(12) United States Patent
Zhou et al.

(10) Patent No.: US 7,919,276 B1
(45) Date of Patent: Apr. 5, 2011

(54) ZA LOOPS OF BROMODOMAINS

(75) Inventors: Ming-Ming Zhou, Greenwich, CT (US); Aneel K. Aggarwal, Edgewater, NJ (US)

(73) Assignee: Mount Sinai School of Medicine, New York, NY (US)

( * ) Notice: Subject to any disclaimer, the term of this patent is extended or adjusted under 35 U.S.C. 154(b) by 0 days.

(21) Appl. No.: 09/510,314

(22) Filed: Feb. 22, 2000

(51) Int. Cl.
*C12P 19/34* (2006.01)

(52) U.S. Cl. ........................................ 435/91.1

(58) Field of Classification Search .................. None
See application file for complete search history.

(56) References Cited

U.S. PATENT DOCUMENTS 5,858,686 A    1/1999   Schlessinger et al. ......... 435/7.8

FOREIGN PATENT DOCUMENTS

| EP | 0124221 | * | 11/1984 |
| WO | WO 98/03652 | * | 1/1998 |

OTHER PUBLICATIONS

Haynes et al., "The bromodomain: a conserved sequence found in human, *Drosophila* and yeast proteins," Nucleic Acids Research, vol. 20 No. 10, p. 2603 (May 1992).*
Archer and Hodin, Curr. Opin. Genet. Biol., 9: 171-74, 1999.
Carson, J. Appl. Crystallogr, 24: 958-61, 1991.
Dhalluin et al., Nature, 399: 491-96, 1999.
Grunstin, Nature, 389: 349-52, 1997.
Jacobson and Pillus, Curr. Opin. Genet. Biol., 9: 175-84, 1999.
Jeanmougin et al., Trends in Biochemical Sciences, 22: 151-53, 1997.
Kiernan et al., EMBO Journal, 18: 6106-118, 1999.
Shuker et al., Science, 274: 1531-34, 1996.
Sobulo et al., PNAS USA, 94: 8732-37, 1997.
Struhl, Genes Dev., 12: 599-606, 1998.
Zhou et al., J. Biol. Chem., 270: 31119-31123, 1995.

* cited by examiner

*Primary Examiner* — Ali R. Salimi
(74) *Attorney, Agent, or Firm* — Klauber & Jackson LLC

(57) ABSTRACT

The present invention provides the structural determination of a bromodomain determined by NMR spectroscopy. The present invention also provides a binding partner for the bromodomain. In addition, the present invention provides methodology for related drug discovery using high throughput drug screening or structure based rational drug design using the three-dimensional data.

2 Claims, 9 Drawing Sheets

Three-Dimensional Structure of the P/CAF Bromodomain

Left-handed bundle

Right-handed bundle

*N*ε-acetyl-lysine

*N*ω-acetyl-histamine

*N*α-acetyl-histidine

SEQUENCE LISTING

<160> NUMBER OF SEQ ID NOS: 47

<210> SEQ ID NO 1
<211> LENGTH: 3014
<212> TYPE: DNA
<213> ORGANISM: Homo sapiens

<400> SEQUENCE: 1
ggggccgcgt cgacgcggaa aagaggccgt ggggggcctc ccagcgctgg cagacaccgt    60

-continued

| | | | | | |
|---|---|---|---|---|---|
| gaggctggca | gccgccggca | cgcacaccta | gtccgcagtc | ccgaggaaca | tgtccgcagc | 120
| cagggcgcgg | agcagagtcc | cgggcaggag | aaccaaggga | gggcgtgtgc | tgtggcggcg | 180
| gcggcagcgg | cagcggagcc | gctagtcccc | tccctcctgg | gggagcagct | gccgccgctg | 240
| ccgccgccgc | caccaccatc | agcgcgcggg | gcccggccag | agcgagccgg | gcgagcggcg | 300
| cgctaggggg | agggcggggg | cggggagggg | ggtgggcgaa | ggggcggga | gggcgtgggg | 360
| ggagggtctc | gctctcccga | ctaccagagc | ccgagggaga | ccctggcggc | ggcggcggcg | 420
| cctgacactc | ggcgcctcct | gccgtgctcc | ggggcggcat | gtccgaggct | ggcggggccg | 480
| ggccgggcg | ctgcggggca | ggagccgggg | caggggccgg | gccgggggcg | ctgccccgc | 540
| agcctgcggc | gcttccgccc | gcgccccgc | agggctcccc | ctgcgccgct | gccgccgggg | 600
| gctcgggcgc | ctgcggtccg | gcgacggcag | tggctgcagc | gggcacggcc | gaaggaccgg | 660
| gaggcggtgg | ctcggcccga | atcgccgtga | agaaagcgca | actacgctcc | gctccgcggg | 720
| ccaagaaact | ggagaaactc | ggagtgtact | ccgcctgcaa | ggccgaggag | tcttgtaaat | 780
| gtaatggctg | gaaaaaccct | aaccctcac | ccactccccc | cagagccgac | ctgcagcaaa | 840
| taattgtcag | tctaacagaa | tcctgtcgga | gttgtagcca | tgccctagct | gctcatgttt | 900
| cccacctgga | gaatgtgtca | gaggaagaaa | tgaacagact | cctgggaata | gtattggatg | 960
| tggaatatct | ctttacctgt | gtccacaagg | aagaagatgc | agataccaaa | caagtttatt | 1020
| tctatctatt | taagctcttg | agaaagtcta | ttttacaaag | aggaaaacct | gtggttgaag | 1080
| gctctttgga | aaagaaaccc | ccatttgaaa | aacctagcat | tgaacagggt | gtgaataact | 1140
| ttgtgcagta | caaatttagt | cacctgccag | caaaagaaag | gcaaacaata | gttgagttgg | 1200
| caaaaatgtt | cctaaaccgc | atcaactatt | ggcatctgga | ggcaccatct | caacgaagac | 1260
| tgcgatctcc | caatgatgat | atttctggat | acaaagagaa | ctacacaagg | tggctgtgtt | 1320
| actgcaacgt | gccacagttc | tgcgacagtc | tacctcggta | cgaaaccaca | caggtgtttg | 1380
| ggagaacatt | gcttcgctcg | gtcttcactg | ttatgaggcg | acaactcctg | gaacaagcaa | 1440
| gacaggaaaa | agataaactg | cctcttgaaa | aacgaactct | aatcctcact | catttcccaa | 1500
| aatttctgtc | catgctagaa | gaagaagtat | atagtcaaaa | ctctcccatc | tgggatcagg | 1560
| attttctctc | agcctcttcc | agaaccagcc | agctaggcat | ccaaacagtt | atcaatccac | 1620
| ctcctgtggc | tgggacaatt | tcatacaatt | caacctcatc | ttcccttgag | cagccaaacg | 1680
| cagggagcag | cagtcctgcc | tgcaaagcct | cttctggact | tgaggcaaac | ccaggagaaa | 1740
| agaggaaaat | gactgattct | catgttctgg | aggaggccaa | gaaacccga | gttatggggg | 1800
| atattccgat | ggaattaatc | aacgaggtta | tgtctaccat | cacggaccct | gcagcaatgc | 1860
| ttggaccaga | gaccaatttt | ctgtcagcac | actcggccag | ggatgaggcg | gcaaggttgg | 1920
| aagagcgcag | gggtgtaatt | gaatttcacg | tggttggcaa | ttccctcaac | cagaaaccaa | 1980
| acaagaagat | cctgatgtgg | ctggttggcc | tacagaacgt | tttctcccac | cagctgcccc | 2040
| gaatgccaaa | agaatacatc | acacggctcg | tctttgaccc | gaaacacaaa | acccttgctt | 2100
| taattaaaga | tggccgtgtt | attggtggta | tctgttccg | tatgttccca | tctcaaggat | 2160
| tcacagagat | tgtcttctgt | gctgtaacct | caaatgagca | agtcaagggc | tatggaacac | 2220
| acctgatgaa | tcatttgaaa | gaatatcaca | taaagcatga | catcctgaac | ttcctcacat | 2280
| atgcagatga | atatgcaatt | ggatacttta | agaaacaggg | tttctccaaa | gaaattaaaa | 2340
| tacctaaaac | caaatatgtt | ggctatatca | aggattatga | aggagccact | ttaatgggat | 2400
| gtgagctaaa | tccacggatc | ccgtacacag | aattttctgt | catcattaaa | aagcagaagg | 2460

-continued

```
agataattaa aaaactgatt gaaagaaaac aggcacaaat tcgaaaagtt taccctggac    2520
tttcatgttt taaagatgga gttcgacaga ttcctataga aagcattcct ggaattagag    2580
agacaggctg gaaaccgagt ggaaaagaga aaagtaaaga gcccagagac cctgaccagc    2640
tttacagcac gctcaagagc atcctccagc aggtgaagag ccatcaaagc gcttggccct    2700
tcatggaacc tgtgaagaga acagaagctc caggatatta tgaagttata aggttcccca    2760
tggatctgaa aaccatgagt gaacgcctca agaataggta ctacgtgtct aagaaattat    2820
tcatggcaga cttacagcga gtctttacca attgcaaaga gtacaacgcc gctgagagtg    2880
aatactacaa atgtgccaat atcctggaga aattcttctt cagtaaaatt aaggaagctg    2940
gattaattga caagtgattt ttttcccc tctgcttctt agaaactcac caagcagtgt    3000
gcctaaagca aggt                                                     3014
```

<210> SEQ ID NO 2
<211> LENGTH: 832
<212> TYPE: PRT
<213> ORGANISM: Homo sapiens

<400> SEQUENCE: 2

```
Met Ser Glu Ala Gly Gly Ala Gly Pro Gly Gly Cys Gly Ala Gly Ala
1               5                   10                  15

Gly Ala Gly Ala Gly Pro Gly Ala Leu Pro Pro Gln Pro Ala Ala Leu
            20                  25                  30

Pro Pro Ala Pro Pro Gln Gly Ser Pro Cys Ala Ala Ala Ala Gly Gly
        35                  40                  45

Ser Gly Ala Cys Gly Pro Ala Thr Ala Val Ala Ala Ala Gly Thr Ala
    50                  55                  60

Glu Gly Pro Gly Gly Gly Gly Ser Ala Arg Ile Ala Val Lys Lys Ala
65                  70                  75                  80

Gln Leu Arg Ser Ala Pro Arg Ala Lys Lys Leu Glu Lys Leu Gly Val
                85                  90                  95

Tyr Ser Ala Cys Lys Ala Glu Glu Ser Cys Lys Cys Asn Gly Trp Lys
            100                 105                 110

Asn Pro Asn Pro Ser Pro Thr Pro Pro Arg Ala Asp Leu Gln Gln Ile
        115                 120                 125

Ile Val Ser Leu Thr Glu Ser Cys Arg Ser Cys Ser His Ala Leu Ala
    130                 135                 140

Ala His Val Ser His Leu Glu Asn Val Ser Glu Glu Met Asn Arg
145                 150                 155                 160

Leu Leu Gly Ile Val Leu Asp Val Glu Tyr Leu Phe Thr Cys Val His
                165                 170                 175

Lys Glu Glu Asp Ala Asp Thr Lys Gln Val Tyr Phe Tyr Leu Phe Lys
            180                 185                 190

Leu Leu Arg Lys Ser Ile Leu Gln Arg Gly Lys Pro Val Val Glu Gly
        195                 200                 205

Ser Leu Glu Lys Lys Pro Pro Phe Glu Lys Pro Ser Ile Glu Gln Gly
    210                 215                 220

Val Asn Asn Phe Val Gln Tyr Lys Phe Ser His Leu Pro Ala Lys Glu
225                 230                 235                 240

Arg Gln Thr Ile Val Glu Leu Ala Lys Met Phe Leu Asn Arg Ile Asn
                245                 250                 255

Tyr Trp His Leu Glu Ala Pro Ser Gln Arg Arg Leu Arg Ser Pro Asn
            260                 265                 270

Asp Asp Ile Ser Gly Tyr Lys Glu Asn Tyr Thr Arg Trp Leu Cys Tyr
```

-continued

```
              275                 280                 285
Cys Asn Val Pro Gln Phe Cys Asp Ser Leu Pro Arg Tyr Glu Thr Thr
290                 295                 300
Gln Val Phe Gly Arg Thr Leu Leu Arg Ser Val Phe Thr Val Met Arg
305                 310                 315                 320
Arg Gln Leu Leu Glu Gln Ala Arg Gln Glu Lys Asp Lys Leu Pro Leu
            325                 330                 335
Glu Lys Arg Thr Leu Ile Leu Thr His Phe Pro Lys Phe Leu Ser Met
            340                 345                 350
Leu Glu Glu Val Tyr Ser Gln Asn Ser Pro Ile Trp Asp Gln Asp
            355                 360                 365
Phe Leu Ser Ala Ser Arg Thr Ser Gln Leu Gly Ile Gln Thr Val
370                 375                 380
Ile Asn Pro Pro Val Ala Gly Thr Ile Ser Tyr Asn Ser Thr Ser
385                 390                 395                 400
Ser Ser Leu Glu Gln Pro Asn Ala Gly Ser Ser Pro Ala Cys Lys
            405                 410                 415
Ala Ser Ser Gly Leu Glu Ala Asn Pro Gly Glu Lys Arg Lys Met Thr
            420                 425                 430
Asp Ser His Val Leu Glu Glu Ala Lys Lys Pro Arg Val Met Gly Asp
            435                 440                 445
Ile Pro Met Glu Leu Ile Asn Glu Val Met Ser Thr Ile Thr Asp Pro
450                 455                 460
Ala Ala Met Leu Gly Pro Glu Thr Asn Phe Leu Ser Ala His Ser Ala
465                 470                 475                 480
Arg Asp Glu Ala Ala Arg Leu Glu Glu Arg Arg Gly Val Ile Glu Phe
            485                 490                 495
His Val Val Gly Asn Ser Leu Asn Gln Lys Pro Asn Lys Lys Ile Leu
            500                 505                 510
Met Trp Leu Val Gly Leu Gln Asn Val Phe Ser His Gln Leu Pro Arg
            515                 520                 525
Met Pro Lys Glu Tyr Ile Thr Arg Leu Val Phe Asp Pro Lys His Lys
            530                 535                 540
Thr Leu Ala Leu Ile Lys Asp Gly Arg Val Ile Gly Gly Ile Cys Phe
545                 550                 555                 560
Arg Met Phe Pro Ser Gln Gly Phe Thr Glu Ile Val Phe Cys Ala Val
            565                 570                 575
Thr Ser Asn Glu Gln Val Lys Gly Tyr Gly Thr His Leu Met Asn His
            580                 585                 590
Leu Lys Glu Tyr His Ile Lys His Asp Ile Leu Asn Phe Leu Thr Tyr
            595                 600                 605
Ala Asp Glu Tyr Ala Ile Gly Tyr Phe Lys Lys Gln Gly Phe Ser Lys
610                 615                 620
Glu Ile Lys Ile Pro Lys Thr Lys Tyr Val Gly Tyr Ile Lys Asp Tyr
625                 630                 635                 640
Glu Gly Ala Thr Leu Met Gly Cys Glu Leu Asn Pro Arg Ile Pro Tyr
            645                 650                 655
Thr Glu Phe Ser Val Ile Ile Lys Lys Gln Lys Glu Ile Ile Lys Lys
            660                 665                 670
Leu Ile Glu Arg Lys Gln Ala Gln Ile Arg Lys Val Tyr Pro Gly Leu
            675                 680                 685
Ser Cys Phe Lys Asp Gly Val Arg Gln Ile Pro Ile Glu Ser Ile Pro
690                 695                 700
```

-continued

```
Gly Ile Arg Glu Thr Gly Trp Lys Pro Ser Gly Lys Glu Lys Ser Lys
705                 710                 715                 720

Glu Pro Arg Asp Pro Asp Gln Leu Tyr Ser Thr Leu Lys Ser Ile Leu
            725                 730                 735

Gln Gln Val Lys Ser His Gln Ser Ala Trp Pro Phe Met Glu Pro Val
        740                 745                 750

Lys Arg Thr Glu Ala Pro Gly Tyr Tyr Glu Val Ile Arg Phe Pro Met
    755                 760                 765

Asp Leu Lys Thr Met Ser Glu Arg Leu Lys Asn Arg Tyr Tyr Val Ser
770                 775                 780

Lys Lys Leu Phe Met Ala Asp Leu Gln Arg Val Phe Thr Asn Cys Lys
785                 790                 795                 800

Glu Tyr Asn Ala Ala Glu Ser Glu Tyr Tyr Lys Cys Ala Asn Ile Leu
                805                 810                 815

Glu Lys Phe Phe Phe Ser Lys Ile Lys Glu Ala Gly Leu Ile Asp Lys
            820                 825                 830

<210> SEQ ID NO 3
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Any amino acid and this region may encompass
      2-3 residues
<220> FEATURE:
<221> NAME/KEY: MOD_RES
<222> LOCATION: (6)..(13)
<223> OTHER INFORMATION: Any amino acid and this region may encompass
      5-8 residues
<220> FEATURE:
<221> NAME/KEY: MOD_RES
<222> LOCATION: (14)
<223> OTHER INFORMATION: Pro, Lys or His
<220> FEATURE:
<221> NAME/KEY: MOD_RES
<222> LOCATION: (15)
<223> OTHER INFORMATION: Any amino acid
<220> FEATURE:
<221> NAME/KEY: MOD_RES
<222> LOCATION: (17)
<223> OTHER INFORMATION: Tyr, Phe or His
<220> FEATURE:
<221> NAME/KEY: MOD_RES
<222> LOCATION: (18)..(22)
<223> OTHER INFORMATION: Any amino acid
<220> FEATURE:
<221> NAME/KEY: MOD_RES
<222> LOCATION: (24)
<223> OTHER INFORMATION: Met, Ile or Val

<400> SEQUENCE: 3

Phe Xaa Xaa Xaa Pro Xaa Xaa Xaa Xaa Xaa Xaa Xaa Xaa Xaa Tyr
1               5                   10                  15

Xaa Xaa Xaa Xaa Xaa Xaa Pro Xaa Asp
                20                  25

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (6)..(6)
<223> OTHER INFORMATION: Acetyl-Lys

<400> SEQUENCE: 4

Ile Ser Tyr Gly Arg Lys Lys Arg Arg Gln Arg Arg
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Acetyl-Lys

<400> SEQUENCE: 5

Ala Arg Lys Ser Thr Gly Gly Lys Ala Pro Arg Lys Gln Leu
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Acetyl-Lys

<400> SEQUENCE: 6

Gln Ser Thr Ser Arg His Lys Lys Leu Met Phe Lys Thr Glu
1               5                   10

<210> SEQ ID NO 7
<211> LENGTH: 110
<212> TYPE: PRT
<213> ORGANISM: Homo sapiens

<400> SEQUENCE: 7

Ser Lys Glu Pro Arg Asp Pro Asp Gln Leu Tyr Ser Thr Leu Lys Ser
1               5                   10                  15

Ile Leu Gln Gln Val Lys Ser His Gln Ser Ala Trp Pro Phe Met Glu
                20                  25                  30

Pro Val Lys Arg Thr Glu Ala Pro Gly Tyr Tyr Glu Val Ile Arg Ser
            35                  40                  45

Pro Met Asp Leu Lys Thr Met Ser Glu Arg Leu Lys Asn Arg Tyr Tyr
        50                  55                  60

Val Ser Lys Lys Leu Phe Met Ala Asp Leu Gln Arg Val Phe Thr Asn
65                  70                  75                  80

Cys Lys Glu Tyr Asn Ala Pro Glu Ser Glu Tyr Tyr Lys Cys Ala Asn
                85                  90                  95

Ile Leu Glu Lys Phe Phe Phe Ser Lys Ile Lys Glu Ala Gly
            100                 105                 110

<210> SEQ ID NO 8
<211> LENGTH: 110
<212> TYPE: PRT
<213> ORGANISM: Homo sapiens
```

-continued

<400> SEQUENCE: 8

```
Gly Lys Glu Leu Lys Asp Pro Asp Gln Leu Tyr Thr Thr Leu Lys Asn
1               5                  10                  15

Leu Leu Ala Gln Ile Lys Ser His Pro Ser Ala Trp Pro Phe Met Glu
            20                  25                  30

Pro Val Lys Lys Ser Glu Ala Pro Asp Tyr Tyr Glu Val Ile Arg Phe
        35                  40                  45

Pro Ile Asp Leu Lys Thr Met Thr Glu Arg Leu Arg Ser Arg Tyr Tyr
    50                  55                  60

Val Thr Arg Lys Leu Phe Val Ala Asp Leu Gln Arg Val Ile Ala Asn
65                  70                  75                  80

Cys Arg Glu Tyr Asn Pro Pro Asp Ser Glu Tyr Cys Arg Cys Ala Ser
                85                  90                  95

Ala Leu Glu Lys Phe Phe Tyr Phe Lys Leu Lys Glu Gly Gly
            100                 105                 110
```

<210> SEQ ID NO 9
<211> LENGTH: 109
<212> TYPE: PRT
<213> ORGANISM: Tetrahymena thermophila

<400> SEQUENCE: 9

```
Leu Lys Lys Ser Lys Glu Arg Ser Phe Asn Leu Gln Cys Ala Asn Val
1               5                  10                  15

Ile Glu Asn Met Lys Arg His Lys Gln Ser Trp Pro Phe Leu Asp Pro
            20                  25                  30

Val Asn Lys Asp Asp Val Pro Asp Tyr Tyr Asp Val Ile Thr Asp Pro
        35                  40                  45

Ile Asp Ile Lys Ala Ile Glu Lys Lys Leu Gln Asn Asn Gln Tyr Val
    50                  55                  60

Asp Lys Asp Gln Phe Ile Lys Asp Val Lys Arg Ile Phe Thr Asn Ala
65                  70                  75                  80

Lys Ile Tyr Asn Gln Pro Asp Thr Ile Tyr Tyr Lys Ala Ala Lys Glu
                85                  90                  95

Leu Glu Asp Phe Val Glu Pro Tyr Leu Thr Lys Leu Lys
            100                 105
```

<210> SEQ ID NO 10
<211> LENGTH: 109
<212> TYPE: PRT
<213> ORGANISM: Saccharomyces cerevisiae

<400> SEQUENCE: 10

```
Ala Gln Arg Pro Lys Arg Gly Pro His Asp Ala Ala Ile Gln Asn Ile
1               5                  10                  15

Leu Thr Glu Leu Gln Asn His Ala Ala Ala Trp Pro Phe Leu Gln Pro
            20                  25                  30

Val Asn Lys Glu Glu Val Pro Asp Tyr Tyr Asp Phe Ile Lys Glu Pro
        35                  40                  45

Met Asp Leu Ser Thr Met Glu Ile Lys Leu Glu Ser Asn Lys Tyr Gln
    50                  55                  60

Lys Met Glu Asp Phe Ile Tyr Asp Ala Arg Leu Val Phe Asn Asn Cys
65                  70                  75                  80

Arg Met Tyr Asn Gly Glu Asn Thr Ser Tyr Tyr Lys Tyr Ala Asn Arg
                85                  90                  95

Leu Glu Lys Phe Phe Asn Asn Lys Val Lys Glu Ile Pro
            100                 105
```

<210> SEQ ID NO 11
<211> LENGTH: 112
<212> TYPE: PRT
<213> ORGANISM: Homo sapiens

<400> SEQUENCE: 11

Lys Lys Ile Phe Lys Pro Glu Glu Leu Arg Gln Ala Leu Met Pro Thr
1               5                   10                  15

Leu Glu Ala Leu Tyr Arg Gln Asp Pro Glu Ser Leu Pro Phe Arg Gln
                20                  25                  30

Pro Val Asp Pro Gln Leu Leu Gly Ile Pro Asp Tyr Phe Asp Ile Val
            35                  40                  45

Lys Ser Pro Met Asp Leu Ser Thr Ile Lys Arg Lys Leu Asp Thr Gly
        50                  55                  60

Gln Tyr Gln Glu Pro Trp Gln Tyr Val Asp Asp Ile Trp Leu Met Phe
65                  70                  75                  80

Asn Asn Ala Trp Leu Tyr Asn Arg Lys Thr Ser Arg Val Tyr Lys Tyr
                85                  90                  95

Cys Ser Lys Leu Ser Glu Val Phe Glu Gln Glu Ile Asp Pro Val Met
            100                 105                 110

<210> SEQ ID NO 12
<211> LENGTH: 112
<212> TYPE: PRT
<213> ORGANISM: Homo sapiens

<400> SEQUENCE: 12

Lys Lys Ile Phe Lys Pro Glu Glu Leu Arg Gln Ala Leu Met Pro Thr
1               5                   10                  15

Leu Glu Ala Leu Tyr Arg Gln Asp Pro Glu Ser Leu Pro Phe Arg Gln
                20                  25                  30

Pro Val Asp Pro Gln Leu Leu Gly Ile Pro Asp Tyr Phe Asp Ile Val
            35                  40                  45

Lys Asn Pro Met Asp Leu Ser Thr Ile Lys Arg Lys Leu Asp Thr Gly
        50                  55                  60

Gln Tyr Gln Glu Pro Trp Gln Tyr Val Asp Asp Val Trp Leu Met Phe
65                  70                  75                  80

Asn Asn Ala Trp Leu Tyr Asn Arg Lys Thr Ser Arg Val Tyr Lys Phe
                85                  90                  95

Cys Ser Lys Leu Ala Glu Val Phe Glu Gln Glu Ile Asp Pro Val Met
            100                 105                 110

<210> SEQ ID NO 13
<211> LENGTH: 112
<212> TYPE: PRT
<213> ORGANISM: Mus musculus

<400> SEQUENCE: 13

Lys Lys Ile Phe Lys Pro Glu Glu Leu Arg Gln Ala Leu Met Pro Thr
1               5                   10                  15

Leu Glu Ala Leu Tyr Arg Gln Asp Pro Glu Ser Leu Pro Phe Arg Gln
                20                  25                  30

Pro Val Asp Pro Gln Leu Leu Gly Ile Pro Asp Tyr Phe Asp Ile Val
            35                  40                  45

Lys Asn Pro Met Asp Leu Ser Thr Ile Lys Arg Lys Leu Asp Thr Gly
        50                  55                  60

Gln Tyr Gln Glu Pro Trp Gln Tyr Val Asp Asp Val Arg Leu Met Phe

```
                65                  70                  75                  80
Asn Asn Ala Trp Leu Tyr Asn Arg Lys Thr Ser Arg Val Tyr Lys Phe
                    85                  90                  95
Cys Ser Lys Leu Ala Glu Val Phe Glu Gln Glu Ile Asp Pro Val Met
                100                 105                 110
```

<210> SEQ ID NO 14
<211> LENGTH: 111
<212> TYPE: PRT
<213> ORGANISM: Caenorhabditis elegans

<400> SEQUENCE: 14

```
Asp Thr Val Phe Ser Gln Glu Asp Leu Ile Lys Phe Leu Leu Pro Val
1               5                   10                  15
Trp Glu Lys Leu Asp Lys Ser Glu Asp Ala Ala Pro Phe Arg Val Pro
                20                  25                  30
Val Asp Ala Lys Leu Leu Asn Ile Pro Asp Tyr His Glu Ile Ile Lys
            35                  40                  45
Arg Pro Met Asp Leu Glu Thr Val His Lys Lys Leu Tyr Ala Gly Gln
        50                  55                  60
Tyr Gln Asn Ala Gly Gln Phe Cys Asp Asp Ile Trp Leu Met Leu Asp
65                  70                  75                  80
Asn Ala Trp Leu Tyr Asn Arg Lys Asn Ser Lys Val Tyr Lys Tyr Gly
                85                  90                  95
Leu Lys Leu Ser Glu Met Phe Val Ser Glu Met Asp Pro Val Met
                100                 105                 110
```

<210> SEQ ID NO 15
<211> LENGTH: 110
<212> TYPE: PRT
<213> ORGANISM: Homo sapiens

<400> SEQUENCE: 15

```
Arg Arg Arg Thr Asp Pro Met Val Thr Leu Ser Ser Ile Leu Glu Ser
1               5                   10                  15
Ile Ile Asn Asp Met Arg Asp Leu Pro Asn Thr Tyr Pro Phe His Thr
                20                  25                  30
Pro Val Asn Ala Lys Val Val Lys Asp Tyr Tyr Lys Ile Ile Thr Arg
            35                  40                  45
Pro Met Asp Leu Gln Thr Leu Arg Glu Asn Val Arg Lys Arg Leu Tyr
        50                  55                  60
Pro Ser Arg Glu Glu Phe Arg Glu His Leu Glu Leu Ile Val Lys Asn
65                  70                  75                  80
Ser Ala Thr Tyr Asn Gly Pro Lys His Ser Leu Thr Gln Ile Ser Gln
                85                  90                  95
Ser Met Leu Asp Leu Cys Asp Glu Lys Leu Lys Glu Lys Glu
                100                 105                 110
```

<210> SEQ ID NO 16
<211> LENGTH: 110
<212> TYPE: PRT
<213> ORGANISM: Mesocricetus auratus

<400> SEQUENCE: 16

```
Arg Arg Arg Thr Asp Pro Met Val Thr Leu Ser Ser Ile Leu Glu Ser
1               5                   10                  15
Ile Ile Asn Asp Met Arg Asp Leu Pro Asn Thr Tyr Pro Phe His Thr
                20                  25                  30
```

```
Pro Val Asn Ala Lys Val Val Lys Asp Tyr Tyr Lys Ile Ile Thr Arg
        35                  40                  45

Pro Met Asp Leu Gln Thr Leu Arg Glu Asn Val Lys Arg Leu Tyr
    50                  55                  60

Pro Ser Arg Glu Glu Phe Arg Glu His Leu Glu Leu Ile Val Lys Asn
 65                  70                  75                  80

Ser Ala Thr Tyr Asn Gly Pro Lys His Ser Leu Thr Gln Ile Ser Gln
                85                  90                  95

Ser Met Leu Asp Leu Cys Asp Glu Lys Leu Lys Glu Lys Glu
            100                 105                 110
```

```
<210> SEQ ID NO 17
<211> LENGTH: 111
<212> TYPE: PRT
<213> ORGANISM: Homo sapiens

<400> SEQUENCE: 17

Leu Leu Asp Asp Asp Asp Gln Val Ala Phe Ser Phe Ile Leu Asp Asn
 1               5                  10                  15

Ile Val Thr Gln Lys Met Met Ala Val Pro Asp Ser Trp Pro Phe His
                20                  25                  30

His Pro Val Asn Lys Lys Phe Val Pro Asp Tyr Tyr Lys Val Ile Val
            35                  40                  45

Asn Pro Met Asp Leu Glu Thr Ile Arg Lys Asn Ile Ser Lys His Lys
    50                  55                  60

Tyr Gln Ser Arg Glu Ser Phe Leu Asp Asp Val Asn Leu Ile Leu Ala
 65                  70                  75                  80

Asn Ser Val Lys Tyr Asn Gly Pro Glu Ser Gln Tyr Thr Lys Thr Ala
                85                  90                  95

Gln Glu Ile Val Asn Val Cys Tyr Gln Thr Leu Thr Glu Tyr Asp
            100                 105                 110
```

```
<210> SEQ ID NO 18
<211> LENGTH: 111
<212> TYPE: PRT
<213> ORGANISM: Mesocricetus auratus

<400> SEQUENCE: 18

Leu Leu Asp Asp Asp Asp Gln Val Ala Phe Ser Phe Ile Leu Asp Asn
 1               5                  10                  15

Ile Val Thr Gln Lys Met Met Ala Val Pro Asp Ser Trp Pro Phe His
                20                  25                  30

His Pro Val Asn Lys Lys Phe Val Pro Asp Tyr Tyr Lys Val Ile Val
            35                  40                  45

Ser Pro Met Asp Leu Glu Thr Ile Arg Lys Asn Ile Ser Lys His Lys
    50                  55                  60

Tyr Gln Ser Arg Glu Ser Phe Leu Asp Asp Val Asn Leu Ile Leu Ala
 65                  70                  75                  80

Asn Ser Val Lys Tyr Asn Gly Ser Glu Ser Gln Tyr Thr Lys Thr Ala
                85                  90                  95

Gln Glu Ile Val Asn Val Cys Tyr Gln Thr Leu Thr Glu Tyr Asp
            100                 105                 110
```

```
<210> SEQ ID NO 19
<211> LENGTH: 111
<212> TYPE: PRT
<213> ORGANISM: Homo sapiens

<400> SEQUENCE: 19
```

```
Lys Pro Gly Arg Val Thr Asn Gln Leu Gln Tyr Leu His Lys Val Val
1               5                   10                  15

Met Lys Ala Leu Trp Lys His Gln Phe Ala Trp Pro Phe Arg Gln Pro
            20                  25                  30

Val Asp Ala Val Lys Leu Gly Leu Pro Asp Tyr His Lys Ile Ile Lys
            35                  40                  45

Gln Pro Met Asp Met Gly Thr Ile Lys Arg Arg Leu Glu Asn Asn Tyr
50                      55                  60

Tyr Trp Ala Ala Ser Glu Cys Met Gln Asp Phe Asn Thr Met Phe Thr
65                  70                  75                  80

Asn Cys Tyr Ile Tyr Asn Lys Pro Thr Asp Asp Ile Val Leu Met Ala
                85                  90                  95

Gln Thr Leu Glu Lys Ile Phe Leu Gln Lys Val Ala Ser Met Pro
            100                 105                 110
```

<210> SEQ ID NO 20
<211> LENGTH: 111
<212> TYPE: PRT
<213> ORGANISM: Homo sapiens

<400> SEQUENCE: 20

```
Lys Pro Gly Arg Lys Thr Asn Gln Leu Gln Tyr Met Gln Asn Val Val
1               5                   10                  15

Val Lys Thr Leu Trp Lys His Gln Phe Ala Trp Pro Phe Tyr Gln Pro
            20                  25                  30

Val Asp Ala Ile Lys Leu Asn Leu Pro Asp Tyr His Lys Ile Ile Lys
            35                  40                  45

Asn Pro Met Asp Met Gly Thr Ile Lys Lys Arg Leu Glu Asn Asn Tyr
50                      55                  60

Tyr Trp Ser Ala Ser Glu Cys Met Gln Asp Phe Asn Thr Met Phe Thr
65                  70                  75                  80

Asn Cys Tyr Ile Tyr Asn Lys Pro Thr Asp Asp Ile Val Leu Met Ala
                85                  90                  95

Gln Ala Leu Glu Lys Ile Phe Leu Gln Lys Val Ala Gly Met Pro
            100                 105                 110
```

<210> SEQ ID NO 21
<211> LENGTH: 111
<212> TYPE: PRT
<213> ORGANISM: Drosophila melanogaster

<400> SEQUENCE: 21

```
Arg Pro Gly Arg Asn Thr Asn Gln Leu Gln Tyr Leu Ile Lys Thr Val
1               5                   10                  15

Met Lys Val Ile Trp Lys His His Phe Ser Trp Pro Phe Gln Gln Pro
            20                  25                  30

Val Asp Ala Lys Lys Leu Asn Leu Pro Asp Tyr His Lys Ile Ile Lys
            35                  40                  45

Gln Pro Met Asp Met Gly Thr Ile Lys Lys Arg Leu Glu Asn Asn Tyr
50                      55                  60

Tyr Trp Ser Ala Lys Glu Thr Ile Gln Asp Phe Asn Thr Met Phe Asn
65                  70                  75                  80

Asn Cys Tyr Val Tyr Asn Lys Pro Gly Glu Asp Val Val Val Met Ala
                85                  90                  95

Gln Thr Leu Glu Lys Val Phe Leu Gln Lys Ile Glu Ser Met Pro
            100                 105                 110
```

```
<210> SEQ ID NO 22
<211> LENGTH: 109
<212> TYPE: PRT
<213> ORGANISM: Saccharomyces cerevisiae

<400> SEQUENCE: 22

Asn Pro Ile Pro Lys His Gln Gln Lys His Ala Leu Leu Ala Ile Lys
1               5                   10                  15

Ala Val Lys Arg Leu Lys Asp Ala Arg Pro Phe Leu Gln Pro Val Asp
            20                  25                  30

Pro Val Lys Leu Asp Ile Pro Phe Tyr Phe Asn Tyr Ile Lys Arg Pro
        35                  40                  45

Met Asp Leu Ser Thr Ile Glu Arg Lys Leu Asn Val Gly Ala Tyr Glu
    50                  55                  60

Val Pro Glu Gln Ile Thr Glu Asp Phe Asn Leu Met Val Asn Asn Ser
65                  70                  75                  80

Ile Lys Phe Asn Gly Pro Asn Ala Gly Ile Ser Gln Met Ala Arg Asn
                85                  90                  95

Ile Gln Ala Ser Phe Glu Lys His Met Leu Asn Met Pro
            100                 105

<210> SEQ ID NO 23
<211> LENGTH: 113
<212> TYPE: PRT
<213> ORGANISM: Homo sapiens

<400> SEQUENCE: 23

Lys Lys Gly Lys Leu Ser Glu Gln Leu Lys His Cys Asn Gly Ile Leu
1               5                   10                  15

Lys Glu Leu Leu Ser Lys Lys His Ala Ala Tyr Ala Trp Pro Phe Tyr
            20                  25                  30

Lys Pro Val Asp Ala Ser Ala Leu Gly Leu His Asp Tyr His Asp Ile
        35                  40                  45

Ile Lys His Pro Met Asp Leu Ser Thr Val Lys Arg Lys Met Glu Asn
    50                  55                  60

Arg Asp Tyr Arg Asp Ala Gln Glu Phe Ala Ala Asp Val Arg Leu Met
65                  70                  75                  80

Phe Ser Asn Cys Tyr Lys Tyr Asn Pro Pro Asp His Asp Val Val Ala
                85                  90                  95

Met Ala Arg Lys Leu Gln Asp Val Phe Glu Phe Arg Tyr Ala Lys Met
            100                 105                 110

Pro

<210> SEQ ID NO 24
<211> LENGTH: 113
<212> TYPE: PRT
<213> ORGANISM: Homo sapiens

<400> SEQUENCE: 24

Lys Lys Gly Lys Leu Ser Glu His Leu Arg Tyr Cys Asp Ser Ile Leu
1               5                   10                  15

Arg Glu Met Leu Ser Lys Lys His Ala Ala Tyr Ala Trp Pro Phe Tyr
            20                  25                  30

Lys Pro Val Asp Ala Glu Ala Leu Glu Leu His Asp Tyr His Asp Ile
        35                  40                  45

Ile Lys His Pro Met Asp Leu Ser Thr Val Lys Arg Lys Met Asp Gly
    50                  55                  60
```

Arg Glu Tyr Pro Asp Ala Gln Gly Phe Ala Ala Asp Val Arg Leu Met
65                  70                  75                  80

Phe Ser Asn Cys Tyr Lys Tyr Asn Pro Pro Asp His Glu Val Val Ala
                85                  90                  95

Met Ala Arg Lys Leu Gln Asp Val Phe Glu Met Arg Phe Ala Lys Met
            100                 105                 110

Pro

<210> SEQ ID NO 25
<211> LENGTH: 113
<212> TYPE: PRT
<213> ORGANISM: Drosophila melanogaster

<400> SEQUENCE: 25

Asn Lys Glu Lys Leu Ser Asp Ala Leu Lys Ser Cys Asn Glu Ile Leu
1               5                   10                  15

Lys Glu Leu Phe Ser Lys Lys His Ser Gly Tyr Ala Trp Pro Phe Tyr
            20                  25                  30

Lys Pro Val Asp Ala Glu Met Leu Gly Leu His Asp Tyr His Asp Ile
        35                  40                  45

Ile Lys Lys Pro Met Asp Leu Gly Thr Val Lys Arg Lys Met Asp Asn
50                  55                  60

Arg Glu Tyr Lys Ser Ala Pro Glu Phe Ala Ala Asp Val Arg Leu Ile
65                  70                  75                  80

Phe Thr Asn Cys Tyr Lys Tyr Asn Pro Pro Asp His Asp Val Val Ala
                85                  90                  95

Met Gly Arg Lys Leu Gln Asp Val Phe Glu Met Arg Tyr Ala Asn Ile
            100                 105                 110

Pro

<210> SEQ ID NO 26
<211> LENGTH: 113
<212> TYPE: PRT
<213> ORGANISM: Saccharomyces cerevisiae

<400> SEQUENCE: 26

Lys Ser Lys Arg Leu Gln Gln Ala Met Lys Phe Cys Gln Ser Val Leu
1               5                   10                  15

Lys Glu Leu Met Ala Lys Lys His Ala Ser Tyr Asn Tyr Pro Phe Leu
            20                  25                  30

Glu Pro Val Asp Pro Val Ser Met Asn Leu Pro Thr Tyr Phe Asp Tyr
        35                  40                  45

Val Lys Glu Pro Met Asp Leu Gly Thr Ile Ala Lys Lys Leu Asn Asp
50                  55                  60

Trp Gln Tyr Gln Thr Met Glu Asp Phe Glu Arg Glu Val Arg Leu Val
65                  70                  75                  80

Phe Lys Asn Cys Tyr Thr Phe Asn Pro Asp Gly Thr Ile Val Asn Met
                85                  90                  95

Met Gly His Arg Leu Glu Glu Val Phe Asn Ser Lys Trp Ala Asp Arg
            100                 105                 110

Pro

<210> SEQ ID NO 27
<211> LENGTH: 108
<212> TYPE: PRT
<213> ORGANISM: Homo sapiens

<400> SEQUENCE: 27

```
Met Glu Met Gln Leu Thr Pro Phe Leu Ile Leu Leu Arg Lys Thr Leu
1               5                   10                  15

Glu Gln Leu Gln Glu Lys Asp Thr Gly Asn Ile Phe Ser Glu Pro Val
            20                  25                  30

Pro Leu Ser Glu Val Pro Asp Tyr Leu Asp His Ile Lys Lys Pro Met
        35                  40                  45

Asp Phe Phe Thr Met Lys Gln Asn Leu Glu Ala Tyr Arg Tyr Leu Asn
    50                  55                  60

Phe Asp Asp Phe Glu Glu Asp Phe Asn Leu Ile Val Ser Asn Cys Leu
65              70                  75                  80

Lys Tyr Asn Ala Lys Asp Thr Ile Phe Tyr Arg Ala Val Arg Leu
                85                  90                  95

Arg Glu Gln Gly Gly Ala Val Val Arg Gln Ala Arg
                100                 105
```

<210> SEQ ID NO 28
<211> LENGTH: 113
<212> TYPE: PRT
<213> ORGANISM: Homo sapiens

<400> SEQUENCE: 28

```
Ser Glu Asp Gln Glu Ala Ile Gln Ala Gln Lys Ile Trp Lys Lys Ala
1               5                   10                  15

Ile Met Leu Val Trp Arg Ala Ala Asn His Arg Tyr Ala Asn Val
            20                  25                  30

Phe Leu Gln Pro Val Thr Asp Asp Ile Ala Pro Gly Tyr His Ser Ile
        35                  40                  45

Val Gln Arg Pro Met Asp Leu Ser Thr Ile Lys Lys Asn Ile Glu Asn
    50                  55                  60

Gly Leu Ile Arg Ser Thr Ala Glu Phe Gln Arg Asp Ile Met Leu Met
65              70                  75                  80

Phe Gln Asn Ala Val Met Tyr Asn Ser Ser Asp His Asp Val Tyr His
                85                  90                  95

Met Ala Val Glu Met Gln Arg Asp Val Leu Glu Gln Ile Gln Gln Phe
                100                 105                 110

Leu
```

<210> SEQ ID NO 29
<211> LENGTH: 106
<212> TYPE: PRT
<213> ORGANISM: Gallus gallus

<400> SEQUENCE: 29

```
Asn Leu Pro Thr Val Asp Pro Ile Ala Val Cys His Glu Leu Tyr Asn
1               5                   10                  15

Thr Ile Arg Asp Tyr Lys Asp Glu Gln Gly Arg Leu Leu Cys Glu Leu
            20                  25                  30

Phe Ile Arg Ala Pro Lys Arg Arg Asn Gln Pro Asp Tyr Tyr Glu Val
        35                  40                  45

Val Ser Gln Pro Ile Asp Leu Met Lys Ile Gln Gln Lys Leu Lys Met
    50                  55                  60

Glu Glu Tyr Asp Asp Val Asn Val Leu Thr Ala Asp Phe Gln Leu Leu
65              70                  75                  80

Phe Asn Asn Ala Lys Ala Tyr Tyr Lys Pro Asp Ser Pro Glu Tyr Lys
                85                  90                  95

Ala Ala Cys Lys Leu Trp Glu Leu Tyr Leu
```

```
                          100             105

<210> SEQ ID NO 30
<211> LENGTH: 112
<212> TYPE: PRT
<213> ORGANISM: Gallus gallus

<400> SEQUENCE: 30

Ser Ser Pro Gly Tyr Leu Lys Glu Ile Leu Glu Gln Leu Leu Glu Ala
1               5                   10                  15

Val Ala Val Ala Thr Asn Pro Ser Gly Arg Leu Ile Ser Glu Leu Phe
            20                  25                  30

Gln Lys Leu Pro Ser Lys Val Gln Tyr Pro Asp Tyr Ala Ile Ile
        35                  40                  45

Lys Glu Pro Ile Asp Leu Lys Thr Ile Ala Gln Arg Ile Gln Asn Gly
    50                  55                  60

Thr Tyr Lys Ser Ile His Ala Met Ala Lys Asp Ile Asp Leu Leu Ala
65                  70                  75                  80

Lys Asn Ala Lys Thr Tyr Asn Glu Pro Gly Ser Gln Val Phe Lys Asp
                85                  90                  95

Ala Asn Ala Ile Lys Lys Ile Phe Asn Met Lys Lys Ala Glu Ile Glu
                100                 105                 110

<210> SEQ ID NO 31
<211> LENGTH: 112
<212> TYPE: PRT
<213> ORGANISM: Gallus gallus

<400> SEQUENCE: 31

Thr Ser Phe Met Asp Thr Ser Asn Pro Leu Tyr Gln Leu Tyr Asp Thr
1               5                   10                  15

Val Arg Ser Cys Arg Asn Asn Gln Gly Gln Leu Ile Ser Glu Pro Phe
            20                  25                  30

Phe Gln Leu Pro Ser Lys Lys Tyr Pro Asp Tyr Gln Gln Ile
        35                  40                  45

Lys Thr Pro Ile Ser Leu Gln Gln Ile Arg Ala Lys Leu Lys Asn His
    50                  55                  60

Glu Tyr Glu Thr Leu Asp Gln Leu Glu Ala Asp Leu Asn Leu Met Phe
65                  70                  75                  80

Glu Asn Ala Lys Arg Tyr Asn Val Pro Asn Ser Ala Ile Tyr Lys Arg
                85                  90                  95

Val Leu Lys Met Gln Gln Val Met Gln Ala Lys Lys Glu Leu Ala
                100                 105                 110

<210> SEQ ID NO 32
<211> LENGTH: 113
<212> TYPE: PRT
<213> ORGANISM: Gallus gallus

<400> SEQUENCE: 32

Ser Lys Lys Asn Met Arg Lys Gln Arg Met Lys Ile Leu Tyr Asn Ala
1               5                   10                  15

Val Leu Glu Ala Arg Glu Ser Gly Thr Gln Arg Arg Leu Cys Asp Leu
            20                  25                  30

Phe Met Val Lys Pro Ser Lys Lys Asp Tyr Pro Asp Tyr Lys Ile
        35                  40                  45

Ile Leu Glu Pro Met Asp Leu Lys Met Ile Glu His Asn Ile Arg Asn
    50                  55                  60
```

-continued

```
Asp Lys Tyr Val Gly Glu Ala Met Ile Asp Met Lys Leu Met
 65                  70                  75                  80

Phe Arg Asn Ala Arg His Tyr Asn Glu Glu Gly Ser Gln Val Tyr Asn
                 85                  90                  95

Asp Ala His Met Leu Glu Lys Ile Leu Lys Glu Lys Arg Lys Glu Leu
            100                 105                 110

Gly

<210> SEQ ID NO 33
<211> LENGTH: 115
<212> TYPE: PRT
<213> ORGANISM: Gallus gallus

<400> SEQUENCE: 33

Lys Lys Ser Lys Tyr Met Thr Pro Met Gln Gln Lys Leu Asn Glu Val
 1                5                  10                  15

Tyr Glu Ala Val Lys Asn Tyr Thr Asp Lys Arg Gly Arg Arg Leu Ser
                 20                  25                  30

Ala Ile Phe Leu Arg Leu Pro Ser Arg Ser Glu Leu Pro Asp Tyr Tyr
            35                  40                  45

Ile Thr Ile Lys Lys Pro Val Asp Met Glu Lys Ile Arg Ser His Met
 50                  55                  60

Met Ala Asn Lys Tyr Gln Asp Ile Asp Ser Met Val Glu Asp Phe Val
 65                  70                  75                  80

Met Met Phe Asn Asn Ala Cys Thr Tyr Asn Glu Pro Glu Ser Leu Ile
                 85                  90                  95

Tyr Lys Asp Ala Leu Val Leu His Lys Val Leu Leu Glu Thr Arg Arg
            100                 105                 110

Glu Ile Glu
        115

<210> SEQ ID NO 34
<211> LENGTH: 112
<212> TYPE: PRT
<213> ORGANISM: Schizosaccharomyces pombe

<400> SEQUENCE: 34

His Asn Ala Pro Phe Asp Lys Thr Lys Phe Asp Glu Val Leu Glu Ala
 1                5                  10                  15

Leu Val Gly Leu Lys Asp Asn Glu Gly Asn Pro Phe Asp Asp Ile Phe
                 20                  25                  30

Glu Glu Leu Pro Ser Lys Arg Tyr Phe Pro Asp Tyr Tyr Gln Ile Ile
            35                  40                  45

Gln Lys Pro Ile Cys Tyr Lys Met Met Arg Asn Lys Ala Lys Thr Gly
 50                  55                  60

Lys Tyr Leu Ser Met Gly Asp Phe Tyr Asp Ile Arg Leu Met Val
 65                  70                  75                  80

Ser Asn Ala Gln Thr Tyr Asn Met Pro Gly Ser Leu Val Tyr Glu Cys
                 85                  90                  95

Ser Val Leu Ile Ala Asn Thr Ala Asn Ser Leu Glu Ser Lys Asp Gly
            100                 105                 110

<210> SEQ ID NO 35
<211> LENGTH: 113
<212> TYPE: PRT
<213> ORGANISM: Schizosaccharomyces pombe

<400> SEQUENCE: 35
```

```
Gly Thr Asn Glu Ile Asp Val Pro Lys Val Ile Gln Asn Ile Leu Asp
 1               5                  10                  15

Ala Leu His Glu Glu Lys Asp Glu Gln Gly Arg Phe Leu Ile Asp Ile
             20                  25                  30

Phe Ile Asp Leu Pro Ser Lys Arg Leu Tyr Pro Asp Tyr Tyr Glu Ile
         35                  40                  45

Ile Lys Ser Pro Met Thr Ile Lys Met Leu Glu Lys Arg Phe Lys Lys
     50                  55                  60

Gly Glu Tyr Thr Thr Leu Glu Ser Phe Val Lys Asp Leu Asn Gln Met
 65                  70                  75                  80

Phe Ile Asn Ala Lys Thr Tyr Asn Ala Pro Gly Ser Phe Val Tyr Glu
                 85                  90                  95

Asp Ala Glu Lys Leu Ser Gln Leu Ser Ser Ser Leu Ile Ser Ser Phe
                100                 105                 110

Ser
```

```
<210> SEQ ID NO 36
<211> LENGTH: 113
<212> TYPE: PRT
<213> ORGANISM: Homo sapiens

<400> SEQUENCE: 36
```

```
Ser Pro Asn Pro Pro Lys Leu Thr Lys Gln Met Asn Ala Ile Ile Asp
 1               5                  10                  15

Thr Val Ile Asn Tyr Lys Asp Ser Ser Gly Arg Gln Leu Ser Glu Val
             20                  25                  30

Phe Ile Gln Leu Pro Ser Arg Lys Glu Leu Pro Glu Tyr Tyr Glu Leu
         35                  40                  45

Ile Arg Lys Pro Val Asp Phe Lys Lys Ile Lys Glu Arg Ile Arg Asn
     50                  55                  60

His Lys Tyr Arg Ser Leu Gly Asp Leu Glu Lys Asp Val Met Leu Leu
 65                  70                  75                  80

Cys His Asn Ala Gln Thr Phe Asn Leu Glu Gly Ser Gln Ile Tyr Glu
                 85                  90                  95

Asp Ser Ile Val Leu Gln Ser Val Phe Lys Ser Ala Arg Gln Lys Ile
                100                 105                 110

Ala
```

```
<210> SEQ ID NO 37
<211> LENGTH: 114
<212> TYPE: PRT
<213> ORGANISM: Homo sapiens

<400> SEQUENCE: 37
```

```
Ser Pro Asn Pro Pro Asn Leu Thr Lys Lys Met Lys Lys Ile Val Asp
 1               5                  10                  15

Ala Val Ile Lys Tyr Lys Asp Ser Ser Ser Gly Arg Gln Leu Ser Glu
             20                  25                  30

Val Phe Ile Gln Leu Pro Ser Arg Lys Glu Leu Pro Glu Tyr Tyr Glu
         35                  40                  45

Leu Ile Arg Lys Pro Val Asp Phe Lys Lys Ile Lys Glu Arg Ile Arg
     50                  55                  60

Asn His Lys Tyr Arg Ser Leu Asn Asp Leu Glu Lys Asp Val Met Leu
 65                  70                  75                  80

Leu Cys Gln Asn Ala Gln Thr Phe Asn Leu Glu Gly Ser Leu Ile Tyr
                 85                  90                  95
```

```
Glu Asp Ser Ile Val Leu Gln Ser Val Phe Thr Ser Val Arg Gln Lys
            100                 105                 110

Ile Glu
```

<210> SEQ ID NO 38
<211> LENGTH: 113
<212> TYPE: PRT
<213> ORGANISM: Gallus gallus

<400> SEQUENCE: 38

```
Ser Pro Asn Pro Pro Lys Leu Thr Lys Gln Met Asn Ala Ile Ile Asp
1               5                   10                  15

Thr Val Ile Asn Tyr Lys Asp Ser Ser Gly Arg Gln Leu Ser Glu Val
            20                  25                  30

Phe Ile Gln Leu Pro Ser Arg Lys Glu Leu Pro Glu Tyr Tyr Glu Leu
        35                  40                  45

Ile Arg Lys Pro Val Asp Phe Lys Lys Ile Lys Glu Arg Ile Arg Asn
50                  55                  60

His Lys Tyr Arg Ser Leu Gly Asp Leu Glu Lys Asp Val Met Leu Leu
65                  70                  75                  80

Cys His Asn Ala Gln Thr Phe Asn Leu Glu Gly Ser Gln Ile Tyr Glu
            85                  90                  95

Asp Ser Ile Val Leu Gln Ser Val Phe Lys Ser Ala Arg Gln Lys Ile
            100                 105                 110

Ala
```

<210> SEQ ID NO 39
<211> LENGTH: 114
<212> TYPE: PRT
<213> ORGANISM: Gallus gallus

<400> SEQUENCE: 39

```
Ser Pro Asn Pro Pro Asn Leu Thr Lys Lys Met Lys Lys Ile Val Asp
1               5                   10                  15

Ala Val Ile Lys Tyr Lys Asp Ser Ser Ser Gly Arg Gln Leu Ser Glu
            20                  25                  30

Val Phe Ile Gln Leu Pro Ser Arg Lys Glu Leu Pro Glu Tyr Tyr Glu
        35                  40                  45

Leu Ile Arg Lys Pro Val Asp Phe Lys Lys Ile Lys Glu Arg Ile Arg
50                  55                  60

Asn His Lys Tyr Arg Ser Leu Asn Asp Leu Glu Lys Asp Val Met Leu
65                  70                  75                  80

Leu Cys Gln Asn Ala Gln Thr Phe Asn Leu Glu Val Ser Leu Ile Tyr
            85                  90                  95

Glu Asp Ser Ile Val Leu Gln Ser Val Phe Thr Ser Val Arg Gln Lys
            100                 105                 110

Ile Glu
```

<210> SEQ ID NO 40
<211> LENGTH: 105
<212> TYPE: PRT
<213> ORGANISM: Homo sapiens

<400> SEQUENCE: 40

```
Ala Lys Leu Ser Pro Ala Asn Gln Arg Lys Cys Glu Arg Val Leu Leu
1               5                   10                  15

Ala Leu Phe Cys His Glu Pro Cys Arg Pro Leu His Gln Leu Ala Thr
            20                  25                  30
```

```
Asp Ser Thr Phe Ser Leu Asp Gln Pro Gly Gly Thr Leu Asp Leu Thr
        35                  40                  45

Leu Ile Arg Ala Arg Leu Gln Glu Lys Leu Ser Pro Pro Tyr Ser Ser
 50                  55                  60

Pro Gln Glu Phe Ala Gln Asp Val Gly Arg Met Phe Lys Gln Phe Asn
 65                  70                  75                  80

Lys Leu Thr Glu Asp Lys Ala Asp Val Gln Ser Ile Ile Gly Leu Gln
                 85                  90                  95

Arg Phe Phe Glu Thr Arg Met Asn Glu
                100                 105

<210> SEQ ID NO 41
<211> LENGTH: 105
<212> TYPE: PRT
<213> ORGANISM: Mus musculus

<400> SEQUENCE: 41

Ala Lys Leu Ser Pro Ala Asn Gln Arg Lys Cys Glu Arg Val Leu Leu
 1               5                  10                  15

Ala Leu Phe Cys His Glu Pro Cys Arg Pro Leu His Gln Leu Ala Thr
                20                  25                  30

Asp Ser Thr Phe Ser Met Glu Gln Pro Gly Gly Thr Leu Asp Leu Thr
        35                  40                  45

Leu Ile Arg Ala Arg Leu Gln Glu Lys Leu Ser Pro Pro Tyr Ser Ser
 50                  55                  60

Pro Gln Glu Phe Ala Gln Asp Val Gly Arg Met Phe Lys Gln Phe Asn
 65                  70                  75                  80

Lys Leu Thr Glu Asp Lys Ala Asp Val Gln Ser Ile Ile Gly Leu Gln
                 85                  90                  95

Arg Phe Phe Glu Thr Arg Met Asn Asp
                100                 105

<210> SEQ ID NO 42
<211> LENGTH: 108
<212> TYPE: PRT
<213> ORGANISM: Mus musculus

<400> SEQUENCE: 42

Thr Lys Leu Thr Pro Ile Asp Lys Arg Lys Cys Glu Arg Leu Leu Leu
 1               5                  10                  15

Phe Leu Tyr Cys His Glu Met Ser Leu Ala Phe Gln Asp Pro Val Pro
                20                  25                  30

Leu Thr Val Pro Asp Tyr Tyr Lys Ile Ile Lys Asn Pro Met Asp Leu
        35                  40                  45

Ser Thr Ile Lys Lys Arg Leu Gln Glu Asp Tyr Cys Met Tyr Thr Lys
 50                  55                  60

Pro Glu Asp Phe Val Ala Asp Phe Arg Leu Ile Phe Gln Asn Cys Ala
 65                  70                  75                  80

Glu Phe Asn Glu Pro Asp Ser Glu Val Ala Asn Ala Gly Ile Lys Leu
                 85                  90                  95

Glu Ser Tyr Phe Glu Glu Leu Leu Lys Asn Leu Tyr
                100                 105

<210> SEQ ID NO 43
<211> LENGTH: 27
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(6)
<223> OTHER INFORMATION: Any amino acid and this region may encompass
      2-3 residues
<220> FEATURE:
<221> NAME/KEY: MOD_RES
<222> LOCATION: (8)..(15)
<223> OTHER INFORMATION: Any amino acid and this region may encompass
      5-8 residues
<220> FEATURE:
<221> NAME/KEY: MOD_RES
<222> LOCATION: (16)
<223> OTHER INFORMATION: Pro, Lys or His
<220> FEATURE:
<221> NAME/KEY: MOD_RES
<222> LOCATION: (17)
<223> OTHER INFORMATION: Any amino acid
<220> FEATURE:
<221> NAME/KEY: MOD_RES
<222> LOCATION: (19)
<223> OTHER INFORMATION: Tyr, Phe or His
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)
<223> OTHER INFORMATION: Met, Ile or Val

<400> SEQUENCE: 43

Xaa Xaa Phe Xaa Xaa Xaa Pro Xaa Xaa Xaa Xaa Xaa Xaa Xaa Xaa Xaa
1               5                   10                  15

Xaa Tyr Xaa Xaa Xaa Xaa Xaa Xaa Pro Xaa Asp
            20                  25

<210> SEQ ID NO 44
<211> LENGTH: 20
<212> TYPE: PRT
<213> ORGANISM: Artificial Sequence
<220> FEATURE:
<223> OTHER INFORMATION: Description of Artificial Sequence: Synthetic
      bromodomain peptide

<400> SEQUENCE: 44

Trp Pro Phe Met Glu Pro Val Lys Arg Thr Glu Ala Pro Gly Tyr Tyr
1               5                   10                  15

Glu Val Ile Arg
            20

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 45

His His His His His His
1               5

<210> SEQ ID NO 46
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Acetyl-Lys

<400> SEQUENCE: 46

Ser Gly Arg Gly Lys Gly Gly Lys Gly Leu Gly Lys
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Acetyl-Lys

<400> SEQUENCE: 47

Arg Lys Ser Thr Gly Gly Lys Ala Pro Arg Lys Gln
1               5                   10
```

ZA LOOPS OF BROMODOMAINS

FIELD OF THE INVENTION

The present invention provides the three-dimensional structure of a histone acetyltransferase bromodomain. The three-dimensional structural information is included in the invention. The present invention also identifies for the first time, that bromodomains can bind to an acetylated binding partners. The interaction between bromodomains and their binding partners play a crucial role in various cellular functions, including in the regulation/modulation of DNA transcription. Therefore, the present invention provides procedures for identifying agents that can modulate the interaction of bromodomains and their binding partners by high throughput drug screening and/or through the use of rational drug design based on the three-dimensional data provided herein.

BACKGROUND OF THE INVENTION

In recent years great strides have been made in the elucidation of the steps involved in intercellular and intracellular signaling. Indeed, the individual steps of the cascade of events involved in a number of cellular signal transduction processes have been determined. For example, intercellular signal transduction generally begins with an intercellular ligand binding the extracellular portion of a receptor of the plasma membrane. The bound receptor then either directly or indirectly initiates the activation of one or more cellular factors. An activated cellular factor may act as transcription factor by entering the nucleus to interact with its corresponding genomic response element, or alternatively, it may interact with other cellular factors depending on the complexity of the process. In either case, one or more transcription factors ultimately bind to one or more specific genomic response elements. This binding plays a crucial role in the up and/or down regulation of the transcription of the specific genes that are under the control of these genomic response elements. However, the process of re-organizing the chromatin of eukaryotic cells, which is a prerequisite for the binding of the transcription factor to the genomic response elements, has remained a mystery.

Chromatin contains several highly conserved histone proteins including: H3, H4, H2A, H2B, and H1. These histone proteins package eukaryotic DNA into repeating nucleosomal units that are folded into higher-order chromatin fibers [Luger and Richmond, *Curr. Opin. Genet. Dev.* 8:140-146 (1998)]. A portion of the histone that comprises roughly a quarter of the protein protrudes from the chromatin surface, and is thereby sensitive to proteolytic enzymes [van Holde, in *Chromatin* (Rich, A. ed., Springer, New York) pages 111-148 (1988); Hect et al., *Cell* 80:583-592 (1995)]. This portion of the histone is known as the "histone tail". Histone tails tend to be free for protein-protein interaction, and are also the portion of the histone most prone to post-translational modification. Such post-translational modification includes acetylation, phosphorylation, methylation, ubiquitination, and ADP-ribosylation [van Holde, in *Chromatin* (Rich, A. ed., Springer, N.Y.) pages 111-148 (1988)].

Of all classes of proteins, histones are amongst the most susceptible to post-translational modification. Perhaps the best studied post-translational modification of histones is the acetylation of specific lysine residues [Grunstin, M., *Nature*, 389:349-352 (1997)]. Indeed, acetylation of histone lysine residues has been suggested to play a pivotal role in chromatin remodeling and gene activation. Consistently, distinct classes of enzymes, namely histone acetyltransferases (HATs) and histone deacetylases (HDACs), acetylate or de-acetylate specific histone lysine residues [Struhl, *Genes Dev.* 12:599-606 (1998)].

Nearly all known nuclear HATs contain an approximately 110 amino acid sequence known as the bromodomain [Jeanmougin et al., *Trends in Biochemical Sciences*, 22:151-153 (1997)], a protein motif that was initially discovered in *Drosophila brahma* protein. Bromodomains are found in a large number of chromatin-associated proteins and have now been identified in approximately 40 proteins, often adjacent to other protein motifs [Jeanmougin et al., *Trends in Biochemical Sciences*, 22:151-153 (1997); Tamkun et al., *Cell*, 68:561-572 (1992): Hanes et al., *Nucleic Acids Research*, 20:2603 (1992)]. Proteins that contain a bromodomain often contain a second bromodomain. However, despite the wide occurrence of bromodomains and their likely role in chromatin regulation, their three-dimensional structure and binding partners heretofore have remained unknown.

Therefore, there is a need to identify a binding partner for a bromodomain. In addition, there is a need to identify agonists or antagonists to the bromodomain-binding partner complex: Since a preferred method of drug-screening relies on structure based drug design, there is also a need to determine the three-dimensional structure of a bromodomain. In this case, once the three dimensional structure of bromodomain is determined, potential agonists and/or potential antagonists can be designed with the aid of computer modeling [Bugg et al., *Scientific American*, December: 92-98 (1993); West et al., *TIPS*, 16:67-74 (1995); Dunbrack et al., *Folding & Design*, 2:27-42 (1997)]. However, heretofore the three-dimensional structure of the bromodomain has remained unknown. Therefore, there is a need for obtaining a form of the bromodomain that is amenable for NMR analysis and/or X-ray crystallographic analysis. Furthermore, there is a need for the determination of the three-dimensional structure of the bromodomain. Finally, there is a need for procedures for related structural based drug design predicated on such structural data.

The citation of any reference herein should not be construed as an admission that such reference is available as "Prior Art" to the instant application.

SUMMARY OF THE INVENTION

The present invention provides, for the first time, that bromodomains bind to acetyl-lysine residues of proteins. The present invention also provides the three-dimensional structure of a bromodomain as well as the three-dimensional structure of a bromodomain-acetyl-histamine complex. The structural information provided can be employed in methods of identifying drugs that can modulate the cellular processes that involve bromodomain-acetyl-lysine interactions. These interactions include chromatin remodeling, which is a required step in eukaryotic transcription. In a particular embodiment, the three-dimensional structural information is used in the design of an inhibitor of leukemia.

The present invention provides an isolated nucleic acid that encodes a peptide consisting of about 21 to 40 amino acids that comprises a ZA loop of a bromodomain. In a preferred embodiment the peptide comprises about 23 to 34 amino acids. The isolated nucleic acid can further comprise a heterologous nucleotide sequence.

In a preferred embodiment the peptide comprises the amino acid sequence of SEQ ID NO:3. In another embodiment the peptide comprises the amino acid sequence of SEQ ID NO:43. In particular embodiments the ZA loop is obtained from the bromodomain having the amino acid sequence of SEQ ID NO:7, or SEQ ID NO:8, or SEQ ID NO:9, or SEQ ID NO:10, or SEQ ID NO:11, or SEQ ID NO:12, or SEQ ID NO:13, or SEQ ID NO:14, or SEQ ID NO:15, or SEQ ID NO:16, or SEQ ID NO:17, or SEQ ID NO:18, or SEQ ID NO:19, or SEQ ID NO:20, or SEQ ID NO:21, or SEQ ID NO:22, or SEQ ID NO:23, or SEQ ID NO:24, or SEQ ID NO:25, or SEQ ID NO:26, or SEQ ID NO:27, or SEQ ID NO:28, or SEQ ID NO:29, or SEQ ID NO:30, or SEQ ID NO: or SEQ ID NO:31, or SEQ ID NO:32, or SEQ ID NO: 33, or SEQ ID NO:34, or SEQ ID NO:35, or SEQ ID NO:36, or SEQ ID NO:37, or SEQ ID NO:38, or SEQ ID NO: or SEQ ID NO:39, or SEQ ID NO:40, or SEQ ID NO:41, or SEQ ID NO:42.

The present invention further provides a recombinant DNA molecule that comprises an isolated nucleic acid of the present invention, as described above, with or without a heterologous nucleotide sequence. Such a recombinant DNA molecule can be operatively linked to an expression control sequence and can be part of an expression vector. The present invention further provides a cell that comprises such an expression vector. The cell can be either a eukaryotic or a prokaryotic cell. The present invention further provides a method of expressing the peptides of the present invention or fragments thereof in this cell. One such method comprises culturing the cell in an appropriate cell culture medium under conditions that provide for expression of the peptide by the cell.

The present invention further provides a peptide consisting of about 21 to 40 amino acids that comprises a ZA loop of a bromodomain. In a preferred embodiment the peptide comprises about 23 to 34 amino acids. The present invention also provides fusion proteins or peptides comprising these peptides.

In a preferred embodiment the peptide comprises the amino acid sequence of SEQ ID NO:3. In another embodiment the peptide comprises the amino acid sequence of SEQ ID NO:43. In particular embodiments the ZA loop is obtained from the bromodomain having the amino acid sequence of SEQ ID NO:7, or SEQ ID NO:8, or SEQ ID NO:9, or SEQ ID NO:10, or SEQ ID NO:11, or SEQ ID NO:12, or SEQ ID NO:13, or SEQ ID NO:14, or SEQ ID NO:15, or SEQ ID NO:16, or SEQ ID NO:17, or SEQ ID NO:18, or SEQ ID NO:19, or SEQ ID NO:20, or SEQ ID NO:21, or SEQ ID NO:22, or SEQ ID NO:23, or SEQ ID NO:24, or SEQ ID NO:25, or SEQ ID NO:26, or SEQ ID NO:27, or SEQ ID NO:28, or SEQ ID NO:29, or SEQ ID NO:30, or SEQ ID NO: or SEQ ID NO:31, or SEQ ID NO:32, or SEQ ID NO: 33, or SEQ ID NO:34, or SEQ ID NO:35, or SEQ ID NO:36, or SEQ ID NO:37, or SEQ ID NO:38, or SEQ ID NO: or SEQ ID NO:39, or SEQ ID NO:40, or SEQ ID NO:41, or SEQ ID NO:42.

The present invention also provides antibodies raised against the peptides/proteins of the present invention, or raised against an antigenic fragment of these proteins/fragments. In a particular embodiment an antibody is raised against a fragment of the ZA loop of a bromodomain. In another embodiment an antibody is raised against a fragment of a protein or peptide that comprises an acetyl-lysine, wherein the protein or peptide can bind to a bromodomain. Such fragments can be conjugated to a carrier protein or be part of a fusion protein. In one embodiment the antibody is a polyclonal antibody. In another embodiment, the antibody is a monoclonal antibody. A hybridoma that makes the monoclonal antibody is also part of the present invention. In a particular embodiment the antibody is a chimeric antibody. Antibodies that can specifically recognize acetyl-lysine residues involved bromodomain binding are also part of the present invention.

In another aspect of the present invention a method is provided for identifying a compound that modulates the affinity of a bromodomain for a ligand (and/or protein) that comprises an acetylated lysine. One such embodiment comprises contacting the bromodomain and the ligand in the presence of a compound under conditions that, the bromodomain and the ligand bind in the absence of the compound. The affinity of the bromodomain for the ligand is then determined (e.g., measured). A compound is identified as a compound that modulates the affinty of the bromodomain for the ligand when there is a change in the affinity of the bromodomain for the ligand in the presence of the compound. When the affinity of the bromodomain for the ligand increases in the presence of the compound, the compound is identified as a promoting agent for the bromodomain-ligand complex. When the affinity of the bromodomain for the ligand decreases in the presence of the compound, the compound is identified as an inhibitor of the bromodomain-ligand complex. In a preferred embodiment, the compound to be tested is pre-selected by performing rational drug design with the set of atomic coordinates obtained from one or more of Tables 1-6. More preferably the selecting is performed in conjunction with computer modeling. In a particular embodiment, the compound is selected by performing rational drug design with the set of atomic coordinates obtained from a set of atomic coordinates defining the three-dimensional structure of a bromodomain consisting of the amino acid sequence of SEQ ID NO:7 alone or with acetyl-histamine.

The present invention also provides a method of identifying a compound that modulates the stability of a bromodomain-acetyl-lysine binding complex. One such embodiment comprises contacting the bromodomain-acetyl-lysine binding complex in the presence of the compound under conditions in which the bromodomain-acetyl-lysine binding complex forms in the absence of the compound. The stability of the bromodomain-acetyl-lysine binding complex is then determined (e.g., measured). A compound is identified as a compound that modulates the stability of the bromodomain-acetyl-lysine binding complex, when there is a change in the stability of the bromodomain-acetyl-lysine binding complex in the presence of that compound. When the stability of the bromodomain-acetyl-lysine binding complex increases in the presence of the compound, the compound is identified as a stabilizing agent. When the stability of the bromodomain-acetyl-lysine binding complex decreases in the presence of the compound, the compound is identified as an inhibitor. In a preferred embodiment, the compound to be tested is pre-selected by performing rational drug design with the set of atomic coordinates obtained from one or more of Tables 1-6. More preferably the selecting is performed in conjunction with computer modeling. In a particular embodiment, the compound is selected by performing rational drug design with the set of atomic coordinates obtained from a set of atomic coordinates defining the three-dimensional structure of a bromodomain consisting of the amino acid sequence of SEQ ID NO:7 alone or with acetyl-histamine.

As anyone having skill in the art of drug development would readily understand, the potential drugs selected by the above methodologies can be refined by re-testing in appropriate drug assays, including those disclosed herein. Chemical analogs of such potential drugs can be obtained (either through chemical synthesis or drug libraries) and be analogously tested. Therefore, methods comprising successive iterations of the steps of the individual drug assays, as exemplified herein, using either repetitive or different binding studies, or transcription activation studies or other such studies are envisioned in the present invention. In addition, potential drugs may be identified first by rapid throughput drug screening, as described below, prior to performing computer modeling on a potential drug using the three-dimensional structure of the bromodomain.

The present invention further comprises all of the potential, selected, and putative compounds (drugs) identified by the methods of the present invention, as well as the final drugs themselves identified with the methods of the present invention.

The present invention further provides a method for identifying a potential binding partner for a protein (e.g., a histone) comprising an acetyl-lysine. One such embodiment comprises contacting the protein with a polypeptide comprising a bromodomain. In a preferred embodiment the bromodomain comprises the amino acid sequence of SEQ ID NO:3. In particular embodiments the bromodomain has the amino acid sequence of SEQ ID NO:7, or SEQ ID NO:8, or SEQ ID NO:9, or SEQ ID NO:10, or SEQ ID NO:11, or SEQ ID NO:12, or SEQ ID NO:13, or SEQ ID NO:14, or SEQ ID NO:15, or SEQ ID NO:16, or SEQ ID NO:17, or SEQ ID NO:18, or SEQ ID NO:19, or SEQ ID NO:20, or SEQ ID NO:21, or SEQ ID NO: 22, or SEQ ID NO:23, or SEQ ID NO:24, or SEQ ID NO:25, or SEQ ID NO:26, or SEQ ID NO:27, or SEQ ID NO:28, or SEQ ID NO:29, or SEQ ID NO:30, or SEQ ID NO: or SEQ ID NO:31, or SEQ ID NO:32, or SEQ ID NO: 33, or SEQ ID NO:34, or SEQ ID NO:35, or SEQ ID NO:36, or SEQ ID NO:37, or SEQ ID NO:38, or SEQ ID NO: or SEQ ID NO:39, or SEQ ID NO:40, or SEQ ID NO:41, or SEQ ID NO:42.

The present invention further provides a method for identifying a protein having a bromodomain. One such embodiment comprises contacting a cellular extract with a peptide comprising an acetyl-lysine.

The present invention further provides agents that can inhibit the binding of a bromodomain with a protein comprising an acetyl-lysine. In one embodiment the agent is ISYGR-AcK-KRRQRR (SEQ ID NO:4). In another embodiment the agent is ARKSTGG-AcK-APRKQL (SEQ ID NO:5). In still another embodiment the agent is QSTSRHK-AcK-LMFKTE (SEQ ID NO:6). In yet another embodiment the agent is an analog of acetyl-lysine such as acetyl-histamine. In still another embodiment the agent is an antibody that recognizes an acetyl-lysine of a protein binding partner of a bromodomain. In a preferred embodiment the agent is an antibody raised against a ZA loop of a bromodomain. These agents can be used as pharmaceuticals in compositions that contain a pharmaceutically acceptable carrier for example, or in the various drug assays of the present invention, serving as controls to demonstrate specificity.

Accordingly, it is a principal object of the present invention to provide the three-dimensional coordinates of a bromodomain.

It is a further object of the present invention to provide the three-dimensional coordinates of a bromodomain complexed with acetyl-histamine.

It is a further object of the present invention to provide an assay for identifying proteins that contain bromodomains that bind proteins that comprise acetyl-lysine.

It is a further object of the present invention to provide methods of identifying drugs that can modulate the bromodomain-acetyl-lysine binding complex.

It is a further object of the present invention to provide methods of identifying drugs that can inhibit the binding of a bromodomain to a protein containing acetyl-lysine.

It is a further object of the present invention to provide methods that incorporate the use of rational design for identifying such drugs.

It is a further object of the present invention to provide a method of identifying drugs that can treat leukemia.

It is a further object of the present invention to provide a method of identifying drugs that can treat and/or prevent AIDS.

These and other aspects of the present invention will be better appreciated by reference to the following drawings and Detailed Description.

BRIEF DESCRIPTION OF THE DRAWINGS

FIGS. 2A-2B shows the stereoview of the $C_a$ trace of 30 superimposed NMR-derived structures of the bromodomain (residues 722-830). The N-terminal four residues (SKEP) (residues 1-4 of SEQ ID NO: 7) which are structurally disordered are omitted for clarity. For the final 30 structures, the root-mean-square deviations (RMSDs) of the backbone and all heavy atoms are 0.63±0.11 Å and 1.15±0.12 Å for residues 723-830, respectively. The RMSDs of the backbone and all heavy atoms for the four α-helices (residues 727-743, 770-776, 785-802, and 807-827), are 0.34±0.04 Å and 0.87±0.06 Å, respectively. FIGS. 2C-2D show the stereoview of the bromodomain structures from the bottom of the protein, which is rotated approximately 90□ from the orientation in FIGS. 2A-2B. FIG. 2E shows the Ribbons [Carson, M., *J. Appl. Crystallogr.* 24:958-961 (1991)] depiction of the averaged minimized NMR structure of the P/CAF bromodomain. The orientation of FIG. 2E is as shown in FIGS. 2A-2B. FIGS. 2F-2G are schematic representations of the overall topology of the up-and-down four-helix bundle folds with the opposite handedness. The left-handed fold is seen in bromodomain, cytochrome $b_5$, and T4 lysozyme (left, FIG. 2F), whereas the right-handed four-helix bundles are observed in proteins such as hemerythrin and cytochrome $b_{562}$ (right, FIG. 2G) [Richardson, J., *Adv. Protein Chem.*, 34:167-339 (1989); Presnell and Cohen, *Proc. Natl. Acad. Sci. USA* 86:6592-6596 (1989)]. FIG. 2H is a molecular surface representation of the electrostatic potential (blue=positive; red=negative) of the bromodomain calculated in GRASP [Nicholls et al., *Biophys. J.* 64:166-170 (1993)]. The hydrophobic and aromatic residues (Tyr809, Tyr802, Tyr760, Ala757, and Val752) located between the ZA and BC loops are indicated.

FIG. 3A shows the superimposed region of the 2D $^{15}$N-HSQC spectra of the bromodomain (approximately 0.5 mM) in its free form (red) and complexed to the AcK-containing H4 peptide (molar ratio 1:6) (black). FIG. 3B is the Ribbon and dotted-surface diagram of the bromodomain depicting the location of the lysine-acetylated H4 peptide binding site. The color coding reflects the chemical shift changes (Δδ) of the backbone amide $^{1}$H and $^{15}$N resonances upon binding to the AcK peptide as observed in the $^{15}$N-HSQC spectra. The normalized weighted average of the chemical shift changes was calculated by $\Delta_{av}/\Delta_{max}=[\Delta\delta_{NH}+\Delta\delta_{N}/25)/2]^{1/2}/\Delta_{max}$, where $\Delta_{max}$ is the maximum weighted chemical shift difference observed for Tyr809 (0.16 ppm). The backbone atoms are color-coded in red, yellow, or green for residues that have $\Delta_{av}/\Delta_{max}$ of >0.6 (Tyr809, Glu808, Asn803, and Ala757), 0.2-0.6 (Ala813, Tyr802, Tyr760, and Val752), or <0.2 (Cys812, Ser807, Cys799, Phe796, and Phe748), respectively. The non-perturbed residues are shown in blue. FIG. 3C shows the chemical structures of acetyl-lysine, acetyl-histamine, and acetyl-histidine.

DETAILED DESCRIPTION OF THE INVENTION

The present invention identifies a general binding partner (ligand) for the protein motif known as the bromodomain. Indeed, by combining structural and site-directed mutagenesis studies the present invention demonstrates that bromodomains can interact specifically with acetyl-lysine (AcK), making them the first protein modules known to exhibit such interactions. Like other modular domains, such as Src homology-2 (SH2) and phosphotyrosine binding (PTB) domains, which specifically interact with phosphotyrosine-containing proteins, the bromodomain/acetyl-lysine recognition provides a means to regulate protein-protein interactions via protein lysine acetylation. The nature of the acetyl-lysine recognition by the bromodomain is similar to that of histone acetyltransferase interaction with acetyl-CoA. The present invention therefore couples for the first time, the functionality of the bromodomain with the HAT activity of coactivators in the regulation of gene transcription.

The present invention further provides both a nuclear magnetic resonance (NMR) structure of the bromodomain from the HAT coactivator P/CAF (p300/CBP-associated factor) as well as the structure for the P/CAF bromodomain in complex with acetyl-histamine. The structure reveals an unusual left-handed up-and-down four-helix bundle.

The results disclosed herein explain prior deletion experiments which showed that the bromodomain is indispensable for the function of GCN5 in yeast. Bromodomain-AcK binding also appears to be important for the assembly and activity of multiprotein complexes in transcriptional activation. The results reported herein therefore, form the foundation for identifying specific biological ligands and for defining the molecular mechanisms by which the extensive family of bromodomains participate in chromatin remodeling and transcriptional activation As disclosed herein, the binding partner for the bromodomain is a peptide or protein comprising an acetyl-lysine (AcK). Interestingly, whereas a free acetyl-lysine does not appear to bind the bromodomain, an analog of the acetyl-lysine, acetyl-histamine, does. This is most likely due to the additional charge present in the free amino acid. Consistently, free acetyl-histidine also does not to bind the bromodomain.

Figure 1:
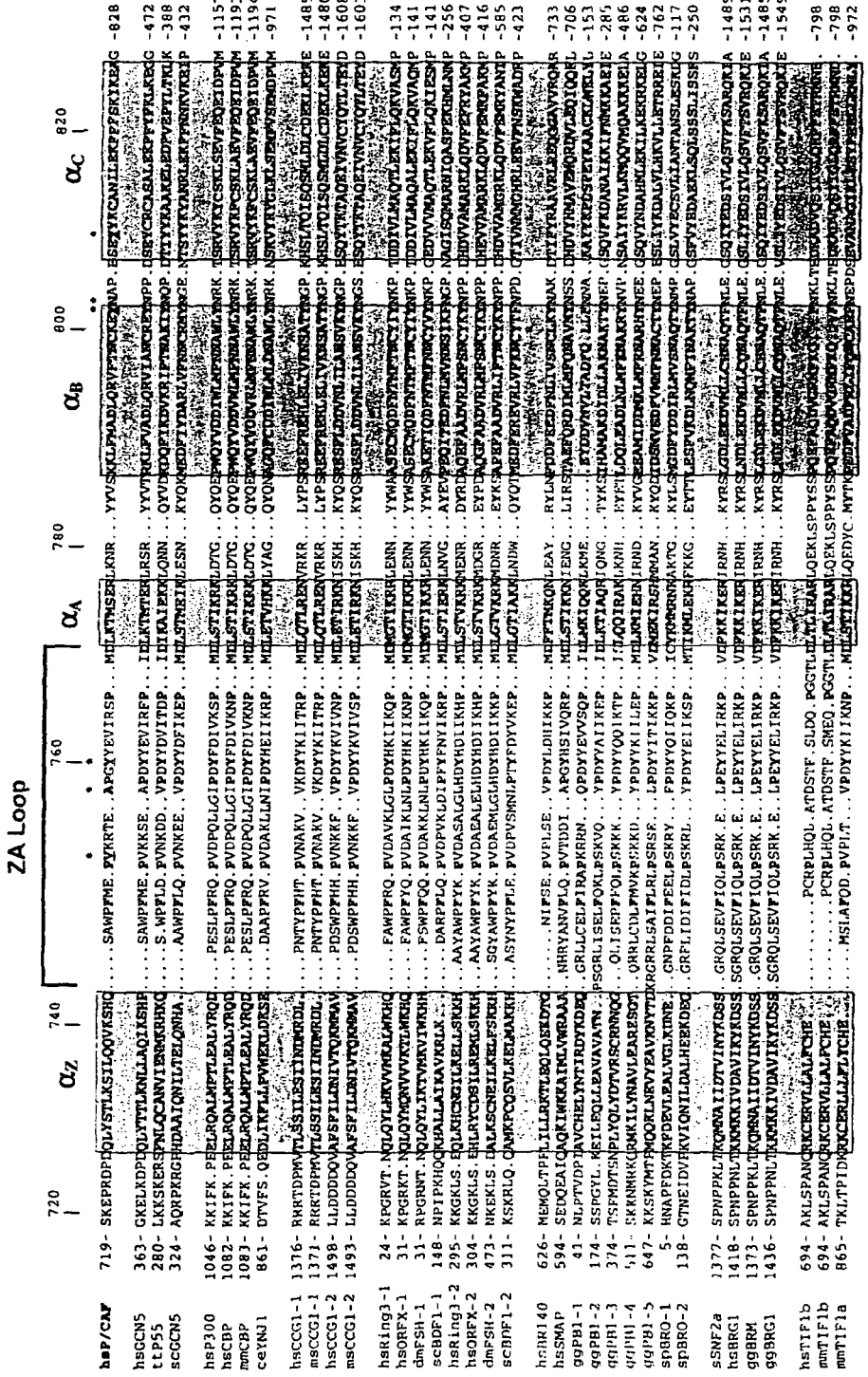
FIG. 1. Structure-based sequence alignment of a selected number of bromodomains (SEQ ID NOS 7-42). The sequences were aligned based on the NMR-derived structure of the P/CAF bromodomain, and the predicated four α-helices are shown in green boxes. Bromodomains are grouped on the basis of the sequence and/or functional similarities as described by Jeanmougin et al., [*Trends in Biochemical Sciences*, 22:151-153 (1997)]. Residue numbers of the P/CAF bromodomain are indicated above its sequence. Three absolutely conserved residues, corresponding to Pro751, Pro767, and Asn803 in the P/CAF bromodomain, are shown in red. Highly conserved residues are colored in blue. The residues of the P/CAF bromodomain that interact with acetyl-histamine, as determined by intermolecular NOEs, are indicated by asterisks. The ZA loop, which is critical for acetyl-lysine binding, for each of the indicated bromodomains is also identified. The underlined residues were changed individually by site-directed mutagenesis to Ala. Genbank accession numbers for the proteins are as indicated in Table 8, in the Example below, along with the SEQ ID NOs. for the bromodomain sequences.
Figure 2A:
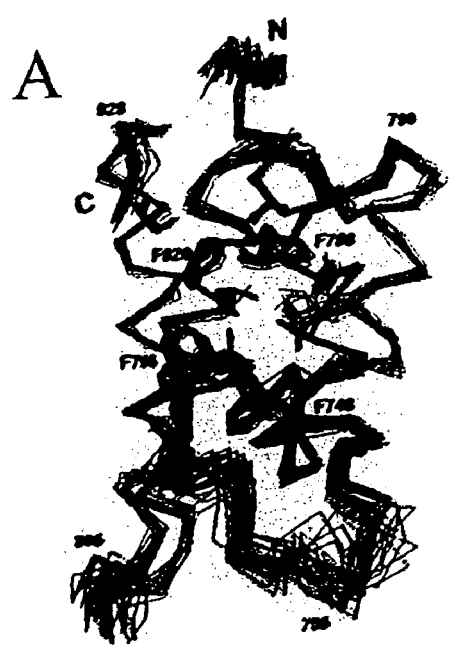
FIGS. 2A-2H depict the structure of the P/CAF bromodomain.
Figure 2B:
Figure 2C:
Figure 2D:
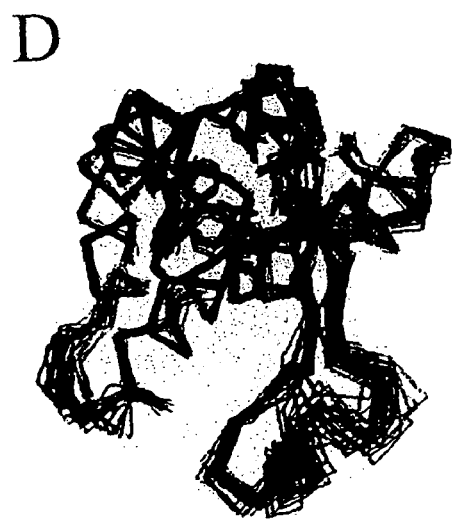

The present invention further provides a key region of the bromodomain for the interaction with its acetyl-lysine binding partner, the ZA loop. The amino acid sequence of the ZA loop is defined in FIG. 1 for a number of bromodomains and is depicted in FIG. 2A for P/CAF. In a particular embodiment, the ZA loop has between about 21 and 40 amino acid residues comprising the amino acid sequence of:

$FX_{2-3}PX_{5-8}J_{P/K/H}XYJ_{Y/F/H}X_5PJ_{M/I/V}D$ (SEQ ID NO:3)

more preferably the ZA loop has about 23 to 34 amino acid residues and comprises the amino acid sequence:

$X_2FX_{2-3}PX_{5-8}J_{P/K/H}XYJ_{Y/F/H}X_5PJ_{M/I/V}D$ (SEQ ID NO:43)

(1) The single letter amino acid code is used in this description, i.e., "F" for phenylalanine; "P" for proline; "Y" for tyrosine; and "D" for aspartic acid.

(2) "X" indicates any amino acid (an undesignated amino acid); and X, $X_2$, $X_{2-3}$, $X_5$, and $X_{5-8}$ indicates one undesignated amino acid, two consecutive undesignated amino acids, two or three consecutive undesignated amino acids, five consecutive undesignated amino acids, and five to eight consecutive undesignated amino acids respectively.

(3) "J" indicates that identity of the amino acid is restricted to a particular group, again the one letter code is used (i) $J_{P/K/H}$ is either proline, lysine or histidine.

(ii) $J_{Y/F/H}$ is either tyrosine, phenylalanine or histidine.

(iii) $J_{M/I/V}$ is either methionine, isoleucine, or valine.

Since this region of the bromodomain is important in binding its acetyl-lysine binding partner, antibodies specifically raised against this region are also included in the present invention. In a particular embodiment, the antibody is a humanized chimeric antibody that can be used in therapeutic treatment. Thus monoclonal, chimeric, and polyclonal antibodies raised against bromodomains, preferably against amino acid residues in the ZA loop region are part of the present invention. In a specific embodiment the antibody is raised against a peptide, fusion peptide or conjugated peptide consisting of amino acid residues 746 to 765 of SEQ ID NO:2, i.e., WPFMEPVKRTEAPGYYEVIR (SEQ ID NO:44). Such antibodies can be used in the treatment of leukemia for example. Alternatively, these antibodies can be used in drug discovery assays.

Thus the present invention provides the first detailed structural information regarding a bromodomain and a bromodomain complexed with its acetylated binding partner. The present invention therefore provides the three-dimensional structure of the bromodomain and a bromodomain acetylated binding partner complex. Since the interaction of the bromodomain with a histone for example, can play a significant role in chromatin remodeling/regulation, the structural information provided herein can be employed in methods of identifying drugs that can modulate basic cell processes by modulating the transcription. In a particular embodiment, the three-dimensional structural information is used in the design of a small organic molecule for the treatment of cancer.

Indeed, the bromodomain and lysine-acetylated protein interaction can now be implicated to play a causal role in the development of a number of diseases including cancers such as leukemia. For example, chromatin remodeling plays a central role in the etiology of viral infection and cancer [Archer and Hodin, *Curr. Opin. Genet. Biol.* 9:171-174 (1999); Jacobson and Pillus, *Curr. Opin. Genet. Biol.* 9:175-184 (1999)]. Both altered histone acetylation/deacetylation and aberrant forms of chromatin-remodeling complexes are associated with human diseases. Furthermore, chromosomal translocation of various cellular genes with those encoding HATs and subunits of chromatin remodeling complexes have been implicated in leukomogenesis. The MOZ (monocytic leukemia zinc finger) and MLL/ALL-1 genes are frequently fused to the gene encoding the co-activator HAT CBP [Sobulo et al., *Proc. Natl. Acad. Sci. USA* 94:8732-8737 (1997)]. The resulting fusion protein MLL-CBP contains the tandem bromodomain-PHD finger-HAT domain of CBP. It also has been shown that both the bromodomain and HAT domain of CBP are required for leukomogenesis, because deletion of either the bromodomain or the HAT domain results in loss of the MLL-CBP fusion protein's ability for cell transform. These results indicate that the CBP bromodomain, and more particularly, the ZA loop of the CBP bromodomain, is an excellent target for developing drugs that interfere with the bromodomain acetyl-lysine interaction that can be used in the treatment of human acute leukemia. In addition, an antibody (e.g., a humanized antibody) raised specifically against a peptide from the ZA loop of the CBP bromodomain could also be effective for treating these conditions.

Furthermore, the human immunodeficiency virus type 1 (HIV-1) trans-activator protein, Tat, is absolutely required for productive HIV viral replication [Jeang and Gatignol, *Curr. Top. Microbiol. Immunol.*, 188:123-144 (1994)]. Recently, it has been shown that HIV-1 Tat transcriptional activity is tightly regulated by lysine acetylation [Kiernan et al., *EMBO Journal* 18:6106-6118 (1999)]. Therefore, the interaction of the acetyl-lysine of Tat with one or more bromodomain-containing proteins associated with chromatin remodeling could mediate gene transcription. Thus, the bromodomain/lysine-acetylated Tat interaction could also serve as a drug target for blocking HIV replication in cells. Similarly, an antibody raised specifically against a peptide from the ZA loop of the bromodomain could also be effective for treating these conditions.

In addition, based on the new structural information disclosed herein, the key amino acid residues for the binding of a given bromodomain and its binding partner can be identified and further elucidated using basic mutagenesis and standard isothermal titration calorimetry, for example. In this case, both the crucial amino acids for the bromodomain and the binding partner (i.e., apart from the acetyl-lysine) can be readily determined and are also part of the present invention.

The results obtained from the structural and functional studies disclosed herein provide the foundation for both high throughput drug screening and structure-based rational drug design. The agents identified by this procedure will be useful for ameliorating conditions involving chromatin remodeling/regulation as indicated above.

Structure based rational drug design is the most efficient method of drug development. However, heretofore, no information has been disclosed regarding the structure of the bromodomain or more importantly, its interaction with the acetyl-lysine of its binding partner. Obtaining detailed structural information requires an extensive NMR or X-ray crystallographic analysis. By determining and then exploiting the detailed structural information of the bromodomain and of the bromodomain/acetyl-histamine (exemplified by NMR analysis below) the present invention provides novel methods for developing new drugs through structure based rational drug design.

Figure 2E:
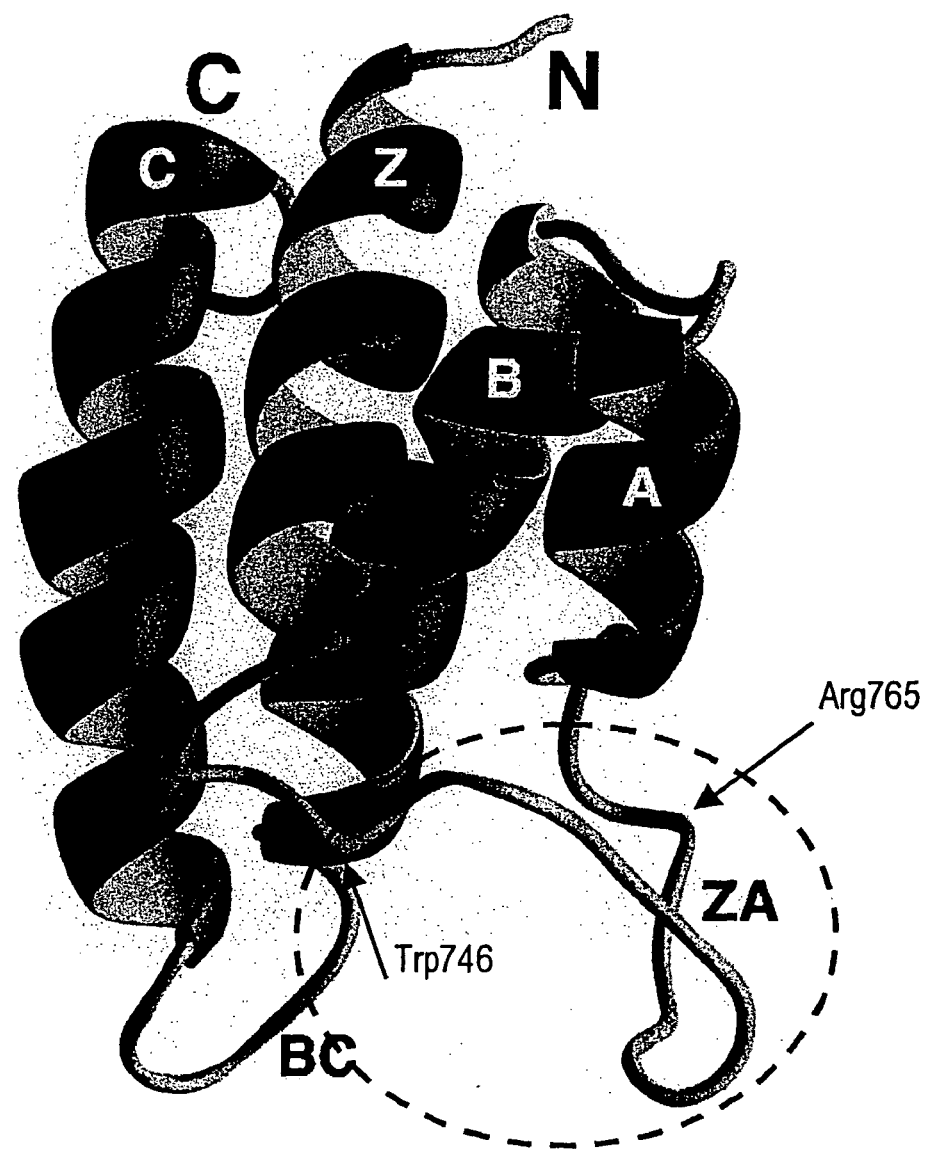
Figure 4:
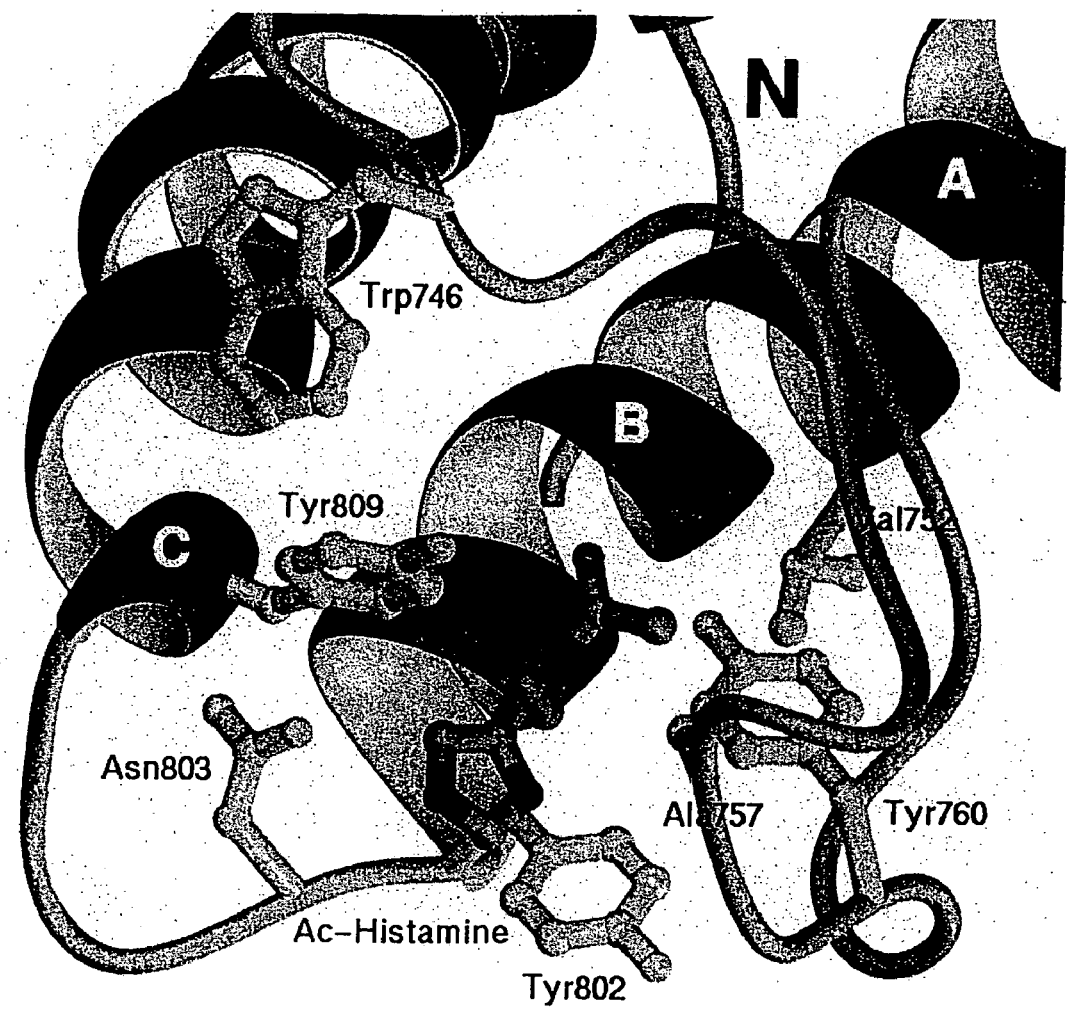
FIG. 4 depicts the acetyl-lysine binding pocket. This is the Ribbons [Carson, M., *J. Appl. Crystallogr.* 24:958-961 (1991)] depiction of a portion of the P/CAF bromodomain complexed with the acetyl-histamine. The ligand is color-coded by atom type.

Thus the present invention provides representative sets of the atomic structure coordinates of the free form of the P/CAF bromodomain (Table 5) and of the P/CAF bromodomain-acetyl-histamine complex (Table 6) which were both obtained by NMR analysis. A Ribbon diagram of the three-dimensional structure of the P/CAF bromodomain is depicted in FIG. 2E, whereas the P/CAF bromodomain acetyl-lysine binding pocket is depicted in FIG. 4. The present invention also provides the NOE-derived distance restraints, and NMR chemical shift assignments of the P/CAF bromodomain. The NMR chemical shift assignments of the P/CAF bromodomain are included in the chemical shift table (Table 1) for the $^1$H-$^{15}$N HSQC spectrum of P/CAF bromodomain. The unambiguous NOE-derived Inter-proton Distance Restraints (Table 2), the ambiguous NOE-derived Inter-proton Distance Restraints (Table 3) and the bonding restraints (Table 4) are also disclosed herein. The sample atomic coordinate data provided enable the skilled artisan to practice the invention. In addition, Tables 1-6 are also capable of being placed into a computer readable form which is also part of the present invention. Furthermore, methods of using these coordinates and chemical shifts and related information (including in computer readable forms) either individually or together in drug assays are also provided. More particularly, such atomic coordinates can be used to identify potential ligands or drugs which will modulate the binding of a bromodomain with its binding partner.

Therefore, if appearing herein, the following terms shall have the definitions set out below.

As used herein a "bromodomain-acetyl-lysine binding complex" is a binding complex between a bromodomain or fragment thereof and either a peptide/polypeptide comprising an acetyl-lysine (or an analog of acetyl-lysine), or a free analog of acetyl-lysine, such as acetyl-histamine disclosed in the Example below. Preferably, the peptide comprises at least six amino acids in addition to the acetyl-lysine. The dissociation constant of a bromodomain-acetyl-lysine binding complex is dependent on whether the lysine residue or analog thereof is acetylated or not, such that the affinity for the bromodomain and the peptide comprising the lysine residue (for example) significantly decreases when that lysine residue is not acetylated.

As used herein a "ZA loop" of a bromodomain is one protion of a bromodomain that is involved in the binding of the bromodomain to the acetyl-lysine. The structure of the ZA loop of the bromodomain of for P/CAF is depicted in FIG. 2A. The ZA loop has between about 20 and 40 amino acids and comprises the amino acid sequence of SEQ ID NO:3. More preferably the ZA loop comprises between about 23 to 34 amino acids and has the amino acid sequence SEQ ID NO:43. The amino acid sequence of the ZA loop for a representative number of individual bromodomains is shown in FIG. 1.

A "polypeptide" or "peptide" comprising a fragment of a bromodomain, such as the ZA loop, or a peptide or polypeptide comprising an acetyl-lysine, as used herein can be the "fragment" alone, or a larger chimeric or fusion peptide/protein which contains the "fragment".

As used herein the terms "fusion protein" and "fusion peptide" are used interchangeably and encompass "chimeric proteins and/or chimeric peptides" and fusion "intein proteins/peptides". A fusion protein comprises at least a portion of a protein or peptide of the present invention, e.g., a bromodomain, joined via a peptide bond to at least a portion of another protein or peptide including e.g., a second bromodomain in a chimeric fusion protein. In a particular embodiment the portion of the bromodomain is antigenic. Fusion proteins can comprise a marker protein or peptide, or a protein or peptide that aids in the isolation and/or purification of the protein, for example.

As used herein, and unless otherwise specified, the terms "agent", "potential drug", "compound", "test compound" or "potential compound" are used interchangeably, and refer to chemicals which potentially have a use as an inhibitor or activator/stabilizer of bromodomain-acetyl-lysine binding.

Therefore, such "agents", "potential drugs", "compounds" and "potential compounds" may be used, as described herein, in drug assays and drug screens and the like.

As used herein a "small organic molecule" is an organic compound, including a peptide [or organic compound complexed with an inorganic compound (e.g., metal)] that has a molecular weight of less than 3 Kilodaltons. Such small organic molecules can be included as agents, etc. as defined above.

As used herein the term "binds to" is meant to include all such specific interactions that result in two or more molecules showing a preference for one another relative to some third molecule. This includes processes such as covalent, ionic, hydrophobic and hydrogen bonding but does not include non-specific associations such as solvent preferences.

As used herein the term "about" signifies that a value is within twenty percent of the indicated value i.e., a peptide containing "about" 20 amino acid residues can contain between 16 and 24 amino acid residues.

General Techniques for Constructing Nucleic Acids that Encode the Bromodomains And Fragments Thereof (Including, ZA Loops); and the Bromodomain Binding Partners of the Present Invention.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

As used herein, the term "gene" refers to an assembly of nucleotides that encode a polypeptide, and includes cDNA and genomic DNA nucleic acids.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogues thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-10.51). For hybridization with shorter nucleic acids, i.e., oligonucleotides, the position of mismatches becomes more important, and the length of the oligonucleotide determines its specificity (see Sambrook et al., supra, 11.7-11.8). Preferably a minimum length for a hybridizable nucleic acid is at least about 12 nucleotides; preferably at least about 18 nucleotides; and more preferably the length is at least about 27 nucleotides; and most preferably 36 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences and synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

As used herein, the term "homologous" in all its grammatical forms refers to the relationship between proteins that possess a "common evolutionary origin," including proteins from superfamilies (e.g., the immunoglobulin superfamily) and homologous proteins from different species (e.g., myosin light chain, etc.) [Reeck et al., Cell, 50:667 (1987)]. Such proteins have sequence homology as reflected by their high degree of sequence similarity.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and not a common evolutionary origin.

Two DNA sequences are "substantially homologous" when at least about 60% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

As used herein an amino acid sequence is 100% "homologous" to a second amino acid sequence if the two amino acid sequences are identical, and/or differ only by neutral or conservative substitutions as defined below. Accordingly, an amino acid sequence is 50% "homologous" to a second amino acid sequence if 50% of the two amino acid sequences are identical, and/or differ only by neutral or conservative substitutions.

As used herein, DNA and protein sequence percent identity can be determined using MacVector 6.0.1, Oxford Molecular Group PLC (1996) and the Clustal W algorithm with the alignment default parameters, and default parameters for identity. These commercially available programs can also be used to determine sequence similarity using the same or analogous default parameters.

The term "corresponding to" is used herein to refer similar or homologous sequences, whether the exact position is identical or different from the molecule to which the similarity or homology is measured. Thus, the term "corresponding to" refers to the sequence similarity, and not the numbering of the amino acid residues or nucleotide bases.

As used herein a "heterologous nucleotide sequence" is a nucleotide sequence that is added to a nucleotide sequence of the present invention by recombinant methods to form a nucleic acid which is not naturally formed in nature. Such nucleic acids can encode fusion proteins or peptides, including chimeric proteins and peptides. Thus the heterologous nucleotide sequence can encode peptides and/or proteins which contain regulatory and/or structural properties. In another such embodiment the heterologous nucleotide can encode a protein or peptide that functions as a means of detecting the protein or peptide encoded by the nucleotide sequence of the present invention after the recombinant nucleic acid is expressed. In still another such embodiment the heterologous nucleotide can function as a means of detecting a nucleotide sequence of the present invention. A heterologous nucleotide sequence can comprise non-coding sequences including restriction sites, regulatory sites, promoters and the like.

The present invention also relates to cloning vectors containing nucleic acids encoding analogs and derivatives of the bromodomains of the present invention and polypeptides/peptides that can bind a bromodomain when a lysine of the polypeptide/peptide is acetylated, including modified fragments, that have the same or homologous functional activity as the individual fragments, and homologs thereof. The production and use of derivatives and analogs related to the fragments are within the scope of the present invention.

Due to the degeneracy of nucleotide coding sequences, other DNA sequences which encode substantially the same amino acid sequence as a nucleic acid encoding a protein comprising bromodomain or bromodomain binding partner (i.e., when post-transcriptionally acetylated) of the present invention for example, may be used in the practice of the present invention. These include but are not limited to allelic genes, homologous genes from other species, which are altered by the substitution of different codons that encode the same amino acid residue within the sequence, thus producing a silent change. Likewise, the peptides and polypeptides of the present invention include, but are not limited to, those containing, as a primary amino acid sequence, analogous portions of their respective amino acid sequences including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, and lysine. The negatively charged (acidic) amino acids include aspartic acid and glutamic acid.

Particularly preferred conserved amino acid exchanges are:

(a) Lys for Arg or vice versa such that a positive charge may be maintained;
(b) Glu for Asp or vice versa such that a negative charge may be maintained;
(c) Ser for Thr or vice versa such that a free —OH can be maintained;
(d) Gln for Asn or vice versa such that a free $NH_2$ can be maintained;
(e) Ile for Leu or for Val or vice versa as roughly equivalent hydrophobic amino acids; and
(f) Phe for Tyr or vice versa as roughly equivalent aromatic amino acids.

A conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein. Specific amino acid residues for the P/CAF bromodomain have been identified that are important for binding, indicating a potential lower stringency for the substitution of the remaining amino acids residues.

All of the peptides/fragments of the present invention can be modified by being placed in a fusion or chimeric peptide or protein, or labeled e.g., to have an N-terminal FLAG-tag, or H6 tag (SEQ ID NO: 45). In a particular embodiment the P/CAF bromodomain fragment can be modified to contain a marker protein such as green fluorescent protein as described in U.S. Pat. No. 5,625,048 filed Apr. 29, 1997 and WO 97/26333, published Jul. 24, 1997 each of which are hereby incorporated by reference herein in their entireties.

The nucleic acids encoding peptides and protein fragments of the present invention and analogs thereof can be produced by various methods known in the art. The manipulations which result in their production can occur at the gene or protein level [Sambrook et al., 1989, supra]. The nucleotide sequence can be cleaved at appropriate sites with restriction endonuclease(s), followed by further enzymatic modification if desired, isolated, and ligated in vitro. In addition a nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis [Hutchinson et al., *J. Biol. Chem.*, 253:6551 (1978); Zoller and Smith, *DNA*, 3:479-488 (1984); Oliphant et al., *Gene*, 44:177 (1986); Hutchinson et al., *Proc. Natl. Acad. Sci. U.S.A.*, 83:710 (1986)], use of TAB® linkers (Pharmacia), etc. PCR techniques are preferred for site directed mutagenesis [see Higuchi, 1989, "Using PCR to Engineer DNA", in *PCR Technology: Principles and Applications for DNA Amplification*, H. Erlich, ed., Stockton Press, Chapter 6, pp. 61-70].

The identified and isolated nucleic acids can then be inserted into an appropriate cloning vector. A large number of vector-host systems known in the art may be used.

Protein Expression and Purification

A bacterial protein expression system can be used to make various stable isotopically labeled ($^{13}C$, $^{15}N$, and $^{2}H$) protein samples that are useful for a three-dimensional NMR structural determination of a protein complex. For example a pET14b (Novagen) bacterial expression vector can be constructed which expresses the recombinant P/CAF bromodomain as an amino-terminal His-tagged fusion protein.

Protein expression and purification can be conducted using standard procedures for His-tagged proteins [Zhou et al., *J. Biol. Chem.* 270:31119-31123 (1995)]. To optimize the level of protein expression, various bacterial growth and expression conditions can be screened, which include different *E. Coli* cell lines, and growth and protein induction temperatures. Generally, it is preferred to obtain the maximum amount of soluble protein while still inducing protein expression with a relatively low IPTG concentration e.g., ~0.2 mM (final concentration) at 16° C. As exemplified below, the bromodomain of P/CAF (residues 719-832 of SEQ ID NO:2 which is SEQ ID NO:7) was subcloned into the pET14b expression vector (Novagen) and expressed in *Escherichia coli* BL21(DE3) cells. Uniformly $^{15}N$- and $^{15}N/^{13}C$-labeled proteins were prepared by growing bacteria in a minimal medium containing $^{15}NH_4Cl$ with or without $^{13}C_6$-glucose. A uniformly $^{15}N/^{13}C$-labeled and fractionally deuterated protein sample was prepared by growing the cells in 75% $^{2}H_2O$. The bromodomain was purified by affinity chromatography on a nickel-IDA column (Invitrogen) followed by the removal of poly-His tag by thrombin cleavage. The final purification of the protein was achieved by size-exclusion chromatography. The acetyl-lysine-containing peptides were prepared on a MilliGen 9050 peptide synthesizer (Perkin Elmer) using Fmoc/HBTU chemistry. Acetyl-lysine was incorporated using the reagent Fmoc-Ac-Lys with HBTU/DIPEA activation. NMR samples contained approximately 1 mM protein in 100 mM phosphate buffer of pH 6.5 and 5 mM perdeuterated DTT and 0.5 mM EDTA in $H_2O/^{2}H_2O$ (9/1) or $^{2}H_2O$.

One major advantage of using the heteronuclear multidimensional approach, as exemplified herein, is that the NMR resonance assignments of a protein are obtained in a sequence-specific manner which assures accuracy and greatly facilitates data analysis and structure determination [Clore, G. M. & Gronenborn, A. M. *Meth. Enzymol.* 239:249-363 (1994)]. In addition, the signal overlapping problems in the protein spectra are minimized by the use of multidimensional NMR spectra, which separates the proton signals according to the chemical shifts of their attached heteronuclei (such as $^{15}N$ and $^{13}C$). This NMR approach has been proven very powerful for structural analysis of large proteins [Clore, G. M. & Gronenborn, A. M. Meth. Enzymol. 239: 249-363 (1994)]. To facilitate sequence-specific resonance assignments for the structural study, a uniformly $^{13}C$, $^{15}N$-labeled and fractionally (75%) deuterated protein sample of the bromodomain can be prepared by growing bacterial cells in 75% $^{2}H_2O$ as exemplified below. Such protein samples can be used for triple-resonance NMR experiments. A triple-labeled protein sample is useful for high-resolution NMR structural studies. Because of the favorable $^{1}H$, $^{13}C$, and $^{15}N$ relaxation rates caused by the partial deuteration of the protein, constant-time triple-resonance NMR spectra can be acquired with higher digital resolution and sensitivity [Sattler, M. & Fesik, S. W. *Structure* 4:1245-1249 (1996)]. In addition, various stable-isotopically labeled (15N and $^{13}$C/$^{15}$N) proteins can also be prepared using this procedure.

Synthetic Polypeptides

The term "polypeptide" is used in its broadest sense to refer to a compound of two or more subunit amino acids, amino acid analogs, or peptidomimetics. The subunits are linked by peptide bonds. The terms "polypeptide", "protein", and "peptide" are used interchangeably herein, though preferably as used herein a "peptide" refers to a compound of at least two but less than fifty subunit amino acids, and a polypeptide or protein refers to compound of fifty or more amino acids. The polypeptides of the present invention may be chemically synthesized or as detailed above, genetically engineered or isolated from natural sources.

In addition, potential drugs or agents that may be tested in the drug screening assays of the present invention may also be chemically synthesized. When the peptide is to be modified, e.g., acetylated, the modification can be at any time during the peptide synthesis, including using an acetyl-lysine as a starting material or acetylating a lysine residue of a peptide after the peptide has been synthesized. In the Example below, the acetyl-lysine-containing peptides were prepared on a MilliGen 9050 peptide synthesizer (Perkin Elmer) using Fmoc/HBTU chemistry. Acetyl-lysine was incorporated using the reagent Fmoc-Ac-Lys with HBTU/DIPEA activation.

Thus, synthetic polypeptides, prepared using the well known techniques of solid phase, liquid phase, or peptide condensation techniques, or any combination thereof, can include natural and unnatural amino acids. Amino acids used for peptide synthesis may be standard Boc (N$^\alpha$-amino protected N$^\alpha$-t-butyloxycarbonyl)amino acid resin with the standard deprotecting, neutralization, coupling and wash protocols of the original solid phase procedure of Merrifield [*J. Am. Chem. Soc.*, 85:2149-2154 (1963)], or the base-labile N$^\alpha$-amino protected 9-fluorenylmethoxycarbonyl(Fmoc) amino acids first described by Carpino and Han [*J. Org. Chem.*, 37:3403-3409 (1972)]. Both Fmoc and Boc N$^\alpha$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other Nu-protecting groups that are familiar to those skilled in this art. Solid phase peptide synthesis may be accomplished by techniques familiar to those in the art and provided, for example, in Stewart and Young [Solid Phase Synthesis, Second Edition, Pierce Chemical Co., Rockford, Ill. (1984)] and Fields and Noble [*Int. J. Pept. Protein Res.*, 35:161-214 (1990)], or using automated synthesizers, such as sold by ABS. Thus, polypeptides of the invention may comprise D-amino acids, a combination of D- and L-amino acids, and various "designer" amino acids (e.g., β-methyl amino acids, Cα-methyl amino acids, and Nα-methyl amino acids, etc.) to convey special properties. Synthetic amino acids include ornithine for lysine, fluorophenylalanine for phenylalanine, and norleucine for leucine or isoleucine. Additionally, by assigning specific amino acids at specific coupling steps, α-helices, β turns, β sheets, γ-turns, and cyclic peptides can be generated.

In a further embodiment, subunits of peptides that confer useful chemical and structural properties will be chosen. For example, peptides comprising D-amino acids will be resistant to L-amino acid-specific proteases in vivo. In addition, the present invention envisions preparing peptides that have more well defined structural properties, and the use of peptidomimetics, and peptidomimetic bonds, such as ester bonds, to prepare peptides with novel properties. In another embodiment, a peptide may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such a molecule would be resistant to peptide bond hydrolysis, e.g., protease activity. Such peptides would provide ligands with unique function and activity, such as extended half-lives in vivo due to resistance to metabolic breakdown, or protease activity. Furthermore, it is well known that in certain systems constrained peptides show enhanced functional activity [Hruby, *Life Sciences*, 31:189-199 (1982); Hruby et al., *Biochem J.*, 268:249-262 (1990)]; the present invention provides a method to produce a constrained peptide that incorporates random sequences at all other positions.

Constrained and cyclic peptides. A constrained, cyclic or rigidized peptide may be prepared synthetically, provided that in at least two positions in the sequence of the peptide an amino acid or amino acid analog is inserted that provides a chemical functional group capable of crosslinking to constrain, cyclise or rigidize the peptide after treatment to form the crosslink. Cyclization will be favored when a turn-inducing amino acid is incorporated. Examples of amino acids capable of crosslinking a peptide are cysteine to form disulfides, aspartic acid to form a lactone or a lactam, and a chelator such as γ-carboxyl-glutamic acid (Gla) (Bachem) to chelate a transition metal and form a cross-link. Protected γ-carboxyl glutamic acid may be prepared by modifying the synthesis described by Zee-Cheng and Olson [*Biophys. Biochem. Res. Commun.*, 94:1128-1132 (1980)]. A peptide in which the peptide sequence comprises at least two amino acids capable of crosslinking may be treated, e.g., by oxidation of cysteine residues to form a disulfide or addition of a metal ion to form a chelate, so as to crosslink the peptide and form a constrained, cyclic or rigidized peptide.

The present invention provides strategies to systematically prepare cross-links. For example, if four cysteine residues are incorporated in the peptide sequence, different protecting groups may be used (Hiskey, in The Peptides: Analysis, Synthesis, Biology, Vol. 3, Gross and Meienhofer, eds., Academic Press: New York, pp. 137-167 (1981); Ponsanti et al., *Tetrahedron*, 46:8255-8266 (1990)]. The first pair of cysteines may be deprotected and oxidized, then the second set may be deprotected and oxidized. In this way a defined set of disulfide cross-links may be formed. Alternatively, a pair of cysteines and a pair of chelating amino acid analogs may be incorporated so that the cross-links are of a different chemical nature.

Non-classical amino acids that induce conformational constraints. The following non-classical amino acids may be incorporated in the peptide in order to introduce particular conformational motifs: 1,2,3,4-tetrahydroisoquinoline-3-carboxylate [Kazmierski et al., *J. Am. Chem. Soc.*, 113:2275-2283 (1991)]; (2S,3S)-methyl-phenylalanine, (2S,3R)-methyl-phenylalanine, (2R,3S)-methyl-phenylalanine and (2R,3R)-methyl-phenylalanine (Kazmierski and Hruby, *Tetrahedron Lett.* (1991)]; 2-aminotetrahydronaphthalene-2-carboxylic acid [Landis, Ph.D. Thesis, University of Arizona (1989)]; hydroxy-1,2,3,4-tetrahydroisoquinoline-3-carboxylate [Miyake et al., *J. Takeda Res. Labs.*, 43:53-76 (1989)]; β-carboline (D and L) [Kazmierski, Ph.D. Thesis, University of Arizona (1988)]; HIC (histidine isoquinoline carboxylic acid) [Zechel et al., *Int. J. Pep. Protein Res.*, 43 (1991)]; and HIC (histidine cyclic urea) (Dharanipragada).

The following amino acid analogs and peptidomimetics may be incorporated into a peptide to induce or favor specific secondary structures: LL-Acp (LL-3-amino-2-propenidone-6-carboxylic acid), a β-turn inducing dipeptide analog [Kemp et al., *J. Org. Chem.*, 50:5834-5838 (1985)]; β-sheet inducing analogs [Kemp et al., *Tetrahedron Lett.,* 29:5081-5082 (1988); β-turn inducing analogs [Kemp et al., *Tetrahedron Lett.,* 29:5057-5060 (1988)]; ∝-helix inducing analogs (Kemp et al., *Tetrahedron Lett.,* 29:4935-4938 (1988)]; γ-turn inducing analogs [Kemp et al., *J. Org. Chem.,* 54:109:115 (1989)]; and analogs provided by the following references: Nagai and Sato, *Tetrahedron Lett.,* 26:647-650 (1985); DiMaio et al., *J. Chem. Soc. Perkin Trans.*, p. 1687 (1989); also a Gly-Ala turn analog [Kahn et al., *Tetrahedron* spectra of mutated proteins can be compared to that of the wild-type protein bromodomain.

Chemical-shift perturbations due to ligand binding have proven to be a reliable and sensitive probe for the ligand binding site of the protein. This is because the chemical-shift changes of the backbone amide groups are likely to reflect any changes in protein conformation and/or hydrogen bonding due to the peptide/ligand binding. To examine the effects of a mutation on the ligand binding (in this case the ligand is a peptide comprising an acetyl-lysine), peptide titration experiments can be conducted by following the changes of $^1$H/$^{15}$N signals of the mutant proteins as a function of the peptide concentration. These experiments indicate whether the acetyl-lysine binding site remains the same or changes in the mutants relative to the wild type protein. The effects of the mutation on the peptide binding affinity can also be examined by NMR spectroscopy. If the mutated proteins result in the reduction of the binding affinity, a change of the exchange phenomenon between the free and the ligand-bound signals should be observed in NMR spectrum. If the reduction in binding affinity causes the peptide binding to change from a slow exchange rate to a fast exchange rate, on the NMR time scale, then the peptide binding affinity can be determined from the NMR titration experiment. From these mutation analyses key amino acid residues that are important for binding a peptide comprising the acetyl-lysine can be identified. Such analysis has been exemplified below.

Protein Structure Determination by NMR Spectroscopy

The NMR results from the present invention are summarized by the atomic structure coordinates of the free form of the P/CAF bromodomain (Table 5) and of the P/CAF bromodomain-acetyl-histamine complex (Table 6). The NMR chemical shift assignments of the P/CAF bromodomain are included in the chemical shift table (Table 1) for the $^1$H-$^{15}$N HSQC spectrum of P/CAF bromodomain. The unambiguous NOE-derived Inter-proton Distance Restraints are in Table 2, the ambiguous NOE-derived Inter-proton Distance Restraints are in Table 3, and the $^1$H bonding restraints are disclosed in Table 4.

Backbone and Side-chain Assignments: Sequence-specific backbone assignment can be achieved by using a suite of deuterium-decoupled triple-resonance 3D NMR experiments which include HNCA, HN(CO)CA, HN(CA)CB, HN(CO-CA)CB, HNCO, and HN(CA)CO experiments [Yamazaki, et al., *J. Am. Chem. Soc.* 116:11655-11666 (1994)]. The water flip-back scheme is used in these NMR pulse programs to minimize amide signal attenuation from water exchange. Sequential side-chain assignments are typically accomplished from a series of 3D NMR experiments with alternative approaches to confirm the assignments. These experiments include 3D $^{15}$N TOCSY-HSQC, HCCH-TOCSY, (H)C(CO)NH-TOCSY, and H(C)(CO)NH-TOCSY [see Clore, G. M. & Gronenborn, A. M. *Meth. Enzymol.* 239:249-363 (1994);Sattler et *Prog. in Nuclear Magnetic Resonance Spec.* 4:93-158 (1999)].

Stereospecific Methyl Groups: Stereospecific assignments of methyl groups of Valine and Leucine residues can be obtained from an analysis of carbon signal multiplet splitting using a fractionally $^{13}$C-labeled protein sample, which can be readily prepared using M9 minimal medium containing 10% $^{13}$C-/90%$^{12}$C-glucose mixture [see Neri, et al., *Biochemistry* 28:7510-7516 (1989)].

Dihedral Angle Restraints: Backbone dihedral angle (Φ) constraints can be generated from the $^3J_{HNH\alpha}$ coupling constants measured in a HNHA-J experiment [see Vuister, G. & Bax, A. *J. Am. Chem. Soc.* 115:7772-7777 (1993)]. Side-chain dihedral angles ($\chi^1$) can be obtained from short mixing time $^{15}$N-edited 3D TOCSY-HSQC [see Clore, et al., *J. Biomol. NMR* 1:13-22 (1991)] and 3D HNHB experiments [see Matson et al., *J. Biomol. NMR* 3:239-244 (1993)], which can also provide stereospecific assignments of β methylene protons.

Hydrogen Bonds Restraints: Amide protons that are involved in hydrogen bonds can be identified from an analysis of amide exchange rates measured from a series of 2D $^1$H/$^{15}$N HSQC spectra recorded after adding $^2$H$_2$O to the protein sample.

NOE Distance Restraints: Distance restraints are obtained from analysis of $^{15}$N, and $^{13}$C-edited 3D NOESY data, which can be collected with different mixing times to minimize spin diffusion problems. The nuclear Overhauser effect (NOE)-derived restraints are categorized as strong (1.8-3 Å), medium (1.8-4 Å) or weak (1.8-5 Å) based on the observed NOE intensities. A recently developed procedure for the iterative automated NOE analysis by using ARIA [see Nilges et al., *Prog. NMR Spectroscopy* 32:107-139 (1998)] can be employed which integrates with X-PLOR for structural calculations. To ensure the success of ARIA/X-PLOR-assisted NOE analysis and structure calculations, the ARIA assigned NOE peaks can be manually confirmed.

Intermolecular NOE Distance Restrains: For the structural determination of a protein/peptide complex, intermolecular NOE distance restraints can be obtained from a $^{13}$C-edited (F$_1$) and $^{15}$N, and $^{13}$C-filtered (F$_3$) 3D NOESY data set collected for a sample containing isotope-labeled protein and non-labeled peptide.

Structure Calculations and Refinements: Structures of the protein can be generated using a distance geometry/simulated annealing protocol with the X-PLOR program [see Nilges, et al., *FEBS Lett.* 229:317-324 (1988); Kuszewski, et al., *J. Biolmol. NMR* 2:33-56 (1992); Brünger, A. T$_m$ X-PLOR Version 3.1: A system for X-Ray crystallography and NMR (Yale University Press, New Haven, Conn., 1993)]. The structure calculations can employ inter-proton distance restraints obtained from $^{15}$N- and $^{13}$C-resolved NOESY spectra. The initial low-resolution structures can be used to facilitate NOE assignments, and help identify hydrogen bonding partners for slowly exchanging amide protons. The experimental restraints of dihedral angles and hydrogen bonds can be included in the distance restraints for structure refinements.

Protein-Structure Based Design of Agonists and Antagonists of the Bromodomain-Acetyl-Lysine Binding Complex Once the three-dimensional structure of the Bromodomain and the Bromodomain-acetyl-lysine binding complex are determined, a potential drug or agent (antagonist or agonist) can be examined through the use of computer modeling using a docking program such as GRAM, DOCK, or AUTODOCK [Dunbrack et al., 1997, supra]. This procedure can include computer fitting of potential agents to the bromodomain, for example, to ascertain how well the shape and the chemical structure of the potential ligand will complement or interfere with the interaction between the bromodomain and the acetyl-lysine [Bugg et al., *Scientific American*, December: 92-98 (1993); West et al., *TIPS,* 16:67-74 (1995)]. Computer programs can also be employed to estimate the attraction, repulsion, and steric hindrance of the agent to the dimer-dimer binding site, for example. Generally the tighter the fit (e.g., the lower the steric hindrance, and/or the greater the attractive force) the more potent the potential drug will be since these properties are consistent with a tighter binding constant. Furthermore, the more specificity in the design of a potential drug the more likely that the drug will not interfere with related proteins. This will minimize potential side-effects due to unwanted interactions with other proteins.

Initially a potential drug could be obtained by screening a random peptide library produced by recombinant bacteriophage for example, [Scott and Smith, *Science,* 249:386-390 (1990); Cwirla et al., *Proc. Natl. Acad. Sci.,* 87:6378-6382 (1990); Devlin et al., *Science,* 249:404-406 (1990)] or a chemical library. An agent selected in this manner could be then be systematically modified by computer modeling programs until one or more promising potential drugs are identified. Such analysis has been shown to be effective in the development of HIV protease inhibitors [Lam et al., *Science* 263:380-384 (1994); Wlodawer et al., *Ann. Rev. Biochem.* 62:543-585 (1993); Appelt, *Perspectives in Drug Discovery and Design* 1:23-48 (1993); Erickson, *Perspectives in Drug Discovery and Design* 1:109-128 (1993)].

Such computer modeling allows the selection of a finite number of rational chemical modifications, as opposed to the countless number of essentially random chemical modifications that could be made, any one of which might lead to a useful drug. Each chemical modification requires additional chemical steps, which while being reasonable for the synthesis of a finite number of compounds, quickly becomes overwhelming if all possible modifications needed to be synthesized. Thus, through the use of the three-dimensional structural analysis disclosed herein and computer modeling, a large number of these compounds can be rapidly screened on the computer monitor screen, and a few likely candidates can be determined without the laborious synthesis of untold numbers of compounds.

Once a potential drug (agonist or antagonist) is identified it can be either selected from a library of chemicals as are commercially available from most large chemical companies including Merck, GlaxoWelcome, Bristol Meyers Squib, Monsanto/Searle, Eli Lilly, Novartis and Pharmacia UpJohn, or alternatively the potential drug may be synthesized de novo. As mentioned above, the de novo synthesis of one or even a relatively small group of specific compounds is reasonable in the art of drug design.

The potential drug can then be tested in any standard binding assay (including in high throughput binding assays) for its ability to bind to the ZA loop of a bromodomain. Alternatively the potential drug can be tested for its ability to modulate the binding of a bromodomain to acetylated histamine, for example. When a suitable potential drug is identified, a second NMR structural analysis can optionally be performed on the binding complex formed between the bromodomain-acetyl-lysine binding complex, or the bromodomain alone and the potential drug. Computer programs that can be used to aid in solving such three-dimensional structures include QUANTA, CHARMM, INSIGHT, SYBYL, MACROMODE, and ICM, MOLMOL, RASMOL, AND GRASP [Kraulis, *J. Appl Crystallogr.* 24:946-950 (1991)]. Most if not all of these programs and others as well can be also obtained from the WorldWideWeb through the internet.

Using the approach described herein and equipped with the structural analysis disclosed herein, the three-dimensional structures of other bromodomain-acetyl-lysine binding complexes can more readily be obtained and analyzed. Such analysis will, in turn, allow corresponding drug screening methodology to be performed using the three-dimensional structures of such related complexes.

For all of the drug screening assays described herein further refinements to the structure of the drug will generally be necessary and can be made by the successive iterations of any and/or all of the steps provided by the particular drug screening assay, including further structural analysis by NMR, for example.

Phage Libraries for Drug Screening

Phage libraries have been constructed which when infected into host *E. coli* produce random peptide sequences of approximately 10 to 15 amino acids [Parmley and Smith, Gene 73:305-318 (1988), Scott and Smith, Science 249:386-249 (1990)]. Specifically, the phage library can be mixed in low dilutions with permissive *E. coli* in low melting point LB agar which is then poured on top of LB agar plates. After incubating the plates at 37° C. for a period of time, small clear plaques in a lawn of *E. coli* will form which represents active phage growth and lysis of the *E. coli*. A representative of these phages can be absorbed to nylon filters by placing dry filters onto the agar plates. The filters can be marked for orientation, removed, and placed in washing solutions to block any remaining absorbent sites. The filters can then be placed in a solution containing, for example, a radioactive bromodomain. After a specified incubation period, the filters can be thoroughly washed and developed for autoradiography. Plaques containing the phage that bind to the radioactive bromodomain can then be identified. These phages can be further cloned and then retested for their ability to bind to the bromodomain as before. Once the phage has been purified, the binding sequence contained within the phage can be determined by standard DNA sequencing techniques. Once the DNA sequence is known, synthetic peptides can be generated which are encoded by these sequences. These peptides can be tested, for example, for their ability to modulate the affinity of the bromodomain for its binding partner (e.g., a protein comprising an acetyl-lysine or a fragment of that protein).

The effective peptide(s) can be synthesized in large quantities for use in in vivo models and eventually in humans to treat certain tumors. It should be emphasized that synthetic peptide production is relatively non-labor intensive, easily manufactured, quality controlled and thus, large quantities of the desired product can be produced quite cheaply. Similar combinations of mass produced synthetic peptides have been used with great success [Patarroyo, *Vaccine,* 10:175-178 (1990)].

Drug Screening Assays

The drug screening assays of the present invention may use any of a number of means for determining the interaction between an agent or drug and a peptide comprising an acetyl-lysine and/or a bromodomain. Thus, standard high throughput drug screening procedures can be employed using a library of low molecular weight compounds, for example that can be screened to identify a binding partner for the bromodoamin. Any such chemical library can be used including those discussed above.

In a particular assay, a bromodomain is placed on or coated onto a solid support. Methods for placing the peptides or proteins on the solid support are well known in the art and include such things as linking biotin to the protein and linking avidin to the solid support. An agent is allowed to equilibrate with the bromodomain to test for binding. Generally, the solid support is washed and agents that are retained are selected as potential drugs. Alternatively, a peptide comprising an acetyl-lysine is placed on or coated onto a solid support. In a particular embodiment of this type, the peptide comprises the amino acid sequence of SEQ ID NO:4.

The agent may be labeled. For example, in one embodiment radiolabeled agents are used to measure the binding of the agent. In another embodiment the agents have fluorescent markers. In yet another embodiment, a Biocore chip (Pharmacia) coated with the bromodomain is used, for example and the change in surface conductivity can be measured.

In addition, since a number of proteins have been identified that contain bromodomains, and the binding partners of many of these proteins are known, the fact that the bromodomain specifically binds to an acetylated lysine as disclosed herein allows the identification and preparation of a number of potential modulators of the bromodomain-acetyl-lysine binding complex based on the amino acid sequences of the binding partners to the proteins. Such potential modulators include: ISYGR-AcK-KRRQRR (SEQ ID NO:4), ARK-STGG-AcK-APRKQL (SEQ ID NO:5) and QSTSRHK-AcK-LMFKTE (SEQ ID NO:6) which bind to the P/CAF bromodomain as shown in the Example, below. Such peptides also can be used, for example, as a starting point for the design of an inhibitor of the bromodomain-acetyl-lysine binding complex.

Alternatively, a drug can be specifically designed to bind to the ZA loop of a bromodomain for example, such as the P/CAF bromodomain, and be assayed through NMR based methodology [Shuker et al., *Science* 274:1531-1534 (1996) hereby incorporated by reference in its entirety.] In a particular embodiment, analogs of the binding partner of the bromodomain can be used in this analysis. One such peptide has the amino acid sequence of SEQ ID NO:4. In another embodiment of this type, the peptide has the amino acid sequence of SEQ ID NO:5. In another such embodiment of this type, the peptide has the amino acid sequence of SEQ ID NO:6.

The assay begins with contacting a compound with a $^{15}$N-labeled bromodomain. Binding of the compound with the ZA loop of the bromodomain can be determined by monitoring the $^{15}$N- or $^1$H-amide chemical shift changes in two dimensional $^{15}$N-heteronuclear single-quantum correlation (15N-HSQC) spectra upon the addition of the compound to the $^{15}$N-labeled bromodomain. Since these spectra can be rapidly obtained, it is feasible to screen a large number of compounds [Shuker et al., *Science* 274:1531-1534 (1996)]. A compound is identified as a potential ligand if it binds to the ZA loop of the bromodomain. In a further embodiment, the potential ligand can then be used as a model structure, and analogs to the compound can be obtained (e.g, from the vast chemical libraries commercially available, or alternatively through de novo synthesis). The analogs are then screened for their ability to bind the ZA loop of the bromodomain thus to obtain a ligand. An analog of the potential ligand is chosen as a ligand when it binds to the ZA loop of the bromodomain with a higher binding affinity than the potential ligand. In a preferred embodiment of this type the analogs are screened by monitoring the $^{15}$N- or $^1$H-amide chemical shift changes in two dimensional $^{15}$N-heteronuclear single-quantum correlation ($^{15}$N-HSQC) spectra upon the addition of the analog to the $^{15}$N-labeled bromodomain as described above.

In another further embodiment, compounds are screened for binding to two nearby sites on the bromodomain. In this case, a compound that binds a first site of the bromodomain does not bind a second nearby site. Binding to the second site can be determined by monitoring changes in a different set of amide chemical shifts in either the original screen or a second screen conducted in the presence of a ligand (or potential ligand) for the first site. From an analysis of the chemical shift changes the approximate location of a potential ligand for the second site is identified. Optimization of the second ligand for binding to the site is then carried out by screening structurally related compounds (e.g., analogs as described above). When ligands for the first site and the second site are identified, their location and orientation in the ternary complex can be determined experimentally either by NMR spectroscopy or X-ray crystallography. On the basis of this structural information, a linked compound is synthesized in which the ligand for the first site and the ligand for the second site are linked. In a preferred embodiment of this type the two ligands are covalently linked. This linked compound is tested to determine if it has a higher binding affinity for the bromodomain than either of the two individual ligands. A linked compound is selected as a ligand when it has a higher binding affinity for the bromodomain than either of the two ligands. In a preferred embodiment the affinity of the linked compound with the bromodomain is determined monitoring the $^{15}$N- or $^1$H-amide chemical shift changes in two dimensional $^{15}$N-heteronuclear single-quantum correlation ($^{15}$N-HSQC) spectra upon the addition of the linked compound to the $^{15}$N-labeled bromodomain as described above.

A larger linked compound can be constructed in an analogous manner, e.g., linking three ligands which bind to three nearby sites on the bromodomain to form a multilinked compound that has an even higher affinity for the bromodomain than the linked compound.

Identification of New Bromodomains

By disclosing that protein bound acetyl-lysine is a binding partner for bromodomains, the present invention provides a method of identifying novel proteins that contain bromodomains. In short, a protein fragment or analog thereof comprising an acetyl-lysine can be used as bait to identify a binding partner that comprises a bromodomain. Any one of a number of procedures can be carried out to identify such a binding partner. One such assay comprises passing a cell extract over the bait peptide which is attached to a solid support. After washing the solid support to remove any non-specific binders, the bromodomain containing protein can be eluted from the solid support with an appropriate eluant. In a particular embodiment, the free bait peptide can be used in the elution. Other methodology includes the use of a yeast two-hybrid system, a GST pull down assay, ELISA, immunometric assays, and a modification of the CORT procedure of Schlessinger et al., (U.S. Pat. No. 5,858,686, Issued on Jan. 12, 1999 which is hereby incorporated by reference in its entirety) for use with the bromodomain-acetyl-lysine binding complex.

Labels

Suitable labels include enzymes, fluorophores (e.g., fluorescein isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the test and control marker gene.

In the instance where a radioactive label, such as the isotopes $^3H$, $^{14}C$, $^{32}P$, $^{35}S$, $^{36}Cl$, $^{51}Cr$, $^{57}CO$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70:419-439 (1980) and in U.S. Pat. No. 4,857,453.

Suitable enzymes include, but are not limited to, alkaline phosphatase, β-galactosidase, green fluorescent protein and its derivatives, luciferase, and horseradish peroxidase.

Other labels for use in the invention include magnetic beads or magnetic resonance imaging labels.

Antibodies to Portions of the Bromodomain that Interact with Acetyl-Lysine

According to the present invention, the bromodomains, and more particularly the ZA loops of the bromodomains and fragments thereof can be produced by a recombinant source, or through chemical synthesis, or through the modification of these peptides and fragments; and derivatives or analogs thereof, including fusion proteins, may be used as an immunogen to generate antibodies that specifically interfere with the formation of the bromodomain-acetyl-lysine binding complex. Similarly, antibodies can be raised against peptides that comprise one or more acetyl-lysine residues which also interfere with the formation of the bromodomain-acetyl-lysine binding complex. Such antibodies include but are not limited to polyclonal, monoclonal, chimeric, single chain, Fab fragments, and a Fab expression library.

Various procedures known in the art may be used for the production of the polyclonal antibodies. For the production of antibody, various host animals can be immunized by injection with the peptide having the amino acid sequence of SEQ ID NO:3, for example, or a derivative (e.g., or fusion protein) thereof, including but not limited to rabbits, mice, rats, sheep, goats, etc. In one embodiment, the peptide can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the peptides or protein fragments of the present invention, or analog, or derivative thereof, any technique that provides for the production of antibody molecules by continuous cell lines in culture may be used. These include but are not limited to the hybridoma technique originally developed by Kohler and Milstein [*Nature*, 256:495-497 (1975)], as well as the trioma technique, the human B-cell hybridoma technique [Kozbor et al., *Immunology Today*, 4:72 (1983); Cote et al., *Proc. Natl. Acad. Sci. U.S.A.*, 80:2026-2030 (1983)], and the EBV-hybridoma technique to produce human monoclonal antibodies [Cole et al., in *Monoclonal Antibodies and Cancer Therapy*, Alan R. Liss, Inc., pp. 77-96 (1985)]. In an additional embodiment of the invention, monoclonal antibodies can be produced in germ-free animals utilizing technology described in PCT/US90/02545. In fact, according to the invention, techniques developed for the production of "chimeric antibodies" [Morrison et al., *J. Bacteriol.*, 159:870 (1984); Neuberger et al., *Nature*, 312:604-608 (1984); Takeda et al., *Nature*, 314:452-454 (1985)] by splicing the genes from a mouse antibody molecule specific for the peptide having the amino acid sequence of SEQ ID NO:3, for example, together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies [U.S. Pat. Nos. 5,476,786 and 5,132,405 to Huston; U.S. Pat. No. 4,946,778] can be adapted to produce specific single chain antibodies. An additional embodiment of the invention utilizes the techniques described for the construction of Fab expression libraries [Huse et al., *Science*, 246:1275-1281 (1989)] to allow rapid and easy identification of monoclonal Fab fragments with the desired specificity.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a ZA loop of a bromodomain, for example, one may assay generated hybridomas for a product which binds to a bromodomain fragment containing such an epitope and choose those which do not cross-react with bromodomain fragments that do not include that epitope.

In a specific embodiment, antibodies that interfere with the formation of the bromodomain-acetyl-lysine complex can be generated. Such antibodies can be tested using the assays described and could potentially be used in anti-cancer therapies.

Administration

According to the invention, the component or components of a therapeutic composition, e.g., an agent of the invention that interferes with the bromodomain-acetyl-lysine binding complex such as the peptide having the amino acid sequence of SEQ ID NOs:4, 5, or 6 and a pharmaceutically acceptable carrier, may be introduced parenterally, transmucosally, e.g., orally, nasally, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration.

In a preferred aspect, the agent of the present invention can cross cellular and nuclear membranes, which would allow for intravenous or oral administration. Strategies are available for such crossing, including but not limited to, increasing the hydrophobic nature of a molecule; introducing the molecule as a conjugate to a carrier, such as a ligand to a specific receptor, targeted to a receptor; and the like.

The present invention also provides for conjugating targeting molecules to such an agent. "Targeting molecule" as used herein shall mean a molecule which, when administered in vivo, localizes to desired location(s). In various embodiments, the targeting molecule can be a peptide or protein, antibody, lectin, carbohydrate, or steroid. In one embodiment, the targeting molecule is a peptide ligand of a receptor on the target cell. In a specific embodiment, the targeting molecule is an antibody. Preferably, the targeting molecule is a monoclonal antibody. In one embodiment, to facilitate crosslinking the antibody can be reduced to two heavy and light chain heterodimers, or the F(ab')$_2$ fragment can be reduced, and crosslinked to the agent via the reduced sulfhydryl. Antibodies for use as targeting molecule are specific for a cell surface antigen.

In another embodiment, the therapeutic compound can be delivered in a vesicle, in particular a liposome [see Langer, Science, 249:1527-1533 (1990); Treat et al., in *Liposomes in the Therapy of Infectious Disease and Cancer*, Lopez-Berestein and Fidler (eds.), Liss: New York, pp. 353-365 (1989); Lopez-Berestein, ibid., pp. 317-327; see generally ibid.].

In yet another embodiment, the therapeutic compound can be delivered in a controlled release system. For example, the agent may be administered using intravenous infusion, an implantable osmotic pump, a transdermal patch, liposomes, or other modes of administration. In one embodiment, a pump may be used [see Langer, supra; Sefton, *CRC Crit. Ref Biomed. Eng.*, 14:201 (1987); Buchwald et al., *Surgery*, 88:507 (1980); Saudek et al., *N. Engl.* 1 Med., 321:574 (1989)]. In another embodiment, polymeric materials can be used [see *Medical Applications of Controlled Release*, Langer and Wise (eds.), CRC Press: Boca Raton, Fla. (1974); *Controlled Drug Bioavailability, Drug Product Design and Performance*, Smolen and Ball (eds.), Wiley: New York (1984); Ranger and Peppas, *J. Macromol. Sci. Rev. Macromol. Chem.*, 23:61 (1983); see also Levy et al., *Science*, 228:190 (1985); During et al., *Ann. Neurol.*, 25:351 (1989); Howard et al., *J. Neurosurg.*, 71:105 (1989)]. In yet another embodiment, a controlled release system can be placed in proximity of the therapeutic target, i.e., the bone marrow, thus requiring only a fraction of the systemic dose [see, e.g., Goodson, in *Medical Applications of Controlled Release*, supra, vol. 2, pp. 115-138 (1984)]. Other controlled release systems are discussed in the review by Langer [Science, 249:1527-1533 (1990)].

Pharmaceutical Compositions. In yet another aspect of the present invention, provided are pharmaceutical compositions of the above. Such pharmaceutical compositions may be for administration for injection, or for oral, pulmonary, nasal or other forms of administration. In general, comprehended by the invention are pharmaceutical compositions comprising effective amounts of a low molecular weight component or components, or derivative products, of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives. See, e.g., Remington's Pharmaceutical Sciences, 18th Ed. [1990, Mack Publishing Co., Easton, Pa. 18042] pages 1435-1712 which are herein incorporated by reference. The compositions may be prepared in liquid form, or may be in dried powder, such as lyophilized form.

Oral Delivery. Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: *Modern Pharmaceutics* Edited by G. S. Banker and C. T. Rhodes Chapter 10, 1979, herein incorporated by reference. In general, the formulation will include an agent of the present invention (or chemically modified forms thereof) and inert ingredients which allow for protection against the stomach environment, and release of the biologically active material in the intestine.

Also specifically contemplated are oral dosage forms of the above derivatized component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. An example of such a moiety is polyethylene glycol.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the protein (or derivative) or by release of the biologically active material beyond the stomach environment, such as in the intestine.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Binders also may be used to hold the therapeutic agent together to form a hard tablet and include materials from natural products such as acacia, tragacanth, starch and gelatin.

An anti-frictional agent may be included in the formulation of the therapeutic to prevent sticking during the formulation process. Lubricants may be used as a layer between the therapeutic and the die wall. Glidants that might improve the flow properties of the drug during formulation and to aid rearrangement during compression also might be added. The glidants may include starch, talc, pyrogenic silica and hydrated silicoaluminate.

In addition, to aid dissolution of the therapeutic into the aqueous environment a surfactant might be added as a wetting agent. Additives which potentially enhance uptake of the protein (or derivative) are for instance the fatty acids oleic acid, linoleic acid and linolenic acid.

Nasal Delivery. Nasal delivery of an agent of the present invention (or derivative) is also contemplated. Nasal delivery allows the passage of a peptide, for example, to the blood stream directly after administering the therapeutic product to the nose, without the necessity for deposition of the product in the lung. Formulations for nasal delivery include those with dextran or cyclodextran.

Transdermal administration. Various and numerous methods are known in the art for transdermal administration of a drug, e.g., via a transdermal patch. Transdermal patches are described in for example, U.S. Pat. No. 5,407,713, issued Apr. 18, 1995 to Rolando et al.; U.S. Pat. No. 5,352,456, issued Oct. 4, 1004 to Fallon et al.; U.S. Pat. No. 5,332,213 issued Aug. 9, 1994 to D'Angelo et al.; U.S. Pat. No. 5,336,168, issued Aug. 9, 1994 to Sibalis; U.S. Pat. No. 5,290,561, issued Mar. 1, 1994 to Farhadieh et al.; U.S. Pat. No. 5,254,346, issued Oct. 19, 1993 to Tucker et al.; U.S. Pat. No. 5,164,189, issued Nov. 17, 1992 to Berger et al.; U.S. Pat. No. 5,163,899, issued Nov. 17, 1992 to Sibalis; U.S. Pat. Nos. 5,088,977 and 5,087,240, both issued Feb. 18, 1992 to Sibalis; U.S. Pat. No. 5,008,110, issued Apr. 16, 1991 to Benecke et al.; and U.S. Pat. No. 4,921,475, issued May 1, 1990 to Sibalis, the disclosure of each of which is incorporated herein by reference in its entirety.

It can be readily appreciated that a transdermal route of administration may be enhanced by use of a dermal penetration enhancer, e.g., such as enhancers described in U.S. Pat. No. 5,164,189 (supra), U.S. Pat. No. 5,008,110 (supra), and U.S. Pat. No. 4,879,119, issued Nov. 7, 1989 to Aruga et al., the disclosure of each of which is incorporated herein by reference in its entirety.

Pulmonary Delivery. Also contemplated herein is pulmonary delivery of the pharmaceutical compositions of the present invention. A pharmaceutical composition of the present invention is delivered to the lungs of a mammal while inhaling and traverses across the lung epithelial lining to the blood stream. Other reports of this include Adjei et al. [*Pharmaceutical Research*, 7:565-569 (1990); Adjei et al., *International Journal of Pharmaceutics*, 63:135-144 (1990) (leuprolide acetate); Braquet et al., *Journal of Cardiovascular Pharmacology*, 13(suppl. 5):143-146 (1989) (endothelin-1); Hubbard et al., *Annals of Internal Medicine*, Vol. III, pp. 206-212 (1989) (α1-antitrypsin); Smith et al., *J. Clin. Invest.*, 84:1145-1146 (1989) (α-1-proteinase); Oswein et al., "Aerosolization of Proteins", *Proceedings of Symposium on Respiratory Drug Delivery II*, Keystone, Colorado, March, (1990) (recombinant human growth hormone); Debs et al., *J. Immunol.*, 140:3482-3488 (1988) (interferon-γ and tumor necrosis factor alpha); Platz et al., U.S. Pat. No. 5,284,656 (granulocyte colony stimulating factor)]. A method and composition for pulmonary delivery of drugs for systemic effect is described in U.S. Pat. No. 5,451,569, issued Sep. 19, 1995 to Wong et al.

A subject in whom administration of an agent of the present invention is an effective therapeutic regiment for cancer, for example, is preferably a human, but can be any animal. Thus, as can be readily appreciated by one of ordinary skill in the art, the methods and pharmaceutical compositions of the present invention are particularly suited to administration to any animal, e.g., for veterinary medical use, particularly for a mammal, and including, but by no means limited to, domestic animals, such as feline or canine subjects, farm animals, including bovine, equine, caprine, ovine, and porcine subjects, wild animals (whether in the wild or in a zoological garden), research animals, such as mice, rats, rabbits, goats, sheep, pigs, dogs, cats, avian species, such as chickens, turkeys, and songbirds.

The present invention may be better understood by reference to the following non-limiting Example, which is provided as exemplary of the invention. The following example is presented in order to more fully illustrate the preferred embodiments of the invention. It should in no way be construed, however, as limiting the broad scope of the invention.

EXAMPLE

Structure and Ligand of a Histone Acetyltransferase Bromodomain

Introduction

The bromodomain is a protein motif comprising approximately 110 amino acids that is found in practically all nuclear histone acetyltransferases (HATs) [Jeanmougin et al., *Trends in Biochemical Sciences*, 22:151-153 (1997)]. However, despite the seemingly requisite occurrence of this motif in HATs, their role in these enzymes is unknown. Indeed, although this motif has also been identified in other chromatin proteins, heretofore not even one binding partner for a bromodomain had been identified.

Materials and Methods

Sample preparation: The bromodomain of P/CAF (residues 719-832 of SEQ ID NO:2) was subcloned into the pET14b expression vector (Novagen) and expressed in *Escherichia coli* BL21(DE3) cells. Uniformly $^{15}$N- and $^{15}$N/$^{13}$C-labelled proteins were prepared by growing bacteria in a minimal medium containing $^{15}$NH$_4$Cl with or without $^{13}$C$_6$-glucose. A uniformly $^{15}$N/$^{13}$C-labelled and fractionally deuterated protein sample was prepared by growing the cells in 75% $^2$H$_2$O. The bromodomain was purified by affinity chromatography on a nickel-IDA column (Invitrogen) followed by the removal of poly-His tag by thrombin cleavage. The final purification of the protein was achieved by size-exclusion chromatography. The acetyl-lysine-containing peptides were prepared on a MilliGen 9050 peptide synthesizer (Perkin Elmer) using Fmoc/HBTU chemistry. Acetyl-lysine was incorporated using the reagent Fmoc-Ac-Lys with HBTU/DIPEA activation. NMR samples contained approximately 1 mM protein in 100 mM phosphate buffer of pH 6.5 and 5 mM perdeuterated DTT and 0.5 mM EDTA in H$_2$O/$^2$H$_2$O (9/1) or $^2$H$_2$O.

NMR spectroscopy: All NMR spectra were acquired at 30° C. on a Bruker DRX600 or DRX500 spectrometer. The backbone assignments of the $^1$H, $^{13}$C, and $^{15}$N resonances were achieved using deuterium-decoupled triple-resonance experiments of HNCACB and HN(CO)CACB [Yamazaki et al., *J. Am. Chem. Soc.* 116:11655-11666 (1994)] recorded using the uniformly $^{15}$N/$^{13}$C-labeled and fractionally deuterated protein. The side-chain atoms were assigned from 3D HCCH-TOCSY [Clore and Gronenborn, *Meth. Enzymol.* 239:249-363 (1994)] and (H)C(CO)NH-TOCSY [Logan et al., *J. Biolmol. NMR* 3:225-231 (1993)] data collected on the uniformly $^{15}$N/$^{13}$C-labeled protein. Stereospecific assignments of methyl groups of the Val and Leu residues were obtained using a fractionally $^{13}$C-labeled sample [Neri et al., *Biochemistry* 28:7510-7516 (1989)]. The NOE-derived distance restraints were obtained from $^{15}$N- or $^{13}$C-edited 3D NOESY spectra. $\phi$-angle restraints were determined based on the $^3J_{HN,H}\alpha$ coupling constants measured in a 3D HNHA spectrum [Clore and Gronenborn, *Meth. Enzymol.* 239:249-363 (1994)]. Slowly exchanging amide protons were identified from a series of 2D $^{15}$N-HSQC spectra recorded after the H$_2$O buffer was changed to a $^2$H$_2$O buffer. The intermolecular NOEs used in defining the structure of the bromodomain/Ac-histamine complex were detected in $^{13}$C-edited (F$_1$), $^{13}$C/$^{15}$N-filtered (F$_3$) 3D NOESY spectrum [Clore and Gronenborn, *Meth. Enzymol.* 239:249-363 (1994)]. All NMR spectra were processed with the NMRPipe/NMRDraw programs and analyzed using NMRView [Johnson and Blevins, *J. Biomol., NMR* 4:603-614 (1994)].

Structure calculations: Structures of the bromodomain were calculated with a distance geometry/simulated annealing protocol using the X-PLOR program [Brunger, A. *X-PLOR Version 3.1: A system for X-Ray crystallography and NMR*, Yale University Press, New Haven, Conn., (1993)]. A total of 1324 manually assigned NOE-derived distance restraints were obtained from the $^{15}$N- and $^{13}$C-edited NOE spectra. Further analysis of the NOE spectra was carried out by the iterative automated assignment procedure using ARIA [Nilges and O'Donoghue, *Prog. NMR Spectroscopy* 32:107-139 (1998)], which integrates with X-PLOR for structure calculations. A total of 1519 unambiguous and 590 ambiguous distance restraints were identified from the NOE data by ARIA, many of which were checked and confirmed manually. The ARIA-assigned distance restraints were in agreement with the structures calculated using only the manually assigned NOE distance restraints, 28 hydrogen-bond distance restraints for 14 hydrogen bonds, and 54$\phi$-angle restraints. The final structure calculations employed a total of 3515 NMR experimental restraints obtained from the manual and the ARIA-assisted assignments, 2843 of which were unambiguously assigned NOE-derived distance restraints that comprise of 1077 intra-residue, 621 sequential, 550 medium-range, and 595 long-range NOEs. For the ensemble of the final 30 structures, no distance and torsional angle restraints were violated by more than 0.3 Å and 5°, respectively. The total, distance violation, and dihedral violation energies were 178.7±2.4 kcal mol$^{-1}$, 41.6±0.9 kcal mol$^{-1}$, and 0.50±0.06 kcal mol$^{-1}$, respectively. The Lennard-Jones potential which was not used during any refinement stage, was −526.2±16.8 kcal mol$^{-1}$ for the final structures. Ramachandran plot analysis of the final structures (residues 727-828) with Procheck-NMR [Laskowski et al., *J. Biolmol. NMR* 8:477-486 (1996)] showed that 71.0±0.6%, 23.8±0.6%, 3.5±0.2%, and 1.7±0.2% of the non-Gly and non-Pro residues were in the most favorable, additionally allowed, generously allowed, and disallowed regions, respectively. The corresponding values for the residues in the four $\alpha$-helices (residues 727-743, 770-776, 785-802, and 807-827) were 88.9±0.4%, 11.0±0.4%, 0.1±0.1%, and 0.0±0.0%, respectively. The structure of the bromodomain/acetyl-histamine complex was determined using the free form structure and additional 25 intermolecular and 5 intra-ligand NOE-derived distance restraints.

Site-directed mutagenesis: Mutant proteins were prepared using the QuickChange site-directed mutagenesis kit (Stratagene). The presence of appropriate mutations was confirmed by DNA sequencing.

Ligand titration: Ligand titration experiments were performed by recording a series of 2D $^{15}$N- and $^{13}$C-HSQC spectra on the uniformly $^{15}$N-, and $^{15}$N/$^{13}$C-labelled bromodomain (~0.3 mM), respectively, in the presence of different amounts of ligand concentration ranging from 0 to approximately 2.0 mM. The protein sample and the stock solutions of the ligands were all prepared in the same aqueous buffer containing 100 mM phosphate and 5 mM perdeuterated DTT at pH 6.5.

The full length nucleic acid sequence of the human p300/CBP-associated factor (P/CAF) was obtained from GenBank. Accession No: U57317.2 (SEQ ID NO:1):

```
  1 ggggccgcgt cgacgcggaa aagaggccgt gggggccctc ccagcgctgg cagacaccgt
 61 gaggctggca gccgccggca cgcacaccta gtccgcagtc ccgaggaaca tgtccgcagc
121 cagggcgcgg agcagagtcc cgggcaggag aaccaaggga gggcgtgtgc tgtggcggcg
```

-continued

```
 181 gcggcagcgg cagcggagcc gctagtcccc tccctcctgg gggagcagct gccgccgctg
 241 ccgccgccgc caccaccatc agcgcgcggg gcccgccag agcgagccgg gcgagcggcg
 301 cgctagggg agggcgggg cggggagggg ggtgggcgaa gggggcggga gggcgtgggg
 361 ggagggtctc gctctcccga ctaccagagc ccgagggaga ccctggcggc ggcggcggcg
 421 cctgacactc ggcgcctcct gccgtgctcc ggggcggcat gtccgaggct ggcggggccg
 481 ggccgggcgg ctgcggggca ggagccgggg cagggccgg gcccggggcg ctgcccccgc
 541 agcctgcggc gcttccgccc gcgcccccgc agggctcccc ctgcgccgct gccgccgggg
 601 gctcgggcgc ctgcggtccg gcgacggcag tggctgcagc gggcacggcc gaaggaccgg
 661 gaggcggtgg ctcggcccga atcgccgtga agaaagcgca actacgctcc gctccgcggg
 721 ccaagaaact ggagaaactc ggagtgtact ccgcctgcaa ggccgaggag tcttgtaaat
 781 gtaatggctg gaaaaaccct aaccctcac ccactccccc cagagccgac ctgcagcaaa
 841 taattgtcag tctaacagaa tcctgtcgga gttgtagcca tgccctagct gctcatgttt
 901 cccacctgga gaatgtgtca gaggaagaaa tgaacagact cctgggaata gtattggatg
 961 tggaatatct ctttacctgt gtccacaagg aagaagatgc agataccaaa caagtttatt
1021 tctatctatt taagctcttg agaaagtcta ttttacaaag aggaaaacct gtggttgaag
1081 gctctttgga aaagaaaccc ccatttgaaa aacctagcat tgaacagggt gtgaataact
1141 ttgtgcagta caaatttagt cacctgccag caaaagaaag gcaaacaata gttgagttgg
1201 caaaaatgtt cctaaaccgc atcaactatt ggcatctgga ggcaccatct caacgaagac
1261 tgcgatctcc caatgatgat atttctggat acaagagaa ctacacaagg tggctgtgtt
1321 actgcaacgt gccacagttc tgcgacagtc tacctcggta cgaaaccaca caggtgtttg
1381 ggagaacatt gcttcgctcg gtcttcactg ttatgaggcg acaactcctg gaacaagcaa
1441 gacaggaaaa agataaactg cctcttgaaa aacgaactct aatcctcact catttcccaa
1501 aatttctgtc catgctagaa gaagaagtat atagtcaaaa ctctcccatc tgggatcagg
1561 attttctctc agcctcttcc agaaccagcc agctaggcat ccaaacagtt atcaatccac
1621 ctcctgtggc tgggacaatt tcatacaatt caacctcatc ttcccttgag cagccaaacg
1681 cagggagcag cagtcctgcc tgcaaagcct cttctggact tgaggcaaac ccaggagaaa
1741 agaggaaaat gactgattct catgttctgg aggaggccaa gaaaccccga gttatggggg
1801 atattccgat ggaattaatc aacgaggtta tgtctaccat cacggaccct gcagcaatgc
1861 ttggaccaga gaccaatttt ctgtcagcac actcggccag ggatgaggcg gcaaggttgg
1921 aagagcgcag gggtgtaatt gaatttcacg tggttggcaa ttccctcaac cagaaaccaa
1981 acaagaagat cctgatgtgg ctggttggcc tacagaacgt tttctcccac cagctgcccc
2041 gaatgccaaa agaatacatc acacggctcg tctttgaccc gaaacacaaa aCccttgctt
2101 taattaaaga tggccgtgtt attggtggta tctgtttccg tatgttccca tctcaaggat
2161 tcacagagat tgtcttctgt gctgtaacct caaatgagca agtcaagggc tatggaacac
2221 acctgatgaa tcatttgaaa gaatatcaca taaagcatga catcctgaac ttcctcacat
2281 atgcagatga atatgcaatt ggatacttta agaaacaggg tttctccaaa gaaattaaaa
2341 tacctaaaac caaatatgtt ggctatatca aggattatga aggagccact ttaatgggat
2401 gtgagctaaa tccacggatc ccgtacacag aatttttctgt catcattaaa aagcagaagg
2461 agataattaa aaaactgatt gaaagaaaac aggcacaaat tcgaaaagtt taccctggac
2521 tttcatgttt taagatgga gttcgacaga ttcctataga aagcattcct ggaattagag
2581 agacaggctg gaaaccgagt ggaaaagaga aaagtaaaga gcccagagac cctgaccagc
```

```
2641 tttacagcac gctcaagagc atcctccagc aggtgaagag ccatcaaagc gcttggccct 2701 tcatggaacc tgtgaagaga acagaagctc caggatatta tgaagttata aggttcccca 2761 tggatctgaa aaccatgagt gaacgcctca agaataggta ctacgtgtct aagaaattat 2821 tcatggcaga cttacagcga gtctttacca attgcaaaga gtacaacgcc gctgagagtg 2881 aatactacaa atgtgccaat atcctggaga aattcttctt cagtaaaatt aaggaagctg 2941 gattaattga caagtgattt tttttccccc tctgcttctt agaaactcac caagcagtgt 3001 gcctaaagca aggt
```

The full length protein sequence of the human p300/CBP-associated factor (P/CAF) was obtained from GenBank. Accession No: U57317.2, (SEQ ID NO:2):

```
  1 MSEAGGAGPG GCGAGAGAGA GPGALPPQPA ALPPAPPQGS PCAAAAGGSG ACGPATAVAA

61 AGTAEGPGGG GSARIAVKKA QLRSAPRAKK LEKLGVYSAC KAEESCKCNG WKNPNPSPTP

121 PRADLQQIIV SLTESCRSCS HALAAHVSHL ENVSEEEMNR LLGIVLDVEY LFTCVHKEED

181 ADTKQVYFYL FKLLRKSILQ RGKPVVEGSL EKKPPFEKPS IEQGVNNFVQ YKFSHLPAKE

241 RQTIVELAKM FLNRINYWHL EAPSQRRLRS PNDDISGYKE NYTRWLCYCN VPQFCDSLPR

301 YETTQVFGRT LLRSVFTVMR RQLLEQARQE KDKLPLEKRT LILTHFPKFL SMLEEEVYSQ

361 NSPIWDQDFL SASSRTSQLG IQTVINPPPV AGTISYNSTS SSLEQPNAGS SSPACKASSG

421 LEANPGEKRK MTDSHVLEEA KKPRVMGDIP MELINEVMST ITDPAAMLGP ETNFLSAHSA

481 RDEAARLEER RGVIEFHVVG NSLNQKPNKK ILMWLVGLQN VFSHQLPRMP KEYITRLVFD

541 PKHKTLALIK DGRVIGGICF RMFPSQGFTE IVFCAVTSNE QVKGYGTHLM NHLKEYHIKH

601 DILNFLTYAD EYAIGYFKKQ GFSKEIKIPK TKYVGYIKDY EGATLMGCEL NPRIPYTEFS

661 VIIKKQKEII KKLIERKQAQ IRKVYPGLSC FKDGVRQIPI ESIPGIRETG WKPSGKEKSK

721 EPRDPDQLYS TLKSILQQVK SHQSAWPFME PVKRTEAPGY YEVIRFPMDL KTMSERLKNR

781 YYVSKKLFMA DLQRVFTNCK EYNAAESEYY KCANILEKFF FSKIKEAGLI DK
```

Results

The P/CAF bromodomain represents an extensive family of bromodomains (FIG. 1). A large number of long-range nuclear Overhauser enhancement (NOE)-derived distance restraints were identified in the NMR data of the P/CAF bromodomain, yielding a well-defined three-dimensional structure (FIGS. 2A-2D). Table 1 shows the NMR chemical shift assignment of the P/CAF bromodomain. Table 2 shows the Unambiguous NOE-derived distance restraints. Table 3 shows the Ambiguous NOE-derived distance restraints. Table 4 shows the Hydrogen bond restraints. The NMR structure coordinates of the P/CAF bromodomain in the free and complexed to acetyl-histamine are shown in Tables 5 and 6, respectively.

Figure 2F:
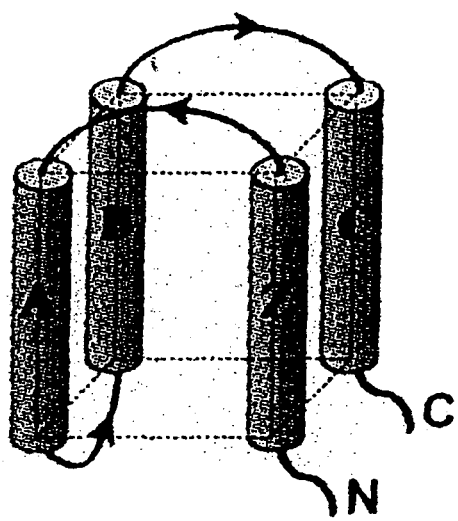
Figure 2G:
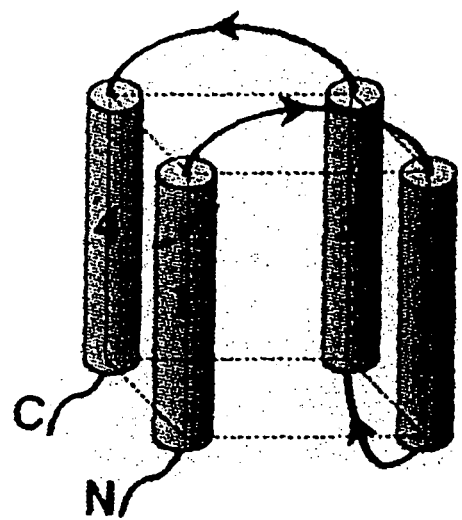
Figure 2H:
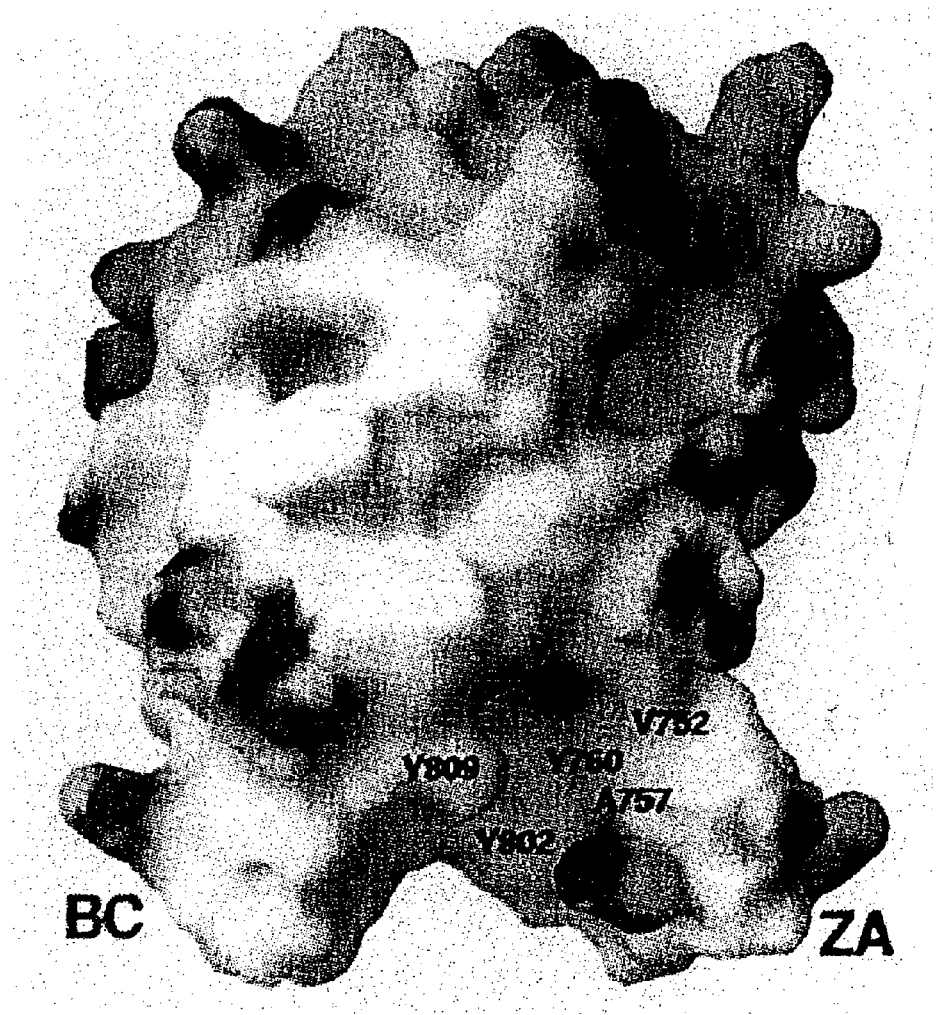

The structure consists of a four-helix bundle (helices $\alpha_Z$, $\alpha_A$, $\alpha_B$, and $\alpha_C$) with a left-handed twist, and a long intervening loop between helices $\alpha_Z$ and $\alpha_A$ (termed the ZA loop, FIG. 2E). The four amphipathic α-helices are packed tightly against one another in an antiparallel manner, with crossing angles for adjacent helices of ~16-20°. The up-and-down four-helix bundle can adapt two topological folds with opposite handedness (FIGS. 2F-2G). The right-handed four-helix bundle fold occurs more commonly and is seen in proteins such as hemerythrin and cytochrome $b_{562}$. The left-handed fold of the bromodomain structure is less common, but also observed in proteins such as cytochrome $b_5$ and T4 lysozyme [Richardson, J., Adv. Protein Chem., 34:167-339 (1989); Presnell and Cohen, Proc. Natl. Acad. Sci. USA 86:6592-6596 (1989)]. This topological difference arises from the orientation of the loop between the first two helices (FIGS. 2F-2G). The right-handed four-helix bundle proteins have a relatively short hairpin-like connection between the first two helices, which makes the "preferred" turn to the right at the top of the first helix [Richardson, J., Adv. Protein Chem., 34:167-339 (1989); Presnell and Cohen, Proc. Natl. Acad. Sci. USA 86:6592-6596 (1989); Weber and Salemme, Nature 287:82-84 (1980)]. In contrast, proteins with the left-handed fold usually have a long loop after the first helix and often contain additional secondary structural elements at the base of the helix bundle [Richardson, J., Adv. Protein Chem., 34:167-339 (1989); Presnell and Cohen, Proc. Natl. Acad. Sci. USA 86:6592-6596 (1989)]. In the bromodomain structure, this long ZA loop has a defined conformation and is packed against the loop between helices $\alpha_B$ and $\alpha_C$ (termed the BC loop) to form a hydrophobic pocket. These tertiary interactions between the two loops appear to favor the left turn of the ZA loop, resulting in the left-handed four-helix bundle fold of the bromodomain. The hydrophobic pocket formed by loops ZA and BC is lined by residues Val752, Ala757, Tyr760, Val763, Tyr802 and Tyr809 (FIG. 2H), and appears to be a site for protein-protein interactions (see below). The pocket is located at one end of the four-helix bundle, opposite to the N- and C-termini of the protein. Interestingly, the ZA loop varies in length amongst different bromodomains, but almost always contains residues corresponding to Phe748, Pro751, Pro758, Tyr760, and Pro767 (FIG. 1). The conservation of these residues within the ZA loop as well as residues within the α-helical regions implies a similar left-handed four-helix bundle structure for the large family of bromodomains (FIG. 1).

Figure 3A:
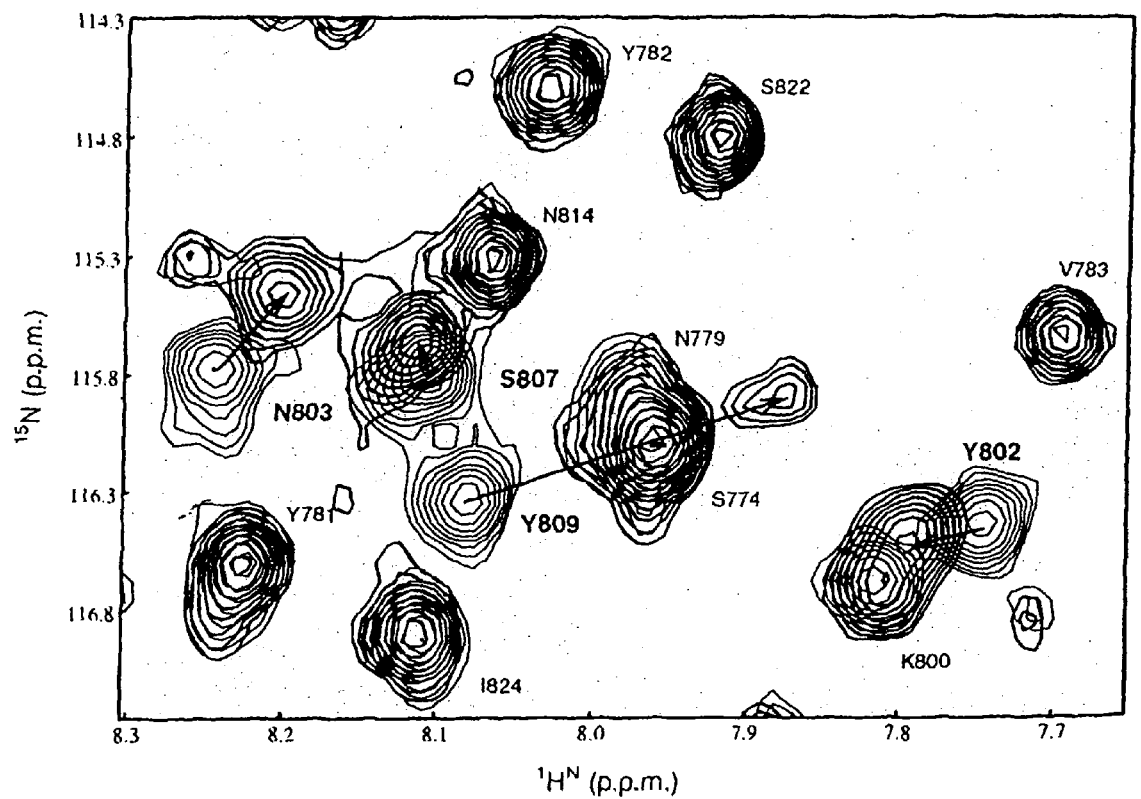
FIGS. 3A-3C show the binding of the P/CAF bromodomain to AcK.

The modular bromodomain structure supports the idea that bromodomain can act as a functional unit for protein-protein interactions. The observation that bromodomains are found in nearly all known nuclear HATs (A-type) that are known to promote transcription-related acetylation of histones on specific lysine residues, but not present in cytoplasmic HATs (B-type), prompted the determination of whether bromodomains can interact with acetyl-lysine (AcK). The NMR titration of the P/CAF bromodomain were performed with a peptide (SGRGKGG-AcK-GLGK) (SEQ ID NO: 46) derived from histone H4, in which Lys8 is acetylated (Lys8 is the major acetylation site in H4 for GCN5, a yeast homologue of P/CAF). Remarkably, the bromodomain could indeed bind the AcK peptide. Moreover, this interaction appeared to be specific, based on the $^{15}$N-HSQC spectra which showed that only a limited number of residues underwent chemical shift changes as a function of peptide concentration (FIG. 3A). Conversely, the NMR titration of the bromodomain with a non-acetylated, but otherwise identical H4 peptide, showed no noticeable chemical shift changes, demonstrating that the interaction between the bromodomain and the lysine-acetylated H4 peptide was dependent upon acetylation of lysine. The dissociation constant ($K_D$) for the AcK peptide was estimated to be 346±54 μM. This binding is likely reinforced through additional interactions between bromodomain-containing proteins and target proteins. Notably, many chromatin-associated proteins contain two or multiple bromodomains (FIG. 1). Indeed, binding with another lysine-acetylated peptide (RKSTGG-AcK-APRKQ) (SEQ ID NO: 47) derived from the major acetylation site on histone H3 (residues 9-20) was also observed. Together, these data demonstrate that the P/CAF bromodomain has the ability to bind AcK peptides in an acetylation dependent manner.

Figure 3B:
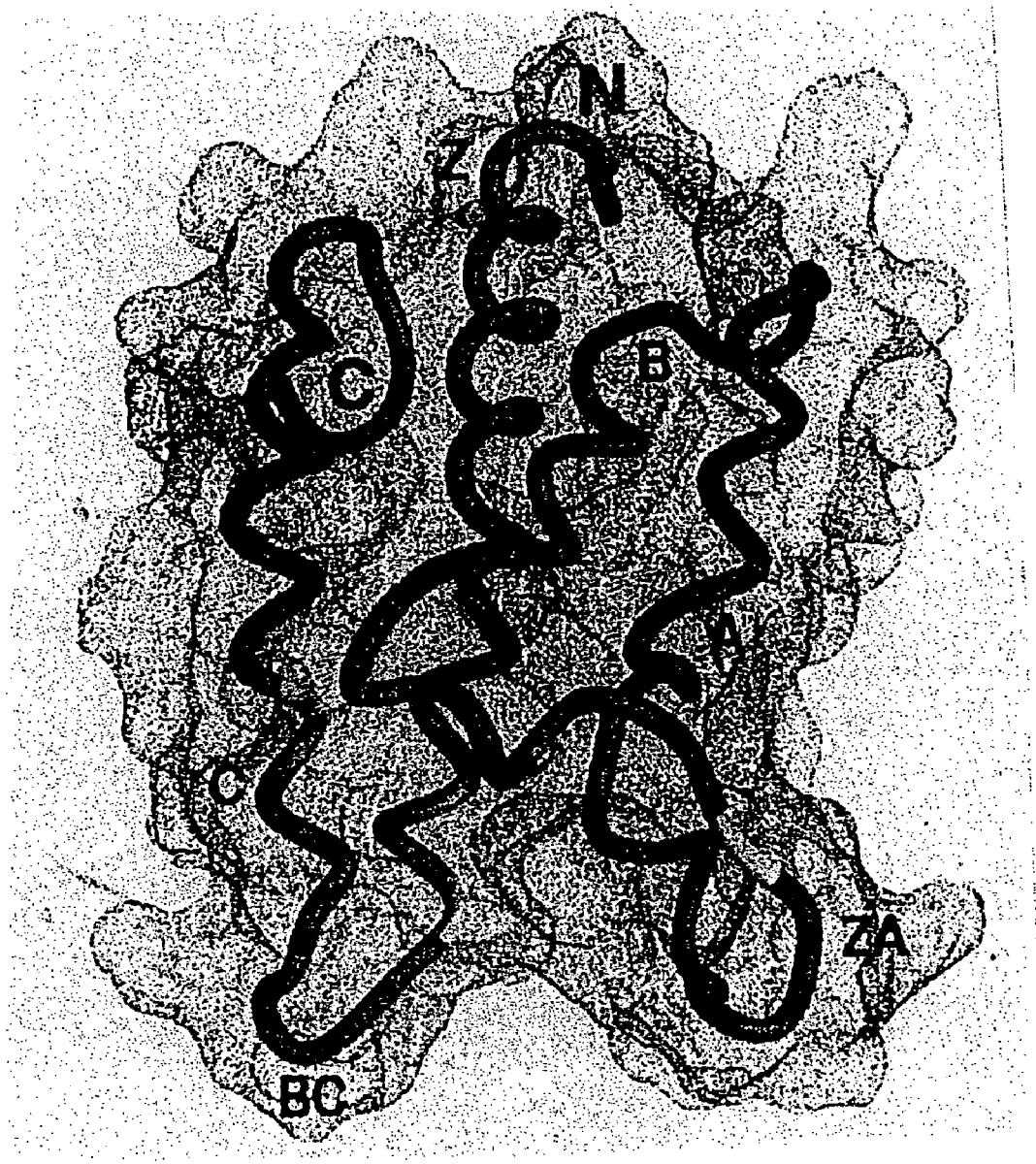
Figure 3C:
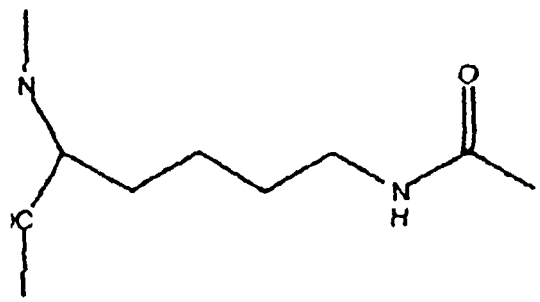
Figure 3C:
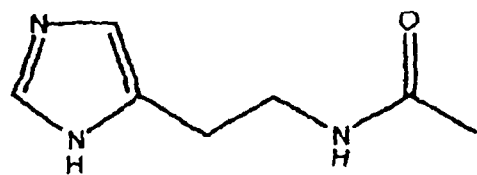
Figure 3C:
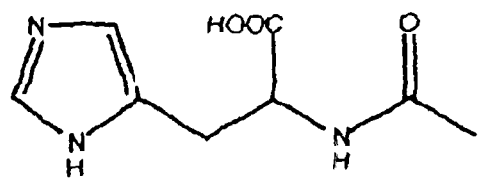

Intriguingly, the bromodomain residues that exhibited the most significant $^1$H and $^{15}$N chemical shift changes on peptide binding are located near the hydrophobic pocket between the ZA and BC loops (FIG. 3B). Because a similar pattern of amide chemical shift changes was observed with the two different AcK-containing peptides, it was surmised that the hydrophobic cavity is the primary binding site for AcK. This hypothesis was further supported by titration with acetyl-histamine, which mimics the chemical structure of the AcK side-chain (FIG. 3C). Both $^{15}$N- and $^{13}$C-HSQC spectra showed that interaction with acetyl-histamine was also acetylation-dependent, involving the same set of residues that showed chemical shift perturbations with similar concentration dependence. It should be noted that the bromodomain did not bind to the amino acids acetyl-lysine or acetyl-histidine alone, possibly due to the presence of the charged amino, carboxyl, or carboxylate group adjacent to the acetyl moiety (FIG. 3C). Taken together, these results strongly suggest that the P/CAF bromodomain can interact with acetyl-lysine-containing proteins in a specific manner, and that this interaction is localized to the bromodomain hydrophobic cavity.

To identify the key residues involved in bromodomain-AcK recognition, the NMR structure of the P/CAF bromodomain in complex with acetyl-histamine was elucidated. As anticipated, the acetylated moiety binds in the bromodomain hydrophobic pocket (FIG. 4). The intermolecular interactions are largely hydrophobic in nature, with the methyl group of acetyl-histamine making extensive contacts with the side-chains of Val752, Ala757, and Tyr760, and the methylene groups of acetyl-histamine displaying specific NOEs to Val752, Ala757, Tyr760, Tyr802, and Tyr809. No intermolecular NOEs were observed for the imidazole ring of acetyl-histamine. From the spectral analysis it is clear that the structure of the bromodomain is very similar in both the free and complex forms.

It is worth noting that the bromodomain-AcK recognition is reminiscent of the interactions between the histone acetyltransferase Hat1 and acetyl-CoA. Although the binding pockets of these two otherwise structurally unrelated proteins are composed of different secondary structural elements, the nature of acetyl-lysine recognition has striking similarities. In particular, Tyr809, Tyr802, Tyr760, and Val752 in the bromodomain appear to be related to Phe220, Phe261, Val254, and Ile217 of Hat1, respectively, in their interactions with the acetyl moiety. This observation may suggest an evolutionary convergent mechanism of acetyl-lysine recognition between bromodomains and histone acetyltransferases.

To determine the relative contributions of residues within the hydrophobic cavity in bromodomain-AcK binding, site-directed mutagenesis was used to alter residues Tyr809, Tyr802, Tyr760, and Val752 (Table 7).

TABLE 7

Structural and Functional Analysis of the P/CAF Bromodomain Mutants

| Bromodomain Proteins | Structural Integrity[a] | H4 AcK-Peptide Binding $K_D$ (μM)[b] |
|---|---|---|
| Wild-Type | ++++ | 346 ± 54 |
| Tyr809Ala | ++++ | No Binding[c] |
| Tyr802Ala | +++ | >10,000[d] |
| Tyr760Ala | +++ | >10,000 |
| Val752Ala | ++ | >10,000 |

[a]The effects of mutations on the structural integrity of the bromodomain were assessed by using the $^{15}$N-HSQC spectra. The amide $^1$H/$^{15}$N resonances of the mutant proteins were compared to those of the wild-type bromodomain to determine if the particular mutations lead to global or local structure disruption. Severe line-broadening of the amide resonances would indicate protein conformational exchange due to a decrease of structure stability resulting from point mutations. Structural integrity of the mutant proteins is expressed here relative to that of the wild-type, using the signs of "++++" for as stable as the wild-type, "+++" for mildly destabilized, "++" for moderately destabilized, and "−" for completely unfolded.
[b]The ligand binding affinity ($K_D$) of the bromodomain proteins was estimated by following chemical shift changes of amide peaks in the $^{15}$N-HSQC spectra as a function of the ligand concentration.
[c]No detectable ligand binding observed in the NMR titration.
[d]Ligand binding affinity was significantly reduced and beyond the limit for reliable measurements by NMR titration.

Substitution of Ala for Tyr809 completely abrogated the bromodomain binding to the lysine-acetylated H4 peptide, while the Tyr802Ala, Tyr760Ala, and Val752Ala mutants had significantly reduced ligand binding affinity. To assess whether these mutations disrupted the overall bromodomain fold, the $^{15}$N-HSQC spectra of the mutants was compared to that of the wild-type protein. For the Tyr809Ala mutant, the amide chemical shifts were only affected for a few residues near the mutation site. However, mutations of the other residues in the hydrophobic binding pocket perturbed the local protein conformation to greater extents, particularly the ZA loop (Table 7). Thus, the NMR structural analysis and the mutagenesis studies show that Tyr809, which is structurally supported by Trp746 and Asn803 (FIG. 4), is essential for the bromodomain interaction with the acetyl group of acetyl-lysine, while residues of Tyr802, Tyr760, and Val752 likely play both structural and functional roles in the recognition. These residues are highly conserved throughout the bromodomain family (FIG. 1), suggesting that recognition of acetyl-lysine may be a feature of bromodomains, in general. Therefore, Val752, Ala757, Tyr760, Tyr802, Asn803, and Tyr809 are key amino acid residues for the P/CAF bromodomain binding to acetyl-lysine.

TABLE 8

Amino Acid Sequences of Bromodomains Identified in FIG. 1

| PROTEIN BD | SEQ ID NO: | GenBank Acc. No. | PROTEIN BD | SEQ ID NO: | GenBank Acc. No. |
|---|---|---|---|---|---|
| hsp/CAF | 7 | U57317 | dmFSH-2 | 25 | |
| hsGCN5 | 8 | U57136 | scBDF1-2 | 26 | |
| ttP55 | 9 | U47321 | hsBR140 | 27 | JC2069 |
| scGCN5 | 10 | Q03330 | hsSMAP | 28 | X87613 |
| hsP300 | 11 | A54277 | ggPB1-1 | 29 | X90849 |
| hsCBP | 12 | S39162 | ggPB1-2 | 30 | |
| mmCBP | 13 | S39161 | ggPB1-3 | 31 | |
| ceYNJ1 | 14 | P34545 | ggPB1-4 | 32 | |
| hsCCG1-1 | 15 | P21675 | ggPB1-5 | 33 | |
| msCCG1-1 | 16 | D26114 | spBRO-1 | 34 | S54260 |
| hsCCG1-2 | 17 | | spBRO-2 | 35 | |
| msCCG1-2 | 18 | | hsSNF2a | 36 | S45251 |
| hsRing3-1 | 19 | P25440 | hsBRG1 | 37 | S39039 |
| hsORFX-1 | 20 | D26362 | ggBRM | 38 | X91638 |
| dmFSH-1 | 21 | P13709 | ggBRG1 | 39 | X91637 |
| scBDF1-1 | 22 | P35817 | hsTIF1b | 40 | X97548 |
| hsRing3-2 | 23 | | mmTIF1b | 41 | X99644 |
| hsORFX-2 | 24 | | mmTIF1a | 42 | S78219 |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are hereby incorporated by reference herein in their entireties.

TABLE 1

NMR Chemical Shift Assignment of the P/CAF Bromodomain

| RES_ID | 715 |
|---|---|
| RES_TYPE | GLY |
| SPIN_SYSTEM_ID | 1 |
| HETEROGENEITY | 100 |
| END_RES_DEF | |
| RES_ID | 716 |
| RES_TYPE | SER |
| SPIN_SYSTEM_ID | 2 |
| HETEROGENEITY | 100 |
| END_RES_DEF | |
| RES_ID | 717 |
| RES_TYPE | HIS |
| SPIN_SYSTEM_ID | 3 |
| HETEROGENEITY | 100 |
| END_RES_DEF | |
| RES_ID | 718 |
| RES_TYPE | MET |
| SPIN_SYSTEM_ID | 4 |
| HETEROGENEITY | 100 |
| END_RES_DEF | |
| RES_ID | 719 |
| RES_TYPE | SER |
| SPIN_SYSTEM_ID | 5 |
| HETEROGENEITY | 100 |
| END_RES_DEF | |
| RES_ID | 720 |

TABLE 1-continued

NMR Chemical Shift Assignment of the P/CAF Bromodomain

| RES_TYPE | LYS |
|---|---|
| SPIN_SYSTEM_ID | 6 |
| HETEROGENEITY | 100 |
| CA | 56.296000 |
| HA | 4.361000 |
| CB | 33.140000 |
| HB1 | 1.882000 |
| HB2 | 1.684000 |
| CG | 25.430000 |
| HG1 | 1.585000 |
| HG2 | 1.433000 |
| CD | 29.834000 |
| HD1 | 1.703000 |
| CE | 41.960000 |
| HE1 | 3.003000 |
| END_RES_DEF | |
| RES_ID | 721 |
| RES_TYPE | GLU |
| SPIN_SYSTEM_ID | 7 |
| HETEROGENEITY | 100 |
| N | 122.990000 |
| HN | 8.317000 |
| CA | 54.620000 |
| HA | 4.540000 |
| CB | 29.830000 |
| HB1 | 2.024000 |
| HB2 | 1.893000 |
| CC | 35.893000 |
| HG1 | 2.271000 |
| END_RES_DEF | |
| RES_ID | 722 |
| RES_TYPE | PRO |
| SPIN_SYSTEM_ID | 8 |
| HETEROGENEITY | 100 |
| CA | 63.430000 |
| HA | 4.393000 |
| CB | 32.030000 |
| HB1 | 2.224000 |
| HB2 | 1.880000 |
| CG | 27.630000 |
| HG1 | 2.028000 |
| CD | 50.760000 |
| HD2 | 3.656000 |
| HD1 | 3.800000 |
| END_RES_DEF | |
| RES_ID | 723 |
| RES_TYPE | ARG |
| SPIN_SYSTEM_ID | 9 |
| HETEROGENEITY | 100 |
| N | 121.192000 |
| HN | 8.416000 |
| CA | 63.430000 |
| HA | 4.331000 |
| CB | 30.930000 |
| HB1 | 1.815000 |
| HB2 | 1.762000 |
| CG | 27.630000 |
| HG1 | 1.681000 |
| CD | 43.603000 |
| HD1 | 3.161000 |
| END_RES_DEF | |
| RES_ID | 724 |
| RES_TYPE | ASP |
| SPIN_SYSTEM_ID | 10 |
| HETEROGENEITY | 100 |
| N | 122.012000 |
| HN | 8.273000 |
| CA | 52.415000 |
| HA | 4.874000 |
| CB | 41.400000 |
| HB1 | 2.754000 |
| HB2 | 2.692000 |
| END_RES_DEF | |
| RES_ID | 725 |
| RES_ | PRO |
| SPIN_SYSTEM_ID | 11 |
| HETEROGENEITY | 100 |
| CA | 65.080000 |

TABLE 1-continued

NMR Chemical Shift Assignment of the P/CAF Bromodomain

| | | |
|---|---|---|
| HA | | 4.329000 |
| CB | | 32.590000 |
| HB1 | | 2.326000 |
| HB2 | | 1.973000 |
| CG | | 27.632000 |
| HG1 | | 2.028000 |
| CD | | 51.310000 |
| HD1 | | 3.866000 |
| END_RES_DEF | | |
| RES_ID | | 726 |
| RES_TYPE | | ASP |
| SPIN_SYSTEM_ID | | 12 |
| HETEROGENEITY | | 100 |
| N | | 119.716000 |
| HN | | 8.397000 |
| CA | | 55.720000 |
| HA | | 4.692000 |
| CB | | 40.550000 |
| HB1 | | 2.792000 |
| HB2 | | 2.730000 |
| END_RES_DEF | | |
| RES_ID | | 727 |
| RES_TYPE | | GLN |
| SPIN_SYSTEM_ID | | 13 |
| HETEROGENEITY | | 100 |
| N | | 121.356000 |
| HN | | 8.196000 |
| CA | | 55.920000 |
| HA | | 4.163000 |
| CB | | 28.730000 |
| HB1 | | 2.148000 |
| CG | | 34.240000 |
| HG1 | | 2.524000 |
| HG2 | | 2.371000 |
| END_RES_DEF | | |
| RES_ID _ | | 728 |
| RES_TYPE | | LEU |
| SPIN_SYSTEM_ID | | 14 |
| HETEROGENEITY | | 100 |
| N | | 121.356000 |
| HN | | 8.210000 |
| CA | | 58.473000 |
| HA | | 4.045000 |
| CB | | 41.400000 |
| HB1 | | 1.847000 |
| HB2 | | 1.555000 |
| CG | | 27.080000 |
| HG | | 1.480000 |
| CD1 | | 25.970000 |
| HD1# | | 0.794000 |
| CD2 | | 23.226000 |
| HD2# | | 0.786000 |
| END_RES_DEF | | |
| RES_ID | | 729 |
| RES_TYPE | | TYR |
| SPIN_SYSTEM_ID | | 15 |
| HETEROGENEITY | | 100 |
| N | | 119.060000 |
| HN | | 8.021000 |
| CA | | 62.320000 |
| HA | | 4.038000 |
| CB | | 38.640000 |
| HB1 | | 3.211000 |
| HB2 | | 3.024000 |
| CD1 | | 134.350000 |
| HD1 | | 7.053000 |
| CE1 | | 119.481000 |
| HE1 | | 6.882000 |
| END_RES_DEF | | |
| RES_ID | | 730 |
| RES_TYPE | | SER |
| SPIN_SYSTEM_ID | | 16 |
| HETEROGENEITY | | 100 |
| N | | 112.173000 |
| HN | | 8.167000 |
| HA | | 3.920000 |
| HB1 | | 3.995000 |
| END_RES_DEF | | |
| RES_ID | | 731 |
| RES_TYPE | | THR |
| SPIN_SYSTEM_ID | | 17 |
| HETEROGENEITY | | 100 |
| N | | 120.372000 |
| HN | | 8.059000 |
| CA | | 66.730000 |
| HA | | 3.924400 |
| CB | | 68.930000 |
| HB | | 4.247000 |
| CG2 | | 21.570000 |
| HG2# | | 1.142000 |
| END_RES_DEF | | |
| RES_ID | | 732 |
| RES_TYPE | | LEU |
| SPIN_SYSTEM_ID | | 18 |
| HETEROGENEITY | | 100 |
| N | | 120.536000 |
| HN | | 8.460000 |
| CA | | 57.920000 |
| HA | | 3.289000 |
| CB | | 39.750000 |
| HB1 | | 1.532000 |
| HB2 | | 0.294000 |
| CG | | 24.880000 |
| HG | | 1.683000 |
| CD1 | | 25.429000 |
| HD1# | | 0.469000 |
| CD2 | | 19.921000 |
| HD2# | | −0.193000 |
| END_RES_DEF | | |
| RES_ID | | 733 |
| RES_TYPE | | LYS |
| SPIN_SYSTEM_ID | | 19 |
| HETEROGENEITY | | 100 |
| N | | 118.568000 |
| HN | | 8.563000 |
| CA | | 60.125000 |
| HA | | 3.679000 |
| CB | | 32.588000 |
| HB1 | | 1.729000 |
| HB2 | | 1.360000 |
| CG | | 24.880000 |
| HG1 | | 1.280000 |
| CD | | 29.835000 |
| HDI | | 1.585000 |
| CE | | 41.960000 |
| HE1 | | 2.918000 |
| END_RES_DEF | | |
| RES_ID | | 734 |
| RES_TYPE | | SER |
| SPIN_SYSTEM_ID | | 20 |
| HETEROGENEITY | | 100 |
| N | | 113.157000 |
| HN | | 7.540000 |
| CA | | 61.227000 |
| HA | | 4.281000 |
| CB | | 63.879000 |
| HB1 | | 4.060000 |
| END_RES_DEF | | |
| RES_ID | | 735 |
| RES_TYPE | | ILE |
| SPIN_ SYSTEM_ID | | 21 |
| HETEROGENEITY | | 100 |
| N | | 120.700000 |
| HN | | 7.951000 |
| CA | | 65.080000 |
| HA | | 3.786000 |
| CB | | 38.095000 |
| HB | | 1.879000 |
| CG1 | | 28.733000 |
| HG11 | | 1.748000 |
| HG12 | | 1.052000 |
| CG2 | | 17.168000 |
| HG2# | | 1.003000 |
| CD1 | | 13.863000 |
| HD1# | | 0.619000 |
| END_RES_DEF | | |

TABLE 1-continued

NMR Chemical Shift Assignment of the P/CAF Bromodomain

| | |
|---|---|
| RES_ID | 736 |
| RES_TYPE | LEU |
| SPIN_SYSTEM_ID | 22 |
| HETEROGENEITY | 100 |
| N | 119.880000 |
| HN | 8.841000 |
| CA | 58.473000 |
| HA | 4.090000 |
| CB | 41.950000 |
| HB1 | 2.090000 |
| HB2 | 1.703000 |
| CG | 27.330000 |
| HG | 1.759000 |
| CD1 | 26.530000 |
| HD1# | 1.061000 |
| CD2 | 23.776000 |
| HD2# | 0.977000 |
| END_RES_DEF | |
| RES_ID | 737 |
| RES_TYPE | GLN |
| SPIN_SYSTEM_ID | 23 |
| HETEROGENEITY | 100 |
| N | 117.256000 |
| HN | 8.505000 |
| CA | 59.020000 |
| HA | 4.032000 |
| CB | 28.182000 |
| HB1 | 2.327000 |
| HB2 | 2.263000 |
| CG | 34.240000 |
| HG1 | 2.536000 |
| HG2 | 2.461000 |
| END_RES_DEF | |
| RES_ID | 738 |
| RESTYPE | GLN |
| SPIN_SYSTEM_ID | 24 |
| HETEROGENEITY | 100 |
| N | 118.896000 |
| HN | 8.033000 |
| CA | 59.574000 |
| HA | 4.196000 |
| CB | 29.835000 |
| HB1 | 2.482000 |
| HB2 | 2.469000 |
| CG | 35.342000 |
| HG1 | 2.840000 |
| HG2 | 2.467000 |
| NE2 | 110.369000 |
| HE21 | 7.022000 |
| HE22 | 6.916000 |
| END_RES_DEF | |
| RES_ID | 739 |
| RES_TYPE | VAL |
| SPIN_SYSTEM_ID | 25 |
| HETEROGENEITY | 100 |
| N | 119.716000 |
| MN | 8.526000 |
| CA | 67.830000 |
| HA | 3.844000 |
| CB | 32.030000 |
| HB | 2.384000 |
| CG1 | 23.330000 |
| HG1# | 1.183000 |
| CG2 | 22.120000 |
| HG2# | 1.033000 |
| END_RES_DEF | |
| RES_ID | 740 |
| RES_TYPE | LYS |
| SPIN_SYSTEM_ID | 26 |
| HETEROGENEITY | 100 |
| N | 114.633000 |
| HN | 8.572000 |
| CA | 59.574000 |
| HA | 3.886000 |
| CB | 32.380000 |
| HB1 | 1.873000 |
| HG1 | 1.022000 |
| HD1 | 1.520000 |
| END_RES_DEF | |
| RES_ID | 741 |
| RES_TYPE | SER |
| SPIN_SYSTEM_ID | 27 |
| HETEROGENEITY | 100 |
| N | 110.369000 |
| HN | 7.557000 |
| CA | 59.024000 |
| HA | 4.448000 |
| CB | 63.980000 |
| HB1 | 4.004000 |
| END_RES_DEF | |
| RES_ID | 742 |
| RES_TYPE | HIS |
| SPIN_SYSTEM_ID | 28 |
| HETEROGENEITY | 100 |
| N | 125.619000 |
| HN | 7.536000 |
| CA | 58.473000 |
| HA | 3.967000 |
| CB | 32.588000 |
| HB1 | 2.990000 |
| HB2 | 2.799000 |
| CD2 | 118.930000 |
| HD2 | 4.978000 |
| CE1 | 138.755000 |
| HE1 | 7.522000 |
| END_RES_DEF | |
| RES_ID | 743 |
| RES_TYPE | GLN |
| SPIN_SYSTEM_ID | 29 |
| HETEROGENEITY | 100 |
| N | 128.571000 |
| HN | 8.543000 |
| CA | 59.125000 |
| HA | 4.209000 |
| CB | 29.834000 |
| HB1 | 2.111000 |
| CG | 33.690000 |
| HG1 | 2.390000 |
| NE2 | 112.173000 |
| HE21 | 7.581000 |
| HE22 | 6.870000 |
| END_RES_DEF | |
| RES_ID | 744 |
| RES_TYPE | SER |
| SPIN_SYSTEM_ID | 30 |
| HETEROGENEITY | 100 |
| N | 119.060000 |
| HN | 11.668000 |
| CA | 60.125000 |
| HA | 4.838000 |
| CB | 63.980000 |
| HB1 | 4.334000 |
| HB2 | 3.926000 |
| END_RES_DEF | |
| RES_ID | 745 |
| RES_TYPE | ALA |
| SPIN_SYSTEM_ID | 31 |
| HETEROGENEITY | 100 |
| N | 117.584000 |
| HN | 7.868000 |
| CA | 53.510000 |
| HA | 4.396000 |
| CB | 20.470000 |
| HB# | 1.688000 |
| END_RES_DEF | |
| RES_ID | 746 |
| RES_TYPE | TRP |
| SPIN_SYSTEM_ID | 32 |
| HETEROGENEITY | 100 |
| N | 116.600000 |
| RN | 7.135000 |
| CA | 60.691000 |
| HA | 4.368000 |
| CB | 27.630000 |
| HB1 | 3.594000 |
| HB2 | 3.351000 |

TABLE 1-continued

NMR Chemical Shift Assignment of the P/CAF Bromodomain

| | |
|---|---|
| CD1 | 128.843000 |
| HD1 | 7.897000 |
| NE1 | 110.861000 |
| HE1 | 10.474000 |
| CE3 | 122.234000 |
| HE3 | 7.336000 |
| CZ2 | 116.177000 |
| HZ2 | 7.382000 |
| CZ3 | 123.336000 |
| HZ3 | 7.197000 |
| CH2 | 126.089000 |
| HH2 | 7.150000 |
| END_RES_DEF | |
| RES_ID | 747 |
| RES_TYPE | PRO |
| SPIN_SYSTEM_ID | 33 |
| HETEROGENEITY | 100 |
| CA | 64.531000 |
| HA | 3.756000 |
| CB | 29.835000 |
| HB1 | 0.487000 |
| HB2 | −0.783000 |
| CG | 26.530000 |
| HG1 | 0.233000 |
| HG2 | −0.931000 |
| CD | 50.212000 |
| HD2 | 1.567000 |
| HD1 | 2.177000 |
| END_RES_DEF | |
| RES_ID | 748 |
| RES_TYPE | PHE |
| SPIN_SYSTEM_ID | 34 |
| HETEROGENEITY | 100 |
| N | 113.321000 |
| HN | 7.585000 |
| CA | 55.719000 |
| HA | 4.930000 |
| CB | 39.202000 |
| HB1 | 3.491000 |
| HB2 | 2.532000 |
| CD1 | 133.248000 |
| HD1 | 7.099000 |
| HE1 | 7.174000 |
| HZ | 7.296000 |
| END_RES_DEF | |
| RES_ID | 749 |
| RES_TYPE | MET |
| SPIN_SYSTEM_ID | 35 |
| HETEROGENEITY | 100 |
| N | 117.748000 |
| HN | 7.115000 |
| CA | 56.820000 |
| HA | 4.286000 |
| CB | 32.590000 |
| HB1 | 2.233000 |
| HB2 | 2.174000 |
| CG | 33.140000 |
| HG1 | 2.851000 |
| CE | 17.168000 |
| HE# | 2.175000 |
| END_RES_DEF | |
| RES_ID | 750 |
| RES_TYPE | GLU |
| SPIN_SYSTEM_ID | 36 |
| HETEROGENEITY | 100 |
| N | 113.813000 |
| HN | 7.709000 |
| CA | 53.516000 |
| HA | 4.849000 |
| CB | 31.487000 |
| HB1 | 2.091000 |
| HB2 | 1.730000 |
| CG | 35.893000 |
| HG1 | 2.164000 |
| END_RES_DEF | |
| RES_ID | 751 |
| RES_TYPE | PRO |
| SPIN_SYSTEM_ID | 37 |
| HETEROGENEITY | 100 |
| CA | 62.879000 |
| HA | 4.242000 |
| CB | 32.040000 |
| HB1 | 2.328000 |
| HB2 | 1.683000 |
| CG | 27.080000 |
| HG1 | 2.126000 |
| HG2 | 1.978000 |
| CD | 50.763000 |
| HD1 | 3.670000 |
| END_RES_DEF | |
| RES_ID | 752 |
| RES_TYPE | VAL |
| SPIN_SYSTEM_ID | 38 |
| HETEROGENEITY | 100 |
| N | 124.450000 |
| HN | 8.124000 |
| CA | 63.430000 |
| HA | 3.553000 |
| CB | 32.580000 |
| HB | 1.145000 |
| CG1 | 21.573000 |
| HG1# | 0.464000 |
| CG2 | 21.573000 |
| HG2# | 0.169000 |
| END_RES_DEF | |
| RES_ID | 753 |
| RES_TYPE | LYS |
| SPIN_SYSTEM_ID | 39 |
| HETEROGENEITY | 100 |
| N | 129.883000 |
| HN | 9.045000 |
| CA | 56.310000 |
| HA | 4.370000 |
| CB | 32.880000 |
| HB1 | 1.873000 |
| HG1 | 1.435000 |
| HD1 | 1.673000 |
| HE1 | 2.985000 |
| END_RES_DEF | |
| RES_ID | 754 |
| RES_TYPE | ARG |
| SPIN_SYSTEM_ID | 40 |
| HETEROGENEITY | 100 |
| N | 120.208000 |
| HN | 8.054000 |
| END_RES_DEF | |
| RES_ID | 755 |
| RES_TYPE | TER |
| SPIN_SYSTEM_ID | 41 |
| HETEROGENEITY | 100 |
| CA | 63.430000 |
| HA | 4.038000 |
| CB | 68.380000 |
| HB | 4.293000 |
| CG2 | 22.670000 |
| HG2# | 1.267000 |
| END_RES_DEF | |
| RES_ID | 756 |
| RES_TYPE | GLU |
| SPIN_SYSTEM_ID | 42 |
| HETEROGENEITY | 100 |
| N | 118.732000 |
| HN | 7.209000 |
| CA | 56.270000 |
| HA | 4.448000 |
| CB | 30.930000 |
| HB1 | 2.174000 |
| HB2 | 2.000000 |
| CG | 36.440000 |
| HG1 | 2.292000 |
| END_RES_DEF | |
| RES_ID | 757 |
| RES_TYPE | ALA |
| SPIN_SYSTEM_ID | 43 |
| HETEROGENEITY | 100 |
| N | 122.504000 |

TABLE 1-continued

NMR Chemical Shift Assignment of the P/CAF Bromodomain

| | |
|---|---|
| HN | 7.379000 |
| CA | 50.220000 |
| HA | 4.937000 |
| CB | 19.370000 |
| HB# | 1.082000 |
| END_RES_DEF | |
| RES_ID | 758 |
| RES_TYPE | PRO |
| SPIN_SYSTEM_ID | 44 |
| HETEROGENEITY | 100 |
| CA | 65.080000 |
| HA | 4.496000 |
| CB | 31.487000 |
| HB1 | 2.374000 |
| HB2 | 2.027000 |
| CG | 27.632000 |
| HG1 | 2.122000 |
| HG2 | 2.038000 |
| CD | 50.212000 |
| HD2 | 3.515000 |
| HD1 | 3.717000 |
| END_RES_DEF | |
| RES_ID | 759 |
| RES_TYPE | GLY |
| SPIN_SYSTEM_ID | 45 |
| HETEROGENEITY | 100 |
| END_RES_DEF | |
| RES_ID | 760 |
| RES_TYPE | TYR |
| SPIN_SYSTEM_ID | 46 |
| HETEROGENEITY | 100 |
| N | 122.504000 |
| HN | 7.945000 |
| CA | 62.328000 |
| HA | 3.536000 |
| CB | 39.750000 |
| HB1 | 2.689000 |
| HB2 | 2.487000 |
| CD1 | 133.799000 |
| HD1 | 5.120000 |
| CE1 | 118.379000 |
| HE1 | 6.070000 |
| END_RES_DEF | |
| RES_ID | 761 |
| RES_TYPE | TYR |
| SPIN_SYSTEM_ID | 47 |
| HETEROGENEITY | 100 |
| N | 113.157000 |
| HN | 8.225000 |
| CA | 60.676000 |
| HA | 4.101000 |
| CB | 37.550000 |
| HB1 | 3.189000 |
| HB2 | 2.801000 |
| CD1 | 134.901000 |
| HD1 | 7.342000 |
| CE1 | 118.930000 |
| HE1 | 6.646000 |
| END_RES_DEF | |
| RES_ID | 762 |
| RES_TYPE | GLU |
| SPIN_SYSTEM_ID | 48 |
| HETEROGENEITY | 100 |
| N | 117.912000 |
| HN | 7.702000 |
| CA | 57.922000 |
| HA | 4.209000 |
| CB | 29.480000 |
| HB1 | 2.086000 |
| CG | 37.545000 |
| HG1 | 2.325000 |
| HG2 | 2.265000 |
| END_RES_DEF | |
| RES_ID | 763 |
| RES_TYPE | VAL |
| SPIN_SYSTEM_ID | 49 |
| HETEROGENEITY | 100 |
| N | 115.453000 |
| HR | 7.135000 |
| CA | 63.430000 |
| HA | 4.077000 |
| CB | 33.690000 |
| HB | 2.015000 |
| CG1 | 21.020000 |
| HG1# | 1.045000 |
| CG2 | 21.574000 |
| HG2# | 0.991000 |
| END_RES_DEF | |
| RES_ID | 764 |
| RES_TYPE | ILE |
| SPIN_SYSTEM_ID | 50 |
| HETEROGENEITY | 100 |
| N | 122.832000 |
| HN | 7.947000 |
| CA | 57.920000 |
| HA | 3.916000 |
| CB | 34.240000 |
| HB | 1.205000 |
| CG1 | 24.878000 |
| HG11 | 0.798000 |
| HG12 | 0.216000 |
| CG2 | 16.617000 |
| HG2# | 0.380000 |
| CD1 | 9.457000 |
| HD1# | 0.537000 |
| END_RES_DEF | |
| RES_ID | 765 |
| RES_TYPE | ARG |
| SPIN_SYSTEM_ID | 51 |
| HETEROGENEITY | 100 |
| N | 125.291000 |
| HN | 7.749000 |
| CA | 57.371000 |
| HA | 3.875000 |
| CB | 30.936000 |
| HB1 | 1.388000 |
| HB2 | 1.211000 |
| CG | 27.080000 |
| HG1 | 1.319000 |
| HG2 | 1.173000 |
| CD | 43.052000 |
| HD1 | 2.971000 |
| END_RES_DEF | |
| RES_ID | 766 |
| RES_TYPE | SER |
| SPIN_SYSTEM_ID | 52 |
| HETEROGENEITY | 100 |
| N | 116.600000 |
| HN | 8.387000 |
| CA | 54.618000 |
| HA | 4.984000 |
| CB | 38.640000 |
| HB1 | 3.034000 |
| HB2 | 2.907000 |
| END_RES_DEF | |
| RES_ID | 767 |
| RES_TYPE | PRO |
| SPIN_SYSTEM_ID | 53 |
| HETEROGENEITY | 100 |
| CA | 63.429000 |
| HA | 4.083000 |
| CB | 32.588000 |
| HB1 | 2.209000 |
| CG | 28.180000 |
| HG1 | 2.177000 |
| HG2 | 1.883000 |
| CD | 50.763000 |
| HD2 | 3.390000 |
| HD2 | 3.623000 |
| END_RES_DEF | |
| RES_ID | 768 |
| RES_TYPE | MET |
| SPIN_SYSTEM_ID | 54 |
| HETEROGENEITY | 100 |
| N | 119.060000 |
| HN | 8.430000 |

TABLE 1-continued

NMR Chemical Shift Assignment of the P/CAF Bromodomain

| | |
|---|---|
| CA | 54.067000 |
| HA | 4.935000 |
| CB | 31.487000 |
| HB1 | 1.989000 |
| HB2 | 1.353000 |
| CG | 30.930000 |
| HG1 | 2.690000 |
| CE | 14.414000 |
| HE# | 1.929000 |
| END_RES_DEF | |
| RES_ID | 769 |
| RES_TYPE | ASP |
| SPIN_SYSTEM_ID | 55 |
| HETEROGENEITY | 100 |
| N | 119.060000 |
| HN | 7.365000 |
| CA | 53.516000 |
| HA | 4.745000 |
| CB | 44.154000 |
| HB1 | 2.371000 |
| END_RES_DEF | |
| RES_ID | 770 |
| RES_TYPE | LEU |
| SPIN_SYSTEM_ID | 56 |
| HETEROGENEITY | 100 |
| N | 116.272000 |
| HN | 9.055000 |
| CA | 57.922000 |
| HA | 4.036000 |
| CB | 41.400000 |
| HB1 | 2.095000 |
| HB2 | 1.395000 |
| CG | 27.080000 |
| HG | 1.713000 |
| CD1 | 27.080000 |
| HD1# | 0.940000 |
| CD2 | 22.675000 |
| HD2# | 0.626000 |
| END_RES_DEF | |
| RES_ID | 771 |
| RES_TYPE | LYS |
| SPIN_SYSTEM_ID | 57 |
| HETEROGENEITY | 100 |
| N | 126.079000 |
| HN | 8.738000 |
| CA | 60.676000 |
| HA | 4.198000 |
| CB | 32.037000 |
| HB1 | 2.330000 |
| HB2 | 2.224000 |
| CG | 25.280000 |
| HG1 | 1.483000 |
| HG2 | 1.403000 |
| CD | 30.385000 |
| HD1 | 1.793000 |
| HD2 | 1.696000 |
| CE | 41.950000 |
| HE1 | 2.965000 |
| END_RES_DEF | |
| RES_ID | 772 |
| RES_TYPE | THR |
| SPIN_SYSTEM_ID | 58 |
| HETEROGENEITY | 100 |
| N | 122.176000 |
| HN | 9.445000 |
| CA | 67.040000 |
| HA | 3.845000 |
| CB | 67.835000 |
| HB | 4.090000 |
| CG2 | 22.124000 |
| HG2# | 1.058000 |
| END_RES_DEF | |
| RES_ID | 773 |
| RES_TYPE | MET |
| SPIN_SYSTEM_ID | 59 |
| HETEROGENEITY | 100 |
| N | 117.912000 |
| HN | 7.862000 |
| CA | 60.676000 |
| HA | 4.319000 |
| CB | 33.342000 |
| HB1 | 2.093000 |
| HB2 | 1.915000 |
| CG | 33.139000 |
| HG1 | 2.621000 |
| HG2 | 2.496000 |
| CE | 16.620000 |
| HE# | 1.241000 |
| END_RES_DEF | |
| RES_ID | 774 |
| RES_TYPE | SER |
| SPIN_SYSTEM_ID | 60 |
| HETEROGENEITY | 100 |
| N | 116.108000 |
| HN | 7.958000 |
| CA | 62.879000 |
| HA | 4.200000 |
| CB | 62.879000 |
| HB1 | 4.368000 |
| HB2 | 4.040000 |
| END_RES_DEF | |
| RES_ID | 775 |
| RES_TYPE | GLU |
| SPIN_SYSTEM_ID | 61 |
| HETEROGENEITY | 100 |
| N | 124.471000 |
| HN | 8.150000 |
| CA | 59.570000 |
| HA | 4.045000 |
| CB | 29.280000 |
| HB1 | 2.246000 |
| HB2 | 2.063000 |
| CG | 36.443000 |
| HG1 | 2.345000 |
| HG2 | 2.176000 |
| END_RES_DEF | |
| RES_ID | 776 |
| RES_TYPE | ARG |
| SPIN_SYSTEM_ID | 62 |
| HETEROGENEITY | 100 |
| N | 120.372000 |
| HN | 8.391000 |
| CA | 60.676000 |
| HA | 3.869000 |
| CB | 30.385000 |
| HB1 | 2.047000 |
| HB2 | 1.076000 |
| CG | 29.284000 |
| HG1 | 1.722000 |
| HG2 | 0.877000 |
| CD | 44.154000 |
| HD1 | 2.578000 |
| HD2 | 2.051000 |
| END_RES_DEF | |
| RES_ID | 777 |
| RES_TYPE | LEU |
| SPIN_SYSTEM_ID | 63 |
| HETEROGENEITY | 100 |
| N | 120.208000 |
| HN | 8.856000 |
| CA | 58.470000 |
| HA | 4.691000 |
| CB | 42.621000 |
| HB1 | 2.295000 |
| HB2 | 1.925000 |
| CG | 27.080000 |
| HG | 1.832000 |
| CD1 | 25.429000 |
| HD1# | 1.067000 |
| CD2 | 27.081000 |
| HD2# | 0.871000 |
| END_RES_DEF | |
| RES_ID | 778 |
| RES_TYPE | LYS |
| SPIN_SYSTEM_ID | 64 |
| HETEROGENEITY | 100 |

TABLE 1-continued

NMR Chemical Shift Assignment of the P/CAF Bromodomain

| | | |
|---|---|---|
| N | | 120.372000 |
| HN | | 7.958000 |
| CA | | 59.574000 |
| HA | | 4.333000 |
| CB | | 32.588000 |
| HB1 | | 2.055000 |
| CG | | 24.878000 |
| HG1 | | 1.596000 |
| CD | | 29.835000 |
| HD1 | | 1.804000 |
| CE | | 41.951000 |
| HE1 | | 2.990000 |
| END_RES_DEF | | |
| RES_ID | | 779 |
| RES_TYPE | | ASN |
| SPIN_SYSTEM_ID | | 65 |
| HETEROGENEITY | | 100 |
| N | | 116.108000 |
| HN | | 7.947000 |
| CA | | 53.510000 |
| HA | | 4.771000 |
| CB | | 38.095000 |
| HB1 | | 3.019000 |
| HB2 | | 2.773000 |
| HD2 | | 112.665000 |
| HD21 | | 7.598000 |
| HD22 | | 6.969000 |
| END_RES_DEF | | |
| RES_ID | | 780 |
| RES_TYPE | | ARG |
| SPIN_SYSTEM_ID | | 66 |
| HETEROGENEITY | | 100 |
| N | | 114.141000 |
| HN | | 8.158000 |
| CA | | 56.821000 |
| HA | | 4.405000 |
| CB | | 25.429000 |
| HB1 | | 2.097000 |
| HB2 | | 2.022000 |
| CG | | 27.632000 |
| HG1 | | 1.539000 |
| HG2 | | 1.534000 |
| CD | | 43.050000 |
| HD1 | | 3.060000 |
| HD2 | | 3.024000 |
| END_RES_DEF | | |
| RES_ID | | 781 |
| RES_TYPE | | TYR |
| SPIN_SYSTEM_ID | | 67 |
| HETEROGENEITY | | 100 |
| N | | 116.764000 |
| HN | | 8.222000 |
| CA | | 60.125000 |
| HA | | 4.064000 |
| CB | | 40.850000 |
| HB1 | | 2.948000 |
| HB2 | | 2.055000 |
| CD1 | | 134.350000 |
| HD1 | | 6.285000 |
| CE1 | | 118.930000 |
| HE1 | | 6.709000 |
| END_RES_DEF | | |
| RES_ID | | 782 |
| RES_TYPE | | TYR |
| SPIN_SYSTEM_ID | | 68 |
| HETEROGENEITY | | 100 |
| N | | 114.633000 |
| HN | | 8.014000 |
| CA | | 57.920000 |
| HA | | 4.528000 |
| CB | | 36.443000 |
| HB1 | | 3.062000 |
| HB2 | | 2.907000 |
| CD1 | | 133.248000 |
| HD1 | | 7.175000 |
| CE1 | | 120.582000 |
| HE1 | | 7.286000 |
| END_RES_DEF | | |
| RES_ID | | 783 |
| RES_TYPE | | VAL |
| SPIN_SYSTEM_ID | | 69 |
| HETEROGENEITY | | 100 |
| N | | 115.780000 |
| HN | | 7.698000 |
| CA | | 62.330000 |
| HA | | 4.083000 |
| CB | | 31.500000 |
| HB | | 2.321000 |
| CG1 | | 21.570000 |
| HG1# | | 0.944000 |
| CG2 | | 18.820000 |
| HG2# | | 0.823000 |
| END_RES_DEF | | |
| RES_ID | | 784 |
| RES_TYPE | | SER |
| SPIN_SYSTEM_ID | | 70 |
| HETEROGENEITY | | 100 |
| N | | 111.353000 |
| HN | | 7.415000 |
| CA | | 55.719000 |
| HA | | 4.741000 |
| CB | | 66.183000 |
| HB1 | | 4.200000 |
| HB2 | | 3.750000 |
| END_RES_DEF | | |
| RES_ID | | 785 |
| RES_TYPE | | LYS |
| SPIN_SYSTEM_ID | | 71 |
| HETEROGENEITY | | 100 |
| CA | | 59.030000 |
| HA | | 4.021000 |
| CB | | 31.590000 |
| END_RES_DEF | | |
| RES_ID | | 786 |
| RES_TYPE | | LYS |
| SPIN_SYSTEM_ID | | 72 |
| HETEROGENEITY | | 100 |
| N | | 120.208000 |
| HN | | 8.244000 |
| CA | | 59.720000 |
| HA | | 4.062000 |
| CB | | 30.385000 |
| HB1 | | 1.779000 |
| CG | | 24.530000 |
| CD | | 28.182000 |
| HD1 | | 1.680000 |
| CE | | 41.670000 |
| HE1 | | 3.137000 |
| HE2 | | 3.045000 |
| END_RES_DEF | | |
| RES_ID | | 787 |
| RES_TYPE | | LEU |
| SPIN_SYSTEM_ID | | 73 |
| HETEROGENEITY | | 100 |
| N | | 118.732000 |
| HN | | 7.422000 |
| CA | | 57.922000 |
| HA | | 4.213000 |
| CB | | 43.603000 |
| HB1 | | 1.996000 |
| HB2 | | 1.891000 |
| CG | | 27.632000 |
| HG | | 1.794000 |
| CD1 | | 25.979000 |
| HD1# | | 0.924000 |
| CD2 | | 23.776000 |
| HD2# | | 0.895000 |
| END_RES_DEF | | |
| RES_ID | | 788 |
| RES_TYPE | | PHE |
| SPIN_SYSTEM_ID | | 74 |
| HETEROGENEITY | | 100 |
| N | | 118.732000 |
| HN | | 6.928000 |
| CA | | 60.676000 |
| HA | | 3.763000 |

TABLE 1-continued

NMR Chemical Shift Assignment of the P/CAF Bromodomain

| | |
|---|---|
| CB | 39.750000 |
| HB1 | 2.945000 |
| HB2 | 2.381000 |
| CD1 | 133.799000 |
| HD1 | 6.400000 |
| CE1 | 131.596000 |
| HE1 | 6.938000 |
| END_RES_DEF | |
| RES_ID | 789 |
| RES_TYPE | MET |
| SPIN_SYSTEM_ID | 75 |
| HETEROGENEITY | 100 |
| N | 116.272000 |
| HN | 8.489000 |
| CA | 59.020000 |
| HA | 3.911000 |
| CB | 32.590000 |
| HB1 | 2.318000 |
| HB2 | 2.208000 |
| CG | 33.140000 |
| HG1 | 2.942000 |
| HG2 | 2.611000 |
| CE | 17.168000 |
| HE# | 2.027000 |
| END_RES_DEF | |
| RES_ID | 790 |
| RES_TYPE | ALA |
| SPIN_SYSTEM_ID | 76 |
| HETEROGENEITY | 100 |
| N | 119.716000 |
| HN | 8.000000 |
| CA | 55.170000 |
| HA | 4.084000 |
| CB | 18.270000 |
| HB# | 1.485000 |
| END_RES_DEF | |
| RES_ID | 791 |
| RES_TYPE | ASP |
| SPIN_SYSTEM_ID | 77 |
| HETEROGENEITY | 100 |
| N | 119.716000 |
| HN | 7.376000 |
| CA | 57.371000 |
| HA | 4.371000 |
| CB | 38.646000 |
| HB1 | 2.730000 |
| END_RES_DEF | |
| RES_ID | 792 |
| RES_TYPE | LEU |
| SPIN_SYSTEM_ID | 78 |
| HETEROGENEITY | 100 |
| N | 119.550000 |
| HN | 7.363000 |
| CA | 57.922000 |
| HA | 3.398000 |
| CB | 40.299000 |
| HB1 | 0.757000 |
| HB2 | 0.442000 |
| CG | 27.632000 |
| HG | 0.707000 |
| CD1 | 24.327000 |
| HD1# | 0.184000 |
| CD2 | 25.979000 |
| HD2# | 0.061000 |
| END_RES_DEF | |
| RES_ID | 793 |
| RES_TYPE | GLN |
| SPIN_SYSTEM_ID | 79 |
| HETEROGENEITY | 100 |
| N | 114.141000 |
| HN | 8.069000 |
| CA | 59.024000 |
| HA | 3.804000 |
| CB | 28.733000 |
| HB1 | 2.157000 |
| HB2 | 2.097000 |
| CG | 35.342000 |
| HG1 | 2.460000 |
| NE2 | 111.353000 |
| HE21 | 7.319000 |
| HE22 | 7.222000 |
| END_RES_DEF | |
| RES_ID | 794 |
| RES_TYPE | ARG |
| SPIN_SYSTEM_ID | 80 |
| HETEROGENEITY | 100 |
| N | 118.568000 |
| HN | 7.382000 |
| CA | 58.473000 |
| HA | 4.078000 |
| CB | 29.835000 |
| HB1 | 1.973000 |
| HB2 | 1.886000 |
| CG | 27.080000 |
| HG1 | 1.742000 |
| CD | 43.603000 |
| HD1 | 3.390000 |
| HD2 | 3.325000 |
| END_RES_DEF | |
| RES_ID | 795 |
| RES_TYPE | VAL |
| SPIN_SYSTEM_ID | 81 |
| HETEROGENEITY | 100 |
| N | 117.912000 |
| HN | 7.013000 |
| CA | 66.730000 |
| HA | 3.0.9000 |
| CB | 30.930000 |
| HB | 1.435000 |
| CG1 | 22.124000 |
| HG1# | 0.479000 |
| CG2 | 21.573000 |
| HG1# | 0.142000 |
| END_RES_DEF | |
| RES_ID | 796 |
| RES_TYPE | PHE |
| SPIN_SYSTEM_ID | 82 |
| HETEROGENEITY | 100 |
| N | 116.928000 |
| HN | 6.357000 |
| CA | 58.470000 |
| HA | 4.161000 |
| CB | 38.096000 |
| HB1 | 3.090000 |
| HB2 | 2.944000 |
| CD1 | 132.147000 |
| HD1 | 6.641000 |
| CE1 | 131.596000 |
| HE1 | 6.456000 |
| CZ | 129.393000 |
| HZ | 6.406000 |
| END_RES_DEF | |
| RES_ID | 797 |
| RES_TYPE | THR |
| SPIN_SYSTEM_ID | 83 |
| HETEROGENEITY | 100 |
| N | 115.289000 |
| HN | 9.047000 |
| CA | 66.734000 |
| HA | 3.838000 |
| CB | 68.380000 |
| HB | 4.210000 |
| CG2 | 22.120000 |
| HG2# | 1.296000 |
| END_RES_DEF | |
| RES_ID | 798 |
| RES_TYPE | ASN |
| SPIN_SYSTEM_ID | 84 |
| HETEROGENEITY | 100 |
| N | 120.700000 |
| HN | 8.846000 |
| CA | 55.170000 |
| HA | 4.315000 |
| CB | 38.090000 |
| HB1 | 2.985000 |
| HB2 | 2.661000 |

TABLE 1-continued

NMR Chemical Shift Assignment of the P/CAF Bromodomain

| | |
|---|---|
| END_RES_DEF | |
| RES_ID | 799 |
| RES_TYPE | CYS |
| SPIN_SYSTEM_ID | 85 |
| HETEROGENEITY | 100 |
| N | 116.928000 |
| HN | 6.893000 |
| CA | 62.157000 |
| HA | 4.405000 |
| CB | 26.530000 |
| HB1 | 3.304000 |
| HB2 | 3.032000 |
| END_RES_DEF | |
| RES_ID | 800 |
| RES_TYPE | LYS |
| SPIN_SYSTEM_ID | 86 |
| HETEROGENEITY | 100 |
| N | 116.764000 |
| HN | 7.799000 |
| CA | 58.473000 |
| HA | 4.204000 |
| CB | 32.588000 |
| HB1 | 1.743000 |
| CG | 25.429000 |
| HG1 | 1.313000 |
| HG2 | 0.138000 |
| CD | 29.835000 |
| HD1 | 1.291000 |
| CE | 41.400000 |
| HE1 | 2.486000 |
| HE2 | 2.421000 |
| END_RES_DEF | |
| RES_ID | 801 |
| RES_TYPE | GLU |
| SPIN_SYSTEM_ID | 87 |
| HETEROGENEITY | 100 |
| N | 117.912000 |
| HN | 7.945000 |
| CA | 57.992000 |
| HA | 4.250000 |
| CB | 30.385000 |
| HB1 | 2.172000 |
| HB2 | 2.003000 |
| CG | 36.994000 |
| HG1 | 2.407000 |
| HG2 | 2.203000 |
| END_RES_DEF | |
| RES_ID | 802 |
| RES_TYPE | TYR |
| SPIN_SYSTEM_ID | 88 |
| HETEROGENEITY | 100 |
| N | 116.600000 |
| HN | 7.744000 |
| CA | 60.676000 |
| HA | 4.369000 |
| CB | 41.400000 |
| HB1 | 2.929000 |
| CD1 | 134.901000 |
| HD1 | 6.989000 |
| CE1 | 119.481000 |
| HE1 | 6.823000 |
| END_RES_DEF | |
| RES_ID | 803 |
| RES_TYPE | ASN |
| SPIN_SYSTEM_ID | 89 |
| HETEROGENEITY | 100 |
| N | 115.944000 |
| HN | 8.241000 |
| CA | 51.864000 |
| HA | 5.024000 |
| CB | 40.849000 |
| HB1 | 3.069000 |
| HB2 | 2.907000 |
| ND2 | 118.732000 |
| HD21 | 8.316000 |
| HD22 | 7.809000 |
| END_RES_DEF | |
| RES_ID | 804 |
| RES_TYPE | ALA |
| SPIN_SYSTEM_ID | 90 |
| HETEROGENEITY | 100 |
| END_RES_DEF | |
| RES_ID | 805 |
| RES_TYPE | PRO |
| SPIN_SYSTEM_ID | 91 |
| HETEROGENEITY | 100 |
| CA | 63.980000 |
| HA | 2.422000 |
| HB1 | 1.949000 |
| HG1 | 1.648000 |
| HG2 | 1.558000 |
| CD | 50.762000 |
| HD2 | 3.601000 |
| HD1 | 3.706000 |
| END_RES_DEF | |
| RES_ID | 806 |
| RES_TYPE | GLU |
| SPIN_SYSTEM_ID | 92 |
| HETEROGENEITY | 100 |
| N | 112.993000 |
| HN | 8.246000 |
| CA | 56.820000 |
| HA | 4.185000 |
| CB | 28.733000 |
| HB1 | 2.095000 |
| HB2 | 1.973000 |
| CG | 36.270000 |
| HG1 | 2.200000 |
| END_RES_DEF | |
| RES_ID | 807 |
| RES_TYPE | SER |
| SPIN_SYSTEM_ID | 93 |
| HETEROGENEITY | 100 |
| N | 115.780000 |
| HN | 8.112000 |
| CA | 58.473000 |
| HA | 4.406000 |
| CB | 66.183000 |
| HB1 | 4.393000 |
| HB2 | 4.157000 |
| END_RES_DEF | |
| RES_ID | 808 |
| RES_TYPE | GLU |
| SPIN_SYSTEM_ID | 94 |
| HETEROGENEITY | 100 |
| N | 123.488000 |
| HN | 9.061000 |
| CA | 59.574000 |
| HA | 4.232000 |
| CB | 29.835000 |
| HB1 | 2.169000 |
| CG | 36.443000 |
| HG1 | 2.528000 |
| END_RES_DEF | |
| RES_ID | 809 |
| RES_TYPE | TYR |
| SPIN_SYSTEM_ID | 95 |
| HETEROGENEITY | 100 |
| N | 116.436000 |
| HN | 8.072000 |
| CA | 60.120000 |
| HA | 3.834000 |
| CB | 37.550000 |
| HB1 | 3.018000 |
| HB2 | 2.738000 |
| CD1 | 132.698000 |
| HD1 | 6.891000 |
| CE1 | 120.032000 |
| HE1 | 7.011000 |
| END_RES_DEF | |
| RES_ID | 810 |
| RES_TYPE | TYR |
| SPIN_SYSTEM_ID | 96 |
| HETEROGENEITY | 100 |
| N | 119.880000 |
| HN | 7.356000 |

TABLE 1-continued

NMR Chemical Shift Assignment of the P/CAF Bromodomain

| | |
|---|---|
| CA | 61.777000 |
| HA | 3.819000 |
| CB | 40.300000 |
| HB1 | 3.390000 |
| HB2 | 2.500000 |
| CD1 | 136.553000 |
| HD1 | 7.094000 |
| CE1 | 119.481000 |
| HE1 | 7.000000 |
| END_RES_DEF | |
| RES_ID | 811 |
| RES_TYPE | LYS |
| SPIN_SYSTEM_ID | 97 |
| HETEROGENEITY | 100 |
| N | 118.076000 |
| HN | 8.072000 |
| CA | 60.676000 |
| HA | 4.204000 |
| CB | 32.588000 |
| HB1 | 2.091000 |
| CG | 25.979000 |
| HG1 | 1.819000 |
| HG2 | 1.582000 |
| CD | 29.834000 |
| HD1 | 1.813000 |
| CE | 41.963000 |
| HE1 | 2.962000 |
| END_RES_DEF | |
| RES_ID | 812 |
| RES_TYPE | CYS |
| SPIN_SYSTEM_ID | 98 |
| HETEROGENEITY | 100 |
| N | 116.764000 |
| HN | 8.520000 |
| CA | 65.087000 |
| HA | 4.202000 |
| CB | 27.080000 |
| HB1 | 3.396000 |
| HB2 | 3.056000 |
| END_RES_DEF | |
| RES_ID | 813 |
| RES_TYPE | ALA |
| SPIN_SYSTEM_ID | 99 |
| HETEROGENEITY | 100 |
| N | 120.700000 |
| HN | 8.315000 |
| CA | 55.563000 |
| HA | 3.834000 |
| CB | 18.270000 |
| HB# | 1.597000 |
| END_RES_DEF | |
| RES_ID | 814 |
| RES_TYPE | ASN |
| SPIN_SYSTEM_ID | 100 |
| HETEROGENEITY | 100 |
| N | 115.453000 |
| HN | 8.068000 |
| CA | 56.270000 |
| HA | 4.329000 |
| CB | 38.646000 |
| HB1 | 2.877000 |
| HB2 | 2.834000 |
| END_RES_DEF | |
| RES_ID | 815 |
| RES_TYPE | ILE |
| SPIN_SYSTEM_ID | 101 |
| HETEROGENEITY | 100 |
| N | 119.880000 |
| HN | 7.912000 |
| CA | 65.080000 |
| HA | 3.646000 |
| CB | 39.197000 |
| HB | 1.924000 |
| CG1 | 29.284000 |
| HG11 | 1.882000 |
| HG12 | 1.201000 |
| CG2 | 17.718000 |
| HG2# | 1.017000 |
| CD1 | 13.863000 |
| HD1# | 0.940000 |
| END_RES_DEF | |
| RES_ID | 816 |
| RES_TYPE | LEU |
| SPIN_SYSTEM_ID | 102 |
| HETEROGENEITY | 100 |
| N | 122.504000 |
| HN | 8.556000 |
| CA | 56.820000 |
| HA | 3.670000 |
| CB | 41.951000 |
| HB1 | 1.405000 |
| HB2 | 1.199000 |
| CG | 26.530000 |
| HG | 1.580000 |
| CD1 | 24.327000 |
| HD1# | 0.701000 |
| CD2 | 25.429000 |
| HD2# | 0.696000 |
| END_RES_DEF | |
| RES_ID | 817 |
| RES_TYPE | GLU |
| SPIN_SYSTEM_ID | 103 |
| HETEROGENEITY | 100 |
| N | 120.700000 |
| HN | 8.073000 |
| CA | 60.125000 |
| HA | 3.185000 |
| CB | 29.835000 |
| HB1 | 1.720000 |
| HB2 | 1.310000 |
| CG | 37.545000 |
| HG1 | 2.001000 |
| HG2 | 1.922000 |
| END_RES_DEF | |
| RES_ID | 818 |
| RES_TYPE | LYS |
| SPIN_SYSTEM_ID | 104 |
| HETEROGENEITY | 100 |
| N | 117.584000 |
| HN | 7.145000 |
| CA | 59.688000 |
| HA | 4.075000 |
| CB | 32.588000 |
| HB1 | 1.929000 |
| CG | 25.644000 |
| HG1 | 1.492000 |
| CD | 29.284000 |
| HD1 | 1.681000 |
| CE | 41.963000 |
| HE1 | 2.964000 |
| END_RES_DEF | |
| RES_ID | 819 |
| RES_TYPE | PHE |
| SPIN_SYSTEM_ID | 105 |
| HETEROGENEITY | 100 |
| N | 121.028000 |
| HN | 7.869000 |
| CA | 61.230000 |
| HA | 4.328000 |
| CB | 39.200000 |
| HB1 | 3.133000 |
| HB2 | 3.047000 |
| CD1 | 113.800000 |
| HD1 | 7.180000 |
| END_RES_DEF | |
| RES_ID | 820 |
| RES_TYPE | PHE |
| SPIN_SYSTEM_ID | 106 |
| HETEROGENEITY | 100 |
| N | 120.700000 |
| HN | 9.126000 |
| CA | 60.691000 |
| HA | 3.961000 |
| CB | 38.640000 |
| HB1 | 3.289000 |
| HB2 | 3.067000 |

TABLE 1-continued

NMR Chemical Shift Assignment of the P/CAF Bromodomain

| | |
|---|---|
| CD1 | 133.248000 |
| HD1 | 6.904000 |
| CE1 | 132.698000 |
| HE1 | 7.011000 |
| END_RES_DEF | |
| RES_ID | 821 |
| RES_TYPE | PHE |
| SPIN_SYSTEM_ID | 107 |
| HETEROGENEITY | 100 |
| N | 118.076000 |
| HN | 8.359000 |
| CA | 61.770000 |
| HA | 3.840000 |
| CB | 38.090000 |
| HB1 | 3.064000 |
| CD1 | 133.248000 |
| HD1 | 7.175000 |
| CE1 | 132.698000 |
| HE1 | 7.294000 |
| CZ | 131.596000 |
| HZ | 7.430000 |
| END_RES_DEF | |
| RES_ID | 822 |
| RES_TYPE | SER |
| SPIN_SYSTEM_ID | 108 |
| HETEROGENEITY | 100 |
| N | 114.961000 |
| HN | 7.906000 |
| CA | 61.773000 |
| HA | 4.200000 |
| CB | 62.879000 |
| HB1 | 4.007000 |
| END_RES_DEF | |
| RES_ID | 823 |
| RES_TYPE | LYS |
| SPIN_SYSTEM_ID | 109 |
| HETEROGENEITY | 100 |
| N | 120.864000 |
| HN | 7.938000 |
| CA | 56.820000 |
| HA | 4.008000 |
| CB | 31.487000 |
| HB1 | 1.730000 |
| HB2 | 1.567000 |
| CG | 23.226000 |
| HG1 | 0.833000 |
| CD | 27.080000 |
| HD1 | 1.403000 |
| CE | 42.501000 |
| HE1 | 2.569000 |
| HE2 | 2.422000 |
| END_RES_DEF | |
| RES_ID | 824 |
| RES_TYPE | ILE |
| SPIN_SYSTEM_ID | 110 |
| HETEROGENEITY | 100 |
| N | 116.928000 |
| HN | 8.101000 |
| CA | 64.530000 |
| HA | 3.818000 |
| CB | 36.990000 |
| HB | 1.746000 |
| CG1 | 26.530000 |
| HG11 | 1.140000 |
| HG12 | 1.073000 |
| CG2 | 18.820000 |
| HG2# | 0.654000 |
| CD1 | 13.312000 |
| HD1# | 0.541000 |
| END_RES_DEF | |
| RES_ID | 825 |
| RES_TYPE | LYS |
| SPIN_SYSTEM_ID | 111 |
| HETEROGENEITY | 100 |
| N | 122.176000 |
| HN | 7.546000 |
| CA | 59.024000 |
| HA | 4.043000 |
| CB | 32.360000 |
| HB1 | 1.879000 |
| HB2 | 1.757000 |
| CG | 24.878000 |
| HG1 | 1.390000 |
| HG2 | 1.302000 |
| CD | 29.284000 |
| HD1 | 1.633000 |
| CE | 41.400000 |
| HE1 | 2.913000 |
| END_RES_DEF | |
| RES_ID | 826 |
| RES_TYPE | GLU |
| SPIN_SYSTEM_ID | 112 |
| HETEROGENEITY | 100 |
| N | 121.192000 |
| HN | 8.063000 |
| CA | 59.024000 |
| HA | 3.995000 |
| CB | 29.834000 |
| HB1 | 2.058000 |
| CG | 36.050000 |
| HG1 | 2.342000 |
| HG2 | 2.205000 |
| END_RES_DEF | |
| RES_ID | 827 |
| RES_TYPE | ALA |
| SPIN_SYSTEM_ID | 113 |
| HETEROGENEITY | 100 |
| N | 117.748000 |
| HN | 7.620000 |
| CA | 52.410000 |
| HA | 4.291000 |
| CB | 19.920000 |
| HB# | 1.358000 |
| END_RES_DEF | |
| RES_ID | 828 |
| RES_TYPE | GLY |
| SPIN_SYSTEM_ID | 114 |
| HETEROGENEITY | 100 |
| N | 126.767000 |
| HN | 7.744000 |
| CA | 45.902000 |
| HA1 | 4.019000 |
| HA2 | 3.935000 |
| END_RES_DEF | |
| RES_ID | 829 |
| RES_TYPE | LEU |
| SPIN_SYSTEM_ID | 115 |
| HETEROGENEITY | 100 |
| N | 117.912000 |
| HN | 7.742000 |
| CA | 55.719000 |
| HA | 4.215000 |
| CB | 43.052000 |
| HB1 | 1.562000 |
| CG | 27.632000 |
| HG | 1.536000 |
| CD1 | 23.776000 |
| HD1# | 0.711000 |
| END_RES_DEF | |
| RES_ID | 830 |
| RES_TYPE | ILE |
| SPIN_SYSTEM_ID | 116 |
| HETEROGENEITY | 100 |
| N | 115.453000 |
| HN | 7.458000 |
| CA | 60.676000 |
| HA | 4.232000 |
| CB | 39.748000 |
| HB | 1.810000 |
| CG1 | 27.080000 |
| HG11 | 1.314000 |
| HG12 | 0.918000 |
| CG2 | 17.718000 |
| HG2# | 0.815000 |
| CD1 | 13.312000 |
| HD1# | 0.794000 |

TABLE 1-continued

NMR Chemical Shift Assignment of the P/CAF Bromodomain

| | |
|---|---|
| END_RES_DEF | |
| RES_ID | 831 |
| RES_TYPE | ASP |
| SPIN_SYSTEM_ID | 117 |
| HETEROGENEITY | 100 |
| N | 123.488000 |
| HN | 8.270000 |
| CA | 54.620000 |
| HA | 4.571000 |
| CB | 41.400000 |
| HB1 | 2.693000 |
| HB2 | 2.540000 |

TABLE 1-continued

NMR Chemical Shift Assignment of the P/CAF Bromodomain

| | |
|---|---|
| END_RES_DEF | |
| RES_ID | 832 |
| RES_TYPE | LYS |
| SPIN_SYSTEM_ID | 118 |
| HETEROGENEITY | 100 |
| N | 125.450000 |
| HN | 7.774000 |
| CA | 57.720000 |
| HA | 4.082000 |
| CB | 33.410000 |
| END_RES_DEF | |

TABLE 2

Unambigous NOE-derived Inter-proton Distance Restraints

```
ASSI (  2141)
    ( ( segid *BrD * and resid 89 and name HN   ) )
    (  segid *BrD * and resid 96 and name HD % )
       4.200  4.200   1.300 peak    2141 weight   0.11000E+01 volume   0.36756E+02 ppm1    8.857 ppm2   7.704
ASSI (13261)
    ( ( segid *BrD * and resid 89 and name HD22) )
    (  segid *BrD * and resid 95 and name HE % )
       3.900  3.800   1.400 peak   13261 weight   0.11000E+01 volume   0.50220E+02 ppm1    8.416 ppm2   7.624
ASSI (13271)
    ( ( segid *BrD * and resid 89 and name HN21) )
    (  segid *BrD * and resid 95 and name HE % )
       4.000  4.000   1.500 peak   13271 weight   0.11000E+01 volume   0.43992E+02 ppm1    8.924 ppm2   7.624
ASSI (  6521)
    ( ( segid *BrD * and resid 46 and name HN   ) )
    (  segid *BrD * and resid 47 and name HD % )
       3.500  3.100   2.000 peak    8521 weight   0.11000E+01 volume   0.10017E+03 ppm1    8.562 ppm2   7.960
ASSI (14401)
    ( ( segid *BrD * and resid 87 and name HN   ) )
    ( ( segid *BrD * and resid 88 and name HB1  ) )
       3.700  3.400   1.000 peak   14401 weight   0.11000E+01 volume   0.72183E+02 ppm1    8.572 ppm2   3.532
ASSI (14401)
    ( ( segid *BrD * and resid 87 and name HN   ) )
    ( ( segid *BrD * and resid 88 and name HB2  ) )
ASSI (15611)
    ( ( segid *BrD * and resid 32 and name HE1  ) )
    ( ( segid *BrD * and resid 94 and name HG2  ) )
       4.500  4.500   1.000 peak   15611 weight   0.11000E+01 volume   0.23846E+02 ppm1   11.082 ppm2   3.143
ASSI (15611)
    ( ( segid *BrD * and resid 32 and name HE1  ) )
    ( ( segid *BrD * and resid 94 and name HG1  ) )
ASSI (    1)
    ( ( segid *BrD * and resid 43 and name HN   ) )
    ( ( segid *BrD * and resid 43 and name HA   ) )
       2.700  1.500   1.800 peak       1 weight   0.11000E+01 volume   0.52965E+03 ppm1    8.001 ppm2   5.544
ASSI (   11)
    ( ( segid *BrD * and resid 43 and name HN   ) )
    (  segid *BrD * and resid 43 and name HB %)
       2.400  1.400   1.400 peak      11 weight   0.11000E+01 volume   0.93421E+03 ppm1    8.001 ppm2   1.689
ASSI (   21)
    ( ( segid *BrD * and resid 43 and name HN   ) )
    ( ( segid *BrD * and resid 42 and name HN   ) )
       2.200  1.200   1.200 peak      21 weight   0.11000E+01 volume   0.18953E+04 ppm1    8.001 ppm2   7.816
ASSI (   31)
    ( ( segid *BrD * and resid 42 and name HN   ) )
    ( ( segid *BrD * and resid 41 and name HB   ) )
       3.300  2.700   2.200 peak      31 weight   0.11000E+01 volume   0.14380E+03 ppm1    7.822 ppm2   4.900
ASSI (   41)
    ( ( segid *BrD * and resid 42 and name HN   ) )
    ( ( segid *BrD * and resid 42 and name HA   ) )
       2.900  2.100   2.100 peak      41 weight   0.11000E+01 volume   0.30790E+03 ppm1    7.824 ppm2   5.053
ASSI (   51)
    ( ( segid *BrD * and resid 42 and name HN   ) )
    ( ( segid *BrD * and resid 42 and name HB2  ) )
       2.700  1.800   1.800 peak      51 weight   0.11000E+01 volume   0.47343E+03 ppm1    7.821 ppm2   2.413
```

TABLE 2-continued

Unambigous NOE-derived Inter-proton Distance Restraints

```
ASSI (   61)
   ( ( segid *BrD * and resid 42 and name HN   ) )
   ( ( segid *BrD * and resid 42 and name HG1  ) )
      3.200  2.600   2.300 peak        61 weight   0.11000E+01 volume   0.16643E+03 ppm1    7.822 ppm2    2.899
ASSI (   71)
   ( ( segid *BrD * and resid 42 and name HN   ) )
   ( ( segid *BrD * and resid 42 and name HB1  ) )
      3.400  2.900   2.100 peak        71 weight   0.11000E+01 volume   0.13090E+03 ppm1    7.821 ppm2    2.790
ASSI (   91)
   ( ( segid *BrD * and resid 99 and name HN   ) )
   (   segid *BrD * and resid 99 and name HB %  ) )
      2.400  1.400   1.400 peak        91 weight   0.11000E+01 volume   0.90687E+03 ppm1    8.936 ppm2    2.208
ASSI (  101)
   ( ( segid *BrD * and resid 99 and name HN   ) )
   ( ( segid *BrD * and resid 99 and name HA   ) )
      2.800  2.000   2.000 peak       101 weight   0.11000E+01 volume   0.42952E+03 ppm1    8.936 ppm2    4.441
ASSI (  121)
   ( ( segid *BrD * and resid 99 and name HN   ) )
   ( ( segid *BrD * and resid 98 and name HN   ) )
      2.700  1.800   1.800 peak       121 weight   0.11000E+01 volume   0.45502E+03 ppm1    8.936 ppm2    9.112
ASSI (  131)
   ( ( segid *BrD * and resid 98 and name HN   ) )
   ( ( segid *BrD * and resid 98 and name HA   ) )
      2.500  1.600   1.600 peak       131 weight   0.11000E+01 volume   0.72592E+03 ppm1    9.125 ppm2    4.811
ASSI (  141)
   ( ( segid *BrD * and resid 98 and name HN   ) )
   ( ( segid *BrD * and resid 98 and name HB1  ) )
      3.300  2.700   2.200 peak       141 weight   0.11000E+01 volume   0.15487E+03 ppm1    9.125 ppm2    4.010
ASSI (  151)
   ( ( segid *BrD * and resid 98 and name HN   ) )
   ( ( segid *BrD * and resid 98 and name HB2  ) )
      2.400  1.400   1.400 peak       151 weight   0.11000E+01 volume   0.95273E+03 ppm1    9.125 ppm2    3.656
ASSI (  171)
   ( ( segid *BrD * and resid 30 and name HN   ) )
   ( ( segid *BrD * and resid 30 and name HA   ) )
      3.100  2.400   2.400 peak       171 weight   0.11000E+01 volume   0.20628E+03 ppm1   12.275 ppm2    5.451
ASSI (  181)
   ( ( segid *BrD * and resid 30 and name HN   ) )
   ( ( segid *BrD * and resid 30 and name HB1  ) )
      3.200  2.600   2.300 peak       181 weight   0.11000E+01 volume   0.16806E+03 ppm1   12.275 ppm2    4.939
ASSI (  191)
   ( ( segid *BrD * and resid 30 and name HN   ) )
   ( ( segid *BrD * and resid 30 and name HB2  ) )
      2.800  2.000   2.000 peak       191 weight   0.11000E+01 volume   0.40863E+03 ppm1   12.275 ppm2    4.538
ASSI (  201)
   ( ( segid *BrD * and resid 30 and name HN   ) )
   ( ( segid *BrD * and resid 29 and name HN   ) )
      3.300  2.700   2.200 peak       201 weight   0.11000E+01 volume   0.51134E+03 ppm1   12.275 ppm2    9.150
ASSI (  211)
   ( ( segid *BrD * and resid 29 and name HN   ) )
   ( ( segid *BrD * and resid 29 and name HA   ) )
      2.700  1.800   1.800 peak       211 weight   0.11000E+01 volume   0.44648E+03 ppm1    9.151 ppm2    4.418
ASSI (  221)
   ( ( segid *BrD * and resid 29 and name HN   ) )
   ( ( segid *BrD * and resid 29 and name HB1  ) )
      2.800  2.000   2.000 peak       221 weight   0.11000E+01 volume   0.39474E+03 ppm1    9.152 ppm2    2.712
ASSI (  231)
   ( ( segid *BrD * and resid 31 and name HN   ) )
   ( ( segid *BrD * and resid 29 and name HA   ) )
      3.400  2.900   2.100 peak       231 weight   0.11000E+01 volume   0.12405E+03 ppm1    8.479 ppm2    4.816
ASSI (  241)
   ( ( segid *BrD * and resid 31 and name HN   ) )
   ( ( segid *BrD * and resid 31 and name HA   ) )
      3.300  2.700   2.200 peak       241 weight   0.11000E+01 volume   0.13933E+03 ppm1    8.479 ppm2    5.003
ASSI (  251)
   ( ( segid *BrD * and resid 31 and name HN   ) )
   (   segid *BrD * and resid 31 and name HB1  ) )
      2.400  1.400   1.400 peak       251 weight   0.11000E+01 volume   0.88455E+03 ppm1    8.480 ppm2    2.307
ASSI (  271)
   ( ( segid *BrD * and resid 28 and name HN   ) )
   ( ( segid *BrD * and resid 28 and name HB2  ) )
      2.500  1.600   1.600 peak       271 weight   0.11000E+01 volume   0.82952E+03 ppm1    8.166 ppm2    3.409
ASSI (  281)
   ( ( segid *BrD * and resid 28 and name HN   ) )
   ( ( segid *BrD * and resid 28 and name HB1  ) )
      2.500  1.600   1.600 peak       281 weight   0.11000E+01 volume   0.71832E+03 ppm1    8.166 ppm2    3.596
```

TABLE 2-continued

Unambigous NOE-derived Inter-proton Distance Restraints

```
ASSI (  291)
   ( ( segid *BrD * and resid 28 and name HN   ) )
   ( ( segid *BrD * and resid 28 and name HA   ) )
      2.700  1.800   1.800 peak       291 weight   0.11000E+01 volume  0.53054E+03 ppm1     8.165 ppm2    4.598
ASSI (  301)
   ( ( segid *BrD * and resid 28 and name HN   ) )
   ( ( segid *BrD * and resid 29 and name HN   ) )
      3.400  2.900   2.100 peak       301 weight   0.11000E+01 volume  0.11688E+03 ppm1     8.166 ppm2    9.164
ASSI (  321)
   ( ( segid *BrD * and resid 32 and name HN   ) )
   ( ( segid *BrD * and resid 32 and name HA   ) )
      2.600  1.700   1.700 peak       321 weight   0.11000E+01 volume  0.66621E+03 ppm1     7.735 ppm2    4.977
ASSI (  331)
   ( ( segid *BrD * and resid 32 and name HN   ) )
   ( ( segid *BrD * and resid 32 and name HB1  ) )
      2.900  2.100   2.100 peak       331 weight   0.11000E+01 volume  0.30872E+03 ppm1     7.740 ppm2    4.201
ASSI (  341)
   ( ( segid *BrD * and resid 32 and name HN   ) )
   ( ( segid *BrD * and resid 32 and name HB2  ) )
      2.600  1.700   1.700 peak       341 weight   0.11000E+01 volume  0.59972E+03 ppm1     7.739 ppm2    3.958
ASSI (  351)
   ( ( segid *BrD * and resid 30 and name HN   ) )
   ( ( segid *BrD * and resid 31 and name HN   ) )
      2.800  2.000   2.000 peak       351 weight   0.11000E+01 volume  0.41861E+03 ppm1    12.275 ppm2    8.477
ASSI (  361)
   ( ( segid *BrD * and resid 105 and name HN  ) )
   ( ( segid *BrD * and resid 105 and name HA  ) )
      3.100  2.400   2.400 peak       361 weight   0.11000E+01 volume  0.22043E+03 ppm1     8.488 ppm2    4.934
ASSI (  371)
   ( ( segid *BrD * and resid 105 and name HN  ) )
   ( ( segid *BrD * and resid 105 and name HB1 ) )
      2.800  2.000   2.000 peak       371 weight   0.11000E+01 volume  0.42542E+03 ppm1     8.487 ppm2    3.740
ASSI (  401)
   ( ( segid *BrD * and resid 106 and name HN  ) )
   ( ( segid *BrD * and resid 105 and name HN  ) )
      2.700  1.800   1.800 peak       401 weight   0.11000E+01 volume  0.44987E+03 ppm1     9.740 ppm2    8.476
ASSI (  411)
   ( ( segid *BrD * and resid 106 and name HN  ) )
   ( ( segid *BrD * and resid 106 and name HA  ) )
      2.600  1.700   1.700 peak       411 weight   0.11000E+01 volume  0.55394E+03 ppm1     9.740 ppm2    4.666
ASSI (  421)
   ( ( segid *BrD * and resid 106 and name HN  ) )
   ( ( segid *BrD * and resid 106 and name HB1 ) )
      2.500  1.600   1.600 peak       421 weight   0.11000E+01 volume  0.71965E+03 ppm1     9.740 ppm2    3.895
ASSI (  431)
   ( ( segid *BrD * and resid 106 and name HN  ) )
   ( ( segid *BrD * and resid 106 and name HB2 ) )
      2.300  1.300   1.300 peak       431 weight   0.11000E+01 volume  0.11998E+04 ppm1     9.740 ppm2    3.674
ASSI (  451)
   ( ( segid *BrD * and resid 107 and name HN  ) )
   ( ( segid *BrD * and resid 106 and name HN  ) )
      2.900  2.100   2.100 peak       451 weight   0.11000E+01 volume  0.34881E+03 ppm1     8.981 ppm2    9.733
ASSI (  461)
   ( ( segid *BrD * and resid 107 and name HN  ) )
   (   segid *BrD * and resid 107 and name HD % )
      3.500  3.100   2.000 peak       461 weight   0.11000E+01 volume  0.11255E+03 ppm1     8.980 ppm2    7.763
ASSI (  471)
   ( ( segid *BrD * and resid 107 and name HN  ) )
   ( ( segid *BrD * and resid 107 and name HA  ) )
      2.600  1.700   1.700 peak       471 weight   0.11000E+01 volume  0.57631E+03 ppm1     8.981 ppm2    4.443
ASSI (  481)
   ( ( segid *BrD * and resid 107 and name HN  ) )
   ( ( segid *BrD * and resid 107 and name HB1 ) )
      3.200  2.600   2.300 peak       481 weight   0.11000E+01 volume  0.16715E+03 ppm1     8.980 ppm2    3.671
ASSI (  501)
   ( ( segid *BrD * and resid 108 and name HN  ) )
   ( ( segid *BrD * and resid 107 and name HN  ) )
      2.600  1.700   1.700 peak       501 weight   0.11000E+01 volume  0.57313E+03 ppm1     8.529 ppm2    8.966
ASSI (  511)
   ( ( segid *BrD * and resid 108 and name HN  ) )
   ( ( segid *BrD * and resid 108 and name HA  ) )
      2.700  1.800   1.800 peak       511 weight   0.11000E+01 volume  0.52916E+03 ppm1     8.526 ppm2    4.811
ASSI (  521)
   ( ( segid *BrD * and resid 108 and name HN  ) )
   ( ( segid *BrD * and resid 108 and name HB1 ) )
      2.400  1.400   1.400 peak       521 weight   0.11000E+01 volume  0.97954E+03 ppm1     8.526 ppm2    4.583
```

TABLE 2-continued

Unambigous NOE-derived Inter-proton Distance Restraints

```
ASSI (  531)
   ( ( segid *BrD * and resid 109 and name HN   ) )
   ( ( segid *BrD * and resid 109 and name HA   ) )
      2.300  1.300   1.300 peak     531 weight  0.11000E+01 volume  0.11922E+04 ppm1     8.572 ppm2   4.615
ASSI (  541)
   ( ( segid *BrD * and resid 110 and name HN   ) )
   ( ( segid *BrD * and resid 109 and name HB2  ) )
      2.900  2.100   2.100 peak     541 weight  0.11000E+01 volume  0.32815E+03 ppm1     8.714 ppm2   2.174
ASSI (  551)
   ( ( segid *BrD * and resid 110 and name HN   ) )
   ( ( segid *BrD * and resid 110 and name HA   ) )
      2.800  2.000   2.000 peak     551 weight  0.11000E+01 volume  0.43619E+03 ppm1     8.714 ppm2   4.451
ASSI (  561)
   ( ( segid *BrD * and resid 110 and name HN   ) )
   ( ( segid *BrD * and resid 110 and name HB   ) )
      2.500  1.600   1.600 peak     551 weight  0.11000E+01 volume   0.77600E+03 ppm1    8.714 ppm2   2.352
ASSI (  581)
   ( ( segid *BrD * and resid 109 and name HN   ) )
   ( ( segid *BrD * and resid 110 and name HN   ) )
      2.800  2.000   2.000 peak     581 weight  0.11000E+01 volume  0.41482E+03 ppm1     8.572 ppm2   8.705
ASSI (  591)
   ( ( segid *BrD * and resid 111 and name HN   ) )
   ( ( segid *BrD * and resid 108 and name HA   ) )
      3.200  2.600   2.300 peak     591 weight  0.11000E+01 volume  0.17690E+03 ppm1     8.168 ppm2   4.807
ASSI (  601)
   ( ( segid *BrD * and resid 111 and name HN   ) )
   ( ( segid *BrD * and resid 111 and name HA   ) )
      2.500  1.600   1.600 peak     601 weight  0.11000E+01 volume  0.71549E+03 ppm1     8.168 ppm2   4.650
ASSI (  621)
   ( ( segid *BrD * and resid 110 and name HN   ) )
   ( ( segid *BrD * and resid 111 and name HN   ) )
      2.800  2.000   2.000 peak     621 weight  0.11000E+01 volume  0.38661E+03 ppm1     8.714 ppm2   6.153
ASSI (  631)
   ( ( segid *BrD * and resid 112 and name HN   ) )
   ( ( segid *BrD * and resid 112 and name HA   ) )
      2.300  1.300   1.300 peak     631 weight  0.11000E+01 volume  0.13944E+04 ppm1     8.667 ppm2   4.607
ASSI (  641)
   ( ( segid *BrD * and resid 112 and name HN   ) )
   ( ( segid *BrD * and resid 112 and name HG1  ) )
      3.400  2.900   2.100 peak     641 weight  0.11000E+01 volume   0.2114E+03 ppm1     8.668 ppm2   2.956
ASSI (  651)
   ( ( segid *BrD * and resid 112 and name HN   ) )
   ( ( segid *BrD * and resid 112 and name HG2  ) )
      3.500  3.100   2.000 peak     651 weight  0.11000E+01 volume  0.96511E+02 ppm1     8.668 ppm2   2.818
ASSI (  661)
   ( ( segid *BrD * and resid 112 and name HN   ) )
   ( ( segid *BrD * and resid 112 and name HB1  ) )
      2.200  1.200   1.200 peak     661 weight  0.11000E+01 volume  0.15417E+04 ppm1     8.668 ppm2   2.667
ASSI (  671)
   ( ( segid *BrD * and resid 113 and name HN   ) )
   ( ( segid *BrD * and resid 113 and name HA   ) )
      2.800  2.000   2.000 peak     671 weight  0.11000E+01 volume  0.42878E+03 ppm1     8.217 ppm2   4.904
ASSI (  681)
   ( ( segid *BrD * and resid 113 and name HN   ) )
   (   segid *BrD * and resid 113 and name HB %  )
      2.400  1.400   1.400 peak     681 weight  0.11000E+01 volume  0.99017E+03 ppm1     8.219 ppm2   1.967
ASSI (  701)
   ( ( segid *BrD * and resid 114 and name HN   ) )
   ( ( segid *BrD * and resid 114 and name HA1  ) )
      2.800  2.000   2.000 peak     701 weight  0.11000E+01 volume  0.42782E+03 ppm1     8.376 ppm2   4.619
ASSI (  721)
   ( ( segid *BrD * and resid 113 and name HN   ) )
   ( ( segid *BrD * and resid 114 and name HN   ) )
      2.800  1.600   1.600 peak     721 weight  0.11000E+01 volume  0.73856E+03 ppm1     8.217 ppm2   8.151
ASSI (  741)
   ( ( segid *BrD * and resid 100 and name HN   ) )
   ( ( segid *BrD * and resid 100 and name HA   ) )
      2.700  1.800   1.800 peak     741 weight  0.11000E+01 volume  0.49224E+03 ppm1     8.669 ppm2   4.938
ASSI (  751)
   ( ( segid *BrD * and resid 100 and name HN   ) )
   ( ( segid *BrD * and resid 100 and name HB2  ) )
      2.400  1.400   1.400 peak     751 weight  0.11000E+01 volume  0.10916E+04 ppm1     8.669 ppm2   3.422
ASSI (  771)
   ( ( segid *BrD * and resid 99 and name HN    ) )
   ( ( segid *BrD * and resid 100 and name HN   ) )
      2.500  1.600   1.600 peak     771 weight  0.11000E+01 volume  0.76441E+03 ppm1     8.936 ppm2   8.664
```

TABLE 2-continued

Unambigous NOE-derived Inter-proton Distance Restraints

```
ASSI (  791)
    ( ( segid *BrD * and resid 97 and name HN    ) )
    ( ( segid *BrD * and resid 97 and name HA    ) )
        2.600   1.700    1.700 peak       791 weight    0.11000E+01 volume    0.58097E+03 ppm1     8.676 ppm2    4.809
ASSI (  811)
    ( ( segid *BrD * and resid 97 and name HN    ) )
    ( ( segid *BrD * and resid 98 and name HN    ) )
        3.00    2.200    2.200 peak       811 weight    0.11000E+01 volume    0.25513E+03 ppm1     8.672 ppm2    9.124
ASSI (  841)
    ( ( segid *BrD * and resid 96 and name HN    ) )
    ( ( segid *BrD * and resid 96 and name HA    ) )
        2.600   1.700    1.700 peak       841 weight    0.11000E+01 volume    0.45098E+03 ppm1     7.977 ppm2    4.433
ASSI (  851)
    ( ( segid *BrD * and resid 96 and name HN    ) )
    ( ( segid *BrD * and resid 96 and name HB1   ) )
        2.800   2.000    2.000 peak       851 weight    0.11000E+01 volume    0.42091E+03 ppm1     7.976 ppm2    1.995
ASSI (  861)
    ( ( segid *BrD * and resid 96 and name HN    ) )
    ( ( segid *BrD * and resid 96 and name HB2   ) )
        2.600   1.700    1.700 peak       861 weight    0.11000E+01 volume    0.54648E+03 ppm1     7.979 ppm2    3.112
ASSI (  871)
    ( ( segid *BrD * and resid 96 and name HN    ) )
    ( ( segid *BrD * and resid 97 and name HN    ) )
        2.600   1.700    1.700 peak       871 weight    0.11000E+01 volume    0.67038E+03 ppm1     7.979 ppm2    8.678
ASSI (  891)
    ( ( segid *BrD * and resid 95 and name HN    ) )
    ( ( segid *BrD * and resid 95 and name HA    ) )
        3.100   2.400    2.400 peak       891 weight    0.11000E+01 volume    0.22376E+03 ppm1     8.669 ppm2    4.443
ASSI (  901)
    ( ( segid *BrD * and resid 95 and name HN    ) )
    ( ( segid *BrD * and resid 95 and name HB1   ) )
        2.600   2.000    2.000 peak       901 weight    0.11000E+01 volume    0.37061E+03 ppm1     8.669 ppm2    3.598
ASSI (  911)
    ( ( segid *BrD * and resid 95 and name HN    ) )
    ( ( segid *BrD * and resid 95 and name HB2   ) )
        2.700   1.800    1.800 peak       911 weight    0.11000E+01 volume    0.54351E+03 ppm1     8.669 ppm2    3.346
ASSI (  921)
    ( ( segid *BrD * and resid 94 and name HN    ) )
    ( ( segid *BrD * and resid 94 and name HA    ) )
        3.300   2.700    2.200 peak       921 weight    0.11000E+01 volume    0.13528E+03 ppm1     9.679 ppm2    4.846
ASSI (  941)
    ( ( segid *BrD * and resid 94 and name HN    ) )
    ( ( segid *BrD * and resid 95 and name HN    ) )
        3.500   3.100    2.000 peak       941 weight    0.11000E+01 volume    0.95054E+02 ppm1     9.679 ppm2    8.670
ASSI (  971)
    ( ( segid *BrD * and resid 93 and name HN    ) )
    ( ( segid *BrD * and resid 93 and name HA    ) )
        3.200   2.600    2.300 peak       971 weight    0.11000E+01 volume    0.16612E+03 ppm1     8.713 ppm2    5.037
ASSI (  981)
    ( ( segid *BrD * and resid 93 and name HN    ) )
    ( ( segid *BrD * and resid 93 and name HB2   ) )
        3.300   2.700    2.200 peak       971 weight    0.11000E+01 volume    0.15761E+03 ppm1     8.713 ppm2    4.753
ASSI ( 1001)
    ( ( segid *BrD * and resid 92 and name HN    ) )
    ( ( segid *BrD * and resid 92 and name HA    ) )
        2.500   1.600    1.600 peak      1001 weight    0.11000E+01 volume    0.71435E+03 ppm1     8.973 ppm2    4.802
ASSI ( 1011)
    ( ( segid *BrD * and resid 92 and name HN    ) )
    ( ( segid *BrD * and resid 93 and name HN    ) )
        2.500   1.600    1.600 peak      1011 weight    0.11000E+01 volume    0.69883E+03 ppm1     8.871 ppm2    8.719
ASSI ( 1031)
    ( ( segid *BrD * and resid 76 and name HN    ) )
    ( ( segid *BrD * and resid 76 and name HA    ) )
        2.500   1.600    1.600 peak      1031 weight    0.11000E+01 volume    0.86678E+03 ppm1     8.611 ppm2    4.688
ASSI ( 1041)
    ( ( segid *BrD * and resid 76 and name HN    ) )
    (   segid *BrD * and resid 76 and name HB %  )
        2.200   1.200    1.200 peak      1041 weight    0.11000E+01 volume    0.16592E+04 ppm1     8.612 ppm2    2.102
ASSI ( 1061)
    ( ( segid *BrD * and resid 77 and name HN    ) )
    ( ( segid *BrD * and resid 77 and name HA    ) )
        2.700   1.800    1.800 peak      1061 weight    0.11000E+01 volume    0.53554E+03 ppm1     7.996 ppm2    4.980
ASSI ( 1071)
    ( ( segid *BrD * and resid 77 and name HN    ) )
    ( ( segid *BrD * and resid 77 and name HB1   ) )
        2.100   1.100    1.100 peak      1071 weight    0.11000E+01 volume    0.22098E+04 ppm1     7.996 ppm2    3.337
```

TABLE 2-continued

Unambigous NOE-derived Inter-proton Distance Restraints

```
ASSI ( 1091)
   ( ( segid *BrD * and resid 76 and name HN   ) )
   ( ( segid *BrD * and resid 77 and name HN   ) )
     2.600  1.700   1.700 peak    1091 weight   0.11000E+01 volume  0.57823E+03 ppm1   8.612 ppm2   7.983
ASSI ( 1111)
   ( ( segid *BrD * and resid 78 and name HN   ) )
   ( ( segid *BrD * and resid 75 and name HA   ) )
     2.800  2.000   2.000 peak    1111 weight   0.11000E+01 volume  0.40919E+03 ppm1   9.106 ppm2   4.527
ASSI ( 1121)
   ( ( segid *BrD * and resid 75 and name HN   ) )
   ( ( segid *BrD * and resid 75 and name HG1  ) )
     2.600  1.700   1.700 peak    1121 weight   0.11000E+01 volume  0.46185E+03 ppm1   9.106 ppm2   3.549
ASSI ( 1131)
   ( ( segid *BrD * and resid 75 and name HN   ) )
   ( ( segid *BrD * and resid 75 and name HG2  ) )
     2.900  2.100   2.100 peak    1131 weight   0.11000E+01 volume  0.30957E+03 ppm1   9.106 ppm2   3.221
ASSI ( 1141)
   ( ( segid *BrD * and resid 75 and name HN   ) )
   ( ( segid *BrD * and resid 75 and name HB1  ) )
     3.100  2.400   2.400 peak    1141 weight   0.11000E+01 volume  0.19539E+03 ppm1   9.106 ppm2   2.919
ASSI ( 1151)
   ( ( segid *BrD * and resid 75 and name HN   ) )
   ( ( segid *BrD * and resid 75 and name HB2  ) )
     2.500  1.600   1.600 peak    1151 weight   0.11000E+01 volume  0.72202E+03 ppm1   9.106 ppm2   2.816
ASSI ( 1171)
   ( ( segid *BrD * and resid 76 and name HN   ) )
   ( ( segid *BrD * and resid 75 and name HN   ) )
     2.700  1.800   1.800 peak    1171 weight   0.11000E+01 volume  0.51792E+03 ppm1   8.613 ppm2   9.085
ASSI ( 1181)
   ( ( segid *BrD * and resid 74 and name HN   ) )
   (   segid *BrD * and resid 74 and name HD %  )
     3.000  2.200   2.200 peak    1181 weight   0.11000E+01 volume  0.24258E+03 ppm1   7.536 ppm2   7.004
ASSI ( 1191)
   ( ( segid *BrD * and resid 74 and name HN   ) )
   ( ( segid *BrD * and resid 74 and name HA   ) )
     3.000  2.200   2.200 peak    1191 weight   0.11000E+01 volume  0.27313E+03 ppm1   7.536 ppm2   4.368
ASSI ( 1201)
   ( ( segid *BrD * and resid 74 and name HN   ) )
   ( ( segid *BrD * and resid 74 and name HB1  ) )
     2.800  2.000   2.000 peak    1201 weight   0.11000E+01 volume  0.42552E+03 ppm1   7.535 ppm2   3.552
ASSI ( 1211)
   ( ( segid *BrD * and resid 74 and name HN   ) )
   ( ( segid *BrD * and resid 74 and name HB2  ) )
     2.700  1.800   1.800 peak    1211 weight   0.11000E+01 volume  0.47386E+03 ppm1   7.536 ppm2   2.983
ASSI ( 1231)
   ( ( segid *BrD * and resid 75 and name HN   ) )
   ( ( segid *BrD * and resid 74 and name HN   ) )
     2.800  2.000   2.000 peak    1231 weight   0.11000E+01 volume  0.42446E+03 ppm1   9.105 ppm2   7.535
ASSI ( 1241)
   ( ( segid *BrD * and resid 70 and name HN   ) )
   ( ( segid *BrD * and resid 70 and name HA   ) )
     2.500  1.600   1.600 peak    1241 weight   0.11000E+01 volume  0.78559E+03 ppm1   8.040 ppm2   5.348
ASSI ( 1251)
   ( ( segid *BrD * and resid 70 and name HN   ) )
   ( ( segid *BrD * and resid 70 and name HB2  ) )
     2.900  2.100   2.100 peak    1251 weight   0.11000E+01 volume  0.29096E+03 ppm1   8.019 ppm2   4.357
ASSI ( 1261)
   ( ( segid *BrD * and resid 69 and name HN   ) )
   ( ( segid *BrD * and resid 69 and name HA   ) )
     2.800  2.000   2.000 peak    1261 weight   0.11000E+01 volume  0.43807E+03 ppm1   8.306 ppm2   4.690
ASSI ( 1271)
   ( ( segid *BrD * and resid 69 and name HN   ) )
   ( ( segid *BrD * and resid 69 and name HB   ) )
     3.300  2.700   2.200 peak    1271 weight   0.11000E+01 volume  0.13733E+03 ppm1   8.306 ppm2   2.921
ASSI ( 1281)
   ( ( segid *BrD * and resid 69 and name HN   ) )
   (   segid *BrD * and resid 69 and name HG1%)
     2.800  2.000   2.000 peak    1281 weight   0.11000E+01 volume  0.40608E+03 ppm1   8.306 ppm2   1.549
ASSI ( 1291)
   ( ( segid *BrD * and resid 69 and name HN   ) )
   (   segid *BrD * and resid 69 and name HG2%)
     3.000  2.200   2.200 peak    1291 weight   0.11000E+01 volume  0.24335E+03 ppm1   8.306 ppm2   1.430
ASSI ( 1301)
   ( ( segid *BrD * and resid 69 and name HN   ) )
   ( ( segid *BrD * and resid 70 and name HN   ) )
     2.800  2.000   2.000 peak    1291 weight   0.11000E+01 volume  0.40402E+03 ppm1   8.306 ppm2   8.022
```

TABLE 2-continued

Unambigous NOE-derived Inter-proton Distance Restraints

```
ASSI ( 1321)
    ( ( segid *BrD * and resid 68 and name HN   ) )
    ( ( segid *BrD * and resid 68 and name HD % )
        2.900  2.100  2.100 peak    1321 weight   0.11000E+01 volume   0.34716E+03 ppm1   8.626 ppm2   7.778
ASSI ( 1331)
    ( ( segid *BrD * and resid 68 and name HN   ) )
    ( ( segid *BrD * and resid 68 and name HA   ) )
        3.200  2.600  2.300 peak    1331 weight   0.11000E+01 volume   0.14288E+03 ppm1   8.626 ppm2   5.142
ASSI ( 1341)
    ( ( segid *BrD * and resid 68 and name HN   ) )
    ( ( segid *BrD * and resid 68 and name HB1  ) )
        3.000  2.200  2.200 peak    1341 weight   0.11000E+01 volume   0.26781E+03 ppm1   8.625 ppm2   3.669
ASSI ( 1351)
    ( ( segid *BrD * and resid 68 and name HN   ) )
    ( ( segid *BrD * and resid 68 and name HB2  ) )
        2.700  1.800  1.800 peak    1351 weight   0.11000E+01 volume   0.52551E+03 ppm1   8.627 ppm2   2.516
ASSI ( 1361)
    ( ( segid *BrD * and resid 68 and name HN   ) )
    ( ( segid *BrD * and resid 69 and name HN   ) )
        3.500  3.100  2.000 peak    1361 weight   0.11000E+01 volume   0.11066E+03 ppm1   8.622 ppm2   6.304
ASSI ( 1381)
    ( ( segid *BrD * and resid 67 and name HN   ) )
    (   segid *BrD * and resid 67 and name HD % )
        3.100  2.400  2.400 peak    1381 weight   0.11000E+01 volume   0.20078E+03 ppm1   8.632 ppm2   6.888
ASSI ( 1391)
    ( ( segid *BrD * and resid 67 and name HN   ) )
    ( ( segid *BrD * and resid 67 and name HA   ) )
        2.800  2.000  2.000 peak    1191 weight   0.11000E+01 volume   0.36081E+03 ppm1   8.632 ppm2   4.671
ASSI ( 1401)
    ( ( segid *BrD * and resid 67 and name HN   ) )
    ( ( segid *BrD * and resid 67 and name HB1  ) )
        2.900  2.100  2.100 peak    1401 weight   0.11000E+01 volume   0.31437E+03 ppm1   8.632 ppm2   3.549
ASSI ( 1411)
    ( ( segid *BrD * and resid 67 and name HN   ) )
    ( ( segid *BrD * and resid 67 and name HB2  ) )
        2.400  1.400  1.400 peak    1411 weight   0.11000E+01 volume   0.92322E+03 ppm1   8.833 ppm2   2.661
ASSI ( 1431)
    ( ( segid *BrD * and resid 68 and name HN   ) )
    ( ( segid *BrD * and resid 67 and name HN   ) )
        2.500  1.600  1.600 peak    1431 weight   0.11000E+01 volume   0.76622E+03 ppm1   8.622 ppm2   8.829
ASSI ( 1441)
    ( ( segid *BrD * and resid 68 and name HN   ) )
    (   segid *BrD * and resid 67 and name HD % )
        3.200  2.600  2.300 peak    1441 weight   0.11000E+01 volume   0.16656E+03 ppm1   8.626 ppm2   6.892
ASSI ( 1451)
    ( ( segid *BrD * and resid 66 and name HN   ) )
    ( ( segid *BrD * and resid 66 and name HA   ) )
        2.200  1.200  1.200 peak    1451 weight   0.11000E+01 volume   0.17604E+04 ppm1   8.763 ppm2   5.001
ASSI ( 1461)
    ( ( segid *BrD * and resid 65 and name HN   ) )
    ( ( segid *BrD * and resid 65 and name HA   ) )
        2.500  1.600  1.600 peak    1461 weight   0.11000E+01 volume   0.81594E+03 ppm1   8.564 ppm2   5.375
ASSI ( 1471)
    ( ( segid *BrD * and resid 65 and name HN   ) )
    ( ( segid *BrD * and resid 65 and name HB1  ) )
        2.600  1.700  1.700 peak    1471 weight   0.11000E+01 volume   0.66517E+03 ppm1   8.566 ppm2   3.627
ASSI ( 1481)
    ( ( segid *BrD * and resid 65 and name HN   ) )
    ( ( segid *BrD * and resid 65 and name HB2  ) )
        2.400  1.400  1.400 peak    1481 weight   0.11000E+01 volume   0.98393E+03 ppm1   8.564 ppm2   3.382
ASSI ( 1491)
    ( ( segid *BrD * and resid 65 and name HN   ) )
    ( ( segid *BrD * and resid 64 and name HB1  ) )
        2.400  1.400  1.400 peak    1491 weight   0.11000E+01 volume   0.10161E+04 ppm1   8.565 ppm2   2.659
ASSI ( 1501)
    ( ( segid *BrD * and resid 65 and name HN   ) )
    ( ( segid *BrD * and resid 66 and name HN   ) )
        2.300  1.300  1.300 peak    1501 weight   0.11000E+01 volume   0.13482E+04 ppm1   8.565 ppm2   8.765
ASSI ( 1521)
    ( ( segid *BrD * and resid 20 and name HN   ) )
    ( ( segid *BrD * and resid 16 and name HA   ) )
        2.700  1.800  1.800 peak    1521 weight   0.11000E+01 volume   0.44067E+03 ppm1   8.146 ppm2   4.527
ASSI ( 1531)
    ( ( segid *BrD * and resid 20 and name HN   ) )
    ( ( segid *BrD * and resid 20 and name HA   ) )
        2.500  1.600  1.600 peak    1531 weight   0.11000E+01 volume   0.84286E+03 ppm1   8.146 ppm2   4.895
```

TABLE 2-continued

Unambigous NOE-derived Inter-proton Distance Restraints

```
ASSI ( 1541)
   ( ( segid *BrD * and resid 20 and name HN   ) )
   ( ( segid *BrD * and resid 20 and name HB1  ) )
     2.300   1.300    1.300  peak    1541  weight   0.11000E+01 volume  0.13472E+04 ppm1   8.147 ppm2   4.669
ASSI ( 1561)
   ( ( segid *BrD * and resid 21 and name HN   ) )
   ( ( segid *BrD * and resid 21 and name HA   ) )
     2.900   2.100    2.100  peak    1561  weight   0.11000E+01 volume  0.31054E+03 ppm1   8.546 ppm2   4.367
ASSI ( 1571)
   ( ( segid *BrD * and resid 21 and name HN   ) )
   ( ( segid *BrD * and resid 21 and name HB   ) )
     2.700   1.800    1.800  peak    1571  weight   0.11000E+01 volume  0.51528E+03 ppm1   8.514 ppm2   2.536
ASSI ( 1581)
   ( ( segid *BrD * and resid 22 and name HN   ) )
   ( ( segid *BrD * and resid 22 and name HA   ) )
     2.700   1.800    1.800  peak    1581  weight   0.11000E+01 volume  0.45405E+03 ppm1   9.456 ppm2   4.712
ASSI ( 1591)
   ( ( segid *BrD * and resid 22 and name HN   ) )
   ( ( segid *BrD * and resid 22 and name HB   ) )
     3.300   2.700    2.200  peak    1591  weight   0.11000E+01 volume  0.13959E+03 ppm1   9.122 ppm2   2.486
ASSI ( 1601)
   ( ( segid *BrD * and resid 23 and name HN   ) )
   ( ( segid *BrD * and resid 23 and name HA   ) )
     2.600   1.700    1.700  peak    1601  weight   0.11000E+01 volume  0.61098E+03 ppm1   9.118 ppm2   4.645
ASSI ( 1611)
   ( ( segid *BrD * and resid 23 and name HN   ) )
   ( ( segid *BrD * and resid 23 and name HG1  ) )
     3.400   2.900    2.100  peak    1611  weight   0.11000E+01 volume  0.11565E+03 ppm1   9.119 ppm2   3.143
ASSI ( 1621)
   ( ( segid *BrD * and resid 23 and name HN   ) )
   ( ( segid *BrD * and resid 23 and name HB1  ) )
     2.900   2.100    2.100  peak    1621  weight   0.11000E+01 volume  0.34650E+03 ppm1   9.118 ppm2   2.939
ASSI ( 1641)
   ( ( segid *BrD * and resid 22 and name HN   ) )
   ( ( segid *BrD * and resid 23 and name HN   ) )
     2.600   1.700    1.700  peak    1641  weight   0.11000E+01 volume  0.57061E+03 ppm1   9.456 ppm2   9.123
ASSI ( 1651)
   ( ( segid *BrD * and resid 15 and name HN   ) )
   (   segid *BrD * and resid 15 and name HD %  )
     3.100   2.400    2.400  peak    1651  weight   0.11000E+01 volume  0.20888E+03 ppm1   8.598 ppm2   7.663
ASSI ( 1661)
   ( ( segid *BrD * and resid 24 and name HN   ) )
   ( ( segid *BrD * and resid 24 and name HA   ) )
     2.800   2.000    2.000  peak    1661  weight   0.11000E+01 volume  0.43492E+03 ppm1   8.681 ppm2   4.775
ASSI ( 1671)
   ( ( segid *BrD * and resid 24 and name HN   ) )
   ( ( segid *BrD * and resid 24 and name HG1  ) )
     2.800   2.000    2.000  peak    1671  weight   0.11000E+01 volume  0.42365E+03 ppm1   8.460 ppm2   3.454
ASSI ( 1681)
   ( ( segid *BrD * and resid 24 and name HN   ) )
   ( ( segid *BrD * and resid 24 and name HB1  ) )
     2.800   2.000    2.000  peak    1681  weight   0.11000E+01 volume  0.37096E+03 ppm1   8.654 ppm2   3.089
ASSI ( 1691)
   ( ( segid *BrD * and resid 24 and name HN   ) )
   ( ( segid *BrD * and resid 23 and name HN   ) )
     2.300   1.300    1.300  peak    1691  weight   0.11000E+01 volume  0.12196E+04 ppm1   8.659 ppm2   9.112
ASSI ( 1711)
   ( ( segid *BrD * and resid 25 and name HN   ) )
   ( ( segid *BrD * and resid 27 and name HN   ) )
     3.600   3.200    1.900  peak    1711  weight   0.11000E+01 volume  0.81722E+02 ppm1   9.134 ppm2   8.155
ASSI ( 1721)
   ( ( segid *BrD * and resid 25 and name HN   ) )
   ( ( segid *BrD * and resid 25 and name HA   ) )
     3.200   2.600    2.300  peak    1721  weight   0.11000E+01 volume  0.14529E+03 ppm1   9.134 ppm2   4.443
ASSI ( 1731)
   ( ( segid *BrD * and resid 25 and name HN   ) )
   ( ( segid *BrD * and resid 25 and name HB   ) )
     2.800   2.000    2.000  peak    1731  weight   0.11000E+01 volume  0.35564E+03 ppm1   9.132 ppm2   2.984
ASSI ( 1741)
   ( ( segid *BrD * and resid 25 and name HN   ) )
   (   segid *BrD * and resid 25 and name HG1%)
     2.600   1.700    1.700  peak    1741  weight   0.11000E+01 volume  0.61322E+03 ppm1   9.133 ppm2   1.799
ASSI ( 1751)
   ( ( segid *BrD * and resid 25 and name HN   ) )
   (   segid *BrD * and resid 25 and name HG2%)
     2.800   2.000    2.000  peak    1751  weight   0.11000E+01 volume  0.35918E+03 ppm1   9.133 ppm2   1.627
```

TABLE 2-continued

Unambigous NOE-derived Inter-proton Distance Restraints

```
ASSI ( 1771)
    ( ( segid *BrD * and resid 24 and name HN   ) )
    ( ( segid *BrD * and resid 25 and name HN   ) )
       2.400   1.400    1.400 peak    1771 weight   0.11000E+01 volume   0.91823E+03 ppm1    8.661 ppm2    9.133
ASSI ( 1791)
    ( ( segid *BrD * and resid 26 and name HN   ) )
    ( ( segid *BrD * and resid 26 and name HA   ) )
       3.000   2.200    2.200 peak    1791 weight   0.11000E+01 volume   0.24501E+03 ppm1    9.196 ppm2    4.488
ASSI ( 1801)
    ( ( segid *BrD * and resid 27 and name HN   ) )
    ( ( segid *BrD * and resid 26 and name HB1  ) )
       2.700   1.800    1.800 peak    1801 weight   0.11000E+01 volume   0.50197E+03 ppm1    8.169 ppm2    2.480
ASSI ( 1811)
    ( ( segid *BrD * and resid 27 and name HN   ) )
    ( ( segid *BrD * and resid 27 and name HA   ) )
       2.700   1.800    1.800 peak    1811 weight   0.11000E+01 volume   0.49453E+03 ppm1    8.170 ppm2    5.055
ASSI ( 1821)
    ( ( segid *BrD * and resid 27 and name HN   ) )
    ( ( segid *BrD * and resid 27 and name HB1  ) )
       2.500   1.600    1.600 peak    1821 weight   0.11000E+01 volume   0.78563E+03 ppm1    8.170 ppm2    4.611
ASSI ( 1831)
    ( ( segid *BrD * and resid 27 and name HN   ) )
    ( ( segid *BrD * and resid 26 and name HN   ) )
       2.600   1.700    1.700 peak    1831 weight   0.11000E+01 volume   0.56681E+03 ppm1    8.149 ppm2    9.179
ASSI ( 1851)
    ( ( segid *BrD * and resid 19 and name HN   ) )
    ( ( segid *BrD * and resid 15 and name HA   ) )
       3.100   2.400    2.400 peak    1851 weight   0.11000E+01 volume   0.20055E+03 ppm1    9.187 ppm2    4.645
ASSI ( 1861)
    ( ( segid *BrD * and resid 19 and name HN   ) )
    ( ( segid *BrD * and resid 19 and name HA   ) )
       2.800   2.000    2.000 peak    1861 weight   0.11000E+01 volume   0.37223E+03 ppm1    9.189 ppm2    4.285
ASSI ( 1881)
    ( ( segid *BrD * and resid 20 and name HN   ) )
    ( ( segid *BrD * and resid 19 and name HN   ) )
       2.800   2.000    2.000 peak    1881 weight   0.11000E+01 volume   0.39357E+03 ppm1    8.146 ppm2    9.170
ASSI ( 1901)
    ( ( segid *BrD * and resid 83 and name HN   ) )
    ( ( segid *BrD * and resid 83 and name HA   ) )
       2.800   2.000    2.000 peak    1901 weight   0.11000E+01 volume   0.35792E+03 ppm1    9.658 ppm2    4.447
ASSI ( 1911)
    ( ( segid *BrD * and resid 83 and name HN   ) )
    ( ( segid *BrD * and resid 83 and name HB   ) )
       2.700   1.800    1.800 peak    1911 weight   0.11000E+01 volume   0.45140E+03 ppm1    9.659 ppm2    4.817
ASSI ( 1921)
    ( ( segid *BrD * and resid 83 and name HN   ) )
    (   segid *BrD * and resid 83 and name HG2%)
       3.000   2.200    2.200 peak    1921 weight   0.11000E+01 volume   0.28097E+03 ppm1    9.659 ppm2    1.910
ASSI ( 1931)
    ( ( segid *BrD * and resid 84 and name HN   ) )
    ( ( segid *BrD * and resid 84 and name HA   ) )
       2.800   2.000    2.000 peak    1931 weight   0.11000E+01 volume   0.37490E+03 ppm1    9.464 ppm2    4.901
ASSI ( 1941)
    ( ( segid *BrD * and resid 84 and name HN   ) )
    ( ( segid *BrD * and resid 84 and name HB1  ) )
       2.800   2.000    2.000 peak    1941 weight   0.11000E+01 volume   0.42690E+03 ppm1    9.463 ppm2    3.592
ASSI ( 1951)
    ( ( segid *BrD * and resid 84 and name HN   ) )
    ( ( segid *BrD * and resid 84 and name HB1  ) )
       3.000   2.200    2.200 peak    1951 weight   0.11000E+01 volume   0.26963E+03 ppm1    9.463 ppm2    3.268
ASSI ( 1971)
    ( ( segid *BrD * and resid 83 and name HN   ) )
    ( ( segid *BrD * and resid 84 and name HN   ) )
       2.600   1.700    1.700 peak    1971 weight   0.11000E+01 volume   0.61276E+03 ppm1    9.658 ppm2    9.450
ASSI ( 1981)
    ( ( segid *BrD * and resid 85 and name HN   ) )
    ( ( segid *BrD * and resid 85 and name HA   ) )
       2.900   2.100    2.100 peak    1981 weight   0.11000E+01 volume   0.32851E+03 ppm1    7.516 ppm2    5.014
ASSI ( 1991)
    ( ( segid *BrD * and resid 85 and name HN   ) )
    ( ( segid *BrD * and resid 85 and name HB1  ) )
       2.800   2.000    2.000 peak    1991 weight   0.11000E+01 volume   0.39507E+03 ppm1    7.516 ppm2    3.919
ASSI ( 2011)
    ( ( segid *BrD * and resid 84 and name HN   ) )
    ( ( segid *BrD * and resid 85 and name HN   ) )
       2.800   2.000    2.000 peak    2011 weight   0.11000E+01 volume   0.37475E+03 ppm1    9.464 ppm2    7.497
```

TABLE 2-continued

Unambigous NOE-derived Inter-proton Distance Restraints

```
ASSI ( 2021)
    ( ( segid *BrD * and resid 86 and name HN   ) )
    ( ( segid *BrD * and resid 85 and name HB1  ) )
       3.200  2.600   2.300  peak    2021  weight   0.11000E+01 volume   0.17051E+03 ppm1   8.423 ppm2   3.911
ASSI ( 2031)
    ( ( segid *BrD * and resid 86 and name HN   ) )
    ( ( segid *BrD * and resid 86 and name HA   ) )
       2.800  2.000   2.000  peak    2031  weight   0.11000E+01 volume   0.42952E+03 ppm1   8.423 ppm2   4.809
ASSI ( 2051)
    ( ( segid *BrD * and resid 85 and name HN   ) )
    ( ( segid *BrD * and resid 86 and name HN   ) )
       2.800  2.000   2.000  peak    2051  weight   0.11000E+01 volume   0.39765E+03 ppm1   7.516 ppm2   8.406
ASSI ( 2061)
    ( ( segid *BrD * and resid 87 and name HN   ) )
    ( ( segid *BrD * and resid 86 and name HB1  ) )
       3.400  2.900   2.100  peak    2061  weight   0.11000E+01 volume   0.11283E+03 ppm1   8.570 ppm2   2.350
ASSI ( 2071)
    ( ( segid *BrD * and resid 87 and name HN   ) )
    ( ( segid *BrD * and resid 87 and name HA   ) )
       2.600  1.700   1.700  peak    2071  weight   0.11000E+01 volume   0.62404E+03 ppm1   8.572 ppm2   4.889
ASSI ( 2081)
    ( ( segid *BrD * and resid 87 and name HN   ) )
    ( ( segid *BrD * and resid 87 and name HG1  ) )
       3.000  2.200   2.200  peak    2081  weight   0.11000E+01 volume   0.28244E+03 ppm1   8.572 ppm2   3.014
ASSI ( 2091)
    ( ( segid *BrD * and resid 87 and name HN   ) )
    ( ( segid *BrD * and resid 87 and name HG2  ) )
       3.000  2.200   2.200  peak    2091  weight   0.11000E+01 volume   0.28579E+03 ppm1   8.570 ppm2   2.810
ASSI ( 2101)
    ( ( segid *BrD * and resid 87 and name HN   ) )
    ( ( segid *BrD * and resid 87 and name HB2  ) )
       2.700  1.800   1.800  peak    2101  weight   0.11000E+01 volume   0.46735E+03 ppm1   8.571 ppm2   2.607
ASSI ( 2111)
    ( ( segid *BrD * and resid 88 and name HN   ) )
    (   segid *BrD * and resid 88 and name HD %  )
       3.300  2.700   2.200  peak    2111  weight   0.11000E+01 volume   0.15320E+03 ppm1   8.355 ppm2   7.595
ASSI ( 2121)
    ( ( segid *BrD * and resid 88 and name HN   ) )
    ( ( segid *BrD * and resid 88 and name HA   ) )
       3.100  2.400   2.400  peak    2121  weight   0.11000E+01 volume   0.22276E+03 ppm1   8.356 ppm2   4.976
ASSI ( 2131)
    ( ( segid *BrD * and resid 88 and name HN   ) )
    ( ( segid *BrD * and resid 88 and name HB1  ) )
       2.500  1.600   1.600  peak    2131  weight   0.11000E+01 volume   0.72297E+03 ppm1   8.354 ppm2   3.536
ASSI ( 2151)
    ( ( segid *BrD * and resid 89 and name HN   ) )
    ( ( segid *BrD * and resid 89 and name HA   ) )
       3.000  2.200   2.200  peak    2151  weight   0.11000E+01 volume   0.26347E+03 ppm1   8.858 ppm2   3.631
ASSI ( 2161)
    ( ( segid *BrD * and resid 89 and name HN   ) )
    ( ( segid *BrD * and resid 89 and name HB1  ) )
       3.000  2.200   2.200  peak    2161  weight   0.11000E+01 volume   0.26996E+03 ppm1   8.858 ppm2   3.671
ASSI ( 2171)
    ( ( segid *BrD * and resid 89 and name HN   ) )
    ( ( segid *BrD * and resid 89 and name HB2  ) )
       2.400  1.400   1.400  peak    2171  weight   0.11000E+01 volume   0.10141E+04 ppm1   8.858 ppm2   3.508
ASSI ( 2191)
    ( ( segid *BrD * and resid 89 and name HN   ) )
    ( ( segid *BrD * and resid 89 and name HN   ) )
       2.600  1.700   1.700  peak    2191  weight   0.11000E+01 volume   0.42488E+03 ppm1   8.355 ppm2   8.848
ASSI ( 2201)
    ( ( segid *BrD * and resid 46 and name HN   ) )
    ( ( segid *BrD * and resid 47 and name HN   ) )
       2.800  2.000   2.000  peak    2201  weight   0.11000E+01 volume   0.36079E+03 ppm1   8.562 ppm2   8.836
ASSI ( 2211)
    ( ( segid *BrD * and resid 46 and name HN   ) )
    ( ( segid *BrD * and resid 46 and name HA   ) )
       2.700  1.800   1.800  peak    2211  weight   0.11000E+01 volume   0.49246E+03 ppm1   8.562 ppm2   4.125
ASSI ( 2221)
    ( ( segid *BrD * and resid 46 and name HN   ) )
    ( ( segid *BrD * and resid 46 and name HB1  ) )
       2.500  1.600   1.600  peak    2221  weight   0.11000E+01 volume   0.82312E+03 ppm1   8.561 ppm2   3.293
ASSI ( 2231)
    ( ( segid *BrD * and resid 46 and name HN   ) )
    ( ( segid *BrD * and resid 46 and name HB2  ) )
       2.500  1.600   1.600  peak    2231  weight   0.11000E+01 volume   0.72605E+03 ppm1   8.542 ppm2   3.098
```

TABLE 2-continued

Unambigous NOE-derived Inter-proton Distance Restraints

```
ASSI (  2241)
  ( ( segid *BrD * and resid 47 and name HN    ) )
  (  segid *BrD * and resid 47 and name HE % )
     3.700   3.400    1.800 peak     2241 weight    0.11000E+01 volume   0.71965E+02 ppm1    8.632 ppm2    7.253
ASSI (  2251)
  ( ( segid *BrD * and resid 47 and name HN    ) )
  ( ( segid *BrD * and resid 47 and name HA    ) )
     2.900   2.100    2.100 peak     2251 weight    0.11000E+01 volume   0.34426E+03 ppm1    8.631 ppm2    4.708
ASSI (  2261)
  ( ( segid *BrD * and resid 47 and name HN    ) )
  ( ( segid *BrD * and resid 47 and name HB1   ) )
     2.800   2.000    2.000 peak     2261 weight    0.11000E+01 volume   0.37063E+03 ppm1    8.633 ppm2    3.807
ASSI (  2271)
  ( ( segid *BrD * and resid 47 and name HN    ) )
  ( ( segid *BrD * and resid 47 and name HB2   ) )
     2.900   2.100    2.100 peak     2271 weight    0.11000E+01 volume   0.34763E+03 ppm1    8.832 ppm2    3.391
ASSI (  2281)
  ( ( segid *BrD * and resid 48 and name HN    ) )
  ( ( segid *BrD * and resid 48 and name HA    ) )
     2.800   2.000    2.000 peak     2281 weight    0.11000E+01 volume   0.37621E+03 ppm1    8.307 ppm2    4.815
ASSI (  2291)
  ( ( segid *BrD * and resid 48 and name HN    ) )
  ( ( segid *BrD * and resid 48 and name HG2   ) )
     3.300   2.700    2.200 peak     2291 weight    0.11000E+01 volume   0.14081E+03 ppm1    8.308 ppm2    2.657
ASSI (  2301)
  ( ( segid *BrD * and resid 48 and name HN    ) )
  ( ( segid *BrD * and resid 48 and name HB1   ) )
     2.400   1.400    1.400 peak     2301 weight    0.11000E+01 volume   0.11018E+04 ppm1    8.308 ppm2    2.498
ASSI (  2321)
  ( ( segid *BrD * and resid 47 and name HN    ) )
  ( ( segid *BrD * and resid 48 and name HN    ) )
     2.700   1.800    1.800 peak     2321 weight    0.11000E+01 volume   0.47004E+03 ppm1    8.832 ppm2    8.310
ASSI (  2341)
  ( ( segid *BrD * and resid 49 and name HN    ) )
  ( ( segid *BrD * and resid 49 and name HA    ) )
     2.600   1.700    1.700 peak     2341 weight    0.11000E+01 volume   0.63035E+03 ppm1    7.762 ppm2    4.690
ASSI (  2351)
  ( ( segid *BrD * and resid 49 and name HN    ) )
  ( ( segid *BrD * and resid 49 and name HB    ) )
     3.100   2.400    2.400 peak     2351 weight    0.11000E+01 volume   0.22961E+03 ppm1    7.762 ppm2    2.611
ASSI (  2361)
  ( ( segid *BrD * and resid 83 and name HN    ) )
  (  segid *BrD * and resid 83 and name HG2%)
     3.300   2.700    2.200 peak     2361 weight    0.11000E+01 volume   0.15115E+03 ppm1    7.762 ppm2    1.586
ASSI (  2381)
  ( ( segid *BrD * and resid 48 and name HN    ) )
  ( ( segid *BrD * and resid 49 and name HN    ) )
     2.400   1.400    1.400 peak     2381 weight    0.11000E+01 volume   0.95252E+03 ppm1    8.308 ppm2    7.742
ASSI (  2391)
  ( ( segid *BrD * and resid 50 and name HN    ) )
  ( ( segid *BrD * and resid 51 and name HN    ) )
     2.600   1.700    1.700 peak     2391 weight    0.11000E+01 volume   0.55801E+03 ppm1    8.559 ppm2    8.318
ASSI (  2401)
  ( ( segid *BrD * and resid 50 and name HN    ) )
  ( ( segid *BrD * and resid 50 and name HA    ) )
     2.700   1.800    1.800 peak     2401 weight    0.11000E+01 volume   0.45800E+03 ppm1    8.564 ppm2    4.525
ASSI (  2421)
  ( ( segid *BrD * and resid 49 and name HN    ) )
  ( ( segid *BrD * and resid 50 and name HN    ) )
     2.400   1.400    1.400 peak     2421 weight    0.11000E+01 volume   0.91502E+03 ppm1    7.762 ppm2    8.554
ASSI (  2431)
  ( ( segid *BrD * and resid 115 and name HN   ) )
  ( ( segid *BrD * and resid 114 and name HA2  ) )
     3.100   2.400    2.400 peak     2431 weight    0.11000E+01 volume   0.20145E+03 ppm1    8.355 ppm2    4.542
ASSI (  2441)
  ( ( segid *BrD * and resid 115 and name HN   ) )
  ( ( segid *BrD * and resid 115 and name HA   ) )
     2.800   2.000    2.000 peak     2441 weight    0.11000E+01 volume   0.38387E+03 ppm1    8.355 ppm2    4.822
ASSI (  2451)
  ( ( segid *BrD * and resid 116 and name HN   ) )
  ( ( segid *BrD * and resid 115 and name HB1  ) )
     2.700   1.800    1.800 peak     2451 weight    0.11000E+01 volume   0.51528E+03 ppm1    8.086 ppm2    2.169
ASSI (  2461)
  ( ( segid *BrD * and resid 116 and name HN   ) )
  ( ( segid *BrD * and resid 116 and name HA   ) )
     2.500   1.600    1.600 peak     2461 weight    0.11000E+01 volume   0.81456E+03 ppm1    8.087 ppm2    4.828
```

TABLE 2-continued

Unambigous NOE-derived Inter-proton Distance Restraints

```
ASSI ( 2471)
    ( ( segid *BrD * and resid 116 and name HN   ) )
    ( ( segid *BrD * and resid 116 and name HB   ) )
        2.600   1.700   1.700 peak    2471 weight   0.11000E+01 volume   0.58085E+03 ppm1    8.086 ppm2   2.419
ASSI ( 2481)
    ( ( segid *BrD * and resid 117 and name HN   ) )
    ( ( segid *BrD * and resid 117 and name HA   ) )
        3.300   2.700   2.200 peak    2481 weight   0.11000E+01 volume   0.15334E+03 ppm1    8.880 ppm2   5.171
ASSI ( 2491)
    ( ( segid *BrD * and resid 117 and name HN   ) )
    ( ( segid *BrD * and resid 117 and name HB1  ) )
        3.300   2.700   2.200 peak    2491 weight   0.11000E+01 volume   0.14660E+03 ppm1    8.879 ppm2   3.300
ASSI ( 2501)
    ( ( segid *BrD * and resid 117 and name HN   ) )
    ( ( segid *BrD * and resid 117 and name HB2  ) )
        2.800   2.000   2.000 peak    2501 weight   0.11000E+01 volume   0.41931E+03 ppm1    8.879 ppm2   3.147
ASSI ( 2511)
    ( ( segid *BrD * and resid 51 and name HN    ) )
    ( ( segid *BrD * and resid 51 and name HA    ) )
        2.300   1.300   1.300 peak    2511 weight   0.11000E+01 volume   0.13843E+04 ppm1    8.377 ppm2   4.475
ASSI ( 2521)
    ( ( segid *BrD * and resid 51 and name HN    ) )
    ( ( segid *BrD * and resid 51 and name HG1   ) )
        2.900   2.100   2.100 peak    2521 weight   0.11000E+01 volume   0.29957E+03 ppm1    8.375 ppm2   1.933
ASSI ( 2531)
    ( ( segid *BrD * and resid 17 and name HN    ) )
    ( ( segid *BrD * and resid 17 and name HB    ) )
        3.000   2.200   2.200 peak    2531 weight   0.11000E+01 volume   0.26023E+03 ppm1    8.679 ppm2   4.860
ASSI ( 2541)
    ( ( segid *BrD * and resid 17 and name HN    ) )
    ( ( segid *BrD * and resid 17 and name HA    ) )
        2.400   1.400   1.400 peak    2541 weight   0.11000E+01 volume   0.10062E+04 ppm1    8.678 ppm2   4.571
ASSI ( 2551)
    ( ( segid *BrD * and resid 17 and name HN    ) )
    (   segid *BrD * and resid 17 and name HG2%)
        3.100   2.400   2.400 peak    2551 weight   0.11000E+01 volume   0.20185E+03 ppm1    8.670 ppm2   1.745
ASSI ( 2561)
    ( ( segid *BrD * and resid 101 and name HN   ) )
    ( ( segid *BrD * and resid 100 and name HB2  ) )
        2.800   2.000   2.000 peak    2561 weight   0.11000E+01 volume   0.38883E+03 ppm1    8.513 ppm2   3.441
ASSI ( 2571)
    ( ( segid *BrD * and resid 101 and name HN   ) )
    ( ( segid *BrD * and resid 101 and name HA   ) )
        2.800   2.000   2.000 peak    2571 weight   0.11000E+01 volume   0.37743E+03 ppm1    8.523 ppm2   4.264
ASSI ( 2591)
    ( ( segid *BrD * and resid 100 and name HN   ) )
    ( ( segid *BrD * and resid 101 and name HN   ) )
        2.600   1.700   1.700 peak    2591 weight   0.11000E+01 volume   0.62929E+03 ppm1    8.669 ppm2   8.521
ASSI ( 2601)
    ( ( segid *BrD * and resid 102 and name HN   ) )
    ( ( segid *BrD * and resid 102 and name HA   ) )
        2.900   2.100   2.100 peak    2601 weight   0.11000E+01 volume   0.34745E+03 ppm1    9.156 ppm2   4.280
ASSI ( 2611)
    ( ( segid *BrD * and resid 102 and name HN   ) )
    ( ( segid *BrD * and resid 101 and name HN   ) )
        2.700   1.800   1.800 peak    2611 weight   0.11000E+01 volume   0.52631E+03 ppm1    9.156 ppm2   8.513
ASSI ( 2641)
    ( ( segid *BrD * and resid 103 and name HN   ) )
    ( ( segid *BrD * and resid 103 and name HA   ) )
        2.800   2.000   2.000 peak    2641 weight   0.11000E+01 volume   0.41836E+03 ppm1    8.695 ppm2   3.800
ASSI ( 2651)
    ( ( segid *BrD * and resid 103 and name HN   ) )
    ( ( segid *BrD * and resid 103 and name HB2  ) )
        2.800   2.000   2.000 peak    2651 weight   0.11000E+01 volume   0.35593E+03 ppm1    8.696 ppm2   1.928
ASSI ( 2661)
    ( ( segid *BrD * and resid 103 and name HN   ) )
    ( ( segid *BrD * and resid 103 and name HB1  ) )
        2.500   1.600   1.600 peak    2661 weight   0.11000E+01 volume   0.72768E+03 ppm1    8.695 ppm2   2.353
ASSI ( 2671)
    ( ( segid *BrD * and resid 103 and name HN   ) )
    ( ( segid *BrD * and resid 103 and name HG2  ) )
        3.200   2.600   2.300 peak    2671 weight   0.11000E+01 volume   0.18331E+03 ppm1    8.695 ppm2   2.529
ASSI ( 2681)
    ( ( segid *BrD * and resid 103 and name HN   ) )
    ( ( segid *BrD * and resid 102 and name HN   ) )
        2.600   1.700   1.700 peak    2681 weight   0.11000E+01 volume   0.48597E+03 ppm1    8.694 ppm2   9.157
```

TABLE 2-continued

Unambigous NOE-derived Inter-proton Distance Restraints

```
ASSI ( 2711)
    ( ( segid *BrD * and resid 104 and name HN   ) )
    ( ( segid *BrD * and resid 104 and name HA   ) )
     2.600  1.700   1.700 peak    2711 weight   0.11000E+01 volume  0.66065E+03 ppm1   7.763 ppm2   4.690
ASSI ( 2731)
    ( ( segid *BrD * and resid 104 and name HN   ) )
    ( ( segid *BrD * and resid 103 and name HN   ) )
     2.800  2.000   2.000 peak    2731 weight   0.11000E+01 volume  0.40496E+03 ppm1   7.763 ppm2   8.680
ASSI ( 2751)
    ( ( segid *BrD * and resid 104 and name HN   ) )
    ( ( segid *BrD * and resid 105 and name HN   ) )
     2.700  1.800   1.800 peak    2751 weight   0.11000E+01 volume  0.54532E+03 ppm1   7.763 ppm2   8.475
ASSI ( 2771)
    ( ( segid *BrD * and resid 79 and name HN   ) )
    (   segid *BrD * and resid 78 and name HG1%)
     3.900  3.800   1.600 peak    2771 weight   0.11000E+01 volume  0.50980E+02 ppm1   8.685 ppm2   0.788
ASSI ( 2781)
    ( ( segid *BrD * and resid 81 and name HN   ) )
    ( ( segid *BrD * and resid 81 and name HA   ) )
     3.300  2.700   2.200 peak    2781 weight   0.11000E+01 volume  0.15663E+03 ppm1   7.640 ppm2   3.711
ASSI ( 2791)
    ( ( segid *BrD * and resid 81 and name HN   ) )
    ( ( segid *BrD * and resid 81 and name HB   ) )
     2.500  1.600   1.600 peak    2791 weight   0.11000E+01 volume  0.72728E+03 ppm1   7.640 ppm2   2.037
ASSI ( 2801)
    ( ( segid *BrD * and resid 81 and name HN   ) )
    (   segid *BrD * and resid 81 and name HG1%)
     2.500  1.600   1.600 peak    2801 weight   0.11000E+01 volume  0.82553E+03 ppm1   7.640 ppm2   1.071
ASSI ( 2811)
    ( ( segid *BrD * and resid 81 and name HN   ) )
    (   segid *BrD * and resid 81 and name HG2%)
     3.100  2.400   2.400 peak    2811 weight   0.11000E+01 volume  0.22921E+03 ppm1   7.640 ppm2   0.751
ASSI ( 2821)
    ( ( segid *BrD * and resid 82 and name HN   ) )
    (   segid *BrD * and resid 82 and name HD %  )
     3.000  2.200   2.200 peak    2821 weight   0.11000E+01 volume  0.28368E+03 ppm1   6.981 ppm2   7.258
ASSI ( 2831)
    ( ( segid *BrD * and resid 82 and name HN   ) )
    ( ( segid *BrD * and resid 82 and name HA   ) )
     2.800  2.000   2.000 peak    2831 weight   0.11000E+01 volume  0.42147E+03 ppm1   6.981 ppm2   4.738
ASSI ( 2841)
    ( ( segid *BrD * and resid 82 and name HN   ) )
    ( ( segid *BrD * and resid 82 and name HB1   ) )
     3.000  2.200   2.200 peak    2841 weight   0.11000E+01 volume  0.27134E+03 ppm1   6.981 ppm2   3.706
ASSI ( 2851)
    ( ( segid *BrD * and resid 82 and name HN   ) )
    ( ( segid *BrD * and resid 82 and name HB2   ) )
     2.600  1.700   1.700 peak    2851 weight   0.11000E+01 volume  0.58897E+03 ppm1   6.981 ppm2   3.556
ASSI ( 2871)
    ( ( segid *BrD * and resid 81 and name HN   ) )
    ( ( segid *BrD * and resid 82 and name HN   ) )
     2.800  2.000   2.000 peak    2871 weight   0.11000E+01 volume  0.36428E+03 ppm1   7.640 ppm2   6.966
ASSI ( 2891)
    ( ( segid *BrD * and resid 82 and name HN   ) )
    ( ( segid *BrD * and resid 83 and name HN   ) )
     2.800  2.000   2.000 peak    2891 weight   0.11000E+01 volume  0.42793E+03 ppm1   6.981 ppm2   9.658
ASSI ( 2901)
    ( ( segid *BrD * and resid 79 and name HN   ) )
    (   segid *BrD * and resid 78 and name HD2%)
     3.900  3.600   1.600 peak    2901 weight   0.11000E+01 volume  0.52951E+02 ppm1   8.684 ppm2   0.666
ASSI ( 2911)
    ( ( segid *BrD * and resid 80 and name HN   ) )
    ( ( segid *BrD * and resid 80 and name HA   ) )
     2.500  1.600   1.600 peak    2911 weight   0.11000E+01 volume  0.82068E+03 ppm1   8.005 ppm2   4.678
ASSI ( 2921)
    ( ( segid *BrD * and resid 80 and name HN   ) )
    ( ( segid *BrD * and resid 81 and name HN   ) )
     2.700  1.800   1.800 peak    2921 weight   0.11000E+01 volume  0.47132E+03 ppm1   8.004 ppm2   7.632
ASSI ( 2941)
    ( ( segid *BrD * and resid 83 and name HN   ) )
    (   segid *BrD * and resid 82 and name HD %  )
     3.400  2.900   2.100 peak    2941 weight   0.11000E+01 volume  0.12712E+03 ppm1   9.658 ppm2   7.248
ASSI ( 2951)
    ( ( segid *BrD * and resid 79 and name HN   ) )
    ( ( segid *BrD * and resid 79 and name HA   ) )
     2.600  1.700   1.700 peak    2951 weight   0.11000E+01 volume  0.57654E+03 ppm1   8.681 ppm2   4.406
```

TABLE 2-continued

Unambigous NOE-derived Inter-proton Distance Restraints

```
ASSI ( 2961)
   ( ( segid *BrD * and resid 79 and name HN   ) )
   ( ( segid *BrD * and resid 79 and name HG1  ) )
     2.900  2.100   2.100 peak    2961 weight   0.11000E+01 volume   0.30890E+03 ppm1    8.681 ppm2    3.055
ASSI ( 2971)
   ( ( segid *BrD * and resid 79 and name HN   ) )
   ( ( segid *BrD * and resid 79 and name HB2  ) )
     2.500  1.600   1.600 peak    2971 weight   0.11000E+01 volume   0.78107E+03 ppm1    8.679 ppm2    2.684
ASSI ( 2981)
   ( ( segid *BrD * and resid 80 and name HN   ) )
   ( ( segid *BrD * and resid 79 and name HN   ) )
     2.700  1.800   1.800 peak    2981 weight   0.11000E+01 volume   0.45960E+03 ppm1    8.006 ppm2    8.676
ASSI ( 3001)
   ( ( segid *BrD * and resid 74 and name HN   ) )
   ( ( segid *BrD * and resid 72 and name HA   ) )
     3.500  3.100   2.000 peak    3001 weight   0.11000E+01 volume   0.94034E+02 ppm1    7.536 ppm2    4.666
ASSI ( 3011)
   ( ( segid *BrD * and resid 73 and name HN   ) )
   ( ( segid *BrD * and resid 73 and name HA   ) )
     2.600  1.700   1.700 peak    3011 weight   0.11000E+01 volume   0.57896E+03 ppm1    8.045 ppm2    4.811
ASSI ( 3021)
   ( ( segid *BrD * and resid 73 and name HN   ) )
   ( ( segid *BrD * and resid 74 and name HN   ) )
     2.800  2.000   2.000 peak    3021 weight   0.11000E+01 volume   0.42186E+03 ppm1    8.049 ppm2    7.542
ASSI ( 3041)
   ( ( segid *BrD * and resid 64 and name HN   ) )
   ( ( segid *BrD * and resid 63 and name HA   ) )
     3.100  2.400   2.400 peak    3041 weight   0.11000E+01 volume   0.20596E+03 ppm1    8.584 ppm2    5.298
ASSI ( 3051)
   ( ( segid *BrD * and resid 64 and name HN   ) )
   ( ( segid *BrD * and resid 64 and name HA   ) )
     2.600  1.700   1.700 peak    3051 weight   0.11000E+01 volume   0.63748E+03 ppm1    8.584 ppm2    4.940
ASSI ( 3061)
   ( ( segid *BrD * and resid 63 and name HN   ) )
   ( ( segid *BrD * and resid 63 and name HA   ) )
     2.900  2.100   2.100 peak    3061 weight   0.11000E+01 volume   0.33289E+03 ppm1    9.473 ppm2    5.302
ASSI ( 3071)
   ( ( segid *BrD * and resid 63 and name HN   ) )
   ( ( segid *BrD * and resid 64 and name HN   ) )
     2.600  1.700   1.700 peak    3071 weight   0.11000E+01 volume   0.48875E+03 ppm1    9.478 ppm2    8.565
ASSI ( 3091)
   ( ( segid *BrD * and resid 38 and name HN   ) )
   ( ( segid *BrD * and resid 38 and name HA   ) )
     3.100  2.400   2.400 peak    3091 weight   0.11000E+01 volume   0.21794E+03 ppm1    8.732 ppm2    4.166
ASSI ( 3101)
   ( ( segid *BrD * and resid 38 and name HN   ) )
   ( ( segid *BrD * and resid 38 and name HB   ) )
     2.500  1.600   1.600 peak    3101 weight   0.11000E+01 volume   0.76036E+03 ppm1    8.731 ppm2    1.767
ASSI ( 3111)
   ( ( segid *BrD * and resid 38 and name HN   ) )
   (  segid *BrD * and resid 38 and name HG1%)
     2.400  1.400   1.400 peak    3111 weight   0.11000E+01 volume   0.94284E+03 ppm1    8.733 ppm2    1.071
ASSI ( 3121)
   ( ( segid *BrD * and resid 38 and name HN   ) )
   (  segid *BrD * and resid 38 and name HG2%)
     4.000  4.000   1.500 peak    3121 weight   0.11000E+01 volume   0.47989E+02 ppm1    8.732 ppm2    0.784
ASSI ( 3131)
   ( ( segid *BrD * and resid 39 and name HN   ) )
   ( ( segid *BrD * and resid 39 and name HA   ) )
     3.400  3.200   1.900 peak    3131 weight   0.11000E+01 volume   0.90084E+02 ppm1    9.653 ppm2    4.977
ASSI ( 3141)
   ( ( segid *BrD * and resid 58 and name HN   ) )
   ( ( segid *BrD * and resid 58 and name HA   ) )
     2.900  2.100   2.100 peak    3141 weight   0.11000E+01 volume   0.34424E+03 ppm1   10.051 ppm2    4.451
ASSI ( 3151)
   ( ( segid *BrD * and resid 58 and name HN   ) )
   ( ( segid *BrD * and resid 58 and name HB   ) )
     2.900  2.100   2.100 peak    3151 weight   0.11000E+01 volume   0.30448E+03 ppm1   10.052 ppm2    4.686
ASSI ( 3161)
   ( ( segid *BrD * and resid 58 and name HN   ) )
   (  segid *BrD * and resid 58 and name HG2%)
     3.700  3.400   1.800 peak    3161 weight   0.11000E+01 volume   0.68430E+02 ppm1   10.051 ppm2    1.674
ASSI ( 3171)
   ( ( segid *BrD * and resid 57 and name HN   ) )
   ( ( segid *BrD * and resid 57 and name HA   ) )
     2.700  1.800   1.800 peak    3171 weight   0.11000E+01 volume   0.45739E+03 ppm1    9.359 ppm2    4.809
```

TABLE 2-continued

Unambigous NOE-derived Inter-proton Distance Restraints

```
ASSI ( 3191)
    ( ( segid *BrD * and resid 58 and name HN   ) )
    ( ( segid *BrD * and resid 57 and name HN   ) )
      2.600  1.700   1.700 peak     3191 weight   0.11000E+01 volume  0.55403E+03 ppm1   10.051 ppm2   9.251
ASSI ( 3201)
    ( ( segid *BrD * and resid 56 and name HN   ) )
    ( ( segid *BrD * and resid 56 and name HA   ) )
      3.100  2.400   2.400 peak     3201 weight   0.11000E+01 volume  0.22011E+03 ppm1    9.478 ppm2   4.622
ASSI ( 3221)
    ( ( segid *BrD * and resid 57 and name HN   ) )
    ( ( segid *BrD * and resid 56 and name HN   ) )
      3.100  2.400   2.400 peak     3221 weight   0.11000E+01 volume  0.21874E+03 ppm1    9.359 ppm2   9.662
ASSI ( 3231)
    ( ( segid *BrD * and resid 79 and name HN   ) )
    ( ( segid *BrD * and resid 78 and name HB2  ) )
      3.200  2.600   2.300 peak     3231 weight   0.11000E+01 volume  0.19421E+03 ppm1    8.680 ppm2   1.049
ASSI ( 3241)
    ( ( segid *BrD * and resid 55 and name HN   ) )
    ( ( segid *BrD * and resid 55 and name HA   ) )
      2.600  1.700   1.700 peak     3241 weight   0.11000E+01 volume  0.57256E+03 ppm1    7.973 ppm2   5.343
ASSI ( 3251)
    ( ( segid *BrD * and resid 55 and name HN   ) )
    ( ( segid *BrD * and resid 55 and name HB1  ) )
      3.200  2.600   2.300 peak     3251 weight   0.11000E+01 volume  0.19260E+03 ppm1    7.975 ppm2   2.971
ASSI ( 3271)
    ( ( segid *BrD * and resid 16 and name HN   ) )
    ( ( segid *BrD * and resid 16 and name HA   ) )
      2.500  1.600   1.600 peak     3271 weight   0.11000E+01 volume  0.81267E+03 ppm1    8.792 ppm2   4.514
ASSI ( 3281)
    ( ( segid *BrD * and resid 15 and name HN   ) )
    ( ( segid *BrD * and resid 11 and name HA   ) )
      3.600  3.200   1.900 peak     3281 weight   0.11000E+01 volume  0.88513E+02 ppm1    8.599 ppm2   4.936
ASSI ( 3291)
    ( ( segid *BrD * and resid 15 and name HN   ) )
    ( ( segid *BrD * and resid 15 and name HA   ) )
      3.000  2.200   2.200 peak     3291 weight   0.11000E+01 volume  0.23859E+03 ppm1    8.599 ppm2   4.615
ASSI ( 3301)
    ( ( segid *BrD * and resid 15 and name HN   ) )
    ( ( segid *BrD * and resid 15 and name HB1  ) )
      2.600  1.700   1.700 peak     3301 weight   0.11000E+01 volume  0.66455E+03 ppm1    8.598 ppm2   3.809
ASSI ( 3311)
    ( ( segid *BrD * and resid 15 and name HN   ) )
    ( ( segid *BrD * and resid 15 and name HB2  ) )
      2.500  1.600   1.600 peak     3211 weight   0.11000E+01 volume  0.74771E+03 ppm1    8.598 ppm2   3.634
ASSI ( 3331)
    ( ( segid *BrD * and resid 16 and name HN   ) )
    ( ( segid *BrD * and resid 15 and name HN   ) )
      2.500  1.600   1.600 peak     3331 weight   0.11000E+01 volume  0.87721E+03 ppm1    8.793 ppm2   4.628
ASSI ( 3341)
    ( ( segid *BrD * and resid 13 and name HN   ) )
    ( ( segid *BrD * and resid 13 and name HA   ) )
      3.200  2.600   2.300 peak     3341 weight   0.11000E+01 volume  0.16876E+03 ppm1    8.801 ppm2   4.773
ASSI ( 3351)
    ( ( segid *BrD * and resid 14 and name HN   ) )
    ( ( segid *BrD * and resid 14 and name HA   ) )
      3.300  2.700   2.200 peak     3351 weight   0.11000E+01 volume  0.15715E+03 ppm1    8.811 ppm2   4.652
ASSI ( 3381)
    ( ( segid *BrD * and resid 13 and name HN   ) )
    ( ( segid *BrD * and resid 13 and name HB1  ) )
      2.300  2.300   1.300 peak     3381 weight   0.11000E+01 volume  0.12106E+04 ppm1    8.807 ppm2   2.758
ASSI ( 3391)
    ( ( segid *BrD * and resid 14 and name HN   ) )
    ( ( segid *BrD * and resid 11 and name HA   ) )
      3.300  2.700   2.200 peak     3391 weight   0.11000E+01 volume  0.15172E+03 ppm1    8.809 ppm2   4.939
ASSI ( 3411)
    ( ( segid *BrD * and resid 34 and name HN   ) )
    ( ( segid *BrD * and resid 31 and name HA   ) )
      2.800  2.000   2.000 peak     3411 weight   0.11000E+01 volume  0.39310E+03 ppm1    8.176 ppm2   5.542
ASSI ( 3421)
    ( ( segid *BrD * and resid 34 and name HN   ) )
    ( ( segid *BrD * and resid 34 and name HB1  ) )
      3.600  3.200   1.900 peak     3421 weight   0.11000E+01 volume  0.86588E+02 ppm1    8.182 ppm2   4.098
ASSI ( 3431)
    ( ( segid *BrD * and resid 34 and name HN   ) )
    ( ( segid *BrD * and resid 34 and name HB2  ) )
      2.700  1.800   1.800 peak     3431 weight   0.11000E+01 volume  0.51957E+03 ppm1    8.182 ppm2   3.143
```

TABLE 2-continued

Unambigous NOE-derived Inter-proton Distance Restraints

```
ASSI ( 3441)
    ( ( segid *BrD * and resid 34 and name HN   ) )
    ( ( segid *BrD * and resid 34 and name HB2  ) )
      3.300  2.700   2.200 peak    3441 weight   0.11000E+01 volume  0.14464E+03 ppm1    7.735 ppm2   3.139
ASSI ( 3451)
    ( ( segid *BrD * and resid 35 and name HN   ) )
    ( ( segid *BrD * and resid 35 and name HA   ) )
      2.800  2.000   2.000 peak    3451 weight   0.11000E+01 volume  0.42792E+03 ppm1    7.734 ppm2   4.699
ASSI ( 3461)
    ( ( segid *BrD * and resid 35 and name HN   ) )
    ( ( segid *BrD * and resid 35 and name HG1  ) )
      2.700  1.800   1.800 peak    3461 weight   0.11000E+01 volume  0.54517E+03 ppm1    7.734 ppm2   3.436
ASSI ( 3471)
    ( ( segid *BrD * and resid 35 and name HN   ) )
    ( ( segid *BrD * and resid 35 and name HB2  ) )
      3.300  2.700   2.200 peak    3471 weight   0.11000E+01 volume  0.15293E+03 ppm1    7.733 ppm2   2.781
ASSI ( 3491)
    ( ( segid *BrD * and resid 34 and name HN   ) )
    ( ( segid *BrD * and resid 35 and name HN   ) )
      2.200  1.200   1.200 peak    3491 weight   0.11000E+01 volume  0.15285E+04 ppm1    8.176 ppm2   7.714
ASSI ( 3501)
    ( ( segid *BrD * and resid 36 and name HN   ) )
    ( ( segid *BrD * and resid 36 and name HA   ) )
      2.600  1.700   1.700 peak    3501 weight   0.11000E+01 volume  0.56896E+03 ppm1    8.320 ppm2   5.456
ASSI ( 3511)
    ( ( segid *BrD * and resid 36 and name HN   ) )
    ( ( segid *BrD * and resid 36 and name HG1  ) )
      3.700  3.400   1.800 peak    3511 weight   0.11000E+01 volume  0.72744E+02 ppm1    8.308 ppm2   2.771
ASSI ( 3521)
    ( ( segid *BrD * and resid 36 and name HN   ) )
    ( ( segid *BrD * and resid 36 and name HB2  ) )
      2.600  1.700   1.700 peak    3521 weight   0.11000E+01 volume  0.65455E+03 ppm1    8.311 ppm2   2.337
ASSI ( 3541)
    ( ( segid *BrD * and resid 35 and name HN   ) )
    ( ( segid *BrD * and resid 36 and name HN   ) )
      2.700  1.800   1.800 peak    3541 weight   0.11000E+01 volume  0.54251E+03 ppm1    7.734 ppm2   6.316
ASSI ( 3561)
    ( ( segid *BrD * and resid 12 and name HN   ) )
    ( ( segid *BrD * and resid 12 and name HA   ) )
      2.100  1.100   1.100 peak    3561 weight   0.11000E+01 volume  0.19935E+04 ppm1    9.021 ppm2   5.292
ASSI ( 3571)
    ( ( segid *BrD * and resid 12 and name HN   ) )
    ( ( segid *BrD * and resid 12 and name HB1  ) )
      2.700  1.800   1.800 peak    3571 weight   0.11000E+01 volume  0.46239E+03 ppm1    9.020 ppm2   3.426
ASSI ( 3581)
    ( ( segid *BrD * and resid 10 and name HN   ) )
    ( ( segid *BrD * and resid 10 and name HA   ) )
      3.500  3.100   2.000 peak    3581 weight   0.11000E+01 volume  0.10021E+03 ppm1    8.885 ppm2   5.482
ASSI ( 3591)
    ( ( segid *BrD * and resid 10 and name HN   ) )
    ( ( segid *BrD * and resid 10 and name HB1  ) )
      3.000  2.200   2.200 peak    3591 weight   0.11000E+01 volume  0.27522E+03 ppm1    8.885 ppm2   3.361
ASSI ( 3611)
    ( ( segid *BrD * and resid 9 and name HN    ) )
    ( ( segid *BrD * and resid 9 and name HB1   ) )
      2.900  2.100   2.100 peak    3611 weight   0.11000E+01 volume   0.3864E+03 ppm1    9.054 ppm2   2.444
ASSI ( 3621)
    ( ( segid *BrD * and resid 9 and name HN    ) )
    ( ( segid *BrD * and resid 10 and name HN   ) )
      3.500  3.100   2.000 peak    3621 weight   0.11000E+01 volume  0.11024E+03 ppm1    9.054 ppm2   8.680
ASSI ( 3641)
    ( ( segid *BrD * and resid 62 and name HN   ) )
    ( ( segid *BrD * and resid 62 and name HD1  ) )
      3.400  2.900   2.100 peak    3641 weight   0.11000E+01 volume  0.12186E+03 ppm1    8.998 ppm2   3.185
ASSI ( 3651)
    ( ( segid *BrD * and resid 62 and name HN   ) )
    ( ( segid *BrD * and resid 61 and name HG2  ) )
      3.000  2.200   2.200 peak    3651 weight   0.11000E+01 volume  0.24395E+03 ppm1    8.999 ppm2   2.783
ASSI ( 3661)
    ( ( segid *BrD * and resid 62 and name HN   ) )
    ( ( segid *BrD * and resid 62 and name HG1  ) )
      2.600  1.700   1.700 peak    3661 weight   0.11000E+01 volume  0.63487E+03 ppm1    8.997 ppm2   2.329
ASSI ( 3681)
    ( ( segid *BrD * and resid 7 and name HN    ) )
    ( ( segid *BrD * and resid 7 and name HA    ) )
      3.100  2.400   2.400 peak    3681 weight   0.11000E+01 volume  0.21276E+03 ppm1    8.924 ppm2   5.147
```

TABLE 2-continued

Unambigous NOE-derived Inter-proton Distance Restraints

```
ASSI ( 3691)
   ( ( segid *BrD * and resid 7 and name HN    ) )
   ( ( segid *BrD * and resid 7 and name HG1   ) )
      3.400  2.900   2.100 peak    3691 weight   0.11000E+01 volume   0.12947E+03 ppm1     8.923 ppm2    2.878
ASSI ( 3701)
   ( ( segid *BrD * and resid 7 and name HN    ) )
   ( ( segid *BrD * and resid 7 and name HB1   ) )
      3.100  2.400   2.400 peak    3701 weight   0.11000E+01 volume   0.20103E+03 ppm1     8.923 ppm2    2.631
ASSI ( 3711)
   ( ( segid *BrD * and resid 7 and name HN    ) )
   ( ( segid *BrD * and resid 7 and name HB2   ) )
      2.700  1.800   1.800 peak    3711 weight   0.11000E+01 volume   0.54229E+03 ppm1     8.924 ppm2    2.500
ASSI ( 3721)
   ( ( segid *BrD * and resid 79 and name HN   ) )
   ( ( segid *BrD * and resid 79 and name HG   ) )
      2.800  2.000   2.000 peak    3721 weight   0.11000E+01 volume   0.38659E+03 ppm1     8.681 ppm2    1.314
ASSI ( 3731)
   ( ( segid *BrD * and resid 78 and name HN   ) )
   ( ( segid *BrD * and resid 78 and name HA   ) )
      2.500  1.600   1.600 peak    3731 weight   0.11000E+01 volume   0.73125E+03 ppm1     7.996 ppm2    4.004
ASSI ( 3741)
   ( ( segid *BrD * and resid 78 and name HN   ) )
   ( ( segid *BrD * and resid 78 and name HA   ) )
      2.900  2.100   2.100 peak    3741 weight   0.11000E+01 volume   0.30830E+03 ppm1     8.381 ppm2    4.689
ASSI ( 3761)
   ( ( segid *BrD * and resid 54 and name HN   ) )
   ( ( segid *BrD * and resid 54 and name HA   ) )
      2.900  2.100   2.100 peak    3761 weight   0.11000E+01 volume   0.30432E+03 ppm1     9.036 ppm2    5.546
ASSI ( 3771)
   ( ( segid *BrD * and resid 54 and name HN   ) )
   ( ( segid *BrD * and resid 54 and name HB1  ) )
      3.400  2.900   2.100 peak    3771 weight   0.11000E+01 volume   0.12506E+03 ppm1     9.036 ppm2    2.596
ASSI ( 3781)
   ( ( segid *BrD * and resid 54 and name HN   ) )
   ( ( segid *BrD * and resid 54 and name HB2  ) )
      3.600  2.200   1.900 peak    3781 weight   0.11000E+01 volume   0.92666E+02 ppm1     9.037 ppm2    1.960
ASSI ( 3791)
   ( ( segid *BrD * and resid 62 and name HN   ) )
   ( ( segid *BrD * and resid 59 and name HA   ) )
      3.200  2.600   2.300 peak    3791 weight   0.11000E+01 volume   0.18605E+03 ppm1     6.996 ppm2    4.900
ASSI ( 3801)
   ( ( segid *BrD * and resid 62 and name HN   ) )
   ( ( segid *BrD * and resid 62 and name HA   ) )
      2.800  2.000   2.000 peak    3801 weight   0.11000E+01 volume   0.36964E+03 ppm1     8.998 ppm2    4.467
ASSI ( 3811)
   ( ( segid *BrD * and resid 72 and name HN   ) )
   ( ( segid *BrD * and resid 72 and name HA   ) )
      3.000  2.200   2.200 peak    3811 weight   0.11000E+01 volume   0.24473E+03 ppm1     8.858 ppm2    4.648
ASSI ( 3821)
   ( ( segid *BrD * and resid 72 and name HN   ) )
   ( ( segid *BrD * and resid 73 and name HN   ) )
      3.700  3.400   1.800 peak    3821 weight   0.11000E+01 volume   0.74895E+02 ppm1     8.856 ppm2    8.033
ASSI ( 3851)
   ( ( segid *BrD * and resid 61 and name HN   ) )
   ( ( segid *BrD * and resid 61 and name HA   ) )
      2.500  1.600   1.600 peak    3851 weight   0.11000E+01 volume   0.82145E+03 ppm1     8.748 ppm2    4.652
ASSI ( 3861)
   ( ( segid *BrD * and resid 65 and name HN   ) )
   ( ( segid *BrD * and resid 62 and name HA   ) )
      3.100  2.400   2.400 peak    3861 weight   0.11000E+01 volume   0.22227E+03 ppm1     8.568 ppm2    4.476
ASSI ( 3871)
   ( ( segid *BrD * and resid 60 and name HN   ) )
   ( ( segid *BrD * and resid 60 and name HA   ) )
      2.400  1.400   1.400 peak    3871 weight   0.11000E+01 volume   0.10791E+04 ppm1     8.569 ppm2    4.808
ASSI ( 3881)
   ( ( segid *BrD * and resid 60 and name HN   ) )
   ( ( segid *BrD * and resid 60 and name HB2  ) )
      2.400  1.400   1.400 peak    3881 weight   0.11000E+01 volume   0.10099E+04 ppm1     8.569 ppm2    4.647
ASSI ( 3891)
   ( ( segid *BrD * and resid 60 and name HN   ) )
   ( ( segid *BrD * and resid 60 and name HB1  ) )
      2.600  1.700   1.700 peak    3891 weight   0.11000E+01 volume   0.65212E+03 ppm1     8.568 ppm2    4.975
ASSI ( 3901)
   ( ( segid *BrD * and resid 59 and name HN   ) )
   ( ( segid *BrD * and resid 59 and name HA   ) )
      3.200  2.600   2.300 peak    3901 weight   0.11000E+01 volume   0.18755E+03 ppm1     8.497 ppm2    4.893
```

TABLE 2-continued

Unambigous NOE-derived Inter-proton Distance Restraints

```
ASSI ( 3921)
    ( ( segid *BrD * and resid 7 and name HN   ) )
    ( ( segid *BrD * and resid 6 and name HA   ) )
       2.600  1.700   1.700  peak    3921  weight   0.11000E+01 volume   0.63166E+03 ppm1    8.924 ppm2    4.968
ASSI ( 3931)
    ( ( segid *BrD * and resid 10 and name HN   ) )
    ( ( segid *BrD * and resid 9 and name HA   ) )
       2.600  1.700   1.700  peak    3931  weight   0.11000E+01 volume   0.55346E+03 ppm1    8.884 ppm2    4.938
ASSI ( 3941)
    ( ( segid *BrD * and resid 13 and name HN   ) )
    ( ( segid *BrD * and resid 12 and name HA   ) )
       3.200  2.600   2.300  peak    3941  weight   0.11000E+01 volume   0.18205E+03 ppm1    8.809 ppm2    5.299
ASSI ( 3951)
    ( ( segid *BrD * and resid 16 and name HN   ) )
    ( ( segid *BrD * and resid 15 and name HB1  ) )
       3.300  2.700   2.200  peak    3951  weight   0.11000E+01 volume   0.13722E+03 ppm1    8.793 ppm2    3.818
ASSI ( 3961)
    ( ( segid *BrD * and resid 16 and name HN   ) )
    ( ( segid *BrD * and resid 15 and name HB2  ) )
       2.500  1.600   1.600  peak    3961  weight   0.11000E+01 volume   0.74092E+03 ppm1    8.793 ppm2    3.631
ASSI ( 3971)
    ( ( segid *BrD * and resid 17 and name HN   ) )
    ( ( segid *BrD * and resid 16 and name HA   ) )
       2.500  1.600   1.600  peak    3971  weight   0.11000E+01 volume   0.82685E+03 ppm1    8.669 ppm2    4.516
ASSI ( 3991)
    ( ( segid *BrD * and resid 18 and name HN   ) )
    ( ( segid *BrD * and resid 18 and name HA   ) )
       3.000  2.200   2.200  peak    3991  weight   0.11000E+01 volume   0.24582E+03 ppm1    9.072 ppm2    3.878
ASSI ( 4001)
    ( ( segid *BrD * and resid 18 and name HN   ) )
    ( ( segid *BrD * and resid 17 and name HB   ) )
       2.800  2.000   2.000  peak    4001  weight   0.11000E+01 volume   0.36663E+03 ppm1    9.072 ppm2    4.848
ASSI ( 4011)
    ( ( segid *BrD * and resid 18 and name HN   ) )
    ( ( segid *BrD * and resid 17 and name HA   ) )
       3.200  2.600   2.300  peak    4011  weight   0.11000E+01 volume   0.18724E+03 ppm1    9.072 ppm2    4.521
ASSI ( 4021)
    ( ( segid *BrD * and resid 18 and name HN   ) )
    (  segid *BrD * and resid 17 and name HG2%)
       3.100  2.400   2.400  peak    4021  weight   0.11000E+01 volume   0.23212E+03 ppm1    9.073 ppm2    1.749
ASSI ( 4041)
    ( ( segid *BrD * and resid 17 and name HN   ) )
    ( ( segid *BrD * and resid 18 and name HN   ) )
       2.600  1.700   1.700  peak    4041  weight   0.11000E+01 volume   0.57514E+03 ppm1    8.469 ppm2    9.062
ASSI ( 4051)
    ( ( segid *BrD * and resid 19 and name HN   ) )
    ( ( segid *BrD * and resid 18 and name HA   ) )
       3.500  3.100   2.000  peak    4051  weight   0.11000E+01 volume   0.95460E+02 ppm1    9.187 ppm2    3.878
ASSI ( 4061)
    ( ( segid *BrD * and resid 20 and name HN   ) )
    ( ( segid *BrD * and resid 19 and name HA   ) )
       3.200  2.600   2.300  peak    4061  weight   0.11000E+01 volume    0.1748E+03 ppm1    8.246 ppm2    4.288
ASSI ( 4071)
    ( ( segid *BrD * and resid 21 and name HN   ) )
    ( ( segid *BrD * and resid 20 and name HA   ) )
       3.400  2.900   2.100  peak    4071  weight   0.11000E+01 volume   0.11425E+03 ppm1    8.545 ppm2    4.869
ASSI ( 4081)
    ( ( segid *BrD * and resid 22 and name HN   ) )
    ( ( segid *BrD * and resid 21 and name HA   ) )
       3.300  2.700   2.200  peak    4081  weight   0.11000E+01 volume   0.15238E+03 ppm1    9.457 ppm2    4.631
ASSI ( 4091)
    ( ( segid *BrD * and resid 23 and name HN   ) )
    ( ( segid *BrD * and resid 22 and name HA   ) )
       3.600  3.200   1.900  peak    4091  weight   0.11000E+01 volume   0.91130E+02 ppm1    9.118 ppm2    4.734
ASSI ( 4101)
    ( ( segid *BrD * and resid 24 and name HN   ) )
    ( ( segid *BrD * and resid 23 and name HA   ) )
       3.500  3.100   2.000  peak    4101  weight   0.11000E+01 volume   0.11008E+03 ppm1    8.661 ppm2    4.640
ASSI ( 4111)
    ( ( segid *BrD * and resid 25 and name HN   ) )
    ( ( segid *BrD * and resid 24 and name HA   ) )
       3.300  2.700   2.200  peak    4111  weight   0.11000E+01 volume   0.14843E+03 ppm1    9.133 ppm2    4.753
ASSI ( 4121)
    ( ( segid *BrD * and resid 25 and name HN   ) )
    ( ( segid *BrD * and resid 24 and name HG2  ) )
       2.500  1.600   1.600  peak    4121  weight   0.11000E+01 volume   0.87462E+03 ppm1    9.131 ppm2    3.059
```

TABLE 2-continued

Unambigous NOE-derived Inter-proton Distance Restraints

```
ASSI ( 4141)
   ( ( segid *BrD * and resid 27 and name HN   ) )
   ( ( segid *BrD * and resid 26 and name HA   ) )
     3.200  2.600   2.300 peak    4141 weight   0.11000E+01 volume   0.18491E+03 ppm1    8.171 ppm2    4.493
ASSI ( 4151)
   ( ( segid *BrD * and resid 28 and name HN   ) )
   ( ( segid *BrD * and resid 27 and name HA   ) )
     3.300  2.700   2.200 peak    4151 weight   0.11000E+01 volume   0.14739E+03 ppm1    8.166 ppm2    5.055
ASSI ( 4161)
   ( ( segid *BrD * and resid 29 and name HN   ) )
   ( ( segid *BrD * and resid 28 and name HA   ) )
     2.400  1.400   1.400 peak    4161 weight   0.11000E+01 volume   0.91502E+03 ppm1    9.151 ppm2    4.574
ASSI ( 4171)
   ( ( segid *BrD * and resid 29 and name HN   ) )
   ( ( segid *BrD * and resid 28 and name HB1  ) )
     3.400  2.900   2.100 peak    4171 weight   0.11000E+01 volume   0.11906E+03 ppm1    9.151 ppm2    3.597
ASSI ( 4181)
   ( ( segid *BrD * and resid 29 and name HN   ) )
   ( ( segid *BrD * and resid 28 and name HB2  ) )
     3.600  3.600   1.700 peak    4181 weight   0.11000E+01 volume   0.65813E+02 ppm1    9.152 ppm2    3.406
ASSI ( 4191)
   ( ( segid *BrD * and resid 30 and name HN   ) )
   ( ( segid *BrD * and resid 29 and name HA   ) )
     3.600  3.200   1.900 peak    4191 weight   0.11000E+01 volume   0.88464E+02 ppm1   12.275 ppm2    4.819
ASSI ( 4201)
   ( ( segid *BrD * and resid 30 and name HN   ) )
   ( ( segid *BrD * and resid 29 and name HB1  ) )
     3.400  2.900   2.100 peak    4201 weight   0.11000E+01 volume   0.11541E+03 ppm1   12.275 ppm2    2.718
ASSI ( 4211)
   ( ( segid *BrD * and resid 30 and name HN   ) )
   ( ( segid *BrD * and resid 29 and name HG1  ) )
     3.600  3.200   1.900 peak    4211 weight   0.11000E+01 volume   0.88536E+02 ppm1   12.275 ppm2    3.024
ASSI ( 4221)
   ( ( segid *BrD * and resid 31 and name HN   ) )
   ( ( segid *BrD * and resid 30 and name HA   ) )
     3.600  3.200   1.900 peak    4221 weight   0.11000E+01 volume   0.86531E+02 ppm1    8.481 ppm2    5.449
ASSI ( 4231)
   ( ( segid *BrD * and resid 31 and name HN   ) )
   ( ( segid *BrD * and resid 30 and name HB1  ) )
     3.000  2.200   2.200 peak    4231 weight   0.11000E+01 volume   0.23699E+03 ppm1    8.480 ppm2    4.491
ASSI ( 4241)
   ( ( segid *BrD * and resid 31 and name HN   ) )
   ( ( segid *BrD * and resid 30 and name HB2  ) )
     3.500  3.100   2.000 peak    4241 weight   0.11000E+01 volume   0.10932E+03 ppm1    8.480 ppm2    4.533
ASSI ( 4251)
   ( ( segid *BrD * and resid 68 and name HN   ) )
   ( ( segid *BrD * and resid 67 and name HB1  ) )
     2.700  1.800   1.800 peak    4251 weight   0.11000E+01 volume   0.47519E+03 ppm1    8.627 ppm2    3.555
ASSI ( 4261)
   ( ( segid *BrD * and resid 32 and name HN   ) )
   (   segid *BrD * and resid 31 and name HB %  )
     2.900  2.100   2.100 peak    4261 weight   0.11000E+01 volume   0.35188E+03 ppm1    7.739 ppm2    2.295
ASSI ( 4271)
   ( ( segid *BrD * and resid 32 and name HN   ) )
   ( ( segid *BrD * and resid 31 and name HN   ) )
     2.300  1.300   1.300 peak    4271 weight   0.11000E+01 volume   0.11812E+04 ppm1    7.739 ppm2    6.475
ASSI ( 4291)
   ( ( segid *BrD * and resid 35 and name HN   ) )
   ( ( segid *BrD * and resid 34 and name HA   ) )
     2.200  2.600   2.300 peak    4291 weight   0.11000E+01 volume   0.17960E+03 ppm1    7.734 ppm2    5.537
ASSI ( 4301)
   ( ( segid *BrD * and resid 36 and name HN   ) )
   ( ( segid *BrD * and resid 37 and name HD1  ) )
     3.500  3.100   2.000 peak    4301 weight   0.11000E+01 volume   0.97101E+02 ppm1    8.309 ppm2    4.227
ASSI ( 4311)
   ( ( segid *BrD * and resid 36 and name HN   ) )
   ( ( segid *BrD * and resid 35 and name HA   ) )
     3.300  2.700   2.200 peak    4311 weight   0.11000E+01 volume   0.16104E+03 ppm1    8.308 ppm2    4.893
ASSI ( 4321)
   ( ( segid *BrD * and resid 36 and name HN   ) )
   ( ( segid *BrD * and resid 35 and name HG1  ) )
     3.700  3.400   1.800 peak    4321 weight   0.11000E+01 volume   0.78555E+02 ppm1    8.307 ppm2    3.458
ASSI ( 4331)
   ( ( segid *BrD * and resid 39 and name HN   ) )
   ( ( segid *BrD * and resid 38 and name HA   ) )
     2.200  1.200   1.200 peak    4331 weight   0.11000E+01 volume   0.15683E+04 ppm1    9.652 ppm2    4.160
```

TABLE 2-continued

Unambigous NOE-derived Inter-proton Distance Restraints

```
ASSI ( 4341)
    ( ( segid *BrD * and resid 39 and name HN  ) )
    ( ( segid *BrD * and resid 38 and name HB  ) )
      3.400  2.900   2.100 peak    4341 weight   0.11000E+01 volume   0.11939E+03 ppm1    9.652 ppm2    1.752
ASSI ( 4351)
    ( ( segid *BrD * and resid 39 and name HN  ) )
    (   segid *BrD * and resid 38 and name HG1%)
      3.600  3.200   1.900 peak    4351 weight   0.11000E+01 volume   0.93234E+02 ppm1    9.652 ppm2    1.071
ASSI ( 4361)
    ( ( segid *BrD * and resid 39 and name HN  ) )
    (   segid *BrD * and resid 38 and name HG2%)
      3.100  2.400   2.400 peak    4361 weight   0.11000E+01 volume   0.20061E+03 ppm1    9.652 ppm2    0.776
ASSI ( 4381)
    ( ( segid *BrD * and resid 43 and name HN  ) )
    ( ( segid *BrD * and resid 42 and name HA  ) )
      2.900  2.100   2.100 peak    4381 weight   0.11000E+01 volume   0.31481E+03 ppm1    8.001 ppm2    5.055
ASSI ( 4391)
    ( ( segid *BrD * and resid 43 and name HN  ) )
    ( ( segid *BrD * and resid 42 and name HB2 ) )
      2.800  2.000   2.000 peak    4391 weight   0.11000E+01 volume   0.36989E+03 ppm1    8.001 ppm2    2.607
ASSI ( 4401)
    ( ( segid *BrD * and resid 43 and name HN  ) )
    ( ( segid *BrD * and resid 42 and name HB1 ) )
      2.900  2.100   2.100 peak    4401 weight   0.11000E+01 volume   0.32280E+03 ppm1    8.001 ppm2    2.781
ASSI ( 4411)
    ( ( segid *BrD * and resid 36 and name HN  ) )
    ( ( segid *BrD * and resid 36 and name HB1 ) )
      2.800  2.000   2.000 peak    4411 weight   0.11000E+01 volume   0.42122E+03 ppm1    8.308 ppm2    2.698
ASSI ( 4421)
    ( ( segid *BrD * and resid 47 and name HN  ) )
    ( ( segid *BrD * and resid 46 and name HA  ) )
      3.300  2.700   2.200 peak    4421 weight   0.11000E+01 volume   0.14320E+03 ppm1    8.832 ppm2    4.139
ASSI ( 4431)
    ( ( segid *BrD * and resid 47 and name HN  ) )
    ( ( segid *BrD * and resid 46 and name HB1 ) )
      3.500  3.100   2.000 peak    4431 weight   0.11000E+01 volume   0.11013E+03 ppm1    8.832 ppm2    3.295
ASSI ( 4441)
    ( ( segid *BrD * and resid 47 and name HN  ) )
    ( ( segid *BrD * and resid 46 and name HB2 ) )
      3.100  2.400   2.400 peak    4441 weight   0.11000E+01 volume   0.20297E+03 ppm1    8.833 ppm2    3.094
ASSI ( 4451)
    ( ( segid *BrD * and resid 48 and name HN  ) )
    ( ( segid *BrD * and resid 47 and name HA  ) )
      3.200  2.600   2.300 peak    4451 weight   0.11000E+01 volume   0.16849E+03 ppm1    8.307 ppm2    4.708
ASSI ( 4461)
    ( ( segid *BrD * and resid 49 and name HN  ) )
    ( ( segid *BrD * and resid 48 and name HA  ) )
      3.000  2.200   2.200 peak    4461 weight   0.11000E+01 volume   0.24376E+03 ppm1    7.762 ppm2    4.816
ASSI ( 4471)
    ( ( segid *BrD * and resid 49 and name HN  ) )
    ( ( segid *BrD * and resid 48 and name HG2 ) )
      4.000  4.000   1.500 peak    4471 weight   0.11000E+01 volume   0.45441E+02 ppm1    7.762 ppm2    2.872
ASSI ( 4481)
    ( ( segid *BrD * and resid 49 and name HN  ) )
    ( ( segid *BrD * and resid 48 and name HB1 ) )
      3.200  2.600   2.300 peak    4481 weight   0.11000E+01 volume   0.17937E+03 ppm1    7.762 ppm2    2.693
ASSI ( 4491)
    ( ( segid *BrD * and resid 50 and name HN  ) )
    ( ( segid *BrD * and resid 49 and name HA  ) )
      2.600  1.700   1.700 peak    4491 weight   0.11000E+01 volume   0.60014E+03 ppm1    8.564 ppm2    4.693
ASSI ( 4501)
    ( ( segid *BrD * and resid 50 and name HN  ) )
    ( ( segid *BrD * and resid 49 and name HB  ) )
      2.900  2.100   2.100 peak    4501 weight   0.11000E+01 volume   0.31627E+03 ppm1    8.564 ppm2    2.622
ASSI ( 4511)
    ( ( segid *BrD * and resid 50 and name HN  ) )
    (   segid *BrD * and resid 49 and name HG2%)
      3.700  3.400   1.800 peak    4511 weight   0.11000E+01 volume   0.77577E+02 ppm1    8.564 ppm2    1.598
ASSI ( 4521)
    ( ( segid *BrD * and resid 55 and name HN  ) )
    ( ( segid *BrD * and resid 54 and name HA  ) )
      2.300  1.300   1.300 peak    4521 weight   0.11000E+01 volume   0.11556E+04 ppm1    7.974 ppm2    5.542
ASSI ( 4531)
    ( ( segid *BrD * and resid 55 and name HN  ) )
    ( ( segid *BrD * and resid 54 and name HB1 ) )
      3.700  3.400   1.800 peak    4531 weight   0.11000E+01 volume   0.71474E+02 ppm1    7.975 ppm2    2.572
```

TABLE 2-continued

Unambigous NOE-derived Inter-proton Distance Restraints

```
ASSI ( 4541)
   (( segid *BrD * and resid 55 and name HN   ))
   (( segid *BrD * and resid 54 and name HB2  ))
      3.100  2.400   2.400  peak    4541 weight   0.11000E+01 volume   0.20373E+03 ppm1    7.975 ppm2   1.956
ASSI ( 4551)
   (( segid *BrD * and resid 56 and name HN   ))
   (( segid *BrD * and resid 55 and name HA   ))
      2.800  2.000   2.000  peak    4551 weight   0.11000E+01 volume   0.38353E+03 ppm1    9.674 ppm2   5.352
ASSI ( 4561)
   (( segid *BrD * and resid 56 and name HN   ))
   (( segid *BrD * and resid 55 and name HB1  ))
      2.400  1.400   1.400  peak    4561 weight   0.11000E+01 volume   0.92127E+03 ppm1    9.679 ppm2   2.978
ASSI ( 4571)
   (( segid *BrD * and resid 57 and name HN   ))
   (( segid *BrD * and resid 56 and name HA   ))
      3.200  2.600   2.300  peak    4571 weight   0.11000E+01 volume   0.16116E+03 ppm1    9.359 ppm2   4.648
ASSI ( 4581)
   (( segid *BrD * and resid 58 and name HN   ))
   (( segid *BrD * and resid 57 and name HA   ))
      3.400  2.900   2.100  peak    4581 weight   0.11000E+01 volume   0.12185E+03 ppm1   10.050 ppm2   4.805
ASSI ( 4591)
   (( segid *BrD * and resid 59 and name HN   ))
   (( segid *BrD * and resid 58 and name HA   ))
      3.400  2.900   2.100  peak    4591 weight   0.11000E+01 volume   0.13191E+03 ppm1    8.498 ppm2   4.449
ASSI ( 4601)
   (( segid *BrD * and resid 59 and name HN   ))
   (( segid *BrD * and resid 58 and name HB   ))
      3.200  2.600   2.300  peak    4601 weight   0.11000E+01 volume   0.18613E+03 ppm1    8.498 ppm2   4.697
ASSI ( 4611)
   (( segid *BrD * and resid 59 and name HN   ))
   (  segid *BrD * and resid 58 and name HG2%)
      3.100  2.400   2.400  peak    4611 weight   0.11000E+01 volume   0.21128E+03 ppm1    8.496 ppm2   1.665
ASSI ( 4631)
   (( segid *BrD * and resid 59 and name HN   ))
   (( segid *BrD * and resid 58 and name HN   ))
      3.200  2.600   2.300  peak    4631 weight   0.11000E+01 volume   0.17034E+03 ppm1   10.051 ppm2   8.489
ASSI ( 4641)
   (( segid *BrD * and resid 61 and name HN   ))
   (( segid *BrD * and resid 61 and name HG1  ))
      2.400  1.400   1.400  peak    4641 weight   0.11000E+01 volume   0.89496E+03 ppm1    8.743 ppm2   2.974
ASSI ( 4651)
   (( segid *BrD * and resid 61 and name HN   ))
   (( segid *BrD * and resid 61 and name HB2  ))
      2.500  1.600   1.600  peak    4651 weight   0.11000E+01 volume   0.72876E+03 ppm1    8.743 ppm2   2.670
ASSI ( 4661)
   (( segid *BrD * and resid 61 and name HN   ))
   (( segid *BrD * and resid 60 and name HA   ))
      3.300  2.700   2.200  peak    4661 weight   0.11000E+01 volume   0.14220E+03 ppm1    8.749 ppm2   4.816
ASSI ( 4691)
   (( segid *BrD * and resid 61 and name HN   ))
   (( segid *BrD * and resid 60 and name HN   ))
      2.400  1.400   1.400  peak    4691 weight   0.11000E+01 volume   0.96369E+03 ppm1    8.566 ppm2   8.734
ASSI ( 4701)
   (( segid *BrD * and resid 62 and name HN   ))
   (( segid *BrD * and resid 61 and name HA   ))
      3.200  2.600   2.300  peak    4701 weight   0.11000E+01 volume   0.17192E+03 ppm1    8.997 ppm2   4.656
ASSI ( 4711)
   (( segid *BrD * and resid 63 and name HN   ))
   (( segid *BrD * and resid 62 and name HN   ))
      2.800  2.000   2.000  peak    4711 weight   0.11000E+01 volume   0.35764E+03 ppm1    9.477 ppm2   8.998
ASSI ( 4731)
   (( segid *BrD * and resid 63 and name HN   ))
   (( segid *BrD * and resid 62 and name HA   ))
      3.600  3.200   1.900  peak    4731 weight   0.11000E+01 volume   0.90728E+02 ppm1    9.472 ppm2   4.481
ASSI ( 4741)
   (( segid *BrD * and resid 65 and name HD21 ))
   (( segid *BrD * and resid 65 and name HB1  ))
      3.500  3.100   2.000  peak    4741 weight   0.11000E+01 volume   0.10454E+03 ppm1    8.206 ppm2   3.637
ASSI ( 4751)
   (( segid *BrD * and resid 65 and name HD22 ))
   (( segid *BrD * and resid 65 and name HB1  ))
      3.500  3.100   2.000  peak    4751 weight   0.11000E+01 volume   0.97769E+02 ppm1    7.576 ppm2   3.637
ASSI ( 4761)
   (( segid *BrD * and resid 65 and name HD21 ))
   (( segid *BrD * and resid 65 and name HB2  ))
      3.200  2.600   2.300  peak    4761 weight   0.11000E+01 volume   0.17538E+03 ppm1    8.205 ppm2   3.393
```

TABLE 2-continued

Unambigous NOE-derived Inter-proton Distance Restraints

```
ASSI ( 4771)
   ( ( segid *BrD * and resid 65 and name HD22) ) )
   ( ( segid *BrD * and resid 65 and name HB2 ) )
      3.400  2.900   2.100 peak    4771 weight   0.11000E+01 volume   0.13182E+03 ppm1   7.576 ppm2   3.393
ASSI ( 4781)
   ( ( segid *BrD * and resid 24 and name HE21) ) )
   ( ( segid *BrD * and resid 24 and name HG1 ) )
      3.400  2.900   2.100 peak    4781 weight   0.11000E+01 volume   0.11561E+03 ppm1   7.634 ppm2   3.459
ASSI ( 4791)
   ( ( segid *BrD * and resid 24 and name HE22) ) )
   ( ( segid *BrD * and resid 24 and name HG1 ) )
      3.600  3.200   1.900 peak    4791 weight   0.11000E+01 volume   0.90204E+02 ppm1   7.523 ppm2   3.474
ASSI ( 4801)
   ( ( segid *BrD * and resid 66 and name HN  ) )
   ( ( segid *BrD * and resid 65 and name HA  ) )
      2.700  1.800   1.800 peak    4801 weight   0.11000E+01 volume   0.48168E+03 ppm1   8.762 ppm2   5.378
ASSI ( 4811)
   ( ( segid *BrD * and resid 66 and name HN  ) )
   ( ( segid *BrD * and resid 65 and name HB1 ) )
      3.400  2.900   2.100 peak    4811 weight   0.11000E+01 volume   0.15537E+03 ppm1   8.759 ppm2   3.608
ASSI ( 4821)
   ( ( segid *BrD * and resid 66 and name HN  ) )
   ( ( segid *BrD * and resid 65 and name HB2 ) )
      3.300  2.700   2.200 peak    4821 weight   0.11000E+01 volume   0.13853E+03 ppm1   8.763 ppm2   3.381
ASSI ( 4831)
   ( ( segid *BrD * and resid 67 and name HN  ) )
   ( ( segid *BrD * and resid 66 and name HA  ) )
      2.800  2.000   2.000 peak    4831 weight   0.11000E+01 volume   0.42855E+03 ppm1   8.832 ppm2   5.009
ASSI ( 4841)
   ( ( segid *BrD * and resid 68 and name HN  ) )
   ( ( segid *BrD * and resid 67 and name HA  ) )
      3.400  2.900   2.100 peak    4841 weight   0.11000E+01 volume   0.12732E+03 ppm1   8.627 ppm2   4.671
ASSI ( 4851)
   ( ( segid *BrD * and resid 68 and name HN  ) )
   ( ( segid *BrD * and resid 67 and name HB2 ) )
      3.300  2.700   2.200 peak    4851 weight   0.11000E+01 volume   0.15213E+03 ppm1   8.626 ppm2   2.662
ASSI ( 4861)
   ( ( segid *BrD * and resid 69 and name HN  ) )
   ( ( segid *BrD * and resid 68 and name HA  ) )
      2.400  1.400   1.400 peak    4861 weight   0.11000E+01 volume   0.95815E+03 ppm1   8.305 ppm2   5.141
ASSI ( 4871)
   ( ( segid *BrD * and resid 69 and name HN  ) )
   ( ( segid *BrD * and resid 68 and name HB1 ) )
      4.500  4.500   1.000 peak    4871 weight   0.11000E+01 volume   0.22391E+02 ppm1   8.304 ppm2   3.669
ASSI ( 4881)
   ( ( segid *BrD * and resid 69 and name HN  ) )
   ( ( segid *BrD * and resid 68 and name HB2 ) )
      3.300  2.700   2.200 peak    4881 weight   0.11000E+01 volume   0.15981E+03 ppm1   8.306 ppm2   3.514
ASSI ( 4891)
   ( ( segid *BrD * and resid 70 and name HN  ) )
   ( ( segid *BrD * and resid 69 and name HA  ) )
      3.00   2.200   2.200 peak    4891 weight   0.11000E+01 volume   0.24443E+03 ppm1   8.039 ppm2   4.690
ASSI ( 4901)
   ( ( segid *BrD * and resid 70 and name HN  ) )
   ( ( segid *BrD * and resid 69 and name HB  ) )
      3.400  2.900   2.100 peak    4901 weight   0.11000E+01 volume   0.12954E+03 ppm1   8.040 ppm2   2.928
ASSI ( 4911)
   ( ( segid *BrD * and resid 70 and name HN  ) )
   (   segid *BrD * and resid 69 and name HG1%)
      3.800  3.600   1.700 peak    4911 weight   0.11000E+01 volume   0.61869E+02 ppm1   8.041 ppm2   1.551
ASSI ( 4921)
   ( ( segid *BrD * and resid 70 and name HN  ) )
   (   segid *BrD * and resid 69 and name HG2%)
      2.700  1.800   1.800 peak    4921 weight   0.11000E+01 volume   0.48346E+03 ppm1   8.040 ppm2   1.430
ASSI ( 4931)
   ( ( segid *BrD * and resid 73 and name HN  ) )
   ( ( segid *BrD * and resid 72 and name HA  ) )
      2.900  2.100   2.100 peak    4931 weight   0.11000E+01 volume   0.30696E+03 ppm1   8.045 ppm2   4.654
ASSI ( 4941)
   ( ( segid *BrD * and resid 74 and name HN  ) )
   ( ( segid *BrD * and resid 73 and name HA  ) )
      3.500  3.100   2.000 peak    4941 weight   0.11000E+01 volume   0.10430E+03 ppm1   7.536 ppm2   4.812
ASSI ( 4951)
   ( ( segid *BrD * and resid 75 and name HN  ) )
   ( ( segid *BrD * and resid 74 and name HA  ) )
      3.500  3.100   2.000 peak    4951 weight   0.11000E+01 volume   0.10099E+03 ppm1   9.106 ppm2   4.361
```

TABLE 2-continued

Unambigous NOE-derived Inter-proton Distance Restraints

```
ASSI ( 4961)
    ( ( segid *BrD * and resid 76 and name HN   ) )
    ( ( segid *BrD * and resid 75 and name HA   ) )
      3.400  2.900   2.100  peak    4961  weight   0.11000E+01  volume   0.11734E+03  ppm1    8.611  ppm2    4.525
ASSI ( 4971)
    ( ( segid *BrD * and resid 76 and name HN   ) )
    ( ( segid *BrD * and resid 75 and name HG1  ) )
      3.000  2.200   2.200  peak    4971  weight   0.11000E+01  volume   0.28326E+03  ppm1    8.611  ppm2    3.549
ASSI ( 4981)
    ( ( segid *BrD * and resid 76 and name HN   ) )
    ( ( segid *BrD * and resid 75 and name HG2  ) )
      3.200  2.600   2.300  peak    4981  weight   0.11000E+01  volume   0.18815E+03  ppm1    8.610  ppm2    3.218
ASSI ( 4991)
    ( ( segid *BrD * and resid 76 and name HN   ) )
    ( ( segid *BrD * and resid 75 and name HB2  ) )
      2.600  1.700   1.700  peak    4991  weight   0.11000E+01  volume   0.61964E+03  ppm1    8.611  ppm2    2.815
ASSI ( 5001)
    ( ( segid *BrD * and resid 76 and name HN   ) )
    ( ( segid *BrD * and resid 75 and name HB1  ) )
      2.600  1.700   1.700  peak    5001  weight   0.11000E+01  volume   0.59739E+03  ppm1    8.611  ppm2    2.925
ASSI ( 5011)
    ( ( segid *BrD * and resid 77 and name HN   ) )
    ( ( segid *BrD * and resid 76 and name HA   ) )
      3.000  2.200   2.200  peak    5011  weight   0.11000E+01  volume   0.25554E+03  ppm1    7.996  ppm2    4.695
ASSI ( 5021)
    ( ( segid *BrD * and resid 77 and name HN   ) )
    (  segid *BrD * and resid 76 and name HB %  )
      2.500  1.600   1.600  peak    5021  weight   0.11000E+01  volume   0.86259E+03  ppm1    7.996  ppm2    2.092
ASSI ( 5031)
    ( ( segid *BrD * and resid 79 and name HN   ) )
    ( ( segid *BrD * and resid 78 and name HA   ) )
      3.300  2.700   2.200  peak    5031  weight   0.11000E+01  volume   0.14659E+03  ppm1    8.681  ppm2    3.995
ASSI ( 5041)
    ( ( segid *BrD * and resid 78 and name HN   ) )
    ( ( segid *BrD * and resid 79 and name HN   ) )
      2.400  1.400   1.400  peak    5041  weight   0.11000E+01  volume   0.10403E+04  ppm1    7.996  ppm2    8.687
ASSI ( 5061)
    ( ( segid *BrD * and resid 80 and name HN   ) )
    ( ( segid *BrD * and resid 80 and name HD1  ) )
      5.300  5.300   0.200  peak    5061  weight   0.11000E+01  volume   0.85899E+01  ppm1    8.006  ppm2    3.997
ASSI ( 5071)
    ( ( segid *BrD * and resid 80 and name HN   ) )
    ( ( segid *BrD * and resid 79 and name HA   ) )
      3.300  2.700   2.200  peak    5071  weight   0.11000E+01  volume   0.15955E+03  ppm1    8.006  ppm2    4.404
ASSI ( 5091)
    ( ( segid *BrD * and resid 80 and name HN   ) )
    ( ( segid *BrD * and resid 79 and name HB2  ) )
      3.200  2.600   2.300  peak    5091  weight   0.11000E+01  volume   0.16421E+03  ppm1    8.006  ppm2    2.704
ASSI ( 5101)
    ( ( segid *BrD * and resid 81 and name HN   ) )
    ( ( segid *BrD * and resid 80 and name HA   ) )
      3.700  3.400   1.800  peak    5101  weight   0.11000E+01  volume   0.77456E+02  ppm1    7.639  ppm2    4.685
ASSI ( 5111)
    ( ( segid *BrD * and resid 82 and name HN   ) )
    ( ( segid *BrD * and resid 81 and name HB   ) )
      2.500  1.600   1.600  peak    5111  weight   0.11000E+01  volume   0.81882E+03  ppm1    6.981  ppm2    2.042
ASSI ( 5121)
    ( ( segid *BrD * and resid 82 and name HN   ) )
    (  segid *BrD * and resid 81 and name HG1%)
      3.200  2.600   2.300  peak    5121  weight   0.11000E+01  volume   0.17066E+03  ppm1    6.981  ppm2    1.086
ASSI ( 5131)
    ( ( segid *BrD * and resid 82 and name HN   ) )
    (  segid *BrD * and resid 81 and name HG2%)
      3.400  2.900   2.100  peak    5131  weight   0.11000E+01  volume   0.12103E+03  ppm1    6.981  ppm2    0.749
ASSI ( 5141)
    ( ( segid *BrD * and resid 83 and name HN   ) )
    ( ( segid *BrD * and resid 82 and name HA   ) )
      3.400  2.900   2.100  peak    5141  weight   0.11000E+01  volume   0.11364E+03  ppm1    9.658  ppm2    4.743
ASSI ( 5151)
    ( ( segid *BrD * and resid 83 and name HN   ) )
    ( ( segid *BrD * and resid 82 and name HB1  ) )
      3.500  3.100   2.000  peak    5151  weight   0.11000E+01  volume   0.10752E+03  ppm1    9.660  ppm2    1.697
ASSI ( 5161)
    ( ( segid *BrD * and resid 83 and name HN   ) )
    ( ( segid *BrD * and resid 82 and name HB2  ) )
      2.800  2.000   2.000  peak    5161  weight   0.11000E+01  volume   0.41394E+03  ppm1    9.658  ppm2    3.551
```

TABLE 2-continued

Unambigous NOE-derived Inter-proton Distance Restraints

```
ASSI ( 5171)
   ( ( segid *BrD * and resid 84 and name HN   ) )
   ( ( segid *BrD * and resid 83 and name HB   ) )
      3.200   2.600    2.300  peak    5171  weight    0.11000E+01 volume   0.19086E+03 ppm1     9.466 ppm2     4.817
ASSI ( 5181)
   ( ( segid *BrD * and resid 84 and name HN   ) )
   ( ( segid *BrD * and resid 83 and name HA   ) )
      3.600   3.200    1.900  peak    5181  weight    0.11000E+01 volume   0.83498E+02 ppm1     9.463 ppm2     4.449
ASSI ( 5191)
   ( ( segid *BrD * and resid 84 and name HN   ) )
   (   segid *BrD * and resid 83 and name HG2%)
      3.500   3.100    2.000  peak    5191  weight    0.11000E+01 volume   0.11050E+03 ppm1     9.463 ppm2     1.903
ASSI ( 5201)
   ( ( segid *BrD * and resid 85 and name HN   ) )
   ( ( segid *BrD * and resid 84 and name HA   ) )
      3.700   3.400    1.800  peak    5201  weight    0.11000E+01 volume   0.79848E+02 ppm1     7.515 ppm2     4.921
ASSI ( 5211)
   ( ( segid *BrD * and resid 85 and name HN   ) )
   ( ( segid *BrD * and resid 84 and name HB2 ) )
      3.400   2.900    2.100  peak    5211  weight    0.11000E+01 volume   0.12439E+03 ppm1     7.516 ppm2     3.268
ASSI ( 5221)
   ( ( segid *BrD * and resid 86 and name HN   ) )
   ( ( segid *BrD * and resid 85 and name HA   ) )
      3.900   3.800    1.600  peak    5221  weight    0.11000E+01 volume   0.50221E+02 ppm1     8.423 ppm2     5.012
ASSI ( 5231)
   ( ( segid *BrD * and resid 86 and name HN   ) )
   ( ( segid *BrD * and resid 85 and name HB2 ) )
      3.300   2.700    2.200  peak    5231  weight    0.11000E+01 volume   0.14503E+03 ppm1     8.423 ppm2     3.639
ASSI ( 5241)
   ( ( segid *BrD * and resid 87 and name HN   ) )
   ( ( segid *BrD * and resid 86 and name HA   ) )
      3.600   3.200    1.900  peak    5241  weight    0.11000E+01 volume   0.84494E+02 ppm1     8.572 ppm2     4.815
ASSI ( 5251)
   ( ( segid *BrD * and resid 88 and name HN   ) )
   ( ( segid *BrD * and resid 87 and name HA   ) )
      3.600   3.200    1.900  peak    5251  weight    0.11000E+01 volume   0.87457E+02 ppm1     8.357 ppm2     4.857
ASSI ( 5261)
   ( ( segid *BrD * and resid 88 and name HN   ) )
   ( ( segid *BrD * and resid 87 and name HB1 ) )
      3.100   2.400    2.400  peak    5261  weight    0.11000E+01 volume   0.23456E+03 ppm1     8.354 ppm2     2.782
ASSI ( 5271)
   ( ( segid *BrD * and resid 88 and name HN   ) )
   ( ( segid *BrD * and resid 87 and name HB2 ) )
      3.200   2.600    2.300  peak    5271  weight    0.11000E+01 volume   0.19424E+03 ppm1     8.354 ppm2     2.614
ASSI ( 5281)
   ( ( segid *BrD * and resid 88 and name HN   ) )
   ( ( segid *BrD * and resid 87 and name HN   ) )
      2.400   1.700    1.700  peak    5281  weight    0.11000E+01 volume   0.67695E+03 ppm1     8.355 ppm2     8.552
ASSI ( 5301)
   ( ( segid *BrD * and resid 89 and name HN   ) )
   ( ( segid *BrD * and resid 88 and name HA   ) )
      3.400   2.900    2.100  peak    5301  weight    0.11000E+01 volume   0.12542E+03 ppm1     8.858 ppm2     4.976
ASSI ( 5311)
   ( ( segid *BrD * and resid 89 and name HD21) )
   ( ( segid *BrD * and resid 89 and name HB2 ) )
      3.900   3.800    1.600  peak    5311  weight    0.11000E+01 volume   0.54504E+02 ppm1     8.923 ppm2     3.516
ASSI ( 5321)
   ( ( segid *BrD * and resid 89 and name HD22) )
   ( ( segid *BrD * and resid 89 and name HB2 ) )
      3.300   2.700    2.200  peak    5321  weight    0.11000E+01 volume   0.13631E+03 ppm1     8.416 ppm2     3.514
ASSI ( 5331)
   ( ( segid *BrD * and resid 89 and name HD21) )
   ( ( segid *BrD * and resid 89 and name HB1 ) )
      5.100   5.100    0.400  peak    5331  weight    0.11000E+01 volume   0.10399E+02 ppm1     8.923 ppm2     3.679
ASSI ( 5341)
   ( ( segid *BrD * and resid 89 and name HD22) )
   ( ( segid *BrD * and resid 89 and name HB1 ) )
      3.900   3.800    1.600  peak    5341  weight    0.11000E+01 volume   0.50137E+02 ppm1     8.416 ppm2     3.676
ASSI ( 5351)
   ( ( segid *BrD * and resid 92 and name HN   ) )
   ( ( segid *BrD * and resid 92 and name HG1  ) )
      2.700   1.800    1.800  peak    5351  weight    0.11000E+01 volume   0.53011E+03 ppm1     8.876 ppm2     3.818
ASSI ( 5361)
   ( ( segid *BrD * and resid 92 and name HN   ) )
   ( ( segid *BrD * and resid 92 and name HB1 ) )
      3.600   3.200    1.900  peak    5361  weight    0.11000E+01 volume   0.93326E+02 ppm1     8.875 ppm2     2.697
```

TABLE 2-continued

Unambigous NOE-derived Inter-proton Distance Restraints

```
ASSI ( 5371)
    ( ( segid *BrD * and resid 92 and name HN   ) )
    ( ( segid *BrD * and resid 92 and name HB2 ) )
      2.500  1.600   1.600 peak    5371 weight    0.11000E+01 volume    0.87608E+03 ppm1      8.875 ppm2    2.576
ASSI ( 5381)
    ( ( segid *BrD * and resid 93 and name HN   ) )
    ( ( segid *BrD * and resid 92 and name HG1 ) )
      3.500  3.100   2.000 peak    5381 weight    0.11000E+01 volume    0.10524E+03 ppm1      8.714 ppm2    2.807
ASSI ( 5391)
    ( ( segid *BrD * and resid 93 and name HN   ) )
    ( ( segid *BrD * and resid 92 and name HB1 ) )
      3.200  2.600   2.300 peak    5391 weight    0.11000E+01 volume    0.36925E+03 ppm1      8.714 ppm2    2.702
ASSI ( 5401)
    ( ( segid *BrD * and resid 93 and name HN   ) )
    ( ( segid *BrD * and resid 92 and name HB2 ) )
      3.300  2.700   2.200 peak    5401 weight    0.11000E+01 volume    0.13613E+03 ppm1      8.714 ppm2    2.580
ASSI ( 5411)
    ( ( segid *BrD * and resid 94 and name HN   ) )
    ( ( segid *BrD * and resid 94 and name HB1 ) )
      2.700  1.800   1.800 peak    5411 weight    0.11000E+01 volume    0.51785E+03 ppm1      9.677 ppm2    2.777
ASSI ( 5421)
    ( ( segid *BrD * and resid 94 and name HN   ) )
    ( ( segid *BrD * and resid 94 and name HG1 ) )
      3.600  3.200   1.900 peak    5421 weight    0.11000E+01 volume    0.65031E+02 ppm1      9.679 ppm2    3.144
ASSI ( 5431)
    ( ( segid *BrD * and resid 94 and name HN   ) )
    ( ( segid *BrD * and resid 93 and name HA   ) )
      3.300  2.700   2.200 peakk   5431 weight    0.11000E+01 volume    0.15989E+03 ppm1      9.678 ppm2    5.042
ASSI ( 5441)
    ( ( segid *BrD * and resid 94 and name HN   ) )
    ( ( segid *BrD * and resid 93 and name HB2 ) )
      3.000  2.200   2.200 peak    5441 weight    0.11000E+01 volume    0.25357E+03 ppm1      9.680 ppm2    6.764
ASSI ( 5451)
    ( ( segid *BrD * and resid 95 and name HN   ) )
    ( ( segid *BrD * and resid 94 and name HA   ) )
      3.600  3.200   1.900 peak    5451 weight    0.11000E+01 volume    0.81131E+02 ppm1      8.669 ppm2    4.839
ASSI ( 5461)
    ( ( segid *BrD * and resid 95 and name HN   ) )
    ( ( segid *BrD * and resid 94 and name HG1 ) )
      3.400  2.900   2.100 peak    5461 weight    0.11000E+01 volume    0.12127E+03 ppm1      8.669 ppm2    3.135
ASSI ( 5471)
    ( ( segid *BrD * and resid 95 and name HN   ) )
    ( ( segid *BrD * and resid 94 and name HB1 ) )
      2.800  2.000   2.000 peak    5471 weight    0.11000E+01 volume    0.41579E+03 ppm1      8.670 ppm2    2.776
ASSI ( 5481)
    ( ( segid *BrD * and resid 96 and name HN   ) )
    ( ( segid *BrD * and resid 95 and name HN   ) )
      2.400  1.400   1.400 peak    5481 weight    0.11000E+01 volume    0.91814E+03 ppm1      7.979 ppm2    8.679
ASSI ( 5501)
    ( ( segid *BrD * and resid 97 and name HN   ) )
    ( ( segid *BrD * and resid 96 and name HA   ) )
      3.300  2.700   2.200 peak    5501 weight    0.11000E+01 volume    0.15786E+03 ppm1      8.677 ppm2    4.426
ASSI ( 5511)
    ( ( segid *BrD * and resid 97 and name HN   ) )
    ( ( segid *BrD * and resid 96 and name HB1 ) )
      3.200  2.600   2.300 peak    5511 weight    0.11000E+01 volume    0.17339E+03 ppm1      8.674 ppm2    3.997
ASSI ( 5521)
    ( ( segid *BrD * and resid 97 and name HN   ) )
    ( ( segid *BrD * and resid 96 and name HB2 ) )
      3.000  2.200   2.200 peak    5521 weight    0.11000E+01 volume    0.24048E+03 ppm1      8.674 ppm2    3.107
ASSI ( 5531)
    ( ( segid *BrD * and resid 99 and name HN   ) )
    ( ( segid *BrD * and resid 98 and name HA   ) )
      3.200  2.400   2.300 peak    5531 weight    0.11000E+01 volume    0.14985E+03 ppm1      8.936 ppm2    4.813
ASSI ( 5541)
    ( ( segid *BrD * and resid 99 and name HN   ) )
    ( ( segid *BrD * and resid 98 and name HB1 ) )
      3.200  2.600   2.300 peak    5541 weight    0.11000E+01 volume    0.16699E+03 ppm1      8.936 ppm2    4.003
ASSI ( 5551)
    ( ( segid *BrD * and resid 99 and name HN   ) )
    ( ( segid *BrD * and resid 98 and name HB2 ) )
      2.900  2.100   2.100 peak    5551 weight    0.11000E+01 volume    0.29941E+03 ppm1      8.936 ppm2    3.463
ASSI ( 5561)
    ( ( segid *BrD * and resid 100 and name HN  ) )
    ( ( segid *BrD * and resid 99 and name HA   ) )
      3.300  2.700   2.200 peak    5561 weight    0.11000E+01 volume    0.14856E+03 ppm1      8.669 ppm2    4.438
```

TABLE 2-continued

Unambigous NOE-derived Inter-proton Distance Restraints

```
ASSI ( 5571)
    ( ( segid *BrD * and resid 100 and name HN   ) )
    ( segid *BrD * and resid 99 and name HB % )
     2.600  1.700   1.700 peak   5571 weight  0.11000E+01 volume  0.56660E+03 ppm1   8.649 ppm2   2.204
ASSI ( 5581)
    ( ( segid *BrD * and resid 100 and name HN   ) )
    ( ( segid *BrD * and resid 101 and name HA   ) )
     3.500  3.100   2.000 peak   5581 weight  0.11000E+01 volume  0.99135E+02 ppm1   8.513 ppm2   4.940
ASSI ( 5591)
    ( ( segid *BrD * and resid 101 and name HN   ) )
    ( ( segid *BrD * and resid 100 and name HB1  ) )
     3.200  2.600   2.300 peak   5591 weight  0.11000E+01 volume  0.18321E+03 ppm1   8.513 ppm2   3.484
ASSI ( 5601)
    ( ( segid *BrD * and resid 102 and name HN   ) )
    ( ( segid *BrD * and resid 101 and name HA   ) )
     3.500  3.100   2.000 peak   5601 weight  0.11000E+01 volume  0.10380E+03 ppm1   9.156 ppm2   4.256
ASSI ( 5611)
    ( ( segid *BrD * and resid 103 and name HN   ) )
    ( ( segid *BrD * and resid 102 and name HA   ) )
     3.500  3.100   2.000 peak   5611 weight  0.11000E+01 volume  0.10037E+03 ppm1   8.696 ppm2   4.277
ASSI ( 5621)
    ( ( segid *BrD * and resid 104 and name HN   ) )
    ( ( segid *BrD * and resid 103 and name HA   ) )
     3.200  2.600   2.300 peak   5621 weight  0.11000E+01 volume  0.16539E+03 ppm1   7.763 ppm2   3.792
ASSI ( 5631)
    ( ( segid *BrD * and resid 104 and name HN   ) )
    ( ( segid *BrD * and resid 103 and name HB1  ) )
     2.800  2.000   2.000 peak   5631 weight  0.11000E+01 volume  0.39404E+03 ppm1   7.762 ppm2   2.327
ASSI ( 5641)
    ( ( segid *BrD * and resid 104 and name HN   ) )
    ( ( segid *BrD * and resid 103 and name HB2  ) )
     3.200  2.600   2.600 peak   5641 weight  0.11000E+01 volume  0.16250E+03 ppm1   7.763 ppm2   1.917
ASSI ( 5651)
    ( ( segid *BrD * and resid 105 and name HN   ) )
    ( ( segid *BrD * and resid 104 and name HA   ) )
     3.200  2.600   2.300 peak   5651 weight  0.11000E+01 volume  0.16160E+03 ppm1   8.488 ppm2   4.688
ASSI ( 5661)
    ( ( segid *BrD * and resid 106 and name HN   ) )
    ( ( segid *BrD * and resid 105 and name HA   ) )
     3.600  3.200   1.900 peak   5661 weight  0.11000E+01 volume  0.94653E+02 ppm1   9.740 ppm2   4.934
ASSI ( 5671)
    ( ( segid *BrD * and resid 107 and name HN   ) )
    ( ( segid *BrD * and resid 106 and name HA   ) )
     3.500  3.100   2.000 peak   5671 weight  0.11000E+01 volume  0.10420E+03 ppm1   8.981 ppm2   4.568
ASSI ( 5681)
    ( ( segid *BrD * and resid 107 and name HN   ) )
    ( ( segid *BrD * and resid 106 and name HB1  ) )
     3.000  2.200   2.200 peak   5681 weight  0.11000E+01 volume  0.25814E+03 ppm1   8.980 ppm2   3.896
ASSI ( 5691)
    ( ( segid *BrD * and resid 108 and name HN   ) )
    ( ( segid *BrD * and resid 107 and name HA   ) )
     3.200  2.600   2.300 peak   5691 weight  0.11000E+01 volume  0.17635E+03 ppm1   8.526 ppm2   4.447
ASSI ( 5701)
    ( ( segid *BrD * and resid 108 and name HN   ) )
    ( ( segid *BrD * and resid 107 and name HB1  ) )
     2.600  1.700   1.700 peak   5701 weight  0.11000E+01 volume  0.68256E+03 ppm1   8.526 ppm2   3.671
ASSI ( 5711)
    ( ( segid *BrD * and resid 109 and name HN   ) )
    ( ( segid *BrD * and resid 108 and name HA   ) )
     3.700  3.400   1.800 peak   5711 weight  0.11000E+01 volume  0.77637E+02 ppm1   8.574 ppm2   4.818
ASSI ( 5721)
    ( ( segid *BrD * and resid 110 and name HN   ) )
    ( ( segid *BrD * and resid 109 and name HA   ) )
     3.700  3.400   1.800 peak   5721 weight  0.11000E+01 volume  0.78233E+02 ppm1   8.714 ppm2   4.615
ASSI ( 5731)
    ( ( segid *BrD * and resid 111 and name HN   ) )
    ( ( segid *BrD * and resid 110 and name HA   ) )
     3.000  2.200   2.200 peak   5731 weight  0.11000E+01 volume  0.28368E+03 ppm1   8.168 ppm2   4.428
ASSI ( 5741)
    ( ( segid *BrD * and resid 111 and name HN   ) )
    ( ( segid *BrD * and resid 110 and name HB   ) )
     2.300  1.300   1.300 peak   5741 weight  0.11000E+01 volume  0.13983E+04 ppm1   8.170 ppm2   2.353
ASSI ( 5751)
    ( ( segid *BrD * and resid 111 and name HN   ) )
    ( ( segid *BrD * and resid 112 and name HN   ) )
     2.800  2.000   2.000 peak   5751 weight  0.11000E+01 volume  0.38572E+03 ppm1   8.168 ppm2   8.663
```

TABLE 2-continued

Unambigous NOE-derived Inter-proton Distance Restraints

ASSI ( 5761)
    ( ( segid *BrD * and resid 113 and name HN   ) )
    ( ( segid *BrD * and resid 112 and name HA   ) )
       2.700  1.800   1.800  peak   5761  weight   0.11000E+01  volume   0.46496E+03  ppm1   8.217  ppm2   4.602
ASSI ( 5771)
    ( ( segid *BrD * and resid 113 and name HN   ) )
    ( ( segid *BrD * and resid 112 and name HG1  ) )
       3.800  3.600   1.700  peak   5771  weight   0.11000E+01  volume   0.43604E+02  ppm1   8.216  ppm2   2.949
ASSI ( 5781)
    ( ( segid *BrD * and resid 113 and name HN   ) )
    ( ( segid *BrD * and resid 112 and name HG2  ) )
       4.100  4.100   1.400  peak   5781  weight   0.11000E+01  volume   0.37977E+02  ppm1   8.217  ppm2   2.812
ASSI ( 5791)
    ( ( segid *BrD * and resid 113 and name HN   ) )
    ( ( segid *BrD * and resid 112 and name HB1  ) )
       2.500  1.600   1.600  peak   5791  weight   0.11000E+01  volume   0.72974E+03  ppm1   8.217  ppm2   2.665
ASSI ( 5801)
    ( ( segid *BrD * and resid 112 and name HN   ) )
    ( ( segid *BrD * and resid 113 and name HN   ) )
       2.500  1.600   1.600  peak   5801  weight   0.11000E+01  volume   0.81801E+03  ppm1   8.668  ppm2   8.185
ASSI ( 5811)
    ( ( segid *BrD * and resid 114 and name HN   ) )
    ( ( segid *BrD * and resid 113 and name HA   ) )
       3.400  2.900   2.100  peak   5811  weight   0.11000E+01  volume   0.12247E+03  ppm1   8.376  ppm2   4.896
ASSI ( 5821)
    ( ( segid *BrD * and resid 114 and name HN   ) )
    (  segid *BrD * and resid 113 and name HB % )
       3.000  2.200   2.200  peak   5821  weight   0.11000E+01  volume   0.28680E+03  ppm1   8.377  ppm2   1.965
ASSI ( 5831)
    ( ( segid *BrD * and resid 115 and name HN   ) )
    ( ( segid *BrD * and resid 114 and name HA1  ) )
       3.500  3.100   2.000  peak   5831  weight   0.11000E+01  volume   0.95188E+02  ppm1   8.355  ppm2   4.626
ASSI ( 5851)
    ( ( segid *BrD * and resid 115 and name HN   ) )
    ( ( segid *BrD * and resid 116 and name HN   ) )
       3.700  3.400   1.800  peak   5851  weight   0.11000E+01  volume   0.76519E+02  ppm1   8.355  ppm2   8.065
ASSI ( 5861)
    ( ( segid *BrD * and resid 117 and name HN   ) )
    ( ( segid *BrD * and resid 116 and name HA   ) )
       2.600  1.700   1.700  peak   5861  weight   0.11000E+01  volume   0.60302E+03  ppm1   8.884  ppm2   4.839
ASSI ( 5871)
    ( ( segid *BrD * and resid 117 and name HN   ) )
    ( ( segid *BrD * and resid 116 and name HB   ) )
       3.100  2.400   2.400  peak   5871  weight   0.11000E+01  volume   0.21223E+03  ppm1   8.876  ppm2   2.417
ASSI ( 5881)
    ( ( segid *BrD * and resid 118 and name HN   ) )
    ( ( segid *BrD * and resid 117 and name HA   ) )
       2.500  1.600   1.600  peak   5881  weight   0.11000E+01  volume   0.81728E+03  ppm1   8.381  ppm2   5.174
ASSI ( 5891)
    ( ( segid *BrD * and resid 79 and name HE21) )
    ( ( segid *BrD * and resid 79 and name HG1 ) )
       3.900  3.800   1.600  peak   5891  weight   0.11000E+01  volume   0.54235E+02  ppm1   7.926  ppm2   3.067
ASSI ( 5901)
    ( ( segid *BrD * and resid 79 and name HE22) )
    ( ( segid *BrD * and resid 79 and name HG1 ) )
       3.500  3.100   2.000  peak   5901  weight   0.11000E+01  volume   0.10842E+03  ppm1   7.829  ppm2   3.067
ASSI ( 5911)
    ( ( segid *BrD * and resid 29 and name HE22) )
    ( ( segid *BrD * and resid 29 and name HG1 ) )
       4.200  4.200   1.300  peak   5911  weight   0.11000E+01  volume   0.35552E+02  ppm1   8.188  ppm2   3.026
ASSI ( 5921)
    ( ( segid *BrD * and resid 29 and name HE22) )
    ( ( segid *BrD * and resid 29 and name HG1 ) )
       3.800  3.600   1.700  peak   5921  weight   0.11000E+01  volume   0.59289E+02  ppm1   7.477  ppm2   3.028
ASSI ( 5931)
    ( ( segid *BrD * and resid 70 and name HN   ) )
    ( ( segid *BrD * and resid 70 and name HB1  ) )
       3.300  2.700   2.200  peak   5931  weight   0.11000E+01  volume   0.15569E+03  ppm1   8.039  ppm2   4.807
ASSI ( 5941)
    ( ( segid *BrD * and resid 18 and name HN   ) )
    ( ( segid *BrD * and resid 18 and name HB1  ) )
       2.700  1.800   1.800  peak   5941  weight   0.11000E+01  volume   0.45519E+03  ppm1   9.072  ppm2   2.113
ASSI ( 5951)
    ( ( segid *BrD * and resid 18 and name HN   ) )
    ( ( segid *BrD * and resid 18 and name HG   ) )
       2.600  1.700   1.700  peak   5951  weight   0.11000E+01  volume   0.61681E+03  ppm1   9.072  ppm2   2.279

TABLE 2-continued

Unambigous NOE-derived Inter-proton Distance Restraints

```
ASSI ( 5961)
   ( ( segid *BrD * and resid 18 and name HN   ) )
   ( ( segid *BrD * and resid 18 and name HD2%) )
      3.000  2.200   2.200 peak    5961 weight   0.11000E+01 volume   0.24628E+03 ppm1    9.076 ppm2   0.416
ASSI ( 5971)
   ( ( segid *BrD * and resid 78 and name HN   ) )
   ( ( segid *BrD * and resid 78 and name HB1  ) )
      3.000  2.200   2.200 peak    5971 weight   0.11000E+01 volume   0.24153E+03 ppm1    7.996 ppm2   1.360
ASSI ( 5981)
   ( ( segid *BrD * and resid 78 and name HN   ) )
   ( ( segid *BrD * and resid 78 and name HB2  ) )
      2.600  1.700   1.700 peak    5981 weight   0.11000E+01 volume   0.64225E+03 ppm1    7.996 ppm2   1.048
ASSI ( 5991)
   ( ( segid *BrD * and resid 78 and name HN   ) )
   (   segid *BrD * and resid 78 and name HD2%)
      3.500  3.100   2.000 peak    5991 weight   0.11000E+01 volume   0.10124E+03 ppm1    7.994 ppm2   0.667
ASSI ( 6001)
   ( ( segid *BrD * and resid 78 and name HN   ) )
   (   segid *BrD * and resid 78 and name HG   ) )
      3.000  2.200   2.200 peak    6001 weight   0.11000E+01 volume   0.26923E+03 ppm1    7.996 ppm2   1.293
ASSI ( 6011)
   ( ( segid *BrD * and resid 78 and name HN   ) )
   (   segid *BrD * and resid 78 and name HD1%)
      3.500  3.100   2.000 peak    6011 weight   0.11000E+01 volume   0.10789E+03 ppm1    7.996 ppm2   0.790
ASSI ( 6021)
   ( ( segid *BrD * and resid 115 and name HN  ) )
   ( ( segid *BrD * and resid 115 and name HB1 ) )
      3.200  2.600   2.300 peak    6021 weight   0.11000E+01 volume   0.18336E+03 ppm1    8.355 ppm2   2.167
ASSI ( 6031)
   ( ( segid *BrD * and resid 115 and name HN  ) )
   (   segid *BrD * and resid 115 and name HD1%)
      2.800  2.000   2.000 peak    6031 weight   0.11000E+01 volume   0.43402E+03 ppm1    8.354 ppm2   1.318
ASSI ( 6041)
   ( ( segid *BrD * and resid 116 and name HN  ) )
   ( ( segid *BrD * and resid 116 and name HG11) )
      2.900  2.100   2.100 peak    6041 weight   0.11000E+01 volume   0.29943E+03 ppm1    8.086 ppm2   1.921
ASSI ( 6051)
   ( ( segid *BrD * and resid 116 and name HN  ) )
   ( ( segid *BrD * and resid 116 and name HG12) )
      3.000  2.200   2.00  peak    6051 weight   0.11000E+01 volume   0.27021E+03 ppm1    8.083 ppm2   1.525
ASSI ( 6061)
   ( ( segid *BrD * and resid 116 and name HN  ) )
   (   segid *BrD * and resid 116 and name HG2%)
      2.500  1.600   1.600 peak    6061 weight   0.11000E+01 volume   0.86711E+03 ppm1    8.084 ppm2   1.420
ASSI ( 6071)
   ( ( segid *BrD * and resid 110 and name HN  ) )
   ( ( segid *BrD * and resid 110 and name HG12) )
      3.000  2.200   2.200 peak    6071 weight   0.11000E+01 volume   0.25527E+03 ppm1    8.714 ppm2   1.679
ASSI ( 6081)
   ( ( segid *BrD * and resid 110 and name HN  ) )
   (   segid *BrD * and resid 110 and name HG2%)
      2.800  2.000   2.000 peak    6081 weight   0.11000E+01 volume   0.42268E+03 ppm1    8.714 ppm2   1.261
ASSI ( 6091)
   ( ( segid *BrD * and resid 110 and name HN  ) )
   (   segid *BrD * and resid 110 and name HD1%)
      3.400  2.900   2.100 peak    6091 weight   0.11000E+01 volume   0.13013E+03 ppm1    8.714 ppm2   1.116
ASSI ( 6101)
   ( ( segid *BrD * and resid 50 and name HN   ) )
   ( ( segid *BrD * and resid 50 and name HB   ) )
      2.400  1.400   1.400 peak    6101 weight   0.11000E+01 volume   0.10564E+04 ppm1    8.564 ppm2   1.812
ASSI ( 6111)
   ( ( segid *BrD * and resid 50 and name HN   ) )
   (   segid *BrD * and resid 50 and name HD1%)
      3.200  2.600   2.300 peak    6111 weight   0.11000E+01 volume   0.17790E+03 ppm1    8.564 ppm2   1.144
ASSI ( 6121)
   ( ( segid *BrD * and resid 50 and name HN   ) )
   ( ( segid *BrD * and resid 50 and name HG12) )
      3.300  2.700   2.200 peak    6121 weight   0.11000E+01 volume   0.13759E+03 ppm1    8.564 ppm2   0.823
ASSI ( 6131)
   ( ( segid *BrD * and resid 50 and name HN   ) )
   (   segid *BrD * and resid 50 and name HG2%)
      3.000  2.200   2.200 peak    6131 weight   0.11000E+01 volume   0.27674E+03 ppm1    8.564 ppm2   0.991
ASSI ( 6141)
   ( ( segid *BrD * and resid 50 and name HN   ) )
   ( ( segid *BrD * and resid 50 and name HG11) )
      4.100  4.100   1.400 peak    6141 weight   0.11000E+01 volume   0.38065E+02 ppm1    8.564 ppm2   1.405
```

TABLE 2-continued

Unambigous NOE-derived Inter-proton Distance Restraints

```
ASSI ( 6151)
    ( ( segid *BrD * and resid 21 and name HN   ) )
    ( ( segid *BrD * and resid 20 and name HB1 ) )
     2.600  1.700   1.700  peak    6151  weight    0.11000E+01 volume   0.62145E+03 ppm1    8.544 ppm2    4.667
ASSI ( 6161)
    ( ( segid *BrD * and resid 20 and name HN   ) )
    ( ( segid *BrD * and resid 21 and name HN   ) )
     2.800  2.000   2.000  peak    6161  weight    0.11000E+01 volume   0.39694E+03 ppm1    8.146 ppm2    8.547
ASSI ( 6191)
    ( ( segid *BrD * and resid 22 and name HN   ) )
    ( ( segid *BrD * and resid 21 and name HN   ) )
     2.800  2.000   2.000  peak    6191  weight    0.11000E+01 volume   0.40962E+03 ppm1    9.455 ppm2    8.532
ASSI ( 6201)
    ( ( segid *BrD * and resid 101 and name HN   ) )
    ( ( segid *BrD * and resid 101 and name HG11) )
     2.400  1.400   1.400  peak    6201  weight    0.11000E+01 volume   0.10700E+04 ppm1    8.514 ppm2    2.489
ASSI ( 6211)
    ( ( segid *BrD * and resid 101 and name HN   ) )
    ( ( segid *BrD * and resid 101 and name HG12) )
     2.800  2.000   2.000  peak    6211  weight    0.11000E+01 volume   0.39771E+03 ppm1    8.513 ppm2    1.808
ASSI ( 6221)
    ( ( segid *BrD * and resid 101 and name HN   ) )
    (   segid *BrD * and resid 101 and name HG2%)
     2.700  1.800   1.800  peak    6221  weight    0.11000E+01 volume   0.49123E+03 ppm1    8.513 ppm2    1.596
ASSI ( 6231)
    ( ( segid *BrD * and resid 21 and name HN   ) )
    ( ( segid *BrD * and resid 21 and name HB   ) )
     2.600  1.700   1.700  peak    6231  weight    0.11000E+01 volume   0.63964E+03 ppm1    8.545 ppm2    2.495
ASSI ( 6241)
    ( ( segid *BrD * and resid 21 and name HN   ) )
    ( ( segid *BrD * and resid 21 and name HG11) )
     2.300  1.300   1.300  peak    6241  weight    0.11000E+01 volume   0.13646E+04 ppm1    8.545 ppm2    2.355
ASSI ( 6251)
    ( ( segid *BrD * and resid 21 and name HN   ) )
    ( ( segid *BrD * and resid 21 and name HG12) )
     3.100  2.400   2.400  peak    6251  weight    0.11000E+01 volume   0.22794E+03 ppm1    8.556 ppm2    1.659
ASSI ( 6261)
    ( ( segid *BrD * and resid 21 and name HN   ) )
    (   segid *BrD * and resid 21 and name HG2%)
     2.600  1.700   1.700  peak    6261  weight    0.11000E+01 volume   0.60538E+03 ppm1    8.556 ppm2    1.605
ASSI ( 6271)
    ( ( segid *BrD * and resid 21 and name HN   ) )
    (   segid *BrD * and resid 21 and name HD1%)
     2.900  2.100   2.100  peak    6271  weight    0.11000E+01 volume   0.30098E+03 ppm1    8.545 ppm2    1.226
ASSI ( 6281)
    ( ( segid *BrD * and resid 87 and name HN   ) )
    ( ( segid *BrD * and resid 87 and name HB1 ) )
     2.800  2.000   2.000  peak    6281  weight    0.11000E+01 volume   0.31963E+03 ppm1    8.570 ppm2    2.771
ASSI ( 6291)
    ( ( segid *BrD * and resid 79 and name HN   ) )
    ( ( segid *BrD * and resid 79 and name HB1 ) )
     2.500  1.600   1.600  peak    6291  weight    0.11000E+01 volume   0.73947E+03 ppm1    8.681 ppm2    2.771
ASSI ( 6301)
    ( ( segid *BrD * and resid 80 and name HN   ) )
    ( ( segid *BrD * and resid 79 and name HB1 ) )
     3.500  3.100   2.000  peak    6301  weight    0.11000E+01 volume   0.10437E+03 ppm1    8.006 ppm2    2.764
ASSI ( 6311)
    ( ( segid *BrD * and resid 23 and name HN   ) )
    ( ( segid *BrD * and resid 23 and name HG2 ) )
     3.200  2.600   2.300  peak    6311  weight    0.11000E+01 volume   0.19029E+03 ppm1    9.120 ppm2    3.068
ASSI ( 6321)
    ( ( segid *BrD * and resid 80 and name HN   ) )
    ( ( segid *BrD * and resid 80 and name HG1 ) )
     3.400  2.900   2.100  peak    6321  weight    0.11000E+01 volume   0.12866E+03 ppm1    8.006 ppm2    2.336
ASSI ( 6331)
    ( ( segid *BrD * and resid 80 and name HN   ) )
    ( ( segid *BrD * and resid 80 and name HB1 ) )
     2.600  2.000   2.000  peak    6331  weight    0.11000E+01 volume   0.38416E+03 ppm1    8.006 ppm2    2.579
ASSI ( 6341)
    ( ( segid *BrD * and resid 80 and name HN   ) )
    ( ( segid *BrD * and resid 80 and name HB2 ) )
     2.600  1.700   1.700  peak    6341  weight    0.11000E+01 volume   0.55298E+03 ppm1    8.006 ppm2    2.497
ASSI ( 6351)
    ( ( segid *BrD * and resid 66 and name HN   ) )
    ( ( segid *BrD * and resid 66 and name HB2 ) )
     3.400  2.900   2.100  peak    6351  weight    0.11000E+01 volume   0.12971E+03 ppm1    8.763 ppm2    2.629
```

TABLE 2-continued

Unambigous NOE-derived Inter-proton Distance Restraints

```
ASSI ( 6361)
    ( ( segid *BrD * and resid 66 and name HN   ) )
    ( ( segid *BrD * and resid 66 and name HG1  ) )
      2.700  1.800   1.800  peak   6361  weight   0.11000E+01 volume   0.45372E+03 ppm1   8.764 ppm2   2.155
ASSI ( 6371)
    ( ( segid *BrD * and resid 9 and name HN   ) )
    ( ( segid *BrD * and resid 9 and name HG1  ) )
      3.600  3.200   1.900  peak   6371  weight   0.11000E+01 volume   0.84495E+02 ppm1   9.053 ppm2   2.254
ASSI ( 6381)
    ( ( segid *BrD * and resid 9 and name HN   ) )
    ( ( segid *BrD * and resid 9 and name HB2  ) )
      3.400  2.900   2.100  peak   6381  weight   0.11000E+01 volume   0.12497E+03 ppm1   9.055 ppm2   2.369
ASSI ( 6391)
    ( ( segid *BrD * and resid 102 and name HN   ) )
    (   segid *BrD * and resid 102 and name HD1%)
      3.100  2.400   2.400  peak   6391  weight   0.11000E+01 volume   0.19704E+03 ppm1   9.156 ppm2   1.310
ASSI ( 6401)
    ( ( segid *BrD * and resid 102 and name HN   ) )
    ( ( segid *BrD * and resid 102 and name HB2  ) )
      2.400  1.400   1.400  peak   6401  weight   0.11000E+01 volume   0.88089E+03 ppm1   9.155 ppm2   1.808
ASSI ( 6411)
    ( ( segid *BrD * and resid 102 and name HN   ) )
    ( ( segid *BrD * and resid 102 and name HB1  ) )
      2.700  1.800   1.800  peak   6411  weight   0.11000E+01 volume   0.47200E+03 ppm1   9.155 ppm2   2.002
ASSI ( 6421)
    ( ( segid *BrD * and resid 102 and name HN   ) )
    ( ( segid *BrD * and resid 102 and name HG   ) )
      3.200  2.600   2.300  peak   6421  weight   0.11000E+01 volume   0.16630E+03 ppm1   9.157 ppm2   2.152
ASSI ( 6431)
    ( ( segid *BrD * and resid 73 and name HN   ) )
    ( ( segid *BrD * and resid 73 and name HB2  ) )
      2.800  2.000   2.000  peak   6431  weight   0.11000E+01 volume   0.37491E+03 ppm1   8.045 ppm2   2.495
ASSI ( 6441)
    ( ( segid *BrD * and resid 73 and name HN   ) )
    ( ( segid *BrD * and resid 73 and name HG   ) )
      3.400  2.900   2.100  peak   6441  weight   0.11000E+01 volume   0.13407E+03 ppm1   8.045 ppm2   2.376
ASSI ( 6451)
    ( ( segid *BrD * and resid 73 and name HN   ) )
    (   segid *BrD * and resid 73 and name HD2%)
      3.600  3.200   1.900  peak   6451  weight   0.11000E+01 volume   0.91167E+02 ppm1   8.049 ppm2   1.491
ASSI ( 6461)
    ( ( segid *BrD * and resid 56 and name HN   ) )
    (   segid *BrD * and resid 56 and name HD1%)
      3.200  2.600   2.300  peak   6461  weight   0.11000E+01 volume   0.17282E+03 ppm1   9.679 ppm2   1.521
ASSI ( 6471)
    ( ( segid *BrD * and resid 56 and name HN   ) )
    ( ( segid *BrD * and resid 56 and name HG   ) )
      2.500  1.600   1.600  peak   6471  weight   0.11000E+01 volume   0.74688E+03 ppm1   9.680 ppm2   2.320
ASSI ( 6481)
    ( ( segid *BrD * and resid 56 and name HN   ) )
    ( ( segid *BrD * and resid 56 and name HB2  ) )
      3.100  2.400   2.400  peak   6481  weight   0.11000E+01 volume   0.21719E+03 ppm1   9.680 ppm2   2.002
ASSI ( 6491)
    ( ( segid *BrD * and resid 22 and name HN   ) )
    (   segid *BrD * and resid 22 and name HD1%)
      3.200  2.600   2.300  peak   6491  weight   0.11000E+01 volume   0.16857E+03 ppm1   9.456 ppm2   1.668
ASSI ( 6501)
    ( ( segid *BrD * and resid 22 and name HN   ) )
    ( ( segid *BrD * and resid 22 and name HB2  ) )
      2.400  1.400   1.400  peak   6501  weight   0.11000E+01 volume   0.10693E+04 ppm1   9.455 ppm2   2.292
ASSI ( 6511)
    ( ( segid *BrD * and resid 22 and name HN   ) )
    ( ( segid *BrD * and resid 22 and name HB1  ) )
      2.700  1.800   1.800  peak   6511  weight   0.11000E+01 volume   0.47530E+03 ppm1   9.455 ppm2   2.693
ASSI ( 6521)
    ( ( segid *BrD * and resid 22 and name HN   ) )
    ( ( segid *BrD * and resid 22 and name HG   ) )
      3.700  3.400   1.800  peak   6521  weight   0.11000E+01 volume   0.69056E+02 ppm1   9.455 ppm2   2.366
ASSI ( 6531)
    ( ( segid *BrD * and resid 63 and name HN   ) )
    (   segid *BrD * and resid 63 and name HD2%)
      3.200  2.600   2.300  peak   6531  weight   0.11000E+01 volume   0.19269E+03 ppm1   9.473 ppm2   1.478
ASSI ( 6541)
    ( ( segid *BrD * and resid 63 and name HN   ) )
    (   segid *BrD * and resid 63 and name HD1%)
      3.100  2.400   2.400  peak   6541  weight   0.11000E+01 volume   0.21627E+03 ppm1   9.472 ppm2   1.674
```

TABLE 2-continued

Unambigous NOE-derived Inter-proton Distance Restraints

```
ASSI (  6561)
    ( ( segid *BrD * and resid 63 and name HN   ) )
    ( ( segid *BrD * and resid 63 and name HB2  ) )
      2.500  1.600    1.600  peak    6561  weight   0.11000E+01  volume   0.86099E+03  ppm1    9.473  ppm2   2.532
ASSI (  6571)
    ( ( segid *BrD * and resid 63 and name HN   ) )
    ( ( segid *BrD * and resid 63 and name HG   ) )
      3.000  2.200    2.00   peak    6571  weight   0.11000E+01  volume   0.26899E+03  ppm1    9.472  ppm2   2.439
ASSI (  6581)
    ( ( segid *BrD * and resid 14 and name HN   ) )
    ( ( segid *BrD * and resid 14 and name HB1  ) )
      2.500  1.600    1.600  peak    6581  weight   0.11000E+01  volume   0.80229E+03  ppm1    8.809  ppm2   2.453
ASSI (  6591)
    ( ( segid *BrD * and resid 14 and name HN   ) )
    ( ( segid *BrD * and resid 14 and name HG   ) )
      3.000  2.200    2.200  peak    6591  weight   0.11000E+01  volume   0.34747E+03  ppm1    8.809  ppm2   2.064
ASSI (  6601)
    ( ( segid *BrD * and resid 14 and name HN   ) )
    ( ( segid *BrD * and resid 14 and name HB2  ) )
      2.500  1.600    1.600  peak    6601  weight   0.11000E+01  volume   0.85081E+03  ppm1    8.809  ppm2   2.164
ASSI (  6611)
    ( ( segid *BrD * and resid 14 and name HN   ) )
    (   segid *BrD * and resid 14 and name HD1%)
      3.200  2.600    2.300  peak    6611  weight   0.11000E+01  volume   0.18673E+03  ppm1    8.809  ppm2   1.401
ASSI (  6621)
    ( ( segid *BrD * and resid 24 and name HN   ) )
    ( ( segid *BrD * and resid 24 and name HG2  ) )
      2.300  1.300    1.300  peak    6621  weight   0.11000E+01  volume   0.12087E+04  ppm1    8.654  ppm2   3.032
ASSI (  6631)
    ( ( segid *BrD * and resid 49 and name HN   ) )
    (   segid *BrD * and resid 49 and name HG1%)
      3.100  2.400    2.400  peak    6631  weight   0.11000E+01  volume   0.20533E+03  ppm1    7.762  ppm2   1.652
ASSI (  6641)
    ( ( segid *BrD * and resid 50 and name HN   ) )
    (   segid *BrD * and resid 49 and name HG1%)
      3.400  2.900    2.100  peak    6641  weight   0.11000E+01  volume   0.12406E+03  ppm1    8.564  ppm2   1.652
ASSI (  6651)
    ( ( segid *BrD * and resid 64 and name HN   ) )
    ( ( segid *BrD * and resid 64 and name HB1  ) )
      2.400  1.400    1.400  peak    6651  weight   0.11000E+01  volume   0.10941E+04  ppm1    8.584  ppm2   2.661
ASSI (  6661)
    ( ( segid *BrD * and resid 64 and name HN   ) )
    ( ( segid *BrD * and resid 64 and name HG1  ) )
      2.700  1.800    1.800  peak    6661  weight   0.11000E+01  volume   0.45034E+03  ppm1    8.584  ppm2   2.210
ASSI (  6671)
    ( ( segid *BrD * and resid 64 and name HN   ) )
    ( ( segid *BrD * and resid 64 and name HD1  ) )
      3.600  3.200    1.900  peak    6671  weight   0.11000E+01  volume   0.82950E+02  ppm1    8.584  ppm2   2.411
ASSI (  6681)
    ( ( segid *BrD * and resid 104 and name HN  ) )
    ( ( segid *BrD * and resid 104 and name HB1 ) )
      2.600  1.700    1.700  peak    6681  weight   0.11000E+01  volume   0.59758E+03  ppm1    7.763  ppm2   2.537
ASSI (  6691)
    ( ( segid *BrD * and resid 104 and name HN  ) )
    ( ( segid *BrD * and resid 104 and name HG1 ) )
      3.000  2.200    2.200  peak    6691  weight   0.11000E+01  volume   0.24911E+03  ppm1    7.763  ppm2   2.099
ASSI (  6701)
    ( ( segid *BrD * and resid 104 and name HN  ) )
    ( ( segid *BrD * and resid 104 and name HD1 ) )
      2.900  2.100    2.100  peak    6701  weight   0.11000E+01  volume   0.30408E+03  ppm1    7.763  ppm2   2.288
ASSI (  6711)
    ( ( segid *BrD * and resid 111 and name HN  ) )
    ( ( segid *BrD * and resid 111 and name HB1 ) )
      2.600  1.700    1.700  peak    6711  weight   0.11000E+01  volume   0.66813E+03  ppm1    8.168  ppm2   2.482
ASSI (  6721)
    ( ( segid *BrD * and resid 111 and name HN  ) )
    ( ( segid *BrD * and resid 111 and name HB2 ) )
      2.400  1.400    1.400  peak    6721  weight   0.11000E+01  volume   0.98067E+03  ppm1    8.170  ppm2   2.376
ASSI (  6731)
    ( ( segid *BrD * and resid 111 and name HN  ) )
    ( ( segid *BrD * and resid 111 and name HG2 ) )
      3.600  3.200    1.900  peak    6731  weight   0.11000E+01  volume   0.88731E+02  ppm1    8.168  ppm2   1.922
ASSI (  6741)
    ( ( segid *BrD * and resid 111 and name HN  ) )
    ( ( segid *BrD * and resid 111 and name HG1 ) )
      3.200  2.600    2.300  peak    6741  weight   0.11000E+01  volume   0.16392E+03  ppm1    8.168  ppm2   2.002
```

TABLE 2-continued

Unambigous NOE-derived Inter-proton Distance Restraints

```
ASSI ( 6761)
    ( ( segid *BrD * and resid 19 and name HN   ) )
    ( ( segid *BrD * and resid 19 and name HB1  ) )
       2.700  1.800   1.800 peak    6761 weight   0.11000E+01 volume   0.53478E+03 ppm1   9.187 ppm2   2.325
ASSI ( 6771)
    ( ( segid *BrD * and resid 19 and name HN   ) )
    ( ( segid *BrD * and resid 19 and name HG1  ) )
       4.000  4.000   1.500 peak    6771 weight   0.11000E+01 volume   0.45358E+02 ppm1   9.188 ppm2   1.879
ASSI ( 6781)
    ( ( segid *BrD * and resid 19 and name HN   ) )
    ( ( segid *BrD * and resid 19 and name HG   ) )
       2.800  2.000   2.000 peak    6781 weight   0.11000E+01 volume   0.38484E+03 ppm1   9.187 ppm2   2.271
ASSI ( 6791)
    ( ( segid *BrD * and resid 12 and name HN   ) )
    ( ( segid *BrD * and resid 11 and name HA   ) )
       3.000  2.200   2.200 peak    6791 weight   0.11000E+01 volume   0.26617E+03 ppm1   9.021 ppm2   4.940
ASSI ( 6801)
    ( ( segid *BrD * and resid 97 and name HN   ) )
    ( ( segid *BrD * and resid 97 and name HB1  ) )
       2.300  1.300   1.300 peak    6801 weight   0.11000E+01 volume   0.12859E+04 ppm1   8.674 ppm2   2.708
ASSI ( 6811)
    ( ( segid *BrD * and resid 97 and name HN   ) )
    ( ( segid *BrD * and resid 97 and name HG2  ) )
       2.900  2.100   2.100 peak    6811 weight   0.11000E+01 volume   0.32919E+03 ppm1   8.674 ppm2   2.193
ASSI ( 6821)
    ( ( segid *BrD * and resid 109 and name HN  ) )
    ( ( segid *BrD * and resid 109 and name HB1 ) )
       2.300  1.300   1.300 peak    6821 weight   0.11000E+01 volume   0.11797E+04 ppm1   8.573 ppm2   2.236
ASSI ( 6831)
    ( ( segid *BrD * and resid 109 and name HN  ) )
    ( ( segid *BrD * and resid 109 and name HB2 ) )
       3.200  2.600   2.100 peak    6831 weight   0.11000E+01 volume   0.19151E+03 ppm1   8.573 ppm2   2.173
ASSI ( 6841)
    ( ( segid *BrD * and resid 109 and name HN  ) )
    ( ( segid *BrD * and resid 109 and name HG1 ) )
       3.700  3.400   1.800 peak    6841 weight   0.11000E+01 volume   0.70793E+02 ppm1   8.574 ppm2   1.439
ASSI ( 6881)
    ( ( segid *BrD * and resid 86 and name HN   ) )
    ( ( segid *BrD * and resid 86 and name HB1  ) )
       2.700  1.800   1.800 peak    6881 weight   0.11000E+01 volume   0.51142E+03 ppm1   8.422 ppm2   2.359
ASSI ( 6891)
    ( ( segid *BrD * and resid 86 and name HN   ) )
    ( ( segid *BrD * and resid 86 and name HG2  ) )
       3.400  2.900   2.100 peak    6891 weight   0.11000E+01 volume   0.13112E+03 ppm1   8.423 ppm2   0.745
ASSI ( 6901)
    ( ( segid *BrD * and resid 86 and name HN   ) )
    ( ( segid *BrD * and resid 86 and name HD1  ) )
       3.800  3.600   1.700 peak    6901 weight   0.11000E+01 volume   0.59192E+02 ppm1   8.423 ppm2   1.862
ASSI ( 6921)
    ( ( segid *BrD * and resid 103 and name HN  ) )
    ( ( segid *BrD * and resid 103 and name HG1 ) )
       3.000  2.200   2.200 peak    6921 weight   0.11000E+01 volume   0.24153E+03 ppm1   8.695 ppm2   2.613
ASSI ( 6931)
    ( ( segid *BrD * and resid 104 and name HN  ) )
    ( ( segid *BrD * and resid 103 and name HG1 ) )
       3.200  2.600   2.300 peak    6931 weight   0.11000E+01 volume   0.18108E+03 ppm1   7.763 ppm2   2.608
ASSI ( 6941)
    ( ( segid *BrD * and resid 48 and name HN   ) )
    ( ( segid *BrD * and resid 48 and name HG1  ) )
       3.300  2.700   2.200 peak    6941 weight   0.11000E+01 volume   0.14027E+03 ppm1   8.307 ppm2   2.909
ASSI ( 6951)
    ( ( segid *BrD * and resid 49 and name HN   ) )
    ( ( segid *BrD * and resid 48 and name HG1  ) )
       4.100  4.100   1.400 peak    6951 weight   0.11000E+01 volume   0.41580E+02 ppm1   7.762 ppm2   2.932
ASSI ( 6961)
    ( ( segid *BrD * and resid 66 and name HN   ) )
    ( ( segid *BrD * and resid 66 and name HB1  ) )
       3.200  2.600   2.300 peak    6941 weight   0.11000E+01 volume   0.17814E+03 ppm1   8.763 ppm2   2.704
ASSI ( 6971)
    ( ( segid *BrD * and resid 35 and name HN   ) )
    ( ( segid *BrD * and resid 35 and name HB1  ) )
       2.900  2.100   2.100 peak    6971 weight   0.11000E+01 volume   0.32270E+03 ppm1   7.734 ppm2   2.850
ASSI ( 6981)
    ( ( segid *BrD * and resid 54 and name HN   ) )
    ( ( segid *BrD * and resid 53 and name HA   ) )
       2.500  1.600   1.600 peak    6981 weight   0.11000E+01 volume   0.78564E+03 ppm1   9.036 ppm2   4.690
```

TABLE 2-continued

Unambigous NOE-derived Inter-proton Distance Restraints

```
ASSI ( 6991)
  ( ( segid *BrD * and resid 38 and name HN   ) )
  ( ( segid *BrD * and resid 37 and name HA   ) )
     2.200  1.200   1.200 peak    6991 weight   0.11000E+01 volume   0.16736E+04 ppm1   8.731 ppm2   4.849
ASSI ( 7001)
  ( ( segid *BrD * and resid 51 and name HN   ) )
  ( ( segid *BrD * and resid 51 and name HB1  ) )
     2.900  2.100   2.100 peak    7001 weight   0.11000E+01 volume   0.35413E+03 ppm1   8.375 ppm2   1.980
ASSI ( 7011)
  ( ( segid *BrD * and resid 51 and name HN   ) )
  ( ( segid *BrD * and resid 51 and name HB2  ) )
     3.000  2.200   2.200 peak    7011 weight   0.11000E+01 volume   0.24666E+03 ppm1   8.375 ppm2   1.818
ASSI ( 7021)
  ( ( segid *BrD * and resid 51 and name HN   ) )
  ( ( segid *BrD * and resid 51 and name HG2  ) )
     3.000  2.200   2.200 peak    7021 weight   0.11000E+01 volume   0.24666E+03 ppm1   8.375 ppm2   1.786
ASSI ( 7041)
  ( ( segid *BrD * and resid 52 and name HN   ) )
  ( ( segid *BrD * and resid 52 and name HA   ) )
     2.900  2.100   2.100 peak    7041 weight   0.11000E+01 volume   0.32203E+03 ppm1   9.004 ppm2   8.591
ASSI ( 7051)
  ( ( segid *BrD * and resid 52 and name HN   ) )
  ( ( segid *BrD * and resid 52 and name HB1  ) )
     2.700  1.800   1.800 peak    7051 weight   0.11000E+01 volume   0.48728E+03 ppm1   9.004 ppm2   3.641
ASSI ( 7061)
  ( ( segid *BrD * and resid 52 and name HN   ) )
  ( ( segid *BrD * and resid 52 and name HB2  ) )
     2.500  1.600   1.600 peak    7061 weight   0.11000E+01 volume   0.72550E+03 ppm1   9.003 ppm2   3.514
ASSI ( 7071)
  ( ( segid *BrD * and resid 52 and name HN   ) )
  ( ( segid *BrD * and resid 51 and name HN   ) )
     2.600  1.700   1.700 peak    7071 weight   0.11000E+01 volume   0.63507E+03 ppm1   9.004 ppm2   3.356
ASSI ( 7091)
  ( ( segid *BrD * and resid 52 and name HN   ) )
  ( ( segid *BrD * and resid 51 and name HA   ) )
     3.000  2.200   2.200 peak    7091 weight   0.11000E+01 volume   0.26640E+03 ppm1   9.004 ppm2   4.482
ASSI ( 7101)
  ( ( segid *BrD * and resid 52 and name HN   ) )
  ( ( segid *BrD * and resid 53 and name HD1  ) )
     3.500  3.100   2.000 peak    7101 weight   0.11000E+01 volume   0.10263E+03 ppm1   9.004 ppm2   4.230
ASSI ( 7111)
  ( ( segid *BrD * and resid 52 and name HN   ) )
  ( ( segid *BrD * and resid 53 and name HD2  ) )
     3.900  3.800   1.600 peak    7111 weight   0.11000E+01 volume   0.57287E+02 ppm1   9.003 ppm2   3.997
ASSI ( 7141)
  ( ( segid *BrD * and resid 59 and name HN   ) )
  ( ( segid *BrD * and resid 59 and name HG2  ) )
     3.300  2.700   2.200 peak    7141 weight   0.11000E+01 volume   0.14988E+03 ppm1   8.496 ppm2   3.103
ASSI ( 7151)
  ( ( segid *BrD * and resid 59 and name HN   ) )
  ( ( segid *BrD * and resid 59 and name HG1  ) )
     3.400  2.900   2.100 peak    7151 weight   0.11000E+01 volume   0.12335E+03 ppm1   8.498 ppm2   3.228
ASSI ( 7161)
  ( ( segid *BrD * and resid 59 and name HN   ) )
  ( ( segid *BrD * and resid 59 and name HB1  ) )
     3.400  2.900   2.100 peak    7161 weight   0.11000E+01 volume   0.11956E+03 ppm1   8.498 ppm2   2.700
ASSI ( 7171)
  ( ( segid *BrD * and resid 59 and name HN   ) )
  ( ( segid *BrD * and resid 59 and name HB2  ) )
     3.200  2.600   2.300 peak    7171 weight   0.11000E+01 volume   0.17215E+03 ppm1   8.499 ppm2   2.504
ASSI ( 7181)
  ( ( segid *BrD * and resid 57 and name HN   ) )
  ( ( segid *BrD * and resid 57 and name HB1  ) )
     2.400  1.400   1.400 peak    7181 weight   0.11000E+01 volume   0.94732E+03 ppm1   9.359 ppm2   2.947
ASSI ( 7191)
  ( ( segid *BrD * and resid 57 and name HN   ) )
  ( ( segid *BrD * and resid 57 and name HB2  ) )
     2.500  1.600   1.600 peak    7191 weight   0.11000E+01 volume   0.75718E+03 ppm1   9.358 ppm2   2.827
ASSI ( 7201)
  ( ( segid *BrD * and resid 57 and name HN   ) )
  ( ( segid *BrD * and resid 57 and name HG1  ) )
     3.600  3.200   1.900 peak    7201 weight   0.11000E+01 volume   0.93147E+02 ppm1   9.359 ppm2   2.088
ASSI ( 7211)
  ( ( segid *BrD * and resid 57 and name HN   ) )
  ( ( segid *BrD * and resid 57 and name HD1  ) )
     4.300  4.300   1.200 peak    7211 weight   0.11000E+01 volume   0.28923E+02 ppm1   9.358 ppm2   2.411
```

TABLE 2-continued

Unambigous NOE-derived Inter-proton Distance Restraints

```
ASSI ( 7221)
  ( ( segid *BrD * and resid 57 and name HN   ) )
  ( ( segid *BrD * and resid 57 and name HD2  ) )
    3.400  2.900   2.100  peak   7221  weight   0.11000E+01  volume   0.13023E+03  ppm1   9.359  ppm2   2.292
ASSI ( 7231)
  ( ( segid *BrD * and resid 26 and name HN   ) )
  ( ( segid *BrD * and resid 26 and name HB1  ) )
    3.300  2.700   2.200  peak   7231  weight   0.11000E+01  volume   0.15703E+03  ppm1   9.195  ppm2   2.463
ASSI ( 7241)
  ( ( segid *BrD * and resid 26 and name HN   ) )
  ( ( segid *BrD * and resid 26 and name HD1  ) )
    3.500  3.100   2.000  peak   7241  weight   0.11000E+01  volume   0.99010E+02  ppm1   9.196  ppm2   2.092
ASSI ( 7261)
  ( ( segid *BrD * and resid 10 and name HN   ) )
  ( ( segid *BrD * and resid 11 and name HD1  ) )
    4.600  4.600   0.900  peak   7261  weight   0.11000E+01  volume   0.20621E+02  ppm1   8.885  ppm2   4.475
ASSI ( 7271)
  ( ( segid *BrD * and resid 10 and name HN   ) )
  ( ( segid *BrD * and resid 9 and name HB1   ) )
    3.400  2.900   2.100  peak   7271  weight   0.11000E+01  volume   0.12456E+03  ppm1   8.883  ppm2   2.422
ASSI ( 7281)
  ( ( segid *BrD * and resid 13 and name HN   ) )
  ( ( segid *BrD * and resid 12 and name HB1  ) )
    3.500  3.100   2.000  peak   7281  weight   0.11000E+01  volume   0.11107E+03  ppm1   8.802  ppm2   3.399
ASSI ( 7301)
  ( ( segid *BrD * and resid 15 and name HN   ) )
  ( ( segid *BrD * and resid 14 and name HN   ) )
    2.900  2.100   2.100  peak   7301  weight   0.11000E+01  volume   0.28889E+03  ppm1   8.597  ppm2   3.417
ASSI ( 7311)
  ( ( segid *BrD * and resid 16 and name HN   ) )
  ( ( segid *BrD * and resid 13 and name HA   ) )
    3.500  3.100   2.000  peak   7311  weight   0.11000E+01  volume   0.96679E+02  ppm1   8.794  ppm2   4.770
ASSI ( 7321)
  ( ( segid *BrD * and resid 15 and name HN   ) )
  (   segid *BrD * and resid 14 and name HD2%)
    3.600  3.200   1.900  peak   7321  weight   0.11000E+01  volume   0.89979E+02  ppm1   8.598  ppm2   1.393
ASSI ( 7331)
  ( ( segid *BrD * and resid 15 and name HN   ) )
  ( ( segid *BrD * and resid 14 and name HB1  ) )
    2.600  1.700   1.700  peak   7331  weight   0.11000E+01  volume   0.65160E+03  ppm1   8.599  ppm2   2.454
ASSI ( 7341)
  ( ( segid *BrD * and resid 15 and name HN   ) )
  ( ( segid *BrD * and resid 14 and name HB2  ) )
    3.600  3.200   1.900  peak   7341  weight   0.11000E+01  volume   0.85197E+02  ppm1   8.598  ppm2   2.162
ASSI ( 7351)
  ( ( segid *BrD * and resid 18 and name HN   ) )
  ( ( segid *BrD * and resid 14 and name HA   ) )
    3.500  3.100   2.000  peak   7351  weight   0.11000E+01  volume   0.10770E+03  ppm1   9.071  ppm2   4.652
ASSI ( 7361)
  ( ( segid *BrD * and resid 21 and name HN   ) )
  ( ( segid *BrD * and resid 18 and name HA   ) )
    3.200  2.600   2.300  peak   7361  weight   0.11000E+01  volume   0.16933E+03  ppm1   8.544  ppm2   3.874
ASSI ( 7371)
  ( ( segid *BrD * and resid 22 and name HN   ) )
  ( ( segid *BrD * and resid 18 and name HA   ) )
    3.700  3.400   1.800  peak   7371  weight   0.11000E+01  volume   0.72924E+02  ppm1   9.456  ppm2   3.896
ASSI ( 7381)
  ( ( segid *BrD * and resid 19 and name HN   ) )
  ( ( segid *BrD * and resid 18 and name HB1  ) )
    2.800  2.000   2.000  peak   7381  weight   0.11000E+01  volume    0.4235E+03  ppm1   9.186  ppm2   2.139
ASSI ( 7391)
  ( ( segid *BrD * and resid 19 and name HN   ) )
  (   segid *BrD * and resid 18 and name HD1%)
    3.800  3.600   1.700  peak   7391  weight   0.11000E+01  volume   0.63600E+02  ppm1   9.189  ppm2   1.084
ASSI ( 7401)
  ( ( segid *BrD * and resid 19 and name HN   ) )
  (   segid *BrD * and resid 18 and name HD2%)
    3.700  3.400   1.800  peak   7401  weight   0.11000E+01  volume   0.71915E+02  ppm1   9.187  ppm2   0.414
ASSI ( 7411)
  ( ( segid *BrD * and resid 20 and name HN   ) )
  ( ( segid *BrD * and resid 19 and name HB1  ) )
    3.200  2.400   2.300  peak   7411  weight   0.11000E+01  volume   0.16507E+03  ppm1   8.146  ppm2   2.336
ASSI ( 7421)
  ( ( segid *BrD * and resid 20 and name HN   ) )
  ( ( segid *BrD * and resid 19 and name HB2  ) )
    3.400  2.900   2.100  peak   7421  weight   0.11000E+01  volume   0.13044E+03  ppm1   8.147  ppm2   1.967
```

TABLE 2-continued

Unambigous NOE-derived Inter-proton Distance Restraints

```
ASSI ( 7431)
    ( ( segid *BrD * and resid 23 and name HN   ) )
    ( ( segid *BrD * and resid 19 and name HA   ) )
       3.600  3.200   1.900  peak    7431  weight   0.11000E+01  volume   0.90645E+02  ppm1    9.120  ppm2    4.286
ASSI ( 7441)
    ( ( segid *BrD * and resid 23 and name HN   ) )
    ( ( segid *BrD * and resid 20 and name HA   ) )
       3.400  2.900   2.100  peak    7441  weight   0.11000E+01  volume   0.11524E+03  ppm1    9.118  ppm2    4.896
ASSI ( 7451)
    ( ( segid *BrD * and resid 20 and name HN   ) )
    ( ( segid *BrD * and resid 22 and name HN   ) )
       3.600  3.200   1.900  peak    7451  weight   0.11000E+01  volume   0.81392E+02  ppm1    8.147  ppm2    9.450
ASSI ( 7471)
    ( ( segid *BrD * and resid 21 and name HN   ) )
    ( ( segid *BrD * and resid 23 and name HN   ) )
       4.100  4.100   1.400  peak    7471  weight   0.11000E+01  volume   0.42834E+02  ppm1    8.545  ppm2    9.230
ASSI ( 7491)
    ( ( segid *BrD * and resid 24 and name HN   ) )
    ( ( segid *BrD * and resid 21 and name HA   ) )
       3.200  2.600   2.300  peak    7491  weight   0.11000E+01  volume   0.16448E+03  ppm1    8.661  ppm2    4.371
ASSI ( 7501)
    ( ( segid *BrD * and resid 26 and name HN   ) )
    ( ( segid *BrD * and resid 23 and name HA   ) )
       3.400  2.900   2.100  peak    7501  weight   0.11000E+01  volume   0.12059E+03  ppm1    9.196  ppm2    4.639
ASSI ( 7511)
    ( ( segid *BrD * and resid 27 and name HN   ) )
    ( ( segid *BrD * and resid 24 and name HA   ) )
       3.200  2.600   2.300  peak    7511  weight   0.11000E+01  volume   0.17746E+03  ppm1    8.170  ppm2    4.777
ASSI ( 7521)
    ( ( segid *BrD * and resid 28 and name HN   ) )
    ( ( segid *BrD * and resid 25 and name HA   ) )
       3.600  3.200   1.900  peak    7521  weight   0.11000E+01  volume   0.92661E+02  ppm1    8.166  ppm2    4.449
ASSI ( 7531)
    ( ( segid *BrD * and resid 26 and name HN   ) )
    ( ( segid *BrD * and resid 25 and name HB   ) )
       2.600  1.700   1.700  peak    7531  weight   0.11000E+01  volume   0.67212E+03  ppm1    9.196  ppm2    2.991
ASSI ( 7541)
    ( ( segid *BrD * and resid 26 and name HN   ) )
    (   segid *BrD * and resid 25 and name HG2%)
       2.900  2.100   2.100  peak    7541  weight   0.11000E+01  volume   0.31151E+03  ppm1    9.196  ppm2    1.640
ASSI ( 7551)
    ( ( segid *BrD * and resid 26 and name HN   ) )
    (   segid *BrD * and resid 25 and name HG1%)
       3.100  2.400   2.400  peak    7551  weight   0.11000E+01  volume   0.21302E+03  ppm1    9.197  ppm2    1.790
ASSI ( 7561)
    ( ( segid *BrD * and resid 43 and name HN   ) )
    ( ( segid *BrD * and resid 44 and name HD1  ) )
       3.400  2.900   2.100  peak    7561  weight   0.11000E+01  volume   0.11281E+03  ppm1    8.001  ppm2    4.324
ASSI ( 7571)
    ( ( segid *BrD * and resid 43 and name HN   ) )
    ( ( segid *BrD * and resid 44 and name HD2  ) )
       3.100  2.400   2.400  peak    7571  weight   0.11000E+01  volume   0.21754E+03  ppm1    8.001  ppm2    4.122
ASSI ( 7581)
    ( ( segid *BrD * and resid 49 and name HN   ) )
    ( ( segid *BrD * and resid 46 and name HA   ) )
       3.900  3.800   1.600  peak    7581  weight   0.11000E+01  volume   0.54216E+02  ppm1    7.763  ppm2    4.143
ASSI ( 7591)
    ( ( segid *BrD * and resid 56 and name HN   ) )
    ( ( segid *BrD * and resid 56 and name HB1  ) )
       2.700  1.800   1.800  peak    7591  weight   0.11000E+01  volume   0.48254E+03  ppm1    9.679  ppm2    2.693
ASSI ( 7601)
    ( ( segid *BrD * and resid 61 and name HN   ) )
    ( ( segid *BrD * and resid 58 and name HA   ) )
       2.900  2.100   2.100  peak    7601  weight   0.11000E+01  volume   0.30089E+03  ppm1    8.749  ppm2    4.452
ASSI ( 7611)
    ( ( segid *BrD * and resid 64 and name HN   ) )
    ( ( segid *BrD * and resid 60 and name HA   ) )
       3.400  2.900   2.100  peak    7611  weight   0.11000E+01  volume   0.11932E+03  ppm1    8.584  ppm2    4.807
ASSI ( 7621)
    ( ( segid *BrD * and resid 66 and name HN   ) )
    ( ( segid *BrD * and resid 66 and name HD1  ) )
       2.900  2.100   2.100  peak    7621  weight   0.11000E+01  volume   0.29994E+03  ppm1    8.759  ppm2    3.667
ASSI ( 7631)
    ( ( segid *BrD * and resid 75 and name HN   ) )
    ( ( segid *BrD * and resid 72 and name HA   ) )
       3.400  2.900   2.100  peak    7631  weight   0.11000E+01  volume   0.13400E+03  ppm1    9.106  ppm2    4.669
```

TABLE 2-continued

Unambigous NOE-derived Inter-proton Distance Restraints

```
ASSI ( 7651)
    ( ( segid *BrD * and resid 79 and name HN   ) )
    ( ( segid *BrD * and resid 76 and name HA   ) )
       3.200  2.600   2.300  peak    7651  weight   0.11000E+01  volume   0.16410E+03  ppm1    8.680  ppm2    4.691
ASSI ( 7661)
    ( ( segid *BrD * and resid 80 and name HN   ) )
    ( ( segid *BrD * and resid 77 and name HA   ) )
       3.700  3.400   1.800  peak    7661  weight   0.11000E+01  volume   0.79484E+02  ppm1    8.006  ppm2    4.969
ASSI ( 7671)
    ( ( segid *BrD * and resid 81 and name HN   ) )
    ( ( segid *BrD * and resid 78 and name HA   ) )
       3.300  2.700   2.200  peak    7671  weight   0.11000E+01  volume   0.15049E+03  ppm1    7.639  ppm2    3.989
ASSI ( 7681)
    ( ( segid *BrD * and resid 82 and name HN   ) )
    ( ( segid *BrD * and resid 79 and name HA   ) )
       3.600  3.200   1.900  peak    7681  weight   0.11000E+01  volume   0.80779E+02  ppm1    6.981  ppm2    4.411
ASSI ( 7701)
    ( ( segid *BrD * and resid 84 and name HN   ) )
    ( ( segid *BrD * and resid 81 and name HA   ) )
       3.500  3.100   2.000  peak    7701  weight   0.11000E+01  volume   0.10576E+03  ppm1    9.463  ppm2    3.705
ASSI ( 7711)
    ( ( segid *BrD * and resid 85 and name HN   ) )
    ( ( segid *BrD * and resid 82 and name HA   ) )
       3.100  2.700   2.200  peak    7711  weight   0.11000E+01  volume   0.13652E+03  ppm1    7.516  ppm2    4.768
ASSI ( 7721)
    ( ( segid *BrD * and resid 89 and name HN   ) )
    ( ( segid *BrD * and resid 86 and name HA   ) )
       3.500  3.100   2.000  peak    7721  weight   0.11000E+01  volume   0.10495E+03  ppm1    8.858  ppm2    4.811
ASSI ( 7731)
    ( ( segid *BrD * and resid 93 and name HN   ) )
    ( ( segid *BrD * and resid 92 and name HA   ) )
       3.600  3.200   1.900  peak    7731  weight   0.11000E+01  volume   0.94491E+02  ppm1    8.712  ppm2    4.796
ASSI ( 7741)
    ( ( segid *BrD * and resid 98 and name HN   ) )
    ( ( segid *BrD * and resid 95 and name HA   ) )
       3.300  2.700   2.200  peak    7741  weight   0.11000E+01  volume   0.14245E+03  ppm1    9.125  ppm2    4.441
ASSI ( 7751)
    ( ( segid *BrD * and resid 77 and name HN   ) )
    ( ( segid *BrD * and resid 75 and name HN   ) )
       3.500  3.100   2.000  peak    7751  weight   0.11000E+01  volume   0.10255E+03  ppm1    7.985  ppm2    9.096
ASSI ( 7761)
    ( ( segid *BrD * and resid 98 and name HN   ) )
    ( ( segid *BrD * and resid 96 and name HN   ) )
       3.900  3.800   1.600  peak    7761  weight   0.11000E+01  volume   0.51137E+02  ppm1    9.125  ppm2    7.963
ASSI ( 7771)
    ( ( segid *BrD * and resid 102 and name HN   ) )
    ( ( segid *BrD * and resid 98 and name HA   ) )
       3.500  3.100   2.000  peak    7771  weight   0.11000E+01  volume   0.10795E+03  ppm1    9.156  ppm2    4.809
ASSI ( 7781)
    ( ( segid *BrD * and resid 102 and name HN   ) )
    ( ( segid *BrD * and resid 99 and name HA   ) )
       3.500  3.100   2.000  peak    7781  weight   0.11000E+01  volume   0.10223E+03  ppm1    9.156  ppm2    4.443
ASSI ( 7791)
    ( ( segid *BrD * and resid 103 and name HN   ) )
    ( ( segid *BrD * and resid 100 and name HA   ) )
       3.000  2.200   2.200  peak    7791  weight   0.11000E+01  volume   0.26822E+03  ppm1    8.696  ppm2    4.932
ASSI ( 7801)
    ( ( segid *BrD * and resid 104 and name HN   ) )
    ( ( segid *BrD * and resid 101 and name HA   ) )
       3.000  2.200   2.200  peak    7801  weight   0.11000E+01  volume   0.25521E+03  ppm1    7.763  ppm2    4.275
ASSI ( 7811)
    ( ( segid *BrD * and resid 102 and name HN   ) )
    ( ( segid *BrD * and resid 104 and name HA   ) )
       4.300  4.300   1.200  peak    7811  weight   0.11000E+01  volume   0.28976E+02  ppm1    9.156  ppm2    7.772
ASSI ( 7831)
    ( ( segid *BrD * and resid 105 and name HN   ) )
    ( ( segid *BrD * and resid 102 and name HA   ) )
       3.300  2.700   2.200  peak    7831  weight   0.11000E+01  volume   0.14640E+03  ppm1    8.488  ppm2    4.290
ASSI ( 7841)
    ( ( segid *BrD * and resid 108 and name HN   ) )
    ( ( segid *BrD * and resid 105 and name HA   ) )
       3.600  3.200   1.900  peak    7841  weight   0.11000E+01  volume   0.82783E+02  ppm1    8.526  ppm2    4.936
ASSI ( 7851)
    ( ( segid *BrD * and resid 16 and name HN   ) )
    ( ( segid *BrD * and resid 16 and name HB1   ) )
       2.900  2.100   2.100  peak    7851  weight   0.11000E+01  volume   0.35014E+03  ppm1    8.794  ppm2    4.587
```

TABLE 2-continued

Unambigous NOE-derived Inter-proton Distance Restraints

```
ASSI ( 7861)
    ( ( segid *BrD * and resid 24 and name HE22) ) )
    ( ( segid *BrD * and resid 24 and name HG2  ) )
        4.100  4.100    1.400  peak    7861  weight   0.11000E+01  volume   0.40620E+02  ppm1    7.523  ppm2    3.068
ASSI ( 7871)
    ( ( segid *BrD * and resid 24 and name HE21) ) )
    ( ( segid *BrD * and resid 24 and name HG2  ) )
        3.500  3.100    2.000  peak    7871  weight   0.11000E+01  volume   0.10084E+03  ppm1    7.629  ppm2    3.067
ASSI ( 7881)
    ( ( segid *BrD * and resid 25 and name HN   ) )
    ( ( segid *BrD * and resid 24 and name HG1  ) )
        3.400  2.900    2.100  peak    7881  weight   0.11000E+01  volume   0.11666E+03  ppm1    9.133  ppm2    3.447
ASSI ( 7891)
    ( ( segid *BrD * and resid 18 and name HN   ) )
    (   segid *BrD * and resid 18 and name HD1%)
        2.900  2.100    2.100  peak    7891  weight   0.11000E+01  volume   0.29964E+03  ppm1    9.072  ppm2    1.068
ASSI ( 7901)
    ( ( segid *BrD * and resid 73 and name HN   ) )
    (   segid *BrD * and resid 73 and name HD1%)
        3.300  2.700    2.200  peak    7901  weight   0.11000E+01  volume   0.15507E+03  ppm1    8.049  ppm2    1.540
ASSI ( 7911)
    ( ( segid *BrD * and resid 73 and name HN   ) )
    ( ( segid *BrD * and resid 73 and name HB1  ) )
        2.800  2.000    2.000  peak    7911  weight   0.11000E+01  volume   0.38621E+03  ppm1    8.045  ppm2    2.590
ASSI ( 7921)
    ( ( segid *BrD * and resid 56 and name HN   ) )
    (   segid *BrD * and resid 56 and name HD2%)
        3.100  2.400    2.400  peak    7921  weight   0.11000E+01  volume   0.19974E+03  ppm1    9.679  ppm2    1.235
ASSI ( 7931)
    ( ( segid *BrD * and resid 22 and name HN   ) )
    (   segid *BrD * and resid 22 and name HD2%)
        3.000  2.200    2.200  peak    7931  weight   0.11000E+01  volume   0.25836E+03  ppm1    9.455  ppm2    1.584
ASSI ( 7941)
    ( ( segid *BrD * and resid 110 and name HN  ) )
    ( ( segid *BrD * and resid 110 and name HG11) )
        2.900  2.100    2.100  peak    7941  weight   0.11000E+01  volume   0.31947E+03  ppm1    8.715  ppm2    1.745
ASSI ( 7951)
    ( ( segid *BrD * and resid 29 and name HN   ) )
    ( ( segid *BrD * and resid 29 and name HG1  ) )
        3.100  2.400    2.400  peak    7951  weight   0.11000E+01  volume   0.23530E+03  ppm1    9.152  ppm2    3.021
ASSI ( 7941)
    ( ( segid *BrD * and resid 23 and name HN   ) )
    ( ( segid *BrD * and resid 23 and name HB2  ) )
        2.400  1.400    1.400  peak    7961  weight   0.11000E+01  volume   0.91388E+03  ppm1    9.120  ppm2    2.851
ASSI ( 7971)
    ( ( segid *BrD * and resid 80 and name HN   ) )
    ( ( segid *BrD * and resid 80 and name HD2  ) )
        4.400  4.400    1.100  peak    7971  weight   0.11000E+01  volume   0.24560E+02  ppm1    8.007  ppm2    3.932
ASSI ( 7981)
    ( ( segid *BrD * and resid 100 and name HN  ) )
    ( ( segid *BrD * and resid 100 and name HB1 ) )
        2.800  2.000    2.000  peak    7981  weight   0.11000E+01  volume   0.39419E+03  ppm1    8.669  ppm2    3.493
ASSI ( 7991)
    ( ( segid *BrD * and resid 19 and name HN   ) )
    ( ( segid *BrD * and resid 19 and name HB2  ) )
        3.000  2.200    2.200  peak    7991  weight   0.11000E+01  volume   0.28394E+03  ppm1    9.187  ppm2    1.971
ASSI ( 8001)
    ( ( segid *BrD * and resid 97 and name HN   ) )
    ( ( segid *BrD * and resid 97 and name HG1  ) )
        2.500  1.600    1.600  peak    8001  weight   0.11000E+01  volume   0.82725E+03  ppm1    8.674  ppm2    2.415
ASSI ( 8011)
    ( ( segid *BrD * and resid 105 and name HN  ) )
    ( ( segid *BrD * and resid 105 and name HB2 ) )
        3.100  2.400    2.400  peak    8011  weight   0.11000E+01  volume   0.23309E+03  ppm1    8.487  ppm2    3.654
ASSI ( 8021)
    ( ( segid *BrD * and resid 12 and name HN   ) )
    ( ( segid *BrD * and resid 12 and name HB2  ) )
        3.100  2.400    2.400  peak    8021  weight   0.11000E+01  volume   0.23285E+03  ppm1    9.021  ppm2    3.337
ASSI ( 8031)
    ( ( segid *BrD * and resid 10 and name HN   ) )
    ( ( segid *BrD * and resid 10 and name HB2  ) )
        3.000  2.200    2.200  peak    8031  weight   0.11000E+01  volume   0.26676E+03  ppm1    8.886  ppm2    3.299
ASSI ( 8041)
    ( ( segid *BrD * and resid 114 and name HN  ) )
    ( ( segid *BrD * and resid 114 and name HA2 ) )
        2.800  2.000    2.000  peak    8041  weight   0.11000E+01  volume   0.43718E+03  ppm1    8.375  ppm2    4.531
```

TABLE 2-continued

Unambigous NOE-derived Inter-proton Distance Restraints

```
ASSI ( 8051)
      ( ( segid *BrD * and resid 85 and name HN   ) )
      ( ( segid *BrD * and resid 85 and name HB2  ) )
         3.100  2.400    2.400 peak    8051 weight    0.11000E+01 volume   0.21741E+03 ppm1    7.517 ppm2    3.603
ASSI ( 8101)
      ( ( segid *BrD * and resid 39 and name HN   ) )
      ( ( segid *BrD * and resid 39 and name HB1  ) )
         2.800  2.000    2.000 peak    8101 weight    0.11000E+01 volume   0.63178E+03 ppm1    9.651 ppm2    2.480
ASSI ( 8111)
      ( ( segid *BrD * and resid 39 and name HN   ) )
      ( ( segid *BrD * and resid 39 and name HD1  ) )
         2.500  1.400    1.600 peak    8111 weight    0.11000E+01 volume   0.74538E+03 ppm1    9.653 ppm2    2.280
ASSI ( 8121)
      ( ( segid *BrD * and resid 39 and name HN   ) )
      ( ( segid *BrD * and resid 39 and name HG1  ) )
         3.100  2.400    2.400 peak    8121 weight    0.11000E+01 volume   0.20991E+03 ppm1    9.651 ppm2    2.042
ASSI ( 8131)
      ( ( segid *BrD * and resid 57 and name HN   ) )
      ( ( segid *BrD * and resid 59 and name HN   ) )
         3.700  3.400    1.800 peak    8131 weight    0.11000E+01 volume   0.75880E+02 ppm1    9.355 ppm2    8.478
ASSI ( 8171)
      ( ( segid *BrD * and resid 57 and name HN   ) )
      ( ( segid *BrD * and resid 56 and name HB1  ) )
         2.800  2.000    2.000 peak    8171 weight    0.11000E+01 volume   0.40297E+03 ppm1    9.359 ppm2    2.782
ASSI ( 8191)
      ( ( segid *BrD * and resid 57 and name HN   ) )
      (   segid *BrD * and resid 56 and name HD1%)
         3.700  3.400    1.800 peak    8191 weight    0.11000E+01 volume   0.68904E+02 ppm1    9.358 ppm2    1.547
ASSI ( 8201)
      ( ( segid *BrD * and resid 57 and name HN   ) )
      ( ( segid *BrD * and resid 57 and name HG2  ) )
         3.700  3.400    1.800 peak    8201 weight    0.11000E+01 volume   0.72664E+02 ppm1    9.361 ppm2    2.011
ASSI ( 8241)
      ( ( segid *BrD * and resid 28 and name HN   ) )
      ( ( segid *BrD * and resid 24 and name HA   ) )
         3.600  3.200    1.900 peak    8241 weight    0.11000E+01 volume   0.82533E+02 ppm1    8.166 ppm2    4.801
ASSI ( 8251)
      ( ( segid *BrD * and resid 28 and name HN   ) )
      ( ( segid *BrD * and resid 28 and name HD2  ) )
         3.800  3.600    1.700 peak    8251 weight    0.11000E+01 volume   0.64220E+02 ppm1    8.166 ppm2    5.585
ASSI ( 8351)
      ( ( segid *BrD * and resid 51 and name HN   ) )
      (   segid *BrD * and resid 50 and name HG2%)
         3.000  2.200    2.200 peak    8351 weight    0.11000E+01 volume   0.27507E+03 ppm1    8.379 ppm2    0.982
ASSI ( 8431)
      ( ( segid *BrD * and resid 117 and name HN  ) )
      (   segid *BrD * and resid 116 and name HG2%)
         3.700  3.400    1.800 peak    8431 weight    0.11000E+01 volume   0.73143E+02 ppm1    8.677 ppm2    1.422
ASSI ( 8471)
      ( ( segid *BrD * and resid 102 and name HN  ) )
      ( ( segid *BrD * and resid 101 and name HB  ) )
         3.000  2.200    2.200 peak    8471 weight    0.11000E+01 volume   0.25477E+03 ppm1    9.156 ppm2    2.531
ASSI ( 8491)
      ( ( segid *BrD * and resid 102 and name HN  ) )
      (   segid *BrD * and resid 101 and name HG2%)
         3.300  2.700    2.200 peak    8491 weight    0.11000E+01 volume   0.14766E+03 ppm1    9.156 ppm2    1.598
ASSI ( 8541)
      ( ( segid *BrD * and resid 46 and name HN   ) )
      (   segid *BrD * and resid 46 and name HD % )
         3.500  3.100    2.000 peak    8541 weight    0.11000E+01 volume   0.10722E+03 ppm1    8.562 ppm2    5.719
ASSI ( 8591)
      ( ( segid *BrD * and resid 43 and name HN   ) )
      ( ( segid *BrD * and resid 41 and name HA   ) )
         3.000  2.200    2.200 peak    8591 weight    0.11000E+01 volume   0.24489E+03 ppm1    8.001 ppm2    4.645
ASSI ( 8671)
      ( ( segid *BrD * and resid 111 and name HN  ) )
      ( ( segid *BrD * and resid 110 and name HG11) )
         3.600  3.200    1.900 peak    8671 weight    0.11000E+01 volume   0.81338E+02 ppm1    8.168 ppm2    1.747
ASSI ( 8701)
      ( ( segid *BrD * and resid 111 and name HN  ) )
      (   segid *BrD * and resid 110 and name HD1%)
         4.000  4.000    1.500 peak    8701 weight    0.11000E+01 volume   0.48240E+02 ppm1    8.168 ppm2    1.148
ASSI ( 8731)
      ( ( segid *BrD * and resid 58 and name HN   ) )
      ( ( segid *BrD * and resid 57 and name HB1  ) )
         3.100  2.400    2.400 peak    8731 weight    0.11000E+01 volume   0.22478E+03 ppm1   10.051 ppm2    2.937
```

TABLE 2-continued

Unambigous NOE-derived Inter-proton Distance Restraints

```
ASSI ( 8741)
     ( ( segid *BrD * and resid 58 and name HN    ) )
     ( ( segid *BrD * and resid 57 and name HB2   ) )
        3.100  2.400   2.400   peak    8741  weight   0.11000E+01  volume  0.21458E+03  ppm1    10.051  ppm2   2.831
ASSI ( 8761)
     ( ( segid *BrD * and resid 58 and name HN    ) )
     ( ( segid *BrD * and resid 57 and name HD1   ) )
        4.300  4.300   1.200   peak    8761  weight   0.11000E+01  volume  0.29553E+02  ppm1    10.051  ppm2   2.400
ASSI ( 8771)
     ( ( segid *BrD * and resid 58 and name HN    ) )
     ( ( segid *BrD * and resid 57 and name HD2   ) )
        3.800  3.600   1.700   peak    8771  weight   0.11000E+01  volume  0.60769E+02  ppm1    10.051  ppm2   2.303
ASSI ( 8781)
     ( ( segid *BrD * and resid 58 and name HN    ) )
     ( ( segid *BrD * and resid 57 and name HG1   ) )
        3.800  3.600   1.700   peak    8781  weight   0.11000E+01  volume  0.60094E+02  ppm1    10.051  ppm2   2.090
ASSI ( 8791)
     ( ( segid *BrD * and resid 58 and name HN    ) )
     ( ( segid *BrD * and resid 57 and name HG2   ) )
        3.800  3.600   1.700   peak    8791  weight   0.11000E+01  volume  0.67776E+02  ppm1    10.051  ppm2   2.010
ASSI ( 8821)
     ( ( segid *BrD * and resid 10 and name HN    ) )
     ( ( segid *BrD * and resid 9  and name HG1   ) )
        4.100  4.100   1.400   peak    8821  weight   0.11000E+01  volume  0.38664E+02  ppm1     8.665  ppm2   2.288
ASSI ( 8831)
     ( ( segid *BrD * and resid 13 and name HN    ) )
     ( ( segid *BrD * and resid 12 and name HB2   ) )
        3.400  2.900   2.100   peak    8831  weight   0.11000E+01  volume  0.11575E+03  ppm1     8.801  ppm2   3.337
ASSI ( 8841)
     ( ( segid *BrD * and resid 14 and name HN    ) )
     ( ( segid *BrD * and resid 12 and name HN    ) )
        2.600  1.700   1.700   peak    8841  weight   0.11000E+01  volume  0.58119E+03  ppm1     8.803  ppm2   9.004
ASSI ( 8921)
     ( ( segid *BrD * and resid 112 and name HN   ) )
     ( ( segid *BrD * and resid 111 and name HB1  ) )
        2.700  1.800   1.800   peak    8921  weight   0.11000E+01  volume  0.52559E+03  ppm1     8.666  ppm2   2.473
ASSI ( 8931)
     ( ( segid *BrD * and resid 112 and name HN   ) )
     ( ( segid *BrD * and resid 111 and name HB2  ) )
        3.100  2.400   2.400   peak    8931  weight   0.11000E+01  volume  0.20903E+03  ppm1     8.667  ppm2   2.363
ASSI ( 8951)
     ( ( segid *BrD * and resid 112 and name HN   ) )
     ( ( segid *BrD * and resid 111 and name HG1  ) )
        3.800  3.600   1.700   peak    8951  weight   0.11000E+01  volume  0.66936E+02  ppm1     8.668  ppm2   1.997
ASSI ( 9001)
     ( ( segid *BrD * and resid 105 and name HN   ) )
     ( ( segid *BrD * and resid 104 and name HB1  ) )
        2.600  1.700   1.700   peak    9001  weight   0.11000E+01  volume  0.67760E+03  ppm1     8.487  ppm2   2.536
ASSI ( 9021)
     ( ( segid *BrD * and resid 105 and name HN   ) )
     ( ( segid *BrD * and resid 104 and name HG1  ) )
        4.800  4.800   0.700   peak    9021  weight   0.11000E+01  volume  0.16288E+02  ppm1     8.485  ppm2   2.099
ASSI ( 9081)
     ( ( segid *BrD * and resid 109 and name HN   ) )
     ( ( segid *BrD * and resid 108 and name HB1  ) )
        2.500  1.600   1.600   peak    9081  weight   0.11000E+01  volume  0.75253E+03  ppm1     8.573  ppm2   4.614
ASSI ( 9141)
     ( ( segid *BrD * and resid 106 and name HN   ) )
     (   segid *BrD * and resid 106 and name HD %  )
        3.700  3.400   1.800   peak    9141  weight   0.11000E+01  volume  0.76595E+02  ppm1     9.740  ppm2   7.511
ASSI ( 9151)
     ( ( segid *BrD * and resid 106 and name HN   ) )
     ( ( segid *BrD * and resid 102 and name HA   ) )
        3.700  3.400   1.800   peak    9151  weight   0.11000E+01  volume  0.78592E+02  ppm1     9.740  ppm2   4.277
ASSI ( 9301)
     ( ( segid *BrD * and resid 63 and name HN    ) )
     ( ( segid *BrD * and resid 60 and name HA    ) )
        3.800  3.600   1.700   peak    9301  weight   0.11000E+01  volume  0.67510E+02  ppm1     9.471  ppm2   4.809
ASSI ( 9321)
     ( ( segid *BrD * and resid 63 and name HN    ) )
     ( ( segid *BrD * and resid 62 and name HB1   ) )
        2.200  1.200   1.200   peak    9321  weight   0.11000E+01  volume  0.14701E+04  ppm1     9.472  ppm2   2.654
ASSI ( 9331)
     ( ( segid *BrD * and resid 63 and name HN    ) )
     ( ( segid *BrD * and resid 61 and name HN    ) )
        3.500  3.100   2.000   peak    9331  weight   0.11000E+01  volume  0.10977E+03  ppm1     9.475  ppm2   8.757
```

TABLE 2-continued

Unambigous NOE-derived Inter-proton Distance Restraints

```
ASSI ( 9351)
    ( ( segid *BrD * and resid 22 and name HN   ) )
    ( ( segid *BrD * and resid 20 and name HA   ) )
       4.100   4.100    1.400  peak    9351  weight   0.11000E+01  volume   0.39214E+02  ppm1    9.458  ppm2    4.872
ASSI ( 9361)
    ( ( segid *BrD * and resid 22 and name HN   ) )
    ( ( segid *BrD * and resid 19 and name HA   ) )
       3.600   3.200    1.900  peak    9361  weight   0.11000E+01  volume   0.85958E+02  ppm1    9.457  ppm2    4.286
ASSI ( 9391)
    ( ( segid *BrD * and resid 22 and name HN   ) )
    ( ( segid *BrD * and resid 21 and name HB   ) )
       2.700   1.800    1.800  peak    9391  weight   0.11000E+01  volume   0.51430E+03  ppm1    9.457  ppm2    2.491
ASSI ( 9551)
    ( ( segid *BrD * and resid 103 and name HN   ) )
    ( ( segid *BrD * and resid 99 and name HA   ) )
       4.600   4.600    0.900  peak    9551  weight   0.11000E+01  volume   0.21373E+02  ppm1    8.695  ppm2    4.441
ASSI ( 9571)
    ( ( segid *BrD * and resid 103 and name HN   ) )
    ( ( segid *BrD * and resid 102 and name HG   ) )
       3.200   2.600    2.300  peak    9571  weight   0.11000E+01  volume   0.17364E+03  ppm1    8.695  ppm2    2.187
ASSI ( 9581)
    ( ( segid *BrD * and resid 103 and name HN   ) )
    (   segid *BrD * and resid 101 and name HG2%)
       3.000   2.200    2.200  peak    9581  weight   0.11000E+01  volume   0.23656E+03  ppm1    8.695  ppm2    1.624
ASSI ( 9591)
    ( ( segid *BrD * and resid 103 and name HN   ) )
    (   segid *BrD * and resid 101 and name HD1%)
       3.600   3.200    1.900  peak    9591  weight   0.11000E+01  volume   0.85679E+02  ppm1    8.695  ppm2    1.308
ASSI ( 9601)
    ( ( segid *BrD * and resid 103 and name HN   ) )
    ( ( segid *BrD * and resid 102 and name HB2  ) )
       3.200   2.600    2.300  peak    9601  weight   0.11000E+01  volume   0.18049E+03  ppm1    8.695  ppm2    1.806
ASSI ( 9691)
    ( ( segid *BrD * and resid 18 and name HN   ) )
    ( ( segid *BrD * and resid 18 and name HB2  ) )
       2.800   2.000    2.000  peak    9691  weight   0.11000E+01  volume   0.37426E+03  ppm1    9.073  ppm2    0.909
ASSI ( 9701)
    ( ( segid *BrD * and resid 64 and name HN   ) )
    ( ( segid *BrD * and resid 61 and name HA   ) )
       3.100   2.400    2.400  peak    9701  weight   0.11000E+01  volume   0.22483E+03  ppm1    8.584  ppm2    4.652
ASSI ( 9711)
    ( ( segid *BrD * and resid 64 and name HN   ) )
    ( ( segid *BrD * and resid 62 and name HA   ) )
       3.900   3.800    1.600  peak    9711  weight   0.11000E+01  volume   0.56508E+02  ppm1    8.583  ppm2    4.488
ASSI ( 9741)
    ( ( segid *BrD * and resid 64 and name HN   ) )
    ( ( segid *BrD * and resid 63 and name HB1  ) )
       2.600   1.700    1.700  peak    9741  weight   0.11000E+01  volume   0.57592E+03  ppm1    8.585  ppm2    2.902
ASSI ( 9931)
    ( ( segid *BrD * and resid 62 and name HN   ) )
    ( ( segid *BrD * and resid 62 and name HB2  ) )
       2.900   2.100    2.100  peak    9931  weight   0.11000E+01  volume   0.30063E+03  ppm1    8.998  ppm2    1.683
ASSI ( 9941)
    ( ( segid *BrD * and resid 62 and name HN   ) )
    ( ( segid *BrD * and resid 62 and name HG2  ) )
       3.700   3.400    1.800  peak    9941  weight   0.11000E+01  volume   0.71463E+02  ppm1    8.998  ppm2    1.484
ASSI ( 9961)
    ( ( segid *BrD * and resid 12 and name HN   ) )
    ( ( segid *BrD * and resid 11 and name HD1  ) )
       2.800   2.000    2.000  peak    9961  weight   0.11000E+01  volume   0.35721E+03  ppm1    9.021  ppm2    4.473
ASSI (10011)
    ( ( segid *BrD * and resid 25 and name HN   ) )
    ( ( segid *BrD * and resid 22 and name HA   ) )
       3.300   2.700    2.00   peak   10011  weight   0.11000E+01  volume   0.14084E+03  ppm1    9.133  ppm2    4.697
ASSI (10041)
    ( ( segid *BrD * and resid 24 and name HN   ) )
    ( ( segid *BrD * and resid 23 and name HB1  ) )
       2.600   1.700    1.700  peak   10041  weight   0.11000E+01  volume   0.58902E+03  ppm1    8.655  ppm2    2.934
ASSI (10051)
    ( ( segid *BrD * and resid 24 and name HN   ) )
    (   segid *BrD * and resid 21 and name HG2%)
       3.600   3.200    1.900  peak   10051  weight   0.11000E+01  volume   0.65488E+02  ppm1    8.656  ppm2    1.610
ASSI (10071)
    ( ( segid *BrD * and resid 24 and name HN   ) )
    ( ( segid *BrD * and resid 20 and name HA   ) )
       3.800   3.600    1.700  peak   10071  weight   0.11000E+01  volume   0.60003E+02  ppm1    8.659  ppm2    4.888
```

TABLE 2-continued

Unambigous NOE-derived Inter-proton Distance Restraints

```
ASSI (10101)
    ( ( segid *BrD * and resid 15 and name HN   ) )
    ( ( segid *BrD * and resid 13 and name HB1 ) )
       3.500   3.100    2.000  peak   10101  weight    0.11000E+01 volume   0.10487E+03 ppm1    8.599 ppm2    2.755
ASSI (10161)
    ( ( segid *BrD * and resid 16 and name HN   ) )
    ( ( segid *BrD * and resid 15 and name HA   ) )
       2.800   2.000    2.000  peak   10161  weight    0.11000E+01 volume   0.35770E+03 ppm1    8.796 ppm2    4.637
ASSI (10171)
    ( ( segid *BrD * and resid 16 and name HN   ) )
    (   segid *BrD * and resid 15 and name HD % )
       3.500   3.100    2.000  peak   10171  weight    0.11000E+01 volume   0.11249E+03 ppm1    8.792 ppm2    7.660
ASSI (10211)
    ( ( segid *BrD * and resid 75 and name HN   ) )
    ( ( segid *BrD * and resid 73 and name HA   ) )
       3.900   3.800    1.600  peak   10211  weight    0.11000E+01 volume   0.50909E+02 ppm1    9.106 ppm2    4.620
ASSI (10271)
    ( ( segid *BrD * and resid 75 and name HN   ) )
    (   segid *BrD * and resid 74 and name HD % )
       3.200   2.600    2.300  peak   10271  weight    0.11000E+01 volume   0.18529E+03 ppm1    9.107 ppm2    7.007
ASSI (10321)
    ( ( segid *BrD * and resid 96 and name HN   ) )
    ( ( segid *BrD * and resid 95 and name HB2 ) )
       2.600   1.700    1.700  peak   10321  weight    0.11000E+01 volume   0.63650E+03 ppm1    7.979 ppm2    3.345
ASSI (10341)
    ( ( segid *BrD * and resid 95 and name HN   ) )
    ( ( segid *BrD * and resid 92 and name HA   ) )
       3.400   2.900    2.100  peak   10341  weight    0.11000E+01 volume   0.12625E+03 ppm1    8.669 ppm2    4.792
ASSI (10361)
    ( ( segid *BrD * and resid 95 and name HN   ) )
    (   segid *BrD * and resid 95 and name HD % )
       3.400   2.900    2.100  peak   10361  weight    0.11000E+01 volume   0.13077E+03 ppm1    8.670 ppm2    7.500
ASSI (10371)
    ( ( segid *BrD * and resid 96 and name HN   ) )
    (   segid *BrD * and resid 96 and name HD % )
       3.300   2.700    2.200  peak   10371  weight    0.11000E+01 volume   0.14891E+03 ppm1    7.979 ppm2    7.701
ASSI (10481)
    ( ( segid *BrD * and resid 78 and name HN   ) )
    ( ( segid *BrD * and resid 75 and name HA   ) )
       3.100   2.400    2.400  peak   10481  weight    0.11000E+01 volume   0.20590E+03 ppm1    7.996 ppm2    4.532
ASSI (10491)
    ( ( segid *BrD * and resid 78 and name HN   ) )
    ( ( segid *BrD * and resid 74 and name HA   ) )
       2.800   2.000    2.000  peak   10491  weight    0.11000E+01 volume   0.36339E+03 ppm1    7.996 ppm2    4.370
ASSI (10511)
    ( ( segid *BrD * and resid 54 and name HN   ) )
    ( ( segid *BrD * and resid 53 and name HB1 ) )
       2.800   2.000    2.000  peak   10511  weight    0.11000E+01 volume   0.43885E+03 ppm1    9.037 ppm2    2.816
ASSI (10521)
    ( ( segid *BrD * and resid 54 and name HN   ) )
    (   segid *BrD * and resid 50 and name HG2%)
       3.400   2.900    2.100  peak   10521  weight    0.11000E+01 volume   0.12606E+03 ppm1    9.036 ppm2    0.987
ASSI (10671)
    ( ( segid *BrD * and resid 82 and name HN   ) )
    ( ( segid *BrD * and resid 78 and name HA   ) )
       3.900   3.800    1.600  peak   10671  weight    0.11000E+01 volume   0.53978E+02 ppm1    6.981 ppm2    4.005
ASSI (10691)
    ( ( segid *BrD * and resid 81 and name HN   ) )
    ( ( segid *BrD * and resid 80 and name HG1 ) )
       3.600   3.200    1.900  peak   10691  weight    0.11000E+01 volume   0.91821E+02 ppm1    7.640 ppm2    2.349
ASSI (10701)
    ( ( segid *BrD * and resid 81 and name HN   ) )
    ( ( segid *BrD * and resid 80 and name HB1 ) )
       3.700   3.400    1.800  peak   10701  weight    0.11000E+01 volume   0.72987E+02 ppm1    7.640 ppm2    2.580
ASSI (10711)
    ( ( segid *BrD * and resid 81 and name HN   ) )
    ( ( segid *BrD * and resid 80 and name HB2 ) )
       3.700   3.400    1.800  peak   10711  weight    0.11000E+01 volume   0.72825E+02 ppm1    7.640 ppm2    2.493
ASSI (10731)
    ( ( segid *BrD * and resid 81 and name HN   ) )
    ( ( segid *BrD * and resid 79 and name HA   ) )
       3.900   3.800    1.600  peak   10731  weight    0.11000E+01 volume   0.55498E+02 ppm1    7.640 ppm2    4.412
ASSI (10791)
    ( ( segid *BrD * and resid 80 and name HN   ) )
    (   segid *BrD * and resid 78 and name HD2%)
       5.500   5.500    0.000  peak   10791  weight    0.11000E+01 volume   0.63252E+00 ppm1    8.014 ppm2    0.668
```

TABLE 2-continued

Unambigous NOE-derived Inter-proton Distance Restraints

```
ASSI (10801)
 ( ( segid *BrD * and resid 80 and name HN    ) )
 ( ( segid *BrD * and resid 78 and name HD1%)
     4.400  4.400   1.100  peak   10801  weight   0.11000E+01 volume   0.27938E+02 ppm1    8.014 ppm2    0.791
ASSI (10831)
 ( ( segid *BrD * and resid 79 and name HN    ) )
 ( ( segid *BrD * and resid 78 and name HB1  ) )
     3.300  2.700   2.200  peak   10831  weight   0.11000E+01 volume   0.14525E+03 ppm1    8.680 ppm2    1.364
ASSI (10911)
 ( ( segid *BrD * and resid 86 and name HN    ) )
 ( ( segid *BrD * and resid 83 and name HA   ) )
     3.300  2.700   2.200  peak   10911  weight   0.11000E+01 volume   0.16077E+03 ppm1    8.423 ppm2    4.445
ASSI (10951)
 ( ( segid *BrD * and resid 87 and name HN    ) )
 ( ( segid *BrD * and resid 86 and name HD1  ) )
     3.500  3.100   2.000  peak   10951  weight   0.11000E+01 volume   0.10515E+03 ppm1    8.571 ppm2    1.898
ASSI (10961)
 ( ( segid *BrD * and resid 86 and name HN    ) )
 ( ( segid *BrD * and resid 87 and name HN   ) )
     3.100  2.400   2.400  peak   10961  weight   0.11000E+01 volume   0.19900E+03 ppm1    8.424 ppm2    6.552
ASSI (10971)
 ( ( segid *BrD * and resid 87 and name HN    ) )
 ( ( segid *BrD * and resid 83 and name HA   ) )
     4.200  4.200   1.300  peak   10971  weight   0.11000E+01 volume   0.36593E+02 ppm1    8.572 ppm2    4.445
ASSI (11061)
 ( ( segid *BrD * and resid 89 and name HN    ) )
 (   segid *BrD * and resid 88 and name HD %  )
     3.200  2.600   2.300  peak   11061  weight   0.11000E+01 volume   0.19134E+03 ppm1    8.858 ppm2    7.596
ASSI (11071)
 ( ( segid *BrD * and resid 89 and name HN    ) )
 ( ( segid *BrD * and resid 91 and name HD1  ) )
     5.300  5.300   0.200  peak   11071  weight   0.11000E+01 volume   0.89575E+01 ppm1    8.858 ppm2    4.559
ASSI (11081)
 ( ( segid *BrD * and resid 89 and name HN    ) )
 ( ( segid *BrD * and resid 91 and name HD2  ) )
     3.800  3.600   1.700  peak   11081  weight   0.11000E+01 volume   0.66703E+02 ppm1    8.858 ppm2    4.400
ASSI (11101)
 ( ( segid *BrD * and resid 89 and name HN    ) )
 ( ( segid *BrD * and resid 87 and name HB1  ) )
     3.800  3.600   1.700  peak   11101  weight   0.11000E+01 volume   0.67773E+02 ppm1    8.858 ppm2    2.779
ASSI (11111)
 ( ( segid *BrD * and resid 89 and name HN    ) )
 ( ( segid *BrD * and resid 87 and name HB2  ) )
     4.200  4.200   1.300  peak   11111  weight   0.11000E+01 volume   0.36189E+02 ppm1    8.865 ppm2    2.610
ASSI (11121)
 ( ( segid *BrD * and resid 92 and name HN    ) )
 ( ( segid *BrD * and resid 91 and name HB1  ) )
     3.200  2.600   2.300  peak   11121  weight   0.11000E+01 volume   0.14770E+03 ppm1    8.876 ppm2    3.059
ASSI (11221)
 ( ( segid *BrD * and resid 30 and name HN    ) )
 ( ( segid *BrD * and resid 28 and name HN   ) )
     4.100  4.100   1.400  peak   11221  weight   0.11000E+01 volume   0.38088E+02 ppm1   12.275 ppm2    6.143
ASSI (11261)
 ( ( segid *BrD * and resid 31 and name HN    ) )
 ( ( segid *BrD * and resid 29 and name HG1  ) )
     5.100  5.100   0.400  peak   11261  weight   0.11000E+01 volume   0.11011E+02 ppm1    8.486 ppm2    2.997
ASSI (11311)
 ( ( segid *BrD * and resid 31 and name HN    ) )
 (   segid *BrD * and resid 102 and name HD1%)
     3.300  2.700   2.200  peak   11311  weight   0.11000E+01 volume   0.14151E+03 ppm1    8.480 ppm2    1.314
ASSI (11331)
 ( ( segid *BrD * and resid 32 and name HN    ) )
 ( ( segid *BrD * and resid 33 and name HD1  ) )
     3.900  3.800   1.600  peak   11331  weight   0.11000E+01 volume   0.57286E+02 ppm1    7.738 ppm2    2.782
ASSI (11341)
 ( ( segid *BrD * and resid 32 and name HN    ) )
 ( ( segid *BrD * and resid 33 and name HD2  ) )
     2.500  1.600   1.600  peak   11341  weight   0.11000E+01 volume   0.82617E+03 ppm1    7.739 ppm2    2.174
ASSI (11381)
 ( ( segid *BrD * and resid 34 and name HN    ) )
 ( ( segid *BrD * and resid 32 and name HA   ) )
     4.200  4.200   1.300  peak   11381  weight   0.11000E+01 volume   0.36612E+02 ppm1    8.183 ppm2    4.975
ASSI (11411)
 ( ( segid *BrD * and resid 34 and name HN    ) )
 ( ( segid *BrD * and resid 33 and name HD1  ) )
     2.600  1.700   1.700  peak   11411  weight   0.11000E+01 volume   0.60528E+03 ppm1    8.181 ppm2    2.784
```

TABLE 2-continued

Unambigous NOE-derived Inter-proton Distance Restraints

```
ASSI (11421)
  ( ( segid *BrD * and resid 34 and name HN   ) )
  ( ( segid *BrD * and resid 33 and name HD2  ) )
      3.300  2.700    2.200  peak   11421  weight    0.11000E+01  volume   0.15559E+03  ppm1    8.184  ppm2    2.174
ASSI (11461)
  ( ( segid *BrD * and resid 34 and name HN   ) )
  ( ( segid *BrD * and resid 33 and name HB1  ) )
      3.500  3.100    2.000  peak   11461  weight    0.11000E+01  volume   0.11065E+03  ppm1    8.178  ppm2    1.094
ASSI (11471)
  ( ( segid *BrD * and resid 34 and name HN   ) )
  ( ( segid *BrD * and resid 33 and name HG1  ) )
      4.100  4.100    1.400  peak   11474  weight    0.11000E+01  volume   0.41672E+02  ppm1    8.177  ppm2    0.840
ASSI (11481)
  ( ( segid *BrD * and resid 34 and name HN   ) )
  ( ( segid *BrD * and resid 33 and name HA   ) )
      3.200  2.600    2.300  peak   11481  weight    0.11000E+01  volume   0.17351E+03  ppm1    8.182  ppm2    4.363
ASSI (11501)
  ( ( segid *BrD * and resid 36 and name HN   ) )
  ( ( segid *BrD * and resid 35 and name HB1  ) )
      4.000  4.000    1.500  peak   11501  weight    0.11000E+01  volume   0.43329E+02  ppm1    8.307  ppm2    2.840
ASSI (11611)
  ( ( segid *BrD * and resid 67 and name HN   ) )
  ( ( segid *BrD * and resid 65 and name HB2  ) )
      3.800  3.600    1.700  peak   11611  weight    0.11000E+01  volume   0.63235E+02  ppm1    8.832  ppm2    3.380
ASSI (11621)
  ( ( segid *BrD * and resid 67 and name HN   ) )
  ( ( segid *BrD * and resid 66 and name HG1  ) )
      3.700  3.400    1.800  peak   11621  weight    0.11000E+01  volume   0.76792E+02  ppm1    8.832  ppm2    2.146
ASSI (11641)
  ( ( segid *BrD * and resid 68 and name HN   ) )
  ( ( segid *BrD * and resid 66 and name HA   ) )
      2.500  1.600    1.600  peak   11641  weight    0.11000E+01  volume   0.80687E+03  ppm1    8.626  ppm2    5.012
ASSI (11681)
  ( ( segid *BrD * and resid 68 and name HN   ) )
  (   segid *BrD * and resid 69 and name HG2%)
      3.400  2.900    2.100  peak   11681  weight    0.11000E+01  volume   0.13257E+03  ppm1    8.626  ppm2    1.437
ASSI (11691)
  ( ( segid *BrD * and resid 68 and name HN   ) )
  (   segid *BrD * and resid 69 and name HG1%)
      3.700  3.400    1.800  peak   11691  weight    0.11000E+01  volume   0.73874E+02  ppm1    8.626  ppm2    1.562
ASSI (11721)
  ( ( segid *BrD * and resid 68 and name HN   ) )
  (   segid *BrD * and resid 69 and name HD % )
      3.500  3.100    2.000  peak   11721  weight    0.11000E+01  volume   0.11106E+03  ppm1    8.306  ppm2    7.782
ASSI (11781)
  ( ( segid *BrD * and resid 70 and name HN   ) )
  ( ( segid *BrD * and resid 68 and name HA   ) )
      3.200  2.600    2.300  peak   11781  weight    0.11000E+01  volume   0.19118E+03  ppm1    8.039  ppm2    5.135
ASSI (11791)
  ( ( segid *BrD * and resid 74 and name HN   ) )
  (   segid *BrD * and resid 73 and name HD2%)
      4.400  4.400    1.100  peak   11791  weight    0.11000E+01  volume   0.24720E+02  ppm1    7.536  ppm2    1.502
ASSI (11801)
  ( ( segid *BrD * and resid 74 and name HN   ) )
  (   segid *BrD * and resid 73 and name HD1%)
      4.100  4.100    1.400  peak   11801  weight    0.11000E+01  volume   0.39673E+02  ppm1    7.536  ppm2    1.531
ASSI (11811)
  ( ( segid *BrD * and resid 74 and name HN   ) )
  ( ( segid *BrD * and resid 73 and name HG   ) )
      3.100  2.400    2.400  peak   11811  weight    0.11000E+01  volume   0.21474E+03  ppm1    7.537  ppm2    2.401
ASSI (11821)
  ( ( segid *BrD * and resid 74 and name HN   ) )
  ( ( segid *BrD * and resid 73 and name HB2  ) )
      2.900  2.100    2.100  peak   11821  weight    0.11000E+01  volume   0.29959E+03  ppm1    7.536  ppm2    2.498
ASSI (11831)
  ( ( segid *BrD * and resid 74 and name HN   ) )
  ( ( segid *BrD * and resid 73 and name HB1  ) )
      3.000  2.200    2.200  peak   11831  weight    0.11000E+01  volume   0.27375E+03  ppm1    7.537  ppm2    2.603
ASSI (11871)
  ( ( segid *BrD * and resid 73 and name HN   ) )
  (   segid *BrD * and resid 76 and name HB % )
      3.300  2.700    2.200  peak   11871  weight    0.11000E+01  volume   0.13672E+03  ppm1    8.046  ppm2    2.116
ASSI (11901)
  ( ( segid *BrD * and resid 74 and name HN   ) )
  (   segid *BrD * and resid 18 and name HD1%)
      3.700  3.400    1.800  peak   11901  weight    0.11000E+01  volume   0.74433E+02  ppm1    7.536  ppm2    1.076
```

TABLE 2-continued

Unambigous NOE-derived Inter-proton Distance Restraints

```
ASSI (11981)
     ( ( segid *BrD * and resid 98 and name HN   ) )
     ( ( segid *BrD * and resid 97 and name HB1  ) )
       2.500  1.600    1.600  peak   11981  weight   0.11000E+01  volume   0.78973E+03  ppm1     9.125  ppm2    2.698
ASSI (11991)
     ( ( segid *BrD * and resid 98 and name HN   ) )
     ( ( segid *BrD * and resid 97 and name HG1  ) )
       3.100  2.400    2.400  peak   11991  weight   0.11000E+01  volume   0.20137E+03  ppm1     9.125  ppm2    2.426
ASSI (12001)
     ( ( segid *BrD * and resid 98 and name HN   ) )
     ( ( segid *BrD * and resid 97 and name HG2  ) )
       3.100  2.400    2.400  peak   12001  weight   0.11000E+01  volume   0.20070E+03  ppm1     9.124  ppm2    2.189
ASSI (12171)
     ( ( segid *BrD * and resid 101 and name HN   ) )
     ( ( segid *BrD * and resid 99 and name HA    ) )
       4.000  4.000    1.500  peak   12171  weight   0.11000E+01  volume   0.46069E+02  ppm1     8.513  ppm2    4.447
ASSI (12181)
     ( ( segid *BrD * and resid 101 and name HN   ) )
     ( ( segid *BrD * and resid 97 and name HA    ) )
       3.100  2.400    2.400  peak   12181  weight   0.11000E+01  volume   0.20943E+03  ppm1     8.513  ppm2    4.811
ASSI (12191)
     ( ( segid *BrD * and resid 103 and name HN   ) )
     ( ( segid *BrD * and resid 102 and name HB1  ) )
       2.800  2.000    2.000  peak   12191  weight   0.11000E+01  volume   0.37773E+03  ppm1     8.696  ppm2    2.012
ASSI (12201)
     ( ( segid *BrD * and resid 104 and name HN   ) )
     ( ( segid *BrD * and resid 100 and name HA   ) )
       3.200  2.600    2.300  peak   12201  weight   0.11000E+01  volume   0.18477E+03  ppm1     7.763  ppm2    4.936
ASSI (12231)
     ( ( segid *BrD * and resid 107 and name HN   ) )
     ( ( segid *BrD * and resid 104 and name HA   ) )
       3.000  2.200    2.200  peak   12231  weight   0.11000E+01  volume   0.26295E+03  ppm1     8.981  ppm2    4.682
ASSI (12321)
     ( ( segid *BrD * and resid 110 and name HN   ) )
     ( ( segid *BrD * and resid 109 and name HD1  ) )
       3.500  3.100    2.000  peak   12321  weight   0.11000E+01  volume   0.10959E+03  ppm1     8.714  ppm2    2.010
ASSI (12331)
     ( ( segid *BrD * and resid 110 and name HN   ) )
     ( ( segid *BrD * and resid 109 and name HB1  ) )
       2.700  1.800    1.800  peak   12331  weight   0.11000E+01  volume   0.48783E+03  ppm1     8.714  ppm2    2.337
ASSI (12341)
     ( ( segid *BrD * and resid 110 and name HN   ) )
     ( ( segid *BrD * and resid 109 and name HG1  ) )
       3.000  2.200    2.200  peak   12341  weight   0.11000E+01  volume   0.26294E+03  ppm1     8.714  ppm2    1.440
ASSI (12351)
     ( ( segid *BrD * and resid 111 and name HN   ) )
     ( ( segid *BrD * and resid 110 and name HG12) )
       3.000  2.200    2.200  peak   12351  weight   0.11000E+01  volume   0.27526E+03  ppm1     8.168  ppm2    1.680
ASSI (12361)
     ( ( segid *BrD * and resid 112 and name HN   ) )
     ( ( segid *BrD * and resid 111 and name HG2  ) )
       3.200  2.600    2.300  peak   12361  weight   0.11000E+01  volume   0.16739E+03  ppm1     8.668  ppm2    3.909
ASSI (12371)
     ( ( segid *BrD * and resid 113 and name HN   ) )
     ( ( segid *BrD * and resid 110 and name HA   ) )
       3.600  3.200    1.900  peak   12371  weight   0.11000E+01  volume   0.80563E+02  ppm1     8.247  ppm2    4.425
ASSI (12381)
     ( ( segid *BrD * and resid 113 and name HN   ) )
     ( ( segid *BrD * and resid 111 and name HB1  ) )
       3.900  3.800    1.600  peak   12381  weight   0.11000E+01  volume   0.57596E+02  ppm1     8.219  ppm2    2.486
ASSI (12391)
     ( ( segid *BrD * and resid 113 and name HN   ) )
     ( ( segid *BrD * and resid 111 and name HB2  ) )
       3.800  3.600    1.700  peak   12391  weight   0.11000E+01  volume   0.67480E+02  ppm1     8.218  ppm2    2.364
ASSI (12531)
     ( ( segid *BrD * and resid 48 and name HN   ) )
     ( ( segid *BrD * and resid 47 and name HB1  ) )
       4.300  4.300    1.200  peak   12531  weight   0.11000E+01  volume   0.28319E+02  ppm1     8.307  ppm2    3.796
ASSI (12541)
     ( ( segid *BrD * and resid 48 and name HN   ) )
     ( ( segid *BrD * and resid 46 and name HA   ) )
       4.000  4.000    1.500  peak   12541  weight   0.11000E+01  volume   0.44246E+02  ppm1     8.307  ppm2    4.152
ASSI (12551)
     ( ( segid *BrD * and resid 48 and name HN   ) )
     ( ( segid *BrD * and resid 47 and name HB2  ) )
       4.200  4.200    1.300  peak   12551  weight   0.11000E+01  volume   0.35395E+02  ppm1     8.307  ppm2    3.408
```

TABLE 2-continued

Unambigous NOE-derived Inter-proton Distance Restraints

```
ASSI (12561)
    ( ( segid *BrD * and resid 47 and name HN   ) )
    ( ( segid *BrD * and resid 46 and name HD % )
       3.500   3.100    2.000  peak    12561  weight    0.11000E+01  volume   0.10097E+03  ppm1    8.832  ppm2    5.727
ASSI (12571)
    ( ( segid *BrD * and resid 47 and name HN   ) )
    (   segid *BrD * and resid 47 and name HD % )
       3.100   2.400    2.400  peak    12571  weight    0.11000E+01  volume   0.23274E+03  ppm1    8.833  ppm2    7.944
ASSI (12631)
    ( ( segid *BrD * and resid 51 and name HN   ) )
    ( ( segid *BrD * and resid 50 and name HA   ) )
       2.600   1.700    1.700  peak    12631  weight    0.11000E+01  volume   0.65616E+03  ppm1    8.377  ppm2    4.523
ASSI (12641)
    ( ( segid *BrD * and resid 52 and name HN   ) )
    ( ( segid *BrD * and resid 51 and name HB1  ) )
       3.400   2.900    2.100  peak    12641  weight    0.11000E+01  volume   0.11270E+03  ppm1    9.003  ppm2    1.995
ASSI (12651)
    ( ( segid *BrD * and resid 52 and name HN   ) )
    (   segid *BrD * and resid 51 and name HG1  ) )
       5.500   5.500    0.000  peak    12651  weight    0.11000E+01  volume   0.88686E+00  ppm1    9.003  ppm2    1.926
ASSI (12661)
    ( ( segid *BrD * and resid 52 and name HN   ) )
    (   segid *BrD * and resid 51 and name HG2  ) )
       3.400   2.900    2.100  peak    12661  weight    0.11000E+01  volume   0.11315E+03  ppm1    9.003  ppm2    1.780
ASSI (12671)
    ( ( segid *BrD * and resid 52 and name HN   ) )
    (   segid *BrD * and resid 51 and name HB2  ) )
       3.200   2.600    2.300  peak    12671  weight    0.11000E+01  volume   0.16847E+03  ppm1    9.004  ppm2    1.818
ASSI (12681)
    ( ( segid *BrD * and resid 52 and name HN   ) )
    (   segid *BrD * and resid 50 and name HG2%)
       2.800   2.000    2.000  peak    12681  weight    0.11000E+01  volume   0.38955E+03  ppm1    9.002  ppm2    0.991
ASSI (12731)
    ( ( segid *BrD * and resid 42 and name HN   ) )
    ( ( segid *BrD * and resid 41 and name HA   ) )
       3.400   2.900    2.100  peak    12731  weight    0.11000E+01  volume   0.12554E+03  ppm1    7.822  ppm2    4.650
ASSI (12771)
    ( ( segid *BrD * and resid 42 and name HN   ) )
    (   segid *BrD * and resid 41 and name HG2%)
       4.200   4.200    1.300  peak    12771  weight    0.11000E+01  volume   0.34295E+02  ppm1    7.821  ppm2    1.874
ASSI (12781)
    ( ( segid *BrD * and resid 97 and name HN   ) )
    (   segid *BrD * and resid 96 and name HD % )
       3.300   2.700    2.200  peak    12781  weight    0.11000E+01  volume   0.12710E+03  ppm1    8.674  ppm2    7.701
ASSI (12791)
    ( ( segid *BrD * and resid 20 and name HN   ) )
    ( ( segid *BrD * and resid 19 and name HG1  ) )
       3.400   2.900    2.100  peak    12791  weight    0.11000E+01  volume   0.11346E+03  ppm1    8.146  ppm2    1.687
ASSI (12801)
    ( ( segid *BrD * and resid 19 and name HN   ) )
    ( ( segid *BrD * and resid 18 and name HB2  ) )
       3.400   2.900    2.100  peak    12801  weight    0.11000E+01  volume   0.11595E+03  ppm1    9.186  ppm2    0.901
ASSI (12811)
    ( ( segid *BrD * and resid 19 and name HN   ) )
    (   segid *BrD * and resid 63 and name HD1%)
       3.100   2.400    2.400  peak    12811  weight    0.11000E+01  volume   0.22952E+03  ppm1    9.186  ppm2    1.442
ASSI (12821)
    ( ( segid *BrD * and resid 19 and name HN   ) )
    (   segid *BrD * and resid 63 and name HD2%)
       3.000   2.200    2.200  peak    12821  weight    0.11000E+01  volume   0.27823E+03  ppm1    9.187  ppm2    1.476
ASSI (12831)
    ( ( segid *BrD * and resid 19 and name HN   ) )
    ( ( segid *BrD * and resid 16 and name HA   ) )
       3.000   2.200    2.200  peak    12831  weight    0.11000E+01  volume   0.27123E+03  ppm1    9.187  ppm2    4.516
ASSI (12871)
    ( ( segid *BrD * and resid 20 and name HN   ) )
    ( ( segid *BrD * and resid 18 and name HG   ) )
       3.800   3.600    1.700  peak    12871  weight    0.11000E+01  volume   0.64336E+02  ppm1    8.147  ppm2    2.290
ASSI (12931)
    ( ( segid *BrD * and resid 23 and name HN   ) )
    ( ( segid *BrD * and resid 22 and name HB1  ) )
       2.600   1.700    1.700  peak    12931  weight    0.11000E+01  volume   0.65704E+03  ppm1    9.120  ppm2    2.697
ASSI (12941)
    ( ( segid *BrD * and resid 23 and name HN   ) )
    ( ( segid *BrD * and resid 22 and name HB2  ) )
       2.800   2.000    2.000  peak    12941  weight    0.11000E+01  volume   0.39331E+03  ppm1    9.122  ppm2    2.110
```

TABLE 2-continued

Unambigous NOE-derived Inter-proton Distance Restraints

ASSI (13051)
( ( segid *BrD * and resid 27 and name HN   ) )
( ( segid *BrD * and resid 26 and name HD1 ) )
   2.700  1.800    1.800  peak   13051  weight    0.11000E+01  volume    0.47384E+03  ppm1    8.168  ppm2    2.127
ASSI (13071)
( ( segid *BrD * and resid 27 and name HN   ) )
( ( segid *BrD * and resid 24 and name HG1 ) )
   3.500  3.100    2.000  peak   13071  weight    0.11000E+01  volume    0.10804E+03  ppm1    8.170  ppm2    3.447
ASSI (13081)
( ( segid *BrD * and resid 27 and name HN   ) )
( ( segid *BrD * and resid 24 and name HG2 ) )
   3.700  3.400    1.800  peak   13081  weight    0.11000E+01  volume    0.74378E+02  ppm1    8.170  ppm2    3.074
ASSI (13141)
( ( segid *BrD * and resid 60 and name HN   ) )
( ( segid *BrD * and resid 59 and name HB2 ) )
   2.900  2.100    2.100  peak   13141  weight    0.11000E+01  volume    0.32659E+03  ppm1    8.565  ppm2    2.522
ASSI (13151)
( ( segid *BrD * and resid 65 and name HN   ) )
( ( segid *BrD * and resid 64 and name HG1 ) )
   3.300  2.700    2.200  peak   13151  weight    0.11000E+01  volume    0.14156E+03  ppm1    8.545  ppm2    2.203
ASSI (13211)
( ( segid *BrD * and resid 15 and name HN   ) )
( ( segid *BrD * and resid 14 and name HG  ) )
   3.700  3.400    1.800  peak   13211  weight    0.11000E+01  volume    0.73008E+02  ppm1    8.597  ppm2    2.087
ASSI (13281)
( ( segid *BrD * and resid 65 and name HD21 ) )
( ( segid *BrD * and resid 64 and name HB1 ) )
   3.600  3.200    1.900  peak   13281  weight    0.11000E+01  volume    0.89819E+02  ppm1    8.205  ppm2    2.662
ASSI (13291)
( ( segid *BrD * and resid 65 and name HD22 ) )
( ( segid *BrD * and resid 64 and name HB1 ) )
   3.600  3.200    1.900  peak   13291  weight    0.11000E+01  volume    0.84418E+02  ppm1    7.576  ppm2    2.662
ASSI (13321)
( ( segid *BrD * and resid 93 and name HN   ) )
( ( segid *BrD * and resid 93 and name HB1 ) )
   4.100  4.100    1.400  peak   13321  weight    0.11000E+01  volume    0.42284E+02  ppm1    8.713  ppm2    5.009
ASSI (13331)
( ( segid *BrD * and resid 94 and name HN   ) )
( ( segid *BrD * and resid 93 and name HB1 ) )
   3.700  3.400    1.800  peak   13331  weight    0.11000E+01  volume    0.78957E+02  ppm1    9.679  ppm2    5.000
ASSI (13341)
( ( segid *BrD * and resid 17 and name HN   ) )
( ( segid *BrD * and resid 16 and name HB1 ) )
   3.400  2.900    2.100  peak   13341  weight    0.11000E+01  volume    0.11732E+03  ppm1    8.670  ppm2    4.602
ASSI (13351)
( ( segid *BrD * and resid 62 and name HN   ) )
( ( segid *BrD * and resid 62 and name HD2 ) )
   2.700  1.800    1.800  peak   13351  weight    0.11000E+01  volume    0.44005E+03  ppm1    8.998  ppm2    2.658
ASSI (13361)
( ( segid *BrD * and resid 86 and name HN   ) )
( ( segid *BrD * and resid 86 and name HG1 ) )
   4.100  4.100    1.400  peak   13361  weight    0.11000E+01  volume    0.42972E+02  ppm1    8.423  ppm2    1.920
ASSI (13371)
( ( segid *BrD * and resid 17 and name HN   ) )
( ( segid *BrD * and resid 17 and name HA  ) )
   2.600  1.700    1.700  peak   13371  weight    0.11000E+01  volume    0.66944E+03  ppm1    8.670  ppm2    4.652
ASSI (13381)
( ( segid *BrD * and resid 18 and name HN   ) )
( ( segid *BrD * and resid 15 and name HA  ) )
   3.800  3.600    1.700  peak   13381  weight    0.11000E+01  volume    0.66429E+02  ppm1    9.073  ppm2    4.620
ASSI (13391)
( ( segid *BrD * and resid 19 and name HN   ) )
( ( segid *BrD * and resid 18 and name HN  ) )
   2.300  1.300    1.300  peak   13391  weight    0.11000E+01  volume    0.12618E+04  ppm1    9.186  ppm2    9.067
ASSI (13401)
( ( segid *BrD * and resid 59 and name HN   ) )
( ( segid *BrD * and resid 56 and name HA  ) )
   3.100  2.400    2.400  peak   13401  weight    0.11000E+01  volume    0.22047E+03  ppm1    8.498  ppm2    4.643
ASSI (13421)
( ( segid *BrD * and resid 79 and name HN   ) )
( ( segid *BrD * and resid 75 and name HA  ) )
   4.000  4.000    1.500  peak   13421  weight    0.11000E+01  volume    0.47743E+02  ppm1    8.680  ppm2    4.518
ASSI (13431)
( ( segid *BrD * and resid 81 and name HN   ) )
( ( segid *BrD * and resid 77 and name HA  ) )
   4.500  4.500    1.000  peak   13431  weight    0.11000E+01  volume    0.23511E+02  ppm1    7.629  ppm2    4.978

TABLE 2-continued

Unambigous NOE-derived Inter-proton Distance Restraints

```
ASSI (13441)
    ( ( segid *BrD * and resid 85 and name HN   ) )
    ( ( segid *BrD * and resid 83 and name HA   ) )
      3.600   3.200    1.900  peak   13441  weight   0.11000E+01 volume   0.85635E+02 ppm1     7.519 ppm2    4.441
ASSI (13451)
    ( ( segid *BrD * and resid 85 and name HN   ) )
    ( ( segid *BrD * and resid 81 and name HA   ) )
      2.500   1.600    1.600  peak   13451  weight   0.11000E+01 volume   0.75325E+03 ppm1     7.517 ppm2    3.646
ASSI (13461)
    ( ( segid *BrD * and resid 88 and name HN   ) )
    ( ( segid *BrD * and resid 84 and name HA   ) )
      2.800   2.000    2.000  peak   13461  weight   0.11000E+01 volume   0.40309E+03 ppm1     8.357 ppm2    4.922
ASSI (13481)
    ( ( segid *BrD * and resid 81 and name HN   ) )
    ( ( segid *BrD * and resid 83 and name HN   ) )
      3.900   3.800    1.600  peak   13481  weight   0.11000E+01 volume   0.50469E+02 ppm1     7.640 ppm2    9.655
ASSI (13491)
    ( ( segid *BrD * and resid 96 and name HN   ) )
    ( ( segid *BrD * and resid 93 and name HA   ) )
      3.700   3.400    1.800  peak   13491  weight   0.11000E+01 volume   0.70852E+02 ppm1     7.981 ppm2    5.013
ASSI (13501)
    ( ( segid *BrD * and resid 109 and name HN   ) )
    ( ( segid *BrD * and resid 105 and name HA   ) )
      4.600   4.600    0.900  peak   13501  weight   0.11000E+01 volume   0.18885E+02 ppm1     8.574 ppm2    4.935
ASSI (13511)
    ( ( segid *BrD * and resid 110 and name HN   ) )
    ( ( segid *BrD * and resid 108 and name HA   ) )
      3.500   3.100    2.000  peak   13511  weight   0.11000E+01 volume   0.11166E+03 ppm1     8.714 ppm2    4.918
ASSI (13521)
    ( ( segid *BrD * and resid 92 and name HN   ) )
    ( ( segid *BrD * and resid 91 and name HA   ) )
      3.200   2.600    2.300  peak   13521  weight   0.11000E+01 volume   0.11000E+01 ppm1     8.873 ppm2    5.343
ASSI (13541)
    ( ( segid *BrD * and resid 98 and name HN   ) )
    ( ( segid *BrD * and resid 100 and name HN   ) )
      2.900   2.100    2.100  peak   13541  weight   0.11000E+01 volume   0.30894E+03 ppm1     9.125 ppm2    8.693
ASSI (13551)
    ( ( segid *BrD * and resid 103 and name HN   ) )
    ( ( segid *BrD * and resid 101 and name HN   ) )
      2.900   2.100    2.100  peak   13551  weight   0.11000E+01 volume   0.34725E+03 ppm1     8.696 ppm2    8.519
ASSI (13561)
    ( ( segid *BrD * and resid 32 and name HN   ) )
    ( ( segid *BrD * and resid 30 and name HA   ) )
      4.400   4.400    1.100  peak   13561  weight   0.11000E+01 volume   0.25941E+02 ppm1     7.739 ppm2    5.445
ASSI (13571)
    ( ( segid *BrD * and resid 24 and name HN   ) )
    ( ( segid *BrD * and resid 23 and name HB2   ) )
      2.800   2.000    2.000  peak   13571  weight   0.11000E+01 volume   0.42825E+03 ppm1     8.655 ppm2    2.870
ASSI (13581)
    ( ( segid *BrD * and resid 73 and name HN   ) )
    ( ( segid *BrD * and resid 75 and name HN   ) )
      4.000   4.000    1.500  peak   13581  weight   0.11000E+01 volume   0.46662E+02 ppm1     8.045 ppm2    9.084
ASSI (13591)
    ( ( segid *BrD * and resid 62 and name HN   ) )
    ( ( segid *BrD * and resid 61 and name HG1   ) )
      3.900   3.800    1.600  peak   13591  weight   0.11000E+01 volume   0.54843E+02 ppm1     8.999 ppm2    2.952
ASSI (13611)
    ( ( segid *BrD * and resid 67 and name HN   ) )
    ( ( segid *BrD * and resid 65 and name HB1   ) )
      2.600   2.000    2.000  peak   13611  weight   0.11000E+01 volume   0.36617E+03 ppm1     8.832 ppm2    3.626
ASSI (13621)
    ( ( segid *BrD * and resid 75 and name HN   ) )
    ( ( segid *BrD * and resid 74 and name HB2   ) )
      3.200   2.600    2.300  peak   13621  weight   0.11000E+01 volume   0.17250E+03 ppm1     9.106 ppm2    2.988
ASSI (13641)
    ( ( segid *BrD * and resid 104 and name HN   ) )
    ( ( segid *BrD * and resid 106 and name HN   ) )
      4.900   4.900    0.600  peak   13641  weight   0.11000E+01 volume   0.14134E+02 ppm1     7.763 ppm2    9.736
ASSI (13671)
    ( ( segid *BrD * and resid 74 and name HN   ) )
    (  segid *BrD * and resid 18 and name HD2%)
      3.900   3.800    1.600  peak   13671  weight   0.11000E+01 volume   0.56031E+02 ppm1     7.545 ppm2    0.414
ASSI (13701)
    ( ( segid *BrD * and resid 61 and name HN   ) )
    ( ( segid *BrD * and resid 61 and name HB1   ) )
      2.800   2.000    2.000  peak   13701  weight   0.11000E+01 volume   0.41690E+03 ppm1     8.743 ppm2    2.837
```

TABLE 2-continued

Unambigous NOE-derived Inter-proton Distance Restraints

```
ASSI (13711)
   ( ( segid *BrD * and resid 62 and name HN   ) )
   ( ( segid *BrD * and resid 61 and name HB1  ) )
    2.800  2.000   2.000 peak    13711 weight   0.11000E+01 volume  0.40898E+03 ppm1    8.998 ppm2    2.853
ASSI (13731)
   ( ( segid *BrD * and resid 25 and name HN   ) )
   ( ( segid *BrD * and resid 21 and name HA   ) )
    2.900  2.100   2.100 peak    13731 weight   0.11000E+01 volume  0.30325E+03 ppm1    9.134 ppm2    4.393
ASSI (13741)
   ( ( segid *BrD * and resid 63 and name HN   ) )
   ( ( segid *BrD * and resid 59 and name HA   ) )
    3.200  2.600   2.300 peak    13741 weight   0.11000E+01 volume  0.16317E+03 ppm1    9.472 ppm2    4.926
ASSI (13761)
   ( ( segid *BrD * and resid 74 and name HN   ) )
   ( ( segid *BrD * and resid 71 and name HA   ) )
    3.200  2.600   2.300 peak    13761 weight   0.11000E+01 volume  0.19208E+03 ppm1    7.534 ppm2    4.622
ASSI (13771)
   ( ( segid *BrD * and resid 75 and name HN   ) )
   ( ( segid *BrD * and resid 71 and name HA   ) )
    3.100  2.400   2.400 peak    13771 weight   0.11000E+01 volume  0.21726E+03 ppm1    9.106 ppm2    4.628
ASSI (13781)
   ( ( segid *BrD * and resid 77 and name HN   ) )
   ( ( segid *BrD * and resid 74 and name HA   ) )
    3.200  2.600   2.300 peak    13781 weight   0.11000E+01 volume  0.16504E+03 ppm1    7.996 ppm2    4.371
ASSI (13791)
   ( ( segid *BrD * and resid 105 and name HN  ) )
   ( ( segid *BrD * and resid 101 and name HA  ) )
    3.200  2.600   2.300 peak    13791 weight   0.11000E+01 volume  0.19414E+03 ppm1    8.487 ppm2    4.253
ASSI (13801)
   ( ( segid *BrD * and resid 26 and name HN   ) )
   ( ( segid *BrD * and resid 24 and name HA   ) )
    3.900  3.800   1.600 peak    13801 weight   0.11000E+01 volume  0.52793E+02 ppm1    9.196 ppm2    4.755
ASSI (13811)
   ( ( segid *BrD * and resid 26 and name HN   ) )
   ( ( segid *BrD * and resid 25 and name HA   ) )
    3.800  3.600   1.700 peak    13811 weight   0.11000E+01 volume  0.62704E+02 ppm1    9.196 ppm2    4.415
ASSI (13821)
   ( ( segid *BrD * and resid 29 and name HN   ) )
   ( ( segid *BrD * and resid 25 and name HA   ) )
    5.500  5.500   0.000 peak    13821 weight   0.11000E+01 volume  0.27795E+01 ppm1    9.152 ppm2    4.452
ASSI (13831)
   ( ( segid *BrD * and resid 54 and name HN   ) )
   ( ( segid *BrD * and resid 55 and name HN   ) )
    2.900  2.100   2.100 peak    13831 weight   0.11000E+01 volume  0.31830E+01 ppm1    9.037 ppm2    7.972
ASSI (13851)
   ( ( segid *BrD * and resid 48 and name HN   ) )
   (   segid *BrD * and resid 47 and name HD %  )
    3.900  3.800   1.600 peak    13851 weight   0.11000E+01 volume  0.57580E+02 ppm1    8.307 ppm2    7.949
ASSI (13861)
   ( ( segid *BrD * and resid 96 and name HN   ) )
   (   segid *BrD * and resid 95 and name HD %  )
    3.500  3.100   2.000 peak    13861 weight   0.11000E+01 volume  0.10869E+03 ppm1    7.979 ppm2    7.498
ASSI (14011)
   ( ( segid *BrD * and resid 108 and name HN  ) )
   (   segid *BrD * and resid 107 and name HD % )
    4.300  4.300   1.200 peak    14011 weight   0.11000E+01 volume  0.30492E+02 ppm1    8.528 ppm2    7.782
ASSI (14881)
   ( ( segid *BrD * and resid 54 and name HN   ) )
   ( ( segid *BrD * and resid 54 and name HG1  ) )
    4.500  4.500   1.000 peak    14881 weight   0.11000E+01 volume  0.23500E+02 ppm1    9.038 ppm2    3.297
ASSI (15591)
   ( ( segid *BrD * and resid 32 and name HE1  ) )
   ( ( segid *BrD * and resid 32 and name HB2  ) )
    4.000  4.000   1.500 peak    15591 weight   0.11000E+01 volume  0.47456E+02 ppm1   11.081 ppm2    3.958
ASSI (15601)
   ( ( segid *BrD * and resid 32 and name HE1  ) )
   ( ( segid *BrD * and resid 32 and name HB1  ) )
    5.200  5.200   0.300 peak    15601 weight   0.11000E+01 volume  0.94290E+01 ppm1   11.081 ppm2    4.201
ASSI (  111)
   ( ( segid *BrD * and resid 99 and name HN   ) )
   ( ( segid *BrD * and resid 34 and name HZ   ) )
    3.100  2.400   2.400 peak      111 weight   0.10000E+01 volume  0.20460E+03 ppm1    8.936 ppm2    7.899
ASSI (  801)
   ( ( segid *BrD * and resid 97 and name HN   ) )
   ( ( segid *BrD * and resid 97 and name HE1  ) )
    4.000  4.000   1.500 peak      801 weight   0.10000E+01 volume  0.47904E+02 ppm1    8.673 ppm2    3.575
```

TABLE 2-continued

Unambigous NOE-derived Inter-proton Distance Restraints

ASSI ( 931)
( ( segid *BrD * and resid 117 and name HN   ) )
( ( segid *BrD * and resid 116 and name HN   ) )
   3.500  3.100   2.000  peak     931  weight   0.10000E+01  volume   0.10704E+03  ppm1     8.883  ppm2     8.075
ASSI ( 1891)
( ( segid *BrD * and resid 83 and name HN   ) )
( ( segid *BrD * and resid 85 and name HN   ) )
   4.000  4.000   1.500  peak    1891  weight   0.10000E+01  volume   0.44105E+02  ppm1     9.660  ppm2     7.505
ASSI ( 2331)
( ( segid *BrD * and resid 49 and name HN   ) )
( ( segid *BrD * and resid 50 and name HA   ) )
   4.000  4.000   1.500  peak    2331  weight   0.10000E+01  volume   0.49544E+02  ppm1     7.761  ppm2     4.525
ASSI ( 2631)
( ( segid *BrD * and resid 103 and name HN   ) )
(   segid *BrD * and resid 82 and name HD % )
   3.800  3.600   1.700  peak    2631  weight   0.10000E+01  volume   0.64814E+02  ppm1     8.695  ppm2     7.246
ASSI ( 3601)
( ( segid *BrD * and resid 9 and name HN   ) )
( ( segid *BrD * and resid 9 and name HA   ) )
   2.900  2.100   2.100  peak    3601  weight   0.10000E+01  volume   0.32855E+03  ppm1     9.052  ppm2     4.936
ASSI ( 3751)
( ( segid *BrD * and resid 56 and name HN   ) )
( ( segid *BrD * and resid 35 and name HA   ) )
   3.200  2.600   2.300  peak    3751  weight   0.10000E+01  volume   0.18743E+03  ppm1     9.678  ppm2     4.895
ASSI ( 4371)
( ( segid *BrD * and resid 40 and name HN   ) )
( ( segid *BrD * and resid 42 and name HA   ) )
   3.400  2.900   2.100  peak    4371  weight   0.10000E+01  volume   0.12104E+03  ppm1     8.662  ppm2     5.021
ASSI ( 4671)
( ( segid *BrD * and resid 61 and name HN   ) )
( ( segid *BrD * and resid 60 and name HB1   ) )
   2.900  2.100   2.100  peak    4671  weight   0.10000E+01  volume   0.31176E+03  ppm1     8.746  ppm2     4.992
ASSI ( 5081)
( ( segid *BrD * and resid 73 and name HN   ) )
( ( segid *BrD * and resid 74 and name HB2   ) )
   3.100  2.400   2.400  peak    5081  weight   0.10000E+01  volume   0.21337E+03  ppm1     8.007  ppm2     3.018
ASSI ( 7641)
( ( segid *BrD * and resid 76 and name HN   ) )
( ( segid *BrD * and resid 73 and name HA   ) )
   3.500  3.100   2.000  peak    7641  weight   0.10000E+01  volume   0.97995E+02  ppm1     8.611  ppm2     4.812
ASSI ( 7691)
( ( segid *BrD * and resid 83 and name HN   ) )
( ( segid *BrD * and resid 80 and name HA   ) )
   2.800  2.000   2.000  peak    7691  weight   0.10000E+01  volume   0.35765E+03  ppm1     9.660  ppm2     4.675
ASSI ( 8061)
( ( segid *BrD * and resid 39 and name HN   ) )
( ( segid *BrD * and resid 38 and name HN   ) )
   4.300  4.300   1.200  peak    8061  weight   0.10000E+01  volume   0.29321E+02  ppm1     9.651  ppm2     8.726
ASSI ( 8071)
( ( segid *BrD * and resid 39 and name HN   ) )
( ( segid *BrD * and resid 42 and name HG1   ) )
   4.100  4.100   1.400  peak    8071  weight   0.10000E+01  volume   0.37403E+02  ppm1     9.657  ppm2     2.891
ASSI ( 8081)
( ( segid *BrD * and resid 39 and name HN   ) )
( ( segid *BrD * and resid 42 and name HB1   ) )
   3.900  3.800   1.600  peak    8081  weight   0.10000E+01  volume   0.55108E+02  ppm1     9.658  ppm2     2.784
ASSI ( 8091)
( ( segid *BrD * and resid 39 and name HN   ) )
( ( segid *BrD * and resid 42 and name HB2   ) )
   4.200  4.200   1.300  peak    8091  weight   0.10000E+01  volume   0.33585E+02  ppm1     9.651  ppm2     2.607
ASSI ( 8141)
( ( segid *BrD * and resid 57 and name HN   ) )
( ( segid *BrD * and resid 36 and name HA   ) )
   3.100  2.400   2.400  peak    8141  weight   0.10000E+01  volume   0.21622E+03  ppm1     9.359  ppm2     5.440
ASSI ( 8151)
( ( segid *BrD * and resid 57 and name HN   ) )
( ( segid *BrD * and resid 58 and name HA   ) )
   4.100  4.100   1.400  peak    8151  weight   0.10000E+01  volume   0.38316E+02  ppm1     9.359  ppm2     4.453
ASSI ( 8161)
( ( segid *BrD * and resid 57 and name HN   ) )
( ( segid *BrD * and resid 37 and name HD1   ) )
   3.700  3.400   1.800  peak    8161  weight   0.10000E+01  volume   0.78885E+02  ppm1     9.359  ppm2     4.288
ASSI ( 8221)
( ( segid *BrD * and resid 114 and name HN   ) )
( ( segid *BrD * and resid 115 and name HG   ) )
   3.800  3.600   1.700  peak    8221  weight   0.10000E+01  volume   0.68239E+02  ppm1     8.377  ppm2     2.169

TABLE 2-continued

Unambigous NOE-derived Inter-proton Distance Restraints

```
OR ( 8221)
   ( ( segid *BrD * and resid 114 and name HN   ) )
   ( ( segid *BrD * and resid 115 and name HB1  ) )
ASSI ( 8231)
   ( ( segid *BrD * and resid 114 and name HN   ) )
   (  segid *BrD * and resid 115 and name HD1%)
      3.700  3.400   1.800  peak    8231  weight   0.10000E+01 volume  0.72638E+02 ppm1  8.375 ppm2  1.308
ASSI ( 8271)
   ( ( segid *BrD * and resid 28 and name HN    ) )
   (  segid *BrD * and resid 31 and name HB %  )
      3.400  2.900   2.100  peak    8271  weight   0.10000E+01 volume  0.12341E+03 ppm1  8.166 ppm2  2.208
ASSI ( 8281)
   ( ( segid *BrD * and resid 28 and name HN    ) )
   ( ( segid *BrD * and resid 26 and name HB1   ) )
      3.700  3.400   1.800  peak    8281  weight   0.10000E+01 volume  0.69844E+02 ppm1  8.166 ppm2  2.476
ASSI ( 8301)
   ( ( segid *BrD * and resid 28 and name HN    ) )
   (  segid *BrD * and resid 102 and name HD1%)
      3.400  2.900   2.100  peak    8301  weight   0.10000E+01 volume  0.11542E+03 ppm1  8.166 ppm2  1.318
ASSI ( 8311)
   ( ( segid *BrD * and resid 118 and name HN   ) )
   ( ( segid *BrD * and resid 116 and name HG12) )
      3.200  2.600   2.300  peak    8311  weight   0.10000E+01 volume  0.19156E+03 ppm1  8.381 ppm2  1.558
ASSI ( 8321)
   ( ( segid *BrD * and resid 118 and name HN   ) )
   (  segid *BrD * and resid 116 and name HD1%)
      4.100  4.100   1.400  peak    8321  weight   0.10000E+01 volume  0.39844E+02 ppm1  8.380 ppm2  1.394
OR ( 8321)
   ( ( segid *BrD * and resid 118 and name HN   ) )
   (  segid *BrD * and resid 116 and name HG2%)
ASSI ( 8331)
   ( ( segid *BrD * and resid 118 and name HN   ) )
   (  segid *BrD * and resid 110 and name HG2%)
      3.400  2.900   2.100  peak    8331  weight   0.10000E+01 volume  0.11494E+03 ppm1  8.381 ppm2  1.296
ASSI ( 8341)
   ( ( segid *BrD * and resid 51 and name HN    ) )
   (  segid *BrD * and resid 50 and name HD1%)
      4.000  4.000   1.500  peak    8341  weight   0.10000E+01 volume  0.45762E+02 ppm1  8.381 ppm2  1.156
ASSI ( 8401)
   ( ( segid *BrD * and resid 38 and name HN    ) )
   ( ( segid *BrD * and resid 37 and name HB2   ) )
      3.000  2.200   2.200  peak    8401  weight   0.10000E+01 volume  0.24692E+03 ppm1  8.733 ppm2  2.290
ASSI ( 8411)
   ( ( segid *BrD * and resid 117 and name HN   ) )
   ( ( segid *BrD * and resid 118 and name HN   ) )
      3.900  3.800   1.600  peak    8411  weight   0.10000E+01 volume  0.55844E+02 ppm1  8.880 ppm2  8.368
ASSI ( 8421)
   ( ( segid *BrD * and resid 117 and name HN   ) )
   ( ( segid *BrD * and resid 118 and name HG11) )
      3.900  3.800   1.600  peak    8421  weight   0.10000E+01 volume  0.57435E+01 ppm1  8.876 ppm2  1.915
ASSI ( 8441)
   ( ( segid *BrD * and resid 7 and name HN     ) )
   ( ( segid *BrD * and resid 6 and name HD1    ) )
      3.800  3.600   1.700  peak    8441  weight   0.10000E+01 volume  0.67409E+02 ppm1  8.923 ppm2  2.338
ASSI ( 8451)
   ( ( segid *BrD * and resid 102 and name HN   ) )
   ( ( segid *BrD * and resid 28 and name HE1   ) )
      3.900  3.800   1.600  peak    8451  weight   0.10000E+01 volume  0.51665E+02 ppm1  9.156 ppm2  8.153
ASSI ( 8461)
   ( ( segid *BrD * and resid 102 and name HN   ) )
   (  segid *BrD * and resid 82 and name HE %  )
      4.100  4.100   1.400  peak    8461  weight   0.10000E+01 volume  0.42485E+02 ppm1  9.156 ppm2  7.050
OR ( 8461)
   ( ( segid *BrD * and resid 102 and name HN   ) )
   (  segid *BrD * and resid 82 and name HZ    )
ASSI ( 8481)
   ( ( segid *BrD * and resid 102 and name HN   ) )
   ( ( segid *BrD * and resid 103 and name HB1  ) )
      3.600  3.200   1.900  peak    8481  weight   0.10000E+01 volume  0.86913E+02 ppm1  9.156 ppm2  2.348
ASSI ( 8501)
   ( ( segid *BrD * and resid 50 and name HN    ) )
   ( ( segid *BrD * and resid 48 and name HA    ) )
      5.100  5.100   0.400  peak    8501  weight   0.10000E+01 volume  0.11267E+02 ppm1  8.564 ppm2  4.822
ASSI ( 8551)
   ( ( segid *BrD * and resid 46 and name HN    ) )
   ( ( segid *BrD * and resid 44 and name HA    ) )
      4.000  4.000   1.500  peak    8551  weight   0.10000E+01 volume  0.43724E+02 ppm1  8.562 ppm2  5.119
```

TABLE 2-continued

Unambigous NOE-derived Inter-proton Distance Restraints

```
ASSI ( 8581)
   ( ( segid *BrD * and resid 46 and name HN   ) )
   ( ( segid *BrD * and resid 43 and name HB % )
     2.800   2.000    2.000   peak    8581  weight   0.10000E+01  volume   0.40920E+03  ppm1    8.562  ppm2   1.692
ASSI ( 8601)
   ( ( segid *BrD * and resid 43 and name HN   ) )
   ( ( segid *BrD * and resid 39 and name HB1  ) )
     4.100   4.100    1.400   peak    8601  weight   0.10000E+01  volume   0.39702E+02  ppm1    8.001  ppm2   2.497
ASSI ( 8611)
   ( ( segid *BrD * and resid 43 and name HN   ) )
   ( ( segid *BrD * and resid 39 and name HD1  ) )
     3.500   3.100    2.000   peak    8611  weight   0.10000E+01  volume   0.96093E+02  ppm1    8.001  ppm2   2.292
ASSI ( 8621)
   ( ( segid *BrD * and resid 43 and name HN   ) )
   (   segid *BrD * and resid 41 and name HG2%)
     4.200   4.200    1.300   peak    8621  weight   0.10000E+01  volume   0.33897E+02  ppm1    8.001  ppm2   1.887
ASSI ( 8631)
   ( ( segid *BrD * and resid 43 and name HN   ) )
   (   segid *BrD * and resid 38 and name HG1%)
     4.300   4.300    1.200   peak    8631  weight   0.10000E+01  volume   0.32108E+02  ppm1    8.002  ppm2   1.058
ASSI ( 8641)
   ( ( segid *BrD * and resid 43 and name HN   ) )
   (   segid *BrD * and resid 38 and name HG2%)
     3.900   3.800    1.600   peak    8641  weight   0.10000E+01  volume   0.57231E+02  ppm1    8.001  ppm2   0.778
ASSI ( 8661)
   ( ( segid *BrD * and resid 111 and name HN   ) )
   ( ( segid *BrD * and resid 112 and name HB1  ) )
     3.800   3.600    1.700   peak    8661  weight   0.10000E+01  volume   0.66898E+02  ppm1    8.167  ppm2   2.659
ASSI ( 8681)
   ( ( segid *BrD * and resid 111 and name HN   ) )
   (   segid *BrD * and resid 110 and name HG2%)
     3.000   2.200    2.200   peak    8681  weight   0.10000E+01  volume   0.28506E+03  ppm1    8.169  ppm2   1.250
ASSI ( 8691)
   ( ( segid *BrD * and resid 111 and name HN   ) )
   (   segid *BrD * and resid 116 and name HD1%)
     3.400   2.900    2.100   peak    8691  weight   0.10000E+01  volume   0.11425E+03  ppm1    8.168  ppm2   1.396
ASSI ( 8711)
   ( ( segid *BrD * and resid 58 and name HN   ) )
   ( ( segid *BrD * and resid 37 and name HD1  ) )
     3.700   3.400    1.800   peak    8711  weight   0.10000E+01  volume   0.73156E+02  ppm1   10.051  ppm2   4.255
ASSI ( 8721)
   ( ( segid *BrD * and resid 58 and name HN   ) )
   ( ( segid *BrD * and resid 59 and name HG2  ) )
     5.500   5.500    0.000   peak    8721  weight   0.10000E+01  volume   0.48442E+00  ppm1   10.051  ppm2   3.087
ASSI ( 8801)
   ( ( segid *BrD * and resid 58 and name HN   ) )
   (   segid *BrD * and resid 54 and name HE % )
     4.600   4.600    0.900   peak    8801  weight   0.10000E+01  volume   0.21191E+02  ppm1   10.050  ppm2   2.534
ASSI ( 8791)
   ( ( segid *BrD * and resid 112 and name HN   ) )
   (   segid *BrD * and resid 110 and name HG2%)
     3.800   3.600    1.700   peak    8971  weight   0.10000E+01  volume   0.60824E+02  ppm1    4.669  ppm2   1.263
ASSI ( 8991)
   ( ( segid *BrD * and resid 105 and name HN   ) )
   ( ( segid *BrD * and resid 106 and name HB1  ) )
     3.500   3.100    2.000   peak    8991  weight   0.10000E+01  volume   0.10888E+03  ppm1    8.487  ppm2   3.870
ASSI ( 9041)
   ( ( segid *BrD * and resid 105 and name HN   ) )
   (   segid *BrD * and resid 102 and name HD2%)
     3.700   3.400    1.800   peak    9041  weight   0.10000E+01  volume   0.76403E+02  ppm1    8.486  ppm2   1.320
OR ( 9041)
   ( ( segid *BrD * and resid 105 and name HN   ) )
   (   segid *BrD * and resid 102 and name HD1%)
ASSI ( 9051)
   ( ( segid *BrD * and resid 105 and name HN   ) )
   (   segid *BrD * and resid 101 and name HG2%)
     3.900   3.800    1.600   peak    9051  weight   0.10000E+01  volume   0.50603E+02  ppm1    8.486  ppm2   1.602
ASSI ( 9131)
   ( ( segid *BrD * and resid 21 and name HN   ) )
   ( ( segid *BrD * and resid 21 and name HG12) )
     3.200   2.600    2.300   peak    9131  weight   0.10000E+01  volume   0.17190E+03  ppm1    8.574  ppm2   1.620
OR ( 9131)
   ( ( segid *BrD * and resid 21 and name HN   ) )
   (   segid *BrD * and resid 21 and name HG2%)
ASSI ( 9211)
   ( ( segid *BrD * and resid 106 and name HN   ) )
   (   segid *BrD * and resid 102 and name HD2%)
     3.800   3.600    1.700   peak    9211  weight   0.10000E+01  volume   0.58744E+02  ppm1    9.740  ppm2   1.314
```

TABLE 2-continued

Unambigous NOE-derived Inter-proton Distance Restraints

```
ASSI ( 9221)
  ( ( segid *BrD * and resid 104 and name HN   ) )
  ( ( segid *BrD * and resid 82 and name HE %  ) )
     4.600  4.600   0.900  peak    9221  weight   0.10000E+01  volume   0.19539E+02  ppm1     9.740  ppm2    7.033
OR ( 9221)
  ( ( segid *BrD * and resid 106 and name HN   ) )
  ( ( segid *BrD * and resid 82 and name HZ    ) )
ASSI ( 9231)
  ( ( segid *BrD * and resid 84 and name HN    ) )
  ( ( segid *BrD * and resid 80 and name HA    ) )
     2.400  1.400   1.400  peak    9231  weight   0.10000E+01  volume   0.97923E+03  ppm1     9.464  ppm2    4.674
ASSI ( 9261)
  ( ( segid *BrD * and resid 84 and name HN    ) )
  (   segid *BrD * and resid 50 and name HD1%)
     4.700  4.700   0.800  peak    9261  weight   0.10000E+01  volume   0.17291E+02  ppm1     9.463  ppm2    1.136
ASSI ( 9271)
  ( ( segid *BrD * and resid 84 and name HN    ) )
  (   segid *BrD * and resid 50 and name HG2%)
     4.800  4.800   0.700  peak    9271  weight   0.10000E+01  volume   0.16063E+02  ppm1     9.464  ppm2    0.994
ASSI ( 9381)
  ( ( segid *BrD * and resid 63 and name HN    ) )
  ( ( segid *BrD * and resid 63 and name HB1   ) )
     2.800  2.000   2.000  peak    9381  weight   0.10000E+01  volume   0.41354E+03  ppm1     9.456  ppm2    2.904
ASSI ( 9411)
  ( ( segid *BrD * and resid 22 and name HN    ) )
  (   segid *BrD * and resid 25 and name HG1%)
     3.600  3.200   1.900  peak    9411  weight   0.10000E+01  volume   0.92991E+02  ppm1     9.456  ppm2    1.979
ASSI ( 9421)
  ( ( segid *BrD * and resid 22 and name HN    ) )
  (   segid *BrD * and resid 21 and name HD1%)
     3.700  3.400   1.800  peak    9421  weight   0.10000E+01  volume   0.76602E+02  ppm1     9.456  ppm2    1.228
ASSI ( 9431)
  ( ( segid *BrD * and resid 63 and name HN    ) )
  (   segid *BrD * and resid 68 and name HD %  )
     3.800  2.600   1.700  peak    9431  weight   0.10000E+01  volume   0.63643E+02  ppm1     9.456  ppm2    7.806
ASSI ( 9481)
  ( ( segid *BrD * and resid 109 and name HN   ) )
  ( ( segid *BrD * and resid 109 and name HD1  ) )
     3.100  2.400   2.400  peak    9481  weight   0.10000E+01  volume   0.19915E+03  ppm1     8.556  ppm2    2.031
ASSI ( 9521)
  ( ( segid *BrD * and resid 103 and name HN   ) )
  (   segid *BrD * and resid 82 and name HE %  )
     3.300  2.700   2.200  peak    9521  weight   0.10000E+01  volume   0.14888E+03  ppm1     8.695  ppm2    7.050
OR ( 9521)
  ( ( segid *BrD * and resid 103 and name HN   ) )
  ( ( segid *BrD * and resid 82 and name HZ    ) )
ASSI ( 9541)
  ( ( segid *BrD * and resid 112 and name HN   ) )
  ( ( segid *BrD * and resid 111 and name HA   ) )
     4.900  4.900   0.600  peak    9541  weight   0.10000E+01  volume   0.13131E+02  ppm1     8.696  ppm2    4.682
ASSI ( 9611)
  ( ( segid *BrD * and resid 99 and name HN    ) )
  (   segid *BrD * and resid 34 and name HE %  )
     3.500  3.100   2.000  peak    9611  weight   0.10000E+01  volume   0.10701E+03  ppm1     8.936  ppm2    7.772
ASSI ( 9671)
  ( ( segid *BrD * and resid 99 and name HN    ) )
  ( ( segid *BrD * and resid 30 and name HB2   ) )
     4.300  4.300   1.200  peak    9671  weight   0.10000E+01  volume   0.29603E+02  ppm1     8.936  ppm2    4.568
ASSI ( 9681)
  ( ( segid *BrD * and resid 18 and name HN    ) )
  (   segid *BrD * and resid 14 and name HD2%)
     3.600  3.200   1.900  peak    9681  weight   0.10000E+01  volume   0.80801E+02  ppm1     9.074  ppm2    1.390
OR ( 9681)
  ( ( segid *BrD * and resid 18 and name HN    ) )
  (   segid *BrD * and resid 14 and name HD1%)
ASSI ( 9751)
  ( ( segid *BrD * and resid 64 and name HN    ) )
  ( ( segid *BrD * and resid 63 and name HB2   ) )
     2.400  1.400   1.400  peak    9751  weight   0.10000E+01  volume   0.10265E+04  ppm1     8.585  ppm2    2.532
ASSI ( 9761)
  ( ( segid *BrD * and resid 64 and name HN    ) )
  (   segid *BrD * and resid 63 and name HD2%)
     3.300  2.700   2.200  peak    9761  weight   0.10000E+01  volume   0.14024E+03  ppm1     8.585  ppm2    1.489
ASSI ( 9811)
  ( ( segid *BrD * and resid 17 and name HN    ) )
  ( ( segid *BrD * and resid 15 and name HB1   ) )
     4.300  4.300   1.200  peak    9811  weight   0.10000E+01  volume   0.29691E+02  ppm1     8.669  ppm2    3.842
```

TABLE 2-continued

Unambigous NOE-derived Inter-proton Distance Restraints

```
ASSI ( 9851)
  ( ( segid *BrD * and resid 40 and name HN   ) )
  (  segid *BrD * and resid 41 and name HG2%)
     2.500  1.600    1.600 peak    9851 weight    0.10000E+01 volume   0.73405E+03 ppm1    8.669 ppm2    1.866
ASSI ( 9871)
  ( ( segid *BrD * and resid 17 and name HN   ) )
  ( ( segid *BrD * and resid 14 and name HD2%)
     4.000  4.000    1.500 peak    9871 weight    0.10000E+01 volume   0.46134E+02 ppm1    8.668 ppm2    1.379
OR ( 9871)
  ( ( segid *BrD * and resid 17 and name HN   ) )
  (  segid *BrD * and resid 14 and name HD1%)
ASSI ( 9881)
  ( ( segid *BrD * and resid 17 and name HN   ) )
  (  segid *BrD * and resid 18 and name HD2%)
     4.600  4.600    0.900 peak    9881 weight    0.10000E+01 volume   0.20602E+02 ppm1    8.669 ppm2    0.394
ASSI ( 9911)
  ( ( segid *BrD * and resid 73 and name HN   ) )
  ( ( segid *BrD * and resid 73 and name HB2  ) )
     3.000  2.200    2.200 peak    9911 weight    0.10000E+01 volume   0.24469E+03 ppm1    8.858 ppm2    2.503
ASSI ( 9951)
  ( ( segid *BrD * and resid 12 and name HN   ) )
  ( ( segid *BrD * and resid 13 and name HA   ) )
     3.800  3.600    1.700 peak    9951 weight    0.10000E+01 volume   0.59337E+02 ppm1    9.021 ppm2    4.770
ASSI ( 9971)
  ( ( segid *BrD * and resid 12 and name HN   ) )
  ( ( segid *BrD * and resid 15 and name HB2  ) )
     4.100  4.100    1.400 peak    9971 weight    0.10000E+01 volume   0.38398E+02 ppm1    9.021 ppm2    3.618
ASSI ( 9981)
  ( ( segid *BrD * and resid 12 and name HN   ) )
  ( ( segid *BrD * and resid 11 and name HB1  ) )
     3.200  2.600    2.300 peak    9981 weight    0.10000E+01 volume   0.16530E+03 ppm1    9.021 ppm2    2.971
ASSI ( 9991)
  ( ( segid *BrD * and resid 12 and name HN   ) )
  ( ( segid *BrD * and resid 11 and name HB2  ) )
     3.300  2.700    2.200 peak    9991 weight    0.10000E+01 volume   0.13633E+03 ppm1    9.022 ppm2    2.611
OR ( 9991)
  ( ( segid *BrD * and resid 12 and name HN   ) )
  ( ( segid *BrD * and resid 11 and name HG1  ) )
ASSI (10021)
  ( ( segid *BrD * and resid 25 and name HN   ) )
  ( ( segid *BrD * and resid 26 and name HD1  ) )
     3.700  3.400    1.800 peak   10021 weight    0.10000E+01 volume   0.73669E+02 ppm1    9.134 ppm2    2.092
ASSI (10031)
  ( ( segid *BrD * and resid 25 and name HN   ) )
  (  segid *BrD * and resid 102 and name HD1%)
     3.800  3.600    1.700 peak   10031 weight    0.10000E+01 volume   0.60868E+02 ppm1    9.133 ppm2    1.295
OR (10031)
  ( ( segid *BrD * and resid 25 and name HN   ) )
  (  segid *BrD * and resid 102 and name HD2%)
ASSI (10061)
  ( ( segid *BrD * and resid 24 and name HN   ) )
  (  segid *BrD * and resid 25 and name HG1%)
     3.600  3.200    1.900 peak   10061 weight    0.10000E+01 volume   0.91063E+02 ppm1    8.657 ppm2    1.798
ASSI (10191)
  ( ( segid *BrD * and resid 16 and name HN   ) )
  ( ( segid *BrD * and resid 18 and name HG   ) )
     3.700  3.400    1.800 peak   10191 weight    0.10000E+01 volume   0.73953E+02 ppm1    8.792 ppm2    2.295
ASSI (10221)
  ( ( segid *BrD * and resid 76 and name HN   ) )
  ( ( segid *BrD * and resid 74 and name HN   ) )
     3.300  2.700    2.200 peak   10221 weight    0.10000E+01 volume   0.15827E+03 ppm1    8.611 ppm2    7.532
ASSI (10251)
  ( ( segid *BrD * and resid 75 and name HN   ) )
  (  segid *BrD * and resid 18 and name HD1%)
     4.200  4.200    1.300 peak   10251 weight    0.10000E+01 volume   0.32785E+02 ppm1    9.105 ppm2    1.056
ASSI (10261)
  ( ( segid *BrD * and resid 76 and name HN   ) )
  (  segid *BrD * and resid 75 and name HB % )
     3.400  2.900    2.100 peak   10261 weight    0.10000E+01 volume   0.13102E+03 ppm1    9.106 ppm2    2.099
ASSI (10291)
  ( ( segid *BrD * and resid 75 and name HN   ) )
  (  segid *BrD * and resid 75 and name HE % )
     3.800  3.600    1.700 peak   10291 weight    0.10000E+01 volume   0.67546E+02 ppm1    9.108 ppm2    2.654
ASSI (10301)
  ( ( segid *BrD * and resid 75 and name HN   ) )
  (  segid *BrD * and resid 18 and name HD2%)
     3.900  3.800    1.600 peak   10301 weight    0.10000E+01 volume   0.57563E+02 ppm1    9.106 ppm2    0.429
```

TABLE 2-continued

Unambigous NOE-derived Inter-proton Distance Restraints

ASSI (10351)
 ( ( segid *BrD * and resid 95 and name HN   ) )
 ( ( segid *BrD * and resid 93 and name HB1  ) )
   2.900  2.100   2.100 peak   10351 weight    0.10000E+01 volume   0.35043E+03 ppm1   8.669 ppm2   5.016
ASSI (10401)
 ( ( segid *BrD * and resid 55 and name HN   ) )
 ( ( segid *BrD * and resid 37 and name HB2  ) )
   3.600  3.200   1.900 peak   10401 weight    0.10000E+01 volume   0.94850E+02 ppm1   7.996 ppm2   2.295
ASSI (10421)
 ( ( segid *BrD * and resid 55 and name HN   ) )
 ( ( segid *BrD * and resid 37 and name HG2  ) )
   2.700  1.800   1.800 peak   10421 weight    0.10000E+01 volume   0.46013E+03 ppm1   7.996 ppm2   2.578
ASSI (10441)
 ( ( segid *BrD * and resid 96 and name HN   ) )
 ( ( segid *BrD * and resid 95 and name HB1  ) )
   3.300  2.700   2.200 peak   10441 weight    0.10000E+01 volume   0.14200E+03 ppm1   7.988 ppm2   3.587
ASSI (10571)
 ( ( segid *BrD * and resid 80 and name HN   ) )
 ( ( segid *BrD * and resid 79 and name HG1  ) )
   2.400  1.400   1.400 peak   10571 weight    0.10000E+01 volume   0.10119E+04 ppm1   7.975 ppm2   3.105
ASSI (10581)
 ( ( segid *BrD * and resid 78 and name HN   ) )
 ( ( segid *BrD * and resid 77 and name HB1  ) )
   3.000  2.200   2.200 peak   10581 weight    0.10000E+01 volume   0.26376E+03 ppm1   7.974 ppm2   3.301
ASSI (10591)
 ( ( segid *BrD * and resid 55 and name HN   ) )
 ( ( segid *BrD * and resid 58 and name HN   ) )
   4.100  4.100   1.400 peak   10591 weight    0.10000E+01 volume   0.42990E+02 ppm1   7.972 ppm2  10.062
ASSI (10621)
 ( ( segid *BrD * and resid 56 and name HN   ) )
 ( ( segid *BrD * and resid 34 and name HB1  ) )
   3.700  3.400   1.800 peak   10621 weight    0.10000E+01 volume   0.69879E+02 ppm1   9.674 ppm2   4.100
ASSI (10641)
 ( ( segid *BrD * and resid 82 and name HN   ) )
 ( ( segid *BrD * and resid 80 and name HB1  ) )
   4.200  4.200   1.300 peak   10641 weight    0.10000E+01 volume   0.33240E+02 ppm1   6.981 ppm2   2.603
ASSI (10651)
 ( ( segid *BrD * and resid 82 and name HN   ) )
 ( ( segid *BrD * and resid 84 and name HB2  ) )
   4.300  4.300   1.200 peak   10651 weight    0.10000E+01 volume   0.31962E+02 ppm1   6.981 ppm2   3.230
ASSI (10661)
 ( ( segid *BrD * and resid 82 and name HN   ) )
 (   segid *BrD * and resid 99 and name HB %  )
   4.100  4.100   1.400 peak   10661 weight    0.10000E+01 volume   0.41756E+02 ppm1   6.981 ppm2   2.202
ASSI (10721)
 ( ( segid *BrD * and resid 81 and name HN   ) )
 ( ( segid *BrD * and resid 77 and name HB1  ) )
   3.900  3.800   1.600 peak   10721 weight    0.10000E+01 volume   0.54085E+02 ppm1   7.641 ppm2   3.310
ASSI (10751)
 ( ( segid *BrD * and resid 80 and name HN   ) )
 ( ( segid *BrD * and resid 77 and name HB1  ) )
   4.400  4.400   1.100 peak   10751 weight    0.10000E+01 volume   0.26321E+02 ppm1   8.005 ppm2   3.322
ASSI (10771)
 ( ( segid *BrD * and resid 80 and name HN   ) )
 ( ( segid *BrD * and resid 81 and name HB   ) )
   3.700  3.400   1.800 peak   10771 weight    0.10000E+01 volume   0.71103E+02 ppm1   8.006 ppm2   2.049
ASSI (10841)
 ( ( segid *BrD * and resid 79 and name HN   ) )
 (   segid *BrD * and resid 76 and name HB %  )
   3.500  3.100   2.000 peak   10841 weight    0.10000E+01 volume   0.10580E+03 ppm1   8.681 ppm2   2.096
ASSI (10881)
 ( ( segid *BrD * and resid 85 and name HN   ) )
 (   segid *BrD * and resid 99 and name HB %  )
   3.900  3.800   1.600 peak   10881 weight    0.10000E+01 volume   0.56660E+02 ppm1   7.515 ppm2   2.208
ASSI (10891)
 ( ( segid *BrD * and resid 85 and name HN   ) )
 (   segid *BrD * and resid 81 and name HG2%)
   4.100  4.100   1.400 peak   10891 weight    0.10000E+01 volume   0.42261E+02 ppm1   7.522 ppm2   0.765
ASSI (10921)
 ( ( segid *BrD * and resid 86 and name HN   ) )
 ( ( segid *BrD * and resid 87 and name HB1  ) )
   3.800  3.600   1.700 peak   10921 weight    0.10000E+01 volume   0.59880E+02 ppm1   8.423 ppm2   2.779
OR (10921)
 ( ( segid *BrD * and resid 86 and name HN   ) )
 ( ( segid *BrD * and resid 87 and name HG2  ) )

TABLE 2-continued

Unambigous NOE-derived Inter-proton Distance Restraints

```
ASSI (10931)
   ( ( segid *BrD * and resid 86 and name HN    ) )
   ( ( segid *BrD * and resid 87 and name HB2 ) )
      3.800   3.600    1.700 peak   10931 weight    0.10000E+01 volume    0.59561E+02 ppm1    8.423 ppm2    2.577
ASSI (10941)
   ( ( segid *BrD * and resid 86 and name HN    ) )
   (   segid *BrD * and resid 99 and name HB % )
      3.600   3.200    1.900 peak   10941 weight    0.10000E+01 volume    0.93545E+02 ppm1    8.423 ppm2    2.210
ASSI (11001)
   ( ( segid *BrD * and resid 87 and name HN    ) )
   (   segid *BrD * and resid 50 and name HD1%)
      3.800   3.600    1.700 peak   11001 weight    0.10000E+01 volume    0.61476E+02 ppm1    8.570 ppm2    1.148
ASSI (11021)
   ( ( segid *BrD * and resid 87 and name HN    ) )
   ( ( segid *BrD * and resid 87 and name HG2 ) )
      4.500   4.500    1.000 peak   11021 weight    0.10000E+01 volume    0.22088E+02 ppm1    8.571 ppm2    0.780
ASSI (11031)
   ( ( segid *BrD * and resid 88 and name HN    ) )
   (   segid *BrD * and resid 50 and name HD1%)
      3.600   3.200    1.900 peak   11031 weight    0.10000E+01 volume    0.90228E+02 ppm1    8.354 ppm2    1.146
ASSI (11041)
   ( ( segid *BrD * and resid 88 and name HN    ) )
   ( ( segid *BrD * and resid 84 and name HB2 ) )
      4.000   4.000    1.500 peak   11041 weight    0.10000E+01 volume    0.46286E+02 ppm1    8.354 ppm2    3.299
ASSI (11051)
   ( ( segid *BrD * and resid 88 and name HN    ) )
   ( ( segid *BrD * and resid 87 and name HG1 ) )
      4.600   4.600    0.900 peak   11051 weight    0.10000E+01 volume    0.19886E+02 ppm1    8.354 ppm2    3.018
ASSI (11161)
   ( ( segid *BrD * and resid 93 and name HN    ) )
   ( ( segid *BrD * and resid 91 and name HD2 ) )
      3.700   3.400    1.800 peak   11161 weight    0.10000E+01 volume    0.78354E+02 ppm1    8.714 ppm2    4.410
ASSI (11171)
   ( ( segid *BrD * and resid 93 and name HN    ) )
   ( ( segid *BrD * and resid 96 and name HB1 ) )
      3.300   2.700    2.200 peak   11171 weight    0.10000E+01 volume    0.14983E+03 ppm1    8.714 ppm2    4.004
ASSI (11191)
   ( ( segid *BrD * and resid 30 and name HN    ) )
   ( ( segid *BrD * and resid 28 and name HB2 ) )
      4.400   4.400    1.100 peak   11191 weight    0.10000E+01 volume    0.26154E+02 ppm1   12.276 ppm2    3.392
ASSI (11201)
   ( ( segid *BrD * and resid 30 and name HN    ) )
   ( ( segid *BrD * and resid 28 and name HB1 ) )
      3.300   2.700    2.200 peak   11201 weight    0.10000E+01 volume    0.15024E+03 ppm1   12.275 ppm2    3.594
ASSI (11211)
   ( ( segid *BrD * and resid 30 and name HN    ) )
   ( ( segid *BrD * and resid 32 and name HN    ) )
      3.600   3.200    1.900 peak   11211 weight    0.10000E+01 volume    0.82022E+02 ppm1   12.276 ppm2    7.741
ASSI (11241)
   ( ( segid *BrD * and resid 31 and name HN    ) )
   ( ( segid *BrD * and resid 28 and name HB1 ) )
      3.600   3.200    1.900 peak   11241 weight    0.10000E+01 volume    0.94685E+02 ppm1    8.480 ppm2    3.594
ASSI (11251)
   ( ( segid *BrD * and resid 31 and name HN    ) )
   ( ( segid *BrD * and resid 28 and name HB2 ) )
      3.800   3.600    1.700 peak   11251 weight    0.10000E+01 volume    0.64760E+02 ppm1    8.481 ppm2    3.389
ASSI (11361)
   ( ( segid *BrD * and resid 32 and name HN    ) )
   (   segid *BrD * and resid 102 and name HD1%)
      4.500   4.500    1.000 peak   11361 weight    0.10000E+01 volume    0.23592E+02 ppm1    7.738 ppm2    1.310
ASSI (11391)
   ( ( segid *BrD * and resid 34 and name HN    ) )
   ( ( segid *BrD * and resid 35 and name HG1 ) )
      3.200   2.600    2.300 peak   11391 weight    0.10000E+01 volume    0.18521E+03 ppm1    8.182 ppm2    3.447
ASSI (11431)
   ( ( segid *BrD * and resid 34 and name HN    ) )
   (   segid *BrD * and resid 31 and name HB % )
      2.900   2.100    2.100 peak   11431 weight    0.10000E+01 volume    0.29794E+03 ppm1    8.179 ppm2    2.301
ASSI (11441)
   ( ( segid *BrD * and resid 34 and name HN    ) )
   (   segid *BrD * and resid 56 and name HD1%)
      3.400   2.900    2.100 peak   11441 weight    0.10000E+01 volume    0.12961E+03 ppm1    8.184 ppm2    1.527
ASSI (11451)
   ( ( segid *BrD * and resid 34 and name HN    ) )
   (   segid *BrD * and resid 102 and name HD1%)
      3.600   3.200    1.900 peak   11451 weight    0.10000E+01 volume    0.84106E+02 ppm1    8.185 ppm2    1.305
```

TABLE 2-continued

Unambigous NOE-derived Inter-proton Distance Restraints

```
ASSI (11521)
    ( ( segid *BrD * and resid 35 and name HN   ) )
    (  segid *BrD * and resid 56 and name HD1%)
       4.500  4.500   1.000 peak  11521 weight    0.10000E+01 volume    0.22012E+02 ppm1    7.734 ppm2   1.553
ASSI (11561)
    ( ( segid *BrD * and resid 36 and name HN   ) )
    ( ( segid *BrD * and resid 57 and name HB1  ) )
       3.400  2.900   2.100 peak  11561 weight    0.10000E+01 volume    0.11642E+03 ppm1    8.308 ppm2   2.953
ASSI (11571)
    ( ( segid *BrD * and resid 66 and name HN   ) )
    (  segid *BrD * and resid 63 and name HD1%)
       4.200  4.200   1.300 peak  11571 weight    0.10000E+01 volume    0.34773E+02 ppm1    8.763 ppm2   1.640
ASSI (11601)
    ( ( segid *BrD * and resid 67 and name HN   ) )
    (  segid *BrD * and resid 68 and name HB %  )
       4.400  4.400   1.100 peak  11601 weight    0.10000E+01 volume    0.26280E+02 ppm1    8.832 ppm2   7.780
ASSI (11651)
    ( ( segid *BrD * and resid 68 and name HN   ) )
    ( ( segid *BrD * and resid 69 and name HB   ) )
       3.700  3.400   1.800 peak  11651 weight    0.10000E+01 volume    0.74566E+02 ppm1    8.626 ppm2   2.947
ASSI (11661)
    ( ( segid *BrD * and resid 68 and name HN   ) )
    (  segid *BrD * and resid 18 and name HD1%)
       5.500  5.500   0.000 peak  11661 weight    0.10000E+01 volume    0.40212E+01 ppm1    8.626 ppm2   1.090
ASSI (11731)
    ( ( segid *BrD * and resid 70 and name HN   ) )
    ( ( segid *BrD * and resid 68 and name HB1  ) )
       3.600  3.200   1.900 peak  11731 weight    0.10000E+01 volume    0.91804E+02 ppm1    8.040 ppm2   3.689
ASSI (11741)
    ( ( segid *BrD * and resid 70 and name HN   ) )
    ( ( segid *BrD * and resid 74 and name HB1  ) )
       3.400  2.900   2.100 peak  11741 weight    0.10000E+01 volume    0.13333E+03 ppm1    8.039 ppm2   3.544
ASSI (11771)
    ( ( segid *BrD * and resid 70 and name HN   ) )
    ( ( segid *BrD * and resid 73 and name HB2  ) )
       3.700  3.400   1.800 peak  11771 weight    0.10000E+01 volume    0.79558E+02 ppm1    8.040 ppm2   2.491
ASSI (11841)
    ( ( segid *BrD * and resid 73 and name HN   ) )
    ( ( segid *BrD * and resid 70 and name HB2  ) )
       3.200  2.600   2.300 peak  11841 weight    0.10000E+01 volume    0.16883E+03 ppm1    8.047 ppm2   4.361
ASSI (11891)
    ( ( segid *BrD * and resid 74 and name HN   ) )
    ( ( segid *BrD * and resid 75 and name HB2  ) )
       4.700  4.700   0.800 peak  11891 weight    0.10000E+01 volume    0.18157E+02 ppm1    7.536 ppm2   2.851
ASSI (11911)
    ( ( segid *BrD * and resid 74 and name HN   ) )
    (  segid *BrD * and resid 76 and name HB %  )
       4.400  4.400   1.100 peak  11911 weight    0.10000E+01 volume    0.27875E+02 ppm1    7.536 ppm2   2.088
ASSI (12031)
    ( ( segid *BrD * and resid 99 and name HN   ) )
    ( ( segid *BrD * and resid 100 and name HB2 ) )
       3.800  3.600   1.7   peak  12031 weight    0.10000E+01 volume    0.61845E+02 ppm1    8.936 ppm2   2.439
ASSI (12041)
    ( ( segid *BrD * and resid 99 and name HN   ) )
    ( ( segid *BrD * and resid 97 and name HB1  ) )
       3.400  2.900   2.100 peak  12041 weight    0.10000E+01 volume    0.12562E+03 ppm1    8.936 ppm2   2.721
ASSI (12061)
    ( ( segid *BrD * and resid 100 and name HN  ) )
    ( ( segid *BrD * and resid 101 and name HA  ) )
       4.000  4.000   1.500 peak  12061 weight    0.10000E+01 volume    0.47923E+02 ppm1    8.669 ppm2   4.289
ASSI (12091)
    ( ( segid *BrD * and resid 100 and name HN  ) )
    ( ( segid *BrD * and resid 101 and name HG11) )
       4.100  4.100   1.400 peak  12091 weight    0.10000E+01 volume    0.39843E+02 ppm1    8.669 ppm2   2.519
OR (12091)
    ( ( segid *BrD * and resid 100 and name HN  ) )
    ( ( segid *BrD * and resid 101 and name HB  ) )
ASSI (12151)
    ( ( segid *BrD * and resid 101 and name HN  ) )
    ( ( segid *BrD * and resid 104 and name HD1 ) )
       3.500  3.100   2.000 peak  12151 weight    0.10000E+01 volume    0.11138E+03 ppm1    8.513 ppm2   2.282
ASSI (12221)
    ( ( segid *BrD * and resid 107 and name HN  ) )
    (  segid *BrD * and resid 106 and name HD %  )
       3.300  2.700   2.200 peak  12221 weight    0.10000E+01 volume    0.14273E+03 ppm1    8.981 ppm2   7.515
```

TABLE 2-continued

Unambigous NOE-derived Inter-proton Distance Restraints

```
ASSI (12241)
   ( ( segid *BrD * and resid 107 and name HN   ) )
   ( ( segid *BrD * and resid 103 and name HG2 ) )
      3.400  2.900   2.100  peak   12241  weight   0.10000E+01  volume   0.11969E+03  ppm1   8.980  ppm2   2.547
ASSI (12271)
   ( ( segid *BrD * and resid 107 and name HN   ) )
   ( ( segid *BrD * and resid 110 and name HG12) )
      4.000  4.000   1.500  peak   12271  weight   0.10000E+01  volume   0.48486E+02  ppm1   8.980  ppm2   1.678
ASSI (12291)
   ( ( segid *BrD * and resid 108 and name HN   ) )
   ( ( segid *BrD * and resid 109 and name HB2 ) )
      5.500  5.500   0.000  peak   12291  weight   0.10000E+01  volume   0.20202E+00  ppm1   8.522  ppm2   2.195
ASSI (12411)
   ( ( segid *BrD * and resid 113 and name HN   ) )
   (   segid *BrD * and resid 17 and name HG2%)
      4.300  4.300   1.200  peak   12411  weight   0.10000E+01  volume   0.28750E+02  ppm1   8.218  ppm2   1.728
ASSI (12431)
   ( ( segid *BrD * and resid 113 and name HN   ) )
   (   segid *BrD * and resid 110 and name HG2%)
      3.400  2.900   2.100  peak   12431  weight   0.10000E+01  volume   0.12771E+03  ppm1   8.218  ppm2   1.275
ASSI (12441)
   ( ( segid *BrD * and resid 115 and name HN   ) )
   (   segid *BrD * and resid 113 and name HB % )
      3.400  2.900   2.100  peak   12441  weight   0.10000E+01  volume   0.11633E+03  ppm1   8.355  ppm2   1.969
ASSI (12451)
   ( ( segid *BrD * and resid 115 and name HN   ) )
   ( ( segid *BrD * and resid 116 and name HG12) )
      5.500  5.500   0.000  peak   12451  weight   0.10000E+01  volume   0.47664E+01  ppm1   8.355  ppm2   1.558
ASSI (12461)
   ( ( segid *BrD * and resid 115 and name HN   ) )
   (   segid *BrD * and resid 110 and name HD1%)
      4.400  4.400   1.100  peak   12461  weight   0.10000E+01  volume   0.26420E+02  ppm1   8.356  ppm2   1.163
ASSI (12471)
   ( ( segid *BrD * and resid 115 and name HN   ) )
   ( ( segid *BrD * and resid 110 and name HB   ) )
      3.700  3.400   1.800  peak   12471  weight   0.10000E+01  volume   0.76081E+02  ppm1   8.355  ppm2   2.346
ASSI (12481)
   ( ( segid *BrD * and resid 117 and name HN   ) )
   ( ( segid *BrD * and resid 116 and name HG12) )
      4.700  4.700   0.800  peak   12481  weight   0.10000E+01  volume   0.17262E+02  ppm1   8.883  ppm2   1.544
ASSI (12491)
   ( ( segid *BrD * and resid 116 and name HN   ) )
   (   segid *BrD * and resid 110 and name HG2%)
      3.200  2.600   2.300  peak   12491  weight   0.10000E+01  volume   0.16590E+03  ppm1   8.083  ppm2   1.277
ASSI (12521)
   ( ( segid *BrD * and resid 116 and name HN   ) )
   (   segid *BrD * and resid 110 and name HD1%)
      3.200  2.600   2.300  peak   12521  weight   0.10000E+01  volume   0.17496E+03  ppm1   8.086  ppm2   1.156
ASSI (12591)
   ( ( segid *BrD * and resid 47 and name HN   ) )
   ( ( segid *BrD * and resid 48 and name HG2 ) )
      4.200  4.200   1.300  peak   12591  weight   0.10000E+01  volume   0.33544E+02  ppm1   8.832  ppm2   2.861
ASSI (12611)
   ( ( segid *BrD * and resid 47 and name HN   ) )
   (   segid *BrD * and resid 43 and name HB % )
      3.800  3.600   1.700  peak   12611  weight   0.10000E+01  volume   0.60519E+02  ppm1   8.832  ppm2   1.700
ASSI (12621)
   ( ( segid *BrD * and resid 49 and name HN   ) )
   ( ( segid *BrD * and resid 50 and name HB   ) )
      3.600  3.200   1.900  peak   12621  weight   0.10000E+01  volume   0.90984E+02  ppm1   7.762  ppm2   2.797
ASSI (12701)
   ( ( segid *BrD * and resid 52 and name HN   ) )
   ( ( segid *BrD * and resid 53 and name HG1  ) )
      3.900  3.800   1.600  peak   12701  weight   0.10000E+01  volume   0.53690E+02  ppm1   9.004  ppm2   2.820
OR (12701)
   ( ( segid *BrD * and resid 52 and name HN   ) )
   ( ( segid *BrD * and resid 53 and name HB1  ) )
ASSI (12741)
   ( ( segid *BrD * and resid 42 and name HN   ) )
   ( ( segid *BrD * and resid 39 and name HB1  ) )
      3.100  2.400   2.400  peak   12741  weight   0.10000E+01  volume   0.21408E+03  ppm1   7.820  ppm2   2.491
ASSI (12751)
   ( ( segid *BrD * and resid 42 and name HN   ) )
   ( ( segid *BrD * and resid 39 and name HD1  ) )
      3.000  2.200   2.200  peak   12751  weight   0.10000E+01  volume   0.29898E+03  ppm1   7.821  ppm2   2.286
```

TABLE 2-continued

Unambigous NOE-derived Inter-proton Distance Restraints

```
ASSI (12761)
   ( ( segid *BrD * and resid 42 and name HN   ) )
   ( ( segid *BrD * and resid 43 and name HB % )
       3.500  3.100    2.000 peak   12761  weight     0.10000E+01 volume   0.10310E+03 ppm1     7.820 ppm2     1.706
ASSI (12851)
   ( ( segid *BrD * and resid 20 and name HN   ) )
   ( ( segid *BrD * and resid 19 and name HD1  ) )
       3.600  3.200    1.900 peak   12851  weight     0.10000E+01 volume   0.82185E+02 ppm1     8.145 ppm2     2.189
ASSI (12881)
   ( ( segid *BrD * and resid 20 and name HN   ) )
   ( ( segid *BrD * and resid 21 and name HG12) )
       3.900  3.800    1.600 peak   12881  weight     0.10000E+01 volume   0.55288E+02 ppm1     8.147 ppm2     1.639
OR (12881)
   ( ( segid *BrD * and resid 20 and name HN   ) )
   (   segid *BrD * and resid 21 and name HG2%)
ASSI (12891)
   ( ( segid *BrD * and resid 20 and name HN   ) )
   (   segid *BrD * and resid 63 and name HD2%)
       3.500  3.100    2.000 peak   12891  weight     0.10000E+01 volume   0.11141E+03 ppm1     8.146 ppm2     1.480
ASSI (12901)
   ( ( segid *BrD * and resid 20 and name HN   ) )
   (   segid *BrD * and resid 17 and name HG2%)
       3.900  2.800    1.600 peak   12901  weight     0.10000E+01 volume   0.53573E+02 ppm1     8.146 ppm2     1.762
ASSI (12991)
   ( ( segid *BrD * and resid 21 and name HN   ) )
   ( ( segid *BrD * and resid 20 and name HN   ) )
       3.800  3.600    1.700 peak   12991  weight     0.10000E+01 volume   0.61946E+02 ppm1     9.119 ppm2     8.121
ASSI (13021)
   ( ( segid *BrD * and resid 26 and name HN   ) )
   ( ( segid *BrD * and resid 28 and name HB2  ) )
       4.200  4.200    1.300 peak   13021  weight     0.10000E+01 volume   0.33211E+02 ppm1     9.196 ppm2     3.393
ASSI (13031)
   ( ( segid *BrD * and resid 26 and name HN   ) )
   ( ( segid *BrD * and resid 35 and name HG1  ) )
       4.500  4.500    1.000 peak   13031  weight     0.10000E+01 volume   0.21672E+02 ppm1     9.195 ppm2     3.493
ASSI (13041)
   ( ( segid *BrD * and resid 26 and name HN   ) )
   (   segid *BrD * and resid 56 and name HD2%)
       4.100  4.100    1.400 peak   13041  weight     0.10000E+01 volume   0.41596E+02 ppm1     9.196 ppm2     1.250
ASSI (13061)
   ( ( segid *BrD * and resid 27 and name HN   ) )
   ( ( segid *BrD * and resid 26 and name HG1  ) )
       3.800  3.600    1.700 peak   13061  weight     0.10000E+01 volume   0.66585E+02 ppm1     8.169 ppm2     1.596
ASSI (13091)
   ( ( segid *BrD * and resid 27 and name HN   ) )
   (   segid *BrD * and resid 35 and name HE % )
       3.600  3.200   1.900 peak    13091  weight     0.10000E+01 volume   0.88198E+02 ppm1     8.169 ppm2     2.809
ASSI (13111)
   ( ( segid *BrD * and resid 59 and name HN   ) )
   (   segid *BrD * and resid 59 and name HE % )
       3.300  2.700    2.200 peak   13111  weight     0.10000E+01 volume   0.15860E+03 ppm1     8.498 ppm2     1.864
ASSI (13131)
   ( ( segid *BrD * and resid 59 and name HN   ) )
   (   segid *BrD * and resid 56 and name HD2%)
       4.300  4.300    1.200 peak   13131  weight     0.10000E+01 volume   0.28520E+02 ppm1     8.499 ppm2     1.239
ASSI (13161)
   ( ( segid *BrD * and resid 60 and name HN   ) )
   ( ( segid *BrD * and resid 59 and name HG1  ) )
       3.600  3.200    1.900 peak   13161  weight     0.10000E+01 volume   0.93397E+02 ppm1     8.565 ppm2     3.213
ASSI (13221)
   ( ( segid *BrD * and resid 32 and name HE1  ) )
   ( ( segid *BrD * and resid 32 and name HD1  ) )
       2.300  1.300    1.300 peak   13221  weight     0.10000E+01 volume   0.12506E+04 ppm1    11.082 ppm2     8.475
ASSI (13231)
   ( ( segid *BrD * and resid 32 and name HE1  ) )
   ( ( segid *BrD * and resid 32 and name HN   ) )
       3.200  2.600    2.300 peak   13231  weight     0.10000E+01 volume   0.18835E+03 ppm1    11.082 ppm2     7.742
OR (13231)
   ( ( segid *BrD * and resid 32 and name HE1  ) )
   ( ( segid *BrD * and resid 32 and name HH2  ) )
ASSI (13241)
   ( ( segid *BrD * and resid 32 and name HE1  ) )
   ( ( segid *BrD * and resid 32 and name HZ2  ) )
       2.500  1.600    1.600 peak   13241  weight     0.10000E+01 volume   0.70734E+03 ppm1    11.082 ppm2     7.984
ASSI (13251)
   ( ( segid *BrD * and resid 32 and name HE1  ) )
   ( ( segid *BrD * and resid 30 and name HA   ) )
       2.100  2.400    2.400 peak   11251  weight     0.10000E+01 volume   0.22949E+03 ppm1    11.082 ppm2     5.450
```

TABLE 2-continued

Unambigous NOE-derived Inter-proton Distance Restraints

```
ASSI (13301)
    ( ( segid *BrD * and resid 76 and name HN    ) )
    ( ( segid *BrD * and resid 77 and name HA    ) )
       4.200  4.200   1.300  peak   13301  weight   0.10000E+01 volume   0.33586E+02 ppm1    8.610 ppm2    4.967
ASSI (13311)
    ( ( segid *BrD * and resid 76 and name HN    ) )
    ( ( segid *BrD * and resid 77 and name HB1   ) )
       4.100  4.100   1.400  peak   13311  weight   0.10000E+01 volume   0.37785E+02 ppm1    8.613 ppm2    3.344
ASSI (13651)
    ( ( segid *BrD * and resid 56 and name HN    ) )
    (   segid *BrD * and resid 61 and name HG1%)
       4.100  4.100   1.400  peak   13651  weight   0.10000E+01 volume   0.38100E+02 ppm1    9.680 ppm2    1.077
ASSI (13661)
    ( ( segid *BrD * and resid 56 and name HN    ) )
    (   segid *BrD * and resid 61 and name HG2%)
       4.200  4.200   1.300  peak   13661  weight   0.10000E+01 volume   0.37875E+02 ppm1    9.681 ppm2    0.743
ASSI (13681)
    ( ( segid *BrD * and resid 74 and name HN    ) )
    (   segid *BrD * and resid 14 and name HD1%)
       4.700  4.700   0.800  peak   13681  weight   0.10000E+01 volume   0.17399E+02 ppm1    7.536 ppm2    1.405
OR (13681)
    ( ( segid *BrD * and resid 74 and name HN    ) )
    (   segid *BrD * and resid 14 and name HD2%)
ASSI (13721)
    ( ( segid *BrD * and resid 16 and name HN    ) )
    ( ( segid *BrD * and resid 17 and name HB    ) )
       4.400  4.400   1.100  peak   13721  weight   0.10000E+01 volume   0.26713E+02 ppm1    8.794 ppm2    4.874
ASSI (13751)
    ( ( segid *BrD * and resid 74 and name HN    ) )
    ( ( segid *BrD * and resid 68 and name HA    ) )
       5.300  5.300   0.200  peak   13751  weight   0.10000E+01 volume   0.82154E+01 ppm1    7.537 ppm2    5.140
ASSI (13881)
    ( ( segid *BrD * and resid 46 and name HN    ) )
    (   segid *BrD * and resid 38 and name HG1%)
       4.600  4.600   0.900  peak   13881  weight   0.10000E+01 volume   0.18836E+02 ppm1    8.562 ppm2    1.082
ASSI (13891)
    ( ( segid *BrD * and resid 62 and name HN    ) )
    ( ( segid *BrD * and resid 67 and name HB1   ) )
       4.100  4.100   1.400  peak   13891  weight   0.10000E+01 volume   0.40043E+02 ppm1    8.998 ppm2    3.557
ASSI (13931)
    ( ( segid *BrD * and resid 116 and name HN   ) )
    (   segid *BrD * and resid 75 and name HE % )
       5.000  5.000   0.500  peak   13931  weight   0.10000E+01 volume   0.12168E+02 ppm1    8.086 ppm2    2.648
ASSI (13941)
    ( ( segid *BrD * and resid 115 and name HN   ) )
    ( ( segid *BrD * and resid 110 and name HA   ) )
       4.100  4.100   1.400  peak   13941  weight   0.10000E+01 volume   0.38338E+02 ppm1    8.355 ppm2    4.419
ASSI (13951)
    ( ( segid *BrD * and resid 114 and name HN   ) )
    ( ( segid *BrD * and resid 112 and name HN   ) )
       4.000  4.000   1.500  peak   13951  weight   0.10000E+01 volume   0.49230E+02 ppm1    8.375 ppm2    8.642
ASSI (13961)
    ( ( segid *BrD * and resid 114 and name HN   ) )
    ( ( segid *BrD * and resid 112 and name HB1  ) )
       5.200  5.200   0.300  peak   13961  weight   0.10000E+01 volume   0.99997E+01 ppm1    8.377 ppm2    2.665
ASSI (14001)
    ( ( segid *BrD * and resid 108 and name HN   ) )
    ( ( segid *BrD * and resid 106 and name HN   ) )
       4.900  4.900   0.600  peak   14001  weight   0.10000E+01 volume   0.12922E+02 ppm1    8.529 ppm2    9.745
ASSI (14021)
    ( ( segid *BrD * and resid 108 and name HN   ) )
    ( ( segid *BrD * and resid 104 and name HA   ) )
       2.700  1.800   1.800  peak   14021  weight   0.10000E+01 volume   0.54819E+03 ppm1    8.526 ppm2    4.663
ASSI (14031)
    ( ( segid *BrD * and resid 108 and name HN   ) )
    ( ( segid *BrD * and resid 110 and name HG12 ) )
       5.200  5.200   0.300  peak   14031  weight   0.10000E+01 volume   0.95149E+01 ppm1    8.521 ppm2    1.696
ASSI (14051)
    ( ( segid *BrD * and resid 107 and name HN   ) )
    ( ( segid *BrD * and resid 108 and name HA   ) )
       4.500  4.500   1.000  peak   14051  weight   0.10000E+01 volume   0.23253E+02 ppm1    8.980 ppm2    4.798
ASSI (14081)
    ( ( segid *BrD * and resid 106 and name HN   ) )
    (   segid *BrD * and resid 21 and name HG2%)
       4.600  4.600   0.900  peak   14081  weight   0.10000E+01 volume   0.21267E+02 ppm1    9.740 ppm2    1.640
```

TABLE 2-continued

Unambigous NOE-derived Inter-proton Distance Restraints

```
ASSI (14091)
   ( ( segid *BrD * and resid 105 and name HN   ) )
   ( ( segid *BrD * and resid 106 and name HA   ) )
      4.500  4.500   1.000  peak   14091  weight   0.10000E+01  volume   0.22190E+02  ppm1    8.487  ppm2    4.568
ASSI (14101)
   ( ( segid *BrD * and resid 105 and name HN   ) )
   ( ( segid *BrD * and resid 103 and name HB2  ) )
      5.000  5.000   0.500  peak   14101  weight   0.10000E+01  volume   0.11917E+02  ppm1    8.487  ppm2    1.661
ASSI (14181)
   ( ( segid *BrD * and resid 100 and name HN   ) )
   ( ( segid *BrD * and resid 34 and name HZ    ) )
      4.700  4.700   0.800  peak   14181  weight   0.10000E+01  volume   0.18067E+02  ppm1    8.675  ppm2    7.907
ASSI (14211)
   ( ( segid *BrD * and resid 100 and name HN   ) )
   ( ( segid *BrD * and resid 97 and name HB1   ) )
      4.400  4.400   1.100  peak   14211  weight   0.10000E+01  volume   0.25437E+02  ppm1    8.669  ppm2    2.715
ASSI (14231)
   ( ( segid *BrD * and resid 99 and name HN    ) )
   ( ( segid *BrD * and resid 101 and name HN   ) )
      4.300  4.300   1.200  peak   14231  weight   0.10000E+01  volume   0.28380E+02  ppm1    8.936  ppm2    8.500
ASSI (14261)
   ( ( segid *BrD * and resid 99 and name HN    ) )
   ( ( segid *BrD * and resid 33 and name HG1   ) )
      5.500  5.500   0.000  peak   14261  weight   0.10000E+01  volume   0.32802E+01  ppm1    8.936  ppm2    0.866
ASSI (14271)
   ( ( segid *BrD * and resid 98 and name HN    ) )
   ( ( segid *BrD * and resid 101 and name HN   ) )
      4.400  4.400   1.100  peak   14271  weight   0.10000E+01  volume   0.25780E+02  ppm1    9.125  ppm2    8.515
ASSI (14291)
   ( ( segid *BrD * and resid 97 and name HN    ) )
   ( ( segid *BrD * and resid 92 and name HB1   ) )
      5.500  5.500   0.000  peak   14291  weight   0.10000E+01  volume   0.62831E+01  ppm1    8.677  ppm2    5.016
OR (14291)
   ( ( segid *BrD * and resid 97 and name HN    ) )
   ( ( segid *BrD * and resid 93 and name HA    ) )
ASSI (14321)
   ( ( segid *BrD * and resid 95 and name HN    ) )
   ( ( segid *BrD * and resid 32 and name HH2   ) )
      3.700  3.400   1.800  peak   14321  weight   0.10000E+01  volume   0.76926E+02  ppm1    8.669  ppm2    7.739
ASSI (14331)
   ( ( segid *BrD * and resid 93 and name HN    ) )
   ( ( segid *BrD * and resid 96 and name HN    ) )
      4.500  4.500   1.000  peak   14331  weight   0.10000E+01  volume   0.22598E+02  ppm1    8.713  ppm2    7.963
ASSI (14351)
   ( ( segid *BrD * and resid 93 and name HN    ) )
   ( ( segid *BrD * and resid 95 and name HB1   ) )
      4.600  4.600   0.900  peak   14351  weight   0.10000E+01  volume   0.20643E+02  ppm1    8.714  ppm2    3.617
ASSI (14381)
   ( ( segid *BrD * and resid 87 and name HN    ) )
   ( ( segid *BrD * and resid 89 and name HD21  ) )
      3.900  3.600   1.600      peak   14381 weight   0.10000E+01  volume   0.54969E+02  ppm1    8.568  ppm2    8.959
ASSI (14391)
   ( ( segid *BrD * and resid 87 and name HN    ) )
   ( ( segid *BrD * and resid 89 and name HN    ) )
      3.600  3.200   1.900  peak   14391  weight   0.10000E+01  volume   0.81305E+02  ppm1    8.568  ppm2    8.838
ASSI (14431)
   ( ( segid *BrD * and resid 85 and name HN    ) )
   ( ( segid *BrD * and resid 87 and name HN    ) )
      4.100  4.100   1.400  peak   14431  weight   0.10000E+01  volume   0.42435E+02  ppm1    7.516  ppm2    8.557
ASSI (14471)
   ( ( segid *BrD * and resid 82 and name HN    ) )
   ( ( segid *BrD * and resid 80 and name HN    ) )
      4.800  4.800   0.700  peak   14471  weight   0.10000E+01  volume   0.16164E+02  ppm1    6.979  ppm2    7.979
ASSI (14521)
   ( ( segid *BrD * and resid 79 and name HN    ) )
   ( ( segid *BrD * and resid 77 and name HA    ) )
      4.800  4.800   0.700  peak   14521  weight   0.10000E+01  volume   0.15931E+02  ppm1    8.679  ppm2    4.968
ASSI (14531)
   ( ( segid *BrD * and resid 79 and name HN    ) )
   (   segid *BrD * and resid 59 and name HE %  )
      4.000  4.000   1.500  peak   14531  weight   0.10000E+01  volume   0.45701E+02  ppm1    8.680  ppm2    1.876
ASSI (14561)
   ( ( segid *BrD * and resid 76 and name HN    ) )
   ( ( segid *BrD * and resid 74 and name HA    ) )
      4.300  4.300   1.200  peak   14561  weight   0.10000E+01  volume   0.31541E+02  ppm1    8.611  ppm2    4.361
```

TABLE 2-continued

Unambigous NOE-derived Inter-proton Distance Restraints

```
ASSI (14601)
   ( ( segid *BrD * and resid 72 and name HN   ) )
   ( ( segid *BrD * and resid 75 and name HB2 ) )
      4.600   4.600    0.900  peak   14601  weight    0.10000E+01  volume   0.21235E+02  ppm1    8.859  ppm2    2.805
ASSI (14611)
   ( ( segid *BrD * and resid 72 and name HN   ) )
   ( ( segid *BrD * and resid 9 and name HB1  ) )
      3.600   3.200    1.900  peak   14611  weight    0.10000E+01  volume   0.90159E+02  ppm1    8.859  ppm2    2.443
ASSI (14661)
   ( ( segid *BrD * and resid 64 and name HN   ) )
   ( ( segid *BrD * and resid 62 and name HN   ) )
      4.100   4.100    1.400  peak   14661  weight    0.10000E+01  volume   0.40125E+02  ppm1    8.585  ppm2    8.966
ASSI (14681)
   ( ( segid *BrD * and resid 64 and name HN   ) )
   ( ( segid *BrD * and resid 65 and name HB2 ) )
      4.800   4.800    0.700  peak   14681  weight    0.10000E+01  volume   0.16509E+02  ppm1    8.584  ppm2    3.383
ASSI (14711)
   ( ( segid *BrD * and resid 63 and name HN   ) )
   (   segid *BrD * and resid 74 and name HD % )
      4.600   4.600    0.900  peak   14711  weight    0.10000E+01  volume   0.18909E+02  ppm1    9.471  ppm2    7.007
ASSI (14741)
   ( ( segid *BrD * and resid 62 and name HN   ) )
   ( ( segid *BrD * and resid 61 and name HN   ) )
      2.600   1.700    1.700  peak   14741  weight    0.10000E+01  volume   0.63142E+03  ppm1    8.997  ppm2    8.742
ASSI (14771)
   ( ( segid *BrD * and resid 62 and name HN   ) )
   ( ( segid *BrD * and resid 65 and name HB2 ) )
      4.200   4.200    1.300  peak   14771  weight    0.10000E+01  volume   0.33744E+02  ppm1    8.999  ppm2    3.355
ASSI (14841)
   ( ( segid *BrD * and resid 57 and name HN   ) )
   ( ( segid *BrD * and resid 35 and name HA   ) )
      3.200   2.600    2.300  peak   14841  weight    0.10000E+01  volume   0.16187E+03  ppm1    9.359  ppm2    4.904
ASSI (14861)
   ( ( segid *BrD * and resid 55 and name HN   ) )
   ( ( segid *BrD * and resid 59 and name HN   ) )
      3.900   3.800    1.600  peak   14861  weight    0.10000E+01  volume   0.53302E+02  ppm1    7.974  ppm2    8.498
ASSI (14891)
   ( ( segid *BrD * and resid 54 and name HN   ) )
   ( ( segid *BrD * and resid 84 and name HB1 ) )
      4.600   4.600    0.900  peak   14891  weight    0.10000E+01  volume   0.21172E+02  ppm1    9.037  ppm2    3.597
ASSI (14981)
   ( ( segid *BrD * and resid 48 and name HN   ) )
   ( ( segid *BrD * and resid 46 and name HB2 ) )
      4.300   4.300    1.200  peak   14981  weight    0.10000E+01  volume   0.30250E+02  ppm1    8.306  ppm2    3.090
ASSI (14991)
   ( ( segid *BrD * and resid 48 and name HN   ) )
   (   segid *BrD * and resid 49 and name HG1%)
      3.700   3.400    1.800  peak   14991  weight    0.10000E+01  volume   0.71559E+02  ppm1    8.305  ppm2    1.639
ASSI (15001)
   ( ( segid *BrD * and resid 92 and name HN   ) )
   ( ( segid *BrD * and resid 89 and name HD22) )
      4.900   4.900    0.600  peak   15001  weight    0.10000E+01  volume   0.14588E+02  ppm1    8.832  ppm2    8.433
ASSI (15011)
   ( ( segid *BrD * and resid 47 and name HN   ) )
   ( ( segid *BrD * and resid 89 and name HN   ) )
      4.000   4.000    1.500  peak   15011  weight    0.10000E+01  volume   0.44203E+02  ppm1    8.832  ppm2    7.759
ASSI (15041)
   ( ( segid *BrD * and resid 43 and name HN   ) )
   ( ( segid *BrD * and resid 42 and name HG1 ) )
      4.000   4.000    1.500  peak   15041  weight    0.10000E+01  volume   0.44922E+02  ppm1    8.000  ppm2    2.889
ASSI (15071)
   ( ( segid *BrD * and resid 35 and name HN   ) )
   ( ( segid *BrD * and resid 33 and name HA   ) )
      4.300   4.300    1.200  peak   15071  weight    0.10000E+01  volume   0.32086E+02  ppm1    7.735  ppm2    4.346
ASSI (15081)
   ( ( segid *BrD * and resid 35 and name HN   ) )
   ( ( segid *BrD * and resid 34 and name HB1 ) )
      3.800   3.600    1.700  peak   15081  weight    0.10000E+01  volume   0.61308E+02  ppm1    7.734  ppm2    4.079
ASSI (15111)
   ( ( segid *BrD * and resid 34 and name HN   ) )
   (   segid *BrD * and resid 81 and name HG2%)
      4.700   4.700    0.800  peak   15111  weight    0.10000E+01  volume   0.17971E+02  ppm1    8.178  ppm2    0.756
ASSI (15131)
   ( ( segid *BrD * and resid 32 and name HN   ) )
   ( ( segid *BrD * and resid 33 and name HG1 ) )
      5.400   5.400    0.100  peak   15131  weight    0.10000E+01  volume   0.80093E+01  ppm1    7.739  ppm2    0.859
```

TABLE 2-continued

Unambigous NOE-derived Inter-proton Distance Restraints

```
ASSI (15141)
   ( ( segid *BrD * and resid 31 and name HN    ) )
   ( ( segid *BrD * and resid 28 and name HN    ) )
       3.200  2.600   2.300 peak   15141 weight   0.10000E+01 volume   0.16166E+03 ppm1     8.480 ppm2    8.159
OR (15141)
   ( ( segid *BrD * and resid 31 and name HN    ) )
   ( ( segid *BrD * and resid 28 and name HE1   ) )
ASSI (15161)
   ( ( segid *BrD * and resid 30 and name HN    ) )
   (   segid *BrD * and resid 31 and name HB %  )
       3.800  3.600   1.700 peak   15161 weight   0.10000E+01 volume   0.65201E+02 ppm1    12.276 ppm2    2.299
ASSI (15171)
   ( ( segid *BrD * and resid 30 and name HN    ) )
   (   segid *BrD * and resid 102 and name HD1%)
       3.900  3.800   1.600 peak   15171 weight   0.10000E+01 volume   0.51602E+02 ppm1    12.275 ppm2    1.315
ASSI (15191)
   ( ( segid *BrD * and resid 29 and name HN    ) )
   ( ( segid *BrD * and resid 31 and name HN    ) )
       5.000  5.000   0.500 peak   15191 weight   0.10000E+01 volume   0.12673E+02 ppm1     9.152 ppm2    8.470
ASSI (15201)
   ( ( segid *BrD * and resid 29 and name HN    ) )
   ( ( segid *BrD * and resid 30 and name HB1   ) )
       4.300  4.300   1.200 peak   15201 weight   0.10000E+01 volume   0.29023E+02 ppm1     9.151 ppm2    4.941
ASSI (15211)
   ( ( segid *BrD * and resid 29 and name HN    ) )
   (   segid *BrD * and resid 101 and name HD1%)
       5.000  5.000   0.500 peak   15211 weight   0.10000E+01 volume   0.12825E+02 ppm1     9.153 ppm2    1.556
ASSI (15261)
   ( ( segid *BrD * and resid 27 and name HN    ) )
   ( ( segid *BrD * and resid 28 and name HB1   ) )
       4.400  4.400   1.100 peak   15261 weight   0.10000E+01 volume   0.27022E+02 ppm1     8.169 ppm2    3.575
ASSI (15291)
   ( ( segid *BrD * and resid 26 and name HN    ) )
   ( ( segid *BrD * and resid 24 and name HN    ) )
       3.500  3.100   2.000 peak   15291 weight   0.10000E+01 volume   0.10602E+03 ppm1     9.196 ppm2    8.655
ASSI (15311)
   ( ( segid *BrD * and resid 25 and name HN    ) )
   ( ( segid *BrD * and resid 24 and name HE22) )
       4.900  4.900   0.600 peak   15311 weight   0.10000E+01 volume   0.14311E+02 ppm1     9.133 ppm2    7.489
ASSI (15361)
   ( ( segid *BrD * and resid 24 and name HN    ) )
   ( ( segid *BrD * and resid 24 and name HE21) )
       4.000  4.000   1.500 peak   15361 weight   0.10000E+01 volume   0.49074E+02 ppm1     8.659 ppm2    7.616
ASSI (15381)
   ( ( segid *BrD * and resid 19 and name HN    ) )
   (   segid *BrD * and resid 75 and name HE %  )
       5.500  5.500   0.000 peak   15381 weight   0.10000E+01 volume   0.38565E-01 ppm1     9.187 ppm2    2.654
ASSI (15391)
   ( ( segid *BrD * and resid 19 and name HN    ) )
   ( ( segid *BrD * and resid 63 and name HG    ) )
       4.500  4.500   1.000 peak   15391 weight   0.10000E+01 volume   0.24115E+02 ppm1     9.188 ppm2    2.454
ASSI (15401)
   ( ( segid *BrD * and resid 18 and name HN    ) )
   ( ( segid *BrD * and resid 21 and name HN    ) )
       3.900  3.800   1.600 peak   15401 weight   0.10000E+01 volume   0.53379E+02 ppm1     9.072 ppm2    8.558
ASSI (15421)
   ( ( segid *BrD * and resid 17 and name HN    ) )
   ( ( segid *BrD * and resid 16 and name HN    ) )
       2.800  2.000   2.000 peak   15421 weight   0.10000E+01 volume   0.36762E+03 ppm1     8.669 ppm2    6.780
ASSI (15441)
   ( ( segid *BrD * and resid 17 and name HN    ) )
   ( ( segid *BrD * and resid 20 and name HN    ) )
       3.500  3.100   2.000 peak   15441 weight   0.10000E+01 volume   0.95968E+02 ppm1     8.668 ppm2    8.154
ASSI (15481)
   ( ( segid *BrD * and resid 15 and name HN    ) )
   (   segid *BrD * and resid 18 and name HD1%)
       5.500  5.500   0.000 peak   15481 weight   0.10000E+01 volume   0.62753E+01 ppm1     8.599 ppm2    1.069
ASSI (15511)
   ( ( segid *BrD * and resid 12 and name HN    ) )
   ( ( segid *BrD * and resid 10 and name HA    ) )
       3.900  3.800   1.600 peak   15511 weight   0.10000E+01 volume   0.54637E+02 ppm1     9.023 ppm2    6.464
ASSI (15531)
   ( ( segid *BrD * and resid 10 and name HN    ) )
   ( ( segid *BrD * and resid 18 and name HD2   ) )
       5.200  5.200   0.300 peak   15531 weight   0.10000E+01 volume   0.99597E+01 ppm1     8.885 ppm2    4.288
```

TABLE 2-continued

Unambigous NOE-derived Inter-proton Distance Restraints

```
ASSI (15551)
   ( ( segid *BrD * and resid 7 and name HN   ) )
   ( ( segid *BrD * and resid 8 and name HD2  ) )
     4.900   4.900   0.600  peak   15551 weight   0.10000E+01  volume   0.14339E+02  ppm1    8.924  ppm2   4.281
ASSI (15631)
   ( ( segid *BrD * and resid 32 and name HE1  ) )
   ( ( segid *BrD * and resid 33 and name HD2  ) )
     3.800   3.600   1.700  peak   15631 weight   0.10000E+01  volume   0.61547E+02  ppm1   11.082  ppm2   2.167
ASSI (15641)
   ( ( segid *BrD * and resid 67 and name HN   ) )
   ( ( segid *BrD * and resid 62 and name HA   ) )
     4.600   4.600   0.900  peak   15641 weight   0.10000E+01  volume   0.20420E+02  ppm1    8.832  ppm2   4.471
ASSI (27052)
   ( ( segid *BrD * and resid 89 and name HB1  ) )
   ( ( segid *BrD * and resid 91 and name HD1  ) )
     3.600   3.200   1.900  peak   27052 weight   0.11000E+01  volume   0.39185E+02  ppm1    3.669  ppm2   4.556
ASSI (27062)
   ( ( segid *BrD * and resid 89 and name HE1  ) )
   ( ( segid *BrD * and resid 91 and name HD2  ) )
     3.700   3.400   1.800  peak   27062 weight   0.11000E+01  volume   0.32055E+02  ppm1    3.473  ppm2   4.556
ASSI (27072)
   ( ( segid *BrD * and resid 89 and name HB2  ) )
   ( ( segid *BrD * and resid 91 and name HD2  ) )
     3.400   2.900   2.100  peak   27072 weight   0.11000E+01  volume   0.54263E+02  ppm1    3.473  ppm2   4.411
ASSI (26992)
   ( ( segid *BrD * and resid 89 and name HA   ) )
   ( ( segid *BrD * and resid 91 and name HG1  ) )
     3.400   2.900   2.100  peak   26992 weight   0.11000E+01  volume   0.54091E+02  ppm1    5.442  ppm2   2.792
OR (26992)
   ( ( segid *BrD * and resid 89 and name HA   ) )
   ( ( segid *BrD * and resid 91 and name HG2  ) )
ASSI (26732)
   ( ( segid *BrD * and resid 94 and name HG1  ) )
   (   segid *BrD * and resid 95 and name HD % )
     3.300   2.700   2.200  peak   26732 weight   0.11000E+01  volume   0.57563E+02  ppm1    3.127  ppm2   7.505
OR (26732)
   ( ( segid *BrD * and resid 94 and name HG2  ) )
   (   segid *BrD * and resid 95 and name HD % )
ASSI (26822)
   ( ( segid *BrD * and resid 94 and name HB2  ) )
   (   segid *BrD * and resid 95 and name HD % )
     3.000   2.200   2.200  peak   26822 weight   0.11000E+01  volume   0.10961E+03  ppm1    2.733  ppm2   7.506
OR (26822)
   ( ( segid *BrD * and resid 94 and name HB1  ) )
   (   segid *BrD * and resid 95 and name HD % )
ASSI (19122)
   (   segid *BrD * and resid 43 and name HB % )
   (   segid *BrD * and resid 47 and name HE % )
     3.900   3.800   1.600  peak   19122 weight   0.11000E+01  volume   0.23047E+02  ppm1    1.697  ppm2   7.267
ASSI (    2)
   ( ( segid *BrD * and resid 93 and name HA   ) )
   ( ( segid *BrD * and resid 93 and name HB2  ) )
     2.100   1.100   1.100  peak       2 weight   0.11000E+01  volume   0.10291E+04  ppm1    5.003  ppm2   4.766
ASSI (   22)
   ( ( segid *BrD * and resid 108 and name HB1 ) )
   ( ( segid *BrD * and resid 108 and name HA  ) )
     1.800   0.800   0.800  peak      22 weight   0.11000E+01  volume   0.21120E+04  ppm1    4.603  ppm2   4.801
ASSI (   32)
   ( ( segid *BrD * and resid 70 and name HA   ) )
   ( ( segid *BrD * and resid 70 and name HB1  ) )
     2.500   1.600   1.600  peak      32 weight   0.11000E+01  volume   0.29221E+03  ppm1    5.344  ppm2   4.786
ASSI (   62)
   ( ( segid *BrD * and resid 70 and name HB2  ) )
   ( ( segid *BrD * and resid 70 and name HA   ) )
     2.500   1.600   1.600  peak      62 weight   0.11000E+01  volume   0.30042E+03  ppm1    4.360  ppm2   5.360
ASSI (   72)
   ( ( segid *BrD * and resid 20 and name HA   ) )
   ( ( segid *BrD * and resid 20 and name HB1  ) )
     2.100   1.100   1.100  peak      72 weight   0.11000E+01  volume   0.10650E+04  ppm1    4.901  ppm2   4.670
ASSI (   92)
   ( ( segid *BrD * and resid 27 and name HA   ) )
   ( ( segid *BrD * and resid 27 and name HB1  ) )
     2.100   1.100   1.100  peak      92 weight   0.11000E+01  volume   0.83585E+03  ppm1    5.050  ppm2   4.617
ASSI (  112)
   ( ( segid *BrD * and resid 38 and name HA   ) )
   (   segid *BrD * and resid 38 and name HG2%)
     2.600   1.700   1.700  peak     112 weight   0.11000E+01  volume   0.24356E+03  ppm1    4.162  ppm2   0.792
```

TABLE 2-continued

Unambigous NOE-derived Inter-proton Distance Restraints

```
ASSI (  132)
   ( ( segid *BrD * and resid 38 and name HB   ) )
   (  segid *BrD * and resid 38 and name HG1%)
      2.400  1.400   1.400 peak       132 weight   0.11000E+01 volume  0.41156E+03 ppm1    1.751 ppm2   1.076
ASSI (  152)
   (  segid *BrD * and resid 38 and name HG2%)
   ( ( segid *BrD * and resid 38 and name HB   ) )
      2.300  1.300   1.300 peak       152 weight   0.11000E+01 volume  0.59973E+03 ppm1    0.808 ppm2   1.776
ASSI (  232)
   ( ( segid *BrD * and resid 81 and name HB   ) )
   (  segid *BrD * and resid 81 and name HG1%)
      2.400  1.400   1.400 peak       232 weight   0.11000E+01 volume  0.37056E+03 ppm1    2.042 ppm2   1.079
ASSI (  242)
   ( ( segid *BrD * and resid 81 and name HB   ) )
   (  segid *BrD * and resid 81 and name HG2%)
      2.300  1.300   1.300 peak       242 weight   0.11000E+01 volume  0.47548E+03 ppm1    2.042 ppm2   0.759
ASSI (  262)
   ( ( segid *BrD * and resid 15 and name HA   ) )
   ( ( segid *BrD * and resid 15 and name HB1  ) )
      2.700  1.800   1.800 peak       262 weight   0.11000E+01 volume  0.20830E+03 ppm1    4.607 ppm2   3.811
ASSI (  322)
   ( ( segid *BrD * and resid 46 and name HB1  ) )
   ( ( segid *BrD * and resid 46 and name HA   ) )
      2.700  1.800   1.800 peak       322 weight   0.11000E+01 volume  0.21305E+03 ppm1    3.274 ppm2   4.143
ASSI (  332)
   ( ( segid *BrD * and resid 46 and name HB2  ) )
   ( ( segid *BrD * and resid 46 and name HA   ) )
      2.700  1.800   1.800 peak       332 weight   0.11000E+01 volume  0.21514E+03 ppm1    3.077 ppm2   4.143
ASSI (  352)
   ( ( segid *BrD * and resid 47 and name HA   ) )
   ( ( segid *BrD * and resid 47 and name HB2  ) )
      2.700  1.800   1.800 peak       352 weight   0.11000E+01 volume  0.22249E+03 ppm1    4.704 ppm2   3.395
ASSI (  362)
   ( ( segid *BrD * and resid 47 and name HB1  ) )
   ( ( segid *BrD * and resid 47 and name HA   ) )
      2.600  1.700   1.700 peak       362 weight   0.11000E+01 volume  0.23254E+03 ppm1    3.815 ppm2   4.721
ASSI (  382)
   ( ( segid *BrD * and resid 67 and name HA   ) )
   ( ( segid *BrD * and resid 67 and name HB1  ) )
      2.400  1.400   1.400 peak       382 weight   0.11000E+01 volume  0.45818E+03 ppm1    4.654 ppm2   3.572
ASSI (  392)
   ( ( segid *BrD * and resid 67 and name HA   ) )
   ( ( segid *BrD * and resid 67 and name HB2  ) )
      2.500  1.600   1.600 peak       392 weight   0.11000E+01 volume  0.31584E+03 ppm1    4.653 ppm2   2.669
ASSI (  422)
   ( ( segid *BrD * and resid 68 and name HB1  ) )
   ( ( segid *BrD * and resid 68 and name HA   ) )
      3.100  2.400   2.400 peak       422 weight   0.11000E+01 volume  0.94493E+02 ppm1    3.669 ppm2   5.143
ASSI (  432)
   ( ( segid *BrD * and resid 68 and name HB2  ) )
   ( ( segid *BrD * and resid 68 and name HA   ) )
      2.700  1.800   1.800 peak       432 weight   0.11000E+01 volume  0.18471E+03 ppm1    3.522 ppm2   5.143
ASSI (  472)
   ( ( segid *BrD * and resid 88 and name HB1  ) )
   ( ( segid *BrD * and resid 88 and name HA   ) )
      2.600  1.700   1.700 peak       472 weight   0.11000E+01 volume  0.28741E+03 ppm1    3.522 ppm2   4.989
ASSI (  492)
   ( ( segid *BrD * and resid 95 and name HA   ) )
   ( ( segid *BrD * and resid 95 and name HB2  ) )
      2.600  1.700   1.700 peak       492 weight   0.11000E+01 volume  0.23932E+03 ppm1    4.459 ppm2   3.361
ASSI (  502)
   ( ( segid *BrD * and resid 95 and name HB1  ) )
   ( ( segid *BrD * and resid 95 and name HA   ) )
      2.600  1.700   1.700 peak       502 weight   0.11000E+01 volume  0.28555E+03 ppm1    3.619 ppm2   4.444
ASSI (  522)
   ( ( segid *BrD * and resid 96 and name HA   ) )
   ( ( segid *BrD * and resid 96 and name HB1  ) )
      2.800  2.000   2.000 peak       522 weight   0.11000E+01 volume  0.17185E+03 ppm1    4.409 ppm2   3.998
ASSI (  532)
   ( ( segid *BrD * and resid 96 and name HA   ) )
   ( ( segid *BrD * and resid 96 and name HB2  ) )
      2.800  2.000   2.000 peak       532 weight   0.11000E+01 volume  0.16898E+03 ppm1    4.409 ppm2   3.118
ASSI (  562)
   ( ( segid *BrD * and resid 31 and name HA   ) )
   (  segid *BrD * and resid 31 and name HB %)
      2.500  1.600   1.600 peak       562 weight   0.11000E+01 volume  0.36354E+03 ppm1    5.000 ppm2   2.315
```

TABLE 2-continued

Unambigous NOE-derived Inter-proton Distance Restraints

```
ASSI (  592)
   ( segid *BrD * and resid 43 and name HB % )
   ( ( segid *BrD * and resid 43 and name HA   ) )
      2.200  1.200   1.200 peak      592 weight   0.11000E+01 volume   0.76123E+03 ppm1    1.700 ppm2    5.539
ASSI (  612)
   ( segid *BrD * and resid 76 and name HB % )
   ( ( segid *BrD * and resid 76 and name HA   ) )
      2.100  1.100   1.100 peak      612 weight   0.11000E+01 volume   0.87848E+03 ppm1    2.093 ppm2    4.687
ASSI (  632)
   ( segid *BrD * and resid 99 and name HB % )
   ( ( segid *BrD * and resid 99 and name HA   ) )
      2.000  1.000   1.000 peak      632 weight   0.11000E+01 volume   0.10742E+04 ppm1    2.190 ppm2    4.440
ASSI (  642)
   ( ( segid *BrD * and resid 113 and name HA   ) )
   ( segid *BrD * and resid 113 and name HB % )
      2.100  1.100   1.100 peak      642 weight   0.11000E+01 volume   0.84264E+03 ppm1    4.901 ppm2    1.979
ASSI (  662)
   ( ( segid *BrD * and resid 34 and name HA   ) )
   ( segid *BrD * and resid 34 and name HB1  ) )
      2.600  1.700   1.700 peak      662 weight   0.11000E+01 volume   0.27701E+03 ppm1    5.542 ppm2    4.307
ASSI (  672)
   ( ( segid *BrD * and resid 34 and name HA   ) )
   ( segid *BrD * and resid 34 and name HB2  ) )
      2.800  2.000   2.000 peak      672 weight   0.11000E+01 volume   0.16922E+03 ppm1    5.542 ppm2    3.146
ASSI (  702)
   ( ( segid *BrD * and resid 74 and name HA   ) )
   ( segid *BrD * and resid 74 and name HB1  ) )
      3.000  2.200   2.200 peak      702 weight   0.11000E+01 volume   0.10996E+03 ppm1    4.359 ppm2    3.563
ASSI (  712)
   ( ( segid *BrD * and resid 74 and name HA   ) )
   ( segid *BrD * and resid 74 and name HB2  ) )
      3.100  2.400   2.400 peak      712 weight   0.11000E+01 volume   0.88126E+02 ppm1    4.361 ppm2    3.000
ASSI (  742)
   ( ( segid *BrD * and resid 82 and name HA   ) )
   ( segid *BrD * and resid 82 and name HB1  ) )
      2.800  2.000   2.000 peak      742 weight   0.11000E+01 volume   0.15835E+03 ppm1    4.755 ppm2    3.695
ASSI (  782)
   ( ( segid *BrD * and resid 82 and name HA   ) )
   ( segid *BrD * and resid 82 and name HB2  ) )
      2.700  1.800   1.800 peak      752 weight   0.11000E+01 volume   0.18532E+03 ppm1    4.755 ppm2    3.573
ASSI (  792)
   ( ( segid *BrD * and resid 106 and name HA   ) )
   ( ( segid *BrD * and resid 106 and name HB1 ) )
      2.700  1.800   1.800 peak      792 weight   0.11000E+01 volume   0.19130E+03 ppm1    4.558 ppm2    3.916
ASSI (  802)
   ( ( segid *BrD * and resid 106 and name HA   ) )
   ( ( segid *BrD * and resid 106 and name HB2 ) )
      2.600  1.700   1.700 peak      802 weight   0.11000E+01 volume   0.25966E+03 ppm1    4.557 ppm2    3.702
ASSI (  842)
   ( ( segid *BrD * and resid 107 and name HB1 ) )
   ( ( segid *BrD * and resid 107 and name HA   ) )
      2.200  1.200   1.200 peak      842 weight   0.11000E+01 volume   0.64742E+03 ppm1    3.671 ppm2    4.435
ASSI (  872)
   ( ( segid *BrD * and resid 65 and name HA   ) )
   ( ( segid *BrD * and resid 65 and name HB1  ) )
      3.600  1.700   1.700 peak      872 weight   0.11000E+01 volume   0.23368E+03 ppm1    5.398 ppm2    3.621
ASSI (  882)
   ( ( segid *BrD * and resid 65 and name HA   ) )
   ( ( segid *BrD * and resid 65 and name HB2  ) )
      2.900  2.100   2.100 peak      882 weight   0.11000E+01 volume   0.14308E+03 ppm1    5.396 ppm2    3.369
ASSI (  892)
   ( ( segid *BrD * and resid 84 and name HA   ) )
   ( ( segid *BrD * and resid 84 and name HB1  ) )
      2.700  1.800   1.800 peak      892 weight   0.11000E+01 volume   0.20950E+03 ppm1    4.904 ppm2    3.606
ASSI (  902)
   ( ( segid *BrD * and resid 84 and name HA   ) )
   ( ( segid *BrD * and resid 84 and name HB2  ) )
      2.600  1.700   1.700 peak      902 weight   0.11000E+01 volume   0.23639E+03 ppm1    4.904 ppm2    3.272
ASSI (  942)
   ( ( segid *BrD * and resid 100 and name HB2 ) )
   ( ( segid *BrD * and resid 100 and name HA   ) )
      2.300  1.300   1.300 peak      942 weight   0.11000E+01 volume   0.53744E+03 ppm1    3.424 ppm2    4.949
ASSI (  952)
   ( ( segid *BrD * and resid 10 and name HA   ) )
   ( ( segid *BrD * and resid 10 and name HB1  ) )
      3.200  2.600   2.300 peak      952 weight   0.11000E+01 volume   0.81254E+02 ppm1    5.478 ppm2    3.354
```

TABLE 2-continued

Unambigous NOE-derived Inter-proton Distance Restraints

```
ASSI (  972)
    ( ( segid *BrD * and resid 12 and name HA   ) )
    ( ( segid *BrD * and resid 12 and name HB1  ) )
      2.700  1.800    1.800 peak       972 weight    0.11000E+01 volume   0.22766E+03 ppm1     5.297 ppm2    3.434
ASSI (  992)
    ( ( segid *BrD * and resid 77 and name HA   ) )
    ( ( segid *BrD * and resid 77 and name HB1  ) )
      2.500  1.600    1.600 peak       992 weight    0.11000E+01 volume   0.33274E+03 ppm1     4.951 ppm2    3.319
ASSI ( 1032)
    ( ( segid *BrD * and resid 117 and name HB2 ) )
    ( ( segid *BrD * and resid 117 and name HA  ) )
      2.700  1.800    1.800 peak      1032 weight    0.11000E+01 volume   0.21830E+03 ppm1     3.127 ppm2    5.167
ASSI ( 1042)
    ( ( segid *BrD * and resid 117 and name HB1 ) )
    ( ( segid *BrD * and resid 117 and name HA  ) )
      2.600  1.700    1.700 peak      1042 weight    0.11000E+01 volume   0.23430E+03 ppm1     3.301 ppm2    5.167
ASSI ( 1052)
    ( ( segid *BrD * and resid 89 and name HA   ) )
    ( ( segid *BrD * and resid 89 and name HB1  ) )
      2.900  2.100    2.100 peak      1052 weight    0.11000E+01 volume   0.12958E+03 ppm1     5.541 ppm2    3.668
ASSI ( 1062)
    ( ( segid *BrD * and resid 89 and name HA   ) )
    ( ( segid *BrD * and resid 89 and name HB2  ) )
      2.800  2.000    2.000 peak      1062 weight    0.11000E+01 volume   0.16727E+03 ppm1     5.641 ppm2    3.491
ASSI ( 1092)
    ( ( segid *BrD * and resid 18 and name HA   ) )
    ( ( segid *BrD * and resid 18 and name HG   ) )
      3.100  2.400    2.400 peak      1092 weight    0.11000E+01 volume   0.85824E+02 ppm1     3.866 ppm2    2.277
ASSI ( 1132)
    (   segid *BrD * and resid 18 and name HD2%)
    ( ( segid *BrD * and resid 18 and name HA   ) )
      2.100  1.100    1.100 peak      1132 weight    0.11000E+01 volume   0.86347E+03 ppm1     0.415 ppm2    3.883
ASSI ( 1142)
    (   segid *BrD * and resid 18 and name HD2%)
    ( ( segid *BrD * and resid 18 and name HG   ) )
      2.500  1.600    1.600 peak      1142 weight    0.11000E+01 volume   0.31482E+03 ppm1     0.419 ppm2    2.274
ASSI ( 1162)
    ( ( segid *BrD * and resid 78 and name HA   ) )
    ( ( segid *BrD * and resid 78 and name HB2  ) )
      2.500  1.600    1.600 peak      1162 weight    0.11000E+01 volume   0.33654E+03 ppm1     3.968 ppm2    1.044
ASSI ( 1172)
    ( ( segid *BrD * and resid 78 and name HA   ) )
    ( ( segid *BrD * and resid 78 and name HG   ) )
      2.900  2.100    2.100 peak      1172 weight    0.11000E+01 volume   0.14454E+03 ppm1     3.967 ppm2    1.270
ASSI ( 1202)
    ( ( segid *BrD * and resid 78 and name HB1  ) )
    ( ( segid *BrD * and resid 78 and name HA   ) )
      2.700  1.800    1.800 peak      1202 weight    0.11000E+01 volume   0.21843E+03 ppm1     1.305 ppm2    4.001
ASSI ( 1212)
    ( ( segid *BrD * and resid 78 and name HB1  ) )
    (   segid *BrD * and resid 78 and name HD1%)
      2.900  2.100    2.100 peak      1212 weight    0.11000E+01 volume   0.13310E+03 ppm1     1.305 ppm2    0.776
ASSI ( 1222)
    ( ( segid *BrD * and resid 78 and name HB1  ) )
    (   segid *BrD * and resid 78 and name HD2%)
      2.700  1.800    1.800 peak      1222 weight    0.11000E+01 volume   0.22009E+03 ppm1     1.305 ppm2    0.673
ASSI ( 1262)
    ( ( segid *BrD * and resid 78 and name HG   ) )
    ( ( segid *BrD * and resid 78 and name HB2  ) )
      2.400  1.400    1.400 peak      1262 weight    0.11000E+01 volume   0.41554E+03 ppm1     1.254 ppm2    1.043
ASSI ( 1282)
    (   segid *BrD * and resid 78 and name HD1%)
    ( ( segid *BrD * and resid 78 and name HA   ) )
      2.400  1.400    1.400 peak      1282 weight    0.11000E+01 volume   0.38399E+03 ppm1     0.761 ppm2    3.998
ASSI ( 1302)
    (   segid *BrD * and resid 78 and name HD1%)
    ( ( segid *BrD * and resid 78 and name HB2  ) )
      2.600  1.700    1.700 peak      1302 weight    0.11000E+01 volume   0.25846E+03 ppm1     0.761 ppm2    1.038
ASSI ( 1312)
    (   segid *BrD * and resid 78 and name HD1%)
    ( ( segid *BrD * and resid 78 and name HG   ) )
      2.200  1.200    1.200 peak      1312 weight    0.11000E+01 volume   0.70030E+03 ppm1     0.761 ppm2    1.270
ASSI ( 1322)
    ( ( segid *BrD * and resid 115 and name HA  ) )
    ( ( segid *BrD * and resid 115 and name HB1 ) )
      2.200  1.200    1.200 peak      1322 weight    0.11000E+01 volume   0.70481E+03 ppm1     4.807 ppm2    2.182
```

TABLE 2-continued

Unambigous NOE-derived Inter-proton Distance Restraints

```
ASSI ( 1352)
    ( segid *BrD* and resid 115 and name HD1%)
    ( ( segid *BrD* and resid 115 and name HG   ) )
      1.300  2.700   2.200 peak    1352 weight  0.11000E+01 volume  0.97922E+02 ppm1   1.352 ppm2   4.829
ASSI ( 1362)
    ( segid *BrD* and resid 115 and name HD1%)
    ( ( segid *BrD* and resid 115 and name HG   ) )
      2.400  1.400   1.400 peak    1362 weight  0.11000E+01 volume  0.44618E+03 ppm1   1.352 ppm2   2.148
ASSI ( 1382)
    ( ( segid *BrD* and resid 116 and name HB   ) )
    ( ( segid *BrD* and resid 116 and name HA   ) )
      2.700  1.800   1.800 peak    1382 weight  0.11000E+01 volume  0.19754E+03 ppm1   2.411 ppm2   4.823
ASSI ( 1402)
    ( ( segid *BrD* and resid 116 and name HB   ) )
    ( ( segid *BrD* and resid 116 and name HG12) )
      2.200  1.200   1.200 peak    1402 weight  0.11000E+01 volume  0.69385E+03 ppm1   2.409 ppm2   1.555
ASSI ( 1422)
    ( ( segid *BrD* and resid 116 and name HG11) )
    ( ( segid *BrD* and resid 116 and name HB   ) )
      2.500  1.600   1.600 peak    1422 weight  0.11000E+01 volume  0.30727E+03 ppm1   1.920 ppm2   2.418
ASSI ( 1432)
    ( segid *BrD* and resid 116 and name HG2%)
    ( ( segid *BrD* and resid 116 and name HA   ) )
      2.500  1.600   1.600 peak    1432 weight  0.11000E+01 volume  0.32118E+03 ppm1   1.403 ppm2   4.823
ASSI ( 1442)
    ( segid *BrD* and resid 116 and name HG2%)
    ( ( segid *BrD* and resid 116 and name HB   ) )
      2.300  1.300   1.300 peak    1442 weight  0.11000E+01 volume  0.50062E+03 ppm1   1.403 ppm2   2.419
ASSI ( 1452)
    ( segid *BrD* and resid 116 and name HD1%)
    ( ( segid *BrD* and resid 116 and name HG12) )
      2.100  1.100   1.100 peak    1452 weight  0.11000E+01 volume  0.85569E+03 ppm1   1.399 ppm2   1.554
ASSI ( 1462)
    ( segid *BrD* and resid 116 and name HD1%)
    ( ( segid *BrD* and resid 116 and name HG11) )
      2.500  1.600   1.600 peak    1462 weight  0.11000E+01 volume  0.33669E+03 ppm1   1.399 ppm2   1.919
ASSI ( 1512)
    ( ( segid *BrD* and resid 110 and name HB   ) )
    ( ( segid *BrD* and resid 110 and name HA   ) )
      2.400  1.400   1.400 peak    1512 weight  0.11000E+01 volume  0.40202E+03 ppm1   2.338 ppm2   4.418
ASSI ( 1542)
    ( segid *BrD* and resid 110 and name HG2%)
    ( ( segid *BrD* and resid 110 and name HA   ) )
      2.200  1.200   1.200 peak    1542 weight  0.11000E+01 volume  0.74299E+03 ppm1   1.251 ppm2   4.418
ASSI ( 1552)
    ( segid *BrD* and resid 110 and name HG2%)
    ( ( segid *BrD* and resid 110 and name HB   ) )
      2.200  1.200   1.200 peak    1552 weight  0.11000E+01 volume  0.70453E+03 ppm1   1.252 ppm2   2.361
ASSI ( 1562)
    ( segid *BrD* and resid 110 and name HG2%)
    ( ( segid *BrD* and resid 110 and name HG11) )
      2.600  1.700   1.700 peak    1562 weight  0.11000E+01 volume  0.27736E+03 ppm1   1.251 ppm2   1.718
ASSI ( 1572)
    ( segid *BrD* and resid 110 and name HG2%)
    ( segid *BrD* and resid 110 and name HD1%)
      2.000  1.000   1.000 peak    1572 weight  0.11000E+01 volume  0.13448E+04 ppm1   1.254 ppm2   1.141
ASSI ( 1602)
    ( segid *BrD* and resid 110 and name HD1%)
    ( ( segid *BrD* and resid 110 and name HA   ) )
      2.200  1.200   1.200 peak    1602 weight  0.11000E+01 volume  0.74125E+03 ppm1   1.154 ppm2   4.420
ASSI ( 1612)
    ( segid *BrD* and resid 110 and name HD1%)
    ( ( segid *BrD* and resid 110 and name HB   ) )
      2.200  1.200   1.200 peak    1612 weight  0.11000E+01 volume  0.75209E+03 ppm1   1.154 ppm2   2.361
ASSI ( 1622)
    ( segid *BrD* and resid 110 and name HD1%)
    ( ( segid *BrD* and resid 110 and name HG11) )
      2.300  1.300   1.300 peak    1622 weight  0.11000E+01 volume  0.59823E+03 ppm1   1.154 ppm2   1.718
ASSI ( 1682)
    ( segid *BrD* and resid 50 and name HD1%)
    ( ( segid *BrD* and resid 50 and name HB   ) )
      2.800  2.000   2.000 peak    1682 weight  0.11000E+01 volume  0.14989E+03 ppm1   1.154 ppm2   1.826
ASSI ( 1692)
    ( segid *BrD* and resid 50 and name HD1%)
    ( ( segid *BrD* and resid 50 and name HG11) )
      2.300  1.300   1.300 peak    1692 weight  0.11000E+01 volume  0.49711E+03 ppm1   1.154 ppm2   1.408
```

TABLE 2-continued

Unambigous NOE-derived Inter-proton Distance Restraints

```
ASSI ( 1702)
    ( segid *BrD * and resid 50 and name HD1%)
    ( ( segid *BrD * and resid 50 and name HG12) )
      2.400  1.400   1.400 peak    1702 weight    0.11000E+01 volume   0.46662E+03 ppm1    1.155 ppm2   0.838
ASSI ( 1712)
    ( segid *BrD * and resid 50 and name HD1%)
    ( segid *BrD * and resid 50 and name HG2%)
      2.400  1.400   1.400 peak    1712 weight    0.11000E+01 volume   0.45288E+03 ppm1    1.154 ppm2   0.994
ASSI ( 1742)
    ( segid *BrD * and resid 50 and name HG2%)
    ( ( segid *BrD * and resid 50 and name HA   ) )
      2.400  1.400   1.400 peak    1742 weight    0.11000E+01 volume   0.43004E+03 ppm1    1.006 ppm2   4.518
ASSI ( 1752)
    ( segid *BrD * and resid 50 and name HG2%)
    ( ( segid *BrD * and resid 50 and name HB   ) )
      2.200  1.200   1.200 peak    1752 weight    0.11000E+01 volume   0.61685E+03 ppm1    1.006 ppm2   1.825
ASSI ( 1762)
    ( segid *BrD * and resid 50 and name HG2%)
    ( ( segid *BrD * and resid 50 and name HG11) )
      2.800  2.000   2.000 peak    1762 weight    0.11000E+01 volume   0.16808E+03 ppm1    1.008 ppm2   1.409
ASSI ( 1772)
    ( segid *BrD * and resid 50 and name HG2%)
    ( ( segid *BrD * and resid 50 and name HG12) )
      2.400  1.400   1.400 peak    1772 weight    0.11000E+01 volume   0.40990E+03 ppm1    1.006 ppm2   0.838
ASSI ( 1792)
    ( ( segid *BrD * and resid 101 and name HA   ) )
    ( segid *BrD * and resid 101 and name HD1%)
      2.700  1.800   1.800 peak    1792 weight    0.11000E+01 volume   0.20691E+03 ppm1    4.262 ppm2   1.578
ASSI ( 1812)
    ( ( segid *BrD * and resid 101 and name HB   ) )
    ( segid *BrD * and resid 101 and name HD1%)
      2.300  1.300   1.300 peak    1812 weight    0.11000E+01 volume   0.50350E+03 ppm1    2.537 ppm2   1.578
ASSI ( 1852)
    ( ( segid *BrD * and resid 101 and name HG11) )
    ( segid *BrD * and resid 101 and name HG2%)
      2.600  1.700   1.700 peak    1852 weight    0.11000E+01 volume   0.23958E+03 ppm1    2.444 ppm2   1.609
ASSI ( 1872)
    ( segid *BrD * and resid 101 and name HG2%)
    ( ( segid *BrD * and resid 101 and name HA   ) )
      2.400  1.400   1.400 peak    1872 weight    0.11000E+01 volume   0.44349E+03 ppm1    1.596 ppm2   4.265
ASSI ( 1882)
    ( segid *BrD * and resid 101 and name HG2%)
    ( ( segid *BrD * and resid 101 and name HB   ) )
      2.200  1.200   1.200 peak    1882 weight    0.11000E+01 volume   0.72150E+03 ppm1    1.600 ppm2   2.536
ASSI ( 1892)
    ( segid *BrD * and resid 101 and name HG2%)
    ( ( segid *BrD * and resid 101 and name HG12) )
      2.300  1.300   1.300 peak    1892 weight    0.11000E+01 volume   0.60307E+03 ppm1    1.598 ppm2   1.806
ASSI ( 1922)
    ( segid *BrD * and resid 101 and name HD1%)
    ( ( segid *BrD * and resid 101 and name HG11) )
      2.300  1.300   1.300 peak    1922 weight    0.11000E+01 volume   0.50142E+03 ppm1    1.550 ppm2   2.467
ASSI ( 1932)
    ( segid *BrD * and resid 101 and name HD1%)
    ( ( segid *BrD * and resid 101 and name HG12) )
      2.200  1.200   1.200 peak    1932 weight    0.11000E+01 volume   0.71179E+03 ppm1    1.550 ppm2   1.806
ASSI ( 1952)
    ( ( segid *BrD * and resid 21 and name HA   ) )
    ( segid *BrD * and resid 21 and name HD1%)
      2.800  2.000   2.000 peak    1952 weight    0.11000E+01 volume   0.16491E+03 ppm1    4.359 ppm2   1.221
ASSI ( 1962)
    ( ( segid *BrD * and resid 21 and name HB   ) )
    ( segid *BrD * and resid 21 and name HG2%)
      3.100  2.400   2.400 peak    1962 weight    0.11000E+01 volume   0.84008E+02 ppm1    2.487 ppm2   1.588
ASSI ( 1982)
    ( ( segid *BrD * and resid 21 and name HG12) )
    ( segid *BrD * and resid 21 and name HD1%)
      2.500  1.600   1.600 peak    1982 weight    0.11000E+01 volume   0.32478E+03 ppm1    1.648 ppm2   1.222
ASSI ( 2012)
    ( segid *BrD * and resid 21 and name HG2%)
    ( ( segid *BrD * and resid 21 and name HG11) )
      2.600  1.700   1.700 peak    2012 weight    0.11000E+01 volume   0.24142E+03 ppm1    1.598 ppm2   2.357
ASSI ( 2022)
    ( segid *BrD * and resid 21 and name HD1%)
    ( ( segid *BrD * and resid 21 and name HB   ) )
      2.500  1.600   1.600 peak    2022 weight    0.11000E+01 volume   0.29587E+03 ppm1    1.206 ppm2   2.508
```

TABLE 2-continued

Unambigous NOE-derived Inter-proton Distance Restraints

```
ASSI ( 2032)
   ( segid *BrD * and resid 21 and name HD1%)
   ( ( segid *BrD * and resid 21 and name HG11 ) )
      2.400  1.400   1.400  peak    2032  weight   0.11000E+01 volume   0.44094E+03 ppm1   1.205 ppm2   2.355
ASSI ( 2042)
   ( segid *BrD * and resid 21 and name HD1%)
   ( segid *BrD * and resid 21 and name HG2%)
      2.300  1.300   1.300  peak    2042  weight   0.11000E+01 volume   0.49870E+03 ppm1   1.205 ppm2   1.586
ASSI ( 2052)
   ( ( segid *BrD * and resid 112 and name HA  ) )
   ( ( segid *BrD * and resid 112 and name HG1 ) )
      2.700  1.800   1.800  peak    2052  weight   0.11000E+01 volume   0.21076E+03 ppm1   4.607 ppm2   2.942
ASSI ( 2072)
   ( ( segid *BrD * and resid 112 and name HB1 ) )
   ( ( segid *BrD * and resid 112 and name HG1 ) )
      2.300  1.300   1.300  peak    2072  weight   0.11000E+01 volume   0.51152E+03 ppm1   2.684 ppm2   2.947
ASSI ( 2092)
   ( ( segid *BrD * and resid 94 and name HA  ) )
   ( segid *BrD * and resid 94 and name HG1 ) )
      2.700  1.800   1.800  peak    2092  weight   0.11000E+01 volume   0.21281E+03 ppm1   4.830 ppm2   3.127
ASSI ( 2112)
   ( ( segid *BrD * and resid 92 and name HG1 ) )
   ( ( segid *BrD * and resid 92 and name HA  ) )
      2.400  1.400   1.400  peak    2112  weight   0.11000E+01 volume   0.46860E+03 ppm1   2.816 ppm2   4.798
ASSI ( 2142)
   ( ( segid *BrD * and resid 87 and name HG1 ) )
   ( ( segid *BrD * and resid 87 and name HA  ) )
      2.900  2.100   2.100  peak    2142  weight   0.11000E+01 volume   0.13435E+03 ppm1   3.030 ppm2   4.874
ASSI ( 2152)
   ( ( segid *BrD * and resid 87 and name HG2 ) )
   ( ( segid *BrD * and resid 87 and name HA  ) )
      2.500  1.600   1.600  peak    2152  weight   0.11000E+01 volume   0.35437E+03 ppm1   2.782 ppm2   4.875
ASSI ( 2172)
   ( ( segid *BrD * and resid 61 and name HG1 ) )
   ( ( segid *BrD * and resid 61 and name HA  ) )
      2.300  1.300   1.300  peak    2172  weight   0.11000E+01 volume   0.47499E+03 ppm1   2.980 ppm2   4.670
ASSI ( 2182)
   ( ( segid *BrD * and resid 61 and name HG2 ) )
   ( ( segid *BrD * and resid 61 and name HA  ) )
      2.800  2.000   2.000  peak    2182  weight   0.11000E+01 volume   0.17452E+03 ppm1   2.832 ppm2   4.670
ASSI ( 2202)
   ( ( segid *BrD * and resid 42 and name HG1 ) )
   ( ( segid *BrD * and resid 42 and name HA  ) )
      2.400  1.400   1.400  peak    2202  weight   0.11000E+01 volume   0.43794E+03 ppm1   2.880 ppm2   5.049
ASSI ( 2222)
   ( ( segid *BrD * and resid 36 and name HG1 ) )
   ( ( segid *BrD * and resid 36 and name HA  ) )
      2.600  1.700   1.700  peak    2222  weight   0.11000E+01 volume   0.28226E+03 ppm1   2.781 ppm2   5.445
ASSI ( 2252)
   ( ( segid *BrD * and resid 79 and name HG1 ) )
   ( ( segid *BrD * and resid 79 and name HA  ) )
      2.600  1.700   1.700  peak    2252  weight   0.11000E+01 volume   0.27675E+03 ppm1   3.033 ppm2   4.417
ASSI ( 2262)
   ( ( segid *BrD * and resid 29 and name HA  ) )
   ( ( segid *BrD * and resid 29 and name HB1 ) )
      2.000  1.000   1.000  peak    2262  weight   0.11000E+01 volume   0.11521E+04 ppm1   4.810 ppm2   2.738
ASSI ( 2272)
   ( ( segid *BrD * and resid 29 and name HG1 ) )
   ( ( segid *BrD * and resid 29 and name HA  ) )
      2.600  1.700   1.700  peak    2272  weight   0.11000E+01 volume   0.24467E+03 ppm1   2.980 ppm2   4.810
ASSI ( 2302)
   ( ( segid *BrD * and resid 23 and name HG1 ) )
   ( ( segid *BrD * and resid 23 and name HA  ) )
      2.500  1.600   1.600  peak    2302  weight   0.11000E+01 volume   0.32948E+03 ppm1   3.124 ppm2   4.638
ASSI ( 2312)
   ( ( segid *BrD * and resid 23 and name HG2 ) )
   ( ( segid *BrD * and resid 23 and name HA  ) )
      2.400  1.400   1.400  peak    2312  weight   0.11000E+01 volume   0.37520E+03 ppm1   3.068 ppm2   4.638
ASSI ( 2322)
   ( ( segid *BrD * and resid 80 and name HD2 ) )
   ( ( segid *BrD * and resid 80 and name HG1 ) )
      2.500  1.600   1.600  peak    2322  weight   0.11000E+01 volume   0.34874E+03 ppm1   3.913 ppm2   2.347
ASSI ( 2342)
   ( ( segid *BrD * and resid 80 and name HD2 ) )
   ( ( segid *BrD * and resid 80 and name HB1 ) )
      2.800  2.000   2.000  peak    2342  weight   0.11000E+01 volume   0.17327E+03 ppm1   3.913 ppm2   2.573
```

TABLE 2-continued

Unambigous NOE-derived Inter-proton Distance Restraints

```
ASSI ( 2372)
    ( ( segid *BrD * and resid 66 and name HA   ) )
    ( ( segid *BrD * and resid 66 and name HD1  ) )
       2.700  1.800    1.800 peak     2372 weight   0.11000E+01 volume   0.22458E+03 ppm1    5.000 ppm2    3.670
ASSI ( 2382)
    ( ( segid *BrD * and resid 66 and name HG2  ) )
    ( ( segid *BrD * and resid 66 and name HD1  ) )
       2.500  1.600    1.600 peak     2382 weight   0.11000E+01 volume   0.35872E+03 ppm1    2.140 ppm2    3.670
ASSI ( 2392)
    ( ( segid *BrD * and resid 9 and name HD1  ) )
    ( ( segid *BrD * and resid 9 and name HG1  ) )
       2.300  1.300    1.300 peak     2392 weight   0.11000E+01 volume   0.51278E+03 ppm1    3.789 ppm2    2.279
ASSI ( 2432)
    ( ( segid *BrD * and resid 35 and name HG1  ) )
    ( ( segid *BrD * and resid 35 and name HA   ) )
       2.900  2.100    2.100 peak     2432 weight   0.11000E+01 volume   0.13495E+03 ppm1    3.422 ppm2    4.901
ASSI ( 2442)
    ( ( segid *BrD * and resid 102 and name HB1  ) )
    ( ( segid *BrD * and resid 102 and name HA   ) )
       2.700  1.800    1.800 peak     2442 weight   0.11000E+01 volume   0.22859E+03 ppm1    1.994 ppm2    4.282
ASSI ( 2452)
    ( ( segid *BrD * and resid 102 and name HB2  ) )
    ( ( segid *BrD * and resid 102 and name HA   ) )
       2.700  1.800    1.800 peak     2452 weight   0.11000E+01 volume   0.18482E+03 ppm1    1.848 ppm2    4.280
ASSI ( 2462)
    ( ( segid *BrD * and resid 102 and name HB1  ) )
    (   segid *BrD * and resid 102 and name HD1%)
       2.500  1.600    1.600 peak     2462 weight   0.11000E+01 volume   0.28966E+03 ppm1    1.992 ppm2    1.325
ASSI ( 2472)
    ( ( segid *BrD * and resid 102 and name HB2  ) )
    (   segid *BrD * and resid 102 and name HD1%)
       2.500  1.600    1.600 peak     2472 weight   0.11000E+01 volume   0.33733E+03 ppm1    1.842 ppm2    1.325
ASSI ( 2532)
    ( ( segid *BrD * and resid 73 and name HA   ) )
    ( ( segid *BrD * and resid 73 and name HB2  ) )
       2.500  1.600    1.600 peak     2532 weight   0.11000E+01 volume   0.31007E+03 ppm1    4.805 ppm2    2.482
ASSI ( 2542)
    ( ( segid *BrD * and resid 73 and name HA   ) )
    ( ( segid *BrD * and resid 73 and name HG   ) )
       2.600  1.700    1.700 peak     2542 weight   0.11000E+01 volume   0.27034E+03 ppm1    4.805 ppm2    2.368
ASSI ( 2572)
    ( ( segid *BrD * and resid 73 and name HB2  ) )
    (   segid *BrD * and resid 73 and name HD1%)
       2.400  1.400    1.400 peak     2572 weight   0.11000E+01 volume   0.37597E+03 ppm1    2.487 ppm2    1.539
ASSI ( 2582)
    (   segid *BrD * and resid 73 and name HD2%)
    ( ( segid *BrD * and resid 73 and name HA   ) )
       2.200  1.200    1.200 peak     2582 weight   0.11000E+01 volume   0.64867E+03 ppm1    1.499 ppm2    4.827
ASSI ( 2592)
    (   segid *BrD * and resid 73 and name HD2%)
    ( ( segid *BrD * and resid 73 and name HG   ) )
       2.100  1.100    1.100 peak     2592 weight   0.11000E+01 volume   0.88262E+03 ppm1    1.500 ppm2    2.367
ASSI ( 2602)
    (   segid *BrD * and resid 56 and name HD2%)
    ( ( segid *BrD * and resid 56 and name HG   ) )
       2.200  1.200    1.200 peak     2602 weight   0.11000E+01 volume   0.64971E+03 ppm1    1.254 ppm2    2.328
ASSI ( 2612)
    (   segid *BrD * and resid 56 and name HD2%)
    ( ( segid *BrD * and resid 56 and name HB1  ) )
       2.700  1.800    1.800 peak     2612 weight   0.11000E+01 volume   0.20000E+03 ppm1    1.254 ppm2    2.703
ASSI ( 2622)
    (   segid *BrD * and resid 56 and name HD2%)
    ( ( segid *BrD * and resid 56 and name HA   ) )
       2.200  1.200    1.200 peak     2622 weight   0.11000E+01 volume   0.63602E+03 ppm1    1.253 ppm2    4.630
ASSI ( 2652)
    ( ( segid *BrD * and resid 22 and name HB1  ) )
    ( ( segid *BrD * and resid 22 and name HA   ) )
       2.400  1.400    1.400 peak     2652 weight   0.11000E+01 volume   0.44257E+03 ppm1    2.682 ppm2    4.723
ASSI ( 2662)
    ( ( segid *BrD * and resid 22 and name HB2  ) )
    ( ( segid *BrD * and resid 22 and name HA   ) )
       2.400  1.400    1.400 peak     2662 weight   0.11000E+01 volume   0.37194E+03 ppm1    2.287 ppm2    4.723
ASSI ( 2682)
    (   segid *BrD * and resid 22 and name HD2%)
    ( ( segid *BrD * and resid 22 and name HA   ) )
       2.200  1.200    1.200 peak     2682 weight   0.11000E+01 volume   0.64884E+03 ppm1    1.599 ppm2    4.723
```

TABLE 2-continued

Unambigous NOE-derived Inter-proton Distance Restraints

```
ASSI ( 2702)
    ( ( segid *BrD * and resid 63 and name HA   ) )
    ( ( segid *BrD * and resid 63 and name HB1  ) )
    2.900  2.100   2.100 peak    2702 weight    0.11000E+01 volume   0.13727E+03 ppm1    5.296 ppm2   2.907
ASSI ( 2712)
    ( ( segid *BrD * and resid 63 and name HA   ) )
    ( ( segid *BrD * and resid 63 and name HB2  ) )
    2.700  1.800   1.800 peak    2712 weight    0.11000E+01 volume   0.18645E+03 ppm1    5.296 ppm2   2.535
ASSI ( 2722)
    ( ( segid *BrD * and resid 63 and name HA   ) )
    ( ( segid *BrD * and resid 63 and name HG   ) )
    2.900  2.100   2.100 peak    2722 weight    0.11000E+01 volume   0.12509E+03 ppm1    5.293 ppm2   2.423
ASSI ( 2732)
    ( ( segid *BrD * and resid 63 and name HA   ) )
    (   segid *BrD * and resid 63 and name HD1%)
    2.700  1.800   1.800 peak    2732 weight    0.11000E+01 volume   0.22485E+03 ppm1    5.296 ppm2   1.649
ASSI ( 2742)
    ( ( segid *BrD * and resid 63 and name HA   ) )
    (   segid *BrD * and resid 63 and name HD2%)
    3.300  2.700   2.200 peak    2742 weight    0.11000E+01 volume   0.65439E+02 ppm1    5.296 ppm2   1.490
ASSI ( 2752)
    ( ( segid *BrD * and resid 63 and name HB2  ) )
    (   segid *BrD * and resid 63 and name HD1%)
    2.500  1.600   1.600 peak    2752 weight    0.11000E+01 volume   0.34992E+03 ppm1    2.538 ppm2   1.653
ASSI ( 2762)
    ( ( segid *BrD * and resid 63 and name HB2  ) )
    (   segid *BrD * and resid 63 and name HD2%)
    2.700  1.800   1.800 peak    2762 weight    0.11000E+01 volume   0.19887E+03 ppm1    2.538 ppm2   1.491
ASSI ( 2772)
    ( ( segid *BrD * and resid 63 and name HB1  ) )
    (   segid *BrD * and resid 63 and name HD1%)
    2.600  1.700   1.700 peak    2772 weight    0.11000E+01 volume   0.26127E+03 ppm1    2.883 ppm2   1.653
ASSI ( 2782)
    ( ( segid *BrD * and resid 63 and name HB1  ) )
    (   segid *BrD * and resid 63 and name HD2%)
    2.600  1.700   1.700 peak    2782 weight    0.11000E+01 volume   0.25187E+03 ppm1    2.883 ppm2   1.491
ASSI ( 2852)
    (   segid *BrD * and resid 14 and name HD2%)
    ( ( segid *BrD * and resid 14 and name HA   ) )
    3.100  2.400   2.400 peak    2852 weight    0.11000E+01 volume   0.89872E+02 ppm1    1.400 ppm2   4.655
ASSI ( 2862)
    (   segid *BrD * and resid 14 and name HD2%)
    ( ( segid *BrD * and resid 14 and name HG   ) )
    2.700  1.800   1.800 peak    2862 weight    0.11000E+01 volume   0.20094E+03 ppm1    1.401 ppm2   2.061
ASSI ( 2872)
    ( ( segid *BrD * and resid 24 and name HA   ) )
    ( ( segid *BrD * and resid 24 and name HG1  ) )
    2.700  1.800   1.800 peak    2872 weight    0.11000E+01 volume   0.22636E+03 ppm1    4.783 ppm2   3.454
ASSI ( 2892)
    ( ( segid *BrD * and resid 24 and name HG2  ) )
    ( ( segid *BrD * and resid 24 and name HA   ) )
    2.400  1.400   1.400 peak    2892 weight    0.11000E+01 volume   0.36992E+03 ppm1    3.076 ppm2   4.784
ASSI ( 2902)
    ( ( segid *BrD * and resid 83 and name HB   ) )
    ( ( segid *BrD * and resid 83 and name HA   ) )
    2.300  1.300   1.300 peak    2902 weight    0.11000E+01 volume   0.54241E+03 ppm1    4.804 ppm2   4.460
ASSI ( 2912)
    ( ( segid *BrD * and resid 17 and name HA   ) )
    ( ( segid *BrD * and resid 17 and name HB   ) )
    2.500  1.600   1.600 peak    2912 weight    0.11000E+01 volume   0.32083E+03 ppm1    4.542 ppm2   4.860
ASSI ( 2932)
    (   segid *BrD * and resid 25 and name HG2%)
    ( ( segid *BrD * and resid 25 and name HB   ) )
    2.300  1.300   1.300 peak    2932 weight    0.11000E+01 volume   0.60381E+03 ppm1    1.650 ppm2   3.005
ASSI ( 2942)
    (   segid *BrD * and resid 25 and name HG1%)
    ( ( segid *BrD * and resid 25 and name HB   ) )
    2.200  1.200   1.200 peak    2942 weight    0.11000E+01 volume   0.72430E+03 ppm1    1.795 ppm2   3.006
ASSI ( 2972)
    ( ( segid *BrD * and resid 49 and name HA   ) )
    ( ( segid *BrD * and resid 49 and name HB   ) )
    2.500  1.600   1.600 peak    2972 weight    0.11000E+01 volume   0.32061E+03 ppm1    4.658 ppm2   2.620
ASSI ( 2992)
    ( ( segid *BrD * and resid 49 and name HA   ) )
    (   segid *BrD * and resid 49 and name HG2%)
    2.900  2.100   2.100 peak    2992 weight    0.11000E+01 volume   0.13480E+03 ppm1    4.658 ppm2   1.570
```

TABLE 2-continued

Unambigous NOE-derived Inter-proton Distance Restraints

```
ASSI ( 3012)
   ( ( segid *BrD * and resid 49 and name HB   ) )
   ( segid *BrD * and resid 49 and name HG2%)
     2.500  1.600    1.600 peak    3012 weight  0.11000E+01 volume  0.36520E+03 ppm1   2.634 ppm2   1.570
ASSI ( 3022)
   ( segid *BrD * and resid 49 and name HG1%)
   ( ( segid *BrD * and resid 49 and name HB   ) )
     2.500  1.600    1.600 peak    3022 weight  0.11000E+01 volume  0.34642E+03 ppm1   1.647 ppm2   2.615
ASSI ( 3042)
   ( segid *BrD * and resid 49 and name HG1%)
   ( ( segid *BrD * and resid 49 and name HA   ) )
     2.700  1.800    1.800 peak    3042 weight  0.11000E+01 volume  0.21850E+03 ppm1   1.647 ppm2   4.679
ASSI ( 3052)
   ( segid *BrD * and resid 69 and name HG1%)
   ( ( segid *BrD * and resid 69 and name HA   ) )
     2.100  1.100    1.100 peak    3052 weight  0.11000E+01 volume  0.91954E+03 ppm1   1.550 ppm2   4.695
ASSI ( 3072)
   ( ( segid *BrD * and resid 58 and name HA   ) )
   ( segid *BrD * and resid 58 and name HB   ) )
     2.200  1.200    1.200 peak    3072 weight  0.11000E+01 volume  0.67241E+03 ppm1   4.456 ppm2   4.703
ASSI ( 3102)
   ( ( segid *BrD * and resid 28 and name HB2 ) )
   ( segid *BrD * and resid 28 and name HA   ) )
     2.800  2.000    2.000 peak    3102 weight  0.11000E+01 volume  0.15370E+03 ppm1   3.372 ppm2   4.582
ASSI ( 3112)
   ( ( segid *BrD * and resid 28 and name HB1 ) )
   ( segid *BrD * and resid 28 and name HA   ) )
     2.800  2.000    2.000 peak    3112 weight  0.11000E+01 volume  0.16666E+03 ppm1   3.571 ppm2   4.582
ASSI ( 3142)
   ( ( segid *BrD * and resid 64 and name HA   ) )
   ( ( segid *BrD * and resid 64 and name HD1 ) )
     3.000  2.200    2.000 peak    3142 weight  0.11000E+01 volume  0.11363E+03 ppm1   4.950 ppm2   2.373
ASSI ( 3162)
   ( ( segid *BrD * and resid 64 and name HB1 ) )
   ( ( segid *BrD * and resid 64 and name HA   ) )
     2.200  1.200    1.200 peak    3162 weight  0.11000E+01 volume  0.77951E+03 ppm1   2.636 ppm2   4.940
ASSI ( 3172)
   ( ( segid *BrD * and resid 64 and name HG1 ) )
   ( ( segid *BrD * and resid 64 and name HA   ) )
     2.500  1.600    1.600 peak    3172 weight  0.11000E+01 volume  0.29624E+03 ppm1   2.190 ppm2   4.938
ASSI ( 3182)
   ( ( segid *BrD * and resid 64 and name HG1 ) )
   ( ( segid *BrD * and resid 64 and name HB1 ) )
     2.300  1.300    1.300 peak    3182 weight  0.11000E+01 volume  0.60420E+03 ppm1   2.190 ppm2   2.662
ASSI ( 3192)
   ( ( segid *BrD * and resid 64 and name HG1 ) )
   ( ( segid *BrD * and resid 64 and name HE1 ) )
     2.500  1.600    1.600 peak    3192 weight  0.11000E+01 volume  0.31904E+03 ppm1   2.190 ppm2   3.597
ASSI ( 3202)
   ( ( segid *BrD * and resid 6 and name HB1 ) )
   ( segid *BrD * and resid 6 and name HA   ) )
     2.400  1.400    1.400 peak    3202 weight  0.11000E+01 volume  0.45358E+03 ppm1   2.489 ppm2   4.969
ASSI ( 3212)
   ( ( segid *BrD * and resid 6 and name HD1 ) )
   ( segid *BrD * and resid 6 and name HA   ) )
     2.800  2.000    2.000 peak    3212 weight  0.11000E+01 volume  0.15911E+03 ppm1   2.310 ppm2   4.972
ASSI ( 3222)
   ( ( segid *BrD * and resid 6 and name HG2 ) )
   ( ( segid *BrD * and resid 6 and name HA   ) )
     2.900  2.100    2.100 peak    3222 weight  0.11000E+01 volume  0.13404E+03 ppm1   2.040 ppm2   4.973
ASSI ( 3232)
   ( ( segid *BrD * and resid 104 and name HG1 ) )
   ( ( segid *BrD * and resid 104 and name HA   ) )
     2.400  1.400    1.400 peak    3232 weight  0.11000E+01 volume  0.41964E+03 ppm1   2.140 ppm2   4.672
ASSI ( 3242)
   ( ( segid *BrD * and resid 104 and name HA   ) )
   ( ( segid *BrD * and resid 104 and name HB1 ) )
     2.100  1.100    1.100 peak    3242 weight  0.11000E+01 volume  0.87442E+03 ppm1   4.657 ppm2   2.537
ASSI ( 3272)
   ( ( segid *BrD * and resid 104 and name HA   ) )
   ( ( segid *BrD * and resid 107 and name HB1 ) )
     2.500  1.600    1.600 peak    3272 weight  0.11000E+01 volume  0.31692E+03 ppm1   4.656 ppm2   3.663
ASSI ( 3292)
   ( ( segid *BrD * and resid 111 and name HB2 ) )
   ( ( segid *BrD * and resid 111 and name HA   ) )
     2.100  1.100    1.100 peak    3292 weight  0.11000E+01 volume  0.10458E+04 ppm1   2.366 ppm2   4.656
```

TABLE 2-continued

Unambigous NOE-derived Inter-proton Distance Restraints

```
ASSI ( 3312)
    (( segid *BrD * and resid 111 and name HA   ))
    (( segid *BrD * and resid 111 and name HG2  ))
      2.800  2.000   2.000 peak    3312 weight   0.11000E+01 volume   0.17232E+03 ppm1    4.656 ppm2   1.918
ASSI ( 3332)
    (( segid *BrD * and resid 111 and name HA   ))
    (( segid *BrD * and resid 111 and name HB1  ))
      2.100  1.100   1.100 peak    3332 weight   0.11000E+01 volume   0.97545E+03 ppm1    4.656 ppm2   2.473
ASSI ( 3362)
    (( segid *BrD * and resid 19 and name HA   ))
    (( segid *BrD * and resid 19 and name HD1  ))
      3.100  2.400   2.400 peak    3362 weight   0.11000E+01 volume   0.91418E+02 ppm1    4.310 ppm2   2.214
ASSI ( 3372)
    (( segid *BrD * and resid 19 and name HB1  ))
    (( segid *BrD * and resid 19 and name HA   ))
      2.500  1.600   1.600 peak    3372 weight   0.11000E+01 volume   0.34161E+03 ppm1    2.290 ppm2   4.297
ASSI ( 3382)
    (( segid *BrD * and resid 19 and name HB1  ))
    (( segid *BrD * and resid 16 and name HA   ))
      3.900  3.800   1.600 peak    3382 weight   0.11000E+01 volume   0.22305E+02 ppm1    2.290 ppm2   4.507
ASSI ( 3392)
    (( segid *BrD * and resid 19 and name HG1  ))
    (( segid *BrD * and resid 19 and name HA   ))
      2.400  1.400   1.400 peak    3392 weight   0.11000E+01 volume   0.37229E+03 ppm1    1.895 ppm2   4.296
ASSI ( 3402)
    (( segid *BrD * and resid 19 and name HG1  ))
    (( segid *BrD * and resid 19 and name HE1  ))
      2.600  1.700   1.700 peak    3402 weight   0.11000E+01 volume   0.28547E+03 ppm1    1.895 ppm2   3.526
ASSI ( 3412)
    (( segid *BrD * and resid 19 and name HD1  ))
    (( segid *BrD * and resid 19 and name HE1  ))
      1.800  0.800   0.800 peak    3412 weight   0.11000E+01 volume   0.21730E+04 ppm1    2.192 ppm2   3.522
ASSI ( 3422)
    (( segid *BrD * and resid 60 and name HA   ))
    (( segid *BrD * and resid 60 and name HB1  ))
      1.700  0.700   0.700 peak    3422 weight   0.11000E+01 volume   0.29577E+04 ppm1    4.805 ppm2   4.995
ASSI ( 3452)
    (( segid *BrD * and resid 11 and name HB1  ))
    (( segid *BrD * and resid 11 and name HA   ))
      2.300  1.300   1.300 peak    3452 weight   0.11000E+01 volume   0.52164E+03 ppm1    2.933 ppm2   4.942
ASSI ( 3462)
    (( segid *BrD * and resid 11 and name HB2  ))
    (( segid *BrD * and resid 11 and name HA   ))
      2.300  1.300   1.300 peak    3462 weight   0.11000E+01 volume   0.61125E+03 ppm1    2.586 ppm2   4.942
ASSI ( 3492)
    (( segid *BrD * and resid 97 and name HA   ))
    (( segid *BrD * and resid 97 and name HB1  ))
      2.300  1.300   1.300 peak    3492 weight   0.11000E+01 volume   0.52974E+03 ppm1    4.805 ppm2   2.704
ASSI ( 3532)
    (( segid *BrD * and resid 109 and name HE2 ))
    (( segid *BrD * and resid 109 and name HD1 ))
      2.500  1.600   1.600 peak    3532 weight   0.11000E+01 volume   0.30326E+03 ppm1    3.029 ppm2   1.994
ASSI ( 3542)
    (( segid *BrD * and resid 109 and name HE2 ))
    (( segid *BrD * and resid 109 and name HG1 ))
      2.700  1.800   1.800 peak    3542 weight   0.11000E+01 volume   0.22719E+03 ppm1    3.027 ppm2   1.411
ASSI ( 3552)
    (( segid *BrD * and resid 109 and name HE1 ))
    (( segid *BrD * and resid 109 and name HG1 ))
      2.600  1.700   1.700 peak    3552 weight   0.11000E+01 volume   0.23490E+03 ppm1    3.176 ppm2   1.411
ASSI ( 3562)
    (( segid *BrD * and resid 109 and name HD1 ))
    (( segid *BrD * and resid 109 and name HE1 ))
      2.700  1.800   1.800 peak    3562 weight   0.11000E+01 volume   0.22693E+03 ppm1    1.994 ppm2   3.195
ASSI ( 3602)
    (( segid *BrD * and resid 86 and name HE2 ))
    (( segid *BrD * and resid 86 and name HG2 ))
      2.900  2.100   2.100 peak    3602 weight   0.11000E+01 volume   0.13036E+03 ppm1    3.080 ppm2   0.766
ASSI ( 3612)
    (( segid *BrD * and resid 86 and name HD1 ))
    (( segid *BrD * and resid 86 and name HG2 ))
      2.300  1.300   1.300 peak    3612 weight   0.11000E+01 volume   0.49629E+03 ppm1    1.896 ppm2   0.765
ASSI ( 3622)
    (( segid *BrD * and resid 86 and name HD1 ))
    (( segid *BrD * and resid 86 and name HE1 ))
      2.600  1.700   1.700 peak    3622 weight   0.11000E+01 volume   0.24556E+03 ppm1    1.892 ppm2   3.093
```

TABLE 2-continued

Unambigous NOE-derived Inter-proton Distance Restraints

```
ASSI ( 3632)
  ( ( segid *BrD * and resid 86 and name HA   ) )
  ( ( segid *BrD * and resid 86 and name HG1  ) )
     2.800  2.000   2.000 peak    3632 weight   0.11000E+01 volume   0.14893E+03 ppm1    4.806 ppm2    1.695
ASSI ( 3682)
  ( ( segid *BrD * and resid 8 and name HG1  ) )
  ( ( segid *BrD * and resid 8 and name HD1  ) )
     2.000  1.000   1.000 peak    3682 weight   0.11000E+01 volume   0.11498E+04 ppm1    2.635 ppm2    4.436
ASSI ( 3692)
  ( ( segid *BrD * and resid 8 and name HG1  ) )
  ( ( segid *BrD * and resid 8 and name HD2  ) )
     2.100  1.100   1.100 peak    3692 weight   0.11000E+01 volume   0.87712E+03 ppm1    2.635 ppm2    4.286
ASSI ( 3702)
  ( ( segid *BrD * and resid 8 and name HB2  ) )
  ( ( segid *BrD * and resid 8 and name HA   ) )
     2.600  1.700   1.700 peak    3702 weight   0.11000E+01 volume   0.24482E+03 ppm1    2.487 ppm2    5.021
ASSI ( 3712)
  ( ( segid *BrD * and resid 8 and name HB1  ) )
  ( ( segid *BrD * and resid 8 and name HA   ) )
     2.400  1.400   1.400 peak    3712 weight   0.11000E+01 volume   0.36862E+03 ppm1    2.831 ppm2    5.021
ASSI ( 3722)
  ( ( segid *BrD * and resid 8 and name HD1  ) )
  ( ( segid *BrD * and resid 7 and name HA   ) )
     2.100  1.100   1.100 peak    3722 weight   0.11000E+01 volume   0.89203E+03 ppm1    4.407 ppm2    5.144
ASSI ( 3732)
  ( ( segid *BrD * and resid 8 and name HD2  ) )
  ( ( segid *BrD * and resid 7 and name HA   ) )
     2.100  1.100   1.100 peak    3732 weight   0.11000E+01 volume   0.93259E+03 ppm1    4.263 ppm2    5.144
ASSI ( 3752)
  ( ( segid *BrD * and resid 44 and name HA   ) )
  ( ( segid *BrD * and resid 44 and name HB1  ) )
     2.400  1.400   1.400 peak    3752 weight   0.11000E+01 volume   0.42716E+03 ppm1    5.098 ppm2    2.973
ASSI ( 3762)
  ( ( segid *BrD * and resid 44 and name HA   ) )
  ( ( segid *BrD * and resid 44 and name HB2  ) )
     2.600  1.700   1.700 peak    3762 weight   0.11000E+01 volume   0.27521E+03 ppm1    5.098 ppm2    2.636
ASSI ( 3792)
  ( ( segid *BrD * and resid 44 and name HB2  ) )
  ( ( segid *BrD * and resid 44 and name HD1  ) )
     2.800  2.000   2.000 peak    3792 weight   0.11000E+01 volume   0.16780E+03 ppm1    2.631 ppm2    4.337
ASSI ( 3802)
  ( ( segid *BrD * and resid 44 and name HB1  ) )
  ( ( segid *BrD * and resid 44 and name HD1  ) )
     2.200  2.600   2.300 peak    3802 weight   0.11000E+01 volume   0.70033E+02 ppm1    2.981 ppm2    4.337
ASSI ( 3822)
  ( ( segid *BrD * and resid 44 and name HG1  ) )
  ( ( segid *BrD * and resid 44 and name HA   ) )
     2.900  2.100   2.100 peak    3822 weight   0.11000E+01 volume   0.14259E+03 ppm1    2.729 ppm2    5.114
ASSI ( 3832)
  ( ( segid *BrD * and resid 44 and name HG2  ) )
  ( ( segid *BrD * and resid 44 and name HA   ) )
     2.700  1.800   1.800 peak    3832 weight   0.11000E+01 volume   0.22601E+03 ppm1    2.645 ppm2    5.114
ASSI ( 3842)
  ( ( segid *BrD * and resid 41 and name HA   ) )
  ( ( segid *BrD * and resid 41 and name HB   ) )
     1.900  0.900   0.900 peak    3842 weight   0.11000E+01 volume   0.19310E+04 ppm1    4.657 ppm2    4.899
ASSI ( 3882)
  ( ( segid *BrD * and resid 103 and name HG2 ) )
  ( ( segid *BrD * and resid 103 and name HA  ) )
     2.800  2.000   2.000 peak    3882 weight   0.11000E+01 volume   0.14970E+03 ppm1    2.519 ppm2    3.789
ASSI ( 3892)
  ( ( segid *BrD * and resid 103 and name HG1 ) )
  ( ( segid *BrD * and resid 103 and name HA  ) )
     2.900  2.100   2.100 peak    3892 weight   0.11000E+01 volume   0.14619E+03 ppm1    2.598 ppm2    3.789
ASSI ( 3912)
  ( ( segid *BrD * and resid 103 and name HG2 ) )
  ( ( segid *BrD * and resid 103 and name HB1 ) )
     3.000  2.200   2.200 peak    3912 weight   0.11000E+01 volume   0.10641E+03 ppm1    2.519 ppm2    2.346
ASSI ( 3922)
  ( ( segid *BrD * and resid 103 and name HG1 ) )
  ( ( segid *BrD * and resid 103 and name HB1 ) )
     3.200  2.600   2.300 peak    3922 weight   0.11000E+01 volume   0.80668E+02 ppm1    2.598 ppm2    2.346
ASSI ( 3942)
  ( ( segid *BrD * and resid 48 and name HA   ) )
  ( ( segid *BrD * and resid 48 and name HG1  ) )
     3.100  2.400   2.400 peak    3942 weight   0.11000E+01 volume   0.93117E+02 ppm1    4.803 ppm2    2.940
```

TABLE 2-continued

Unambigous NOE-derived Inter-proton Distance Restraints

```
ASSI ( 3952)
    ( ( segid *BrD * and resid 48 and name HA   ) )
    ( ( segid *BrD * and resid 48 and name HG2 ) )
       3.000  2.200   2.200 peak    3952 weight   0.11000E+01 volume  0.10971E+03 ppm1    4.803 ppm2   2.851
ASSI ( 3982)
    (   segid *BrD * and resid 50 and name HD1%)
    ( ( segid *BrD * and resid 50 and name HA   ) )
       2.300  1.300   1.300 peak    3982 weight   0.11000E+01 volume  0.51678E+03 ppm1    1.155 ppm2   4.518
ASSI ( 4012)
    (   segid *BrD * and resid 110 and name HD1%)
    ( ( segid *BrD * and resid 110 and name HG12) )
       2.600  1.700   1.700 peak    4012 weight   0.11000E+01 volume  0.27804E+03 ppm1    1.154 ppm2   1.652
ASSI ( 4022)
    (   segid *BrD * and resid 110 and name HG2%)
    ( ( segid *BrD * and resid 110 and name HG12) )
       2.500  1.600   1.600 peak    4022 weight   0.11000E+01 volume  0.35399E+03 ppm1    1.253 ppm2   1.651
ASSI ( 4032)
    ( ( segid *BrD * and resid 110 and name HB   ) )
    ( ( segid *BrD * and resid 110 and name HG12) )
       3.300  2.700   2.200 peak    4032 weight   0.11000E+01 volume  0.60399E+02 ppm1    2.338 ppm2   1.651
ASSI ( 4052)
    ( ( segid *BrD * and resid 24 and name HB1 ) )
    ( ( segid *BrD * and resid 24 and name HG1 ) )
       2.600  1.700   1.700 peak    4052 weight   0.11000E+01 volume  0.27715E+03 ppm1    3.076 ppm2   3.453
ASSI ( 4062)
    ( ( segid *BrD * and resid 80 and name HD1 ) )
    ( ( segid *BrD * and resid 80 and name HG1 ) )
       2.400  1.400   1.400 peak    4062 weight   0.11000E+01 volume  0.37330E+03 ppm1    3.956 ppm2   2.347
ASSI ( 4072)
    ( ( segid *BrD * and resid 80 and name HD1 ) )
    ( ( segid *BrD * and resid 80 and name HB1 ) )
       2.700  1.800   1.800 peak    4072 weight   0.11000E+01 volume  0.22342E+03 ppm1    3.956 ppm2   2.573
ASSI ( 4112)
    ( ( segid *BrD * and resid 101 and name HA   ) )
    ( ( segid *BrD * and resid 101 and name HB   ) )
       2.600  1.700   1.700 peak    4112 weight   0.11000E+01 volume  0.25152E+03 ppm1    4.263 ppm2   2.535
ASSI ( 4122)
    ( ( segid *BrD * and resid 101 and name HA   ) )
    ( ( segid *BrD * and resid 101 and name HG11) )
       2.600  1.700   1.700 peak    4122 weight   0.11000E+01 volume  0.23036E+03 ppm1    4.263 ppm2   2.469
ASSI ( 4132)
    ( ( segid *BrD * and resid 101 and name HA   ) )
    ( ( segid *BrD * and resid 101 and name HG12) )
       2.500  1.600   1.600 peak    4132 weight   0.11000E+01 volume  0.31941E+03 ppm1    4.261 ppm2   1.806
ASSI ( 4142)
    (   segid *BrD * and resid 38 and name HG1%)
    ( ( segid *BrD * and resid 38 and name HA   ) )
       2.300  1.300   1.300 peak    4142 weight   0.11000E+01 volume  0.50428E+03 ppm1    1.058 ppm2   4.168
ASSI ( 4162)
    (   segid *BrD * and resid 81 and name HG2%)
    ( ( segid *BrD * and resid 81 and name HA   ) )
       2.400  1.400   1.400 peak    4162 weight   0.11000E+01 volume  0.38926E+03 ppm1    0.761 ppm2   3.716
ASSI ( 4182)
    (   segid *BrD * and resid 81 and name HG1%)
    ( ( segid *BrD * and resid 81 and name HA   ) )
       2.400  1.400   1.400 peak    4182 weight   0.11000E+01 volume  0.43496E+03 ppm1    1.059 ppm2   3.716
ASSI ( 4212)
    ( ( segid *BrD * and resid 69 and name HB   ) )
    ( ( segid *BrD * and resid 69 and name HA   ) )
       2.200  1.200   1.200 peak    4212 weight   0.11000E+01 volume  0.67869E+03 ppm1    2.929 ppm2   4.696
ASSI ( 4222)
    ( ( segid *BrD * and resid 18 and name HA   ) )
    ( ( segid *BrD * and resid 18 and name HB1 ) )
       2.800  2.000   2.000 peak    4222 weight   0.11000E+01 volume  0.15123E+03 ppm1    3.866 ppm2   2.131
ASSI ( 4272)
    ( ( segid *BrD * and resid 116 and name HB   ) )
    (   segid *BrD * and resid 116 and name HD1%)
       2.500  1.600   1.600 peak    4272 weight   0.11000E+01 volume  0.31982E+03 ppm1    2.409 ppm2   1.399
ASSI ( 4282)
    ( ( segid *BrD * and resid 110 and name HA   ) )
    ( ( segid *BrD * and resid 110 and name HG11) )
       3.100  2.400   2.400 peak    4282 weight   0.11000E+01 volume  0.90397E+02 ppm1    2.338 ppm2   1.718
ASSI ( 4302)
    ( ( segid *BrD * and resid 50 and name HA   ) )
    ( ( segid *BrD * and resid 50 and name HG11) )
       2.600  1.700   1.700 peak    4302 weight   0.11000E+01 volume  0.24102E+03 ppm1    4.506 ppm2   1.409
```

TABLE 2-continued

Unambigous NOE-derived Inter-proton Distance Restraints

```
ASSI ( 4322)
   ( ( segid *BrD * and resid 50 and name HB   ) )
   ( ( segid *BrD * and resid 50 and name HG12) )
     2.700  1.800   1.800 peak    4322 weight   0.11000E+01 volume   0.20938E+03 ppm1   1.797 ppm2   0.840
ASSI ( 4332)
   ( ( segid *BrD * and resid 50 and name HB   ) )
   ( ( segid *BrD * and resid 50 and name HG11) )
     2.700  1.800   1.800 peak    4332 weight   0.11000E+01 volume   0.20876E+03 ppm1   1.797 ppm2   1.407
ASSI ( 4342)
   ( ( segid *BrD * and resid 50 and name HB   ) )
   ( ( segid *BrD * and resid 50 and name HA   ) )
     3.000  2.200   2.200 peak    4342 weight   0.11000E+01 volume   0.11875E+03 ppm1   1.797 ppm2   4.516
ASSI ( 4382)
   ( ( segid *BrD * and resid 21 and name HA   ) )
   ( ( segid *BrD * and resid 21 and name HB   ) )
     2.700  1.800   1.800 peak    4382 weight   0.11000E+01 volume   0.19816E+03 ppm1   4.359 ppm2   2.515
ASSI ( 4392)
   ( ( segid *BrD * and resid 21 and name HA   ) )
   ( ( segid *BrD * and resid 21 and name HG12) )
     2.600  1.700   1.700 peak    4392 weight   0.11000E+01 volume   0.25295E+03 ppm1   4.358 ppm2   1.653
ASSI ( 4402)
   ( ( segid *BrD * and resid 21 and name HA   ) )
   ( ( segid *BrD * and resid 21 and name HG11) )
     2.600  1.700   1.700 peak    4402 weight   0.11000E+01 volume   0.24995E+03 ppm1   4.358 ppm2   2.357
ASSI ( 4412)
   ( ( segid *BrD * and resid 21 and name HB   ) )
   ( ( segid *BrD * and resid 21 and name HG11) )
     2.900  2.100   2.100 peak    4412 weight   0.11000E+01 volume   0.13199E+03 ppm1   2.487 ppm2   2.354
ASSI ( 4472)
   ( ( segid *BrD * and resid 21 and name HG12) )
   ( ( segid *BrD * and resid 21 and name HB   ) )
     2.800  2.000   2.000 peak    4472 weight   0.11000E+01 volume   0.17027E+03 ppm1   1.642 ppm2   2.511
ASSI ( 4482)
   ( ( segid *BrD * and resid 21 and name HG12) )
   ( ( segid *BrD * and resid 21 and name HG11) )
     2.200  1.200   1.200 peak    4482 weight   0.11000E+01 volume   0.65087E+03 ppm1   1.642 ppm2   2.357
ASSI ( 4502)
   (   segid *BrD * and resid 21 and name HG2%)
   ( ( segid *BrD * and resid 21 and name HA   ) )
     2.400  1.400   1.400 peak    4502 weight   0.11000E+01 volume   0.39582E+03 ppm1   1.596 ppm2   4.369
ASSI ( 4512)
   ( ( segid *BrD * and resid 36 and name HG1  ) )
   ( ( segid *BrD * and resid 36 and name HB2  ) )
     2.100  1.100   1.100 peak    4512 weight   0.11000E+01 volume   0.10618E+04 ppm1   2.781 ppm2   2.342
ASSI ( 4562)
   ( ( segid *BrD * and resid 9 and name HG1  ) )
   ( ( segid *BrD * and resid 9 and name HA   ) )
     2.800  2.000   2.000 peak    4562 weight   0.11000E+01 volume   0.15274E+03 ppm1   2.236 ppm2   4.940
ASSI ( 4582)
   ( ( segid *BrD * and resid 9 and name HA   ) )
   ( ( segid *BrD * and resid 9 and name HB2  ) )
     2.400  1.400   1.400 peak    4582 weight   0.11000E+01 volume   0.39636E+03 ppm1   4.953 ppm2   2.285
ASSI ( 4592)
   ( ( segid *BrD * and resid 35 and name HB2  ) )
   ( ( segid *BrD * and resid 35 and name HG1  ) )
     2.600  1.700   1.700 peak    4592 weight   0.11000E+01 volume   0.27554E+03 ppm1   2.781 ppm2   3.447
ASSI ( 4602)
   ( ( segid *BrD * and resid 35 and name HB1  ) )
   ( ( segid *BrD * and resid 35 and name HG1  ) )
     3.000  2.200   2.200 peak    4602 weight   0.11000E+01 volume   0.10522E+03 ppm1   2.838 ppm2   3.447
ASSI ( 4632)
   (   segid *BrD * and resid 73 and name HD1%)
   ( ( segid *BrD * and resid 73 and name HG   ) )
     2.100  1.100   1.100 peak    4632 weight   0.11000E+01 volume   0.81939E+03 ppm1   1.549 ppm2   2.368
ASSI ( 4642)
   ( ( segid *BrD * and resid 56 and name HA   ) )
   ( ( segid *BrD * and resid 56 and name HB1  ) )
     2.500  1.600   1.600 peak    4642 weight   0.11000E+01 volume   0.31507E+03 ppm1   4.606 ppm2   2.694
ASSI ( 4652)
   (   segid *BrD * and resid 22 and name HD2%)
   ( ( segid *BrD * and resid 22 and name HB1  ) )
     2.500  1.600   1.600 peak    4652 weight   0.11000E+01 volume   0.35307E+03 ppm1   1.600 ppm2   2.702
ASSI ( 4662)
   ( ( segid *BrD * and resid 22 and name HA   ) )
   ( ( segid *BrD * and resid 22 and name HG   ) )
     2.400  1.400   1.400 peak    4662 weight   0.11000E+01 volume   0.43065E+03 ppm1   4.704 ppm2   2.360
```

TABLE 2-continued

Unambigous NOE-derived Inter-proton Distance Restraints

```
ASSI ( 4722)
   (( segid *BrD * and resid 14 and name HA    ))
   (( segid *BrD * and resid 14 and name HB1   ))
     2.400  1.400   1.400 peak    4722 weight    0.11000E+01 volume   0.40350E+03 ppm1    4.655 ppm2    2.464
ASSI ( 4732)
   (( segid *BrD * and resid 14 and name HA    ))
   (( segid *BrD * and resid 14 and name HB2   ))
     2.500  1.600   1.600 peak    4732 weight    0.11000E+01 volume   0.34201E+03 ppm1    4.655 ppm2    2.159
ASSI ( 4742)
   (( segid *BrD * and resid 14 and name HA    ))
   (( segid *BrD * and resid 14 and name HG    ))
     2.800  2.000   2.000 peak    4742 weight    0.11000E+01 volume   0.16298E+03 ppm1    4.655 ppm2    2.062
ASSI ( 4752)
   (  segid *BrD * and resid 14 and name HD2%)
   (( segid *BrD * and resid 14 and name HB2   ))
     2.900  2.100   2.100 peak    4752 weight    0.11000E+01 volume   0.12176E+03 ppm1    1.401 ppm2    2.255
ASSI ( 4762)
   (  segid *BrD * and resid 14 and name HD2%)
   (( segid *BrD * and resid 14 and name HB1   ))
     2.200  1.200   1.200 peak    4762 weight    0.11000E+01 volume   0.78049E+03 ppm1    1.401 ppm2    2.466
ASSI ( 4782)
   (( segid *BrD * and resid 24 and name HB2   ))
   (( segid *BrD * and resid 24 and name HG1   ))
     2.700  1.800   1.800 peak    4782 weight    0.11000E+01 volume   0.20235E+03 ppm1    2.989 ppm2    3.453
ASSI ( 4812)
   (( segid *BrD * and resid 25 and name HA    ))
   (  segid *BrD * and resid 25 and name HG2%)
     2.600  1.700   1.700 peak    4812 weight    0.11000E+01 volume   0.28433E+03 ppm1    4.412 ppm2    1.637
ASSI ( 4822)
   (  segid *BrD * and resid 25 and name HG1%)
   (( segid *BrD * and resid 25 and name HA    ))
     2.300  1.300   1.300 peak    4822 weight    0.11000E+01 volume   0.50491E+03 ppm1    1.796 ppm2    4.427
ASSI ( 4832)
   (( segid *BrD * and resid 30 and name HB1   ))
   (( segid *BrD * and resid 30 and name HA    ))
     2.700  1.800   1.800 peak    4832 weight    0.11000E+01 volume   0.18839E+03 ppm1    4.907 ppm2    5.445
ASSI ( 4852)
   (( segid *BrD * and resid 30 and name HA    ))
   (( segid *BrD * and resid 30 and name HB2   ))
     2.900  2.100   2.100 peak    4852 weight    0.11000E+01 volume   0.13412E+03 ppm1    5.444 ppm2    4.533
ASSI ( 4862)
   (( segid *BrD * and resid 104 and name HE1  ))
   (( segid *BrD * and resid 104 and name HD1  ))
     1.900  0.900   0.900 peak    4862 weight    0.11000E+01 volume   0.17529E+04 ppm1    3.571 ppm2    2.290
ASSI ( 4912)
   (( segid *BrD * and resid 57 and name HG1   ))
   (( segid *BrD * and resid 57 and name HA    ))
     2.400  1.400   1.400 peak    4912 weight    0.11000E+01 volume   0.42230E+03 ppm1    2.110 ppm2    4.800
ASSI ( 4922)
   (( segid *BrD * and resid 97 and name HE1   ))
   (( segid *BrD * and resid 97 and name HG2   ))
     2.200  1.200   1.200 peak    4922 weight    0.11000E+01 volume   0.69710E+03 ppm1    3.569 ppm2    2.172
ASSI ( 4932)
   (( segid *BrD * and resid 109 and name HA   ))
   (( segid *BrD * and resid 109 and name HB2  ))
     2.000  1.000   1.000 peak    4932 weight    0.11000E+01 volume   0.10760E+04 ppm1    4.653 ppm2    2.149
ASSI ( 4942)
   (( segid *BrD * and resid 109 and name HA   ))
   (( segid *BrD * and resid 109 and name HB1  ))
     2.000  1.000   1.000 peak    4942 weight    0.11000E+01 volume   0.13416E+04 ppm1    4.653 ppm2    2.321
ASSI ( 4962)
   (( segid *BrD * and resid 109 and name HB2  ))
   (( segid *BrD * and resid 109 and name HG1  ))
     2.500  1.600   1.600 peak    4962 weight    0.11000E+01 volume   0.29632E+03 ppm1    2.141 ppm2    1.417
ASSI ( 4972)
   (( segid *BrD * and resid 109 and name HB1  ))
   (( segid *BrD * and resid 109 and name HG1  ))
     2.500  1.600   1.600 peak    4972 weight    0.11000E+01 volume   0.36408E+03 ppm1    2.334 ppm2    1.417
ASSI ( 4982)
   (( segid *BrD * and resid 109 and name HG1  ))
   (( segid *BrD * and resid 109 and name HA   ))
     2.700  1.800   1.800 peak    4982 weight    0.11000E+01 volume   0.22259E+03 ppm1    1.399 ppm2    4.639
ASSI ( 5002)
   (( segid *BrD * and resid 109 and name HE2  ))
   (( segid *BrD * and resid 109 and name HA   ))
     2.800  2.000   2.000 peak    5002 weight    0.11000E+01 volume   0.16510E+03 ppm1    3.029 ppm2    4.639
```

TABLE 2-continued

Unambigous NOE-derived Inter-proton Distance Restraints

```
ASSI ( 5012)
     ( ( segid *BrD * and resid 86 and name HG2 ) )
     ( ( segid *BrD * and resid 86 and name HA   ) )
       2.800  2.000   2.000 peak    5012 weight   0.11000E+01 volume   0.18063E+03 ppm1    0.761 ppm2    4.812
ASSI ( 5022)
     (  segid *BrD * and resid 41 and name HG2%)
     ( ( segid *BrD * and resid 41 and name HA   ) )
       2.200  1.200   1.200 peak    5022 weight   0.11000E+01 volume   0.76022E+03 ppm1    1.844 ppm2    4.671
ASSI ( 5032)
     (  segid *BrD * and resid 41 and name HG2%)
     ( ( segid *BrD * and resid 41 and name HB   ) )
       2.000  1.000   1.000 peak    5032 weight   0.11000E+01 volume   0.12138E+04 ppm1    1.845 ppm2    4.901
ASSI ( 5042)
     (  segid *BrD * and resid 58 and name HG2%)
     ( ( segid *BrD * and resid 58 and name HA   ) )
       2.000  1.000   1.000 peak    5042 weight   0.11000E+01 volume   0.10840E+04 ppm1    1.649 ppm2    4.451
ASSI ( 5052)
     (  segid *BrD * and resid 58 and name HG2%)
     ( ( segid *BrD * and resid 58 and name HB   ) )
       1.900  0.900   0.900 peak    5052 weight   0.11000E+01 volume   0.14547E+04 ppm1    1.649 ppm2    4.705
ASSI ( 5062)
     (  segid *BrD * and resid 17 and name HG2%)
     ( ( segid *BrD * and resid 17 and name HA   ) )
       2.300  1.300   1.300 peak    5062 weight   0.11000E+01 volume   0.54601E+03 ppm1    1.747 ppm2    4.542
ASSI ( 5072)
     (  segid *BrD * and resid 17 and name HG2%)
     ( ( segid *BrD * and resid 17 and name HB   ) )
       2.100  1.100   1.100 peak    5072 weight   0.11000E+01 volume   0.92706E+03 ppm1    1.745 ppm2    4.861
ASSI ( 5082)
     (  segid *BrD * and resid 83 and name HG2%)
     ( ( segid *BrD * and resid 83 and name HB   ) )
       2.100  1.100   1.100 peak    5082 weight   0.11000E+01 volume   0.10099E+04 ppm1    1.893 ppm2    4.805
ASSI ( 5092)
     (  segid *BrD * and resid 83 and name HG2%)
     ( ( segid *BrD * and resid 83 and name HA   ) )
       2.200  1.200   1.200 peak    5092 weight   0.11000E+01 volume   0.64890E+03 ppm1    1.894 ppm2    4.460
ASSI ( 5122)
     ( ( segid *BrD * and resid 37 and name HA   ) )
     ( ( segid *BrD * and resid 37 and name HG1  ) )
       2.800  2.000   2.000 peak    5122 weight   0.11000E+01 volume   0.14935E+03 ppm1    4.853 ppm2    2.725
ASSI ( 5132)
     ( ( segid *BrD * and resid 37 and name HA   ) )
     ( ( segid *BrD * and resid 37 and name HG2  ) )
       3.200  2.600   2.300 peak    5132 weight   0.11000E+01 volume   0.80336E+02 ppm1    4.853 ppm2    2.587
ASSI ( 5162)
     ( ( segid *BrD * and resid 37 and name HG2  ) )
     ( ( segid *BrD * and resid 37 and name HD1  ) )
       2.300  1.300   1.300 peak    5162 weight   0.11000E+01 volume   0.49428E+03 ppm1    2.585 ppm2    4.291
ASSI ( 5172)
     ( ( segid *BrD * and resid 37 and name HG1  ) )
     ( ( segid *BrD * and resid 37 and name HD1  ) )
       2.500  1.600   1.600 peak    5172 weight   0.11000E+01 volume   0.34945E+03 ppm1    2.733 ppm2    4.290
ASSI ( 5182)
     ( ( segid *BrD * and resid 37 and name HG1  ) )
     ( ( segid *BrD * and resid 37 and name HB1  ) )
       2.300  1.300   1.300 peak    5182 weight   0.11000E+01 volume   0.51291E+03 ppm1    2.733 ppm2    2.961
ASSI ( 5192)
     ( ( segid *BrD * and resid 37 and name HG2  ) )
     ( ( segid *BrD * and resid 37 and name HB1  ) )
       2.300  1.300   1.300 peak    5192 weight   0.11000E+01 volume   0.56233E+03 ppm1    2.584 ppm2    2.961
ASSI ( 5202)
     ( ( segid *BrD * and resid 37 and name HB1  ) )
     ( ( segid *BrD * and resid 37 and name HA   ) )
       2.200  1.200   1.200 peak    5202 weight   0.11000E+01 volume   0.64791E+03 ppm1    2.935 ppm2    4.858
ASSI ( 5212)
     ( ( segid *BrD * and resid 37 and name HB2  ) )
     ( ( segid *BrD * and resid 37 and name HA   ) )
       2.400  1.400   1.400 peak    5212 weight   0.11000E+01 volume   0.38926E+03 ppm1    2.290 ppm2    4.858
ASSI ( 5222)
     ( ( segid *BrD * and resid 37 and name HB1  ) )
     ( ( segid *BrD * and resid 37 and name HD1  ) )
       3.600  3.200   1.900 peak    5222 weight   0.11000E+01 volume   0.35025E+02 ppm1    2.935 ppm2    4.298
ASSI ( 5272)
     ( ( segid *BrD * and resid 53 and name HD1  ) )
     ( ( segid *BrD * and resid 52 and name HA   ) )
       3.300  2.700   2.200 peak    5272 weight   0.11000E+01 volume   0.65454E+02 ppm1    4.214 ppm2    5.584
```

TABLE 2-continued

Unambigous NOE-derived Inter-proton Distance Restraints

```
ASSI ( 5272)
    ( ( segid *BrD * and resid 53 and name HB1 ) )
    ( ( segid *BrD * and resid 53 and name HA   ) )
    2.200  1.200   1.200 peak    5282 weight   0.11000E+01 volume  0.77735E+03 ppm1   2.780 ppm2   4.686
ASSI ( 5292)
    ( ( segid *BrD * and resid 53 and name HG2 ) )
    ( ( segid *BrD * and resid 53 and name HA   ) )
    2.900  2.100   2.100 peak    5292 weight   0.11000E+01 volume  0.13443E+03 ppm1   2.487 ppm2   4.687
ASSI ( 5302)
    ( ( segid *BrD * and resid 51 and name HA   ) )
    ( ( segid *BrD * and resid 51 and name HG2 ) )
    2.300  1.300   1.300 peak    5302 weight   0.11000E+01 volume  0.54723E+03 ppm1   4.459 ppm2   1.796
ASSI ( 5312)
    ( ( segid *BrD * and resid 51 and name HA   ) )
    ( ( segid *BrD * and resid 51 and name HG1 ) )
    2.400  1.400   1.400 peak    5312 weight   0.11000E+01 volume  0.38819E+03 ppm1   4.459 ppm2   1.946
ASSI ( 5332)
    ( ( segid *BrD * and resid 51 and name HB1 ) )
    ( ( segid *BrD * and resid 51 and name HA   ) )
    2.700  1.800   1.800 peak    5332 weight   0.11000E+01 volume  0.20757E+03 ppm1   1.945 ppm2   4.468
ASSI ( 5342)
    ( ( segid *BrD * and resid 51 and name HB2 ) )
    ( ( segid *BrD * and resid 51 and name HA   ) )
    2.400  1.400   1.400 peak    5342 weight   0.11000E+01 volume  0.37628E+03 ppm1   1.795 ppm2   4.468
ASSI ( 5372)
    ( ( segid *BrD * and resid 51 and name HG1 ) )
    ( ( segid *BrD * and resid 51 and name HD1 ) )
    2.800  2.000   2.00  peak    5372 weight   0.11000E+01 volume  0.16452E+03 ppm1   1.946 ppm2   3.606
ASSI ( 5382)
    ( ( segid *BrD * and resid 51 and name HG2 ) )
    ( ( segid *BrD * and resid 51 and name HD1 ) )
    2.400  1.400   1.400 peak    5382 weight   0.11000E+01 volume  0.40668E+03 ppm1   1.796 ppm2   3.606
ASSI ( 5392)
    ( ( segid *BrD * and resid 51 and name HD1 ) )
    ( ( segid *BrD * and resid 51 and name HB1 ) )
    2.500  1.600   1.600 peak    5392 weight   0.11000E+01 volume  0.36659E+03 ppm1   3.577 ppm2   1.945
ASSI ( 5402)
    ( ( segid *BrD * and resid 51 and name HD1 ) )
    ( ( segid *BrD * and resid 51 and name HB2 ) )
    2.400  1.400   1.400 peak    5402 weight   0.11000E+01 volume  0.38417E+03 ppm1   3.577 ppm2   1.795
ASSI ( 5412)
    ( ( segid *BrD * and resid 51 and name HD1 ) )
    ( ( segid *BrD * and resid 51 and name HA   ) )
    2.700  1.800   1.800 peak    5412 weight   0.11000E+01 volume  0.20141E+03 ppm1   3.578 ppm2   4.463
ASSI ( 5422)
    ( ( segid *BrD * and resid 52 and name HA   ) )
    ( ( segid *BrD * and resid 52 and name HB1 ) )
    2.500  1.600   1.600 peak    5422 weight   0.11000E+01 volume  0.31370E+03 ppm1   5.592 ppm2   3.654
ASSI ( 5432)
    ( ( segid *BrD * and resid 52 and name HA   ) )
    ( ( segid *BrD * and resid 52 and name HB2 ) )
    2.800  2.000   2.000 peak    5432 weight   0.11000E+01 volume  0.16779E+03 ppm1   5.592 ppm2   3.533
ASSI ( 5462)
    ( ( segid *BrD * and resid 75 and name HG2 ) )
    ( ( segid *BrD * and resid 75 and name HA   ) )
    2.700  1.800   1.800 peak    5462 weight   0.11000E+01 volume  0.19830E+03 ppm1   3.228 ppm2   4.517
ASSI ( 5482)
    ( ( segid *BrD * and resid 75 and name HG2 ) )
    ( ( segid *BrD * and resid 75 and name HB2 ) )
    2.600  1.700   1.700 peak    5482 weight   0.11000E+01 volume  0.27353E+03 ppm1   3.227 ppm2   2.847
ASSI ( 5492)
    ( ( segid *BrD * and resid 75 and name HG1 ) )
    ( ( segid *BrD * and resid 75 and name HB2 ) )
    2.300  1.300   1.300 peak    5492 weight   0.11000E+01 volume  0.48028E+03 ppm1   3.523 ppm2   2.847
ASSI ( 5502)
    ( ( segid *BrD * and resid 75 and name HG1 ) )
    ( ( segid *BrD * and resid 75 and name HB1 ) )
    2.700  1.800   1.800 peak    5502 weight   0.11000E+01 volume  0.21586E+03 ppm1   3.523 ppm2   2.931
ASSI ( 5512)
    ( ( segid *BrD * and resid 75 and name HG2 ) )
    ( ( segid *BrD * and resid 75 and name HB1 ) )
    2.700  1.800   1.800 peak    5512 weight   0.11000E+01 volume  0.21836E+03 ppm1   3.227 ppm2   2.931
ASSI ( 5522)
    ( ( segid *BrD * and resid 75 and name HA   ) )
    ( ( segid *BrD * and resid 75 and name HG1 ) )
    2.800  2.000   2.000 peak    5522 weight   0.11000E+01 volume  0.16121E+03 ppm1   4.509 ppm2   3.530
```

TABLE 2-continued

Unambigous NOE-derived Inter-proton Distance Restraints

```
ASSI ( 5542)
    ( ( segid *BrD * and resid 19 and name HB2 ) )
    ( ( segid *BrD * and resid 16 and name HA   ) )
     2.900  2.100   2.100  peak     5542  weight    0.11000E+01  volume   0.12463E+03  ppm1    1.989  ppm2    4.807
ASSI ( 5552)
    ( ( segid *BrD * and resid 19 and name HB2 ) )
    ( ( segid *BrD * and resid 19 and name HA   ) )
     2.600  1.700   1.700  peak     5552  weight    0.11000E+01  volume   0.27005E+03  ppm1    1.989  ppm2    4.297
ASSI ( 5582)
    ( ( segid *BrD * and resid 54 and name HA   ) )
    ( ( segid *BrD * and resid 54 and name HB2 ) )
     3.000  2.200   2.200  peak     5582  weight    0.11000E+01  volume   0.10290E+03  ppm1    5.543  ppm2    1.964
ASSI ( 5592)
    ( ( segid *BrD * and resid 97 and name HG2 ) )
    ( ( segid *BrD * and resid 97 and name HE1 ) )
     3.100  2.400   2.400  peak     5592  weight    0.11000E+01  volume   0.89029E+02  ppm1    2.436  ppm2    3.572
ASSI ( 5622)
    ( ( segid *BrD * and resid 89 and name HG2 ) )
    ( ( segid *BrD * and resid 89 and name HA   ) )
     2.400  1.400   1.400  peak     5622  weight    0.11000E+01  volume   0.39102E+03  ppm1    3.137  ppm2    4.911
ASSI ( 5632)
    ( ( segid *BrD * and resid 59 and name HG1 ) )
    ( ( segid *BrD * and resid 59 and name HA   ) )
     3.000  2.200   2.200  peak     5632  weight    0.11000E+01  volume   0.11482E+03  ppm1    3.228  ppm2    4.911
ASSI ( 5642)
    ( ( segid *BrD * and resid 13 and name HG2 ) )
    ( ( segid *BrD * and resid 13 and name HA   ) )
     2.300  1.300   1.300  peak     5642  weight    0.11000E+01  volume   0.56353E+03  ppm1    2.978  ppm2    4.775
ASSI ( 5652)
    ( ( segid *BrD * and resid 13 and name HG1 ) )
    ( ( segid *BrD * and resid 13 and name HA   ) )
     2.800  2.000   2.000  peak     5652  weight    0.11000E+01  volume   0.18150E+03  ppm1    3.131  ppm2    4.775
ASSI ( 5672)
    ( ( segid *BrD * and resid 57 and name HA   ) )
    ( ( segid *BrD * and resid 57 and name HD1 ) )
     2.600  1.700   1.700  peak     5672  weight    0.11000E+01  volume   0.27608E+03  ppm1    4.805  ppm2    2.387
ASSI ( 5682)
    ( ( segid *BrD * and resid 57 and name HA   ) )
    ( ( segid *BrD * and resid 57 and name HG2 ) )
     2.900  2.100   2.100  peak     5682  weight    0.11000E+01  volume   0.12195E+03  ppm1    4.805  ppm2    2.016
ASSI ( 5712)
    ( ( segid *BrD * and resid 57 and name HB2 ) )
    ( ( segid *BrD * and resid 57 and name HA   ) )
     2.500  1.600   1.600  peak     5712  weight    0.11000E+01  volume   0.35277E+03  ppm1    2.843  ppm2    4.800
ASSI ( 5722)
    ( ( segid *BrD * and resid 57 and name HB1 ) )
    ( ( segid *BrD * and resid 57 and name HA   ) )
     2.400  1.400   1.400  peak     5722  weight    0.11000E+01  volume   0.42344E+03  ppm1    2.935  ppm2    4.798
ASSI ( 5732)
    ( ( segid *BrD * and resid 57 and name HE1 ) )
    ( ( segid *BrD * and resid 57 and name HG2 ) )
     2.200  1.200   1.200  peak     5732  weight    0.11000E+01  volume   0.67766E+03  ppm1    3.572  ppm2    2.017
ASSI ( 5752)
    ( ( segid *BrD * and resid 57 and name HD2 ) )
    ( ( segid *BrD * and resid 57 and name HA   ) )
     2.600  1.700   1.700  peak     5752  weight    0.11000E+01  volume   0.24171E+03  ppm1    2.295  ppm2    4.800
ASSI ( 5762)
    ( ( segid *BrD * and resid 57 and name HD1 ) )
    ( ( segid *BrD * and resid 57 and name HE1 ) )
     2.100  1.100   1.100  peak     5762  weight    0.11000E+01  volume   0.83932E+03  ppm1    2.387  ppm2    3.591
ASSI ( 5772)
    ( ( segid *BrD * and resid 57 and name HD2 ) )
    ( ( segid *BrD * and resid 57 and name HE1 ) )
     2.100  1.100   1.100  peak     5772  weight    0.11000E+01  volume   0.96087E+03  ppm1    2.289  ppm2    3.591
ASSI ( 5792)
    ( ( segid *BrD * and resid 12 and name HA   ) )
    ( ( segid *BrD * and resid 12 and name HB2 ) )
     2.700  1.800   1.800  peak     5792  weight    0.11000E+01  volume   0.22035E+03  ppm1    5.297  ppm2    3.338
ASSI ( 5812)
    ( ( segid *BrD * and resid 57 and name HG1 ) )
    ( ( segid *BrD * and resid 57 and name HE1 ) )
     2.600  1.700   1.700  peak     5812  weight    0.11000E+01  volume   0.23002E+03  ppm1    2.099  ppm2    3.890
ASSI ( 5822)
    ( ( segid *BrD * and resid 26 and name HA   ) )
    ( ( segid *BrD * and resid 26 and name HB1 ) )
     2.100  1.100   1.100  peak     5822  weight    0.11000E+01  volume   0.10358E+04  ppm1    4.509  ppm2    2.482
```

TABLE 2-continued

Unambigous NOE-derived Inter-proton Distance Restraints

```
ASSI ( 5832)
    ( ( segid *BrD * and resid 26 and name HA   ) )
    ( ( segid *BrD * and resid 26 and name HD1  ) )
      2.700  1.800   1.800 peak    5832 weight   0.11000E+01 volume   0.18918E+03 ppm1    4.509 ppm2    2.109
ASSI ( 5842)
    ( ( segid *BrD * and resid 26 and name HA   ) )
    ( ( segid *BrD * and resid 26 and name HG1  ) )
      3.200  2.600   2.300 peak    5842 weight   0.11000E+01 volume   0.75991E+02 ppm1    4.509 ppm2    1.629
ASSI ( 5852)
    ( ( segid *BrD * and resid 10 and name HA   ) )
    ( ( segid *BrD * and resid 10 and name HB2  ) )
      2.800  2.000   2.000 peak    5852 weight   0.11000E+01 volume   0.18381E+03 ppm1    5.478 ppm2    3.300
ASSI ( 5862)
    ( ( segid *BrD * and resid 56 and name HA   ) )
    ( ( segid *BrD * and resid 56 and name HB2  ) )
      2.800  2.000   2.000 peak    5862 weight   0.11000E+01 volume   0.18369E+03 ppm1    4.607 ppm2    2.003
ASSI ( 5872)
    (   segid *BrD * and resid 56 and name HD2%)
    ( ( segid *BrD * and resid 56 and name HB2  ) )
      2.600  1.700   1.700 peak    5872 weight   0.11000E+01 volume   0.24752E+03 ppm1    1.254 ppm2    2.004
ASSI ( 5882)
    (   segid *BrD * and resid 69 and name HG1%)
    ( ( segid *BrD * and resid 69 and name HB   ) )
      2.100  1.100   1.100 peak    5882 weight   0.11000E+01 volume   0.96122E+03 ppm1    1.548 ppm2    2.922
ASSI ( 5892)
    (   segid *BrD * and resid 69 and name HG2%)
    ( ( segid *BrD * and resid 69 and name HB   ) )
      2.100  1.100   1.100 peak    5892 weight   0.11000E+01 volume   0.91489E+03 ppm1    1.424 ppm2    2.919
ASSI ( 5902)
    (   segid *BrD * and resid 69 and name HG2%)
    ( ( segid *BrD * and resid 69 and name HA   ) )
      2.600  1.700   1.700 peak    5902 weight   0.11000E+01 volume   0.28227E+03 ppm1    1.425 ppm2    4.696
ASSI ( 5912)
    (   segid *BrD * and resid 78 and name HD2%)
    ( ( segid *BrD * and resid 78 and name HA   ) )
      2.800  2.000   2.000 peak    5912 weight   0.11000E+01 volume   0.18293E+03 ppm1    0.662 ppm2    3.999
ASSI ( 5922)
    (   segid *BrD * and resid 78 and name HD2%)
    ( ( segid *BrD * and resid 78 and name HB2  ) )
      2.600  1.700   1.700 peak    5922 weight   0.11000E+01 volume   0.24706E+03 ppm1    0.662 ppm2    1.039
ASSI ( 5932)
    (   segid *BrD * and resid 78 and name HD2%)
    ( ( segid *BrD * and resid 78 and name HG   ) )
      2.300  1.300   1.300 peak    5932 weight   0.11000E+01 volume   0.60283E+03 ppm1    0.662 ppm2    1.270
ASSI ( 5962)
    ( ( segid *BrD * and resid 18 and name HA   ) )
    (   segid *BrD * and resid 18 and name HD1%)
      2.600  1.700   1.700 peak    5962 weight   0.11000E+01 volume   0.27810E+03 ppm1    3.867 ppm2    1.079
ASSI ( 5982)
    (   segid *BrD * and resid 18 and name HD1%)
    ( ( segid *BrD * and resid 18 and name HG   ) )
      2.700  1.800   1.800 peak    5982 weight   0.11000E+01 volume   0.22916E+03 ppm1    1.057 ppm2    2.278
ASSI ( 5992)
    (   segid *BrD * and resid 18 and name HD2%)
    ( ( segid *BrD * and resid 18 and name HB1  ) )
      2.600  1.700   1.700 peak    5992 weight   0.11000E+01 volume   0.25721E+03 ppm1    0.418 ppm2    2.137
ASSI ( 6002)
    ( ( segid *BrD * and resid 102 and name HG  ) )
    (   segid *BrD * and resid 102 and name HD1%)
      2.300  1.300   1.300 peak    6002 weight   0.11000E+01 volume   0.47853E+03 ppm1    2.141 ppm2    1.324
ASSI ( 6012)
    ( ( segid *BrD * and resid 73 and name HB1  ) )
    (   segid *BrD * and resid 73 and name HD2%)
      2.300  1.300   1.300 peak    6012 weight   0.11000E+01 volume   0.54334E+03 ppm1    2.583 ppm2    1.483
ASSI ( 6052)
    ( ( segid *BrD * and resid 73 and name HA   ) )
    ( ( segid *BrD * and resid 73 and name HB1  ) )
      2.400  1.400   1.400 peak    6052 weight   0.11000E+01 volume   0.44904E+03 ppm1    4.809 ppm2    2.594
ASSI ( 6072)
    (   segid *BrD * and resid 73 and name HD1%)
    ( ( segid *BrD * and resid 73 and name HA   ) )
      2.500  1.600   1.600 peak    6072 weight   0.11000E+01 volume   0.30560E+03 ppm1    1.549 ppm2    4.825
ASSI ( 6112)
    ( ( segid *BrD * and resid 56 and name HB1  ) )
    (   segid *BrD * and resid 56 and name HD1%)
      2.700  1.800   1.800 peak    6112 weight   0.11000E+01 volume   0.20480E+03 ppm1    2.685 ppm2    1.538
```

TABLE 2-continued

Unambigous NOE-derived Inter-proton Distance Restraints

```
ASSI (  6122)
    (( segid *BrD * and resid 56 and name HB2  ))
    (  segid *BrD * and resid 56 and name HD1%)
      2.900  2.100   2.100  peak    6122  weight   0.11000E+01  volume  0.13067E+03  ppm1   1.994  ppm2   1.538
ASSI (  6162)
    (( segid *BrD * and resid 56 and name HG   ))
    (  segid *BrD * and resid 56 and name HD1%)
      2.300  1.300   1.300  peak    6162  weight   0.11000E+01  volume  0.52968E+03  ppm1   2.339  ppm2   1.539
ASSI (  6212)
    (( segid *BrD * and resid 22 and name HA   ))
    (  segid *BrD * and resid 22 and name HD1%)
      2.500  1.600   1.600  peak    6212  weight   0.11000E+01  volume  0.33531E+03  ppm1   4.706  ppm2   1.648
ASSI (  6232)
    (  segid *BrD * and resid 22 and name HD1%)
    (( segid *BrD * and resid 22 and name HB1  ))
      2.400  1.400   1.400  peak    6232  weight   0.11000E+01  volume  0.37274E+03  ppm1   1.648  ppm2   2.702
ASSI (  6242)
    (  segid *BrD * and resid 22 and name HD1%)
    (( segid *BrD * and resid 22 and name HG   ))
      2.200  1.200   1.200  peak    6242  weight   0.11000E+01  volume  0.77165E+03  ppm1   1.648  ppm2   2.361
ASSI (  6272)
    (  segid *BrD * and resid 63 and name HD2%)
    (( segid *BrD * and resid 63 and name HG   ))
      2.600  1.700   1.700  peak    6272  weight   0.11000E+01  volume  0.24631E+03  ppm1   1.498  ppm2   2.424
ASSI (  6282)
    (  segid *BrD * and resid 63 and name HD1%)
    (( segid *BrD * and resid 63 and name HG   ))
      2.700  1.800   1.800  peak    6282  weight   0.11000E+01  volume  0.21403E+03  ppm1   1.649  ppm2   2.424
ASSI (  6322)
    (( segid *BrD * and resid 66 and name HG2  ))
    (( segid *BrD * and resid 66 and name HD2  ))
      2.500  1.600   1.600  peak    6322  weight   0.11000E+01  volume  0.35570E+03  ppm1   2.140  ppm2   3.637
ASSI (  6352)
    (( segid *BrD * and resid 66 and name HD2  ))
    (( segid *BrD * and resid 66 and name HA   ))
      2.500  1.600   1.600  peak    6352  weight   0.11000E+01  volume  0.30900E+03  ppm1   3.631  ppm2   4.998
ASSI (  6392)
    (( segid *BrD * and resid 100 and name HB1  ))
    (( segid *BrD * and resid 100 and name HA   ))
      2.100  1.100   1.100  peak    6392  weight   0.11000E+01  volume  0.94220E+03  ppm1   3.455  ppm2   4.949
ASSI (  6412)
    (( segid *BrD * and resid 114 and name HA1  ))
    (( segid *BrD * and resid 114 and name HA2  ))
      2.100  1.100   1.100  peak    6412  weight   0.11000E+01  volume  0.97579E+03  ppm1   4.600  ppm2   4.522
ASSI (  6432)
    (( segid *BrD * and resid 85 and name HA   ))
    (( segid *BrD * and resid 85 and name HB1  ))
      2.700  1.800   1.800  peak    6432  weight   0.11000E+01  volume  0.21987E+03  ppm1   5.001  ppm2   3.906
ASSI (  6442)
    (( segid *BrD * and resid 85 and name HA   ))
    (( segid *BrD * and resid 85 and name HB2  ))
      2.800  2.000   2.000  peak    6442  weight   0.11000E+01  volume  0.16015E+03  ppm1   5.000  ppm2   3.621
ASSI (  6492)
    (( segid *BrD * and resid 98 and name HA   ))
    (( segid *BrD * and resid 98 and name HB1  ))
      2.800  2.000   2.000  peak    6492  weight   0.11000E+01  volume  0.16821E+03  ppm1   4.804  ppm2   4.014
ASSI (  6502)
    (( segid *BrD * and resid 98 and name HA   ))
    (( segid *BrD * and resid 98 and name HB2  ))
      2.700  1.800   1.800  peak    6502  weight   0.11000E+01  volume  0.19206E+03  ppm1   4.804  ppm2   3.660
ASSI (  6512)
    (( segid *BrD * and resid 32 and name HA   ))
    (( segid *BrD * and resid 32 and name HB2  ))
      2.700  1.800   1.800  peak    6512  weight   0.11000E+01  volume  0.22944E+03  ppm1   4.953  ppm2   3.965
ASSI (  6522)
    (( segid *BrD * and resid 32 and name HA   ))
    (( segid *BrD * and resid 32 and name HB1  ))
      2.700  1.800   1.800  peak    6522  weight   0.11000E+01  volume  0.20617E+03  ppm1   4.954  ppm2   4.206
ASSI (  6552)
    (( segid *BrD * and resid 11 and name HA   ))
    (( segid *BrD * and resid 11 and name HG1  ))
      2.600  1.700   1.700  peak    6552  weight   0.11000E+01  volume  0.23807E+03  ppm1   4.951  ppm2   2.635
ASSI (  6562)
    (( segid *BrD * and resid 53 and name HG1  ))
    (( segid *BrD * and resid 53 and name HA   ))
      2.700  1.800   1.800  peak    6562  weight   0.11000E+01  volume  0.20893E+03  ppm1   2.784  ppm2   4.687
```

TABLE 2-continued

Unambigous NOE-derived Inter-proton Distance Restraints

```
ASSI ( 6572)
    ( ( segid *BrD * and resid 31 and name HA   ) )
    ( segid *BrD * and resid 102 and name HD1%)
       2.500  1.600    1.600 peak    6572 weight    0.11000E+01 volume   0.36090E+03 ppm1    5.000 ppm2    1.323
ASSI ( 6612)
    ( segid *BrD * and resid 31 and name HB % )
    ( segid *BrD * and resid 102 and name HD1%)
       2.500  1.600    1.600 peak    6612 weight    0.11000E+01 volume   0.31261E+03 ppm1    2.289 ppm2    1.320
ASSI ( 6642)
    ( ( segid *BrD * and resid 43 and name HA   ) )
    ( ( segid *BrD * and resid 44 and name HD2  ) )
       2.400  1.400    1.400 peak    6642 weight    0.11000E+01 volume   0.39497E+03 ppm1    5.547 ppm2    4.127
ASSI ( 6662)
    ( segid *BrD * and resid 43 and name HB % )
    ( ( segid *BrD * and resid 44 and name HD2  ) )
       2.700  1.800    1.800 peak    6662 weight    0.11000E+01 volume   0.20471E+03 ppm1    1.700 ppm2    4.135
ASSI ( 6672)
    ( segid *BrD * and resid 43 and name HB % )
    ( segid *BrD * and resid 46 and name HB1  ) )
       2.600  1.700    1.700 peak    6672 weight    0.11000E+01 volume   0.27100E+03 ppm1    1.697 ppm2    3.295
ASSI ( 6682)
    ( segid *BrD * and resid 43 and name HB % )
    ( ( segid *BrD * and resid 46 and name HB2  ) )
       2.700  1.800    1.800 peak    6682 weight    0.11000E+01 volume   0.19809E+03 ppm1    1.697 ppm2    3.100
ASSI ( 6732)
    ( ( segid *BrD * and resid 76 and name HA   ) )
    ( ( segid *BrD * and resid 79 and name HB1  ) )
       2.800  2.000    2.000 peak    6732 weight    0.11000E+01 volume   0.46513E+03 ppm1    4.656 ppm2    2.774
ASSI ( 6872)
    ( segid *BrD * and resid 113 and name HB % )
    ( segid *BrD * and resid 17 and name HG2%)
       2.500  1.600    1.600 peak    6872 weight    0.11000E+01 volume   0.31889E+03 ppm1    1.994 ppm2    1.750
ASSI ( 6882)
    ( ( segid *BrD * and resid 79 and name HA   ) )
    ( ( segid *BrD * and resid 79 and name HB1  ) )
       2.700  1.800    1.800 peak    6882 weight    0.11000E+01 volume   0.19089E+03 ppm1    4.409 ppm2    2.781
ASSI ( 6892)
    ( ( segid *BrD * and resid 79 and name HA   ) )
       2.200  1.200    1.200 peak    6892 weight    0.11000E+01 volume   0.79324E+03 ppm1    4.409 ppm2    2.678
ASSI ( 6912)
    ( segid *BrD * and resid 43 and name HB % )
    ( ( segid *BrD * and resid 44 and name HD1  ) )
       2.900  2.100    2.100 peak    6912 weight    0.11000E+01 volume   0.13650E+03 ppm1    1.700 ppm2    4.337
ASSI ( 6942)
    ( segid *BrD * and resid 25 and name HG1%)
    ( segid *BrD * and resid 102 and name HD1%)
       2.700  1.800    1.800 peak    6942 weight    0.11000E+01 volume   0.21235E+03 ppm1    1.795 ppm2    1.323
ASSI ( 6962)
    ( segid *BrD * and resid 25 and name HG1%)
    ( segid *BrD * and resid 78 and name HD1%)
       3.000  2.200    2.200 peak    6962 weight    0.11000E+01 volume   0.99662E+02 ppm1    1.798 ppm2    0.774
ASSI ( 6972)
    ( segid *BrD * and resid 25 and name HG1%)
    ( segid *BrD * and resid 78 and name HD2%)
       2.800  2.000    2.000 peak    6972 weight    0.11000E+01 volume   0.15213E+03 ppm1    1.797 ppm2    0.673
ASSI ( 6992)
    ( segid *BrD * and resid 25 and name HG2%)
    ( segid *BrD * and resid 102 and name HD1%)
       2.200  1.200    1.200 peak    6992 weight    0.11000E+01 volume   0.77265E+03 ppm1    1.646 ppm2    1.324
ASSI ( 7002)
    ( segid *BrD * and resid 25 and name HG2%)
    ( segid *BrD * and resid 78 and name HD1%)
       2.800  2.000    2.000 peak    7002 weight    0.11000E+01 volume   0.16697E+03 ppm1    1.646 ppm2    0.775
ASSI ( 7022)
    ( ( segid *BrD * and resid 38 and name HB   ) )
    ( ( segid *BrD * and resid 38 and name HA   ) )
       2.800  2.000    2.000 peak    7022 weight    0.11000E+01 volume   0.17527E+03 ppm1    1.751 ppm2    4.170
ASSI ( 7032)
    ( segid *BrD * and resid 38 and name HG2%)
    ( segid *BrD * and resid 43 and name HB % )
       2.200  1.200    1.200 peak    7032 weight    0.11000E+01 volume   0.74974E+03 ppm1    0.808 ppm2    1.715
ASSI ( 7092)
    ( ( segid *BrD * and resid 81 and name HA   ) )
    ( ( segid *BrD * and resid 81 and name HB   ) )
       2.800  2.000    2.000 peak    7092 weight    0.11000E+01 volume   0.15198E+03 ppm1    3.718 ppm2    2.037
```

TABLE 2-continued

Unambigous NOE-derived Inter-proton Distance Restraints

```
ASSI ( 7102)
  ( ( segid *BrD * and resid 81 and name HB   ) )
  ( ( segid *BrD * and resid 78 and name HA   ) )
    3.100  2.400   2.400 peak    7102 weight   0.11000E+01 volume  0.98817E+02 ppm1   2.042 ppm2   4.000
ASSI ( 7122)
  ( segid *BrD * and resid 81 and name HG1%)
  ( ( segid *BrD * and resid 78 and name HA   ) )
    2.600  1.700   1.700 peak    7122 weight   0.11000E+01 volume  0.25254E+03 ppm1   1.059 ppm2   3.999
ASSI ( 7172)
  ( segid *BrD * and resid 81 and name HG2%)
  ( ( segid *BrD * and resid 34 and name HB1 ) )
    2.600  1.700   1.700 peak    7172 weight   0.11000E+01 volume  0.27152E+03 ppm1   0.755 ppm2   4.106
ASSI ( 7192)
  ( ( segid *BrD * and resid 17 and name HA   ) )
  ( ( segid *BrD * and resid 20 and name HB1 ) )
    3.200  2.600   2.300 peak    7192 weight   0.11000E+01 volume  0.76028E+02 ppm1   4.542 ppm2   4.671
ASSI ( 7252)
  ( segid *BrD * and resid 17 and name HG2%)
  ( segid *BrD * and resid 102 and name HD2%)
    5.500  5.500   0.000 peak    7252 weight   0.11000E+01 volume  0.56051E+00 ppm1   1.745 ppm2   1.320
ASSI ( 7272)
  ( segid *BrD * and resid 17 and name HG2%)
  ( segid *BrD * and resid 18 and name HD2%)
    2.800  2.000   2.000 peak    7272 weight   0.11000E+01 volume  0.14970E+03 ppm1   1.747 ppm2   0.409
ASSI ( 7352)
  ( segid *BrD * and resid 58 and name HG2%)
  ( segid *BrD * and resid 54 and name HE % )
    2.400  1.400   1.400 peak    7352 weight   0.11000E+01 volume  0.41514E+03 ppm1   1.849 ppm2   2.963
ASSI ( 7482)
  ( ( segid *BrD * and resid 32 and name HA   ) )
  ( ( segid *BrD * and resid 35 and name HG1 ) )
    2.900  2.100   2.100 peak    7482 weight   0.11000E+01 volume  0.12205E+03 ppm1   4.953 ppm2   3.451
ASSI ( 7492)
  ( ( segid *BrD * and resid 32 and name HA   ) )
  ( ( segid *BrD * and resid 33 and name HD1 ) )
    2.900  2.100   2.100 peak    7492 weight   0.11000E+01 volume  0.14430E+03 ppm1   4.952 ppm2   2.776
ASSI ( 7502)
  ( ( segid *BrD * and resid 62 and name HA   ) )
  ( ( segid *BrD * and resid 62 and name HB1 ) )
    2.700  1.800   1.800 peak    7502 weight   0.11000E+01 volume  0.21435E+03 ppm1   4.457 ppm2   2.657
ASSI ( 7522)
  ( ( segid *BrD * and resid 62 and name HA   ) )
  ( ( segid *BrD * and resid 62 and name HG2 ) )
    2.800  2.000   2.000 peak    7522 weight   0.11000E+01 volume  0.15009E+03 ppm1   4.457 ppm2   1.478
ASSI ( 7532)
  ( ( segid *BrD * and resid 62 and name HA   ) )
  ( ( segid *BrD * and resid 62 and name HB2 ) )
    3.000  2.200   2.200 peak    7532 weight   0.11000E+01 volume  0.10361E+03 ppm1   4.457 ppm2   1.681
ASSI ( 7622)
  ( ( segid *BrD * and resid 74 and name HA   ) )
  ( segid *BrD * and resid 59 and name HE % )
    3.100  2.400   2.400 peak    7652 weight   0.11000E+01 volume  0.93787E+02 ppm1   4.361 ppm2   1.879
ASSI ( 7662)
  ( ( segid *BrD * and resid 74 and name HB1 ) )
  ( ( segid *BrD * and resid 71 and name HA   ) )
    3.100  2.400   2.400 peak    7662 weight   0.11000E+01 volume  0.98803E+02 ppm1   3.576 ppm2   4.627
ASSI ( 7722)
  ( ( segid *BrD * and resid 105 and name HA  ) )
  ( ( segid *BrD * and resid 108 and name HB1 ) )
    3.100  2.400   2.400 peak    7722 weight   0.11000E+01 volume  0.93160E+02 ppm1   4.902 ppm2   4.582
ASSI ( 7752)
  ( ( segid *BrD * and resid 107 and name HA  ) )
  ( ( segid *BrD * and resid 110 and name HB  ) )
    2.800  2.000   2.000 peak    7752 weight   0.11000E+01 volume  0.15544E+03 ppm1   4.410 ppm2   2.360
ASSI ( 7742)
  ( ( segid *BrD * and resid 96 and name HA   ) )
  ( segid *BrD * and resid 99 and name HB % )
    3.400  2.900   2.100 peak    7762 weight   0.11000E+01 volume  0.54211E+02 ppm1   4.409 ppm2   2.206
ASSI ( 7772)
  ( ( segid *BrD * and resid 107 and name HA  ) )
  ( ( segid *BrD * and resid 110 and name HG11) )
    3.100  2.400   2.400 peak    7772 weight   0.11000E+01 volume  0.86608E+02 ppm1   4.408 ppm2   1.715
ASSI ( 7782)
  ( ( segid *BrD * and resid 107 and name HA  ) )
  ( ( segid *BrD * and resid 110 and name HG12) )
    2.900  2.100   2.100 peak    7782 weight   0.11000E+01 volume  0.14800E+03 ppm1   4.408 ppm2   1.661
```

TABLE 2-continued

Unambigous NOE-derived Inter-proton Distance Restraints

```
ASSI ( 7792)
    ( ( segid *BrD * and resid 107 and name HA   ) )
    (  segid *BrD * and resid 110 and name HG2%)
       3.100  2.400   2.400 peak    7792 weight   0.11000E+01 volume  0.86153E+02 ppm1    4.408 ppm2    1.261
ASSI ( 7802)
    ( ( segid *BrD * and resid 107 and name HA   ) )
    (  segid *BrD * and resid 110 and name HD1%)
       3.000  2.200   2.200 peak    7802 weight   0.11000E+01 volume  0.11960E+03 ppm1    4.408 ppm2    1.141
ASSI ( 7872)
    ( ( segid *BrD * and resid 89 and name HA    ) )
    ( ( segid *BrD * and resid 91 and name HD2   ) )
       2.700  1.800   1.800 peak    7872 weight   0.11000E+01 volume  0.22343E+03 ppm1    5.641 ppm2    4.407
ASSI ( 7892)
    ( ( segid *BrD * and resid 100 and name HA   ) )
    ( ( segid *BrD * and resid 103 and name HB2  ) )
       2.900  2.100   2.100 peak    7892 weight   0.11000E+01 volume  0.12930E+03 ppm1    4.952 ppm2    1.897
ASSI ( 7922)
    ( ( segid *BrD * and resid 100 and name HB1  ) )
    ( ( segid *BrD * and resid 97 and name HA    ) )
       2.600  1.700   1.700 peak    7922 weight   0.11000E+01 volume  0.24354E+03 ppm1    3.455 ppm2    4.798
ASSI ( 7932)
    ( ( segid *BrD * and resid 100 and name HB2  ) )
    ( ( segid *BrD * and resid 97 and name HA    ) )
       2.600  1.700   1.700 peak    7932 weight   0.11000E+01 volume  0.23409E+03 ppm1    3.424 ppm2    4.799
ASSI ( 7962)
    ( ( segid *BrD * and resid 12 and name HA    ) )
    ( ( segid *BrD * and resid 15 and name HB2   ) )
       2.900  2.100   2.100 peak    7962 weight   0.11000E+01 volume  0.12451E+03 ppm1    5.298 ppm2    3.646
ASSI ( 7972)
    ( ( segid *BrD * and resid 12 and name HA    ) )
    ( ( segid *BrD * and resid 15 and name HB1   ) )
       3.100  2.400   2.400 peak    7972 weight   0.11000E+01 volume  0.81954E+02 ppm1    5.297 ppm2    3.812
ASSI ( 8032)
    ( ( segid *BrD * and resid 77 and name HA    ) )
    ( ( segid *BrD * and resid 80 and name HG1   ) )
       3.000  2.200   2.200 peak    8032 weight   0.11000E+01 volume  0.10885E+03 ppm1    4.952 ppm2    2.347
ASSI ( 8062)
    ( ( segid *BrD * and resid 85 and name HB2   ) )
    ( ( segid *BrD * and resid 82 and name HA    ) )
       3.000  2.200   2.200 peak    8062 weight   0.11000E+01 volume  0.10120E+03 ppm1    3.621 ppm2    4.753
ASSI ( 8072)
    ( ( segid *BrD * and resid 98 and name HB2   ) )
    ( ( segid *BrD * and resid 95 and name HA    ) )
       3.100  2.400   2.400 peak    8072 weight   0.11000E+01 volume  0.94016E+02 ppm1    3.667 ppm2    4.447
ASSI ( 8102)
    ( ( segid *BrD * and resid 63 and name HB1   ) )
    ( ( segid *BrD * and resid 60 and name HA    ) )
       2.600  1.700   1.700 peak    8102 weight   0.11000E+01 volume  0.27762E+03 ppm1    2.883 ppm2    4.808
ASSI ( 8112)
    ( ( segid *BrD * and resid 63 and name HB2   ) )
    ( ( segid *BrD * and resid 60 and name HA    ) )
       2.700  1.800   1.800 peak    8112 weight   0.11000E+01 volume  0.20887E+03 ppm1    2.538 ppm2    4.809
ASSI ( 8142)
    (  segid *BrD * and resid 63 and name HD1%)
    ( ( segid *BrD * and resid 18 and name HB2   ) )
       2.800  2.000   2.000 peak    8142 weight   0.11000E+01 volume  0.16157E+03 ppm1    1.649 ppm2    0.919
ASSI ( 8152)
    (  segid *BrD * and resid 63 and name HD1%)
    (  segid *BrD * and resid 18 and name HD1%)
       2.700  1.800   1.800 peak    8152 weight   0.11000E+01 volume  0.20633E+03 ppm1    1.646 ppm2    1.085
ASSI ( 8162)
    (  segid *BrD * and resid 63 and name HD1%)
    ( ( segid *BrD * and resid 18 and name HB1   ) )
       2.400  1.400   1.400 peak    8162 weight   0.11000E+01 volume  0.38153E+03 ppm1    1.649 ppm2    2.139
ASSI ( 8172)
    (  segid *BrD * and resid 63 and name HD1%)
    ( ( segid *BrD * and resid 19 and name HA    ) )
       2.400  1.400   1.400 peak    8172 weight   0.11000E+01 volume  0.45741E+03 ppm1    1.501 ppm2    4.295
ASSI ( 8182)
    ( ( segid *BrD * and resid 14 and name HB2   ) )
    ( ( segid *BrD * and resid 14 and name HG    ) )
       3.100  2.400   2.400 peak    8182 weight   0.11000E+01 volume  0.92156E+02 ppm1    2.145 ppm2    2.059
ASSI ( 8192)
    ( ( segid *BrD * and resid 14 and name HB1   ) )
    ( ( segid *BrD * and resid 14 and name HG    ) )
       2.600  1.700   1.700 peak    8192 weight   0.11000E+01 volume  0.23309E+03 ppm1    2.444 ppm2    2.059
```

TABLE 2-continued

Unambigous NOE-derived Inter-proton Distance Restraints

```
ASSI ( 8222)
   ( segid *BrD * and resid 14 and name HD2%)
   ( segid *BrD * and resid 18 and name HD2%)
     2.500  1.600    1.600   peak    8222  weight   0.11000E+01 volume   0.31711E+03 ppm1   1.401 ppm2   0.409
ASSI ( 8232)
   ( segid *BrD * and resid 14 and name HD2%)
   ( segid *BrD * and resid 18 and name HD1%)
     2.400  1.400    1.400   peak    8232  weight   0.11000E+01 volume   0.46026E+03 ppm1   1.401 ppm2   1.085
ASSI ( 8302)
   ( ( segid *BrD * and resid 18 and name HA   ) )
   ( ( segid *BrD * and resid 18 and name HB2  ) )
     2.700  1.800    1.800   peak    8302  weight   0.11000E+01 volume   0.20320E+03 ppm1   3.867 ppm2   0.920
ASSI ( 8392)
   ( segid *BrD * and resid 18 and name HD1%)
   ( ( segid *BrD * and resid 18 and name HB2  ) )
     2.400  1.400    1.400   peak    8392  weight   0.11000E+01 volume   0.39910E+03 ppm1   1.057 ppm2   0.925
ASSI ( 8402)
   ( segid *BrD * and resid 18 and name HD1%)
   ( ( segid *BrD * and resid 74 and name HB1  ) )
     3.000  2.200    2.200   peak    8402  weight   0.11000E+01 volume   0.10291E+03 ppm1   1.056 ppm2   3.563
ASSI ( 8412)
   ( segid *BrD * and resid 18 and name HD1%)
   ( ( segid *BrD * and resid 74 and name HB2  ) )
     2.900  2.100    2.100   peak    8412  weight   0.11000E+01 volume   0.13686E+03 ppm1   1.057 ppm2   2.998
ASSI ( 8442)
   ( segid *BrD * and resid 18 and name HD2%)
   ( segid *BrD * and resid 14 and name HD1%)
     2.900  2.100    2.100   peak    8442  weight   0.11000E+01 volume   0.12935E+03 ppm1   0.412 ppm2   1.417
ASSI ( 8452)
   ( segid *BrD * and resid 18 and name HD2%)
   ( ( segid *BrD * and resid 18 and name HB2  ) )
     2.800  2.000    2.000   peak    8452  weight   0.11000E+01 volume   0.15454E+03 ppm1   0.415 ppm2   0.917
ASSI ( 8462)
   ( segid *BrD * and resid 18 and name HD2%)
   ( segid *BrD * and resid 102 and name HD2%)
     5.500  5.500    0.000   peak    8462  weight   0.11000E+01 volume   0.22428E+01 ppm1   0.416 ppm2   1.320
ASSI ( 8552)
   ( ( segid *BrD * and resid 22 and name HB1  ) )
   ( ( segid *BrD * and resid 19 and name HA   ) )
     2.600  1.700    1.700   peak    8552  weight   0.11000E+01 volume   0.27759E+03 ppm1   2.682 ppm2   4.295
ASSI ( 8562)
   ( ( segid *BrD * and resid 22 and name HB2  ) )
   ( segid *BrD * and resid 22 and name HD2%)
     2.500  1.600    1.600   peak    8562  weight   0.11000E+01 volume   0.30282E+03 ppm1   2.286 ppm2   1.671
ASSI ( 8602)
   ( ( segid *BrD * and resid 22 and name HA   ) )
   ( ( segid *BrD * and resid 25 and name HB   ) )
     2.600  1.700    1.700   peak    8602  weight   0.11000E+01 volume   0.25484E+03 ppm1   4.706 ppm2   2.980
ASSI ( 8652)
   ( segid *BrD * and resid 56 and name HD1%)
   ( ( segid *BrD * and resid 56 and name HA   ) )
     2.500  1.600    1.600   peak    8652  weight   0.11000E+01 volume   0.34489E+03 ppm1   1.544 ppm2   4.638
ASSI ( 8672)
   ( segid *BrD * and resid 56 and name HD2%)
   ( segid *BrD * and resid 78 and name HD2%)
     2.900  2.100    2.300   peak    8672  weight   0.11000E+01 volume   0.14779E+03 ppm1   1.253 ppm2   0.674
ASSI ( 8682)
   ( segid *BrD * and resid 56 and name HD2%)
   ( segid *BrD * and resid 78 and name HD1%)
     2.300  1.300    1.300   peak    8682  weight   0.11000E+01 volume   0.48347E+03 ppm1   2.254 ppm2   0.767
ASSI ( 8722)
   ( ( segid *BrD * and resid 73 and name HA   ) )
   ( segid *BrD * and resid 76 and name HB % )
     2.700  1.800    1.800   peak    8722  weight   0.11000E+01 volume   0.22156E+03 ppm1   4.805 ppm2   2.101
ASSI ( 8742)
   ( segid *BrD * and resid 73 and name HD1%)
   ( ( segid *BrD * and resid 73 and name HB1  ) )
     2.400  1.400    1.400   peak    8742  weight   0.11000E+01 volume   0.42630E+03 ppm1   1.549 ppm2   2.594
ASSI ( 8752)
   ( ( segid *BrD * and resid 78 and name HA   ) )
   ( segid *BrD * and resid 59 and name HE % )
     3.300  2.700    2.200   peak    8752  weight   0.11000E+01 volume   0.67002E+03 ppm1   3.967 ppm2   1.876
ASSI ( 8782)
   ( ( segid *BrD * and resid 78 and name HB1  ) )
   ( segid *BrD * and resid 59 and name HE % )
     3.200  2.600    2.300   peak    8782  weight   0.11000E+01 volume   0.75592E+02 ppm1   1.307 ppm2   1.876
```

TABLE 2-continued

Unambigous NOE-derived Inter-proton Distance Restraints

```
ASSI ( 8792)
  ( ( segid *BrD * and resid 78 and name HB2  ) )
  (  segid *BrD * and resid 59 and name HE %  )
    2.900  2.100    2.100 peak    8792 weight   0.11000E+01 volume   0.13248E+03 ppm1    1.054 ppm2    1.876
ASSI ( 8802)
  ( ( segid *BrD * and resid 78 and name HB1  ) )
  ( ( segid *BrD * and resid 75 and name HA   ) )
    3.100  2.400    2.400 peak    8802 weight   0.11000E+01 volume   0.93675E+02 ppm1    1.305 ppm2    4.820
ASSI ( 8812)
  ( ( segid *BrD * and resid 78 and name HG   ) )
  (  segid *BrD * and resid 59 and name HE %  )
    3.200  2.600    2.300 peak    8812 weight   0.11000E+01 volume   0.81269E+02 ppm1    1.254 ppm2    1.878
ASSI ( 8822)
  (  segid *BrD * and resid 78 and name HD2%)
  (  segid *BrD * and resid 81 and name HG1%)
    2.600  1.700    1.700 peak    8822 weight   0.11000E+01 volume   0.25375E+03 ppm1    0.761 ppm2    1.078
ASSI ( 8852)
  (  segid *BrD * and resid 78 and name HD1%)
  (  segid *BrD * and resid 59 and name HE %  )
    2.900  2.100    2.100 peak    8852 weight   0.11000E+01 volume   0.13937E+03 ppm1    0.761 ppm2    1.878
ASSI ( 8872)
  (  segid *BrD * and resid 78 and name HD2%)
  (  segid *BrD * and resid 25 and name HG2%)
    2.600  1.700    1.700 peak    8872 weight   0.11000E+01 volume   0.25847E+03 ppm1    0.662 ppm2    1.637
ASSI ( 8892)
  (  segid *BrD * and resid 78 and name HD2%)
  (  segid *BrD * and resid 81 and name HG1%)
    2.800  2.000    2.000 peak    8892 weight   0.11000E+01 volume   0.17974E+03 ppm1    0.662 ppm2    1.078
ASSI ( 8912)
  (  segid *BrD * and resid 78 and name HD2%)
  (  segid *BrD * and resid 59 and name HE %  )
    2.600  1.700    1.700 peak    8912 weight   0.11000E+01 volume   0.24075E+03 ppm1    0.662 ppm2    1.875
ASSI ( 8922)
  ( ( segid *BrD * and resid 102 and name HA   ) )
  ( ( segid *BrD * and resid 105 and name HB1  ) )
    2.800  2.000    2.000 peak    8922 weight   0.11000E+01 volume   0.18319E+03 ppm1    4.263 ppm2    3.742
ASSI ( 8932)
  ( ( segid *BrD * and resid 102 and name HA   ) )
  ( ( segid *BrD * and resid 105 and name HB2  ) )
    2.700  1.800    1.800 peak    8932 weight   0.11000E+01 volume   0.21483E+03 ppm1    4.263 ppm2    3.674
ASSI ( 8952)
  ( ( segid *BrD * and resid 102 and name HB1  ) )
  ( ( segid *BrD * and resid 99 and name HA    ) )
    2.900  2.100    2.100 peak    8952 weight   0.11000E+01 volume   0.14144E+03 ppm1    1.993 ppm2    4.442
ASSI ( 8972)
  (  segid *BrD * and resid 102 and name HD1%)
  ( ( segid *BrD * and resid 25 and name HA   ) )
    2.700  1.800    1.800 peak    8972 weight   0.11000E+01 volume   0.20447E+03 ppm1    1.303 ppm2    4.424
ASSI ( 8982)
  (  segid *BrD * and resid 102 and name HD1%)
  ( ( segid *BrD * and resid 103 and name HB1  ) )
    3.000  2.200    2.200 peak    8982 weight   0.11000E+01 volume   0.11841E+03 ppm1    1.302 ppm2    3.760
ASSI ( 8992)
  (  segid *BrD * and resid 102 and name HD1%)
  ( ( segid *BrD * and resid 105 and name HB2  ) )
    2.800  2.000    2.000 peak    8992 weight   0.11000E+01 volume   0.16956E+03 ppm1    1.303 ppm2    3.689
ASSI ( 9002)
  (  segid *BrD * and resid 102 and name HD1%)
  ( ( segid *BrD * and resid 28 and name HB1  ) )
    2.600  1.700    1.700 peak    9002 weight   0.11000E+01 volume   0.27744E+03 ppm1    1.303 ppm2    3.603
ASSI ( 9012)
  (  segid *BrD * and resid 102 and name HD1%)
  ( ( segid *BrD * and resid 28 and name HB2  ) )
    2.800  2.000    2.000 peak    9012 weight   0.11000E+01 volume   0.15194E+03 ppm1    1.303 ppm2    3.402
ASSI ( 9062)
  ( ( segid *BrD * and resid 115 and name HB1  ) )
  (  segid *BrD * and resid 115 and name HD1%)
    2.300  1.300    1.300 peak    9062 weight   0.11000E+01 volume   0.58334E+03 ppm1    2.190 ppm2    1.348
ASSI ( 9082)
  ( ( segid *BrD * and resid 21 and name HA   ) )
  ( ( segid *BrD * and resid 24 and name HB1  ) )
    3.000  2.200    2.200 peak    9082 weight   0.11000E+01 volume   0.11815E+03 ppm1    4.360 ppm2    3.074
ASSI ( 9092)
  ( ( segid *BrD * and resid 21 and name HB   ) )
  ( ( segid *BrD * and resid 18 and name HA   ) )
    2.800  2.000    2.000 peak    9092 weight   0.11000E+01 volume   0.16218E+03 ppm1    2.488 ppm2    3.884
```

TABLE 2-continued

Unambigous NOE-derived Inter-proton Distance Restraints

```
ASSI ( 9182)
   ( segid *BrD * and resid 21 and name HD1%)
   ( segid *BrD * and resid 18 and name HD2%)
      2.900  2.100    2.100  peak    9182  weight   0.11000E+01  volume   0.13133E+03  ppm1    1.203  ppm2    0.410
ASSI ( 9222)
   ( segid *BrD * and resid 21 and name HD1%)
   ( ( segid *BrD * and resid 18 and name HA   ) )
      2.900  2.100    2.100  peak    9222  weight   0.11000E+01  volume   0.13713E+03  ppm1    1.205  ppm2    3.883
ASSI ( 9242)
   ( ( segid *BrD * and resid 50 and name HG11) )
   ( ( segid *BrD * and resid 50 and name HG12) )
      2.500  1.600    1.600  peak    9242  weight   0.11000E+01  volume   0.31586E+03  ppm1    1.397  ppm2    0.834
ASSI ( 9292)
   ( segid *BrD * and resid 50 and name HG2%)
   ( ( segid *BrD * and resid 53 and name HB1  ) )
      2.700  1.800    1.800  peak    9292  weight   0.11000E+01  volume   0.22449E+03  ppm1    1.006  ppm2    2.820
ASSI ( 9302)
   ( segid *BrD * and resid 50 and name HG2%)
   ( ( segid *BrD * and resid 53 and name HG2  ) )
      3.100  2.400    2.400  peak    9302  weight   0.11000E+01  volume   0.95431E+02  ppm1    1.006  ppm2    2.500
ASSI ( 9312)
   ( segid *BrD * and resid 50 and name HG2%)
   ( ( segid *BrD * and resid 84 and name HB2  ) )
      2.800  2.000    2.000  peak    9312  weight   0.11000E+01  volume   0.16689E+03  ppm1    1.004  ppm2    3.271
ASSI ( 9322)
   ( segid *BrD * and resid 50 and name HG2%)
   ( ( segid *BrD * and resid 53 and name HA   ) )
      2.500  1.600    1.600  peak    9322  weight   0.11000E+01  volume   0.33859E+03  ppm1    1.008  ppm2    4.690
ASSI ( 9332)
   ( ( segid *BrD * and resid 101 and name HA   ) )
   ( ( segid *BrD * and resid 104 and name HD1  ) )
      3.000  2.200    2.200  peak    9332  weight   0.11000E+01  volume   0.11803E+03  ppm1    4.265  ppm2    2.302
ASSI ( 9342)
   ( ( segid *BrD * and resid 101 and name HB   ) )
   ( ( segid *BrD * and resid 98 and name HA   ) )
      2.500  1.600    1.600  peak    9342  weight   0.11000E+01  volume   0.31366E+03  ppm1    2.533  ppm2    4.810
ASSI ( 9372)
   ( ( segid *BrD * and resid 101 and name HG11) )
   ( ( segid *BrD * and resid 101 and name HG12) )
      2.300  1.300    1.300  peak    9372  weight   0.11000E+01  volume   0.48997E+03  ppm1    2.444  ppm2    1.807
ASSI ( 9422)
   ( segid *BrD * and resid 101 and name HD1%)
   ( ( segid *BrD * and resid 98 and name HA   ) )
      2.600  1.700    1.700  peak    9422  weight   0.11000E+01  volume   0.26958E+03  ppm1    1.547  ppm2    4.810
ASSI ( 9432)
   ( ( segid *BrD * and resid 110 and name HA   ) )
   ( ( segid *BrD * and resid 110 and name HG12) )
      3.000  2.200    2.200  peak    9432  weight   0.11000E+01  volume   0.11168E+03  ppm1    4.411  ppm2    1.652
ASSI ( 9442)
   ( ( segid *BrD * and resid 110 and name HA   ) )
   ( segid *BrD * and resid 113 and name HB % )
      2.700  1.800    1.800  peak    9442  weight   0.11000E+01  volume   0.20383E+03  ppm1    4.411  ppm2    1.976
ASSI ( 9712)
   ( ( segid *BrD * and resid 24 and name HA   ) )
   ( ( segid *BrD * and resid 24 and name HB2  ) )
      2.500  1.600    1.600  peak    9712  weight   0.11000E+01  volume   0.10771E+03  ppm1    4.784  ppm2    2.989
ASSI ( 9762)
   ( ( segid *BrD * and resid 23 and name HA   ) )
   ( ( segid *BrD * and resid 23 and name HB2  ) )
      2.300  1.300    1.300  peak    9762  weight   0.11000E+01  volume   0.47366E+03  ppm1    4.653  ppm2    2.857
ASSI ( 9772)
   ( ( segid *BrD * and resid 23 and name HA   ) )
   ( ( segid *BrD * and resid 23 and name HB1  ) )
      2.400  1.400    1.400  peak    9772  weight   0.11000E+01  volume   0.38629E+03  ppm1    4.653  ppm2    2.930
ASSI ( 9782)
   ( ( segid *BrD * and resid 13 and name HB1  ) )
   ( ( segid *BrD * and resid 13 and name HA   ) )
      2.900  2.100    2.100  peak    9782  weight   0.11000E+01  volume   0.14088E+03  ppm1    2.733  ppm2    4.775
ASSI ( 9802)
   ( ( segid *BrD * and resid 103 and name HA   ) )
   ( ( segid *BrD * and resid 103 and name HB2  ) )
      2.900  2.100    2.100  peak    9802  weight   0.11000E+01  volume   0.13225E+03  ppm1    3.769  ppm2    1.897
ASSI ( 9812)
   ( ( segid *BrD * and resid 103 and name HA   ) )
   ( ( segid *BrD * and resid 103 and name HB1  ) )
      2.800  2.000    2.000  peak    9812  weight   0.11000E+01  volume   0.16112E+03  ppm1    3.769  ppm2    2.346
```

TABLE 2-continued

Unambigous NOE-derived Inter-proton Distance Restraints

```
ASSI ( 9822)
    ( ( segid *BrD * and resid 103 and name HA   ) )
    ( ( segid *BrD * and resid 106 and name HB1  ) )
      2.800  2.000   2.000 peak    9822 weight   0.11000E+01 volume   0.15761E+03 ppm1    3.769 ppm2    3.917
ASSI ( 9832)
    ( ( segid *BrD * and resid 103 and name HA   ) )
    ( ( segid *BrD * and resid 106 and name HB2  ) )
      2.800  2.000   2.000 peak    9832 weight   0.11000E+01 volume   0.15186E+03 ppm1    3.769 ppm2    3.702
ASSI ( 9862)
    ( ( segid *BrD * and resid 10 and name HA   ) )
    ( ( segid *BrD * and resid 11 and name HD1  ) )
      3.000  2.200   2.200 peak    9862 weight   0.11000E+01 volume   0.11074E+03 ppm1    5.479 ppm2    4.464
ASSI ( 9872)
    ( ( segid *BrD * and resid 22 and name HB2  ) )
    ( ( segid *BrD * and resid 19 and name HA   ) )
      2.800  2.000   2.000 peak    9872 weight   0.11000E+01 volume   0.16684E+03 ppm1    2.286 ppm2    4.297
ASSI ( 9912)
    ( ( segid *BrD * and resid 36 and name HB1  ) )
    ( ( segid *BrD * and resid 36 and name HA   ) )
      2.700  1.800   1.800 peak    9912 weight   0.11000E+01 volume   0.21618E+03 ppm1    2.685 ppm2    5.445
ASSI ( 9922)
    ( ( segid *BrD * and resid 36 and name HB2  ) )
    ( ( segid *BrD * and resid 36 and name HA   ) )
      2.800  2.000   2.000 peak    9922 weight   0.11000E+01 volume   0.17054E+03 ppm1    2.340 ppm2    5.444
ASSI ( 9932)
    ( ( segid *BrD * and resid 36 and name HB1  ) )
    ( ( segid *BrD * and resid 37 and name HD1  ) )
      5.500  5.500   0.000 peak    9932 weight   0.11000E+01 volume   0.21944E+00 ppm1    2.686 ppm2    4.296
ASSI ( 9942)
    ( ( segid *BrD * and resid 36 and name HB2  ) )
    ( ( segid *BrD * and resid 37 and name HD1  ) )
      3.900  3.800   1.600 peak    9942 weight   0.11000E+01 volume   0.23373E+02 ppm1    2.341 ppm2    4.296
ASSI ( 9942)
    ( ( segid *BrD * and resid 36 and name HG1  ) )
    ( ( segid *BrD * and resid 37 and name HD1  ) )
      2.600  1.700   1.700 peak    9952 weight   0.11000E+01 volume   0.23785E+03 ppm1    2.781 ppm2    4.289
ASSI ( 9962)
    ( ( segid *BrD * and resid 54 and name HB1  ) )
    ( ( segid *BrD * and resid 54 and name HA   ) )
      2.900  2.100   2.100 peak    9962 weight   0.11000E+01 volume   0.14616E+03 ppm1    2.585 ppm2    5.542
ASSI ( 9982)
    ( ( segid *BrD * and resid 54 and name HB2  ) )
    ( ( segid *BrD * and resid 54 and name HG1  ) )
      2.900  2.100   2.100 peak    9982 weight   0.11000E+01 volume   0.13342E+03 ppm1    2.947 ppm2    3.304
ASSI (10042)
    ( ( segid *BrD * and resid 54 and name HA   ) )
    ( ( segid *BrD * and resid 54 and name HG1  ) )
      3.400  2.900   2.100 peak   10042 weight   0.11000E+01 volume   0.51922E+02 ppm1    5.541 ppm2    3.304
ASSI (10062)
    ( ( segid *BrD * and resid 35 and name HA   ) )
    ( ( segid *BrD * and resid 35 and name HB2  ) )
      3.000  2.200   2.200 peak   10062 weight   0.11000E+01 volume   0.10268E+03 ppm1    4.904 ppm2    2.781
ASSI (10062)
    ( ( segid *BrD * and resid 35 and name HA   ) )
    ( ( segid *BrD * and resid 35 and name HB1  ) )
      3.100  2.400   2.400 peak   10072 weight   0.11000E+01 volume   0.86087E+02 ppm1    4.904 ppm2    2.831
ASSI (10112)
    ( ( segid *BrD * and resid 70 and name HB1  ) )
    (   segid *BrD * and resid 69 and name HG2%)
      4.700  4.700   0.800 peak   10112 weight   0.11000E+01 volume   0.77364E+01 ppm1    4.756 ppm2    1.427
ASSI (10122)
    ( ( segid *BrD * and resid 70 and name HB2  ) )
    (   segid *BrD * and resid 69 and name HG2%)
      4.800  4.800   0.700 peak   10122 weight   0.11000E+01 volume   0.67595E+01 ppm1    4.359 ppm2    1.428
ASSI (10132)
    ( ( segid *BrD * and resid 70 and name HB2  ) )
    (   segid *BrD * and resid 69 and name HG1%)
      3.200  2.600   2.300 peak   10132 weight   0.11000E+01 volume   0.71826E+02 ppm1    4.360 ppm2    1.543
ASSI (10232)
    ( ( segid *BrD * and resid 7 and name HB1  ) )
    ( ( segid *BrD * and resid 7 and name HA   ) )
      2.800  2.000   2.000 peak   10232 weight   0.11000E+01 volume   0.15716E+03 ppm1    2.634 ppm2    5.143
ASSI (10232)
    ( ( segid *BrD * and resid 7 and name HB2  ) )
    ( ( segid *BrD * and resid 7 and name HA   ) )
      2.900  2.100   2.100 peak   10242 weight   0.11000E+01 volume   0.13922E+03 ppm1    2.501 ppm2    5.143
```

TABLE 2-continued

Unambigous NOE-derived Inter-proton Distance Restraints

```
ASSI (10252)
    ( ( segid *BrD * and resid 42 and name HA   ) )
    ( ( segid *BrD * and resid 42 and name HB1  ) )
      2.400  1.400   1.400  peak  10252  weight   0.11000E+01 volume   0.37492E+03 ppm1    5.051 ppm2    2.784
ASSI (10292)
    ( ( segid *BrD * and resid 42 and name HB2  ) )
    ( ( segid *BrD * and resid 42 and name HA   ) )
      2.300  1.300   1.300  peak  10292  weight   0.11000E+01 volume   0.49547E+03 ppm1    2.586 ppm2    5.046
ASSI (10312)
    ( ( segid *BrD * and resid 87 and name HA   ) )
    ( ( segid *BrD * and resid 87 and name HB2  ) )
      2.400  1.400   1.400  peak  10312  weight   0.11000E+01 volume   0.37361E+03 ppm1    4.858 ppm2    2.581
ASSI (10322)
    ( ( segid *BrD * and resid 87 and name HA   ) )
    ( ( segid *BrD * and resid 87 and name HB1  ) )
      2.500  1.600   1.600  peak  10322  weight   0.11000E+01 volume   0.30668E+03 ppm1    4.854 ppm2    2.780
ASSI (10332)
    ( ( segid *BrD * and resid 87 and name HB1  ) )
    ( ( segid *BrD * and resid 84 and name HA   ) )
      2.600  1.700   1.700  peak  10332  weight   0.11000E+01 volume   0.28367E+03 ppm1    2.779 ppm2    4.873
ASSI (10342)
    ( ( segid *BrD * and resid 87 and name HB2  ) )
    ( ( segid *BrD * and resid 84 and name HA   ) )
      2.100  1.100   1.100  peak  10342  weight   0.11000E+01 volume   0.80939E+03 ppm1    2.585 ppm2    4.873
ASSI (10352)
    ( ( segid *BrD * and resid 87 and name HB2  ) )
    ( ( segid *BrD * and resid 87 and name HG1  ) )
      2.300  1.300   1.300  peak  10352  weight   0.11000E+01 volume   0.47273E+03 ppm1    2.585 ppm2    3.021
ASSI (10392)
    ( ( segid *BrD * and resid 87 and name HG2  ) )
    (   segid *BrD * and resid 50 and name HD1%)
      3.500  3.100   2.000  peak  10392  weight   0.11000E+01 volume   0.42729E+02 ppm1    2.782 ppm2    1.145
ASSI (10402)
    ( ( segid *BrD * and resid 48 and name HA   ) )
    ( ( segid *BrD * and resid 48 and name HB1  ) )
      2.400  1.400   1.400  peak  10402  weight   0.11000E+01 volume   0.46141E+03 ppm1    4.803 ppm2    2.729
ASSI (10422)
    ( ( segid *BrD * and resid 94 and name HA   ) )
    ( ( segid *BrD * and resid 94 and name HB1  ) )
      2.300  1.300   1.300  peak  10422  weight   0.11000E+01 volume   0.56402E+03 ppm1    4.831 ppm2    2.731
ASSI (10452)
    ( ( segid *BrD * and resid 92 and name HB2  ) )
    ( ( segid *BrD * and resid 92 and name HA   ) )
      2.300  1.300   1.300  peak  10452  weight   0.11000E+01 volume   0.48724E+03 ppm1    2.570 ppm2    4.798
ASSI (10462)
    ( ( segid *BrD * and resid 92 and name HB1  ) )
    ( ( segid *BrD * and resid 92 and name HA   ) )
      2.000  1.000   1.000  peak  10462  weight   0.11000E+01 volume   0.12901E+04 ppm1    2.694 ppm2    4.798
ASSI (10482)
    ( ( segid *BrD * and resid 112 and name HB1 ) )
    ( ( segid *BrD * and resid 109 and name HA  ) )
      2.400  1.400   1.400  peak  10482  weight   0.11000E+01 volume   0.44320E+03 ppm1    2.684 ppm2    4.638
ASSI (10492)
    ( ( segid *BrD * and resid 112 and name HB1 ) )
    ( ( segid *BrD * and resid 112 and name HA  ) )
      2.400  1.400   1.400  peak  10492  weight   0.11000E+01 volume   0.38447E+03 ppm1    2.684 ppm2    4.587
ASSI (10532)
    ( ( segid *BrD * and resid 75 and name HA   ) )
    ( ( segid *BrD * and resid 75 and name HB1  ) )
      2.500  1.600   1.600  peak  10532  weight   0.11000E+01 volume   0.36144E+03 ppm1    4.509 ppm2    2.931
ASSI (10542)
    ( ( segid *BrD * and resid 75 and name HA   ) )
    ( ( segid *BrD * and resid 75 and name HB2  ) )
      2.400  1.400   1.400  peak  10542  weight   0.11000E+01 volume   0.39358E+03 ppm1    4.509 ppm2    2.847
ASSI (10552)
    ( ( segid *BrD * and resid 75 and name HG1  ) )
    (   segid *BrD * and resid 75 and name HE % )
      2.600  1.700   1.700  peak  10552  weight   0.11000E+01 volume   0.23961E+03 ppm1    3.523 ppm2    2.662
ASSI (10562)
    ( ( segid *BrD * and resid 75 and name HG2  ) )
    (   segid *BrD * and resid 75 and name HE % )
      2.600  1.700   1.700  peak  10562  weight   0.11000E+01 volume   0.23485E+03 ppm1    3.227 ppm2    2.662
ASSI (10632)
    ( ( segid *BrD * and resid 66 and name HA   ) )
    ( ( segid *BrD * and resid 66 and name HG1  ) )
      2.600  1.700   1.700  peak  10632  weight   0.11000E+01 volume   0.25166E+03 ppm1    5.000 ppm2    2.181
```

TABLE 2-continued

Unambigous NOE-derived Inter-proton Distance Restraints

```
ASSI (10642)
    ( ( segid *BrD * and resid 66 and name HG2 ) )
    ( ( segid *BrD * and resid 66 and name HA   ) )
    2.500  1.600   1.600  peak   10642  weight   0.11000E+01 volume   0.30460E+03 ppm1    2.141 ppm2   4.998
ASSI (10652)
    ( ( segid *BrD * and resid 66 and name HA   ) )
    ( ( segid *BrD * and resid 66 and name HB1  ) )
    2.300  1.300   1.300  peak   10652  weight   0.11000E+01 volume   0.48749E+03 ppm1    5.000 ppm2   2.702
ASSI (10662)
    ( ( segid *BrD * and resid 66 and name HA   ) )
    ( ( segid *BrD * and resid 66 and name HB2  ) )
    2.100  1.100   1.100  peak   10662  weight   0.11000E+01 volume   0.87656E+03 ppm1    5.000 ppm2   2.608
ASSI (10672)
    ( ( segid *BrD * and resid 80 and name HB2  ) )
    ( ( segid *BrD * and resid 77 and name HA   ) )
    2.600  1.700   1.700  peak   10672  weight   0.11000E+01 volume   0.24800E+03 ppm1    2.536 ppm2   4.951
ASSI (10682)
    ( ( segid *BrD * and resid 80 and name HB1  ) )
    ( ( segid *BrD * and resid 77 and name HA   ) )
    2.600  1.700   1.700  peak   10682  weight   0.11000E+01 volume   0.24031E+03 ppm1    2.583 ppm2   4.951
ASSI (10692)
    ( ( segid *BrD * and resid 80 and name HB2  ) )
    ( ( segid *BrD * and resid 80 and name HA   ) )
    3.000  2.200   2.200  peak   10692  weight   0.11000E+01 volume   0.11905E+03 ppm1    2.536 ppm2   4.671
ASSI (10702)
    ( ( segid *BrD * and resid 80 and name HB1  ) )
    ( ( segid *BrD * and resid 80 and name HA   ) )
    2.900  2.100   2.100  peak   10702  weight   0.11000E+01 volume   0.13820E+03 ppm1    2.584 ppm2   4.672
ASSI (10752)
    ( ( segid *BrD * and resid 80 and name HA   ) )
    ( ( segid *BrD * and resid 80 and name HG1  ) )
    2.300  1.300   1.300  peak   10752  weight   0.11000E+01 volume   0.52255E+03 ppm1    4.655 ppm2   2.339
ASSI (10762)
    ( ( segid *BrD * and resid 80 and name HA   ) )
    (   segid *BrD * and resid 83 and name HG2%)
    3.200  2.600   2.300  peak   10762  weight   0.11000E+01 volume   0.74419E+02 ppm1    4.655 ppm2   1.901
ASSI (10792)
    ( ( segid *BrD * and resid 9 and name HA    ) )
    ( ( segid *BrD * and resid 9 and name HB1   ) )
    2.500  1.600   1.600  peak   10792  weight   0.11000E+01 volume   0.30562E+03 ppm1    4.953 ppm2   2.434
ASSI (10802)
    ( ( segid *BrD * and resid 20 and name HA   ) )
    ( ( segid *BrD * and resid 23 and name HB1  ) )
    2.800  2.000   2.000  peak   10802  weight   0.11000E+01 volume   0.14886E+03 ppm1    4.901 ppm2   2.931
ASSI (10812)
    ( ( segid *BrD * and resid 20 and name HA   ) )
    ( ( segid *BrD * and resid 23 and name HB2  ) )
    2.900  2.100   2.100  peak   10812  weight   0.11000E+01 volume   0.14118E+03 ppm1    4.901 ppm2   2.857
ASSI (10822)
    ( ( segid *BrD * and resid 27 and name HB1  ) )
    ( ( segid *BrD * and resid 24 and name HA   ) )
    2.500  1.600   1.600  peak   10822  weight   0.11000E+01 volume   0.34604E+03 ppm1    4.608 ppm2   4.788
ASSI (10932)
    ( ( segid *BrD * and resid 108 and name HA  ) )
    ( ( segid *BrD * and resid 111 and name HB1 ) )
    2.900  2.100   2.100  peak   10932  weight   0.11000E+01 volume   0.13575E+03 ppm1    4.801 ppm2   2.475
ASSI (10942)
    ( ( segid *BrD * and resid 108 and name HA  ) )
    ( ( segid *BrD * and resid 111 and name HB2 ) )
    3.000  2.200   2.200  peak   10942  weight   0.11000E+01 volume   0.11676E+03 ppm1    4.803 ppm2   2.351
ASSI (10952)
    ( ( segid *BrD * and resid 108 and name HA  ) )
    ( ( segid *BrD * and resid 111 and name HD1 ) )
    3.200  2.600   2.300  peak   10952  weight   0.11000E+01 volume   0.76235E+02 ppm1    4.803 ppm2   2.237
ASSI (11002)
    ( ( segid *BrD * and resid 44 and name HG2  ) )
    ( ( segid *BrD * and resid 44 and name HD1  ) )
    2.300  1.300   1.300  peak   11002  weight   0.11000E+01 volume   0.53477E+03 ppm1    2.645 ppm2   4.337
ASSI (11032)
    ( ( segid *BrD * and resid 44 and name HD1  ) )
    ( ( segid *BrD * and resid 43 and name HA   ) )
    2.300  1.300   1.300  peak   11032  weight   0.11000E+01 volume   0.59437E+03 ppm1    4.312 ppm2   5.541
ASSI (11092)
    ( ( segid *BrD * and resid 11 and name HA   ) )
    ( ( segid *BrD * and resid 14 and name HB1  ) )
    3.000  2.200   2.200  peak   11092  weight   0.11000E+01 volume   0.11894E+03 ppm1    4.951 ppm2   2.471
```

TABLE 2-continued

Unambigous NOE-derived Inter-proton Distance Restraints

```
ASSI (11112)
   ( ( segid *BrD * and resid 11 and name HD1 ) )
   ( ( segid *BrD * and resid 10 and name HB2 ) )
      2.800  2.000    2.000 peak   11112 weight    0.11000E+01 volume   0.15710E+03 ppm1    4.457 ppm2    3.300
ASSI (11122)
   ( ( segid *BrD * and resid 11 and name HD1 ) )
   ( ( segid *BrD * and resid 10 and name HB1 ) )
      3.000  2.200    2.000 peak   11122 weight    0.11000E+01 volume   0.11776E+03 ppm1    4.457 ppm2    3.355
ASSI (11152)
   ( ( segid *BrD * and resid 37 and name HD1 ) )
   ( ( segid *BrD * and resid 36 and name HA  ) )
      3.400  2.900    2.100 peak   11152 weight    0.11000E+01 volume   0.48585E+02 ppm1    4.262 ppm2    5.446
ASSI (11182)
   ( ( segid *BrD * and resid 53 and name HD2 ) )
   (   segid *BrD * and resid 50 and name HG2%)
      3.400  2.900    2.100 peak   11182 weight    0.11000E+01 volume   0.47917E+02 ppm1    4.015 ppm2    0.993
ASSI (11212)
   ( ( segid *BrD * and resid 53 and name HG1 ) )
   ( ( segid *BrD * and resid 53 and name HD1 ) )
      2.800  2.000    2.000 peak   11212 weight    0.11000E+01 volume   0.15118E+03 ppm1    2.784 ppm2    4.209
ASSI (11222)
   ( ( segid *BrD * and resid 53 and name HG2 ) )
   ( ( segid *BrD * and resid 53 and name HD1 ) )
      2.800  2.000    2.000 peak   11272 weight    0.11000E+01 volume   0.15165E+03 ppm1    2.490 ppm2    4.210
ASSI (11232)
   ( ( segid *BrD * and resid 53 and name HG2 ) )
   ( ( segid *BrD * and resid 53 and name HD2 ) )
      2.900  2.100    2.100 peak   11232 weight    0.11000E+01 volume   0.12572E+03 ppm1    2.486 ppm2    4.011
ASSI (11242)
   ( ( segid *BrD * and resid 53 and name HG1 ) )
   ( ( segid *BrD * and resid 53 and name HD2 ) )
      3.100  2.400    2.400 peak   11242 weight    0.11000E+01 volume   0.94017E+02 ppm1    2.784 ppm2    4.011
ASSI (11252)
   ( ( segid *BrD * and resid 53 and name HG1 ) )
   (   segid *BrD * and resid 50 and name HG2%)
      4.300  4.300    1.200 peak   11252 weight    0.11000E+01 volume   0.13261E+02 ppm1    2.784 ppm2    0.993
ASSI (11272)
   ( ( segid *BrD * and resid 19 and name HB1 ) )
   (   segid *BrD * and resid 63 and name HD2%)
      3.000  2.200    2.200 peak   11272 weight    0.11000E+01 volume   0.10292E+03 ppm1    2.290 ppm2    1.492
ASSI (11292)
   ( ( segid *BrD * and resid 19 and name HB1 ) )
   (   segid *BrD * and resid 63 and name HD1%)
      3.300  2.700    2.200 peak   11292 weight    0.11000E+01 volume   0.56479E+02 ppm1    2.290 ppm2    1.655
ASSI (11302)
   ( ( segid *BrD * and resid 19 and name HB2 ) )
   (   segid *BrD * and resid 63 and name HD1%)
      3.400  2.900    2.100 peak   11302 weight    0.11000E+01 volume   0.52899E+02 ppm1    1.988 ppm2    1.655
ASSI (11392)
   ( ( segid *BrD * and resid 97 and name HA  ) )
   ( ( segid *BrD * and resid 97 and name HG1 ) )
      2.400  1.400    1.400 peak   11392 weight    0.11000E+01 volume   0.40873E+03 ppm1    4.805 ppm2    2.436
ASSI (11422)
   ( ( segid *BrD * and resid 97 and name HB1 ) )
   ( ( segid *BrD * and resid 94 and name HA  ) )
      2.200  1.200    1.200 peak   11422 weight    0.11000E+01 volume   0.64841E+03 ppm1    2.685 ppm2    4.830
ASSI (11442)
   ( ( segid *BrD * and resid 97 and name HD1 ) )
   ( ( segid *BrD * and resid 97 and name HA  ) )
      3.600  3.200    1.900 peak   11442 weight    0.11000E+01 volume   0.36224E+02 ppm1    2.420 ppm2    4.800
ASSI (11472)
   ( ( segid *BrD * and resid 86 and name HB1 ) )
   ( ( segid *BrD * and resid 86 and name HA  ) )
      2.400  1.400    1.400 peak   11472 weight    0.11000E+01 volume   0.38167E+03 ppm1    2.340 ppm2    4.807
ASSI (11482)
   ( ( segid *BrD * and resid 86 and name HB1 ) )
   ( ( segid *BrD * and resid 86 and name HG2 ) )
      2.900  2.100    2.100 peak   11482 weight    0.11000E+01 volume   0.12261E+03 ppm1    2.340 ppm2    0.766
ASSI (11612)
   ( ( segid *BrD * and resid 64 and name HB1 ) )
   ( ( segid *BrD * and resid 61 and name HA  ) )
      2.300  1.300    1.300 peak   11612 weight    0.11000E+01 volume   0.48201E+03 ppm1    2.636 ppm2    4.667
ASSI (11622)
   ( ( segid *BrD * and resid 64 and name HG1 ) )
   ( ( segid *BrD * and resid 61 and name HA  ) )
      2.600  1.700    1.700 peak   11622 weight    0.11000E+01 volume   0.27263E+03 ppm1    2.190 ppm2    4.667
```

TABLE 2-continued

Unambigous NOE-derived Inter-proton Distance Restraints

```
ASSI (11692)
    ( ( segid *BrD * and resid 6 and name HA   ) )
    ( ( segid *BrD * and resid 6 and name HB2  ) )
    2.400  1.400   1.400  peak   11692  weight   0.11000E+01  volume   0.40526E+03  ppm1    4.972  ppm2    2.291
ASSI (11702)
    ( ( segid *BrD * and resid 72 and name HD1  ) )
    ( ( segid *BrD * and resid 72 and name HA   ) )
    2.600  1.700   1.700  peak   11702  weight   0.11000E+01  volume   0.26243E+03  ppm1    2.291  ppm2    4.646
ASSI (11712)
    ( ( segid *BrD * and resid 62 and name HD1  ) )
    ( ( segid *BrD * and resid 62 and name HG1  ) )
    2.700  1.800   1.800  peak   11712  weight   0.11000E+01  volume   0.19040E+03  ppm1    3.177  ppm2    2.323
ASSI (11732)
    ( ( segid *BrD * and resid 62 and name HD2  ) )
    ( ( segid *BrD * and resid 62 and name HG2  ) )
    3.200  2.600   2.300  peak   11732  weight   0.11000E+01  volume   0.69523E+02  ppm1    2.629  ppm2    1.480
ASSI (11742)
    ( ( segid *BrD * and resid 62 and name HD1  ) )
    ( ( segid *BrD * and resid 59 and name HA   ) )
    3.100  2.400   2.400  peak   11742  weight   0.11000E+01  volume   0.81736E+02  ppm1    3.177  ppm2    4.911
ASSI (11782)
    ( ( segid *BrD * and resid 91 and name HG1  ) )
    ( ( segid *BrD * and resid 91 and name HD2  ) )
    3.000  2.200   2.200  peak   11782  weight   0.11000E+01  volume   0.11953E+03  ppm1    2.779  ppm2    4.406
ASSI (11802)
    ( ( segid *BrD * and resid 91 and name HA   ) )
    ( ( segid *BrD * and resid 91 and name HB1  ) )
    2.700  1.800   1.800  peak   11802  weight   0.11000E+01  volume   0.18443E+03  ppm1    5.347  ppm2    2.978
ASSI (11812)
    ( ( segid *BrD * and resid 91 and name HA   ) )
    ( ( segid *BrD * and resid 91 and name HG1  ) )
    3.700  3.400   1.800  peak   11812  weight   0.11000E+01  volume   0.32384E+02  ppm1    5.347  ppm2    2.788
ASSI (11852)
    ( ( segid *BrD * and resid 91 and name HD1  ) )
    ( ( segid *BrD * and resid 91 and name HA   ) )
    2.700  1.800   1.800  peak   11852  weight   0.11000E+01  volume   0.19122E+03  ppm1    4.559  ppm2    5.642
ASSI (11882)
    ( ( segid *BrD * and resid 91 and name HD2  ) )
    ( ( segid *BrD * and resid 89 and name HB1  ) )
    2.800  2.000   2.000  peak   11882  weight   0.11000E+01  volume   0.16587E+03  ppm1    4.410  ppm2    3.668
ASSI (11912)
    ( ( segid *BrD * and resid 91 and name HB2  ) )
    ( ( segid *BrD * and resid 91 and name HD1  ) )
    3.700  3.400   1.800  peak   11912  weight   0.11000E+01  volume    031825E+02  ppm1    2.730  ppm2    4.559
ASSI (11922)
    ( ( segid *BrD * and resid 91 and name HD1  ) )
    ( ( segid *BrD * and resid 91 and name HB1  ) )
    3.400  2.900   2.100  peak   11922  weight   0.11000E+01  volume   0.50256E+02  ppm1    2.978  ppm2    4.559
ASSI (11942)
    ( ( segid *BrD * and resid 91 and name HB2  ) )
    ( ( segid *BrD * and resid 91 and name HA   ) )
    2.800  2.000   2.000  peak   11942  weight   0.11000E+01  volume   0.17033E+03  ppm1    2.725  ppm2    5.378
ASSI (11952)
    ( ( segid *BrD * and resid 33 and name HA   ) )
    ( ( segid *BrD * and resid 33 and name HG2  ) )
    3.000  2.200   2.200  peak   11952  weight   0.11000E+01  volume   0.10731E+03  ppm1    4.361  ppm2   -0.319
ASSI (11962)
    ( ( segid *BrD * and resid 33 and name HA   ) )
    ( ( segid *BrD * and resid 33 and name HB2  ) )
    2.700  1.800   1.800  peak   11962  weight   0.11000E+01  volume   0.20069E+03  ppm1    4.361  ppm2   -0.166
ASSI (11972)
    ( ( segid *BrD * and resid 33 and name HA   ) )
    ( ( segid *BrD * and resid 33 and name HB1  ) )
    2.700  1.800   1.800  peak   11972  weight   0.11000E+01  volume   0.18669E+03  ppm1    4.360  ppm2    1.083
ASSI (12032)
    ( ( segid *BrD * and resid 33 and name HG1  ) )
    ( ( segid *BrD * and resid 33 and name HB2  ) )
    2.900  2.100   2.100  peak   12032  weight   0.11000E+01  volume   0.13883E+03  ppm1    0.858  ppm2   -0.165
ASSI (12042)
    ( ( segid *BrD * and resid 33 and name HG2  ) )
    ( ( segid *BrD * and resid 33 and name HB2  ) )
    2.900  2.100   2.100  peak   12042  weight   0.11000E+01  volume   0.12386E+03  ppm1   -0.324  ppm2   -0.169
ASSI (12062)
    ( ( segid *BrD * and resid 33 and name HD1  ) )
    ( ( segid *BrD * and resid 33 and name HG1  ) )
    3.000  2.200   2.200  peak   12062  weight   0.11000E+01  volume   0.11534E+03  ppm1    2.780  ppm2    0.864
```

TABLE 2-continued

Unambigous NOE-derived Inter-proton Distance Restraints

```
ASSI (12072)
    ( ( segid *BrD * and resid 33 and name HD2 ) )
    ( ( segid *BrD * and resid 33 and name HG1 ) )
      3.100  2.400    2.400 peak   12072 weight    0.11000E+01 volume   0.97683E+02 ppm1    2.189 ppm2    0.864
ASSI (12082)
    ( ( segid *BrD * and resid 33 and name HD1 ) )
    ( ( segid *BrD * and resid 33 and name HG2 ) )
      2.900  2.100    2.100 peak   12082 weight    0.11000E+01 volume   0.13242E+03 ppm1    2.780 ppm2   -0.319
ASSI (12092)
    ( ( segid *BrD * and resid 33 and name HD2 ) )
    ( ( segid *BrD * and resid 33 and name HG2 ) )
      2.900  2.100    2.100 peak   12092 weight    0.11000E+01 volume   0.13995E+03 ppm1    2.189 ppm2   -0.319
ASSI (12102)
    ( ( segid *BrD * and resid 33 and name HB1 ) )
    ( ( segid *BrD * and resid 33 and name HG2 ) )
      2.900  2.100    2.100 peak   12102 weight    0.11000E+01 volume   0.14146E+03 ppm1    1.051 ppm2   -0.316
ASSI (12132)
    ( ( segid *BrD * and resid 33 and name HB1 ) )
    ( ( segid *BrD * and resid 33 and name HG1 ) )
      3.300  2.400    2.400 peak   12132 weight    0.11000E+01 volume   0.94205E+02 ppm1    1.059 ppm2    0.859
ASSI (12182)
    ( ( segid *BrD * and resid 35 and name HA  ) )
    ( ( segid *BrD * and resid 36 and name HB1 ) )
      4.100  4.100    1.400 peak   12182 weight    0.11000E+01 volume   0.16299E+02 ppm1    4.904 ppm2    2.685
ASSI (12222)
    ( ( segid *BrD * and resid 59 and name HG2 ) )
    (   segid *BrD * and resid 59 and name HE % )
      2.300  1.300    1.300 peak   12222 weight    0.11000E+01 volume   0.52760E+03 ppm1    3.137 ppm2    1.875
ASSI (12242)
    ( ( segid *BrD * and resid 59 and name HB2 ) )
    (   segid *BrD * and resid 59 and name HE % )
      2.700  1.800    1.800 peak   12242 weight    0.11000E+01 volume   0.19334E+03 ppm1    2.487 ppm2    1.876
ASSI (12252)
    ( ( segid *BrD * and resid 59 and name HA  ) )
    ( ( segid *BrD * and resid 59 and name HB2 ) )
      3.300  2.700    2.200 peak   12252 weight    0.11000E+01 volume   0.59031E+02 ppm1    4.903 ppm2    2.487
ASSI (12262)
    ( ( segid *BrD * and resid 59 and name HA  ) )
    ( ( segid *BrD * and resid 62 and name HB1 ) )
      3.100  2.400    2.400 peak   12262 weight    0.11000E+01 volume   0.90578E+02 ppm1    4.903 ppm2    2.657
ASSI (12272)
    ( ( segid *BrD * and resid 59 and name HA  ) )
    ( ( segid *BrD * and resid 62 and name HB2 ) )
      2.900  2.100    2.100 peak   12272 weight    0.11000E+01 volume   0.13057E+03 ppm1    4.903 ppm2    1.670
ASSI (12312)
    ( ( segid *BrD * and resid 61 and name HB1 ) )
    ( ( segid *BrD * and resid 61 and name HA  ) )
      2.500  1.600    1.600 peak   12312 weight    0.11000E+01 volume   0.30078E+03 ppm1    2.826 ppm2    4.673
ASSI (12322)
    ( ( segid *BrD * and resid 61 and name HB1 ) )
    ( ( segid *BrD * and resid 58 and name HA  ) )
      3.000  2.200    2.200 peak   12322 weight    0.11000E+01 volume   0.10826E+03 ppm1    2.826 ppm2    4.453
ASSI (12332)
    ( ( segid *BrD * and resid 61 and name HB2 ) )
    ( ( segid *BrD * and resid 58 and name HA  ) )
      2.400  1.400    1.400 peak   12332 weight    0.11000E+01 volume   0.42931E+03 ppm1    2.679 ppm2    4.453
ASSI (12342)
    ( ( segid *BrD * and resid 61 and name HB2 ) )
    ( ( segid *BrD * and resid 61 and name HA  ) )
      2.100  1.100    1.100 peak   12342 weight    0.11000E+01 volume   0.81117E+03 ppm1    2.679 ppm2    4.673
ASSI (12392)
    (   segid *BrD * and resid 102 and name HD2%)
    ( ( segid *BrD * and resid 102 and name HG  ) )
      2.000  1.000    1.000 peak   12392 weight    0.11000E+01 volume   0.13682E+04 ppm1    1.304 ppm2    2.159
ASSI (12402)
    (   segid *BrD * and resid 102 and name HD2%)
    ( ( segid *BrD * and resid 102 and name HB1 ) )
      2.400  1.400    1.400 peak   12402 weight    0.11000E+01 volume   0.42022E+03 ppm1    1.304 ppm2    2.020
ASSI (12422)
    (   segid *BrD * and resid 102 and name HD2%)
    (   segid *BrD * and resid 31 and name HB % )
      3.500  3.100    2.000 peak   12422 weight    0.11000E+01 volume   0.40319E+02 ppm1    1.305 ppm2    2.315
ASSI (12432)
    (   segid *BrD * and resid 14 and name HD1%)
    ( ( segid *BrD * and resid 14 and name HG  ) )
      2.400  1.400    1.400 peak   12432 weight    0.11000E+01 volume   0.38368E+03 ppm1    1.402 ppm2    2.062
```

TABLE 2-continued

Unambigous NOE-derived Inter-proton Distance Restraints

```
ASSI (12442)
    ( segid *BrD * and resid 14 and name HD1%)
    ( ( segid *BrD * and resid 14 and name HB2  ) )
      2.300  1.300   1.300  peak   12442  weight   0.11000E+01 volume   0.51224E+03 ppm1    1.402 ppm2    2.155
ASSI (12452)
    ( segid *BrD * and resid 14 and name HD1%)
    ( ( segid *BrD * and resid 14 and name HB1  ) )
      2.300  1.300   1.300  peak   12452  weight   0.11000E+01 volume   0.51311E+03 ppm1    1.402 ppm2    2.468
ASSI (12462)
    ( segid *BrD * and resid 14 and name HD1%)
    ( ( segid *BrD * and resid 14 and name HA   ) )
      2.600  1.700   1.700  peak   12462  weight   0.11000E+01 volume   0.23971E+03 ppm1    1.401 ppm2    4.655
ASSI (12472)
    ( segid *BrD * and resid 14 and name HD1%)
    ( segid *BrD * and resid 18 and name HD1%)
      2.500  1.600   1.600  peak   12472  weight   0.11000E+01 volume   0.29352E+03 ppm1    1.402 ppm2    1.084
ASSI (12602)
    ( segid *BrD * and resid 59 and name HE % )
    ( ( segid *BrD * and resid 59 and name HB1  ) )
      2.700  1.800   1.800  peak   12602  weight   0.11000E+01 volume   0.21211E+03 ppm1    1.847 ppm2    2.707
ASSI (12602)
    ( segid *BrD * and resid 59 and name HE % )
    ( ( segid *BrD * and resid 59 and name HG1  ) )
      3.100  2.400   2.400  peak   12622  weight   0.11000E+01 volume   0.88634E+02 ppm1    1.848 ppm2    3.230
ASSI (12662)
    ( segid *BrD * and resid 54 and name HE % )
    ( ( segid *BrD * and resid 54 and name HB2  ) )
      2.700  1.800   1.800  peak   12662  weight   0.11000E+01 volume   0.21213E+03 ppm1    2.535 ppm2    1.964
ASSI (12682)
    ( segid *BrD * and resid 54 and name HE % )
    ( ( segid *BrD * and resid 54 and name HG1  ) )
      2.500  1.600   1.600  peak   12682  weight   0.11000E+01 volume   0.35414E+03 ppm1    2.535 ppm2    3.307
ASSI (12772)
    ( segid *BrD * and resid 50 and name HG2%)
    ( ( segid *BrD * and resid 84 and name HB1  ) )
      2.900  2.100   2.100  peak   12772  weight   0.11000E+01 volume   0.14057E+03 ppm1    1.004 ppm2    3.605
ASSI (12802)
    ( ( segid *BrD * and resid 78 and name HB2  ) )
    ( ( segid *BrD * and resid 75 and name HA   ) )
      3.300  2.700   2.200  peak   12802  weight   0.11000E+01 volume   0.66311E+02 ppm1    1.054 ppm2    4.517
ASSI (12902)
    ( segid *BrD * and resid 38 and name HG1%)
    ( segid *BrD * and resid 43 and name HB % )
      2.800  2.000   2.000  peak   12902  weight   0.11000E+01 volume   0.17186E+03 ppm1    1.059 ppm2    1.715
ASSI (12912)
    ( ( segid *BrD * and resid 25 and name HA   ) )
    ( ( segid *BrD * and resid 28 and name HB2  ) )
      3.400  2.900   2.100  peak   12912  weight   0.11000E+01 volume   0.50976E+02 ppm1    4.412 ppm2    3.406
ASSI (12922)
    ( ( segid *BrD * and resid 25 and name HA   ) )
    ( ( segid *BrD * and resid 28 and name HB1  ) )
      3.400  2.900   2.100  peak   12922  weight   0.11000E+01 volume   0.50637E+02 ppm1    4.412 ppm2    3.607
ASSI (12932)
    ( ( segid *BrD * and resid 25 and name HB   ) )
    ( ( segid *BrD * and resid 25 and name HA   ) )
      2.600  1.700   1.700  peak   12932  weight   0.11000E+01 volume   0.25503E+03 ppm1    2.979 ppm2    4.436
ASSI (12942)
    ( ( segid *BrD * and resid 99 and name HA   ) )
    ( segid *BrD * and resid 102 and name HD1%)
      3.500  3.100   2.000  peak   12942  weight   0.11000E+01 volume   0.42963E+02 ppm1    4.458 ppm2    1.321
ASSI (12952)
    ( segid *BrD * and resid 17 and name HG2%)
    ( segid *BrD * and resid 18 and name HD1%)
      3.100  2.400   2.400  peak   12952  weight   0.11000E+01 volume   0.90746E+02 ppm1    1.745 ppm2    1.083
ASSI (12982)
    ( ( segid *BrD * and resid 98 and name HB1  ) )
    ( ( segid *BrD * and resid 95 and name HA   ) )
      3.200  2.600   2.300  peak   12982  weight   0.11000E+01 volume   0.76248E+02 ppm1    4.013 ppm2    4.445
ASSI (13062)
    ( segid *BrD * and resid 56 and name HD1%)
    ( ( segid *BrD * and resid 34 and name HB2  ) )
      2.900  2.100   2.100  peak   13062  weight   0.11000E+01 volume   0.13096E+03 ppm1    1.546 ppm2    3.143
ASSI (13152)
    ( ( segid *BrD * and resid 81 and name HA   ) )
    ( ( segid *BrD * and resid 84 and name HB2  ) )
      3.300  2.700   2.200  peak   13152  weight   0.11000E+01 volume   0.59764E+02 ppm1    3.718 ppm2    3.278
```

TABLE 2-continued

Unambigous NOE-derived Inter-proton Distance Restraints

```
ASSI (13162)
     ( ( segid *BrD * and resid 85 and name HA    ) )
     ( ( segid *BrD * and resid 88 and name HB1  ) )
        3.400   2.900    2.100  peak   13162  weight   0.11000E+01  volume   0.52965E+02  ppm1    5.003  ppm2    3.532
ASSI (13172)
     ( ( segid *BrD * and resid 86 and name HB1  ) )
     ( ( segid *BrD * and resid 83 and name HA   ) )
        3.700   3.400    1.800  peak   13172  weight   0.11000E+01  volume   0.32755E+02  ppm1    2.340  ppm2    4.462
ASSI (13182)
     (   segid *BrD * and resid 54 and name HE % )
     ( ( segid *BrD * and resid 54 and name HA   ) )
        2.300   1.300    1.300  peak   13182  weight   0.11000E+01  volume   0.48303E+03  ppm1    2.535  ppm2    5.543
ASSI (13212)
     ( ( segid *BrD * and resid 47 and name HA   ) )
     ( ( segid *BrD * and resid 50 and name HB   ) )
        3.600   3.200    1.900  peak   13212  weight   0.11000E+01  volume   0.37838E+02  ppm1    4.704  ppm2    1.823
ASSI (13222)
     (   segid *BrD * and resid 81 and name HG2%)
     (   segid *BrD * and resid 34 and name HB2  ) )
        2.800   2.000    2.000  peak   13222  weight   0.11000E+01  volume   0.16892E+03  ppm1    0.756  ppm2    3.149
ASSI (13252)
     ( ( segid *BrD * and resid 34 and name HB2  ) )
     (   segid *BrD * and resid 56 and name HG   ) )
        3.100   2.400    2.400  peak   13252  weight   0.11000E+01  volume   0.87944E+02  ppm1    3.127  ppm2    2.323
ASSI (13262)
     ( ( segid *BrD * and resid 34 and name HB1  ) )
     (   segid *BrD * and resid 56 and name HG   ) )
        3.200   2.600    2.300  peak   13262  weight   0.11000E+01  volume   0.75137E+02  ppm1    4.108  ppm2    2.322
ASSI (13362)
     (   segid *BrD * and resid 18 and name HD1%)
     ( ( segid *BrD * and resid 18 and name HB1  ) )
        2.300   1.300    1.300  peak   13362  weight   0.11000E+01  volume   0.50793E+03  ppm1    1.058  ppm2    2.128
ASSI (13372)
     ( ( segid *BrD * and resid 14 and name HB1  ) )
     (   segid *BrD * and resid 18 and name HD1%)
        4.000   4.000    1.500  peak   13372  weight   0.11000E+01  volume   0.18693E+02  ppm1    2.441  ppm2    1.084
ASSI (13382)
     (   segid *BrD * and resid 25 and name HG1%)
     ( ( segid *BrD * and resid 22 and name HA   ) )
        2.600   1.700    1.700  peak   13382  weight   0.11000E+01  volume   0.28896E+03  ppm1    1.795  ppm2    4.720
ASSI (13402)
     ( ( segid *BrD * and resid 102 and name HB2 ) )
     ( ( segid *BrD * and resid 99 and name HA   ) )
        2.600   1.700    1.700  peak   13402  weight   0.11000E+01  volume   0.26245E+03  ppm1    1.842  ppm2    4.441
ASSI (13422)
     ( ( segid *BrD * and resid 21 and name HA   ) )
     (   segid *BrD * and resid 18 and name HD2%)
        3.700   3.400    1.800  peak   13422  weight   0.11000E+01  volume   0.29780E+02  ppm1    2.487  ppm2    0.409
ASSI (13432)
     ( ( segid *BrD * and resid 57 and name HA   ) )
     ( ( segid *BrD * and resid 60 and name HB2  ) )
        2.700   1.800    1.800  peak   13432  weight   0.11000E+01  volume   0.19090E+03  ppm1    4.805  ppm2    4.625
ASSI (13442)
     ( ( segid *BrD * and resid 57 and name HA   ) )
     ( ( segid *BrD * and resid 60 and name HB1  ) )
        2.900   2.100    2.100  peak   13442  weight   0.11000E+01  volume   0.14250E+03  ppm1    4.805  ppm2    5.000
ASSI (13482)
     (   segid *BrD * and resid 58 and name HG2%)
     ( ( segid *BrD * and resid 62 and name HD2  ) )
        2.800   2.000    2.000  peak   13482  weight   0.11000E+01  volume   0.17578E+03  ppm1    1.651  ppm2    2.644
ASSI (13492)
     ( ( segid *BrD * and resid 61 and name HB1  ) )
     (   segid *BrD * and resid 58 and name HG2%)
        3.600   3.200    1.900  peak   13492  weight   0.11000E+01  volume   0.34592E+02  ppm1    2.826  ppm2    1.662
ASSI (13512)
     (   segid *BrD * and resid 59 and name HE % )
     ( ( segid *BrD * and resid 59 and name HA   ) )
        3.100   2.400    2.400  peak   13512  weight   0.11000E+01  volume   0.83827E+02  ppm1    1.848  ppm2    4.913
ASSI (13522)
     (   segid *BrD * and resid 59 and name HE % )
     (   segid *BrD * and resid 56 and name HD2%)
        3.400   2.900    2.100  peak   13522  weight   0.11000E+01  volume   0.55813E+02  ppm1    1.848  ppm2    1.271
ASSI (13542)
     ( ( segid *BrD * and resid 21 and name HA   ) )
     ( ( segid *BrD * and resid 24 and name HB2  ) )
        3.200   2.600    2.300  peak   13542  weight   0.11000E+01  volume   0.69544E+02  ppm1    4.360  ppm2    2.989
```

TABLE 2-continued

Unambigous NOE-derived Inter-proton Distance Restraints

```
ASSI (13552)
   ( ( segid *BrD * and resid 74 and name HB2 ) )
   ( ( segid *BrD * and resid 71 and name HA    ) )
      3.300  2.700    2.200   peak   13552  weight    0.11000E+01  volume   0.56669E+02  ppm1    2.974  ppm2    4.624
ASSI (13652)
   (  segid *BrD * and resid 58 and name HG2%)
   ( ( segid *BrD * and resid 62 and name HD1  ) )
      2.800  2.000    2.000   peak   13652  weight    0.11000E+01  volume   0.18084E+03  ppm1    1.649  ppm2    3.182
ASSI (13662)
   ( ( segid *BrD * and resid 32 and name HA   ) )
   (  segid *BrD * and resid 31 and name HB % )
      3.700  3.400    1.800   peak   13662  weight    0.11000E+01  volume   0.29121E+02  ppm1    4.952  ppm2    2.312
ASSI (13702)
   ( ( segid *BrD * and resid 42 and name HB1  ) )
   (  segid *BrD * and resid 43 and name HB % )
      3.800  3.600    1.700   peak   13702  weight    0.11000E+01  volume   0.26752E+02  ppm1    2.785  ppm2    1.712
ASSI (13722)
   ( ( segid *BrD * and resid 59 and name HA   ) )
   ( ( segid *BrD * and resid 62 and name HD2  ) )
      2.600  1.700    1.700   peak   13722  weight    0.11000E+01  volume   0.25810E+03  ppm1    4.903  ppm2    2.634
ASSI (13742)
   ( ( segid *BrD * and resid 63 and name HG   ) )
   ( ( segid *BrD * and resid 63 and name HB1  ) )
      2.300  1.300    1.300   peak   13742  weight    0.11000E+01  volume   0.59564E+03  ppm1    2.437  ppm2    2.905
ASSI (13902)
   ( ( segid *BrD * and resid 70 and name HB1  ) )
   (  segid *BrD * and resid 69 and name HG1%)
      3.700  3.400    1.800   peak   13902  weight    0.11000E+01  volume   0.30896E+02  ppm1    4.756  ppm2    1.544
ASSI (13912)
   (  segid *BrD * and resid 101 and name HG2%)
   ( ( segid *BrD * and resid 98 and name HA   ) )
      2.800  2.000    2.000   peak   13912  weight    0.11000E+01  volume   0.17496E+03  ppm1    1.596  ppm2    4.810
ASSI (13932)
   ( ( segid *BrD * and resid 101 and name HG12) )
   ( ( segid *BrD * and resid 98 and name HA   ) )
      3.400  2.900    2.100   peak   13932  weight    0.11000E+01  volume   0.55145E+02  ppm1    1.797  ppm2    4.808
ASSI (13942)
   ( ( segid *BrD * and resid 98 and name HA   ) )
   ( ( segid *BrD * and resid 101 and name HG11) )
      3.300  2.700    2.200   peak   13942  weight    0.11000E+01  volume   0.65568E+02  ppm1    4.804  ppm2    2.469
ASSI (14002)
   ( ( segid *BrD * and resid 53 and name HB1  ) )
   ( ( segid *BrD * and resid 53 and name HD1  ) )
      2.800  2.000    2.000   peak   14002  weight    0.11000E+01  volume   0.16043E+03  ppm1    2.781  ppm2    4.208
ASSI (14012)
   ( ( segid *BrD * and resid 53 and name HB1  ) )
   ( ( segid *BrD * and resid 53 and name HD2  ) )
      3.000  2.200    2.200   peak   14012  weight    0.11000E+01  volume   0.10929E+03  ppm1    2.781  ppm2    4.010
ASSI (14072)
   ( ( segid *BrD * and resid 79 and name HA   ) )
   ( ( segid *BrD * and resid 82 and name HB2  ) )
      3.000  2.200    2.200   peak   14072  weight    0.11000E+01  volume   0.11123E+03  ppm1    4.409  ppm2    3.606
ASSI (14082)
   ( ( segid *BrD * and resid 79 and name HA   ) )
   ( ( segid *BrD * and resid 82 and name HB1  ) )
      3.300  2.700    2.200   peak   14082  weight    0.11000E+01  volume   0.67314E+02  ppm1    4.409  ppm2    3.697
ASSI (14092)
   ( ( segid *BrD * and resid 79 and name HB2  ) )
   ( ( segid *BrD * and resid 76 and name HA   ) )
      2.400  1.400    1.400   peak   14092  weight    0.11000E+01  volume   0.38186E+03  ppm1    2.680  ppm2    4.683
ASSI (14182)
   ( ( segid *BrD * and resid 94 and name HA   ) )
   ( ( segid *BrD * and resid 97 and name HD1  ) )
      3.200  2.600    2.300   peak   14182  weight    0.11000E+01  volume   0.68636E+02  ppm1    4.830  ppm2    2.434
ASSI (14252)
   ( ( segid *BrD * and resid 113 and name HA   ) )
   (  segid *BrD * and resid 17 and name HG2%)
      3.600  3.200    1.900   peak   14252  weight    0.11000E+01  volume   0.37471E+02  ppm1    4.901  ppm2    1.750
ASSI (14552)
   ( ( segid *BrD * and resid 11 and name HB2  ) )
   ( ( segid *BrD * and resid 11 and name HD1  ) )
      2.700  1.800    1.800   peak   14552  weight    0.11000E+01  volume   0.21551E+03  ppm1    2.580  ppm2    4.460
ASSI (14572)
   ( ( segid *BrD * and resid 14 and name HB2  ) )
   ( ( segid *BrD * and resid 11 and name HA   ) )
      3.300  2.700    2.200   peak   14572  weight    0.11000E+01  volume   0.58722E+02  ppm1    2.145  ppm2    4.942
```

TABLE 2-continued

Unambigous NOE-derived Inter-proton Distance Restraints

```
ASSI (14592)
    ( segid *BrD * and resid 102 and name HD2%)
    ( ( segid *BrD * and resid 31 and name HA   ) )
        3.400   2.900    2.100  peak   14592  weight    0.11000E+01  volume   0.51768E+02  ppm1    1.303  ppm2    4.984
ASSI (14612)
    ( segid *BrD * and resid 102 and name HD2%)
    ( segid *BrD * and resid 25 and name HG2%)
        2.300   1.300    1.300  peak   14612  weight    0.11000E+01  volume   0.50747E+03  ppm1    1.305  ppm2    1.633
ASSI (14622)
    ( segid *BrD * and resid 102 and name HD2%)
    ( ( segid *BrD * and resid 25 and name HA   ) )
        2.700   1.800    1.800  peak   14622  weight    0.11000E+01  volume   0.22785E+03  ppm1    1.305  ppm2    4.425
ASSI (14662)
    ( ( segid *BrD * and resid 18 and name HB2 ) )
    ( ( segid *BrD * and resid 18 and name HG  ) )
        3.100   2.400    2.400  peak   14662  weight    0.11000E+01  volume   0.98423E+02  ppm1    0.911  ppm2    2.274
ASSI (14772)
    ( ( segid *BrD * and resid 36 and name HA  ) )
    ( segid *BrD * and resid 37 and name HG2 ) )
        5.500   5.500    0.000  peak   14772  weight    0.11000E+01  volume   0.48374E+00  ppm1    5.447  ppm2    2.587
ASSI (14812)
    ( ( segid *BrD * and resid 42 and name HB2 ) )
    ( segid *BrD * and resid 43 and name HB % )
        3.200   2.600    2.300  peak   14812  weight    0.11000E+01  volume   0.74053E+02  ppm1    2.586  ppm2    1.710
ASSI (14822)
    ( ( segid *BrD * and resid 35 and name HA  ) )
    ( ( segid *BrD * and resid 36 and name HB2 ) )
        3.800   3.600    1.700  peak   14822  weight    0.11000E+01  volume   0.27804E+02  ppm1    4.904  ppm2    2.340
ASSI (14942)
    ( ( segid *BrD * and resid 46 and name HA  ) )
    ( segid *BrD * and resid 88 and name HE % )
        2.700   1.800    1.800  peak   14942  weight    0.11000E+01  volume   0.19889E+03  ppm1    4.163  ppm2    7.421
ASSI (14962)
    ( ( segid *BrD * and resid 46 and name HA  ) )
    ( segid *BrD * and resid 46 and name HE % )
        3.600   3.200    1.900  peak   14962  weight    0.11000E+01  volume   0.36218E+02  ppm1    4.164  ppm2    6.689
ASSI (14992)
    ( ( segid *BrD * and resid 46 and name HB2 ) )
    ( segid *BrD * and resid 46 and name HE % )
        3.700   3.400    1.800  peak   14992  weight    0.11000E+01  volume   0.28675E+02  ppm1    3.078  ppm2    6.689
ASSI (15062)
    ( ( segid *BrD * and resid 28 and name HB2 ) )
    ( ( segid *BrD * and resid 28 and name HD2 ) )
        3.100   2.400    2.400  peak   15062  weight    0.11000E+01  volume   0.98530E+02  ppm1    3.372  ppm2    5.575
ASSI (15072)
    ( ( segid *BrD * and resid 28 and name HB1 ) )
    ( ( segid *BrD * and resid 28 and name HD2 ) )
        3.200   2.600    2.300  peak   15072  weight    0.11000E+01  volume   0.74212E+02  ppm1    3.570  ppm2    5.575
ASSI (15122)
    ( ( segid *BrD * and resid 67 and name HB1 ) )
    ( segid *BrD * and resid 67 and name HE % )
        4.100   4.100    1.400  peak   15122  weight    0.11000E+01  volume   0.17734E+02  ppm1    2.639  ppm2    7.315
ASSI (15292)
    ( ( segid *BrD * and resid 47 and name HA  ) )
    ( segid *BrD * and resid 46 and name HD % )
        4.100   4.100    1.400  peak   15292  weight    0.11000E+01  volume   0.16402E+02  ppm1    4.705  ppm2    5.762
ASSI (15322)
    ( ( segid *BrD * and resid 47 and name HB2 ) )
    ( segid *BrD * and resid 47 and name HE % )
        3.400   2.900    2.100  peak   15322  weight    0.11000E+01  volume   0.56146E+02  ppm1    1.375  ppm2    7.271
ASSI (15332)
    ( ( segid *BrD * and resid 47 and name HB1 ) )
    ( segid *BrD * and resid 47 and name HE % )
        3.200   2.600    2.300  peak   15332  weight    0.11000E+01  volume   0.74345E+02  ppm1    1.816  ppm2    7.271
ASSI (15352)
    ( ( segid *BrD * and resid 32 and name HB2 ) )
    ( ( segid *BrD * and resid 32 and name HE3 ) )
        2.600   1.700    1.700  peak   15352  weight    0.11000E+01  volume   0.27498E+03  ppm1    1.962  ppm2    7.952
ASSI (15432)
    ( ( segid *BrD * and resid 74 and name HB1 ) )
    ( segid *BrD * and resid 74 and name HD % )
        2.900   2.100    2.100  peak   15432  weight    0.11000E+01  volume   0.14689E+03  ppm1    3.576  ppm2    6.998
ASSI (15482)
    ( ( segid *BrD * and resid 74 and name HB2 ) )
    ( segid *BrD * and resid 74 and name HE % )
        3.600   2.200    1.900  peak   15482  weight    0.11000E+01  volume   0.37941E+02  ppm1    2.985  ppm2    7.533
```

TABLE 2-continued

Unambigous NOE-derived Inter-proton Distance Restraints

```
ASSI (15492)
   ( ( segid *BrD * and resid 74 and name HB1 ) )
   (  segid *BrD * and resid 74 and name HE % )
      2.800  2.000   2.000 peak   15492 weight   0.11000E+01 volume   0.16094E+03 ppm1     3.571 ppm2    7.535
ASSI (15602)
   ( ( segid *BrD * and resid 82 and name HB2 ) )
   (  segid *BrD * and resid 82 and name HE % )
      3.000  2.200   2.200 peak   15602 weight   0.11000E+01 volume   0.11655E+03 ppm1     3.573 ppm2    7.069
ASSI (15612)
   ( ( segid *BrD * and resid 82 and name HB1 ) )
   (  segid *BrD * and resid 82 and name HE % )
      2.800  2.000   2.000 peak   15612 weight   0.11000E+01 volume   0.15106E+03 ppm1     3.672 ppm2    7.069
ASSI (15732)
   ( ( segid *BrD * and resid 82 and name HA   ) )
   (  segid *BrD * and resid 82 and name HE % )
      3.200  2.600   2.300 peak   15732 weight   0.11000E+01 volume   0.68425E+02 ppm1     4.755 ppm2    7.063
ASSI (15742)
   ( ( segid *BrD * and resid 82 and name HA   ) )
   (  segid *BrD * and resid 82 and name HD % )
      2.100  1.100   1.100 peak   15742 weight   0.11000E+01 volume   0.82972E+03 ppm1     4.755 ppm2    7.259
ASSI (15792)
   ( ( segid *BrD * and resid 15 and name HA   ) )
   (  segid *BrD * and resid 18 and name HD2%)
      4.600  4.600   0.900 peak   15792 weight   0.11000E+01 volume   0.83712E+01 ppm1     4.607 ppm2    0.408
ASSI (16522)
   ( ( segid *BrD * and resid 107 and name HA   ) )
   (  segid *BrD * and resid 107 and name HE % )
      2.700  1.800   1.800 peak   16522 weight   0.11000E+01 volume   0.21131E+03 ppm1     4.410 ppm2    7.901
ASSI (16532)
   ( ( segid *BrD * and resid 96 and name HA   ) )
   (  segid *BrD * and resid 96 and name HE % )
      2.800  2.000   2.000 peak   16532 weight   0.11000E+01 volume   0.16900E+03 ppm1     4.410 ppm2    7.607
ASSI (16692)
   ( ( segid *BrD * and resid 52 and name HA   ) )
   ( ( segid *BrD * and resid 53 and name HG2 ) )
      5.500  5.500   0.000 peak   16692 weight   0.11000E+01 volume   0.97221E+00 ppm1     5.592 ppm2    2.494
ASSI (16822)
   ( ( segid *BrD * and resid 105 and name HB1 ) )
   ( ( segid *BrD * and resid 105 and name HA   ) )
      2.600  1.700   1.700 peak   16822 weight   0.11000E+01 volume   0.25358E+03 ppm1     3.721 ppm2    4.932
ASSI (17182)
   ( ( segid *BrD * and resid 105 and name HB2 ) )
   ( ( segid *BrD * and resid 105 and name HA   ) )
      2.400  1.400   1.400 peak   17182 weight   0.11000E+01 volume   0.43854E+03 ppm1     3.668 ppm2    4.932
ASSI (17202)
   ( ( segid *BrD * and resid 105 and name HB2 ) )
   (  segid *BrD * and resid 105 and name HD % )
      2.200  1.200   1.200 peak   17202 weight   0.11000E+01 volume   0.67242E+03 ppm1     3.720 ppm2    7.788
ASSI (17242)
   ( ( segid *BrD * and resid 105 and name HA   ) )
   (  segid *BrD * and resid 105 and name HD % )
      2.200  1.200   1.200 peak   17242 weight   0.11000E+01 volume   0.69463E+03 ppm1     4.903 ppm2    7.787
ASSI (17292)
   ( ( segid *BrD * and resid 116 and name HA   ) )
   ( ( segid *BrD * and resid 116 and name HG12) )
      2.800  2.000   2.000 peak   17292 weight   0.11000E+01 volume   0.16843E+03 ppm1     4.804 ppm2    1.554
ASSI (17302)
   ( ( segid *BrD * and resid 116 and name HA   ) )
   ( ( segid *BrD * and resid 116 and name HG11) )
      3.100  2.400   2.400 peak   17302 weight   0.11000E+01 volume   0.94615E+02 ppm1     4.804 ppm2    1.917
ASSI (17412)
   ( ( segid *BrD * and resid 34 and name HB2 ) )
   (  segid *BrD * and resid 34 and name HD % )
      2.900  2.100   2.100 peak   17412 weight   0.11000E+01 volume   0.12277E+03 ppm1     3.125 ppm2    7.705
ASSI (17652)
   (  segid *BrD * and resid 81 and name HG2%)
   ( ( segid *BrD * and resid 34 and name HA   ) )
      2.500  1.600   1.600 peak   17652 weight   0.11000E+01 volume   0.31158E+03 ppm1     0.760 ppm2    5.542
ASSI (17662)
   (  segid *BrD * and resid 81 and name HG2%)
   ( ( segid *BrD * and resid 55 and name HA   ) )
      2.600  1.700   1.700 peak   17662 weight   0.11000E+01 volume   0.23078E+03 ppm1     0.755 ppm2    5.266
ASSI (17722)
   ( ( segid *BrD * and resid 33 and name HG1 ) )
   ( ( segid *BrD * and resid 33 and name HA   ) )
      3.100  2.400   2.400 peak   17722 weight   0.11000E+01 volume   0.93743E+02 ppm1     0.859 ppm2    4.354
```

TABLE 2-continued

Unambigous NOE-derived Inter-proton Distance Restraints

```
ASSI (17812)
    ( ( segid *BrD * and resid 33 and name HD2 ) )
    ( ( segid *BrD * and resid 33 and name HB2 ) )
       3.000  2.200    2.200  peak   17812  weight    0.11000E+01 volume   0.10412E+03 ppm1    2.190 ppm2    −0.162
ASSI (17822)
    ( ( segid *BrD * and resid 33 and name HD1 ) )
    ( ( segid *BrD * and resid 33 and name HB2 ) )
       3.000  2.200    2.200  peak   17822  weight    0.11000E+01 volume   0.99908E+02 ppm1    2.782 ppm2    −0.162
ASSI (17832)
    ( ( segid *BrD * and resid 33 and name HD2 ) )
    ( ( segid *BrD * and resid 33 and name HA  ) )
       3.900  3.800    1.600  peak   17832  weight    0.11000E+01 volume   0.24295E+02 ppm1    2.190 ppm2     4.354
ASSI (17842)
    ( ( segid *BrD * and resid 33 and name HD1 ) )
    ( ( segid *BrD * and resid 33 and name HA  ) )
       3.800  3.600    1.700  peak   17842  weight    0.11000E+01 volume   0.26770E+02 ppm1    2.785 ppm2     4.353
ASSI (17862)
    ( ( segid *BrD * and resid 33 and name HD2 ) )
    ( ( segid *BrD * and resid 32 and name HA  ) )
       3.300  2.700    2.200  peak   17862  weight    0.11000E+01 volume   0.11000E+01 ppm1    2.190 ppm2     4.981
ASSI (17872)
    ( ( segid *BrD * and resid 33 and name HD1 ) )
    ( ( segid *BrD * and resid 32 and name HH2 ) )
       5.500  5.500    0.000  peak   17872  weight    0.11000E+01 volume   0.61193E+03 ppm1    2.783 ppm2     7.797
ASSI (17882)
    ( ( segid *BrD * and resid 33 and name HD2 ) )
    ( ( segid *BrD * and resid 32 and name HH2 ) )
       5.500  5.500    0.000  peak   17882  weight    0.11000E+01 volume   0.56139E+03 ppm1    2.191 ppm2     7.797
ASSI (17912)
    ( ( segid *BrD * and resid 33 and name HB1 ) )
    ( ( segid *BrD * and resid 33 and name HD2 ) )
       3.900  3.800    1.600  peak   17912  weight    0.11000E+01 volume   0.21009E+02 ppm1    1.056 ppm2     2.190
ASSI (17942)
    ( ( segid *BrD * and resid 33 and name HB1 ) )
    ( ( segid *BrD * and resid 33 and name HD1 ) )
       3.300  2.700    2.200  peak   17942  weight    0.11000E+01 volume   0.67464E+02 ppm1    1.056 ppm2     2.792
ASSI (18062)
    ( ( segid *BrD * and resid 75 and name HG1 ) )
    (   segid *BrD * and resid 110 and name HG2%)
       4.000  4.000    1.500  peak   18062  weight    0.11000E+01 volume   0.20766E+02 ppm1    3.522 ppm2     1.262
ASSI (18082)
    ( ( segid *BrD * and resid 75 and name HG2 ) )
    (   segid *BrD * and resid 110 and name HD1%)
       3.400  2.900    2.100  peak   18082  weight    0.11000E+01 volume   0.48309E+02 ppm1    3.226 ppm2     1.140
ASSI (18092)
    ( ( segid *BrD * and resid 75 and name HG2 ) )
    (   segid *BrD * and resid 110 and name HG2%)
       4.100  4.100    1.400  peak   18092  weight    0.11000E+01 volume   0.17226E+02 ppm1    3.226 ppm2     1.262
ASSI (18162)
    ( ( segid *BrD * and resid 53 and name HB1 ) )
    ( ( segid *BrD * and resid 52 and name HA  ) )
       5.500  5.500    0.000  peak   18162  weight    0.11000E+01 volume   0.54558E+00 ppm1    2.784 ppm2     5.582
ASSI (18172)
    ( ( segid *BrD * and resid 53 and name HB1 ) )
    (   segid *BrD * and resid 46 and name HE % )
       2.600  1.700    1.700  peak   18172  weight    0.11000E+01 volume   0.27274E+03 ppm1    2.783 ppm2     6.688
ASSI (18182)
    ( ( segid *BrD * and resid 53 and name HB1 ) )
    (   segid *BrD * and resid 47 and name HE % )
       2.500  1.600    1.600  peak   18182  weight    0.11000E+01 volume   0.34975E+03 ppm1    2.783 ppm2     7.267
ASSI (18192)
    ( ( segid *BrD * and resid 53 and name HA  ) )
    (   segid *BrD * and resid 47 and name HD % )
       3.100  2.400    2.400  peak   18192  weight    0.11000E+01 volume   0.93621E+02 ppm1    2.777 ppm2     7.962
ASSI (18222)
    (   segid *BrD * and resid 35 and name HE % )
    ( ( segid *BrD * and resid 35 and name HG1 ) )
       2.300  1.300    1.300  peak   18222  weight    0.11000E+01 volume   0.50180E+03 ppm1    2.781 ppm2     3.448
ASSI (18292)
    (   segid *BrD * and resid 35 and name HE % )
    ( ( segid *BrD * and resid 35 and name HA  ) )
       2.700  1.800    1.800  peak   18292  weight    0.11000E+01 volume   0.21224E+03 ppm1    2.782 ppm2     4.901
ASSI (18452)
    ( ( segid *BrD * and resid 75 and name HG2 ) )
    (   segid *BrD * and resid 74 and name HD % )
       3.400  2.900    2.100  peak   18452  weight    0.11000E+01 volume   0.49200E+02 ppm1    3.227 ppm2     6.999
```

TABLE 2-continued

Unambigous NOE-derived Inter-proton Distance Restraints

```
ASSI (18462)
    ( ( segid *BrD * and resid 75 and name HG1 ) )
    ( segid *BrD * and resid 74 and name HD % )
      3.100  2.400   2.400  peak   18462  weight   0.11000E+01  volume  0.92286E+02  ppm1    3.524  ppm2   7.001
ASSI (18512)
    ( segid *BrD * and resid 75 and name HE % )
    ( ( segid *BrD * and resid 75 and name HA   ) )
      2.900  2.100   2.100  peak   18512  weight   0.11000E+01  volume  0.12672E+03  ppm1    2.635  ppm2   4.518
ASSI (18752)
    ( segid *BrD * and resid 75 and name HE % )
    ( segid *BrD * and resid 18 and name HD2%)
      3.800  3.600   1.700  peak   18752  weight   0.11000E+01  volume  0.27479E+02  ppm1    2.634  ppm2   0.416
ASSI (18792)
    ( segid *BrD * and resid 75 and name HE % )
    ( segid *BrD * and resid 110 and name HG2%)
      2.700  1.800   1.800  peak   18792  weight   0.11000E+01  volume  0.21896E+03  ppm1    2.634  ppm2   1.262
ASSI (18802)
    ( segid *BrD * and resid 75 and name HE % )
    ( segid *BrD * and resid 110 and name HD1%)
      2.600  1.700   1.700  peak   18802  weight   0.11000E+01  volume  0.24635E+03  ppm1    2.634  ppm2   1.140
ASSI (19032)
    ( ( segid *BrD * and resid 75 and name HA   ) )
    ( segid *BrD * and resid 74 and name HD % )
      2.600  1.700   1.700  peak   19032  weight   0.11000E+01  volume  0.28302E+03  ppm1    4.508  ppm2   6.998
ASSI (19112)
    ( segid *BrD * and resid 43 and name HB % )
    ( segid *BrD * and resid 88 and name HE % )
      2.900  2.100   2.100  peak   19112  weight   0.11000E+01  volume  0.13802E+03  ppm1    1.700  ppm2   7.416
ASSI (19132)
    ( segid *BrD * and resid 43 and name HB % )
    ( segid *BrD * and resid 88 and name HD % )
      4.900  4.900   0.600  peak   19132  weight   0.11000E+01  volume  0.55356E+01  ppm1    1.697  ppm2   7.609
ASSI (19142)
    ( segid *BrD * and resid 43 and name HB % )
    ( segid *BrD * and resid 46 and name HE % )
      3.400  2.900   2.100  peak   19142  weight   0.11000E+01  volume  0.52712E+02  ppm1    1.697  ppm2   6.689
ASSI (19162)
    ( segid *BrD * and resid 43 and name HB % )
    ( segid *BrD * and resid 46 and name HD % )
      2.600  1.700   1.700  peak   19162  weight   0.11000E+01  volume  0.28846E+03  ppm1    1.697  ppm2   5.753
ASSI (19852)
    ( ( segid *BrD * and resid 102 and name HA   ) )
    ( ( segid *BrD * and resid 102 and name HG   ) )
      2.700  1.800   1.800  peak   19852  weight   0.11000E+01  volume  0.19930E+03  ppm1    4.263  ppm2   2.157
ASSI (20082)
    ( ( segid *BrD * and resid 102 and name HA   ) )
    ( ( segid *BrD * and resid 102 and name HG11 ) )
      2.400  1.400   1.400  peak   20082  weight   0.11000E+01  volume  0.38344E+03  ppm1    4.411  ppm2   1.718
ASSI (20232)
    ( segid *BrD * and resid 17 and name HG2%)
    ( ( segid *BrD * and resid 18 and name HA   ) )
      3.100  2.400   2.400  peak   20232  weight   0.11000E+01  volume  0.91939E+02  ppm1    1.747  ppm2   3.882
ASSI (20342)
    ( ( segid *BrD * and resid 53 and name HA   ) )
    ( ( segid *BrD * and resid 53 and name HD1  ) )
      3.300  2.700   2.200  peak   20342  weight   0.11000E+01  volume  0.66608E+02  ppm1    4.696  ppm2   4.210
ASSI (20372)
    ( ( segid *BrD * and resid 53 and name HA   ) )
    ( segid *BrD * and resid 47 and name HE % )
      3.900  3.800   1.600  peak   20372  weight   0.11000E+01  volume  0.22677E+02  ppm1    4.696  ppm2   7.260
ASSI (20422)
    ( ( segid *BrD * and resid 53 and name HD2  ) )
    ( ( segid *BrD * and resid 53 and name HA   ) )
      3.200  2.600   2.300  peak   20422  weight   0.11000E+01  volume  0.75265E+02  ppm1    4.015  ppm2   4.696
ASSI (20432)
    ( ( segid *BrD * and resid 53 and name HD1  ) )
    ( segid *BrD * and resid 50 and name HG2%)
      3.400  2.900   2.100  peak   20432  weight   0.11000E+01  volume  0.50650E+02  ppm1    4.214  ppm2   0.993
ASSI (20462)
    ( ( segid *BrD * and resid 53 and name HG1  ) )
    ( segid *BrD * and resid 46 and name HE % )
      3.600  3.200   1.900  peak   20462  weight   0.11000E+01  volume  0.35265E+02  ppm1    2.784  ppm2   6.689
ASSI (20472)
    ( ( segid *BrD * and resid 53 and name HG1  ) )
    ( segid *BrD * and resid 47 and name HE % )
      2.500  1.600   1.600  peak   20472  weight   0.11000E+01  volume  0.29199E+03  ppm1    2.784  ppm2   7.267
```

TABLE 2-continued

Unambigous NOE-derived Inter-proton Distance Restraints

```
ASSI (20482)
  ( ( segid *BrD * and resid 53 and name HG2 ) )
  (  segid *BrD * and resid 47 and name HE % )
    2.600  1.700    1.700  peak   20482  weight   0.11000E+01  volume  0.27122E+03  ppm1   2.486  ppm2   7.267
ASSI (20492)
  ( ( segid *BrD * and resid 53 and name HG2 ) )
  (  segid *BrD * and resid 47 and name HD % )
    2.400  1.400    1.400  peak   20492  weight   0.11000E+01  volume  0.38647E+03  ppm1   2.486  ppm2   7.958
ASSI (20502)
  ( ( segid *BrD * and resid 53 and name HG1 ) )
  (  segid *BrD * and resid 47 and name HD % )
    2.800  2.000    2.000  peak   20502  weight   0.11000E+01  volume  0.18213E+03  ppm1   2.784  ppm2   7.958
ASSI (20502)
  ( ( segid *BrD * and resid 53 and name HG1 ) )
  ( ( segid *BrD * and resid 52 and name HA   ) )
    5.500  5.500    0.000  peak   20522  weight   0.11000E+01  volume  0.58337E+01  ppm1   2.784  ppm2   5.587
ASSI (20602)
  ( ( segid *BrD * and resid 61 and name HG2 ) )
  ( ( segid *BrD * and resid 58 and name HA   ) )
    2.500  1.600    1.600  peak   20602  weight   0.11000E+01  volume  0.31153E+03  ppm1   2.831  ppm2   4.452
ASSI (20612)
  ( ( segid *BrD * and resid 61 and name HG1 ) )
  ( ( segid *BrD * and resid 58 and name HA   ) )
    2.500  1.600    1.600  peak   20612  weight   0.11000E+01  volume  0.36307E+03  ppm1   2.980  ppm2   4.452
ASSI (20702)
  ( ( segid *BrD * and resid 80 and name HA   ) )
  ( ( segid *BrD * and resid 83 and name HB   ) )
    1.400  0.500    0.800  peak   20702  weight   0.11000E+01  volume  0.11465E+05  ppm1   4.656  ppm2   4.804
ASSI (20772)
  ( ( segid *BrD * and resid 58 and name HB   ) )
  ( ( segid *BrD * and resid 54 and name HA   ) )
    3.400  2.900    2.100  peak   20772  weight   0.11000E+01  volume  0.51113E+02  ppm1   4.702  ppm2   5.544
ASSI (20782)
  (  segid *BrD * and resid 58 and name HG2%)
  ( ( segid *BrD * and resid 54 and name HA   ) )
    2.800  2.000    2.000  peak   20782  weight   0.11000E+01  volume  0.15234E+03  ppm1   1.648  ppm2   5.542
ASSI (20882)
  ( ( segid *BrD * and resid 62 and name HD1 ) )
  ( ( segid *BrD * and resid 62 and name HA   ) )
    3.100  2.400    2.400  peak   20882  weight   0.11000E+01  volume  0.94082E+02  ppm1   3.177  ppm2   4.476
ASSI (20892)
  ( ( segid *BrD * and resid 62 and name HD2 ) )
  ( ( segid *BrD * and resid 62 and name HA   ) )
    3.000  2.200    2.200  peak   20892  weight   0.11000E+01  volume  0.10111E+03  ppm1   2.634  ppm2   4.476
ASSI (20902)
  ( ( segid *BrD * and resid 62 and name HD1 ) )
  (  segid *BrD * and resid 67 and name HE % )
    4.400  4.400    1.100  peak   20902  weight   0.11000E+01  volume  0.11575E+02  ppm1   3.177  ppm2   7.316
ASSI (20912)
  ( ( segid *BrD * and resid 62 and name HD1 ) )
  (  segid *BrD * and resid 67 and name HD % )
    3.700  3.400    1.800  peak   20912  weight   0.11000E+01  volume  0.30541E+02  ppm1   3.177  ppm2   6.893
ASSI (20922)
  ( ( segid *BrD * and resid 62 and name HD2 ) )
  (  segid *BrD * and resid 67 and name HD % )
    3.400  2.900    2.100  peak   20922  weight   0.11000E+01  volume   0.5284E+02  ppm1   2.634  ppm2   6.893
ASSI (20932)
  ( ( segid *BrD * and resid 62 and name HD2 ) )
  (  segid *BrD * and resid 67 and name HE % )
    3.100  2.400    2.400  peak   20932  weight   0.11000E+01  volume  0.91289E+02  ppm1   2.634  ppm2   7.315
ASSI (20952)
  ( ( segid *BrD * and resid 62 and name HB1 ) )
  ( ( segid *BrD * and resid 62 and name HD1 ) )
    3.200  2.600    2.300  peak   20952  weight   0.11000E+01  volume  0.71708E+02  ppm1   2.641  ppm2   3.183
ASSI (20962)
  ( ( segid *BrD * and resid 62 and name HB2 ) )
  ( ( segid *BrD * and resid 62 and name HG1 ) )
    3.000  2.200    2.200  peak   20962  weight   0.11000E+01  volume  0.10075E+03  ppm1   1.699  ppm2   2.325
ASSI (20972)
  ( ( segid *BrD * and resid 62 and name HG2 ) )
  ( ( segid *BrD * and resid 62 and name HB1 ) )
    2.700  1.800    1.800  peak   20972  weight   0.11000E+01  volume  0.20830E+03  ppm1   2.641  ppm2   1.479
ASSI (21012)
  ( ( segid *BrD * and resid 62 and name HG2 ) )
  ( ( segid *BrD * and resid 62 and name HD1 ) )
    3.100  2.400    2.400  peak   21012  weight   0.11000E+01  volume  0.87215E+02  ppm1   1.501  ppm2   3.182
```

TABLE 2-continued

Unambigous NOE-derived Inter-proton Distance Restraints

```
ASSI (21022)
    ( ( segid *BrD * and resid 62 and name HG1  ) )
    ( ( segid *BrD * and resid 62 and name HA   ) )
        2.900  2.100   2.100  peak   21022  weight   0.11000E+01  volume   0.13858E+03  ppm1   2.340  ppm2   4.474
ASSI (21162)
    ( ( segid *BrD * and resid 63 and name HA   ) )
    ( ( segid *BrD * and resid 86 and name HG2  ) )
        4.600  4.600   0.700  peak   21162  weight   0.11000E+01  volume   0.66244E+01  ppm1   4.459  ppm2   0.766
ASSI (21512)
    ( ( segid *BrD * and resid 38 and name HB   ) )
    (   segid *BrD * and resid 46 and name HE % )
        3.400  2.900   2.100  peak   21512  weight   0.11000E+01  volume   0.54169E+02  ppm1   1.747  ppm2   5.745
ASSI (21522)
    ( ( segid *BrD * and resid 38 and name HB   ) )
    (   segid *BrD * and resid 47 and name HE % )
        4.500  4.500   1.000  peak   21522  weight   0.11000E+01  volume   0.90841E+01  ppm1   1.751  ppm2   7.259
ASSI (21532)
    ( ( segid *BrD * and resid 38 and name HB   ) )
    (   segid *BrD * and resid 46 and name HE % )
        4.500  4.500   1.000  peak   21532  weight   0.11000E+01  volume   0.97356E+01  ppm1   1.747  ppm2   6.689
ASSI (21602)
    (   segid *BrD * and resid 81 and name HG1%)
    ( ( segid *BrD * and resid 34 and name HB2  ) )
        3.300  2.700   2.200  peak   21602  weight   0.11000E+01  volume   0.56657E+02  ppm1   1.056  ppm2   3.146
ASSI (21622)
    (   segid *BrD * and resid 81 and name HG1%)
    ( ( segid *BrD * and resid 55 and name HA   ) )
        2.400  1.400   1.400  peak   21622  weight   0.11000E+01  volume   0.44267E+03  ppm1   1.056  ppm2   5.367
ASSI (21632)
    (   segid *BrD * and resid 81 and name HG1%)
    ( ( segid *BrD * and resid 34 and name HA   ) )
        2.800  2.000   2.000  peak   21632  weight   0.11000E+01  volume   0.15411E+03  ppm1   1.056  ppm2   5.542
ASSI (21762)
    (   segid *BrD * and resid 81 and name HG2%)
    ( ( segid *BrD * and resid 78 and name HA   ) )
        2.600  1.700   1.700  peak   21762  weight   0.11000E+01  volume   0.24983E+03  ppm1   0.760  ppm2   4.004
ASSI (21832)
    (   segid *BrD * and resid 50 and name HD1%)
    (   segid *BrD * and resid 49 and name HG1%)
        2.900  2.100   2.100  peak   21832  weight   0.11000E+01  volume   0.14668E+03  ppm1   1.155  ppm2   1.645
ASSI (21842)
    (   segid *BrD * and resid 50 and name HD1%)
    (   segid *BrD * and resid 49 and name HG2%)
        2.400  1.400   1.400  peak   21842  weight   0.11000E+01  volume   0.37404E+03  ppm1   1.155  ppm2   1.571
ASSI (21852)
    ( ( segid *BrD * and resid 49 and name HB   ) )
    (   segid *BrD * and resid 88 and name HD % )
        3.400  2.900   2.100  peak   21852  weight   0.11000E+01  volume   0.48521E+02  ppm1   2.634  ppm2   7.606
ASSI (21862)
    ( ( segid *BrD * and resid 49 and name HB   ) )
    (   segid *BrD * and resid 88 and name HE % )
        3.400  2.900   2.100  peak   21862  weight   0.11000E+01  volume   0.55049E+02  ppm1   2.634  ppm2   7.414
ASSI (21872)
    ( ( segid *BrD * and resid 49 and name HB   ) )
    ( ( segid *BrD * and resid 46 and name HA   ) )
        3.700  3.400   1.800  peak   21872  weight   0.11000E+01  volume   0.31537E+02  ppm1   2.634  ppm2   4.143
ASSI (21912)
    (   segid *BrD * and resid 50 and name HD1%)
    ( ( segid *BrD * and resid 87 and name HB2  ) )
        2.600  1.700   1.700  peak   21912  weight   0.11000E+01  volume   0.24085E+03  ppm1   1.155  ppm2   2.603
ASSI (21922)
    (   segid *BrD * and resid 50 and name HD1%)
    ( ( segid *BrD * and resid 87 and name HB1  ) )
        2.400  1.400   1.400  peak   21922  weight   0.11000E+01  volume   0.36901E+03  ppm1   1.155  ppm2   2.778
ASSI (21932)
    (   segid *BrD * and resid 50 and name HD1%)
    ( ( segid *BrD * and resid 87 and name HG1  ) )
        3.700  3.400   1.800  peak   21932  weight   0.11000E+01  volume   0.32396E+02  ppm1   1.155  ppm2   3.028
ASSI (21942)
    (   segid *BrD * and resid 50 and name HD1%)
    ( ( segid *BrD * and resid 84 and name HB2  ) )
        2.700  1.800   1.800  peak   21942  weight   0.11000E+01  volume   0.22842E+03  ppm1   1.155  ppm2   3.272
ASSI (21962)
    (   segid *BrD * and resid 50 and name HD1%)
    ( ( segid *BrD * and resid 84 and name HB1  ) )
        2.600  1.700   1.700  peak   21962  weight   0.11000E+01  volume   0.28478E+03  ppm1   1.155  ppm2   3.606
```

TABLE 2-continued

Unambigous NOE-derived Inter-proton Distance Restraints

```
ASSI (21992)
   ( segid *BrD * and resid 50 and name HD1%)
   ( ( segid *BrD * and resid 88 and name HA   ) )
     2.700  1.800   1.800  peak   21992  weight   0.11000E+01 volume   0.19153E+03 ppm1   1.155  ppm2   4.988
ASSI (22002)
   ( segid *BrD * and resid 50 and name HD1%)
   ( ( segid *BrD * and resid 84 and name HA   ) )
     2.300  1.300   1.300  peak   22002  weight   0.11000E+01 volume   0.57384E+03 ppm1   1.155  ppm2   4.915
ASSI (22052)
   ( ( segid *BrD * and resid 50 and name HB   ) )
   ( segid *BrD * and resid 46 and name HE % )
     3.000  2.200   2.200  peak   22052  weight   0.11000E+01 volume   0.99146E+02 ppm1   1.797  ppm2   6.689
ASSI (22092)
   ( segid *BrD * and resid 50 and name HG2%)
   ( ( segid *BrD * and resid 52 and name HA   ) )
     3.500  3.100   2.000  peak   22092  weight   0.11000E+01 volume   0.46395E+02 ppm1   1.006  ppm2   5.587
ASSI (22102)
   ( segid *BrD * and resid 50 and name HG2%)
   ( segid *BrD * and resid 46 and name HD % )
     3.700  3.400   1.800  peak   22102  weight   0.11000E+01 volume   0.30083E+02 ppm1   1.007  ppm2   5.745
ASSI (22152)
   ( segid *BrD * and resid 50 and name HG2%)
   ( segid *BrD * and resid 47 and name HE % )
     4.300  4.300   1.200  peak   22152  weight   0.11000E+01 volume   0.12530E+02 ppm1   1.007  ppm2   7.259
ASSI (22162)
   ( segid *BrD * and resid 50 and name HG2%)
   ( segid *BrD * and resid 46 and name HE % )
     2.500  1.600   1.600  peak   22162  weight   0.11000E+01 volume   0.31318E+03 ppm1   1.007  ppm2   6.689
ASSI (22172)
   ( segid *BrD * and resid 50 and name HG2%)
   ( ( segid *BrD * and resid 84 and name HA   ) )
     2.900  2.100   2.100  peak   22172  weight   0.11000E+01 volume   0.14754E+03 ppm1   1.007  ppm2   4.915
ASSI (22192)
   ( segid *BrD * and resid 50 and name HG2%)
   ( segid *BrD * and resid 49 and name HG2%)
     3.700  3.400   1.800  peak   22192  weight   0.11000E+01 volume   0.30274E+02 ppm1   1.006  ppm2   1.570
ASSI (22262)
   ( ( segid *BrD * and resid 50 and name HG12) )
   ( ( segid *BrD * and resid 50 and name HA   ) )
     3.300  2.700   2.200  peak   22262  weight   0.11000E+01 volume   0.57888E+02 ppm1   0.809  ppm2   4.522
ASSI (22342)
   ( segid *BrD * and resid 69 and name HG2%)
   ( ( segid *BrD * and resid 70 and name HA   ) )
     3.500  3.100   2.000  peak   22342  weight   0.11000E+01 volume   0.43395E+02 ppm1   1.427  ppm2   5.356
ASSI (22512)
   ( segid *BrD * and resid 49 and name HG1%)
   ( segid *BrD * and resid 88 and name HE % )
     2.300  1.300   1.300  peak   22512  weight   0.11000E+01 volume   0.52744E+03 ppm1   1.646  ppm2   7.419
ASSI (22522)
   ( segid *BrD * and resid 49 and name HG1%)
   ( segid *BrD * and resid 88 and name HD % )
     2.500  1.600   1.600  peak   22522  weight   0.11000E+01 volume   0.29406E+03 ppm1   1.646  ppm2   7.604
ASSI (22652)
   ( ( segid *BrD * and resid 7 and name HB1  ) )
   ( ( segid *BrD * and resid 7 and name HA   ) )
     3.000  2.200   2.200  peak   22652  weight   0.11000E+01 volume   0.11329E+03 ppm1   2.880  ppm2   5.143
ASSI (22792)
   ( ( segid *BrD * and resid 104 and name HB1  ) )
   ( ( segid *BrD * and resid 101 and name HA   ) )
     2.300  1.300   1.300  peak   22792  weight   0.11000E+01 volume   0.53105E+03 ppm1   2.537  ppm2   4.267
ASSI (22872)
   ( ( segid *BrD * and resid 6 and name HE1  ) )
   ( ( segid *BrD * and resid 6 and name HA   ) )
     2.100  1.100   1.100  peak   22872  weight   0.11000E+01 volume   0.98321E+03 ppm1   3.610  ppm2   4.972
ASSI (22942)
   ( ( segid *BrD * and resid 44 and name HD2  ) )
   ( ( segid *BrD * and resid 44 and name HA   ) )
     3.100  2.400   2.400  peak   22942  weight   0.11000E+01 volume   0.83098E+02 ppm1   4.114  ppm2   5.114
ASSI (23162)
   ( ( segid *BrD * and resid 8 and name HG1  ) )
   ( ( segid *BrD * and resid 8 and name HA   ) )
     2.600  1.700   1.700  peak   23162  weight   0.11000E+01 volume   0.28012E+03 ppm1   2.635  ppm2   5.021
ASSI (23172)
   ( ( segid *BrD * and resid 8 and name HG1  ) )
   ( ( segid *BrD * and resid 8 and name HA   ) )
     4.100  4.100   1.400  peak   23172  weight   0.11000E+01 volume   0.17156E+02 ppm1   2.635  ppm2   5.477
```

TABLE 2-continued

Unambigous NOE-derived Inter-proton Distance Restraints

```
ASSI (23302)
   ( ( segid *BrD * and resid 9 and name HD1  ) )
   ( ( segid *BrD * and resid 9 and name HA   ) )
      2.900  2.100   2.100 peak   23302 weight   0.11000E+01 volume   0.13154E+03 ppm1    3.768 ppm2    4.940
ASSI (23352)
   ( ( segid *BrD * and resid 9 and name HD1  ) )
   ( ( segid *BrD * and resid 9 and name HB1  ) )
      2.400  1.400   1.400 peak   23352 weight   0.11000E+01 volume   0.39945E+03 ppm1    3.768 ppm2    2.434
ASSI (23362)
   ( ( segid *BrD * and resid 9 and name HD1  ) )
   ( ( segid *BrD * and resid 9 and name HB2  ) )
      2.300  1.300   1.300 peak   23362 weight   0.11000E+01 volume   0.50335E+03 ppm1    3.768 ppm2    2.385
ASSI (23542)
   ( ( segid *BrD * and resid 11 and name HA   ) )
   ( ( segid *BrD * and resid 11 and name HD1  ) )
      2.600  1.700   1.700 peak   23542 weight   0.11000E+01 volume   0.23295E+03 ppm1    4.951 ppm2    4.459
ASSI (23552)
   (  segid *BrD * and resid 14 and name HD2%)
   ( ( segid *BrD * and resid 11 and name HA   ) )
      2.500  1.600   1.600 peak   23552 weight   0.11000E+01 volume   0.34571E+03 ppm1    1.401 ppm2    4.947
ASSI (23692)
   ( ( segid *BrD * and resid 14 and name HB2  ) )
   (  segid *BrD * and resid 18 and name HD1%)
      2.900  2.100   2.100 peak   23692 weight   0.11000E+01 volume   0.14113E+03 ppm1    2.143 ppm2    1.084
ASSI (23702)
   ( ( segid *BrD * and resid 17 and name HA   ) )
   (  segid *BrD * and resid 17 and name HG2%)
      3.400  2.900   2.100 peak   23702 weight   0.11000E+01 volume   0.49626E+02 ppm1    4.656 ppm2    1.750
ASSI (23722)
   ( ( segid *BrD * and resid 14 and name HG   ) )
   (  segid *BrD * and resid 18 and name HD2%)
      3.200  2.600   2.300 peak   23722 weight   0.11000E+01 volume   0.69871E+02 ppm1    2.044 ppm2    0.415
ASSI (23752)
   ( ( segid *BrD * and resid 14 and name HA   ) )
   ( ( segid *BrD * and resid 17 and name HB   ) )
      2.100  1.100   1.100 peak   23752 weight   0.11000E+01 volume   0.89711E+03 ppm1    4.656 ppm2    4.854
ASSI (23852)
   (  segid *BrD * and resid 14 and name HD1%)
   ( ( segid *BrD * and resid 11 and name HA   ) )
      2.200  1.200   1.200 peak   23852 weight   0.11000E+01 volume   0.75160E+03 ppm1    1.402 ppm2    4.947
ASSI (23952)
   ( ( segid *BrD * and resid 18 and name HB2  ) )
   ( ( segid *BrD * and resid 15 and name HA   ) )
      3.200  2.600   2.300 peak   23952 weight   0.11000E+01 volume   0.79651E+02 ppm1    0.911 ppm2    4.630
ASSI (23962)
   ( ( segid *BrD * and resid 18 and name HB1  ) )
   ( ( segid *BrD * and resid 15 and name HA   ) )
      3.100  2.400   2.400 peak   23962 weight   0.11000E+01 volume   0.98332E+02 ppm1    2.144 ppm2    4.626
ASSI (24042)
   (  segid *BrD * and resid 18 and name HD2%)
   ( ( segid *BrD * and resid 17 and name HA   ) )
      2.900  2.100   2.100 peak   24042 weight   0.11000E+01 volume   0.13399E+03 ppm1    0.414 ppm2    4.860
ASSI (24052)
   (  segid *BrD * and resid 18 and name HD2%)
   (  segid *BrD * and resid 74 and name HD %  )
      2.500  1.600   1.600 peak   24052 weight   0.11000E+01 volume   0.29789E+03 ppm1    0.415 ppm2    6.998
ASSI (24062)
   (  segid *BrD * and resid 18 and name HD2%)
   (  segid *BrD * and resid 74 and name HE %  )
      2.700  1.800   1.800 peak   24062 weight   0.11000E+01 volume   0.22219E+03 ppm1    0.415 ppm2    7.534
ASSI (24072)
   (  segid *BrD * and resid 18 and name HD2%)
   ( ( segid *BrD * and resid 74 and name HB1  ) )
      3.200  2.600   2.300 peak   24072 weight   0.11000E+01 volume   0.70185E+02 ppm1    0.419 ppm2    3.565
ASSI (24072)
   (  segid *BrD * and resid 18 and name HD2%)
   ( ( segid *BrD * and resid 74 and name HB2  ) )
      2.900  2.100   2.100 peak   24082 weight   0.11000E+01 volume   0.13658E+03 ppm1    0.415 ppm2    2.995
ASSI (24092)
   (  segid *BrD * and resid 18 and name HD2%)
   (  segid *BrD * and resid 63 and name HD1%)
      3.200  2.600   2.300 peak   24092 weight   0.11000E+01 volume   0.72579E+02 ppm1    0.414 ppm2    1.648
ASSI (24132)
   (  segid *BrD * and resid 18 and name HD2%)
   ( ( segid *BrD * and resid 74 and name HA   ) )
      3.400  2.900   2.100 peak   24132 weight   0.11000E+01 volume   0.52592E+02 ppm1    0.414 ppm2    4.378
```

TABLE 2-continued

Unambigous NOE-derived Inter-proton Distance Restraints

```
ASSI (24162)
   ( segid *BrD * and resid 18 and name HD1%)
   ( segid *BrD * and resid 74 and name HE % )
     3.000  2.200   2.200  peak   24162  weight   0.11000E+01  volume   0.10145E+03  ppm1   1.058  ppm2   7.536
ASSI (24162)
   ( segid *BrD * and resid 18 and name HD1%)
   ( segid *BrD * and resid 74 and name HD % )
     2.600  1.700   1.700  peak   24182  weight   0.11000E+01  volume   0.27877E+03  ppm1   1.056  ppm2   6.998
ASSI (24212)
   ( segid *BrD * and resid 18 and name HD1%)
   ( ( segid *BrD * and resid 74 and name HA  ) )
     3.200  2.600   2.300  peak   24212  weight   0.11000E+01  volume   0.48587E+02  ppm1   1.056  ppm2   4.378
ASSI (24212)
   ( segid *BrD * and resid 63 and name HD1%)
   ( ( segid *BrD * and resid 19 and name HA  ) )
     2.600  1.700   1.700  peak   24522  weight   0.11000E+01  volume   0.26998E+03  ppm1   1.647  ppm2   4.297
ASSI (24662)
   ( segid *BrD * and resid 63 and name HD2%)
   ( segid *BrD * and resid 18 and name HD1%)
     2.700  1.800   1.800  peak   24662  weight   0.11000E+01  volume   0.19359E+03  ppm1   1.498  ppm2   1.090
ASSI (24672)
   ( segid *BrD * and resid 63 and name HD2%)
   ( ( segid *BrD * and resid 18 and name HB2 ) )
     5.500  5.500   0.000  peak   24672  weight   0.11000E+01  volume   0.20841E+01  ppm1   1.498  ppm2   0.925
ASSI (24742)
   ( ( segid *BrD * and resid 19 and name HB2 ) )
   ( ( segid *BrD * and resid 19 and name HE1 ) )
     4.000  4.000   1.500  peak   24742  weight   0.11000E+01  volume   0.20066E+02  ppm1   1.989  ppm2   3.525
ASSI (24752)
   ( ( segid *BrD * and resid 19 and name HB1 ) )
   ( ( segid *BrD * and resid 19 and name HE1 ) )
     3.300  2.700   2.200  peak   24752  weight   0.11000E+01  volume   0.65557E+02  ppm1   2.290  ppm2   3.525
ASSI (24762)
   ( ( segid *BrD * and resid 19 and name HG1 ) )
   ( ( segid *BrD * and resid 16 and name HA  ) )
     2.900  2.100   2.100  peak   24762  weight   0.11000E+01  volume   0.12763E+03  ppm1   1.894  ppm2   4.508
ASSI (24812)
   ( ( segid *BrD * and resid 19 and name HD1 ) )
   ( ( segid *BrD * and resid 16 and name HA  ) )
     2.300  1.300   1.300  peak   24812  weight   0.11000E+01  volume   0.50116E+03  ppm1   2.192  ppm2   4.507
ASSI (24872)
   ( ( segid *BrD * and resid 23 and name HG1 ) )
   ( ( segid *BrD * and resid 20 and name HA  ) )
     3.100  2.400   2.400  peak   24872  weight   0.11000E+01  volume   0.91712E+02  ppm1   3.124  ppm2   4.893
ASSI (24902)
   ( ( segid *BrD * and resid 24 and name HG1 ) )
   ( ( segid *BrD * and resid 21 and name HA  ) )
     3.200  2.600   2.300  peak   24902  weight   0.11000E+01  volume   0.67606E+02  ppm1   3.469  ppm2   4.370
ASSI (24912)
   ( ( segid *BrD * and resid 24 and name HG2 ) )
   ( ( segid *BrD * and resid 21 and name HA  ) )
     2.600  1.700   1.700  peak   24912  weight   0.11000E+01  volume   0.26410E+03  ppm1   3.076  ppm2   4.370
ASSI (24932)
   ( ( segid *BrD * and resid 24 and name HA  ) )
   ( ( segid *BrD * and resid 24 and name HB1 ) )
     2.200  1.200   1.200  peak   24932  weight   0.11000E+01  volume   0.62910E+03  ppm1   4.784  ppm2   3.074
ASSI (25432)
   ( ( segid *BrD * and resid 85 and name HB1 ) )
   ( ( segid *BrD * and resid 82 and name HA  ) )
     3.100  2.400   2.400  peak   25432  weight   0.11000E+01  volume   0.87929E+02  ppm1   3.917  ppm2   4.753
ASSI (25552)
   ( ( segid *BrD * and resid 101 and name HG12) )
   ( ( segid *BrD * and resid 101 and name HB  ) )
     2.300  1.300   1.300  peak   25552  weight   0.11000E+01  volume   0.55437E+03  ppm1   1.797  ppm2   2.538
ASSI (25612)
   ( segid *BrD * and resid 21 and name HG2%)
   ( ( segid *BrD * and resid 18 and name HA  ) )
     3.000  2.200   2.200  peak   25612  weight   0.11000E+01  volume   0.11187E+03  ppm1   1.599  ppm2   3.890
ASSI (26032)
   ( segid *BrD * and resid 110 and name HD1%)
   ( ( segid *BrD * and resid 75 and name HG1 ) )
     3.400  2.900   2.100  peak   26032  weight   0.11000E+01  volume   0.51048E+02  ppm1   1.155  ppm2   3.524
ASSI (26172)
   ( segid *BrD * and resid 110 and name HG2%)
   ( segid *BrD * and resid 18 and name HD2%)
     4.400  4.400   1.100  peak   26172  weight   0.11000E+01  volume   0.11733E+02  ppm1   1.254  ppm2   0.408
```

TABLE 2-continued

Unambigous NOE-derived Inter-proton Distance Restraints

```
ASSI (26182)
   ( segid *BrD * and resid 110 and name HD1%)
   ( segid *BrD * and resid 18 and name HD2%)
      3.000  2.200   2.200  peak  26182  weight   0.11000E+01  volume   0.11735E+03  ppm1   1.153  ppm2   0.410
ASSI (26302)
   ( segid *BrD * and resid 116 and name HD1%)
   ( ( segid *BrD * and resid 116 and name HA  ) )
      2.500  1.600   1.600  peak  26302  weight   0.11000E+01  volume   0.31414E+03  ppm1   1.401  ppm2   4.826
ASSI (26562)
   ( ( segid *BrD * and resid 103 and name HA  ) )
   ( segid *BrD * and resid 106 and name HD % )
      3.100  2.400   2.400  peak  26562  weight   0.11000E+01  volume   0.97052E+02  ppm1   3.768  ppm2   7.514
ASSI (26592)
   ( ( segid *BrD * and resid 103 and name HB1 ) )
   ( ( segid *BrD * and resid 100 and name HA  ) )
      2.700  1.800   1.800  peak  26592  weight   0.11000E+01  volume   0.20226E+03  ppm1   2.338  ppm2   4.946
ASSI (26642)
   ( ( segid *BrD * and resid 103 and name HB2 ) )
   ( ( segid *BrD * and resid 103 and name HG2 ) )
      2.000  1.000   1.000  peak  26642  weight   0.11000E+01  volume   0.14101E+04  ppm1   1.893  ppm2   2.520
ASSI (26652)
   ( ( segid *BrD * and resid 103 and name HB2 ) )
   ( ( segid *BrD * and resid 103 and name HG1 ) )
      2.200  1.200   1.200  peak  26652  weight   0.11000E+01  volume   0.62174E+03  ppm1   1.893  ppm2   2.598
ASSI (26662)
   ( ( segid *BrD * and resid 103 and name HG2 ) )
   ( ( segid *BrD * and resid 100 and name HA  ) )
      3.500  3.100   2.000  peak  26662  weight   0.11000E+01  volume   0.45243E+02  ppm1   2.519  ppm2   4.497
ASSI (26672)
   ( ( segid *BrD * and resid 103 and name HG1 ) )
   ( ( segid *BrD * and resid 100 and name HA  ) )
      3.900  3.800   1.600  peak  26672  weight   0.11000E+01  volume   0.23440E+02  ppm1   2.598  ppm2   4.947
ASSI (26722)
   ( ( segid *BrD * and resid 94 and name HG1 ) )
   ( ( segid *BrD * and resid 32 and name HH2 ) )
      2.900  2.100   2.100  peak  26722  weight   0.11000E+01  volume   0.14855E+03  ppm1   3.129  ppm2   7.788
ASSI (26782)
   ( ( segid *BrD * and resid 94 and name HB1 ) )
   ( ( segid *BrD * and resid 32 and name HZ2 ) )
      2.500  1.600   1.600  peak  26782  weight   0.11000E+01  volume   0.35938E+03  ppm1   2.735  ppm2   7.998
ASSI (26792)
   ( ( segid *BrD * and resid 94 and name HB1 ) )
   ( ( segid *BrD * and resid 32 and name HH2 ) )
      3.000  2.200   2.200  peak  26792  weight   0.11000E+01  volume   0.10089E+03  ppm1   2.733  ppm2   7.785
ASSI (26842)
   ( ( segid *BrD * and resid 94 and name HG1 ) )
   ( ( segid *BrD * and resid 94 and name HB1 ) )
      2.200  1.200   1.200  peak  26842  weight   0.11000E+01  volume   0.72439E+03  ppm1   3.123  ppm2   2.731
ASSI (26862)
   ( ( segid *BrD * and resid 87 and name HG2 ) )
   ( ( segid *BrD * and resid 86 and name HD1 ) )
      3.600  3.200   1.900  peak  26862  weight   0.11000E+01  volume   0.34874E+02  ppm1   2.782  ppm2   1.900
ASSI (26882)
   ( ( segid *BrD * and resid 87 and name HB1 ) )
   ( ( segid *BrD * and resid 87 and name HG1 ) )
      2.400  1.400   1.400  peak  26882  weight   0.11000E+01  volume   0.47090E+03  ppm1   2.779  ppm2   3.021
ASSI (27152)
   ( ( segid *BrD * and resid 80 and name HD2 ) )
   ( ( segid *BrD * and resid 80 and name HA  ) )
      2.400  1.400   1.400  peak  27152  weight   0.11000E+01  volume   0.41973E+03  ppm1   3.912  ppm2   4.678
ASSI (27162)
   ( ( segid *BrD * and resid 80 and name HD1 ) )
   ( ( segid *BrD * and resid 80 and name HA  ) )
      2.600  1.700   1.700  peak  27162  weight   0.11000E+01  volume   0.27730E+03  ppm1   3.962  ppm2   4.677
ASSI (27212)
   ( ( segid *BrD * and resid 77 and name HB1 ) )
   ( ( segid *BrD * and resid 74 and name HA  ) )
      2.800  2.000   2.000  peak  27212  weight   0.11000E+01  volume   0.16302E+03  ppm1   3.225  ppm2   4.378
ASSI (27242)
   ( ( segid *BrD * and resid 80 and name HB2 ) )
   ( ( segid *BrD * and resid 80 and name HD1 ) )
      2.900  2.100   2.100  peak  27242  weight   0.11000E+01  volume   0.12614E+03  ppm1   2.536  ppm2   3.955
ASSI (27252)
   ( ( segid *BrD * and resid 80 and name HB2 ) )
   ( ( segid *BrD * and resid 80 and name HD2 ) )
      2.800  2.000   2.000  peak  27252  weight   0.11000E+01  volume   0.14981E+03  ppm1   2.536  ppm2   3.890
```

TABLE 2-continued

Unambigous NOE-derived Inter-proton Distance Restraints

```
ASSI (27312)
    ( ( segid *BrD * and resid 56 and name HG    ) )
    ( ( segid *BrD * and resid 34 and name HA    ) )
      5.500   5.500    0.000 peak   27312 weight   0.11000E+01 volume   0.47841E+00 ppm1    2.338 ppm2    5.542
ASSI (27352)
    ( ( segid *BrD * and resid 55 and name HB1   ) )
    ( ( segid *BrD * and resid 55 and name HA    ) )
      2.200   1.200    1.200 peak   27352 weight   0.11000E+01 volume   0.72273E+03 ppm1    2.979 ppm2    5.366
ASSI (27412)
    (   segid *BrD * and resid 81 and name HG1%)
    ( ( segid *BrD * and resid 34 and name HB1   ) )
      3.100   2.400    2.400 peak   27412 weight   0.11000E+01 volume   0.93003E+02 ppm1    1.058 ppm2    4.106
ASSI (27512)
    (   segid *BrD * and resid 22 and name HD2%)
    ( ( segid *BrD * and resid 22 and name HG    ) )
      1.900   0.900    0.900 peak   27512 weight   0.11000E+01 volume   0.14735E+04 ppm1    1.599 ppm2    2.362
ASSI (27522)
    (   segid *BrD * and resid 22 and name HD2%)
    ( ( segid *BrD * and resid 22 and name HB2   ) )
      2.200   1.200    1.200 peak   27522 weight   0.11000E+01 volume   0.70123E+03 ppm1    1.599 ppm2    2.286
ASSI (27682)
    (   segid *BrD * and resid 73 and name HD2%)
    ( ( segid *BrD * and resid 73 and name HB2   ) )
      2.900   2.100    2.100 peak   27682 weight   0.11000E+01 volume   0.12667E+03 ppm1    1.600 ppm2    2.483
ASSI (27922)
    (   segid *BrD * and resid 78 and name HD1%)
    (   segid *BrD * and resid 82 and name HD %  )
      3.600   3.200    1.900 peak   27922 weight   0.11000E+01 volume   0.39776E+02 ppm1    0.760 ppm2    7.259
ASSI (27972)
    (   segid *BrD * and resid 78 and name HD2%)
    (   segid *BrD * and resid 82 and name HD %  )
      3.400   2.900    2.100 peak   27972 weight   0.11000E+01 volume   0.49710E+02 ppm1    0.662 ppm2    7.259
ASSI (28242)
    (   segid *BrD * and resid 56 and name HD1%)
    ( ( segid *BrD * and resid 34 and name HB1   ) )
      3.000   2.200    2.200 peak   28242 weight   0.11000E+01 volume   0.10505E+03 ppm1    1.549 ppm2    4.110
ASSI (28282)
    (   segid *BrD * and resid 56 and name HD2%)
    ( ( segid *BrD * and resid 34 and name HA    ) )
      3.800   3.600    1.700 peak   28282 weight   0.11000E+01 volume   0.25930E+02 ppm1    1.253 ppm2    5.540
ASSI (28312)
    (   segid *BrD * and resid 56 and name HD2%)
    ( ( segid *BrD * and resid 34 and name HB1   ) )
      3.400   2.900    2.100 peak   28312 weight   0.11000E+01 volume   0.48455E+02 ppm1    1.253 ppm2    4.110
ASSI (28362)
    (   segid *BrD * and resid 56 and name HD2%)
    ( ( segid *BrD * and resid 34 and name HB2   ) )
      3.200   2.600    2.300 peak   28362 weight   0.11000E+01 volume   0.68625E+02 ppm1    1.254 ppm2    3.134
ASSI (28672)
    (   segid *BrD * and resid 102 and name HD1%)
    ( ( segid *BrD * and resid 102 and name HA   ) )
      2.100   1.100    1.100 peak   28672 weight   0.11000E+01 volume   0.89519E+03 ppm1    1.303 ppm2    4.282
ASSI (28712)
    (   segid *BrD * and resid 102 and name HD2%)
    ( ( segid *BrD * and resid 102 and name HB2  ) )
      2.000   1.000    1.000 peak   28712 weight   0.11000E+01 volume   0.12274E+04 ppm1    1.303 ppm2    1.832
ASSI (28802)
    ( ( segid *BrD * and resid 115 and name HG   ) )
    ( ( segid *BrD * and resid 115 and name HA   ) )
      2.400   1.400    1.400 peak   28802 weight   0.11000E+01 volume   0.40182E+03 ppm1    2.143 ppm2    4.828
ASSI (28962)
    (   segid *BrD * and resid 56 and name HD1%)
    ( ( segid *BrD * and resid 34 and name HA    ) )
      3.200   2.600    2.300 peak   28962 weight   0.11000E+01 volume   0.68400E+02 ppm1    1.544 ppm2    5.540
ASSI (28982)
    ( ( segid *BrD * and resid 59 and name HG2   ) )
    ( ( segid *BrD * and resid 56 and name HA    ) )
      2.400   1.400    1.400 peak   28982 weight   0.11000E+01 volume   0.37484E+03 ppm1    3.137 ppm2    4.636
ASSI (29062)
    (   segid *BrD * and resid 59 and name HE %  )
    ( ( segid *BrD * and resid 56 and name HA    ) )
      3.100   2.400    2.400 peak   29062 weight   0.11000E+01 volume   0.84530E+02 ppm1    1.847 ppm2    4.636
ASSI (29122)
    (   segid *BrD * and resid 59 and name HE %  )
    (   segid *BrD * and resid 74 and name HE %  )
      2.400   1.400    1.400 peak   29122 weight   0.11000E+01 volume   0.44730E+03 ppm1    1.848 ppm2    7.535
```

TABLE 2-continued

Unambigous NOE-derived Inter-proton Distance Restraints

```
ASSI (29182)
     ( segid *BrD * and resid 54 and name HE % ) )
     ( ( segid *BrD * and resid 58 and name HB    ) )
       3.000  2.200    2.200   peak   29182  weight    0.11000E+01  volume   0.12060E+03  ppm1    2.536  ppm2    4.696
ASSI (29282)
     ( ( segid *BrD * and resid 54 and name HB1 ) )
     ( ( segid *BrD * and resid 54 and name HG1 ) )
       2.800  2.000    2.000   peak   29282  weight    0.11000E+01  volume   0.16180E+03  ppm1    2.985  ppm2    3.304
ASSI (29312)
     ( ( segid *BrD * and resid 44 and name HB2 ) )
     ( ( segid *BrD * and resid 44 and name HD2 ) )
       3.500  3.100    2.000   peak   29312  weight    0.11000E+01  volume   0.45332E+02  ppm1    2.634  ppm2    4.126
ASSI (29342)
     ( ( segid *BrD * and resid 44 and name HG2 ) )
     ( ( segid *BrD * and resid 43 and name HA   ) )
       3.600  3.200    1.900   peak   29342  weight    0.11000E+01  volume   0.36619E+02  ppm1    2.645  ppm2    5.542
ASSI (29362)
     ( ( segid *BrD * and resid 44 and name HD1 ) )
     ( segid *BrD * and resid 44 and name HA    ) )
       3.200  2.600    2.300   peak   29362  weight    0.11000E+01  volume   0.69345E+02  ppm1    4.310  ppm2    5.114
ASSI (29422)
     ( ( segid *BrD * and resid 91 and name HB1 ) )
     ( ( segid *BrD * and resid 91 and name HD2 ) )
       2.600  1.700    1.700   peak   29422  weight    0.11000E+01  volume   0.26299E+03  ppm1    2.978  ppm2    4.407
ASSI (29432)
     ( ( segid *BrD * and resid 91 and name HB2 ) )
     ( ( segid *BrD * and resid 91 and name HD2 ) )
       2.800  2.000    2.000   peak   29432  weight    0.11000E+01  volume   0.15191E+03  ppm1    2.730  ppm2    4.407
ASSI (29492)
     ( ( segid *BrD * and resid 79 and name HG1 ) )
     ( ( segid *BrD * and resid 76 and name HA   ) )
       2.400  1.400    1.400   peak   29492  weight    0.11000E+01  volume   0.46894E+03  ppm1    3.033  ppm2    4.680
ASSI (29612)
     ( ( segid *BrD * and resid 70 and name HA   ) )
     ( segid *BrD * and resid 69 and name HG1%)
       4.000  4.000    1.500   peak   29612  weight    0.11000E+01  volume   0.20014E+02  ppm1    5.346  ppm2    1.547
ASSI (29932)
     ( ( segid *BrD * and resid 66 and name HB2 ) )
     ( ( segid *BrD * and resid 66 and name HD2 ) )
       2.700  1.800    1.800   peak   29932  weight    0.11000E+01  volume   0.20564E+03  ppm1    2.641  ppm2    3.633
ASSI (29942)
     ( ( segid *BrD * and resid 66 and name HB1 ) )
     ( ( segid *BrD * and resid 66 and name HD2 ) )
       2.600  1.700    1.700   peak   29942  weight    0.11000E+01  volume   0.23040E+03  ppm1    2.701  ppm2    3.636
ASSI (29942)
     ( ( segid *BrD * and resid 66 and name HB2 ) )
     ( ( segid *BrD * and resid 66 and name HD1 ) )
       2.600  1.700    1.700   peak   29952  weight    0.11000E+01  volume   0.23393E+03  ppm1    2.633  ppm2    3.670
ASSI (29962)
     ( ( segid *BrD * and resid 66 and name HB1 ) )
     ( ( segid *BrD * and resid 66 and name HD1 ) )
       2.700  1.800    1.800   peak   29962  weight    0.11000E+01  volume   0.22124E+03  ppm1    2.701  ppm2    3.669
ASSI (30032)
     ( ( segid *BrD * and resid 51 and name HA   ) )
     ( ( segid *BrD * and resid 52 and name HA   ) )
       4.100  4.100    1.400   peak   30032  weight    0.11000E+01  volume   0.17278E+02  ppm1    4.459  ppm2    5.585
ASSI (30052)
     ( ( segid *BrD * and resid 86 and name HD1 ) )
     ( ( segid *BrD * and resid 86 and name HA   ) )
       3.500  3.100    2.000   peak   30052  weight    0.11000E+01  volume   0.45287E+02  ppm1    1.895  ppm2    4.810
ASSI (30162)
     ( ( segid *BrD * and resid 64 and name HA   ) )
     ( segid *BrD * and resid 15 and name HE % )
       2.400  1.400    1.400   peak   30162  weight    0.11000E+01  volume   0.39658E+03  ppm1    4.950  ppm2    7.485
ASSI (30202)
     ( ( segid *BrD * and resid 64 and name HE1 ) )
     ( ( segid *BrD * and resid 64 and name HA   ) )
       2.300  1.300    1.300   peak   30202  weight    0.11000E+01  volume   0.49260E+03  ppm1    3.597  ppm2    4.939
ASSI (30342)
     ( ( segid *BrD * and resid 86 and name HB1 ) )
     ( segid *BrD * and resid 96 and name HD % )
       2.700  1.800    1.800   peak   30342  weight    0.11000E+01  volume   0.18798E+03  ppm1    2.337  ppm2    7.722
ASSI (30352)
     ( ( segid *BrD * and resid 86 and name HB1 ) )
     ( segid *BrD * and resid 96 and name HE % )
       2.700  1.800    1.800   peak   30352  weight    0.11000E+01  volume   0.21345E+03  ppm1    2.338  ppm2    7.602
```

TABLE 2-continued

Unambigous NOE-derived Inter-proton Distance Restraints

```
ASSI (30392)
    ( ( segid *BrD * and resid 86 and name HE1 ) )
    ( ( segid *BrD * and resid 86 and name HA  ) )
      3.100  2.400   2.400  peak   30392  weight   0.11000E+01  volume   0.90505E+02  ppm1   3.080  ppm2   4.808
ASSI (30402)
    ( ( segid *BrD * and resid 86 and name HE1 ) )
    ( ( segid *BrD * and resid 86 and name HB1 ) )
      2.200  1.200   1.200  peak   30402  weight   0.11000E+01  volume   0.64111E+03  ppm1   3.079  ppm2   2.370
ASSI (30412)
    ( ( segid *BrD * and resid 86 and name HE1 ) )
    ( ( segid *BrD * and resid 86 and name HG1 ) )
      2.900  2.100   2.100  peak   30412  weight   0.11000E+01  volume   0.14017E+03  ppm1   3.079  ppm2   1.896
ASSI (30512)
    ( ( segid *BrD * and resid 109 and name HE1 ) )
    ( ( segid *BrD * and resid 109 and name HA  ) )
      2.900  2.100   2.100  peak   30512  weight   0.11000E+01  volume   0.12187E+03  ppm1   3.176  ppm2   4.639
ASSI (30522)
    ( ( segid *BrD * and resid 109 and name HD1 ) )
    ( ( segid *BrD * and resid 109 and name HA  ) )
      1.900  0.900   0.900  peak   30522  weight   0.11000E+01  volume   0.17943E+04  ppm1   1.994  ppm2   4.639
ASSI (30622)
    ( ( segid *BrD * and resid 109 and name HB1 ) )
    ( ( segid *BrD * and resid 106 and name HA  ) )
      2.400  1.400   1.400  peak   30622  weight   0.11000E+01  volume   0.44758E+03  ppm1   2.334  ppm2   4.575
ASSI (30632)
    ( ( segid *BrD * and resid 109 and name HB2 ) )
    ( ( segid *BrD * and resid 106 and name HA  ) )
      2.700  1.800   1.800  peak   30632  weight   0.11000E+01  volume   0.21060E+03  ppm1   2.139  ppm2   4.573
ASSI (30732)
    ( ( segid *BrD * and resid 97 and name HG2 ) )
    ( ( segid *BrD * and resid 97 and name HA  ) )
      2.400  1.400   1.400  peak   30732  weight   0.11000E+01  volume   0.42305E+03  ppm1   2.143  ppm2   4.800
ASSI (30802)
    ( ( segid *BrD * and resid 104 and name HD1 ) )
    ( ( segid *BrD * and resid 104 and name HA  ) )
      1.700  0.700   0.700  peak   30802  weight   0.11000E+01  volume   0.32351E+04  ppm1   2.269  ppm2   4.671
ASSI (30862)
    ( ( segid *BrD * and resid 111 and name HG1 ) )
    ( ( segid *BrD * and resid 111 and name HA  ) )
      2.500  1.600   1.600  peak   30862  weight   0.11000E+01  volume   0.32568E+03  ppm1   2.000  ppm2   4.670
ASSI (30872)
    ( ( segid *BrD * and resid 111 and name HD1 ) )
    ( ( segid *BrD * and resid 111 and name HA  ) )
      2.500  1.600   1.600  peak   30872  weight   0.11000E+01  volume   0.34175E+03  ppm1   2.240  ppm2   4.656
ASSI (30912)
    ( ( segid *BrD * and resid 111 and name HE1 ) )
    ( ( segid *BrD * and resid 111 and name HA  ) )
      2.200  1.200   1.200  peak   30912  weight   0.11000E+01  volume   0.72636E+03  ppm1   3.520  ppm2   4.656
ASSI (31022)
    ( ( segid *BrD * and resid 72 and name HD1 ) )
    ( ( segid *BrD * and resid 72 and name HE2 ) )
      2.200  1.200   1.200  peak   31022  weight   0.11000E+01  volume   0.72521E+03  ppm1   2.287  ppm2   3.654
ASSI (31032)
    ( ( segid *BrD * and resid 72 and name HD1 ) )
    ( ( segid *BrD * and resid 72 and name HE1 ) )
      2.300  1.300   1.300  peak   31032  weight   0.11000E+01  volume   0.50216E+03  ppm1   2.287  ppm2   3.744
ASSI (31042)
    ( ( segid *BrD * and resid 72 and name HB1 ) )
    ( ( segid *BrD * and resid 72 and name HE1 ) )
      2.200  1.200   1.200  peak   31042  weight   0.11000E+01  volume   0.79378E+03  ppm1   2.387  ppm2   3.744
ASSI (31052)
    ( ( segid *BrD * and resid 72 and name HB1 ) )
    ( ( segid *BrD * and resid 72 and name HE2 ) )
      1.900  0.900   0.900  peak   31052  weight   0.11000E+01  volume   0.15518E+04  ppm1   2.386  ppm2   3.652
ASSI ( 1632)
    (  segid *BrD * and resid 110 and name HD1%)
    ( ( segid *BrD * and resid 78 and name HB1 ) )
      2.100  2.100   2.400  peak    1632  weight   0.10000E+01  volume   0.10163E+04  ppm1   1.154  ppm2   1.309
ASSI ( 4042)
    ( ( segid *BrD * and resid 79 and name HG1 ) )
    ( ( segid *BrD * and resid 80 and name HG1 ) )
      3.700  3.400   1.800  peak    4042  weight   0.10000E+01  volume   0.30439E+02  ppm1   3.029  ppm2   2.351
ASSI ( 4882)
    ( ( segid *BrD * and resid 19 and name HD1 ) )
    (  segid *BrD * and resid 63 and name HD2%)
      2.700  1.800   1.800  peak    4882  weight   0.10000E+01  volume   0.22363E+03  ppm1   2.191  ppm2   1.495
```

TABLE 2-continued

Unambigous NOE-derived Inter-proton Distance Restraints

```
ASSI ( 4902)
    ( ( segid *BrD * and resid 97 and name HB1 ) )
    ( segid *BrD * and resid 101 and name HD1%)
       3.000  2.200    2.200 peak    4902 weight   0.10000E+01 volume   0.10809E+03 ppm1     2.683 ppm2    1.580
ASSI ( 4992)
    ( ( segid *BrD * and resid 37 and name HG2 ) )
    ( ( segid *BrD * and resid 58 and name HA   ) )
       4.200  4.200    1.300 peak    4992 weight   0.10000E+01 volume   0.14817E+02 ppm1     2.586 ppm2    5.380
ASSI ( 6092)
    ( ( segid *BrD * and resid 115 and name HG  ) )
    ( segid *BrD * and resid 110 and name HG2%)
       3.700  3.400    1.800 peak    6092 weight   0.10000E+01 volume   0.29496E+02 ppm1     2.140 ppm2    1.222
ASSI ( 6222)
    ( segid *BrD * and resid 22 and name HD2%)
    ( segid *BrD * and resid 56 and name HD2%)
       2.300  1.300    1.300 peak    6222 weight   0.10000E+01 volume   0.52799E+03 ppm1     1.599 ppm2    1.246
ASSI ( 6602)
    ( segid *BrD * and resid 31 and name HB % )
    ( segid *BrD * and resid 56 and name HD2%)
       2.500  1.600    1.600 peak    6602 weight   0.10000E+01 volume   0.34161E+03 ppm1     2.291 ppm2    1.539
ASSI ( 6792)
    ( segid *BrD * and resid 99 and name HB % )
    ( ( segid *BrD * and resid 82 and name HA   ) )
       3.000  2.200    2.200 peak    6792 weight   0.10000E+01 volume   0.12038E+03 ppm1     2.190 ppm2    4.752
ASSI ( 6832)
    ( segid *BrD * and resid 99 and name HB % )
    ( ( segid *BrD * and resid 86 and name HG2 ) )
       3.000  2.200    2.200 peak    6832 weight   0.10000E+01 volume   0.11935E+03 ppm1     2.191 ppm2    0.765
ASSI ( 6852)
    ( segid *BrD * and resid 113 and name HB % )
    ( segid *BrD * and resid 110 and name HG2%)
       2.800  2.000    2.000 peak    6852 weight   0.10000E+01 volume   0.15622E+03 ppm1     1.991 ppm2    1.221
ASSI ( 6862)
    ( segid *BrD * and resid 113 and name HB % )
    ( segid *BrD * and resid 18 and name HD1%)
       4.900  4.900    0.600 peak    6862 weight   0.10000E+01 volume   0.56980E+01 ppm1     1.991 ppm2    1.066
ASSI ( 6902)
    ( ( segid *BrD * and resid 31 and name HA   ) )
    ( ( segid *BrD * and resid 31 and name HD1  ) )
       3.300  2.700    2.200 peak    6902 weight   0.10000E+01 volume   0.60152E+02 ppm1     5.000 ppm2    2.794
ASSI ( 6952)
    ( segid *BrD * and resid 25 and name HG2%)
    ( segid *BrD * and resid 25 and name HB % )
       2.500  1.600    1.600 peak    6952 weight   0.10000E+01 volume   0.32952E+03 ppm1     1.650 ppm2    2.320
ASSI ( 6982)
    ( segid *BrD * and resid 25 and name HG2%)
    ( segid *BrD * and resid 56 and name HD2%)
       2.500  1.600    1.600 peak    6982 weight   0.10000E+01 volume   0.36117E+03 ppm1     1.646 ppm2    1.252
ASSI ( 7362)
    ( segid *BrD * and resid 25 and name HG2%)
    ( ( segid *BrD * and resid 102 and name HG   ) )
       2.900  2.100    2.100 peak    7362 weight   0.10000E+01 volume   0.13044E+03 ppm1     1.647 ppm2    2.157
ASSI ( 7412)
    ( ( segid *BrD * and resid 46 and name HA   ) )
    ( segid *BrD * and resid 49 and name HG1%)
       3.400  2.900    2.100 peak    7412 weight   0.10000E+01 volume   0.55913E+02 ppm1     4.164 ppm2    1.645
ASSI ( 7422)
    ( ( segid *BrD * and resid 46 and name HA   ) )
    ( segid *BrD * and resid 43 and name HB % )
       3.600  3.200    1.900 peak    7422 weight   0.10000E+01 volume   0.39252E+02 ppm1     4.164 ppm2    1.718
ASSI ( 7442)
    ( ( segid *BrD * and resid 68 and name HA   ) )
    ( segid *BrD * and resid 63 and name HD1%)
       3.700  3.400    1.800 peak    7442 weight   0.10000E+01 volume   0.32100E+02 ppm1     5.146 ppm2    1.652
ASSI ( 7462)
    ( ( segid *BrD * and resid 68 and name HB2 ) )
    ( segid *BrD * and resid 18 and name HD1%)
       3.100  2.400    2.400 peak    7462 weight   0.10000E+01 volume   0.95501E+02 ppm1     3.522 ppm2    1.083
ASSI ( 7472)
    ( ( segid *BrD * and resid 68 and name HB1 ) )
    ( segid *BrD * and resid 18 and name HD1%)
       3.100  2.400    2.400 peak    7472 weight   0.10000E+01 volume   0.86786E+02 ppm1     3.669 ppm2    1.084
ASSI ( 8082)
    ( ( segid *BrD * and resid 98 and name HA   ) )
    ( ( segid *BrD * and resid 30 and name HB2  ) )
       2.900  2.100    2.100 peak    8082 weight   0.10000E+01 volume   0.14301E+03 ppm1     4.802 ppm2    4.530
```

TABLE 2-continued

Unambigous NOE-derived Inter-proton Distance Restraints

```
ASSI ( 8132)
    ( segid *BrD * and resid 63 and name HD1%)
    ( ( segid *BrD * and resid 15 and name HA   ) )
      2.800  2.000   2.000 peak    8132 weight  0.10000E+01 volume  0.17717E+03 ppm1   1.646 ppm2  4.624
ASSI ( 8252)
    ( ( segid *BrD * and resid 109 and name HG1 ) )
    ( ( segid *BrD * and resid 109 and name HD1 ) )
      2.700  1.800   1.800 peak    8252 weight  0.10000E+01 volume  0.20695E+03 ppm1   1.401 ppm2  1.989
ASSI ( 8282)
    ( ( segid *BrD * and resid 18 and name HA   ) )
    ( ( segid *BrD * and resid 21 and name HG12) )
      3.300  2.700   2.200 peak    8282 weight  0.10000E+01 volume  0.61204E+02 ppm1   3.866 ppm2  1.640
ASSI ( 8362)
    ( ( segid *BrD * and resid 18 and name HG   ) )
    ( segid *BrD * and resid 14 and name HD2%)
      3.100  2.400   2.400 peak    8362 weight  0.10000E+01 volume  0.89516E+02 ppm1   2.290 ppm2  1.418
OR ( 8362)
    ( ( segid *BrD * and resid 18 and name HG   ) )
    ( segid *BrD * and resid 14 and name HD1%)
ASSI ( 8422)
    ( segid *BrD * and resid 18 and name HD1%)
    ( ( segid *BrD * and resid 14 and name HG   ) )
      2.700  1.800   1.800 peak    8422 weight  0.10000E+01 volume  0.21908E+03 ppm1   1.058 ppm2  2.070
ASSI ( 8432)
    ( segid *BrD * and resid 18 and name HD1%)
    ( ( segid *BrD * and resid 15 and name HA   ) )
      2.700  1.800   1.800 peak    8432 weight  0.10000E+01 volume  0.20923E+03 ppm1   1.057 ppm2  4.626
ASSI ( 8512)
    ( segid *BrD * and resid 22 and name HD2%)
    ( segid *BrD * and resid 78 and name HD2%)
      3.300  2.700   2.700 peak    8512 weight  0.10000E+01 volume  0.62220E+02 ppm1   1.599 ppm2  0.677
ASSI ( 8522)
    ( segid *BrD * and resid 22 and name HD2%)
    ( segid *BrD * and resid 59 and name HE % )
      2.900  2.100   2.100 peak    8522 weight  0.10000E+01 volume  0.12491E+03 ppm1   1.599 ppm2  1.679
ASSI ( 8532)
    ( segid *BrD * and resid 22 and name HD1%)
    ( ( segid *BrD * and resid 60 and name HA   ) )
      2.600  1.700   1.700 peak    8532 weight  0.10000E+01 volume  0.23265E+03 ppm1   1.645 ppm2  4.809
ASSI ( 8582)
    ( ( segid *BrD * and resid 22 and name HB2  ) )
    ( segid *BrD * and resid 63 and name HD2%)
      2.600  1.700   1.700 peak    8582 weight  0.10000E+01 volume  0.24738E+03 ppm1   2.286 ppm2  1.494
ASSI ( 8612)
    ( ( segid *BrD * and resid 56 and name HB1  ) )
    ( ( segid *BrD * and resid 35 and name HA   ) )
      2.800  2.000   2.000 peak    8612 weight  0.10000E+01 volume  0.17130E+03 ppm1   2.685 ppm2  4.900
ASSI ( 8632)
    ( segid *BrD * and resid 56 and name HD1%)
    ( segid *BrD * and resid 81 and name HG2%)
      3.800  3.600   1.700 peak    8632 weight  0.10000E+01 volume  0.24706E+02 ppm1   1.547 ppm2  0.758
ASSI ( 8642)
    ( ( segid *BrD * and resid 116 and name HG12) )
    ( ( segid *BrD * and resid 116 and name HG11) )
      2.000  1.000   1.000 peak    8642 weight  0.10000E+01 volume  0.13013E+04 ppm1   1.548 ppm2  1.921
ASSI ( 8702)
    ( segid *BrD * and resid 56 and name HD2%)
    ( segid *BrD * and resid 81 and name HG1%)
      2.400  1.400   1.400 peak    8702 weight  0.10000E+01 volume  0.46717E+03 ppm1   1.254 ppm2  1.080
ASSI ( 8832)
    ( segid *BrD * and resid 78 and name HD1%)
    ( ( segid *BrD * and resid 18 and name HB2  ) )
      4.100  4.100   1.400 peak    8832 weight  0.10000E+01 volume  0.15698E+02 ppm1   0.761 ppm2  0.924
ASSI ( 8882)
    ( segid *BrD * and resid 78 and name HD1%)
    ( segid *BrD * and resid 18 and name HD2%)
      3.000  2.200   2.200 peak    8882 weight  0.10000E+01 volume  0.10893E+03 ppm1   0.662 ppm2  0.427
ASSI ( 8942)
    ( ( segid *BrD * and resid 102 and name HA  ) )
    ( segid *BrD * and resid 101 and name HG2%)
      3.100  2.400   2.400 peak    8942 weight  0.10000E+01 volume  0.83720E+02 ppm1   4.263 ppm2  1.612
ASSI ( 9102)
    ( ( segid *BrD * and resid 21 and name HG12) )
    ( segid *BrD * and resid 102 and name HD2%)
      3.700  3.400   1.800 peak    9102 weight  0.10000E+01 volume  0.31128E+02 ppm1   1.648 ppm2  1.320
OR ( 9102)
    ( ( segid *BrD * and resid 21 and name HG12) )
    ( segid *BrD * and resid 102 and name HD1%)
```

TABLE 2-continued

Unambigous NOE-derived Inter-proton Distance Restraints

ASSI ( 9122)
  ( segid *BrD * and resid 21 and name HG2%)
  ( segid *BrD * and resid 110 and name HD1%)
    2.900  2.100  2.100  peak   9122  weight   0.10000E+01  volume   0.12723E+03  ppm1   1.600  ppm2   1.143
ASSI ( 9132)
  ( segid *BrD * and resid 21 and name HG2%)
  ( segid *BrD * and resid 78 and name HD2%)
    3.400  2.900  2.100  peak   9132  weight   0.10000E+01  volume   0.50284E+02  ppm1   1.596  ppm2   0.670
ASSI ( 9172)
  ( segid *BrD * and resid 21 and name HD1%)
  ( segid *BrD * and resid 17 and name HG2%)
    2.500  1.600  1.600  peak   9172  weight   0.10000E+01  volume   0.33280E+03  ppm1   1.205  ppm2   1.748
ASSI ( 9402)
  ( segid *BrD * and resid 21 and name HG2%)
  ( ( segid *BrD * and resid 106 and name HA ) )
    2.600  1.700  1.700  peak   9402  weight   0.10000E+01  volume   0.25016E+03  ppm1   1.597  ppm2   4.536
ASSI ( 9412)
  ( segid *BrD * and resid 101 and name HG2%)
  ( ( segid *BrD * and resid 30 and name HB1 ) )
    2.800  2.000  2.000  peak   9412  weight   0.10000E+01  volume   0.17182E+03  ppm1   1.598  ppm2   4.928
ASSI ( 9462)
  ( ( segid *BrD * and resid 110 and name HB ) )
  ( ( segid *BrD * and resid 115 and name HB1 ) )
    3.000  2.200  2.200  peak   9462  weight   0.10000E+01  volume   0.11040E+03  ppm1   2.338  ppm2   2.182
ASSI ( 9502)
  ( segid *BrD * and resid 110 and name HG2%)
  ( ( segid *BrD * and resid 115 and name HB1 ) )
    2.500  1.600  1.600  peak   9502  weight   0.10000E+01  volume   0.34762E+03  ppm1   1.252  ppm2   2.182
ASSI ( 9512)
  ( segid *BrD * and resid 110 and name HG2%)
  ( ( segid *BrD * and resid 116 and name HG12 ) )
    2.500  1.600  1.600  peak   9512  weight   0.10000E+01  volume   0.33972E+03  ppm1   1.253  ppm2   1.586
ASSI ( 9572)
  ( segid *BrD * and resid 110 and name HD1%)
  ( segid *BrD * and resid 78 and name HD1%)
    3.800  3.600  1.700  peak   9572  weight   0.10000E+01  volume   0.27664E+02  ppm1   1.154  ppm2   0.750
ASSI ( 9602)
  ( segid *BrD * and resid 110 and name HD1%)
  ( segid *BrD * and resid 78 and name HD2%)
    3.400  2.900  2.100  peak   9602  weight   0.10000E+01  volume   0.49420E+02  ppm1   1.154  ppm2   0.674
ASSI ( 9622)
  ( segid *BrD * and resid 116 and name HG2%)
  ( segid *BrD * and resid 110 and name HG2%)
    2.800  2.000  2.000  peak   9622  weight   0.10000E+01  volume   0.18357E+03  ppm1   1.401  ppm2   1.271
ASSI ( 9632)
  ( segid *BrD * and resid 116 and name HD1%)
  ( segid *BrD * and resid 110 and name HD1%)
    2.100  1.100  1.100  peak   9632  weight   0.10000E+01  volume   0.89032E+03  ppm1   1.399  ppm2   1.152
ASSI ( 9992)
  ( ( segid *BrD * and resid 54 and name HB2 ) )
  ( ( segid *BrD * and resid 59 and name HB2 ) )
    2.700  1.800  1.800  peak   9992  weight   0.10000E+01  volume   0.19570E+03  ppm1   1.947  ppm2   2.490
ASSI (10032)
  ( ( segid *BrD * and resid 54 and name HA ) )
  ( ( segid *BrD * and resid 54 and name HB2 ) )
    3.000  2.200  2.200  peak  10032  weight   0.10000E+01  volume   0.99741E+02  ppm1   5.541  ppm2   2.481
ASSI (10142)
  ( ( segid *BrD * and resid 70 and name HB2 ) )
  ( ( segid *BrD * and resid 73 and name HB1 ) )
    4.100  4.100  1.400  peak  10142  weight   0.10000E+01  volume   0.17585E+02  ppm1   4.360  ppm2   2.597
ASSI (10172)
  ( ( segid *BrD * and resid 52 and name HB2 ) )
  ( ( segid *BrD * and resid 60 and name HG1 ) )
    4.200  4.200  1.300  peak  10172  weight   0.10000E+01  volume   0.15368E+02  ppm1   3.522  ppm2   2.345
ASSI (10512)
  ( ( segid *BrD * and resid 61 and name HG1 ) )
  ( ( segid *BrD * and resid 60 and name HB2 ) )
    2.700  1.800  1.800  peak  10512  weight   0.10000E+01  volume   0.19616E+03  ppm1   2.980  ppm2   4.588
ASSI (10842)
  ( ( segid *BrD * and resid 30 and name HB2 ) )
  ( segid *BrD * and resid 102 and name HD1%)
    3.200  2.600  2.300  peak  10842  weight   0.10000E+01  volume   0.80809E+02  ppm1   4.510  ppm2   1.320
ASSI (10912)
  ( ( segid *BrD * and resid 93 and name HB1 ) )
  ( ( segid *BrD * and resid 91 and name HG1 ) )
    3.700  3.400  1.800  peak  10912  weight   0.10000E+01  volume   0.32594E+02  ppm1   5.000  ppm2   2.798

TABLE 2-continued

Unambigous NOE-derived Inter-proton Distance Restraints

ASSI (10922)
( ( segid *BrD * and resid 93 and name HB2 ) )
( ( segid *BrD * and resid 91 and name HG1 ) )
    3.700  3.400    1.800   peak   10922   weight    0.10000E+01  volume    0.31695E+02  ppm1     4.755  ppm2     2.799
ASSI (10962)
( ( segid *BrD * and resid 44 and name HA   ) )
( ( segid *BrD * and resid 41 and name HA   ) )
    4.600  4.600    0.900   peak   10962   weight    0.10000E+01  volume    0.78869E+01  ppm1     5.099  ppm2     4.654
ASSI (11342)
( ( segid *BrD * and resid 19 and name HG1 ) )
(  segid *BrD * and resid 63 and name HD2%)
    3.100  2.400    2.400   peak   11342   weight    0.10000E+01  volume    0.91996E+02  ppm1     1.889  ppm2     1.493
ASSI (11372)
( ( segid *BrD * and resid 26 and name HA   ) )
(  segid *BrD * and resid 31 and name HB % )
    2.200  1.200    1.200   peak   11372   weight    0.10000E+01  volume    0.67300E+03  ppm1     4.509  ppm2     2.311
ASSI (11382)
( ( segid *BrD * and resid 26 and name HA   ) )
(  segid *BrD * and resid 35 and name HE % )
    2.800  2.000    2.000   peak   11382   weight    0.10000E+01  volume    0.18352E+03  ppm1     4.509  ppm2     2.783
ASSI (11502)
( ( segid *BrD * and resid 86 and name HE1 ) )
( ( segid *BrD * and resid 83 and name HA   ) )
    2.900  2.100    2.100   peak   11502   weight    0.10000E+01  volume    0.14787E+03  ppm1     3.080  ppm2     4.460
ASSI (11572)
( ( segid *BrD * and resid 109 and name HB1 ) )
(  segid *BrD * and resid 21 and name HG2%)
    3.500  3.100    2.000   peak   11572   weight    0.10000E+01  volume    0.46118E+02  ppm1     2.334  ppm2     1.587
ASSI (11642)
( ( segid *BrD * and resid 6 and name HB2 ) )
( ( segid *BrD * and resid 7 and name HG1 ) )
    3.100  2.400    2.400   peak   11642   weight    0.10000E+01  volume    0.90515E+02  ppm1     2.291  ppm2     2.876
ASSI (11752)
( ( segid *BrD * and resid 55 and name HB1 ) )
( ( segid *BrD * and resid 37 and name HA   ) )
    2.800  2.000    2.000   peak   11752   weight    0.10000E+01  volume    0.16032E+03  ppm1     2.979  ppm2     4.860
ASSI (11832)
( ( segid *BrD * and resid 91 and name HA   ) )
( ( segid *BrD * and resid 92 and name HB2 ) )
    3.500  3.100    2.000   peak   11832   weight    0.10000E+01  volume    0.43713E+02  ppm1     5.347  ppm2     2.571
ASSI (12292)
(  segid *BrD * and resid 81 and name HG2%)
( ( segid *BrD * and resid 56 and name HG   ) )
    3.300  2.700    2.200   peak   12292   weight    0.10000E+01  volume    0.58134E+02  ppm1     0.761  ppm2     2.323
ASSI (12502)
( ( segid *BrD * and resid 54 and name HG1 ) )
( ( segid *BrD * and resid 59 and name HB2 ) )
    4.000  4.000    1.500   peak   12502   weight    0.10000E+01  volume    0.18992E+02  ppm1     3.288  ppm2     2.467
ASSI (12632)
(  segid *BrD * and resid 59 and name HE % )
( ( segid *BrD * and resid 77 and name HB1 ) )
    2.500  1.600    1.600   peak   12632   weight    0.10000E+01  volume    0.30644E+03  ppm1     1.848  ppm2     3.321
ASSI (12732)
( ( segid *BrD * and resid 71 and name HA   ) )
(  segid *BrD * and resid 18 and name HD1%)
    3.700  3.400    1.800   peak   12732   weight    0.10000E+01  volume    0.29522E+02  ppm1     4.608  ppm2     1.084
ASSI (12752)
( ( segid *BrD * and resid 71 and name HA   ) )
(  segid *BrD * and resid 18 and name HD2%)
    3.300  2.700    2.200   peak   12752   weight    0.10000E+01  volume    0.66213E+02  ppm1     4.607  ppm2     0.409
ASSI (12872)
( ( segid *BrD * and resid 62 and name HD1 ) )
( ( segid *BrD * and resid 59 and name HB2 ) )
    3.500  3.100    2.000   peak   12872   weight    0.10000E+01  volume    0.44554E+02  ppm1     3.177  ppm2     2.484
ASSI (13092)
( ( segid *BrD * and resid 54 and name HG1 ) )
(  segid *BrD * and resid 81 and name HG1%)
    3.400  2.900    2.100   peak   13092   weight    0.10000E+01  volume    0.51686E+02  ppm1     3.288  ppm2     1.075
ASSI (13112)
( ( segid *BrD * and resid 73 and name HB2 ) )
( ( segid *BrD * and resid 68 and name HA   ) )
    3.000  2.200    2.200   peak   13112   weight    0.10000E+01  volume    0.10760E+03  ppm1     2.486  ppm2     5.142
ASSI (13122)
( ( segid *BrD * and resid 73 and name HB1 ) )
( ( segid *BrD * and resid 68 and name HA   ) )
    2.900  2.100    2.100   peak   13122   weight    0.10000E+01  volume    0.13268E+03  ppm1     2.583  ppm2     5.141

TABLE 2-continued

Unambigous NOE-derived Inter-proton Distance Restraints

```
ASSI (13232)
    ( ( segid *BrD * and resid 46 and name HB1 ) )
    (   segid *BrD * and resid 38 and name HG2%)
      3.500  3.100   2.000 peak   13232 weight    0.10000E+01 volume   0.45934E+02 ppm1    3.275 ppm2   0.790
ASSI (13282)
    ( ( segid *BrD * and resid 56 and name HA    ) )
    (   segid *BrD * and resid 22 and name HD2%)
      3.100  2.400   2.400 peak   13282 weight    0.10000E+01 volume   0.86018E+02 ppm1    4.607 ppm2   1.637
OR (13282)
    ( ( segid *BrD * and resid 56 and name HA    ) )
    (   segid *BrD * and resid 22 and name HD1%)
ASSI (13312)
    ( ( segid *BrD * and resid 116 and name HG12) )
    (   segid *BrD * and resid 110 and name HD1%)
      2.700  1.800   1.800 peak   13312 weight    0.10000E+01 volume   0.18778E+03 ppm1    1.548 ppm2   1.145
ASSI (13332)
    (   segid *BrD * and resid 22 and name HD1%)
    ( ( segid *BrD * and resid 63 and name HB2 ) )
      2.500  1.600   1.600 peak   13332 weight    0.10000E+01 volume   0.34390E+03 ppm1    1.648 ppm2   2.516
ASSI (13412)
    (   segid *BrD * and resid 25 and name HG1%)
    (   segid *BrD * and resid 56 and name HD2%)
      2.900  2.100   2.100 peak   13412 weight    0.10000E+01 volume   0.12726E+03 ppm1    1.795 ppm2   1.252
ASSI (13572)
    ( ( segid *BrD * and resid 49 and name HB    ) )
    ( ( segid *BrD * and resid 50 and name HG11) )
      5.500  5.500   0.000 peak   13572 weight    0.10000E+01 volume   0.27123E−01 ppm1    2.634 ppm2   1.417
ASSI (13582)
    ( ( segid *BrD * and resid 49 and name HB    ) )
    (   segid *BrD * and resid 50 and name HD1%)
      4.000  4.000   1.500 peak   13582 weight    0.10000E+01 volume   0.18896E+02 ppm1    2.634 ppm2   1.148
ASSI (13682)
    (   segid *BrD * and resid 54 and name HE % )
    ( ( segid *BrD * and resid 57 and name HG1 ) )
      3.600  3.200   1.900 peak   13682 weight    0.10000E+01 volume   0.37432E+02 ppm1    2.537 ppm2   2.101
ASSI (13732)
    ( ( segid *BrD * and resid 63 and name HA    ) )
    ( ( segid *BrD * and resid 68 and name HB1 ) )
      3.500  3.100   2.000 peak   13732 weight    0.10000E+01 volume   0.44471E+02 ppm1    5.296 ppm2   3.662
ASSI (13752)
    (   segid *BrD * and resid 63 and name HD2%)
    ( ( segid *BrD * and resid 19 and name HB2 ) )
      2.700  1.800   1.800 peak   13752 weight    0.10000E+01 volume   0.20264E+03 ppm1    1.498 ppm2   1.996
ASSI (13772)
    ( ( segid *BrD * and resid 64 and name HA    ) )
    (   segid *BrD * and resid 63 and name HD2%)
      4.000  4.000   1.500 peak   13772 weight    0.10000E+01 volume   0.18294E+02 ppm1    4.951 ppm2   1.488
ASSI (13792)
    (   segid *BrD * and resid 49 and name HG1%)
    (   segid *BrD * and resid 50 and name HG2%)
      3.800  3.600   1.700 peak   13792 weight    0.10000E+01 volume   0.26015E+02 ppm1    1.646 ppm2   1.009
ASSI (13812)
    ( ( segid *BrD * and resid 76 and name HA    ) )
    ( ( segid *BrD * and resid 80 and name HB2 ) )
      4.200  4.200   1.300 peak   13812 weight    0.10000E+01 volume   0.14558E+02 ppm1    4.656 ppm2   2.508
ASSI (13832)
    ( ( segid *BrD * and resid 56 and name HB1 ) )
    ( ( segid *BrD * and resid 34 and name HB2 ) )
      3.100  2.400   2.400 peak   13832 weight    0.10000E+01 volume   0.92421E+02 ppm1    2.685 ppm2   3.159
ASSI (13842)
    ( ( segid *BrD * and resid 67 and name HB2 ) )
    ( ( segid *BrD * and resid 62 and name HA    ) )
      3.400  2.900   2.100 peak   13842 weight    0.10000E+01 volume   0.56015E+02 ppm1    2.636 ppm2   4.483
ASSI (13862)
    (   segid *BrD * and resid 69 and name HG2%)
    (   segid *BrD * and resid 18 and name HD1%)
      3.600  3.200   1.900 peak   13862 weight    0.10000E+01 volume   0.35688E+02 ppm1    1.425 ppm2   1.030
ASSI (13872)
    (   segid *BrD * and resid 69 and name HG2%)
    ( ( segid *BrD * and resid 18 and name HB2 ) )
      5.500  5.500   0.000 peak   13872 weight    0.10000E+01 volume   0.14355E+01 ppm1    1.425 ppm2   0.880
ASSI (13892)
    ( ( segid *BrD * and resid 12 and name HA    ) )
    (   segid *BrD * and resid 14 and name HD2%)
      3.000  2.200   2.200 peak   13892 weight    0.10000E+01 volume   0.11539E+03 ppm1    5.298 ppm2   1.382
OR (13892)
    ( ( segid *BrD * and resid 12 and name HA    ) )
    (   segid *BrD * and resid 14 and name HD1%)
```

TABLE 2-continued

Unambigous NOE-derived Inter-proton Distance Restraints

```
ASSI (13982)
   ( ( segid *BrD * and resid 74 and name HA   ) )
   ( ( segid *BrD * and resid 68 and name HB2 ) )
      3.600  3.200   1.900 peak   13982 weight   0.10000E+01 volume   0.36366E+02 ppm1    4.360 ppm2    3.499
ASSI (14032)
   (  segid *BrD * and resid 76 and name HB % )
   ( ( segid *BrD * and resid 80 and name HG1 ) )
      2.800  2.000   2.000 peak   14032 weight   0.10000E+01 volume   0.17944E+03 ppm1    2.091 ppm2    2.344
ASSI (14052)
   (  segid *BrD * and resid 14 and name HD1%)
   ( ( segid *BrD * and resid 70 and name HA   ) )
      2.700  1.800   1.800 peak   14052 weight   0.10000E+01 volume   0.21486E+03 ppm1    1.402 ppm2    5.362
ASSI (14112)
   ( ( segid *BrD * and resid 14 and name HA   ) )
   (  segid *BrD * and resid 113 and name HB % )
      3.100  2.400   2.400 peak   14112 weight   0.10000E+01 volume   0.82177E+02 ppm1    4.655 ppm2    1.987
ASSI (14212)
   ( ( segid *BrD * and resid 98 and name HB2 ) )
   ( ( segid *BrD * and resid 30 and name HB1 ) )
      3.700  3.400   1.800 peak   14212 weight   0.10000E+01 volume   0.32251E+02 ppm1    3.667 ppm2    4.933
ASSI (14222)
   ( ( segid *BrD * and resid 99 and name HA   ) )
   ( ( segid *BrD * and resid 102 and name HG  ) )
      3.400  2.900   2.100 peak   14222 weight   0.10000E+01 volume   0.54061E+02 ppm1    4.459 ppm2    2.136
ASSI (14242)
   ( ( segid *BrD * and resid 99 and name HA   ) )
   ( ( segid *BrD * and resid 82 and name HB2 ) )
      3.000  2.200   2.200 peak   14242 weight   0.10000E+01 volume   0.10335E+03 ppm1    4.457 ppm2    3.581
ASSI (14262)
   ( ( segid *BrD * and resid 64 and name HA   ) )
   ( ( segid *BrD * and resid 33 and name HD2 ) )
      3.100  2.700   2.200 peak   14262 weight   0.10000E+01 volume   0.61370E+02 ppm1    9.000 ppm2    2.218
ASSI (14272)
   (  segid *BrD * and resid 31 and name HB % )
   ( ( segid *BrD * and resid 25 and name HA   ) )
      3.000  2.200   2.200 peak   14272 weight   0.10000E+01 volume   0.10586E+03 ppm1    2.289 ppm2    4.437
ASSI (14292)
   ( ( segid *BrD * and resid 110 and name HB  ) )
   (  segid *BrD * and resid 115 and name HD1%)
      5.500  5.500   0.000 peak   14292 weight   0.10000E+01 volume   0.49515E+00 ppm1    2.338 ppm2    1.318
ASSI (14302)
   (  segid *BrD * and resid 63 and name HD2%)
   ( ( segid *BrD * and resid 22 and name HB1 ) )
      2.500  1.600   1.600 peak   14302 weight   0.10000E+01 volume   0.30120E+03 ppm1    1.498 ppm2    2.695
ASSI (14332)
   ( ( segid *BrD * and resid 103 and name HA  ) )
   ( ( segid *BrD * and resid 102 and name HB2 ) )
      3.500  3.300   2.000 peak   14332 weight   0.10000E+01 volume   0.41084E+02 ppm1    3.769 ppm2    1.830
ASSI (14352)
   ( ( segid *BrD * and resid 106 and name HA  ) )
   ( ( segid *BrD * and resid 109 and name HG1 ) )
      4.000  4.000   1.500 peak   14352 weight   0.10000E+01 volume   0.19913E+02 ppm1    4.555 ppm2    1.4395
ASSI (14382)
   ( ( segid *BrD * and resid 15 and name HA   ) )
   ( ( segid *BrD * and resid 14 and name HG   ) )
      3.800  3.600   1.700 peak   14382 weight   0.10000E+01 volume   0.25435E+02 ppm1    4.606 ppm2    2.042
ASSI (14442)
   ( ( segid *BrD * and resid 110 and name HA  ) )
   ( ( segid *BrD * and resid 115 and name HB1 ) )
      2.800  2.000   2.000 peak   14442 weight   0.10000E+01 volume   0.18018E+03 ppm1    4.411 ppm2    2.181
OR (14442)
   ( ( segid *BrD * and resid 110 and name HA  ) )
   ( ( segid *BrD * and resid 115 and name HG  ) )
ASSI (14452)
   (  segid *BrD * and resid 110 and name HG2%)
   (  segid *BrD * and resid 115 and name HD1%)
      2.600  1.700   1.700 peak   14452 weight   0.10000E+01 volume   0.23487E+03 ppm1    1.254 ppm2    1.330
ASSI (14512)
   ( ( segid *BrD * and resid 111 and name HG1 ) )
   (  segid *BrD * and resid 110 and name HG2%)
      3.600  3.200   1.900 peak   14512 weight   0.10000E+01 volume   0.36391E+02 ppm1    1.989 ppm2    1.278
ASSI (14652)
   ( ( segid *BrD * and resid 18 and name HA   ) )
   ( ( segid *BrD * and resid 21 and name HG11) )
      3.700  3.400   1.800 peak   14652 weight   0.10000E+01 volume   0.30202E+02 ppm1    3.866 ppm2    2.351
```

TABLE 2-continued

Unambigous NOE-derived Inter-proton Distance Restraints

```
ASSI (14672)
   ( segid *BrD * and resid 18 and name HD1%)
   ( ( segid *BrD * and resid 63 and name HG   ) )
      3.100  2.400    2.400  peak   14672  weight    0.10000E+01  volume   0.91159E+02  ppm1    1.057  ppm2    2.467
ASSI (14702)
   ( segid *BrD * and resid 21 and name HD1%)
   ( segid *BrD * and resid 63 and name HD2%)
      2.300  2.300    2.200  peak   14702  weight    0.10000E+01  volume   0.60922E+03  ppm1    1.205  ppm2    1.458
ASSI (14752)
   ( segid *BrD * and resid 54 and name HE % )
   ( segid *BrD * and resid 81 and name HG1%)
      3.700  3.400    1.800  peak   14752  weight    0.10000E+01  volume   0.28669E+02  ppm1    2.535  ppm2    1.075
ASSI (14762)
   ( ( segid *BrD * and resid 51 and name HA   ) )
   ( ( segid *BrD * and resid 53 and name HD1  ) )
      5.500  5.500    0.000  peak   14762  weight    0.10000E+01  volume   0.89215E-01  ppm1    4.460  ppm2    4.222
ASSI (14782)
   ( ( segid *BrD * and resid 36 and name HA   ) )
   ( ( segid *BrD * and resid 57 and name HB1  ) )
      2.300  1.300    1.300  peak   14782  weight    0.10000E+01  volume   0.40436E+03  ppm1    5.446  ppm2    2.956
ASSI (15012)
   ( ( segid *BrD * and resid 46 and name HB1  ) )
   ( segid *BrD * and resid 38 and name HG1%)
      4.000  4.000    1.500  peak   15012  weight    0.10000E+01  volume   0.20055E+02  ppm1    3.275  ppm2    1.075
ASSI (15032)
   ( ( segid *BrD * and resid 46 and name HB1  ) )
   ( segid *BrD * and resid 47 and name HD % )
      4.500  4.500    1.000  peak   15032  weight    0.10000E+01  volume   0.96365E+01  ppm1    3.276  ppm2    7.934
ASSI (15042)
   ( ( segid *BrD * and resid 46 and name HB2  ) )
   ( segid *BrD * and resid 47 and name HD % )
      3.200  2.600    2.300  peak   15042  weight    0.10000E+01  volume   0.71990E+02  ppm1    3.077  ppm2    7.933
ASSI (15052)
   ( ( segid *BrD * and resid 46 and name HA   ) )
   ( segid *BrD * and resid 49 and name HG2%)
      3.600  3.200    1.900  peak   15052  weight    0.10000E+01  volume   0.38868E+02  ppm1    4.165  ppm2    1.571
ASSI (15092)
   ( ( segid *BrD * and resid 28 and name HB2  ) )
   ( segid *BrD * and resid 31 and name HB % )
      2.800  2.000    2.000  peak   15092  weight    0.10000E+01  volume   0.15966E+03  ppm1    3.374  ppm2    2.312
ASSI (15182)
   ( ( segid *BrD * and resid 67 and name HB1  ) )
   ( ( segid *BrD * and resid 62 and name HB2  ) )
      4.000  4.000    1.500  peak   15182  weight    0.10000E+01  volume   0.19603E+02  ppm1    3.572  ppm2    1.693
ASSI (15192)
   ( ( segid *BrD * and resid 67 and name HB1  ) )
   ( ( segid *BrD * and resid 62 and name HG2  ) )
      4.400  4.400    1.100  peak   15192  weight    0.10000E+01  volume   0.11003E+02  ppm1    3.572  ppm2    1.474
ASSI (15402)
   ( ( segid *BrD * and resid 82 and name HB2  ) )
   ( segid *BrD * and resid 99 and name HB % )
      3.000  2.200    2.200  peak   15402  weight    0.10000E+01  volume   0.10991E+03  ppm1    3.572  ppm2    2.206
ASSI (15412)
   ( ( segid *BrD * and resid 82 and name HB1  ) )
   ( segid *BrD * and resid 99 and name HB % )
      2.900  2.100    2.100  peak   15412  weight    0.10000E+01  volume   0.12753E+03  ppm1    3.672  ppm2    2.206
ASSI (15552)
   ( ( segid *BrD * and resid 82 and name HB2  ) )
   ( ( segid *BrD * and resid 103 and name HB2 ) )
      3.700  3.400    1.800  peak   15552  weight    0.10000E+01  volume   0.31328E+02  ppm1    3.573  ppm2    1.897
ASSI (15592)
   ( ( segid *BrD * and resid 107 and name HB1 ) )
   ( ( segid *BrD * and resid 103 and name HG2 ) )
      3.100  2.400    2.400  peak   15592  weight    0.10000E+01  volume   0.86957E+02  ppm1    3.670  ppm2    2.540
ASSI (15712)
   ( ( segid *BrD * and resid 107 and name HB1 ) )
   ( segid *BrD * and resid 107 and name HD % )
      2.200  1.200    1.200  peak   15712  weight    0.10000E+01  volume   0.63746E+03  ppm1    3.673  ppm2    7.827
ASSI (15812)
   ( ( segid *BrD * and resid 15 and name HA   ) )
   ( ( segid *BrD * and resid 18 and name HA   ) )
      3.300  2.700    2.200  peak   15812  weight    0.10000E+01  volume   0.67333E+02  ppm1    4.606  ppm2    3.900
ASSI (15882)
   ( ( segid *BrD * and resid 15 and name HB1  ) )
   ( segid *BrD * and resid 63 and name HD1%)
      4.000  4.000    1.500  peak   15882  weight    0.10000E+01  volume   0.19033E+02  ppm1    3.815  ppm2    1.652
```

TABLE 2-continued

Unambigous NOE-derived Inter-proton Distance Restraints

```
ASSI (15932)
    ( ( segid *BrD * and resid 82 and name HB1 ) )
    ( ( segid *BrD * and resid 107 and name HZ   ) )
      2.600  1.700    1.700 peak   15932 weight    0.10000E+01 volume   0.26167E+03 ppm1    3.670 ppm2    8.022
ASSI (16052)
    ( ( segid *BrD * and resid 68 and name HA   ) )
    ( ( segid *BrD * and resid 73 and name HG   ) )
      4.000  4.000    1.500 peak   16052 weight    0.10000E+01 volume   0.20921E+02 ppm1    5.148 ppm2    2.367
ASSI (16062)
    ( ( segid *BrD * and resid 68 and name HB2 ) )
    (   segid *BrD * and resid 74 and name HD % )
      3.600  3.200    1.900 peak   16062 weight    0.10000E+01 volume   0.38285E+02 ppm1    3.522 ppm2    6.998
ASSI (16112)
    ( ( segid *BrD * and resid 68 and name HB1 ) )
    ( ( segid *BrD * and resid 62 and name HD1 ) )
      4.500  4.500    1.000 peak   16112 weight    0.10000E+01 volume   0.90000E+01 ppm1    3.669 ppm2    3.146
ASSI (16122)
    ( ( segid *BrD * and resid 68 and name HB2 ) )
    ( ( segid *BrD * and resid 62 and name HD1 ) )
      3.500  3.100    2.000 peak   16122 weight    0.10000E+01 volume   0.43825E+02 ppm1    3.522 ppm2    3.149
ASSI (16132)
    ( ( segid *BrD * and resid 68 and name HB1 ) )
    ( ( segid *BrD * and resid 63 and name HB1 ) )
      3.600  3.200    1.900 peak   16132 weight    0.10000E+01 volume   0.35724E+02 ppm1    3.669 ppm2    2.883
ASSI (16152)
    ( ( segid *BrD * and resid 68 and name HB2 ) )
    ( ( segid *BrD * and resid 63 and name HB1 ) )
      3.500  3.100    2.000 peak   16152 weight    0.10000E+01 volume   0.44106E+02 ppm1    3.522 ppm2    2.884
ASSI (16162)
    ( ( segid *BrD * and resid 68 and name HB2 ) )
    ( ( segid *BrD * and resid 62 and name HB1 ) )
      4.100  4.100    1.400 peak  16162 weight     0.10000E+01 volume   0.16622E+02 ppm1    3.522 ppm2    2.605
ASSI (16212)
    ( ( segid *BrD * and resid 88 and name HA   ) )
    (   segid *BrD * and resid 49 and name HG2%)
      3.200  2.600    2.300 peak   16212 weight    0.10000E+01 volume   0.71276E+02 ppm1    4.999 ppm2    1.571
ASSI (16312)
    ( ( segid *BrD * and resid 88 and name HB1 ) )
    (   segid *BrD * and resid 95 and name HD % )
      3.500  3.100    2.000 peak   16312 weight    0.10000E+01 volume   0.47079E+02 ppm1    3.524 ppm2    7.496
ASSI (16382)
    ( ( segid *BrD * and resid 19 and name HE1 ) )
    (   segid *BrD * and resid 63 and name HD2%)
      3.500  3.100    2.000 peak   16382 weight    0.10000E+01 volume   0.45471E+02 ppm1    3.522 ppm2    1.495
ASSI (16422)
    ( ( segid *BrD * and resid 66 and name HD2 ) )
    (   segid *BrD * and resid 69 and name HG1%)
      4.900  4.900    0.600 peak   16422 weight    0.10000E+01 volume   0.59473E+01 ppm1    3.621 ppm2    1.562
ASSI (16432)
    ( ( segid *BrD * and resid 66 and name HD2 ) )
    (   segid *BrD * and resid 63 and name HD1%)
      4.700  4.700    0.800 peak   16432 weight    0.10000E+01 volume   0.72449E+01 ppm1    3.620 ppm2    1.645
ASSI (16492)
    ( ( segid *BrD * and resid 96 and name HA   ) )
    ( ( segid *BrD * and resid 86 and name HA   ) )
      2.200  1.200    1.200 peak   16492 weight    0.10000E+01 volume   0.78759E+03 ppm1    4.409 ppm2    4.802
ASSI (16502)
    ( ( segid *BrD * and resid 96 and name HA   ) )
    ( ( segid *BrD * and resid 86 and name HG2 ) )
      4.100  4.100    1.400 peak   16502 weight    0.10000E+01 volume   0.17647E+02 ppm1    4.409 ppm2    0.758
ASSI (16612)
    ( ( segid *BrD * and resid 96 and name HB2 ) )
    (   segid *BrD * and resid 96 and name HE % )
      3.400  2.900    2.100 peak   16612 weight    0.10000E+01 volume   0.47985E+02 ppm1    3.134 ppm2    7.633
ASSI (16662)
    ( ( segid *BrD * and resid 96 and name HB1 ) )
    (   segid *BrD * and resid 99 and name HB % )
      4.200  4.200    1.300 peak   16662 weight    0.10000E+01 volume   0.14266E+02 ppm1    4.008 ppm2    2.227
ASSI (16672)
    ( ( segid *BrD * and resid 96 and name HB2 ) )
    (   segid *BrD * and resid 99 and name HB % )
      4.200  4.200    1.300 peak   16672 weight    0.10000E+01 volume   0.13986E+02 ppm1    3.125 ppm2    2.209
ASSI (16682)
    ( ( segid *BrD * and resid 52 and name HA   ) )
    ( ( segid *BrD * and resid 53 and name HG1 ) )
      4.300  4.300    1.200 peak   16682 weight    0.10000E+01 volume   0.11894E+02 ppm1    5.589 ppm2    2.819
```

TABLE 2-continued

Unambigous NOE-derived Inter-proton Distance Restraints

```
OR (16682)
    ( ( segid *BrD * and resid 52 and name HA   ) )
    ( ( segid *BrD * and resid 53 and name HB1  ) )
ASSI (16792)
    ( ( segid *BrD * and resid 95 and name HB2  ) )
    ( ( segid *BrD * and resid 85 and name HA   ) )
      2.700  1.800   1.800  peak   16792  weight   0.10000E+01  volume   0.22870E+03  ppm1   3.375  ppm2   4.995
ASSI (16842)
    ( ( segid *BrD * and resid 15 and name HB2  ) )
    ( ( segid *BrD * and resid 15 and name HA   ) )
      2.200  1.200   1.200  peak   16842  weight   0.10000E+01  volume   0.62256E+03  ppm1   3.677  ppm2   4.618
ASSI (16882)
    ( ( segid *BrD * and resid 106 and name HA  ) )
    (   segid *BrD * and resid 82 and name HE % )
      4.100  4.100   1.400  peak   16882  weight   0.10000E+01  volume   0.17840E+02  ppm1   4.557  ppm2   7.039
OR (16882)
    ( ( segid *BrD * and resid 106 and name HA  ) )
    ( ( segid *BrD * and resid 82 and name HZ   ) )
ASSI (16892)
    ( ( segid *BrD * and resid 106 and name HA  ) )
    (   segid *BrD * and resid 106 and name HD % )
      2.200  1.200   1.200  peak   16892  weight   0.10000E+01  volume   0.63095E+03  ppm1   4.556  ppm2   7.511
ASSI (16902)
    ( ( segid *BrD * and resid 106 and name HA  ) )
    (   segid *BrD * and resid 106 and name HE % )
      3.000  2.200   2.200  peak   16902  weight   0.10000E+01  volume   0.10421E+03  ppm1   4.558  ppm2   7.634
ASSI (16932)
    ( ( segid *BrD * and resid 57 and name HA   ) )
    ( ( segid *BrD * and resid 36 and name HA   ) )
      5.500  5.500   0.000  peak   16932  weight   0.10000E+01  volume   0.15155E+01  ppm1   4.804  ppm2   5.444
ASSI (16972)
    ( ( segid *BrD * and resid 106 and name HB2 ) )
    (   segid *BrD * and resid 82 and name HE % )
      3.000  2.200   2.200  peak   16972  weight   0.10000E+01  volume   0.99455E+02  ppm1   3.676  ppm2   7.053
ASSI (17032)
    ( ( segid *BrD * and resid 62 and name HA   ) )
    ( ( segid *BrD * and resid 67 and name HB1  ) )
      2.400  1.400   1.400  peak   17032  weight   0.10000E+01  volume   0.47084E+03  ppm1   4.462  ppm2   3.576
ASSI (17072)
    ( ( segid *BrD * and resid 95 and name HA   ) )
    ( ( segid *BrD * and resid 32 and name HH2  ) )
      2.800  2.000   2.000  peak   17072  weight   0.10000E+01  volume   0.16966E+03  ppm1   4.462  ppm2   7.790
ASSI (17192)
    ( ( segid *BrD * and resid 20 and name HA   ) )
    ( ( segid *BrD * and resid 23 and name HG2  ) )
      2.400  1.400   1.400  peak   17192  weight   0.10000E+01  volume   0.43323E+03  ppm1   4.903  ppm2   3.069
ASSI (17342)
    ( ( segid *BrD * and resid 97 and name HA   ) )
    (   segid *BrD * and resid 96 and name HD % )
      2.800  2.000   2.000  peak   17342  weight   0.10000E+01  volume   0.15398E+03  ppm1   4.807  ppm2   7.719
ASSI (17352)
    ( ( segid *BrD * and resid 34 and name HB2  ) )
    (   segid *BrD * and resid 102 and name HD1%)
      3.900  3.800   1.600  peak   17352  weight   0.10000E+01  volume   0.22025E+02  ppm1   3.127  ppm2   1.319
OP (17352)
    ( ( segid *BrD * and resid 34 and name HB2  ) )
    (   segid *BrD * and resid 102 and name HD2%)
ASSI (17372)
    ( ( segid *BrD * and resid 34 and name HB1  ) )
    (   segid *BrD * and resid 102 and name HD1%)
      4.300  4.300   1.200  peak   17372  weight   0.10000E+01  volume   0.12013E+02  ppm1   4.114  ppm2   1.317
OR (17372)
    ( ( segid *BrD * and resid 34 and name HB1  ) )
    (   segid *BrD * and resid 102 and name HD2%)
ASSI (17452)
    ( ( segid *BrD * and resid 34 and name HB2  ) )
    (   segid *BrD * and resid 34 and name HE % )
      3.800  3.600   1.700  peak   17452  weight   0.10000E+01  volume   0.24806E+02  ppm1   3.122  ppm2   7.774
ASSI (17502)
    ( ( segid *BrD * and resid 34 and name HA   ) )
    ( ( segid *BrD * and resid 35 and name HA   ) )
      4.600  4.600   0.900  peak   17502  weight   0.10000E+01  volume   0.81169E+01  ppm1   5.544  ppm2   4.907
ASSI (17562)
    (   segid *BrD * and resid 81 and name HG2%)
    ( ( segid *BrD * and resid 34 and name HZ   ) )
      3.500  3.100   2.000  peak   17562  weight   0.10000E+01  volume   0.45996E+02  ppm1   0.759  ppm2   7.903
```

TABLE 2-continued

Unambigous NOE-derived Inter-proton Distance Restraints

```
ASSI (17572)
   ( segid *BrD * and resid 81 and name HG2%)
   ( segid *BrD * and resid 34 and name HD % )
      2.500  1.600    1.600  peak   17572  weight   0.10000E+01  volume   0.32265E+03  ppm1    0.761  ppm2   7.706
ASSI (17632)
   ( segid *BrD * and resid 81 and name HG2%)
   ( segid *BrD * and resid 82 and name HD % )
      2.300  1.300    1.300  peak   17632  weight   0.10000E+01  volume   0.48682E+03  ppm1    0.763  ppm2   7.263
ASSI (17642)
   ( segid *BrD * and resid 81 and name HG2%)
   ( segid *BrD * and resid 82 and name HE % )
      2.800  2.000    2.000  peak   17642  weight   0.10000E+01  volume   0.15950E+03  ppm1    0.760  ppm2   7.063
ASSI (17712)
   ( ( segid *BrD * and resid 33 and name HG1 ) )
   ( ( segid *BrD * and resid 95 and name HA  ) )
      3.000  2.200    2.200  peak   17712  weight   0.10000E+01  volume   0.11633E+03  ppm1    0.859  ppm2   4.452
ASSI (17732)
   ( ( segid *BrD * and resid 33 and name HG1 ) )
   ( ( segid *BrD * and resid 98 and name HB1 ) )
      3.400  2.900    2.100  peak   17732  weight   0.10000E+01  volume   0.51004E+02  ppm1    0.859  ppm2   4.020
ASSI (17742)
   ( ( segid *BrD * and resid 33 and name HG1 ) )
   ( ( segid *BrD * and resid 98 and name HB2 ) )
      3.100  2.400    2.400  peak   17742  weight   0.10000E+01  volume   0.94735E+02  ppm1    0.859  ppm2   3.654
ASSI (17762)
   ( ( segid *BrD * and resid 33 and name HG2 ) )
   ( ( segid *BrD * and resid 95 and name HA  ) )
      3.400  2.900    2.100  peak   17762  weight   0.10000E+01  volume   0.53514E+02  ppm1   -0.324  ppm2   4.444
ASSI (17782)
   ( ( segid *BrD * and resid 33 and name HD1 ) )
   ( segid *BrD * and resid 31 and name HB % )
      3.500  3.100    2.000  peak   17782  weight   0.10000E+01  volume   0.42246E+02  ppm1    2.782  ppm2   2.304
ASSI (17902)
   ( ( segid *BrD * and resid 33 and name HD2 ) )
   ( segid *BrD * and resid 34 and name HD % )
      3.900  3.800    1.600  peak   17902  weight   0.10000E+01  volume   0.21155E+02  ppm1    2.190  ppm2   7.707
ASSI (17952)
   ( ( segid *BrD * and resid 33 and name HB1 ) )
   ( ( segid *BrD * and resid 95 and name HA  ) )
      3.800  3.600    1.700  peak   17952  weight   0.10000E+01  volume   0.26579E+02  ppm1    1.055  ppm2   4.443
ASSI (17962)
   ( ( segid *BrD * and resid 33 and name HB2 ) )
   ( ( segid *BrD * and resid 95 and name HA  ) )
      3.900  3.800    1.600  peak   17962  weight   0.10000E+01  volume   0.22889E+02  ppm1   -0.176  ppm2   4.444
ASSI (17982)
   ( ( segid *BrD * and resid 33 and name HB2 ) )
   ( segid *BrD * and resid 34 and name HD % )
      3.700  3.400    1.800  peak   17982  weight   0.10000E+01  volume   0.30273E+02  ppm1   -0.174  ppm2   7.699
ASSI (18012)
   ( ( segid *BrD * and resid 75 and name HG1 ) )
   ( ( segid *BrD * and resid 71 and name HA  ) )
      3.200  2.600    2.300  peak   18012  weight   0.10000E+01  volume   0.74474E+02  ppm1    3.524  ppm2   4.662
ASSI (18052)
   ( ( segid *BrD * and resid 59 and name HG1 ) )
   ( ( segid *BrD * and resid 59 and name HB2 ) )
      2.600  1.700    1.700  peak   18052  weight   0.10000E+01  volume   0.28930E+03  ppm1    3.227  ppm2   2.482
OR (18052)
   ( ( segid *BrD * and resid 59 and name HG2 ) )
   ( ( segid *BrD * and resid 59 and name HB2 ) )
ASSI (18102)
   ( ( segid *BrD * and resid 75 and name HG2 ) )
   ( segid *BrD * and resid 115 and name HD1%)
      4.400  4.400    1.100  peak   18102  weight   0.10000E+01  volume   0.10857E+02  ppm1    3.226  ppm2   1.327
ASSI (18112)
   ( ( segid *BrD * and resid 59 and name HG2 ) )
   ( segid *BrD * and resid 22 and name HD1%)
      4.100  4.100    1.400  peak   18112  weight   0.10000E+01  volume   0.16621E+02  ppm1    3.226  ppm2   1.661
OR (18112)
   ( ( segid *BrD * and resid 59 and name HG1 ) )
   ( segid *BrD * and resid 22 and name HD1%)
ASSI (18122)
   ( ( segid *BrD * and resid 75 and name HG1 ) )
   ( ( segid *BrD * and resid 115 and name HB1 ) )
      3.500  3.100    2.000  peak   18122  weight   0.10000E+01  volume   0.47142E+02  ppm1    3.522  ppm2   2.165
ASSI (18142)
   ( ( segid *BrD * and resid 75 and name HG1 ) )
   ( segid *BrD * and resid 113 and name HB % )
      3.900  3.800    1.600  peak   18142  weight   0.10000E+01  volume   0.23045E+02  ppm1    3.523  ppm2   1.996
```

TABLE 2-continued

Unambigous NOE-derived Inter-proton Distance Restraints

```
ASSI (18282)
   ( segid *BrD * and resid 35 and name HE % )
   ( ( segid *BrD * and resid 60 and name HB1 ) )
      2.800  2.000   2.000 peak  18282 weight   0.10000E+01 volume   0.18338E+03 ppm1   2.782 ppm2   4.972
ASSI (18302)
   ( segid *BrD * and resid 35 and name HE % )
   ( ( segid *BrD * and resid 59 and name HG2 ) )
      3.400  2.900   2.100 peak  18302 weight   0.10000E+01 volume   0.50813E+02 ppm1   2.782 ppm2   3.248
OR (18302)
   ( segid *BrD * and resid 35 and name HE % )
   ( ( segid *BrD * and resid 59 and name HG1 ) )
ASSI (18312)
   ( segid *BrD * and resid 35 and name HE % )
   ( ( segid *BrD * and resid 34 and name HB2 ) )
      3.000  2.200   2.200 peak  18312 weight   0.10000E+01 volume   0.11214E+03 ppm1   2.782 ppm2   3.101
ASSI (18352)
   ( segid *BrD * and resid 35 and name HE % )
   ( segid *BrD * and resid 56 and name HD1%)
      2.800  2.000   2.000 peak  18352 weight   0.10000E+01 volume   0.15609E+03 ppm1   2.782 ppm2   2.529
ASSI (18362)
   ( segid *BrD * and resid 35 and name HE % )
   ( ( segid *BrD * and resid 57 and name HB1 ) )
      2.400  1.400   1.400 peak  18362 weight   0.10000E+01 volume   0.43055E+03 ppm1   2.782 ppm2   2.938
ASSI (18382)
   ( segid *BrD * and resid 35 and name HE % )
   ( ( segid *BrD * and resid 26 and name HB1 ) )
      2.500  1.600   1.600 peak  18382 weight   0.10000E+01 volume   0.28204E+03 ppm1   2.781 ppm2   2.460
ASSI (18492)
   ( ( segid *BrD * and resid 59 and name HG1 ) )
   ( segid *BrD * and resid 74 and name HE % )
      5.000  5.000   0.500 peak  18492 weight   0.10000E+01 volume   0.50782E+01 ppm1   3.226 ppm2   7.552
OR (18492)
   ( ( segid *BrD * and resid 59 and name HG2 ) )
   ( segid *BrD * and resid 74 and name HE % )
ASSI (18542)
   ( segid *BrD * and resid 75 and name HE % )
   ( ( segid *BrD * and resid 17 and name HB  ) )
      3.000  2.200   2.200 peak  18542 weight   0.10000E+01 volume   0.10304E+03 ppm1   2.634 ppm2   4.826
ASSI (18642)
   ( segid *BrD * and resid 75 and name HE % )
   ( ( segid *BrD * and resid 110 and name HA  ) )
      3.400  2.900   2.100 peak  18642 weight   0.10000E+01 volume   0.51911E+02 ppm1   2.634 ppm2   4.427
ASSI (18662)
   ( segid *BrD * and resid 75 and name HE % )
   ( ( segid *BrD * and resid 74 and name HB1 ) )
      2.900  2.100   2.100 peak  18662 weight   0.10000E+01 volume   0.13576E+03 ppm1   2.634 ppm2   3.595
ASSI (18682)
   ( segid *BrD * and resid 75 and name HE % )
   ( ( segid *BrD * and resid 74 and name HB2 ) )
      3.000  2.200   2.200 peak  18682 weight   0.10000E+01 volume   0.11929E+03 ppm1   2.634 ppm2   3.003
ASSI (18722)
   ( segid *BrD * and resid 75 and name HE % )
   ( ( segid *BrD * and resid 75 and name HB1 ) )
      3.700  3.400   1.800 peak  18722 weight   0.10000E+01 volume   0.33115E+02 ppm1   2.634 ppm2   2.906
ASSI (18732)
   ( segid *BrD * and resid 75 and name HE % )
   ( ( segid *BrD * and resid 75 and name HB2 ) )
      2.100  2.100   2.400 peak  18732 weight   0.10000E+01 volume   0.10446E+04 ppm1   2.634 ppm2   2.824
ASSI (18762)
   ( segid *BrD * and resid 75 and name HE % )
   ( segid *BrD * and resid 78 and name HD2%)
      4.900  4.900   0.600 peak  18762 weight   0.10000E+01 volume   0.60943E+01 ppm1   2.634 ppm2   0.676
ASSI (18772)
   ( segid *BrD * and resid 75 and name HE % )
   ( segid *BrD * and resid 14 and name HD1%)
      2.600  1.700   1.700 peak  18772 weight   0.10000E+01 volume   0.27797E+03 ppm1   2.634 ppm2   1.425
OR (18772)
   ( segid *BrD * and resid 75 and name HE % )
   ( segid *BrD * and resid 14 and name HD2%)
ASSI (18782)
   ( segid *BrD * and resid 75 and name HE % )
   ( segid *BrD * and resid 115 and name HD1%)
      2.800  2.000   2.000 peak  18782 weight   0.10000E+01 volume   0.15408E+03 ppm1   2.634 ppm2   1.327
ASSI (18812)
   ( segid *BrD * and resid 75 and name HE % )
   ( ( segid *BrD * and resid 116 and name HG12) )
      3.600  3.200   1.900 peak  18812 weight   0.10000E+01 volume   0.36651E+02 ppm1   2.635 ppm2   1.547
```

TABLE 2-continued

Unambigous NOE-derived Inter-proton Distance Restraints

```
ASSI (18862)
   ( segid *BrD * and resid 75 and name HE % )
   ( ( segid *BrD * and resid 116 and name HG11) )
      4.600   4.600    0.900  peak   18862  weight   0.10000E+01  volume   0.79723E+01  ppm1   2.635  ppm2   1.914
ASSI (18872)
   ( segid *BrD * and resid 75 and name HE % )
   ( segid *BrD * and resid 59 and name HE % )
      3.500   3.100    2.000  peak   18872  weight   0.10000E+01  volume   0.40230E+02  ppm1   2.635  ppm2   1.865
ASSI (18882)
   ( segid *BrD * and resid 75 and name HE % )
   ( segid *BrD * and resid 113 and name HB % )
      2.700   1.800    1.800  peak   18882  weight   0.10000E+01  volume   0.22578E+03  ppm1   2.634  ppm2   1.986
ASSI (18892)
   ( segid *BrD * and resid 75 and name HE % )
   ( ( segid *BrD * and resid 18 and name HG   ) )
      2.400   1.400    1.400  peak   18892  weight   0.10000E+01  volume   0.37764E+03  ppm1   2.636  ppm2   2.250
ASSI (18902)
   ( segid *BrD * and resid 75 and name HE % )
   ( ( segid *BrD * and resid 115 and name HB1 ) )
      2.500   1.600    1.600  peak   18902  weight   0.10000E+01  volume   0.35880E+03  ppm1   2.635  ppm2   2.199
ASSI (18932)
   ( segid *BrD * and resid 75 and name HE % )
   ( ( segid *BrD * and resid 14 and name HB1 ) )
      3.700   3.400    1.800  peak   18932  weight   0.10000E+01  volume   0.29255E+02  ppm1   2.636  ppm2   2.444
ASSI (18952)
   ( ( segid *BrD * and resid 57 and name HB2 ) )
   ( ( segid *BrD * and resid 37 and name HD1 ) )
      3.200   2.600    2.300  peak   18952  weight   0.10000E+01  volume   0.68763E+02  ppm1   2.847  ppm2   4.289
ASSI (18992)
   ( ( segid *BrD * and resid 57 and name HB2 ) )
   ( ( segid *BrD * and resid 36 and name HA   ) )
      3.700   3.400    1.800  peak   18992  weight   0.10000E+01  volume   0.28694E+02  ppm1   2.842  ppm2   5.444
ASSI (19072)
   ( ( segid *BrD * and resid 31 and name HA   ) )
   ( ( segid *BrD * and resid 34 and name HZ   ) )
      3.100   2.400    2.400  peak   19072  weight   0.10000E+01  volume   0.98899E+02  ppm1   5.001  ppm2   7.893
ASSI (19092)
   ( ( segid *BrD * and resid 31 and name HA   ) )
   ( ( segid *BrD * and resid 30 and name HA   ) )
      2.800   2.000    2.000  peak   19092  weight   0.10000E+01  volume   0.15610E+03  ppm1   5.001  ppm2   5.428
ASSI (19172)
   ( ( segid *BrD * and resid 43 and name HA   ) )
   ( segid *BrD * and resid 88 and name HE % )
      3.300   2.700    2.200  peak   19172  weight   0.10000E+01  volume   0.58224E+02  ppm1   5.547  ppm2   7.417
ASSI (19182)
   ( ( segid *BrD * and resid 43 and name HA   ) )
   ( ( segid *BrD * and resid 44 and name HG1 ) )
      2.900   2.100    2.100  peak   19182  weight   0.10000E+01  volume   0.12258E+03  ppm1   5.544  ppm2   2.735
ASSI (19192)
   ( ( segid *BrD * and resid 43 and name HA   ) )
   ( ( segid *BrD * and resid 44 and name HG2 ) )
      3.100   2.400    2.400  peak   19192  weight   0.10000E+01  volume   0.97301E+02  ppm1   5.544  ppm2   2.646
OR (19192)
   ( ( segid *BrD * and resid 43 and name HA   ) )
   ( ( segid *BrD * and resid 44 and name HB2 ) )
ASSI (19202)
   ( ( segid *BrD * and resid 43 and name HA   ) )
   ( segid *BrD * and resid 38 and name HG2%)
      3.500   3.100    2.000  peak   19202  weight   0.10000E+01  volume   0.42319E+02  ppm1   5.544  ppm2   0.799
ASSI (19212)
   ( segid *BrD * and resid 43 and name HB % )
   ( ( segid *BrD * and resid 42 and name HG1 ) )
      3.600   3.200    1.900  peak   19212  weight   0.10000E+01  volume   0.35927E+02  ppm1   1.697  ppm2   2.898
ASSI (19242)
   ( segid *BrD * and resid 43 and name HB % )
   ( segid *BrD * and resid 50 and name HD1%)
      5.400   5.400    0.100  peak   19242  weight   0.10000E+01  volume   0.31463E+01  ppm1   1.697  ppm2   1.148
ASSI (19272)
   ( segid *BrD * and resid 43 and name HB % )
   ( ( segid *BrD * and resid 39 and name HG1 ) )
      3.300   2.700    2.200  peak   19272  weight   0.10000E+01  volume   0.60793E+02  ppm1   1.697  ppm2   2.032
ASSI (19282)
   ( segid *BrD * and resid 43 and name HB % )
   ( ( segid *BrD * and resid 38 and name HB   ) )
      3.000   2.200    2.200  peak   19282  weight   0.10000E+01  volume   0.12013E+03  ppm1   1.697  ppm2   1.790
```

TABLE 2-continued

Unambigous NOE-derived Inter-proton Distance Restraints

ASSI (19312)
 ( segid *BrD * and resid 31 and name HB % )
 ( segid *BrD * and resid 25 and name HG1%)
  3.200  2.600  2.300  peak  19312  weight  0.10000E+01  volume  0.68019E+02  ppm1  2.289  ppm2  1.832
ASSI (19352)
 ( segid *BrD * and resid 31 and name HB % )
 ( ( segid *BrD * and resid 35 and name HB1 ) )
  3.400  2.900  2.100  peak  19352  weight  0.10000E+01  volume  0.48169E+02  ppm1  2.289  ppm2  2.841
ASSI (19362)
 ( segid *BrD * and resid 31 and name HB % )
 ( ( segid *BrD * and resid 28 and name HB1 ) )
  2.400  1.400  1.400  peak  19362  weight  0.10000E+01  volume  0.37768E+03  ppm1  2.289  ppm2  3.581
ASSI (19372)
 ( segid *BrD * and resid 31 and name HB % )
 ( ( segid *BrD * and resid 35 and name HG1 ) )
  2.500  1.600  1.600  peak  19372  weight  0.10000E+01  volume  0.30400E+03  ppm1  2.289  ppm2  3.427
ASSI (19382)
 ( segid *BrD * and resid 31 and name HB % )
 ( ( segid *BrD * and resid 34 and name HB2 ) )
  4.200  4.200  1.300  peak  19382  weight  0.10000E+01  volume  0.14651E+02  ppm1  2.289  ppm2  3.134
ASSI (19392)
 ( segid *BrD * and resid 31 and name HB % )
 ( ( segid *BrD * and resid 28 and name HA   ) )
  3.100  2.400  2.400  peak  19392  weight  0.10000E+01  volume  0.87183E+02  ppm1  2.289  ppm2  4.582
ASSI (19422)
 ( segid *BrD * and resid 31 and name HB % )
 ( segid *BrD * and resid 34 and name HE % )
  3.500  3.100  2.000  peak  19422  weight  0.10000E+01  volume  0.44223E+02  ppm1  2.289  ppm2  7.803
ASSI (19482)
 ( segid *BrD * and resid 76 and name HB % )
 ( ( segid *BrD * and resid 79 and name HB2 ) )
  3.300  2.700  2.200  peak  19482  weight  0.10000E+01  volume  0.66817E+02  ppm1  2.092  ppm2  2.662
ASSI (19492)
 ( segid *BrD * and resid 76 and name HB % )
 ( ( segid *BrD * and resid 80 and name HB2 ) )
  2.800  2.000  2.000  peak  19492  weight  0.10000E+01  volume  0.15977E+03  ppm1  2.092  ppm2  2.564
OR (19492)
 ( segid *BrD * and resid 76 and name HB % )
 ( ( segid *BrD * and resid 80 and name HB1 ) )
ASSI (19502)
 ( segid *BrD * and resid 76 and name HB % )
 ( ( segid *BrD * and resid 80 and name HB2 ) )
  2.700  1.800  1.800  peak  19502  weight  0.10000E+01  volume  0.21436E+03  ppm1  2.092  ppm2  2.507
ASSI (19522)
 ( segid *BrD * and resid 76 and name HB % )
 ( ( segid *BrD * and resid 77 and name HA   ) )
  2.800  2.000  2.000  peak  19522  weight  0.10000E+01  volume  0.15327E+03  ppm1  2.092  ppm2  4.963
ASSI (19552)
 ( segid *BrD * and resid 76 and name HB % )
 ( ( segid *BrD * and resid 51 and name HB2 ) )
  2.500  1.600  1.600  peak  19552  weight  0.10000E+01  volume  0.32487E+03  ppm1  2.092  ppm2  1.783
OR (19552)
 ( segid *BrD * and resid 76 and name HB % )
 ( ( segid *BrD * and resid 51 and name HG2 ) )
ASSI (19572)
 ( segid *BrD * and resid 76 and name HB % )
 ( segid *BrD * and resid 116 and name HG2%)
  3.600  3.200  1.900  peak  19572  weight  0.10000E+01  volume  0.35020E+03  ppm1  2.092  ppm2  1.432
ASSI (19582)
 ( segid *BrD * and resid 73 and name HD2%)
 ( ( segid *BrD * and resid 68 and name HA   ) )
  2.800  2.000  2.000  peak  19582  weight  0.10000E+01  volume  0.16681E+03  ppm1  1.600  ppm2  5.143
ASSI (19632)
 ( ( segid *BrD * and resid 76 and name HA   ) )
 ( ( segid *BrD * and resid 80 and name HG1 ) )
  3.100  2.400  2.400  peak  19632  weight  0.10000E+01  volume  0.95067E+02  ppm1  4.656  ppm2  2.327
ASSI (19642)
 ( segid *BrD * and resid 99 and name HB % )
 ( ( segid *BrD * and resid 34 and name HZ   ) )
  2.200  2.200  2.300  peak  19642  weight  0.10000E+01  volume  0.65240E+03  ppm1  2.190  ppm2  7.903
ASSI (19652)
 ( segid *BrD * and resid 99 and name HB % )
 ( segid *BrD * and resid 34 and name HE % )
  2.300  1.300  1.300  peak  19652  weight  0.10000E+01  volume  0.50164E+03  ppm1  2.190  ppm2  7.781
ASSI (19672)
 ( segid *BrD * and resid 99 and name HB % )
 ( segid *BrD * and resid 82 and name HD % )
  2.500  1.600  1.600  peak  19672  weight  0.10000E+01  volume  0.36039E+03  ppm1  2.190  ppm2  7.259

TABLE 2-continued

Unambigous NOE-derived Inter-proton Distance Restraints

```
ASSI (19692)
    ( segid *BrD * and resid 99 and name HB % )
    ( ( segid *BrD * and resid 85 and name HA   ) )
      3.100  2.400    2.400  peak   19692  weight   0.10000E+01 volume   0.92786E+02 ppm1    2.190 ppm2    5.005
ASSI (19702)
    ( segid *BrD * and resid 99 and name HB % )
    ( ( segid *BrD * and resid 100 and name HA   ) )
      3.000  2.200    2.200  peak   19702  weight   0.10000E+01 volume   0.10441E+03 ppm1    2.190 ppm2    4.948
ASSI (19752)
    ( segid *BrD * and resid 99 and name HB % )
    ( ( segid *BrD * and resid 103 and name HG1 ) )
      3.000  2.200    2.200  peak   19752  weight   0.10000E+01 volume   0.10256E+03 ppm1    2.190 ppm2    2.613
ASSI (19772)
    ( segid *BrD * and resid 76 and name HB % )
    ( ( segid *BrD * and resid 79 and name HB1 ) )
      3.500  3.100    2.000  peak   19772  weight   0.10000E+01 volume   0.45000E+02 ppm1    2.092 ppm2    2.784
ASSI (19792)
    ( ( segid *BrD * and resid 99 and name HA   ) )
    ( segid *BrD * and resid 34 and name HZ   ) )
      2.600  1.700    1.700  peak   19792  weight   0.10000E+01 volume   0.26558E+03 ppm1    4.459 ppm2    7.901
ASSI (19802)
    ( ( segid *BrD * and resid 99 and name HA   ) )
    ( segid *BrD * and resid 34 and name HE % )
      2.700  1.800    1.800  peak   19802  weight   0.10000E+01 volume   0.21467E+03 ppm1    4.459 ppm2    7.771
ASSI (19812)
    ( ( segid *BrD * and resid 99 and name HA   ) )
    ( segid *BrD * and resid 82 and name HE % )
      3.200  2.600    2.300  peak   19812  weight   0.10000E+01 volume   0.71395E+02 ppm1    4.457 ppm2    7.073
ASSI (19822)
    ( ( segid *BrD * and resid 99 and name HA   ) )
    ( segid *BrD * and resid 82 and name HD % )
      2.800  2.000    2.000  peak   19822  weight   0.10000E+01 volume   0.15492E+03 ppm1    4.459 ppm2    7.259
ASSI (19832)
    ( ( segid *BrD * and resid 99 and name HA   ) )
    ( ( segid *BrD * and resid 100 and name HA   ) )
      2.800  2.000    2.000  peak   19832  weight   0.10000E+01 volume   0.16591E+03 ppm1    4.458 ppm2    4.950
ASSI (19842)
    ( ( segid *BrD * and resid 99 and name HA   ) )
    ( ( segid *BrD * and resid 103 and name HB2 ) )
      2.600  1.700    1.700  peak   19842  weight   0.10000E+01 volume   0.24667E+03 ppm1    4.458 ppm2    1.922
ASSI (19882)
    ( ( segid *BrD * and resid 113 and name HA   ) )
    ( segid *BrD * and resid 110 and name HG2%)
      3.600  3.200    1.900  peak   19882  weight   0.10000E+01 volume   0.35803E+02 ppm1    4.903 ppm2    1.222
ASSI (19902)
    ( ( segid *BrD * and resid 113 and name HA   ) )
    ( ( segid *BrD * and resid 112 and name HB1 ) )
      3.400  2.900    2.100  peak   19902  weight   0.10000E+01 volume   0.48759E+02 ppm1    4.903 ppm2    2.670
ASSI (19912)
    ( ( segid *BrD * and resid 113 and name HA   ) )
    ( ( segid *BrD * and resid 110 and name HA   ) )
      3.500  3.100    2.000  peak   19912  weight   0.10000E+01 volume   0.44605E+02 ppm1    4.903 ppm2    4.419
ASSI (19922)
    ( ( segid *BrD * and resid 113 and name HA   ) )
    ( ( segid *BrD * and resid 14 and name HA   ) )
      3.100  2.400    2.400  peak   19922  weight   0.10000E+01 volume   0.84488E+02 ppm1    4.903 ppm2    4.663
ASSI (19962)
    ( ( segid *BrD * and resid 113 and name HA   ) )
    ( segid *BrD * and resid 115 and name HD1%)
      4.000  4.000    1.500  peak   19962  weight   0.10000E+01 volume   0.18572E+02 ppm1    4.899 ppm2    1.313
ASSI (19992)
    ( segid *BrD * and resid 113 and name HB % )
    ( ( segid *BrD * and resid 14 and name HB1 ) )
      3.300  2.700    2.200  peak   19992  weight   0.10000E+01 volume   0.60405E+02 ppm1    1.991 ppm2    2.442
ASSI (20032)
    ( segid *BrD * and resid 113 and name HB % )
    ( ( segid *BrD * and resid 14 and name HG   ) )
      2.100  2.100    2.400  peak   20032  weight   0.10000E+01 volume   0.86636E+03 ppm1    1.994 ppm2    2.059
ASSI (20042)
    ( segid *BrD * and resid 113 and name HB % )
    ( segid *BrD * and resid 18 and name HD2%)
      4.200  4.200    1.300  peak   20042  weight   0.10000E+01 volume   0.14101E+02 ppm1    1.993 ppm2    0.408
ASSI (20052)
    ( segid *BrD * and resid 113 and name HB % )
    ( segid *BrD * and resid 115 and name HD1%)
      2.400  1.400    1.400  peak   20052  weight   0.10000E+01 volume   0.47259E+03 ppm1    1.993 ppm2    1.319
```

TABLE 2-continued

Unambigous NOE-derived Inter-proton Distance Restraints

```
ASSI (20072)
   ( ( segid *BrD * and resid 110 and name HA   ) )
   (  segid *BrD * and resid 115 and name HD1%)
      2.500  1.800   1.800 peak   20072 weight   0.10000E+01 volume   0.33630E+03 ppm1    4.409 ppm2    1.319
ASSI (20192)
   ( ( segid *BrD * and resid 17 and name HB   ) )
   (  segid *BrD * and resid 115 and name HD1%)
      3.200  2.600   2.300 peak   20192 weight   0.10000E+01 volume   0.76060E+02 ppm1    4.854 ppm2    1.327
ASSI (20212)
   ( ( segid *BrD * and resid 17 and name HA   ) )
   (  segid *BrD * and resid 21 and name HD1%)
      4.600  4.600   0.900 peak   20212 weight   0.10000E+01 volume   0.88717E+01 ppm1    4.542 ppm2    1.224
ASSI (20242)
   (  segid *BrD * and resid 17 and name HG2%)
   (  segid *BrD * and resid 75 and name HE % )
      2.600  1.700   1.700 peak   20242 weight   0.10000E+01 volume   0.27619E+03 ppm1    1.747 ppm2    2.619
ASSI (20252)
   (  segid *BrD * and resid 17 and name HG2%)
   (  segid *BrD * and resid 21 and name HB   ) )
      3.000  2.200   2.200 peak   20252 weight   0.10000E+01 volume   0.10098E+03 ppm1    1.747 ppm2    2.507
ASSI (20272)
   (  segid *BrD * and resid 17 and name HG2%)
   ( ( segid *BrD * and resid 115 and name HB1 ) )
      3.500  3.100   2.000 peak   20272 weight   0.10000E+01 volume   0.46134E+02 ppm1    1.747 ppm2    2.214
ASSI (20292)
   (  segid *BrD * and resid 17 and name HG2%)
   ( ( segid *BrD * and resid 109 and name HB2 ) )
      2.600  1.700   1.700 peak   20292 weight   0.10000E+01 volume   0.25743E+03 ppm1    1.747 ppm2    2.149
ASSI (20302)
   (  segid *BrD * and resid 17 and name HG2%)
   ( ( segid *BrD * and resid 18 and name HB2 ) )
      4.600  4.600   0.900 peak   20302 weight   0.10000E+01 volume   0.84610E+01 ppm1    1.747 ppm2    0.904
ASSI (20312)
   ( ( segid *BrD * and resid 41 and name HB   ) )
   ( ( segid *BrD * and resid 39 and name HD1 ) )
      3.300  2.700   2.200 peak   20312 weight   0.10000E+01 volume   0.67487E+02 ppm1    4.903 ppm2    2.271
ASSI (20332)
   ( ( segid *BrD * and resid 41 and name HB   ) )
   ( ( segid *BrD * and resid 44 and name HD2 ) )
      3.500  3.100   2.000 peak   20332 weight   0.10000E+01 volume   0.42717E+02 ppm1    4.656 ppm2    4.143
ASSI (20382)
   ( ( segid *BrD * and resid 41 and name HA   ) )
   ( ( segid *BrD * and resid 44 and name HD2 ) )
      2.900  2.100   2.100 peak   20382 weight   0.10000E+01 volume   0.13674E+03 ppm1    4.656 ppm2    4.308
ASSI (20532)
   (  segid *BrD * and resid 41 and name HG2%)
   ( ( segid *BrD * and resid 42 and name HA   ) )
      3.400  2.900   2.100 peak   20532 weight   0.10000E+01 volume   0.51387E+02 ppm1    1.845 ppm2    5.062
ASSI (20542)
   (  segid *BrD * and resid 41 and name HG2%)
   ( ( segid *BrD * and resid 39 and name HG1 ) )
      2.600  1.700   1.700 peak   20542 weight   0.10000E+01 volume   0.28354E+03 ppm1    1.844 ppm2    2.019
ASSI (20562)
   (  segid *BrD * and resid 41 and name HG2%)
   ( ( segid *BrD * and resid 39 and name HD1 ) )
      2.900  2.100   2.100 peak   20562 weight   0.10000E+01 volume   0.13596E+03 ppm1    1.844 ppm2    2.296
ASSI (20572)
   (  segid *BrD * and resid 41 and name HG2%)
   ( ( segid *BrD * and resid 39 and name HB1 ) )
      3.200  2.600   2.300 peak   20572 weight   0.10000E+01 volume   0.75085E+02 ppm1    1.845 ppm2    2.466
ASSI (20592)
   ( ( segid *BrD * and resid 112 and name HG1 ) )
   ( ( segid *BrD * and resid 112 and name HA   ) )
      2.400  1.400   1.400 peak   20592 weight   0.10000E+01 volume   0.44748E+03 ppm1    2.832 ppm2    4.585
ASSI (20712)
   ( ( segid *BrD * and resid 67 and name HA   ) )
   ( ( segid *BrD * and resid 68 and name HA   ) )
      2.800  2.000   2.000 peak   20712 weight   0.10000E+01 volume   0.17530E+03 ppm1    4.656 ppm2    5.111
ASSI (20802)
   (  segid *BrD * and resid 25 and name HG2%)
   (  segid *BrD * and resid 82 and name HE % )
      2.900  2.100   2.100 peak   20802 weight   0.10000E+01 volume   0.13726E+03 ppm1    1.648 ppm2    7.026
OR (20802)
   (  segid *BrD * and resid 25 and name HG2%)
   ( ( segid *BrD * and resid 82 and name HZ   ) )
```

TABLE 2-continued

Unambigous NOE-derived Inter-proton Distance Restraints

```
ASSI (20812)
   ( segid *BrD * and resid 58 and name HG2%)
   ( segid *BrD * and resid 68 and name HE % )
      3.200  2.600   2.300 peak   20812 weight   0.10000E+01 volume   0.69885E+02 ppm1   1.651 ppm2   7.920
ASSI (20852)
   ( segid *BrD * and resid 25 and name HG2%)
   (( segid *BrD * and resid 31 and name HA   ))
      3.400  2.900   2.100 peak   20852 weight   0.10000E+01 volume   0.55839E+02 ppm1   1.649 ppm2   4.980
ASSI (20862)
   (( segid *BrD * and resid 62 and name HD1  ))
   (( segid *BrD * and resid 62 and name HB2  ))
      2.900  2.100   2.100 peak   20862 weight   0.10000E+01 volume   0.12367E+03 ppm1   3.175 ppm2   1.710
ASSI (20872)
   (( segid *BrD * and resid 62 and name HD2  ))
   (( segid *BrD * and resid 62 and name HB2  ))
      3.000  2.200   2.200 peak   20872 weight   0.10000E+01 volume   0.11189E+03 ppm1   2.633 ppm2   1.711
ASSI (20992)
   (( segid *BrD * and resid 62 and name HB1  ))
   ( segid *BrD * and resid 68 and name HE % )
      3.100  2.400   2.400 peak   20992 weight   0.10000E+01 volume   0.97455E+02 ppm1   2.638 ppm2   7.905
ASSI (21082)
   ( segid *BrD * and resid 83 and name HG2%)
   (( segid *BrD * and resid 87 and name HG2 ))
      3.000  2.200   2.200 peak   21082 weight   0.10000E+01 volume   0.11102E+03 ppm1   1.895 ppm2   2.784
ASSI (21142)
   (( segid *BrD * and resid 83 and name HB   ))
   (( segid *BrD * and resid 80 and name HG1  ))
      3.400  2.900   2.100 peak   21142 weight   0.10000E+01 volume   0.55703E+02 ppm1   4.803 ppm2   2.360
ASSI (21192)
   ( segid *BrD * and resid 83 and name HG2%)
   (( segid *BrD * and resid 87 and name HG1  ))
      2.100  1.100   1.100 peak   21192 weight   0.10000E+01 volume   0.10489E+04 ppm1   1.895 ppm2   3.028
ASSI (21202)
   ( segid *BrD * and resid 83 and name HG2%)
   (( segid *BrD * and resid 87 and name HB2  ))
      3.400  2.900   2.100 peak   21202 weight   0.10000E+01 volume   0.47828E+02 ppm1   1.899 ppm2   2.597
ASSI (21292)
   ( segid *BrD * and resid 25 and name HG1%)
   ( segid *BrD * and resid 106 and name HD % )
      2.500  2.500   2.000 peak   21292 weight   0.10000E+01 volume   0.35912E+03 ppm1   1.795 ppm2   7.515
ASSI (21322)
   ( segid *BrD * and resid 25 and name HG1%)
   ( segid *BrD * and resid 82 and name HE % )
      3.500  3.100   2.000 peak   21322 weight   0.10000E+01 volume   0.43989E+02 ppm1   1.795 ppm2   7.026
OR (21322)
   ( segid *BrD * and resid 25 and name HG1%)
   (( segid *BrD * and resid 82 and name HZ   ))
ASSI (21392)
   (( segid *BrD * and resid 25 and name HB   ))
   ( segid *BrD * and resid 102 and name HD1%)
      3.600  3.200   1.900 peak   21392 weight   0.10000E+01 volume   0.35593E+02 ppm1   2.979 ppm2   1.327
OR (21392)
   (( segid *BrD * and resid 25 and name HB   ))
   ( segid *BrD * and resid 102 and name HD2%)
ASSI (21402)
   (( segid *BrD * and resid 25 and name HB   ))
   (( segid *BrD * and resid 76 and name HD2%))
      4.400  4.400   1.100 peak   21402 weight   0.10000E+01 volume   0.11302E+02 ppm1   2.979 ppm2   0.676
ASSI (21422)
   ( segid *BrD * and resid 25 and name HG1%)
   (( segid *BrD * and resid 102 and name HG   ))
      3.500  3.100   2.000 peak   21422 weight   0.10000E+01 volume   0.43674E+02 ppm1   1.795 ppm2   2.157
ASSI (21452)
   ( segid *BrD * and resid 25 and name HG1%)
   (( segid *BrD * and resid 106 and name HB1  ))
      4.300  4.300   1.200 peak   21452 weight   0.10000E+01 volume   0.18856E+02 ppm1   1.796 ppm2   3.907
ASSI (21462)
   ( segid *BrD * and resid 25 and name HG1%)
   (( segid *BrD * and resid 21 and name HA    ))
      2.700  1.800   1.800 peak   21462 weight   0.10000E+01 volume   0.21023E+03 ppm1   1.797 ppm2   4.369
ASSI (21472)
   ( segid *BrD * and resid 25 and name HG1%)
   (( segid *BrD * and resid 102 and name HA   ))
      3.400  2.900   2.100 peak   21472 weight   0.10000E+01 volume   0.48930E+02 ppm1   1.796 ppm2   4.297
ASSI (21562)
   ( segid *BrD * and resid 81 and name HG2%)
   (( segid *BrD * and resid 82 and name HA    ))
      2.900  2.100   2.100 peak   21562 weight   0.10000E+01 volume   0.12812E+03 ppm1   0.760 ppm2   4.753
```

TABLE 2-continued

Unambigous NOE-derived Inter-proton Distance Restraints

```
ASSI (21582)
   ( segid *BrD * and resid 38 and name HG1%)
   ( ( segid *BrD * and resid 37 and name HA   ) )
       3.300  2.700   2.200 peak   21582  weight   0.10000E+01 volume  0.64039E+02 ppm1    1.056 ppm2   4.859
ASSI (21672)
   ( segid *BrD * and resid 81 and name HG1%)
   ( segid *BrD * and resid 34 and name HD % )
       3.400  2.900   2.100 peak   21672  weight   0.10000E+01 volume  0.52778E+02 ppm1    1.056 ppm2   7.706
ASSI (21702)
   ( segid *BrD * and resid 38 and name HG2%)
   ( ( segid *BrD * and resid 41 and name HA   ) )
       4.900  4.900   0.600 peak   21702  weight   0.10000E+01 volume  0.56291E+01 ppm1    0.808 ppm2   4.646
ASSI (21732)
   ( segid *BrD * and resid 81 and name HG2%)
   ( segid *BrD * and resid 56 and name HD2%)
       2.600  1.700   1.700 peak   21732  weight   0.10000E+01 volume  0.28103E+03 ppm1    0.760 ppm2   1.238
ASSI (21742)
   ( segid *BrD * and resid 81 and name HG2%)
   ( segid *BrD * and resid 102 and name HD1%)
       3.900  3.800   1.600 peak   21742  weight   0.10000E+01 volume  0.21895E+02 ppm1    0.760 ppm2   1.319
OR (21742)
   ( segid *BrD * and resid 81 and name HG2%)
   ( segid *BrD * and resid 102 and name HD2%)
ASSI (21752)
   ( segid *BrD * and resid 81 and name HG2%)
   ( ( segid *BrD * and resid 84 and name HB2  ) )
       3.000  2.200   2.200 peak   21752  weight   0.10000E+01 volume  0.11571E+03 ppm1    0.763 ppm2   3.296
ASSI (21772)
   ( ( segid *BrD * and resid 81 and name HB   ) )
   ( segid *BrD * and resid 78 and name HD2%)
       3.200  2.600   2.300 peak   21772  weight   0.10000E+01 volume  0.80152E+02 ppm1    2.042 ppm2   0.683
ASSI (21802)
   ( ( segid *BrD * and resid 81 and name HA   ) )
   ( ( segid *BrD * and resid 80 and name HB1  ) )
       3.900  3.800   1.600 peak   21802  weight   0.10000E+01 volume  0.23614E+02 ppm1    3.719 ppm2   2.564
OR (21802)
   ( ( segid *BrD * and resid 81 and name HA   ) )
   ( ( segid *BrD * and resid 80 and name HB2  ) )
ASSI (21812)
   ( ( segid *BrD * and resid 81 and name HA   ) )
   ( ( segid *BrD * and resid 80 and name HB1  ) )
       3.600  3.200   1.900 peak   21812  weight   0.10000E+01 volume  0.37077E+02 ppm1    3.719 ppm2   2.597
ASSI (21902)
   ( ( segid *BrD * and resid 49 and name HA   ) )
   ( segid *BrD * and resid 50 and name HD1%)
       4.100  4.100   1.400 peak   21902  weight   0.10000E+01 volume  0.17504E+02 ppm1    4.656 ppm2   1.140
ASSI (21952)
   ( segid *BrD * and resid 50 and name HD1%)
   ( ( segid *BrD * and resid 88 and name HB1  ) )
       2.400  1.400   1.400 peak   21952  weight   0.10000E+01 volume  0.36864E+03 ppm1    1.155 ppm2   3.535
ASSI (21972)
   ( segid *BrD * and resid 50 and name HD1%)
   ( ( segid *BrD * and resid 46 and name HA   ) )
       4.100  4.100   1.400 peak   21972  weight   0.10000E+01 volume  0.16984E+02 ppm1    1.155 ppm2   4.151
ASSI (22022)
   ( segid *BrD * and resid 50 and name HD1%)
   ( segid *BrD * and resid 88 and name HD % )
       3.100  2.400   2.400 peak   22022  weight   0.10000E+01 volume  0.82494E+02 ppm1    1.155 ppm2   7.606
ASSI (22042)
   ( ( segid *BrD * and resid 50 and name HA   ) )
   ( ( segid *BrD * and resid 51 and name HB1  ) )
       4.800  4.800   0.700 peak   22042  weight   0.10000E+01 volume  0.67010E+01 ppm1    1.797 ppm2   1.966
OR (22042)
   ( ( segid *BrD * and resid 50 and name HA   ) )
   ( ( segid *BrD * and resid 51 and name HG1  ) )
ASSI (22132)
   ( ( segid *BrD * and resid 50 and name HA   ) )
   ( segid *BrD * and resid 49 and name HG2%)
       2.500  1.600   1.600 peak   22132  weight   0.10000E+01 volume  0.30657E+03 ppm1    4.506 ppm2   1.570
ASSI (22142)
   ( ( segid *BrD * and resid 50 and name HA   ) )
   ( segid *BrD * and resid 49 and name HG1%)
       3.800  3.600   1.700 peak   22142  weight   0.10000E+01 volume  0.27941E+02 ppm1    4.506 ppm2   1.646
ASSI (22212)
   ( segid *BrD * and resid 50 and name HG2%)
   ( ( segid *BrD * and resid 51 and name HB1  ) )
       4.000  4.000   1.500 peak   22212  weight   0.10000E+01 volume  0.20287E+02 ppm1    1.007 ppm2   1.954
```

TABLE 2-continued

Unambigous NOE-derived Inter-proton Distance Restraints

```
ASSI (22222)
   ( ( segid *BrD * and resid 84 and name HA    ) )
   ( ( segid *BrD * and resid 83 and name HG2%) )
      4.100  4.100    1.400  peak  22222  weight   0.10000E+01  volume   0.17290E+02  ppm1   4.903  ppm2   1.913
ASSI (22232)
   ( ( segid *BrD * and resid 84 and name HA    ) )
   ( ( segid *BrD * and resid 87 and name HG1  ) )
      3.500  3.100    2.000  peak  22232  weight   0.10000E+01  volume   0.41523E+02  ppm1   4.904  ppm2   3.010
ASSI (22242)
   ( ( segid *BrD * and resid 84 and name HA    ) )
   ( ( segid *BrD * and resid 88 and name HB1  ) )
      3.100  2.400    2.400  peak  22242  weight   0.10000E+01  volume   0.82426E+02  ppm1   4.904  ppm2   3.533
ASSI (22322)
   (   segid *BrD * and resid 69 and name HG1%)
   ( ( segid *BrD * and resid 66 and name HA    ) )
      2.800  2.000    2.000  peak  22322  weight   0.10000E+01  volume   0.17920E+03  ppm1   1.551  ppm2   4.989
ASSI (22332)
   (   segid *BrD * and resid 69 and name HG1%)
   ( ( segid *BrD * and resid 68 and name HA    ) )
      5.000  5.000    0.500  peak  22332  weight   0.10000E+01  volume   0.51283E+01  ppm1   1.551  ppm2   5.141
ASSI (22372)
   (   segid *BrD * and resid 69 and name HG2%)
   (   segid *BrD * and resid 66 and name HB1  ) )
      4.000  4.000    1.900  peak  22372  weight   0.10000E+01  volume   0.19974E+02  ppm1   1.428  ppm2   2.726
ASSI (22382)
   (   segid *BrD * and resid 69 and name HG2%)
   ( ( segid *BrD * and resid 11 and name HB2  ) )
      3.100  2.400    2.400  peak  22382  weight   0.10000E+01  volume   0.94687E+02  ppm1   1.425  ppm2   2.612
ASSI (22452)
   (   segid *BrD * and resid 69 and name HG2%)
   (   segid *BrD * and resid 63 and name HD1%)
      2.400  1.400    1.400  peak  22452  weight   0.10000E+01  volume   0.42940E+03  ppm1   1.425  ppm2   1.659
ASSI (22482)
   (   segid *BrD * and resid 49 and name HG2%)
   ( ( segid *BrD * and resid 50 and name HG12) )
      4.000  4.000    1.500  peak  22482  weight   0.10000E+01  volume   0.18478E+02  ppm1   1.548  ppm2   0.808
ASSI (22492)
   (   segid *BrD * and resid 49 and name HG2%)
   ( ( segid *BrD * and resid 87 and name HA    ) )
      4.900  4.900    0.600  peak  22492  weight   0.10000E+01  volume   0.59811E+01  ppm1   1.549  ppm2   4.854
ASSI (22552)
   (   segid *BrD * and resid 49 and name HG1%)
   ( ( segid *BrD * and resid 50 and name HG12) )
      4.800  4.800    0.700  peak  22552  weight   0.10000E+01  volume   0.66669E+01  ppm1   1.647  ppm2   0.835
ASSI (22592)
   ( ( segid *BrD * and resid 57 and name HG2  ) )
   ( ( segid *BrD * and resid 36 and name HA    ) )
      3.500  3.100    2.000  peak  22592  weight   0.10000E+01  volume   0.41488E+02  ppm1   2.016  ppm2   5.446
ASSI (22612)
   ( ( segid *BrD * and resid 42 and name HA    ) )
   (   segid *BrD * and resid 43 and name HB %  )
      4.300  4.300    1.200  peak  22612  weight   0.10000E+01  volume   0.12059E+02  ppm1   5.050  ppm2   1.710
ASSI (22632)
   ( ( segid *BrD * and resid 42 and name HA    ) )
   ( ( segid *BrD * and resid 44 and name HD1  ) )
      4.200  4.200    1.300  peak  22632  weight   0.10000E+01  volume   0.14713E+02  ppm1   5.051  ppm2   4.337
ASSI (22642)
   ( ( segid *BrD * and resid 42 and name HA    ) )
   ( ( segid *BrD * and resid 43 and name HA    ) )
      4.000  4.000    1.500  peak  22642  weight   0.10000E+01  volume   0.19305E+02  ppm1   5.051  ppm2   5.550
ASSI (22682)
   ( ( segid *BrD * and resid 117 and name HA   ) )
   ( ( segid *BrD * and resid 116 and name HA   ) )
      3.200  2.600    2.300  peak  22682  weight   0.10000E+01  volume   0.76840E+02  ppm1   5.148  ppm2   4.826
ASSI (22722)
   ( ( segid *BrD * and resid 117 and name HA   ) )
   (   segid *BrD * and resid 116 and name HD1%)
      4.300  4.300    1.200  peak  22722  weight   0.10000E+01  volume   0.13070E+02  ppm1   5.149  ppm2   1.409
OR (22722)
   ( ( segid *BrD * and resid 117 and name HA   ) )
   (   segid *BrD * and resid 116 and name HG2%)
ASSI (22732)
   ( ( segid *BrD * and resid 7 and name HB1   ) )
   ( ( segid *BrD * and resid 8 and name HD2   ) )
      2.800  2.000    2.000  peak  22732  weight   0.10000E+01  volume   0.18127E+03  ppm1   2.636  ppm2   4.287
```

TABLE 2-continued

Unambigous NOE-derived Inter-proton Distance Restraints

```
ASSI (22742)
     ( ( segid *BrD * and resid 37 and name HA   ) )
     ( ( segid *BrD * and resid 38 and name HA   ) )
        3.900   3.800    1.600  peak    22742  weight    0.10000E+01  volume    0.21223E+02  ppm1    4.853  ppm2    4.167
ASSI (22752)
     ( ( segid *BrD * and resid 37 and name HA   ) )
     ( ( segid *BrD * and resid 38 and name HB   ) )
        5.500   5.500    0.000  peak    22752  weight    0.10000E+01  volume    0.13492E+00  ppm1    4.853  ppm2    1.759
ASSI (22852)
     ( ( segid *BrD * and resid 59 and name HB2 ) )
     (   segid *BrD * and resid 56 and name HD2%)
        3.300   2.700    2.200  peak    22852  weight    0.10000E+01  volume    0.58772E+02  ppm1    2.486  ppm2    1.246
ASSI (22882)
     ( ( segid *BrD * and resid 8 and name HD2  ) )
     ( ( segid *BrD * and resid 8 and name HA   ) )
        3.300   2.700    2.200  peak    22882  weight    0.10000E+01  volume    0.65959E+02  ppm1    4.261  ppm2    5.021
ASSI (22892)
     ( ( segid *BrD * and resid 8 and name HD1  ) )
     ( ( segid *BrD * and resid 8 and name HA   ) )
        2.800   2.000    2.000  peak    22892  weight    0.10000E+01  volume    0.15205E+03  ppm1    4.407  ppm2    5.019
ASSI (22932)
     ( ( segid *BrD * and resid 37 and name HD1 ) )
     ( ( segid *BrD * and resid 37 and name HA  ) )
        3.000   2.200    2.200  peak    22932  weight    0.10000E+01  volume    0.11242E+03  ppm1    4.261  ppm2    4.859
ASSI (22952)
     ( ( segid *BrD * and resid 44 and name HD2 ) )
     ( ( segid *BrD * and resid 42 and name HA  ) )
        3.600   3.200    1.900  peak    22952  weight    0.10000E+01  volume    0.34019E+02  ppm1    4.114  ppm2    5.046
ASSI (22962)
     ( ( segid *BrD * and resid 91 and name HD2 ) )
     ( ( segid *BrD * and resid 93 and name HB2 ) )
        3.000   2.200    2.200  peak    22962  weight    0.10000E+01  volume    0.11249E+03  ppm1    4.409  ppm2    4.745
ASSI (22992)
     ( ( segid *BrD * and resid 11 and name HD1 ) )
     ( ( segid *BrD * and resid 11 and name HB1 ) )
        2.500   1.600    1.600  peak    22992  weight    0.10000E+01  volume    0.33828E+03  ppm1    4.457  ppm2    2.945
ASSI (23012)
     ( ( segid *BrD * and resid 8 and name HD1  ) )
     ( ( segid *BrD * and resid 8 and name HB1  ) )
        3.300   2.700    2.200  peak    23012  weight    0.10000E+01  volume    0.56548E+02  ppm1    4.409  ppm2    2.849
ASSI (23022)
     ( ( segid *BrD * and resid 44 and name HD1 ) )
     ( ( segid *BrD * and resid 44 and name HG1 ) )
        2.100   1.100    1.100  peak    23022  weight    0.10000E+01  volume    0.84503E+03  ppm1    4.311  ppm2    2.727
ASSI (23062)
     ( ( segid *BrD * and resid 37 and name HD1 ) )
     ( ( segid *BrD * and resid 37 and name HB2 ) )
        3.200   2.600    2.300  peak    23062  weight    0.10000E+01  volume    0.68384E+02  ppm1    4.261  ppm2    2.287
ASSI (23082)
     ( ( segid *BrD * and resid 91 and name HD1 ) )
     ( ( segid *BrD * and resid 61 and name HG1 ) )
        2.600   1.700    1.700  peak    23082  weight    0.10000E+01  volume    0.26320E+03  ppm1    4.557  ppm2    2.784
ASSI (23092)
     ( ( segid *BrD * and resid 44 and name HD2 ) )
     ( ( segid *BrD * and resid 44 and name HG1 ) )
        2.300   1.300    1.300  peak    23092  weight    0.10000E+01  volume    0.51719E+03  ppm1    4.114  ppm2    2.735
ASSI (23102)
     ( ( segid *BrD * and resid 44 and name HD2 ) )
     ( ( segid *BrD * and resid 44 and name HG2 ) )
        2.300   1.300    1.300  peak    23102  weight    0.10000E+01  volume    0.54971E+03  ppm1    4.114  ppm2    2.654
ASSI (23112)
     ( ( segid *BrD * and resid 11 and name HD1 ) )
     ( ( segid *BrD * and resid 11 and name HG1 ) )
        2.600   1.700    1.700  peak    23112  weight    0.10000E+01  volume    0.26059E+03  ppm1    4.454  ppm2    2.648
ASSI (23122)
     ( ( segid *BrD * and resid 44 and name HD2 ) )
     ( ( segid *BrD * and resid 44 and name HB1 ) )
        2.700   1.800    1.800  peak    23122  weight    0.10000E+01  volume    0.21568E+03  ppm1    4.124  ppm2    2.973
ASSI (23202)
     ( ( segid *BrD * and resid 44 and name HG2 ) )
     ( ( segid *BrD * and resid 41 and name HA  ) )
        3.200   2.600    2.300  peak    23202  weight    0.10000E+01  volume    0.75568E+02  ppm1    2.615  ppm2    4.666
ASSI (23242)
     ( ( segid *BrD * and resid 11 and name HG1 ) )
     (   segid *BrD * and resid 69 and name HG1%)
        3.200   2.600    2.300  peak    23242  weight    0.10000E+01  volume    0.73085E+02  ppm1    2.635  ppm2    1.547
```

TABLE 2-continued

Unambigous NOE-derived Inter-proton Distance Restraints

```
ASSI (23272)
   ( ( segid *BrD * and resid 11 and name HG1  ) )
   (  segid *BrD * and resid 14 and name HD2%)
       3.500  3.100   2.000 peak   23272 weight   0.10000E+01 volume   0.45861E+02 ppm1    2.635 ppm2    1.376
OR (23272)
   ( ( segid *BrD * and resid 11 and name HG1  ) )
   (  segid *BrD * and resid 14 and name HD1%)
ASSI (23292)
   ( ( segid *BrD * and resid 91 and name HG1  ) )
   ( ( segid *BrD * and resid 89 and name HA   ) )
       4.600  4.600   0.900 peak   23292 weight   0.10000E+01 volume   0.80378E+01 ppm1    2.784 ppm2    5.646
ASSI (23372)
   ( ( segid *BrD * and resid 9 and name HD1   ) )
   (  segid *BrD * and resid 14 and name HD1%)
       3.700  3.400   1.800 peak   23372 weight   0.10000E+01 volume   0.32255E+02 ppm1    3.768 ppm2    1.425
OR (23372)
   ( ( segid *BrD * and resid 9 and name HD1   ) )
   (  segid *BrD * and resid 14 and name HD2%)
ASSI (23402)
   ( ( segid *BrD * and resid 100 and name HA  ) )
   ( ( segid *BrD * and resid 86 and name HE1  ) )
       3.500  3.100   2.000 peak   23402 weight   0.10000E+01 volume   0.44085E+02 ppm1    4.952 ppm2    3.093
ASSI (23422)
   ( ( segid *BrD * and resid 9 and name HB2   ) )
   ( ( segid *BrD * and resid 8 and name HA    ) )
       3.000  2.200   2.200 peak   23422 weight   0.10000E+01 volume   0.11322E+03 ppm1    2.388 ppm2    5.029
ASSI (23472)
   ( ( segid *BrD * and resid 6 and name HA    ) )
   ( ( segid *BrD * and resid 6 and name HG1   ) )
       1.900  0.900   0.900 peak   23472 weight   0.10000E+01 volume   0.18609E+04 ppm1    4.952 ppm2    2.214
ASSI (23572)
   ( ( segid *BrD * and resid 11 and name HB2  ) )
   ( ( segid *BrD * and resid 10 and name HA   ) )
       3.600  3.200   1.900 peak   23572 weight   0.10000E+01 volume   0.38586E+02 ppm1    2.585 ppm2    5.477
ASSI (23592)
   ( ( segid *BrD * and resid 12 and name HA   ) )
   ( ( segid *BrD * and resid 11 and name HA   ) )
       4.600  4.600   0.900 peak   23592 weight   0.10000E+01 volume   0.79375E+01 ppm1    5.297 ppm2    4.948
ASSI (23602)
   ( ( segid *BrD * and resid 29 and name HG1  ) )
   ( ( segid *BrD * and resid 27 and name HA   ) )
       3.900  3.800   1.600 peak   23602 weight   0.10000E+01 volume   0.21350E+02 ppm1    2.978 ppm2    5.022
ASSI (23632)
   ( ( segid *BrD * and resid 13 and name HB1  ) )
   ( ( segid *BrD * and resid 113 and name HA  ) )
       2.700  1.800   1.800 peak   23632 weight   0.10000E+01 volume   0.21427E+03 ppm1    2.733 ppm2    4.920
ASSI (23642)
   ( ( segid *BrD * and resid 13 and name HG2  ) )
   ( ( segid *BrD * and resid 113 and name HA  ) )
       3.200  2.600   2.300 peak   23642 weight   0.10000E+01 volume   0.71312E+02 ppm1    2.978 ppm2    4.920
ASSI (23652)
   ( ( segid *BrD * and resid 13 and name HB1  ) )
   ( ( segid *BrD * and resid 12 and name HB2  ) )
       2.900  2.100   2.100 peak   23652 weight   0.10000E+01 volume   0.14282E+03 ppm1    2.732 ppm2    3.359
ASSI (23672)
   ( ( segid *BrD * and resid 14 and name HA   ) )
   (  segid *BrD * and resid 18 and name HD2%)
       3.300  2.700   2.200 peak   23672 weight   0.10000E+01 volume   0.64900E+02 ppm1    4.654 ppm2    0.409
ASSI (23712)
   ( ( segid *BrD * and resid 111 and name HA  ) )
   (  segid *BrD * and resid 110 and name HG2%)
       2.400  1.400   1.400 peak   23712 weight   0.10000E+01 volume   0.44849E+03 ppm1    4.656 ppm2    1.246
ASSI (23732)
   ( ( segid *BrD * and resid 14 and name HB2  ) )
   (  segid *BrD * and resid 14 and name HD2%)
       2.200  1.200   1.200 peak   23732 weight   0.10000E+01 volume   0.70287E+03 ppm1    2.142 ppm2    1.402
OR (23732)
   ( ( segid *BrD * and resid 14 and name HB2  ) )
   (  segid *BrD * and resid 14 and name HD1%)
ASSI (23762)
   (  segid *BrD * and resid 14 and name HD2%)
   ( ( segid *BrD * and resid 70 and name HA   ) )
       3.100  2.400   2.400 peak   23762 weight   0.10000E+01 volume   0.94978E+02 ppm1    1.401 ppm2    5.359
ASSI (23802)
   (  segid *BrD * and resid 14 and name HD2%)
   ( ( segid *BrD * and resid 15 and name HB1  ) )
       3.800  3.600   1.700 peak   23802 weight   0.10000E+01 volume   0.26555E+02 ppm1    1.401 ppm2    1.785
```

TABLE 2-continued

Unambigous NOE-derived Inter-proton Distance Restraints

```
ASSI (23842)
   ( segid *BrD * and resid 14 and name HD2%)
   ( segid *BrD * and resid 75 and name HE % )
      2.600  1.700   1.700  peak   23842  weight   0.10000E+01  volume   0.23698E+03  ppm1   1.401  ppm2   2.619
ASSI (23882)
   (( segid *BrD * and resid 18 and name HA   ))
   (( segid *BrD * and resid 17 and name HB   ))
      3.500  3.100   2.000  peak   23882  weight   0.10000E+01  volume   0.41356E+02  ppm1   3.867  ppm2   4.867
ASSI (23922)
   (( segid *BrD * and resid 18 and name HB1  ))
   ( segid *BrD * and resid 63 and name HD2%)
      3.900  3.800   1.600  peak   23922  weight   0.10000E+01  volume   0.21833E+02  ppm1   2.144  ppm2   1.492
ASSI (23972)
   (( segid *BrD * and resid 18 and name HB2  ))
   ( segid *BrD * and resid 74 and name HE % )
      1.200  2.600   2.300  peak   23972  weight   0.10000E+01  volume   0.77951E+02  ppm1   0.911  ppm2   7.523
ASSI (23982)
   (( segid *BrD * and resid 18 and name HB2  ))
   ( segid *BrD * and resid 74 and name HD % )
      3.700  3.400   1.600  peak   23982  weight   0.10000E+01  volume   0.32246E+02  ppm1   0.911  ppm2   7.014
ASSI (24022)
   (( segid *BrD * and resid 18 and name HG   ))
   ( segid *BrD * and resid 115 and name HD1%)
      4.500  4.500   1.000  peak   24022  weight   0.10000E+01  volume   0.94731E+01  ppm1   2.290  ppm2   1.137
ASSI (24032)
   ( segid *BrD * and resid 18 and name HD2%)
   (( segid *BrD * and resid 75 and name HA   ))
      3.400  2.900   2.100  peak   24032  weight   0.10000E+01  volume   0.52852E+02  ppm1   0.415  ppm2   4.541
ASSI (24202)
   ( segid *BrD * and resid 18 and name HD1%)
   (( segid *BrD * and resid 17 and name HB   ))
      3.900  3.800   1.600  peak   24202  weight   0.10000E+01  volume   0.21965E+02  ppm1   1.056  ppm2   4.859
ASSI (24232)
   ( segid *BrD * and resid 18 and name HD1%)
   (( segid *BrD * and resid 15 and name HB1  ))
      2.700  3.400   1.800  peak   24232  weight   0.10000E+01  volume   0.32596E+02  ppm1   1.056  ppm2   3.801
ASSI (24262)
   ( segid *BrD * and resid 18 and name HD1%)
   ( segid *BrD * and resid 78 and name HD2%)
      3.500  3.100   2.000  peak   24262  weight   0.10000E+01  volume   0.41978E+02  ppm1   1.056  ppm2   0.676
ASSI (24272)
   ( segid *BrD * and resid 18 and name HD1%)
   (( segid *BrD * and resid 69 and name HA   ))
      3.400  2.900   2.100  peak   24272  weight   0.10000E+01  volume   0.49516E+02  ppm1   1.057  ppm2   4.692
ASSI (24302)
   (( segid *BrD * and resid 63 and name HA   ))
   (( segid *BrD * and resid 68 and name HB2  ))
      3.300  2.700   2.700  peak   24302  weight   0.10000E+01  volume   0.61304E+02  ppm1   5.294  ppm2   3.557
ASSI (24452)
   (( segid *BrD * and resid 63 and name HG   ))
   (( segid *BrD * and resid 68 and name HB2  ))
      3.400  2.900   2.100  peak   24452  weight   0.10000E+01  volume   0.51423E+02  ppm1   2.437  ppm2   3.516
ASSI (24462)
   (( segid *BrD * and resid 63 and name HG   ))
   (( segid *BrD * and resid 15 and name HA   ))
      2.500  2.500   2.000  peak   24462  weight   0.10000E+01  volume   0.29838E+03  ppm1   2.437  ppm2   4.645
ASSI (24482)
   ( segid *BrD * and resid 63 and name HD1%)
   (( segid *BrD * and resid 18 and name HA   ))
      3.600  3.200   1.900  peak   24482  weight   0.10000E+01  volume   0.38413E+02  ppm1   1.649  ppm2   3.878
ASSI (24512)
   ( segid *BrD * and resid 63 and name HD1%)
   (( segid *BrD * and resid 68 and name HB2  ))
      2.900  2.100   2.100  peak   24512  weight   0.10000E+01  volume   0.12238E+03  ppm1   1.649  ppm2   3.527
ASSI (24542)
   ( segid *BrD * and resid 63 and name HD1%)
   ( segid *BrD * and resid 74 and name HD % )
      3.200  2.600   2.300  peak   24542  weight   0.10000E+01  volume   0.76917E+02  ppm1   1.648  ppm2   7.006
ASSI (24682)
   (( segid *BrD * and resid 19 and name HA   ))
   ( segid *BrD * and resid 22 and name HD2%)
      3.100  2.400   2.400  peak   24682  weight   0.10000E+01  volume   0.84277E+02  ppm1   4.311  ppm2   1.588
ASSI (24702)
   (( segid *BrD * and resid 19 and name HA   ))
   (( segid *BrD * and resid 19 and name HE1  ))
      3.100  2.400   2.400  peak   24702  weight   0.10000E+01  volume   0.84024E+02  ppm1   4.310  ppm2   3.544
```

TABLE 2-continued

Unambigous NOE-derived Inter-proton Distance Restraints

```
ASSI (24782)
    ( ( segid *BrD * and resid 19 and name HG1 ) )
    (  segid *BrD * and resid 15 and name HE % )
       3.300  2.700   2.200  peak   24782  weight   0.10000E+01  volume   0.57959E+02  ppm1   1.895  ppm2   7.487
ASSI (24832)
    ( ( segid *BrD * and resid 19 and name HD1 ) )
    (  segid *BrD * and resid 15 and name HE % )
       2.400  1.400   1.400  peak   24832  weight   0.10000E+01  volume   0.37891E+03  ppm1   2.191  ppm2   7.469
ASSI (24842)
    ( ( segid *BrD * and resid 19 and name HD1 ) )
    (  segid *BrD * and resid 63 and name HD1%)
       2.200  2.200   2.300  peak   24842  weight   0.10000E+01  volume   0.74438E+03  ppm1   2.191  ppm2   1.654
ASSI (24882)
    ( ( segid *BrD * and resid 23 and name HG1 ) )
    ( ( segid *BrD * and resid 19 and name HG1 ) )
       2.600  1.700   1.700  peak   24882  weight   0.10000E+01  volume   0.24553E+03  ppm1   3.124  ppm2   1.888
ASSI (24892)
    ( ( segid *BrD * and resid 23 and name HG2 ) )
    ( ( segid *BrD * and resid 19 and name HG1 ) )
       2.500  1.600   1.600  peak   24892  weight   0.10000E+01  volume   0.29588E+03  ppm1   3.068  ppm2   1.888
ASSI (25012)
    ( ( segid *BrD * and resid 21 and name HB  ) )
    (  segid *BrD * and resid 106 and name HD % )
       2.400  1.400   1.400  peak   25012  weight   0.10000E+01  volume   0.42303E+03  ppm1   2.486  ppm2   7.519
ASSI (25022)
    ( ( segid *BrD * and resid 21 and name HG12) )
    (  segid *BrD * and resid 106 and name HD % )
       4.300  4.300   1.200  peak   25022  weight   0.10000E+01  volume   0.12393E+02  ppm1   1.648  ppm2   7.511
ASSI (25072)
    ( ( segid *BrD * and resid 21 and name HG12) )
    (  segid *BrD * and resid 17 and name HG2%)
       2.800  2.000   2.000  peak   25072  weight   0.10000E+01  volume   0.15768E+03  ppm1   1.648  ppm2   1.746
ASSI (25082)
    ( ( segid *BrD * and resid 21 and name HG11) )
    (  segid *BrD * and resid 17 and name HG2%)
       2.200  1.200   1.200  peak   25082  weight   0.10000E+01  volume   0.65857E+03  ppm1   2.336  ppm2   1.746
ASSI (25092)
    ( ( segid *BrD * and resid 21 and name HG11) )
    (  segid *BrD * and resid 102 and name HD2%)
       3.800  3.600   1.700  peak   25092  weight   0.10000E+01  volume   0.25380E+02  ppm1   2.338  ppm2   1.322
OR (25092)
    ( ( segid *BrD * and resid 21 and name HG11) )
    (  segid *BrD * and resid 102 and name HD1%)
ASSI (25102)
    ( ( segid *BrD * and resid 21 and name HG12) )
    ( ( segid *BrD * and resid 20 and name HB1  ) )
       3.300  2.700   2.200  peak   25102  weight   0.10000E+01  volume   0.61127E+02  ppm1   1.648  ppm2   4.647
ASSI (25132)
    ( ( segid *BrD * and resid 62 and name HG1 ) )
    ( ( segid *BrD * and resid 62 and name HG2 ) )
       2.200  1.200   1.200  peak   25132  weight   0.10000E+01  volume   0.61439E+03  ppm1   2.336  ppm2   1.498
ASSI (25192)
    (  segid *BrD * and resid 21 and name HD1%)
    (  segid *BrD * and resid 102 and name HD2%)
       2.800  2.000   2.000  peak   25192  weight   0.10000E+01  volume   0.17249E+03  ppm1   1.205  ppm2   1.312
ASSI (25202)
    (  segid *BrD * and resid 21 and name HD1%)
    ( ( segid *BrD * and resid 18 and name HB2  ) )
       3.400  2.900   2.100  peak   25202  weight   0.10000E+01  volume   0.54202E+02  ppm1   1.205  ppm2   0.902
ASSI (25272)
    (  segid *BrD * and resid 21 and name HG2%)
    (  segid *BrD * and resid 106 and name HE % )
       2.800  2.000   2.000  peak   25272  weight   0.10000E+01  volume   0.17880E+03  ppm1   1.599  ppm2   7.638
ASSI (25302)
    (  segid *BrD * and resid 21 and name HG2%)
    ( ( segid *BrD * and resid 82 and name HZ   ) )
       3.500  3.100   2.000  peak   25302  weight   0.10000E+01  volume   0.42795E+02  ppm1   1.599  ppm2   6.998
ASSI (25312)
    (  segid *BrD * and resid 101 and name HG2%)
    ( ( segid *BrD * and resid 30 and name HA   ) )
       3.500  3.100   2.000  peak   25312  weight   0.10000E+01  volume   0.43138E+02  ppm1   1.599  ppm2   5.444
ASSI (25322)
    ( ( segid *BrD * and resid 101 and name HA   ) )
    ( ( segid *BrD * and resid 100 and name HA   ) )
       3.400  2.900   2.100  peak   25322  weight   0.10000E+01  volume   0.52950E+02  ppm1   4.261  ppm2   4.948
```

TABLE 2-continued

Unambigous NOE-derived Inter-proton Distance Restraints

```
ASSI (25332)
   ( ( segid *BrD * and resid 101 and name HA    ) )
   ( ( segid *BrD * and resid 100 and name HB1   ) )
      3.100  2.400   2.400  peak   25332  weight  0.10000E+01  volume  0.82741E+02  ppm1   4.261  ppm2   3.475
ASSI (25342)
   ( ( segid *BrD * and resid 101 and name HB    ) )
   ( ( segid *BrD * and resid 30 and name HB2    ) )
      3.200  2.600   2.300  peak   25342  weight  0.10000E+01  volume  0.74692E+02  ppm1   2.536  ppm2   4.525
ASSI (25352)
   ( ( segid *BrD * and resid 101 and name HB    ) )
   ( ( segid *BrD * and resid 30 and name HB1    ) )
      2.900  2.100   2.100  peak   25352  weight  0.10000E+01  volume  0.14018E+03  ppm1   2.536  ppm2   4.932
ASSI (25362)
   ( ( segid *BrD * and resid 101 and name HB    ) )
   (   segid *BrD * and resid 102 and name HD1%)
      3.500  3.100   2.000  peak   25362  weight  0.10000E+01  volume  0.47210E+02  ppm1   2.536  ppm2   1.311
ASSI (25382)
   ( ( segid *BrD * and resid 98 and name HA    ) )
   (   segid *BrD * and resid 102 and name HD1%)
      5.100  5.100   0.400  peak   25382  weight  0.10000E+01  volume  0.44968E+01  ppm1   4.804  ppm2   1.311
ASSI (25402)
   ( ( segid *BrD * and resid 98 and name HA    ) )
   ( ( segid *BrD * and resid 30 and name HA    ) )
      3.300  2.700   2.200  peak   25402  weight  0.10000E+01  volume  0.66772E+02  ppm1   4.804  ppm2   5.444
ASSI (25412)
   ( ( segid *BrD * and resid 98 and name HA    ) )
   (   segid *BrD * and resid 34 and name HE % )
      3.700  3.400   1.800  peak   25412  weight  0.10000E+01  volume  0.30316E+02  ppm1   4.804  ppm2   7.779
ASSI (25422)
   ( ( segid *BrD * and resid 98 and name HB1   ) )
   ( ( segid *BrD * and resid 30 and name HB1   ) )
      2.900  2.100   2.100  peak   25422  weight  0.10000E+01  volume  0.12678E+03  ppm1   4.013  ppm2   4.933
ASSI (25442)
   ( ( segid *BrD * and resid 98 and name HB1   ) )
   ( ( segid *BrD * and resid 30 and name HB2   ) )
      3.300  2.700   2.200  peak   25442  weight  0.10000E+01  volume  0.62906E+02  ppm1   4.015  ppm2   4.533
ASSI (25452)
   ( ( segid *BrD * and resid 85 and name HB2   ) )
   (   segid *BrD * and resid 99 and name HB % )
      2.500  1.600   1.600  peak   25452  weight  0.10000E+01  volume  0.29534E+03  ppm1   3.620  ppm2   2.206
ASSI (25462)
   ( ( segid *BrD * and resid 85 and name HB1   ) )
   (   segid *BrD * and resid 99 and name HB % )
      2.800  2.000   2.000  peak   25462  weight  0.10000E+01  volume  0.15410E+03  ppm1   3.916  ppm2   2.206
ASSI (25502)
   ( ( segid *BrD * and resid 98 and name HB2   ) )
   ( ( segid *BrD * and resid 34 and name HZ    ) )
      2.900  2.100   2.100  peak   25502  weight  0.10000E+01  volume  0.12121E+03  ppm1   3.670  ppm2   7.893
ASSI (25512)
   ( ( segid *BrD * and resid 85 and name HB2   ) )
   (   segid *BrD * and resid 34 and name HE % )
      2.400  1.400   1.400  peak   25512  weight  0.10000E+01  volume  0.45042E+03  ppm1   3.620  ppm2   7.779
ASSI (25522)
   ( ( segid *BrD * and resid 85 and name HB1   ) )
   (   segid *BrD * and resid 34 and name HE % )
      2.500  1.600   1.600  peak   25522  weight  0.10000E+01  volume  0.32323E+03  ppm1   3.917  ppm2   7.778
ASSI (25562)
   (   segid *BrD * and resid 101 and name HD1%)
   ( ( segid *BrD * and resid 30 and name HB2   ) )
      3.500  3.100   2.000  peak   25562  weight  0.10000E+01  volume  0.41073E+02  ppm1   1.551  ppm2   4.532
ASSI (25572)
   (   segid *BrD * and resid 101 and name HD1%)
   ( ( segid *BrD * and resid 30 and name HB1   ) )
      3.000  2.200   2.200  peak   25572  weight  0.10000E+01  volume  0.10658E+03  ppm1   1.549  ppm2   4.932
ASSI (25582)
   (   segid *BrD * and resid 21 and name HG2%)
   (   segid *BrD * and resid 18 and name HD2%)
      3.600  3.200   1.900  peak   25582  weight  0.10000E+01  volume  0.38225E+02  ppm1   1.599  ppm2   0.408
ASSI (25642)
   (   segid *BrD * and resid 21 and name HG2%)
   ( ( segid *BrD * and resid 24 and name HG2   ) )
      3.600  3.200   1.900  peak   25642  weight  0.10000E+01  volume  0.38422E+02  ppm1   1.599  ppm2   3.069
ASSI (25652)
   (   segid *BrD * and resid 21 and name HG2%)
   ( ( segid *BrD * and resid 109 and name HE2  ) )
      4.000  4.000   1.500  peak   25652  weight  0.10000E+01  volume  0.20266E+02  ppm1   1.599  ppm2   3.012
```

TABLE 2-continued

Unambigous NOE-derived Inter-proton Distance Restraints

```
ASSI (25722)
    ( segid *BrD * and resid 21 and name HG2%)
    ( ( segid *BrD * and resid 109 and name HB2 ) )
      2.700  1.800   1.800 peak  25722 weight  0.10000E+01 volume  0.18743E+03 ppm1   1.599 ppm2  2.157
ASSI (25752)
    ( segid *BrD * and resid 101 and name HD1%)
    ( ( segid *BrD * and resid 102 and name HB1 ) )
      3.100  2.400   2.400 peak  25752 weight  0.10000E+01 volume  0.84468E+02 ppm1   1.549 ppm2  1.970
ASSI (25812)
    ( ( segid *BrD * and resid 110 and name HB  ) )
    ( segid *BrD * and resid 116 and name HD1%)
      2.300  1.300   1.300 peak  25812 weight  0.10000E+01 volume  0.58301E+03 ppm1   2.338 ppm2  1.410
ASSI (25822)
    ( ( segid *BrD * and resid 110 and name HG11) )
    ( segid *BrD * and resid 78 and name HD2%)
      4.000  4.000   1.500 peak  25822 weight  0.10000E+01 volume  0.19996E+02 ppm1   1.697 ppm2  0.676
ASSI (25842)
    ( segid *BrD * and resid 110 and name HD1%)
    ( ( segid *BrD * and resid 75 and name HA   ) )
      3.100  2.400   2.400 peak  25842 weight  0.10000E+01 volume  0.86474E+02 ppm1   1.154 ppm2  4.511
ASSI (25852)
    ( segid *BrD * and resid 110 and name HG2%)
    ( ( segid *BrD * and resid 114 and name HA1 ) )
      4.200  4.200   1.300 peak  25852 weight  0.10000E+01 volume  0.14960E+02 ppm1   1.254 ppm2  4.569
ASSI (25952)
    ( segid *BrD * and resid 110 and name HG2%)
    ( segid *BrD * and resid 107 and name HD % )
      3.200  2.600   2.300 peak  25952 weight  0.10000E+01 volume  0.71378E+02 ppm1   1.251 ppm2  7.789
ASSI (26002)
    ( segid *BrD * and resid 110 and name HD1%)
    ( segid *BrD * and resid 106 and name HE % )
      2.500  1.600   1.600 peak  26002 weight  0.10000E+01 volume  0.29658E+03 ppm1   1.155 ppm2  7.638
ASSI (26012)
    ( segid *BrD * and resid 110 and name HD1%)
    ( segid *BrD * and resid 106 and name HD % )
      2.700  1.800   1.800 peak  26012 weight  0.10000E+01 volume  0.22034E+03 ppm1   1.155 ppm2  7.529
ASSI (26082)
    ( segid *BrD * and resid 110 and name HD1%)
    ( ( segid *BrD * and resid 118 and name HB1 ) )
      2.300  1.200   1.300 peak  26082 weight  0.10000E+01 volume  0.91139E+03 ppm1   1.194 ppm2  2.182
ASSI (26092)
    ( segid *BrD * and resid 110 and name HG2%)
    ( ( segid *BrD * and resid 111 and name HB1 ) )
      3.400  2.900   2.100 peak  26092 weight  0.10000E+01 volume  0.52641E+02 ppm1   1.254 ppm2  2.493
ASSI (26122)
    ( segid *BrD * and resid 110 and name HG2%)
    ( ( segid *BrD * and resid 116 and name HG11) )
      3.700  3.400   1.800 peak  26122 weight  0.10000E+01 volume  0.30456E+02 ppm1   1.254 ppm2  1.918
ASSI (26132)
    ( segid *BrD * and resid 110 and name HD1%)
    ( ( segid *BrD * and resid 116 and name HG11) )
      3.300  2.700   2.200 peak  26132 weight  0.10000E+01 volume  0.58180E+02 ppm1   1.154 ppm2  1.918
ASSI (26142)
    ( segid *BrD * and resid 110 and name HD1%)
    ( segid *BrD * and resid 113 and name HB % )
      2.400  1.400   1.400 peak  26142 weight  0.10000E+01 volume  0.40630E+03 ppm1   1.154 ppm2  1.978
ASSI (26212)
    ( segid *BrD * and resid 116 and name HG2%)
    ( ( segid *BrD * and resid 117 and name HA   ) )
      4.200  4.200   1.300 peak  26212 weight  0.10000E+01 volume  0.13762E+02 ppm1   1.401 ppm2  5.168
ASSI (26222)
    ( segid *BrD * and resid 116 and name HG2%)
    ( ( segid *BrD * and resid 79 and name HB2 ) )
      3.200  2.600   2.300 peak  26222 weight  0.10000E+01 volume  0.79045E+02 ppm1   1.401 ppm2  2.662
ASSI (26242)
    ( segid *BrD * and resid 116 and name HG2%)
    ( ( segid *BrD * and resid 115 and name HB1 ) )
      3.800  3.600   1.700 peak  26242 weight  0.10000E+01 volume  0.25845E+02 ppm1   1.401 ppm2  2.175
ASSI (26252)
    ( segid *BrD * and resid 116 and name HG2%)
    ( ( segid *BrD * and resid 116 and name HG11) )
      2.700  1.800   1.800 peak  26252 weight  0.10000E+01 volume  0.22212E+03 ppm1   1.401 ppm2  1.906
ASSI (26262)
    ( segid *BrD * and resid 116 and name HG2%)
    ( segid *BrD * and resid 110 and name HD1%)
      2.400  2.400   2.100 peak  26262 weight  0.10000E+01 volume  0.45578E+03 ppm1   1.401 ppm2  1.140
```

TABLE 2-continued

Unambigous NOE-derived Inter-proton Distance Restraints

```
ASSI (26322)
 ( segid *BrD * and resid 116 and name HD1%)
 ( ( segid *BrD * and resid 107 and name HA   ) )
    3.200  2.600   2.300  peak   26322  weight   0.10000E+01  volume  0.76194E+02  ppm1   1.401  ppm2   4.427
ASSI (26372)
 ( segid *BrD * and resid 116 and name HD1%)
 ( ( segid *BrD * and resid 75 and name HG1  ) )
    3.200  2.600   2.300  peak   26372  weight   0.10000E+01  volume  0.79368E+02  ppm1   1.401  ppm2   3.508
ASSI (26382)
 ( segid *BrD * and resid 116 and name HD1%)
 ( ( segid *BrD * and resid 79 and name HB2  ) )
    3.400  2.900   2.100  peak   26382  weight   0.10000E+01  volume  0.54400E+02  ppm1   1.401  ppm2   2.662
ASSI (26402)
 ( segid *BrD * and resid 116 and name HD1%)
 ( ( segid *BrD * and resid 110 and name HG11) )
    2.600  1.700   1.700  peak   26402  weight   0.10000E+01  volume  0.24061E+03  ppm1   1.401  ppm2   1.718
ASSI (26412)
 ( segid *BrD * and resid 116 and name HD1%)
 ( ( segid *BrD * and resid 110 and name HG12) )
    2.100  1.100   1.100  peak   26412  weight   0.10000E+01  volume  0.93798E+03  ppm1   1.401  ppm2   1.637
ASSI (26432)
 ( segid *BrD * and resid 116 and name HD1%)
 ( ( segid *BrD * and resid 78 and name HB2  ) )
    2.400  2.400   2.100  peak   26432  weight   0.10000E+01  volume  0.39159E+03  ppm1   1.399  ppm2   1.078
ASSI (26472)
 ( segid *BrD * and resid 116 and name HD1%)
 ( segid *BrD * and resid 78 and name HD2%)
    4.900  4.900   0.600  peak   26472  weight   0.10000E+01  volume  0.55118E+01  ppm1   1.399  ppm2   0.680
ASSI (26482)
 ( segid *BrD * and resid 116 and name HD1%)
 ( segid *BrD * and resid 110 and name HG2%)
    2.000  1.000   1.000  peak   26482  weight   0.10000E+01  volume  0.13707E+04  ppm1   1.399  ppm2   1.237
ASSI (26502)
 ( segid *BrD * and resid 63 and name HD2%)
 ( ( segid *BrD * and resid 60 and name HA   ) )
    2.300  1.300   1.300  peak   26502  weight   0.10000E+01  volume  0.60749E+03  ppm1   1.501  ppm2   4.818
ASSI (26522)
 ( ( segid *BrD * and resid 116 and name HB  ) )
 ( ( segid *BrD * and resid 115 and name HB1 ) )
    4.400  4.400   1.100  peak   26522  weight   0.10000E+01  volume  0.11059E+02  ppm1   2.432  ppm2   2.200
ASSI (26532)
 ( ( segid *BrD * and resid 116 and name HB  ) )
 ( segid *BrD * and resid 110 and name HG2%)
    3.600  3.200   1.900  peak   26532  weight   0.10000E+01  volume  0.35446E+02  ppm1   2.409  ppm2   1.263
ASSI (26542)
 ( ( segid *BrD * and resid 116 and name HB  ) )
 ( segid *BrD * and resid 110 and name HD1%)
    3.300  2.700   2.200  peak   26542  weight   0.10000E+01  volume  0.65125E+02  ppm1   2.409  ppm2   1.149
ASSI (26682)
 ( ( segid *BrD * and resid 103 and name HG2 ) )
 ( ( segid *BrD * and resid 104 and name HA  ) )
    3.300  2.700   2.200  peak   26682  weight   0.10000E+01  volume  0.56609E+02  ppm1   2.519  ppm2   4.679
ASSI (26692)
 ( ( segid *BrD * and resid 94 and name HG1  ) )
 ( ( segid *BrD * and resid 93 and name HB1  ) )
    5.400  5.400   0.100  peak   26692  weight   0.10000E+01  volume  0.32972E+01  ppm1   3.127  ppm2   5.038
OR (26692)
 ( ( segid *BrD * and resid 94 and name HG1  ) )
 ( ( segid *BrD * and resid 93 and name HA   ) )
ASSI (26702)
 ( ( segid *BrD * and resid 94 and name HG1  ) )
 ( ( segid *BrD * and resid 95 and name HA   ) )
    3.700  3.400   1.800  peak   26702  weight   0.10000E+01  volume  0.33522E+02  ppm1   3.132  ppm2   4.448
ASSI (26752)
 ( ( segid *BrD * and resid 94 and name HG1  ) )
 ( ( segid *BrD * and resid 97 and name HD1  ) )
    2.600  1.700   1.700  peak   26752  weight   0.10000E+01  volume  0.26306E+03  ppm1   3.127  ppm2   2.401
ASSI (26872)
 ( ( segid *BrD * and resid 86 and name HD1  ) )
 ( ( segid *BrD * and resid 87 and name HG1  ) )
    2.700  1.800   1.800  peak   26872  weight   0.10000E+01  volume  0.22393E+03  ppm1   1.892  ppm2   3.028
ASSI (26902)
 ( ( segid *BrD * and resid 36 and name HG1  ) )
 ( ( segid *BrD * and resid 57 and name HG2  ) )
    3.500  3.100   2.000  peak   26902  weight   0.10000E+01  volume  0.44296E+02  ppm1   2.781  ppm2   2.003
```

TABLE 2-continued

Unambigous NOE-derived Inter-proton Distance Restraints

```
ASSI (26922)
     ( ( segid *BrD * and resid 37 and name HB1 ) )
     ( ( segid *BrD * and resid 54 and name HA   ) )
       4.000  4.000   1.500  peak   26922  weight   0.10000E+01 volume   0.19758E+02 ppm1    2.930 ppm2    5.542
ASSI (26952)
     ( ( segid *BrD * and resid 37 and name HG1 ) )
     ( ( segid *BrD * and resid 36 and name HA   ) )
       5.300  5.300   0.200  peak   26952  weight   0.10000E+01 volume   0.36066E+01 ppm1    2.733 ppm2    5.444
ASSI (26962)
     ( ( segid *BrD * and resid 112 and name HG2 ) )
     ( ( segid *BrD * and resid 111 and name HG2 ) )
       3.400  2.900   2.100  peak   26962  weight   0.10000E+01 volume   0.56268E+02 ppm1    2.815 ppm2    1.898
ASSI (26972)
     ( ( segid *BrD * and resid 61 and name HB2 ) )
     (   segid *BrD * and resid 58 and name HG2%)
       3.000  2.200   2.200  peak   26972  weight   0.10000E+01 volume   0.11517E+03 ppm1    2.684 ppm2    1.644
ASSI (27022)
     ( ( segid *BrD * and resid 89 and name HA   ) )
     ( ( segid *BrD * and resid 93 and name HB2 ) )
       3.700  1.400   1.800  peak   27022  weight   0.10000E+01 volume   0.31951E+02 ppm1    5.642 ppm2    4.745
ASSI (27032)
     ( ( segid *BrD * and resid 89 and name HB1 ) )
     ( ( segid *BrD * and resid 96 and name HB2 ) )
       3.300  2.700   2.200  peak   27032  weight   0.10000E+01 volume   0.59751E+02 ppm1    3.669 ppm2    3.117
ASSI (27082)
     ( ( segid *BrD * and resid 100 and name HB2 ) )
     (   segid *BrD * and resid 101 and name HD1%)
       4.000  4.000   1.500  peak   27082  weight   0.10000E+01 volume   0.18249E+02 ppm1    3.421 ppm2    1.572
OR (27082)
     ( ( segid *BrD * and resid 100 and name HB2 ) )
     (   segid *BrD * and resid 101 and name HG2%)
ASSI (27092)
     ( ( segid *BrD * and resid 100 and name HB2 ) )
     ( ( segid *BrD * and resid 101 and name HA   ) )
       4.000  4.000   1.500  peak   27092  weight   0.10000E+01 volume   0.18330E+02 ppm1    3.423 ppm2    4.265
ASSI (27102)
     ( ( segid *BrD * and resid 100 and name HB2 ) )
     ( ( segid *BrD * and resid 101 and name HG11) )
       2.700  1.800   1.800  peak   27102  weight   0.10000E+01 volume   0.20958E+03 ppm1    3.423 ppm2    2.458
ASSI (27112)
     ( ( segid *BrD * and resid 100 and name HB2 ) )
     (   segid *BrD * and resid 99 and name HB % )
       3.400  2.900   2.100  peak   27112  weight   0.10000E+01 volume   0.49005E+02 ppm1    3.423 ppm2    2.206
ASSI (27142)
     ( ( segid *BrD * and resid 80 and name HD1 ) )
     ( ( segid *BrD * and resid 77 and name HA   ) )
       3.100  2.400   2.400  peak   27142  weight   0.10000E+01 volume   0.85246E+02 ppm1    3.962 ppm2    4.963
ASSI (27172)
     ( ( segid *BrD * and resid 80 and name HD2 ) )
     ( ( segid *BrD * and resid 84 and name HB2 ) )
       4.100  4.100   1.400  peak   27172  weight   0.10000E+01 volume   0.16098E+02 ppm1    3.913 ppm2    3.276
ASSI (27192)
     ( ( segid *BrD * and resid 80 and name HD2 ) )
     ( ( segid *BrD * and resid 83 and name HB   ) )
       3.400  2.900   2.100  peak   27192  weight   0.10000E+01 volume   0.47687E+02 ppm1    3.912 ppm2    4.808
ASSI (27202)
     ( ( segid *BrD * and resid 80 and name HD2 ) )
     ( ( segid *BrD * and resid 52 and name HA   ) )
       3.900  3.800   1.600  peak   27202  weight   0.10000E+01 volume   0.23078E+02 ppm1    3.902 ppm2    8.583
ASSI (27322)
     ( ( segid *BrD * and resid 56 and name HG   ) )
     (   segid *BrD * and resid 81 and name HG1%)
       3.400  2.900   2.100  peak   27322  weight   0.10000E+01 volume   0.49600E+02 ppm1    2.339 ppm2    1.079
ASSI (27342)
     ( ( segid *BrD * and resid 55 and name HB1 ) )
     ( ( segid *BrD * and resid 34 and name HA   ) )
       3.300  2.700   2.200  peak   27342  weight   0.10000E+01 volume   0.66937E+02 ppm1    2.979 ppm2    5.539
ASSI (27362)
     ( ( segid *BrD * and resid 55 and name HB1 ) )
     (   segid *BrD * and resid 81 and name HG1%)
       3.900  3.800   1.600  peak   27362  weight   0.10000E+01 volume   0.24126E+02 ppm1    2.979 ppm2    1.075
ASSI (27372)
     ( ( segid *BrD * and resid 38 and name HA   ) )
     ( ( segid *BrD * and resid 39 and name HA   ) )
       3.500  3.100   2.000  peak   27372  weight   0.10000E+01 volume   0.46123E+02 ppm1    4.163 ppm2    4.972
```

TABLE 2-continued

Unambigous NOE-derived Inter-proton Distance Restraints

```
ASSI (27392)
     ( ( segid *BrD * and resid 55 and name HB1 ) )
     ( ( segid *BrD * and resid 36 and name HA    ) )
        3.400  2.900   2.100 peak   27392 weight  0.10000E+01 volume  0.54954E+02 ppm1    2.979 ppm2    5.442
ASSI (27442)
     (  segid *BrD * and resid 69 and name HG1%)
     (  segid *BrD * and resid 18 and name HD1%)
        2.400  2.400   2.100 peak   27442 weight  0.10000E+01 volume  0.37353E+03 ppm1    1.547 ppm2    1.091
ASSI (27452)
     (  segid *BrD * and resid 22 and name HD2%)
     (  segid *BrD * and resid 25 and name HG1%)
        2.500  1.600   1.600 peak   27452 weight  0.10000E+01 volume  0.30318E+03 ppm1    1.599 ppm2    1.788
ASSI (27472)
     (  segid *BrD * and resid 22 and name HD2%)
     ( ( segid *BrD * and resid 25 and name HB   ) )
        3.400  2.900   2.100 peak   27472 weight  0.10000E+01 volume  0.54052E+02 ppm1    1.599 ppm2    3.003
ASSI (27492)
     (  segid *BrD * and resid 22 and name HD2%)
     ( ( segid *BrD * and resid 60 and name HA   ) )
        2.300  1.300   1.300 peak   27492 weight  0.10000E+01 volume  0.56630E+03 ppm1    1.599 ppm2    4.809
ASSI (27552)
     (  segid *BrD * and resid 22 and name HD2%)
     (  segid *BrD * and resid 74 and name HE % )
        2.300  2.300   2.200 peak   27552 weight  0.10000E+01 volume  0.54070E+03 ppm1    1.599 ppm2    7.529
ASSI (27572)
     (  segid *BrD * and resid 22 and name HD1%)
     ( ( segid *BrD * and resid 60 and name HB1 ) )
        3.200  2.600   2.300 peak   27572 weight  0.10000E+01 volume  0.80681E+02 ppm1    1.645 ppm2    4.990
ASSI (27582)
     (  segid *BrD * and resid 22 and name HD1%)
     (  segid *BrD * and resid 74 and name HE % )
        2.200  1.200   1.200 peak   27582 weight  0.10000E+01 volume  0.62438E+03 ppm1    1.446 ppm2    7.529
ASSI (27632)
     (  segid *BrD * and resid 73 and name HD1%)
     ( ( segid *BrD * and resid 68 and name HA   ) )
        2.500  1.600   1.600 peak   27632 weight  0.10000E+01 volume  0.31070E+03 ppm1    1.549 ppm2    5.143
ASSI (27662)
     (  segid *BrD * and resid 73 and name HD1%)
     ( ( segid *BrD * and resid 70 and name HB2 ) )
        1.100  2.400   2.400 peak   27662 weight  0.10000E+01 volume  0.86052E+02 ppm1    1.549 ppm2    4.362
ASSI (27692)
     (  segid *BrD * and resid 73 and name HD2%)
     (  segid *BrD * and resid 76 and name HB % )
        2.800  2.000   2.000 peak   27692 weight  0.10000E+01 volume  0.17686E+03 ppm1    1.500 ppm2    2.106
ASSI (27722)
     ( ( segid *BrD * and resid 48 and name HA   ) )
     (  segid *BrD * and resid 49 and name HG1%)
        3.000  2.200   2.200 peak   27722 weight  0.10000E+01 volume  0.11137E+03 ppm1    4.803 ppm2    1.652
ASSI (27772)
     ( ( segid *BrD * and resid 73 and name HB2 ) )
     ( ( segid *BrD * and resid 70 and name HB2 ) )
        3.400  2.900   2.100 peak   27772 weight  0.10000E+01 volume  0.55069E+02 ppm1    2.487 ppm2    4.377
ASSI (27822)
     ( ( segid *BrD * and resid 78 and name HA   ) )
     ( ( segid *BrD * and resid 77 and name HB1 ) )
        3.800  3.600   1.700 peak   27822 weight  0.10000E+01 volume  0.26285E+02 ppm1    1.967 ppm2    3.312
ASSI (27842)
     ( ( segid *BrD * and resid 78 and name HB2 ) )
     ( ( segid *BrD * and resid 116 and name HG11) )
        3.700  3.400   1.800 peak   27842 weight  0.10000E+01 volume  0.31985E+02 ppm1    1.056 ppm2    1.954
ASSI (27872)
     ( ( segid *BrD * and resid 78 and name HB2 ) )
     ( ( segid *BrD * and resid 79 and name HA   ) )
        4.100  4.100   1.400 peak   27872 weight  0.10000E+01 volume  0.17221E+02 ppm1    1.056 ppm2    4.411
ASSI (27882)
     ( ( segid *BrD * and resid 78 and name HG   ) )
     ( ( segid *BrD * and resid 75 and name HA   ) )
        5.500  5.500   0.000 peak   27882 weight  0.10000E+01 volume  0.22274E+01 ppm1    1.254 ppm2    4.509
ASSI (27892)
     ( ( segid *BrD * and resid 78 and name HG   ) )
     ( ( segid *BrD * and resid 82 and name HZ   ) )
        2.500  2.500   2.000 peak   27892 weight  0.10000E+01 volume  0.30077E+03 ppm1    1.254 ppm2    7.047
OR (27892)
     ( ( segid *BrD * and resid 78 and name HG   ) )
     (  segid *BrD * and resid 82 and name HE % )
```

TABLE 2-continued

Unambigous NOE-derived Inter-proton Distance Restraints

```
ASSI (27912)
    ( ( segid *BrD * and resid 78 and name HB2  ) )
    (  segid *BrD * and resid 106 and name HD % )
      3.600   3.200     1.900  peak    27912  weight    0.10000E+01  volume   0.34865E+02  ppm1     1.056  ppm2    7.532
ASSI (27942)
    (  segid *BrD * and resid 78 and name HD1%)
    (  segid *BrD * and resid 106 and name HE % )
      2.600   1.700     1.700  peak    27942  weight    0.10000E+01  volume   0.24618E+03  ppm1     0.760  ppm2    7.635
ASSI (27982)
    (  segid *BrD * and resid 78 and name HD2%)
    (  segid *BrD * and resid 106 and name HE % )
      2.200   1.200     1.200  peak    27982  weight    0.10000E+01  volume   0.76393E+03  ppm1     0.662  ppm2    7.526
ASSI (27992)
    (  segid *BrD * and resid 78 and name HD2%)
    ( ( segid *BrD * and resid 82 and name HZ   ) )
      2.100   1.100     1.100  peak    27992  weight    0.10000E+01  volume   0.83417E+03  ppm1     0.662  ppm2    7.031
OR (27992)
    (  segid *BrD * and resid 78 and name HD2%)
    (  segid *BrD * and resid 82 and name HE % )
ASSI (28012)
    (  segid *BrD * and resid 78 and name HD2%)
    (  segid *BrD * and resid 106 and name HE % )
      2.900   2.100     2.100  peak    28012  weight    0.10000E+01  volume   0.14234E+03  ppm1     0.662  ppm2    7.637
ASSI (28032)
    (  segid *BrD * and resid 78 and name HD1%)
    ( ( segid *BrD * and resid 22 and name HA   ) )
      3.500   3.100     2.000  peak    28032  weight    0.10000E+01  volume   0.43609E+02  ppm1     0.761  ppm2    4.727
ASSI (28062)
    (  segid *BrD * and resid 78 and name HD1%)
    ( ( segid *BrD * and resid 75 and name HA   ) )
      3.500   3.100     2.000  peak    28062  weight    0.10000E+01  volume   0.46405E+02  ppm1     0.761  ppm2    4.525
ASSI (28102)
    (  segid *BrD * and resid 78 and name HD1%)
    ( ( segid *BrD * and resid 106 and name HB1  ) )
      4.700   4.700     0.800  peak    28102  weight    0.10000E+01  volume   0.77501E+01  ppm1     0.761  ppm2    2.918
ASSI (28122)
    (  segid *BrD * and resid 78 and name HD2%)
    ( ( segid *BrD * and resid 106 and name HB2  ) )
      2.900   2.100     2.100  peak    28122  weight    0.10000E+01  volume   0.14435E+03  ppm1     0.662  ppm2    2.703
ASSI (28132)
    (  segid *BrD * and resid 78 and name HD2%)
    ( ( segid *BrD * and resid 106 and name HB1  ) )
      2.900   2.100     2.100  peak    28132  weight    0.10000E+01  volume   0.12276E+03  ppm1     0.662  ppm2    3.919
ASSI (28192)
    (  segid *BrD * and resid 78 and name HD1%)
    ( ( segid *BrD * and resid 81 and name HB   ) )
      2.700   1.800     1.800  peak    28192  weight    0.10000E+01  volume   0.18524E+03  ppm1     0.760  ppm2    2.043
ASSI (28202)
    (  segid *BrD * and resid 78 and name HD1%)
    (  segid *BrD * and resid 22 and name HD2%)
      2.500   1.600     1.600  peak    28202  weight    0.10000E+01  volume   0.29008E+03  ppm1     0.761  ppm2    1.590
ASSI (28232)
    (  segid *BrD * and resid 78 and name HD1%)
    (  segid *BrD * and resid 18 and name HD2%)
      3.300   2.700     2.200  peak    28232  weight    0.10000E+01  volume   0.64808E+02  ppm1     0.760  ppm2    0.424
ASSI (28262)
    (  segid *BrD * and resid 56 and name HD2%)
    (  segid *BrD * and resid 74 and name HE % )
      4.100   4.100     1.400  peak    28262  weight    0.10000E+01  volume   0.17777E+02  ppm1     1.254  ppm2    7.534
ASSI (28272)
    (  segid *BrD * and resid 56 and name HD2%)
    (  segid *BrD * and resid 82 and name HE % )
      3.400   2.900     2.100  peak    28272  weight    0.10000E+01  volume   0.54803E+02  ppm1     1.253  ppm2    7.041
OR (28272)
    (  segid *BrD * and resid 56 and name HD2%)
    ( ( segid *BrD * and resid 82 and name HZ   ) )
ASSI (28292)
    (  segid *BrD * and resid 56 and name HD2%)
    ( ( segid *BrD * and resid 55 and name HA   ) )
      3.500   3.100     2.000  peak    28292  weight    0.10000E+01  volume   0.41030E+02  ppm1     1.254  ppm2    5.371
ASSI (28322)
    (  segid *BrD * and resid 56 and name HD2%)
    ( ( segid *BrD * and resid 26 and name HA   ) )
      3.100   2.400     2.400  peak    28322  weight    0.10000E+01  volume   0.83493E+02  ppm1     1.254  ppm2    4.509
ASSI (28342)
    (  segid *BrD * and resid 56 and name HD2%)
    ( ( segid *BrD * and resid 22 and name HA   ) )
      3.000   2.200     2.200  peak    28342  weight    0.10000E+01  volume   0.99805E+02  ppm1     1.251  ppm2    4.733
```

TABLE 2-continued

Unambigous NOE-derived Inter-proton Distance Restraints

```
ASSI (28352)
    ( segid *BrD * and resid 56 and name HD2%)
    ( ( segid *BrD * and resid 78 and name HA   ) )
      3.800  3.600   1.700  peak  28352  weight   0.10000E+01  volume   0.27666E+02  ppm1    1.254  ppm2   3.996
ASSI (28372)
    ( segid *BrD * and resid 56 and name HD2%)
    ( ( segid *BrD * and resid 25 and name HB   ) )
      3.500  3.100   2.000  peak  28372  weight   0.10000E+01  volume   0.41722E+02  ppm1    1.254  ppm2   3.002
ASSI (28402)
    ( ( segid *BrD * and resid 56 and name HB1 ) )
    ( ( segid *BrD * and resid 35 and name HG1 ) )
      3.800  3.600   1.700  peak  28402  weight   0.10000E+01  volume   0.28628E+02  ppm1    2.684  ppm2   3.451
ASSI (28412)
    ( ( segid *BrD * and resid 56 and name HB2 ) )
    ( ( segid *BrD * and resid 35 and name HG1 ) )
      4.000  4.000   1.500  peak  28412  weight   0.10000E+01  volume   0.20241E+02  ppm1    1.993  ppm2   3.443
ASSI (28442)
    ( ( segid *BrD * and resid 102 and name HB1 ) )
    ( segid *BrD * and resid 82 and name HE % )
      2.900  2.100   2.100  peak  28442  weight   0.10000E+01  volume   0.13708E+03  ppm1    1.993  ppm2   7.064
ASSI (28472)
    ( ( segid *BrD * and resid 102 and name HB2 ) )
    ( segid *BrD * and resid 34 and name HE % )
      3.200  2.600   2.300  peak  28472  weight   0.10000E+01  volume   0.70904E+02  ppm1    1.842  ppm2   7.778
ASSI (28502)
    ( ( segid *BrD * and resid 102 and name HB2 ) )
    ( segid *BrD * and resid 81 and name HG2%)
      3.600  3.200   1.900  peak  28502  weight   0.10000E+01  volume   0.34445E+02  ppm1    1.842  ppm2   0.766
ASSI (28532)
    ( ( segid *BrD * and resid 102 and name HG   ) )
    ( segid *BrD * and resid 82 and name HE % )
      2.500  1.400   1.400  peak  28532  weight   0.10000E+01  volume   0.29286E+03  ppm1    2.141  ppm2   7.041
ASSI (28562)
    ( segid *BrD * and resid 102 and name HD2%)
    ( segid *BrD * and resid 82 and name HD % )
      3.600  3.200   1.900  peak  28562  weight   0.10000E+01  volume   0.38923E+02  ppm1    1.303  ppm2   7.245
ASSI (28582)
    ( segid *BrD * and resid 102 and name HD2%)
    ( segid *BrD * and resid 106 and name HD % )
      3.100  2.400   2.400  peak  28582  weight   0.10000E+01  volume   0.86642E+02  ppm1    1.303  ppm2   7.534
ASSI (28622)
    ( segid *BrD * and resid 102 and name HD2%)
    ( ( segid *BrD * and resid 28 and name HD2 ) )
      3.100  2.400   2.400  peak  28622  weight   0.10000E+01  volume   0.83600E+02  ppm1    1.303  ppm2   5.553
ASSI (28632)
    ( segid *BrD * and resid 102 and name HD2%)
    ( ( segid *BrD * and resid 106 and name HA   ) )
      2.800  2.000   2.000  peak  28632  weight   0.10000E+01  volume   0.15974E+03  ppm1    1.303  ppm2   4.525
ASSI (28642)
    ( segid *BrD * and resid 102 and name HD2%)
    ( ( segid *BrD * and resid 21 and name HA   ) )
      3.500  3.100   2.100  peak  28642  weight   0.10000E+01  volume   0.44750E+02  ppm1    1.303  ppm2   4.354
ASSI (28662)
    ( segid *BrD * and resid 102 and name HD1%)
    ( ( segid *BrD * and resid 28 and name HD2 ) )
      3.200  2.600   2.300  peak  28662  weight   0.10000E+01  volume   0.73304E+02  ppm1    1.303  ppm2   5.574
ASSI (28702)
    ( segid *BrD * and resid 102 and name HD2%)
    ( ( segid *BrD * and resid 106 and name HB1 ) )
      3.600  3.200   1.900  peak  28702  weight   0.10000E+01  volume   0.36289E+02  ppm1    1.303  ppm2   3.882
ASSI (28722)
    ( segid *BrD * and resid 102 and name HD2%)
    ( ( segid *BrD * and resid 21 and name HB   ) )
      3.200  2.600   2.300  peak  28722  weight   0.10000E+01  volume   0.68526E+02  ppm1    1.305  ppm2   2.473
ASSI (28752)
    ( segid *BrD * and resid 102 and name HD2%)
    ( segid *BrD * and resid 78 and name HD2%)
      3.400  2.900   2.100  peak  28752  weight   0.10000E+01  volume   0.55554E+02  ppm1    1.303  ppm2   0.676
ASSI (28782)
    ( segid *BrD * and resid 115 and name HD1%)
    ( segid *BrD * and resid 17 and name HG2%)
      2.200  1.200   1.200  peak  28782  weight   0.10000E+01  volume   0.67664E+03  ppm1    1.352  ppm2   1.750
ASSI (28792)
    ( ( segid *BrD * and resid 66 and name HG2 ) )
    ( ( segid *BrD * and resid 65 and name HA   ) )
      3.000  2.200   2.200  peak  28792  weight   0.10000E+01  volume   0.10599E+03  ppm1    2.141  ppm2   5.395
```

TABLE 2-continued

Unambigous NOE-derived Inter-proton Distance Restraints

```
ASSI (28812)
   ( ( segid *BrD * and resid 115 and name HB1  ) )
   ( ( segid *BrD * and resid 110 and name HA    ) )
      2.400  1.400   1.400 peak   28812 weight   0.10000E+01 volume   0.45932E+03 ppm1   2.190 ppm2   4.419
ASSI (28822)
   ( ( segid *BrD * and resid 115 and name HG    ) )
   ( ( segid *BrD * and resid 110 and name HA    ) )
      2.800  2.000   2.000 peak   28822 weight   0.10000E+01 volume   0.18123E+03 ppm1   2.139 ppm2   4.426
ASSI (28842)
   ( ( segid *BrD * and resid 115 and name HG    ) )
   (   segid *BrD * and resid 110 and name HD1%)
      3.400  2.900   2.100 peak   28842 weight   0.10000E+01 volume   0.47604E+02 ppm1   2.139 ppm2   1.140
ASSI (28852)
   ( ( segid *BrD * and resid 115 and name HB1  ) )
   (   segid *BrD * and resid 113 and name HB % )
      3.600  3.200   1.900 peak   28852 weight   0.10000E+01 volume   0.39467E+02 ppm1   2.190 ppm2   1.978
ASSI (28872)
   ( ( segid *BrD * and resid 115 and name HB1  ) )
   ( ( segid *BrD * and resid 110 and name HG12) )
      2.600  2.600   1.900 peak   28872 weight   0.10000E+01 volume   0.26332E+03 ppm1   2.190 ppm2   1.661
ASSI (28882)
   ( ( segid *BrD * and resid 115 and name HB1  ) )
   (   segid *BrD * and resid 116 and name HD1%)
      2.200  1.200   1.200 peak   28882 weight   0.10000E+01 volume   0.69706E+03 ppm1   2.188 ppm2   1.424
OR (28882)
   ( ( segid *BrD * and resid 115 and name HB1  ) )
   (   segid *BrD * and resid 116 and name HG2%)
ASSI (28892)
   ( ( segid *BrD * and resid 115 and name HB1  ) )
   ( ( segid *BrD * and resid 116 and name HG12) )
      4.000  4.000   1.500 peak   28892 weight   0.10000E+01 volume   0.19745E+02 ppm1   2.188 ppm2   1.583
ASSI (28912)
   ( ( segid *BrD * and resid 115 and name HA   ) )
   (   segid *BrD * and resid 110 and name HG2%)
      3.400  2.900   2.100 peak   28912 weight   0.10000E+01 volume   0.51456E+02 ppm1   4.807 ppm2   1.263
ASSI (28932)
   (   segid *BrD * and resid 56 and name HD1%)
   ( ( segid *BrD * and resid 35 and name HG1   ) )
      3.600  3.200   1.900 peak   28932 weight   0.10000E+01 volume   0.33849E+02 ppm1   1.549 ppm2   3.451
ASSI (28942)
   (   segid *BrD * and resid 56 and name HD1%)
   ( ( segid *BrD * and resid 35 and name HA    ) )
      2.800  2.000   2.000 peak   28942 weight   0.10000E+01 volume   0.16319E+03 ppm1   1.548 ppm2   4.900
ASSI (29012)
   (   segid *BrD * and resid 59 and name HE % )
   ( ( segid *BrD * and resid 81 and name HB    ) )
      2.500  2.500   2.000 peak   29012 weight   0.10000E+01 volume   0.32346E+03 ppm1   1.848 ppm2   2.018
ASSI (29042)
   (   segid *BrD * and resid 59 and name HE % )
   ( ( segid *BrD * and resid 54 and name HB2   ) )
      1.800  1.800   2.700 peak   29042 weight   0.10000E+01 volume   0.22344E+04 ppm1   1.848 ppm2   1.944
ASSI (29052)
   (   segid *BrD * and resid 59 and name HE % )
   ( ( segid *BrD * and resid 74 and name HB2   ) )
      3.900  3.800   1.600 peak   29052 weight   0.10000E+01 volume   0.23714E+02 ppm1   1.848 ppm2   3.002
ASSI (29132)
   (   segid *BrD * and resid 59 and name HE % )
   ( ( segid *BrD * and resid 77 and name HA    ) )
      3.600  3.200   1.900 peak   29132 weight   0.10000E+01 volume   0.36305E+02 ppm1   1.847 ppm2   4.966
ASSI (29132)
   (   segid *BrD * and resid 59 and name HE % )
   ( ( segid *BrD * and resid 75 and name HA    ) )
      4.500  4.500   1.000 peak   29142 weight   0.10000E+01 volume   0.98620E+01 ppm1   1.847 ppm2   4.516
ASSI (29172)
   (   segid *BrD * and resid 54 and name HE % )
   ( ( segid *BrD * and resid 58 and name HA    ) )
      3.500  3.100   2.000 peak   29172 weight   0.10000E+01 volume   0.40557E+02 ppm1   2.536 ppm2   4.468
ASSI (29222)
   (   segid *BrD * and resid 54 and name HE % )
   ( ( segid *BrD * and resid 57 and name HB2   ) )
      2.800  2.000   2.000 peak   29222 weight   0.10000E+01 volume   0.17311E+03 ppm1   2.536 ppm2   2.881
ASSI (29232)
   (   segid *BrD * and resid 54 and name HE % )
   ( ( segid *BrD * and resid 59 and name HG2   ) )
      2.900  2.100   2.100 peak   29232 weight   0.10000E+01 volume   0.12717E+03 ppm1   2.535 ppm2   3.199
OR (29232)
   (   segid *BrD * and resid 54 and name HE % )
   ( ( segid *BrD * and resid 59 and name HG1   ) )
```

TABLE 2-continued

Unambigous NOE-derived Inter-proton Distance Restraints

```
ASSI (29292)
   ( ( segid *BrD * and resid 54 and name HB2 ) )
   ( ( segid *BrD * and resid 81 and name HG1%)
      3.200  2.600   2.300 peak   29292 weight   0.10000E+01 volume   0.80321E+02 ppm1   1.947 ppm2   1.083
ASSI (29302)
   ( segid *BrD * and resid 54 and name HE % )
   ( segid *BrD * and resid 59 and name HE % )
      3.000  2.200   2.200 peak   29302 weight   0.10000E+01 volume   0.10558E+03 ppm1   2.535 ppm2   1.863
ASSI (29382)
   ( ( segid *BrD * and resid 33 and name HA   ) )
   ( ( segid *BrD * and resid 32 and name HZ3  ) )
      3.200  2.600   2.300 peak   29382 weight   0.10000E+01 volume   0.67859E+02 ppm1   4.361 ppm2   7.811
ASSI (29472)
   ( ( segid *BrD * and resid 91 and name HG1  ) )
   ( ( segid *BrD * and resid 93 and name HB1  ) )
      3.700  3.400   1.800 peak   29472 weight   0.10000E+01 volume   0.32210E+02 ppm1   2.779 ppm2   5.018
OR (29472)
   ( ( segid *BrD * and resid 91 and name HG1  ) )
   ( ( segid *BrD * and resid 93 and name HA   ) )
ASSI (29602)
   ( ( segid *BrD * and resid 70 and name HA   ) )
   ( ( segid *BrD * and resid 73 and name HB2  ) )
      3.600  3.200   1.900 peak   29602 weight   0.10000E+01 volume   0.37115E+02 ppm1   5.346 ppm2   2.483
ASSI (29622)
   ( ( segid *BrD * and resid 70 and name HB2  ) )
   ( ( segid *BrD * and resid 9 and name HB1   ) )
      3.100  2.400   2.400 peak   29622 weight   0.10000E+01 volume   0.85748E+02 ppm1   4.360 ppm2   2.443
ASSI (29632)
   ( ( segid *BrD * and resid 70 and name HB1  ) )
   ( ( segid *BrD * and resid 9 and name HB1   ) )
      3.600  1.200   1.900 peak   29632 weight   0.10000E+01 volume   0.38576E+02 ppm1   4.755 ppm2   2.442
ASSI (29642)
   ( ( segid *BrD * and resid 93 and name HB2  ) )
   ( ( segid *BrD * and resid 91 and name HD1  ) )
      2.300  1.300   1.300 peak   29642 weight   0.10000E+01 volume   0.51818E+03 ppm1   4.753 ppm2   4.550
ASSI (29652)
   ( ( segid *BrD * and resid 93 and name HB1  ) )
   ( ( segid *BrD * and resid 91 and name HD1  ) )
      2.900  2.100   2.100 peak   29652 weight   0.10000E+01 volume   0.14178E+03 ppm1   5.000 ppm2   4.550
ASSI (29662)
   ( ( segid *BrD * and resid 93 and name HB1  ) )
   ( ( segid *BrD * and resid 94 and name HB1  ) )
      3.100  2.400   2.400 peak   29662 weight   0.10000E+01 volume   0.83013E+02 ppm1   5.000 ppm2   2.731
ASSI (29672)
   ( ( segid *BrD * and resid 93 and name HA   ) )
   ( ( segid *BrD * and resid 91 and name HG1  ) )
      3.100  2.400   2.400 peak   29672 weight   0.10000E+01 volume   0.87723E+02 ppm1   5.003 ppm2   2.798
ASSI (29692)
   ( ( segid *BrD * and resid 108 and name HA  ) )
   ( ( segid *BrD * and resid 111 and name HG2 ) )
      4.300  4.300   1.200 peak   29692 weight   0.10000E+01 volume   0.13311E+02 ppm1   4.804 ppm2   1.905
ASSI (29752)
   ( ( segid *BrD * and resid 30 and name HA   ) )
   ( segid *BrD * and resid 102 and name HD1%)
      4.200  4.200   1.300 peak   29752 weight   0.10000E+01 volume   0.14252E+02 ppm1   5.445 ppm2   1.327
ASSI (29772)
   ( ( segid *BrD * and resid 30 and name HB2  ) )
   ( ( segid *BrD * and resid 28 and name HE1  ) )
      3.300  2.700   2.200 peak   29772 weight   0.10000E+01 volume   0.60630E+02 ppm1   4.808 ppm2   8.090
ASSI (29782)
   ( ( segid *BrD * and resid 30 and name HB2  ) )
   ( segid *BrD * and resid 101 and name HG2%)
      3.200  2.600   2.300 peak   29782 weight   0.10000E+01 volume   0.72004E+02 ppm1   4.507 ppm2   1.604
ASSI (29792)
   ( ( segid *BrD * and resid 27 and name HB1  ) )
   ( ( segid *BrD * and resid 24 and name HB2  ) )
      3.400  2.900   2.100 peak   29792 weight   0.10000E+01 volume   0.52302E+02 ppm1   4.607 ppm2   3.077
OR (29792)
   ( ( segid *BrD * and resid 27 and name HB1  ) )
   ( ( segid *BrD * and resid 24 and name HG2  ) )
ASSI (29832)
   ( ( segid *BrD * and resid 66 and name HD2  ) )
   ( ( segid *BrD * and resid 65 and name HA   ) )
      4.000  4.000   1.500 peak   29832 weight   0.10000E+01 volume   0.19067E+02 ppm1   3.631 ppm2   5.390
ASSI (29842)
   ( ( segid *BrD * and resid 66 and name HD1  ) )
   ( ( segid *BrD * and resid 65 and name HA   ) )
      4.300  4.300   1.200 peak   29842 weight   0.10000E+01 volume   0.12737E+02 ppm1   3.673 ppm2   5.390
```

TABLE 2-continued

Unambigous NOE-derived Inter-proton Distance Restraints

```
ASSI (29852)
  ( ( segid *BrD * and resid 66 and name HD1 ) )
  (  segid *BrD * and resid 15 and name HE % )
     2.800  2.000    2.000 peak   29852 weight   0.10000E+01 volume   0.17551E+03 ppm1    1.673 ppm2    7.488
ASSI (29882)
  ( ( segid *BrD * and resid 66 and name HD2 ) )
  (  segid *BrD * and resid 15 and name HE % )
     2.700  1.800    1.800 peak   29882 weight   0.10000E+01 volume   0.20920E+03 ppm1    3.631 ppm2    7.488
ASSI (29912)
  ( ( segid *BrD * and resid 66 and name HA  ) )
  ( ( segid *BrD * and resid 65 and name HA  ) )
     3.500  3.100    2.000 peak   29912 weight   0.10000E+01 volume   0.40427E+02 ppm1    5.001 ppm2    5.387
ASSI (29922)
  ( ( segid *BrD * and resid 66 and name HB2 ) )
  ( ( segid *BrD * and resid 65 and name HA  ) )
     4.700  4.700    0.800 peak   29922 weight   0.10000E+01 volume   0.75028E+01 ppm1    2.634 ppm2    5.395
ASSI (29982)
  ( ( segid *BrD * and resid 66 and name HB2 ) )
  (  segid *BrD * and resid 69 and name HG1%)
     3.900  3.800    1.600 peak   29982 weight   0.10000E+01 volume   0.23433E+02 ppm1    2.633 ppm2    1.550
ASSI (29992)
  ( ( segid *BrD * and resid 66 and name HB1 ) )
  (  segid *BrD * and resid 69 and name HG1%)
     3.900  3.800    1.600 peak   29992 weight   0.10000E+01 volume   0.22947E+02 ppm1    2.701 ppm2    1.551
ASSI (30022)
  ( ( segid *BrD * and resid 51 and name HA  ) )
  ( ( segid *BrD * and resid 53 and name HD2 ) )
     5.500  5.500    0.000 peak   30022 weight   0.10000E+01 volume   0.72129E−01 ppm1    4.459 ppm2    4.011
ASSI (30062)
  ( ( segid *BrD * and resid 103 and name HB2 ) )
  ( ( segid *BrD * and resid 82 and name HB1 ) )
     3.100  2.400    2.400 peak   30062 weight   0.10000E+01 volume   0.91298E+02 ppm1    1.896 ppm2    3.706
ASSI (30132)
  ( ( segid *BrD * and resid 116 and name HG11) )
  (  segid *BrD * and resid 107 and name HE % )
     2.900  2.100    2.100 peak   30132 weight   0.10000E+01 volume   0.12243E+03 ppm1    1.946 ppm2    7.891
ASSI (30142)
  ( ( segid *BrD * and resid 116 and name HG11) )
  (  segid *BrD * and resid 107 and name HD % )
     3.100  2.400    2.400 peak   30142 weight   0.10000E+01 volume   0.96863E+02 ppm1    1.946 ppm2    7.835
ASSI (30182)
  ( ( segid *BrD * and resid 66 and name HG1 ) )
  (  segid *BrD * and resid 63 and name HD2%)
     3.500  3.100    2.000 peak   30182 weight   0.10000E+01 volume   0.45416E+02 ppm1    2.190 ppm2    1.489
ASSI (30262)
  ( ( segid *BrD * and resid 86 and name HG1 ) )
  (  segid *BrD * and resid 96 and name HD % )
     3.700  3.400    1.800 peak   30262 weight   0.10000E+01 volume   0.30501E+02 ppm1    1.891 ppm2    7.722
ASSI (30322)
  ( ( segid *BrD * and resid 86 and name HG2 ) )
  ( ( segid *BrD * and resid 87 and name HG1 ) )
     3.400  2.900    2.100 peak   30322 weight   0.10000E+01 volume   0.52723E+02 ppm1    0.760 ppm2    3.028
ASSI (30362)
  ( ( segid *BrD * and resid 103 and name HB2 ) )
  (  segid *BrD * and resid 99 and name HB % )
     2.300  1.300    1.300 peak   30362 weight   0.10000E+01 volume   0.49767E+03 ppm1    1.892 ppm2    2.206
ASSI (30422)
  ( ( segid *BrD * and resid 86 and name HE1 ) )
  (  segid *BrD * and resid 99 and name HB % )
     2.500  1.600    1.600 peak   30422 weight   0.10000E+01 volume   0.29716E+03 ppm1    3.078 ppm2    2.206
ASSI (30492)
  ( ( segid *BrD * and resid 109 and name HE2 ) )
  ( ( segid *BrD * and resid 106 and name HA  ) )
     3.000  2.200    2.200 peak   30492 weight   0.10000E+01 volume   0.11843E+03 ppm1    3.029 ppm2    4.591
ASSI (30502)
  ( ( segid *BrD * and resid 109 and name HE1 ) )
  ( ( segid *BrD * and resid 106 and name HA  ) )
     3.800  3.600    1.700 peak   30502 weight   0.10000E+01 volume   0.25593E+02 ppm1    3.177 ppm2    4.590
ASSI (30532)
  ( ( segid *BrD * and resid 109 and name HD1 ) )
  ( ( segid *BrD * and resid 112 and name HG1 ) )
     3.300  2.700    2.200 peak   30532 weight   0.10000E+01 volume   0.67000E+02 ppm1    1.994 ppm2    2.968
ASSI (30682)
  ( ( segid *BrD * and resid 109 and name HA  ) )
  (  segid *BrD * and resid 21 and name HG2%)
     3.600  3.200    1.900 peak   30682 weight   0.10000E+01 volume   0.34166E+02 ppm1    4.656 ppm2    1.588
```

TABLE 2-continued

Unambigous NOE-derived Inter-proton Distance Restraints

```
ASSI (30702)
  ( ( segid *BrD * and resid 109 and name HA    ) )
  ( ( segid *BrD * and resid 112 and name HG1  ) )
    3.800  3.600   1.700 peak     30702 weight   0.10000E+01 volume   0.20614E+02 ppm1    4.653 ppm2   2.964
ASSI (30722)
  ( ( segid *BrD * and resid 109 and name HA    ) )
  ( ( segid *BrD * and resid 112 and name HG2  ) )
    3.200  2.600   2.300 peak     30722 weight   0.10000E+01 volume   0.68767E+02 ppm1    4.653 ppm2   2.823
ASSI (30772)
  ( ( segid *BrD * and resid 104 and name HB1  ) )
  (   segid *BrD * and resid 105 and name HB %  )
    3.200  2.600   2.300 peak     30772 weight   0.10000E+01 volume   0.81070E+02 ppm1    2.536 ppm2   7.819
ASSI (30922)
  ( ( segid *BrD * and resid 19 and name HB1   ) )
  (   segid *BrD * and resid 15 and name HE %   )
    3.200  2.600   2.300 peak     30922 weight   0.10000E+01 volume   0.75523E+02 ppm1    2.289 ppm2   7.486
ASSI (30962)
  ( ( segid *BrD * and resid 59 and name HB2   ) )
  ( ( segid *BrD * and resid 56 and name HA    ) )
    2.300  1.300   1.300 peak     30962 weight   0.10000E+01 volume   0.51425E+03 ppm1    2.486 ppm2   4.646
ASSI (31062)
  ( ( segid *BrD * and resid 22 and name HG    ) )
  (   segid *BrD * and resid 74 and name HE %   )
    2.500  2.500   2.000 peak     31062 weight   0.10000E+01 volume   0.34749E+03 ppm1    2.388 ppm2   7.497
ASSI (31162)
  ( ( segid *BrD * and resid 54 and name HG1  ) )
  ( ( segid *BrD * and resid 77 and name HA    ) )
    1.100  2.400   2.400 peak     11162 weight   0.10000E+01 volume   0.89147E+02 ppm1    3.288 ppm2   4.964
ASSI (    13)
  (   segid *BrD * and resid 46 and name HD %   )
  (   segid *BrD * and resid 88 and name HE %   )
    2.900  2.100   2.100 peak         13 weight  0.11000E+01 volume   0.62066E+02 ppm1    5.758 ppm2   7.421
ASSI (    23)
  (   segid *BrD * and resid 47 and name HD %   )
  (   segid *BrD * and resid 47 and name HE %   )
    3.200  2.600   2.300 peak         23 weight  0.11000E+01 volume   0.31210E+02 ppm1    5.758 ppm2   7.261
ASSI (    43)
  (   segid *BrD * and resid 46 and name HE %   )
  (   segid *BrD * and resid 88 and name HE %   )
    3.800  3.600   1.700 peak         43 weight  0.11000E+01 volume   0.11086E+02 ppm1    6.688 ppm2   7.421
ASSI (    53)
  (   segid *BrD * and resid 46 and name HE %   )
  (   segid *BrD * and resid 47 and name HE %   )
    4.000  4.000   1.500 peak         53 weight  0.11000E+01 volume   0.78634E+01 ppm1    6.688 ppm2   7.261
ASSI (    93)
  (   segid *BrD * and resid 46 and name HD %   )
  ( ( segid *BrD * and resid 46 and name HA    ) )
    2.600  1.700   1.700 peak         93 weight  0.11000E+01 volume   0.11748E+03 ppm1    5.758 ppm2   4.154
ASSI (   103)
  (   segid *BrD * and resid 46 and name HE %   )
  ( ( segid *BrD * and resid 88 and name HB1  ) )
    2.300  1.300   1.300 peak        103 weight  0.11000E+01 volume   0.25301E+01 ppm1    6.688 ppm2   3.527
ASSI (   113)
  (   segid *BrD * and resid 46 and name HE %   )
  ( ( segid *BrD * and resid 46 and name HB1  ) )
    3.300  2.700   2.200 peak        113 weight  0.11000E+01 volume   0.27341E+02 ppm1    6.688 ppm2   3.279
ASSI (   133)
  (   segid *BrD * and resid 46 and name HD %   )
  ( ( segid *BrD * and resid 46 and name HB2  ) )
    2.500  1.600   1.600 peak        133 weight  0.11000E+01 volume   0.14809E+03 ppm1    5.758 ppm2   3.104
ASSI (   153)
  (   segid *BrD * and resid 46 and name HE %   )
  (   segid *BrD * and resid 50 and name HD1%)
    3.000  2.200   2.200 peak        153 weight  0.11000E+01 volume   0.42674E+02 ppm1    4.685 ppm2   1.148
ASSI (   273)
  ( ( segid *BrD * and resid 28 and name HE1  ) )
  ( ( segid *BrD * and resid 28 and name HA    ) )
    3.600  3.200   1.900 peak        273 weight  0.11000E+01 volume   0.14248E+02 ppm1    8.129 ppm2   4.533
ASSI (   333)
  (   segid *BrD * and resid 67 and name HD %   )
  (   segid *BrD * and resid 68 and name HD %   )
    3.000  2.200   2.200 peak        333 weight  0.11000E+01 volume   0.41792E+02 ppm1    6.873 ppm2   7.772
ASSI (   343)
  (   segid *BrD * and resid 67 and name HD %   )
  ( ( segid *BrD * and resid 68 and name HA    ) )
    2.800  2.000   2.000 peak        343 weight  0.11000E+01 volume   0.64783E+02 ppm1    6.874 ppm2   5.146
```

TABLE 2-continued

Unambigous NOE-derived Inter-proton Distance Restraints

```
ASSI (  353)
    ( segid *BrD * and resid 67 and name HD % )
    ( ( segid *BrD * and resid 67 and name HA   ) )
    2.500  1.600   1.600 peak      353 weight   0.11000E+01 volume   0.12803E+03 ppm1   6.872 ppm2   4.678
ASSI (  373)
    ( segid *BrD * and resid 67 and name HD % )
    ( ( segid *BrD * and resid 67 and name HB1 ) )
    2.300  1.300   1.300 peak      373 weight   0.11000E+01 volume   0.22980E+03 ppm1   6.874 ppm2   3.570
ASSI (  383)
    ( segid *BrD * and resid 67 and name HE % )
    ( segid *BrD * and resid 68 and name HD % )
    2.900  2.100   2.100 peak      383 weight   0.11000E+01 volume   0.60490E+02 ppm1   7.293 ppm2   7.780
ASSI (  403)
    ( segid *BrD * and resid 67 and name HE % )
    ( segid *BrD * and resid 68 and name HE % )
    2.400  1.400   1.400 peak      403 weight   0.11000E+01 volume   0.16942E+01 ppm1   7.293 ppm2   7.888
ASSI (  433)
    ( segid *BrD * and resid 67 and name HE % )
    ( ( segid *BrD * and resid 67 and name HA   ) )
    3.000  2.200   2.200 peak      433 weight   0.11000E+01 volume   0.50708E+02 ppm1   7.292 ppm2   4.679
ASSI (  463)
    ( segid *BrD * and resid 47 and name HE % )
    ( segid *BrD * and resid 46 and name HD % )
    2.900  2.100   2.100 peak      463 weight   0.11000E+01 volume   0.56184E+02 ppm1   7.246 ppm2   5.744
ASSI (  493)
    ( segid *BrD * and resid 47 and name HE % )
    ( ( segid *BrD * and resid 47 and name HA   ) )
    3.300  2.700   2.200 peak      493 weight   0.11000E+01 volume   0.27001E+02 ppm1   7.246 ppm2   4.711
ASSI (  503)
    ( segid *BrD * and resid 47 and name HD % )
    ( ( segid *BrD * and resid 47 and name HA   ) )
    2.200  1.200   1.200 peak      503 weight   0.11000E+01 volume   0.29622E+03 ppm1   7.942 ppm2   4.693
ASSI (  543)
    ( ( segid *BrD * and resid 32 and name HD1 ) )
    ( ( segid *BrD * and resid 30 and name HA  ) )
    2.600  1.700   1.700 peak      543 weight   0.11000E+01 volume   0.10449E+03 ppm1   8.455 ppm2   5.452
ASSI (  563)
    ( ( segid *BrD * and resid 32 and name HD1 ) )
    ( ( segid *BrD * and resid 32 and name HB2 ) )
    2.900  2.100   2.100 peak      563 weight   0.11000E+01 volume   0.53265E+02 ppm1   8.456 ppm2   3.942
ASSI (  603)
    ( segid *BrD * and resid 74 and name HD % )
    ( ( segid *BrD * and resid 74 and name HA   ) )
    2.500  1.600   1.600 peak      603 weight   0.11000E+01 volume   0.15470E+03 ppm1   7.013 ppm2   4.373
ASSI (  843)
    ( segid *BrD * and resid 15 and name HD % )
    ( ( segid *BrD * and resid 15 and name HA   ) )
    1.900  0.900   0.900 peak      843 weight   0.11000E+01 volume   0.61725E+03 ppm1   7.664 ppm2   4.621
ASSI (  863)
    ( segid *BrD * and resid 15 and name HD % )
    ( ( segid *BrD * and resid 15 and name HB1 ) )
    2.400  1.400   1.400 peak      863 weight   0.11000E+01 volume   0.19360E+03 ppm1   7.664 ppm2   2.818
ASSI (  873)
    ( segid *BrD * and resid 15 and name HD % )
    ( ( segid *BrD * and resid 15 and name HB2 ) )
    2.000  1.000   1.000 peak      873 weight   0.11000E+01 volume   0.48925E+03 ppm1   7.664 ppm2   3.643
ASSI (  893)
    ( segid *BrD * and resid 15 and name HE % )
    ( ( segid *BrD * and resid 15 and name HA   ) )
    3.500  3.100   2.000 peak      893 weight   0.11000E+01 volume   0.17907E+02 ppm1   7.478 ppm2   4.635
ASSI (  903)
    ( segid *BrD * and resid 15 and name HE % )
    ( ( segid *BrD * and resid 15 and name HB2 ) )
    4.000  4.000   1.500 peak      903 weight   0.11000E+01 volume   0.77515E+01 ppm1   7.478 ppm2   3.643
ASSI (  993)
    ( segid *BrD * and resid 68 and name HE % )
    ( segid *BrD * and resid 74 and name HD % )
    3.100  2.400   2.400 peak      993 weight   0.11000E+01 volume   0.39808E+02 ppm1   7.850 ppm2   6.998
ASSI ( 1003)
    ( segid *BrD * and resid 68 and name HE % )
    ( segid *BrD * and resid 67 and name HD % )
    2.900  2.100   2.100 peak     1003 weight   0.11000E+01 volume   0.57511E+02 ppm1   7.850 ppm2   6.896
ASSI ( 1063)
    ( segid *BrD * and resid 68 and name HE % )
    ( ( segid *BrD * and resid 68 and name HA   ) )
    2.900  2.100   2.100 peak     1063 weight   0.11000E+01 volume   0.51154E+02 ppm1   7.850 ppm2   5.146
```

TABLE 2-continued

Unambigous NOE-derived Inter-proton Distance Restraints

```
ASSI ( 1213)
   ( segid *BrD * and resid 68 and name HD % )
   ( ( segid *BrD * and resid 68 and name HB1 ) )
     2.000  1.000   1.000 peak     1213 weight   0.11000E+01 volume   0.59736E+03 ppm1    7.757 ppm2    3.673
ASSI ( 1263)
   ( segid *BrD * and resid 88 and name HD % )
   ( segid *BrD * and resid 46 and name HE % )
     2.800  2.000   2.000 peak     1263 weight   0.11000E+01 volume   0.62764E+02 ppm1    7.618 ppm2    6.692
ASSI ( 1283)
   ( segid *BrD * and resid 88 and name HD % )
   ( segid *BrD * and resid 46 and name HD % )
     3.100  2.400   2.400 peak     1283 weight   0.11000E+01 volume   0.38726E+02 ppm1    7.616 ppm2    5.745
ASSI ( 1303)
   ( segid *BrD * and resid 88 and name HD % )
   ( ( segid *BrD * and resid 88 and name HA   ) )
     2.200  1.200   1.200 peak     1303 weight   0.11000E+01 volume   0.31179E+03 ppm1    7.616 ppm2    4.999
ASSI ( 1313)
   ( segid *BrD * and resid 88 and name HE % )
   ( ( segid *BrD * and resid 88 and name HA   ) )
     2.800  2.000   2.000 peak     1313 weight   0.11000E+01 volume   0.64049E+02 ppm1    7.410 ppm2    4.999
ASSI ( 1323)
   ( segid *BrD * and resid 88 and name HD % )
   ( ( segid *BrD * and resid 46 and name HA   ) )
     3.100  2.400   2.400 peak     1323 weight   0.11000E+01 volume   0.38562E+02 ppm1    7.618 ppm2    4.154
ASSI ( 1363)
   ( segid *BrD * and resid 88 and name HD % )
   ( ( segid *BrD * and resid 88 and name HB1 ) )
     2.300  1.300   1.300 peak     1363 weight   0.11000E+01 volume   0.21010E+03 ppm1    7.616 ppm2    3.531
ASSI ( 1403)
   ( segid *BrD * and resid 96 and name HD % )
   ( ( segid *BrD * and resid 96 and name HA   ) )
     2.400  1.400   1.400 peak     1403 weight   0.11000E+01 volume   0.18299E+03 ppm1    7.711 ppm2    4.431
ASSI ( 1413)
   ( segid *BrD * and resid 96 and name HD % )
   ( ( segid *BrD * and resid 96 and name HB1 ) )
     2.400  1.400   1.400 peak     1413 weight   0.11000E+01 volume   0.19687E+03 ppm1    7.712 ppm2    3.996
ASSI ( 1503)
   ( segid *BrD * and resid 34 and name HD % )
   ( ( segid *BrD * and resid 31 and name HA   ) )
     2.200  1.200   1.200 peak     1503 weight   0.11000E+01 volume   0.28381E+03 ppm1    7.708 ppm2    4.985
ASSI ( 1583)
   ( segid *BrD * and resid 107 and name HE % )
   ( ( segid *BrD * and resid 107 and name HB1 ) )
     3.200  2.600   2.300 peak     1583 weight   0.11000E+01 volume   0.29123E+02 ppm1    7.896 ppm2    3.674
ASSI ( 1793)
   ( segid *BrD * and resid 95 and name HD % )
   ( ( segid *BrD * and resid 95 and name HB2 ) )
     3.400  2.900   2.100 peak     1793 weight   0.11000E+01 volume   0.22641E+02 ppm1    7.478 ppm2    3.352
ASSI ( 1833)
   ( segid *BrD * and resid 95 and name HD % )
   ( ( segid *BrD * and resid 95 and name HA   ) )
     2.100  1.100   1.100 peak     1833 weight   0.11000E+01 volume   0.35285E+03 ppm1    7.478 ppm2    4.446
ASSI ( 1883)
   ( segid *BrD * and resid 95 and name HE % )
   ( ( segid *BrD * and resid 95 and name HA   ) )
     3.400  2.900   2.100 peak     1883 weight   0.11000E+01 volume   0.23591E+02 ppm1    7.617 ppm2    4.446
ASSI ( 1943)
   ( segid *BrD * and resid 95 and name HE % )
   ( ( segid *BrD * and resid 32 and name HH2 ) )
     1.800  0.800   0.800 peak     1943 weight   0.11000E+01 volume   0.97461E+03 ppm1    7.619 ppm2    7.785
ASSI ( 1963)
   ( segid *BrD * and resid 95 and name HE % )
   ( ( segid *BrD * and resid 32 and name HZ2 ) )
     3.400  2.900   2.100 peak     1963 weight   0.11000E+01 volume   0.21109E+02 ppm1    7.618 ppm2    8.002
ASSI ( 2023)
   ( ( segid *BrD * and resid 32 and name HH2 ) )
   ( ( segid *BrD * and resid 32 and name HZ2 ) )
     2.100  1.100   1.100 peak     2023 weight   0.11000E+01 volume   0.40155E+03 ppm1    7.757 ppm2    8.004
ASSI ( 2133)
   ( ( segid *BrD * and resid 82 and name HA   ) )
   ( segid *BrD * and resid 82 and name HD % )
     2.600  1.700   1.700 peak     2133 weight   0.11000E+01 volume   0.10557E+03 ppm1    7.013 ppm2    7.261
ASSI (  163)
   ( segid *BrD * and resid 46 and name HE % )
   ( segid *BrD * and resid 38 and name HG1%)
     3.000  2.200   2.200 peak      163 weight   0.10000E+01 volume   0.48608E+02 ppm1    6.688 ppm2    1.076
```

TABLE 2-continued

Unambigous NOE-derived Inter-proton Distance Restraints

```
ASSI (  183)
   ( segid *BrD * and resid 46 and name HD % )
   ( ( segid *BrD * and resid 50 and name HB   ) )
      3.100  2.400    2.400 peak       183 weight    0.10000E+01 volume   0.36832E+02 ppm1    5.758 ppm2    1.791
ASSI (  253)
   ( ( segid *BrD * and resid 28 and name HE1  ) )
   ( segid *BrD * and resid 101 and name HG2%)
      2.800  2.000    2.000 peak       253 weight    0.10000E+01 volume   0.66486E+02 ppm1    8.130 ppm2    1.601
ASSI (  263)
   ( ( segid *BrD * and resid 28 and name HE1  ) )
   ( segid *BrD * and resid 101 and name HD1%)
      2.600  1.700    1.700 peak       263 weight    0.10000E+01 volume   0.12057E+03 ppm1    8.129 ppm2    1.528
ASSI (  283)
   ( ( segid *BrD * and resid 28 and name HE1  ) )
   ( ( segid *BrD * and resid 30 and name HB1  ) )
      2.900  2.100    2.100 peak       283 weight    0.10000E+01 volume   0.53269E+02 ppm1    8.129 ppm2    4.927
ASSI (  733)
   ( segid *BrD * and resid 74 and name HE % )
   ( segid *BrD * and resid 63 and name HD1%)
      3.700  3.400    1.800 peak       733 weight    0.10000E+01 volume   0.13584E+02 ppm1    7.524 ppm2    1.704
ASSI (  793)
   ( segid *BrD * and resid 82 and name HE % )
   ( segid *BrD * and resid 106 and name HD % )
      3.500  3.100    2.000 peak       793 weight    0.10000E+01 volume   0.18520E+02 ppm1    7.060 ppm2    7.494
ASSI ( 1113)
   ( segid *BrD * and resid 68 and name HD % )
   ( ( segid *BrD * and resid 62 and name HD2  ) )
      2.600  1.700    1.700 peak      1113 weight    0.10000E+01 volume   0.11215E+03 ppm1    7.758 ppm2    2.595
ASSI ( 1133)
   ( segid *BrD * and resid 68 and name HD % )
   ( ( segid *BrD * and resid 62 and name HB2  ) )
      2.800  2.000    2.000 peak      1133 weight    0.10000E+01 volume   0.66541E+02 ppm1    7.757 ppm2    1.718
ASSI ( 1173)
   ( segid *BrD * and resid 105 and name HD % )
   ( segid *BrD * and resid 102 and name HD2%)
      2.800  2.000    2.000 peak      1173 weight    0.10000E+01 volume   0.71257E+02 ppm1    7.758 ppm2    1.338
OR ( 1173)
   ( segid *BrD * and resid 105 and name HD % )
   ( segid *BrD * and resid 102 and name HD1%)
ASSI ( 1353)
   ( segid *BrD * and resid 88 and name HE % )
   ( ( segid *BrD * and resid 88 and name HB1  ) )
      3.400  2.900    2.100 peak      1353 weight    0.10000E+01 volume   0.21121E+02 ppm1    7.413 ppm2    3.527
ASSI ( 1423)
   ( segid *BrD * and resid 96 and name HD % )
   ( ( segid *BrD * and resid 100 and name HB1  ) )
      3.100  2.400    2.400 peak      1423 weight    0.10000E+01 volume   0.40018E+02 ppm1    7.711 ppm2    3.454
OR ( 1423)
   ( segid *BrD * and resid 96 and name HD % )
   ( ( segid *BrD * and resid 100 and name HB2  ) )
ASSI ( 1613)
   ( segid *BrD * and resid 107 and name HD % )
   ( ( segid *BrD * and resid 106 and name HB1  ) )
      3.600  3.200    1.900 peak      1613 weight    0.10000E+01 volume   0.14818E+02 ppm1    7.803 ppm2    3.953
ASSI ( 1663)
   ( segid *BrD * and resid 107 and name HD % )
   ( ( segid *BrD * and resid 103 and name HA   ) )
      3.100  2.400    2.400 peak      1663 weight    0.10000E+01 volume   0.38863E+02 ppm1    7.803 ppm2    3.804
ASSI ( 1753)
   ( segid *BrD * and resid 106 and name HE % )
   ( segid *BrD * and resid 75 and name HA   )
      3.700  3.400    1.800 peak      1753 weight    0.10000E+01 volume   0.13649E+02 ppm1    7.617 ppm2    4.534
ASSI ( 1803)
   ( segid *BrD * and resid 95 and name HD % )
   ( ( segid *BrD * and resid 65 and name HA   ) )
      3.300  2.700    2.200 peak      1803 weight    0.10000E+01 volume   0.27238E+02 ppm1    7.478 ppm2    4.985
ASSI ( 1853)
   ( segid *BrD * and resid 95 and name HD % )
   ( ( segid *BrD * and resid 85 and name HB1  ) )
      3.300  2.700    2.200 peak      1853 weight    0.10000E+01 volume   0.27537E+02 ppm1    7.479 ppm2    3.920
ASSI ( 1863)
   ( segid *BrD * and resid 95 and name HD % )
   ( ( segid *BrD * and resid 33 and name HB1  ) )
      3.200  2.600    2.300 peak      1863 weight    0.10000E+01 volume   0.30330E+02 ppm1    7.478 ppm2    1.047
ASSI ( 1903)
   ( segid *BrD * and resid 95 and name HE % )
   ( ( segid *BrD * and resid 33 and name HA   ) )
      3.500  3.100    2.000 peak      1903 weight    0.10000E+01 volume   0.17985E+02 ppm1    7.618 ppm2    4.343
```

TABLE 2-continued

Unambigous NOE-derived Inter-proton Distance Restraints

```
ASSI ( 2003)
    ( ( segid *BrD * and resid 32 and name HH2 ) )
    (  segid *BrD * and resid 95 and name HD % )
      4.300  4.300   1.200 peak      2003 weight   0.10000E+01 volume  0.52192E+01 ppm1   7.757 ppm2   7.509
ASSI ( 2143)
    ( ( segid *BrD * and resid 82 and name HZ   ) )
    (  segid *BrD * and resid 106 and name HD % )
      3.800  3.600   1.700 peak      2143 weight   0.10000E+01 volume  0.11127E+02 ppm1   7.013 ppm2   7.509
ASSI ( 2183)
    (  segid *BrD * and resid 107 and name HE % )
    ( ( segid *BrD * and resid 79 and name HG1 ) )
      3.500  3.100   2.000 peak      2183 weight   0.10000E+01 volume  0.19805E+02 ppm1   7.897 ppm2   3.060
ASSI (   54)
    (  segid *BrD * and resid 47 and name HD % )
    ( ( segid *BrD * and resid 47 and name HB1 ) )
      2.200  1.200   1.200 peak        54 weight   0.10000E+01 volume  0.95356E+03 ppm1   7.970 ppm2   3.806
ASSI (   64)
    (  segid *BrD * and resid 47 and name HD % )
    ( ( segid *BrD * and resid 47 and name HB2 ) )
      2.300  1.300   1.300 peak        64 weight   0.10000E+01 volume  0.78871E+03 ppm1   7.970 ppm2   3.415
ASSI (  144)
    (  segid *BrD * and resid 67 and name HD % )
    (  segid *BrD * and resid 67 and name HE % )
      2.000  1.000   1.000 peak       144 weight   0.10000E+01 volume  0.18744E+04 ppm1   6.900 ppm2   7.321
ASSI (  214)
    (  segid *BrD * and resid 47 and name HD % )
    ( ( segid *BrD * and resid 47 and name HB2 ) )
      2.200  1.200   1.200 peak       214 weight   0.10000E+01 volume  0.10973E+04 ppm1   6.899 ppm2   2.664
ASSI (  274)
    (  segid *BrD * and resid 68 and name HD % )
    ( ( segid *BrD * and resid 68 and name HA  ) )
      2.400  1.400   1.400 peak       274 weight   0.10000E+01 volume  0.56412E+03 ppm1   7.778 ppm2   5.140
ASSI (  294)
    (  segid *BrD * and resid 68 and name HD % )
    ( ( segid *BrD * and resid 68 and name HB2 ) )
      2.300  1.300   1.300 peak       294 weight   0.10000E+01 volume  0.81340E+03 ppm1   7.778 ppm2   3.546
ASSI (  354)
    (  segid *BrD * and resid 88 and name HD % )
    (  segid *BrD * and resid 88 and name HE % )
      2.000  1.000   1.000 peak       354 weight   0.10000E+01 volume  0.17752E+04 ppm1   7.612 ppm2   7.418
ASSI (  454)
    ( ( segid *BrD * and resid 32 and name HD1 ) )
    ( ( segid *BrD * and resid 32 and name HA  ) )
      3.000  2.200   2.200 peak       454 weight   0.10000E+01 volume  0.17821E+03 ppm1   8.491 ppm2   4.977
ASSI (  474)
    ( ( segid *BrD * and resid 32 and name HD1 ) )
    ( ( segid *BrD * and resid 32 and name HB1 ) )
      3.100  2.400   2.400 peak       474 weight   0.10000E+01 volume  0.14234E+03 ppm1   8.490 ppm2   4.213
ASSI ( 1694)
    (  segid *BrD * and resid 34 and name HE % )
    ( ( segid *BrD * and resid 34 and name HB1 ) )
      3.300  2.700   2.200 peak      1694 weight   0.10000E+01 volume  0.91431E+02 ppm1   7.781 ppm2   4.116
ASSI ( 1834)
    (  segid *BrD * and resid 96 and name HD % )
    (  segid *BrD * and resid 96 and name HE % )
      1.900  0.900   0.900 peak      1834 weight   0.10000E+01 volume  0.29744E+04 ppm1   7.724 ppm2   7.614
ASSI ( 1914)
    (  segid *BrD * and resid 96 and name HD % )
    ( ( segid *BrD * and resid 96 and name HB2 ) )
      2.200  1.200   1.200 peak      1914 weight   0.10000E+01 volume  0.99570E+03 ppm1   7.726 ppm2   3.124
ASSI ( 2024)
    (  segid *BrD * and resid 34 and name HD % )
    ( ( segid *BrD * and resid 34 and name HB1 ) )
      2.500  1.600   1.600 peak      2024 weight   0.10000E+01 volume  0.48715E+03 ppm1   7.714 ppm2   4.115
ASSI ( 2084)
    (  segid *BrD * and resid 15 and name HD % )
    (  segid *BrD * and resid 15 and name HE % )
      1.900  0.900   0.900 peak      2084 weight   0.10000E+01 volume  0.28924E+04 ppm1   7.689 ppm2   7.483
ASSI ( 2474)
    (  segid *BrD * and resid 96 and name HE % )
    ( ( segid *BrD * and resid 96 and name HB1 ) )
      3.300  2.700   2.200 peak      2474 weight   0.10000E+01 volume  0.86809E+02 ppm1   7.611 ppm2   4.001
ASSI ( 2554)
    (  segid *BrD * and resid 74 and name HE % )
    (  segid *BrD * and resid 74 and name HD % )
      2.000  1.000   1.000 peak      2554 weight   0.10000E+01 volume  0.18278E+04 ppm1   7.539 ppm2   7.006
```

TABLE 2-continued

Unambigous NOE-derived Inter-proton Distance Restraints

```
ASSI ( 3204)
  ( segid *BrD * and resid 82 and name HD % )
  ( ( segid *BrD * and resid 82 and name HB1 ) )
     2.400  1.400   1.400 peak    3204 weight  0.10000E+01 volume  0.67788E+03 ppm1   7.265 ppm2   3.708
ASSI ( 3214)
  ( segid *BrD * and resid 82 and name HD % )
  ( ( segid *BrD * and resid 82 and name HB2 ) )
     2.300  1.300   1.300 peak    3214 weight  0.10000E+01 volume  0.77298E+03 ppm1   7.262 ppm2   3.571
ASSI ( 3304)
  ( segid *BrD * and resid 82 and name HD % )
  ( segid *BrD * and resid 82 and name HE % )
     2.100  1.100   1.100 peak    3304 weight  0.10000E+01 volume  0.12642E+04 ppm1   7.262 ppm2   7.076
ASSI ( 3644)
  ( segid *BrD * and resid 74 and name HD % )
  ( ( segid *BrD * and resid 74 and name HB2 ) )
     2.400  1.400   1.400 peak    3644 weight  0.10000E+01 volume  0.64123E+03 ppm1   7.005 ppm2   3.007
ASSI ( 3894)
  ( segid *BrD * and resid 46 and name HD % )
  ( segid *BrD * and resid 46 and name HE % )
     2.000  1.000   1.000 peak    3894 weight  0.10000E+01 volume  0.17599E+04 ppm1   5.743 ppm2   6.687
ASSI ( 3914)
  ( segid *BrD * and resid 46 and name HD % )
  ( ( segid *BrD * and resid 46 and name HB1 ) )
     2.400  1.400   1.400 peak    3914 weight  0.10000E+01 volume  0.61947E+03 ppm1   5.740 ppm2   3.304
ASSI ( 4064)
  ( ( segid *BrD * and resid 28 and name HD2 ) )
  ( ( segid *BrD * and resid 28 and name HA   ) )
     3.000  2.200   2.200 peak    4064 weight  0.10000E+01 volume  0.15484E+03 ppm1   5.577 ppm2   4.586
ASSI (   84)
  ( segid *BrD * and resid 82 and name HD % )
  ( ( segid *BrD * and resid 103 and name HA   ) )
     2.900  2.100   2.100 peak      84 weight  0.10000E+01 volume  0.22432E+03 ppm1   7.265 ppm2   3.790
ASSI (  174)
  ( segid *BrD * and resid 67 and name HD % )
  ( ( segid *BrD * and resid 62 and name HA   ) )
     3.300  2.700   2.200 peak     174 weight  0.10000E+01 volume  0.89209E+02 ppm1   6.899 ppm2   4.490
ASSI (  244)
  ( segid *BrD * and resid 67 and name HD % )
  ( ( segid *BrD * and resid 62 and name HB2 ) )
     2.900  2.100   2.100 peak     244 weight  0.10000E+01 volume  0.21286E+03 ppm1   6.899 ppm2   1.706
ASSI (  254)
  ( segid *BrD * and resid 67 and name HD % )
  ( segid *BrD * and resid 73 and name HD1%)
     3.500  3.100   2.000 peak     254 weight  0.10000E+01 volume  0.64742E+02 ppm1   6.899 ppm2   3.545
ASSI (  464)
  ( ( segid *BrD * and resid 32 and name HD1 ) )
  ( ( segid *BrD * and resid 29 and name HA   ) )
     3.300  2.700   2.200 peak     464 weight  0.10000E+01 volume  0.97341E+02 ppm1   8.490 ppm2   4.814
ASSI (  494)
  ( ( segid *BrD * and resid 32 and name HD1 ) )
  ( ( segid *BrD * and resid 33 and name HD1 ) )
     5.500  5.500   0.000 peak     494 weight  0.10000E+01 volume  0.38880E-03 ppm1   8.490 ppm2   2.781
ASSI (  504)
  ( ( segid *BrD * and resid 32 and name HD1 ) )
  ( ( segid *BrD * and resid 33 and name HD2 ) )
     4.000  4.000   1.500 peak     504 weight  0.10000E+01 volume  0.30117E+02 ppm1   8.490 ppm2   2.211
ASSI (  564)
  ( ( segid *BrD * and resid 107 and name HZ   ) )
  ( ( segid *BrD * and resid 79 and name HB1 ) )
     3.100  2.400   2.400 peak     564 weight  0.10000E+01 volume  0.14239E+03 ppm1   8.008 ppm2   2.802
ASSI (  624)
  ( ( segid *BrD * and resid 107 and name HZ   ) )
  ( ( segid *BrD * and resid 79 and name HA   ) )
     3.000  2.200   2.200 peak     624 weight  0.10000E+01 volume  0.17938E+03 ppm1   8.058 ppm2   4.439
ASSI (  634)
  ( ( segid *BrD * and resid 107 and name HZ   ) )
  ( segid *BrD * and resid 107 and name HE % )
     2.000  1.000   1.000 peak     634 weight  0.10000E+01 volume  0.19583E+04 ppm1   8.058 ppm2   7.927
ASSI (  644)
  ( ( segid *BrD * and resid 107 and name HZ   ) )
  ( segid *BrD * and resid 107 and name HD % )
     2.500  2.500   2.000 peak     644 weight  0.10000E+01 volume  0.49678E+03 ppm1   8.058 ppm2   7.793
ASSI (  664)
  ( ( segid *BrD * and resid 107 and name HZ   ) )
  ( ( segid *BrD * and resid 79 and name HG1 ) )
     2.700  1.800   1.800 peak     664 weight  0.10000E+01 volume  0.34018E+03 ppm1   8.059 ppm2   2.994
```

TABLE 2-continued

Unambigous NOE-derived Inter-proton Distance Restraints

```
ASSI (  694)
   ( ( segid *BrD * and resid 32 and name HZ2 ) )
   ( ( segid *BrD * and resid 94 and name HG1 ) )
      2.500  1.600   1.600 peak      694 weight   0.10000E+01 volume  0.45123E+03 ppm1   8.008 ppm2    3.154
ASSI (  714)
   ( ( segid *BrD * and resid 32 and name HZ2 ) )
   ( ( segid *BrD * and resid 32 and name HZ3 ) )
      2.100  2.100   2.400 peak      714 weight   0.10000E+01 volume  0.13157E+04 ppm1   8.004 ppm2    7.797
ASSI (  724)
   ( ( segid *BrD * and resid 32 and name HE3 ) )
   ( ( segid *BrD * and resid 33 and name HG2 ) )
      3.200  2.600   2.300 peak      724 weight   0.10000E+01 volume  0.11962E+03 ppm1   7.959 ppm2   -0.311
ASSI (  804)
   ( ( segid *BrD * and resid 32 and name HZ2 ) )
   ( ( segid *BrD * and resid 97 and name HB1 ) )
      2.700  1.800   1.800 peak      804 weight   0.10000E+01 volume  0.29399E+03 ppm1   7.961 ppm2    2.667
ASSI (  854)
   ( ( segid *BrD * and resid 32 and name HE3 ) )
   ( ( segid *BrD * and resid 32 and name HA  ) )
      2.900  2.100   2.100 peak      854 weight   0.10000E+01 volume  0.19220E+03 ppm1   7.957 ppm2    4.976
ASSI (  864)
   ( ( segid *BrD * and resid 32 and name HE3 ) )
   ( ( segid *BrD * and resid 33 and name HA  ) )
      2.600  1.700   1.700 peak      864 weight   0.10000E+01 volume  0.35337E+03 ppm1   7.956 ppm2    4.361
ASSI (  874)
   ( ( segid *BrD * and resid 32 and name HE3 ) )
   ( ( segid *BrD * and resid 32 and name HB1 ) )
      2.800  2.000   2.000 peak      874 weight   0.10000E+01 volume  0.24249E+03 ppm1   7.958 ppm2    3.966
ASSI (  984)
   (   segid *BrD * and resid 107 and name HE % )
   ( ( segid *BrD * and resid 103 and name HA  ) )
      3.000  2.200   2.200 peak      984 weight   0.10000E+01 volume  0.17386E+03 ppm1   7.925 ppm2    3.742
ASSI ( 1024)
   ( ( segid *BrD * and resid 34 and name HZ  ) )
   ( ( segid *BrD * and resid 102 and name HB2 ) )
      2.500  1.600   1.600 peak     1024 weight   0.10000E+01 volume  0.46463E+03 ppm1   7.926 ppm2    1.813
ASSI ( 1144)
   ( ( segid *BrD * and resid 34 and name HZ  ) )
   ( ( segid *BrD * and resid 102 and name HB1 ) )
      2.900  2.100   2.100 peak     1144 weight   0.10000E+01 volume  0.21471E+03 ppm1   7.900 ppm2    1.967
ASSI ( 1154)
   ( ( segid *BrD * and resid 34 and name HZ  ) )
   ( ( segid *BrD * and resid 98 and name HB1 ) )
      3.300  2.700   2.700 peak     1154 weight   0.10000E+01 volume  0.95962E+02 ppm1   7.899 ppm2    4.001
ASSI ( 1194)
   (   segid *BrD * and resid 107 and name HE % )
   ( ( segid *BrD * and resid 79 and name HA  ) )
      2.300  1.300   1.300 peak     1194 weight   0.10000E+01 volume  0.84240E+03 ppm1   7.889 ppm2    4.391
ASSI ( 1224)
   (   segid *BrD * and resid 68 and name HE % )
   ( ( segid *BrD * and resid 62 and name HD1 ) )
      3.100  2.400   2.400 peak     1224 weight   0.10000E+01 volume  0.13020E+03 ppm1   7.892 ppm2    3.172
ASSI ( 1314)
   (   segid *BrD * and resid 68 and name HE % )
   (   segid *BrD * and resid 73 and name HD2%)
      4.100  4.100   1.400 peak     1314 weight   0.10000E+01 volume  0.23932E+02 ppm1   7.892 ppm2    1.496
ASSI ( 1344)
   ( ( segid *BrD * and resid 32 and name HE3 ) )
   ( ( segid *BrD * and resid 33 and name HD2 ) )
      3.200  2.600   2.300 peak     1344 weight   0.10000E+01 volume  0.10782E+03 ppm1   7.956 ppm2    2.212
ASSI ( 1434)
   ( ( segid *BrD * and resid 32 and name HZ3 ) )
   ( ( segid *BrD * and resid 32 and name HE3 ) )
      1.800  0.800   0.800 peak     1434 weight   0.10000E+01 volume  0.39856E+04 ppm1   7.812 ppm2    7.954
ASSI ( 1454)
   (   segid *BrD * and resid 34 and name HE % )
   (   segid *BrD * and resid 102 and name HD1%)
      2.900  2.100   2.100 peak     1454 weight   0.10000E+01 volume  0.19468E+03 ppm1   7.808 ppm2    1.268
ASSI ( 1464)
   (   segid *BrD * and resid 107 and name HD % )
   (   segid *BrD * and resid 110 and name HD1%)
      2.800  2.000   2.000 peak     1464 weight   0.10000E+01 volume  0.23444E+03 ppm1   7.810 ppm2    1.153
ASSI ( 1474)
   (   segid *BrD * and resid 107 and name HD % )
   (   segid *BrD * and resid 116 and name HD1%)
      2.600  1.700   1.700 peak     1474 weight   0.10000E+01 volume  0.36349E+03 ppm1   7.806 ppm2    1.399
```

TABLE 2-continued

Unambigous NOE-derived Inter-proton Distance Restraints

```
ASSI ( 1494)
    ( segid *BrD * and resid 107 and name HD % )
    ( ( segid *BrD * and resid 107 and name HA   ) )
      2.300  1.300   1.300 peak    1494 weight   0.10000E+01 volume   0.85611E+03 ppm1   7.803 ppm2   4.440
ASSI ( 1524)
    ( segid *BrD * and resid 105 and name HD % )
    ( ( segid *BrD * and resid 105 and name HB1  ) )
      2.300  1.300   1.300 peak    1524 weight   0.10000E+01 volume   0.86322E+03 ppm1   7.798 ppm2   3.741
ASSI ( 1564)
    ( segid *BrD * and resid 34 and name HE % )
    ( ( segid *BrD * and resid 28 and name HD2 ) )
      3.000  2.200   2.200 peak    1564 weight   0.10000E+01 volume   0.16881E+03 ppm1   7.794 ppm2   5.562
ASSI ( 1594)
    ( ( segid *BrD * and resid 32 and name HZ3  ) )
    ( segid *BrD * and resid 95 and name HE % )
      2.600  1.700   1.700 peak    1594 weight   0.10000E+01 volume   0.36507E+03 ppm1   7.791 ppm2   7.630
ASSI ( 1634)
    ( segid *BrD * and resid 34 and name HE % )
    ( segid *BrD * and resid 102 and name HB2  ) )
      3.200  2.600   2.300 peak    1634 weight   0.10000E+01 volume   0.12088E+03 ppm1   7.790 ppm2   2.032
ASSI ( 1644)
    ( segid *BrD * and resid 34 and name HE % )
    ( ( segid *BrD * and resid 98 and name HB1  ) )
      2.700  1.800   1.800 peak    1644 weight   0.10000E+01 volume   0.32157E+03 ppm1   7.784 ppm2   4.016
ASSI ( 1724)
    ( segid *BrD * and resid 107 and name HD % )
    ( ( segid *BrD * and resid 103 and name HG2 ) )
      2.400  2.400   2.100 peak    1724 weight   0.10000E+01 volume   0.57448E+03 ppm1   7.778 ppm2   2.487
ASSI ( 1754)
    ( ( segid *BrD * and resid 32 and name HZ3  ) )
    ( ( segid *BrD * and resid 33 and name HB1  ) )
      2.700  1.800   1.800 peak    1754 weight   0.10000E+01 volume   0.30103E+03 ppm1   7.780 ppm2   1.088
ASSI ( 1764)
    ( segid *BrD * and resid 34 and name HE % )
    ( segid *BrD * and resid 81 and name HG2%)
      3.000  2.200   2.200 peak    1764 weight   0.10000E+01 volume   0.16442E+03 ppm1   7.781 ppm2   0.762
ASSI ( 1794)
    ( segid *BrD * and resid 68 and name HD % )
    ( segid *BrD * and resid 73 and name HD1%)
      2.600  1.700   1.700 peak    1794 weight   0.10000E+01 volume   0.42209E+03 ppm1   7.781 ppm2   1.543
ASSI ( 1904)
    ( segid *BrD * and resid 34 and name HD % )
    ( ( segid *BrD * and resid 34 and name HZ   ) )
      2.600  1.700   1.700 peak    1904 weight   0.10000E+01 volume   0.35620E+03 ppm1   7.719 ppm2   7.901
ASSI ( 1954)
    ( segid *BrD * and resid 34 and name HD % )
    ( ( segid *BrD * and resid 85 and name HB1  ) )
      3.000  2.200   2.200 peak    1954 weight   0.10000E+01 volume   0.18188E+03 ppm1   7.714 ppm2   3.920
ASSI ( 2124)
    ( segid *BrD * and resid 15 and name HD % )
    ( segid *BrD * and resid 63 and name HD1%)
      2.500  1.600   1.600 peak    2124 weight   0.10000E+01 volume   0.44171E+03 ppm1   7.689 ppm2   1.641
ASSI ( 2164)
    ( segid *BrD * and resid 15 and name HD % )
    ( ( segid *BrD * and resid 16 and name HA   ) )
      2.600  1.700   1.700 peak    2164 weight   0.10000E+01 volume   0.41516E+03 ppm1   7.650 ppm2   4.538
ASSI ( 2224)
    ( segid *BrD * and resid 106 and name HE % )
    ( segid *BrD * and resid 75 and name HE % )
      3.000  2.200   2.200 peak    2224 weight   0.10000E+01 volume   0.17361E+03 ppm1   7.646 ppm2   2.666
ASSI ( 2234)
    ( segid *BrD * and resid 106 and name HE % )
    ( ( segid *BrD * and resid 78 and name HB1  ) )
      2.900  2.100   2.100 peak    2234 weight   0.10000E+01 volume   0.21480E+03 ppm1   7.647 ppm2   1.333
ASSI ( 2244)
    ( segid *BrD * and resid 106 and name HE % )
    ( ( segid *BrD * and resid 78 and name HB1  ) )
      2.600  1.700   1.700 peak    2244 weight   0.10000E+01 volume   0.42179E+03 ppm1   7.647 ppm2   1.268
OR ( 2244)
    ( segid *BrD * and resid 106 and name HE % )
    ( ( segid *BrD * and resid 78 and name HG   ) )
ASSI ( 2264)
    ( segid *BrD * and resid 106 and name HE % )
    ( ( segid *BrD * and resid 106 and name HB1 ) )
      3.400  2.900   2.100 peak    2264 weight   0.10000E+01 volume   0.80420E+02 ppm1   7.644 ppm2   3.919
```

TABLE 2-continued

Unambigous NOE-derived Inter-proton Distance Restraints

```
ASSI ( 2414)
    ( segid *BrD * and resid 106 and name HE % )
    ( segid *BrD * and resid 17 and name HG2%)
      4.000  4.000   1.500 peak     2414 weight   0.10000E+01 volume   0.29483E+02 ppm1    7.616 ppm2   1.706
ASSI ( 2484)
    ( segid *BrD * and resid 96 and name HE % )
    ( ( segid *BrD * and resid 86 and name HE1 ) )
      3.000  2.200   2.200 peak     2484 weight   0.10000E+01 volume   0.16268E+03 ppm1    7.611 ppm2   3.106
ASSI ( 2504)
    ( segid *BrD * and resid 106 and name HE % )
    ( ( segid *BrD * and resid 21 and name HG11 ) )
      2.500  1.600   1.600 peak     2504 weight   0.10000E+01 volume   0.54543E+03 ppm1    7.611 ppm2   2.274
ASSI ( 2514)
    ( segid *BrD * and resid 106 and name HE % )
    ( ( segid *BrD * and resid 18 and name HG    ) )
      2.600  1.700   1.700 peak     2514 weight   0.10000E+01 volume   0.40048E+03 ppm1    7.611 ppm2   2.274
ASSI ( 2574)
    ( segid *BrD * and resid 74 and name HE % )
    ( segid *BrD * and resid 63 and name HD2%)
      2.900  2.100   2.100 peak     2574 weight   0.10000E+01 volume   0.18991E+03 ppm1    7.539 ppm2   1.496
ASSI ( 2614)
    ( segid *BrD * and resid 106 and name HD % )
    ( ( segid *BrD * and resid 21 and name HG11 ) )
      3.200  2.600   2.300 peak     2614 weight   0.10000E+01 volume   0.10679E+03 ppm1    7.535 ppm2   2.308
ASSI ( 2654)
    ( segid *BrD * and resid 106 and name HD % )
    ( segid *BrD * and resid 21 and name HG2%)
      2.000  1.000   1.000 peak     2654 weight   0.10000E+01 volume   0.21819E+04 ppm1    7.541 ppm2   1.580
ASSI ( 2674)
    ( segid *BrD * and resid 74 and name HE % )
    ( ( segid *BrD * and resid 78 and name HG    ) )
      2.500  1.600   1.600 peak     2674 weight   0.10000E+01 volume   0.54850E+03 ppm1    7.529 ppm2   1.266
ASSI ( 2694)
    ( segid *BrD * and resid 74 and name HE % )
    ( segid *BrD * and resid 78 and name HD1%)
      2.500  1.600   1.600 peak     2694 weight   0.10000E+01 volume   0.46858E+03 ppm1    7.530 ppm2   0.780
ASSI ( 2754)
    ( segid *BrD * and resid 106 and name HD % )
    ( ( segid *BrD * and resid 106 and name HB1 ) )
      2.300  1.300   1.300 peak     2754 weight   0.10000E+01 volume   0.86816E+03 ppm1    7.524 ppm2   1.919
ASSI ( 2774)
    ( segid *BrD * and resid 106 and name HD % )
    ( ( segid *BrD * and resid 106 and name HB2 ) )
      2.400  1.400   1.400 peak     2774 weight   0.10000E+01 volume   0.63063E+02 ppm1    7.524 ppm2   3.708
ASSI ( 2834)
    ( segid *BrD * and resid 106 and name HD % )
    ( segid *BrD * and resid 107 and name HE % )
      3.400  2.900   2.100 peak     2834 weight   0.10000E+01 volume   0.82229E+02 ppm1    7.513 ppm2   7.940
ASSI ( 3074)
    ( segid *BrD * and resid 67 and name HE % )
    ( segid *BrD * and resid 73 and name HD1%)
      4.000  4.000   1.500 peak     3074 weight   0.10000E+01 volume   0.28072E+02 ppm1    7.318 ppm2   1.545
ASSI ( 3144)
    ( segid *BrD * and resid 47 and name HE % )
    ( ( segid *BrD * and resid 46 and name HB2 ) )
      3.000  2.200   2.200 peak     3144 weight   0.10000E+01 volume   0.17782E+03 ppm1    7.270 ppm2   3.075
ASSI ( 3224)
    ( segid *BrD * and resid 82 and name HD % )
    ( ( segid *BrD * and resid 103 and name HG1 ) )
      3.100  2.400   2.400 peak     3224 weight   0.10000E+01 volume   0.12400E+03 ppm1    7.264 ppm2   2.595
ASSI ( 3234)
    ( segid *BrD * and resid 82 and name HD % )
    ( ( segid *BrD * and resid 103 and name HB1 ) )
      3.200  2.600   2.300 peak     3234 weight   0.10000E+01 volume   0.10914E+03 ppm1    7.266 ppm2   2.374
ASSI ( 3254)
    ( segid *BrD * and resid 82 and name HD % )
    ( ( segid *BrD * and resid 81 and name HB   ) )
      3.200  2.600   2.300 peak     3254 weight   0.10000E+01 volume   0.12188E+03 ppm1    7.266 ppm2   2.032
ASSI ( 3264)
    ( segid *BrD * and resid 82 and name HD % )
    ( ( segid *BrD * and resid 103 and name HB2 ) )
      3.100  2.400   2.400 peak     3264 weight   0.10000E+01 volume   0.13715E+03 ppm1    7.266 ppm2   1.902
ASSI ( 3314)
    ( segid *BrD * and resid 82 and name HD % )
    ( segid *BrD * and resid 102 and name HD2%)
      3.100  2.400   2.400 peak     3314 weight   0.10000E+01 volume   0.13023E+03 ppm1    7.261 ppm2   1.332
```

TABLE 2-continued

Unambigous NOE-derived Inter-proton Distance Restraints

```
OR ( 3314)
   ( segid *BrD * and resid 82 and name HD % )
   ( segid *BrD * and resid 102 and name HD1%)
ASSI ( 3354)
   ( segid *BrD * and resid 82 and name HE % )
   ( ( segid *BrD * and resid 106 and name HB1  ) )
    3.000  2.200   2.200  peak    3354  weight   0.10000E+01  volume   0.15234E+03  ppm1   7.069  ppm2   3.922
ASSI ( 3364)
   ( segid *BrD * and resid 82 and name HE % )
   ( ( segid *BrD * and resid 103 and name HA   ) )
    3.000  2.200   2.200  peak    3364  weight   0.10000E+01  volume   0.15996E+02  ppm1   7.070  ppm2   3.789
ASSI ( 3404)
   ( segid *BrD * and resid 82 and name HE % )
   ( ( segid *BrD * and resid 102 and name HB2  ) )
    2.900  2.100   2.100  peak    3404  weight   0.10000E+01  volume   0.20703E+03  ppm1   7.070  ppm2   1.838
ASSI ( 3424)
   ( segid *BrD * and resid 82 and name HE % )
   ( segid *BrD * and resid 102 and name HD2%)
    2.400  1.400   1.400  peak    3424  weight   0.10000E+01  volume   0.67243E+03  ppm1   7.070  ppm2   1.333
ASSI ( 3444)
   ( segid *BrD * and resid 82 and name HE % )
   ( segid *BrD * and resid 107 and name HD % )
    3.500  3.100   2.000  peak    3444  weight   0.10000E+01  volume   0.65231E+02  ppm1   7.069  ppm2   7.777
ASSI ( 3444)
   ( segid *BrD * and resid 82 and name HE % )
   ( segid *BrD * and resid 78 and name HD2%)
    2.900  2.100   2.100  peak    3464  weight   0.10000E+01  volume   0.20065E+03  ppm1   7.067  ppm2   0.680
ASSI ( 3514)
   ( ( segid *BrD * and resid 82 and name HZ   ) )
   ( segid *BrD * and resid 102 and name HD2%)
    3.200  2.600   2.300  peak    3514  weight   0.10000E+01  volume   0.11748E+03  ppm1   7.021  ppm2   1.331
ASSI ( 3524)
   ( ( segid *BrD * and resid 82 and name HZ   ) )
   ( segid *BrD * and resid 78 and name HD2%)
    2.800  2.000   2.000  peak    3524  weight   0.10000E+01  volume   0.25407E+03  ppm1   7.017  ppm2   0.681
ASSI ( 3574)
   ( segid *BrD * and resid 74 and name HD % )
   ( segid *BrD * and resid 68 and name HD % )
    2.800  2.000   2.000  peak    3574  weight   0.10000E+01  volume   0.24279E+03  ppm1   7.005  ppm2   7.777
ASSI ( 3654)
   ( segid *BrD * and resid 74 and name HD % )
   ( segid *BrD * and resid 75 and name HE % )
    3.300  2.700   2.200  peak    3654  weight   0.10000E+01  volume   0.90985E+02  ppm1   7.005  ppm2   2.667
ASSI ( 3684)
   ( segid *BrD * and resid 74 and name HD % )
   ( segid *BrD * and resid 59 and name HE % )
    2.600  1.700   1.700  peak    3684  weight   0.10000E+01  volume   0.36097E+03  ppm1   7.005  ppm2   1.885
ASSI ( 3754)
   ( segid *BrD * and resid 67 and name HD % )
   ( ( segid *BrD * and resid 62 and name HG2  ) )
    3.400  2.900   2.100  peak    3754  weight   0.10000E+01  volume   0.78199E+02  ppm1   6.899  ppm2   1.496
ASSI ( 3804)
   ( segid *BrD * and resid 46 and name HE % )
   ( ( segid *BrD * and resid 53 and name HA   ) )
    3.100  2.400   2.400  peak    3804  weight   0.10000E+01  volume   0.13088E+03  ppm1   6.686  ppm2   4.701
ASSI ( 3944)
   ( segid *BrD * and resid 46 and name HD % )
   ( segid *BrD * and resid 38 and name HG1%)
    3.400  2.900   2.100  peak    3944  weight   0.10000E+01  volume   0.75575E+02  ppm1   5.740  ppm2   1.088
ASSI ( 4024)
   ( ( segid *BrD * and resid 52 and name HA   ) )
   ( ( segid *BrD * and resid 53 and name HD2  ) )
    3.400  2.900   2.100  peak    4024  weight   0.10000E+01  volume   0.78758E+02  ppm1   5.589  ppm2   4.017
ASSI ( 4054)
   ( ( segid *BrD * and resid 28 and name HD2  ) )
   ( ( segid *BrD * and resid 34 and name HZ   ) )
    2.800  2.000   2.000  peak    4054  weight   0.10000E+01  volume   0.24761E+03  ppm1   5.577  ppm2   7.924
ASSI ( 4114)
   ( ( segid *BrD * and resid 34 and name HA   ) )
   ( segid *BrD * and resid 34 and name HD % )
    2.300  1.300   1.300  peak    4114  weight   0.10000E+01  volume   0.78719E+03  ppm1   5.547  ppm2   7.713
ASSI ( 4204)
   ( segid *BrD * and resid 34 and name HD % )
   ( segid *BrD * and resid 56 and name HD1%)
    2.900  2.100   2.100  peak    4204  weight   0.10000E+01  volume   0.22356E+03  ppm1   7.714  ppm2   1.544
```

TABLE 2-continued

Unambigous NOE-derived Inter-proton Distance Restraints

```
ASSI (  4264)
    (  segid *BrD * and resid 34 and name HE % )
    ( ( segid *BrD * and resid 31 and name HA   ) )
     2.500  1.600   1.600 peak     4264 weight   0.10000E+01 volume   0.48557E+03 ppm1    7.781 ppm2    4.993
ASSI (  4304)
    (  segid *BrD * and resid 107 and name HD % )
    (  segid *BrD * and resid 106 and name HD % )
     2.800  2.000   2.000 peak     4304 weight   0.10000E+01 volume   0.27783E+03 ppm1    7.802 ppm2    7.517
ASSI (  4324)
    ( ( segid *BrD * and resid 82 and name HZ    ) )
    ( ( segid *BrD * and resid 103 and name HA   ) )
     3.300  2.700   2.200 peak     4324 weight   0.10000E+01 volume   0.96267E+02 ppm1    7.031 ppm2    3.790
ASSI (  4364)
    (  segid *BrD * and resid 107 and name HE % )
    ( ( segid *BrD * and resid 78 and name HB2 ) )
     3.400  2.900   2.100 peak     4364 weight   0.10000E+01 volume   0.78224E+02 ppm1    7.888 ppm2    1.085
ASSI (     5)
    ( ( segid *AcH * and resid 201 and name HA1 ) )
    (  segid *BrD * and resid 38 and name HG1%)
     2.600  1.700   1.700 peak        5 weight   0.11000E+01 volume   0.16527E+03 ppm1    4.029 ppm2    1.081
OR (     5)
    ( ( segid *AcH * and resid 201 and name HA2 ) )
    (  segid *BrD * and resid 38 and name HG1%)
ASSI (    15)
    ( ( segid *AcH * and resid 201 and name HA1 ) )
    (  segid *BrD * and resid 38 and name HG2%)
     2.600  1.700   1.700 peak       15 weight   0.11000E+01 volume   0.14933E+03 ppm1    4.026 ppm2    0.723
OR (    15)
    ( ( segid *AcH * and resid 201 and name HA2 ) )
    (  segid *BrD * and resid 38 and name HG2%)
ASSI (    25)
    ( ( segid *AcH * and resid 201 and name HA1 ) )
    (  segid *BrD * and resid 43 and name HB % )
     2.600  1.700   1.700 peak       25 weight   0.11000E+01 volume   0.16374E+03 ppm1    4.023 ppm2    1.609
ASSI (    35)
    ( ( segid *AcH * and resid 201 and name HB2 ) )
    (  segid *BrD * and resid 43 and name HB % )
     2.600  1.700   1.700 peak       35 weight   0.11000E+01 volume   0.16831E+03 ppm1    3.428 ppm2    1.601
ASSI (    45)
    ( ( segid *AcH * and resid 201 and name HB2 ) )
    (  segid *BrD * and resid 38 and name HG1%)
     2.700  1.800   1.800 peak       45 weight   0.11000E+01 volume   0.14392E+03 ppm1    3.430 ppm2    1.074
OR (    45)
    ( ( segid *AcH * and resid 201 and name HB1 ) )
    (  segid *BrD * and resid 38 and name HG1%)
ASSI (    55)
    ( ( segid *AcH * and resid 201 and name HB2 ) )
    (  segid *BrD * and resid 38 and name HG2%)
     2.600  1.700   1.700 peak       55 weight   0.11000E+01 volume   0.14742E+03 ppm1    3.430 ppm2    0.723
OR (    55)
    ( ( segid *AcH * and resid 201 and name HB1 ) )
    (  segid *BrD * and resid 38 and name HG2%)
ASSI (    65)
    ( ( segid *AcH * and resid 201 and name HD1 ) )
    (  segid *BrD * and resid 43 and name HB % )
     2.600  1.700   1.700 peak       65 weight   0.11000E+01 volume   0.15413E+03 ppm1    8.179 ppm2    1.608
ASSI (    75)
    ( ( segid *AcH * and resid 201 and name HD2 ) )
    (  segid *BrD * and resid 43 and name HB % )
     2.700  1.800   1.800 peak       75 weight   0.11000E+01 volume   0.13471E+03 ppm1    7.682 ppm2    1.592
ASSI (    85)
    ( ( segid *AcH * and resid 201 and name HD2 ) )
    (  segid *BrD * and resid 38 and name HG1%)
     2.700  1.800   1.800 peak       85 weight   0.11000E+01 volume   0.12532E+03 ppm1    7.680 ppm2    1.066
ASSI (    95)
    ( ( segid *AcH * and resid 201 and name HD2 ) )
    (  segid *BrD * and resid 38 and name HG2%)
     2.700  1.800   1.800 peak       95 weight   0.11000E+01 volume   0.12585E+03 ppm1    7.690 ppm2    0.691
ASSI (   105)
    (  segid *BrD * and resid 200 and name HA % )
    (  segid *BrD * and resid 38 and name HG2%)
     2.600  1.700   1.700 peak      105 weight   0.11000E+01 volume   0.16395E+03 ppm1    2.547 ppm2    0.727
ASSI (   115)
    (  segid *AcH * and resid 200 and name HA % )
    (  segid *BrD * and resid 38 and name HG1%)
     2.400  1.400   1.400 peak      115 weight   0.11000E+01 volume   0.29029E+03 ppm1    2.548 ppm2    1.072
```

TABLE 2-continued

Unambigous NOE-derived Inter-proton Distance Restraints

```
ASSI (  125)
   ( segid *AcH * and resid 200 and name HA % )
   ( segid *BrD * and resid 43 and name HB % )
      2.700  1.800   1.800 peak       125 weight   0.11000E+01 volume   0.13320E+03 ppm1    2.538 ppm2    1.603
ASSI (  135)
   ( segid *AcH * and resid 200 and name HA % )
   ( ( segid *BrD * and resid 38 and name HA   ) )
      2.600  1.700   1.700 peak       135 weight   0.11000E+01 volume   0.17326E+03 ppm1    2.548 ppm2    4.209
ASSI (  145)
   ( segid *AcH * and resid 200 and name HA % )
   ( ( segid *BrD * and resid 43 and name HA   ) )
      2.700  1.800   1.800 peak       145 weight   0.11000E+01 volume   0.12382E+03 ppm1    2.547 ppm2    5.520
ASSI (   6)
   ( ( segid *AcH * and resid 201 and name HA1 ) )
   ( segid *BrD * and resid 46 and name HE % )
      2.700  1.800   1.800 peak         6 weight   0.11000E+01 volume   0.14312E+02 ppm1    4.007 ppm2    6.648
OR (     6)
   ( ( segid *AcH * and resid 201 and name HA2 ) )
   ( segid *BrD * and resid 46 and name HE % )
ASSI (   16)
   ( ( segid *AcH * and resid 201 and name HA2 ) )
   ( segid *BrD * and resid 95 and name HD % )
      2.700  1.800   1.800 peak        16 weight   0.11000E+01 volume   0.13924E+03 ppm1    4.015 ppm2    7.481
OR (    16)
   ( ( segid *AcH * and resid 201 and name HA1 ) )
   ( segid *BrD * and resid 95 and name HD % )
ASSI (   26)
   ( ( segid *AcH * and resid 201 and name HB1 ) )
   ( segid *BrD * and resid 95 and name HD % )
      2.600  1.700   1.700 peak        26 weight   0.11000E+01 volume   0.15229E+03 ppm1    3.429 ppm2    7.481
OR (    26)
   ( ( segid *AcH * and resid 201 and name HB2 ) )
   ( segid *BrD * and resid 95 and name HD % )
ASSI (   36)
   ( ( segid *AcH * and resid 201 and name HA1 ) )
   ( segid *BrD * and resid 88 and name HD % )
      2.500  1.600   1.600 peak        36 weight   0.11000E+01 volume   0.18465E+03 ppm1    4.015 ppm2    7.637
OR (    36)
   ( ( segid *AcH * and resid 201 and name HA2 ) )
   ( segid *BrD * and resid 88 and name HD % )
ASSI (   46)
   ( ( segid *AcH * and resid 201 and name HB2 ) )
   ( segid *BrD * and resid 88 and name HD % )
      2.700  1.800   1.800 peak        46 weight   0.11000E+01 volume   0.13938E+03 ppm1    3.429 ppm2    7.637
OR (    46)
   ( ( segid *AcH * and resid 201 and name HB1 ) )
   ( segid *BrD * and resid 88 and name HD % )
ASSI (   56)
   ( ( segid *AcH * and resid 201 and name HA2 ) )
   ( segid *BrD * and resid 95 and name HE % )
      2.600  1.700   1.700 peak        56 weight   0.11000E+01 volume   0.16075E+03 ppm1    4.015 ppm2    7.585
OR (    56)
   ( ( segid *AcH * and resid 201 and name HA1 ) )
   ( segid *BrD * and resid 95 and name HE % )
ASSI (   66)
   ( ( segid *AcH * and resid 201 and name HB1 ) )
   ( segid *BrD * and resid 95 and name HE % )
      2.600  1.700   1.700 peak        66 weight   0.11000E+01 volume   0.16293E+03 ppm1    3.429 ppm2    7.585
ASSI (   76)
   ( segid *AcH * and resid 200 and name HA % )
   ( segid *BrD * and resid 95 and name HE % )
      2.700  1.800   1.800 peak        76 weight   0.11000E+01 volume   0.14049E+03 ppm1    2.542 ppm2    7.585
ASSI (   86)
   ( ( segid *AcH * and resid 201 and name HA1 ) )
   ( segid *BrD * and resid 88 and name HE % )
      2.600  1.700   1.700 peak        86 weight   0.11000E+01 volume   0.16796E+03 ppm1    4.019 ppm2    7.358
OR (    86)
   ( ( segid *AcH * and resid 201 and name HA2 ) )
   ( segid *BrD * and resid 88 and name HE % )
ASSI (   96)
   ( ( segid *AcH * and resid 201 and name HB2 ) )
   ( segid *BrD * and resid 88 and name HE % )
      2.600  1.700   1.700 peak        96 weight   0.11000E+01 volume   0.16763E+03 ppm1    3.430 ppm2    7.358
OR (    96)
   ( ( segid *AcH * and resid 201 and name HB1 ) )
   ( segid *BrD * and resid 88 and name HE % )
```

TABLE 2-continued

Unambigous NOE-derived Inter-proton Distance Restraints

```
ASSI (    7)
   ( segid *AcH * and resid 200 and name HA % )
   ( ( segid *AcH * and resid 201 and name HN   ) )
      2.700  1.800   1.800 peak        7 weight   0.11000E+01 volume   0.12000E+03 ppm1      3.430 ppm2     7.358
ASSI (   17)
   ( segid *AcH * and resid 200 and name HA % )
   ( ( segid *AcH * and resid 201 and name HA1  ) )
      2.700  1.800   1.800 peak       17 weight   0.11000E+01 volume   0.12000E+03 ppm1      3.430 ppm2     7.358
ASSI (   27)
   ( ( segid *AcH * and resid 201 and name HB2  ) )
   ( ( segid *AcH * and resid 201 and name HD1  ) )
      2.700  1.800   1.800 peak       27 weight   0.11000E+01 volume   0.12000E+03 ppm1      3.430 ppm2     7.358
OR (    27)
   ( ( segid *AcH * and resid 201 and name HB1  ) )
   ( ( segid *AcH * and resid 201 and name HD1  ) )
ASSI (   37)
   ( ( segid *AcH * and resid 201 and name HB1  ) )
   ( ( segid *AcH * and resid 201 and name HN   ) )
      2.700  1.800   1.800 peak       37 weight   0.11000E+01 volume   0.12000E+03 ppm1      3.430 ppm2     7.358
OR (    37)
   ( ( segid *AcH * and resid 201 and name HB2  ) )
   ( ( segid *AcH * and resid 201 and name HN   ) )
ASSI (   47)
   ( ( segid *AcH * and resid 201 and name HA2  ) )
   ( ( segid *AcH * and resid 201 and name HN   ) )
      2.700  1.800   1.800 peak       47 weight   0.11000E+01 volume   0.12000E+03 ppm1      3.430 ppm2     7.358
OR (    47)
   ( ( segid *AcH * and resid 201 and name HA1  ) )
   ( ( segid *AcH * and resid 201 and name HN   ) )
```

TABLE 3

Ambiguous NOE-derived Inter-proton Distance Restraints

```
ASSI  {311}
     {{ segid "BrD" and resid 32 and name HN  }}
     {{ segid "BrD" and resid 35 and name HG1}}
        4.200  4.200  1.300 peak      311 weight   0.10000E♦01 volume   0.35526E♦02 ppm1   7.738      ppm2  3.430
OR    {311}
     {{ segid "BrD" and resid 32 and name HN  }}
     {{ segid "BrD" and resid 28 and name HB2}}
ASSI  {391}
     {{ segid "BrD" and resid 106 and name HN  }}
     {  segid "BrD" and resid 105 and name HD1}
        3.100  2.400  2.400 peak      391 weight   0.10000E♦01 volume   0.20417E♦03 ppm1   9.740      ppm2  7.778
OR    {391}
     {{ segid "BrD" and resid 106 and name HN  }}
     {{ segid "BrD" and resid 104 and name HN  }}
OR    {391}
     {{ segid "BrD" and resid 106 and name HN  }}
     {  segid "BrD" and resid 107 and name HD4}
ASSI  {731}
     {{ segid "BrD" and resid 100 and name HN}}
     {{ segid "BrD" and resid 97 and name HA  }}
        3.300  2.700  2.200 peak      731 weight   0.10000E♦01 volume   0.15089E♦02 ppm1   3.671      ppm2  4.801
OR    {731}
     {{ segid "BrD" and resid 100 and name HN}}
     {{ segid "BrD" and resid 98 and name HA  }}
ASSI  {781}
     {{ segid "BrD" and resid 97 and name HN  }}
     {{ segid "BrD" and resid 98 and name HG1}}
        4.000  4.000  1.500 peak      781 weight   0.10000E♦01 volume   0.45845E♦02 ppm1   8.671      ppm2  3.671
OR    {781}
     {{ segid "BrD" and resid 97 and name HN  }}
     {{ segid "BrD" and resid 85 and name HB2}}
ASSI  {831}
     {{ segid "BrD" and resid 96 and name HN  }}
     {{ segid "BrD" and resid 97 and name HB1}}
        3.200  2.600  2.300 peak      831 weight   0.10000E♦01 volume   0.17645E♦02 ppm1   7.977      ppm2  2.728
OR    {831}
     {{ segid "BrD" and resid 78 and name HN  }}
     {{ segid "BrD" and resid 79 and name HB2}}
```

TABLE 3-continued

Ambiguous NOE-derived Inter-proton Distance Restraints

```
OR      {831}
        {{ segid "BrD" and resid 77 and name HN  }}
        {{ segid "BrD" and resid 79 and name HB2}}
OR      {831}
        {{ segid "BrD" and resid 96 and name HN  }}
        {{ segid "BrD" and resid 92 and name HB1}}
OR      {831}
        {{ segid "BrD" and resid 78 and name HN  }}
        {{ segid "BrD" and resid 79 and name HB1}}
ASSI    {1051}
        {{ segid "BrD" and resid 76 and name HN  }}
        {{ segid "BrD" and resid 73 and name HB2}}
           5.000  5.000  0.500 peak     1051 weight    0.10000E+01 volume   0.12021E+02 ppm1  8.612   ppm2  2.497
OR      {1051}
        {{ segid "BrD" and resid 76 and name HN  }}
        {{ segid "BrD" and resid 80 and name HB2}}
ASSI    {1101}
        {{ segid "BrD" and resid 75 and name HN  }}
        {{ segid "BrD" and resid 18 and name HG  }}
           5.500  5.500  0.000 peak     1101 weight    0.10000E+01 volume   0.63178E+01 ppm1  9.107   ppm2  2.294
OR      {1101}
        {{ segid "BrD" and resid 75 and name HN  }}
        {{ segid "BrD" and resid 72 and name HD1}}
OR      {1101}
        {{ segid "BrD" and resid 98 and name HN  }}
        {  segid "BrD" and resid 31 and name HB4 }
ASSI    {1551}
        {{ segid "BrD" and resid 21 and name HN   }}
        {{ segid "BrD" and resid 24 and name HE22}}
           3.400  2.900  2.100 peak     1551 weight    0.10000E+01 volume   0.12608E+03 ppm1  8.544   ppm2  7.515
OR      {1551}
        {{ segid "BrD" and resid 21 and name HN   }}
        {  segid "BrD" and resid 106 and name HD4}
OR      {1551}
        {{ segid "BrD" and resid 109 and name HN  }}
        {  segid "BrD" and resid 106 and name HD4}
OR      {1551}
        {{ segid "BrD" and resid 64 and name HN  }}
        {  segid "BrD" and resid 15 and name HE4}}
ASSI    {1781}
        {{ segid "BrD" and resid 26 and name HN  }}
        {{ segid "BrD" and resid 22 and name HB1}}
           3.400  2.900  2.100 peak     1781 weight    0.10000E+01 volume   0.12549E+03 ppm1  9.196   ppm2  2.672
OR      {1781}
        {{ segid "BrD" and resid 26 and name HN  }}
        {{ segid "BrD" and resid 56 and name HB1}}
ASSI    {2721}
        {{ segid "BrD" and resid 104 and name HN  }}
        {{ segid "BrD" and resid 105 and name HB2}}
           3.300  2.700  2.200 peak     2721 weight    0.10000E+01 volume   0.14753E+03 ppm1  7.763   ppm2  3.671
OR      {2721}
        {{ segid "BrD" and resid 104 and name HN  }}
        {{ segid "BrD" and resid 107 and name HB1}}
OR      {2721}
        {{ segid "BrD" and resid 104 and name HN  }}
        {{ segid "BrD" and resid 106 and name HB2}}
ASSI    {3261}
        {{ segid "BrD" and resid 16 and name HN  }}
        {{ segid "BrD" and resid 13 and name HG2}}
           4.100  4.100  1.400 peak     3261 weight    0.10000E+01 volume   0.35526E+02 ppm1  6.794   ppm2  2.994
OR      {3261}
        {{ segid "BrD" and resid 16 and name HN  }}
        {{ segid "BrD" and resid 11 and name HB1}}
ASSI    {3361}
        {{ segid "BrD" and resid 13 and name HN  }}
        {{ segid "BrD" and resid 13 and name HG1}}
           4.100  4.100  1.300 peak     3361 weight    0.10000E+01 volume   0.40202E+02 ppm1  8.809   ppm2  3.103
OR      {3361}
        {{ segid "BrD" and resid 14 and name HN  }}
        {{ segid "BrD" and resid 13 and name HG1}}
ASSI    {3371}
        {{ segid "BrD" and resid 13 and name HN  }}
        {{ segid "BrD" and resid 13 and name HG2}}
           3.300  2.700  2.200 peak     3371 weight    0.10000E+01 volume   0.14859E+03 ppm1  8.802   ppm2  2.987
OR      {3371}
        {{ segid "BrD" and resid 14 and name HN  }}
        {{ segid "BrD" and resid 13 and name HG2}}
```

TABLE 3-continued

Ambiguous NOE-derived Inter-proton Distance Restraints

```
ASSI    {3401}
        {{ segid "BrD" and resid 13 and name HN }}
        {{ segid "BrD" and resid 11 and name HD1}}
            3.800  3.600  1.700 peak    3401 weight    0.10000E+01 volume   0.67241E+02 ppm1  8.810   ppm2  4.488
OR      {3401}
        {{ segid "BrD" and resid 14 and name HN }}
        {{ segid "BrD" and resid 11 and name HD1}}
OR      {3401}
        {{ segid "BrD" and resid 14 and name HN }}
        {{ segid "BrD" and resid 16 and name HA }}
ASSI    {3671}
        {{ segid "BrD" and resid 102 and name HN }}
        {{ segid "BrD" and resid 30 and name HB1 }}
            3.800  3.600  1.700 peak    3671 weight    0.10000E+01 volume   0.58619E+02 ppm1  9.156   ppm2  4.934
OR      {3671}
        {{ segid "BrD" and resid 102 and name HN }}
        {{ segid "BrD" and resid 100 and name HA }}
ASSI    {3841}
        {{ segid "BrD" and resid 103 and name HN }}
        {{ segid "BrD" and resid 100 and name HA }}
            3.000  2.200  2.200 peak    3841 weight    0.10000E+01 volume   0.24821E+03 ppm1  8.661   ppm2  4.900
OR      {3841}
        {{ segid "BrD" and resid 40 and name HN }}
        {{ segid "BrD" and resid 41 and name HB }}
ASSI    {3911}
        {{ segid "BrD" and resid 59 and name HN }}
        {{ segid "BrD" and resid 57 and name HB1}}
            3.500  3.100  2.000 peak    3911 weight    0.10000E+01 volume   0.98690E+02 ppm1  8.496   ppm2  2.969
OR      {3911}
        {{ segid "BrD" and resid 59 and name HN }}
        {{ segid "BrD" and resid 61 and name HG1}}
OR      {3911}
        {{ segid "BrD" and resid 31 and name HN }}
        {{ segid "BrD" and resid 29 and name HG1}}
OR      {3911}
        {{ segid "BrD" and resid 59 and name HN }}
        {{ segid "BrD" and resid 55 and name HB1}}
ASSI    {4131}
        {{ segid "BrD" and resid 25 and name HN }}
        {{ segid "BrD" and resid 21 and name HB }}
            3.800  3.600  1.700 peak    4131 weight    0.10000E+01 volume   0.59139E+02 ppm1  9.133   ppm2  2.465
OR      {4131}
        {{ segid "BrD" and resid 25 and name HN }}
        {{ segid "BrD" and resid 26 and name HB1}}
ASSI    {6751}
        {{ segid "BrD" and resid 111 and name HN }}
        {{ segid "BrD" and resid 111 and name HD1}}
            3.200  2.600  2.300 peak    6751 weight    0.10000E+01 volume   0.16212E+03 ppm1  8.168   ppm2  2.204
OR      {6751}
        {{ segid "BrD" and resid 111 and name HN }}
        {{ segid "BrD" and resid 109 and name HB2}}
ASSI    {6861}
        {{ segid "BrD" and resid 21 and name HN }}
        {{ segid "BrD" and resid 24 and name HG2}}
            3.400  2.900  2.100 peak    6861 weight    0.10000E+01 volume   0.12194E+03 ppm1  8.574   ppm2  3.072
OR      {6861}
        {{ segid "BrD" and resid 21 and name HN }}
        {{ segid "BrD" and resid 24 and name HG2}}
OR      {6861}
        {{ segid "BrD" and resid 21 and name HN }}
        {{ segid "BrD" and resid 23 and name HB1}}
OR      {6861}
        {{ segid "BrD" and resid 21 and name HN }}
        {{ segid "BrD" and resid 24 and name HB1}}
ASSI    {6871}
        {{ segid "BrD" and resid 21 and name HN }}
        {{ segid "BrD" and resid 22 and name HB1}}
            3.300  2.700  2.200 peak    6871 weight    0.10000E+01 volume   0.15992E+03 ppm1  8.573   ppm2  2.702
OR      {6871}
        {{ segid "BrD" and resid 64 and name HN }}
        {{ segid "BrD" and resid 61 and name HB1}}
OR      {6871}
        {{ segid "BrD" and resid 109 and name HN }}
        {{ segid "BrD" and resid 112 and name HB1}}
OR      {6871}
        {{ segid "BrD" and resid 64 and name HN }}
        {{ segid "BrD" and resid 22 and name HG1}}
```

TABLE 3-continued

Ambiguous NOE-derived Inter-proton Distance Restraints

```
ASSI    {6911}
        {{ segid "BrD" and resid 86 and name HN  }}
        {{ segid "BrD" and resid 86 and name HE1}}
            3.700  3.400  1.800 peak     6911 weight    0.10000E+01 volume  0.78171E+02 ppm1  8.423    ppm2  3.044
OR      {6911}
        {{ segid "BrD" and resid 86 and name HN  }}
        {{ segid "BrD" and resid 87 and name HG1}}
ASSI    {7031}
        {{ segid "BrD" and resid 92 and name HN  }}
        {{ segid "BrD" and resid 80 and name HN  }}
            4.200  4.200  1.300 peak     7031 weight    0.10000E+01 volume  0.35356E+02 ppm1  9.003    ppm2  7.979
OR      {7031}
        {{ segid "BrD" and resid 52 and name HN  }}
        {{ segid "BrD" and resid 77 and name HN  }}
OR      {7031}
        {{ segid "BrD" and resid 52 and name HN  }}
        {{ segid "BrD" and resid 47 and name HD1}}
ASSI    {7121}
        {{ segid "BrD" and resid 89 and name HD21}}
        {{ segid "BrD" and resid 85 and name HA   }}
            3.700  3.400  1.800 peak     7121 weight    0.10000E+01 volume  0.76700E+02 ppm1  8.923    ppm2  5.021
OR      {7121}
        {{ segid "BrD" and resid 89 and name HD21}}
        {{ segid "BrD" and resid 93 and name HB1  }}
ASSI    {7131}
        {{ segid "BrD" and resid 89 and name HD22}}
        {{ segid "BrD" and resid 85 and name HA   }}
            3.600  3.200  1.900 peak     7131 weight    0.10000E+01 volume  0.84076E+02 ppm1  8.416    ppm2  5.021
OR      {7131}
        {{ segid "BrD" and resid 89 and name HD22}}
        {{ segid "BrD" and resid 93 and name HB1  }}
ASSI    {7251}
        {{ segid "BrD" and resid 26 and name HN   }}
        {  segid "BrD" and resid 22 and name HD24 }
            3.00   2.200  2.200 peak     7251 weight    0.10000E+01 volume  0.24489E+03 ppm1  9.196    ppm2  1.549
OR      {7251}
        {{ segid "BrD" and resid 26 and name HN   }}
        {  segid "BrD" and resid 56 and name HD14}
ASSI    {8181}
        {{ segid "BrD" and resid 57 and name HN   }}
        {  segid "BrD" and resid 25 and name HG24}
            4.100  4.100  1.400 peak     8181 weight    0.10000E+01 volume  0.42960E+02 ppm1  9.359    ppm2  1.667
OR      {8181}
        {{ segid "BrD" and resid 57 and name HN   }}
        {  segid "BrD" and resid 58 and name HG24}
OR      {8181}
        {{ segid "BrD" and resid 57 and name HN   }}
        {  segid "BrD" and resid 22 and name HD14}
ASSI    {8211}
        {{ segid "BrD" and resid 114 and name HN }}
        {{ segid "BrD" and resid 111 and name HB2}}
            4.000  4.000  1.500 peak     8211weight     0.10000E+01 volume  0.47918E+02 ppm1  8.377    ppm2  2.377
OR      {8211}
        {{ segid "BrD" and resid 114 and name HN }}
        {{ segid "BrD" and resid 110 and name HB }}
ASSI    {8261}
        {{ segid "BrD" and resid 28 and name HN }}
        {{ segid "BrD" and resid 25 and name HB }}
            4.200  4.200  1.300 peak     8261 weight    0.10000E+01 volume  0.36987E+02 ppm1  8.166    ppm2  3.014
OR      {8261}
        {{ segid "BrD" and resid 28 and name HN }}
        {{ segid "BrD" and resid 29 and name HG1}}
ASSI    {8291}
        {{ segid "BrD" and resid 28 and name HN   }}
        {{ segid "BrD" and resid 25 and name HG24}}
            4.400  4.400  1.100 peak     8291 weight    0.10000E+01 volume  0.24897E+02 ppm1  8.164    ppm2  1.639
OR      {8291}
        {{ segid "BrD" and resid 28 and name HN   }}
        {{ segid "BrD" and resid 26 and name HG24}}
ASSI    {8381}
        {{ segid "BrD" and resid 61 and name HN  }}
        {  segid "BrD" and resid 58 and name HG1 }}
            3.400  2.900  2.100 peak     8381 weight    0.10000E+01 volume  0.13119E+03 ppm1  8.743    ppm2  1.674
OR      {8381}
        {{ segid "BrD" and resid 61 and name HN   }}
        {  segid "BrD" and resid 22 and name HD14}}
```

TABLE 3-continued

Ambiguous NOE-derived Inter-proton Distance Restraints

| | | | | | | | | | | | |
|---|---|---|---|---|---|---|---|---|---|---|---|
| OR | {8381} | | | | | | | | | | |
| | {{ segid "BrD" and resid 38 and name HN }} | | | | | | | | | | |
| | { segid "BrD" and resid 43 and name HB4}} | | | | | | | | | | |
| ASSI | {8391} | | | | | | | | | | |
| | {{ segid "BrD" and resid 38 and name HN }} | | | | | | | | | | |
| | {{ segid "BrD" and resid 39 and name HG1}} | | | | | | | | | | |
| | 4.000 4.000 1.900 peak 8391 weight | 0.10000E+01 volume | 0.49211E+02 ppm1 8.743 | ppm2 2.008 | | | | | | | |
| OR | {8391} | | | | | | | | | | |
| | {{ segid "BrD" and resid 61 and name HN }} | | | | | | | | | | |
| | {{ segid "BrD" and resid 57 and name HG2}} | | | | | | | | | | |
| ASSI | {8511} | | | | | | | | | | |
| | {{ segid "BrD" and resid 50 and name HN }} | | | | | | | | | | |
| | {{ segid "BrD" and resid 53 and name HG1}} | | | | | | | | | | |
| | 3.700 3.400 1.800 peak 8511weight | 0.10000E+01 volume | 0.70210E+02 ppm1 8.564 | ppm2 2.814 | | | | | | | |
| OR | {8511} | | | | | | | | | | |
| | {{ segid "BrD" and resid 50 and name HN }} | | | | | | | | | | |
| | {{ segid "BrD" and resid 53 and name HB1}} | | | | | | | | | | |
| OR | {8511} | | | | | | | | | | |
| | {{ segid "BrD" and resid 50 and name HN }} | | | | | | | | | | |
| | {{ segid "BrD" and resid 87 and name HB1}} | | | | | | | | | | |
| OR | {8511} | | | | | | | | | | |
| | {{ segid "BrD" and resid 46 and name HN }} | | | | | | | | | | |
| | {{ segid "BrD" and resid 83 and name HG1}} | | | | | | | | | | |
| OR | {8511} | | | | | | | | | | |
| | {{ segid "BrD" and resid 44 and name HN }} | | | | | | | | | | |
| | {{ segid "BrD" and resid 53 and name HB1}} | | | | | | | | | | |
| ASSI | {8751} | | | | | | | | | | |
| | {{ segid "BrD" and resid 58 and name HN }} | | | | | | | | | | |
| | {{ segid "BrD" and resid 37 and name HG1}} | | | | | | | | | | |
| | 3.400 2.900 2.100 peak 8751 weight | 0.10000E+01 volume | 0.12911E+03 ppm1 10.051 | ppm2 2.747 | | | | | | | |
| OR | {8751} | | | | | | | | | | |
| | {{ segid "BrD" and resid 58 and name HN }} | | | | | | | | | | |
| | { segid "BrD" and resid 35 and name HE4}} | | | | | | | | | | |
| ASSI | {8861} | | | | | | | | | | |
| | {{ segid "BrD" and resid 9 and name HN }} | | | | | | | | | | |
| | {{ segid "BrD" and resid 8 and name HG1}} | | | | | | | | | | |
| | 3.400 3.200 1.900 peak 8841 weight | 0.10000E+01 volume | 0.86153E+02 ppm1 9.052 | ppm2 2.631 | | | | | | | |
| OR | {8861} | | | | | | | | | | |
| | {{ segid "BrD" and resid 9 and name HN }} | | | | | | | | | | |
| | {{ segid "BrD" and resid 7 and name HB1}} | | | | | | | | | | |
| ASSI | {8891} | | | | | | | | | | |
| | {{ segid "BrD" and resid 103 and name HN }} | | | | | | | | | | |
| | {{ segid "BrD" and resid 100 and name HA }} | | | | | | | | | | |
| | 4.000 4.000 1.500 peak 8891 weight | 0.10000E+01 volume | 0.44524E+02 ppm1 8.668 | ppm2 4.917 | | | | | | | |
| OR | {8891} | | | | | | | | | | |
| | {{ segid "BrD" and resid 112 and name HN }} | | | | | | | | | | |
| | {{ segid "BrD" and resid 113 and name HA }} | | | | | | | | | | |
| ASSI | {8901} | | | | | | | | | | |
| | {{ segid "BrD" and resid 112 and name HN }} | | | | | | | | | | |
| | {{ segid "BrD" and resid 108 and name HA }} | | | | | | | | | | |
| | 3.400 2.900 2.100 peak 8901 weight | 0.10000E+01 volume | 0.11279E+03 ppm1 8.668 | ppm2 4.805 | | | | | | | |
| OR | {8901} | | | | | | | | | | |
| | {{ segid "BrD" and resid 103 and name HN}} | | | | | | | | | | |
| | {{ segid "BrD" and resid 82 and name HA }} | | | | | | | | | | |
| OR | {8901} | | | | | | | | | | |
| | {{ segid "BrD" and resid 103 and name HN}} | | | | | | | | | | |
| | {{ segid "BrD" and resid 98 and name HA }} | | | | | | | | | | |
| ASSI | {8911} | | | | | | | | | | |
| | {{ segid "BrD" and resid 102 and name HN}} | | | | | | | | | | |
| | {{ segid "BrD" and resid 99 and name HA }} | | | | | | | | | | |
| | 3.500 3.100 2.000 peak 8911 weight | 0.10000E+01 volume | 0.10762E+03 ppm1 8.668 | ppm2 4.426 | | | | | | | |
| OR | {8911} | | | | | | | | | | |
| | {{ segid "BrD" and resid 112 and name HN }} | | | | | | | | | | |
| | {{ segid "BrD" and resid 110 and name HA }} | | | | | | | | | | |
| ASSI | {8941} | | | | | | | | | | |
| | {{ segid "BrD" and resid 103 and name HN }} | | | | | | | | | | |
| | { segid "BrD" and resid 99 and name HB4 } | | | | | | | | | | |
| | 2.900 2.100 2.100 peak 8941 weight | 0.10000E+01 volume | 0.29817E+03 ppm1 8.667 | ppm2 2.178 | | | | | | | |
| OR | {8941} | | | | | | | | | | |
| | {{ segid "BrD" and resid 103 and name HN }} | | | | | | | | | | |
| | {{ segid "BrD" and resid 102 and name HG }} | | | | | | | | | | |
| OR | {8941} | | | | | | | | | | |
| | {{ segid "BrD" and resid 112 and name HN }} | | | | | | | | | | |
| | {{ segid "BrD" and resid 109 and name HB2}} | | | | | | | | | | |
| ASSI | {9011} | | | | | | | | | | |
| | {{ segid "BrD" and resid 105 and name HN }} | | | | | | | | | | |
| | {{ segid "BrD" and resid 104 and name HD1}} | | | | | | | | | | |
| | 3.100 2.400 2.400 peak 9011 weight | 0.10000E+01 volume | 0.22428E+03 ppm1 8.487 | ppm2 2.294 | | | | | | | |

TABLE 3-continued

Ambiguous NOE-derived Inter-proton Distance Restraints

| | | | | | | | | | | | | |
|---|---|---|---|---|---|---|---|---|---|---|---|---|
| OR | {9011} | | | | | | | | | | | |
| | {{ segid "BrD" and resid 105 and name HN }} | | | | | | | | | | | |
| | {{ segid "BrD" and resid 103 and name HB1}} | | | | | | | | | | | |
| ASSI | {9031} | | | | | | | | | | | |
| | {{ segid "BrD" and resid 105 and name HN }} | | | | | | | | | | | |
| | {{ segid "BrD" and resid 102 and name HB2}} | | | | | | | | | | | |
| | 3.800 | 3.600 | 1.700 peak | 9031 weight | 0.10000E♦01 volume | 0.62331E♦02 ppm1 | 8.487 | ppm2 | 1.809 | | | |
| OR | {9031} | | | | | | | | | | | |
| | {{ segid "BrD" and resid 109 and name HN }} | | | | | | | | | | | |
| | { segid "BrD" and resid 25 and name HG14} | | | | | | | | | | | |
| ASSI | {9091} | | | | | | | | | | | |
| | {{ segid "BrD" and resid 109 and name HN }} | | | | | | | | | | | |
| | {{ segid "BrD" and resid 106 and name HB2}} | | | | | | | | | | | |
| | 3.800 | 3.600 | 1.700 peak | 9091 weight | 0.10000E♦01 volume | 0.64318E♦02 ppm1 | 8.574 | ppm2 | 3.678 | | | |
| OR | {9091} | | | | | | | | | | | |
| | {{ segid "BrD" and resid 109 and name HN }} | | | | | | | | | | | |
| | {{ segid "BrD" and resid 107 and name HB1}} | | | | | | | | | | | |
| OR | {9091} | | | | | | | | | | | |
| | {{ segid "BrD" and resid 109 and name HN }} | | | | | | | | | | | |
| | {{ segid "BrD" and resid 105 and name HB21}} | | | | | | | | | | | |
| OR | {9091} | | | | | | | | | | | |
| | {{ segid "BrD" and resid 64 and name HN }} | | | | | | | | | | | |
| | {{ segid "BrD" and resid 68 and name HB1}} | | | | | | | | | | | |
| ASSI | {9101} | | | | | | | | | | | |
| | {{ segid "BrD" and resid 64 and name HN }} | | | | | | | | | | | |
| | {{ segid "BrD" and resid 63 and name HB2}} | | | | | | | | | | | |
| | 2.900 | 2.100 | 2.100 peak | 9101 weight | 0.10000E♦01 volume | 0.30416E♦03 ppm1 | 8.573 | ppm2 | 2.498 | | | |
| OR | {9101} | | | | | | | | | | | |
| | {{ segid "BrD" and resid 21 and name HN }} | | | | | | | | | | | |
| | {{ segid "BrD" and resid 21 and name HB }} | | | | | | | | | | | |
| ASSI | {9111} | | | | | | | | | | | |
| | {{ segid "BrD" and resid 21 and name HN }} | | | | | | | | | | | |
| | {{ segid "BrD" and resid 17 and name HG24}} | | | | | | | | | | | |
| | 3.500 | 3.100 | 2.000 peak | 9111 weight | 0.10000E♦01 volume | 0.10029E♦03 ppm1 | 8.574 | ppm2 | 1.725 | | | |
| OR | {9111} | | | | | | | | | | | |
| | {{ segid "BrD" and resid 109 and name HN }} | | | | | | | | | | | |
| | { segid "BrD" and resid 17 and name HG24} | | | | | | | | | | | |
| ASSI | {9161} | | | | | | | | | | | |
| | {{ segid "BrD" and resid 106 and name HN }} | | | | | | | | | | | |
| | {{ segid "BrD" and resid 104 and name HB1}} | | | | | | | | | | | |
| | 3.900 | 3.800 | 1.600 peak | 9161 weight | 0.10000E♦01 volume | 0.56197E♦02 ppm1 | 9.740 | ppm2 | 2.560 | | | |
| OR | {9161} | | | | | | | | | | | |
| | {{ segid "BrD" and resid 106 and name HN }} | | | | | | | | | | | |
| | {{ segid "BrD" and resid 103 and name HG2}} | | | | | | | | | | | |
| ASSI | {9171} | | | | | | | | | | | |
| | {{ segid "BrD" and resid 106 and name HN }} | | | | | | | | | | | |
| | {{ segid "BrD" and resid 109 and name HB1}} | | | | | | | | | | | |
| | 4.000 | 4.000 | 1.500 peak | 9171 weight | 0.10000E♦01 volume | 0.47299E♦02 ppm1 | 9.739 | ppm2 | 2.318 | | | |
| OR | {9171} | | | | | | | | | | | |
| | {{ segid "BrD" and resid 106 and name HN }} | | | | | | | | | | | |
| | {{ segid "BrD" and resid 103 and name HB1}} | | | | | | | | | | | |
| OR | {9171} | | | | | | | | | | | |
| | {{ segid "BrD" and resid 106 and name HN }} | | | | | | | | | | | |
| | {{ segid "BrD" and resid 104 and name HD1}} | | | | | | | | | | | |
| OR | {9171} | | | | | | | | | | | |
| | {{ segid "BrD" and resid 106 and name HN }} | | | | | | | | | | | |
| | {{ segid "BrD" and resid 21 and name HG11}} | | | | | | | | | | | |
| ASSI | {9181} | | | | | | | | | | | |
| | {{ segid "BrD" and resid 106 and name HN }} | | | | | | | | | | | |
| | {{ segid "BrD" and resid 102 and name HG }} | | | | | | | | | | | |
| | 4.100 | 4.100 | 1.400 peak | 9181 weight | 0.10000E♦01 volume | 0.40041E♦02 ppm1 | 9.742 | ppm2 | 2.150 | | | |
| OR | {9181} | | | | | | | | | | | |
| | {{ segid "BrD" and resid 106 and name HN }} | | | | | | | | | | | |
| | {{ segid "BrD" and resid 109 and name HB2}} | | | | | | | | | | | |
| ASSI | {9191} | | | | | | | | | | | |
| | {{ segid "BrD" and resid 106 and name HN }} | | | | | | | | | | | |
| | {{ segid "BrD" and resid 102 and name HB1}} | | | | | | | | | | | |
| | 4.200 | 4.200 | 1.300 peak | 9191 weight | 0.10000E♦01 volume | 0.35794E♦02 ppm1 | 9.740 | ppm2 | 2.002 | | | |
| OR | {9191} | | | | | | | | | | | |
| | {{ segid "BrD" and resid 106 and name HN }} | | | | | | | | | | | |
| | {{ segid "BrD" and resid 109 and name HD1}} | | | | | | | | | | | |
| ASSI | {9201} | | | | | | | | | | | |
| | {{ segid "BrD" and resid 106 and name HN }} | | | | | | | | | | | |
| | {{ segid "BrD" and resid 102 and name HG1}} | | | | | | | | | | | |
| | 3.900 | 3.800 | 1.600 peak | 9201 weight | 0.10000E♦01 volume | 0.56492E♦02 ppm1 | 9.739 | ppm2 | 1.786 | | | |
| OR | {9201} | | | | | | | | | | | |
| | {{ segid "BrD" and resid 106 and name HN }} | | | | | | | | | | | |
| | { segid "BrD" and resid 25 and name HG14}} | | | | | | | | | | | |

TABLE 3-continued

Ambiguous NOE-derived Inter-proton Distance Restraints

```
ASSI    {9241}
        {{ segid "BrD" and resid 84 and name HN }}
        {{ segid "BrD" and resid 80 and name HD2}}
            3.700  3.400  1.800 peak    9241 weight    0.10000E+01 volume  0.69670E+02 ppm1  9.464    ppm2  3.908
OR      {9241}
        {{ segid "BrD" and resid 84 and name HN }}
        {{ segid "BrD" and resid 85 and name HB1}}
ASSI    {9251}
        {{ segid "BrD" and resid 42 and name HN }}
        {{ segid "BrD" and resid 42 and name HG1}}
            3.700  3.400  1.800 peak    9251 weight    0.10000E+01 volume  0.78060E+02 ppm1  9.463    ppm2  2.352
OR      {9251}
        {{ segid "BrD" and resid 84 and name HN }}
        {{ segid "BrD" and resid 80 and name HG1}}
OR      {9251}
        {{ segid "BrD" and resid 84 and name HN }}
        {{ segid "BrD" and resid 86 and name HB1}}
ASSI    {9281}
        {{ segid "BrD" and resid 80 and name HN }}
        {{ segid "BrD" and resid 84 and name HN }}
            3.300  2.700  2.200 peak    9281 weight    0.10000E+01 volume  0.13642E+03 ppm1  9.462    ppm2  8.001
OR      {9281}
        {{ segid "BrD" and resid 84 and name HN }}
        {{ segid "BrD" and resid 107 and name HZ}}
OR      {9281}
        {{ segid "BrD" and resid 63 and name HN }}
        {{ segid "BrD" and resid 70 and name HN }}
ASSI    {9311}
        {{ segid "BrD" and resid 22 and name HN }}
        {{ segid "BrD" and resid 22 and name HA }}
            4.200  4.200  1.300 peak    9311 weight    0.10000E+01 volume  0.39671E+02 ppm1  9.472    ppm2  4.678
OR      {9311}
        {{ segid "BrD" and resid 84 and name HN }}
        {{ segid "BrD" and resid 80 and name HA }}
ASSI    {9341}
        {{ segid "BrD" and resid 63 and name HN }}
        { segid "BrD" and resid 74 and name HE4}
            2.900  2.100  2.100 peak    9341 weight    0.10000E+01 volume  0.30219E+03 pmm1  9.456    ppm2  7.530
OR      {9341}
        {{ segid "BrD" and resid 22 and name HN }}
        { segid "BrD" and resid 104 and name HD4}
ASSI    {9371}
        {{ segid "BrD" and resid 22 and name HN }}
        {{ segid "BrD" and resid 24 and name HG2}}
            3.400  2.900  2.100 peak    9371 weight    0.10000E+01 volume  0.12105E+03 ppm1  9.456    ppm2  3.066
OR      {9371}
        {{ segid "BrD" and resid 22 and name HN }}
        {{ segid "BrD" and resid 23 and name HG2}}
OR      {9371}
        {{ segid "BrD" and resid 63 and name HN }}
        {{ segid "BrD" and resid 59 and name HG2}}
ASSI    {9441}
        {{ segid "BrD" and resid 109 and name HN }}
        {{ segid "BrD" and resid 109 and name HB2}}
            3.900  3.800  1.600 peak    9441 weight    0.10000E+01 volume  0.55505E+02 ppm1  8.557    ppm2  2.173
OR      {9441}
        {{ segid "BrD" and resid 64 and name HN }}
        {{ segid "BrD" and resid 64 and name HG1}}
ASSI    {9451}
        {{ segid "BrD" and resid 21 and name HN }}
        {{ segid "BrD" and resid 24 and name HG2}}
            3.900  3.800  1.600 peak    9451 weight    0.10000E+01 volume  0.53501E+02 ppm1  8.556    ppm2  3.108
OR      {9451}
        {{ segid "BrD" and resid 21 and name HN }}
        {{ segid "BrD" and resid 24 and name HB2}}
OR      {9451}
        {{ segid "BrD" and resid 21 and name HN }}
        {{ segid "BrD" and resid 23 and name HG1}}
OR      {9451}
        {{ segid "BrD" and resid 21 and name HN }}
        {{ segid "BrD" and resid 24 and name HB1}}
ASSI    {9461}
        {{ segid "BrD" and resid 64 and name HN }}
        {{ segid "BrD" and resid 61 and name HB1}}
            3.700  3.400  1.800 peak    9461 weight    0.10000E+01 volume  0.72347E+02 ppm1  8.544    ppm2  2.891
OR      {9461}
        {{ segid "BrD" and resid 21 and name HN }}
        {{ segid "BrD" and resid 23 and name HB2}}
```

TABLE 3-continued

Ambiguous NOE-derived Inter-proton Distance Restraints

```
ASSI  {9491}
      {{ segid "BrD" and resid 21 and name HN  }}
      {{ segid "BrD" and resid 19 and name HB2}}
          3.300  2.700  2.200 peak     9491 weight    0.10000E+01 volume  0.14127E+03 ppm1  8.556    ppm2  1.929
OR    {9491}
      {{ segid "BrD" and resid 109 and name HN  }}
      {{ segid "BrD" and resid 111 and name HG2}}
OR    {9491}
      {{ segid "BrD" and resid 109 and name HN  }}
      {  segid "BrD" and resid 113 and name HB4}
OR    {9491}
      {{ segid "BrD" and resid 64 and name HN  }}
      {{ segid "BrD" and resid 19 and name HB2}}
ASSI  {9501}
      {{ segid "BrD" and resid 21 and name HN    }}
      {  segid "BrD" and resid 17 and name HG24}
          3.300  2.700  2.200 peak     9501 weight    0.10000E+01 volume  0.14396E+03 ppm1  8.556    ppm2  1.762
OR    {9501}
      {{ segid "BrD" and resid 109 and name HN  }}
      {  segid "BrD" and resid 17 and name HG24}
OR    {9501}
      {{ segid "BrD" and resid 21 and name HN    }}
      {  segid "BrD" and resid 25 and name HG14}
ASSI  {9531}
      {{ segid "BrD" and resid 17 and name HN }}
      {{ segid "BrD" and resid 13 and name HA }}
          3.600  3.200  1.900 peak     9531 weight    0.10000E+01 volume  0.86367E+02 ppm1  8.695    ppm2  4.805
OR    {9531}
      {{ segid "BrD" and resid 112 and name HN }}
      {{ segid "BrD" and resid 106 and name HA }}
OR    {9531}
      {{ segid "BrD" and resid 103 and name HN}}
      {{ segid "BrD" and resid 82 and name HA  }}
ASSI  {9561}
      {{ segid "BrD" and resid 103 and name HN }}
      {{ segid "BrD" and resid 106 and name HB2}}
          3.300  2.700  2.200 peak     9561 weight    0.10000E+01 volume  0.15504E+03 ppm1  8.694    ppm2  3.641
OR    {9561}
      {{ segid "BrD" and resid 103 and name HN }}
      {{ segid "BrD" and resid 82 and name HB1 }}
OR    {9561}
      {{ segid "BrD" and resid 103 and name HN }}
      {{ segid "BrD" and resid 105 and name HB2}}
OR    {9561}
      {{ segid "BrD" and resid 103 and name HN }}
      {{ segid "BrD" and resid 107 and name HB1}}
ASSI  {9631}
      {{ segid "BrD" and resid 99 and name HN  }}
      {{ segid "BrD" and resid 100 and name HA}}
          3.900  3.800  1.600 peak     9631 weight    0.10000E+01 volume  0.94041E+02 pmm1  6.936    ppm2  4.947
OR    {9631}
      {{ segid "BrD" and resid 99 and name HN  }}
      {{ segid "BrD" and resid 30 and name HB1}}
ASSI  {9641}
      {{ segid "BrD" and resid 99 and name HN     }}
      {{ segid "BrD" and resid 101 and name HG11}}
          3.900  3.800  1.600 peak     9641 weight    0.10000E+01 volume  0.56248E+02 ppm1  8.935    ppm2  2.460
OR    {9641}
      {{ segid "BrD" and resid 99 and name HN  }}
      {{ segid "BrD" and resid 97 and name HG1}}
ASSI  {9651}
      {{ segid "BrD" and resid 99 and name HN    }}
      {{ segid "BrD" and resid 103 and name HB2}}
          5.500  5.900  0.000 peak     9651 weight    0.10000E+01 volume  0.57216E+02 ppm1  8.936    ppm2  1.920
OR    {9651}
      {{ segid "BrD" and resid 99 and name HN  }}
      {{ segid "BrD" and resid 86 and name HG1}}
ASSI  {9721}
      {{ segid "BrD" and resid 64 and name HN  }}
      {{ segid "BrD" and resid 64 and name HE1}}
          4.000  4.000  1.900 peak     9721 weight    0.10000E+01 volume  0.46621E+02 ppm1  8.586    ppm2  3.626
OR    {9721}
      {{ segid "BrD" and resid 64 and name HN  }}
      {{ segid "BrD" and resid 65 and name HB1}}
ASSI  {9731}
      {{ segid "BrD" and resid 21 and name HN     }}
      {{ segid "BrD" and resid 109 and name HE1}}
          3.800  3.600  1.700 peak     9731 weight    0.10000E+01 volume  0.59335E+02 ppm1  8.584    ppm2  3.146
```

TABLE 3-continued

Ambiguous NOE-derived Inter-proton Distance Restraints

| | |
|---|---|
| OR | {9731} |
| | {{ segid "BrD" and resid 21 and name HN }} |
| | {{ segid "BrD" and resid 23 and name HG1}} |
| ASSI | {9801} |
| | {{ segid "BrD" and resid 103 and name HN }} |
| | {{ segid "BrD" and resid 106 and name HB2}} |
| | 4.600  4.600  0.900 peak   9801 weight   0.10000E♦01 volume   0.19838E♦02 ppm1  8.669   ppm2  3.659 |
| OR | {9801} |
| | {{ segid "BrD" and resid 17 and name HN }} |
| | {{ segid "BrD" and resid 15 and name HB2}} |
| OR | {9801} |
| | {{ segid "BrD" and resid 103 and name HN }} |
| | {{ segid "BrD" and resid 82 and name HB1 }} |
| OR | {9801} |
| | {{ segid "BrD" and resid 103 and name HN }} |
| | {{ segid "BrD" and resid 105 and name HB2}} |
| ASSI | {9821} |
| | {{ segid "BrD" and resid 17 and name HN }} |
| | {{ segid "BrD" and resid 13 and name HG2}} |
| | 3.700  3.400  1.800 peak   9821 weight   0.10000E♦01 volume   0.70791E♦02 ppm1  8.668   ppm2  2.943 |
| OR | {9821} |
| | {{ segid "BrD" and resid 17 and name HN }} |
| | {{ segid "BrD" and resid 11 and name HB1}} |
| ASSI | {9831} |
| | {{ segid "BrD" and resid 17 and name HN }} |
| | {{ segid "BrD" and resid 18 and name HG }} |
| | 3.000  2.200  2.200 peak   9831 weight   0.10000E♦01 volume   0.24267E♦03 ppm1  8.669   ppm2  2.284 |
| OR | {9831} |
| | {{ segid "BrD" and resid 40 and name HN }} |
| | {{ segid "BrD" and resid 39 and name HD1}} |
| OR | {9831} |
| | {{ segid "BrD" and resid 103 and name HN }} |
| | {{ segid "BrD" and resid 104 and name HD1}} |
| ASSI | {9841} |
| | {{ segid "BrD" and resid 103 and name HN }} |
| | {{ segid "BrD" and resid 104 and name HB1}} |
| | 4.500  4.500  1.000 peak   9841 weight   0.10000E♦01 volume   0.24419E♦02 ppm1  8.669   ppm2  1.973 |
| OR | {9841} |
| | {{ segid "BrD" and resid 17 and name   HN}} |
| | {  segid "BrD" and resid 113 and name HB4} |
| ASSI | {9861} |
| | {{ segid "BrD" and resid 17 and name HN }} |
| | {{ segid "BrD" and resid 14 and name HB2}} |
| | 3.500  3.100  2.000 peak   9861 weight   0.10000E♦01 volume   0.99899E♦02 ppm1  8.668   ppm2  2.125 |
| OR | {9861} |
| | {{ segid "BrD" and resid 17 and name HN }} |
| | {{ segid "BrD" and resid 18 and name HB1}} |
| OR | {9861} |
| | {{ segid "BrD" and resid 103 and name HN }} |
| | {{ segid "BrD" and resid 104 and name HG1}} |
| ASSI | {10081} |
| | {{ segid "BrD" and resid 24 and name HN }} |
| | {{ segid "BrD" and resid 21 and name HB }} |
| | 4.300  4.300  1.200 peak   10081 weight   0.10000E♦01 volume   0.28058E♦02 ppm1  8.666   ppm2  2.481 |
| OR | {10061} |
| | {{ segid "BrD" and resid 24 and name HN }} |
| | {{ segid "BrD" and resid 26 and name HB1}} |
| ASSI | {10181} |
| | {{ segid "BrD" and resid 16 and name HN }} |
| | {{ segid "BrD" and resid 14 and name HB2}} |
| | 4.100  4.100  1.400 peak   10181 weight   0.10000E♦01 volume   0.40626E♦02 ppm1  8.785   ppm2  2.129 |
| OR | {10181} |
| | {{ segid "BrD" and resid 16 and name HN }} |
| | {{ segid "BrD" and resid 18 and name HB1}} |
| ASSI | {10201} |
| | {{ segid "BrD" and resid 16 and name HN }} |
| | {{ segid "BrD" and resid 19 and name HB2}} |
| | 3.900  3.800  1.600 peak   10201 weight   0.10000E♦01 volume   0.57921E♦02 ppm1  8.791   ppm2  1.963 |
| OR | {10201} |
| | {{ segid "BrD" and resid 16 and name HN }} |
| | {  segid "BrD" and resid 113 and name HB1} |
| ASSI | {10241} |
| | {{ segid "BrD" and resid 75 and name HN }} |
| | {{ segid "BrD" and resid 78 and name HB1}} |
| | 3.900  3.800  1.600 peak   10241 weight   0.10000E♦01 volume   0.50050E♦02 ppm1  9.106   ppm2  1.347 |
| OR | {10241} |
| | {{ segid "BrD" and resid 75 and name HN   }} |
| | {  segid "BrD" and resid 115 and name HD14} |

TABLE 3-continued

Ambiguous NOE-derived Inter-proton Distance Restraints

```
ASSI  {10281}
      {{ segid "BrD" and resid 98 and name HN  }}
      {{ segid "BrD" and resid 97 and name HG1}}
         4.000  4.000  1.500 peak    10281 weight   0.10000E♦01 volume  0.43323E♦02 ppm1  9.106   ppm2 2.456
OR    {10281}
      {{ segid "BrD" and resid 98 and name HN  }}
      {{ segid "BrD" and resid 97 and name HD1}}
OR    {10281}
      {{ segid "BrD" and resid 98 and name HN    }}
      {{ segid "BrD" and resid 101 and name HG11}}
ASSI  {10331}
      {{ segid "BrD" and resid 96 and name HN  }}
      {{ segid "BrD" and resid 97 and name HG1}}
         3.900  3.800  1.600 peak    10331 weight   0.10000E♦01 volume  0.52289E♦02 ppm1  7.977   ppm2 2.412
OR    {10331}
      {{ segid "BrD" and resid 77 and name HN  }}
      {{ segid "BrD" and resid 73 and name HG  }}
OR    {10331}
      {{ segid "BrD" and resid 96 and name HN  }}
      {{ segid "BrD" and resid 97 and name HD1}}
OR    {10331}
      {{ segid "BrD" and resid 77 and name HN  }}
      {{ segid "BrD" and resid 72 and name HB1}}
ASSI  {10381}
      {{ segid "BrD" and resid 78 and name HN    }}
      {{ segid "BrD" and resid 116 and name HG11}}
         3.900  3.800  1.600 peak    10381 weight   0.10000E♦01 volume  0.51654E♦02 ppm1  7.996   ppm2 1.888
OR    {10381}
      {{ segid "BrD" and resid 77 and name HN    }}
      {{ segid "BrD" and resid 116 and name HG11}}
ASSI  {10391}
      {{ segid "BrD" and resid 78 and name HN   }}
      {  segid "BrD" and resid 22 and name HD24}
         3.500  3.100  2.000 peak    10391 weight   0.10000E♦01 volume  0.99200E♦02 ppm1  7.996   ppm2 1.604
OR    {10391}
      {{ segid "BrD" and resid 55 and name HN   }}
      {  segid "BrD" and resid 22 and name HD24}
OR    {10391}
      {{ segid "BrD" and resid 78 and name HN   }}
      {  segid "BrD" and resid 29 and name HG24}
OR    {10391}
      {{ segid "BrD" and resid 77 and name HN   }}
      {  segid "BrD" and resid 22 and name HD24}
OR    {10391}
      {{ segid "BrD" and resid 55 and name HN   }}
      {  segid "BrD" and resid 25 and name HG24}
ASSI  {10411}
      {{ segid "BrD" and resid 77 and name HN  }}
      {{ segid "BrD" and resid 80 and name HB2}}
         2.800  2.000  2.000 peak    10411 weight   0.10000E♦01 volume  0.43395E♦03 ppm1  7.996   ppm2 2.456
OR    {10411}
      {{ segid "BrD" and resid 78 and name HN  }}
      {{ segid "BrD" and resid 80 and name HB2}}
ASSI  {10431}
      {{ segid "BrD" and resid 55 and name HN  }}
      {{ segid "BrD" and resid 37 and name HG1}}
         2.600  1.700  1.700 peak    10431 weight   0.10000E♦01 volume  0.60264E♦03 ppm1  7.996   ppm2 2.722
OR    {10431}
      {{ segid "BrD" and resid 78 and name HN  }}
      {{ segid "BrD" and resid 79 and name HB2}}
ASSI  {10471}
      {{ segid "BrD" and resid 96 and name HN }}
      {{ segid "BrD" and resid 94 and name HA }}
         3.900  3.800  1.600 peak    10471 weight   0.10000E♦01 volume  0.5287E♦02  ppm1  7.984   ppm2 4.814
OR    {10471}
      {{ segid "BrD" and resid 96 and name HN }}
      {{ segid "BrD" and resid 84 and name HA }}
OR    {10471}
      {{ segid "BrD" and resid 96 and name HN }}
      {{ segid "BrD" and resid 92 and name HA }}
ASSI  {10501}
      {{ segid "BrD" and resid 80 and name HN }}
      {{ segid "BrD" and resid 80 and name HA }}
         2.800  2.000  2.000 peak    10501 weight   0.10000E♦01 volume  0.42726E♦03 ppm1  7.974   ppm2 4.691
OR    {10501}
      {{ segid "BrD" and resid 80 and name HN }}
      {{ segid "BrD" and resid 76 and name HA }}
```

TABLE 3-continued

Ambiguous NOE-derived Inter-proton Distance Restraints

```
ASSI  {10541}
      {{ segid "BrD" and resid 55 and name HN   }}
      {  segid "BrD" and resid 58 and name HG24}
         3.900  3.100  2.000 peak     10541 weight   0.10000E♦01 volume   0.11084E♦03 ppm1  7.974     ppm2  1.670
OR    {10541}
      {{ segid "BrD" and resid 78 and name HN   }}
      {  segid "BrD" and resid 22 and name HD14}
OR    {10541}
      {{ segid "BrD" and resid 78 and name HN   }}
      {{ segid "BrD" and resid 110 and name HG12}}
OR    {10541}
      {{ segid "BrD" and resid 55 and name HN }}
      {  segid "BrD" and resid 43 and name HB4}
OR    {10541}
      {{ segid "BrD" and resid 78 and name HN   }}
      {  segid "BrD" and resid 25 and name HG24}
OR    {10541}
      {{ segid "BrD" and resid 55 and name HN   }}
      {  segid "BrD" and resid 29 and name HG24}
OR    {10541}
      {{ segid "BrD" and resid 78 and name HN   }}
      {  segid "BrD" and resid 63 and name HD14}
OR    {10541}
      {{ segid "BrD" and resid 55 and name HN   }}
      {  segid "BrD" and resid 22 and name HD14}
ASSI  {10551}
      {{ segid "BrD" and resid 78 and name HN   }}
      {{ segid "BrD" and resid 78 and name HB2}}
         3.400  2.900  2.100 peak     10551 weight   0.10000E♦01 volume   0.13253E♦03 ppm1  7.975     ppm2  1.068
OR    {10551}
      {{ segid "BrD" and resid 80 and name HN   }}
      {  segid "BrD" and resid 81 and name HG14}
OR    {10551}
      {{ segid "BrD" and resid 78 and name HN   }}
      {  segid "BrD" and resid 81 and name HG14}
OR    {10551}
      {{ segid "BrD" and resid 55 and name HN   }}
      {  segid "BrD" and resid 81 and name HG14}
ASSI  {10611}
      {{ segid "BrD" and resid 56 and name HN   }}
      {{ segid "BrD" and resid 34 and name HB2}}
         2.100  2.400  2.400 peak     10611 weight   0.10000E♦01 volume   0.21458E♦03 ppm1  9.680     ppm2  3.118
OR    {10411}
      {{ segid "BrD" and resid 56 and name HN   }}
      {{ segid "BrD" and resid 59 and name HG2}}
ASSI  {10631}
      {{ segid "BrD" and resid 82 and name HN   }}
      {  segid "BrD" and resid 83 and name HG24}
         3.500  3.100  2.00  peak     10631 weight   0.10000E♦01 volume   0.97408E♦02 ppm1  6.984     ppm2  1.909
OR    {10631}
      {{ segid "BrD" and resid 82 and name HN   }}
      {{ segid "BrD" and resid 103 and name HB2}}
ASSI  {10781}
      {{ segid "BrD" and resid 80 and name HN   }}
      {  segid "BrD" and resid 83 and name HG24}
         3.900  3.800  1.600 peak     10781 weight   0.10000E♦01 volume   0.97791E♦02 ppm1  8.004     ppm2  1.932
OR    {10781}
      {{ segid "BrD" and resid 80 and name HN   }}
      {{ segid "BrD" and resid 114 and name HG11}}
OR    {10781}
      {{ segid "BrD" and resid 80 and name HN   }}
      {{ segid "BrD" and resid 54 and name HB2}}
ASSI  {10811}
      {{ segid "BrD" and resid 80 and name HN   }}
      {  segid "BrD" and resid 81 and name HG14}
         3.600  3.200  1.900 peak     10811 weight   0.10000E♦01 volume   0.94809E♦02 ppm1  8.005     ppm2  1.064
OR    {10811}
      {{ segid "BrD" and resid 80 and name HN   }}
      {{ segid "BrD" and resid 78 and name HB2}}
ASSI  {10901}
      {{ segid "BrD" and resid 85 and name HN   }}
      {{ segid "BrD" and resid 86 and name HG1}}
         3.800  3.400  1.700 peak     10901 weight   0.10000E♦01 volume   0.64876E♦02 ppm1  7.916     ppm2  1.905
OR    {10901}
      {{ segid "BrD" and resid 85 and name HN   }}
      {  segid "BrD" and resid 83 and name HG24}}
```

TABLE 3-continued

Ambiguous NOE-derived Inter-proton Distance Restraints

```
ASSI  {10981}
         {{ segid "BrD" and resid 87 and name HN }}
         {{ segid "BrD" and resid 85 and name HA }}
             3.900  3.800  1.600 peak    10981 weight    0.10000E+01 volume   0.57856E+02 ppm1  8.572    ppm2  5.005
  OR   {10981}
         {{ segid "BrD" and resid 87 and name HN }}
         {{ segid "BrD" and resid 88 and name HA }}
ASSI  {10991}
         {{ segid "BrD" and resid 87 and name HN }}
         {{ segid "BrD" and resid 85 and name HB2}}
             3.300  2.600  2.300 peak    10991 weight    0.10000E+01 volume   0.17351E+03 ppm1  8.571    ppm2  3.639
  OR   {10991}
         {{ segid "BrD" and resid 87 and name HN }}
         {{ segid "BrD" and resid 95 and name HB1}}
ASSI  {11181}
         {{ segid "BrD" and resid 93 and name HN }}
         {{ segid "BrD" and resid 91 and name HB1}}
             3.000  2.200  2.200 peak    11181 weight    0.10000E+01 volume   0.28245E+03 ppm1  8.714    ppm2  3.075
  OR   {11181}
         {{ segid "BrD" and resid 93 and name HN }}
         {{ segid "BrD" and resid 96 and name HB2}}
ASSI  {11231}
         {{ segid "BrD" and resid 31 and name HN }}
         {{ segid "BrD" and resid 98 and name HB1}}
             3.900  3.800  1.600 peak    11231 weight    0.10000E+01 volume   0.56370E+02 ppm1  8.481    ppm2  3.992
  OR   {11231}
         {{ segid "BrD" and resid 31 and name HN }}
         {{ segid "BrD" and resid 32 and name HB2}}
ASSI  {11271}
         {{ segid "BrD" and resid 31 and name HN }}
         {{ segid "BrD" and resid 33 and name HG1}}
             4.100  4.100  1.400 peak    11271 weight    0.10000E+01 volume   0.42900E+02 ppm1  8.480    ppm2  2.781
  OR   {11271}
         {{ segid "BrD" and resid 59 and name HN }}
         {{ segid "BrD" and resid 61 and name HG2}}
ASSI  {11301}
         {{ segid "BrD" and resid 31 and name HN    }}
         {  segid "BrD" and resid 101 and name HD14}
             3.800  3.600  1.700 peak    11301 weight    0.10000E+01 volume   0.60718E+02 ppm1  8.479    ppm2  1.542
  OR   {11301}
         {{ segid "BrD" and resid 31 and name HN    }}
         {  segid "BrD" and resid 56 and name HD14}
ASSI  {11321}
         {{ segid "BrD" and resid 59 and name HN    }}
         {  segid "BrD" and resid 81 and name HG14}
             4.200  4.200  1.300 peak    11321 weight    0.10000E+01 volume   0.33324E+02 ppm1  8.480    ppm2  1.110
  OR   {11321}
         {{ segid "BrD" and resid 31 and name HN }}
         {{ segid "BrD" and resid 33 and name HB1}}
ASSI  {11531}
         {{ segid "BrD" and resid 104 and name HN   }}
         {  segid "BrD" and resid 102 and name HD24}
             4.700  4.700  0.800 peak    11531 weight    0.10000E+01 volume   0.14001E+02 ppm1  7.735    ppm2  1.282
  OR   {11531}
         {{ segid "BrD" and resid 35 and name HN    }}
         {  segid "BrD" and resid 102 and name HD14}
  OR   {11531}
         {{ segid "BrD" and resid 104 and name HN   }}
         {  segid "BrD" and resid 102 and name HD14}
ASSI  {11541}
         {{ segid "BrD" and resid 35 and name HN }}
         {{ segid "BrD" and resid 32 and name HB2}}
             3.400  2.900  2.100 peak    11541 weight    0.10000E+01 volume   0.13237E+03 ppm1  7.734    ppm2  3.923
  OR   {11541}
         {{ segid "BrD" and resid 104 and name HN }}
         {{ segid "BrD" and resid 106 and name HB1}}
ASSI  {11591}
         {{ segid "BrD" and resid 66 and name HN }}
         {{ segid "BrD" and resid 69 and name HB }}
             3.600  3.200  1.900 peak    11591 weight    0.10000E+01 volume   0.90637E+02 ppm1  8.764    ppm2  2.939
  OR   {11591}
         {{ segid "BrD" and resid 66 and name HN }}
         {{ segid "BrD" and resid 43 and name HB1}}
ASSI  {11631}
         {{ segid "BrD" and resid 67 and name HN    }}
         {  segid "BrD" and resid 63 and name HD14}
             3.500  3.100  2.000 peak    11631 weight    0.10000E+01 volume   0.99713E+02 ppm1  8.832    ppm2  1.678
```

TABLE 3-continued

Ambiguous NOE-derived Inter-proton Distance Restraints

| | | | | | | | | | | | |
|---|---|---|---|---|---|---|---|---|---|---|---|
| OR | {11631} | | | | | | | | | | |
| | {{ segid "BrD" and resid 67 and name HN }} | | | | | | | | | | |
| | {{ segid "BrD" and resid 62 and name HB2}} | | | | | | | | | | |
| ASSI | {11671} | | | | | | | | | | |
| | {{ segid "BrD" and resid 68 and name HN }} | | | | | | | | | | |
| | { segid "BrD" and resid 63 and name HD14} | | | | | | | | | | |
| | 3.600 | 3.200 | 1.900 peak | 11671 weight | 0.10000E+01 | volume | 0.92729E+02 | ppm1 | 8.626 | ppm2 | 1.684 |
| OR | {11671} | | | | | | | | | | |
| | {{ segid "BrD" and resid 68 and name HN }} | | | | | | | | | | |
| | {{ segid "BrD" and resid 62 and name HB2}} | | | | | | | | | | |
| ASSI | {11701} | | | | | | | | | | |
| | {{ segid "BrD" and resid 69 and name HN }} | | | | | | | | | | |
| | {{ segid "BrD" and resid 63 and name HG }} | | | | | | | | | | |
| | 3.400 | 2.900 | 2.100 peak | 11701 weight | 0.10000E+01 | volume | 0.12326E+03 | ppm1 | 8.306 | ppm2 | 2.476 |
| OR | {11701} | | | | | | | | | | |
| | {{ segid "BrD" and resid 69 and name HN }} | | | | | | | | | | |
| | {{ segid "BrD" and resid 73 and name HB2}} | | | | | | | | | | |
| ASSI | {11711} | | | | | | | | | | |
| | {{ segid "BrD" and resid 69 and name HN }} | | | | | | | | | | |
| | {{ segid "BrD" and resid 66 and name HB2}} | | | | | | | | | | |
| | 3.800 | 3.600 | 1.700 peak | 11711 weight | 0.10000E+01 | volume | 0.68030E+02 | ppm1 | 8.306 | ppm2 | 2.614 |
| OR | {11711} | | | | | | | | | | |
| | {{ segid "BrD" and resid 69 and name HN }} | | | | | | | | | | |
| | {{ segid "BrD" and resid 11 and name HB2}} | | | | | | | | | | |
| OR | {11711} | | | | | | | | | | |
| | {{ segid "BrD" and resid 69 and name HN }} | | | | | | | | | | |
| | {{ segid "BrD" and resid 73 and name HB1}} | | | | | | | | | | |
| ASSI | {11751} | | | | | | | | | | |
| | {{ segid "BrD" and resid 70 and name HN }} | | | | | | | | | | |
| | {{ segid "BrD" and resid 73 and name HG }} | | | | | | | | | | |
| | 4.200 | 4.200 | 1.300 peak | 11751 weight | 0.10000E+01 | volume | 0.36902E+02 | ppm1 | 8.039 | ppm2 | 2.374 |
| OR | {11751} | | | | | | | | | | |
| | {{ segid "BrD" and resid 70 and name HN }} | | | | | | | | | | |
| | {{ segid "BrD" and resid 9 and name HB2 }} | | | | | | | | | | |
| ASSI | {11761} | | | | | | | | | | |
| | {{ segid "BrD" and resid 70 and name HN }} | | | | | | | | | | |
| | {{ segid "BrD" and resid 73 and name HB1}} | | | | | | | | | | |
| | 3.500 | 3.100 | 2.000 peak | 11761 weight | 0.10000E+01 | volume | 0.95470E+02 | ppm1 | 8.040 | ppm2 | 2.594 |
| OR | {11761} | | | | | | | | | | |
| | {{ segid "BrD" and resid 70 and name HN }} | | | | | | | | | | |
| | {{ segid "BrD" and resid 11 and name HB2}} | | | | | | | | | | |
| ASSI | {11851} | | | | | | | | | | |
| | {{ segid "BrD" and resid 73 and name HN }} | | | | | | | | | | |
| | {{ segid "BrD" and resid 74 and name HB1}} | | | | | | | | | | |
| | 3.600 | 3.200 | 1.900 peak | 11851 weight | 0.10000E+01 | volume | 0.82682E+02 | ppm1 | 8.045 | ppm2 | 3.572 |
| OR | {11851} | | | | | | | | | | |
| | {{ segid "BrD" and resid 73 and name HN }} | | | | | | | | | | |
| | {{ segid "BrD" and resid 75 and name HG1}} | | | | | | | | | | |
| ASSI | {11931} | | | | | | | | | | |
| | {{ segid "BrD" and resid 23 and name HN }} | | | | | | | | | | |
| | {{ segid "BrD" and resid 22 and name HA }} | | | | | | | | | | |
| | 3.800 | 3.600 | 1.700 peak | 11931 weight | 0.10000E+01 | volume | 0.64947E+02 | ppm1 | 9.125 | ppm2 | 4.688 |
| OR | {11931} | | | | | | | | | | |
| | {{ segid "BrD" and resid 75 and name HN }} | | | | | | | | | | |
| | {{ segid "BrD" and resid 72 and name HA }} | | | | | | | | | | |
| ASSI | {11941} | | | | | | | | | | |
| | {{ segid "BrD" and resid 98 and name HN }} | | | | | | | | | | |
| | {{ segid "BrD" and resid 100 and name HB2}} | | | | | | | | | | |
| | 4.000 | 4.000 | 1.500 peak | 11941 weight | 0.10000E+01 | volume | 0.47235E+02 | ppm1 | 9.125 | ppm2 | 3.411 |
| OR | {11941} | | | | | | | | | | |
| | {{ segid "BrD" and resid 23 and name HN }} | | | | | | | | | | |
| | {{ segid "BrD" and resid 24 and name HG1}} | | | | | | | | | | |
| ASSI | {12011} | | | | | | | | | | |
| | {{ segid "BrD" and resid 23 and name HN }} | | | | | | | | | | |
| | { segid "BrD" and resid 22 and name HD24} | | | | | | | | | | |
| | 3.800 | 3.600 | 1.700 peak | 12011 weight | 0.10000E+01 | volume | 0.60927E+02 | ppm1 | 9.125 | ppm2 | 1.594 |
| OR | {12011} | | | | | | | | | | |
| | {{ segid "BrD" and resid 23 and name HN }} | | | | | | | | | | |
| | { segid "BrD" and resid 21 and name HG24} | | | | | | | | | | |
| ASSI | {12021} | | | | | | | | | | |
| | {{ segid "BrD" and resid 98 and name HN }} | | | | | | | | | | |
| | {{ segid "BrD" and resid 30 and name HB1}} | | | | | | | | | | |
| | 4.00 | 4.000 | 1.500 peak | 12021 weight | 0.10000E+01 | volume | 0.46966E+02 | ppm1 | 9.124 | ppm2 | 4.936 |
| OR | {12021} | | | | | | | | | | |
| | {{ segid "BrD" and resid 23 and name HN }} | | | | | | | | | | |
| | {{ segid "BrD" and resid 60 and name HB1}} | | | | | | | | | | |

TABLE 3-continued

Ambiguous NOE-derived Inter-proton Distance Restraints

| | | | | | | | | | | | | |
|---|---|---|---|---|---|---|---|---|---|---|---|---|
| OR | {12021} | | | | | | | | | | | |
| | {{ segid "BrD" and resid 98 and name HN }} | | | | | | | | | | | |
| | {{ segid "BrD" and resid 100 and name HA}} | | | | | | | | | | | |
| OR | {12021} | | | | | | | | | | | |
| | {{ segid "BrD" and resid 23 and name HN }} | | | | | | | | | | | |
| | {{ segid "BrD" and resid 64 and name HA }} | | | | | | | | | | | |
| ASSI | {12071} | | | | | | | | | | | |
| | {{ segid "BrD" and resid 100 and name HN }} | | | | | | | | | | | |
| | {{ segid "BrD" and resid 98 and name HB2 }} | | | | | | | | | | | |
| | 4.100 | 4.100 | 1.400 peak | 12071 weight | 0.10000E♦01 volume | 0.37827E♦02 ppm1 | 8.669 | ppm2 | 3.641 | | | |
| OR | {12071} | | | | | | | | | | | |
| | {{ segid "BrD" and resid 100 and name HN }} | | | | | | | | | | | |
| | {{ segid "BrD" and resid 85 and name HB2 }} | | | | | | | | | | | |
| ASSI | {12101} | | | | | | | | | | | |
| | {{ segid "BrD" and resid 100 and name HN }} | | | | | | | | | | | |
| | {{ segid "BrD" and resid 103 and name HB1}} | | | | | | | | | | | |
| | 2.000 | 2.000 | 2.900 peak | 12101 weight | 0.10000E♦01 volume | 0.26537E♦04 ppm1 | 8.669 | ppm2 | 2.323 | | | |
| OR | {12101} | | | | | | | | | | | |
| | {{ segid "BrD" and resid 100 and name HN }} | | | | | | | | | | | |
| | {{ segid "BrD" and resid 104 and name HD1}} | | | | | | | | | | | |
| ASSI | {12111} | | | | | | | | | | | |
| | {{ segid "BrD" and resid 100 and name HN }} | | | | | | | | | | | |
| | {{ segid "BrD" and resid 103 and name HB2}} | | | | | | | | | | | |
| | 4.100 | 4.100 | 1.400 peak | 12111 weight | 0.10000E♦01 volume | 0.37921E♦02 ppm1 | 8.669 | ppm2 | 1.892 | | | |
| OR | {12111} | | | | | | | | | | | |
| | {{ segid "BrD" and resid 100 and name HN }} | | | | | | | | | | | |
| | {{ segid "BrD" and resid 86 and name HG1 }} | | | | | | | | | | | |
| ASSI | {12141} | | | | | | | | | | | |
| | {{ segid "BrD" and resid 100 and name HN}} | | | | | | | | | | | |
| | { segid "BrD" and resid 96 and name HG1} | | | | | | | | | | | |
| | 4.300 | 4.300 | 1.200 peak | 12141 weight | 0.10000E♦01 volume | 0.30609E♦02 ppm1 | 8.669 | ppm2 | 7.737 | | | |
| OR | {12141} | | | | | | | | | | | |
| | {{ segid "BrD" and resid 100 and name HN }} | | | | | | | | | | | |
| | {{ segid "BrD" and resid 104 and name HN }} | | | | | | | | | | | |
| ASSI | {12251} | | | | | | | | | | | |
| | {{ segid "BrD" and resid 107 and name HN }} | | | | | | | | | | | |
| | {{ segid "BrD" and resid 110 and name HB }} | | | | | | | | | | | |
| | 3.700 | 3.400 | 1.800 peak | 12251 weight | 0.10000E♦01 volume | 0.79191E♦02 ppm1 | 8.980 | ppm2 | 2.348 | | | |
| OR | {12251} | | | | | | | | | | | |
| | {{ segid "BrD" and resid 107 and name HN }} | | | | | | | | | | | |
| | {{ segid "BrD" and resid 103 and name HB1}} | | | | | | | | | | | |
| OR | {12251} | | | | | | | | | | | |
| | {{ segid "BrD" and resid 107 and name HN }} | | | | | | | | | | | |
| | {{ segid "BrD" and resid 109 and name HB1}} | | | | | | | | | | | |
| ASSI | {12261} | | | | | | | | | | | |
| | {{ segid "BrD" and resid 107 and name HN }} | | | | | | | | | | | |
| | {{ segid "BrD" and resid 102 and name HB2}} | | | | | | | | | | | |
| | 5.500 | 5.500 | 0.000 peak | 12261 weight | 0.10000E♦01 volume | 0.35919E♦00 ppm1 | 8.980 | ppm2 | 1.797 | | | |
| OR | {12261} | | | | | | | | | | | |
| | {{ segid "BrD" and resid 107 and name HN }} | | | | | | | | | | | |
| | { segid "BrD" and resid 25 and name HG14} | | | | | | | | | | | |
| ASSI | {12281} | | | | | | | | | | | |
| | {{ segid "BrD" and resid 108 and name HN }} | | | | | | | | | | | |
| | {{ segid "BrD" and resid 103 and name HG2}} | | | | | | | | | | | |
| | 4.100 | 4.100 | 1.400 peak | 12281 weight | 0.10000E♦01 volume | 0.42059E♦02 ppm1 | 8.522 | ppm2 | 2.529 | | | |
| OR | {12281} | | | | | | | | | | | |
| | {{ segid "BrD" and resid 108 and name HN }} | | | | | | | | | | | |
| | {{ segid "BrD" and resid 104 and name HB1}} | | | | | | | | | | | |
| ASSI | {12301} | | | | | | | | | | | |
| | {{ segid "BrD" and resid 108 and name HN }} | | | | | | | | | | | |
| | { segid "BrD" and resid 116 and name HD14} | | | | | | | | | | | |
| | 3.900 | 3.800 | 1.600 peak | 12301 weight | 0.10000E♦01 volume | 0.52230E♦02 ppm1 | 8.521 | ppm2 | 1.422 | | | |
| OR | {12301} | | | | | | | | | | | |
| | {{ segid "BrD" and resid 108 and name HN }} | | | | | | | | | | | |
| | {{ segid "BrD" and resid 109 and name HG1}} | | | | | | | | | | | |
| ASSI | {12311} | | | | | | | | | | | |
| | {{ segid "BrD" and resid 108 and name HN }} | | | | | | | | | | | |
| | {{ segid "BrD" and resid 110 and name HB }} | | | | | | | | | | | |
| | 4.100 | 4.100 | 1.400 peak | 12311 weight | 0.10000E♦01 volume | 0.41867E♦02 ppm1 | 8.522 | ppm2 | 2.331 | | | |
| OR | {12311} | | | | | | | | | | | |
| | {{ segid "BrD" and resid 108 and name HN }} | | | | | | | | | | | |
| | {{ segid "BrD" and resid 109 and name HB1}} | | | | | | | | | | | |
| ASSI | {12401} | | | | | | | | | | | |
| | {{ segid "BrD" and resid 113 and name HN }} | | | | | | | | | | | |
| | {{ segid "BrD" and resid 115 and name HG }} | | | | | | | | | | | |
| | 3.300 | 2.700 | 2.200 peak | 12401 weight | 0.10000E♦01 volume | 0.16014E♦03 ppm1 | 8.218 | ppm2 | 2.152 | | | |

TABLE 3-continued

Ambiguous NOE-derived Inter-proton Distance Restraints

| | | | | | | | | | | | | |
|---|---|---|---|---|---|---|---|---|---|---|---|---|
| OR | {12401} | | | | | | | | | | | |
| | {{ segid "BrD" and resid 113 and name HN }} | | | | | | | | | | | |
| | {{ segid "BrD" and resid 115 and name HB1}} | | | | | | | | | | | |
| OR | {12401} | | | | | | | | | | | |
| | {{ segid "BrD" and resid 113 and name HN }} | | | | | | | | | | | |
| | {{ segid "BrD" and resid 109 and name HB2}} | | | | | | | | | | | |
| ASSI | {12501} | | | | | | | | | | | |
| | {{ segid "BrD" and resid 116 and name HN}} | | | | | | | | | | | |
| | {{ segid "BrD" and resid 71 and name HA }} | | | | | | | | | | | |
| | 4.300 | 4.300 | 1.200 | peak | 12501 | weight | 0.10000E♦01 | volume | 0.28782E♦02 | ppm1 | 8.087 | ppm2 4.664 |
| OR | {12501} | | | | | | | | | | | |
| | {{ segid "BrD" and resid 116 and name HN}} | | | | | | | | | | | |
| | {{ segid "BrD" and resid 72 and name HA }} | | | | | | | | | | | |
| OR | {12501} | | | | | | | | | | | |
| | {{ segid "BrD" and resid 116 and name HN }} | | | | | | | | | | | |
| | {{ segid "BrD" and resid 114 and name HA1}} | | | | | | | | | | | |
| OR | {12501} | | | | | | | | | | | |
| | {{ segid "BrD" and resid 116 and name HN}} | | | | | | | | | | | |
| | {{ segid "BrD" and resid 76 and name HA }} | | | | | | | | | | | |
| ASSI | {12511} | | | | | | | | | | | |
| | {{ segid "BrD" and resid 116 and name HN}} | | | | | | | | | | | |
| | {{ segid "BrD" and resid 75 and name HA }} | | | | | | | | | | | |
| | 3.600 | 3.200 | 1.900 | peak | 12511 | weight | 0.10000E♦01 | volume | 0.81005E♦02 | ppm1 | 8.087 | ppm2 4.526 |
| OR | {12511} | | | | | | | | | | | |
| | {{ segid "BrD" and resid 116 and name HN }} | | | | | | | | | | | |
| | {{ segid "BrD" and resid 114 and name HA2}} | | | | | | | | | | | |
| ASSI | {12601} | | | | | | | | | | | |
| | {{ segid "BrD" and resid 92 and name HN }} | | | | | | | | | | | |
| | {{ segid "BrD" and resid 92 and name HB1}} | | | | | | | | | | | |
| | 4.100 | 4.100 | 1.400 | peak | 12601 | weight | 0.10000E♦01 | volume | 0.37922E♦02 | ppm1 | 8.831 | ppm2 2.695 |
| OR | {12601} | | | | | | | | | | | |
| | {{ segid "BrD" and resid 92 and name HN }} | | | | | | | | | | | |
| | {{ segid "BrD" and resid 91 and name HB2}} | | | | | | | | | | | |
| ASSI | {12841} | | | | | | | | | | | |
| | {{ segid "BrD" and resid 19 and name HN }} | | | | | | | | | | | |
| | {{ segid "BrD" and resid 17 and name HB }} | | | | | | | | | | | |
| | 3.800 | 3.600 | 1.700 | peak | 12841 | weight | 0.10000E♦01 | volume | 0.59211E♦02 | ppm1 | 9.187 | ppm2 4.880 |
| OR | {12841} | | | | | | | | | | | |
| | {{ segid "BrD" and resid 19 and name HN }} | | | | | | | | | | | |
| | {{ segid "BrD" and resid 20 and name HA }} | | | | | | | | | | | |
| ASSI | {12861} | | | | | | | | | | | |
| | {{ segid "BrD" and resid 20 and name HN }} | | | | | | | | | | | |
| | {{ segid "BrD" and resid 63 and name HG }} | | | | | | | | | | | |
| | 4.000 | 4.000 | 1.500 | peak | 12861 | weight | 0.10000E♦01 | volume | 0.43415E♦02 | ppm1 | 8.147 | ppm2 2.471 |
| OR | {12861} | | | | | | | | | | | |
| | {{ segid "BrD" and resid 20 and name HN }} | | | | | | | | | | | |
| | {{ segid "BrD" and resid 21 and name HB }} | | | | | | | | | | | |
| ASSI | {12951} | | | | | | | | | | | |
| | {{ segid "BrD" and resid 23 and name HN }} | | | | | | | | | | | |
| | { segid "BrD" and resid 25 and name HG14}} | | | | | | | | | | | |
| | 3.800 | 3.600 | 1.700 | peak | 12951 | weight | 0.10000E♦01 | volume | 0.65890E♦02 | ppm1 | 9.119 | ppm2 1.823 |
| OR | {12951} | | | | | | | | | | | |
| | {{ segid "BrD" and resid 98 and name HN }} | | | | | | | | | | | |
| | {{ segid "BrD" and resid 101 and name HG12}} | | | | | | | | | | | |
| ASSI | {12961} | | | | | | | | | | | |
| | {{ segid "BrD" and resid 23 and name HN }} | | | | | | | | | | | |
| | { segid "BrD" and resid 22 and name HD14} | | | | | | | | | | | |
| | 3.100 | 2.400 | 2.400 | peak | 12961 | weight | 0.10000E♦01 | volume | 0.23452E♦03 | ppm1 | 9.120 | ppm2 1.646 |
| OR | {12961} | | | | | | | | | | | |
| | {{ segid "BrD" and resid 23 and name HN }} | | | | | | | | | | | |
| | {{ segid "BrD" and resid 21 and name HG12}} | | | | | | | | | | | |
| OR | {12961} | | | | | | | | | | | |
| | {{ segid "BrD" and resid 23 and name HN }} | | | | | | | | | | | |
| | { segid "BrD" and resid 21 and name HG24} | | | | | | | | | | | |
| OR | {12961} | | | | | | | | | | | |
| | {{ segid "BrD" and resid 23 and name HN }} | | | | | | | | | | | |
| | { segid "BrD" and resid 25 and name HG24} | | | | | | | | | | | |
| ASSI | {12971} | | | | | | | | | | | |
| | {{ segid "BrD" and resid 98 and name HN }} | | | | | | | | | | | |
| | { segid "BrD" and resid 101 and name HD14} | | | | | | | | | | | |
| | 3.900 | 3.800 | 1.600 | peak | 12971 | weight | 0.10000E♦01 | volume | 0.50522E♦02 | ppm1 | 9.119 | ppm2 1.514 |
| OR | {12971} | | | | | | | | | | | |
| | {{ segid "BrD" and resid 23 and name HN }} | | | | | | | | | | | |
| | { segid "BrD" and resid 63 and name HD24} | | | | | | | | | | | |
| ASSI | {12981} | | | | | | | | | | | |
| | {{ segid "BrD" and resid 94 and name HN }} | | | | | | | | | | | |
| | {{ segid "BrD" and resid 100 and name HB2}} | | | | | | | | | | | |
| | 3.400 | 2.900 | 2.100 | peak | 12981 | weight | 0.10000E♦01 | volume | 0.12055E♦03 | ppm1 | 9.119 | ppm2 3.467 |

TABLE 3-continued

Ambiguous NOE-derived Inter-proton Distance Restraints

| | |
|---|---|
| OR | {12981} |
| | {{ segid "BrD" and resid 23 and name HN }} |
| | {{ segid "BrD" and resid 24 and name HG1}} |
| OR | {12981} |
| | {{ segid "BrD" and resid 98 and name HN }} |
| | {{ segid "BrD" and resid 100 and name HB1}} |
| ASSI | {13001} |
| | {{ segid "BrD" and resid 98 and name HN }} |
| | { segid "BrD" and resid 95 and name HD4} |
| | 3.900  3.800  1.600 peak  13001 weight  0.10000E+01 volume  0.54095E+02 ppm1  9.119  ppm2  7.520 |
| OR | {13001} |
| | {{ segid "BrD" and resid 23 and name HN }} |
| | {{ segid "BrD" and resid 24 and name HE22}} |
| OR | {13001} |
| | {{ segid "BrD" and resid 23 and name HN }} |
| | { segid "BrD" and resid 74 and name HE4} |
| ASSI | {13011} |
| | {{ segid "BrD" and resid 26 and name HN }} |
| | { segid "BrD" and resid 31 and name HB4} |
| | 3.500  3.100  2.000 peak  13011 weight  0.10000E+01 volume  0.10060E+03 ppm1  9.196  ppm2  2.308 |
| OR | {13011} |
| | {{ segid "BrD" and resid 26 and name HN }} |
| | {{ segid "BrD" and resid 22 and name HB2}} |
| ASSI | {13121} |
| | {{ segid "BrD" and resid 59 and name HN }} |
| | {{ segid "BrD" and resid 56 and name HB2}} |
| | 3.800  3.600  1.700 peak  13121 weight  0.10000E+01 volume  0.59266E+02 ppm1  8.496  ppm2  2.008 |
| OR | {13121} |
| | {{ segid "BrD" and resid 59 and name HN }} |
| | {{ segid "BrD" and resid 57 and name HG2}} |
| OR | {13121} |
| | {{ segid "BrD" and resid 31 and name HN }} |
| | {{ segid "BrD" and resid 102 and name HB1}} |
| ASSI | {13171} |
| | {{ segid "BrD" and resid 60 and name HN }} |
| | {{ segid "BrD" and resid 57 and name HB2}} |
| | 3.900  3.100  2.000 peak  13171 weight  0.10000E+01 volume  0.10295E+03 ppm1  8.564  ppm2  2.858 |
| OR | {13171} |
| | {{ segid "BrD" and resid 60 and name HN }} |
| | {{ segid "BrD" and resid 61 and name HB1}} |
| OR | {13171} |
| | {{ segid "BrD" and resid 65 and name HN }} |
| | {{ segid "BrD" and resid 61 and name HB1}} |
| ASSI | {13181} |
| | {{ segid "BrD" and resid 60 and name HN }} |
| | {{ segid "BrD" and resid 22 and name HG }} |
| | 3.800  3.600  1.700 peak  13161 weight  0.10000E+01 volume  0.61364E+02 ppm1  8.565  ppm2  2.336 |
| OR | {13181} |
| | {{ segid "BrD" and resid 65 and name HN }} |
| | {{ segid "BrD" and resid 62 and name HG1}} |
| OR | {13181} |
| | {{ segid "BrD" and resid 60 and name HN }} |
| | {{ segid "BrD" and resid 56 and name HG }} |
| OR | {13181} |
| | {{ segid "BrD" and resid 60 and name HN }} |
| | {{ segid "BrD" and resid 22 and name HB2}} |
| OR | {13181} |
| | {{ segid "BrD" and resid 60 and name HN }} |
| | {{ segid "BrD" and resid 57 and name HD2}} |
| ASSI | {13191} |
| | {{ segid "BrD" and resid 60 and name HN }} |
| | { segid "BrD" and resid 22 and name HD14} |
| | 3.200  2.600  2.300 peak  13191 weight  0.10000E+01 volume  0.17809E+03 ppm1  8.568  ppm2  1.666 |
| OR | {13191} |
| | {{ segid "BrD" and resid 65 and name HN }} |
| | { segid "BrD" and resid 63 and name HD14} |
| OR | {13191} |
| | {{ segid "BrD" and resid 60 and name HN }} |
| | { segid "BrD" and resid 58 and name HG24} |
| ASSI | {13201} |
| | {{ segid "BrD" and resid 65 and name HN }} |
| | { segid "BrD" and resid 63 and name HD24} |
| | 3.600  3.200  1.900 peak  13201 weight  0.10000E+01 volume  0.81304E+02 ppm1  8.565  ppm2  1.497 |
| OR | {13201} |
| | {{ segid "BrD" and resid 65 and name HN }} |
| | {{ segid "BrD" and resid 62 and name HG2}} |

TABLE 3-continued

Ambiguous NOE-derived Inter-proton Distance Restraints

```
OR        {13201}
          {{ segid "BrD" and resid 60 and name HN   }}
          {  segid "BrD" and resid 63 and name HD24}
ASSI      {13631}
          {{ segid "BrD" and resid 84 and name HN }}
          {{ segid "BrD" and resid 82 and name HN }}
             4.000  4.000  1.900 peak     13631 weight    0.10000E+01 volume   0.44090E+02 ppm1  9.463    ppm2  6.981
OR        {13631}
          {{ segid "BrD" and resid 63 and name HN  }}
          {  segid "BrD" and resid 74 and name HD4}
ASSI      {13691}
          {{ segid "BrD" and resid 22 and name HN}}
          {{ segid "BrD" and resid 22 and name HB2}}
             3.700  3.400  1.800 peak     13691 weight    0.10000E+01 volume   0.68904E+02 ppm1  9.473    ppm2  3.333
OR        {13691}
          {{ segid "BrD" and resid 22 and name HN   }}
          {{ segid "BrD" and resid 21 and name HG11}}
OR        {13691}
          {{ segid "BrD" and resid 22 and name HN }}
          {{ segid "BrD" and resid 22 and name HG }}
ASSI      {13971}
          {{ segid "BrD" and resid 114 and name HN }}
          {{ segid "BrD" and resid 112 and name HG2}}
             4.900  4.900  0.600 peak     13971 weight    0.10000E+01 volume   0.14499E+02 ppm1  8.377    ppm2  2.786
OR        {13971}
          {{ segid "BrD" and resid 114 and name HN }}
          {{ segid "BrD" and resid 13 and name HB1 }}
ASSI      {14061}
          {{ segid "BrD" and resid 107 and name HN   }}
          {  segid "BrD" and resid 110 and name HG24}
             4.800  4.800  0.700 peak     14061 weight    0.10000E+01 volume   0.19271E+02 ppm1  8.980    ppm2  1.260
OR        {10461}
          {{ segid "BrD" and resid 107 and name HN }}
          {  segid "BrD" and resid 21 and name HD14}
ASSI      {14071}
          {{ segid "BrD" and resid 106 and name HN }}
          {{ segid "BrD" and resid 107 and name HA }}
             4.600  4.600  0.900 peak     14071 weight    0.10000E+01 volume   0.20479E+02 ppm1  9.742    ppm2  4.447
OR        {14071}
          {{ segid "BrD" and resid 106 and name HN}}
          {{ segid "BrD" and resid 99 and name HA  }}
ASSI      {14131}
          {{ segid "BrD" and resid 104 and name HN }}
          {{ segid "BrD" and resid 102 and name HB2}}
             3.700  3.400  1.800 peak     14131 weight    0.10000E+01 volume   0.76948E+02 ppm1  7.763    ppm2  1.816
OR        {14131}
          {{ segid "BrD" and resid 104 and name HN   }}
          {{ segid "BrD" and resid 101 and name HG12}}
ASSI      {14141}
          {{ segid "BrD" and resid 103 and name HN }}
          {{ segid "BrD" and resid 106 and name HB1}}
             3.600  3.200  1.900 peak     14141 weight    0.10000E+01 volume   0.92105E+02 ppm1  8.695    ppm2  3.908
OR        {14141}
          {{ segid "BrD" and resid 17 and name HN }}
          {{ segid "BrD" and resid 18 and name HA }}
ASSI      {14151}
          {{ segid "BrD" and resid 102 and name HN }}
          {{ segid "BrD" and resid 105 and name HB2}}
             4.000  4.000  1.500 peak     14151 weight    0.10000E+01 volume   0.49406E+02 ppm1  9.156    ppm2  3.635
OR        {14151}
          {{ segid "BrD" and resid 102 and name HN }}
          {{ segid "BrD" and resid 98 and name HB2 }}
OR        {14151}
          {{ segid "BrD" and resid 102 and name HN }}
          {{ segid "BrD" and resid 106 and name HB2}}
ASSI      {14161}
          {{ segid "BrD" and resid 102 and name HN }}
          {{ segid "BrD" and resid 103 and name HA }}
             5.000  5.000  0.500 peak     14161 weight    0.10000E+01 volume   0.12711E+02 ppm1  9.156    ppm2  3.783
OR        {14161}
          {{ segid "BrD" and resid 102 and name HN }}
          {{ segid "BrD" and resid 105 and name HB1}}
ASSI      {14171}
          {{ segid "BrD" and resid 101 and name HN }}
          {{ segid "BrD" and resid 104 and name HN }}
             4.300  4.300  1.200 peak     14171 weight    0.10000E+01 volume   0.29353E+02 ppm1  8.513    ppm2  7.761
```

TABLE 3-continued

Ambiguous NOE-derived Inter-proton Distance Restraints

```
OR      {14171}
        {{ segid "BrD" and resid 101 and name HN}}
        {  segid "BrD" and resid 34 and name HE4}
ASSI    {14201}
        {{ segid "BrD" and resid 100 and name HN }}
        {{ segid "BrD" and resid 86 and name HE1 }}
          4.100  4.100  1.400 peak     14201 weight    0.10000E♦01 volume   0.38990E♦02 ppm1  8.667   ppm2  3.092
OR      {14201}
        {{ segid "BrD" and resid 100 and name HN }}
        {{ segid "BrD" and resid 96 and name HB2 }}
ASSI    {14221}
        {{ segid "BrD" and resid 100 and name HN   }}
        {{ segid "BrD" and resid 101 and name HG12}}
          4.800  4.800  0.700 peak     14221 weight    0.10000E♦01 volume   0.14931E♦02 ppm1  8.669   ppm2  1.806
OR      {14221}
        {{ segid "BrD" and resid 100 and name HN }}
        {{ segid "BrD" and resid 102 and name HB2}}
ASSI    {14241}
        {{ segid "BrD" and resid 99 and name HN }}
        {{ segid "BrD" and resid 96 and name HB2}}
          4.900  4.900  0.600 peak     14241 weight    0.10000E♦01 volume   0.14325E♦02 ppm1  8.940   ppm2  3.103
OR      {14241}
        {{ segid "BrD" and resid 99 and name HN }}
        {{ segid "BrD" and resid 94 and name HG1}}
OR      {14241}
        {{ segid "BrD" and resid 99 and name HN }}
        {{ segid "BrD" and resid 86 and name HE1}}
ASSI    {14251}
        {{ segid "BrD" and resid 99 and name HN   }}
        {  segid "BrD" and resid 81 and name HG24}
          5.500  5.500  0.000 peak     14251 weight    0.10000E♦01 volume   0.30696E♦01 ppm1  6.934   ppm2  0.748
OR      {14251}
        {{ segid "BrD" and resid 99 and name HN }}
        {{ segid "BrD" and resid 86 and name HG2}}
ASSI    {14281}
        {{ segid "BrD" and resid 98 and name HN }}
        {{ segid "BrD" and resid 32 and name HH2}}
          3.800  3.600  1.700 peak     14281 weight    0.10000E♦01 volume   0.66237E♦02 ppm1  9.125   ppm2  7.750
OR      {14281}
        {{ segid "BrD" and resid 98 and name HN }}
        {  segid "BrD" and resid 34 and name HE4}
OR      {14281}
        {{ segid "BrD" and resid 79 and name HN }}
        {  segid "BrD" and resid 68 and name HD4}
ASSI    {14301}
        {{ segid "BrD" and resid 96 and name HN }}
        {  segid "BrD" and resid 99 and name HB4}
          3.600  3.200  1.900 peak     14301 weight    0.10000E♦01 volume   0.84940E♦02 ppm1  7.977   ppm2  2.199
OR      {14301}
        {{ segid "BrD" and resid 96 and name HN }}
        {{ segid "BrD" and resid 97 and name HG2}}
ASSI    {14311}
        {{ segid "BrD" and resid 77 and name HN   }}
        {  segid "BrD" and resid 73 and name HD14}
          4.900  4.900  0.600 peak     14311 weight    0.10000E♦01 volume   0.13346E♦02 ppm1  7.981   ppm2  1.543
OR      {14311}
        {{ segid "BrD" and resid 78 and name HN    }}
        {{ segid "BrD" and resid 116 and name HG12}}
OR      {14311}
        {{ segid "BrD" and resid 78 and name HN   }}
        {  segid "BrD" and resid 96 and name HD14}
OR      {14311}
        {{ segid "BrD" and resid 77 and name HN    }}
        {{ segid "BrD" and resid 116 and name HG12}}
OR      {14311}
        {{ segid "BrD" and resid 96 and name HN   }}
        {  segid "BrD" and resid 101 and name HD14}
ASSI    {14441}
        {{ segid "BrD" and resid 63 and name HN }}
        {{ segid "BrD" and resid 79 and name HG1}}
          4.600  4.600  0.900 peak     14441 weight    0.10000E♦01 volume   0.19968E♦02 ppm1  9.658   ppm2  3.046
OR      {14441}
        {{ segid "BrD" and resid 83 and name HN }}
        {{ segid "BrD" and resid 87 and name HG1}}
ASSI    {14451}
        {{ segid "BrD" and resid 83 and name HN }}
        {{ segid "BrD" and resid 80 and name HG1}}
          9.900  9.500  0.000 peak     14451 weight    0.10000E♦01 volume   0.45437E♦00 ppm1  9.658   ppm2  2.374
```

TABLE 3-continued

Ambiguous NOE-derived Inter-proton Distance Restraints

```
OR      {14461}
        {{ segid "BrD" and resid 83 and name HN  }}
        {{ segid "BrD" and resid 86 and name HB1}}
ASSI    {14461}
        {{ segid "BrD" and resid 83 and name HN  }}
        {{ segid "BrD" and resid 86 and name HG2}}
          5.000  5.000  0.900 peak      14461 weight    0.10000E+01 volume   0.12633E+02 ppm1  9.657    ppm2  0.743
OR      {14461}
        {{ segid "BrD" and resid 83 and name HN   }}
        {  segid "BrD" and resid 81 and name HG24}
ASSI    {14511}
        {{ segid "BrD" and resid 79 and name HN   }}
        {  segid "BrD" and resid 106 and name HE4}
          3.600  3.200  1.900 peak      14511 weight    0.10000E+01 volume   0.86513E+02 ppm1  8.680    ppm2  7.621
OR      {14511}
        {{ segid "BrD" and resid 79 and name HN }}
        {{ segid "BrD" and resid 81 and name HN }}
ASSI    {14591}
        {{ segid "BrD" and resid 72 and name HN }}
        {{ segid "BrD" and resid 73 and name HA }}
          4.100  4.100  1.400 peak      14591 weight    0.10000E+01 volume   0.40514E+02 ppm1  8.858    ppm2  4.801
OR      {14591}
        {{ segid "BrD" and resid 72 and name HN  }}
        {{ segid "BrD" and resid 70 and name HB1}}
OR      {14591}
        {{ segid "BrD" and resid 72 and name HN  }}
        {{ segid "BrD" and resid 115 and name HA}}
ASSI    {14631}
        {{ segid "BrD" and resid 66 and name HN }}
        {{ segid "BrD" and resid 47 and name HA }}
          4.400  4.400  1.100 peak      14631 weight    0.10000E+01 volume   0.25627E+02 ppm1  8.762    ppm2  4.678
OR      {14631}
        {{ segid "BrD" and resid 66 and name HN }}
        {{ segid "BrD" and resid 69 and name HA }}
OR      {14631}
        {{ segid "BrD" and resid 66 and name HN }}
        {{ segid "BrD" and resid 61 and name HA }}
ASSI    {14641}
        {{ segid "BrD" and resid 60 and name HN }}
        {{ segid "BrD" and resid 62 and name HN }}
          4.200  4.200  1.300 peak      14641 weight    0.10000E+01 volume   0.32935E+02 ppm1  8.568    ppm2  8.968
OR      {14641}
        {{ segid "BrD" and resid 69 and name HN }}
        {{ segid "BrD" and resid 62 and name HN }}
ASSI    {14691}
        {{ segid "BrD" and resid 69 and name HN   }}
        {{ segid "BrD" and resid 65 and name HD22}}
          4.200  4.200  1.300 peak      14651 weight    0.10000E+01 volume   0.33097E+02 ppm1  8.566    ppm2  7.569
OR      {14651}
        {{ segid "BrD" and resid 60 and name HN  }}
        {  segid "BrD" and resid 74 and name HE4}
ASSI    {14751}
        {{ segid "BrD" and resid 62 and name HN }}
        {{ segid "BrD" and resid 64 and name HN }}
          2.800  2.000  2.000 peak      14751 weight    0.10000E+01 volume   0.39549E+03 ppm1  8.998    ppm2  8.976
OR      {14791}
        {{ segid "BrD" and resid 62 and name HN }}
        {{ segid "BrD" and resid 60 and name HN }}
ASSI    {14791}
        {{ segid "BrD" and resid 38 and name HN  }}
        {{ segid "BrD" and resid 39 and name HG2}}
          3.900  3.800  1.600 peak      14791 weight    0.10000E+01 volume   0.52365E+02 ppm1  6.742    ppm2  2.547
OR      {14791}
        {{ segid "BrD" and resid 61 and name HN  }}
        {  segid "BrD" and resid 54 and name HE4}
OR      {14791}
        {{ segid "BrD" and resid 61 and name HN  }}
        {{ segid "BrD" and resid 59 and name HB2}}
OR      {14791}
        {{ segid "BrD" and resid 61 and name HN  }}
        {{ segid "BrD" and resid 63 and name HB2}}
ASSI    {14801}
        {{ segid "BrD" and resid 65 and name HN }}
        {{ segid "BrD" and resid 63 and name HN }}
          4.400  4.400  1.100 peak      14801 weight    0.10000E+01 volume   0.24650E+02 ppm1  8.570    ppm2  9.470
OR      {14801}
        {{ segid "BrD" and resid 60 and name HN }}
        {{ segid "BrD" and resid 63 and name HN }}
```

TABLE 3-continued

Ambiguous NOE-derived Inter-proton Distance Restraints

```
ASSI    {14821}
        {{ segid "BrD" and resid 59 and name HN }}
        {{ segid "BrD" and resid 55 and name HN }}
          3.600  3.200  1.900 peak    14821 weight   0.10000E+01 volume  0.84273E+02 ppm1  8.498   ppm2  7.974
OR      {14821}
        {{ segid "BrD" and resid 31 and name HN }}
        {{ segid "BrD" and resid 32 and name HE2}}
ASSI    {14901}
        {{ segid "BrD" and resid 54 and name HN }}
        {{ segid "BrD" and resid 55 and name HB1}}
          4.200  4.200  1.100 peak    14901 weight   0.10000E+01 volume  0.25948E+02 ppm1  9.039   ppm2  2.965
OR      {14901}
        {{ segid "BrD" and resid 54 and name HN }}
        {{ segid "BrD" and resid 37 and name HB1}}
ASSI    {14921}
        {{ segid "BrD" and resid 54 and name HN   }}
        {  segid "BrD" and resid 81 and name HG14}
          4.000  4.000  1.900 peak    14921 weight   0.10000E+01 volume  0.46529E+02 ppm1  9.037   ppm2  1.081
OR      {14921}
        {{ segid "BrD" and resid 54 and name HN   }}
        {  segid "BrD" and resid 38 and name HG14}
ASSI    {14931}
        {{ segid "BrD" and resid 52 and name HN   }}
        {  segid "BrD" and resid 50 and name HD14}
          5.500  5.500  0.000 peak    14931 weight   0.10000E+01 volume  0.20319E+01 ppm1  9.004   ppm2  1.110
OR      {14931}
        {{ segid "BrD" and resid 52 and name HN   }}
        {  segid "BrD" and resid 81 and name HG14}
ASSI    {15021}
        {{ segid "BrD" and resid 50 and name HN }}
        {{ segid "BrD" and resid 49 and name HB }}
          3.400  2.900  2.100 peak    15021 weight   0.10000E+01 volume  0.11615E+03 ppm1  8.562   ppm2  2.642
OR      {15021}
        {{ segid "BrD" and resid 46 and name HN }}
        {{ segid "BrD" and resid 44 and name HB2}}
ASSI    {15091}
        {{ segid "BrD" and resid 35 and name HN }}
        {{ segid "BrD" and resid 33 and name HB1}}
          5.000  5.000  0.500 peak    15091 weight   0.10000E+01 volume  0.12752E+02 ppm1  7.725   ppm2  1.073
OR      {15091}
        {{ segid "BrD" and resid 35 and name HN   }}
        {  segid "BrD" and resid 81 and name HG14}
ASSI    {15181}
        {{ segid "BrD" and resid 30 and name HN    }}
        {  segid "BrD" and resid 101 and name HG24}
          3.900  2.800  1.600 peak    15181 weight   0.10000E+01 volume  0.50580E+02 ppm1 12.275   ppm2  1.601
OR      {15181}
        {{ segid "BrD" and resid 30 and name HN   }}
        {  segid "BrD" and resid 25 and name HG24}
ASSI    {15221}
        {{ segid "BrD" and resid 28 and name HN }}
        {{ segid "BrD" and resid 32 and name HN }}
          4.200  4.200  1.300 peak    15221 weight   0.10000E+01 volume  0.33692E+02 ppm1  8.166   ppm2  7.752
OR      {15221}
        {{ segid "BrD" and resid 28 and name HN  }}
        {  segid "BrD" and resid 34 and name HE4}
ASSI    {15331}
        {{ segid "BrD" and resid 25 and name HN  }}
        {  segid "BrD" and resid 31 and name HB4}
          4.500  4.500  1.000 peak    15331 weight   0.10000E+01 volume  0.22185E+02 ppm1  9.133   ppm2  2.295
OR      {15331}
        {{ segid "BrD" and resid 25 and name HN }}
        {{ segid "BrD" and resid 22 and name HB2}}
ASSI    {15341}
        {{ segid "BrD" and resid 24 and name HN }}
        {{ segid "BrD" and resid 27 and name HN }}
          3.700  3.400  1.800 peak    15341 weight   0.10000E+01 volume  0.78760E+02 ppm1  8.660   ppm2  8.147
OR      {15341}
        {{ segid "BrD" and resid 24 and name HN }}
        {{ segid "BrD" and resid 20 and name HN }}
ASSI    {15411}
        {{ segid "BrD" and resid 18 and name HN  }}
        {{ segid "BrD" and resid 21 and name HG12}}
          4.300  4.300  1.200 peak    15411 weight   0.10000E+01 volume  0.29441E+02 ppm1  9.077   ppm2  1.642
OR      {15411}
        {{ segid "BrD" and resid 18 and name HN   }}
        {  segid "BrD" and resid 63 and name HG14}
```

TABLE 3-continued

Ambiguous NOE-derived Inter-proton Distance Restraints

```
OR      {15411}
        {{ segid "BrD" and resid 18 and name HN   }}
        {  segid "BrD" and resid 21 and name HG24}
ASSI    {15451}
        {{ segid "BrD" and resid 17 and name HN   }}
        {  segid "BrD" and resid 15 and name HD4}
           4.700  4.700  0.800 peak    15451 weight    0.10000E+01 volume   0.16799E+02 ppm1  8.669    ppm2  7.656
OR      {15451}
        {{ segid "BrD" and resid 17 and name HN   }}
        {  segid "BrD" and resid 106 and name HE4}
ASSI    {15461}
        {{ segid "BrD" and resid 16 and name HN   }}
        {  segid "BrD" and resid 14 and name HD24}
           4.800  4.800  0.700 peak    15461 weight    0.10000E+01 volume   0.14734E+02 ppm1  8.791    ppm2  1.430
OR      {15461}
        {{ segid "BrD" and resid 16 and name HN   }}
        {  segid "BrD" and resid 69 and name HG24}
OR      {15461}
        {{ segid "BrD" and resid 16 and name HN   }}
        {  segid "BrD" and resid 14 and name HD14}
ASSI    {15491}
        {{ segid "BrD" and resid 14 and name HN  }}
        {{ segid "BrD" and resid 15 and name HB1}}
           5.000  5.000  0.500 peak    15491 weight    0.10000E+01 volume   0.11598E+02 ppm1  8.609    ppm2  3.823
OR      {15491}
        {{ segid "BrD" and resid 13 and name HN  }}
        {{ segid "BrD" and resid 15 and name HB1}}
ASSI    {15501}
        {{ segid "BrD" and resid 14 and name HN  }}
        {{ segid "BrD" and resid 15 and name HB2}}
           5.100  5.100  0.400 peak    15501 weight    0.10000E+01 volume   0.11421E+02 ppm1  8.809    ppm2  3.641
OR      {15501}
        {{ segid "BrD" and resid 13 and name HN  }}
        {{ segid "BrD" and resid 15 and name HB2}}
ASSI    {15581}
        {{ segid "BrD" and resid 32 and name HE1 }}
        {{ segid "BrD" and resid 30 and name HB1 }}
           4.800  4.800  0.700 peak    15581 weight    0.10000E+01 volume   0.19339E+02 ppm1 11.082    ppm2  4.955
OR      {15581}
        {{ segid "BrD" and resid 32 and name HE1}}
        {{ segid "BrD" and resid 32 and name HA  }}
ASSI    {15621}
        {{ segid "BrD" and resid 32 and name HE1 }}
        {{ segid "BrD" and resid 33 and name HD1 }}
           4.200  4.200  1.300 peak    15621 weight    0.10000E+01 volume   0.36353E+02 ppm1 11.082    ppm2  2.779
OR      {15621}
        {{ segid "BrD" and resid 32 and name HE1 }}
        {{ segid "BrD" and resid 94 and name HB1 }}
ASSI    {862}
        {{ segid "BrD" and resid 95 and name HB2}}
        {{ segid "BrD" and resid 95 and name HA  }}
           2.900  2.100  2.100 peak      862 weight    0.10000E+01 volume   0.13207E+03 ppm1  3.373    ppm2  4.477
OR      {862}
        {{ segid "BrD" and resid 65 and name HB2}}
        {{ segid "BrD" and resid 62 and name HA  }}
ASSI    {5972}
        {  segid "BrD" and resid 14 and name HD14}
        {{ segid "BrD" and resid 68 and name HB1  }}
           2.800  2.800  2.000 peak     5972 weight    0.10000E+01 volume   0.16306E+03 ppm1  1.057    ppm2  3.667
OR      {5972}
        {  segid "BrD" and resid 16 and name HD14}
        {{ segid "BrD" and resid 15 and name HB2 }}
ASSI    {6172}
        {  segid "BrD" and resid 56 and name HD14}
        {{ segid "BrD" and resid 26 and name HA   }}
           3.00   2.200  2.200 peak     6172 weight    0.10000E+01 volume   0.11879E+03 ppm1  1.546    ppm2  4.502
OR      {6172}
        {{ segid "BrD" and resid 116 and name HG12}}
        {{ segid "BrD" and resid 75 and name HA    }}
ASSI    {6592}
        {  segid "BrD" and resid 31 and name HB4 }
        {  segid "BrD" and resid 35 and name HE4 }
           3.000  2.200  2.200 peak     6592 weight    0.10000E+01 volume   0.12050E+03 ppm1  2.289    ppm2  2.779
OR      {6592}
        {  segid "BrD" and resid 31 and name HB4}
        {{ segid "BrD" and resid 33 and name HD1}}
```

TABLE 3-continued

Ambiguous NOE-derived Inter-proton Distance Restraints

```
ASSI  {6622}
      {  segid "BrD" and resid 31 and name HB4}
      {{ segid "BrD" and resid 56 and name HB2}}
         3.200  2.600  2.300 peak    6622 weight   0.10000E+01 volume  0.78528E+02 ppm1  2.291  ppm2  1.994
OR    {6622}
      {  segid "BrD" and resid 31 and name HB4 }
      {{ segid "BrD" and resid 102 and name HB1}}
ASSI  {6812}
      {  segid "BrD" and resid 99 and name HB4}}
      {{ segid "BrD" and resid 85 and name HB2}}
         2.500  1.600  1.600 peak    6812 weight   0.10000E+01 volume  0.30669E+03 ppm1  2.190  ppm2  3.645
OR    {6812}
      {  segid "BrD" and resid 99 and name HB4}
      {{ segid "BrD" and resid 82 and name HB1}}
ASSI  {6822}
      {  segid "BrD" and resid 99 and name HB4 }}
      {{ segid "BrD" and resid 103 and name HB2}}
         2.900  2.100  2.100 peak    6822 weight   0.10000E+01 volume  0.12780E+03 ppm1  2.190  ppm2  1.903
OR    {6822}
      {  segid "BrD" and resid 99 and name HB4}
      {{ segid "BrD" and resid 86 and name HG1}}
ASSI  {7132}
      {  segid "BrD" and resid 38 and name HG14}
      {{ segid "BrD" and resid 46 and name HB1  }}
         2.600  1.700  1.700 peak    7132 weight   0.10000E+01 volume  0.23427E+03 ppm1  1.057  ppm2  3.306
OR    {7132}
      {  segid "BrD" and resid 81 and name HG14}
      {{ segid "BrD" and resid 77 and name HB1  }}
ASSI  {7142}
      {  segid "BrD" and resid 81 and name HG14}
      {{ segid "BrD" and resid 59 and name HB2  }}
         2.800  2.000  2.000 peak    7142 weight   0.10000E+01 volume  0.18258E+03 ppm1  1.058  ppm2  2.475
OR    {7142}
      {  segid "BrD" and resid 38 and name HG14}
      {{ segid "BrD" and resid 52 and name HG2  }}
ASSI  {7152}
      {  segid "BrD" and resid 81 and name HG14}
      {{ segid "BrD" and resid 54 and name HB2  }}
         2.800  2.000  2.000 peak    7152 weight   0.10000E+01 volume  0.17360E+03 ppm1  1.097  ppm2  1.962
OR    {7152}
      {  segid "BrD" and resid 81 and name HG14}
      {{ segid "BrD" and resid 56 and name HB2  }}
ASSI  {7222}
      {{ segid "BrD" and resid 17 and name HB   }}
      {  segid "BrD" and resid 14 and name HD24}
         3.200  2.600  2.300 peak    7222 weight   0.10000E+01 volume  0.77701E+02 ppm1  4.854  ppm2  1.424
OR    {7222}
      {{ segid "BrD" and resid 17 and name HE   }}
      {  segid "BrD" and resid 14 and name HD14}
OR    {7222}
      {{ segid "BrD" and resid 17 and name HE   }}
      {{ segid "BrD" and resid 109 and name HG1}}
ASSI  {7232}
      {{ segid "BrD" and resid 17 and name HB   }}
      {  segid "BrD" and resid 115 and name HD14}
         3.400  2.900  2.100 peak    7232 weight   0.10000E+01 volume  0.48663E+02 ppm1  4.854  ppm2  1.377
OR    {7232}
      {{ segid "BrD" and resid 17 and name HE   }}
      {  segid "BrD" and resid 14 and name HD24}
ASSI  {7262}
      {  segid "BrD" and resid 17 and name HG24 }
      {  segid "BrD" and resid 21 and name HD14 }
         2.400  1.400  1.400 peak    7262 weight   0.10000E+01 volume  0.43712E+03 ppm1  1.747  ppm2  1.221
OR    {7262}
      {  segid "BrD" and resid 17 and name HG24 }
      {  segid "BrD" and resid 110 and name HG24}
ASSI  {7392}
      {{ segid "BrD" and resid 15 and name HA }}
      {{ segid "BrD" and resid 18 and name HG }}
         3.800  3.600  1.700 peak    7392 weight   0.10000E+01 volume  0.25131E+02 ppm1  4.605  ppm2  2.314
OR    {7392}
      {{ segid "BrD" and resid 15 and name HA }}
      {{ segid "BrD" and resid 19 and name HB1}}
ASSI  {7742}
      {{ segid "BrD" and resid 106 and name HA }}
      {  segid "BrD" and resid 25 and name HG14}
         3.400  2.900  2.100 peak    7742 weight   0.10000E+01 volume  0.51959E+02 ppm1  4.597  ppm2  1.817
```

TABLE 3-continued

Ambiguous NOE-derived Inter-proton Distance Restraints

| | |
|---|---|
| OR | {7742} |
| | {{ segid "BrD" and resid 106 and name HA }} |
| | {{ segid "BrD" and resid 102 and name HB2}} |
| ASSI | {8052} |
| | {{ segid "BrD" and resid 77 and name HB1 }} |
| | {{ segid "BrD" and resid 80 and name HB2 }} |
| | 3.300  2.700  2.200 peak    8052 weight    0.10000E♦01 volume  0.59988E♦02 ppm1  3.325    ppm2  2.564 |
| OR | {8052} |
| | {{ segid "BrD" and resid 77 and name HB1 }} |
| | {{ segid "BrD" and resid 54 and name HB1 }} |
| OR | {8052} |
| | {{ segid "BrD" and resid 77 and name HB1 }} |
| | {  segid "BrD" and resid 54 and name HE4 } |
| ASSI | {8122} |
| | {{ segid "BrD" and resid 63 and name HA }} |
| | {{ segid "BrD" and resid 62 and name HB1}} |
| | 3.700  3.400  1.800 peak    8122 weight    0.10000E♦01 volume  0.30661E♦02 ppm1  5.296    ppm2  2.660 |
| OR | {8122} |
| | {{ segid "BrD" and resid 63 and name HA }} |
| | {{ segid "BrD" and resid 67 and name HB2}} |
| OR | {8122} |
| | {{ segid "BrD" and resid 63 and name HA }} |
| | {{ segid "BrD" and resid 64 and name HB1}} |
| ASSI | {8212} |
| | {{ segid "BrD" and resid 109 and name HG1 }} |
| | {{ segid "BrD" and resid 109 and name HB1 }} |
| | 2.200  1.200  1.200 peak    8212 weight    0.10000E♦01 volume  0.72542E♦03 ppm1  1.401    ppm2  2.310 |
| OR | {8212} |
| | {  segid "BrD" and resid 14 and name HD24} |
| | {{ segid "BrD" and resid 18 and name HG  }} |
| ASSI | {8492} |
| | {  segid "BrD" and resid 18 and name HD24} |
| | {{ segid "BrD" and resid 14 and name HA  }} |
| | 2.700  1.800  1.800 peak    8492 weight    0.10000E♦01 volume  0.19700E♦03 ppm1  0.414    ppm2  4.626 |
| OR | {8492} |
| | {  segid "BrD" and resid 18 and name HD24} |
| | {{ segid "BrD" and resid 15 and name HA  }} |
| OR | {8492} |
| | {  segid "BrD" and resid 18 and name HD24} |
| | {{ segid "BrD" and resid 71 and name HA  }} |
| ASSI | {8542} |
| | {  segid "BrD" and resid 22 and name HD14} |
| | {{ segid "BrD" and resid 60 and name HB2 }} |
| | 2.600  1.700  1.700 peak    8542 weight    0.10000E♦01 volume  0.24926E♦03 ppm1  1.645    ppm2  4.629 |
| OR | {8542} |
| | {  segid "BrD" and resid 22 and name HD14} |
| | {{ segid "BrD" and resid 23 and name HA  }} |
| OR | {8542} |
| | {  segid "BrD" and resid 22 and name HD14} |
| | {{ segid "BrD" and resid 56 and name HA  }} |
| OR | {8542} |
| | {  segid "BrD" and resid 22 and name HD14} |
| | {{ segid "BrD" and resid 61 and name HA  }} |
| ASSI | {8662} |
| | { segid "BrD" and resid 56 and name HD24 } |
| | { segid "BrD" and resid 22 and name HD24 } |
| | 2.200  1.200  1.200 peak    8662 weight    0.10000E♦01 volume  0.65442E♦03 ppm1  1.254    ppm2  1.635 |
| OR | {8662} |
| | { segid "BrD" and resid 56 and name HD24 } |
| | { segid "BrD" and resid 25 and name HG24 } |
| ASSI | {8712} |
| | { segid "BrD" and resid 56 and name HD14 } |
| | { segid "BrD" and resid 102 and name HD14} |
| | 2.600  1.700  1.700 peaak   8712 weight    0.10000E♦01 volume  0.26563E♦03 ppm1  1.547    ppm2  1.321 |
| OR | {8712} |
| | { segid "BrD" and resid 56 and name HD14 } |
| | { segid "BrD" and resid 102 and name HD24} |
| OR | {8712} |
| | {{ segid "BrD" and resid 116 and name HG12}} |
| | {  segid "BrD" and resid 115 and name HD14 } |
| ASSI | {8962} |
| | {{ segid "BrD" and resid 56 and name HB2 }} |
| | {  segid "BrD" and resid 25 and name HG24} |
| | 3.700  3.400  1.800 peak    8962 weight    0.10000E♦01 volume  0.31139E♦02 ppm1  1.994    ppm2  1.627 |
| OR | {8962} |
| | {{ segid "BrD" and resid 102 and name HB1 }} |
| | {  segid "BrD" and resid 101 and name HG24} |

TABLE 3-continued

Ambiguous NOE-derived Inter-proton Distance Restraints

```
OR      {8962}
        {{ segid "BrD" and resid 56 and name HB2  }}
        {  segid "BrD" and resid 22 and name HD24}
ASSI    {9112}
        { segid "BrD" and resid 21 and name HG24 }
        { segid "BrD" and resid 102 and name HD24}
           2.600  1.700  1.700 peak    9112 weight    0.10000E+01 volume  0.28598E+03 ppm1  1.600    ppm2  1.324
OR      {9112}
        { segid "BrD" and resid 101 and name HG24 }
        { segid "BrD" and resid 102 and name HD14 }
ASSI    {9142}
        { segid "BrD" and resid 21 and name HG24 }
        { segid "BrD" and resid 78 and name HD14 }
           3.800  3.600  1.700 peak    9142 weight    0.10000E+01 volume  0.27968E+02 ppm1  1.596    ppm2  0.772
OR      {9142}
        { segid "BrD" and resid 21 and name HG24 }
        { segid "BrD" and resid 81 and name HG24 }
ASSI    {9192}
        { segid "BrD" and resid 21 and name HD14 }
        { segid "BrD" and resid 18 and name HD14 }
           2.500  1.600  1.600 peak    9192 weight    0.10000E+01 volume  0.36076E+03 ppm1  1.205    ppm2  1.068
OR      {9192}
        {  segid "BrD" and resid 21 and name HD14}
        {{ segid "BrD" and resid 78 and name HB2 }}
ASSI    {9662}
        {{ segid "BrD" and resid 79 and name HG1   }}
        {  segid "BrD" and resid 83 and name HG24}
           3.000  2.200  2.200 peak    9662 weight    0.10000E+01 volume  0.10300E+03 ppm1  3.031    ppm2  1.900
OR      {9662}
        {{ segid "BrD" and resid 79 and name HG1   }}
        {{ segid "BrD" and resid 116 and name HG11}}
ASSI    {10002}
        {{ segid "BrD" and resid 54 and name HB1  }}
        {  segid "BrD" and resid 81 and name HG14}
           3.600  3.200  1.900 peak   10002 weight    0.10000E+01 volume  0.33897E+02 ppm1  2.585    ppm2  1.083
OR      {10002}
        {{ segid "BrD" and resid 42 and name HB2  }}
        {  segid "BrD" and resid 38 and name HG14}
ASSI    {10092}
        {{ segid "BrD" and resid 35 and name HG1}}
        {{ segid "BrD" and resid 32 and name HA  }}
           3.100  2.400  2.400 peak   10092 weight    0.10000E+01 volume  0.97444E+02 ppm1  3.422    ppm2  4.972
OR      {10092}
        {{ segid "BrD" and resid 35 and name HG1}}
        {{ segid "BrD" and resid 31 and name HA  }}
ASSI    {10182}
        {{ segid "BrD" and resid 52 and name HB1 }}
        {{ segid "BrD" and resid 80 and name HG1 }}
           4.100  4.100  1.400 peak   10182 weight    0.10000E+01 volume  0.17926E+02 ppm1  3.621    ppm2  2.345
OR      {10182}
        {{ segid "BrD" and resid 84 and name HB1 }}
        {{ segid "BrD" and resid 80 and name HG1 }}
ASSI    {10302}
        {{ segid "BrD" and resid 42 and name HG1 }}
        {{ segid "BrD" and resid 39 and name HD1 }}
           3.000  2.200  2.200 peak   10302 weight    0.10000E+01 volume  0.10808E+03 ppm1  2.880    ppm2  2.298
OR      {10302}
        {{ segid "BrD" and resid 7 and name HG1 }}
        {{ segid "BrD" and resid 6 and name HB2 }}
ASSI    {10412}
        {{ segid "BrD" and resid 48 and name HA  }}
        {{ segid "BrD" and resid 48 and name HB1}}
           2.800  2.000  2.000 peak   10412 weight    0.10000E+01 volume  0.17461E+03 ppm1  4.831    ppm2  2.762
OR      {10412}
        {{ segid "BrD" and resid 87 and name HA  }}
        {{ segid "BrD" and resid 87 and name HB1}}
ASSI    {10502}
        {{ segid "BrD" and resid 112 and name HB1}}
        {  segid "BrD" and resid 113 and name HB4}
           2.700  1.800  1.800 peak    1002 weight    0.10000E+01 volume  0.19681E+03 ppm1  2.684    ppm2  1.985
OR      {10502}
        {{ segid "BrD" and resid 112 and name HB  }}
        {{ segid "BrD" and resid 109 and name HD1}}
ASSI    {10602}
        {{ segid "BrD" and resid 23 and name HA }}
        {{ segid "BrD" and resid 19 and name HA }}
           3.500  3.100  2.000 peak   10602 weight    0.10000E+01 volume  0.44566E+02 ppm1  4.656    ppm2  4.278
```

TABLE 3-continued

Ambiguous NOE-derived Inter-proton Distance Restraints

```
OR      {10602}
        {{ segid "BrD" and resid 104 and name HA }}
        {{ segid "BrD" and resid 101 and name HA }}
ASSI    {10902}
        {{ segid "BrD" and resid 70 and name HB1 }}
        {{ segid "BrD" and resid 11 and name HG1 }}
          3.200  2.600  2.300 peak    10902 weight    0.10000E+01 volume   0.71093E+02 ppm1  4.755    ppm2  2.646
OR      {10902}
        {{ segid "BrD" and resid 70 and name HB1}}
        {  segid "BrD" and resid 75 and name HE4}
OR      {10902}
        {{ segid "BrD" and resid 93 and name HB2 }}
        {{ segid "BrD" and resid 97 and name HB1 }}
OR      {10902}
        {{ segid "BrD" and resid 70 and name HB1 }}
        {{ segid "BrD" and resid 62 and name HB1 }}
OR      {10902}
        {{ segid "BrD" and resid 70 and name HB1}}
        {{ segid "BrD" and resid 8 and name HG1  }}
ASSI    {11592}
        {{ segid "BrD" and resid 109 and name HB2}}
        {  segid "BrD" and resid 21 and name HD14}
          3.400  2.900  2.100 peak    11592 weight    0.10000E+01 volume   0.47849E+02 ppm1  2.141    ppm2  1.222
OR      {11592}
        {{ segid "BrD" and resid 109 and name HB2 }}
        {  segid "BrD" and resid 110 and name HG24}
ASSI    {11652}
        {{ segid "BrD" and resid 59 and name HB2 }}
        {  segid "BrD" and resid 58 and name HG24}
          2.900  2.100  2.100 peak    11652 weight    0.10000E+01 volume   0.12259E+03 ppm1  2.487    ppm2  1.660
OR      {11652}
        {{ segid "BrD" and resid 59 and name HB2 }}
        {  segid "BrD" and resid 22 and name HD14}
ASSI    {12162}
        {{ segid "BrD" and resid 18 and name HA   }}
        {  segid "BrD" and resid 21 and name HG24}
          3.600  3.200  1.900 peak    12162 weight    0.10000E+01 volume   0.38701E+02 ppm1  3.866    ppm2  1.591
OR      {12162}
        {{ segid "BrD" and resid 16 and name HA   }}
        {  segid "BrD" and resid 22 and name HD24}
ASSI    {12172}
        {{ segid "BrD" and resid 6 and name HA }}
        {{ segid "BrD" and resid 6 and name HG2}}
          2.500  1.600  1.600 peak    12172 weight    0.10000E+01 volume   0.31535E+03 ppm1  4.951    ppm2  2.033
OR      {12172}
        {{ segid "BrD" and resid 39 and name HA }}
        {{ segid "BrD" and resid 39 and name HG1}}
ASSI    {12302}
        {{ segid "BrD" and resid 86 and name HG2}}
        {{ segid "BrD" and resid 83 and name HA }}
          3.600  3.200  1.900 peak    12302 weight    0.10000E+01 volume   0.36612E+02 ppm1  0.760    ppm2  4.450
OR      {12302}
        {{ segid "BrD" and resid 86 and name HG2}}
        {{ segid "BrD" and resid 96 and name HA }}
ASSI    {12572}
        {  segid "BrD" and resid 59 and name HE4 }
        {  segid "BrD" and resid 22 and name HD14}
          2.700  1.600  1.800 peak    12572 weight    0.10000E+01 volume   0.19213E+03 ppm1  1.848    ppm2  1.645
OR      {12572}
        {  segid "BrD" and resid 59 and name HE4 }
        {  segid "BrD" and resid 63 and name HD14}
ASSI    {12722}
        {  segid "BrD" and resid 18 and name HD14}
        {{ segid "BrD" and resid 68 and name HB2 }}
          3.400  2.900  2.100 peak    12722 weight    0.10000E+01 volume   0.56232E+02 ppm1  1.056    ppm2  3.513
OR      {12722}
        {  segid "BrD" and resid 18 and name HD14}
        {{ segid "BrD" and resid 75 and name HG1  }}
ASSI    {12742}
        {{ segid "BrD" and resid 72 and name HA    }}
        {  segid "BrD" and resid 116 and name HG24}
          3.000  2.200  2.300 peak    12742 weight    0.10000E+01 volume   0.10372E+03 ppm1  4.496    ppm2  1.414
OR      {12742}
        {{ segid "BrD" and resid 67 and name HA   }}
        {  segid "BrD" and resid 69 and name HG24}
OR      {12742}
        {{ segid "BrD" and resid 111 and name HA   }}
        {  segid "BrD" and resid 116 and name HD14}
```

TABLE 3-continued

Ambiguous NOE-derived Inter-proton Distance Restraints

```
ASSI  {12862}
      {{ segid "BrD" and resid 62 and name HD1}}
      {  segid "BrD" and resid 54 and name HE4}
        3.000  2.200  2.200 peak    12862 weight  0.10000E+01 volume  0.10219E+03 ppm1  3.177   ppm2  2.569
OR    {12862}
      {{ segid "BrD" and resid 62 and name HD1 }}
      {{ segid "BrD" and resid 63 and name HB2 }}
OR    {12862}
      {{ segid "BrD" and resid 62 and name HD1 }}
      {{ segid "BrD" and resid 54 and name HB1 }}
ASSI  {13242}
      {{ segid "BrD" and resid 46 and name HB2  }}
      {  segid "BrD" and resid 38 and name HG24}
        3.50   3.100  2.000 peak    13242 weight  0.10000E+01 volume  0.46826E+02 ppm1  3.080   ppm2  0.791
OR    {13242}
      {{ segid "BrD" and resid 46 and name HB2  }}
      {{ segid "BrD" and resid 50 and name HG12}}
ASSI  {13322}
      {  segid "BrD" and resid 78 and name HD24 }
      {  segid "BrD" and resid 21 and name HG24 }
        2.700  1.800  1.800 peak    13322 weight  0.10000E+01 volume  0.21424E+03 ppm1  0.662   ppm2  1.590
OR    {13322}
      {  segid "BrD" and resid 78 and name HD24 }
      {  segid "BrD" and resid 22 and name HD24 }
ASSI  {13352}
      {  segid "BrD" and resid 18 and name HD24}
      {{ segid "BrD" and resid 14 and name HB1  }}
        4.200  4.200  1.300 peak    13355 weight  0.10000E+01 volume  0.14746E+02 ppm1  0.415   ppm2  2.451
OR    {13352}
      {  segid "BrD" and resid 18 and name HD24 }
      {{ segid "BrD" and resid 21 and name HB   }}
ASSI  {13392}
      {  segid "BrD" and resid 25 and name HG14}
      {{ segid "BrD" and resid 28 and name HA   }}
        2.800  2.000  2.000 peak    13392 weight  0.10000E+01 volume  0.16152E+03 ppm1  1.795   ppm2  4.566
OR    {13392}
      {  segid "BrD" and resid 25 and name HG24 }
      {{ segid "BrD" and resid 106 and name HA  }}
ASSI  {13592}
      {  segid "BrD" and resid 56 and name HD24}
      {{ segid "BrD" and resid 99 and name HB2  }}
        2.600  1.700  1.700 peak    13592 weight  0.10000E+01 volume  0.24679E+03 ppm1  1.254   ppm2  2.499
OR    {13592}
      {  segid "BrD" and resid 56 and name HD24}
      {  segid "BrD" and resid 54 and name HE4  }
OR    {13592}
      {  segid "BrD" and resid 56 and name HD24}
      {{ segid "BrD" and resid 26 and name HB1  }}
ASSI  {13602}
      {  segid "BrD" and resid 54 and name HE4}
      {{ segid "BrD" and resid 37 and name HB2}}
        2.500  1.600  1.600 peak    13602 weight  0.10000E+01 volume  0.34655E+03 ppm1  2.535   ppm2  2.323
OR    {13602}
      {  segid "BrD" and resid 54 and name HE4}
      {{ segid "BrD" and resid 56 and name HG   }}
ASSI  {13762}
      {  segid "BrD" and resid 63 and name HD24}
      {{ segid "BrD" and resid 19 and name HB1  }}
        2.300  1.300  1.300 peak    13762 weight  0.10000E+01 volume  0.59623E+03 ppm1  1.498   ppm2  2.318
OR    {13762}
      {  segid "BrD" and resid 63 and name HD24}
      {{ segid "BrD" and resid 22 and name HB2  }}
ASSI  {13952}
      {  segid "BrD" and resid 14 and name HD14}
      {{ segid "BrD" and resid 14 and name HA   }}
        2.700  1.600  1.600 peak    13952 weight  0.10000E+01 volume  0.20699E+03 ppm1  1.402   ppm2  4.687
OR    {13952}
      {  segid "BrD" and resid 14 and name HD14}
      {{ segid "BrD" and resid 69 and name HA   }}
ASSI  {14042}
      {  segid "BrD" and resid 76 and name HB4  }
      {  segid "BrD" and resid 73 and name HD14 }
        3.100  2.400  2.400 peak    14042 weight  0.10000E+01 volume  0.97985E+02 ppm1  2.092   ppm2  1.540
OR    {14042}
      {  segid "BrD" and resid 76 and name HB4   }}
      {{ segid "BrD" and resid 116 and name HG12}}
```

TABLE 3-continued

Ambiguous NOE-derived Inter-proton Distance Restraints

```
ASSI  {14162}
      {{ segid "BrD" and resid 15 and name HA    }}
      {  segid "BrD" and resid 63 and name HD24}
         3.600  3.200  1.900 peak     14162 weight    0.10000E+01 volume   0.37938E+02 ppm1  4.609     ppm2  1.490
OR    {14162}
      {{ segid "BrD" and resid 60 and name HB2 }}
      { segid "BrD" and resid 63 and name HD24}
ASSI  {14192}
      {{ segid "BrD" and resid 62 and name HA }}
      {{ segid "BrD" and resid 68 and name HB2}}
         3.700  3.400  1.800 peak     14192 weight    0.10000E+01 volume   0.29812E+02 ppm1  4.459     ppm2  1.504
OR    {14192}
      {{ segid "BrD" and resid 95 and name HA  }}
      {{ segid "BrD" and resid 89 and name HB2}}
ASSI  {14202}
      {{ segid "BrD" and resid 95 and name HA  }}
      {{ segid "BrD" and resid 98 and name HB2}}
         3.200  2.600  2.300 peak     14202 weight    0.10000E+01 volume   0.81269E+02 ppm1  4.462     ppm2  3.701
OR    {14202}
      {{ segid "BrD" and resid 62 and name HA }}
      {{ segid "BrD" and resid 68 and name HB1}}
ASSI  {14312}
      {  segid "BrD" and resid 22 and name HD24}
      {{ segid "BrD" and resid 59 and name HB2 }}
         2.700  1.800  1.800 peak     14312 weight    0.10000E+01 volume   0.21510E+03 ppm1  1.599     ppm2  2.501
OR    {14312}
      {  segid "BrD" and resid 22 and name HD24}
      {{ segid "BrD" and resid 21 and name HB   }}
OR    {14312}
      {  segid "BrD" and resid 22 and name HD24}
      {{ segid "BrD" and resid 63 and name HB2 }}
OR    {14312}
      {  segid "BrD" and resid 22 and name HD24}
      {{ segid "BrD" and resid 26 and name HB1 }}
ASSI  {14432}
      {  segid "BrD" and resid 21 and name HD14}
      {{ segid "BrD" and resid 18 and name HB1  }}
         2.700  1.800  1.800 peak     14432 weight    0.10000E+01 volume   0.19246E+03 ppm1  1.205     ppm2  2.148
OR    {14432}
      {  segid "BrD" and resid 21 and name HD14}
      {{ segid "BrD" and resid 102 and name HG  }}
ASSI  {14462}
      { segid "BrD" and resid 110 and name HD14 }
      { segid "BrD" and resid 116 and name HD14 }
         2.100  1.100  1.100 peak     14462 weight    0.10000E+01 volume   0.89267E+03 ppm1  1.154     ppm2  1.387
OR    {14462}
      { segid "BrD" and resid 110 and name HD14 }
      { segid "BrD" and resid 115 and name HD14 }
ASSI  {14602}
      { segid "BrD" and resid 18 and name HD14  }
      { segid "BrD" and resid 115 and name HD14}
         3.500  3.100  2.000 peak     14602 weight    0.10000E+01 volume   0.42578E+02 ppm1  1.057     ppm2  1.327
OR    {14602}
      {  segid "BrD" and resid 18 and name HD14}
      {{ segid "BrD" and resid 78 and name HB1 }}
ASSI  {14642}
      {{ segid "BrD" and resid 16 and name HA    }}
      {  segid "BrD" and resid 102 and name HD24}
         4.400  4.400  1.100 peak     14642 weight    0.10000E+01 volume   0.11486E+02 ppm1  3.867     ppm2  1.320
OR    {14642}
      {{ segid "BrD" and resid 18 and name HA    }}
      {  segid "BrD" and resid 115 and name HD14}
OR    {14642}
      {{ segid "BrD" and resid 18 and name HA  }}
      {{ segid "BrD" and resid 78 and name HB1}}
ASSI  {14682}
      {  segid "BrD" and resid 22 and name HD14}
      {{ segid "BrD" and resid 64 and name HG1  }}
         3.000  2.200  2.200 peak     14682 weight    0.10000E+01 volume   0.10496E+03 ppm1  1.645     ppm2  2.186
OR    {14682}
      {{ segid "BrD" and resid 110 and name HG12}}
      {{ segid "BrD" and resid 115 and name HB1  }}
ASSI  {14692}
      {  segid "BrD" and resid 63 and name HD24}
      {{ segid "BrD" and resid 19 and name HD1  }}
         2.300  1.300  1.300 peak     14692 weight    0.10000E+01 volume   0.59246E+03 ppm1  1.498     ppm2  2.191
```

TABLE 3-continued

Ambiguous NOE-derived Inter-proton Distance Restraints

| | | | | | | | | | | | | |
|---|---|---|---|---|---|---|---|---|---|---|---|---|
| OR | {14692} | | | | | | | | | | | |
| | { segid "BrD" and resid 63 and name HD24} | | | | | | | | | | | |
| | {{ segid "BrD" and resid 64 and name HG1 }} | | | | | | | | | | | |
| ASSI | {14792} | | | | | | | | | | | |
| | { segid "BrD" and resid 22 and name HD24} | | | | | | | | | | | |
| | {{ segid "BrD" and resid 56 and name HA }} | | | | | | | | | | | |
| | 2.600 | 1.700 | 1.700 peak | 14792 weight | 0.10000E◆01 volume | 0.26795E◆03 ppm1 | 1.599 | ppm2 | 4.639 | | | |
| OR | {14792} | | | | | | | | | | | |
| | { segid "BrD" and resid 22 and name HD24} | | | | | | | | | | | |
| | {{ segid "BrD" and resid 60 and name HB2 }} | | | | | | | | | | | |
| ASSI | {14802} | | | | | | | | | | | |
| | {{ segid "BrD" and resid 86 and name HD1}} | | | | | | | | | | | |
| | {{ segid "BrD" and resid 83 and name HA }} | | | | | | | | | | | |
| | 2.700 | 1.800 | 1.800 peak | 14802 weight | 0.10000E◆01 volume | 0.19483E◆03 ppm1 | 1.896 | ppm2 | 4.461 | | | |
| OR | {14802} | | | | | | | | | | | |
| | {{ segid "BrD" and resid 103 and name HB2}} | | | | | | | | | | | |
| | {{ segid "BrD" and resid 99 and name HA }} | | | | | | | | | | | |
| ASSI | {14862} | | | | | | | | | | | |
| | {{ segid "BrD" and resid 54 and name HA }} | | | | | | | | | | | |
| | { segid "BrD" and resid 81 and name HG14} | | | | | | | | | | | |
| | 3.800 | 3.600 | 1.700 peak | 14862 weight | 0.10000E◆01 volume | 0.25126E◆02 ppm1 | 5.543 | ppm2 | 1.076 | | | |
| OR | {14862} | | | | | | | | | | | |
| | {{ segid "BrD" and resid 54 and name HA }} | | | | | | | | | | | |
| | { segid "BrD" and resid 38 and name HG14} | | | | | | | | | | | |
| ASSI | {14872} | | | | | | | | | | | |
| | { segid "BrD" and resid 81 and name HG14} | | | | | | | | | | | |
| | {{ segid "BrD" and resid 80 and name HB2 }} | | | | | | | | | | | |
| | 2.900 | 2.100 | 2.100 peak | 14872 weight | 0.10000E◆01 volume | 0.14378E◆03 ppm1 | 1.058 | ppm2 | 2.565 | | | |
| OR | {14872} | | | | | | | | | | | |
| | { segid "BrD" and resid 81 and name HG14} | | | | | | | | | | | |
| | {{ segid "BrD" and resid 80 and name HB1 }} | | | | | | | | | | | |
| OR | {14872} | | | | | | | | | | | |
| | { segid "BrD" and resid 81 and name HG14} | | | | | | | | | | | |
| | { segid "BrD" and resid 54 and name HE4 } | | | | | | | | | | | |
| OR | {14872} | | | | | | | | | | | |
| | { segid "BrD" and resid 81 and name HG14} | | | | | | | | | | | |
| | {{ segid "BrD" and resid 54 and name HB1 }} | | | | | | | | | | | |
| ASSI | {14882} | | | | | | | | | | | |
| | { segid "BrD" and resid 81 and name HG14} | | | | | | | | | | | |
| | {{ segid "BrD" and resid 56 and name HG }} | | | | | | | | | | | |
| | 3.500 | 3.100 | 2.000 peak | 14882 weight | 0.10000E◆01 volume | 0.44935E◆02 ppm1 | 1.058 | ppm2 | 2.328 | | | |
| OR | {14882} | | | | | | | | | | | |
| | { segid "BrD" and resid 38 and name HG14} | | | | | | | | | | | |
| | {{ segid "BrD" and resid 37 and name HB2 }} | | | | | | | | | | | |
| ASSI | {15202} | | | | | | | | | | | |
| | {{ segid "BrD" and resid 72 and name HA }} | | | | | | | | | | | |
| | {{ segid "BrD" and resid 79 and name HG2}} | | | | | | | | | | | |
| | 4.000 | 4.000 | 1.500 peak | 15202 weight | 0.10000E◆01 volume | 0.18586E◆02 ppm1 | 4.656 | ppm2 | 3.224 | | | |
| OR | {15202} | | | | | | | | | | | |
| | {{ segid "BrD" and resid 61 and name HA }} | | | | | | | | | | | |
| | {{ segid "BrD" and resid 59 and name HG2}} | | | | | | | | | | | |
| OR | {15202} | | | | | | | | | | | |
| | {{ segid "BrD" and resid 61 and name HA }} | | | | | | | | | | | |
| | {{ segid "BrD" and resid 59 and name HG1}} | | | | | | | | | | | |
| ASSI | {15382} | | | | | | | | | | | |
| | {{ segid "BrD" and resid 74 and name HA }} | | | | | | | | | | | |
| | { segid "BrD" and resid 75 and name HE4} | | | | | | | | | | | |
| | 3.200 | 2.600 | 2.300 peak | 15382 weight | 0.10000E◆01 volume | 0.70547E◆02 ppm1 | 4.362 | ppm2 | 2.693 | | | |
| OR | {15382} | | | | | | | | | | | |
| | {{ segid "BrD" and resid 74 and name HA }} | | | | | | | | | | | |
| | {{ segid "BrD" and resid 59 and name HB1}} | | | | | | | | | | | |
| ASSI | {15392} | | | | | | | | | | | |
| | {{ segid "BrD" and resid 74 and name HB1 }} | | | | | | | | | | | |
| | {{ segid "BrD" and resid 73 and name HB2 }} | | | | | | | | | | | |
| | 3.200 | 2.600 | 2.300 peak | 15392 weight | 0.10000E◆01 volume | 0.74692E◆02 ppm1 | 3.572 | ppm2 | 2.471 | | | |
| OR | {15392} | | | | | | | | | | | |
| | {{ segid "BrD" and resid 74 and name HB1}} | | | | | | | | | | | |
| | {{ segid "BrD" and resid 63 and name HG }} | | | | | | | | | | | |
| ASSI | {15532} | | | | | | | | | | | |
| | {{ segid "BrD" and resid 82 and name HB2 }} | | | | | | | | | | | |
| | {{ segid "BrD" and resid 103 and name HB1}} | | | | | | | | | | | |
| | 3.100 | 2.400 | 2.400 peak | 15932 weight | 0.10000E◆01 volume | 0.91508E◆02 ppm1 | 3.973 | ppm2 | 2.344 | | | |
| OR | {15532} | | | | | | | | | | | |
| | {{ segid "BrD" and resid 82 and name HB2 }} | | | | | | | | | | | |
| | {{ segid "BrD" and resid 84 and name HB1 }} | | | | | | | | | | | |

TABLE 3-continued

Ambiguous NOE-derived Inter-proton Distance Restraints

```
ASSI  {15542}
      {{ segid "BrD" and resid 82 and name HB1 }}
      {{ segid "BrD" and resid 103 and name HB1}}
         3.100  2.400  2.400 peak    15542 weight   0.10000E+01 volume  0.94295E+02 ppm1  3.672   ppm2  2.344
OR    {15542}
      {{ segid "BrD" and resid 107 and name HB1}}
      {{ segid "BrD" and resid 110 and name HB }}
OR    {15542}
      {{ segid "BrD" and resid 107 and name HB1 }}
      {{ segid "BrD" and resid 103 and name HB1 }}
OR    {15542}
      {{ segid "BrD" and resid 106 and name HB2 }}
      {{ segid "BrD" and resid 109 and name HB1 }}
OR    {15542}
      {{ segid "BrD" and resid 106 and name HB2 }}
      {{ segid "BrD" and resid 21 and name HG11 }}
ASSI  {15562}
      {{ segid "BrD" and resid 82 and name HB1  }}
      {{ segid "BrD" and resid 106 and name HB2}}
         3.900  3.100  2.000 peak    15562 weight   0.10000E+01 volume  0.43748E+02 ppm1  3.671   ppm2  1.897
OR    {15562}
      {{ segid "BrD" and resid 82 and name HB1  }}
      {  segid "BrD" and resid 83 and name HG24}
ASSI  {15572}
      {{ segid "BrD" and resid 106 and name HB2 }}
      {{ segid "BrD" and resid 110 and name HG11}}
         5.500  5.500  0.000 peak    15572 weight   0.10000E+01 volume  0.17071E+01 ppm1  3.671   ppm2  1.722
OR    {15572}
      {{ segid "BrD" and resid 107 and name HB1  }}
      {{ segid "BrD" and resid 110 and name HG11}}
OR    {15572}
      {{ segid "BrD" and resid 106 and name HB2}}
      {  segid "BrD" and resid 17 and name HG24}
ASSI  {15582}
      {{ segid "BrD" and resid 15 and name HB2  }}
      {  segid "BrD" and resid 63 and name HD14}
         3.300  2.700  2.200 peak    15582 weight   0.10000E+01 volume  0.63482E+02 ppm1  3.671   ppm2  1.653
OR    {15582}
      {{ segid "BrD" and resid 106 and name HB2 }}
      {{ segid "BrD" and resid 110 and name HG12}}
OR    {15582}
      {{ segid "BrD" and resid 107 and name HB1  }}
      {{ segid "BrD" and resid 110 and name HG12}}
ASSI  {15722}
      {{ segid "BrD" and resid 52 and name HB1 }}
      {{ segid "BrD" and resid 80 and name HB1 }}
         4.700  4.700  0.800 peak    15722 weight   0.10000E+01 volume  0.74610E+01 ppm1  3.620   ppm2  2.597
OR    {15722}
      {{ segid "BrD" and resid 84 and name HB1 }}
      {{ segid "BrD" and resid 87 and name HB2 }}
OR    {15722}
      {{ segid "BrD" and resid 84 and name HB1 }}
      {{ segid "BrD" and resid 80 and name HB1 }}
OR    {15722}
      {{ segid "BrD" and resid 65 and name HB1 }}
      {{ segid "BrD" and resid 64 and name HB1 }}
ASSI  {16012}
      {{ segid "BrD" and resid 68 and name HA   }}
      {  segid "BrD" and resid 69 and name HG24}
         3.700  3.400  1.800 peak    16012 weight   0.10000E+01 volume  0.30406E+02 ppm1  5.148   ppm2  1.433
OR    {16012}
      {{ segid "BrD" and resid 68 and name HA   }}
      {  segid "BrD" and resid 14 and name HD24}
ASSI  {16172}
      {{ segid "BrD" and resid 68 and name HB1 }}
      {  segid "BrD" and resid 63 and name HD14}
         3.600  3.200  1.900 peak    16172 weight   0.10000E+01 volume  0.37293E+02 ppm1  3.668   ppm2  1.645
OR    {16172}
      {{ segid "BrD" and resid 68 and name HB1 }}
      {  segid "BrD" and resid 22 and name HD14}
ASSI  {16182}
      {{ segid "BrD" and resid 66 and name HB2 }}
      {  segid "BrD" and resid 63 and name HD14}
         3.600  3.600  1.700 peak    16182 weight   0.10000E+01 volume  0.27740E+02 ppm1  3.522   ppm2  1.645
OR    {16182}
      {{ segid "BrD" and resid 68 and name HB2 }}
      {  segid "BrD" and resid 22 and name HD14}
```

TABLE 3-continued

Ambiguous NOE-derived Inter-proton Distance Restraints

```
ASSI    {16362}
        {{ segid "BrD" and resid 97 and name HE1   }}
        {  segid "BrD" and resid 101 and name HD14}
           3.000  2.200  2.200 peak    16362 weight    0.10000E♦01 volume   0.11543E♦03 ppm1  3.971    ppm2  1.540
OR      {16362}
        {{ segid "BrD" and resid 64 and name HE1   }}
        {  segid "BrD" and resid 22 and name HD24}
OR      {16362}
        {{ segid "BrD" and resid 97 and name HE1   }}
        {  segid "BrD" and resid 101 and name HG24}
ASSI    {16372}
        {{ segid "BrD" and resid 88 and name HB1  }}
        {{ segid "BrD" and resid 50 and name HG11}}
           2.900  2.100  2.100 peak    16372 weight    0.10000E♦01 volume   0.13106E♦03 ppm1  3.522    ppm2  1.401
OR      {16372}
        {{ segid "BrD" and resid 111 and name HE1  }}
        {  segid "BrD" and resid 116 and name HD14}
ASSI    {16482}
        {{ segid "BrD" and resid 96 and name HA   }}
        {{ segid "BrD" and resid 85 and name HB1}}
           3.800  3.600  1.700 peak    16482 weight    0.10000E♦01 volume   0.24632E♦02 ppm1  4.409    ppm2  3.891
OR      {16482}
        {{ segid "BrD" and resid 107 and name HA  }}
        {{ segid "BrD" and resid 106 and name HB1}}
ASSI    {16572}
        {{ segid "BrD" and resid 96 and name HB2}}
        {{ segid "BrD" and resid 86 and name HA   }}
           4.100  4.100  1.400 peak    16972 weight    0.10000E♦01 volume   0.16756E♦02 ppm1  3.132    ppm2  4.804
OR      {16572}
        {{ segid "BrD" and resid 96 and name HB2}}
        {{ segid "BrD" and resid 92 and name HA   }}
ASSI    {16582}
        {{ segid "BrD" and resid 96 and name HB1}}
        {{ segid "BrD" and resid 92 and name HA   }}
           3.800  3.600  1.700 peak    16582 weight    0.10000E♦01 volume   0.28094E♦02 ppm1  4.004    ppm2  4.808
OR      {16582}
        {{ segid "BrD" and resid 96 and name HB1}}
        {{ segid "BrD" and resid 97 and name HA   }}
OR      {16582}
        {{ segid "BrD" and resid 96 and name HB1}}
        {{ segid "BrD" and resid 94 and name HA   }}
ASSI    {16782}
        {{ segid "BrD" and resid 95 and name HB1}}
        {{ segid "BrD" and resid 85 and name HA   }}
           3.200  2.600  2.300 peak    16782 weight    0.10000E♦01 volume   0.73175E♦02 ppm1  3.620    ppm2  4.995
OR      {16782}
        {{ segid "BrD" and resid 95 and name HB1 }}
        {{ segid "BrD" and resid 93 and name HB1 }}
OR      {16782}
        {{ segid "BrD" and resid 84 and name HB1}}
        {{ segid "BrD" and resid 85 and name HA   }}
ASSI    {16852}
        {{ segid "BrD" and resid 82 and name HB1  }}
        {  segid "BrD" and resid 107 and name HE4}
           3.000  2.200  2.200 peak    16852 weight    0.10000E♦01 volume   0.10680E♦03 ppm1  3.670    ppm2  7.896
OR      {16852}
        {{ segid "BrD" and resid 107 and name HB1}}
        {  segid "BrD" and resid 107 and name HE4}
ASSI    {17112}
        {{ segid "BrD" and resid 95 and name HB2 }}
        {{ segid "BrD" and resid 32 and name HH2 }}
           3.500  3.100  2.000 peak    17112 weight    0.10000E♦01 volume   0.46090E♦02 ppm1  3.366    ppm2  7.754
OR      {17112}
        {{ segid "BrD" and resid 95 and name HB2}}
        {  segid "BrD" and resid 34 and name HE4}
OR      {17112}
        {{ segid "BrD" and resid 95 and name HB2}}
        {  segid "BrD" and resid 96 and name HD4}
ASSI    {17122}
        {{ segid "BrD" and resid 105 and name HB1}}
        {  segid "BrD" and resid 25 and name HG14}
           3.400  2.900  2.100 peak    17122 weight    0.10000E♦01 volume   0.47791E♦02 ppm1  3.721    ppm2  1.824
OR      {17122}
        {{ segid "BrD" and resid 105 and name HB1 }}
        {{ segid "BrD" and resid 102 and name HB2 }}
```

TABLE 3-continued

Ambiguous NOE-derived Inter-proton Distance Restraints

```
ASSI  {17132}
      {{ segid "BrD" and resid 106 and name HB2 }}
      {{ segid "BrD" and resid 102 and name HB2 }}
         3.500  3.100  2.000 peak     17132 weight    0.10000E+01 volume   0.42104E+02 ppm1  3.668     ppm2  1.824
OR    {17132}
      {{ segid "BrD" and resid 105 and name HB2}}
      {  segid "BrD" and resid 25 and name HG14}
OR    {17132}
      {{ segid "BrD" and resid 106 and name HB2}}
      {  segid "BrD" and resid 25 and name HG14}
ASSI  {17142}
      {{ segid "BrD" and resid 106 and name HB2}}
      {  segid "BrD" and resid 21 and name HG24}
         3.700  3.400  1.800 peak     17142 weight    0.10000E+01 volume   0.28702E+02 ppm1  3.668     ppm2  1.612
OR    {17142}
      {{ segid "BrD" and resid 105 and name HB2 }}
      {  segid "BrD" and resid 101 and name HG24}
OR    {17142}
      {{ segid "BrD" and resid 105 and name HB2}}
      {  segid "BrD" and resid 21 and name HG24}
ASSI  {17272}
      {{ segid "BrD" and resid 116 and name HA   }}
      {  segid "BrD" and resid 110 and name HG24}
         4.000  4.000  1.500 peak     17272 weight    0.10000E+01 volume   0.18200E+02 ppm1  4.804     ppm2  1.262
OR    {17272}
      {{ segid "BrD" and resid 57 and name HA   }}
      {  segid "BrD" and resid 56 and name HD24}
ASSI  {17322}
      {{ segid "BrD" and resid 59 and name HA  }}
      {{ segid "BrD" and resid 62 and name HG2}}
         4.200  4.200  1.300 peak     17322 weight    0.10000E+01 volume   0.13830E+02 ppm1  4.903     ppm2  1.490
OR    {17322}
      {{ segid "BrD" and resid 20 and name HA   }}
      {  segid "BrD" and resid 63 and name HD24}
ASSI  {17492}
      {{ segid "BrD" and resid 34 and name HA }}
      {{ segid "BrD" and resid 31 and name HA }}
         3.300  2.700  2.200 peak     17492 weight    0.10000E+01 volume   0.57702E+02 ppm1  5.544     ppm2  4.989
OR    {17492}
      {{ segid "BrD" and resid 34 and name HA }}
      {{ segid "BrD" and resid 32 and name HA }}
ASSI  {17522}
      {{ segid "BrD" and resid 34 and name HA  }}
      {  segid "BrD" and resid 54 and name HE4}
         4.000  4.000  1.900 peak     17522 weight    0.10000E+01 volume   0.19574E+02 ppm1  5.544     ppm2  2.564
OR    {17522}
      {{ segid "BrD" and resid 34 and name HA  }}
      {{ segid "BrD" and resid 37 and name HG2}}
ASSI  {17682}
      {{ segid "BrD" and resid 33 and name HG1 }}
      {{ segid "BrD" and resid 32 and name HE3 }}
         4.900  4.900  0.600 peak     17682 weight    0.10000E+01 volume   0.94467E+01 ppm1  0.859     ppm2  7.926
OR    {17682}
      {{ segid "BrD" and resid 33 and name HG1}}
      {{ segid "BrD" and resid 34 and name HZ  }}
ASSI  {17692}
      {{ segid "BrD" and resid 33 and name HG1 }}
      {{ segid "BrD" and resid 32 and name HE3 }}
         4.000  4.000  1.900 peak     17692 weight    0.10000E+01 volume   0.18980E+02 ppm1  0.859     ppm2  7.803
OR    {17692}
      {{ segid "BrD" and resid 33 and name HG1}}
      {  segid "BrD" and resid 34 and name HE4}
ASSI  {17702}
      {{ segid "BrD" and resid 33 and name HG1 }}
      {{ segid "BrD" and resid 32 and name HH2 }}
         4.100  4.100  1.400 peak     17702 weight    0.10000E+01 volume   016294E+02 ppm1  0.859     ppm2  7.745
OR    {17702}
      {{ segid "BrD" and resid 33 and name HG1}}
      {  segid "BrD" and resid 34 and name HE4}
ASSI  {17892}
      {{ segid "BrD" and resid 33 and name HD1}}
      {  segid "BrD" and resid 34 and name HD4}
         3.400  2.900  2.100 peak     17892 weight    0.10000E+01 volume   0.51743E+02 ppm1  2.783     ppm2  7.720
OR    {17892}
      {{ segid "BrD" and resid 33 and name HD1 }}
      {{ segid "BrD" and resid 32 and name HH2 }}
```

TABLE 3-continued

Ambiguous NOE-derived Inter-proton Distance Restraints

```
ASSI    {17972}
        {{ segid "BrD" and resid 33 and name HB2 }}
        {{ segid "BrD" and resid 32 and name HZ3 }}
            3.500  3.100  2.000 peak    17972 weight   0.10000E+01 volume   0.44678E+02 ppm1  -0.176   ppm2 7.789
OR      {17972}
        {{ segid "BrD" and resid 33 and name HB2}}
        { segid "BrD" and resid 34 and name HE4}
ASSI    {18022}
        {{ segid "BrD" and resid 59 and name HG2 }}
        {{ segid "BrD" and resid 60 and name HB2 }}
            3.200  2.600  2.300 peak    18022 weight   0.10000E+01 volume   0.69043E+02 ppm1   3.227   ppm2 4.664
OR      {18022}
        {{ segid "BrD" and resid 75 and name HG2}}
        {{ segid "BrD" and resid 72 and name HA  }}
OR      {18022}
        {{ segid "BrD" and resid 59 and name HG1 }}
        {{ segid "BrD" and resid 60 and name HB2 }}
OR      {18022}
        {{ segid "BrD" and resid 59 and name HG2}}
        {{ segid "BrD" and resid 58 and name HB  }}
OR      {18022}
        {{ segid "BrD" and resid 59 and name HG1}}
        {{ segid "BrD" and resid 58 and name HB  }}
ASSI    {18032}
        {{ segid "BrD" and resid 75 and name HG2 }}
        {{ segid "BrD" and resid 74 and name HB1 }}
            3.400  2.900  2.100 peak    18032 weight   0.10000E+01 volume   0.48637E+02 ppm1   3.226   ppm2 3.597
OR      {18032}
        {{ segid "BrD" and resid 59 and name HG1 }}
        {{ segid "BrD" and resid 74 and name HB1 }}
OR      {18032}
        {{ segid "BrD" and resid 59 and name HG2 }}
        {{ segid "BrD" and resid 74 and name HB1 }}
OR      {18032}
        {{ segid "BrD" and resid 59 and name HG1 }}
        {{ segid "BrD" and resid 67 and name HB1 }}
ASSI    {18252}
        { segid "BrD" and resid 35 and name HE4}
        {{ segid "BrD" and resid 60 and name HB2}}
            3.500  3.100  2.000 peak    18252 weight   0.10000E+01 volume   0.44998E+02 ppm1   2.782   ppm2 4.631
OR      {18252}
        { segid "BrD" and resid 35 and name HE4}
        {{ segid "BrD" and resid 56 and name HA  }}
ASSI    {18332}
        { segid "BrD" and resid 35 and name HE4}
        {{ segid "BrD" and resid 25 and name HB  }}
            3.700  3.400  1.800 peak    18332 weight   0.10000E+01 volume   0.33097E+02 ppm1   2.782   ppm2 3.003
OR      {18332}
        { segid "BrD" and resid 35 and name HE4}
        {{ segid "BrD" and resid 55 and name HB1}}
ASSI    {18342}
        { segid "BrD" and resid 35 and name HE4}}
        {{ segid "BrD" and resid 35 and name HB1}}
            1.700  1.700  2.800 peak    18342 weight   0.10000E+01 volume   0.31604E+04 ppm1   2.781   ppm2 2.841
OR      {18342}
        { segid "BrD" and resid 35 and name HE4}
        {{ segid "BrD" and resid 57 and name HB2}}
ASSI    {18392}
        { segid "BrD" and resid 35 and name HE4}}
        {{ segid "BrD" and resid 57 and name HD1}}
            2.500  1.600  1.600 peak    18392 weight   0.10000E+01 volume   0.33173E+03 ppm1   2.782   ppm2 2.361
OR      {18392}
        { segid "BrD" and resid 35 and name HE4}
        {{ segid "BrD" and resid 56 and name HG  }}
ASSI    {18402}
        { segid "BrD" and resid 35 and name HE4 }
        { segid "BrD" and resid 31 and name HB4 }
            2.300  1.300  1.300 peak    18402 weight   0.10000E+01 volume   0.54118E+03 ppm1   2.782   ppm2 2.312
OR      {18402}
        { segid "BrD" and resid 35 and name HE4}
        {{ segid "BrD" and resid 57 and name HD2}}
OR      {18402}
        { segid "BrD" and resid 35 and name HE4}
        {{ segid "BrD" and resid 56 and name HG  }}
ASSI    {18432}
        { segid "BrD" and resid 35 and name HE4}
        {{ segid "BrD" and resid 57 and name HG1}}
            2.800  2.000  2.000 peak    18432 weight   0.10000E+01 volume   0.16595E+03 ppm1   2.780   ppm2 2.118
```

TABLE 3-continued

Ambiguous NOE-derived Inter-proton Distance Restraints

```
OR      {18432}
        { segid "BrD" and resid 35 and name HE4}
        {{ segid "BrD" and resid 26 and name HD1}}
ASSI    {18522}
        { segid "BrD" and resid 75 and name HE4}
        {{ segid "BrD" and resid 71 and name HA  }}
          2.600  1.700  1.700 peak      18522 weight    0.10000E◆01 volume   0.24378E◆03 ppm1  2.635    ppm2  4.663
OR      {18522}
        { segid "BrD" and resid 75 and name HE4}
        {{ segid "BrD" and resid 14 and name HA  }}
ASSI    {18532}
        { segid "BrD" and resid 75 and name HE4}
        {{ segid "BrD" and resid 110 and name HA}}
          4.200  4.200  1.300 peak      18532 weight    0.10000E◆01 volume   0.13873E◆02 ppm1  2.633    ppm2  4.383
OR      {18532}
        { segid "BrD" and resid 75 and name HE4}
        {{ segid "BrD" and resid 74 and name HA  }}
ASSI    {18592}
        { segid "BrD" and resid 75 and name HE4 }
        { segid "BrD" and resid 74 and name HE4 }
          3.600  3.200  1.900 peak      18592 weight    0.10000E◆01 volume   0.36365E◆02 ppm1  2.634    ppm2  7.552
OR      {18592}
        { segid "BrD" and resid 75 and name HE4 }
        { segid "BrD" and resid 106 and name HD4}
ASSI    {18822}
        { segid "BrD" and resid 75 and name HE4  }
        {{ segid "BrD" and resid 116 and name HG12}}
          3.300  2.700  2.200 peak      18822 weight    0.10000E◆01 volume   0.58079E◆02 ppm1  2.635    ppm2  1.988
OR      {18822}
        { segid "BrD" and resid 75 and name HE4 }
        { segid "BrD" and resid 21 and name HG24}
ASSI    {18832}
        { segid "BrD" and resid 752 and name HE4 }
        { segid "BrD" and resid 63 and name HD14 }
          3.400  2.900  2.100 peak      18832 weight    0.10000E◆01 volume   0.54622E◆02 ppm1  2.635    ppm2  1.657
OR      {18832}
        { segid "BrD" and resid 75 and name HE4   }
        {{ segid "BrD" and resid 110 and name HG12}}
OR      {18832}
        { segid "BrD" and resid 75 and name HE4  }
        {{ segid "BrD" and resid 21 and name HG12}}
ASSI    {18912}
        { segid "BrD" and resid 75 and name HE4 }}
        {{ segid "BrD" and resid 14 and name HB2 }}
          2.700  1.800  1.800 peak      18912 weight    0.10000E◆01 volume   0.20227E◆03 ppm1  2.635    ppm2  2.216
OR      {18912}
        { segid "BrD" and resid 79 and name HE4}
        {{ segid "BrD" and resid 115 and name HG}}
ASSI    {18942}
        { segid "BrD" and resid 75 and name HE4  }
        {{ segid "BrD" and resid 21 and name HG11}}
          3.700  3.400  1.800 peak      18942 weight    0.10000E◆01 volume   0.30880E◆02 ppm1  2.636    ppm2  2.344
OR      {18942}
        { segid "BrD" and resid 75 and name HE4}
        {{ segid "BrD" and resid 110 and name HB}}
OR      {18942}
        { segid "BrD" and resid 75 and name HE4  }
        {{ segid "BrD" and resid 109 and name HB1}}
ASSI    {18962}
        {{ segid "BrD" and resid 57 and name HB1 }}
        {{ segid "BrD" and resid 37 and name HD1 }}
          3.100  2.400  2.400 peak      18962 weight    0.10000E◆01 volume   0.84483E◆02 ppm1  2.931    ppm2  4.289
OR      {18962}
        {{ segid "BrD" and resid 37 and name HB1 }}
        {{ segid "BrD" and resid 37 and name HD1 }}
ASSI    {19022}
        {{ segid "BrD" and resid 75 and name HA  }}
        {{ segid "BrD" and resid 78 and name HB2 }}
          2.500  1.600  1.600 peak      19022 weight    0.10000E◆01 volume   0.30551E◆03 ppm1  4.508    ppm2  1.043
OR      {19022}
        {{ segid "BrD" and resid 79 and name HA  }}
        { segid "BrD" and resid 18 and name HD14 }
ASSI    {19222}
        { segid "BrD" and resid 43 and name HB4}
        {{ segid "BrD" and resid 42 and name HB1}}
          4.500  4.500  1.000 peak      19222 weight    0.10000E◆01 volume   0.92899E◆01 ppm1  1.697    ppm2  2.768
```

TABLE 3-continued

Ambiguous NOE-derived Inter-proton Distance Restraints

| | | | | | | | | | | | |
|---|---|---|---|---|---|---|---|---|---|---|---|
| OR | {19222} | | | | | | | | | | |
| | { segid "BrD" and resid 43 and name HB4} | | | | | | | | | | |
| | {{ segid "BrD" and resid 44 and name HG1}} | | | | | | | | | | |
| ASSI | {19332} | | | | | | | | | | |
| | { segid "BrD" and resid 31 and name HB4} | | | | | | | | | | |
| | {{ segid "BrD" and resid 26 and name HB1}} | | | | | | | | | | |
| | 3.600 3.200 1.900 peak 19332 weight | 0.10000E+01 volume | 0.33671E+02 ppm1 2.289 | ppm2 2.466 |
| OR | {19332} | | | | | | | | | | |
| | { segid "BrD" and resid 31 and name HB4} | | | | | | | | | | |
| | {{ segid "BrD" and resid 21 and name HB }} | | | | | | | | | | |
| ASSI | {19342} | | | | | | | | | | |
| | { segid "BrD" and resid 31 and name HB4}} | | | | | | | | | | |
| | {{ segid "BrD" and resid 56 and name HB1}} | | | | | | | | | | |
| | 3.300 2.700 2.200 peak 19342 weight | 0.10000E+01 volume | 0.60076E+02 ppm1 2.289 | ppm2 2.719 |
| OR | {19342} | | | | | | | | | | |
| | { segid "BrD" and resid 31 and name HB4} | | | | | | | | | | |
| | {{ segid "BrD" and resid 29 and name HB1}} | | | | | | | | | | |
| ASSI | {19402} | | | | | | | | | | |
| | { segid "BrD" and resid 31 and name HE4} | | | | | | | | | | |
| | {{ segid "BrD" and resid 29 and name HA }} | | | | | | | | | | |
| | 3.600 3.200 1.900 peak 19402 weight | 0.10000E+01 volume | 0.34186E+02 ppm1 2.289 | ppm2 4.810 |
| OR | {19402} | | | | | | | | | | |
| | { segid "BrD" and resid 31 and name HB4} | | | | | | | | | | |
| | {{ segid "BrD" and resid 24 and name HA }} | | | | | | | | | | |
| ASSI | {19452} | | | | | | | | | | |
| | {{ segid "BrD" and resid 73 and name HB2}} | | | | | | | | | | |
| | {{ segid "BrD" and resid 72 and name HA }} | | | | | | | | | | |
| | 3.800 3.600 1.700 peak 19452 weight | 0.10000E+01 volume | 0.27108E+02 ppm1 2.486 | ppm2 4.672 |
| OR | {19452} | | | | | | | | | | |
| | {{ segid "BrD" and resid 73 and name HB2}} | | | | | | | | | | |
| | {{ segid "BrD" and resid 69 and name HA }} | | | | | | | | | | |
| ASSI | {19462} | | | | | | | | | | |
| | {{ segid "BrD" and resid 73 and name HB1}} | | | | | | | | | | |
| | {{ segid "BrD" and resid 72 and name HA }} | | | | | | | | | | |
| | 3.900 3.800 1.600 peak 19462 weight | 0.10000E+01 volume | 0.22198E+02 ppm1 2.583 | ppm2 4.672 |
| OR | {19462} | | | | | | | | | | |
| | {{ segid "BrD" and resid 73 and name HB1}} | | | | | | | | | | |
| | {{ segid "BrD" and resid 69 and name HA }} | | | | | | | | | | |
| ASSI | {19472} | | | | | | | | | | |
| | { segid "BrD" and resid 99 and name HB4} | | | | | | | | | | |
| | {{ segid "BrD" and resid 86 and name HB1}} | | | | | | | | | | |
| | 2.400 1.400 1.400 peak 19872 weight | 0.10000E+01 volume | 0.42300E+03 ppm1 2.190 | ppm2 2.359 |
| OR | {19472} | | | | | | | | | | |
| | { segid "BrD" and resid 99 and name HE4 } | | | | | | | | | | |
| | {{ segid "BrD" and resid 103 and name HB1}} | | | | | | | | | | |
| ASSI | {19561} | | | | | | | | | | |
| | { segid "BrD" and resid 76 and name HB4} | | | | | | | | | | |
| | {{ segid "BrD" and resid 51 and name HB1}} | | | | | | | | | | |
| | 1.800 1.800 2.700 peak 19562 weight | 0.10000E+01 volume | 0.21948E+04 ppm1 2.092 | ppm2 1.946 |
| OR | {19562} | | | | | | | | | | |
| | { segid "BrD" and resid 76 and name HB4 }} | | | | | | | | | | |
| | {{ segid "BrD" and resid 116 and name HG11}} | | | | | | | | | | |
| OR | {19562} | | | | | | | | | | |
| | { segid "BrD" and resid 76 and name HB4} | | | | | | | | | | |
| | {{ segid "BrD" and resid 51 and name HG1}} | | | | | | | | | | |
| ASSI | {19712} | | | | | | | | | | |
| | { segid "BrD" and resid 99 and name HB4} | | | | | | | | | | |
| | {{ segid "BrD" and resid 98 and name HB1}} | | | | | | | | | | |
| | 3.300 2.700 2.200 peak 19712 weight | 0.10000E+01 volume | 0.62693E+02 ppm1 2.190 | ppm2 3.988 |
| OR | {19712} | | | | | | | | | | |
| | { segid "BrD" and resid 99 and name HB4} | | | | | | | | | | |
| | {{ segid "BrD" and resid 96 and name HB1}} | | | | | | | | | | |
| ASSI | {19862} | | | | | | | | | | |
| | {{ segid "BrD" and resid 102 and name HA }} | | | | | | | | | | |
| | {{ segid "BrD" and resid 105 and name HA }} | | | | | | | | | | |
| | 4.200 4.200 1.300 peak 19862 weight | 0.10000E+01 volume | 0.13941E+02 ppm1 4.261 | ppm2 4.924 |
| OR | {19862} | | | | | | | | | | |
| | {{ segid "BrD" and resid 102 and name HA }} | | | | | | | | | | |
| | {{ segid "BrD" and resid 30 and name HB1 }} | | | | | | | | | | |
| ASSI | {19872} | | | | | | | | | | |
| | {{ segid "BrD" and resid 102 and name HA }} | | | | | | | | | | |
| | { segid "BrD" and resid 105 and name HD4} | | | | | | | | | | |
| | 2.700 1.800 1.800 peak 19872 weight | 0.10000E+01 volume | 0.22737E+03 ppm1 4.261 | ppm2 7.779 |
| OR | {19872} | | | | | | | | | | |
| | {{ segid "BrD" and resid 102 and name HA}} | | | | | | | | | | |
| | { segid "BrD" and resid 34 and name HE4} | | | | | | | | | | |

TABLE 3-continued

Ambiguous NOE-derived Inter-proton Distance Restraints

```
ASSI   {19892}
       {{ segid "BrD" and resid 113 and name HA }}
       {{ segid "BrD" and resid 115 and name HG }}
          3.600  3.200  1.900 peak    19892 weight   0.10000E+01 volume  0.36454E+02 ppm1  4.903    ppm2  2.133
OR     {19892}
       {{ segid "BrD" and resid 113 and name HA }}
       {{ segid "BrD" and resid 14 and name HB2 }}
ASSI   {19932}
       {{ segid "BrD" and resid 113 and name HA }}
       {{ segid "BrD" and resid 112 and name HA }}
          3.400  2.900  2.100 peak    19932 weight   0.10000E+01 volume  0.56030E+02 ppm1  4.903    ppm2  4.598
OR     {19932}
       {{ segid "BrD" and resid 113 and name HA }}
       {{ segid "BrD" and resid 114 and name HA1}}
ASSI   {19972}
       { segid "BrD" and resid 113 and name HB4}
       { segid "BrD" and resid 75 and name HE4 }
          3.400  2.900  2.100 peak    19972 weight   0.10000E+01 volume  0.53194E+02 ppm1  1.991    ppm2  2.662
OR     {19972}
       { segid "BrD" and resid 113 and name HB4}
       {{ segid "BrD" and resid 112 and name HB1}}
ASSI   {20002}
       { segid "BrD" and resid 113 and name HB4}
       {{ segid "BrD" and resid 18 and name HG   }}
          2.700  1.800  1.800 peak    20002 weight   0.10000E+01 volume  0.18667E+03 ppm1  1.991    ppm2  2.304
OR     {20002}
       { segid "BrD" and resid 113 and name HB4}
       {{ segid "BrD" and resid 110 and name HB }}
OR     {20002}
       { segid "BrD" and resid 113 and name HB4}
       {{ segid "BrD" and resid 109 and name HB }}
ASSI   {20012}
       { segid "BrD" and resid 113 and name HB4}
       {{ segid "BrD" and resid 110 and name HB }}
          3.900  3.800  1.600 peak    20012 weight   0.10000E+01 volume  0.22660E+02 ppm1  1.990    ppm2  2.369
OR     {20012}
       { segid "BrD" and resid 113 and name HB4}
       {{ segid "BrD" and resid 109 and name HB }}
ASSI   {20022}
       { segid "BrD" and resid 113 and name HB4}
       {{ segid "BrD" and resid 115 and name HG }}
          3.300  2.700  2.200 peak     2002 weight   0.10000E+01 volume  0.61319E+02 ppm1  1.990    ppm2  2.135
OR     {20022}
       { segid "BrD" and resid 113 and name HB4}
       {{ segid "BrD" and resid 14 and name HB2 }}
ASSI   {20062}
       {{ segid "BrD" and resid 110 and name HA   }}
       { segid "BrD" and resid 116 and name HD14}
          3.100  2.400  2.400 peak    20062 weight   0.10000E+01 volume  0.82911E+02 ppm1  4.411    ppm2  1.410
OR     {20062}
       {{ segid "BrD" and resid 110 and name HA }}
       {{ segid "BrD" and resid 109 and name HG1}}
ASSI   {20122}
       { segid "BrD" and resid 113 and name HB4}
       {{ segid "BrD" and resid 114 and name HA1}}
          3.700  3.400  1.800 peak    20122 weight   0.10000E+01 volume  0.29578E+02 ppm1  1.994    ppm2  4.564
OR     {20122}
       { segid "BrD" and resid 113 and name HB4}
       {{ segid "BrD" and resid 17 and name HA   }}
ASSI   {20152}
       { segid "BrD" and resid 113 and name HB4 }}
       { segid "BrD" and resid 14 and name HD14 }
          2.700  1.800  1.800 peak    20152 weight   0.10000E+01 volume  0.21357E+03 ppm1  1.995    ppm2  1.425
OR     {20152}
       { segid "BrD" and resid 113 and name HB4 }
       { segid "BrD" and resid 14 and name HD24 }
OR     {20152}
       { segid "BrD" and resid 113 and name HB4}
       {{ segid "BrD" and resid 109 and name HG1}}
ASSI   {20182}
       {{ segid "BrD" and resid 17 and name HB }}
       {{ segid "BrD" and resid 14 and name HB2}}
          3.400  2.900  2.100 peak    20182 weight   0.10000E+01 volume  0.54504E+02 ppm1  4.853    ppm2  2.149
OR     {20182}
       {{ segid "BrD" and resid 17 and name HB }}
       {{ segid "BrD" and resid 18 and name HB1}}
```

TABLE 3-continued

Ambiguous NOE-derived Inter-proton Distance Restraints

```
OR      {20182}
        {{ segid "BrD" and resid 17 and name HB   }}
        {{ segid "BrD" and resid 109 and name HB2}}
ASSI    {20202}
        {{ segid "BrD" and resid 17 and name HB   }}
        {  segid "BrD" and resid 21 and name HD14}
           4.300  4.300  1.200 peak    20202 weight   0.10000E+01 volume  0.12632E+02 ppm1  4.853   ppm2  1.222
OR      {20202}
        {{ segid "BrD" and resid 17 and name HB   }}
        {  segid "BrD" and resid 110 and name HG24}
ASSI    {20222}
        {  segid "BrD" and resid 17 and name HG24}
        {{ segid "BrD" and resid 14 and name HA   }}
           2.200  1.200  1.200 peak    20222 weight   0.10000E+01 volume  0.69704E+03 ppm1  1.747   ppm2  4.666
OR      {20222}
        {  segid "BrD" and resid 17 and name HG24}}
        {{ segid "BrD" and resid 109 and name HA  }}
OR      {20222}
        {  segid "BrD" and resid 17 and name HG24}
        {{ segid "BrD" and resid 20 and name HB1  }}
ASSI    {20262}
        {  segid "BrD" and resid 17 and name HG24}
        {{ segid "BrD" and resid 109 and name HB1}}
           2.500  1.600  1.600 peak    20262 weight   0.10000E+01 volume  0.34655E+03 ppm1  3.747   ppm2  2.352
OR      {20262}
        {  segid "BrD" and resid 17 and name HG24}
        {{ segid "BrD" and resid 21 and name HG11}}
ASSI    {20322}
        {{ segid "BrD" and resid 20 and name HB1  }}
        {{ segid "BrD" and resid 21 and name HG11}}
           2.300  2.300  2.200 peak    20322 weight   0.10000E+01 volume  0.47333E+02 ppm1  4.656   ppm2  2.320
OR      {20322}
        {{ segid "BrD" and resid 20 and name HB1  }}
        {{ segid "BrD" and resid 19 and name HB1  }}
OR      {20322}
        {{ segid "BrD" and resid 20 and name HB1  }}
        {{ segid "BrD" and resid 109 and name HB1}}
ASSI    {20632}
        {{ segid "BrD" and resid 112 and name HG2 }}
        {{ segid "BrD" and resid 109 and name HD1 }}
           3.100  2.400  2.400 peak    20632 weight   0.10000E+01 volume  0.87177E+02 ppm1  2.832   ppm2  1.997
OR      {20632}
        {{ segid "BrD" and resid 112 and name HG2 }}
        {{ segid "BrD" and resid 111 and name HG1 }}
OR      {20632}
        {{ segid "BrD" and resid 112 and name HG2}}
        {  segid "BrD" and resid 113 and name HB4}
ASSI    {20652}
        {{ segid "BrD" and resid 111 and name HA   }}
        {  segid "BrD" and resid 115 and name HD14}
           3.800  3.600  1.700 peak    20652 weight   0.10000E+01 volume  0.25940E+02 ppm1  4.656   ppm2  1.319
OR      {20652}
        {{ segid "BrD" and resid 104 and name HA   }}
        {  segid "BrD" and resid 102 and name HD24}
OR      {20652}
        {{ segid "BrD" and resid 72 and name HA    }}
        {  segid "BrD" and resid 115 and name HD14}}
OR      {20652}
        {{ segid "BrD" and resid 104 and name HA   }}
        {  segid "BrD" and resid 102 and name HD14}
OR      {20652}
        {{ segid "BrD" and resid 72 and name HA }}
        {{ segid "BrD" and resid 78 and name HB1}}
ASSI    {20662}
        {{ segid "BrD" and resid 61 and name HA  }}
        {{ segid "BrD" and resid 62 and name HB2}}
           3.300  2.700  2.200 peak    20662 weight   0.10000E+01 volume  0.56653E+02 ppm1  4.656   ppm2  1.710
OR      {20662}
        {{ segid "BrD" and resid 67 and name HA  }}
        {{ segid "BrD" and resid 62 and name HB2}}
OR      {20662}
        {{ segid "BrD" and resid 111 and name HA   }}
        {{ segid "BrD" and resid 110 and name HG11}}
ASSI    {20672}
        {{ segid "BrD" and resid 33 and name HA  }}
        {{ segid "BrD" and resid 26 and name HG1}}
           3.300  2.700  2.200 peak    20672 weight   0.10000E+01 volume  0.58313E+02 ppm1  4.656   ppm2  1.661
```

TABLE 3-continued

Ambiguous NOE-derived Inter-proton Distance Restraints

```
OR      {20672}
        {{ segid "BrD" and resid 23 and name HA   }}
        {  segid "BrD" and resid 22 and name HD14}
OR      {20672}
        {{ segid "BrD" and resid 61 and name HA   }}
        {  segid "BrD" and resid 22 and name HD14}
OR      {20672}
        {{ segid "BrD" and resid 61 and name HA }}
        {{ segid "BrD" and resid 62 and name HB2}}
OR      {20672}
        {{ segid "BrD" and resid 23 and name HA   }}
        {  segid "BrD" and resid 25 and name HG24}
OR      {20672}
        {{ segid "BrD" and resid 61 and name HA   }}
        {  segid "BrD" and resid 58 and name HG24}
OR      {20672}
        {{ segid "BrD" and resid 67 and name HA }}
        {{ segid "BrD" and resid 62 and name HB2}}
ASSI    {20682}
        {{ segid "BrD" and resid 67 and name HA   }}
        {  segid "BrD" and resid 69 and name HG14}
           3.700  1.800  1.800 peak     20682 weight    0.10000E◆01 volume   0.18983E◆03 ppm1  4.656    ppm2  1.547
OR      {20682}
        {{ segid "BrD" and resid 67 and name HA   }}
        {  segid "BrD" and resid 73 and name HD14}
ASSI    {20792}
        {  segid "BrD" and resid 25 and name HG24}
        {  segid "BrD" and resid 74 and name HE4 }
           3.100  2.400  2.400 peak     20792 weight    0.10000E◆01 volume   0.98567E◆02 ppm1  1.648    ppm2  7.517
OR      {20792}
        {  segid "BrD" and resid 25 and name HG24}
        {  segid "BrD" and resid 106 and name HD4 }
OR      {20792}
        {  segid "BrD" and resid 58 and name HG24}
        {  segid "BrD" and resid 74 and name HE4 }
ASSI    {20822}
        {  segid "BrD" and resid 25 and name HG24}
        {  segid "BrD" and resid 34 and name HE4 }
           3.300  2.700  2.200 peak     20822 weight    0.10000E◆01 volume   0.60371E◆02 ppm1  1.650    ppm2  7.791
OR      {20822}
        {  segid "BrD" and resid 58 and name HG24}
        {  segid "BrD" and resid 68 and name HD4 }
ASSI    {20842}
        {  segid "BrD" and resid 25 and name HG24}
        {{ segid "BrD" and resid 102 and name HA }}
           3.600  3.200  1.900 peak     20842 weight    0.10000E◆01 volume   0.35063E◆02 ppm1  1.649    ppm2  4.282
OR      {20842}
        {  segid "BrD" and resid 58 and name HG24}
        {{ segid "BrD" and resid 37 and name HD1 }}
ASSI    {21092}
        {  segid "BrD" and resid 58 and name HG24}
        {{ segid "BrD" and resid 61 and name HG2 }}
           2.600  1.700  1.700 peak     21092 weight    0.10000E◆01 volume   0.23144E◆03 ppm1  1.648    ppm2  2.833
OR      {21092}
        {  segid "BrD" and resid 58 and name HG24}
        {{ segid "BrD" and resid 61 and name HB1 }}
OR      {21092}
        {  segid "BrD" and resid 58 and name HG24}
        {{ segid "BrD" and resid 57 and name HB2 }}
ASSI    {21102}
        {  segid "BrD" and resid 25 and name HG24}
        {{ segid "BrD" and resid 56 and name HB1 }}
           2.500  1.600  1.600 peak     21102 weight    0.10000E◆01 volume   0.34384E◆03 ppm1  1.649    ppm2  2.700
OR      {21102}
        {  segid "BrD" and resid 58 and name HG24}
        {{ segid "BrD" and resid 61 and name HB2 }}
OR      {21102}
        {  segid "BrD" and resid 58 and name HG24}
        {{ segid "BrD" and resid 37 and name HG1 }}
OR      {21102}
        {  segid "BrD" and resid 25 and name HG24}
        {{ segid "BrD" and resid 22 and name HB1 }}
ASSI    {21112}
        {  segid "BrD" and resid 58 and name HG24}
        {  segid "BrD" and resid 54 and name HE4 }
           2.500  1.600  1.600 peak     21112 weight    0.10000E◆01 volume   0.2059E◆03  ppm1  1.649    ppm2  2.508
```

TABLE 3-continued

Ambiguous NOE-derived Inter-proton Distance Restraints

```
OR      {21112}
        { segid "BrD" and resid 25 and name HG24}
        {{ segid "BrD" and resid 26 and name HB1  }}
ASSI    {21132}
        {{ segid "BrD" and resid 83 and name HB  }}
        {{ segid "BrD" and resid 79 and name HG1}}
          5.000  5.000  0.500 peak     21132 weight    0.10000E+01 volume   0.54051E+01 ppm1  4.804   ppm2  3.028
OR      {21132}
        {{ segid "BrD" and resid 83 and name HB  }}
        {{ segid "BrD" and resid 87 and name HG1}}
ASSI    {21152}
        {{ segid "BrD" and resid 58 and name HA  }}
        { segid "BrD" and resid 54 and name HE4}
          3.500  3.100  2.000 peak     21152 weight    0.10000E+01 volume   0.43944E+02 ppm1  4.459   ppm2  2.572
OR      {21152}
        {{ segid "BrD" and resid 83 and name HA  }}
        {{ segid "BrD" and resid 87 and name HB2}}
ASSI    {21222}
        { segid "BrD" and resid 83 and name HG24}
        {{ segid "BrD" and resid 80 and name HG1 }}
          3.000  2.200  2.200 peak     21222 weight    0.10000E+01 volume   0.98918E+02 ppm1  1.894   ppm2  2.366
OR      {21222}
        { segid "BrD" and resid 83 and name HG24}
        {{ segid "BrD" and resid 86 and name HB1 }}
ASSI    {21382}
        {{ segid "BrD" and resid 25 and name HB    }}
        { segid "BrD" and resid 102 and name HD14}
          5.400  5.400  0.100 peak     21382 weight    0.10000E+01 volume   0.33979E+01 ppm1  2.980   ppm2  1.273
OR      {21382}
        {{ segid "BrD" and resid 25 and name HB    }}
        { segid "BrD" and resid 56 and name HD24}
ASSI    {21432}
        { segid "BrD" and resid 25 and name HG14}
        { segid "BrD" and resid 31 and name HB4  }
          3.300  2.700  2.200 peak     21432 weight    0.10000E+01 volume   0.60830E+02 ppm1  1.795   ppm2  2.320
OR      {21432}
        { segid "BrD" and resid 25 and name HG14}
        {{ segid "BrD" and resid 21 and name HG11}}
ASSI    {21442}
        { segid "BrD" and resid 25 and name HG14}
        {{ segid "BrD" and resid 105 and name HB1}}
          2.600  1.700  1.700 peak     21442 weight    0.10000E+01 volume   0.23532E+03 ppm1  1.796   ppm2  3.695
OR      {21442}
        { segid "BrD" and resid 25 and name HG14}
        {{ segid "BrD" and resid 105 and name HB2}}
OR      {21442}
        { segid "BrD" and resid 25 and name HG14}
        {{ segid "BrD" and resid 106 and name HB2}}
ASSI    {21502}
        {{ segid "BrD" and resid 38 and name HA  }}
        {{ segid "BrD" and resid 39 and name HD1}}
          3.600  3.200  1.900 peak     21502 weight    0.10000E+01 volume   0.37412E+02 ppm1  4.163   ppm2  2.291
OR      {21502}
        {{ segid "BrD" and resid 38 and name HA  }}
        {{ segid "BrD" and resid 37 and name HB2}}
ASSI    {21552}
        { segid "BrD" and resid 81 and name HG24}
        {{ segid "BrD" and resid 31 and name HA   }}
          3.000  2.200  2.200 peak     21552 weight    0.10000E+01 volume   0.11144E+03 ppm1  0.760   ppm2  4.981
OR      {21552}
        { segid "BrD" and resid 81 and name HG24}
        {{ segid "BrD" and resid 85 and name HA   }}
OR      {21552}
        { segid "BrD" and resid 81 and name HG24}
        {{ segid "BrD" and resid 77 and name HA   }}
ASSI    {21572}
        { segid "BrD" and resid 81 and name HG14}
        {{ segid "BrD" and resid 77 and name HA   }}
          3.200  2.600  2.300 peak     21572 weight    0.10000E+01 volume   0.78059E+02 ppm1  1.056   ppm2  4.972
OR      {21572}
        { segid "BrD" and resid 38 and name HG14}
        {{ segid "BrD" and resid 39 and name HA   }}
ASSI    {21592}
        { segid "BrD" and resid 38 and name HG14}
        {{ segid "BrD" and resid 53 and name HA   }}
          3.100  2.400  2.400 peak     21592 weight    0.10000E+01 volume   0.93082E+02 ppm1  1.056   ppm2  4.664
```

TABLE 3-continued

Ambiguous NOE-derived Inter-proton Distance Restraints

| | | | | | | | | | | | | |
|---|---|---|---|---|---|---|---|---|---|---|---|---|
| OR | {21592} | | | | | | | | | | | |
| | { segid "BrD" and resid 81 and name HG14} | | | | | | | | | | | |
| | {{ segid "BrD" and resid 80 and name HA }} | | | | | | | | | | | |
| OR | {21592} | | | | | | | | | | | |
| | { segid "BrD" and resid 81 and name HG14} | | | | | | | | | | | |
| | {{ segid "BrD" and resid 53 and name HA }} | | | | | | | | | | | |
| ASSI | {21612} | | | | | | | | | | | |
| | { segid "BrD" and resid 38 and name HG14} | | | | | | | | | | | |
| | {{ segid "BrD" and resid 37 and name HB1 }} | | | | | | | | | | | |
| | 3.800 3.600 1.700 peak 21612 weight | 0.10000E◆01 volume | 0.25206E◆02 ppm1 1.056 | ppm2 2.966 | | | | | | | | |
| OR | {21612} | | | | | | | | | | | |
| | { segid "BrD" and resid 81 and name HG14} | | | | | | | | | | | |
| | {{ segid "BrD" and resid 55 and name HB1 }} | | | | | | | | | | | |
| ASSI | {21652} | | | | | | | | | | | |
| | { segid "BrD" and resid 38 and name HG14} | | | | | | | | | | | |
| | { segid "BrD" and resid 47 and name HE4 }} | | | | | | | | | | | |
| | 3.100 2.400 2.400 peak 21652 weight | 0.10000E◆01 volume | 0.89355E◆02 ppm1 1.056 | ppm2 7.259 | | | | | | | | |
| OR | {21652} | | | | | | | | | | | |
| | { segid "BrD" and resid 81 and name HG14} | | | | | | | | | | | |
| | { segid "BrD" and resid 82 and name HD4 } | | | | | | | | | | | |
| ASSI | {21792} | | | | | | | | | | | |
| | {{ segid "BrD" and resid 81 and name HB }} | | | | | | | | | | | |
| | {{ segid "BrD" and resid 82 and name HB2}} | | | | | | | | | | | |
| | 3.900 3.800 1.600 peak 21792 weight | 0.10000E◆01 volume | 0.21639E◆02 ppm1 2.042 | ppm2 3.573 | | | | | | | | |
| OR | {21792} | | | | | | | | | | | |
| | {{ segid "BrD" and resid 81 and name HB }} | | | | | | | | | | | |
| | {{ segid "BrD" and resid 84 and name HB1}} | | | | | | | | | | | |
| ASSI | {21982} | | | | | | | | | | | |
| | { segid "BrD" and resid 50 and name HD14} | | | | | | | | | | | |
| | {{ segid "BrD" and resid 49 and name HA }} | | | | | | | | | | | |
| | 3.000 2.200 2.200 peak 21982 weight | 0.10000E◆01 volume | 0.11219E◆03 ppm1 1.153 | ppm2 4.692 | | | | | | | | |
| OR | {21982} | | | | | | | | | | | |
| | { segid "BrD" and resid 50 and name HD14} | | | | | | | | | | | |
| | {{ segid "BrD" and resid 53 and name HA }} | | | | | | | | | | | |
| OR | {21982} | | | | | | | | | | | |
| | { segid "BrD" and resid 50 and name HD14}} | | | | | | | | | | | |
| | {{ segid "BrD" and resid 47 and name HA }} | | | | | | | | | | | |
| ASSI | {22072} | | | | | | | | | | | |
| | { segid "BrD" and resid 50 and name HD14 } | | | | | | | | | | | |
| | { segid "BrD" and resid 38 and name HG14 } | | | | | | | | | | | |
| | 3.800 3.600 1.700 peak 22072 weight | 0.10000E◆01 volume | 0.25153E◆02 ppm1 1.154 | ppm2 1.078 | | | | | | | | |
| OR | {22072} | | | | | | | | | | | |
| | { segid "BrD" and resid 50 and name HD14 } | | | | | | | | | | | |
| | { segid "BrD" and resid 81 and name HG14 } | | | | | | | | | | | |
| ASSI | {22432} | | | | | | | | | | | |
| | { segid "BrD" and resid 69 and name HG24} | | | | | | | | | | | |
| | {{ segid "BrD" and resid 19 and name HB2 }} | | | | | | | | | | | |
| | 5.500 5.500 0.000 peak 22432 weight | 0.10000E◆01 volume | 0.51248E◆00 ppm1 1.425 | ppm2 1.993 | | | | | | | | |
| OR | {22432} | | | | | | | | | | | |
| | { segid "BrD" and resid 69 and name HG24 } | | | | | | | | | | | |
| | { segid "BrD" and resid 113 and name HB4 } | | | | | | | | | | | |
| ASSI | {22502} | | | | | | | | | | | |
| | { segid "BrD" and resid 25 and name HG24} | | | | | | | | | | | |
| | { segid "BrD" and resid 35 and name HE4 } | | | | | | | | | | | |
| | 2.900 2.100 2.100 peak 22502 weight | 0.10000E◆01 volume | 0.14480E◆03 ppm1 1.633 | ppm2 2.752 | | | | | | | | |
| OR | {22502} | | | | | | | | | | | |
| | { segid "BrD" and resid 49 and name HG14} | | | | | | | | | | | |
| | {{ segid "BrD" and resid 48 and name HB }} | | | | | | | | | | | |
| OR | {22502} | | | | | | | | | | | |
| | { segid "BrD" and resid 58 and name HG24} | | | | | | | | | | | |
| | {{ segid "BrD" and resid 37 and name HG1 }} | | | | | | | | | | | |
| ASSI | {22622} | | | | | | | | | | | |
| | {{ segid "BrD" and resid 42 and name HA }} | | | | | | | | | | | |
| | {{ segid "BrD" and resid 44 and name HD2}} | | | | | | | | | | | |
| | 4.000 4.000 1.500 peak 22622 weight | 0.10000E◆01 volume | 0.20863E◆02 ppm1 5.051 | ppm2 4.133 | | | | | | | | |
| OR | {22622} | | | | | | | | | | | |
| | {{ segid "BrD" and resid 42 and name HA }} | | | | | | | | | | | |
| | {{ segid "BrD" and resid 38 and name HA }} | | | | | | | | | | | |
| ASSI | {22802} | | | | | | | | | | | |
| | {{ segid "BrD" and resid 104 and name HB1 }} | | | | | | | | | | | |
| | {{ segid "BrD" and resid 105 and name HB2 }} | | | | | | | | | | | |
| | 3.200 2.600 2.300 peak 22802 weight | 0.10000E◆01 volume | 0.76681E◆02 ppm1 2.536 | ppm2 3.662 | | | | | | | | |
| OR | {22802} | | | | | | | | | | | |
| | {{ segid "BrD" and resid 104 and name HB1 }} | | | | | | | | | | | |
| | {{ segid "BrD" and resid 107 and name HB1 }} | | | | | | | | | | | |

TABLE 3-continued

Ambiguous NOE-derived Inter-proton Distance Restraints

```
ASSI    {22862}
        {{ segid "BrD" and resid 64 and name HE1}}
        {{ segid "BrD" and resid 19 and name HA  }}
          3.600  3.200  1.900 peak     22862 weight    0.10000E+01 volume  0.38596E+02 ppm1  3.573    ppm2  4.285
OR      {22862}
        {{ segid "BrD" and resid 57 and name HE1 }}
        {{ segid "BrD" and resid 37 and name HD1 }}
ASSI    {22912}
        {{ segid "BrD" and resid 60 and name HB1 }}
        {{ segid "BrD" and resid 22 and name HB2 }}
          4.100  4.100  1.400 peak     22912 weight    0.10000E+01 volume  0.16339E+02 ppm1  5.001    ppm2  2.312
OR      {22912}
        {{ segid "BrD" and resid 60 and name HB1}}
        {{ segid "BrD" and resid 56 and name HG  }}
ASSI    {23002}
        {{ segid "BrD" and resid 37 and name HD1 }}
        {{ segid "BrD" and resid 57 and name HB1 }}
          3.100  2.400  2.400 peak     23002 weight    0.10000E+01 volume  0.82823E+02 ppm1  4.285    ppm2  2.966
OR      {23002}
        {{ segid "BrD" and resid 37 and name HD1 }}
        {{ segid "BrD" and resid 37 and name HB1 }}
OR      {23002}
        {{ segid "BrD" and resid 44 and name HD1 }}
        {{ segid "BrD" and resid 44 and name HB1 }}
ASSI    {23042}
        {{ segid "BrD" and resid 37 and name HD1 }}
        {{ segid "BrD" and resid 37 and name HG2 }}
          2.000  1.000  1.000 peak     23042 weight    0.10000E+01 volume  0.14416E+04 ppm1  4.261    ppm2  2.621
OR      {23042}
        {{ segid "BrD" and resid 8 and name HD2 }}
        {{ segid "BrD" and resid 8 and name HG1 }}
ASSI    {23052}
        {{ segid "BrD" and resid 8 and name HD1 }}
        {{ segid "BrD" and resid 8 and name HB2 }}
          3.600  3.200  1.900 peak     23052 weight    0.10000E+01 volume  0.37937E+02 ppm1  4.409    ppm2  2.499
OR      {23052}
        {{ segid "BrD" and resid 8 and name HD1 }}
        {{ segid "BrD" and resid 7 and name HB2 }}
ASSI    {23212}
        {{ segid "BrD" and resid 44 and name HG2}}
        {{ segid "BrD" and resid 44 and name HA  }}
          3.100  2.400  2.400 peak     23212 weight    0.10000E+01 volume  0.93859E+02 ppm1  2.635    ppm2  5.120
OR      {23212}
        {{ segid "BrD" and resid 8 and name HG1}}
        {{ segid "BrD" and resid 7 and name HA  }}
ASSI    {23252}
        {{ segid "BrD" and resid 11 and name HG1  }}
        {  segid "BrD" and resid 69 and name HG24}
          3.000  2.200  2.200 peak     23252 weight    0.10000E+01 volume  0.10852E+03 ppm1  2.635    ppm2  1.417
OR      {23252}
        {{ segid "BrD" and resid 11 and name HG1  }}
        {  segid "BrD" and resid 14 and name HD24}
ASSI    {23382}
        {{ segid "BrD" and resid 100 and name HA }}
        {{ segid "BrD" and resid 101 and name HA }}
          5.500  5.500  0.000 peak     23382 weight    0.10000E+01 volume  0.24494E+01 ppm1  4.952    ppm2  4.256
OR      {23382}
        {{ segid "BrD" and resid 6 and name HA  }}
        {{ segid "BrD" and resid 8 and name HD2}}
ASSI    {23392}
        {{ segid "BrD" and resid 100 and name HA}}
        {{ segid "BrD" and resid 99 and name HA  }}
          3.200  2.600  2.300 peak     23392 weight    0.10000E+01 volume  0.72079E+02 ppm1  4.952    ppm2  4.444
OR      {23392}
        {{ segid "BrD" and resid 6 and name HA  }}
        {{ segid "BrD" and resid 8 and name HD1}}
ASSI    {23512}
        {{ segid "BrD" and resid 10 and name HA }}
        {{ segid "BrD" and resid 11 and name HA }}
          3.400  2.900  2.100 peak     23512 weight    0.10000E+01 volume  0.53886E+02 ppm1  5.477    ppm2  4.939
OR      {23512}
        {{ segid "BrD" and resid 10 and name HA}}
        {{ segid "BrD" and resid 9 and name HA  }}
ASSI    {23582}
        {{ segid "BrD" and resid 12 and name HA }}
        {{ segid "BrD" and resid 15 and name HA }}
          3.600  3.200  1.900 peak     23582 weight    0.10000E+01 volume  0.33831E+02 ppm1  5.297    ppm2  4.627
```

TABLE 3-continued

Ambiguous NOE-derived Inter-proton Distance Restraints

```
OR      {23582}
        {{ segid "BrD" and resid 12 and name HA  }}
        {{ segid "BrD" and resid 16 and name HB1}}
OR      {23582}
        {{ segid "BrD" and resid 12 and name HA  }}
        {{ segid "BrD" and resid 14 and name HA  }}
ASSI    {23682}
        {{ segid "BrD" and resid 14 and name HA   }}
        {  segid "BrD" and resid 18 and name HD14}
          3.300  2.700  2.200 peak    23682 weight    0.10000E♦01 volume   0.67221E♦02 ppm1  4.656    ppm2  1.083
OR      {23682}
        {{ segid "BrD" and resid 80 and name HA   }}
        {  segid "BrD" and resid 81 and name HG14}
ASSI    {23772}
        {  segid "BrD" and resid 14 and name HD24}}
        {{ segid "BrD" and resid 15 and name HA   }}
          2.400  1.400  1.400 peak    23772 weight    0.10000E♦01 volume   0.36871E♦03 ppm1  1.400    ppm2  4.574
OR      {23772}
        {{ segid "BrD" and resid 109 and name HG1}}
        {{ segid "BrD" and resid 17 and name HA   }}
ASSI    {23792}
        {  segid "BrD" and resid 14 and name HD24}
        {{ segid "BrD" and resid 18 and name HA   }}
          3.900  3.800  1.600 peak    23792 weight    0.10000E♦01 volume   0.23831E♦02 ppm1  1.401    ppm2  3.889
OR      {23792}
        {{ segid "BrD" and resid 109 and name HG1}}
        {{ segid "BrD" and resid 18 and name HA   }}
ASSI    {23872}
        {{ segid "BrD" and resid 18 and name HA  }}
        {  segid "BrD" and resid 74 and name HE4}
          2.900  2.100  2.100 peak    23872 weight    0.10000E♦01 volume   0.13092E♦03 ppm1  3.866    ppm2  7.534
OR      {23872}
        {{ segid "BrD" and resid 18 and name HA   }}
        {  segid "BrD" and resid 106 and name HD4}
ASSI    {23892}
        {{ segid "BrD" and resid 18 and name HA }}
        {{ segid "BrD" and resid 15 and name HA }}
          2.900  2.100  2.100 peak    23892 weight    0.10000E♦01 volume   0.13327E♦03 ppm1  3.867    ppm2  4.631
OR      {23892}
        {{ segid "BrD" and resid 18 and name HA }}
        {{ segid "BrD" and resid 20 and name HB1}}
OR      {23892}
        {{ segid "BrD" and resid 16 and name HA }}
        {{ segid "BrD" and resid 14 and name HA }}
ASSI    {23902}
        {{ segid "BrD" and resid 16 and name HA }}
        {{ segid "BrD" and resid 17 and name HA }}
          2.800  3.600  1.700 peak    23902 weight    0.10000E♦01 volume   0.26018E♦02 ppm1  3.867    ppm2  4.541
OR      {23902}
        {{ segid "BrD" and resid 16 and name HA  }}
        {{ segid "BrD" and resid 106 and name HA}}
ASSI    {23912}
        {{ segid "BrD" and resid 18 and name HB1  }}
        {{ segid "BrD" and resid 14 and name HD24}}
          3.400  2.900  2.100 peak    23912 weight    0.10000E♦01 volume   0.53944E♦02 ppm1  2.140    ppm2  1.433
OR      {23912}
        {{ segid "BrD" and resid 18 and name HB1 }}
        {  segid "BrD" and resid 69 and name HG24}
ASSI    {23942}
        {{ segid "BrD" and resid 18 and name HB2 }}
        {  segid "BrD" and resid 14 and name HD24}
          4.100  4.100  1.400 peak    23942 weight    0.10000E♦01 volume   0.16641E♦02 ppm1  0.911    ppm2  1.415
OR      {23942}
        {{ segid "BrD" and resid 18 and name HB2 }}
        {  segid "BrD" and resid 69 and name HG24}
ASSI    {24102}
        {  segid "BrD" and resid 18 and name HD24 }
        {  segid "BrD" and resid 21 and name HG24 }
          5.500  5.500  0.000 peak    24102 weight    0.10000E♦01 volume   0.18200E♦00 ppm1  0.415    ppm2  1.596
OR      {24102}
        {  segid "BrD" and resid 18 and name HD24 }
        {  segid "BrD" and resid 22 and name HD24 }
ASSI    {24112}
        {  segid "BrD" and resid 18 and name HD24 }
        {  segid "BrD" and resid 115 and name HD14}
          2.800  2.000  2.000 peak    24112 weight    0.10000E♦01 volume   0.15952E♦03 ppm1  0.416    ppm2  1.377
```

TABLE 3-continued

Ambiguous NOE-derived Inter-proton Distance Restraints

```
OR    {24112}
      { segid "BrD" and resid 18 and name HD24 }
      { segid "BrD" and resid 14 and name HD24 }
OR    {24112}
      { segid "BrD" and resid 18 and name HD24 }
      { segid "BrD" and resid 14 and name HD14 }
ASSI  {24122}
      { segid "BrD" and resid 16 and name HD24 }
      { segid "BrD" and resid 113 and name HB4 }
        3.900  3.800  1.600 peak    24122 weight   0.10000E+01 volume   0.21917E+02 ppm1  0.415   ppm2  1.986
OR    {24122}
      {  segid "BrD" and resid 18 and name HD24}
      {{ segid "BrD" and resid 19 and name HB2  }}
ASSI  {24292}
      {  segid "BrD" and resid 18 and name HN  }
      {{ segid "BrD" and resid 106 and name HN}}
        3.900  3.800  1.600 peak    24292 weight   0.10000E+01 volume   0.23222E+02 ppm1  0.416   ppm2  3.650
OR    {24292}
      {  segid "BrD" and resid 18 and name HD24}
      {{ segid "BrD" and resid 68 and name HB1  }}
OR    {24292}
      {  segid "BrD" and resid 18 and name HD24}
      {{ segid "BrD" and resid 15 and name HB2  }}
ASSI  {24492}
      {  segid "BrD" and resid 63 and name HD14}
      {{ segid "BrD" and resid 68 and name HB   }}
        2.800  2.000  2.000 peak    24492 weight   0.10000E+01 volume   0.15293E+03 ppm1  1.649   ppm2  3.671
OR    {24492}
      {  segid "BrD" and resid 63 and name HD14}
      {{ segid "BrD" and resid 15 and name HB2  }}
ASSI  {24502}
      {  segid "BrD" and resid 63 and name HD14}
      {{ segid "BrD" and resid 66 and name HD2  }}
        3.000  2.200  2.200 peak    24502 weight   0.10000E+01 volume   0.10614E+03 ppm1  1.649   ppm2  1.614
OR    {24502}
      {  segid "BrD" and resid 63 and name HD14}
      {{ segid "BrD" and resid 64 and name HE1  }}
ASSI  {24532}
      {  segid "BrD" and resid 63 and name HD14}
      {{ segid "BrD" and resid 16 and name HA   }}
        3.500  3.100  2.000 peak    24632 weight   0.10000E+01 volume   0.45951E+02 ppm1  1.649   ppm2  4.516
OR    {24532}
      {  segid "BrD" and resid 63 and name HD14}
      {{ segid "BrD" and resid 17 and name HA   }}
ASSI  {24602}
      {  segid "BrD" and resid 63 and name HD24}
      {{ segid "BrD" and resid 19 and name HE1  }}
        3.400  2.900  2.100 peak    24602 weight   0.10000E+01 volume   0.54742E+02 ppm1  1.900   ppm2  3.524
OR    {24602}
      {  segid "BrD" and resid 63 and name HD24}
      {{ segid "BrD" and resid 68 and name HB2  }}
ASSI  {24692}
      {{ segid "BrD" and resid 19 and name HA }}
      {{ segid "BrD" and resid 22 and name HG }}
        3.000  2.200  2.200 peak    24692 weight   0.10000E+01 volume   0.10572E+03 ppm1  4.310   ppm2  2.293
OR    {24692}
      {{ segid "BrD" and resid 19 and name HA }}
      {{ segid "BrD" and resid 64 and name HD1}}
ASSI  {24712}
      {{ segid "BrD" and resid 19 and name HA }}
      {{ segid "BrD" and resid 23 and name HA }}
        3.700  3.400  1.800 peak    24712 weight   0.10000E+01 volume   0.31255E+02 ppm1  4.310   ppm2  4.677
OR    {24712}
      {{ segid "BrD" and resid 19 and name HA }}
      {{ segid "BrD" and resid 22 and name HA }}
OR    {24712}
      {{ segid "BrD" and resid 19 and name HA }}
      {{ segid "BrD" and resid 20 and name HB1}}
ASSI  {24722}
      {{ segid "BrD" and resid 19 and name HB2}}
      {{ segid "BrD" and resid 15 and name HA }}
        3.800  3.600  1.700 peak    24722 weight   0.10000E+01 volume   0.24706E+03 ppm1  1.989   ppm2  4.974
OR    {24722}
      {{ segid "BrD" and resid 19 and name HB2 }}
      {{ segid "BrD" and resid 16 and name HB1 }}
```

TABLE 3-continued

Ambiguous NOE-derived Inter-proton Distance Restraints

```
ASSI    {24732}
        {{ segid "BrD" and resid 19 and name HB2}}
        {{ segid "BrD" and resid 15 and name HA  }}
           3.800  3.600  1.700 peak    24732 weight    0.10000E+01 volume   0.28161E+02 ppm1  1.989    ppm2  4.631
OR      {24732}
        {{ segid "BrD" and resid 19 and name HB2 }}
        {{ segid "BrD" and resid 20 and name HB1 }}
ASSI    {24772}
        {{ segid "BrD" and resid 19 and name HG1}}
        {{ segid "BrD" and resid 20 and name HA  }}
           4.200  4.200  1.300 peak    24772 weight    0.10000E+01 volume   0.15236E+02 ppm1  1.895    ppm2  4.891
OR      {24772}
        {{ segid "BrD" and resid 86 and name HG1}}
        {{ segid "BrD" and resid 87 and name HA  }}
OR      {24772}
        {{ segid "BrD" and resid 19 and name HG  }}
        {{ segid "BrD" and resid 64 and name HA  }}
ASSI    {24822}
        {{ segid "BrD" and resid 19 and name HD1}}
        {{ segid "BrD" and resid 15 and name HA  }}
           4.100  4.100  1.400 peak    24822 weight    0.10000E+01 volume   0.14533E+02 ppm1  2.190    ppm2  4.643
OR      {24822}
        {{ segid "BrD" and resid 19 and name HD1 }}
        {{ segid "BrD" and resid 20 and name HB1 }}
ASSI    {24852}
        {{ segid "BrD" and resid 97 and name HE1}}
        {{ segid "BrD" and resid 97 and name HA  }}
           2.000  2.000  2.500 peak    24852 weight    0.10000E+01 volume   0.10950E+04 ppm1  3.571    ppm2  4.802
OR      {24852}
        {{ segid "BrD" and resid 57 and name HE1}}
        {{ segid "BrD" and resid 57 and name HA  }}
ASSI    {24982}
        {{ segid "BrD" and resid 21 and name HA  }}
        {  segid "BrD" and resid 106 and name HD4}
           3.600  3.200  1.900 peak    24982 weight    0.10000E+01 volume   0.38794E+02 ppm1  4.358    ppm2  7.517
OR      {24982}
        {{ segid "BrD" and resid 33 and name HA  }}
        {  segid "BrD" and resid 95 and name HD4}
ASSI    {24992}
        {{ segid "BrD" and resid 21 and name HA }}
        {{ segid "BrD" and resid 22 and name HA }}
           2.000  2.000  2.500 peak    24992 weight    0.10000E+01 volume   0.12406E+04 ppm1  4.360    ppm2  4.671
OR      {24992}
        {{ segid "BrD" and resid 21 and name HA  }}
        {{ segid "BrD" and resid 20 and name HB1}}
ASSI    {25052}
        {{ segid "BrD" and resid 21 and name HG12}}
        {{ segid "BrD" and resid 18 and name HB1  }}
           3.500  3.100  2.000 peak    25052 weight    0.10000E+01 volume   0.40558E+02 ppm1  1.648    ppm2  2.141
OR      {25052}
        {{ segid "BrD" and resid 21 and name HG12 }}
        {{ segid "BrD" and resid 109 and name HB2 }}
ASSI    {25112}
        {{ segid "BrD" and resid 21 and name HG12 }}
        {{ segid "BrD" and resid 109 and name HG1 }}
           3.900  3.800  1.600 peak    25112 weight    0.10000E+01 volume   0.24225E+02 ppm1  1.648    ppm2  1.387
OR      {25112}
        {{ segid "BrD" and resid 21 and name HG12 }}
        {  segid "BrD" and resid 115 and name HD14}
OR      {25112}
        {{ segid "BrD" and resid 21 and name HG14 }}
        {  segid "BrD" and resid 14 and name HD24 }
ASSI    {25152}
        {  segid "BrD" and resid 21 and name HD14}
        {{ segid "BrD" and resid 106 and name HA }}
           2.600  1.700  1.700 peak    25152 weight    0.10000E+01 volume   0.24691E+03 ppm1  1.205    ppm2  4.456
OR      {25152}
        {  segid "BrD" and resid 21 and name HD14}
        {{ segid "BrD" and resid 17 and name HA   }}
OR      {25152}
        {  segid "BrD" and resid 21 and name HD14}
        {  segid "BrD" and resid 75 and name HA   }
ASSI    {25162}
        {  segid "BrD" and resid 21 and name HD14}
        {{ segid "BrD" and resid 20 and name HA   }}
           5.500  5.500  0.000 peak    25162 weight    0.10000E+01 volume   0.64481E+01 ppm1  1.205    ppm2  4.907
```

TABLE 3-continued

Ambiguous NOE-derived Inter-proton Distance Restraints

```
OR      {25162}
        {  segid "BrD" and resid 21 and name HD14}
        {{ segid "BrD" and resid 105 and name HA  }}
OR      {25162}
        {  segid "BrD" and resid 21 and name HD14}
        {{ segid "BrD" and resid 59 and name HA   }}
ASSI    {25172}
        {  segid "BrD" and resid 21 and name HD14}
        {{ segid "BrD" and resid 17 and name HB   }}
          3.100  2.400  2.400  peak    25172 weight   0.10000E◆01 volume   0.95979E◆02 ppm1  1.205    ppm2  4.863
OR      {25172}
        {  segid "BrD" and resid 21 and name HD14}
        {{ segid "BrD" and resid 20 and name HA   }}
ASSI    {25182}
        {  segid "BrD" and resid 21 and name HD14}
        {  segid "BrD" and resid 74 and name HE4  }
          2.600  1.700  1.700  peak    25182 weight   0.10000E◆01 volume   0.25847E◆03 ppm1  1.204    ppm2  7.536
OR      {25182}
        {  segid "BrD" and resid 21 and name HD14 }
        {  segid "BrD" and resid 106 and name HD4 }
ASSI    {25392}
        {{ segid "BrD" and resid 98 and name HA  }}
        {{ segid "BrD" and resid 101 and name HA}}
          3.400  2.900  2.100  peak    25392 weight   0.10000E◆01 volume   0.50125E◆02 ppm1  4.804    ppm2  4.265
OR      {25392}
        {{ segid "BrD" and resid 98 and name HA  }}
        {{ segid "BrD" and resid 102 and name HA}}
ASSI    {25602}
        {  segid "BrD" and resid 21 and name HG24}
        {{ segid "BrD" and resid 20 and name HB1  }}
          3.400  2.900  2.100  peak    25602 weight   0.10000E◆01 volume   0.54447E◆02 ppm1  1.596    ppm2  4.657
OR      {25602}
        {  segid "BrD" and resid 21 and name HG24}
        {{ segid "BrD" and resid 109 and name HA }}
ASSI    {25622}
        {  segid "BrD" and resid 21 and name HG24}
        {{ segid "BrD" and resid 105 and name HB1}}
          3.400  2.900  2.100  peak    25622 weight   0.10000E◆01 volume   0.55968E◆02 ppm1  1.599    ppm2  3.736
OR      {25622}
        {  segid "BrD" and resid 101 and name HG24}
        {{ segid "BrD" and resid 105 and name HB1 }}
ASSI    {25632}
        {  segid "BrD" and resid 21 and name HG24}
        {{ segid "BrD" and resid 106 and name HB2}}
          4.400  4.400  1.100  peak    25632 weight   0.10000E◆01 volume   0.10843E◆02 ppm1  1.599    ppm2  3.662
OR      {25632}
        {  segid "BrD" and resid 21 and name HG24}
        {{ segid "BrD" and resid 105 and name HB2}}
ASSI    {25672}
        {  segid "BrD" and resid 101 and name HD14}
        {{ segid "BrD" and resid 97 and name HB1   }}
          3.100  2.400  2.400  peak    25672 weight   0.10000E◆01 volume   0.84040E◆02 ppm1  1.550    ppm2  2.702
OR      {25672}
        {  segid "BrD" and resid 101 and name HD14}
        {{ segid "BrD" and resid 29 and name HB1   }}
ASSI    {25692}
        {  segid "BrD" and resid 101 and name HD14}
        {{ segid "BrD" and resid 97 and name HG2   }}
          3.800  3.600  1.700  peak    25692 weight   0.10000E◆01 volume   0.27614E◆02 ppm1  1.550    ppm2  2.167
OR      {25692}
        {  segid "BrD" and resid 101 and name HD14}
        {  segid "BrD" and resid 99 and name HB4  }
OR      {25692}
        {  segid "BrD" and resid 101 and name HD14}}
        {{ segid "BrD" and resid 33 and name HD2   }}
ASSI    {25702}
        {  segid "BrD" and resid 21 and name HG24}
        {  segid "BrD" and resid 75 and name HE4  }
          4.300  4.300  1.200  peak    25702 weight   0.10000E◆01 volume   0.11881E◆02 ppm1  1.599    ppm2  2.654
OR      {25702}
        {  segid "BrD" and resid 21 and name HG24}
        {{ segid "BrD" and resid 22 and name HB1  }}
OR      {25702}
        {  segid "BrD" and resid 101 and name HG24}
        {{ segid "BrD" and resid 97 and name HB1   }}
```

TABLE 3-continued

Ambiguous NOE-derived Inter-proton Distance Restraints

```
ASSI    {25732}
        { segid "BrD" and resid 101 and name HG24}
        {{ segid "BrD" and resid 102 and name HB1 }}
          2.600  1.700  1.700 peak     25732 weight    0.10000E+01 volume   0.25581E+03 ppm1  1.599    ppm2  2.011
OR      {25732}
        { segid "BrD" and resid 21 and name HG24}
        {{ segid "BrD" and resid 109 and name HD1}}
ASSI    {25772}
        { segid "BrD" and resid 21 and name HG24 }
        { segid "BrD" and resid 18 and name HD14 }
          3.200  2.600  2.300 peak     25772 weight    0.10000E+01 volume   0.75349E+02 ppm1  1.599    ppm2  1.059
OR      {25772}
        { segid "BrD" and resid 21 and name HG24 }
        {{ segid "BrD" and resid 78 and name HB2  }}
OR      {25772}
        { segid "BrD" and resid 21 and name HG24 }
        { segid "BrD" and resid 81 and name HG14 }
ASSI    {25832}
        {{ segid "BrD" and resid 110 and name HB }}
        {{ segid "BrD" and resid 104 and name HA }}
          3.800  3.600  1.700 peak     25832 weight    0.10000E+01 volume   0.26102E+02 ppm1  2.338    ppm2  4.823
OR      {25832}
        {{ segid "BrD" and resid 110 and name HB }}
        {{ segid "BrD" and resid 115 and name HA }}
ASSI    {25861}
        { segid "BrD" and resid 110 and name HG24}
        {{ segid "BrD" and resid 114 and name HA   }}
          3.100  2.400  2.400 peak     25862 weight    0.10000E+01 volume   0.90313E+02 ppm1  1.254    ppm2  4.509
OR      {25852}
        { segid "BrD" and resid 110 and name HG24}
        {{ segid "BrD" and resid 75 and name HA    }}
ASSI    {25872}
        { segid "BrD" and resid 110 and name HD14}
        {{ segid "BrD" and resid 14 and name HA    }}
          2.800  2.000  2.000 peak     25872 weight    0.10000E+01 volume   0.15296E+03 ppm1  1.154    ppm2  4.655
OR      {25872}
        { segid "BrD" and resid 110 and name HD14}
        {{ segid "BrD" and resid 71 and name HA    }}
OR      {25872}
        { segid "BrD" and resid 110 and name HD14}
        {{ segid "BrD" and resid 111 and name HA   }}
OR      {25872}
        { segid "BrD" and resid 110 and name HD14}
        {{ segid "BrD" and resid 109 and name HA   }}
ASSI    {25882}
        { segid "BrD" and resid 110 and name HG24}
        {{ segid "BrD" and resid 115 and name HA   }}
          2.800  2.000  2.000 peak     25882 weight    0.10000E+01 volume   0.15787E+03 ppm1  1.253    ppm2  4.824
OR      {25882}
        { segid "BrD" and resid 110 and name HG24}
        {{ segid "BrD" and resid 116 and name HA   }}
ASSI    {25892}
        { segid "BrD" and resid 110 and name HD14}
        {{ segid "BrD" and resid 17 and name HB    }}
          3.100  2.400  2.400 peak     25892 weight    0.10000E+01 volume   0.95882E+02 ppm1  1.154    ppm2  4.824
OR      {25892}
        { segid "BrD" and resid 110 and name HD14}
        {{ segid "BrD" and resid 115 and name HA   }}
ASSI    {25902}
        { segid "BrD" and resid 110 and name HD14}
        {{ segid "BrD" and resid 106 and name HA   }}
          3.000  2.200  2.200 peak     25902 weight    0.10000E+01 volume   0.11502E+03 ppm1  1.154    ppm2  4.568
OR      {25902}
        { segid "BrD" and resid 110 and name HD14}
        {{ segid "BrD" and resid 17 and name HA    }}
OR      {25902}
        { segid "BrD" and resid 110 and name HD14}
        {{ segid "BrD" and resid 114 and name HA1  }}
ASSI    {26022}
        { segid "BrD" and resid 110 and name HD14}
        {{ segid "BrD" and resid 106 and name HB2  }}
          3.200  2.600  2.300 peak     26022 weight    0.10000E+01 volume   0.70430E+02 ppm1  1.154    ppm2  3.670
OR      {26022}
        { segid "BrD" and resid 110 and name HD14}
        {{ segid "BrD" and resid 107 and name HB1  }}
```

TABLE 3-continued

Ambiguous NOE-derived Inter-proton Distance Restraints

```
ASSI  {26042}
      {  segid "BrD" and resid 110 and name HG24}
      {{ segid "BrD" and resid 107 and name HB1  }}
        3.600  3.200  1.900 peak    26042 weight    0.10000E+01 volume  0.38059E+02 ppm1  1.251    ppm2  3.671
OR    {26042}
      {  segid "BrD" and resid 110 and name HG24}
      {{ segid "BrD" and resid 106 and name HB2  }}
ASSI  {26202}
      {  segid "BrD" and resid 116 and name HG24}
      {{ segid "BrD" and resid 76 and name HA    }}
        2.600  1.700  1.700 peak    26202 weight    0.10000E+01 volume  0.28885E+03 ppm1  1.401    ppm2  4.655
OR    {26202}
      {  segid "BrD" and resid 116 and name HG24}
      {{ segid "BrD" and resid 72 and name HA    }}
ASSI  {26312}
      {  segid "BrD" and resid 116 and name HD14}
      {{ segid "BrD" and resid 76 and name HA    }}
        3.800  3.600  1.700 peak    26312 weight    0.10000E+01 volume  0.26059E+02 ppm1  1.401    ppm2  4.655
OR    {26312}
      {  segid "BrD" and resid 116 and name HD14}
      {{ segid "BrD" and resid 118 and name HA   }}
OR    {26312}
      {  segid "BrD" and resid 116 and name HD14}
      {{ segid "BrD" and resid 111 and name HA   }}
OR    {26312}
      {  segid "BrD" and resid 116 and name HD14}
      {{ segid "BrD" and resid 71 and name HA    }}
OR    {26312}
      {  segid "BrD" and resid 116 and name HD14}
      {{ segid "BrD" and resid 72 and name HA    }}
ASSI  {26352}
      {  segid "BrD" and resid 116 and name HG24}
      {{ segid "BrD" and resid 79 and name HA    }}
        3.600  3.200  1.900 peak    26352 weight    0.10000E+01 volume  0.36722E+02 ppm1  1.400    ppm2  4.428
OR    {26352}
      {  segid "BrD" and resid 116 and name HG24}
      {{ segid "BrD" and resid 107 and name HA   }}
ASSI  {26362}
      {  segid "BrD" and resid 116 and name HD14}
      {{ segid "BrD" and resid 107 and name HB1  }}
        3.800  3.600  1.700 peak    26362 weight    0.10000E+01 volume  0.28562E+02 ppm1  1.401    ppm2  3.662
OR    {26362}
      {  segid "BrD" and resid 116 and name HD14}
      {{ segid "BrD" and resid 106 and name HB2  }}
ASSI  {26512}
      {{ segid "BrD" and resid 116 and name HB}}
      {{ segid "BrD" and resid 76 and name HA   }}
        3.300  2.700  2.200 peak    26512 weight    0.10000E+01 volume  0.66907E+02 ppm1  2.410    ppm2  4.655
OR    {26512}
      {{ segid "BrD" and resid 116 and name HB  }}
      {{ segid "BrD" and resid 118 and name HA  }}
OR    {26512}
      {{ segid "BrD" and resid 116 and name HB}}
      {{ segid "BrD" and resid 72 and name HA   }}
ASSI  {27012}
      {{ segid "BrD" and resid 89 and name HA   }}
      {{ segid "BrD" and resid 88 and name HA   }}
        3.600  3.200  1.900 peak    27012 weight    0.10000E+01 volume  0.33743E+02 ppm1  5.642    ppm2  5.005
OR    {27012}
      {{ segid "BrD" and resid 89 and name HA   }}
      {{ segid "BrD" and resid 93 and name HB1  }}
ASSI  {27292}
      {{ segid "BrD" and resid 80 and name HG1  }}
      {{ segid "BrD" and resid 92 and name HB1  }}
        3.300  2.700  2.200 peak    27292 weight    0.10000E+01 volume  0.41197E+02 ppm1  2.341    ppm2  3.649
OR    {27292}
      {{ segid "BrD" and resid 73 and name HG   }}
      {{ segid "BrD" and resid 68 and name HB1  }}
ASSI  {27302}
      {{ segid "BrD" and resid 80 and name HG1  }}
      {{ segid "BrD" and resid 77 and name HB1  }}
        4.600  4.600  0.900 peak    27302 weight    0.10000E+01 volume  0.87654E+01 ppm1  2.341    ppm2  3.311
OR    {27302}
      {{ segid "BrD" and resid 73 and name HG   }}
      {{ segid "BrD" and resid 77 and name HB1  }}
OR    {27302}
      {{ segid "BrD" and resid 73 and name HG   }}
      {{ segid "BrD" and resid 54 and name HG1  }}
```

TABLE 3-continued

Ambiguous NOE-derived Inter-proton Distance Restraints

```
OR      {27302}
        {{ segid "BrD" and resid 56 and name HG   }}
        {{ segid "BrD" and resid 54 and name HG1}}
OR      {27302}
        {{ segid "BrD" and resid 56 and name HG   }}
        {{ segid "BrD" and resid 77 and name HB1}}
ASSI    {27332}
        {{ segid "BrD" and resid 56 and name HG   }}
        {  segid "BrD" and resid 81 and name HG24}
          3.600  3.200  1.900 peak     27332 weight    0.10000E◆01 volume   0.35670E◆02 ppm1  2.338    ppm2 0.758
OR      {27332}
        {{ segid "BrD" and resid 22 and name HG   }}
        {  segid "BrD" and resid 78 and name HD14}
ASSI    {27462}
        {  segid "BrD" and resid 22 and name HD14}
        {{ segid "BrD" and resid 25 and name HB   }}
          3.800  3.600  1.700 peak     27462 weight    0.10000E◆01 volume   0.26281E◆02 ppm1  1.648    ppm2 2.995
OR      {27462}
        {  segid "BrD" and resid 22 and name HD14}
        {{ segid "BrD" and resid 61 and name HG1  }}
OR      {27462}
        {  segid "BrD" and resid 22 and name HD14}
        {{ segid "BrD" and resid 74 and name HB2  }}
ASSI    {27482}
        {  segid "BrD" and resid 22 and name HD24}
        {{ segid "BrD" and resid 26 and name HA   }}
          3.200  2.600  2.300 peak     27482 weight    0.10000E◆01 volume   0.77977E◆02 ppm1  1.599    ppm2 4.492
OR      {27482}
        {  segid "BrD" and resid 22 and name HD24}
        {{ segid "BrD" and resid 58 and name HA   }}
ASSI    {27502}
        {  segid "BrD" and resid 22 and name HD24}
        {{ segid "BrD" and resid 59 and name HA   }}
          3.200  2.600  2.300 peak     27502 weight    0.10000E◆01 volume   0.74913E◆02 ppm1  1.599    ppm2 4.901
OR      {27502}
        {  segid "BrD" and resid 22 and name HD24}
        {{ segid "BrD" and resid 35 and name HA   }}
OR      {27502}
        {  segid "BrD" and resid 22 and name HD24}
        {{ segid "BrD" and resid 20 and name HA   }}
ASSI    {27542}
        {  segid "BrD" and resid 22 and name HD24}
        {{ segid "BrD" and resid 56 and name HB2  }}
          4.000  4.000  1.500 peak     27542 weight    0.10000E◆01 volume   0.19846E◆02 ppm1  1.599    ppm2 2.011
OR      {27542}
        {  segid "BrD" and resid 22 and name HD24}
        {{ segid "BrD" and resid 81 and name HB   }}
ASSI    {27562}
        {  segid "BrD" and resid 22 and name HD14}
        {{ segid "BrD" and resid 64 and name HA   }}
          3.300  2.700  2.200 peak     27562 weight    0.10000E◆01 volume   0.62753E◆02 ppm1  1.645    ppm2 4.911
OR      {27562}
        {  segid "BrD" and resid 22 and name HD14}
        {{ segid "BrD" and resid 59 and name HA   }}
ASSI    {27592}
        {{ segid "BrD" and resid 110 and name HG12 }}
        {  segid "BrD" and resid 115 and name HD14 }}
          3.300  2.700  2.200 peak     27592 weight    0.10000E◆01 volume   0.61111E◆02 ppm1  1.646    ppm2 1.321
OR      {27592}
        {{ segid "BrD" and resid 110 and name HG12}}
        {{ segid "BrD" and resid 78 and name HB1    }}
OR      {27592}
        {  segid "BrD" and resid 22 and name HD14  }
        {  segid "BrD" and resid 102 and name HD24 }
OR      {27592}
        {{ segid "BrD" and resid 110 and name HG12 }}
        {  segid "BrD" and resid 102 and name HD24 }
ASSI    {27622}
        {  segid "BrD" and resid 73 and name HD24}
        {{ segid "BrD" and resid 74 and name HA   }}
          3.000  2.200  2.200 peak     27622 weight    0.10000E◆01 volume   0.10007E◆03 ppm1  1.500    ppm2 4.362
OR      {27622}
        {  segid "BrD" and resid 73 and name HD24}
        {{ segid "BrD" and resid 70 and name HB2  }}
ASSI    {27832}
        {{ segid "BrD" and resid 78 and name HA }}
        {{ segid "BrD" and resid 82 and name HZ }}
          3.500  3.100  3.000 peak     27832 weight    0.10000E◆01 volume   0.44344E◆02 ppm1  3.966    ppm2 7.023
```

TABLE 3-continued

Ambiguous NOE-derived Inter-proton Distance Restraints

```
OR      {27832}
        {{ segid "BrD" and resid 78 and name HA   }}
        {  segid "BrD" and resid 74 and name HD4}
ASSI    {27852}
        {{ segid "BrD" and resid 78 and name HB2  }}
        {{ segid "BrD" and resid 116 and name HG12}}
           4.700  4.700  0.800 peak    27852 weight   0.10000E+01 volume  0.74355E+01 ppm1  1.056    ppm2  1.531
OR      {27852}
        {{ segid "BrD" and resid 78 and name HB2  }}
        {  segid "BrD" and resid 56 and name HD14}
ASSI    {27862}
        {{ segid "BrD" and resid 78 and name HB2  }}
        {{ segid "BrD" and resid 110 and name HG12}}
           3.700  3.400  1.800 peak    27862 weight   0.10000E+01 volume  0.33112E+02 ppm1  1.054    ppm2  1.629
OR      {27862}
        {{ segid "BrD" and resid 78 and name HB2  }}
        {  segid "BrD" and resid 21 and name HG24}}
OR      {27862}
        {{ segid "BrD" and resid 78 and name HB2  }}
        {  segid "BrD" and resid 22 and name HD24}
OR      {27862}
        {{ segid "BrD" and resid 78 and name HB2  }}
        {{ segid "BrD" and resid 21 and name HG12}}
ASSI    {27962}
        {  segid "BrD" and resid 78 and name HD14}
        {  segid "BrD" and resid 74 and name HD4  }
           2.200  2.200  2.300 peak    27962 weight   0.10000E+01 volume  0.80433E+03 ppm1  0.761    ppm2  7.031
OR      {27962}
        {  segid "BrD" and resid 78 and name HD14}
        {  segid "BrD" and resid 82 and name HE4  }
ASSI    {28022}
        {  segid "BrD" and resid 78 and name HD24}
        {{ segid "BrD" and resid 22 and name HA   }}
           3.100  2.400  2.400 peak    28022 weight   0.10000E+01 volume  0.92248E+02 ppm1  0.662    ppm2  4.727
OR      {28022}
        {  segid "BrD" and resid 78 and name HD24}
        {{ segid "BrD" and resid 82 and name HA   }}
ASSI    {28042}
        {  segid "BrD" and resid 78 and name HD24}
        {{ segid "BrD" and resid 56 and name HA   }}
           3.600  3.200  1.900 peak    28042 weight   0.10000E+01 volume  0.33967E+02 ppm1  0.662    ppm2  4.631
OR      {28042}
        {  segid "BrD" and resid 78 and name HD24}
        {{ segid "BrD" and resid 76 and name HA   }}
OR      {28042}
        {  segid "BrD" and resid 78 and name HD24}
        {{ segid "BrD" and resid 80 and name HA   }}
OR      {28042}
        {  segid "BrD" and resid 78 and name HD24}
        {{ segid "BrD" and resid 104 and name HA  }}
OR      {28042}
        {  segid "BrD" and resid 78 and name HD24}
        {{ segid "BrD" and resid 20 and name HB1  }}
OR      {28042}
        {{ segid "BrD" and resid 78 and name HD24}}
        {{ segid "BrD" and resid 109 and name HA  }}
OR      {28042}
        {  segid "BrD" and resid 78 and name HD24}
        {{ segid "BrD" and resid 14 and name HA   }}
OR      {28042}
        {  segid "BrD" and resid 78 and name HD24}
        {{ segid "BrD" and resid 71 and name HA   }}
OR      {28042}
        {  segid "BrD" and resid 78 and name HD24}
        {{ segid "BrD" and resid 15 and name HA   }}
ASSI    {28052}
        {  segid "BrD" and resid 78 and name HD14}
        {{ segid "BrD" and resid 56 and name HA   }}
           3.800  3.600  1.700 peak    28052 weight   0.10000E+01 volume  0.28600E+02 ppm1  0.761    ppm2  4.631
OR      {28052}
        {  segid "BrD" and resid 78 and name HD14}
        {{ segid "BrD" and resid 76 and name HA   }}
OR      {28052}
        {  segid "BrD" and resid 78 and name HD14}
        {{ segid "BrD" and resid 80 and name HA   }}
OR      {28052}
        {  segid "BrD" and resid 78 and name HD14}
        {{ segid "BrD" and resid 60 and name HB2  }}
```

TABLE 3-continued

Ambiguous NOE-derived Inter-proton Distance Restraints

```
ASSI  {28072}
      {  segid "BrD" and resid 78 and name HD14}
      {{ segid "BrD" and resid 79 and name HA    }}
         3.400  2.900  2.100 peak    28072 weight   0.10000E+01 volume  0.48389E+02 ppm1  0.761  ppm2  4.428
OR    {28072}
      {  segid "BrD" and resid 78 and name HD14}
      {{ segid "BrD" and resid 25 and name HA   }}
OR    {28072}
      {  segid "BrD" and resid 78 and name HD14}
      {{ segid "BrD" and resid 107 and name HA  }}
OR    {28072}
      {  segid "BrD" and resid 78 and name HD14}
      {{ segid "BrD" and resid 99 and name HA   }}
ASSI  {28082}
      {  segid "BrD" and resid 78 and name HD24}
      {{ segid "BrD" and resid 106 and name HA  }}
         3.000  2.200  2.200 peak    28082 weight   0.10000E+01 volume  0.10774E+03 ppm1  0.662  ppm2  4.529
OR    {28082}
      {  segid "BrD" and resid 78 and name HD24}
      {{ segid "BrD" and resid 75 and name HA   }}
ASSI  {28092}
      {  segid "BrD" and resid 78 and name HD24}
      {{ segid "BrD" and resid 79 and name HA   }}
         2.900  2.100  2.100 peak    28092 weight   0.10000E+01 volume  0.12398E+03 ppm1  0.662  ppm2  4.427
OR    {28092}
      {  segid "BrD" and resid 78 and name HD24}
      {{ segid "BrD" and resid 107 and name HA  }}
ASSI  {28112}
      {  segid "BrD" and resid 78 and name HD14 }
      {{ segid "BrD" and resid 106 and name HB2 }}
         3.200  2.600  2.300 peak    28112 weight   0.10000E+01 volume  0.76864E+02 ppm1  0.760  ppm2  3.711
OR    {28112}
      {  segid "BrD" and resid 78 and name HD14}
      {{ segid "BrD" and resid 81 and name HA   }}
ASSI  {28142}
      {  segid "BrD" and resid 78 and name HD24}
      {{ segid "BrD" and resid 25 and name HB   }}
         3.900  3.800  1.600 peak    28142 weight   0.10000E+01 volume  0.22598E+02 ppm1  0.662  ppm2  3.005
OR    {28142}
      {  segid "BrD" and resid 78 and name HD24}
      {{ segid "BrD" and resid 79 and name HG1  }}
OR    {28142}
      {  segid "BrD" and resid 78 and name HD24}
      {{ segid "BrD" and resid 74 and name HB2  }}
ASSI  {28152}
      {  segid "BrD" and resid 78 and name HD24 }
      {{ segid "BrD" and resid 21 and name HG11 }}
         3.600  3.200  1.900 peak    28152 weight   0.10000E+01 volume  0.38156E+02 ppm1  0.662  ppm2  2.347
OR    {28152}
      {  segid "BrD" and resid 78 and name HD24}
      {{ segid "BrD" and resid 56 and name HG   }}
OR    {28152}
      {  segid "BrD" and resid 78 and name HD24}
      {{ segid "BrD" and resid 22 and name HG   }}
ASSI  {28162}
      {  segid "BrD" and resid 78 and name HD24}}
      {  segid "BrD" and resid 75 and name HE4  }}
         4.300  4.300  1.200 peak    28162 weight   0.10000E+01 volume  0.12997E+02 ppm1  0.662  ppm2  2.670
OR    {28162}
      {  segid "BrD" and resid 78 and name HD24}
      {{ segid "BrD" and resid 79 and name HB2  }}
OR    {28162}
      {  segid "BrD" and resid 78 and name HD24}
      {{ segid "BrD" and resid 22 and name HB1  }}
ASSI  {28172}
      {  segid "BrD" and resid 78 and name HD14}
      {{ segid "BrD" and resid 74 and name HB2  }}
         3.800  3.600  1.700 peak    28172 weight   0.10000E+01 volume  0.27394E+02 ppm1  0.760  ppm2  3.003
OR    {28172}
      {  segid "BrD" and resid 78 and name HD14}}
      {{ segid "BrD" and resid 25 and name HB   }}
ASSI  {28302}
      {  segid "BrD" and resid 56 and name HD24}
      {{ segid "BrD" and resid 35 and name HA   }}
         2.600  1.700  1.700 peak    28302 weight   0.10000E+01 volume  0.27298E+03 ppm1  1.254  ppm2  4.907
OR    {28302}
      {  segid "BrD" and resid 56 and name HD24}
      {{ segid "BrD" and resid 59 and name HA   }}
```

TABLE 3-continued

Ambiguous NOE-derived Inter-proton Distance Restraints

```
ASSI    {28332}
        {   segid "BrD" and resid 56 and name HD24}
        {{  segid "BrD" and resid 25 and name HA    }}
            5.000  5.000  0.500 peak     28332 weight    0.10000E+01 volume   0.51532E+01 ppm1  1.253    ppm2  4.441
OR      {28332}
        {   segid "BrD" and resid 56 and name HD24}
        {{  segid "BrD" and resid 58 and name HA    }}
ASSI    {28482}
        {{  segid "BrD" and resid 86 and name HB2   }}
        {   segid "BrD" and resid 81 and name HG24}
            3.700  3.400  1.800 peak     28482 weight    0.10000E+01 volume   0.33282E+02 ppm1  1.993    ppm2  0.766
OR      {28482}
        {{  segid "BrD" and resid 102 and name HB1}}
        {   segid "BrD" and resid 81 and name HG24}
ASSI    {28552}
        {{  segid "BrD" and resid 102 and name HG}}
        {{  segid "BrD" and resid 25 and name HA    }}
            4.000  4.000  1.500 peak     28552 weight    0.10000E+01 volume   0.18876E+02 ppm1  2.141    ppm2  4.445
OR      {28552}
        {{  segid "BrD" and resid 102 and name HN}}
        {{  segid "BrD" and resid 99 and name HA    }}
OR      {28552}
        {{  segid "BrD" and resid 97 and name HG2}}
        {{  segid "BrD" and resid 96 and name HA    }}
ASSI    {28592}
        {   segid "BrD" and resid 102 and name HD24}
        {{  segid "BrD" and resid 34 and name HZ    }}
            3.700  3.400  1.800 peak     28592 weight    0.10000E+01 volume   0.30371E+02 ppm1  1.303    ppm2  7.899
OR      {28592}
        {   segid "BrD" and resid 102 and name HD24}
        {   segid "BrD" and resid 107 and name HE4  }
ASSI    {28602}
        {   segid "BrD" and resid 102 and name HD24}
        {   segid "BrD" and resid 34 and name HE4   }
            2.000  2.000  2.500 peak     28602 weight    0.10000E+01 volume   0.10851E+04 ppm1  1.303    ppm2  7.771
OR      {28602}
        {   segid "BrD" and resid 102 and name HD24}
        {   segid "BrD" and resid 105 and name HD4  }
ASSI    {28682}
        {   segid "BrD" and resid 102 and name HD14}
        {{  segid "BrD" and resid 28 and name HA    }}
            4.000  4.000  1.500 peak     28682 weight    0.10000E+01 volume   0.20825E+02 ppm1  1.303    ppm2  4.581
OR      {28682}
        {   segid "BrD" and resid 102 and name HD14}
        {{  segid "BrD" and resid 106 and name HA   }}
ASSI    {28692}
        {   segid "BrD" and resid 102 and name HD14}
        {{  segid "BrD" and resid 30 and name HB2   }}
            2.700  1.800  1.800 peak     28692 weight    0.10000E+01 volume   0.20830E+03 ppm1  1.303    ppm2  4.526
OR      {28692}
        {   segid "BrD" and resid 102 and name HD14}
        {{  segid "BrD" and resid 28 and name HA    }}
ASSI    {28772}
        {   segid "BrD" and resid 102 and name HD24}
        {   segid "BrD" and resid 78 and name HD14  }
            3.500  3.100  2.000 peak     28772 weight    0.10000E+01 volume   0.44195E+02 ppm1  1.304    ppm2  0.760
OR      {28772}
        {   segid "BrD" and resid 102 and name HD24}
        {   segid "BrD" and resid 81 and name HG24  }
ASSI    {28862}
        {{  segid "BrD" and resid 115 and name HB1  }}
        {{  segid "BrD" and resid 110 and name HG11}}
            3.300  2.700  2.200 peak     28862 weight    0.10000E+01 volume   0.61541E+02 ppm1  2.190    ppm2  1.742
OR      {28862}
        {{  segid "BrD" and resid 115 and name HB1}}
        {   segid "BrD" and resid 17 and name HG24}
ASSI    {28952}
        {   segid "BrD" and resid 56 and name HD14}
        {{  segid "BrD" and resid 31 and name HA    }}
            3.100  2.400  2.400 peak     28952 weight    0.10000E+01 volume   0.92579E+02 ppm1  1.548    ppm2  4.984
OR      {28952}
        {   segid "BrD" and resid 56 and name HD14}
        {   segid "BrD" and resid 60 and name HB1   }
ASSI    {29002}
        {   segid "BrD" and resid 59 and name HE4   }
        {   segid "BrD" and resid 76 and name HB4   }
            3.500  3.100  2.00 peak      29002 weight    0.10000E+01 volume   0.43704E+02 ppm1  1.848    ppm2  2.108
```

TABLE 3-continued

Ambiguous NOE-derived Inter-proton Distance Restraints

```
OR      {29002}
        { segid "BrD" and resid 59 and name HE4}
        {{ segid "BrD" and resid 18 and name HB1}}
OR      {29002}
        { segid "BrD" and resid 59 and name HE4}
        {{ segid "BrD" and resid 102 and name HG }}
ASSI    {29022}
        { segid "BrD" and resid 59 and name HE4}
        {{ segid "BrD" and resid 22 and name HB2}}
         3.400  2.900  2.100 peak    29022 weight   0.10000E+01 volume   0.52140E+02 ppm1  1.848    ppm2  2.292
OR      {29022}
        { segid "BrD" and resid 59 and name HE4}
        {{ segid "BrD" and resid 18 and name HG }}
OR      {29022}
        { segid "BrD" and resid 59 and name HE4 }
        { segid "BrD" and resid 31 and name HB4 }
ASSI    {29032}
        { segid "BrD" and resid 59 and name HE4}
        {{ segid "BrD" and resid 56 and name HG }}
         3.700  3.400  1.800 peak    29032 weight   0.10000E+01 volume   0.29631E+02 ppm1  1.848    ppm2  2.361
OR      {29032}
        { segid "BrD" and resid 59 and name HE4}
        {{ segid "BrD" and resid 22 and name HG }}
OR      {29032}
        { segid "BrD" and resid 59 and name HE4}
        {{ segid "BrD" and resid 73 and name HG }}
OR      {29032}
        { segid "BrD" and resid 59 and name HE4 }
        {{ segid "BrD" and resid 21 and name HG11}}
ASSI    {29072}
        { segid "BrD" and resid 59 and name HE4}
        {{ segid "BrD" and resid 22 and name HA }}
         4.200  4.200  1.300 peak    29072 weight   0.10000E+01 volume   0.14615E+02 ppm1  1.848    ppm2  4.719
OR      {29072}
        { segid "BrD" and resid 59 and name HE4}
        {{ segid "BrD" and resid 58 and name HB }}
OR      {29072}
        { segid "BrD" and resid 59 and name HE4}
        {{ segid "BrD" and resid 69 and name HA }}
OR      {29072}
        { segid "BrD" and resid 59 and name HE4}
        {{ segid "BrD" and resid 53 and name HA }}
ASSI    {29152}
        { segid "BrD" and resid 59 and name HE4 }
        { segid "BrD" and resid 73 and name HD24}
         3.600  3.200  1.900 peak    29152 weight   0.10000E+01 volume   0.38252E+02 ppm1  1.848    ppm2  1.462
OR      {29152}
        { segid "BrD" and resid 59 and name HE4 }
        { segid "BrD" and resid 63 and name HD24}
OR      {29152}
        { segid "BrD" and resid 59 and name HE4}
        {{ segid "BrD" and resid 62 and name HG2}}
ASSI    {29192}
        { segid "BrD" and resid 54 and name HE4}
        {{ segid "BrD" and resid 60 and name HB1}}
         3.200  2.600  2.300 peak    29192 weight   0.10000E+01 volume   0.76364E+02 ppm1  2.536    ppm2  4.964
OR      {29192}
        { segid "BrD" and resid 54 and name HE4}
        {{ segid "BrD" and resid 77 and name HA }}
ASSI    {29202}
        { segid "BrD" and resid 54 and name HE4}
        {{ segid "BrD" and resid 55 and name HB1}}
         3.700  3.400  1.800 peak    29202 weight   0.10000E+01 volume   0.30281E+02 ppm1  2.535    ppm2  2.955
OR      {29202}
        { segid "BrD" and resid 54 and name HE4}
        {{ segid "BrD" and resid 37 and name HB1}}
ASSI    {29252}
        { segid "BrD" and resid 54 and name HE4 }
        { segid "BrD" and resid 35 and name HE4 }
         2.500  2.500  2.000 peak    29252 weight   0.10000E+01 volume   0.29954E+03 ppm1  2.535    ppm2  2.801
OR      {29252}
        { segid "BrD" and resid 54 and name HE4}
        {{ segid "BrD" and resid 53 and name HB1}}
OR      {29252}
        { segid "BrD" and resid 54 and name HE4}
        {{ segid "BrD" and resid 61 and name HG2}}
```

TABLE 3-continued

Ambiguous NOE-derived Inter-proton Distance Restraints

```
OR      {29252}
        {  segid "BrD" and resid 54 and name HE4}
        {{ segid "BrD" and resid 36 and name HG1}}
ASSI    {29262}
        {  segid "BrD" and resid 54 and name HE4}
        {{ segid "BrD" and resid 37 and name HG1}}
           2.600  1.700  1.700 peak    29262 weight   0.10000E♦01 volume   0.23100E♦03 ppm1  2.535    ppm2  2.722
OR      {29262}
        {  segid "BrD" and resid 54 and name HE4}
        {{ segid "BrD" and resid 59 and name HB1}}
ASSI    {29582}
        {{ segid "BrD" and resid 79 and name HA   }}
        {{ segid "BrD" and resid 116 and name HG11}}
           4.100  4.100  1.400 peak    29582 weight   0.10000E♦01 volume   0.16991E♦02 ppm1  4.409    ppm2  1.897
OR      {29582}
        {{ segid "BrD" and resid 79 and name HA   }}
        {{ segid "BrD" and resid 103 and name HB2}}
ASSI    {29682}
        {{ segid "BrD" and resid 108 and name HA  }}
        {{ segid "BrD" and resid 111 and name HG1}}
           4.100  4.100  1.400 peak    29682 weight   0.10000E♦01 volume   0.16470E♦02 ppm1  4.804    ppm2  2.003
OR      {29682}
        {{ segid "BrD" and resid 108 and name HA  }}
        {{ segid "BrD" and resid 109 and name HD1}}
ASSI    {29702}
        {{ segid "BrD" and resid 15 and name HA  }}
        {{ segid "BrD" and resid 19 and name HB2}}
           2.800  2.000  2.000 peak    29702 weight   0.10000E♦01 volume   0.16053E♦03 ppm1  4.607    ppm2  1.986
OR      {29702}
        {{ segid "BrD" and resid 108 and name HB1}}
        {{ segid "BrD" and resid 109 and name HD1}}
OR      {29702}
        {{ segid "BrD" and resid 60 and name HB2 }}
        {{ segid "BrD" and resid 56 and name HB2 }}
ASSI    {29712}
        {{ segid "BrD" and resid 15 and name HA  }}
        {{ segid "BrD" and resid 18 and name HB1}}
           3.100  2.400  2.400 peak    29712 weight   0.10000E♦01 volume   0.92305E♦02 ppm1  4.807    ppm2  2.182
OR      {29712}
        {{ segid "BrD" and resid 60 and name HB2 }}
        {{ segid "BrD" and resid 64 and name HG1 }}
ASSI    {29722}
        {{ segid "BrD" and resid 15 and name HA   }}
        {  segid "BrD" and resid 14 and name HD24}
           3.900  3.800  1.600 peak    29722 weight   0.10000E♦01 volume   0.22638E♦02 ppm1  4.607    ppm2  1.417
OR      {29722}
        {{ segid "BrD" and resid 15 and name HA   }}
        {  segid "BrD" and resid 69 and name HG24}
ASSI    {29732}
        {{ segid "BrD" and resid 30 and name HA }}
        {{ segid "BrD" and resid 98 and name HA }}
           2.600  1.700  1.700 peak    29732 weight   0.10000E♦01 volume   0.26724E♦03 ppm1  5.445    ppm2  4.810
OR      {29732}
        {{ segid "BrD" and resid 30 and name HA }}
        {{ segid "BrD" and resid 29 and name HA }}
ASSI    {30592}
        {{ segid "BrD" and resid 109 and name HB1}}
        {  segid "BrD" and resid 21 and name HD14}
           3.700  3.400  1.800 peak    30592 weight   0.10000E♦01 volume   0.31262E♦02 ppm1  2.334    ppm2  1.222
OR      {30592}
        {{ segid "BrD" and resid 109 and name HB1 }}
        {  segid "BrD" and resid 110 and name HG24}
ASSI    {30672}
        {{ segid "BrD" and resid 109 and name HB2}}
        {{ segid "BrD" and resid 110 and name HA }}
           3.600  3.200  1.900 peak    30672 weight   0.10000E♦01 volume   0.39278E♦02 ppm1  2.141    ppm2  4.378
OR      {30672}
        {{ segid "BrD" and resid 109 and name HB2}}
        {{ segid "BrD" and resid 107 and name HA }}
ASSI    {30952}
        {{ segid "BrD" and resid 75 and name HA }}
        {{ segid "BrD" and resid 78 and name HG }}
           3.800  3.600  1.700 peak    30952 weight   0.10000E♦01 volume   0.28077E♦02 ppm1  4.509    ppm2  1.260
OR      {30952}
        {{ segid "BrD" and resid 26 and name HA   }}
        {  segid "BrD" and resid 56 and name HD24}
```

TABLE 3-continued

Ambiguous NOE-derived Inter-proton Distance Restraints

```
ASSI    {83}
        {   segid "BrD" and resid 46 and name HD4}
        {{  segid "BrD" and resid 47 and name HA  }}
            2.300  2.300  2.200 peak     83 weight   0.10000E+01 volume  0.20163E+03 ppm1  5.758    ppm2  4.692
OR      {83}
        {   segid "BrD" and resid 46 and name HD4}
        {{  segid "BrD" and resid 53 and name HA  }}
ASSI    {533}
        {   segid "BrD" and resid 47 and name HE4}
        {{  segid "BrD" and resid 35 and name HB  }}
            3.200  2.600  2.300 peak    533 weight   0.10000E+01 volume  0.34245E+02 ppm1  7.246    ppm2  1.776
OR      {533}
        {   segid "BrD" and resid 47 and name HE4}
        {{  segid "BrD" and resid 50 and name HB  }}
ASSI    {643}
        {   segid "BrD" and resid 74 and name HD4}
        {{  segid "BrD" and resid 71 and name HA  }}
            3.100  2.400  2.400 peak    643 weight   0.10000E+01 volume  0.35394E+02 ppm1  7.012    ppm2  4.622
OR      {643}
        {   segid "BrD" and resid 74 and name HD4}
        {{  segid "BrD" and resid 15 and name HA  }}
OR      {643}
        {   segid "BrD" and resid 74 and name HD4}
        {{  segid "BrD" and resid 76 and name HA  }}
OR      {643}
        {   segid "BrD" and resid 74 and name HD4}
        {{  segid "BrD" and resid 56 and name HA  }}
OR      {643}
        {   segid "BrD" and resid 74 and name HD4}
        {{  segid "BrD" and resid 72 and name HA  }}
OR      {643}
        {   segid "BrD" and resid 74 and name HD4}
        {{  segid "BrD" and resid 14 and name HA  }}
ASSI    {1142}
        {   segid "BrD" and resid 105 and name HD4 }
        {   segid "BrD" and resid 101 and name HG24}
            3.100  2.400  2.400 peak   1143 weight   0.10000E+01 volume  0.36890E+02 ppm1  7.758    ppm2  1.631
OR      {1143}
        {   segid "BrD" and resid 105 and name HD4 }
        {   segid "BrD" and resid 21 and name HG24 }
ASSI    {1393}
        {   segid "BrD" and resid 96 and name HD4}
        {{  segid "BrD" and resid 86 and name HA  }}
            2.200  2.200  2.300 peak   1393 weight   0.10000E+01 volume  0.26898E+03 ppm1  7.711    ppm2  4.810
OR      {1392}
        {   segid "BrD" and resid 96 and name HD4}
        {{  segid "BrD" and resid 93 and name HA  }}
ASSI    {1763}
        {   segid "BrD" and resid 106 and name HE4}
        {{  segid "BrD" and resid 107 and name HA  }}
            3.400  2.900  2.100 peak   1763 weight   0.10000E+01 volume  0.21871E+02 ppm1  7.617    ppm2  4.431
OR      {1763}
        {   segid "BrD" and resid 106 and name HE4}
        {{  segid "BrD" and resid 79 and name HA   }}
OR      {1763}
        {   segid "BrD" and resid 106 and name HE4}
        {{  segid "BrD" and resid 110 and name HA  }}
ASSI    {1783}
        {   segid "BrD" and resid 106 and name HE4}
        {   segid "BrD" and resid 74 and name HD4 }
            3.700  3.400  1.800 peak   1783 weight   0.10000E+01 volume  0.13672E+02 ppm1  7.617    ppm2  7.027
OR      {1783}
        {   segid "BrD" and resid 106 and name HE4}
        {   segid "BrD" and resid 82 and name HE4  }
OR      {1783}
        {   segid "BrD" and resid 106 and name HE4}
        {{  segid "BrD" and resid 82 and name HZ   }}
ASSI    {1813}
        {   segid "BrD" and resid 95 and name HD4}
        {{  segid "BrD" and resid 94 and name HA  }}
            3.300  2.700  2.200 peak   1813 weight   0.10000E+01 volume  0.28141E+02 ppm1  7.678    ppm2  4.810
OR      {1813}
        {   segid "BrD" and resid 95 and name HD4}
        {{  segid "BrD" and resid 86 and name HA  }}
ASSI    {1893}
        {   segid "BrD" and resid 96 and name HE4}
        {{  segid "BrD" and resid 96 and name HA  }}
            3.600  3.200  1.900 peak   1893 weight   0.10000E+01 volume  0.14793E+03 ppm1  7.618    ppm2  4.387
```

TABLE 3-continued

Ambiguous NOE-derived Inter-proton Distance Restraints

```
OR     {1893}
       {  segid "BrD" and resid 95 and name HE4}
       {{ segid "BrD" and resid 33 and name HA  }}
ASSI   {2063}
       {{ segid "BrD" and resid 32 and name HZ3}}
       {{ segid "BrD" and resid 32 and name HA  }}
         5.500  5.500  0.000 peak     2063 weight    0.10000E+01 volume  0.11153E-03 ppm1  7.804    ppm2  4.971
OR     {2063}
       {{ segid "BrD" and resid 32 and name HZ3}}
       {{ segid "BrD" and resid 93 and name HB1}}
OR     {2063}
       {{ segid "BrD" and resid 32 and name HZ3}}
       {{ segid "BrD" and resid 85 and name HA  }}
ASSI   {24}
       {  segid "BrD" and resid 46 and name HE4}
       {{ segid "BrD" and resid 50 and name HB  }}
         3.600  3.200  1.900 peak      124 weight    0.10000E+01 volume  0.55296E+02 ppm1  6.687    ppm2  1.777
OR     {24}
       {  segid "BrD" and resid 46 and name HE4}
       {{ segid "BrD" and resid 38 and name HB  }}
ASSI   {94}
       {  segid "BrD" and resid 82 and name HD4}}
       {{ segid "BrD" and resid 79 and name HA  }}
         2.200  1.200  1.200 peak       94 weight    0.10000E+01 volume  0.10359E+04 ppm1  7.266    ppm2  4.424
OR     {94}
       {  segid "BrD" and resid 85 and name HD4}
       {{ segid "BrD" and resid 99 and name HA  }}
ASSI   {104}
       {  segid "BrD" and resid 47 and name HE4}
       {{ segid "BrD" and resid 53 and name HG2}}
         2.500  1.600  1.600 peak      104 weight    0.10000E+01 volume  0.51584E+03 ppm1  7.270    ppm2  2.504
OR     {104}
       {  segid "BrD" and resid 82 and name HD4  }
       {{ segid "BrD" and resid 103 and name HG2}}
ASSI   {124}
       {  segid "BrD" and resid 47 and name HD4  }}
       {{ segid "BrD" and resid 50 and name HG12}}
         3.600  3.200  1.900 peak      124 weight    0.10000E+01 volume  0.55730E+02 ppm1  7.970    ppm2  0.780
OR     {124}
       {  segid "BrD" and resid 47 and name HD4  }
       {  segid "BrD" and resid 38 and name HG24}
ASSI   {134}
       {  segid "BrD" and resid 47 and name HD4}
       {{ segid "BrD" and resid 83 and name HD2}}
         2.900  2.100  2.300 peak      134 weight    0.10000E+01 volume  0.18431E+03 ppm1  7.970    ppm2  4.007
OR     {134}
       {{ segid "BrD" and resid 32 and name HZ2}}
       {{ segid "BrD" and resid 98 and name HB1}}
ASSI   {554}
       {{ segid "BrD" and resid 28 and name HE1}}
       {{ segid "BrD" and resid 30 and name HB2}}
         2.900  2.100  2.100 peak      554 weight    0.10000E+01 volume  0.21924E+03 ppm1  8.154    ppm2  4.538
OR     {554}
       {{ segid "BrD" and resid 28 and name HE1}}
       {{ segid "BrD" and resid 28 and name HA  }}
ASSI   {574}
       {  segid "BrD" and resid 68 and name HE4}
       {{ segid "BrD" and resid 59 and name HA  }}
         3.200  2.600  2.300 peak      574 weight    0.10000E+01 volume  0.10500E+03 ppm1  7.921    ppm2  4.930
OR     {574}
       {{ segid "BrD" and resid 32 and name HE3}}
       {{ segid "BrD" and resid 32 and name HA  }}
ASSI   {604}
       {{ segid "BrD" and resid 107 and name HZ}}
       {{ segid "BrD" and resid 83 and name HB  }}
         3.500  3.100  2.000 peak      604 weight    0.10000E+01 volume  0.65660E+02 ppm1  8.063    ppm2  4.784
OR     {604}
       {{ segid "BrD" and resid 107 and name HZ}}
       {{ segid "BrD" and resid 82 and name HA  }}
ASSI   {614}
       {{ segid "BrD" and resid 107 and name HZ}}
       {{ segid "BrD" and resid 80 and name HA  }}
         3.300  2.700  2.200 peak      614 weight    0.10000E+01 volume  0.96219E+02 ppm1  8.062    ppm2  4.673
OR     {614}
       {{ segid "BrD" and resid 107 and name HZ}}
       {{ segid "BrD" and resid 118 and name HA}}
```

TABLE 3-continued

Ambiguous NOE-derived Inter-proton Distance Restraints

| | | | | | | | | | | | | |
|---|---|---|---|---|---|---|---|---|---|---|---|---|
| OR | {614} |
| | {{ segid "BrD" and resid 107 and name HZ}} |
| | {{ segid "BrD" and resid 76 and name HA }} |
| ASSI | {704} |
| | {{ segid "BrD" and resid 107 and name HZ }} |
| | {{ segid "BrD" and resid 79 and name HB1 }} |
| | 2.800 2.000 2.000 peak 704 weight 0.10000E+01 volume 0.25291E+03 ppm1 8.009 ppm2 2.758 |
| OR | {704} |
| | {{ segid "BrD" and resid 32 and name HZ2}} |
| | {{ segid "BrD" and resid 94 and name HB1}} |
| ASSI | {794} |
| | {{ segid "BrD" and resid 32 and name HE3}} |
| | {{ segid "BrD" and resid 32 and name HB2}} |
| | 2.600 1.700 1.700 peak 794 weight 0.10000E+01 volume 0.29954E+03 ppm1 7.960 ppm2 4.212 |
| OR | {794} |
| | { segid "BrD" and resid 47 and name HD4} |
| | {{ segid "BrD" and resid 53 and name HD1}} |
| ASSI | {964} |
| | {{ segid "BrD" and resid 34 and name HZ }} |
| | {{ segid "BrD" and resid 28 and name HD2}} |
| | 4.200 4.200 1.300 peak 964 weight 0.10000E+01 volume 0.22395E+02 ppm1 7.928 ppm2 5.579 |
| OR | {964} |
| | {{ segid "BrD" and resid 34 and name HZ}} |
| | {{ segid "BrD" and resid 34 and name HA}} |
| ASSI | {974} |
| | {{ segid "BrD" and resid 34 and name HZ}} |
| | {{ segid "BrD" and resid 98 and name HA}} |
| | 3.800 3.600 1.700 peak 974 weight 0.10000E+01 volume 0.41681E+02 ppm1 7.929 ppm2 4.791 |
| OR | {974} |
| | {{ segid "BrD" and resid 34 and name HZ}} |
| | {{ segid "BrD" and resid 82 and name HA}} |
| ASSI | {1044} |
| | { segid "BrD" and resid 107 and name HE4}} |
| | {{ segid "BrD" and resid 79 and name HA }} |
| | 2.300 1.300 1.300 peak 1044 weight 0.10000E+01 volume 0.88364E+03 ppm1 7.921 ppm2 4.440 |
| OR | {1044} |
| | {{ segid "BrD" and resid 34 and name HZ}} |
| | {{ segid "BrD" and resid 99 and name HA}} |
| ASSI | {1074} |
| | {{ segid "BrD" and resid 34 and name HZ }} |
| | { segid "BrD" and resid 102 and name HD14} |
| | 2.900 2.100 2.100 peak 1074 weight 0.10000E+01 volume 0.20962E+03 ppm1 7.924 ppm2 1.333 |
| OR | {1074} |
| | { segid "BrD" and resid 107 and name HE4} |
| | {{ segid "BrD" and resid 78 and name HB1 }} |
| ASSI | {1084} |
| | {{ segid "BrD" and resid 34 and name HZ}} |
| | {{ segid "BrD" and resid 98 and name HA}} |
| | 4.000 4.000 1.500 peak 1084 weight 0.10000E+01 volume 0.28521E+02 ppm1 7.913 ppm2 4.791 |
| OR | {1084} |
| | {{ segid "BrD" and resid 34 and name HZ}} |
| | {{ segid "BrD" and resid 82 and name HA}} |
| OR | {1084} |
| | { segid "BrD" and resid 68 and name HE4} |
| | {{ segid "BrD" and resid 73 and name HA }} |
| ASSI | {1094} |
| | { segid "BrD" and resid 107 and name HE4} |
| | {{ segid "BrD" and resid 118 and name HA }} |
| | 3.200 2.600 2.300 peak 1094 weight 0.10000E+01 volume 0.10760E+03 ppm1 7.918 ppm2 4.683 |
| OR | {1094} |
| | { segid "BrD" and resid 107 and name HE4} |
| | {{ segid "BrD" and resid 76 and name HA }} |
| OR | {1094} |
| | { segid "BrD" and resid 68 and name HE4} |
| | {{ segid "BrD" and resid 58 and name HB }} |
| OR | {1094} |
| | { segid "BrD" and resid 68 and name HE4} |
| | {{ segid "BrD" and resid 67 and name HA }} |
| OR | {1094} |
| | { segid "BrD" and resid 107 and name HE4} |
| | {{ segid "BrD" and resid 104 and name HA }} |
| OR | {1094} |
| | { segid "BrD" and resid 107 and name HE4} |
| | {{ segid "BrD" and resid 80 and name HA }} |
| OR | {1094} |
| | { segid "BrD" and resid 68 and name HZ4}} |
| | {{ segid "BrD" and resid 69 and name HA }} |

TABLE 3-continued

Ambiguous NOE-derived Inter-proton Distance Restraints

```
ASSI  {1104}
      {{ segid "BrD" and resid 34 and name HZ  }}
      {  segid "BrD" and resid 99 and name HB4}}
       2.400  1.400  1.400 peak    1104 weight   0.10000E♦01 volume  0.63603E♦03 ppm1  7.907   ppm2  2.212
OR    {1104}
      {{ segid "BrD" and resid 34 and name HZ  }}
      {{ segid "BrD" and resid 33 and name HD2}}
ASSI  {1114}
      { segid "BrD" and resid 68 and name HE4 }
      { segid "BrD" and resid 68 and name HD4 }
       2.100  1.300  1.100 peak    1114 weight   0.10000E♦01 volume  0.15242E♦04 ppm1  7.904   ppm2  7.776
OR    {1114}
      { segid "BrD" and resid 107 and name HE4 }
      { segid "BrD" and resid 107 and name HD4 }
OR    {1114}
      {{ segid "BrD" and resid 34 and name HZ  }}
      {  segid "BrD" and resid 34 and name HE4}
ASSI  {1124}
      {{ segid "BrD" and resid 34 and name HZ  }}
      {{ segid "BrD" and resid 98 and name HB2}}
       2.500  1.600  1.600 peak    1124 weight   0.10000E♦01 volume  0.54441E♦03 ppm1  7.898   ppm2  3.659
OR    {1124}
      {  segid "BrD" and resid 107 and name HE4}
      {{ segid "BrD" and resid 82 and name HB1  }}
OR    {1124}
      {  segid "BrD" and resid 68 and name HE4}
      {{ segid "BrD" and resid 68 and name HB1}}
ASSI  {1134}
      {  segid "BrD" and resid 68 and name HE4}
      {{ segid "BrD" and resid 62 and name HG1}}
       3.600  3.200  1.900 peak    1134 weight   0.10000E♦01 volume  0.60159E♦02 ppm1  7.900   ppm2  2.343
OR    {1134}
      {  segid "BrD" and resid 68 and name HE4}
      {{ segid "BrD" and resid 73 and name HG  }}
ASSI  {1164}
      {  segid "BrD" and resid 68 and name HE4}
      {{ segid "BrD" and resid 62 and name HG1}}
       3.200  2.600  2.300 peak    1164 weight   0.10000E♦01 volume  0.12306E♦03 ppm1  7.896   ppm2  2.374
OR    {1164}
      {  segid "BrD" and resid 68 and name HE4}
      {{ segid "BrD" and resid 73 and name HG  }}
OR    {1164}
      {  segid "BrD" and resid 107 and name HE4}
      {{ segid "BrD" and resid 116 and name HB  }}
ASSI  {1204}
      {  segid "BrD" and resid 68 and name HE4}
      {{ segid "BrD" and resid 68 and name HB2}}
       2.500  1.600  1.600 peak    1204 weight   0.10000E♦01 volume  0.47618E♦03 ppm1  7.892   ppm2  3.546
OR    {1204}
      {  segid "BrD" and resid 68 and name HE4}
      {{ segid "BrD" and resid 67 and name HB1}}
OR    {1204}
      {  segid "BrD" and resid 107 and name HE4}
      {{ segid "BrD" and resid 82 and name HB2  }}
OR    {1204}
      {{ segid "BrD" and resid 34 and name HZ  }}
      {{ segid "BrD" and resid 82 and name HB2}}
ASSI  {1244}
      {  segid "BrD" and resid 107 and name HE4}
      {{ segid "BrD" and resid 79 and name HB2  }}
       2.500  1.600  1.600 peak    1244 weight   0.10000E♦01 volume  0.54491E♦03 ppm1  7.891   ppm2  2.644
OR    {1244}
      {  segid "BrD" and resid 68 and name HE4}
      {{ segid "BrD" and resid 62 and name HD2}}
ASSI  {1254}
      {  segid "BrD" and resid 107 and name HE4 }}
      {{ segid "BrD" and resid 116 and name HG11}}
       2.700  1.800  1.800 peak    1254 weight   0.10000E♦01 volume  0.30083E♦03 ppm1  7.891   ppm2  1.886
OR    {1254}
      { segid "BrD" and resid 68 and name HE4 }
      { segid "BrD" and resid 59 and name HE4 }
OR    {1254}
      {  segid "BrD" and resid 107 and name HE4}
      {{ segid "BrD" and resid 103 and name HB2}}
ASSI  {1274}
      {{ segid "BrD" and resid 34 and name HZ}}
      {{ segid "BrD" and resid 98 and name HA}}
       3.400  2.900  2.100 peak    1274 weight   0.10000E♦01 volume  0.84175E♦02 ppm1  7.888   ppm2  4.815
```

TABLE 3-continued

Ambiguous NOE-derived Inter-proton Distance Restraints

```
OR      {1274}
        {  segid "BrD" and resid 68 and name HE4}
        {{ segid "BrD" and resid 73 and name HA  }}
ASSI    {1284}
        {  segid "BrD" and resid 107 and name HE4}
        {{ segid "BrD" and resid 103 and name HG2}}
           2.500  1.600  1.600 peak     1284 weight    0.10000E+01 volume   0.45504E+03 ppm1  7.689    ppm2  2.554
OR      {1284}
        {  segid "BrD" and resid 68 and name HE4}
        {{ segid "BrD" and resid 54 and name HB1}}
ASSI    {1294}
        {  segid "BrD" and resid 107 and name HE4}
        {{ segid "BrD" and resid 116 and name HB  }}
           3.300  2.700  2.200 peak     1294 weight    0.10000E+01 volume   0.10144E+03 ppm1  7.888    ppm2  2.422
OR      {1294}
        {{ segid "BrD" and resid 34 and name HZ    }}
        {{ segid "BrD" and resid 101 and name HG11}}
ASSI    {1304}
        {  segid "BrD" and resid 68 and name HE4  }
        {  segid "BrD" and resid 56 and name HG24}
           2.600  1.700  1.700 peak     1304 weight    0.10000E+01 volume   0.38056E+03 ppm1  7.888    ppm2  1.656
OR      {1304}
        {  segid "BrD" and resid 107 and name HE4  }
        {{ segid "BrD" and resid 110 and name HG12}}
ASSI    {1444}
        {  segid "BrD" and resid 107 and name HD4}
        {{ segid "BrD" and resid 104 and name HA  }}
           2.900  2.100  2.100 peak     1444 weight    0.10000E+01 volume   0.19434E+03 ppm1  7.811    ppm2  4.684
OR      {1444}
        {  segid "BrD" and resid 105 and name HD4}
        {{ segid "BrD" and resid 104 and name HA  }}
OR      {1444}
        {  segid "BrD" and resid 107 and name HD4}
        {{ segid "BrD" and resid 118 and name HA  }}
OR      {1444}
        {  segid "BrD" and resid 105 and name HD4}
        {{ segid "BrD" and resid 109 and name HA  }}
ASSI    {1504}
        {  segid "BrD" and resid 105 and name HD4}
        {{ segid "BrD" and resid 105 and name HA  }}
           2.400  1.400  1.400 peak     1504 weight    0.10000E+01 volume   0.65395E+03 ppm1  7.798    ppm2  4.926
OR      {1504}
        {  segid "BrD" and resid 68 and name HD4}
        {{ segid "BrD" and resid 59 and name HA  }}
ASSI    {1514}
        {  segid "BrD" and resid 107 and name HD4}
        {{ segid "BrD" and resid 106 and name HA  }}
           2.800  2.000  2.000 peak     1514 weight    0.10000E+01 volume   0.27794E+03 ppm1  7.798    ppm2  4.572
OR      {1514}
        {  segid "BrD" and resid 105 and name HD4}
        {{ segid "BrD" and resid 106 and name HA  }}
OR      {1514}
        {  segid "BrD" and resid 105 and name HD4}
        {{ segid "BrD" and resid 108 and name HB1}}
ASSI    {1534}
        {  segid "BrD" and resid 105 and name HD4}
        {{ segid "BrD" and resid 105 and name HB2}}
           2.200  1.200  1.200 peak     1534 weight    0.10000E+01 volume   0.11824E+04 ppm1  7.799    ppm2  3.674
OR      {1534}
        {  segid "BrD" and resid 107 and name HD4}
        {{ segid "BrD" and resid 107 and name HB1}}
OR      {1534}
        {  segid "BrD" and resid 68 and name HD4}
        {{ segid "BrD" and resid 68 and name HB1}}
ASSI    {1554}
        {  segid "BrD" and resid 34 and name HE4  }
        {{ segid "BrD" and resid 102 and name HB2}}
           2.500  2.500  2.000 peak     1554 weight    0.10000E+01 volume   0.46212E+03 ppm1  7.799    ppm2  1.819
OR      {1554}
        {  segid "BrD" and resid 68 and name HD4  }
        {  segid "BrD" and resid 59 and name HE4  }
ASSI    {1574}
        {  segid "BrD" and resid 105 and name HD4}
        {{ segid "BrD" and resid 102 and name HA  }}
           2.800  2.000  2.000 peak     1574 weight    0.10000E+01 volume   0.27340E+03 ppm1  7.797    ppm2  4.278
OR      {1574}
        {  segid "BrD" and resid 105 and name HD4}
        {{ segid "BrD" and resid 101 and name HA  }}
```

TABLE 3-continued

Ambiguous NOE-derived Inter-proton Distance Restraints

| | |
|---|---|
| OR | {1574} |
| | { segid "BrD" and resid 34 and name HE4} |
| | {{ segid "BrD" and resid 102 and name HA}} |
| ASSI | {1614} |
| | { segid "BrD" and resid 68 and name HD4} |
| | {{ segid "BrD" and resid 74 and name HB2}} |
| | 2.900  2.100  2.100 peak   1614 weight   0.10000E+01 volume   0.20510E+03 ppm1  7.790   ppm2  3.010 |
| OR | {1614} |
| | { segid "BrD" and resid 105 and name HD4} |
| | {{ segid "BrD" and resid 109 and name HE2}} |
| ASSI | {1624} |
| | { segid "BrD" and resid 34 and name HE4}} |
| | {{ segid "BrD" and resid 33 and name HD1}} |
| | 2.800  2.000  2.000 peak   1624 weight   0.10000E+01 volume   0.23703E+03 ppm1  7.786   ppm2  2.796 |
| OR | {1624} |
| | {{ segid "BrD" and resid 32 and name HZ3}} |
| | {{ segid "BrD" and resid 33 and name HD1}} |
| OR | {1624} |
| | {{ segid "BrD" and resid 107 and name HD4}} |
| | {{ segid "BrD" and resid 79 and name HB1 }} |
| OR | {1624} |
| | {{ segid "BrD" and resid 32 and name HH2}} |
| | {{ segid "BrD" and resid 33 and name HD1}} |
| ASSI | {1654} |
| | { segid "BrD" and resid 34 and name HE4} |
| | {{ segid "BrD" and resid 85 and name HB1}} |
| | 2.600  1.700  1.700 peak   1654 weight   0.10000E+01 volume   0.36960E+03 ppm1  7.784   ppm2  3.920 |
| OR | {1654} |
| | { segid "BrD" and resid 107 and name HD4} |
| | {{ segid "BrD" and resid 106 and name HB1}} |
| ASSI | {1664} |
| | { segid "BrD" and resid 34 and name HE4 } |
| | { segid "BrD" and resid 99 and name HB4 } |
| | 2.400  1.400  1.400 peak   1664 weight   0.10000E+01 volume   0.66064E+03 ppm1  7.786   ppm2  2.211 |
| OR | {1664} |
| | { segid "BrD" and resid 34 and name HE4} |
| | {{ segid "BrD" and resid 33 and name HD2}} |
| ASSI | {1674} |
| | {{ segid "BrD" and resid 32 and name HH2}} |
| | {{ segid "BrD" and resid 33 and name HG1}} |
| | 3.300  2.700  2.200 peak   1674 weight   0.10000E+01 volume   0.96894E+02 ppm1  7.786   ppm2  0.876 |
| OR | {1674} |
| | {{ segid "BrD" and resid 32 and name HZ3}} |
| | {{ segid "BrD" and resid 33 and name HG1}} |
| OR | {1674} |
| | { segid "BrD" and resid 34 and name HE4} |
| | {{ segid "BrD" and resid 33 and name HG1}} |
| ASSI | {1684} |
| | { segid "BrD" and resid 34 and name HE4} |
| | {{ segid "BrD" and resid 98 and name HA }} |
| | 3.400  2.900  2.100 peak   1684 weight   0.10000E+01 volume   0.73775E+02 ppm1  7.783   ppm2  4.815 |
| OR | {1684} |
| | {{ segid "BrD" and resid 32 and name HH2}} |
| | {{ segid "BrD" and resid 94 and name HA }} |
| OR | {1684} |
| | { segid "BrD" and resid 68 and name HD4} |
| | {{ segid "BrD" and resid 73 and name HA }} |
| OR | {1684} |
| | { segid "BrD" and resid 107 and name HD4} |
| | {{ segid "BrD" and resid 108 and name HA }} |
| OR | {1684} |
| | { segid "BrD" and resid 68 and name HD4} |
| | {{ segid "BrD" and resid 60 and name HA }} |
| OR | {1684} |
| | {{ segid "BrD" and resid 32 and name HH2}} |
| | {{ segid "BrD" and resid 98 and name HA }} |
| OR | {1684} |
| | { segid "BrD" and resid 34 and name HE4} |
| | {{ segid "BrD" and resid 86 and name HA }} |
| OR | {1684} |
| | { segid "BrD" and resid 107 and name HD4} |
| | {{ segid "BrD" and resid 116 and name HA }} |
| OR | {1684} |
| | { segid "BrD" and resid 105 and name HD4} |
| | {{ segid "BrD" and resid 106 and name HA}} |
| OR | {1684} |
| | {{ segid "BrD" and resid 32 and name HZ3}} |
| | {{ segid "BrD" and resid 94 and name HA }} |

TABLE 3-continued

Ambiguous NOE-derived Inter-proton Distance Restraints

```
ASSI  {1704}
      {   segid "BrD" and resid 68 and name HD4}
      {{ segid "BrD" and resid 62 and name HD1}}
         2.700  1.800  1.800 peak    1704 weight    0.10000E+01 volume  0.31213E+03 ppm1  7.787   ppm2  3.153
  OR  {1704}
      {   segid "BrD" and resid 105 and name HD4}
      {{ segid "BrD" and resid 109 and name HE1}}
ASSI  {1714}
      {   segid "BrD" and resid 68 and name HD4}
      {{ segid "BrD" and resid 62 and name HB1}}
         2.300  1.300  1.300 peak    1714 weight    0.10000E+01 volume  0.79418E+03 ppm1  7.779   ppm2  2.602
  OR  {1714}
      {   segid "BrD" and resid 107 and name HD4}
      {{ segid "BrD" and resid 103 and name HG1}}
  OR  {1714}
      {   segid "BrD" and resid 68 and name HD4}
      {{ segid "BrD" and resid 62 and name HD2}}
ASSI  {1734}
      {   segid "BrD" and resid 68 and name HD4}
      {{ segid "BrD" and resid 62 and name HG1}}
         2.900  2.100  2.100 peak    1734 weight    0.10000E+01 volume  0.18466E+03 ppm1  7.781   ppm2  2.324
  OR  {1734}
      {  segid "BrD" and resid 34 and name HE4 }
      {  segid "BrD" and resid 31 and name HB4 }
  OR  {1734}
      {   segid "BrD" and resid 107 and name HD4}
      {{ segid "BrD" and resid 110 and name HB  }}
  OR  {1734}
      {   segid "BrD" and resid 68 and name HD4}
      {{ segid "BrD" and resid 73 and name HG  }}
ASSI  {1744}
      {   segid "BrD" and resid 107 and name HD4 }
      {{ segid "BrD" and resid 110 and name HG12}}
         2.300  1.300  1.300 peak    1744 weight    0.10000E+01 volume  0.92480E+03 ppm1  7.781   ppm2  1.641
  OR  {1744}
      {{ segid "BrD" and resid 34 and name HE4 }
      {{ segid "BrD" and resid 25 and name HG24}
ASSI  {1784}
      {   segid "BrD" and resid 68 and name HD4}
      {{ segid "BrD" and resid 62 and name HG1}}
         2.800  2.000  2.000 peak    1784 weight    0.10000E+01 volume  0.24728E+03 ppm1  7.781   ppm2  2.374
  OR  {1784}
      {   segid "BrD" and resid 107 and name HD4}
      {{ segid "BrD" and resid 110 and name HB  }}
  OR  {1784}
      {   segid "BrD" and resid 68 and name HD4}
      {{ segid "BrD" and resid 73 and name HG  }}
ASSI  {1804}
      {   segid "BrD" and resid 68 and name HD4}
      {{ segid "BrD" and resid 62 and name HG2}}
         2.700  1.800  1.800 peak    1804 weight    0.10000E+01 volume  0.30580E+03 ppm1  7.781   ppm2  1.503
  OR  {1804}
      { segid "BrD" and resid 68 and name HD4 }
      { segid "BrD" and resid 73 and name HD24}
ASSI  {1884}
      {   segid "BrD" and resid 96 and name HD4}
      {{ segid "BrD" and resid 92 and name HB1}}
         2.900  2.100  2.100 peak    1884 weight    0.10000E+01 volume  0.22072E+03 ppm1  7.726   ppm2  2.666
  OR  {1884}
      {   segid "BrD" and resid 34 and name HD4}
      {   segid "BrD" and resid 56 and name HB1}}
ASSI  {1924}
      { segid "BrD" and resid 96 and name HD4 }
      { segid "BrD" and resid 99 and name HB4 }
         2.500  1.600  1.600 peak    1924 weight    0.10000E+01 volume  0.55506E+03 ppm1  7.721   ppm2  2.211
  OR  {1924}
      {   segid "BrD" and resid 34 and name HD4}
      {{ segid "BrD" and resid 33 and name HD2}}
ASSI  {1964}
      {   segid "BrD" and resid 96 and name HD4}
      {{ segid "BrD" and resid 92 and name HG1}}
         2.800  2.000  2.000 peak    1964 weight    0.10000E+01 volume  0.22599E+03 ppm1  7.714   ppm2  2.796
  OR  {1964}
      {   segid "BrD" and resid 34 and name HD4}
      {{ segid "BrD" and resid 33 and name HD1}}
  OR  {1964}
      { segid "BrD" and resid 34 and name HD4 }
      { segid "BrD" and resid 35 and name HE4 }
```

TABLE 3-continued

Ambiguous NOE-derived Inter-proton Distance Restraints

```
ASSI  {1974}
      { segid "BrD" and resid 96 and name HD4}
      {{ segid "BrD" and resid 86 and name HB1}}
         2.300  2.300  2.200 peak    1974 weight    0.10000E+01 volume  0.79213E+03 ppm1  7.717   ppm2  2.321
OR    {1974}
      { segid "BrD" and resid 34 and name HD4 }
      { segid "BrD" and resid 31 and name HB4 }
ASSI  {1994}
      { segid "BrD" and resid 34 and name HD4 }
      { segid "BrD" and resid 81 and name HG24}
         2.400  1.400  1.400 peak    1994 weight    0.10000E+01 volume  0.69140E+03 ppm1  7.717   ppm2  0.762
OR    {1994}
      { segid "BrD" and resid 96 and name HD4}
      {{ segid "BrD" and resid 86 and name HG2}}
ASSI  {2054}
      { segid "BrD" and resid 34 and name HD4}
      {{ segid "BrD" and resid 81 and name HB }}
         2.900  2.100  2.100 peak    2054 weight    0.10000E+01 volume  0.18901E+03 ppm1  7.709   ppm2  2.033
OR    {2054}
      { segid "BrD" and resid 34 and name HD4}
      {{ segid "BrD" and resid 54 and name HB2}}
ASSI  {2064}
      { segid "BrD" and resid 34 and name HD4}
      {{ segid "BrD" and resid 33 and name HB1}}
         2.800  2.000  2.000 peak    2064 weight    0.10000E+01 volume  0.24003E+03 ppm1  7.714   ppm2  1.088
OR    {2064}
      { segid "BrD" and resid 34 and name HD4 }
      { segid "BrD" and resid 81 and name HG14}
ASSI  {2134}
      { segid "BrD" and resid 15 and name HD4}
      {{ segid "BrD" and resid 19 and name HE1}}
         4.000  4.000  1.500 peak    2134 weight    0.10000E+01 volume  0.29314E+02 ppm1  7.692   ppm2  3.512
OR    {2134}
      { segid "BrD" and resid 96 and name HD4}
      {{ segid "BrD" and resid 89 and name HB2}}
ASSI  {2274}
      { segid "BrD" and resid 106 and name HE4}
      { segid "BrD" and resid 59 and name HE4 }
         3.400  2.900  2.100 peak    2274 weight    0.10000E+01 volume  0.79128E+02 ppm1  7.640   ppm2  1.820
OR    {2274}
      { segid "BrD" and resid 106 and name HE4 }
      { segid "BrD" and resid 25 and name HG14 }
ASSI  {2294}
      { segid "BrD" and resid 106 and name HE4 }
      { segid "BrD" and resid 21 and name HG24 }
         2.600  1.700  1.700 peak    2294 weight    0.10000E+01 volume  0.41702E+03 ppm1  7.643   ppm2  1.593
OR    {2294}
      { segid "BrD" and resid 106 and name HE4 }
      {{ segid "BrD" and resid 116 and name HG12}}
ASSI  {2314}
      { segid "BrD" and resid 106 and name HE4 }
      {{ segid "BrD" and resid 106 and name HB2}}
         4.000  4.000  1.500 peak    2314 weight    0.10000E+01 volume  0.29399E+02 ppm1  7.633   ppm2  3.693
OR    {2314}
      { segid "BrD" and resid 95 and name HE4}
      {{ segid "BrD" and resid 89 and name HB1}}
OR    {2314}
      { segid "BrD" and resid 88 and name HD4}
      {{ segid "BrD" and resid 89 and name HB1}}
OR    {2314}
      { segid "BrD" and resid 106 and name HE4}
      {{ segid "BrD" and resid 107 and name HB1}}
ASSI  {2324}
      { segid "BrD" and resid 106 and name HE4 }
      { segid "BrD" and resid 21 and name HG24 }
         2.600  1.700  1.700 peak    2324 weight    0.10000E+01 volume  0.43383E+03 ppm1  7.616   ppm2  1.576
OR    {2324}
      { segid "BrD" and resid 88 and name HD4 }
      {{ segid "BrD" and resid 49 and name HG24}}
OR    {2324}
      { segid "BrD" and resid 106 and name HE4 }
      {{ segid "BrD" and resid 116 and name HG12}}
ASSI  {2334}
      { segid "BrD" and resid 95 and name HE4}
      {{ segid "BrD" and resid 33 and name HB1}}
         2.900  2.100  2.100 peak    2334 weight    0.10000E+01 volume  0.19423E+03 ppm1  7.623   ppm2  1.095
```

TABLE 3-continued

Ambiguous NOE-derived Inter-proton Distance Restraints

```
OR      {2334}
        { segid "BrD" and resid 106 and name HE4 }
        { segid "BrD" and resid 18 and name HD14 }
ASSI    {2334}
        { segid "BrD" and resid 95 and name HE4}}
        {{ segid "BrD" and resid 32 and name HZ2}}
            3.300  2.700  2.200 peak     2344 weight    0.10000E+01 volume   0.91993E+02 ppm1  7.615   ppm2  8.004
OR      {2344}
        { segid "BrD" and resid 106 and name HE4}
        {{ segid "BrD" and resid 107 and name HZ  }}
ASSI    {2354}
        { segid "BrD" and resid 95 and name HE4}
        {{ segid "BrD" and resid 95 and name HA  }}
            3.000  2.200  2.200 peak     2354 weight    0.10000E+01 volume   0.18109E+03 ppm1  7.619   ppm2  4.448
OR      {2354}
        { segid "BrD" and resid 96 and name HE4}
        {{ segid "BrD" and resid 96 and name HA  }}
OR      {2354}
        { segid "BrD" and resid 106 and name HE4}
        {{ segid "BrD" and resid 107 and name HA }}
OR      {2354}
        { segid "BrD" and resid 106 and name HE4}
        {{ segid "BrD" and resid 79 and name HA  }}
ASSI    {2364}
        { segid "BrD" and resid 95 and name HE4}
        {{ segid "BrD" and resid 33 and name HA  }}
            3.200  2.600  2.300 peak     2364 weight    0.10000E+01 volume   0.11374E+03 ppm1  7.617   ppm2  4.366
OR      {2364}
        { segid "BrD" and resid 106 and name HE4}
        {{ segid "BrD" and resid 21 and name HA  }}
ASSI    {2374}
        { segid "BrD" and resid 88 and name HD4}
        {{ segid "BrD" and resid 87 and name HB1}}
            3.000  2.200  2.200 peak     2374 weight    0.10000E+01 volume   0.17346E+03 ppm1  7.619   ppm2  2.771
OR      {2374}
        { segid "BrD" and resid 106 and name HE4}
        {{ segid "BrD" and resid 79 and name HB1 }}
OR      {2374}
        { segid "BrD" and resid 95 and name HE4}
        {{ segid "BrD" and resid 33 and name HD1}}
OR      {2374}
        { segid "BrD" and resid 88 and name HD4}
        {{ segid "BrD" and resid 87 and name HG2}}
ASSI    {2404}
        { segid "BrD" and resid 106 and name HE4}
        { segid "BrD" and resid 75 and name HE4 }
            2.800  2.000  2.000 peak     2404 weight    0.10000E+01 volume   0.24430E+03 ppm1  7.615   ppm2  2.618
OR      {2404}
        { segid "BrD" and resid 88 and name HD4}
        {{ segid "BrD" and resid 49 and name HB  }}
ASSI    {2424}
        { segid "BrD" and resid 88 and name HD4 }
        { segid "BrD" and resid 49 and name HG14}
            2.600  1.700  1.700 peak     2424 weight    0.10000E+01 volume   0.35230E+03 ppm1  7.616   ppm2  1.658
OR      {2424}
        { segid "BrD" and resid 106 and name HE4}
        {{ segid "BrD" and resid 21 and name HG12}}
ASSI    {2454}
        { segid "BrD" and resid 106 and name HE4}
        {{ segid "BrD" and resid 17 and name HB   }}
            2.500  1.600  1.600 peak     2454 weight    0.10000E+01 volume   0.48101E+03 ppm1  7.611   ppm2  4.815
OR      {2454}
        { segid "BrD" and resid 96 and name HE4}
        {{ segid "BrD" and resid 86 and name HA  }}
OR      {2454}
        { segid "BrD" and resid 96 and name HE4}
        {{ segid "BrD" and resid 97 and name HA  }}
OR      {2454}
        { segid "BrD" and resid 86 and name HD4}
        {{ segid "BrD" and resid 87 and name HA  }}
OR      {2454}
        { segid "BrD" and resid 96 and name HE4}
        {{ segid "BrD" and resid 92 and name HA  }}
OR      {2454}
        { segid "BrD" and resid 95 and name HE4}
        {{ segid "BrD" and resid 94 and name HA  }}
```

TABLE 3-continued

Ambiguous NOE-derived Inter-proton Distance Restraints

| | | | | | | | | | | | | |
|---|---|---|---|---|---|---|---|---|---|---|---|---|
ASSI {2524}
{ segid "BrD" and resid 106 and name HE4 }
{{ segid "BrD" and resid 116 and name HG11}}
    3.000  2.200  2.200 peak    2524 weight    0.10000E+01 volume    0.18273E+03 ppm1  7.611    ppm2  1.925
OR  {2524}
{ segid "BrD" and resid 96 and name HE4}
{{ segid "BrD" and resid 86 and name HG1}}
OR  {2524}
{ segid "BrD" and resid 96 and name HE4}
{{ segid "BrD" and resid 86 and name HD1}}
ASSI {2544}
{ segid "BrD" and resid 106 and name HD4}
{{ segid "BrD" and resid 107 and name HA }}
    3.100  2.400  2.400 peak    2544 weight    0.10000E+01 volume    0.12798E+03 ppm1  7.938    ppm2  4.390
OR  {2544}
{ segid "BrD" and resid 106 and name HD4}
{{ segid "BrD" and resid 79 and name HA }}
OR  {2544}
{ segid "BrD" and resid 74 and name HE4}
{{ segid "BrD" and resid 74 and name HA }}
ASSI {2604}
{ segid "BrD" and resid 74 and name HE4}
{{ segid "BrD" and resid 59 and name HB1}}
    2.500  1.600  1.600 peak    2604 weight    0.10000E+01 volume    0.55016E+03 ppm1  7.534    ppm2  2.695
OR  {2604}
{ segid "BrD" and resid 74 and name HE4}
{{ segid "BrD" and resid 22 and name HB1}}
ASSI {2624}
{ segid "BrD" and resid 106 and name HD4}
{{ segid "BrD" and resid 109 and name HB2}}
    3.000  2.200  2.200 peak    2624 weight    0.10000E+01 volume    0.15519E+03 ppm1  7.524    ppm2  2.146
OR  {2624}
{ segid "BrD" and resid 74 and name HE4}
{{ segid "BrD" and resid 18 and name HB1}}
ASSI {2644}
{ segid "BrD" and resid 74 and name HE4}
{{ segid "BrD" and resid 63 and name HB2}}
    2.300  1.300  1.300 peak    2644 weight    0.10000E+01 volume    0.82012E+03 ppm1  7.931    ppm2  2.521
OR  {2664}
{ segid "BrD" and resid 106 and name HD4}
{{ segid "BrD" and resid 21 and name HB }}
ASSI {2664}
{ segid "BrD" and resid 106 and name HD4 }
{ segid "BrD" and resid 102 and name HD24}
    2.800  2.000  2.000 peak    2664 weight    0.10000E+01 volume    0.24374E+03 ppm1  7.930    ppm2  1.331
OR  {2664}
{ segid "BrD" and resid 74 and name HE4}
{{ segid "BrD" and resid 78 and name HB1}}
ASSI {2784}
{ segid "BrD" and resid 74 and name HE4}
{{ segid "BrD" and resid 68 and name HB2}}
    2.900  2.100  2.100 peak    2784 weight    0.10000E+01 volume    0.21978E+03 ppm1  7.530    ppm2  3.559
OR  {2784}
{ segid "BrD" and resid 74 and name HE4}
{{ segid "BrD" and resid 74 and name HB1}}
OR  {2784}
{ segid "BrD" and resid 95 and name HD4}
{{ segid "BrD" and resid 88 and name HB1}}
ASSI {2804}
{ segid "BrD" and resid 95 and name HD4}
{{ segid "BrD" and resid 32 and name HH2}}
    2.800  2.000  2.000 peak    2804 weight    0.10000E+01 volume    0.23332E+03 ppm1  7.520    ppm2  7.793
OR  {2804}
{ segid "BrD" and resid 106 and name HD4 }
{ segid "BrD" and resid 107 and name HD4 }
ASSI {2814}
{ segid "BrD" and resid 106 and name HD4}
{{ segid "BrD" and resid 78 and name HB2 }}
    3.000  2.200  2.200 peak    2814 weight    0.10000E+01 volume    0.16253E+03 ppm1  7.520    ppm2  1.080
OR  {2814}
{ segid "BrD" and resid 74 and name HE4 }
{ segid "BrD" and resid 18 and name HD14}
OR  {2814}
{ segid "BrD" and resid 95 and name HD4}
{{ segid "BrD" and resid 33 and name HB1}}

TABLE 3-continued

Ambiguous NOE-derived Inter-proton Distance Restraints

```
ASSI  {2914}
      {  segid "BrD" and resid 18 and name HE4}
      {{ segid "BrD" and resid 19 and name HE1}}
         2.900  2.100  2.100 peak    2914 weight    0.10000E+01 volume   0.20135E+03 ppm1  7.488   ppm2  3.545
OR    {2914}
      {  segid "BrD" and resid 95 and name HD4}
      {{ segid "BrD" and resid 88 and name HB1}}
ASSI  {3164}
      {  segid "BrD" and resid 82 and name HD4 }
      {{ segid "BrD" and resid 103 and name HB1}}
         2.700  1.800  1.800 peak    3164 weight    0.10000E+01 volume   0.29307E+03 ppm1  7.270   ppm2  2.309
OR    {3164}
      {  segid "BrD" and resid 47 and name HE4}
      {{ segid "BrD" and resid 37 and name HB2}}
ASSI  {3284}
      {  segid "BrD" and resid 82 and name HD4 }
      {  segid "BrD" and resid 34 and name HE4 }
         2.800  2.000  2.000 peak    3284 weight    0.10000E+01 volume   0.24491E+03 ppm1  7.263   ppm2  7.800
OR    {3284}
      {  segid "BrD" and resid 82 and name HD4 }
      {  segid "BrD" and resid 107 and name HD4}
ASSI  {3324}
      {  segid "BrD" and resid 82 and name HE4}
      {{ segid "BrD" and resid 79 and name HA  }}
         2.900  2.100  2.100 peak    3324 weight    0.10000E+01 volume   0.20070E+03 ppm1  7.074   ppm2  4.440
OR    {3324}
      {  segid "BrD" and resid 82 and name HE4}
      {{ segid "BrD" and resid 107 and name HA}}
ASSI  {3394}
      {  segid "BrD" and resid 82 and name HE4}
      {{ segid "BrD" and resid 81 and name HB }}
         2.600  1.700  1.700 peak    3394 weight    0.10000E+01 volume   0.37424E+03 ppm1  7.069   ppm2  2.032
OR    {3394}
      {  segid "BrD" and resid 82 and name HE4 }
      {{ segid "BrD" and resid 102 and name HB1}}
ASSI  {3414}
      {  segid "BrD" and resid 82 and name HE4 }
      {  segid "BrD" and resid 25 and name HG24}
         3.400  2.900  2.100 peak    3414 weight    0.10000E+01 volume   0.73603E+02 ppm1  7.067   ppm2  1.641
OR    {3414}
      {  segid "BrD" and resid 82 and name HE4   }
      {{ segid "BrD" and resid 110 and name HG12}}
ASSI  {3474}
      {{ segid "BrD" and resid 82 and name HZ  }}
      {{ segid "BrD" and resid 102 and name HG}}
         2.800  2.000  2.000 peak    3474 weight    0.10000E+01 volume   0.23859E+03 ppm1  7.025   ppm2  2.163
OR    {3474}
      {  segid "BrD" and resid 74 and name HD4}
      {{ segid "BrD" and resid 18 and name HB1}}
ASSI  {3484}
      {  segid "BrD" and resid 74 and name HD4 }
      {  segid "BrD" and resid 78 and name HD14}
         2.900  2.100  2.100 peak    3484 weight    0.10000E+01 volume   0.18792E+03 ppm1  7.023   ppm2  0.780
OR    {3484}
      {{ segid "BrD" and resid 82 and name HZ   }}
      {  segid "BrD" and resid 78 and name HD14}
ASSI  {3494}
      {  segid "BrD" and resid 74 and name HD4}
      {{ segid "BrD" and resid 68 and name HB1}}
         2.900  2.100  2.100 peak    3494 weight    0.10000E+01 volume   0.19853E+03 ppm1  7.022   ppm2  3.708
OR    {3494}
      {{ segid "BrD" and resid 82 and name HZ   }}
      {{ segid "BrD" and resid 106 and name HB2}}
ASSI  {3504}
      {{ segid "BrD" and resid 82 and name HZ}}
      {{ segid "BrD" and resid 81 and name HB}}
         3.100  2.400  2.400 peak    3504 weight    0.10000E+01 volume   0.12383E+03 ppm1  7.023   ppm2  2.034
OR    {3504}
      {  segid "BrD" and resid 74 and name HD4}
      {{ segid "BrD" and resid 14 and name HG }}
ASSI  {3544}
      {  segid "BrD" and resid 74 and name HD4}
      {{ segid "BrD" and resid 18 and name HG }}
         3.400  2.900  2.100 peak    3544 weight    0.10000E+01 volume   0.82384E+02 ppm1  7.005   ppm2  2.307
OR    {3544}
      {{ segid "BrD" and resid 82 and name HZ   }}
      {{ segid "BrD" and resid 103 and name HB1}}
```

TABLE 3-continued

Ambiguous NOE-derived Inter-proton Distance Restraints

| | | | | | | | | |
|---|---|---|---|---|---|---|---|---|
| OR | {3544} | | | | | | | |
| | { segid "BrD" and resid 74 and name HD4 } | | | | | | | |
| | {{ segid "BrD" and resid 21 and name HG11}} | | | | | | | |
| OR | {3544} | | | | | | | |
| | { segid "BrD" and resid 74 and name HD4} | | | | | | | |
| | {{ segid "BrD" and resid 62 and name HG1}} | | | | | | | |
| OR | {3544} | | | | | | | |
| | { segid "BrD" and resid 74 and name HD4} | | | | | | | |
| | {{ segid "BrD" and resid 73 and name HG }} | | | | | | | |
| OR | {3544} | | | | | | | |
| | {{ segid "BrD" and resid 82 and name HZ }} | | | | | | | |
| | {{ segid "BrD" and resid 21 and name HG11}} | | | | | | | |
| ASSI | {3554} | | | | | | | |
| | { segid "BrD" and resid 74 and name HD4 } | | | | | | | |
| | { segid "BrD" and resid 63 and name HD14} | | | | | | | |
| | 2.500  1.600  1.600 peak     3554 weight | 0.10000E♦01 | volume | 0.51806E♦03 | ppm1 | 7.009 | ppm2 | 1.643 |
| OR | {3554} | | | | | | | |
| | { segid "BrD" and resid 74 and name HD4 } | | | | | | | |
| | { segid "BrD" and resid 22 and name HD14} | | | | | | | |
| ASSI | {3564} | | | | | | | |
| | { segid "BrD" and resid 74 and name HD4 } | | | | | | | |
| | { segid "BrD" and resid 68 and name HE4 } | | | | | | | |
| | 3.100  2.400  2.400 peak     3564 weight | 0.10000E♦01 | volume | 0.13987E♦03 | ppm1 | 7.005 | ppm2 | 7.889 |
| OR | {3564} | | | | | | | |
| | {{ segid "BrD" and resid 82 and name HZ }} | | | | | | | |
| | { segid "BrD" and resid 107 and name HE4} | | | | | | | |
| ASSI | {3584} | | | | | | | |
| | { segid "BrD" and resid 74 and name HD4 } | | | | | | | |
| | { segid "BrD" and resid 106 and name HE4} | | | | | | | |
| | 3.000  2.200  2.200 peak     3584 weight | 0.10000E♦01 | volume | 0.17632E♦03 | ppm1 | 7.005 | ppm2 | 7.647 |
| OR | {3584} | | | | | | | |
| | {{ segid "BrD" and resid 82 and name HZ }} | | | | | | | |
| | { segid "BrD" and resid 106 and name HE4} | | | | | | | |
| ASSI | {3604} | | | | | | | |
| | { segid "BrD" and resid 74 and name HD4} | | | | | | | |
| | {{ segid "BrD" and resid 71 and name HA }} | | | | | | | |
| | 3.300  2.700  2.200 peak     3604 weight | 0.10000E♦01 | volume | 0.95504E♦02 | ppm1 | 7.005 | ppm2 | 4.636 |
| OR | {3604} | | | | | | | |
| | { segid "BrD" and resid 74 and name HD4} | | | | | | | |
| | {{ segid "BrD" and resid 15 and name HA }} | | | | | | | |
| OR | {3604} | | | | | | | |
| | { segid "BrD" and resid 74 and name HD4} | | | | | | | |
| | {{ segid "BrD" and resid 76 and name HA }} | | | | | | | |
| OR | {3604} | | | | | | | |
| | { segid "BrD" and resid 74 and name HD4} | | | | | | | |
| | {{ segid "BrD" and resid 56 and name HA }} | | | | | | | |
| OR | {3604} | | | | | | | |
| | { segid "BrD" and resid 74 and name HD4} | | | | | | | |
| | {{ segid "BrD" and resid 72 and name HA }} | | | | | | | |
| OR | {3604} | | | | | | | |
| | { segid "BrD" and resid 74 and name HD4} | | | | | | | |
| | {{ segid "BrD" and resid 14 and name HA }} | | | | | | | |
| OR | {3604} | | | | | | | |
| | { segid "BrD" and resid 74 and name HD4} | | | | | | | |
| | {{ segid "BrD" and resid 67 and name HA }} | | | | | | | |
| OR | {3604} | | | | | | | |
| | { segid "BrD" and resid 74 and name HD4} | | | | | | | |
| | {{ segid "BrD" and resid 60 and name HB2}} | | | | | | | |
| OR | {3604} | | | | | | | |
| | {{ segid "BrD" and resid 85 and name HZ }} | | | | | | | |
| | {{ segid "BrD" and resid 104 and name HA}} | | | | | | | |
| ASSI | {3634} | | | | | | | |
| | { segid "BrD" and resid 74 and name HD4}} | | | | | | | |
| | {{ segid "BrD" and resid 75 and name HG2}} | | | | | | | |
| | 3.100  2.400  2.400 peak     3634 weight | 0.10000E♦01 | volume | 0.12756E♦03 | ppm1 | 7.004 | ppm2 | 3.221 |
| OR | {3634} | | | | | | | |
| | { segid "BrD" and resid 74 and name HD4} | | | | | | | |
| | {{ segid "BrD" and resid 59 and name HG1}} | | | | | | | |
| OR | {3634} | | | | | | | |
| | { segid "BrD" and resid 74 and name HD4} | | | | | | | |
| | {{ segid "BrD" and resid 59 and name HG2}} | | | | | | | |
| ASSI | {3664} | | | | | | | |
| | { segid "BrD" and resid 74 and name HD4} | | | | | | | |
| | {{ segid "BrD" and resid 63 and name HB2}} | | | | | | | |
| | 3.600  3.200  1.900 peak     3664 weight | 0.10000E♦01 | volume | 0.57581E♦02 | ppm1 | 7.005 | ppm2 | 2.520 |
| OR | {3664} | | | | | | | |
| | {{ segid "BrD" and resid 85 and name HZ}} | | | | | | | |
| | {{ segid "BrD" and resid 21 and name HB}} | | | | | | | |

TABLE 3-continued

Ambiguous NOE-derived Inter-proton Distance Restraints

```
ASSI    {3674}
        {{ segid "BrD" and resid 82 and name HZ}}
        {{ segid "BrD" and resid 21 and name HB}}
           3.700  3.400  1.800 peak    3674 weight    0.10000E+01 volume   0.46728E+02 ppm1  7.004   ppm2  2.494
OR      {3674}
        {  segid "BrD" and resid 74 and name HD4 }
        {{ segid "BrD" and resid 59 and name HB2}}
OR      {3674}
        {  segid "BrD" and resid 74 and name HD4 }
        {{ segid "BrD" and resid 73 and name HB2}}
ASSI    {3694}
        {  segid "BrD" and resid 74 and name HD4  }
        {  segid "BrD" and resid 63 and name HD24}
           3.500  3.100  2.000 peak    3694 weight    0.10000E+01 volume   0.62447E+02 ppm1  7.005   ppm2  1.496
OR      {3694}
        {  segid "BrD" and resid 74 and name HD4  }
        {  segid "BrD" and resid 73 and name HD24}
ASSI    {3854}
        {  segid "BrD" and resid 46 and name HE4  }
        {{ segid "BrD" and resid 50 and name HG12}}
           2.700  1.800  1.800 peak    3854 weight    0.10000E+01 volume   0.29261E+03 ppm1  6.687   ppm2  0.795
OR      {3894}
        {  segid "BrD" and resid 46 and name HE4  }
        {  segid "BrD" and resid 38 and name HG24}}
ASSI    {3954}
        {  segid "BrD" and resid 46 and name HD4  }
        {{ segid "BrD" and resid 50 and name HG12}}
           3.200  2.600  2.300 peak    3954 weight    0.10000E+01 volume   0.11437E+03 ppm1  5.740   ppm2  0.796
OR      {3954}
        {  segid "BrD" and resid 46 and name HD4  }
        {  segid "BrD" and resid 38 and name HG24}
ASSI    {4144}
        {  segid "BrD" and resid 74 and name HD4  }
        {{ segid "BrD" and resid 78 and name HG   }}
           3.400  2.900  2.100 peak    4144 weight    0.10000E+01 volume   0.77150E+02 ppm1  7.005   ppm2  1.249
OR      {4144}
        {{ segid "BrD" and resid 82 and name HZ}}
        {{ segid "BrD" and resid 78 and name HG}}
ASSI    {4154}
        {  segid "BrD" and resid 74 and name HE4  }
        {  segid "BrD" and resid 22 and name HD14}
           2.400  1.400  1.400 peak    4154 weight    0.10000E+01 volume   0.70341E+03 ppm1  7.534   ppm2  1.676
OR      {4154}
        {  segid "BrD" and resid 106 and name HD4}
        {{ segid "BrD" and resid 21 and name HG12}}
ASSI    {4174}
        {  segid "BrD" and resid 96 and name HD4}
        {{ segid "BrD" and resid 100 and name HA}}
           3.100  2.400  2.400 peak    4174 weight    0.10000E+01 volume   0.13533E+03 ppm1  7.689   ppm2  4.927
OR      {4174}
        {  segid "BrD" and resid 34 and name HD4}
        {{ segid "BrD" and resid 35 and name HA  }}
OR      {4174}
        {  segid "BrD" and resid 15 and name HD4}
        {{ segid "BrD" and resid 64 and name HA  }}
OR      {4174}
        {  segid "BrD" and resid 15 and name HD4}
        {{ segid "BrD" and resid 11 and name HA  }}
OR      {4174}
        {  segid "BrD" and resid 34 and name HD4}
        {{ segid "BrD" and resid 32 and name HA  }}
ASSI    {4224}
        {  segid "BrD" and resid 88 and name HD4  }
        {{ segid "BrD" and resid 50 and name HG12}}
           3.100  2.400  2.400 peak    4224 weight    0.10000E+01 volume   0.12837E+03 ppm1  7.615   ppm2  0.845
OR      {4224}
        {  segid "BrD" and resid 95 and name HE4}
        {{ segid "BrD" and resid 33 and name HG1}}
ASSI    {4234}
        {  segid "BrD" and resid 96 and name HE4  }
        {  segid "BrD" and resid 99 and name HB4  }
           3.300  2.700  2.200 peak    4234 weight    0.10000E+01 volume   0.94963E+02 ppm1  7.611   ppm2  2.178
OR      {4234}
        {  segid "BrD" and resid 106 and name HE4}
        {{ segid "BrD" and resid 18 and name HB1  }}
OR      {4234}
        {  segid "BrD" and resid 106 and name HE4}
        {{ segid "BrD" and resid 109 and name HB2}}
```

TABLE 3-continued

Ambiguous NOE-derived Inter-proton Distance Restraints

```
OR     {4234}
       { segid "BrD" and resid 106 and name HE4}
       {{ segid "BrD" and resid 115 and name HB1}}
OR     {4234}
       { segid "BrD" and resid 106 and name HE4}
       {{ segid "BrD" and resid 115 and name HG }}
ASSI   {4244}
       { segid "BrD" and resid 106 and name HE4 }
       { segid "BrD" and resid 78 and name HD14 }
         3.100  2.400  2.400 peak    4244 weight   0.10000E♦01 volume  0.14012E♦03 ppm1  7.616   ppm2  0.763
OR     {4244}
       { segid "BrD" and resid 96 and name HE4}
       {{ segid "BrD" and resid 86 and name HG2}}
ASSI   {4284}
       { segid "BrD" and resid 74 and name HE4}
       {{ segid "BrD" and resid 74 and name HB2}}
         3.000  2.200  2.200 peak    4284 weight   0.10000E♦01 volume  0.18031E♦03 ppm1  7.534   ppm2  3.010
OR     {4284}
       { segid "BrD" and resid 106 and name HD4}
       {{ segid "BrD" and resid 109 and name HE2}}
ASSI   {4344}
       {{ segid "BrD" and resid 34 and name HZ }}
       {{ segid "BrD" and resid 28 and name HD2}}
         3.100  2.400  2.400 peak    4344 weight   0.10000E♦01 volume  0.12962E♦03 ppm1  7.904   ppm2  5.555
OR     {4344}
       { segid "BrD" and resid 68 and name HE4}
       {{ segid "BrD" and resid 54 and name HA  }}
ASSI   {4354}
       { segid "BrD" and resid 106 and name HD4}
       {{ segid "BrD" and resid 78 and name HB2 }}
         2.900  2.100  2.100 peak    4354 weight   0.10000E♦01 volume  0.19182E♦03 ppm1  7.539   ppm2  1.089
OR     {4354}
       { segid "BrD" and resid 74 and name HE4 }
       { segid "BrD" and resid 18 and name HD14}
```

TABLE 4

Hydrogen Bonding Restraints

!Helix Z

| | | | | |
|---|---|---|---|---|
| assign (residue 19 and name HN ) | (residue 15 and name O ) | 1.80 | 0.0 | 0.40 |
| assign (residue 19 and name N ) | (residue 15 and name O ) | 2.80 | 0.30 | 0.40 |
| assign (residue 22 and name HN ) | (residue 18 and name O ) | 1.80 | 0.0 | 0.40 |
| assign (residue 22 and name N ) | (residue 18 and name O ) | 2.80 | 0.30 | 0.40 |
| assign (residue 23 and name HN ) | (residue 19 and name O ) | 1.80 | 0.0 | 0.40 |
| assign (residue 23 and name N ) | (residue 19 and name O ) | 2.80 | 0.30 | 0.40 |
| assign (residue 24 and name HN ) | (residue 20 and name O ) | 1.80 | 0.0 | 0.40 |
| assign (residue 24 and name N ) | (residue 20 and name O ) | 2.80 | 0.30 | 0.40 |
| assign (residue 25 and name HN ) | (residue 21 and name O ) | 1.80 | 0.0 | 0.40 |
| assign (residue 25 and name N ) | (residue 21 and name O ) | 2.80 | 0.30 | 0.40 |

!Helix B

| | | | | |
|---|---|---|---|---|
| assign (residue 75 and name HN ) | (residue 71 and name O ) | 1.80 | 0.0 | 0.40 |
| assign (residue 75 and name N ) | (residue 71 and name O ) | 2.80 | 0.30 | 0.40 |
| !assign (residue 77 and name HN ) | (residue 73 and name O ) | 1.80 | 0.0 | 0.40 |
| !assign (residue 77 and name N ) | (residue 73 and name O ) | 2.80 | 0.30 | 0.40 |
| assign (residue 78 and name HN ) | (residue 74 and name O ) | 1.80 | 0.0 | 0.40 |
| assign (residue 78 and name N ) | (residue 74 and name O ) | 2.80 | 0.30 | 0.40 |
| assign (residue 79 and name HN ) | (residue 75 and name O ) | 1.80 | 0.0 | 0.40 |
| assign (residue 79 and name N ) | (residue 75 and name O ) | 2.80 | 0.30 | 0.40 |
| !assign (residue 80 and name HN ) | (residue 76 and name O ) | 1.80 | 0.0 | 0.40 |
| !assign (residue 80 and name N ) | (residue 76 and name O ) | 2.80 | 0.30 | 0.40 |
| assign (residue 81 and name HN ) | (residue 77 and name O ) | 1.80 | 0.0 | 0.40 |
| assign (residue 81 and name N ) | (residue 77 and name O ) | 2.80 | 0.30 | 0.40 |
| assign (residue 82 and name HN ) | (residue 78 and name O ) | 1.80 | 0.0 | 0.40 |
| assign (residue 82 and name N ) | (residue 78 and name O ) | 2.80 | 0.30 | 0.40 |

!Helix C

| | | | | |
|---|---|---|---|---|
| assign (residue 102 and name HN ) | (residue 98 and name O ) | 1.80 | 0.0 | 0.40 |
| assign (residue 102 and name N ) | (residue 98 and name O ) | 2.80 | 0.30 | 0.40 |
| assign (residue 103 and name HN ) | (residue 99 and name O ) | 1.80 | 0.0 | 0.40 |
| assign (residue 103 and name N ) | (residue 99 and name O ) | 2.80 | 0.30 | 0.40 |
| assign (residue 104 and name HN ) | (residue 100 and name O ) | 1.80 | 0.0 | 0.40 |
| assign (residue 104 and name N ) | (residue 100 and name O ) | 2.80 | 0.30 | 0.40 |
| assign (residue 105 and name HN ) | (residue 101 and name O ) | 1.80 | 0.0 | 0.40 |
| assign (residue 105 and name N ) | (residue 101 and name O ) | 2.80 | 0.30 | 0.40 |

TABLE 5

Atomic Structure Coordinates of the
Free Form of the P/CAF Bromodomain

REMARK FILENAME= "/bloch2/chris/BROMO_XPLOR_ARIA32/structures/its/brd_187.pdb"
REMARK initial random number seed: 1.342676E+11
REMARK --------------------------------------------------------------------------------
REMARK overall, bonds, angles, improper, vdw, noe, cdih
REMARK energies: 157.923, 9.10626, 73.1523, 0, 23.1819, 36.4277, 0.228429
REMARK --------------------------------------------------------------------------------
REMARK bonds, angles, impropers, noe, cdih
REMARK rms-dev,: 2.1641968-03, 0.165411, 50.3111, 1.418985E−02, 0.263503
REMARK --------------------------------------------------------------------------------
REMARK noe, cdih
REMARK violations.: 2, 0
REMARK --------------------------------------------------------------------------------
REMARK DATE: 29-Nov.-98 06:51:33 created by user:

| ATOM | 1 | CA | GLY | 1 | 27.208 | 16.825 | −6.349 | 1.00 | 0.00 |
|---|---|---|---|---|---|---|---|---|---|
| ATOM | 2 | HA1 | GLY | 1 | 26.763 | 14.827 | −6.369 | 1.00 | 0.00 |
| ATOM | 3 | HA2 | GLY | 1 | 26.041 | 17.914 | −6.357 | 1.00 | 0.00 |
| ATOM | 4 | C | GLY | 1 | 27.720 | 15.412 | −6.490 | 1.00 | 0.00 |
| ATOM | 5 | O | GLY | 1 | 28.656 | 15.263 | −7.438 | 1.00 | 0.00 |
| ATOM | 6 | N | GLY | 1 | 26.194 | 17.289 | −7.337 | 1.00 | 0.00 |
| ATOM | 7 | HT1 | GLY | 1 | 26.586 | 18.049 | −7.923 | 1.00 | 0.00 |
| ATOM | 8 | HT2 | GLY | 1 | 25.350 | 17.641 | −6.843 | 1.00 | 0.00 |
| ATOM | 9 | HT3 | GLY | 1 | 25.914 | 16.498 | −7.955 | 1.00 | 0.00 |
| ATOM | 10 | N | SER | 2 | 27.113 | 14.431 | −6.024 | 1.00 | 0.00 |
| ATOM | 11 | HN | SER | 2 | 26.376 | 14.625 | −5.409 | 1.00 | 0.00 |
| ATOM | 12 | CA | SER | 2 | 27.516 | 13.044 | −6.226 | 1.00 | 0.00 |
| ATOM | 13 | HA | SER | 2 | 28.481 | 13.047 | −6.712 | 1.00 | 0.00 |
| ATOM | 14 | CB | SER | 2 | 27.638 | 12.329 | −4.878 | 1.00 | 0.00 |
| ATOM | 15 | HB1 | SER | 2 | 26.904 | 12.729 | −4.193 | 1.00 | 0.00 |
| ATOM | 16 | HB2 | SER | 2 | 27.462 | 11.373 | −5.017 | 1.00 | 0.00 |
| ATOM | 17 | OG | SER | 2 | 28.927 | 12.508 | −4.319 | 1.00 | 0.00 |
| ATOM | 18 | HG | SER | 2 | 29.571 | 12.014 | −4.832 | 1.00 | 0.00 |
| ATOM | 19 | C | SER | 2 | 26.919 | 12.308 | −7.114 | 1.00 | 0.00 |
| ATOM | 20 | O | SER | 2 | 25.320 | 12.288 | −6.835 | 1.00 | 0.00 |
| ATOM | 21 | N | HIS | 3 | 27.022 | 11.698 | −8.183 | 1.00 | 0.00 |
| ATOM | 22 | HN | HIS | 3 | 27.986 | 11.747 | −8.351 | 1.00 | 0.00 |
| ATOM | 23 | CA | HIS | 3 | 26.173 | 10.955 | −9.106 | 1.00 | 0.00 |
| ATOM | 24 | HA | HIS | 3 | 25.197 | 11.295 | −8.967 | 1.00 | 0.00 |
| ATOM | 25 | CB | HIS | 3 | 26.594 | 11.222 | −10.553 | 1.00 | 0.00 |
| ATOM | 26 | HB1 | HIS | 3 | 26.616 | 12.288 | −10.723 | 1.00 | 0.00 |
| ATOM | 27 | HB2 | HIS | 3 | 27.581 | 10.814 | −10.714 | 1.00 | 0.00 |
| ATOM | 28 | CG | HIS | 3 | 25.671 | 10.612 | −11.561 | 1.00 | 0.00 |
| ATOM | 29 | ND1 | HIS | 3 | 25.965 | 10.494 | −12.900 | 1.00 | 0.00 |
| ATOM | 30 | HD1 | HIS | 3 | 26.820 | 10.790 | −13.320 | 1.00 | 0.00 |
| ATOM | 31 | CD2 | HIS | 3 | 24.433 | 10.080 | −11.420 | 1.00 | 0.00 |
| ATOM | 32 | HD2 | HIS | 3 | 23.870 | 10.003 | −10.501 | 1.00 | 0.00 |
| ATOM | 33 | CE1 | HIS | 3 | 24.981 | 9.918 | −13.537 | 1.00 | 0.00 |
| ATOM | 34 | HE1 | HIS | 3 | 24.945 | 9.698 | −14.594 | 1.00 | 0.00 |
| ATOM | 35 | NE2 | HIS | 3 | 24.028 | 9.658 | −12.662 | 1.00 | 0.00 |
| ATOM | 36 | HE2 | HIS | 3 | 23.171 | 9.230 | −12.868 | 1.00 | 0.00 |
| ATOM | 37 | C | HIS | 3 | 26.233 | 9.459 | −8.817 | 1.00 | 0.00 |
| ATOM | 38 | O | HIS | 3 | 26.214 | 8.638 | −9.734 | 1.00 | 0.00 |
| ATOM | 39 | N | MET | 4 | 26.305 | 9.111 | −7.536 | 1.00 | 0.00 |
| ATOM | 40 | HN | MET | 4 | 26.314 | 9.811 | −6.850 | 1.00 | 0.00 |
| ATOM | 41 | CA | MET | 4 | 26.364 | 7.713 | −7.120 | 1.00 | 0.00 |
| ATOM | 42 | HA | MET | 4 | 26.144 | 7.105 | −7.998 | 1.00 | 0.00 |
| ATOM | 43 | CB | MET | 4 | 27.755 | 7.374 | −6.591 | 1.00 | 0.00 |
| ATOM | 44 | HB1 | MET | 4 | 28.456 | 8.117 | −6.944 | 1.00 | 0.00 |
| ATOM | 45 | HB2 | MET | 4 | 27.730 | 7.400 | −5.512 | 1.00 | 0.00 |
| ATOM | 46 | CG | MET | 4 | 28.254 | 6.005 | −7.024 | 1.00 | 0.00 |
| ATOM | 47 | HG1 | MET | 4 | 27.433 | 5.306 | −6.972 | 1.00 | 0.00 |
| ATOM | 48 | HG2 | MET | 4 | 28.606 | 6.071 | −8.043 | 1.00 | 0.00 |
| ATOM | 49 | SD | MET | 4 | 29.597 | 5.394 | −5.988 | 1.00 | 0.00 |
| ATOM | 50 | CE | MET | 4 | 28.922 | 3.825 | −5.449 | 1.00 | 0.00 |
| ATOM | 51 | HE1 | MET | 4 | 29.243 | 3.623 | −4.416 | 1.00 | 0.00 |
| ATOM | 52 | HE2 | MET | 4 | 29.273 | 3.039 | −6.102 | 1.00 | 0.00 |
| ATOM | 53 | HE3 | MET | 4 | 27.843 | 1.866 | −5.481 | 1.00 | 0.00 |
| ATOM | 54 | C | MET | 4 | 25.310 | 7.413 | −6.067 | 1.00 | 0.00 |
| ATOM | 55 | O | MET | 4 | 25.333 | 7.983 | −4.977 | 1.00 | 0.00 |
| ATOM | 56 | N | SER | 5 | 24.386 | 6.517 | −6.398 | 1.00 | 0.00 |
| ATOM | 57 | HN | SER | 5 | 24.422 | 6.098 | −7.283 | 1.00 | 0.00 |
| ATOM | 58 | CA | SER | 5 | 23.321 | 6.141 | −5.476 | 1.00 | 0.00 |
| ATOM | 59 | HA | SER | 5 | 23.780 | 5.750 | −4.580 | 1.00 | 0.00 |
| ATOM | 60 | CB | SER | 5 | 22.479 | 7.366 | −5.111 | 1.00 | 0.00 |
| ATOM | 61 | HB1 | SER | 5 | 22.188 | 7.882 | −6.014 | 1.00 | 0.00 |
| ATOM | 62 | HB2 | SER | 5 | 23.062 | 8.029 | −4.490 | 1.00 | 0.00 |
| ATOM | 63 | OG | SER | 5 | 21.309 | 6.990 | −4.405 | 1.00 | 0.00 |
| ATOM | 64 | HG | SER | 5 | 21.060 | 7.693 | −3.800 | 1.00 | 0.00 |

TABLE 5-continued

Atomic Structure Coordinates of the
Free Form of the P/CAF Bromodomain

| ATOM | 65 | C | SER | 5 | 22.431 | 5.062 | −6.084 | 1.00 | 0.00 |
|---|---|---|---|---|---|---|---|---|---|
| ATOM | 66 | O | SER | 5 | 21.471 | 5.362 | −6.794 | 1.00 | 0.00 |
| ATOM | 67 | N | LYS | 6 | 22.756 | 3.805 | −5.800 | 1.00 | 0.00 |
| ATOM | 68 | HN | LYS | 6 | 23.532 | 3.630 | −5.228 | 1.00 | 0.00 |
| ATOM | 69 | CA | LYS | 6 | 21.987 | 2.680 | −6.319 | 1.00 | 0.00 |
| ATOM | 70 | HA | LYS | 6 | 21.642 | 2.942 | −7.308 | 1.00 | 0.00 |
| ATOM | 71 | CB | LYS | 6 | 22.869 | 1.433 | −6.409 | 1.00 | 0.00 |
| ATOM | 72 | HB1 | LYS | 6 | 22.266 | 0.563 | −6.192 | 1.00 | 0.00 |
| ATOM | 73 | HB2 | LYS | 6 | 23.655 | 1.508 | −5.673 | 1.00 | 0.00 |
| ATOM | 74 | CG | LYS | 6 | 23.510 | 1.238 | −7.773 | 1.00 | 0.00 |
| ATOM | 75 | HG1 | LYS | 6 | 24.045 | 2.136 | −8.041 | 1.00 | 0.00 |
| ATOM | 76 | HG2 | LYS | 6 | 24.201 | 0.409 | −7.721 | 1.00 | 0.00 |
| ATOM | 77 | CD | LYS | 6 | 22.469 | 0.947 | −8.842 | 1.00 | 0.00 |
| ATOM | 78 | HD1 | LYS | 6 | 21.794 | 1.787 | −8.911 | 1.00 | 0.00 |
| ATOM | 79 | HD2 | LYS | 6 | 22.970 | 0.804 | −9.788 | 1.00 | 0.00 |
| ATOM | 80 | CE | LYS | 6 | 21.669 | −0.304 | −8.514 | 1.00 | 0.00 |
| ATOM | 81 | HE1 | LYS | 6 | 21.107 | −0.129 | −7.608 | 1.00 | 0.00 |
| ATOM | 82 | HE2 | LYS | 6 | 20.987 | −0.501 | −9.327 | 1.00 | 0.00 |
| ATOM | 83 | NZ | LYS | 6 | 22.548 | −1.489 | −8.317 | 1.00 | 0.00 |
| ATOM | 84 | HZ1 | LYS | 6 | 23.320 | −1.481 | −9.014 | 1.00 | 0.00 |
| ATOM | 85 | HZ2 | LYS | 6 | 21.999 | −2.365 | −8.435 | 1.00 | 0.00 |
| ATOM | 86 | HZ3 | LYS | 6 | 22.958 | −1.476 | −7.362 | 1.00 | 0.00 |
| ATOM | 87 | C | LYS | 6 | 20.776 | 2.397 | −5.436 | 1.00 | 0.00 |
| ATOM | 88 | O | LYS | 6 | 20.863 | 1.638 | −4.471 | 1.00 | 0.00 |
| ATOM | 89 | N | GLU | 7 | 19.646 | 3.011 | −5.771 | 1.00 | 0.00 |
| ATOM | 90 | HN | GLU | 7 | 19.637 | 3.606 | −4.992 | 1.00 | 0.00 |
| ATOM | 91 | CA | GLU | 7 | 18.420 | 2.829 | −5.005 | 1.00 | 0.00 |
| ATOM | 92 | HA | GLU | 7 | 18.531 | 1.926 | −4.418 | 1.00 | 0.00 |
| ATOM | 93 | CB | GLU | 7 | 18.200 | 4.011 | −4.064 | 1.00 | 0.00 |
| ATOM | 94 | HB | GLU | 7 | 18.505 | 4.915 | −4.567 | 1.00 | 0.00 |
| ATOM | 95 | HB2 | GLU | 7 | 17.148 | 4.078 | −3.828 | 1.00 | 0.00 |
| ATOM | 96 | CO | GLU | 7 | 18.979 | 3.904 | −2.761 | 1.00 | 0.00 |
| ATOM | 97 | HG1 | GLU | 7 | 19.744 | 3.154 | −2.876 | 1.00 | 0.00 |
| ATOM | 98 | HG2 | GLU | 7 | 19.430 | 4.860 | −2.948 | 1.00 | 0.00 |
| ATOM | 99 | CO | GLU | 7 | 18.095 | 3.519 | −1.989 | 1.00 | 0.00 |
| ATOM | 100 | OE1 | GLU | 7 | 17.118 | 4.243 | −1.312 | 1.00 | 0.00 |
| ATOM | 101 | OE2 | GLU | 7 | 18.383 | 2.483 | −0.947 | 1.00 | 0.00 |
| ATOM | 102 | C | GLU | 7 | 17.215 | 2.662 | −5.928 | 1.00 | 0.00 |
| ATOM | 103 | O | GLU | 7 | 16.278 | 3.461 | −5.886 | 1.00 | 0.00 |
| ATOM | 104 | N | PRO | 8 | 17.218 | 1.617 | −6.772 | 1.00 | 0.00 |
| ATOM | 105 | CA | PRO | 8 | 16.120 | 1.352 | −7.702 | 1.00 | 0.00 |
| ATOM | 106 | HA | PRO | 8 | 15.785 | 2.256 | −8.189 | 1.00 | 0.00 |
| ATOM | 107 | CB | PRO | 8 | 16.760 | 0.419 | −8.727 | 1.00 | 0.00 |
| ATOM | 108 | HB1 | PRO | 8 | 17.200 | 1.002 | −9.523 | 1.00 | 0.00 |
| ATOM | 109 | HB2 | PRO | 8 | 16.011 | −0.245 | −9.130 | 1.00 | 0.00 |
| ATOM | 110 | CG | PRO | 8 | 17.796 | −0.327 | −7.958 | 1.00 | 0.00 |
| ATOM | 111 | HG1 | PRO | 8 | 17.357 | −1.209 | −7.908 | 1.00 | 0.00 |
| ATOM | 112 | HG2 | PRO | 8 | 18.607 | −0.608 | −8.414 | 1.00 | 0.00 |
| ATOM | 113 | CO | PRO | 8 | 18.294 | 0.613 | −6.869 | 1.00 | 0.00 |
| ATOM | 114 | HD1 | PRO | 8 | 18.429 | 0.085 | −5.936 | 1.00 | 0.00 |
| ATOM | 115 | HD2 | PRO | 8 | 19.220 | 1.076 | −7.197 | 1.00 | 0.00 |
| ATOM | 116 | C | PRO | 8 | 14.938 | 0.669 | −7.021 | 1.00 | 0.00 |
| ATOM | 117 | O | PRO | 8 | 13.782 | 0.924 | −7.360 | 1.00 | 0.00 |
| ATOM | 118 | N | ARG | 9 | 15.236 | −0.196 | −6.057 | 1.00 | 0.00 |
| ATOM | 119 | HN | ARG | 9 | 16.176 | −0.357 | −5.833 | 1.00 | 0.00 |
| ATOM | 120 | CA | ARG | 9 | 14.199 | −0.917 | −5.328 | 1.00 | 0.00 |
| ATOM | 121 | HA | ARG | 9 | 13.522 | −0.189 | −4.906 | 1.00 | 0.00 |
| ATOM | 122 | CB | ARG | 9 | 13.421 | −1.630 | −6.279 | 1.00 | 0.00 |
| ATOM | 123 | HB1 | ARG | 9 | 12.812 | −2.904 | −5.695 | 1.00 | 0.00 |
| ATOM | 124 | HB2 | ARG | 9 | 12.778 | −1.222 | −6.898 | 1.00 | 0.00 |
| ATOM | 125 | CG | ARG | 9 | 14.313 | −2.661 | −7.188 | 1.00 | 0.00 |
| ATOM | 126 | HG1 | ARG | 9 | 14.295 | −2.236 | −8.181 | 1.00 | 0.00 |
| ATOM | 127 | HG2 | ARG | 9 | 15.322 | −2.640 | −6.801 | 1.00 | 0.00 |
| ATOM | 128 | CD | ARG | 9 | 13.843 | −4.106 | −7.262 | 1.00 | 0.00 |
| ATOM | 129 | HD1 | ARG | 9 | 13.831 | −4.518 | −6.264 | 1.00 | 0.00 |
| ATOM | 130 | HD2 | ARG | 9 | 12.844 | −4.125 | −7.671 | 1.00 | 0.00 |
| ATOM | 131 | NE | ARG | 9 | 14.714 | −4.926 | −8.102 | 1.00 | 0.00 |
| ATOM | 132 | HE | ARG | 9 | 15.302 | −4.464 | −8.735 | 1.00 | 0.00 |
| ATOM | 133 | CZ | ARG | 9 | 14.745 | −6.255 | −8.093 | 1.00 | 0.00 |
| ATOM | 134 | NH1 | ARG | 9 | 13.960 | −6.908 | −7.208 | 1.00 | 0.00 |
| ATOM | 135 | HH11 | ARG | 9 | 13.342 | −6.401 | −6.606 | 1.00 | 0.00 |
| ATOM | 136 | HH12 | ARG | 9 | 13.985 | −7.907 | −7.172 | 1.00 | 0.00 |
| ATOM | 137 | NH2 | ARG | 9 | 15.563 | −6.932 | −8.850 | 1.00 | 0.00 |
| ATOM | 138 | HH21 | ARG | 9 | 16.157 | −6.444 | −9.489 | 1.00 | 0.00 |
| ATOM | 139 | HH22 | ARG | 9 | 15.585 | −7.931 | −8.810 | 1.00 | 0.00 |
| ATOM | 140 | C | ARG | 9 | 14.800 | −1.744 | −4.196 | 1.00 | 0.00 |
| ATOM | 141 | O | ARG | 9 | 14.421 | −2.897 | −3.991 | 1.00 | 0.00 |

TABLE 5-continued

Atomic Structure Coordinates of the
Free Form of the P/CAF Bromodomain

| ATOM | 142 | N    | ASP | 10 | 15.732 | −1.144 | −3.458 | 1.00 | 0.00 |
|------|-----|------|-----|----|--------|--------|--------|------|------|
| ATOM | 143 | HN   | ASP | 10 | 15.988 | −0.223 | −3.673 | 1.00 | 0.00 |
| ATOM | 144 | CA   | ASP | 10 | 16.393 | −1.824 | −2.345 | 1.00 | 0.00 |
| ATOM | 145 | HA   | ASP | 10 | 17.087 | −2.540 | −2.760 | 1.00 | 0.00 |
| ATOM | 146 | CB   | ASP | 10 | 17.169 | −0.813 | −1.497 | 1.00 | 0.00 |
| ATOM | 147 | HB1  | ASP | 10 | 17.594 | −0.061 | −2.146 | 1.00 | 0.00 |
| ATOM | 148 | HB2  | ASP | 10 | 16.490 | −0.341 | −0.802 | 1.00 | 0.00 |
| ATOM | 149 | CG   | ASP | 10 | 18.292 | −1.457 | −0.708 | 1.00 | 0.00 |
| ATOM | 150 | OD1  | ASP | 10 | 18.771 | −2.532 | −1.126 | 1.00 | 0.00 |
| ATOM | 151 | OD2  | ASP | 10 | 18.692 | −0.886 | 0.328  | 1.00 | 0.00 |
| ATOM | 152 | C    | ASP | 10 | 15.383 | −2.565 | −1.468 | 1.00 | 0.00 |
| ATOM | 153 | O    | ASP | 10 | 14.728 | −1.961 | −0.619 | 1.00 | 0.00 |
| ATOM | 154 | N    | PRO | 11 | 15.249 | −3.889 | −1.658 | 1.00 | 0.00 |
| ATOM | 155 | CA   | PRO | 11 | 14.309 | −4.709 | −0.887 | 1.00 | 0.00 |
| ATOM | 156 | HA   | PRO | 11 | 13.311 | −5.297 | −0.920 | 1.00 | 0.00 |
| ATOM | 157 | CB   | PRO | 11 | 14.326 | −6.068 | −1.607 | 1.00 | 0.00 |
| ATOM | 158 | HB1  | PRO | 11 | 13.311 | −6.399 | −1.772 | 1.00 | 0.00 |
| ATOM | 159 | HB2  | PRO | 11 | 14.849 | −6.791 | −0.999 | 1.00 | 0.00 |
| ATOM | 160 | CG   | PRO | 11 | 15.036 | −5.829 | −2.899 | 1.00 | 0.00 |
| ATOM | 161 | HG1  | PRO | 11 | 15.582 | −6.715 | −3.188 | 1.00 | 0.00 |
| ATOM | 162 | HG2  | PRO | 11 | 14.324 | −9.561 | −3.666 | 1.00 | 0.00 |
| ATOM | 163 | CD   | PRO | 11 | 15.981 | −4.692 | −2.646 | 1.00 | 0.00 |
| ATOM | 164 | HD1  | PRO | 11 | 16.155 | −4.133 | −3.552 | 1.00 | 0.00 |
| ATOM | 165 | HD2  | PRO | 11 | 16.911 | −9.096 | −2.237 | 1.00 | 0.00 |
| ATOM | 166 | C    | PRO | 11 | 14.732 | −4.881 | 0.972  | 1.00 | 0.00 |
| ATOM | 167 | O    | PRO | 11 | 13.991 | −9.446 | 1.375  | 1.00 | 0.00 |
| ATOM | 168 | N    | ASP | 12 | 15.926 | −4.397 | 0.912  | 1.00 | 0.00 |
| ATOM | 169 | HN   | ASP | 12 | 16.477 | −3.954 | 0.236  | 1.00 | 0.00 |
| ATOM | 170 | CA   | ASP | 12 | 16.430 | −4.508 | 2.276  | 1.00 | 0.00 |
| ATOM | 171 | HA   | ASP | 12 | 16.402 | −5.551 | 2.554  | 1.00 | 0.00 |
| ATOM | 172 | CB   | ASP | 12 | 17.874 | −4.008 | 2.352  | 1.00 | 0.00 |
| ATOM | 173 | HB1  | ASP | 12 | 18.146 | −3.873 | 3.389  | 1.00 | 0.00 |
| ATOM | 174 | HB2  | ASP | 12 | 17.948 | −3.061 | 1.839  | 1.00 | 0.00 |
| ATOM | 175 | CG   | ASP | 12 | 18.856 | −4.975 | 1.721  | 1.00 | 0.00 |
| ATOM | 176 | OD1  | ASP | 12 | 18.870 | −6.157 | 2.125  | 1.00 | 0.00 |
| ATOM | 177 | OD2  | ASP | 12 | 19.615 | −4.549 | 0.824  | 1.00 | 0.00 |
| ATOM | 178 | C    | ASP | 12 | 15.555 | −3.719 | 3.243  | 1.00 | 0.00 |
| ATOM | 179 | O    | ASP | 12 | 14.689 | −4.282 | 3.913  | 1.00 | 0.00 |
| ATOM | 180 | N    | GLN | 13 | 15.785 | −2.412 | 3.309  | 1.00 | 0.00 |
| ATOM | 181 | HN   | GLN | 13 | 16.486 | −2.020 | 2.744  | 1.00 | 0.00 |
| ATOM | 182 | CA   | GLN | 13 | 15.012 | −1.546 | 4.191  | 1.00 | 0.00 |
| ATOM | 183 | HA   | GLN | 13 | 15.115 | −1.923 | 5.197  | 1.00 | 0.00 |
| ATOM | 184 | CB   | GLN | 13 | 15.550 | −0.115 | 4.134  | 1.00 | 0.00 |
| ATOM | 185 | HB1  | GLN | 13 | 15.055 | 0.411  | 3.331  | 1.00 | 0.00 |
| ATOM | 186 | HB2  | GLN | 13 | 16.610 | −0.149 | 3.931  | 1.00 | 0.00 |
| ATOM | 187 | CG   | GLN | 13 | 15.336 | 0.669  | 5.420  | 1.00 | 0.00 |
| ATOM | 188 | HG1  | GLN | 13 | 15.288 | −0.025 | 6.244  | 1.00 | 0.00 |
| ATOM | 189 | HG2  | GLN | 13 | 14.403 | 1.208  | 5.347  | 1.00 | 0.00 |
| ATOM | 190 | CD   | GLN | 13 | 16.450 | 1.682  | 5.687  | 1.00 | 0.00 |
| ATOM | 191 | OE1  | GLN | 13 | 16.879 | 2.391  | 4.790  | 1.00 | 0.00 |
| ATOM | 192 | HE2  | GLN | 13 | 16.930 | 1.695  | 6.925  | 1.00 | 0.00 |
| ATOM | 193 | HE21 | GLN | 13 | 17.691 | 2.320  | 7.125  | 1.00 | 0.00 |
| ATOM | 194 | HE22 | GLN | 13 | 16.543 | 1.085  | 7.587  | 1.00 | 0.00 |
| ATOM | 195 | C    | GLN | 13 | 13.518 | −1.566 | 3.807  | 1.00 | 0.00 |
| ATOM | 196 | O    | GLN | 13 | 12.658 | −1.499 | 4.666  | 1.00 | 0.00 |
| ATOM | 197 | N    | LEU | 14 | 13.278 | −1.666 | 2.509  | 1.00 | 0.00 |
| ATOM | 198 | HN   | LEU | 14 | 14.025 | −1.723 | 1.877  | 1.00 | 0.00 |
| ATOM | 199 | CA   | LEU | 14 | 11.914 | −1.713 | 1.999  | 1.00 | 0.00 |
| ATOM | 200 | HA   | LEU | 14 | 11.445 | −0.764 | 2.212  | 1.00 | 0.00 |
| ATOM | 201 | CB   | LEU | 14 | 11.939 | −1.932 | 0.481  | 1.00 | 0.00 |
| ATOM | 202 | HB1  | LEU | 14 | 12.218 | −1.001 | 0.012  | 1.00 | 0.00 |
| ATOM | 203 | HB2  | LEU | 14 | 12.702 | −2.664 | 0.261  | 1.00 | 0.00 |
| ATOM | 204 | CG   | LEU | 14 | 10.625 | −2.407 | −0.145 | 1.00 | 0.00 |
| ATOM | 205 | HG   | LEU | 14 | 9.801  | −1.900 | 0.333  | 1.00 | 0.00 |
| ATOM | 206 | CO1  | LEU | 14 | 10.592 | −2.066 | −1.624 | 1.00 | 0.00 |
| ATOM | 207 | HD11 | LEU | 14 | 11.506 | −2.403 | −2.095 | 1.00 | 0.00 |
| ATOM | 208 | HD12 | LEU | 14 | 10.499 | −0.997 | −1.749 | 1.00 | 0.00 |
| ATOM | 209 | HD13 | LEU | 14 | 9.749  | −2.556 | −2.091 | 1.00 | 0.00 |
| ATOM | 210 | CO2  | LEU | 14 | 10.444 | −3.902 | 0.064  | 1.00 | 0.00 |
| ATOM | 211 | HD21 | LEU | 14 | 11.402 | −4.354 | 0.275  | 1.00 | 0.00 |
| ATOM | 212 | HD22 | LEU | 14 | 10.026 | −4.344 | −0.828 | 1.00 | 0.00 |
| ATOM | 213 | HD23 | LEU | 14 | 9.777  | −4.071 | 0.897  | 1.00 | 0.00 |
| ATOM | 214 | C    | LEU | 14 | 11.121 | −2.822 | 2.688  | 1.00 | 0.00 |
| ATOM | 215 | O    | LEU | 14 | 10.019 | −2.595 | 3.188  | 1.00 | 0.00 |
| ATOM | 216 | N    | TYR | 15 | 11.697 | −4.018 | 2.715  | 1.00 | 0.00 |
| ATOM | 217 | HN   | TYR | 15 | 12.579 | −4.131 | 2.303  | 1.00 | 0.00 |
| ATOM | 218 | CA   | TYR | 15 | 11.061 | −5.167 | 3.350  | 1.00 | 0.00 |

TABLE 5-continued

Atomic Structure Coordinates of the Free Form of the P/CAF Bromodomain

| ATOM | 219 | HA | TYR | 15 | 10.125 | −5.357 | 2.843 | 1.00 | 0.00 |
|---|---|---|---|---|---|---|---|---|---|
| ATOM | 220 | CB | TYR | 15 | 11.964 | −6.394 | 3.218 | 1.00 | 0.00 |
| ATOM | 221 | HB1 | TYR | 15 | 12.163 | −6.569 | 2.713 | 1.00 | 0.00 |
| ATOM | 222 | HB2 | TYR | 15 | 12.896 | −6.200 | 3.728 | 1.00 | 0.00 |
| ATOM | 223 | CG | TYR | 15 | 11.374 | −7.659 | 3.798 | 1.00 | 0.00 |
| ATOM | 224 | CD1 | TYR | 15 | 12.076 | −8.408 | 4.734 | 1.00 | 0.00 |
| ATOM | 225 | HD1 | TYR | 15 | 13.051 | −8.070 | 5.053 | 1.00 | 0.00 |
| ATOM | 226 | CD2 | TYR | 15 | 10.121 | −8.111 | 3.402 | 1.00 | 0.00 |
| ATOM | 227 | HD2 | TYR | 15 | 9.564 | −7.543 | 2.471 | 1.00 | 0.00 |
| ATOM | 228 | CE1 | TYR | 15 | 11.542 | −9.565 | 5.268 | 1.00 | 0.00 |
| ATOM | 229 | HE1 | TYR | 15 | 12.102 | −10.132 | 5.998 | 1.00 | 0.00 |
| ATOM | 230 | CE2 | TYR | 15 | 9.582 | −9.269 | 3.929 | 1.00 | 0.00 |
| ATOM | 231 | HE2 | TYR | 15 | 8.606 | −9.604 | 3.610 | 1.00 | 0.00 |
| ATOM | 232 | CZ | TYR | 15 | 10.296 | −9.991 | 4.860 | 1.00 | 0.00 |
| ATOM | 233 | OH | TYR | 15 | 9.761 | −11.145 | 5.388 | 1.00 | 0.00 |
| ATOM | 234 | HH | TYR | 15 | 10.392 | −11.863 | 5.295 | 1.00 | 0.00 |
| ATOM | 235 | C | TYR | 15 | 10.776 | −4.888 | 4.821 | 1.0 | 0.00 |
| ATOM | 236 | O | TYR | 15 | 9.750 | −5.307 | 5.356 | 1.00 | 0.00 |
| ATOM | 237 | N | SER | 16 | 11.694 | −4.181 | 5.471 | 1.00 | 0.00 |
| ATOM | 238 | HN | SER | 16 | 12.487 | −3.869 | 4.989 | 1.00 | 0.00 |
| ATOM | 239 | CA | SER | 16 | 11.535 | −3.836 | 6.878 | 1.00 | 0.00 |
| ATOM | 240 | NA | SER | 16 | 11.318 | −4.746 | 7.420 | 1.00 | 0.00 |
| ATOM | 241 | CB | SER | 16 | 12.824 | −3.220 | 7.425 | 1.00 | 0.00 |
| ATOM | 242 | HB1 | SER | 16 | 13.672 | −3.768 | 7.042 | 1.00 | 0.00 |
| ATOM | 243 | HB2 | SER | 16 | 12.889 | −2.189 | 7.111 | 1.00 | 0.00 |
| ATOM | 244 | OG | SER | 16 | 12.852 | −3.268 | 8.841 | 1.00 | 0.00 |
| ATOM | 245 | HG | SER | 16 | 13.743 | −3.741 | 9.137 | 1.00 | 0.00 |
| ATOM | 246 | C | SER | 16 | 10.373 | −2.867 | 7.061 | 1.00 | 0.00 |
| ATOM | 247 | O | SER | 16 | 9.746 | −2.824 | 8.120 | 1.00 | 0.00 |
| ATOM | 248 | N | THR | 17 | 10.087 | −2.096 | 6.017 | 1.00 | 0.00 |
| ATOM | 249 | HN | THR | 17 | 10.615 | −2.189 | 5.195 | 1.00 | 0.00 |
| ATOM | 250 | CA | THR | 17 | 8.980 | −1.146 | 6.049 | 1.00 | 0.00 |
| ATOM | 251 | HA | THR | 17 | 8.965 | −0.685 | 7.025 | 1.00 | 0.00 |
| ATOM | 252 | CD | THR | 17 | 9.182 | −0.061 | 4.982 | 1.00 | 0.00 |
| ATOM | 253 | HO | THR | 17 | 9.399 | −0.507 | 4.037 | 1.00 | 0.00 |
| ATOM | 254 | OG1 | THR | 17 | 10.278 | 0.771 | 9.316 | 1.00 | 0.00 |
| ATOM | 255 | HG1 | THR | 17 | 10.098 | 1.223 | 6.144 | 1.00 | 0.00 |
| ATOM | 256 | CG2 | THR | 17 | 7.971 | 0.832 | 4.783 | 1.00 | 0.00 |
| ATOM | 257 | HG21 | THR | 17 | 7.078 | 0.224 | 4.720 | 1.00 | 0.00 |
| ATOM | 258 | HG22 | THR | 17 | 8.088 | 1.395 | 3.867 | 1.00 | 0.00 |
| ATOM | 259 | HG23 | THR | 17 | 7.883 | 1.513 | 5.616 | 1.00 | 0.00 |
| ATOM | 260 | C | THR | 17 | 7.662 | −1.866 | 5.821 | 1.00 | 0.00 |
| ATOM | 261 | O | THR | 17 | 6.756 | −1.792 | 6.646 | 1.00 | 0.00 |
| ATOM | 262 | N | LEU | 18 | 7.574 | −2.569 | 4.697 | 1.00 | 0.00 |
| ATOM | 263 | HN | LEU | 18 | 8.339 | −2.578 | 4.083 | 1.00 | 0.00 |
| ATOM | 264 | CA | LEU | 18 | 6.369 | −3.302 | 4.330 | 1.00 | 0.00 |
| ATOM | 265 | HA | LEU | 18 | 5.555 | −2.597 | 4.289 | 1.00 | 0.00 |
| ATOM | 266 | CE | LEU | 18 | 6.550 | −3.928 | 2.955 | 1.00 | 0.00 |
| ATOM | 267 | HE1 | LEU | 18 | 7.307 | −4.694 | 3.026 | 1.00 | 0.00 |
| ATOM | 268 | HE2 | LEU | 18 | 9.619 | −4.389 | 2.661 | 1.00 | 0.00 |
| ATOM | 269 | CG | LEU | 18 | 6.964 | −2.940 | 1.875 | 1.00 | 0.00 |
| ATOM | 270 | HG | LEU | 18 | 7.969 | −2.603 | 2.075 | 1.00 | 0.00 |
| ATOM | 271 | CO1 | LEU | 18 | 6.954 | −3.607 | 0.510 | 1.00 | 0.00 |
| ATOM | 272 | HD11 | LEU | 18 | 7.945 | −3.963 | 0.274 | 1.00 | 0.00 |
| ATOM | 273 | HD12 | LEU | 18 | 6.640 | −2.894 | −0.236 | 1.00 | 0.00 |
| ATOM | 274 | HD13 | LEU | 18 | 6.270 | −4.442 | 0.524 | 1.00 | 0.00 |
| ATOM | 275 | CO2 | LEU | 18 | 6.048 | −1.722 | 1.899 | 1.00 | 0.00 |
| ATOM | 276 | HD21 | LEU | 18 | 5.138 | −1.963 | 2.430 | 1.00 | 0.00 |
| ATOM | 277 | HD22 | LEU | 18 | 5.811 | −1.428 | 0.889 | 1.00 | 0.00 |
| ATOM | 278 | HD23 | LEU | 18 | 6.549 | −0.908 | 2.401 | 1.00 | 0.00 |
| ATOM | 279 | C | LEU | 18 | 6.037 | −4.076 | 5.349 | 1.00 | 0.00 |
| ATOM | 280 | O | LEU | 18 | 4.961 | −4.072 | 9.942 | 1.00 | 0.00 |
| ATOM | 281 | N | LYS | 19 | 6.956 | −5.310 | 9.541 | 1.00 | 0.00 |
| ATOM | 282 | HN | LYS | 19 | 7.802 | −5.262 | 5.048 | 1.00 | 0.00 |
| ATOM | 283 | CA | LYS | 19 | 6.798 | −6.372 | 6.514 | 1.00 | 0.00 |
| ATOM | 284 | HA | LYS | 19 | 5.946 | −6.995 | 6.158 | 1.00 | 0.00 |
| ATOM | 285 | CB | LYS | 19 | 8.029 | −7.225 | 6.608 | 1.00 | 0.00 |
| ATOM | 286 | HB1 | LYS | 19 | 8.522 | −7.243 | 5.674 | 1.00 | 0.00 |
| ATOM | 287 | HB2 | LYS | 19 | 7.748 | −8.232 | 6.897 | 1.00 | 0.00 |
| ATOM | 288 | CG | LYS | 19 | 9.033 | −6.730 | 7.669 | 1.00 | 0.00 |
| ATOM | 289 | HG1 | LYS | 19 | 8.693 | −7.018 | 8.653 | 1.00 | 0.00 |
| ATOM | 290 | HG2 | LYS | 19 | 9.096 | −5.653 | 7.608 | 1.00 | 0.00 |
| ATOM | 291 | CD | LYS | 19 | 10.412 | −7.319 | 7.429 | 1.00 | 0.00 |
| ATOM | 292 | HD1 | LYS | 19 | 10.559 | −7.440 | 6.365 | 1.00 | 0.00 |
| ATOM | 293 | HD2 | LYS | 19 | 11.156 | −6.643 | 7.823 | 1.00 | 0.00 |
| ATOM | 294 | CE | LYS | 19 | 10.567 | −8.671 | 8.106 | 1.00 | 0.00 |
| ATOM | 295 | HE1 | LYS | 19 | 9.987 | −9.401 | 7.560 | 1.00 | 0.00 |

TABLE 5-continued

Atomic Structure Coordinates of the Free Form of the P/CAF Bromodomain

| ATOM | 296 | HE2 | LYS | 19 | 10.193 | −8.598 | 9.117 | 1.00 | 0.00 |
|---|---|---|---|---|---|---|---|---|---|
| ATOM | 297 | N2 | LYS | 19 | 11.988 | −9.115 | 8.146 | 1.00 | 0.00 |
| ATOM | 298 | HZ1 | LYS | 19 | 12.044 | −10.147 | 8.030 | 1.00 | 0.00 |
| ATOM | 299 | HZ2 | LYS | 19 | 12.418 | −8.855 | 9.057 | 1.00 | 0.00 |
| ATOM | 300 | HZ3 | LYS | 19 | 12.526 | −8.661 | 7.380 | 1.00 | 0.00 |
| ATOM | 301 | C | LYS | 19 | 6.349 | −5.772 | 7.863 | 1.00 | 0.00 |
| ATOM | 302 | O | LYS | 19 | 5.624 | −6.390 | 8.646 | 1.00 | 0.00 |
| ATOM | 303 | N | SER | 20 | 6.797 | −4.542 | 8.100 | 1.00 | 0.00 |
| ATOM | 304 | HN | SER | 20 | 7.346 | −4.092 | 7.419 | 1.00 | 0.00 |
| ATOM | 305 | CA | SER | 20 | 6.482 | −3.841 | 9.336 | 1.00 | 0.00 |
| ATOM | 306 | HA | SER | 20 | 6.548 | −4.551 | 10.141 | 1.00 | 0.00 |
| ATOM | 307 | CB | SER | 20 | 7.481 | −2.708 | 9.581 | 1.00 | 0.00 |
| ATOM | 308 | HB1 | SER | 20 | 7.647 | −2.171 | 8.659 | 1.00 | 0.00 |
| ATOM | 309 | HB2 | SER | 20 | 8.416 | −3.123 | 9.929 | 1.00 | 0.00 |
| ATOM | 310 | OG | SER | 20 | 6.996 | −1.801 | 10.556 | 1.00 | 0.00 |
| ATOM | 311 | HG | SER | 20 | 7.552 | −1.841 | 11.337 | 1.00 | 0.00 |
| ATOM | 312 | C | SER | 20 | 5.070 | −3.268 | 9.292 | 1.00 | 0.00 |
| ATOM | 313 | O | SER | 20 | 4.188 | −3.752 | 10.016 | 1.00 | 0.00 |
| ATOM | 314 | N | ILE | 21 | 4.851 | −2.311 | 8.423 | 1.00 | 0.00 |
| ATOM | 315 | HN | ILE | 21 | 5.590 | −1.989 | 7.866 | 1.00 | 0.00 |
| ATOM | 316 | CA | ILE | 21 | 3.531 | −1.717 | 8.268 | 1.00 | 0.00 |
| ATOM | 317 | HA | ILE | 21 | 3.312 | −1.154 | 9.164 | 1.00 | 0.00 |
| ATOM | 318 | CB | ILE | 21 | 3.477 | −0.752 | 7.069 | 1.00 | 0.00 |
| ATOM | 319 | HB | ILE | 21 | 2.442 | −0.564 | 6.839 | 1.00 | 0.00 |
| ATOM | 320 | CG1 | ILE | 21 | 4.155 | −1.368 | 5.846 | 1.00 | 0.00 |
| ATOM | 321 | HGI1 | ILE | 21 | 4.819 | −0.640 | 5.404 | 1.00 | 0.00 |
| ATOM | 322 | HGI2 | ILE | 21 | 4.723 | −2.227 | 6.152 | 1.00 | 0.00 |
| ATOM | 323 | CO2 | ILE | 21 | 4.130 | 0.573 | 7.427 | 1.00 | 0.00 |
| ATOM | 324 | HG21 | ILE | 21 | 3.498 | 1.385 | 7.101 | 1.00 | 0.00 |
| ATOM | 325 | HG22 | ILE | 21 | 5.089 | 0.644 | 6.935 | 1.00 | 0.00 |
| ATOM | 326 | HG23 | ILE | 21 | 4.268 | 0.630 | 8.496 | 1.00 | 0.00 |
| ATOM | 327 | CD1 | ILE | 21 | 3.185 | −1.819 | 4.782 | 1.00 | 0.00 |
| ATOM | 328 | HD11 | ILE | 21 | 2.645 | −2.684 | 5.134 | 1.00 | 0.00 |
| ATOM | 329 | HD12 | ILE | 21 | 3.729 | −2.074 | 3.885 | 1.00 | 0.00 |
| ATOM | 330 | HD13 | ILE | 21 | 2.489 | −1.022 | 4.568 | 1.00 | 0.00 |
| ATOM | 331 | C | ILE | 21 | 2.472 | −2.801 | 8.095 | 1.00 | 0.00 |
| ATOM | 332 | O | ILE | 21 | 1.487 | −2.838 | 8.823 | 1.00 | 0.00 |
| ATOM | 333 | N | LEU | 22 | 2.710 | −3.715 | 7.164 | 1.00 | 0.00 |
| ATOM | 334 | HN | LEU | 22 | 3.520 | −3.646 | 6.622 | 1.00 | 0.00 |
| ATOM | 335 | CA | LEU | 22 | 1.785 | −4.812 | 6.920 | 1.00 | 0.00 |
| ATOM | 336 | HA | LEU | 22 | 0.864 | −4.390 | 6.544 | 1.00 | 0.00 |
| ATOM | 337 | CB | LRU | 22 | 2.361 | −5.772 | 5.874 | 1.00 | 0.00 |
| ATOM | 338 | HB1 | LEU | 22 | 1.785 | −6.685 | 9.900 | 1.00 | 0.00 |
| ATOM | 339 | HB2 | LEU | 22 | 3.379 | −6.000 | 6.147 | 1.00 | 0.00 |
| ATOM | 340 | CG | LEU | 22 | 2.360 | −5.245 | 4.439 | 1.00 | 0.00 |
| ATOM | 341 | HG | LEU | 22 | 3.054 | −4.421 | 4.365 | 1.00 | 0.00 |
| ATOM | 342 | CD1 | LEU | 22 | 2.815 | −6.329 | 3.474 | 1.00 | 0.00 |
| ATOM | 343 | HD11 | LEU | 22 | 2.102 | −6.416 | 2.668 | 1.00 | 0.00 |
| ATOM | 344 | HD12 | LEU | 22 | 2.885 | −7.271 | 3.997 | 1.00 | 0.00 |
| ATOM | 345 | HD13 | LEU | 22 | 3.783 | −6.069 | 3.071 | 1.00 | 0.00 |
| ATOM | 346 | CD2 | LEU | 22 | 0.980 | −4.733 | 4.097 | 1.00 | 0.00 |
| ATOM | 347 | HD21 | LEU | 22 | 0.926 | −3.671 | 4.243 | 1.00 | 0.00 |
| ATOM | 348 | HD22 | LEU | 22 | 0.234 | −5.242 | 4.647 | 1.00 | 0.00 |
| ATOM | 349 | HD23 | LEU | 22 | 0.803 | −4.924 | 3.008 | 1.00 | 0.00 |
| ATOM | 350 | C | LEU | 22 | 1.493 | −5.568 | 8.214 | 1.00 | 0.00 |
| ATOM | 351 | O | LEU | 22 | 0.340 | −5.862 | 8.525 | 1.00 | 0.00 |
| ATOM | 352 | N | GLN | 23 | 2.546 | −5.868 | 8.971 | 1.00 | 0.00 |
| ATOM | 353 | HN | GLN | 23 | 3.447 | −5.617 | 8.646 | 1.00 | 0.00 |
| ATOM | 354 | CA | GLN | 23 | 2.402 | −6.598 | 10.226 | 1.00 | 0.00 |
| ATOM | 355 | HA | GLN | 23 | 2.066 | −7.596 | 9.989 | 1.00 | 0.00 |
| ATOM | 356 | CB | GLN | 23 | 3.754 | −6.684 | 10.940 | 1.00 | 0.00 |
| ATOM | 357 | HB1 | GLN | 23 | 3.588 | −6.635 | 12.006 | 1.00 | 0.00 |
| ATOM | 358 | HB2 | GLN | 23 | 4.360 | −5.842 | 10.640 | 1.00 | 0.00 |
| ATOM | 359 | CG | GLN | 23 | 4.528 | −7.958 | 10.637 | 1.00 | 0.00 |
| ATOM | 360 | HG1 | GLN | 23 | 4.592 | −8.082 | 9.566 | 1.00 | 0.00 |
| ATOM | 361 | HG2 | GLN | 23 | 5.523 | −7.865 | 11.048 | 1.00 | 0.00 |
| ATOM | 362 | CD | GLN | 23 | 3.875 | −9.191 | 11.231 | 1.00 | 0.00 |
| ATOM | 363 | OE1 | GLN | 23 | 3.304 | −9.141 | 12.320 | 1.00 | 0.00 |
| ATOM | 364 | NE2 | GLN | 23 | 3.958 | −10.308 | 10.517 | 1.00 | 0.00 |
| ATOM | 365 | HE21 | GLN | 23 | 3.545 | −11.120 | 10.879 | 1.00 | 0.00 |
| ATOM | 366 | HE22 | GLN | 23 | 4.429 | −10.275 | 9.658 | 1.00 | 0.00 |
| ATOM | 367 | C | GLN | 23 | 1.374 | −9.941 | 11.151 | 1.00 | 0.00 |
| ATOM | 368 | O | GLN | 23 | 0.462 | −6.604 | 11.646 | 1.00 | 0.00 |
| ATOM | 369 | N | GLN | 24 | 1.542 | −4.645 | 11.404 | 1.00 | 0.00 |
| ATOM | 370 | HN | GLN | 24 | 2.303 | −4.175 | 11.002 | 1.00 | 0.00 |
| ATOM | 371 | CA | GLN | 24 | 0.659 | −3.920 | 12.317 | 1.00 | 0.00 |
| ATOM | 372 | HA | GLN | 24 | 0.414 | −4.980 | 13.142 | 1.00 | 0.00 |

TABLE 5-continued

Atomic Structure Coordinates of the
Free Form of the P/CAF Bromodomain

| ATOM | 373 | CB | GLN | 24 | 1.369 | −2.679 | 12.863 | 1.00 | 0.00 |
|------|-----|------|-----|----|-------|--------|--------|------|------|
| ATOM | 374 | HB1 | GLN | 24 | 2.330 | −2.973 | 13.260 | 1.00 | 0.00 |
| ATOM | 375 | HB2 | GLN | 24 | 0.774 | −2.298 | 13.699 | 1.00 | 0.00 |
| ATOM | 376 | CG | GLN | 24 | 1.996 | −1.602 | 11.817 | 1.00 | 0.00 |
| ATOM | 377 | HG1 | GLN | 24 | 0.680 | −1.044 | 11.689 | 1.00 | 0.00 |
| ATOM | 378 | HG2 | GLN | 24 | 1.860 | −2.077 | 10.885 | 1.00 | 0.00 |
| ATOM | 379 | CD | GLN | 24 | 2.702 | −0.638 | 12.200 | 1.00 | 0.00 |
| ATOM | 380 | OE1 | GLN | 24 | 3.210 | −0.671 | 13.320 | 1.00 | 0.00 |
| ATOM | 381 | NE2 | GLN | 24 | 3.082 | 0.227 | 11.266 | 1.00 | 0.00 |
| ATOM | 382 | HE21 | GLN | 24 | 2.633 | 0.199 | 10.395 | 1.00 | 0.00 |
| ATOM | 383 | HE22 | GLN | 24 | 3.795 | 0.862 | 11.486 | 1.00 | 0.00 |
| ATOM | 384 | C | GLN | 24 | −0.658 | −3.911 | 11.654 | 1.00 | 0.00 |
| ATOM | 385 | G | GLN | 24 | −1.727 | −3.682 | 12.237 | 1.00 | 0.00 |
| ATOM | 386 | N | VSL | 25 | −0.577 | −2.936 | 10.456 | 1.00 | 0.00 |
| ATOM | 387 | HN | VAL | 25 | 0.298 | −2.811 | 10.047 | 1.00 | 0.00 |
| ATOM | 388 | CA | VAL | 25 | −1.769 | −2.477 | 9.740 | 1.00 | 0.00 |
| ATOM | 389 | HA | VAL | 25 | −2.119 | −1.597 | 10.251 | 1.00 | 0.00 |
| ATOM | 390 | CB | VAL | 25 | −1.454 | −2.089 | 8.285 | 1.00 | 0.00 |
| ATOM | 391 | HB | VAL | 25 | −2.344 | −1.670 | 7.845 | 1.00 | 0.00 |
| ATOM | 392 | CG1 | VAL | 25 | −0.364 | −1.025 | 8.239 | 1.00 | 0.00 |
| ATOM | 393 | HG11 | VAL | 25 | −0.774 | −0.102 | 7.858 | 1.00 | 0.00 |
| ATOM | 394 | HG12 | VAL | 25 | 0.404 | −1.358 | 7.591 | 1.00 | 0.00 |
| ATOM | 395 | HG13 | VAL | 25 | 0.024 | −0.863 | 9.234 | 1.00 | 0.00 |
| ATOM | 396 | CG | VAL | 25 | −1.061 | −3.301 | 7.473 | 1.00 | 0.00 |
| ATOM | 397 | HG21 | VAL | 25 | −1.924 | −3.934 | 7.330 | 1.00 | 0.00 |
| ATOM | 398 | HG22 | VAL | 25 | −0.295 | −3.848 | 7.997 | 1.00 | 0.00 |
| ATOM | 399 | HG23 | VAL | 25 | −0.684 | −2.982 | 6.511 | 1.00 | 0.00 |
| ATOM | 400 | C | VAL | 25 | −2.865 | −3.536 | 9.760 | 1.00 | 0.00 |
| ATOM | 401 | O | VAL | 25 | −4.042 | −3.213 | 9.907 | 1.00 | 0.00 |
| ATOM | 402 | N | LYS | 26 | −2.478 | −4.805 | 9.670 | 1.00 | 0.00 |
| ATOM | 403 | HN | LYS | 26 | −1.925 | −9.013 | 9.579 | 1.00 | 0.00 |
| ATOM | 404 | CA | LYS | 26 | −3.448 | −5.893 | 9.728 | 1.00 | 0.00 |
| ATOM | 405 | HA | LYS | 26 | −4.076 | −5.827 | 8.892 | 1.00 | 0.00 |
| ATOM | 406 | CB | LYS | 26 | −2.739 | −7.248 | 9.740 | 1.00 | 0.00 |
| ATOM | 407 | HB1 | LYS | 26 | −2.064 | −7.280 | 10.582 | 1.00 | 0.00 |
| ATOM | 408 | HB2 | LYS | 26 | −0.479 | −8.026 | 9.853 | 1.00 | 0.00 |
| ATOM | 409 | CG | LYS | 26 | −1.940 | −7.530 | 8.479 | 1.00 | 0.00 |
| ATOM | 410 | HG1 | LYS | 26 | −2.552 | −8.102 | 7.797 | 1.00 | 0.00 |
| ATOM | 411 | HG2 | LYS | 26 | −1.665 | −6.591 | 8.020 | 1.00 | 0.00 |
| ATOM | 412 | CD | LYS | 26 | −0.679 | −8.317 | 8.790 | 1.00 | 0.00 |
| ATOM | 413 | HD1 | LYS | 26 | −0.295 | −7.995 | 9.747 | 1.00 | 0.00 |
| ATOM | 414 | HD2 | LYS | 26 | 0.054 | −8.123 | 8.020 | 1.00 | 0.00 |
| ATOM | 415 | CE | LYS | 26 | −0.955 | −9.811 | 8.844 | 1.00 | 0.00 |
| ATOM | 416 | HE1 | LYS | 26 | −0.358 | −10.245 | 9.632 | 1.00 | 0.00 |
| ATOM | 417 | HE2 | LYS | 26 | −2.002 | −9.962 | 9.062 | 1.00 | 0.00 |
| ATOM | 418 | NZ | LYS | 26 | −0.625 | −10.486 | 7.558 | 1.00 | 0.00 |
| ATOM | 419 | HZ1 | LYS | 26 | 0.302 | −10.951 | 7.627 | 1.00 | 0.00 |
| ATOM | 420 | HZ2 | LYS | 26 | −0.595 | −9.790 | 6.787 | 1.00 | 0.00 |
| ATOM | 421 | HZ3 | LYS | 26 | −1.345 | −11.203 | 7.326 | 1.00 | 0.00 |
| ATOM | 422 | C | LYS | 26 | −4.318 | −5.750 | 10.973 | 1.00 | 0.00 |
| ATOM | 423 | O | LYS | 26 | −9.496 | −6.109 | 10.969 | 1.00 | 0.00 |
| ATOM | 424 | N | SER | 27 | −3.724 | −5.203 | 12.029 | 1.00 | 0.00 |
| ATOM | 425 | HN | SER | 27 | −2.783 | −4.928 | 11.957 | 1.00 | 0.00 |
| ATOM | 426 | CA | SER | 27 | −4.407 | −4.970 | 13.281 | 1.00 | 0.00 |
| ATOM | 427 | HA | SER | 27 | −9.407 | −9.436 | 13.209 | 1.00 | 0.00 |
| ATOM | 428 | CB | SER | 27 | −3.669 | −5.589 | 14.452 | 1.00 | 0.00 |
| ATOM | 429 | HB1 | SER | 27 | −2.861 | −4.927 | 14.735 | 1.00 | 0.00 |
| ATOM | 430 | HB2 | SER | 27 | −3.267 | −6.542 | 14.152 | 1.00 | 0.00 |
| ATOM | 431 | OG | SER | 27 | −4.914 | −5.777 | 15.573 | 1.00 | 0.00 |
| ATOM | 432 | HG | SER | 27 | −5.402 | −9.986 | 15.273 | 1.00 | 0.00 |
| ATOM | 433 | C | SER | 27 | −4.643 | −3.481 | 13.919 | 1.00 | 0.00 |
| ATOM | 434 | O | SER | 27 | −4.887 | −3.082 | 14.646 | 1.00 | 0.00 |
| ATOM | 435 | N | HIS | 28 | −4.516 | −2.692 | 12.457 | 1.00 | 0.00 |
| ATOM | 436 | HN | HIS | 28 | −4.367 | −3.088 | 11.578 | 1.00 | 0.00 |
| ATOM | 437 | CA | HIS | 28 | −4.755 | −1.267 | 12.552 | 1.00 | 0.00 |
| ATOM | 438 | HA | HIS | 28 | −4.393 | −4.936 | 13.515 | 1.00 | 0.00 |
| ATOM | 439 | CB | HIS | 28 | −4.006 | −0.912 | 11.456 | 1.00 | 0.00 |
| ATOM | 440 | HB1 | HIS | 28 | −2.948 | −0.428 | 11.622 | 1.00 | 0.00 |
| ATOM | 441 | HB2 | HIS | 28 | −4.266 | −0.930 | 10.496 | 1.00 | 0.00 |
| ATOM | 442 | CG | HIS | 28 | −4.292 | 0.956 | 11.417 | 1.00 | 0.00 |
| ATOM | 443 | ND1 | HIS | 28 | −4.264 | 1.759 | 12.538 | 1.00 | 0.00 |
| ATOM | 444 | HD1 | HIS | 28 | −4.083 | 1.459 | 13.494 | 1.00 | 0.00 |
| ATOM | 445 | CD2 | HIS | 28 | −4.969 | 1.777 | 10.077 | 1.00 | 0.00 |
| ATOM | 446 | HD2 | HIS | 28 | −4.665 | 1.487 | 9.340 | 1.00 | 0.00 |
| ATOM | 447 | CE1 | HIS | 28 | −4.900 | 3.006 | 12.191 | 1.00 | 0.00 |
| ATOM | 448 | HE1 | HIS | 28 | −4.587 | 3.892 | 12.899 | 1.00 | 0.00 |
| ATOM | 449 | HE2 | HIS | 28 | −4.719 | 3.042 | 10.886 | 1.00 | 0.00 |

TABLE 5-continued

Atomic Structure Coordinates of the
Free Form of the P/CAF Bromodomain

| ATOM | 450 | HE3 | HIS | 28 | −4.935 | 3.844 | 10.367 | 1.00 | 0.00 |
|---|---|---|---|---|---|---|---|---|---|
| ATOM | 451 | C | HIS | 28 | −6.246 | −1.009 | 12.480 | 1.00 | 0.00 |
| ATOM | 452 | O | HIS | 28 | −6.982 | −1.724 | 11.800 | 1.00 | 0.00 |
| ATOM | 453 | N | GLN | 29 | −6.690 | −0.007 | 13.241 | 1.00 | 0.00 |
| ATOM | 454 | HN | GLN | 29 | −6.048 | 0.472 | 13.779 | 1.00 | 0.00 |
| ATOM | 455 | CA | GLN | 29 | −8.109 | 0.272 | 13.334 | 1.00 | 0.00 |
| ATOM | 456 | HA | GLN | 29 | −8.640 | −0.668 | 13.358 | 1.00 | 0.00 |
| ATOM | 457 | CB | GLN | 29 | −8.371 | 1.007 | 14.638 | 1.00 | 0.00 |
| ATOM | 458 | HB1 | GLN | 29 | −9.433 | 1.108 | 14.832 | 1.00 | 0.00 |
| ATOM | 459 | HB2 | GLN | 29 | −8.012 | 2.021 | 14.552 | 1.00 | 0.00 |
| ATOM | 460 | CG | GLN | 29 | −7.670 | 0.341 | 15.809 | 1.00 | 0.00 |
| ATOM | 461 | HG1 | GLN | 29 | −7.180 | −0.56 | 15.445 | 1.00 | 0.00 |
| ATOM | 462 | HG2 | GLN | 29 | −6.929 | 1.021 | 16.203 | 1.00 | 0.00 |
| ATOM | 463 | CD | GLN | 29 | −8.622 | −0.040 | 16.925 | 1.00 | 0.00 |
| ATOM | 464 | OE1 | GLN | 29 | −8.364 | 0.234 | 18.097 | 1.00 | 0.00 |
| ATOM | 465 | HE2 | GLN | 29 | −9.730 | −0.676 | 16.566 | 1.00 | 0.00 |
| ATOM | 466 | HE21 | GLN | 29 | −9.870 | −0.861 | 15.613 | 1.00 | 0.00 |
| ATOM | 467 | HE22 | GLN | 29 | −10.363 | −0.935 | 17.267 | 1.00 | 0.00 |
| ATOM | 468 | C | GLN | 29 | −8.607 | 1.069 | 12.132 | 1.00 | 0.00 |
| ATOM | 469 | O | GLN | 29 | −9.794 | 1.378 | 12.034 | 1.00 | 0.00 |
| ATOM | 470 | N | SER | 60 | −7.711 | 1.348 | 11.191 | 1.00 | 0.00 |
| ATOM | 471 | HN | SER | 30 | −6.789 | 1.096 | 11.306 | 1.00 | 0.00 |
| ATOM | 472 | CA | SER | 30 | −8.082 | 2.036 | 9.969 | 1.00 | 0.00 |
| ATOM | 473 | HA | SER | 30 | −9.149 | 2.199 | 9.989 | 1.00 | 0.00 |
| ATOM | 474 | CB | SER | 30 | −7.375 | 3.385 | 9.874 | 1.00 | 0.00 |
| ATOM | 475 | HB1 | SER | 30 | −6.450 | 3.269 | 9.324 | 1.00 | 0.00 |
| ATOM | 476 | HB2 | SER | 30 | −8.013 | 4.090 | 9.362 | 1.00 | 0.00 |
| ATOM | 477 | OG | SER | 30 | −7.079 | 0.891 | 11.163 | 1.00 | 0.00 |
| ATOM | 478 | HG | SER | 30 | −7.871 | 0.870 | 11.705 | 1.00 | 0.00 |
| ATOM | 479 | C | SER | 30 | −7.741 | 1.184 | 8.740 | 1.00 | 0.00 |
| ATOM | 480 | O | SER | 30 | −8.056 | 1.962 | 7.611 | 1.00 | 0.00 |
| ATOM | 481 | N | ALA | 31 | −7.089 | 0.039 | 8.962 | 1.00 | 0.00 |
| ATOM | 482 | HN | ALA | 31 | −6.867 | −0.224 | 9.880 | 1.00 | 0.00 |
| ATOM | 483 | CA | ALA | 31 | −6.726 | −0.855 | 7.868 | 1.00 | 0.00 |
| ATOM | 484 | HA | ALA | 31 | −6.413 | −0.246 | 7.034 | 1.00 | 0.00 |
| ATOM | 485 | CB | ALA | 31 | −5.590 | −1.732 | 8.272 | 1.00 | 0.00 |
| ATOM | 486 | HB1 | ALA | 31 | −5.218 | −2.301 | 7.417 | 1.00 | 0.00 |
| ATOM | 487 | HB2 | ALA | 31 | −5.865 | −2.407 | 9.054 | 1.00 | 0.00 |
| ATOM | 488 | HB3 | ALA | 31 | −4.746 | −1.111 | 8.629 | 1.00 | 0.00 |
| ATOM | 489 | C | ALA | 31 | −7.906 | −1.726 | 7.433 | 1.00 | 0.00 |
| ATOM | 490 | O | ALA | 31 | −7.795 | −2.496 | 6.480 | 1.00 | 0.00 |
| ATOM | 491 | N | TRP | 32 | −9.040 | −1.990 | 8.119 | 1.00 | 0.00 |
| ATOM | 492 | HN | TRP | 32 | −9.072 | −0.974 | 8.879 | 1.00 | 0.00 |
| ATOM | 493 | CA | TRP | 32 | −10.222 | −2.384 | 7.799 | 1.00 | 0.00 |
| ATOM | 494 | HA | TRP | 32 | −9.960 | −3.416 | 7.971 | 1.00 | 0.00 |
| ATOM | 495 | CB | TRP | 32 | −11.389 | −2.030 | 8.736 | 1.00 | 0.00 |
| ATOM | 496 | HB2 | TRP | 32 | −11.167 | −2.390 | 9.730 | 1.00 | 0.00 |
| ATOM | 497 | HB2 | TRP | 32 | −12.289 | −2.507 | 8.377 | 1.00 | 0.00 |
| ATOM | 498 | CG | TRP | 32 | −11.644 | −0.566 | 8.823 | 1.00 | 0.00 |
| ATOM | 499 | CD1 | TRP | 32 | −11.330 | 0.268 | 9.857 | 1.00 | 0.00 |
| ATOM | 500 | HD1 | TRP | 32 | −10.462 | −0.052 | 10.776 | 1.00 | 0.00 |
| ATOM | 501 | CD2 | TRP | 32 | −12.255 | 0.241 | 7.823 | 1.00 | 0.00 |
| ATOM | 502 | NE1 | TRP | 32 | −11.699 | 1.554 | 9.949 | 1.00 | 0.00 |
| ATOM | 503 | HE1 | TRP | 32 | −11.582 | 2.335 | 10.128 | 1.00 | 0.00 |
| ATOM | 504 | CE2 | TRP | 32 | −12.259 | 1.564 | 8.298 | 1.00 | 0.00 |
| ATOM | 505 | CE3 | TRP | 32 | −12.759 | −0.025 | 6.552 | 1.00 | 0.00 |
| ATOM | 506 | HE3 | TRP | 32 | −12.751 | −1.026 | 6.146 | 1.00 | 0.00 |
| ATOM | 507 | CZ2 | TRP | 32 | −12.780 | 2.612 | 7.590 | 1.00 | 0.00 |
| ATOM | 508 | HZ2 | TRP | 32 | −12.798 | 3.627 | 7.923 | 1.00 | 0.00 |
| ATOM | 509 | CZ3 | TRP | 32 | −13.278 | 1.012 | 5.816 | 1.00 | 0.00 |
| ATOM | 510 | HZ3 | TRP | 32 | −13.671 | 0.827 | 4.829 | 1.00 | 0.00 |
| ATOM | 511 | CH2 | TRP | 32 | −13.284 | 2.314 | 6.317 | 1.00 | 0.00 |
| ATOM | 512 | HH2 | TRP | 32 | −13.669 | 3.090 | 5.697 | 1.00 | 0.00 |
| ATOM | 513 | C | TRP | 32 | −10.647 | −2.291 | 6.323 | 1.00 | 0.00 |
| ATOM | 514 | O | TRP | 32 | −11.197 | −3.202 | 5.769 | 1.00 | 0.00 |
| ATOM | 515 | N | PRO | 33 | −10.400 | −1.102 | 5.633 | 1.00 | 0.00 |
| ATOM | 516 | CA | PRO | 33 | −10.776 | −0.964 | 4.229 | 1.00 | 0.00 |
| ATOM | 517 | HA | PRO | 33 | −11.746 | −1.400 | 4.038 | 1.00 | 0.00 |
| ATOM | 518 | CB | PRO | 33 | −10.842 | 0.590 | 3.996 | 1.00 | 0.00 |
| ATOM | 519 | HB1 | PRO | 33 | −10.273 | 0.798 | 3.113 | 1.00 | 0.00 |
| ATOM | 520 | HB2 | PRO | 33 | −11.870 | 0.844 | 3.892 | 1.00 | 0.00 |
| ATOM | 521 | CG | PRO | 33 | −10.257 | 1.205 | 5.213 | 1.00 | 0.00 |
| ATOM | 522 | HG1 | PRO | 33 | −9.438 | 1.839 | 4.913 | 1.00 | 0.00 |
| ATOM | 523 | HG2 | PRO | 33 | −11.008 | 1.791 | 5.713 | 1.00 | 0.00 |
| ATOM | 524 | CD | PRO | 33 | −9.749 | 0.125 | 6.125 | 1.00 | 0.00 |
| ATOM | 525 | HD1 | PRO | 33 | −8.693 | 0.063 | 6.011 | 1.00 | 0.00 |
| ATOM | 526 | HD2 | PRO | 33 | −10.014 | 0.330 | 7.146 | 1.00 | 0.00 |

TABLE 5-continued

Atomic Structure Coordinates of the
Free Form of the P/CAF Bromodomain

| ATOM | 527 | C | PRO | 33 | −9.748 | −1.604 | 3.299 | 1.00 | 0.00 |
|---|---|---|---|---|---|---|---|---|---|
| ATOM | 528 | O | PRO | 33 | −10.097 | −2.161 | 2.299 | 1.00 | 0.00 |
| ATOM | 529 | N | PHE | 34 | −8.481 | −1.522 | 3.688 | 1.00 | 0.00 |
| ATOM | 530 | HN | PHE | 34 | −8.271 | −1.075 | 4.533 | 1.00 | 0.00 |
| ATOM | 531 | CA | PHE | 34 | −7.393 | −2.109 | 2.910 | 1.00 | 0.00 |
| ATOM | 532 | HA | PHE | 34 | −7.546 | −1.870 | 1.872 | 1.00 | 0.00 |
| ATOM | 533 | CB | PHE | 34 | −6.043 | −1.529 | 3.044 | 1.00 | 0.00 |
| ATOM | 534 | HB1 | PHE | 34 | −5.395 | −1.497 | 2.486 | 1.00 | 0.00 |
| ATOM | 535 | HB2 | PHE | 34 | −5.608 | −2.168 | 4.098 | 1.00 | 0.00 |
| ATOM | 536 | CG | PHE | 34 | −6.120 | −0.134 | 3.900 | 1.00 | 0.00 |
| ATOM | 537 | CD1 | PHE | 34 | −6.997 | 0.794 | 3.361 | 1.00 | 0.00 |
| ATOM | 538 | HD1 | PHE | 34 | −7.638 | 0.503 | 2.542 | 1.00 | 0.00 |
| ATOM | 539 | CD2 | PHE | 34 | −5.300 | 0.255 | 4.946 | 1.00 | 0.00 |
| ATOM | 540 | HD2 | PHE | 34 | −4.611 | −0.459 | 5.373 | 1.00 | 0.00 |
| ATOM | 541 | CE1 | PHE | 34 | −7.069 | 2.077 | 3.868 | 1.00 | 0.00 |
| ATOM | 542 | HE1 | PHE | 34 | −7.761 | 2.789 | 3.443 | 1.00 | 0.00 |
| ATOM | 543 | CE2 | PHE | 34 | −5.368 | 1.936 | 5.459 | 1.00 | 0.00 |
| ATOM | 544 | HE2 | PHE | 34 | −4.728 | 1.824 | 6.279 | 1.00 | 0.00 |
| ATOM | 545 | CZ | PHE | 34 | −6.252 | 2.450 | 4.917 | 1.00 | 0.00 |
| ATOM | 546 | HZ | PHE | 34 | −6.304 | 3.453 | 5.314 | 1.00 | 0.00 |
| ATOM | 547 | C | PHE | 34 | −7.400 | −3.624 | 3.053 | 1.00 | 0.00 |
| ATOM | 548 | O | PHE | 34 | −7.293 | −4.349 | 2.065 | 1.00 | 0.00 |
| ATOM | 549 | N | MET | 35 | −7.543 | −4.100 | 4.285 | 1.00 | 0.00 |
| ATOM | 550 | HN | MET | 35 | −7.635 | −3.476 | 5.015 | 1.00 | 0.00 |
| ATOM | 551 | CA | MET | 35 | −7.587 | −5.534 | 4.541 | 1.00 | 0.00 |
| ATOM | 552 | HA | MET | 35 | −6.624 | −5.948 | 4.283 | 1.00 | 0.00 |
| ATOM | 553 | CB | MET | 35 | −7.868 | −9.802 | 6.021 | 1.00 | 0.00 |
| ATOM | 554 | HB1 | MET | 35 | −8.472 | −4.998 | 6.413 | 1.00 | 0.00 |
| ATOM | 555 | HB2 | MET | 35 | −8.415 | −6.729 | 6.110 | 1.00 | 0.00 |
| ATOM | 556 | CG | MET | 35 | −6.609 | −5.910 | 6.848 | 1.00 | 0.00 |
| ATOM | 557 | HG1 | MET | 35 | −6.714 | −5.267 | 7.730 | 1.00 | 0.00 |
| ATOM | 558 | HG2 | MET | 35 | −5.766 | −5.582 | 6.278 | 1.00 | 0.00 |
| ATOM | 559 | SD | MET | 35 | −6.296 | −7.591 | 7.437 | 1.00 | 0.00 |
| ATOM | 560 | CE | MET | 35 | −4.848 | −8.011 | 6.470 | 1.00 | 0.00 |
| ATOM | 561 | HE1 | MET | 35 | −4.248 | −8.726 | 7.011 | 1.00 | 0.00 |
| ATOM | 562 | HE2 | MET | 35 | −4.268 | −7.119 | 6.285 | 1.00 | 0.00 |
| ATOM | 563 | HE3 | MET | 35 | −5.157 | −8.441 | 5.529 | 1.00 | 0.00 |
| ATOM | 564 | C | MET | 35 | −8.656 | −6.194 | 3.674 | 1.00 | 0.00 |
| ATOM | 565 | O | MET | 35 | −9.847 | −5.924 | 3.827 | 1.00 | 0.00 |
| ATOM | 566 | N | GLU | 36 | −8.219 | −7.049 | 2.751 | 1.00 | 0.00 |
| ATOM | 567 | HN | GLU | 36 | −7.299 | −7.208 | 2.671 | 1.00 | 0.00 |
| ATOM | 568 | CA | GLU | 36 | −9.128 | −7.729 | 1.829 | 1.00 | 0.00 |
| ATOM | 569 | HA | GLU | 36 | −8.598 | −8.569 | 1.409 | 1.00 | 0.00 |
| ATOM | 570 | CB | GLU | 36 | −10.371 | −8.248 | 2.962 | 1.00 | 0.00 |
| ATOM | 571 | HB1 | GLU | 36 | −11.151 | −7.504 | 2.496 | 1.00 | 0.00 |
| ATOM | 572 | HB2 | GLU | 36 | −10.122 | −8.406 | 3.601 | 1.00 | 0.00 |
| ATOM | 573 | CG | GLU | 36 | −10.907 | −9.553 | 1.996 | 1.00 | 0.00 |
| ATOM | 574 | HG1 | GLU | 36 | −10.073 | −10.192 | 1.748 | 1.00 | 0.00 |
| ATOM | 575 | HG2 | GLU | 36 | −11.473 | −9.338 | 1.102 | 1.00 | 0.00 |
| ATOM | 576 | CO | GLU | 36 | −11.806 | −10.289 | 2.972 | 1.00 | 0.00 |
| ATOM | 577 | OE1 | GLU | 36 | −11.522 | −11.469 | 3.266 | 1.00 | 0.00 |
| ATOM | 578 | OE2 | GLU | 36 | −12.794 | −9.685 | 3.440 | 1.00 | 0.00 |
| ATOM | 579 | C | GLU | 36 | −9.543 | −6.792 | 0.696 | 1.00 | 0.00 |
| ATOM | 580 | O | GLU | 36 | −10.414 | −5.939 | 0.873 | 1.00 | 0.00 |
| ATOM | 581 | N | PRO | 37 | −8.913 | −6.929 | −0.486 | 1.00 | 0.00 |
| ATOM | 582 | CA | PRO | 37 | −9.200 | −6.075 | −1.644 | 1.00 | 0.00 |
| ATOM | 583 | HA | PRO | 37 | −9.135 | −5.029 | −1.386 | 1.00 | 0.00 |
| ATOM | 584 | CB | PRO | 37 | −8.087 | −6.425 | −2.646 | 1.00 | 0.00 |
| ATOM | 585 | HB1 | PRO | 37 | −7.650 | −5.515 | −3.031 | 1.00 | 0.00 |
| ATOM | 586 | HB2 | PRO | 37 | −8.504 | −6.999 | −3.461 | 1.00 | 0.00 |
| ATOM | 587 | CG | PRO | 37 | −7.087 | −7.224 | −1.876 | 1.00 | 0.00 |
| ATOM | 588 | HG1 | PRO | 37 | −6.627 | −7.957 | −2.522 | 1.00 | 0.00 |
| ATOM | 589 | HG2 | PRO | 37 | −6.338 | −6.570 | −1.455 | 1.00 | 0.00 |
| ATOM | 590 | CD | PRO | 37 | −7.857 | −7.904 | −0.784 | 1.00 | 0.00 |
| ATOM | 591 | HD1 | PRO | 37 | −7.229 | −8.071 | 0.077 | 1.00 | 0.00 |
| ATOM | 592 | HD2 | PRO | 37 | −8.276 | −8.834 | −1.137 | 1.00 | 0.00 |
| ATOM | 593 | C | PRO | 37 | −10.569 | −6.357 | −2.254 | 1.00 | 0.00 |
| ATOM | 594 | O | PRO | 37 | −11.467 | −6.866 | −1.584 | 1.00 | 0.00 |
| ATOM | 595 | N | VAL | 38 | −10.720 | −6.015 | −3.531 | 1.00 | 0.00 |
| ATOM | 596 | HN | VAL | 38 | −9.967 | −5.610 | −4.008 | 1.00 | 0.00 |
| ATOM | 597 | CA | VAL | 38 | −11.979 | −6.221 | −4.237 | 1.00 | 0.00 |
| ATOM | 598 | HA | VAL | 38 | −12.777 | −5.845 | −3.614 | 1.00 | 0.00 |
| ATOM | 599 | CB | VAL | 38 | −12.006 | −5.450 | −5.571 | 1.00 | 0.00 |
| ATOM | 600 | HB | VAL | 38 | −11.238 | −9.856 | −6.213 | 1.00 | 0.00 |
| ATOM | 601 | CG1 | VAL | 38 | −11.704 | −3.977 | −5.342 | 1.00 | 0.00 |
| ATOM | 602 | HG11 | VAL | 38 | −12.002 | −3.410 | −6.212 | 1.00 | 0.00 |
| ATOM | 603 | HG12 | VAL | 38 | −10.645 | −3.845 | −5.174 | 1.00 | 0.00 |

TABLE 5-continued

Atomic Structure Coordinates of the
Free Form of the P/CAF Bromodomain

| ATOM | 604 | HG13 | VAL | 38 | −12.290 | −3.628 | −4.479 | 1.00 | 0.00 |
|---|---|---|---|---|---|---|---|---|---|
| ATOM | 605 | CG2 | VAL | 38 | −13.347 | −5.625 | −6.266 | 1.00 | 0.00 |
| ATOM | 606 | HG21 | VAL | 38 | −13.431 | −6.636 | −6.639 | 1.00 | 0.00 |
| ATOM | 607 | HG22 | VAL | 38 | −13.419 | −4.931 | −7.090 | 1.00 | 0.00 |
| ATOM | 608 | HG23 | VAL | 38 | −14.145 | −5.434 | −5.563 | 1.00 | 0.00 |
| ATOM | 609 | C | VAL | 38 | −12.222 | −7.700 | −4.513 | 1.00 | 0.00 |
| ATOM | 610 | O | VAL | 38 | −11.293 | −8.508 | −4.492 | 1.00 | 0.00 |
| ATOM | 611 | N | LYS | 39 | −13.477 | −8.047 | −4.775 | 1.00 | 0.00 |
| ATOM | 612 | HN | LYS | 39 | −14.173 | −7.357 | −4.773 | 1.00 | 0.00 |
| ATOM | 613 | CA | LYS | 39 | −11.850 | −9.431 | −5.053 | 1.00 | 0.00 |
| ATOM | 614 | HA | LYS | 39 | −12.960 | −10.036 | −4.968 | 1.00 | 0.00 |
| ATOM | 615 | CB | LYS | 39 | −14.898 | −9.939 | −4.047 | 1.00 | 0.00 |
| ATOM | 616 | HB1 | LYS | 39 | −15.855 | −9.996 | −4.546 | 1.00 | 0.00 |
| ATOM | 617 | HB2 | LYS | 39 | −14.615 | −10.931 | −3.727 | 1.00 | 0.00 |
| ATOM | 618 | CG | LYS | 39 | −15.065 | −9.072 | −2.804 | 1.00 | 0.00 |
| ATOM | 619 | HG1 | LYS | 39 | −14.989 | −8.033 | −3.086 | 1.00 | 0.00 |
| ATOM | 620 | HG2 | LYS | 39 | −14.283 | −9.319 | −2.099 | 1.00 | 0.00 |
| ATOM | 621 | CD | LYS | 39 | −16.414 | −9.301 | −2.144 | 1.00 | 0.00 |
| ATOM | 622 | HD1 | LYS | 39 | −17.168 | −8.758 | −2.693 | 1.00 | 0.00 |
| ATOM | 623 | HD2 | LYS | 39 | −16.640 | −10.397 | −2.164 | 1.00 | 0.00 |
| ATOM | 624 | CE | LYS | 39 | −16.415 | −8.824 | −0.701 | 1.00 | 0.00 |
| ATOM | 625 | HE1 | LYS | 39 | −16.995 | −9.516 | −0.107 | 1.00 | 0.00 |
| ATOM | 626 | HE2 | LYS | 39 | −15.398 | −8.806 | −0.340 | 1.00 | 0.00 |
| ATOM | 627 | NZ | LYS | 39 | −17.002 | −7.462 | −0.567 | 1.00 | 0.00 |
| ATOM | 628 | HZ1 | LYS | 39 | −17.552 | −7.225 | −1.417 | 1.00 | 0.00 |
| ATOM | 629 | HZ2 | LYS | 39 | −16.246 | −6.758 | −0.448 | 1.00 | 0.00 |
| ATOM | 630 | HZ3 | LYS | 39 | −17.630 | −7.423 | 0.261 | 1.00 | 0.00 |
| ATOM | 631 | C | LYS | 39 | −14.399 | −9.563 | −6.469 | 1.00 | 0.00 |
| ATOM | 632 | O | LYS | 39 | −13.886 | −10.337 | −7.278 | 1.00 | 0.00 |
| ATOM | 633 | N | ARG | 40 | −15.448 | −8.801 | −6.759 | 1.00 | 0.00 |
| ATOM | 634 | HN | ARG | 40 | −15.810 | −8.206 | −6.070 | 1.00 | 0.00 |
| ATOM | 635 | CA | ARG | 40 | −16.078 | −8.826 | −8.074 | 1.00 | 0.00 |
| ATOM | 636 | HA | ARG | 40 | −15.347 | −8.504 | −8.800 | 1.00 | 0.00 |
| ATOM | 637 | CB | ARG | 40 | −16.534 | −10.246 | −8.417 | 1.00 | 0.00 |
| ATOM | 638 | HB1 | ARG | 40 | −15.676 | −10.822 | −8.729 | 1.00 | 0.00 |
| ATOM | 639 | HB2 | ARG | 40 | −17.240 | −10.197 | −9.234 | 1.00 | 0.00 |
| ATOM | 640 | CG | ARG | 40 | −17.198 | −10.968 | −7.256 | 1.00 | 0.00 |
| ATOM | 641 | HG1 | ARG | 40 | −18.190 | −10.565 | −7.115 | 1.00 | 0.00 |
| ATOM | 642 | HG2 | ARG | 40 | −16.612 | −10.809 | −6.363 | 1.00 | 0.00 |
| ATOM | 643 | CD | ARG | 40 | −17.305 | −12.462 | −7.916 | 1.00 | 0.00 |
| ATOM | 644 | HD1 | ARG | 40 | −16.418 | −12.788 | −8.008 | 1.00 | 0.00 |
| ATOM | 645 | HD2 | ARG | 40 | −18.173 | −12.645 | −8.133 | 1.00 | 0.00 |
| ATOM | 646 | NE | ARG | 40 | −17.434 | −13.225 | −6.277 | 1.00 | 0.00 |
| ATOM | 647 | HE | ARG | 40 | −17.683 | −12.705 | −5.466 | 1.00 | 0.00 |
| ATOM | 648 | CZ | ARG | 40 | −17.235 | −14.937 | −6.197 | 1.00 | 0.00 |
| ATOM | 649 | NH1 | ARG | 40 | −16.898 | −15.225 | −7.279 | 1.00 | 0.00 |
| ATOM | 650 | HH11 | ARG | 40 | −16.794 | −14.758 | −8.157 | 1.00 | 0.00 |
| ATOM | 651 | HH12 | ARG | 40 | −16.748 | −16.212 | −7.217 | 1.00 | 0.00 |
| ATOM | 652 | NH2 | ARG | 40 | −17.371 | −15.160 | −5.034 | 1.00 | 0.00 |
| ATOM | 653 | HH21 | ARG | 40 | −17.624 | −14.644 | −4.216 | 1.00 | 0.00 |
| ATOM | 654 | HH22 | ARG | 40 | −17.220 | −16.147 | −4.976 | 1.00 | 0.00 |
| ATOM | 655 | C | ARG | 40 | −17.268 | −7.874 | −8.116 | 1.00 | 0.00 |
| ATOM | 656 | O | ARG | 40 | −17.442 | −7.122 | −9.074 | 1.00 | 0.00 |
| ATOM | 657 | N | THR | 41 | −18.081 | −7.910 | −7.065 | 1.00 | 0.00 |
| ATOM | 658 | HN | THR | 41 | −17.886 | −8.930 | −6.332 | 1.00 | 0.00 |
| ATOM | 659 | CA | THR | 41 | −19.252 | −7.047 | −6.971 | 1.00 | 0.00 |
| ATOM | 660 | HA | THN | 41 | −19.928 | −6.751 | −7.973 | 1.00 | 0.00 |
| ATOM | 661 | CB | THR | 41 | −20.418 | −7.806 | −6.335 | 1.00 | 0.00 |
| ATOM | 662 | HB | THR | 41 | −20.623 | −8.689 | −6.922 | 1.00 | 0.00 |
| ATOM | 663 | OG1 | THR | 41 | −21.586 | −7.003 | −6.313 | 1.00 | 0.00 |
| ATOM | 664 | HG1 | THR | 41 | −21.499 | −6.331 | −5.634 | 1.00 | 0.00 |
| ATOM | 665 | OG2 | THR | 41 | −20.109 | −8.252 | −4.916 | 1.00 | 0.00 |
| ATOM | 666 | HG21 | THR | 41 | −19.793 | −7.409 | −4.335 | 1.00 | 0.00 |
| ATOM | 667 | HG22 | THR | 41 | −19.381 | −9.020 | −4.923 | 1.00 | 0.00 |
| ATOM | 668 | HG23 | THR | 41 | −21.045 | −8.644 | −4.477 | 1.00 | 0.00 |
| ATOM | 669 | C | THR | 41 | −18.940 | −5.797 | −6.155 | 1.00 | 0.00 |
| ATOM | 670 | O | THR | 41 | −19.962 | −4.791 | −6.338 | 1.00 | 0.00 |
| ATOM | 671 | N | GLU | 42 | −17.969 | −9.915 | −5.254 | 1.00 | 0.00 |
| ATOM | 672 | HN | GLU | 42 | −17.511 | −6.776 | −5.156 | 1.00 | 0.00 |
| ATOM | 673 | CA | GLU | 42 | −17.570 | −4.797 | −4.408 | 1.00 | 0.00 |
| ATOM | 674 | HA | GLU | 42 | −18.437 | −4.480 | −3.847 | 1.00 | 0.00 |
| ATOM | 675 | CB | GLU | 42 | −16.478 | −5.238 | −3.432 | 1.00 | 0.00 |
| ATOM | 676 | HB1 | GLU | 42 | −15.513 | −5.015 | −3.864 | 1.00 | 0.00 |
| ATOM | 677 | HB2 | GLU | 42 | −16.556 | −6.304 | −3.279 | 1.00 | 0.00 |
| ATOM | 678 | CG | GLU | 42 | −16.561 | −4.556 | −2.076 | 1.00 | 0.00 |
| ATOM | 679 | HG1 | GLU | 42 | −17.313 | −9.094 | −1.482 | 1.00 | 0.00 |
| ATOM | 680 | HG2 | GLU | 42 | −16.845 | −3.524 | −2.224 | 1.00 | 0.00 |

TABLE 5-continued

Atomic Structure Coordinates of the
Free Form of the P/CAF Bromodomain

| ATOM | 681 | CD | GLU | 42 | −15.246 | −4.592 | −1.323 | 1.00 | 0.00 |
|---|---|---|---|---|---|---|---|---|---|
| ATOM | 682 | OE1 | GLU | 42 | −14.293 | −3.913 | −1.760 | 1.00 | 0.00 |
| ATOM | 683 | OE2 | GLU | 42 | −15.169 | −5.000 | −0.297 | 1.00 | 0.00 |
| ATOM | 684 | C | GLU | 42 | −17.072 | −3.626 | −5.249 | 1.00 | 0.00 |
| ATOM | 685 | O | GLU | 42 | −17.374 | −2.468 | −4.959 | 1.00 | 0.00 |
| ATOM | 686 | N | ALA | 43 | −16.304 | −0.935 | −6.288 | 1.00 | 0.00 |
| ATOM | 687 | HN | ALA | 43 | −16.098 | −4.877 | −6.467 | 1.00 | 0.00 |
| ATOM | 688 | CA | ALA | 43 | −15.762 | −2.908 | −7.171 | 1.00 | 0.00 |
| ATOM | 689 | HA | ALA | 43 | −16.392 | −2.035 | −7.091 | 1.00 | 0.00 |
| ATOM | 690 | CB | ALA | 43 | −14.359 | −2.518 | −6.730 | 1.00 | 0.00 |
| ATOM | 691 | HB1 | ALA | 43 | −14.122 | −3.016 | −5.801 | 1.00 | 0.00 |
| ATOM | 692 | HB2 | ALA | 43 | −14.310 | −1.449 | −6.587 | 1.00 | 0.00 |
| ATOM | 693 | HB3 | ALA | 43 | −13.648 | −2.813 | −7.487 | 1.00 | 0.00 |
| ATOM | 694 | C | ALA | 43 | −15.753 | −3.381 | −8.623 | 1.00 | 0.00 |
| ATOM | 695 | O | ALA | 43 | −14.707 | −3.745 | −9.159 | 1.00 | 0.00 |
| ATOM | 696 | N | PRO | 44 | −16.925 | −3.378 | −9.280 | 1.00 | 0.00 |
| ATOM | 697 | CA | PRO | 44 | −17.051 | −3.815 | −10.673 | 1.00 | 0.00 |
| ATOM | 698 | HA | PRO | 44 | −16.945 | −4.794 | −10.841 | 1.00 | 0.00 |
| ATOM | 699 | CB | PRO | 44 | −18.558 | −4.006 | −10.840 | 1.00 | 0.00 |
| ATOM | 700 | HB1 | PRO | 44 | −18.842 | −3.787 | −11.859 | 1.00 | 0.00 |
| ATOM | 701 | HB2 | PRO | 44 | −18.824 | −9.024 | −10.597 | 1.00 | 0.00 |
| ATOM | 702 | CG | PRO | 44 | −19.165 | −3.039 | −9.884 | 1.00 | 0.00 |
| ATOM | 703 | HG1 | PRO | 44 | −19.259 | −2.070 | −10.392 | 1.00 | 0.00 |
| ATOM | 704 | HG2 | PRO | 44 | −20.133 | −3.397 | −9.564 | 1.00 | 0.00 |
| ATOM | 705 | CD | PRO | 44 | −18.224 | −2.963 | −8.711 | 1.00 | 0.00 |
| ATOM | 706 | HD1 | PRO | 44 | −18.173 | −1.993 | −8.334 | 1.00 | 0.00 |
| ATOM | 707 | HD2 | PRO | 44 | −18.987 | −3.642 | −7.932 | 1.00 | 0.00 |
| ATOM | 708 | C | PRO | 44 | −16.932 | −2.775 | −11.662 | 1.00 | 0.00 |
| ATOM | 709 | O | PRO | 44 | −16.263 | −3.090 | −12.821 | 1.00 | 0.00 |
| ATOM | 710 | N | GLY | 45 | −16.394 | −1.536 | −11.200 | 1.00 | 0.00 |
| ATOM | 711 | HN | GLY | 45 | −16.627 | −1.340 | −10.268 | 1.00 | 0.00 |
| ATOM | 712 | CA | GLY | 45 | −15.915 | −0.810 | −13.089 | 1.00 | 0.00 |
| ATOM | 713 | HA1 | GLY | 45 | −19.960 | −10.397 | −2.164 | 1.00 | 0.00 |
| ATOM | 714 | HA2 | GLY | 45 | −16.940 | −0.385 | −11.950 | 1.00 | 0.00 |
| ATOM | 715 | C | GLY | 45 | −14.491 | −0.059 | −11.747 | 1.00 | 0.00 |
| ATOM | 716 | O | GLY | 45 | −14.104 | −1.111 | −11.883 | 1.00 | 0.00 |
| ATOM | 717 | N | TYR | 46 | −13.676 | −1.020 | −11.327 | 1.00 | 0.00 |
| ATOM | 718 | HN | TYR | 46 | −14.018 | −1.934 | −11.241 | 1.00 | 0.00 |
| ATOM | 719 | CA | TYR | 46 | −12.282 | −0.748 | −10.995 | 1.00 | 0.00 |
| ATOM | 720 | HA | TYR | 46 | −12.243 | −0.805 | −10.488 | 1.00 | 0.00 |
| ATOM | 721 | CB | TYR | 46 | −11.739 | −1.832 | −10.062 | 1.00 | 0.00 |
| ATOM | 722 | HB1 | TYR | 46 | −10.765 | −2.142 | −10.411 | 1.00 | 0.00 |
| ATOM | 723 | HB2 | TYR | 46 | −12.408 | −2.680 | −10.078 | 1.00 | 0.00 |
| ATOM | 724 | CG | TYR | 46 | −11.595 | −1.382 | −8.625 | 1.00 | 0.00 |
| ATOM | 725 | CD1 | TYR | 46 | −10.623 | −1.931 | −7.799 | 1.00 | 0.00 |
| ATOM | 726 | HD1 | TYR | 46 | −9.964 | −2.690 | −8.196 | 1.00 | 0.00 |
| ATOM | 727 | CD2 | TYR | 46 | −12.402 | −0.408 | −8.095 | 1.00 | 0.00 |
| ATOM | 728 | HD2 | TYR | 46 | −13.194 | 0.029 | −8.724 | 1.00 | 0.00 |
| ATOM | 729 | CE1 | TYR | 46 | −10.487 | −1.922 | −6.486 | 1.00 | 0.00 |
| ATOM | 730 | HE1 | TYR | 46 | −9.725 | −1.960 | −5.859 | 1.00 | 0.00 |
| ATOM | 731 | CE2 | TYR | 46 | −12.301 | −0.007 | −6.783 | 1.00 | 0.00 |
| ATOM | 732 | HE2 | TYR | 46 | −12.964 | −0.766 | −6.389 | 1.00 | 0.00 |
| ATOM | 733 | CZ | TYR | 46 | −11.330 | −0.553 | −5.983 | 1.00 | 0.00 |
| ATOM | 734 | OH | TYR | 46 | −11.199 | −0.143 | −4.676 | 1.00 | 0.00 |
| ATOM | 735 | HH | TYR | 46 | −10.892 | −0.877 | −4.139 | 1.00 | 0.00 |
| ATOM | 736 | C | TYR | 46 | −11.427 | −0.671 | −12.296 | 1.00 | 0.00 |
| ATOM | 737 | O | TYR | 46 | −11.940 | −0.764 | −12.072 | 1.00 | 0.00 |
| ATOM | 738 | N | TYR | 47 | −10.120 | −0.506 | −2.804 | 1.00 | 0.00 |
| ATOM | 739 | HN | TYR | 47 | −9.772 | −0.440 | −11.159 | 1.00 | 0.00 |
| ATOM | 740 | CA | TYR | 47 | −9.189 | −0.421 | −13.195 | 1.00 | 0.00 |
| ATOM | 741 | HA | TYR | 47 | −8.188 | −0.506 | −12.800 | 1.00 | 0.00 |
| ATOM | 742 | CB | TYR | 47 | −9.433 | −1.567 | −14.181 | 1.00 | 0.00 |
| ATOM | 743 | HB1 | TYR | 47 | −10.224 | −1.285 | −14.860 | 1.00 | 0.00 |
| ATOM | 744 | HB2 | TYR | 47 | −8.929 | −1.748 | −14.743 | 1.00 | 0.00 |
| ATOM | 745 | CG | TYR | 47 | −9.833 | −2.862 | −13.914 | 1.00 | 0.00 |
| ATOM | 746 | CD1 | TYR | 47 | −10.796 | −8.715 | −14.109 | 1.00 | 0.00 |
| ATOM | 747 | HD1 | TYR | 47 | −11.188 | −3.443 | −15.057 | 1.00 | 0.00 |
| ATOM | 748 | CD2 | TYR | 47 | −9.290 | −3.229 | −12.290 | 1.00 | 0.00 |
| ATOM | 749 | HD2 | TYR | 47 | −8.972 | −2.974 | −11.818 | 1.00 | 0.00 |
| ATOM | 750 | CE1 | TYR | 47 | −11.124 | −4.899 | −13.496 | 1.00 | 0.00 |
| ATOM | 751 | HE1 | TYR | 47 | −11.843 | −5.550 | −13.971 | 1.00 | 0.00 |
| ATOM | 752 | CE1 | TYR | 47 | −9.693 | −4.411 | −11.674 | 1.00 | 0.00 |
| ATOM | 753 | HE2 | TYR | 47 | −9.219 | −4.679 | −10.722 | 1.00 | 0.00 |
| ATOM | 754 | CZ | TYR | 47 | −10.970 | −9.242 | −12.280 | 1.00 | 0.00 |
| ATOM | 755 | OH | TYR | 47 | −10.934 | −6.421 | −11.671 | 1.00 | 0.00 |
| ATOM | 756 | HH | TYR | 47 | −10.193 | −6.958 | −11.919 | 1.00 | 0.00 |
| ATOM | 757 | C | TYR | 47 | −9.318 | 0.917 | −13.916 | 1.00 | 0.00 |

TABLE 5-continued

Atomic Structure Coordinates of the
Free Form of the P/CAF Bromodomain

| | | | | | | | | | |
|---|---|---|---|---|---|---|---|---|---|
| ATOM | 758 | O | TYR | 47 | −8.360 | 1.686 | −13.992 | 1.00 | 0.00 |
| ATOM | 759 | N | GLU | 48 | −10.904 | 1.184 | −14.451 | 1.00 | 0.00 |
| ATOM | 760 | HN | GLU | 48 | −11.227 | 0.529 | −14.362 | 1.00 | 0.00 |
| ATOM | 761 | CA | GLU | 48 | −10.754 | 2.425 | −15.175 | 1.00 | 0.00 |
| ATOM | 762 | HA | GLU | 48 | −10.103 | 2.441 | −16.037 | 1.00 | 0.00 |
| ATOM | 763 | CB | GLU | 48 | −12.209 | 2.478 | −19.648 | 1.00 | 0.00 |
| ATOM | 764 | HB1 | GLU | 48 | −12.854 | 2.529 | −14.784 | 1.00 | 0.00 |
| ATOM | 765 | HB2 | GLU | 48 | −12.349 | 3.368 | −16.244 | 1.00 | 0.00 |
| ATOM | 766 | CG | GLU | 48 | −12.621 | 1.276 | −16.482 | 1.00 | 0.00 |
| ATOM | 767 | HG1 | GLU | 48 | −12.135 | 1.337 | −17.444 | 1.00 | 0.00 |
| ATOM | 768 | HG2 | GLU | 48 | −12.304 | 0.376 | −15.976 | 1.00 | 0.00 |
| ATOM | 769 | CD | GLU | 48 | −14.120 | 1.204 | −16.702 | 1.00 | 0.00 |
| ATOM | 770 | OE1 | GLU | 48 | −14.858 | 1.919 | −19.994 | 1.00 | 0.00 |
| ATOM | 771 | OE2 | GLU | 48 | −14.554 | 0.433 | −17.584 | 1.00 | 0.00 |
| ATOM | 772 | C | GLU | 48 | −10.445 | 3.639 | −14.306 | 1.00 | 0.00 |
| ATOM | 773 | O | GLU | 48 | −10.136 | 4.716 | −14.815 | 1.00 | 0.00 |
| ATOM | 774 | N | VAL | 49 | −10.929 | 3.459 | −12.992 | 1.00 | 0.00 |
| ATOM | 775 | HN | VAL | 49 | −10.761 | 2.578 | −12.644 | 1.00 | 0.00 |
| ATOM | 776 | CA | VAL | 49 | −10.261 | 4.545 | −12.059 | 1.00 | 0.00 |
| ATOM | 777 | HA | VAL | 49 | −9.905 | 5.392 | −12.624 | 1.00 | 0.00 |
| ATOM | 778 | CB | VAL | 49 | −11.542 | 4.971 | −11.313 | 1.00 | 0.00 |
| ATOM | 779 | HB | VAL | 49 | −12.308 | 5.171 | −12.047 | 1.00 | 0.00 |
| ATOM | 780 | CG1 | VAL | 49 | −12.033 | 3.853 | −10.407 | 1.00 | 0.00 |
| ATOM | 781 | HG11 | VAL | 49 | −11.630 | 3.991 | −9.414 | 1.00 | 0.00 |
| ATOM | 782 | HG12 | VAL | 49 | −11.705 | 2.901 | −10.799 | 1.00 | 0.00 |
| ATOM | 783 | HG13 | VAL | 49 | −13.112 | 3.872 | −10.364 | 1.00 | 0.00 |
| ATOM | 784 | CG2 | VAL | 49 | −11.301 | 6.246 | −10.518 | 1.00 | 0.00 |
| ATOM | 785 | HG21 | VAL | 49 | −10.706 | 6.020 | −9.646 | 1.00 | 0.00 |
| ATOM | 786 | HG22 | VAL | 49 | −12.249 | 6.661 | −10.209 | 1.00 | 0.00 |
| ATOM | 787 | HG23 | VAL | 49 | −10.779 | 6.963 | −11.135 | 1.00 | 0.00 |
| ATOM | 788 | C | VAL | 49 | −9.195 | 4.160 | −11.026 | 1.00 | 0.00 |
| ATOM | 789 | O | VAL | 49 | −8.861 | 4.956 | −10.148 | 1.00 | 0.00 |
| ATOM | 790 | N | ILE | 50 | −8.665 | 2.941 | −11.130 | 1.00 | 0.00 |
| ATOM | 791 | HN | ILE | 50 | −8.958 | 2.347 | −11.847 | 1.00 | 0.00 |
| ATOM | 792 | CA | ILE | 50 | −7.644 | 2.474 | −10.204 | 1.00 | 0.00 |
| ATOM | 793 | HA | ILE | 50 | −7.342 | 3.309 | −9.589 | 1.00 | 0.00 |
| ATOM | 794 | CB | ILE | 50 | −8.182 | 1.365 | −9.282 | 1.00 | 0.00 |
| ATOM | 795 | HB | ILE | 50 | −8.267 | 0.458 | −9.861 | 1.00 | 0.00 |
| ATOM | 796 | CG1 | ILE | 50 | −9.559 | 1.747 | −8.737 | 1.00 | 0.00 |
| ATOM | 797 | HG11 | ILE | 50 | −10.222 | 1.952 | −9.564 | 1.00 | 0.00 |
| ATOM | 798 | HG12 | ILE | 50 | −9.952 | 0.921 | −8.162 | 1.00 | 0.00 |
| ATOM | 799 | CG2 | ILE | 50 | −7.210 | 1.105 | −8.142 | 1.00 | 0.00 |
| ATOM | 800 | HG21 | ILE | 50 | −6.248 | 1.528 | −8.387 | 1.00 | 0.00 |
| ATOM | 801 | HG22 | ILE | 50 | −7.108 | 0.041 | −7.991 | 1.00 | 0.00 |
| ATOM | 802 | HG23 | ILE | 50 | −7.986 | 1.961 | −7.238 | 1.00 | 0.00 |
| ATOM | 803 | CD1 | ILE | 50 | −9.540 | 2.967 | −7.843 | 1.00 | 0.00 |
| ATOM | 804 | HD11 | ILE | 50 | −9.670 | 3.855 | −8.443 | 1.00 | 0.00 |
| ATOM | 805 | HD12 | ILE | 50 | −8.992 | 3.019 | −7.325 | 1.00 | 0.00 |
| ATOM | 806 | HD13 | ILE | 50 | −10.341 | 2.898 | −7.123 | 1.00 | 0.00 |
| ATOM | 807 | C | ILE | 50 | −6.428 | 1.945 | −10.953 | 1.00 | 0.00 |
| ATOM | 808 | O | ILE | 50 | −6.557 | 1.228 | −11.945 | 1.00 | 0.00 |
| ATOM | 809 | N | ARG | 51 | −9.248 | 2.301 | −10.466 | 1.00 | 0.00 |
| ATOM | 810 | HN | ARG | 51 | −5.216 | 2.877 | −9.676 | 1.00 | 0.00 |
| ATOM | 811 | CA | ARG | 51 | −4.000 | 1.873 | −12.114 | 1.00 | 0.00 |
| ATOM | 812 | HA | ARG | 51 | −4.014 | 2.198 | −6.212 | 1.00 | 0.00 |
| ATOM | 813 | CB | ARG | 51 | −2.811 | 2.519 | −10.373 | 1.00 | 0.00 |
| ATOM | 814 | HB1 | ARG | 51 | −3.181 | 3.123 | −9.597 | 1.00 | 0.00 |
| ATOM | 815 | HB2 | ARG | 51 | −2.177 | 1.740 | −9.975 | 1.00 | 0.00 |
| ATOM | 816 | CG | ARG | 51 | −1.967 | 3.403 | −11.277 | 1.00 | 0.00 |
| ATOM | 817 | HG1 | ARG | 51 | −2.041 | 3.037 | −12.291 | 1.00 | 0.00 |
| ATOM | 818 | HG2 | ARG | 51 | −0.939 | 3.398 | −10.950 | 1.00 | 0.00 |
| ATOM | 819 | CD | ARG | 51 | −2.433 | 4.849 | −11.240 | 1.00 | 0.00 |
| ATOM | 820 | HD1 | ARG | 51 | −2.996 | 5.010 | −10.332 | 1.00 | 0.00 |
| ATOM | 821 | HD2 | ARG | 51 | −1.566 | 5.493 | −11.244 | 1.00 | 0.00 |
| ATOM | 822 | NE | ARG | 51 | −3.275 | 5.184 | −12.365 | 1.00 | 0.00 |
| ATOM | 823 | HE | ARG | 51 | −4.217 | 5.390 | −12.212 | 1.00 | 0.00 |
| ATOM | 824 | CZ | ARG | 51 | −2.832 | 5.226 | −13.638 | 1.00 | 0.00 |
| ATOM | 825 | NH1 | ARG | 51 | −1.562 | 4.953 | −13.904 | 1.00 | 0.00 |
| ATOM | 826 | NH11 | ARG | 51 | −1.231 | 4.984 | −14.846 | 1.00 | 0.00 |
| ATOM | 827 | NH12 | ARG | 51 | −0.936 | 4.716 | −13.161 | 1.00 | 0.00 |
| ATOM | 828 | NH2 | ARG | 51 | −3.699 | 5.539 | −14.626 | 1.00 | 0.00 |
| ATOM | 829 | NH21 | ARG | 51 | −3.323 | 5.969 | −15.568 | 1.00 | 0.00 |
| ATOM | 830 | NH22 | ARG | 51 | −4.617 | 5.746 | −14.430 | 1.00 | 0.00 |
| ATOM | 831 | C | ARG | 51 | −3.864 | 0.394 | −11.096 | 1.00 | 0.00 |
| ATOM | 832 | O | ARG | 51 | −4.094 | −0.319 | −12.061 | 1.00 | 0.00 |
| ATOM | 833 | N | SER | 52 | −3.479 | −0.182 | −9.901 | 1.00 | 0.00 |
| ATOM | 834 | HN | SER | 52 | −3.310 | 0.403 | −9.134 | 1.00 | 0.00 |

TABLE 5-continued

Atomic Structure Coordinates of the
Free Form of the P/CAF Bromodomain

| ATOM | 835 | CA | SER | 52 | −3.307 | −1.622 | −9.751 | 1.00 | 0.00 |
|------|-----|------|-----|----|--------|--------|---------|------|------|
| ATOM | 836 | HA | SER | 52 | −3.766 | −2.101 | −10.603 | 1.00 | 0.00 |
| ATOM | 837 | CB | SER | 52 | −1.820 | −1.980 | −9.715 | 1.00 | 0.00 |
| ATOM | 838 | HB1 | SER | 52 | −1.690 | −3.005 | −10.027 | 1.00 | 0.00 |
| ATOM | 839 | HB2 | SER | 52 | −1.447 | −1.860 | −8.708 | 1.00 | 0.00 |
| ATOM | 840 | OG | SER | 52 | −1.072 | −1.143 | −10.580 | 1.00 | 0.00 |
| ATOM | 841 | HG | SER | 52 | −0.287 | −1.608 | −10.877 | 1.00 | 0.00 |
| ATOM | 842 | C | SER | 52 | −3.993 | −2.128 | −8.488 | 1.00 | 0.00 |
| ATOM | 843 | O | SER | 52 | −0.393 | −2.308 | −7.452 | 1.00 | 0.00 |
| ATOM | 844 | N | PRO | 53 | −5.310 | −2.379 | −8.565 | 1.00 | 0.00 |
| ATOM | 845 | CA | PRO | 53 | −4.087 | −2.882 | −7.435 | 1.00 | 0.00 |
| ATOM | 846 | HA | PRO | 53 | −6.390 | −2.083 | −6.773 | 1.00 | 0.00 |
| ATOM | 847 | CB | PRO | 53 | −7.313 | −3.484 | −8.111 | 1.00 | 0.00 |
| ATOM | 848 | HB1 | PRO | 53 | −8.160 | −3.415 | −7.450 | 1.00 | 0.00 |
| ATOM | 849 | HB2 | PRO | 53 | −7.122 | −4.519 | −8.355 | 1.00 | 0.00 |
| ATOM | 850 | CG | PRO | 53 | −7.512 | −2.661 | −9.337 | 1.00 | 0.00 |
| ATOM | 851 | HG1 | PRO | 53 | −7.963 | −3.263 | −10.110 | 1.00 | 0.00 |
| ATOM | 852 | HG2 | PRO | 53 | −8.139 | −1.812 | −9.109 | 1.00 | 0.00 |
| ATOM | 853 | CD | PRO | 53 | −6.145 | −2.197 | −9.770 | 1.00 | 0.00 |
| ATOM | 854 | HD1 | PRO | 53 | −5.780 | −2.805 | −10.584 | 1.00 | 0.00 |
| ATOM | 855 | HD2 | PRO | 53 | −6.176 | −1.197 | −10.060 | 1.00 | 0.00 |
| ATOM | 856 | C | PRO | 53 | −9.340 | −3.947 | −6.639 | 1.00 | 0.00 |
| ATOM | 857 | O | PRO | 53 | −5.425 | −5.137 | −6.943 | 1.00 | 0.00 |
| ATOM | 858 | N | MET | 54 | −4.609 | −3.512 | −5.619 | 1.00 | 0.00 |
| ATOM | 859 | HN | MET | 54 | −4.581 | −2.592 | −5.426 | 1.00 | 0.00 |
| ATOM | 860 | CA | MET | 54 | −3.850 | −4.424 | −4.777 | 1.00 | 0.00 |
| ATOM | 861 | HA | MET | 54 | −4.303 | −5.405 | −4.859 | 1.00 | 0.00 |
| ATOM | 862 | CB | MET | 54 | −2.398 | −4.508 | −5.253 | 1.00 | 0.00 |
| ATOM | 863 | HB1 | MET | 54 | −2.390 | −4.624 | −6.327 | 1.00 | 0.00 |
| ATOM | 864 | HB2 | MET | 54 | −1.897 | −3.587 | −4.995 | 1.00 | 0.00 |
| ATOM | 865 | CG | MET | 54 | −1.615 | −5.660 | −4.644 | 1.00 | 0.00 |
| ATOM | 866 | HG1 | MET | 54 | −1.472 | −5.464 | −3.592 | 1.00 | 0.00 |
| ATOM | 867 | HG2 | MET | 54 | −0.653 | −5.720 | −5.132 | 1.00 | 0.00 |
| ATOM | 868 | SD | MET | 54 | −2.452 | −7.247 | −4.826 | 1.00 | 0.00 |
| ATOM | 869 | CE | MET | 54 | −3.383 | −7.311 | −3.298 | 1.00 | 0.00 |
| ATOM | 870 | HE1 | MET | 54 | −2.905 | −7.997 | −2.612 | 1.00 | 0.00 |
| ATOM | 871 | HE2 | MET | 54 | −4.388 | −7.650 | −3.501 | 1.00 | 0.00 |
| ATOM | 872 | HE2 | MET | 54 | −3.418 | −6.327 | −2.857 | 1.00 | 0.00 |
| ATOM | 873 | C | MET | 54 | −3.897 | −3.984 | −3.320 | 1.00 | 0.00 |
| ATOM | 874 | O | MET | 54 | −2.937 | −3.415 | −2.802 | 1.00 | 0.00 |
| ATOM | 875 | N | ASP | 55 | −5.026 | −4.240 | −2.667 | 1.00 | 0.00 |
| ATOM | 876 | HN | ASP | 55 | −5.755 | −4.699 | −3.134 | 1.00 | 0.00 |
| ATOM | 877 | CA | ASP | 55 | −5.201 | −3.870 | −1.269 | 1.00 | 0.00 |
| ATOM | 878 | HA | ASP | 55 | −4.803 | −2.874 | −1.139 | 1.00 | 0.00 |
| ATOM | 879 | CB | ASP | 55 | −6.690 | −3.863 | −0.906 | 1.00 | 0.00 |
| ATOM | 880 | HB1 | ASP | 55 | −6.811 | −3.495 | 0.102 | 1.00 | 0.00 |
| ATOM | 881 | HB2 | ASP | 55 | −7.075 | −4.869 | −0.964 | 1.00 | 0.00 |
| ATOM | 882 | GC | ASP | 55 | −7.506 | −2.985 | −1.835 | 1.00 | 0.00 |
| ATOM | 883 | OD1 | ASP | 55 | −7.575 | −3.302 | −3.041 | 1.00 | 0.00 |
| ATOM | 884 | OD2 | ASP | 55 | −8.074 | −1.981 | −1.357 | 1.00 | 0.00 |
| ATOM | 885 | C | ASP | 55 | −4.435 | −4.826 | −0.360 | 1.00 | 0.00 |
| ATOM | 886 | O | ASP | 55 | −3.578 | −5.580 | −0.819 | 1.00 | 0.00 |
| ATOM | 887 | N | LEU | 56 | −4.739 | −4.786 | 0.931 | 1.00 | 0.00 |
| ATOM | 888 | HN | LEU | 56 | −5.426 | −4.163 | 1.242 | 1.00 | 0.00 |
| ATOM | 889 | CA | LEU | 56 | −4.069 | −5.644 | 1.898 | 1.00 | 0.00 |
| ATOM | 890 | HA | LEU | 56 | −3.012 | −5.620 | 1.683 | 1.00 | 0.00 |
| ATOM | 891 | CB | LEU | 56 | −4.305 | −5.115 | 3.318 | 1.00 | 0.00 |
| ATOM | 892 | HB1 | LEU | 56 | −4.223 | −5.939 | 4.008 | 1.00 | 0.00 |
| ATOM | 893 | HB2 | LEU | 56 | −5.306 | −4.729 | 3.371 | 1.00 | 0.00 |
| ATOM | 894 | CG | LEU | 56 | −3.343 | −4.015 | 3.770 | 1.00 | 0.00 |
| ATOM | 895 | HG | LEU | 56 | −3.605 | −3.702 | 4.770 | 1.00 | 0.00 |
| ATOM | 896 | CD1 | LEU | 56 | −3.425 | −2.802 | 2.859 | 1.00 | 0.00 |
| ATOM | 897 | HD11 | LEU | 56 | −3.644 | −1.924 | 3.449 | 1.00 | 0.00 |
| ATOM | 898 | HD12 | LEU | 56 | −4.204 | −2.950 | 2.132 | 1.00 | 0.00 |
| ATOM | 899 | HD13 | LEU | 56 | −2.481 | −2.668 | 2.352 | 1.00 | 0.00 |
| ATOM | 900 | CD2 | LEU | 56 | −1.929 | −4.544 | 3.801 | 1.00 | 0.00 |
| ATOM | 901 | HD21 | LEU | 56 | −1.279 | −3.850 | 3.291 | 1.00 | 0.00 |
| ATOM | 902 | HD22 | LEU | 56 | −1.898 | −5.500 | 3.303 | 1.00 | 0.00 |
| ATOM | 903 | HD23 | LEU | 56 | −1.611 | −4.656 | 4.824 | 1.00 | 0.00 |
| ATOM | 904 | C | LEU | 56 | −4.568 | −7.0811 | 1.773 | 1.00 | 0.00 |
| ATOM | 905 | O | LEU | 56 | −5.294 | −7.404 | 0.835 | 1.00 | 0.00 |
| ATOM | 906 | N | LYS | 57 | −4.152 | −7.939 | 2.706 | 1.00 | 0.00 |
| ATOM | 907 | HN | LYS | 57 | −3.564 | −7.617 | 3.417 | 1.00 | 0.00 |
| ATOM | 908 | CA | LYS | 57 | −4.555 | −9.347 | 2.715 | 1.00 | 0.00 |
| ATOM | 909 | HA | LYS | 57 | −4.259 | −9.758 | 3.669 | 1.00 | 0.00 |
| ATOM | 910 | CB | LYS | 57 | −6.075 | −9.490 | 2.976 | 1.00 | 0.00 |
| ATOM | 911 | HB1 | LYS | 57 | −6.549 | −9.007 | 3.418 | 1.00 | 0.00 |

TABLE 5-continued

Atomic Structure Coordinates of the
Free Form of the P/CAF Bromodomain

| ATOM | 912 | HB2 | LYS | 57 | −6.396 | −9.008 | 1.668 | 1.00 | 0.00 |
|------|-----|------|-----|----|--------|---------|-------|------|------|
| ATOM | 913 | CG | LYS | 57 | −6.542 | −10.935 | 2.530 | 1.00 | 0.00 |
| ATOM | 914 | HG1 | LYS | 57 | −6.160 | −11.395 | 1.629 | 1.00 | 0.00 |
| ATOM | 915 | HG2 | LYS | 57 | −7.622 | −10.954 | 2.517 | 1.00 | 0.00 |
| ATOM | 916 | CD | LYS | 57 | −6.049 | −11.720 | 3.736 | 1.00 | 0.00 |
| ATOM | 917 | HD1 | LYS | 57 | −9.944 | −11.047 | 4.573 | 1.00 | 0.00 |
| ATOM | 918 | HD2 | LYS | 57 | −9.090 | −12.157 | 3.498 | 1.00 | 0.00 |
| ATOM | 919 | CE | LYS | 57 | −7.017 | −12.831 | 4.112 | 1.00 | 0.00 |
| ATOM | 920 | HE1 | LYS | 57 | −7.967 | −12.640 | 3.635 | 1.00 | 0.00 |
| ATOM | 921 | HE2 | LYS | 57 | −6.621 | −13.771 | 3.759 | 1.00 | 0.00 |
| ATOM | 922 | NZ | LYS | 57 | −7.223 | −12.915 | 5.585 | 1.00 | 0.00 |
| ATOM | 923 | HZ1 | LYS | 57 | −6.363 | −12.609 | 6.084 | 1.00 | 0.00 |
| ATOM | 924 | HZ2 | LYS | 57 | −7.441 | −13.894 | 5.860 | 1.00 | 0.00 |
| ATOM | 925 | HZ3 | LYS | 57 | −8.013 | −12.302 | 5.871 | 1.00 | 0.00 |
| ATOM | 926 | C | LYS | 57 | −3.855 | −10.144 | 1.617 | 1.00 | 0.00 |
| ATOM | 927 | O | LYS | 57 | −3.197 | −11.146 | 1.895 | 1.00 | 0.00 |
| ATOM | 928 | N | THR | 58 | −4.014 | −9.714 | 0.370 | 1.00 | 0.00 |
| ATOM | 929 | HN | THR | 58 | −4.511 | −8.913 | 0.201 | 1.00 | 0.00 |
| ATOM | 930 | CA | THR | 58 | −3.403 | −10.411 | −0.755 | 1.00 | 0.00 |
| ATOM | 931 | HA | THR | 58 | −3.409 | −11.465 | −0.527 | 1.00 | 0.00 |
| ATOM | 932 | CB | THR | 58 | −4.223 | −10.177 | −2.031 | 1.00 | 0.00 |
| ATOM | 933 | HB | THR | 58 | −4.448 | −9.126 | −2.112 | 1.00 | 0.00 |
| ATOM | 934 | OG1 | THR | 58 | −5.448 | −10.887 | −1.970 | 1.00 | 0.00 |
| ATOM | 935 | HG1 | THR | 58 | −5.974 | −10.557 | −1.238 | 1.00 | 0.00 |
| ATOM | 936 | CG2 | THR | 58 | −3.515 | −10.598 | −3.304 | 1.00 | 0.00 |
| ATOM | 937 | HG21 | THR | 58 | −4.236 | −11.003 | −3.999 | 1.00 | 0.00 |
| ATOM | 938 | HG22 | THR | 58 | −2.775 | −11.349 | −3.073 | 1.00 | 0.00 |
| ATOM | 939 | HG23 | THR | 58 | −3.031 | −9.740 | −3.747 | 1.00 | 0.00 |
| ATOM | 940 | C | THR | 58 | −1.956 | −9.961 | −0.952 | 1.00 | 0.00 |
| ATOM | 941 | O | THR | 58 | −1.093 | −10.759 | −1.318 | 1.00 | 0.00 |
| ATOM | 942 | N | MET | 59 | −1.697 | −8.682 | −0.701 | 1.00 | 0.00 |
| ATOM | 943 | HN | MET | 59 | −2.426 | −8.092 | −0.413 | 1.00 | 0.00 |
| ATOM | 944 | CA | MET | 59 | −0.355 | −8.132 | −0.851 | 1.00 | 0.00 |
| ATOM | 945 | HA | MET | 59 | 0.020 | −8.431 | −1.819 | 1.00 | 0.00 |
| ATOM | 946 | CB | MET | 59 | −0.404 | −6.609 | −0.783 | 1.00 | 0.00 |
| ATOM | 947 | HB1 | MET | 59 | 0.536 | −6.209 | −1.138 | 1.00 | 0.00 |
| ATOM | 948 | HB2 | MET | 59 | −1.200 | −6.252 | −1.423 | 1.00 | 0.00 |
| ATOM | 949 | CG | MET | 59 | −0.650 | −6.072 | 0.617 | 1.00 | 0.00 |
| ATOM | 950 | HG1 | MET | 59 | −1.503 | −6.585 | 1.032 | 1.00 | 0.00 |
| ATOM | 951 | HG2 | MET | 59 | 0.218 | −6.279 | 1.223 | 1.00 | 0.00 |
| ATOM | 952 | SD | MET | 59 | −0.969 | −4.297 | 0.643 | 1.00 | 0.00 |
| ATOM | 953 | CE | MET | 59 | 0.230 | −3.715 | −0.554 | 1.00 | 0.00 |
| ATOM | 954 | HE1 | MET | 59 | 0.178 | −4.324 | −1.443 | 1.00 | 0.00 |
| ATOM | 955 | HE2 | MET | 59 | 1.221 | −3.779 | −0.131 | 1.00 | 0.00 |
| ATOM | 956 | HE3 | MET | 59 | 0.016 | −2.688 | −0.808 | 1.00 | 0.00 |
| ATOM | 957 | C | MET | 59 | 0.582 | −8.669 | 0.228 | 1.00 | 0.00 |
| ATOM | 958 | O | MET | 59 | 1.701 | −9.092 | −0.061 | 1.00 | 0.00 |
| ATOM | 959 | N | SER | 60 | 0.126 | −8.621 | 1.476 | 1.00 | 0.00 |
| ATOM | 960 | HN | SER | 60 | −0.772 | −8.270 | 1.644 | 1.00 | 0.00 |
| ATOM | 961 | CA | SER | 60 | 0.925 | −9.088 | 2.601 | 1.00 | 0.00 |
| ATOM | 962 | HA | SER | 60 | 1.789 | −8.445 | 2.682 | 1.00 | 0.00 |
| ATOM | 963 | CB | SER | 60 | 0.117 | −9.004 | 3.898 | 1.00 | 0.00 |
| ATOM | 964 | HB1 | SER | 60 | 0.214 | −8.013 | 4.315 | 1.00 | 0.00 |
| ATOM | 965 | HB2 | SER | 60 | −0.922 | −9.205 | 3.686 | 1.00 | 0.00 |
| ATOM | 966 | OG | SER | 60 | 0.979 | −9.946 | 4.852 | 1.00 | 0.00 |
| ATOM | 967 | HG | SER | 60 | 1.273 | −9.548 | 5.383 | 1.00 | 0.00 |
| ATOM | 968 | C | SER | 60 | 1.401 | −10.917 | 2.372 | 1.00 | 0.00 |
| ATOM | 969 | O | SER | 60 | 2.417 | −10.939 | 2.923 | 1.00 | 0.00 |
| ATOM | 970 | N | GLU | 61 | 0.665 | −11.258 | 1.591 | 1.00 | 0.00 |
| ATOM | 971 | HN | GLU | 61 | −0.134 | −10.867 | 1.137 | 1.00 | 0.00 |
| ATOM | 972 | CA | GLU | 61 | 1.022 | −12.636 | 1.249 | 1.00 | 0.00 |
| ATOM | 973 | HA | GLU | 61 | 1.138 | −13.156 | 2.186 | 1.00 | 0.00 |
| ATOM | 974 | CB | GLU | 61 | −0.084 | −13.309 | 0.435 | 1.00 | 0.00 |
| ATOM | 975 | HB1 | GLU | 61 | 0.025 | −14.380 | 0.516 | 1.00 | 0.00 |
| ATOM | 976 | HB2 | GLU | 61 | 0.021 | −13.022 | −0.601 | 1.00 | 0.00 |
| ATOM | 977 | CG | GLU | 61 | −1.484 | −12.937 | 0.891 | 1.00 | 0.00 |
| ATOM | 978 | HG1 | GLU | 61 | −1.460 | −12.730 | 1.951 | 1.00 | 0.00 |
| ATOM | 979 | HG2 | GLU | 61 | −1.797 | −12.091 | 0.360 | 1.00 | 0.00 |
| ATOM | 980 | CD | GLU | 61 | −2.493 | −14.039 | 0.636 | 1.00 | 0.00 |
| ATOM | 981 | OE1 | GLU | 61 | −2.755 | −14.830 | 1.567 | 1.00 | 0.00 |
| ATOM | 982 | OE2 | GLU | 61 | −3.020 | −14.112 | −0.494 | 1.00 | 0.00 |
| ATOM | 983 | C | GLU | 61 | 2.338 | −12.695 | 0.485 | 1.00 | 0.00 |
| ATOM | 984 | O | GLU | 61 | 0.295 | −13.334 | 0.922 | 1.00 | 0.00 |
| ATOM | 985 | N | ARG | 62 | 2.382 | −12.013 | −0.654 | 1.00 | 0.00 |
| ATOM | 986 | HN | ARG | 62 | 1.588 | −11.524 | −0.949 | 1.00 | 0.00 |
| ATOM | 987 | CA | ARG | 62 | 3.978 | −11.980 | −1.479 | 1.00 | 0.00 |
| ATOM | 988 | HA | ARG | 62 | 3.752 | −12.979 | −1.846 | 1.00 | 0.00 |

TABLE 5-continued

Atomic Structure Coordinates of the
Free Form of the P/CAF Bromodomain

| ATOM | 989 | CB | ARG | 62 | 3.368 | −11.045 | −2.672 | 1.00 | 0.00 |
|---|---|---|---|---|---|---|---|---|---|
| ATOM | 990 | HB1 | ARG | 62 | 4.330 | −10.804 | −3.101 | 1.00 | 0.00 |
| ATOM | 991 | HB2 | ARG | 62 | 2.898 | −10.136 | −2.326 | 1.00 | 0.00 |
| ATOM | 992 | CG | ARG | 62 | 2.496 | −11.652 | −3.761 | 1.00 | 0.00 |
| ATOM | 993 | HG1 | ARG | 62 | 1.895 | −12.438 | −3.328 | 1.00 | 0.00 |
| ATOM | 994 | HG2 | ARG | 62 | 3.131 | −13.065 | −4.528 | 1.00 | 0.00 |
| ATOM | 995 | CD | ARG | 62 | 1.576 | −10.619 | −4.389 | 1.00 | 0.00 |
| ATOM | 996 | HD1 | ARG | 62 | 2.043 | −9.647 | −4.320 | 1.00 | 0.00 |
| ATOM | 997 | HD2 | ARG | 62 | 0.645 | −10.609 | −3.845 | 1.00 | 0.00 |
| ATOM | 998 | NE | ARG | 62 | 1.299 | −10.916 | −5.792 | 1.00 | 0.00 |
| ATOM | 999 | HE | ARG | 62 | 1.697 | −10.330 | −6.467 | 1.00 | 0.00 |
| ATOM | 1000 | CZ | ARG | 62 | 0.541 | −11.931 | −6.194 | 1.00 | 0.00 |
| ATOM | 1001 | NH1 | ARG | 62 | 0.336 | −12.136 | −7.488 | 1.00 | 0.00 |
| ATOM | 1002 | HH11 | ARG | 62 | 0.793 | −11.927 | −8.163 | 1.00 | 0.00 |
| ATOM | 1003 | HH12 | ARG | 62 | −0.235 | −12.900 | −7.789 | 1.00 | 0.00 |
| ATOM | 1004 | NH2 | ARG | 62 | −0.014 | −12.742 | −5.303 | 1.00 | 0.00 |
| ATOM | 1005 | HH21 | ARG | 62 | 0.139 | −12.590 | −4.326 | 1.00 | 0.00 |
| ATOM | 1006 | HH22 | ARG | 62 | −0.583 | −13.505 | −5.608 | 1.00 | 0.00 |
| ATOM | 1007 | C | ARG | 62 | 4.790 | −11.542 | −0.664 | 1.00 | 0.00 |
| ATOM | 1008 | O | ARG | 62 | 5.781 | −12.266 | −0.574 | 1.00 | 0.00 |
| ATOM | 1009 | N | LEU | 63 | 4.700 | −10.366 | −0.092 | 1.00 | 0.00 |
| ATOM | 1010 | HN | LEU | 63 | 3.882 | −9.835 | −0.149 | 1.00 | 0.00 |
| ATOM | 1011 | CA | LEU | 63 | 9.792 | −9.853 | 0.768 | 1.00 | 0.00 |
| ATOM | 1012 | HA | LEU | 63 | 6.634 | −9.663 | 0.117 | 1.00 | 0.00 |
| ATOM | 1013 | CB | LEU | 63 | 5.384 | −8.546 | 1.450 | 1.00 | 0.00 |
| ATOM | 1014 | HB1 | LEU | 63 | 9.208 | −7.805 | 0.685 | 1.00 | 0.00 |
| ATOM | 1015 | HB2 | LEU | 63 | 4.460 | −8.716 | 1.982 | 1.00 | 0.00 |
| ATOM | 1016 | CG | LEU | 63 | 6.413 | −7.984 | 2.436 | 1.00 | 0.00 |
| ATOM | 1017 | HG | LEU | 63 | 7.141 | −8.747 | 2.663 | 1.00 | 0.00 |
| ATOM | 1018 | CD1 | LEU | 63 | 7.148 | −6.804 | 1.825 | 1.00 | 0.00 |
| ATOM | 1019 | HD11 | LEU | 63 | 6.457 | −5.991 | 1.672 | 1.00 | 0.00 |
| ATOM | 1020 | HD12 | LEU | 63 | 7.975 | −7.097 | 0.877 | 1.00 | 0.00 |
| ATOM | 1021 | HD13 | LEU | 63 | 7.917 | −6.487 | 2.492 | 1.00 | 0.00 |
| ATOM | 1022 | CD2 | LEU | 63 | 9.741 | −7.580 | 3.738 | 1.00 | 0.00 |
| ATOM | 1023 | HD21 | LEU | 63 | 4.709 | −7.899 | 3.726 | 1.00 | 0.00 |
| ATOM | 1024 | HD22 | LEU | 63 | 9.785 | −6.907 | 3.848 | 1.00 | 0.00 |
| ATOM | 1025 | HD23 | LEU | 63 | 6.252 | −8.049 | 4.565 | 1.00 | 0.00 |
| ATOM | 1026 | C | LEU | 63 | 6.204 | −10.880 | 1.817 | 1.00 | 0.00 |
| ATOM | 1027 | O | LEU | 63 | 7.391 | −11.134 | 2.019 | 1.00 | 0.00 |
| ATOM | 1028 | N | LYS | 64 | 9.212 | −11.475 | 2.475 | 1.00 | 0.00 |
| ATOM | 1029 | HN | LYS | 64 | 4.284 | −11.235 | 2.262 | 1.00 | 0.00 |
| ATOM | 1030 | CA | LYS | 64 | 5.469 | −12.487 | 3.492 | 1.00 | 0.00 |
| ATOM | 1031 | HA | LYS | 64 | 5.942 | −12.002 | 4.333 | 1.00 | 0.00 |
| ATOM | 1032 | CB | LYS | 64 | 4.155 | −13.122 | 3.953 | 1.00 | 0.00 |
| ATOM | 1033 | HB1 | LYS | 64 | 3.506 | −13.240 | 3.098 | 1.00 | 0.00 |
| ATOM | 1034 | HB2 | LYS | 64 | 4.365 | −14.094 | 4.372 | 1.00 | 0.00 |
| ATOM | 1035 | CG | LYS | 64 | 3.416 | −12.301 | 5.000 | 1.00 | 0.00 |
| ATOM | 1036 | HG1 | LYS | 64 | 3.615 | −11.294 | 4.828 | 1.00 | 0.00 |
| ATOM | 1037 | HG2 | LYS | 64 | 2.396 | −12.488 | 4.907 | 1.00 | 0.00 |
| ATOM | 1038 | CD | LYS | 64 | 3.899 | −12.660 | 6.408 | 1.00 | 0.00 |
| ATOM | 1039 | HD1 | LYS | 64 | 3.007 | −13.038 | 6.997 | 1.00 | 0.00 |
| ATOM | 1040 | HD2 | LYS | 64 | 4.618 | −13.428 | 6.391 | 1.00 | 0.00 |
| ATOM | 1041 | CE | LYS | 64 | 4.426 | −11.459 | 7.141 | 1.00 | 0.00 |
| ATOM | 1042 | HE1 | LYS | 64 | 4.711 | −10.712 | 6.414 | 1.00 | 0.00 |
| ATOM | 1043 | HE2 | LYS | 64 | 0.663 | −11.096 | 7.790 | 1.00 | 0.00 |
| ATOM | 1044 | NZ | LYS | 64 | 5.618 | −11.817 | 7.959 | 1.00 | 0.00 |
| ATOM | 1045 | HZ1 | LYS | 64 | 6.086 | −12.655 | 7.560 | 1.00 | 0.00 |
| ATOM | 1046 | HZ2 | LYS | 64 | 5.332 | −12.025 | 8.936 | 1.00 | 0.00 |
| ATOM | 1047 | HZ3 | LYS | 64 | 6.295 | −11.028 | 7.968 | 1.00 | 0.00 |
| ATOM | 1048 | C | LYS | 64 | 6.407 | −13.962 | 2.953 | 1.00 | 0.00 |
| ATOM | 1049 | O | LYS | 64 | 7.299 | −14.082 | 3.677 | 1.00 | 0.00 |
| ATOM | 1050 | N | ASN | 65 | 6.296 | −13.879 | 1.671 | 1.00 | 0.00 |
| ATOM | 1051 | HN | ASN | 65 | 5.569 | −13.420 | 1.143 | 1.00 | 0.00 |
| ATOM | 1052 | CA | ASN | 65 | 7.103 | −14.872 | 1.023 | 1.00 | 0.00 |
| ATOM | 1053 | HA | ASN | 65 | 7.632 | −15.410 | 1.795 | 1.00 | 0.00 |
| ATOM | 1054 | CB | ASN | 65 | 6.254 | −15.855 | 0.214 | 1.00 | 0.00 |
| ATOM | 1055 | HB1 | ASN | 65 | 6.762 | −16.082 | −0.712 | 1.00 | 0.00 |
| ATOM | 1056 | HB2 | ASN | 65 | 9.299 | −19.400 | −0.006 | 1.00 | 0.00 |
| ATOM | 1057 | CG | ASN | 65 | 6.006 | −17.155 | 0.954 | 1.00 | 0.00 |
| ATOM | 1058 | OD1 | ASN | 65 | 6.244 | −18.239 | 0.433 | 1.00 | 0.00 |
| ATOM | 1059 | ND2 | ASN | 65 | 5.501 | −17.092 | 2.178 | 1.00 | 0.00 |
| ATOM | 1060 | HD21 | ASN | 65 | 5.318 | −16.156 | 2.930 | 1.00 | 0.00 |
| ATOM | 1061 | HD22 | ASN | 65 | 5.331 | −17.877 | 2.679 | 1.00 | 0.00 |
| ATOM | 1062 | C | ASN | 65 | 8.122 | −14.195 | 0.119 | 1.00 | 0.00 |
| ATOM | 1063 | O | ASN | 65 | 8.532 | −14.749 | −0.901 | 1.00 | 0.00 |
| ATOM | 1064 | N | ARG | 66 | 8.535 | −12.995 | 0.510 | 1.00 | 0.00 |
| ATOM | 1065 | HN | ARG | 66 | 8.174 | −12.614 | 1.338 | 1.00 | 0.00 |

TABLE 5-continued

Atomic Structure Coordinates of the
Free Form of the P/CAF Bromodomain

| ATOM | 1066 | CA | ARG | 66 | 9.524 | −12.235 | −0.247 | 1.00 | 0.00 |
|---|---|---|---|---|---|---|---|---|---|
| ATOM | 1067 | HA | ARG | 66 | 9.535 | −11.232 | 0.148 | 1.00 | 0.00 |
| ATOM | 1068 | CB | ARG | 66 | 10.919 | −12.848 | −0.092 | 1.00 | 0.00 |
| ATOM | 1069 | HB1 | ARG | 66 | 11.122 | −13.471 | −0.950 | 1.00 | 0.00 |
| ATOM | 1070 | HB2 | ARG | 66 | 11.643 | −12.091 | −0.063 | 1.00 | 0.00 |
| ATOM | 1071 | CG | ARG | 66 | 11.100 | −13.692 | 1.161 | 1.00 | 0.00 |
| ATOM | 1072 | HG1 | ARG | 66 | 11.963 | −14.321 | 1.031 | 1.00 | 0.00 |
| ATOM | 1073 | HG2 | ARG | 66 | 10.225 | −14.307 | 1.303 | 1.00 | 0.00 |
| ATOM | 1074 | CD | ARG | 66 | 11.298 | −12.825 | 2.392 | 1.00 | 0.00 |
| ATOM | 1075 | HD1 | ARG | 66 | 11.969 | −12.017 | 2.143 | 1.00 | 0.00 |
| ATOM | 1076 | HD2 | ARG | 66 | 10.342 | −12.420 | 2.689 | 1.00 | 0.00 |
| ATOM | 1077 | NE | ARG | 66 | 11.860 | −13.580 | 3.509 | 1.00 | 0.00 |
| ATOM | 1078 | HE | ARG | 66 | 12.826 | −13.512 | 3.663 | 1.00 | 0.00 |
| ATOM | 1079 | CZ | ARG | 66 | 11.136 | −14.344 | 4.319 | 1.00 | 0.00 |
| ATOM | 1080 | NH1 | ARG | 66 | 11.719 | −14.994 | 5.314 | 1.00 | 0.00 |
| ATOM | 1081 | HH11 | ARG | 66 | 12.706 | −14.917 | 5.455 | 1.00 | 0.00 |
| ATOM | 1082 | HH12 | ARG | 66 | 11.173 | −15.573 | 5.923 | 1.00 | 0.00 |
| ATOM | 1083 | NH2 | ARG | 66 | 9.827 | −14.454 | 4.136 | 1.00 | 0.00 |
| ATOM | 1084 | HH21 | ARG | 66 | 9.384 | −13.963 | 3.387 | 1.00 | 0.00 |
| ATOM | 1085 | HH22 | ARG | 66 | 9.284 | −15.030 | 4.747 | 1.00 | 0.00 |
| ATOM | 1086 | C | ARG | 66 | 9.193 | −12.177 | −1.725 | 1.00 | 0.00 |
| ATOM | 1087 | O | ARG | 66 | 10.018 | −12.041 | −2.590 | 1.00 | 0.00 |
| ATOM | 1088 | N | TYR | 67 | 7.862 | −12.285 | −2.002 | 1.00 | 0.00 |
| ATOM | 1089 | HN | TYR | 67 | 7.230 | −12.408 | −1.266 | 1.00 | 0.00 |
| ATOM | 1090 | CA | TYR | 67 | 7.364 | −12.275 | −3.374 | 1.00 | 0.00 |
| ATOM | 1091 | HA | TYR | 67 | 8.129 | −12.804 | −4.006 | 1.00 | 0.00 |
| ATOM | 1092 | CB | TYR | 67 | 6.091 | −13.117 | −3.475 | 1.00 | 0.00 |
| ATOM | 1093 | HB1 | TYR | 67 | 6.193 | −13.995 | −2.856 | 1.00 | 0.00 |
| ATOM | 1094 | HB2 | TYR | 67 | 5.259 | −12.530 | −3.121 | 1.00 | 0.00 |
| ATOM | 1095 | CG | TYR | 67 | 5.747 | −13.566 | −4.881 | 1.00 | 0.00 |
| ATOM | 1096 | CD1 | TYR | 67 | 6.113 | −14.835 | −5.326 | 1.00 | 0.00 |
| ATOM | 1097 | HD | TYR | 67 | 6.628 | −15.506 | −4.654 | 1.00 | 0.00 |
| ATOM | 1098 | CD2 | TYR | 67 | 5.107 | −12.720 | −5.761 | 1.00 | 0.00 |
| ATOM | 1099 | HD2 | TYR | 67 | 4.827 | −11.731 | −5.427 | 1.00 | 0.00 |
| ATOM | 1100 | CE1 | TYR | 67 | 5.811 | −15.247 | −6.611 | 1.00 | 0.00 |
| ATOM | 1101 | HE1 | TYR | 67 | 6.089 | −16.237 | −6.940 | 1.00 | 0.00 |
| ATOM | 1102 | CE2 | TYR | 67 | 4.798 | −13.123 | −7.044 | 1.00 | 0.00 |
| ATOM | 1103 | HE2 | TYR | 67 | 4.281 | −12.449 | −7.711 | 1.00 | 0.00 |
| ATOM | 1104 | CZ | TYR | 67 | 5.153 | −14.387 | −7.466 | 1.00 | 0.00 |
| ATOM | 1105 | OH | TYR | 67 | 4.850 | −14.793 | −8.745 | 1.00 | 0.00 |
| ATOM | 1106 | HH | TYR | 67 | 4.026 | −15.286 | −8.737 | 1.00 | 0.00 |
| ATOM | 1107 | C | TYR | 67 | 7.066 | −10.860 | −3.859 | 1.00 | 0.00 |
| ATOM | 1108 | O | TYR | 67 | 6.990 | −10.616 | −9.063 | 1.00 | 0.00 |
| ATOM | 1109 | N | TYR | 68 | 6.859 | −9.937 | −2.925 | 1.00 | 0.00 |
| ATOM | 1110 | HN | TYR | 68 | 6.909 | −10.187 | −1.978 | 1.00 | 0.00 |
| ATOM | 1111 | CA | TYR | 68 | 6.515 | −8.568 | −3.280 | 1.00 | 0.00 |
| ATOM | 1112 | HA | TYR | 68 | 6.570 | −8.478 | −4.355 | 1.00 | 0.00 |
| ATOM | 1113 | CB | TYR | 68 | 5.089 | −8.263 | −2.821 | 1.00 | 0.00 |
| ATOM | 1114 | HB1 | TYR | 68 | 4.746 | −9.065 | −2.186 | 1.00 | 0.00 |
| ATOM | 1115 | HB2 | TYR | 68 | 5.096 | −7.348 | −2.256 | 1.00 | 0.00 |
| ATOM | 1116 | CG | TYR | 68 | 4.089 | −8.103 | −3.946 | 1.00 | 0.00 |
| ATOM | 1117 | CD1 | TYR | 68 | 4.278 | −8.729 | −5.174 | 1.00 | 0.00 |
| ATOM | 1118 | HD1 | TYR | 68 | 5.157 | −9.336 | −5.327 | 1.00 | 0.00 |
| ATOM | 1119 | CD2 | TYR | 68 | 2.946 | −7.334 | −3.772 | 1.00 | 0.00 |
| ATOM | 1120 | HD2 | TYR | 68 | 2.783 | −6.844 | −2.823 | 1.00 | 0.00 |
| ATOM | 1121 | CE1 | TYR | 68 | 3.359 | −8.582 | −6.196 | 1.00 | 0.00 |
| ATOM | 1122 | HE1 | TYR | 68 | 3.523 | −9.075 | −7.143 | 1.00 | 0.00 |
| ATOM | 1123 | CE2 | TYR | 68 | 2.022 | −7.185 | −4.789 | 1.00 | 0.00 |
| ATOM | 1124 | HE2 | TYR | 68 | 1.141 | −6.591 | −4.633 | 1.00 | 0.00 |
| ATOM | 1125 | CZ | TYR | 68 | 2.233 | −7.811 | −5.998 | 1.00 | 0.00 |
| ATOM | 1126 | OH | TYR | 68 | 1.315 | −7.665 | −7.012 | 1.00 | 0.00 |
| ATOM | 1127 | HH | TYR | 68 | 0.444 | −7.518 | −6.637 | 1.00 | 0.00 |
| ATOM | 1128 | C | TYR | 68 | 7.484 | −7.570 | −2.656 | 1.00 | 0.00 |
| ATOM | 1129 | O | TYR | 68 | 7.096 | −6.457 | −2.303 | 1.00 | 0.00 |
| ATOM | 1130 | N | VAL | 69 | 8.744 | −7.967 | −2.529 | 1.00 | 0.00 |
| ATOM | 1131 | HN | VAL | 69 | 9.000 | −8.862 | −2.835 | 1.00 | 0.00 |
| ATOM | 1132 | CA | VAL | 69 | 9.761 | −7.086 | −1.962 | 1.00 | 0.00 |
| ATOM | 1133 | HA | VAL | 69 | 9.284 | −6.461 | −1.221 | 1.00 | 0.00 |
| ATOM | 1134 | CB | VAL | 69 | 10.907 | −7.854 | −1.276 | 1.00 | 0.00 |
| ATOM | 1135 | HB | VAL | 69 | 11.715 | −7.964 | −1.984 | 1.00 | 0.00 |
| ATOM | 1136 | CG1 | VAL | 69 | 10.465 | −9.242 | −0.846 | 1.00 | 0.00 |
| ATOM | 1137 | HG11 | VAL | 69 | 9.487 | −9.183 | −0.393 | 1.00 | 0.00 |
| ATOM | 1138 | HG12 | VAL | 69 | 11.171 | −9.640 | −0.133 | 1.00 | 0.00 |
| ATOM | 1139 | HG13 | VAL | 69 | 10.423 | −9.887 | −1.712 | 1.00 | 0.00 |
| ATOM | 1140 | CG2 | VAL | 69 | 11.422 | −7.099 | −0.090 | 1.00 | 0.00 |
| ATOM | 1141 | HG21 | VAL | 69 | 12.197 | −7.619 | 0.411 | 1.00 | 0.00 |
| ATOM | 1142 | HG22 | VAL | 69 | 10.608 | −6.872 | 0.597 | 1.00 | 0.00 |

TABLE 5-continued

Atomic Structure Coordinates of the
Free Form of the P/CAF Bromodomain

| ATOM | 1143 | HG23 | VAL | 69 | 11.822 | −6.118 | −0.438 | 1.00 | 0.00 |
|---|---|---|---|---|---|---|---|---|---|
| ATOM | 1144 | C | VAL | 69 | 10.352 | −6.198 | −3.043 | 1.00 | 0.00 |
| ATOM | 1145 | O | VAL | 69 | 11.543 | −6.272 | −3.345 | 1.00 | 0.00 |
| ATOM | 1146 | N | SER | 70 | 9.507 | −5.372 | −3.634 | 1.00 | 0.00 |
| ATOM | 1147 | HN | SER | 70 | 8.566 | −5.371 | −3.359 | 1.00 | 0.00 |
| ATOM | 1148 | CA | SER | 70 | 9.934 | −4.491 | −4.703 | 1.00 | 0.00 |
| ATOM | 1149 | HA | SER | 70 | 10.985 | −4.285 | −4.564 | 1.00 | 0.00 |
| ATOM | 1150 | CB | SER | 70 | 9.734 | −9.190 | −6.045 | 1.00 | 0.00 |
| ATOM | 1151 | HB1 | SER | 70 | 10.626 | −5.749 | −6.289 | 1.00 | 0.00 |
| ATOM | 1152 | HB2 | SER | 70 | 8.898 | −5.868 | −5.966 | 1.00 | 0.00 |
| ATOM | 1153 | OG | SER | 70 | 9.476 | −4.258 | −7.081 | 1.00 | 0.00 |
| ATOM | 1154 | HG | SER | 70 | 10.175 | −3.600 | −7.102 | 1.00 | 0.00 |
| ATOM | 1155 | C | SER | 70 | 9.164 | −3.179 | −4.657 | 1.00 | 0.00 |
| ATOM | 1156 | O | SER | 70 | 7.969 | −3.158 | −4.359 | 1.00 | 0.00 |
| ATOM | 1157 | N | LYS | 71 | 9.861 | −2.083 | −4.924 | 1.00 | 0.00 |
| ATOM | 1158 | HN | LYS | 71 | 10.816 | −2.163 | −5.131 | 1.00 | 0.00 |
| ATOM | 1159 | CA | LYS | 71 | 9.258 | −0.761 | −4.863 | 1.00 | 0.00 |
| ATOM | 1160 | HA | LYS | 71 | 8.988 | −0.582 | −3.832 | 1.00 | 0.00 |
| ATOM | 1161 | CB | LYS | 71 | 10.271 | 0.305 | −5.297 | 1.00 | 0.00 |
| ATOM | 1162 | HB1 | LYS | 71 | 11.076 | 0.332 | −4.577 | 1.00 | 0.00 |
| ATOM | 1163 | HB2 | LYS | 71 | 10.673 | 0.029 | −6.261 | 1.00 | 0.00 |
| ATOM | 1164 | CG | LYS | 71 | 9.687 | 1.706 | −5.409 | 1.00 | 0.00 |
| ATOM | 1165 | HG1 | LYS | 71 | 9.954 | 2.267 | −4.528 | 1.00 | 0.00 |
| ATOM | 1166 | HG2 | LYS | 71 | 8.613 | 1.638 | −5.482 | 1.00 | 0.00 |
| ATOM | 1167 | CD | LYS | 71 | 10.218 | 2.433 | −6.634 | 1.00 | 0.00 |
| ATOM | 1168 | HD1 | LYS | 71 | 11.033 | 1.863 | −7.054 | 1.00 | 0.00 |
| ATOM | 1169 | HD2 | LYS | 71 | 9.424 | 2.521 | −7.360 | 1.00 | 0.00 |
| ATOM | 1170 | CE | LYS | 71 | 10.721 | 3.824 | −6.282 | 1.00 | 0.00 |
| ATOM | 1171 | HE1 | LYS | 71 | 11.466 | 3.737 | −5.506 | 1.00 | 0.00 |
| ATOM | 1172 | HE2 | LYS | 71 | 9.891 | 4.412 | −5.919 | 1.00 | 0.00 |
| ATOM | 1173 | NZ | LYS | 71 | 11.323 | 4.511 | −7.457 | 1.00 | 0.00 |
| ATOM | 1174 | HZ1 | LYS | 71 | 10.580 | 4.970 | −8.023 | 1.00 | 0.00 |
| ATOM | 1175 | HZ2 | LYS | 71 | 11.823 | 3.823 | −8.056 | 1.00 | 0.00 |
| ATOM | 1176 | HZ3 | LYS | 71 | 12.000 | 5.234 | −7.141 | 1.00 | 0.00 |
| ATOM | 1177 | C | LYS | 71 | 7.984 | −0.678 | −5.707 | 1.00 | 0.00 |
| ATOM | 1178 | O | LYS | 71 | 6.898 | −1.000 | −5.224 | 1.00 | 0.00 |
| ATOM | 1179 | N | LYS | 72 | 8.116 | −0.244 | −6.964 | 1.00 | 0.00 |
| ATOM | 1180 | HN | LYS | 72 | 9.002 | 0.015 | −7.290 | 1.00 | 0.00 |
| ATOM | 1181 | CA | LYS | 72 | 6.963 | −0.053 | −7.846 | 1.00 | 0.00 |
| ATOM | 1182 | HA | LYS | 72 | 6.511 | 0.892 | −7.580 | 1.00 | 0.00 |
| ATOM | 1183 | CB | LYS | 72 | 7.419 | 0.008 | −9.305 | 1.00 | 0.00 |
| ATOM | 1184 | HB1 | LYS | 72 | 8.261 | 0.680 | −9.379 | 1.00 | 0.00 |
| ATOM | 1185 | HB2 | LYS | 72 | 7.728 | −0.979 | −9.615 | 1.00 | 0.00 |
| ATOM | 1186 | CG | LYS | 72 | 6.339 | 0.491 | −10.258 | 1.00 | 0.00 |
| ATOM | 1187 | HG1 | LYS | 72 | 6.588 | 0.174 | −11.260 | 1.00 | 0.00 |
| ATOM | 1188 | HG2 | LYS | 72 | 5.394 | 0.057 | −9.965 | 1.00 | 0.00 |
| ATOM | 1189 | CD | LYS | 72 | 6.214 | 2.005 | −10.238 | 1.00 | 0.00 |
| ATOM | 1190 | HD1 | LYS | 72 | 5.264 | 2.284 | −10.669 | 1.00 | 0.00 |
| ATOM | 1191 | HD2 | LYS | 72 | 6.261 | 2.347 | −9.214 | 1.00 | 0.00 |
| ATOM | 1192 | CE | LYS | 72 | 7.329 | 2.668 | −11.031 | 1.00 | 0.00 |
| ATOM | 1193 | HE1 | LYS | 72 | 7.643 | 3.559 | −10.508 | 1.00 | 0.00 |
| ATOM | 1194 | HE2 | LYS | 72 | 8.160 | 1.981 | −11.102 | 1.00 | 0.00 |
| ATOM | 1195 | NZ | LYS | 72 | 6.889 | 3.041 | −12.403 | 1.00 | 0.00 |
| ATOM | 1196 | HZ1 | LYS | 72 | 7.488 | 3.805 | −12.775 | 1.00 | 0.00 |
| ATOM | 1197 | HZ2 | LYS | 72 | 5.902 | 3.366 | −12.386 | 1.00 | 0.00 |
| ATOM | 1198 | HZ3 | LYS | 72 | 6.961 | 2.219 | −13.037 | 1.00 | 0.00 |
| ATOM | 1199 | C | LYS | 72 | 5.915 | −1.152 | −7.680 | 1.00 | 0.00 |
| ATOM | 1200 | O | LYS | 72 | 4.723 | −0.913 | −7.869 | 1.00 | 0.00 |
| ATOM | 1201 | N | LEU | 73 | 6.357 | −2.345 | −7.305 | 1.00 | 0.00 |
| ATOM | 1202 | HN | LEU | 73 | 7.318 | −2.480 | −7.168 | 1.00 | 0.00 |
| ATOM | 1203 | CA | LEU | 73 | 5.446 | −3.462 | −7.101 | 1.00 | 0.00 |
| ATOM | 1204 | HA | LEU | 73 | 4.802 | −3.527 | −7.966 | 1.00 | 0.00 |
| ATOM | 1205 | CB | LEU | 73 | 6.231 | −4.764 | −6.964 | 1.00 | 0.00 |
| ATOM | 1206 | HB1 | LEU | 73 | 6.470 | −4.910 | −5.922 | 1.00 | 0.00 |
| ATOM | 1207 | HB2 | LEU | 73 | 7.192 | −4.656 | −7.512 | 1.00 | 0.00 |
| ATOM | 1208 | CG | LEU | 73 | 5.508 | −6.014 | −7.466 | 1.00 | 0.00 |
| ATOM | 1209 | HG | LEU | 73 | 4.553 | −6.094 | −6.966 | 1.00 | 0.00 |
| ATOM | 1210 | CD1 | LEU | 73 | 6.315 | −7.262 | −7.145 | 1.00 | 0.00 |
| ATOM | 1211 | HD11 | LEU | 73 | 6.321 | −7.421 | −6.076 | 1.00 | 0.00 |
| ATOM | 1212 | HD12 | LEU | 73 | 7.128 | −7.136 | −7.496 | 1.00 | 0.00 |
| ATOM | 1213 | HD13 | LEU | 73 | 5.868 | −8.115 | −7.633 | 1.00 | 0.00 |
| ATOM | 1214 | CD2 | LEU | 73 | 5.247 | −5.915 | −8.961 | 1.00 | 0.00 |
| ATOM | 1215 | HD21 | LEU | 73 | 4.982 | −6.889 | −9.345 | 1.00 | 0.00 |
| ATOM | 1216 | HD22 | LEU | 73 | 6.138 | −5.562 | −9.459 | 1.00 | 0.00 |
| ATOM | 1217 | HD23 | LEU | 73 | 4.437 | −5.224 | −9.140 | 1.00 | 0.00 |
| ATOM | 1218 | C | LEU | 73 | 4.587 | −3.247 | −9.861 | 1.00 | 0.00 |
| ATOM | 1219 | O | LEU | 73 | 3.375 | −3.093 | −5.958 | 1.00 | 0.00 |

TABLE 5-continued

Atomic Structure Coordinates of the
Free Form of the P/CAF Bromodomain

| ATOM | 1220 | N | PHE | 74 | 5.218 | −3.316 | −4.693 | 1.00 | 0.00 |
|---|---|---|---|---|---|---|---|---|---|
| ATOM | 1221 | HN | PHE | 74 | 6.184 | −3.474 | −4.678 | 1.00 | 0.00 |
| ATOM | 1222 | CA | PHE | 74 | 4.513 | −3.144 | −3.434 | 1.00 | 0.00 |
| ATOM | 1223 | HA | PHE | 74 | 3.549 | −3.622 | −3.526 | 1.00 | 0.00 |
| ATOM | 1224 | CH | PHE | 74 | 5.290 | −3.809 | −2.305 | 1.00 | 0.00 |
| ATOM | 1225 | HB1 | PHE | 74 | 6.174 | −3.224 | −2.095 | 1.00 | 0.00 |
| ATOM | 1226 | HB2 | PHE | 74 | 5.587 | −4.799 | −2.614 | 1.00 | 0.00 |
| ATOM | 1227 | CG | PHE | 74 | 4.504 | −3.929 | −1.033 | 1.00 | 0.00 |
| ATOM | 1228 | CD1 | PHE | 74 | 4.062 | −9.163 | −0.989 | 1.00 | 0.00 |
| ATOM | 1229 | HD1 | PHE | 74 | 4.271 | −6.043 | −1.166 | 1.00 | 0.00 |
| ATOM | 1230 | CD2 | PHE | 74 | 4.223 | −2.807 | −0.277 | 1.00 | 0.00 |
| ATOM | 1231 | HD2 | PHE | 74 | 4.578 | −1.842 | −0.610 | 1.00 | 0.00 |
| ATOM | 1232 | CE1 | PHE | 74 | 3.350 | −5.272 | 0.993 | 1.00 | 0.00 |
| ATOM | 1233 | HE1 | PHE | 74 | 3.006 | −6.238 | 0.930 | 1.00 | 0.00 |
| ATOM | 1234 | CE2 | PHE | 74 | 3.518 | −2.911 | 0.903 | 1.00 | 0.00 |
| ATOM | 1235 | HE2 | PHE | 74 | 1.316 | −2.029 | 1.489 | 1.00 | 0.00 |
| ATOM | 1236 | CZ | PHE | 74 | 3.087 | −4.144 | 1.342 | 1.00 | 0.00 |
| ATOM | 1237 | HZ | PHE | 74 | 2.924 | −4.223 | 2.257 | 1.00 | 0.00 |
| ATOM | 1238 | C | PHE | 74 | 4.000 | −1.670 | −3.113 | 1.00 | 0.00 |
| ATOM | 1239 | O | PHE | 74 | 3.172 | −1.236 | −2.879 | 1.00 | 0.00 |
| ATOM | 1240 | N | MET | 75 | 5.392 | −0.902 | −3.095 | 1.00 | 0.00 |
| ATOM | 1241 | HN | MET | 75 | 6.262 | −1.309 | −3.281 | 1.00 | 0.00 |
| ATOM | 1242 | CA | MET | 75 | 5.324 | 0.929 | −2.788 | 1.00 | 0.00 |
| ATOM | 1243 | HA | MET | 75 | 5.190 | 0.628 | −1.721 | 1.00 | 0.00 |
| ATOM | 1244 | CB | MET | 75 | 6.617 | 1.240 | −3.192 | 1.00 | 0.00 |
| ATOM | 1245 | HB1 | MET | 75 | 6.403 | 2.289 | −3.330 | 1.00 | 0.00 |
| ATOM | 1246 | HB2 | MET | 75 | 6.964 | 0.834 | −4.124 | 1.00 | 0.00 |
| ATOM | 1247 | CG | MET | 75 | 7.738 | 1.120 | −2.171 | 1.00 | 0.00 |
| ATOM | 1248 | HG1 | MET | 75 | 8.668 | 1.379 | −2.652 | 1.00 | 0.00 |
| ATOM | 1249 | HG2 | MET | 75 | 7.546 | 1.818 | −1.373 | 1.00 | 0.00 |
| ATOM | 1250 | SD | MET | 75 | 7.907 | −0.529 | −1.461 | 1.00 | 0.00 |
| ATOM | 1251 | CE | MET | 75 | 7.869 | −0.193 | 0.288 | 1.00 | 0.00 |
| ATOM | 1252 | HE1 | MET | 75 | 8.136 | −1.036 | 0.851 | 1.00 | 0.00 |
| ATOM | 1253 | HE2 | MET | 75 | 6.875 | 0.161 | 0.564 | 1.00 | 0.00 |
| ATOM | 1254 | HE2 | MET | 75 | 8.569 | 0.638 | 0.506 | 1.00 | 0.00 |
| ATOM | 1255 | C | MET | 75 | 4.136 | 1.176 | −3.488 | 1.00 | 0.00 |
| ATOM | 1256 | O | MET | 75 | 3.495 | 2.073 | −2.942 | 1.00 | 0.00 |
| ATOM | 1257 | N | ALA | 76 | 3.826 | 0.692 | −4.687 | 1.00 | 0.00 |
| ATOM | 1258 | HN | ALA | 76 | 4.346 | −0.055 | −5.060 | 1.00 | 0.00 |
| ATOM | 1259 | CA | ALA | 76 | 2.659 | 1.177 | −5.404 | 1.00 | 0.00 |
| ATOM | 1260 | HA | ALA | 76 | 2.666 | 2.259 | −5.381 | 1.00 | 0.00 |
| ATOM | 1261 | CB | ALA | 76 | 2.669 | 0.723 | −4.853 | 1.00 | 0.00 |
| ATOM | 1262 | HB1 | ALA | 76 | 3.441 | 1.251 | −7.393 | 1.00 | 0.00 |
| ATOM | 1263 | HB2 | ALA | 76 | 1.706 | 0.935 | −7.300 | 1.00 | 0.00 |
| ATOM | 1264 | HB3 | ALA | 76 | 2.858 | −0.338 | −6.895 | 1.00 | 0.00 |
| ATOM | 1265 | C | ALA | 76 | 1.409 | 0.682 | −4.714 | 1.00 | 0.00 |
| ATOM | 1266 | O | ALA | 76 | 0.613 | 1.472 | −4.236 | 1.00 | 0.00 |
| ATOM | 1267 | N | ASP | 77 | 1.286 | −0.640 | −4.600 | 1.00 | 0.00 |
| ATOM | 1268 | HN | ASP | 77 | 1.977 | −1.214 | −4.989 | 1.00 | 0.00 |
| ATOM | 1269 | CA | ASP | 77 | 0.136 | −1.260 | −3.941 | 1.00 | 0.00 |
| ATOM | 1270 | HA | ASP | 77 | −0.692 | −1.239 | −4.637 | 1.00 | 0.00 |
| ATOM | 1271 | CB | ASP | 77 | 0.454 | −2.714 | −3.586 | 1.00 | 0.00 |
| ATOM | 1272 | HB1 | ASP | 77 | 1.280 | −2.736 | −2.891 | 1.00 | 0.00 |
| ATOM | 1273 | HB2 | ASP | 77 | −0.413 | −3.164 | −3.124 | 1.00 | 0.00 |
| ATOM | 1274 | CG | ASP | 77 | 0.831 | −3.537 | −4.802 | 1.00 | 0.00 |
| ATOM | 1275 | OD1 | ASP | 77 | 0.295 | −3.261 | −5.896 | 1.00 | 0.00 |
| ATOM | 1276 | OD2 | ASP | 77 | 1.666 | −4.455 | −4.661 | 1.00 | 0.00 |
| ATOM | 1277 | C | ASP | 77 | −0.266 | −0.491 | −2.685 | 1.00 | 0.00 |
| ATOM | 1278 | O | ASP | 77 | −1.436 | −0.169 | −2.498 | 1.00 | 0.00 |
| ATOM | 1279 | N | LEU | 78 | 0.718 | −0.155 | −1.857 | 1.00 | 0.00 |
| ATOM | 1280 | HN | LEU | 78 | 1.639 | −0.417 | −2.071 | 1.00 | 0.00 |
| ATOM | 1281 | CA | LEU | 78 | 0.464 | 0.617 | −0.649 | 1.00 | 0.00 |
| ATOM | 1282 | HA | LEU | 78 | −0.294 | 0.104 | −0.077 | 1.00 | 0.00 |
| ATOM | 1283 | CB | LEU | 78 | 1.744 | 0.724 | 0.185 | 1.00 | 0.00 |
| ATOM | 1284 | HB1 | LEU | 78 | 1.931 | 1.768 | 0.378 | 1.00 | 0.00 |
| ATOM | 1285 | HB2 | LEU | 78 | 2.562 | 0.336 | −0.402 | 1.00 | 0.00 |
| ATOM | 1286 | CO | LEU | 78 | 1.726 | −0.014 | 1.529 | 1.00 | 0.00 |
| ATOM | 1287 | HG | LEU | 78 | 2.742 | −0.221 | 1.827 | 1.00 | 0.00 |
| ATOM | 1288 | CD1 | LEU | 78 | 0.998 | −1.347 | 1.413 | 1.00 | 0.00 |
| ATOM | 1289 | HD11 | LEU | 78 | −0.066 | −1.174 | 1.360 | 1.00 | 0.00 |
| ATOM | 1290 | HD12 | LEU | 78 | 1.222 | −1.955 | 2.277 | 1.00 | 0.00 |
| ATOM | 1291 | HD13 | LEU | 78 | 1.327 | −1.855 | 0.521 | 1.00 | 0.00 |
| ATOM | 1292 | CO2 | LEU | 78 | 1.094 | 0.844 | 2.606 | 1.00 | 0.00 |
| ATOM | 1293 | HD21 | LEU | 78 | 1.126 | 1.880 | 2.303 | 1.00 | 0.00 |
| ATOM | 1294 | HD22 | LEU | 78 | 1.641 | 0.721 | 3.529 | 1.00 | 0.00 |
| ATOM | 1295 | HD23 | LEU | 78 | 0.068 | 0.541 | 2.752 | 1.00 | 0.00 |
| ATOM | 1296 | C | LEU | 78 | −0.045 | 2.009 | −1.009 | 1.00 | 0.00 |

TABLE 5-continued

Atomic Structure Coordinates of the
Free Form of the P/CAF Bromodomain

| ATOM | 1297 | O | LEU | 78 | −1.164 | 2.385 | −0.657 | 1.00 | 0.00 |
|---|---|---|---|---|---|---|---|---|---|
| ATOM | 1298 | N | GLN | 79 | 0.780 | 2.760 | −1.731 | 1.00 | 0.00 |
| ATOM | 1299 | HN | GLN | 79 | 1.649 | 2.393 | −1.995 | 1.00 | 0.00 |
| ATOM | 1300 | CA | GLN | 79 | 0.410 | 4.097 | −2.184 | 1.00 | 0.00 |
| ATOM | 1301 | HA | GLN | 79 | 0.357 | 4.744 | −1.321 | 1.00 | 0.00 |
| ATOM | 1302 | CB | GLN | 79 | 1.478 | 4.621 | −3.154 | 1.00 | 0.00 |
| ATOM | 1303 | HB1 | GLN | 79 | 1.727 | 3.833 | −3.850 | 1.00 | 0.00 |
| ATOM | 1304 | HB2 | GLN | 79 | 2.362 | 4.879 | −2.591 | 1.00 | 0.00 |
| ATOM | 1305 | CG | GLN | 79 | 1.052 | 5.840 | −3.958 | 1.00 | 0.00 |
| ATOM | 1306 | HG1 | GLN | 79 | 0.674 | 9.507 | −4.913 | 1.00 | 0.00 |
| ATOM | 1307 | HG2 | GLN | 79 | 0.270 | 6.356 | −3.421 | 1.00 | 0.00 |
| ATOM | 1308 | CD | GLN | 79 | 2.194 | 6.807 | −4.202 | 1.00 | 0.00 |
| ATOM | 1309 | OE1 | GLN | 79 | 2.596 | 7.551 | −3.307 | 1.00 | 0.00 |
| ATOM | 1310 | HE2 | GLN | 79 | 2.722 | 6.801 | −5.420 | 1.00 | 0.00 |
| ATOM | 1311 | HE21 | GLN | 79 | 3.462 | 7.416 | −5.607 | 1.00 | 0.00 |
| ATOM | 1312 | HE22 | GLN | 79 | 2.350 | 6.182 | −6.083 | 1.00 | 0.00 |
| ATOM | 1313 | C | GLN | 79 | −0.953 | 4.061 | −2.870 | 1.00 | 0.00 |
| ATOM | 1314 | O | GLN | 79 | −1.745 | 4.997 | −2.768 | 1.00 | 0.00 |
| ATOM | 1315 | N | ARG | 80 | −1.205 | 2.961 | −3.563 | 1.00 | 0.00 |
| ATOM | 1316 | HN | ARG | 80 | −0.522 | 2.263 | −3.602 | 1.00 | 0.00 |
| ATOM | 1317 | CA | ARG | 80 | −2.439 | 2.755 | −4.287 | 1.00 | 0.00 |
| ATOM | 1318 | HA | ARG | 80 | −2.705 | 3.686 | −4.766 | 1.00 | 0.00 |
| ATOM | 1319 | CB | ARG | 80 | −2.211 | 1.682 | −5.363 | 1.00 | 0.00 |
| ATOM | 1320 | HB1 | ARG | 80 | −1.193 | 1.505 | −5.449 | 1.00 | 0.00 |
| ATOM | 1321 | HB2 | ARG | 80 | −2.686 | 0.767 | −5.059 | 1.00 | 0.00 |
| ATOM | 1322 | CG | ARG | 80 | −2.725 | 2.063 | −6.740 | 1.00 | 0.00 |
| ATOM | 1323 | HG1 | ARG | 80 | −2.057 | 2.795 | −7.171 | 1.00 | 0.00 |
| ATOM | 1324 | HG2 | ARG | 80 | −2.742 | 1.180 | −7.363 | 1.00 | 0.00 |
| ATOM | 1325 | CD | ARG | 80 | −4.122 | 2.649 | −6.682 | 1.00 | 0.00 |
| ATOM | 1326 | HD1 | ARG | 80 | −4.422 | 2.735 | −5.653 | 1.00 | 0.00 |
| ATOM | 1327 | HD2 | ARG | 80 | −4.792 | 1.982 | −7.193 | 1.00 | 0.00 |
| ATOM | 1328 | NE | ARG | 80 | −4.186 | 3.968 | −7.310 | 1.00 | 0.00 |
| ATOM | 1329 | HE | ARG | 80 | −3.338 | 4.403 | −7.534 | 1.00 | 0.00 |
| ATOM | 1330 | CZ | ARG | 80 | −5.322 | 4.595 | −7.594 | 1.00 | 0.00 |
| ATOM | 1331 | NH1 | ARG | 80 | −6.486 | 4.030 | −7.305 | 1.00 | 0.00 |
| ATOM | 1332 | HH11 | ARG | 80 | −7.339 | 4.505 | −7.519 | 1.00 | 0.00 |
| ATOM | 1333 | HH12 | ARG | 80 | −6.509 | 3.129 | −6.872 | 1.00 | 0.00 |
| ATOM | 1334 | NH2 | ARG | 80 | −5.294 | 5.790 | −8.168 | 1.00 | 0.00 |
| ATOM | 1335 | HH21 | ARG | 80 | −4.418 | 6.219 | −8.386 | 1.00 | 0.00 |
| ATOM | 1336 | HH22 | ARG | 80 | −6.149 | 6.263 | −8.380 | 1.00 | 0.00 |
| ATOM | 1337 | C | ARG | 80 | −3.562 | 2.353 | −3.329 | 1.00 | 0.00 |
| ATOM | 1338 | O | ARG | 80 | −4.715 | 2.740 | −3.513 | 1.00 | 0.00 |
| ATOM | 1339 | N | VAL | 81 | −3.210 | 1.620 | −2.273 | 1.00 | 0.00 |
| ATOM | 1340 | HN | VAL | 81 | −2.271 | 1.367 | −2.155 | 1.00 | 0.00 |
| ATOM | 1341 | CA | VAL | 81 | −4.189 | 1.231 | −1.261 | 1.00 | 0.00 |
| ATOM | 1342 | HA | VAL | 81 | −4.947 | 0.630 | −1.742 | 1.00 | 0.00 |
| ATOM | 1343 | CB | VAL | 81 | −3.543 | 0.387 | −0.129 | 1.00 | 0.00 |
| ATOM | 1344 | HB | VAL | 81 | −2.648 | 0.893 | 0.201 | 1.00 | 0.00 |
| ATOM | 1345 | CG1 | VAL | 81 | −3.147 | −0.988 | −0.645 | 1.00 | 0.00 |
| ATOM | 1346 | HG11 | VAL | 81 | −2.073 | −1.089 | −0.614 | 1.00 | 0.00 |
| ATOM | 1347 | HG12 | VAL | 81 | −3.491 | −1.105 | −1.661 | 1.00 | 0.00 |
| ATOM | 1348 | HG13 | VAL | 81 | −3.597 | −1.750 | −0.023 | 1.00 | 0.00 |
| ATOM | 1349 | CG2 | VAL | 81 | −4.476 | 0.247 | 1.070 | 1.00 | 0.00 |
| ATOM | 1350 | HG21 | VAL | 81 | −5.364 | −0.291 | 0.774 | 1.00 | 0.00 |
| ATOM | 1351 | HG22 | VAL | 81 | −4.752 | 1.228 | 1.429 | 1.00 | 0.00 |
| ATOM | 1352 | HG23 | VAL | 81 | −3.972 | −0.295 | 1.857 | 1.00 | 0.00 |
| ATOM | 1353 | C | VAL | 81 | −4.844 | 2.481 | −0.674 | 1.00 | 0.00 |
| ATOM | 1354 | O | VAL | 81 | −6.050 | 2.507 | −0.427 | 1.00 | 0.00 |
| ATOM | 1355 | N | PHE | 82 | −4.037 | 3.515 | −0.459 | 1.00 | 0.00 |
| ATOM | 1356 | HN | PHE | 82 | −3.086 | 3.434 | −0.684 | 1.00 | 0.00 |
| ATOM | 1357 | CA | PHE | 82 | −4.533 | 4.774 | 0.080 | 1.00 | 0.00 |
| ATOM | 1358 | HA | PHE | 82 | −5.269 | 4.545 | 0.837 | 1.00 | 0.00 |
| ATOM | 1359 | CB | PHE | 82 | −3.390 | 5.972 | 0.717 | 1.00 | 0.00 |
| ATOM | 1360 | HB1 | PHE | 82 | −2.807 | 6.034 | −0.065 | 1.00 | 0.00 |
| ATOM | 1361 | HB2 | PHE | 82 | −3.810 | 6.342 | 1.348 | 1.00 | 0.00 |
| ATOM | 1362 | CG | PHE | 82 | −2.455 | 4.746 | 1.561 | 1.00 | 0.00 |
| ATOM | 1363 | CD1 | PHE | 82 | −2.850 | 3.520 | 2.077 | 1.00 | 0.00 |
| ATOM | 1364 | HD1 | PHE | 82 | −3.841 | 3.149 | 1.861 | 1.00 | 0.00 |
| ATOM | 1365 | CD2 | PHE | 82 | −1.180 | 9.209 | 1.850 | 1.00 | 0.00 |
| ATOM | 1366 | HD2 | PHE | 82 | −0.862 | 6.163 | 1.457 | 1.00 | 0.00 |
| ATOM | 1367 | CE1 | PHE | 82 | −1.988 | 2.768 | 2.853 | 1.00 | 0.00 |
| ATOM | 1368 | HE1 | PHE | 82 | −2.307 | 1.815 | 3.248 | 1.00 | 0.00 |
| ATOM | 1369 | CE2 | PHE | 82 | −0.316 | 4.462 | 2.627 | 1.00 | 0.00 |
| ATOM | 1370 | HE2 | PHE | 82 | 0.675 | 4.834 | 2.842 | 1.00 | 0.00 |
| ATOM | 1371 | CZ | PHE | 82 | −0.721 | 3.242 | 3.131 | 1.00 | 0.00 |
| ATOM | 1372 | HZ | PHE | 82 | −0.047 | 2.659 | 3.741 | 1.00 | 0.00 |
| ATOM | 1373 | C | PHE | 82 | −5.194 | 5.601 | −1.016 | 1.00 | 0.00 |

TABLE 5-continued

Atomic Structure Coordinates of the
Free Form of the P/CAF Bromodomain

| ATOM | 1374 | O    | PHE | 82 | −6.353  | 5.997  | −0.895 | 1.00 | 0.00 |
|------|------|------|-----|----|---------|--------|--------|------|------|
| ATOM | 1375 | N    | THR | 83 | −4.450  | 5.849  | −2.089 | 1.00 | 0.00 |
| ATOM | 1376 | HN   | THR | 83 | −3.536  | 5.499  | −2.129 | 1.00 | 0.00 |
| ATOM | 1377 | CA   | THR | 83 | −4.968  | 6.616  | −3.215 | 1.00 | 0.00 |
| ATOM | 1378 | HA   | THR | 83 | −5.151  | 7.624  | −2.875 | 1.00 | 0.00 |
| ATOM | 1379 | CB   | THR | 83 | −3.941  | 6.649  | −4.390 | 1.00 | 0.00 |
| ATOM | 1380 | HH   | THR | 83 | −3.649  | 5.627  | −4.588 | 1.00 | 0.00 |
| ATOM | 1381 | OG1  | THR | 83 | −2.784  | 7.369  | −3.953 | 1.00 | 0.00 |
| ATOM | 1382 | HG1  | THR | 83 | −2.246  | 6.812  | −3.382 | 1.00 | 0.00 |
| ATOM | 1383 | CG2  | THR | 83 | −4.464  | 7.286  | −5.619 | 1.00 | 0.00 |
| ATOM | 1384 | HG21 | THR | 83 | −3.654  | 7.404  | −6.323 | 1.00 | 0.00 |
| ATOM | 1385 | HG22 | THR | 83 | −4.884  | 8.255  | −5.389 | 1.00 | 0.00 |
| ATOM | 1386 | HG23 | THR | 83 | −5.228  | 6.656  | −6.049 | 1.00 | 0.00 |
| ATOM | 1387 | C    | THR | 83 | −6.278  | 6.017  | −3.711 | 1.00 | 0.00 |
| ATOM | 1388 | O    | THR | 83 | −7.211  | 6.740  | −4.033 | 1.00 | 0.00 |
| ATOM | 1389 | N    | ASN | 84 | −6.333  | 4.690  | −3.754 | 1.00 | 0.00 |
| ATOM | 1390 | HN   | ASN | 84 | −5.550  | 4.170  | −3.476 | 1.00 | 0.00 |
| ATOM | 1391 | CA   | ASN | 84 | −7.533  | 3.987  | −4.190 | 1.00 | 0.00 |
| ATOM | 1392 | HA   | ASN | 84 | −7.822  | 4.381  | −5.153 | 1.00 | 0.00 |
| ATOM | 1393 | CB   | ASN | 84 | −7.250  | 2.491  | −4.321 | 1.00 | 0.00 |
| ATOM | 1394 | HB1  | ASN | 84 | −6.457  | 2.342  | −5.039 | 1.00 | 0.00 |
| ATOM | 1395 | HB2  | ASN | 84 | −6.919  | 2.107  | −3.362 | 1.00 | 0.00 |
| ATOM | 1396 | CG   | ASN | 84 | −8.464  | 1.707  | −4.778 | 1.00 | 0.00 |
| ATOM | 1397 | OD1  | ASN | 84 | −9.459  | 2.282  | −5.218 | 1.00 | 0.00 |
| ATOM | 1398 | ND2  | ASN | 84 | −8.388  | 0.385  | −4.672 | 1.00 | 0.00 |
| ATOM | 1399 | HD21 | ASN | 84 | −7.564  | −0.004 | −4.312 | 1.00 | 0.00 |
| ATOM | 1400 | HD22 | ASN | 84 | −9.158  | −0.147 | −4.960 | 1.00 | 0.00 |
| ATOM | 1401 | C    | ASN | 84 | −8.670  | 4.212  | −3.201 | 1.00 | 0.00 |
| ATOM | 1402 | O    | ASN | 84 | −9.656  | 4.879  | −3.514 | 1.00 | 0.00 |
| ATOM | 1403 | N    | CYS | 85 | −8.520  | 3.657  | −2.003 | 1.00 | 0.00 |
| ATOM | 1404 | HN   | CYS | 85 | −7.708  | 3.142  | −1.812 | 1.00 | 0.00 |
| ATOM | 1405 | CA   | CYS | 85 | −9.526  | 3.808  | −0.961 | 1.00 | 0.00 |
| ATOM | 1406 | HA   | CYS | 85 | −10.414 | 3.280  | −1.276 | 1.00 | 0.00 |
| ATOM | 1407 | CB   | CYS | 85 | −9.028  | 3.205  | 0.354  | 1.00 | 0.00 |
| ATOM | 1408 | HB1  | CYS | 85 | −9.789  | 3.329  | 1.109  | 1.00 | 0.00 |
| ATOM | 1409 | HB2  | CYS | 85 | −8.132  | 3.724  | 0.665  | 1.00 | 0.00 |
| ATOM | 1410 | SG   | CYS | 85 | −8.635  | 1.443  | 0.257  | 1.00 | 0.00 |
| ATOM | 1411 | HG   | CYS | 85 | −9.362  | 0.955  | 0.652  | 1.00 | 0.00 |
| ATOM | 1412 | C    | CYS | 85 | −9.873  | 5.278  | −0.759 | 1.00 | 0.00 |
| ATOM | 1413 | O    | CYS | 85 | −10.996 | 5.613  | −0.398 | 1.00 | 0.00 |
| ATOM | 1414 | N    | LYS | 86 | −8.898  | 6.150  | −0.993 | 1.00 | 0.00 |
| ATOM | 1415 | HN   | LYS | 86 | −8.021  | 5.820  | −1.281 | 1.00 | 0.00 |
| ATOM | 1416 | CA   | LYS | 86 | −9.102  | 7.586  | −0.840 | 1.00 | 0.00 |
| ATOM | 1417 | HA   | LYS | 86 | −9.725  | 7.741  | 0.029  | 1.00 | 0.00 |
| ATOM | 1418 | CB   | LYS | 86 | −7.758  | 8.290  | −0.623 | 1.00 | 0.00 |
| ATOM | 1419 | HB1  | LYS | 86 | −7.355  | 7.984  | 0.330  | 1.00 | 0.00 |
| ATOM | 1420 | HB2  | LYS | 86 | −7.078  | 7.990  | −1.405 | 1.00 | 0.00 |
| ATOM | 1421 | CG   | LYS | 86 | −7.853  | 9.807  | −0.632 | 1.00 | 0.00 |
| ATOM | 1422 | HG1  | LYS | 86 | −8.858  | 10.091 | −0.901 | 1.00 | 0.00 |
| ATOM | 1423 | HG2  | LYS | 86 | −7.625  | 10.178 | 0.356  | 1.00 | 0.00 |
| ATOM | 1424 | CD   | LYS | 86 | −6.882  | 10.424 | −1.626 | 1.00 | 0.00 |
| ATOM | 1425 | HD1  | LYS | 86 | −7.437  | 11.020 | −2.324 | 1.00 | 0.00 |
| ATOM | 1426 | HD2  | LYS | 86 | −6.363  | 9.633  | −2.147 | 1.00 | 0.00 |
| ATOM | 1427 | CE   | LYS | 86 | −5.860  | 11.308 | −0.930 | 1.00 | 0.00 |
| ATOM | 1428 | HE1  | LYS | 86 | −5.744  | 10.970 | 0.090  | 1.00 | 0.00 |
| ATOM | 1429 | HE2  | LYS | 86 | −4.916  | 11.221 | −1.447 | 1.00 | 0.00 |
| ATOM | 1430 | NZ   | LYS | 86 | −6.276  | 12.738 | −0.922 | 1.00 | 0.00 |
| ATOM | 1431 | HZ1  | LYS | 86 | −6.207  | 13.125 | 0.041  | 1.00 | 0.00 |
| ATOM | 1432 | HZ2  | LYS | 86 | −7.260  | 12.825 | −1.249 | 1.00 | 0.00 |
| ATOM | 1433 | HZ3  | LYS | 86 | −5.663  | 13.292 | −1.552 | 1.00 | 0.00 |
| ATOM | 1434 | C    | LYS | 86 | −9.805  | 8.175  | −2.060 | 1.00 | 0.00 |
| ATOM | 1435 | O    | LYS | 86 | −10.579 | 9.126  | −1.943 | 1.00 | 0.00 |
| ATOM | 1436 | N    | GLU | 87 | −9.518  | 7.615  | −3.230 | 1.00 | 0.00 |
| ATOM | 1437 | HN   | GLU | 87 | −8.883  | 6.869  | −3.259 | 1.00 | 0.00 |
| ATOM | 1438 | CA   | GLU | 87 | −10.101 | 8.103  | −4.474 | 1.00 | 0.00 |
| ATOM | 1439 | HA   | GLU | 87 | −10.101 | 9.183  | −4.435 | 1.00 | 0.00 |
| ATOM | 1440 | CB   | GLU | 87 | −9.256  | 7.649  | −5.665 | 1.00 | 0.00 |
| ATOM | 1441 | HB1  | GLU | 87 | −9.884  | 7.607  | −6.542 | 1.00 | 0.00 |
| ATOM | 1442 | HB2  | GLU | 87 | −8.869  | 6.662  | −5.462 | 1.00 | 0.00 |
| ATOM | 1443 | CG   | GLU | 87 | −8.084  | 8.570  | −5.963 | 1.00 | 0.00 |
| ATOM | 1444 | HG1  | GLU | 87 | −7.726  | 8.989  | −5.033 | 1.00 | 0.00 |
| ATOM | 1445 | HG2  | GLU | 87 | −7.296  | 7.993  | −6.424 | 1.00 | 0.00 |
| ATOM | 1446 | CD   | GLU | 87 | −8.460  | 9.707  | −6.893 | 1.00 | 0.00 |
| ATOM | 1447 | OE1  | GLU | 87 | −9.484  | 9.583  | −7.597 | 1.00 | 0.00 |
| ATOM | 1448 | OE2  | GLU | 87 | −7.732  | 10.721 | −6.916 | 1.00 | 0.00 |
| ATOM | 1449 | C    | GLU | 87 | −11.539 | 7.621  | −4.645 | 1.00 | 0.00 |
| ATOM | 1450 | O    | GLU | 87 | −12.422 | 8.397  | −5.010 | 1.00 | 0.00 |

TABLE 5-continued

Atomic Structure Coordinates of the
Free Form of the P/CAF Bromodomain

| ATOM | 1451 | N    | TYR | 88 | −11.769 | 6.338  | −4.387 | 1.00 | 0.00 |
|------|------|------|-----|----|---------|--------|--------|------|------|
| ATOM | 1452 | HN   | TYR | 88 | −11.023 | 5.763  | −4.109 | 1.00 | 0.00 |
| ATOM | 1453 | CA   | TYR | 88 | −13.100 | 5.757  | −4.536 | 1.00 | 0.00 |
| ATOM | 1454 | HA   | TYR | 88 | −13.528 | 6.144  | −5.449 | 1.00 | 0.00 |
| ATOM | 1455 | CB   | TYR | 88 | −13.000 | 4.234  | −4.639 | 1.00 | 0.00 |
| ATOM | 1456 | HB1  | TYR | 88 | −12.032 | 3.971  | −5.040 | 1.00 | 0.00 |
| ATOM | 1457 | HB2  | TYR | 88 | −13.104 | 3.806  | −3.653 | 1.00 | 0.00 |
| ATOM | 1458 | CG   | TYR | 88 | −14.054 | 3.612  | −5.527 | 1.00 | 0.00 |
| ATOM | 1459 | CD1  | TYR | 88 | −15.165 | 2.982  | −4.982 | 1.00 | 0.00 |
| ATOM | 1460 | HD1  | TYR | 88 | −15.273 | 2.942  | −3.908 | 1.00 | 0.00 |
| ATOM | 1461 | CD2  | TYR | 88 | −13.935 | 3.651  | −6.911 | 1.00 | 0.00 |
| ATOM | 1462 | HD2  | TYR | 88 | −13.076 | 4.136  | −7.350 | 1.00 | 0.00 |
| ATOM | 1463 | CE1  | TYR | 88 | −16.130 | 2.410  | −5.790 | 1.00 | 0.00 |
| ATOM | 1464 | HE1  | TYR | 88 | −16.987 | 1.925  | −5.347 | 1.00 | 0.00 |
| ATOM | 1465 | CE2  | TYR | 88 | −14.894 | 3.081  | −7.726 | 1.00 | 0.00 |
| ATOM | 1466 | HE2  | TYR | 88 | −14.785 | 3.122  | −8.800 | 1.00 | 0.00 |
| ATOM | 1467 | CZ   | TYR | 88 | −15.990 | 2.463  | −7.161 | 1.00 | 0.00 |
| ATOM | 1468 | OH   | TYR | 88 | −16.947 | 1.893  | −7.969 | 1.00 | 0.00 |
| ATOM | 1469 | HH   | TYR | 88 | −17.473 | 2.584  | −8.378 | 1.00 | 0.00 |
| ATOM | 1470 | C    | TYR | 88 | −14.010 | 6.137  | −3.368 | 1.00 | 0.00 |
| ATOM | 1471 | O    | TYR | 88 | −14.555 | 5.265  | −2.691 | 1.00 | 0.00 |
| ATOM | 1472 | N    | ASN | 89 | −14.187 | 7.439  | −3.150 | 1.00 | 0.00 |
| ATOM | 1473 | HN   | ASN | 89 | −13.737 | 8.087  | −3.727 | 1.00 | 0.00 |
| ATOM | 1474 | CA   | ASN | 89 | −19.038 | 7.925  | −2.070 | 1.00 | 0.00 |
| ATOM | 1475 | HA   | ASN | 89 | −15.852 | 7.102  | −1.736 | 1.00 | 0.00 |
| ATOM | 1476 | CB   | ASN | 89 | −14.185 | 8.416  | −0.899 | 1.00 | 0.00 |
| ATOM | 1477 | HB1  | ASN | 89 | −14.820 | 8.581  | −0.042 | 1.00 | 0.00 |
| ATOM | 1478 | HB2  | ASN | 89 | −13.704 | 9.344  | −1.173 | 1.00 | 0.00 |
| ATOM | 1479 | CG   | ASN | 89 | −13.111 | 7.419  | −0.917 | 1.00 | 0.00 |
| ATOM | 1480 | OD1  | ASN | 89 | −12.001 | 7.796  | −0.149 | 1.00 | 0.00 |
| ATOM | 1481 | ND2  | ASN | 89 | −13.444 | 6.136  | −0.609 | 1.00 | 0.00 |
| ATOM | 1482 | HD21 | ASN | 89 | −12.769 | 9.467  | −0.377 | 1.00 | 0.00 |
| ATOM | 1483 | HD22 | ASN | 89 | −14.348 | 5.910  | −0.912 | 1.00 | 0.00 |
| ATOM | 1484 | C    | ASN | 89 | −15.944 | 9.048  | −2.552 | 1.00 | 0.00 |
| ATOM | 1485 | O    | ASN | 89 | −15.701 | 10.222 | −2.272 | 1.00 | 0.00 |
| ATOM | 1486 | N    | ALA | 90 | −16.997 | 8.680  | −3.272 | 1.00 | 0.00 |
| ATOM | 1487 | HN   | ALA | 90 | −17.141 | 7.728  | −3.456 | 1.00 | 0.00 |
| ATOM | 1488 | CA   | ALA | 90 | −17.954 | 9.655  | −3.783 | 1.00 | 0.00 |
| ATOM | 1489 | HA   | ALA | 90 | −17.486 | 10.184 | −4.999 | 1.00 | 0.00 |
| ATOM | 1490 | CB   | ALA | 90 | −19.185 | 8.946  | −4.326 | 1.00 | 0.00 |
| ATOM | 1491 | HB1  | ALA | 90 | −19.230 | 7.944  | −3.926 | 1.00 | 0.00 |
| ATOM | 1492 | HB2  | ALA | 90 | −19.124 | 8.901  | −5.404 | 1.00 | 0.00 |
| ATOM | 1493 | HB3  | ALA | 90 | −20.072 | 9.490  | −4.035 | 1.00 | 0.00 |
| ATOM | 1494 | C    | ALA | 90 | −18.356 | 10.662 | −2.705 | 1.00 | 0.00 |
| ATOM | 1495 | O    | ALA | 90 | −18.383 | 11.868 | −2.952 | 1.00 | 0.00 |
| ATOM | 1496 | N    | PRO | 91 | −18.657 | 10.179 | −1.487 | 1.00 | 0.00 |
| ATOM | 1497 | CA   | PRO | 91 | −19.087 | 11.011 | −0.381 | 1.00 | 0.00 |
| ATOM | 1498 | HA   | PRO | 91 | −19.505 | 11.951 | −0.717 | 1.00 | 0.00 |
| ATOM | 1499 | CB   | PRO | 91 | −20.176 | 10.140 | 0.237  | 1.00 | 0.00 |
| ATOM | 1500 | HB1  | PRO | 91 | −20.271 | 10.369 | 1.289  | 1.00 | 0.00 |
| ATOM | 1501 | HB2  | PRO | 91 | −21.115 | 10.323 | −0.263 | 1.00 | 0.00 |
| ATOM | 1502 | CG   | PRO | 91 | −19.704 | 8.730  | 0.022  | 1.00 | 0.00 |
| ATOM | 1503 | HG1  | PRO | 91 | −20.537 | 8.104  | −0.298 | 1.00 | 0.00 |
| ATOM | 1504 | HG2  | PRO | 91 | −19.249 | 8.358  | 0.929  | 1.00 | 0.00 |
| ATOM | 1505 | CD   | PRO | 91 | −18.679 | 8.764  | −1.094 | 1.00 | 0.00 |
| ATOM | 1506 | HD1  | PRO | 91 | −17.713 | 8.492  | −0.724 | 1.00 | 0.00 |
| ATOM | 1507 | HD2  | PRO | 91 | −18.988 | 8.139  | −1.919 | 1.00 | 0.00 |
| ATOM | 1508 | C    | PRO | 91 | −17.976 | 11.264 | 0.633  | 1.00 | 0.00 |
| ATOM | 1509 | O    | PRO | 91 | −18.242 | 11.671 | 1.766  | 1.00 | 0.00 |
| ATOM | 1510 | N    | GLU | 92 | −16.734 | 11.007 | 0.234  | 1.00 | 0.00 |
| ATOM | 1511 | HN   | GLU | 92 | −16.582 | 10.671 | −0.674 | 1.00 | 0.00 |
| ATOM | 1512 | CA   | GLU | 92 | −15.596 | 11.174 | 1.132  | 1.00 | 0.00 |
| ATOM | 1513 | HA   | GLU | 92 | −14.728 | 10.745 | 0.654  | 1.00 | 0.00 |
| ATOM | 1514 | CB   | GLU | 92 | −15.340 | 12.658 | 1.408  | 1.00 | 0.00 |
| ATOM | 1515 | HB1  | GLU | 92 | −14.454 | 12.750 | 2.020  | 1.00 | 0.00 |
| ATOM | 1516 | HB2  | GLU | 92 | −16.183 | 13.062 | 1.949  | 1.00 | 0.00 |
| ATOM | 1517 | CG   | GLU | 92 | −19.139 | 13.487 | 0.150  | 1.00 | 0.00 |
| ATOM | 1518 | HG1  | GLU | 92 | −15.062 | 12.821 | −0.696 | 1.00 | 0.00 |
| ATOM | 1519 | HG2  | GLU | 92 | −15.993 | 14.135 | 0.021  | 1.00 | 0.00 |
| ATOM | 1520 | CD   | GLU | 92 | −13.888 | 14.343 | 0.208  | 1.00 | 0.00 |
| ATOM | 1521 | OE1  | GLU | 92 | −13.118 | 14.335 | −0.775 | 1.00 | 0.00 |
| ATOM | 1522 | OE2  | GLU | 92 | −13.679 | 15.021 | 1.236  | 1.00 | 0.00 |
| ATOM | 1523 | C    | GLU | 92 | −15.843 | 10.432 | 2.436  | 1.00 | 0.00 |
| ATOM | 1524 | O    | GLU | 92 | −15.529 | 10.925 | 3.519  | 1.00 | 0.00 |
| ATOM | 1525 | N    | SER | 93 | −16.427 | 9.248  | 2.313  | 1.00 | 0.00 |
| ATOM | 1526 | HN   | SER | 93 | −16.649 | 8.919  | 1.417  | 1.00 | 0.00 |
| ATOM | 1527 | CA   | SER | 93 | −16.725 | 8.412  | 3.463  | 1.00 | 0.00 |

TABLE 5-continued

Atomic Structure Coordinates of the
Free Form of the P/CAF Bromodomain

| ATOM | 1528 | HA | SER | 93 | −17.495 | 8.899 | 4.042 | 1.00 | 0.00 |
|---|---|---|---|---|---|---|---|---|---|
| ATOM | 1529 | CB | SER | 93 | −17.234 | 7.048 | 2.986 | 1.00 | 0.00 |
| ATOM | 1530 | HB1 | SER | 93 | −17.222 | 6.360 | 3.809 | 1.00 | 0.00 |
| ATOM | 1531 | HB2 | SER | 93 | −18.243 | 7.152 | 2.615 | 1.00 | 0.00 |
| ATOM | 1532 | OG | SER | 93 | −15.418 | 6.536 | 1.947 | 1.00 | 0.00 |
| ATOM | 1533 | HG | SER | 93 | −16.849 | 6.678 | 1.101 | 1.00 | 0.00 |
| ATOM | 1534 | C | SER | 93 | −15.490 | 8.232 | 4.335 | 1.00 | 0.00 |
| ATOM | 1535 | O | SER | 93 | −14.447 | 8.833 | 4.082 | 1.00 | 0.00 |
| ATOM | 1536 | N | GLU | 94 | −15.601 | 7.370 | 5.338 | 1.00 | 0.00 |
| ATOM | 1537 | HN | GLU | 94 | −16.455 | 6.913 | 5.485 | 1.00 | 0.00 |
| ATOM | 1538 | CA | GLU | 94 | −14.485 | 7.092 | 6.230 | 1.00 | 0.00 |
| ATOM | 1539 | HA | GLU | 94 | −14.213 | 8.017 | 6.717 | 1.00 | 0.00 |
| ATOM | 1540 | CB | GLU | 94 | −14.901 | 6.073 | 7.292 | 1.00 | 0.00 |
| ATOM | 1541 | HB1 | GLU | 94 | −14.489 | 5.109 | 7.031 | 1.00 | 0.00 |
| ATOM | 1542 | HB2 | GLU | 94 | −15.979 | 6.003 | 7.305 | 1.00 | 0.00 |
| ATOM | 1543 | CG | GLU | 94 | −14.430 | 6.427 | 8.693 | 1.00 | 0.00 |
| ATOM | 1544 | HG1 | GLU | 94 | −13.974 | 7.082 | 8.416 | 1.00 | 0.00 |
| ATOM | 1545 | HG2 | GLU | 94 | −15.229 | 6.939 | 9.209 | 1.00 | 0.00 |
| ATOM | 1546 | CD | GLU | 94 | −14.035 | 5.207 | 9.502 | 1.00 | 0.00 |
| ATOM | 1547 | OE1 | GLU | 94 | −13.155 | 5.336 | 10.379 | 1.00 | 0.00 |
| ATOM | 1548 | OE2 | GLU | 94 | −14.604 | 4.123 | 9.257 | 1.00 | 0.00 |
| ATOM | 1549 | C | GLU | 94 | −13.274 | 6.569 | 5.457 | 1.00 | 0.00 |
| ATOM | 1550 | O | GLU | 94 | −12.160 | 6.551 | 5.979 | 1.00 | 0.00 |
| ATOM | 1551 | N | TYR | 95 | −13.493 | 6.137 | 4.214 | 1.00 | 0.00 |
| ATOM | 1552 | HN | TYR | 95 | −14.397 | 6.168 | 3.841 | 1.00 | 0.00 |
| ATOM | 1553 | CA | TYR | 95 | −12.412 | 5.611 | 3.393 | 1.00 | 0.00 |
| ATOM | 1554 | HA | TYR | 95 | −11.977 | 4.775 | 3.916 | 1.00 | 0.00 |
| ATOM | 1555 | CA | TYR | 95 | −12.947 | 5.131 | 2.045 | 1.00 | 0.00 |
| ATOM | 1556 | HB1 | TYR | 95 | −13.630 | 5.870 | 1.653 | 1.00 | 0.00 |
| ATOM | 1557 | HB2 | TYR | 95 | −12.119 | 5.016 | 1.365 | 1.00 | 0.00 |
| ATOM | 1558 | CG | TYR | 95 | −13.678 | 3.807 | 2.104 | 1.00 | 0.00 |
| ATOM | 1559 | CD1 | TYR | 95 | −13.724 | 2.972 | 0.996 | 1.00 | 0.00 |
| ATOM | 1560 | HD1 | TYR | 95 | −13.227 | 3.279 | 0.087 | 1.00 | 0.00 |
| ATOM | 1561 | CD2 | TYR | 95 | −14.325 | 3.394 | 3.263 | 1.00 | 0.00 |
| ATOM | 1562 | HD2 | TYR | 95 | −14.303 | 4.030 | 4.132 | 1.00 | 0.00 |
| ATOM | 1563 | CE1 | TYR | 95 | −14.390 | 1.762 | 1.040 | 1.00 | 0.00 |
| ATOM | 1564 | HE1 | TYR | 95 | −14.413 | 1.126 | 0.167 | 1.00 | 0.00 |
| ATOM | 1565 | CE2 | TYR | 95 | −14.994 | 2.187 | 3.314 | 1.00 | 0.00 |
| ATOM | 1566 | HE2 | TYR | 95 | −15.487 | 3.884 | 4.227 | 1.00 | 0.00 |
| ATOM | 1567 | CZ | TYR | 95 | −15.023 | 1.374 | 2.202 | 1.00 | 0.00 |
| ATOM | 1568 | OH | TYR | 95 | −15.687 | 0.170 | 2.250 | 1.00 | 0.00 |
| ATOM | 1569 | HH | TYR | 95 | −15.098 | −0.934 | 1.974 | 1.00 | 0.00 |
| ATOM | 1570 | C | TYR | 95 | −11.338 | 6.671 | 3.177 | 1.00 | 0.00 |
| ATOM | 1571 | O | TYR | 95 | −10.170 | 6.352 | 2.951 | 1.00 | 0.00 |
| ATOM | 1572 | N | TYR | 96 | −11.743 | 7.934 | 3.243 | 1.00 | 0.00 |
| ATOM | 1573 | HN | TYR | 96 | −12.686 | 8.125 | 3.432 | 1.00 | 0.00 |
| ATOM | 1574 | CA | TYR | 96 | −10.816 | 9.049 | 3.073 | 1.00 | 0.00 |
| ATOM | 1575 | HA | TYR | 96 | −10.140 | 8.795 | 2.268 | 1.00 | 0.00 |
| ATOM | 1576 | CB | TYR | 96 | −11.579 | 10.321 | 2.712 | 1.00 | 0.00 |
| ATOM | 1577 | HB1 | TYR | 96 | −12.376 | 10.073 | 2.027 | 1.00 | 0.00 |
| ATOM | 1578 | HB2 | TYR | 96 | −12.001 | 10.745 | 3.611 | 1.00 | 0.00 |
| ATOM | 1579 | CG | TYR | 96 | −10.717 | 11.378 | 2.060 | 1.00 | 0.00 |
| ATOM | 1580 | CD1 | TYR | 96 | −10.257 | 11.219 | 0.759 | 1.00 | 0.00 |
| ATOM | 1581 | HD1 | TYR | 96 | −10.524 | 10.326 | 0.213 | 1.00 | 0.00 |
| ATOM | 1582 | CD2 | TYR | 96 | −10.364 | 12.533 | 2.745 | 1.00 | 0.00 |
| ATOM | 1583 | HD2 | TYR | 96 | −10.714 | 12.672 | 3.758 | 1.00 | 0.00 |
| ATOM | 1584 | CE1 | TYR | 96 | −9.471 | 12.183 | 0.159 | 1.00 | 0.00 |
| ATOM | 1585 | HE1 | TYR | 96 | −9.120 | 12.039 | −0.892 | 1.00 | 0.00 |
| ATOM | 1586 | CE2 | TYR | 96 | −9.576 | 13.901 | 2.152 | 1.00 | 0.00 |
| ATOM | 1587 | HE2 | TYR | 96 | −9.312 | 14.393 | 2.701 | 1.00 | 0.00 |
| ATOM | 1588 | CZ | TYR | 96 | −9.131 | 13.320 | 0.859 | 1.00 | 0.00 |
| ATOM | 1589 | OH | TYR | 96 | −8.347 | 14.282 | 0.269 | 1.00 | 0.00 |
| ATOM | 1590 | HH | TYR | 96 | −8.832 | 14.690 | −0.456 | 1.00 | 0.00 |
| ATOM | 1591 | C | TYR | 96 | −10.009 | 9.267 | 4.346 | 1.00 | 0.00 |
| ATOM | 1592 | O | TYR | 96 | −8.884 | 9.764 | 4.303 | 1.00 | 0.00 |
| ATOM | 1593 | N | LYS | 97 | −10.593 | 8.888 | 5.476 | 1.00 | 0.00 |
| ATOM | 1594 | HN | LYS | 97 | −11.496 | 8.503 | 9.445 | 1.00 | 0.00 |
| ATOM | 1595 | CA | LYS | 97 | −9.917 | 9.050 | 6.771 | 1.00 | 0.00 |
| ATOM | 1596 | HA | LYS | 97 | −9.515 | 10.043 | 6.806 | 1.00 | 0.00 |
| ATOM | 1597 | CB | LYS | 97 | −10.960 | 8.901 | 7.898 | 1.00 | 0.00 |
| ATOM | 1598 | HB1 | LYS | 97 | −11.380 | 7.906 | 7.859 | 1.00 | 0.00 |
| ATOM | 1599 | HB2 | LYS | 97 | −10.457 | 9.033 | 8.845 | 1.00 | 0.00 |
| ATOM | 1600 | CG | LYS | 97 | −12.100 | 9.903 | 7.820 | 1.00 | 0.00 |
| ATOM | 1601 | HG1 | LYS | 97 | −12.840 | 9.937 | 7.124 | 1.00 | 0.00 |
| ATOM | 1602 | HG2 | LYS | 97 | −11.711 | 10.849 | 7.473 | 1.00 | 0.00 |
| ATOM | 1603 | CD | LYS | 97 | −12.796 | 10.107 | 9.176 | 1.00 | 0.00 |
| ATOM | 1604 | HD1 | LYS | 97 | −13.665 | 10.674 | 9.042 | 1.00 | 0.00 |

TABLE 5-continued

Atomic Structure Coordinates of the
Free Form of the P/CAF Bromodomain

| ATOM | 1605 | HD2 | LYS | 97 | −12.990 | 9.142 | 9.601 | 1.00 | 0.00 |
|---|---|---|---|---|---|---|---|---|---|
| ATOM | 1606 | CE | LYS | 97 | −11.842 | 10.897 | 10.131 | 1.00 | 0.00 |
| ATOM | 1607 | HE1 | LYS | 97 | −10.927 | 11.105 | 9.614 | 1.00 | 0.00 |
| ATOM | 1608 | HE2 | LYS | 97 | −11.618 | 10.218 | 10.972 | 1.00 | 0.00 |
| ATOM | 1609 | NZ | LYS | 97 | −12.471 | 12.111 | 10.629 | 1.00 | 0.00 |
| ATOM | 1610 | HZ1 | LYS | 97 | −11.831 | 12.917 | 10.476 | 1.00 | 0.00 |
| ATOM | 1611 | HZ2 | LYS | 97 | −12.672 | 12.031 | 11.646 | 1.00 | 0.00 |
| ATOM | 1612 | HZ3 | LYS | 97 | −13.362 | 12.289 | 10.123 | 1.00 | 0.00 |
| ATOM | 1613 | C | LYS | 97 | −8.816 | 8.031 | 6.955 | 1.00 | 0.00 |
| ATOM | 1614 | O | LYS | 97 | −7.664 | 8.395 | 7.189 | 1.00 | 0.00 |
| ATOM | 1615 | N | CYS | 98 | −9.167 | 6.753 | 6.861 | 1.00 | 0.00 |
| ATOM | 1616 | HN | CYS | 98 | −10.105 | 6.529 | 6.684 | 1.00 | 0.00 |
| ATOM | 1617 | CA | CYS | 98 | −8.203 | 5.671 | 7.039 | 1.00 | 0.00 |
| ATOM | 1618 | HA | CYS | 98 | −7.970 | 5.609 | 8.092 | 1.00 | 0.00 |
| ATOM | 1619 | CB | CYS | 98 | −8.816 | 4.348 | 6.588 | 1.00 | 0.00 |
| ATOM | 1620 | NB1 | CYS | 98 | −8.039 | 3.600 | 6.531 | 1.00 | 0.00 |
| ATOM | 1621 | HB2 | CYS | 98 | −9.554 | 4.040 | 7.311 | 1.00 | 0.00 |
| ATOM | 1622 | SG | CYS | 98 | −9.627 | 4.426 | 4.976 | 1.00 | 0.00 |
| ATOM | 1623 | HG | CYS | 98 | −10.366 | 5.034 | 5.045 | 1.00 | 0.00 |
| ATOM | 1624 | C | CYS | 98 | −6.914 | 5.931 | 6.268 | 1.00 | 0.00 |
| ATOM | 1625 | O | CYS | 98 | −9.817 | 5.796 | 6.814 | 1.00 | 0.00 |
| ATOM | 1626 | N | ALA | 99 | −7.045 | 6.278 | 4.991 | 1.00 | 0.00 |
| ATOM | 1627 | HN | ALA | 99 | −7.939 | 6.375 | 4.607 | 1.00 | 0.00 |
| ATOM | 1628 | CA | ALA | 99 | −5.885 | 6.991 | 4.158 | 1.00 | 0.00 |
| ATOM | 1629 | HA | ALA | 99 | −5.339 | 5.629 | 4.029 | 1.00 | 0.00 |
| ATOM | 1630 | CB | ALA | 99 | −6.319 | 7.042 | 2.785 | 1.00 | 0.00 |
| ATOM | 1631 | HB1 | ALA | 99 | −6.855 | 6.255 | 2.275 | 1.00 | 0.00 |
| ATOM | 1632 | HB2 | ALA | 99 | −5.448 | 7.317 | 2.209 | 1.00 | 0.00 |
| ATOM | 1633 | HB3 | ALA | 99 | −6.963 | 7.902 | 2.897 | 1.00 | 0.00 |
| ATOM | 1634 | C | ALA | 99 | −4.977 | 7.570 | 4.828 | 1.00 | 0.00 |
| ATOM | 1635 | O | ALA | 99 | −3.764 | 7.398 | 4.871 | 1.00 | 0.00 |
| ATOM | 1636 | N | ASN | 100 | −5.581 | 8.613 | 5.379 | 1.00 | 0.00 |
| ATOM | 1637 | HN | ASN | 100 | −6.555 | 8.685 | 5.321 | 1.00 | 0.00 |
| ATOM | 1638 | CA | ASN | 100 | −4.826 | 9.660 | 6.094 | 1.00 | 0.00 |
| ATOM | 1639 | HA | ASN | 100 | −4.202 | 10.142 | 5.316 | 1.00 | 0.00 |
| ATOM | 1640 | CB | ASN | 100 | −5.778 | 10.695 | 6.658 | 1.00 | 0.00 |
| ATOM | 1641 | HB1 | ASN | 100 | −6.720 | 10.640 | 6.130 | 1.00 | 0.00 |
| ATOM | 1642 | HB2 | ASN | 100 | −5.943 | 10.459 | 7.699 | 1.00 | 0.00 |
| ATOM | 1643 | CG | ASN | 100 | −5.230 | 12.106 | 6.548 | 1.00 | 0.00 |
| ATOM | 1644 | OD1 | ASN | 100 | −5.097 | 12.798 | 7.577 | 1.00 | 0.00 |
| ATOM | 1645 | ND2 | ASN | 100 | −4.910 | 12.541 | 5.354 | 1.00 | 0.00 |
| ATOM | 1646 | HD21 | ASN | 100 | −4.553 | 13.449 | 5.267 | 1.00 | 0.00 |
| ATOM | 1647 | HD22 | ASN | 100 | −5.042 | 11.934 | 4.595 | 1.00 | 0.00 |
| ATOM | 1648 | C | ASN | 100 | −3.935 | 9.073 | 7.144 | 1.00 | 0.00 |
| ATOM | 1649 | O | ASN | 100 | −2.862 | 9.602 | 7.434 | 1.00 | 0.00 |
| ATOM | 1650 | N | ILE | 101 | −4.386 | 7.975 | 7.743 | 1.00 | 0.00 |
| ATOM | 1651 | HN | ILE | 101 | −5.248 | 7.599 | 7.467 | 1.00 | 0.00 |
| ATOM | 1652 | CA | ILE | 101 | −3.630 | 7.318 | 8.803 | 1.00 | 0.00 |
| ATOM | 1653 | HA | ILE | 101 | −3.193 | 8.088 | 9.422 | 1.00 | 0.00 |
| ATOM | 1654 | CB | ILE | 101 | −4.541 | 6.450 | 9.691 | 1.00 | 0.00 |
| ATOM | 1655 | HB | ILE | 101 | −4.890 | 9.618 | 9.105 | 1.00 | 0.00 |
| ATOM | 1656 | CG1 | ILE | 101 | −5.743 | 7.274 | 10.166 | 1.00 | 0.00 |
| ATOM | 1657 | HG11 | ILE | 101 | −6.325 | 7.575 | 9.308 | 1.00 | 0.00 |
| ATOM | 1658 | HG12 | ILE | 101 | −5.387 | 8.193 | 10.682 | 1.00 | 0.00 |
| ATOM | 1659 | CG2 | ILE | 101 | −3.761 | 5.909 | 10.879 | 1.00 | 0.00 |
| ATOM | 1660 | HG21 | ILE | 101 | −4.431 | 5.373 | 11.934 | 1.00 | 0.00 |
| ATOM | 1661 | HG22 | ILE | 101 | −3.108 | 6.727 | 11.418 | 1.00 | 0.00 |
| ATOM | 1662 | HG23 | ILE | 101 | −2.990 | 9.240 | 10.924 | 1.00 | 0.00 |
| ATOM | 1663 | CD1 | ILE | 101 | −6.689 | 6.823 | 11.107 | 1.00 | 0.00 |
| ATOM | 1664 | HD11 | ILE | 101 | −7.168 | 7.226 | 11.749 | 1.00 | 0.00 |
| ATOM | 1665 | HD12 | ILE | 101 | −6.075 | 5.842 | 11.709 | 1.00 | 0.00 |
| ATOM | 1666 | HD13 | ILE | 101 | −7.384 | 5.966 | 10.534 | 1.00 | 0.00 |
| ATOM | 1667 | C | ILE | 101 | −2.911 | 6.497 | 8.226 | 1.00 | 0.00 |
| ATOM | 1668 | O | ILE | 101 | −1.335 | 6.807 | 8.332 | 1.00 | 0.00 |
| ATOM | 1669 | N | LEU | 102 | −2.876 | 9.343 | 7.590 | 1.00 | 0.00 |
| ATOM | 1670 | HN | LEU | 102 | −3.829 | 9.117 | 7.527 | 1.00 | 0.00 |
| ATOM | 1671 | CA | LEU | 102 | −1.886 | 4.457 | 6.972 | 1.00 | 0.00 |
| ATOM | 1672 | HA | LEU | 102 | −1.350 | 3.953 | 7.763 | 1.00 | 0.00 |
| ATOM | 1673 | CB | LEU | 102 | −2.569 | 3.416 | 6.082 | 1.00 | 0.00 |
| ATOM | 1674 | HB1 | LEU | 102 | −3.630 | 3.443 | 6.283 | 1.00 | 0.00 |
| ATOM | 1675 | HB2 | LEU | 102 | −2.408 | 3.700 | 5.053 | 1.00 | 0.00 |
| ATOM | 1676 | CG | LEU | 102 | −2.083 | 1.971 | 6.260 | 1.00 | 0.00 |
| ATOM | 1677 | HG | LEU | 102 | −2.423 | 1.382 | 5.420 | 1.00 | 0.00 |
| ATOM | 1678 | CD1 | LEU | 102 | −2.676 | 1.364 | 7.523 | 1.00 | 0.00 |
| ATOM | 1679 | HD11 | LEU | 102 | −1.943 | 1.395 | 8.316 | 1.00 | 0.00 |
| ATOM | 1680 | HD12 | LEU | 102 | −2.958 | 0.338 | 7.332 | 1.00 | 0.00 |
| ATOM | 1681 | HD13 | LEU | 102 | −3.549 | 1.928 | 7.818 | 1.00 | 0.00 |

TABLE 5-continued

Atomic Structure Coordinates of the
Free Form of the P/CAF Bromodomain

| ATOM | 1682 | CD2 | LEU | 102 | −0.559 | 1.903 | 6.290 | 1.00 | 0.00 |
|---|---|---|---|---|---|---|---|---|---|
| ATOM | 1683 | HD21 | LEU | 102 | −0.147 | 2.788 | 5.827 | 1.00 | 0.00 |
| ATOM | 1684 | HD22 | LEU | 102 | −0.224 | 1.027 | 5.749 | 1.00 | 0.00 |
| ATOM | 1685 | HD23 | LEU | 102 | −0.220 | 1.841 | 7.313 | 1.00 | 0.00 |
| ATOM | 1686 | C | LEU | 102 | −0.897 | 5.265 | 6.139 | 1.00 | 0.00 |
| ATOM | 1687 | O | LEU | 102 | 0.301 | 4.991 | 6.137 | 1.00 | 0.00 |
| ATOM | 1688 | N | GLU | 103 | −1.414 | 6.266 | 5.433 | 1.00 | 0.00 |
| ATOM | 1689 | HN | GLU | 103 | −2.377 | 6.439 | 5.484 | 1.00 | 0.00 |
| ATOM | 1690 | CA | GLU | 103 | −0.581 | 7.132 | 4.612 | 1.00 | 0.00 |
| ATOM | 1691 | HA | GLU | 103 | −0.056 | 6.514 | 3.900 | 1.00 | 0.00 |
| ATOM | 1692 | CE | GLU | 103 | −1.446 | 8.146 | 3.857 | 1.00 | 0.00 |
| ATOM | 1693 | HB1 | GLU | 103 | −1.912 | 8.808 | 4.972 | 1.00 | 0.00 |
| ATOM | 1694 | HB2 | GLU | 103 | −2.220 | 7.612 | 3.320 | 1.00 | 0.00 |
| ATOM | 1695 | CG | GLU | 103 | −0.670 | 8.991 | 2.860 | 1.00 | 0.00 |
| ATOM | 1696 | HG1 | GLU | 103 | −1.083 | 8.832 | 1.874 | 1.00 | 0.00 |
| ATOM | 1697 | HG2 | GLU | 103 | 0.364 | 8.680 | 2.871 | 1.00 | 0.00 |
| ATOM | 1698 | CD | GLU | 103 | −0.734 | 10.472 | 3.178 | 1.00 | 0.00 |
| ATOM | 1699 | OE1 | GLU | 103 | −1.856 | 10.996 | 3.342 | 1.00 | 0.00 |
| ATOM | 1700 | OE2 | GLU | 103 | 0.337 | 11.108 | 3.264 | 1.00 | 0.00 |
| ATOM | 1701 | C | GLU | 103 | 0.439 | 7.898 | 5.478 | 1.00 | 0.00 |
| ATOM | 1702 | O | GLU | 103 | 1.644 | 7.658 | 5.334 | 1.00 | 0.00 |
| ATOM | 1703 | N | LYS | 104 | −0.052 | 8.675 | 6.405 | 1.00 | 0.00 |
| ATOM | 1704 | HN | LYS | 104 | −1.024 | 8.786 | 6.480 | 1.00 | 0.00 |
| ATOM | 1705 | CA | LYS | 104 | 0.821 | 9.417 | 7.306 | 1.00 | 0.00 |
| ATOM | 1706 | HA | LYS | 104 | 1.329 | 10.172 | 6.725 | 1.00 | 0.00 |
| ATOM | 1707 | CB | LYS | 104 | −0.003 | 10.100 | 8.399 | 1.00 | 0.00 |
| ATOM | 1708 | HB1 | LYS | 104 | −0.949 | 9.589 | 8.492 | 1.00 | 0.00 |
| ATOM | 1709 | HB2 | LYS | 104 | 0.530 | 10.024 | 9.335 | 1.00 | 0.00 |
| ATOM | 1710 | CG | LYS | 104 | −0.278 | 11.569 | 8.125 | 1.00 | 0.00 |
| ATOM | 1711 | HG1 | LYS | 104 | 0.635 | 12.128 | 8.261 | 1.00 | 0.00 |
| ATOM | 1712 | HG2 | LYS | 104 | −1.026 | 11.920 | 8.820 | 1.00 | 0.00 |
| ATOM | 1713 | CD | LYS | 104 | −0.782 | 11.786 | 6.708 | 1.00 | 0.00 |
| ATOM | 1714 | HD1 | LYS | 104 | −0.960 | 10.824 | 6.248 | 1.00 | 0.00 |
| ATOM | 1715 | HD2 | LYS | 104 | −0.031 | 12.322 | 6.147 | 1.00 | 0.00 |
| ATOM | 1716 | CE | LYS | 104 | −2.073 | 12.589 | 6.695 | 1.00 | 0.00 |
| ATOM | 1717 | HE1 | LYS | 104 | −2.601 | 12.384 | 5.775 | 1.00 | 0.00 |
| ATOM | 1718 | HE2 | LYS | 104 | −2.680 | 12.283 | 7.534 | 1.00 | 0.00 |
| ATOM | 1719 | HZ | LYS | 104 | −1.817 | 14.053 | 6.791 | 1.00 | 0.00 |
| ATOM | 1720 | HZ1 | LYS | 104 | −2.239 | 14.433 | 7.661 | 1.00 | 0.00 |
| ATOM | 1721 | HZ2 | LYS | 104 | −2.233 | 14.543 | 5.973 | 1.00 | 0.00 |
| ATOM | 1722 | HZ3 | LYS | 104 | −0.793 | 14.236 | 6.806 | 1.00 | 0.00 |
| ATOM | 1723 | C | LYS | 104 | 1.860 | 8.497 | 7.941 | 1.00 | 0.00 |
| ATOM | 1724 | O | LYS | 104 | 2.995 | 8.903 | 8.184 | 1.00 | 0.00 |
| ATOM | 1725 | N | PHE | 105 | 1.460 | 7.259 | 8.213 | 1.00 | 0.00 |
| ATOM | 1726 | HN | PHE | 105 | 0.540 | 6.997 | 7.997 | 1.00 | 0.00 |
| ATOM | 1727 | CA | PHE | 105 | 2.351 | 6.279 | 8.824 | 1.00 | 0.00 |
| ATOM | 1728 | HA | PHE | 105 | 2.951 | 6.790 | 9.562 | 1.00 | 0.00 |
| ATOM | 1729 | CB | PHE | 105 | 1.536 | 5.184 | 9.515 | 1.00 | 0.00 |
| ATOM | 1730 | HB1 | PHE | 105 | 2.007 | 4.228 | 9.338 | 1.00 | 0.00 |
| ATOM | 1731 | HB2 | PHE | 105 | 0.540 | 5.171 | 9.097 | 1.00 | 0.00 |
| ATOM | 1732 | CG | PHE | 105 | 1.411 | 5.369 | 11.001 | 1.00 | 0.00 |
| ATOM | 1733 | CD1 | PHE | 105 | 0.521 | 6.294 | 11.524 | 1.00 | 0.00 |
| ATOM | 1734 | HD1 | PHE | 105 | −0.083 | 6.887 | 10.853 | 1.00 | 0.00 |
| ATOM | 1735 | CD2 | PHE | 105 | 2.177 | 4.614 | 11.874 | 1.00 | 0.00 |
| ATOM | 1736 | HD2 | PHE | 105 | 2.872 | 3.889 | 11.478 | 1.00 | 0.00 |
| ATOM | 1737 | CE1 | PHE | 105 | 0.400 | 6.465 | 12.890 | 1.00 | 0.00 |
| ATOM | 1738 | HE1 | PHE | 105 | −0.296 | 7.190 | 13.285 | 1.00 | 0.00 |
| ATOM | 1739 | CE2 | PHE | 105 | 2.061 | 4.780 | 13.241 | 1.00 | 0.00 |
| ATOM | 1740 | HE2 | PHE | 105 | 2.665 | 4.186 | 13.911 | 1.00 | 0.00 |
| ATOM | 1741 | CZ | PHE | 105 | 1.172 | 5.707 | 13.750 | 1.00 | 0.00 |
| ATOM | 1742 | HZ | PHE | 105 | 1.079 | 5.838 | 14.818 | 1.00 | 0.00 |
| ATOM | 1743 | C | PHE | 105 | 3.279 | 5.655 | 7.785 | 1.00 | 0.00 |
| ATOM | 1744 | O | PHE | 105 | 4.491 | 5.871 | 7.808 | 1.00 | 0.00 |
| ATOM | 1745 | N | PHE | 106 | 2.702 | 4.870 | 6.882 | 1.00 | 0.00 |
| ATOM | 1746 | HN | PHE | 106 | 1.732 | 4.732 | 6.922 | 1.00 | 0.00 |
| ATOM | 1747 | CA | PHE | 106 | 3.470 | 4.199 | 5.841 | 1.00 | 0.00 |
| ATOM | 1748 | HA | PHE | 106 | 4.078 | 3.441 | 6.316 | 1.00 | 0.00 |
| ATOM | 1749 | CB | PHE | 106 | 2.532 | 3.526 | 4.839 | 1.00 | 0.00 |
| ATOM | 1750 | HB1 | PHE | 106 | 1.881 | 2.844 | 5.366 | 1.00 | 0.00 |
| ATOM | 1751 | HB2 | PHE | 106 | 1.937 | 4.281 | 4.351 | 1.00 | 0.00 |
| ATOM | 1752 | CG | PHE | 106 | 3.254 | 2.795 | 3.777 | 1.00 | 0.00 |
| ATOM | 1753 | CD1 | PHE | 106 | 3.931 | 1.590 | 4.091 | 1.00 | 0.00 |
| ATOM | 1754 | HD1 | PHE | 106 | 3.928 | 1.235 | 5.109 | 1.00 | 0.00 |
| ATOM | 1755 | CD2 | PHE | 106 | 3.267 | 3.202 | 2.469 | 1.00 | 0.00 |
| ATOM | 1756 | HD | PHE | 106 | 2.743 | 4.111 | 2.214 | 1.00 | 0.00 |
| ATOM | 1757 | CE1 | PHE | 106 | 4.601 | 0.879 | 3.118 | 1.00 | 0.00 |
| ATOM | 1758 | HE1 | PHE | 106 | 5.122 | −0.029 | 3.376 | 1.00 | 0.00 |

TABLE 5-continued

Atomic Structure Coordinates of the
Free Form of the P/CAF Bromodomain

| ATOM | 1759 | CE2 | PHE | 106 | 3.941 | 2.500 | 1.491 | 1.00 | 0.00 |
|---|---|---|---|---|---|---|---|---|---|
| ATOM | 1760 | HE2 | PHE | 106 | 3.935 | 2.853 | 0.471 | 1.00 | 0.00 |
| ATOM | 1761 | CZ | PHE | 106 | 4.605 | 1.334 | 1.814 | 1.00 | 0.00 |
| ATOM | 1762 | HZ | PHE | 106 | 5.125 | 0.780 | 1.050 | 1.00 | 0.00 |
| ATOM | 1763 | C | PHE | 106 | 4.388 | 5.173 | 5.110 | 1.00 | 0.00 |
| ATOM | 1764 | O | PHE | 106 | 5.610 | 5.033 | 5.148 | 1.00 | 0.00 |
| ATOM | 1765 | N | PHE | 107 | 3.795 | 4.155 | 4.434 | 1.00 | 0.00 |
| ATOM | 1766 | HN | PHE | 107 | 2.814 | 6.212 | 4.432 | 1.00 | 0.00 |
| ATOM | 1767 | CA | PHE | 107 | 4.575 | 7.140 | 3.686 | 1.00 | 0.00 |
| ATOM | 1768 | HA | PHE | 107 | 5.076 | 6.616 | 2.885 | 1.00 | 0.00 |
| ATOM | 1769 | CB | PHE | 107 | 3.662 | 8.212 | 3.077 | 1.00 | 0.00 |
| ATOM | 1770 | HB1 | PHE | 107 | 2.932 | 8.510 | 3.811 | 1.00 | 0.00 |
| ATOM | 1771 | HB2 | PHE | 107 | 4.263 | 9.070 | 2.810 | 1.00 | 0.00 |
| ATOM | 1772 | CG | PHE | 107 | 2.918 | 7.770 | 1.838 | 1.00 | 0.00 |
| ATOM | 1773 | CD1 | PHE | 107 | 3.038 | 6.475 | 1.348 | 1.00 | 0.00 |
| ATOM | 1774 | HD1 | PHE | 107 | 3.674 | 5.771 | 1.863 | 1.00 | 0.00 |
| ATOM | 1775 | CD2 | PHE | 107 | 2.098 | 8.660 | 1.160 | 1.00 | 0.00 |
| ATOM | 1776 | HD2 | PHE | 107 | 1.995 | 9.670 | 1.528 | 1.00 | 0.00 |
| ATOM | 1777 | CE1 | PHE | 107 | 2.356 | 6.080 | 0.214 | 1.00 | 0.00 |
| ATOM | 1778 | HE1 | PHE | 107 | 2.460 | 9.069 | −0.154 | 1.00 | 0.00 |
| ATOM | 1779 | CE2 | PHE | 107 | 1.413 | 8.268 | 0.025 | 1.00 | 0.00 |
| ATOM | 1780 | HE2 | PHE | 107 | 0.777 | 8.972 | −0.492 | 1.00 | 0.00 |
| ATOM | 1781 | CZ | PHE | 107 | 1.542 | 6.977 | −0.449 | 1.00 | 0.00 |
| ATOM | 1782 | HZ | PHE | 107 | 1.007 | 6.669 | −1.336 | 1.00 | 0.00 |
| ATOM | 1783 | C | PHE | 107 | 5.636 | 7.787 | 4.571 | 1.00 | 0.00 |
| ATOM | 1784 | O | PHE | 107 | 6.638 | 8.301 | 4.075 | 1.00 | 0.00 |
| ATOM | 1785 | N | SER | 108 | 5.411 | 7.766 | 5.883 | 1.00 | 0.00 |
| ATOM | 1786 | HN | SER | 108 | 4.619 | 7.305 | 6.227 | 1.00 | 0.00 |
| ATOM | 1787 | CA | SER | 108 | 6.391 | 8.287 | 6.826 | 1.00 | 0.00 |
| ATOM | 1788 | HA | SER | 108 | 6.805 | 9.173 | 6.400 | 1.00 | 0.00 |
| ATOM | 1789 | CB | SER | 108 | 5.730 | 8.643 | 8.157 | 1.00 | 0.00 |
| ATOM | 1790 | HB1 | SER | 108 | 6.468 | 8.997 | 8.942 | 1.00 | 0.00 |
| ATOM | 1791 | HB2 | SER | 108 | 4.940 | 7.938 | 8.364 | 1.00 | 0.00 |
| ATOM | 1792 | OG | SER | 108 | 5.181 | 9.949 | 8.121 | 1.00 | 0.00 |
| ATOM | 1793 | HG | SER | 108 | 4.501 | 9.993 | 7.445 | 1.00 | 0.00 |
| ATOM | 1794 | C | SER | 108 | 7.471 | 7.243 | 7.042 | 1.00 | 0.00 |
| ATOM | 1795 | O | SER | 108 | 8.647 | 7.561 | 7.216 | 1.00 | 0.00 |
| ATOM | 1796 | N | LYS | 109 | 7.049 | 5.986 | 6.994 | 1.00 | 0.00 |
| ATOM | 1797 | HN | LYS | 109 | 6.100 | 5.811 | 6.828 | 1.00 | 0.00 |
| ATOM | 1798 | CA | LYS | 109 | 7.953 | 4.860 | 7.124 | 1.00 | 0.00 |
| ATOM | 1799 | HA | LYS | 109 | 8.620 | 9.053 | 7.991 | 1.00 | 0.00 |
| ATOM | 1800 | CB | LYS | 109 | 7.149 | 3.591 | 7.401 | 1.00 | 0.00 |
| ATOM | 1801 | HB1 | LYS | 109 | 6.225 | 3.607 | 6.795 | 1.00 | 0.00 |
| ATOM | 1802 | HB2 | LYS | 109 | 7.741 | 2.737 | 7.126 | 1.00 | 0.00 |
| ATOM | 1803 | CG | LYS | 109 | 6.734 | 3.440 | 8.856 | 1.00 | 0.00 |
| ATOM | 1804 | HG1 | LYS | 109 | 9.820 | 2.866 | 8.902 | 1.00 | 0.00 |
| ATOM | 1805 | HG2 | LYS | 109 | 6.566 | 4.421 | 9.276 | 1.00 | 0.00 |
| ATOM | 1806 | CD | LYS | 109 | 7.802 | 2.732 | 9.670 | 1.00 | 0.00 |
| ATOM | 1807 | HD1 | LYS | 109 | 8.751 | 3.219 | 9.500 | 1.00 | 0.00 |
| ATOM | 1808 | HD2 | LYS | 109 | 7.544 | 2.794 | 10.717 | 1.00 | 0.00 |
| ATOM | 1809 | CE | LYS | 109 | 7.919 | 1.269 | 9.276 | 1.00 | 0.00 |
| ATOM | 1810 | HE1 | LYS | 109 | 6.930 | 0.835 | 9.254 | 1.00 | 0.00 |
| ATOM | 1811 | HE2 | LYS | 109 | 8.359 | 1.209 | 8.292 | 1.00 | 0.00 |
| ATOM | 1812 | NZ | LYS | 109 | 8.763 | 0.502 | 10.233 | 1.00 | 0.00 |
| ATOM | 1813 | HZ1 | LYS | 109 | 8.800 | −0.499 | 9.955 | 1.00 | 0.00 |
| ATOM | 1814 | HZ2 | LYS | 109 | 8.368 | 0.570 | 11.192 | 1.00 | 0.00 |
| ATOM | 1815 | HZ3 | LYS | 109 | 9.731 | 0.883 | 10.241 | 1.00 | 0.00 |
| ATOM | 1816 | C | LYS | 109 | 8.769 | 4.700 | 5.846 | 1.00 | 0.00 |
| ATOM | 1817 | O | LYS | 109 | 9.948 | 4.348 | 5.882 | 1.00 | 0.00 |
| ATOM | 1818 | N | ILE | 110 | 8.127 | 4.989 | 4.717 | 1.00 | 0.00 |
| ATOM | 1819 | HN | ILE | 110 | 7.193 | 5.283 | 4.765 | 1.00 | 0.00 |
| ATOM | 1820 | CA | ILE | 110 | 8.780 | 4.928 | 3.416 | 1.00 | 0.00 |
| ATOM | 1821 | HA | ILE | 110 | 8.993 | 3.891 | 3.187 | 1.00 | 0.00 |
| ATOM | 1822 | CB | ILE | 110 | 7.850 | 5.488 | 2.313 | 1.00 | 0.00 |
| ATOM | 1823 | HB | ILE | 110 | 7.508 | 6.464 | 2.626 | 1.00 | 0.00 |
| ATOM | 1824 | CG1 | ILE | 110 | 6.640 | 4.570 | 2.129 | 1.00 | 0.00 |
| ATOM | 1825 | HG11 | ILE | 110 | 5.898 | 5.077 | 1.532 | 1.00 | 0.00 |
| ATOM | 1826 | HG12 | ILE | 110 | 6.221 | 4.342 | 3.093 | 1.00 | 0.00 |
| ATOM | 1827 | CG2 | ILE | 110 | 8.593 | 5.651 | 0.996 | 1.00 | 0.00 |
| ATOM | 1828 | HG21 | ILE | 110 | 8.729 | 6.702 | 0.786 | 1.00 | 0.00 |
| ATOM | 1829 | HG22 | ILE | 110 | 8.022 | 5.196 | 0.201 | 1.00 | 0.00 |
| ATOM | 1830 | HG23 | ILE | 110 | 9.556 | 5.169 | 1.070 | 1.00 | 0.00 |
| ATOM | 1831 | CD1 | ILE | 110 | 6.973 | 3.260 | 1.449 | 1.00 | 0.00 |
| ATOM | 1832 | HD11 | ILE | 110 | 6.748 | 2.442 | 2.117 | 1.00 | 0.00 |
| ATOM | 1833 | HD12 | ILE | 110 | 8.023 | 3.242 | 1.201 | 1.00 | 0.00 |
| ATOM | 1834 | HD13 | ILE | 110 | 6.688 | 3.162 | 0.548 | 1.00 | 0.00 |
| ATOM | 1835 | C | ILE | 110 | 10.088 | 5.717 | 3.438 | 1.00 | 0.00 |

TABLE 5-continued

Atomic Structure Coordinates of the Free Form of the P/CAF Bromodomain

| | | | | | | | | |
|---|---|---|---|---|---|---|---|---|
| ATOM | 1836 | O | ILE | 110 | 11.129 | 5.225 | 3.008 | 1.00 | 0.00 |
| ATOM | 1837 | N | LYS | 111 | 10.018 | 6.946 | 3.946 | 1.00 | 0.00 |
| ATOM | 1838 | HN | LYS | 111 | 9.153 | 7.278 | 4.263 | 1.00 | 0.00 |
| ATOM | 1839 | CA | LYS | 111 | 11.184 | 7.828 | 4.017 | 1.00 | 0.00 |
| ATOM | 1840 | HA | LYS | 111 | 11.336 | 8.250 | 3.035 | 1.00 | 0.00 |
| ATOM | 1841 | CB | LYS | 111 | 10.921 | 8.963 | 5.009 | 1.00 | 0.00 |
| ATOM | 1842 | HB1 | LYS | 111 | 11.572 | 8.840 | 5.861 | 1.00 | 0.00 |
| ATOM | 1843 | HB2 | LYS | 111 | 9.894 | 8.907 | 5.340 | 1.00 | 0.00 |
| ATOM | 1844 | CG | LYS | 111 | 11.156 | 10.346 | 4.425 | 1.00 | 0.00 |
| ATOM | 1845 | HG1 | LYS | 111 | 11.692 | 10.245 | 3.493 | 1.00 | 0.00 |
| ATOM | 1846 | HG2 | LYS | 111 | 11.746 | 10.925 | 5.121 | 1.00 | 0.00 |
| ATOM | 1847 | CD | LYS | 111 | 9.847 | 11.073 | 4.164 | 1.00 | 0.00 |
| ATOM | 1848 | HD1 | LYS | 111 | 10.065 | 12.076 | 3.827 | 1.00 | 0.00 |
| ATOM | 1849 | HD2 | LYS | 111 | 9.280 | 11.114 | 5.083 | 1.00 | 0.00 |
| ATOM | 1850 | CE | LYS | 111 | 9.018 | 10.367 | 3.104 | 1.00 | 0.00 |
| ATOM | 1851 | HE1 | LYS | 111 | 8.683 | 9.419 | 3.499 | 1.00 | 0.00 |
| ATOM | 1852 | HE2 | LYS | 111 | 9.636 | 10.195 | 2.235 | 1.00 | 0.00 |
| ATOM | 1853 | NZ | LYS | 111 | 7.830 | 11.169 | 2.702 | 1.00 | 0.00 |
| ATOM | 1854 | HZ1 | LYS | 111 | 7.360 | 11.560 | 3.543 | 1.00 | 0.00 |
| ATOM | 1855 | HZ2 | LYS | 111 | 7.191 | 10.571 | 2.187 | 1.00 | 0.00 |
| ATOM | 1856 | HZ3 | LYS | 111 | 8.121 | 11.954 | 2.084 | 1.00 | 0.00 |
| ATOM | 1857 | C | LYS | 111 | 12.448 | 7.070 | 4.425 | 1.00 | 0.00 |
| ATOM | 1858 | O | LYS | 111 | 13.491 | 7.199 | 3.785 | 1.00 | 0.00 |
| ATOM | 1859 | N | GLU | 112 | 12.347 | 6.285 | 5.491 | 1.00 | 0.00 |
| ATOM | 1860 | HN | GLU | 112 | 11.489 | 6.225 | 5.962 | 1.00 | 0.00 |
| ATOM | 1861 | CA | GLU | 112 | 13.485 | 5.516 | 9.983 | 1.00 | 0.00 |
| ATOM | 1862 | HA | GLU | 112 | 14.297 | 6.205 | 6.161 | 1.00 | 0.00 |
| ATOM | 1863 | CB | GLU | 112 | 13.126 | 4.819 | 7.296 | 1.00 | 0.00 |
| ATOM | 1864 | HB1 | GLU | 112 | 12.159 | 4.390 | 7.189 | 1.00 | 0.00 |
| ATOM | 1865 | HB2 | GLU | 112 | 13.864 | 4.058 | 7.500 | 1.00 | 0.00 |
| ATOM | 1866 | CG | GLU | 112 | 13.070 | 5.760 | 8.489 | 1.00 | 0.00 |
| ATOM | 1867 | HG1 | GLU | 112 | 12.440 | 5.320 | 9.249 | 1.00 | 0.00 |
| ATOM | 1868 | HG2 | GLU | 112 | 12.644 | 6.700 | 8.169 | 1.00 | 0.00 |
| ATOM | 1869 | CD | GLU | 112 | 14.437 | 6.026 | 9.087 | 1.00 | 0.00 |
| ATOM | 1870 | OE1 | GLU | 112 | 14.843 | 5.277 | 10.001 | 1.00 | 0.00 |
| ATOM | 1871 | OE2 | GLU | 112 | 15.103 | 6.984 | 8.641 | 1.00 | 0.00 |
| ATOM | 1872 | C | GLU | 112 | 13.934 | 4.484 | 4.954 | 1.00 | 0.00 |
| ATOM | 1873 | O | GLU | 112 | 15.128 | 4.228 | 4.798 | 1.00 | 0.00 |
| ATOM | 1874 | N | ALA | 113 | 12.970 | 3.892 | 4.297 | 1.00 | 0.00 |
| ATOM | 1875 | HN | ALA | 113 | 12.037 | 4.138 | 4.430 | 1.00 | 0.00 |
| ATOM | 1876 | CA | ALA | 113 | 13.263 | 2.883 | 3.245 | 1.00 | 0.00 |
| ATOM | 1877 | HA | ALA | 113 | 14.151 | 2.356 | 3.550 | 1.00 | 0.00 |
| ATOM | 1878 | CB | ALA | 113 | 12.128 | 1.872 | 3.167 | 1.00 | 0.00 |
| ATOM | 1879 | HB1 | ALA | 113 | 11.209 | 2.380 | 2.915 | 1.00 | 0.00 |
| ATOM | 1880 | HB2 | ALA | 113 | 12.018 | 1.381 | 4.123 | 1.00 | 0.00 |
| ATOM | 1881 | HB3 | ALA | 113 | 12.393 | 1.136 | 2.409 | 1.00 | 0.00 |
| ATOM | 1882 | C | ALA | 113 | 13.513 | 3.513 | 1.873 | 1.00 | 0.00 |
| ATOM | 1883 | O | ALA | 113 | 13.917 | 2.823 | 0.936 | 1.00 | 0.00 |
| ATOM | 1884 | N | GLY | 114 | 13.276 | 4.818 | 1.793 | 1.00 | 0.00 |
| ATOM | 1885 | HN | GLY | 114 | 12.946 | 5.324 | 2.923 | 1.00 | 0.00 |
| ATOM | 1886 | CA | GLY | 114 | 13.468 | 5.488 | 0.480 | 1.00 | 0.00 |
| ATOM | 1887 | HA1 | GLY | 114 | 14.518 | 5.464 | 0.226 | 1.00 | 0.00 |
| ATOM | 1888 | HA2 | GLY | 114 | 13.192 | 6.516 | 0.573 | 1.00 | 0.00 |
| ATOM | 1889 | C | GLY | 114 | 12.679 | 4.830 | −0.634 | 1.00 | 0.00 |
| ATOM | 1890 | O | GLY | 114 | 13.227 | 4.056 | −1.417 | 1.00 | 0.00 |
| ATOM | 1891 | N | LEU | 115 | 11.383 | 5.123 | −0.690 | 1.00 | 0.00 |
| ATOM | 1892 | HN | LEU | 115 | 11.006 | 5.743 | −0.033 | 1.00 | 0.00 |
| ATOM | 1893 | CA | LEU | 115 | 10.508 | 4.534 | −1.697 | 1.00 | 0.00 |
| ATOM | 1894 | HA | LEU | 115 | 11.123 | 4.180 | −2.510 | 1.00 | 0.00 |
| ATOM | 1895 | CB | LEU | 115 | 9.724 | 3.363 | −1.104 | 1.00 | 0.00 |
| ATOM | 1896 | HB1 | LEU | 115 | 9.340 | 3.668 | −0.144 | 1.00 | 0.00 |
| ATOM | 1897 | HB2 | LEU | 115 | 8.890 | 3.167 | −1.754 | 1.00 | 0.00 |
| ATOM | 1898 | CG | LEU | 115 | 10.497 | 2.058 | −0.907 | 1.00 | 0.00 |
| ATOM | 1899 | HG | LEU | 115 | 9.793 | 1.246 | −0.833 | 1.00 | 0.00 |
| ATOM | 1900 | CD1 | LEU | 115 | 11.280 | 2.102 | 0.391 | 1.00 | 0.00 |
| ATOM | 1901 | HD11 | LEU | 115 | 10.719 | 1.597 | 1.166 | 1.00 | 0.00 |
| ATOM | 1902 | HD12 | LEU | 115 | 11.440 | 3.130 | 0.676 | 1.00 | 0.00 |
| ATOM | 1903 | HD13 | LEU | 115 | 12.231 | 1.611 | 0.255 | 1.00 | 0.00 |
| ATOM | 1904 | CD2 | LEU | 115 | 11.414 | 1.774 | −2.087 | 1.00 | 0.00 |
| ATOM | 1905 | HD21 | LEU | 115 | 11.066 | 2.313 | −2.953 | 1.00 | 0.00 |
| ATOM | 1906 | HD22 | LEU | 115 | 11.409 | 0.715 | −2.298 | 1.00 | 0.00 |
| ATOM | 1907 | HD23 | LEU | 115 | 12.418 | 2.086 | −1.846 | 1.00 | 0.00 |
| ATOM | 1908 | C | LEU | 115 | 9.509 | 5.550 | −2.237 | 1.00 | 0.00 |
| ATOM | 1909 | O | LEU | 115 | 9.388 | 6.653 | −1.709 | 1.00 | 0.00 |
| ATOM | 1910 | N | ILE | 116 | 8.752 | 5.124 | −3.252 | 1.00 | 0.00 |
| ATOM | 1911 | HN | ILE | 116 | 8.896 | 4.217 | −3.594 | 1.00 | 0.00 |
| ATOM | 1912 | CA | ILE | 116 | 7.707 | 5.945 | −3.865 | 1.00 | 0.00 |

TABLE 5-continued

Atomic Structure Coordinates of the
Free Form of the P/CAF Bromodomain

| ATOM | 1913 | HA | ILE | 116 | 7.395 | 5.441 | −4.768 | 1.00 | 0.00 |
|---|---|---|---|---|---|---|---|---|---|
| ATOM | 1914 | CB | ILE | 116 | 6.469 | 6.061 | −2.949 | 1.00 | 0.00 |
| ATOM | 1915 | HB | ILE | 116 | 6.730 | 6.669 | −2.097 | 1.00 | 0.00 |
| ATOM | 1916 | CG1 | ILE | 116 | 6.037 | 4.676 | −2.458 | 1.00 | 0.00 |
| ATOM | 1917 | HG11 | ILE | 116 | 5.298 | 4.265 | −3.135 | 1.00 | 0.00 |
| ATOM | 1918 | HG12 | ILE | 116 | 6.898 | 4.026 | −2.435 | 1.00 | 0.00 |
| ATOM | 1919 | CG2 | ILE | 116 | 5.326 | 6.743 | −3.681 | 1.00 | 0.00 |
| ATOM | 1920 | HG21 | ILE | 116 | 5.006 | 7.609 | −3.121 | 1.00 | 0.00 |
| ATOM | 1921 | HG22 | ILE | 116 | 4.502 | 6.052 | −3.779 | 1.00 | 0.00 |
| ATOM | 1922 | HG23 | ILE | 116 | 5.659 | 7.050 | −4.661 | 1.00 | 0.00 |
| ATOM | 1923 | CD1 | ILE | 116 | 5.433 | 4.694 | −1.073 | 1.00 | 0.00 |
| ATOM | 1924 | HD11 | ILE | 116 | 6.172 | 5.032 | −0.363 | 1.00 | 0.00 |
| ATOM | 1925 | HD12 | ILE | 116 | 5.110 | 3.698 | −0.809 | 1.00 | 0.00 |
| ATOM | 1926 | HD13 | ILE | 116 | 4.586 | 5.363 | −1.057 | 1.00 | 0.00 |
| ATOM | 1927 | C | ILE | 116 | 8.213 | 7.340 | −4.246 | 1.00 | 0.00 |
| ATOM | 1928 | O | ILE | 116 | 8.498 | 7.601 | −5.415 | 1.00 | 0.00 |
| ATOM | 1929 | N | ASP | 117 | 8.305 | 8.240 | −3.268 | 1.00 | 0.00 |
| ATOM | 1930 | HN | ASP | 117 | 8.072 | 7.979 | −2.355 | 1.00 | 0.00 |
| ATOM | 1931 | CA | ASP | 117 | 8.776 | 9.600 | −3.515 | 1.00 | 0.00 |
| ATOM | 1932 | HA | ASP | 117 | 8.982 | 10.054 | −3.558 | 1.00 | 0.00 |
| ATOM | 1933 | CB | ASP | 117 | 10.063 | 9.583 | −4.345 | 1.00 | 0.00 |
| ATOM | 1934 | HB1 | ASP | 117 | 9.902 | 10.133 | −9.260 | 1.00 | 0.00 |
| ATOM | 1935 | HB2 | ASP | 117 | 10.317 | 8.560 | −4.583 | 1.00 | 0.00 |
| ATOM | 1936 | CG | ASP | 117 | 11.233 | 10.208 | −3.610 | 1.00 | 0.00 |
| ATOM | 1937 | OD1 | ASP | 117 | 11.977 | 11.368 | −3.920 | 1.00 | 0.00 |
| ATOM | 1938 | OD2 | ASP | 117 | 11.804 | 9.538 | −2.724 | 1.00 | 0.00 |
| ATOM | 1939 | C | ASP | 117 | 7.708 | 10.424 | −4.226 | 1.00 | 0.00 |
| ATOM | 1940 | O | ASP | 117 | 8.020 | 11.293 | −5.041 | 1.00 | 0.00 |
| ATOM | 1941 | N | LYS | 118 | 6.448 | 10.150 | −3.906 | 1.00 | 0.00 |
| ATOM | 1942 | HN | LYS | 118 | 6.264 | 9.447 | −3.247 | 1.00 | 0.00 |
| ATOM | 1943 | CA | LYS | 118 | 5.332 | 10.869 | −4.908 | 1.00 | 0.00 |
| ATOM | 1944 | HA | LYS | 118 | 9.619 | 11.184 | −5.496 | 1.00 | 0.00 |
| ATOM | 1945 | CB | LYS | 118 | 4.114 | 9.952 | −4.628 | 1.00 | 0.00 |
| ATOM | 1946 | HB1 | LYS | 118 | 3.696 | 9.798 | −3.644 | 1.00 | 0.00 |
| ATOM | 1947 | HB2 | LYS | 118 | 4.432 | 9.001 | −5.028 | 1.00 | 0.00 |
| ATOM | 1948 | CG | LYS | 118 | 3.021 | 10.506 | −5.527 | 1.00 | 0.00 |
| ATOM | 1949 | HG1 | LYS | 118 | 3.175 | 10.140 | −6.531 | 1.00 | 0.00 |
| ATOM | 1950 | HG2 | LYS | 118 | 3.077 | 11.585 | −5.522 | 1.00 | 0.00 |
| ATOM | 1951 | CD | LYS | 118 | 1.642 | 10.081 | −5.053 | 1.00 | 0.00 |
| ATOM | 1952 | HD1 | LYS | 118 | 1.422 | 9.100 | −5.449 | 1.00 | 0.00 |
| ATOM | 1953 | HD2 | LYS | 118 | 1.637 | 10.044 | −3.974 | 1.00 | 0.00 |
| ATOM | 1954 | CE | LYS | 118 | 0.569 | 11.052 | −5.518 | 1.00 | 0.00 |
| ATOM | 1955 | HE1 | LYS | 118 | −0.025 | 11.347 | −4.666 | 1.00 | 0.00 |
| ATOM | 1956 | HE2 | LYS | 118 | 1.048 | 11.922 | −5.942 | 1.00 | 0.00 |
| ATOM | 1957 | NZ | LYS | 118 | −0.324 | 10.443 | −6.543 | 1.00 | 0.00 |
| ATOM | 1958 | HZ1 | LYS | 118 | −0.734 | 9.558 | −6.180 | 1.00 | 0.00 |
| ATOM | 1959 | HZ2 | LYS | 118 | 0.214 | 10.234 | −7.408 | 1.00 | 0.00 |
| ATOM | 1960 | HZ3 | LYS | 118 | −1.097 | 11.099 | −6.778 | 1.00 | 0.00 |
| ATOM | 1961 | C | LYS | 118 | 4.974 | 12.103 | −3.687 | 1.00 | 0.00 |
| ATOM | 1962 | OT1 | LYS | 118 | 4.769 | 13.177 | −4.291 | 1.00 | 0.00 |
| ATOM | 1963 | OT2 | LYS | 118 | 4.901 | 11.986 | −2.445 | 1.00 | 0.00 |
| END | | | | | | | | | |

TABLE 6

Atomic Structure Coordinates of the
P/CAF Bromodomain/Acetyl-Histamine Complex

REMARK
FILENAME= */bloch2/chris/COMPLEX_XPLOR_ARIA7/structures/its/complex_83. "REMARK
initial random number seed: 5.960359E+10REMARK
---------------------------------------------------------------------------------REMARK
overall, bonds, angles, improper, vdw, noe, cdihREMARK energies; 154.107, 9.85626,
72.1621, 0, 22.2303, 16.0191, 0.204524REMARK
---------------------------------------------------------------------------------REMARK
bonds, angles, impropers, noe, cdihREMARK rma-dev.: 2.214961E−
03, 0.361077, 52.7899, 1.40651E−02, 0.249335REMARK
---------------------------------------------------------------------------------REMARK
noe, cdihREMARK violations.: 2, OREMARK
---------------------------------------------------------------------------------REMARK DATE:05-
Dec.-98 15:11:47 created by user:ATOM        1   CA    ACE   200   −14.018
    2.661       −4.709      1.00    0.00   Ach   ATOM    2   HA1   ACK   200   −14.803
    1.912       −4.998      1.00    0.00   AcH   ATOM    3   HA2   ACE   200   −13.320
    2.304       −5.428      1.00    0.00   AcH   ATOM    4   HA3   ACE   200   −14.491

TABLE 6-continued

Atomic Structure Coordinates of the
P/CAF Bromodomain/Acetyl-Histamine Complex

| | | | | | | | | | | |
|---|---|---|---|---|---|---|---|---|---|---|
| 3.572 | −5.067 | 1.00 | 0.00 | AcH | ATOM | 5 | C | ACE | 200 | −13.332 |
| 2.936 | −3.376 | 1.00 | 0.00 | AcH | ATOM | 6 | O | ACE | 200 | −12.385 |
| 2.238 | −3.012 | 1.00 | 0.00 | AcH | ATOM | 7 | N | HIM | 201 | −13.773 |
| 3.967 | −2.663 | 1.00 | 0.00 | AcH | ATOM | 8 | HN | HIM | 201 | −13.586 |
| 4.875 | −2.982 | 1.00 | 0.00 | AcH | ATOM | 9 | CA | HIM | 201 | −14.521 |
| 3.827 | −1.417 | 1.00 | 0.00 | AcH | ATOM | 10 | HA1 | HIM | 201 | −13.833 |
| 3.589 | −0.620 | 1.00 | 0.00 | AcH | ATOM | 11 | HA1 | HIM | 201 | −15.236 |
| 3.025 | −1.526 | 1.00 | 0.00 | AcH | ATOM | 12 | CB | HIM | 201 | −15.268 |
| 5.100 | −1.055 | 1.00 | 0.00 | AcH | ATOM | 13 | HB1 | HIM | 201 | −14.591 |
| 5.940 | −1.107 | 1.00 | 0.00 | AcH | ATOM | 14 | HB2 | HIM | 201 | −15.669 |
| 5.009 | −0.056 | 1.00 | 0.00 | AcH | ATOM | 15 | CG | HIM | 201 | −16.397 |
| 5.329 | −2.010 | 1.00 | 0.00 | AcH | ATOM | 16 | ND1 | HIM | 201 | −17.392 |
| 6.259 | −1.793 | 1.00 | 0.00 | AcH | ATOM | 17 | HD1 | HIM | 201 | −17.421 |
| 6.906 | −1.057 | 1.00 | 0.00 | AcH | ATOM | 18 | CD | HIM | 201 | −16.680 |
| 4.796 | −3.204 | 1.00 | 0.00 | AcH | ATOM | 19 | HD2 | HIM | 201 | −16.026 |
| 4.116 | −3.779 | 1.00 | 0.00 | AcH | ATOM | 20 | CE1 | HIM | 201 | −18.316 |
| 6.135 | −2.729 | 1.00 | 0.00 | AcH | ATOM | 21 | HE1 | HIM | 201 | −19.220 |
| 6.722 | −2.806 | 1.00 | 0.00 | AcH | ATOM | 22 | NE2 | HIM | 201 | −17.912 |
| 5.221 | −3.592 | 1.00 | 0.00 | AcH | ATOM | 23 | CA | GLY | 1 | 27.272 |
| 16.667 | −0.366 | 1.00 | 0.00 | BrD | ATOM | 24 | HA1 | GLY | 1 | 28.103 |
| 16.198 | −0.871 | 1.00 | 0.00 | BrD | ATOM | 25 | HA2 | GLY | 1 | 26.478 |
| 15.945 | −0.255 | 1.00 | 0.00 | BrD | ATOM | 26 | C | GLY | 1 | 27.724 |
| 17.114 | 1.011 | 1.00 | 0.00 | BrD | ATOM | 27 | O | GLY | 1 | 28.713 |
| 17.834 | 1.144 | 1.00 | 0.00 | BrD | ATOM | 28 | N | GLY | 1 | 26.780 |
| 17.800 | −1.198 | 1.00 | 0.00 | BrD | ATOM | 29 | HT1 | GLY | 1 | 25.769 |
| 17.963 | −1.018 | 1.00 | 0.00 | BrD | ATOM | 30 | HT2 | GLY | 1 | 26.911 |
| 17.584 | −2.207 | 1.00 | 0.00 | BrD | ATOM | 31 | HT3 | GLY | 1 | 27.307 |
| 18.667 | −0.970 | 1.00 | 0.00 | BrD | ATOM | 32 | N | SER | 2 | 26.999 |
| 16.682 | 2.037 | 1.00 | 0.00 | BrD | ATOM | 33 | HN | SER | 2 | 26.222 |
| 16.110 | 1.866 | 1.00 | 0.00 | BrD | ATOM | 34 | CA | SER | 2 | 27.328 |
| 17.043 | 3.411 | 1.00 | 0.00 | BrD | ATOM | 35 | HA | SER | 2 | 28.283 |
| 17.546 | 3.401 | 1.00 | 0.00 | BrD | ATOM | 36 | CB | SER | 2 | 26.269 |
| 17.992 | 3.975 | 1.00 | 0.00 | BrD | ATOM | 37 | HB1 | SER | 2 | 26.705 |
| 18.588 | 4.762 | 1.00 | 0.00 | BrD | ATOM | 38 | HB2 | SER | 2 | 25.448 |
| 17.414 | 4.174 | 1.00 | 0.00 | BrD | ATOM | 39 | OG | SER | 2 | 25.771 |
| 18.857 | 2.969 | 1.00 | 0.00 | BrD | ATOM | 40 | HG | SER | 2 | 26.478 |
| 19.429 | 2.660 | 1.00 | 0.00 | BrD | ATOM | 41 | C | SER | 2 | 27.435 |
| 15.601 | 4.290 | 1.00 | 0.00 | BrD | ATOM | 42 | O | SER | 2 | 26.900 |
| 14.744 | 3.956 | 1.00 | 0.00 | BrD | ATOM | 43 | N | HIS | 3 | 28.131 |
| 15.935 | 5.415 | 1.00 | 0.00 | BrD | ATOM | 44 | HN | HIS | 3 | 28.534 |
| 16.803 | 5.627 | 1.00 | 0.00 | BrD | ATOM | 45 | CA | HIS | 3 | 28.308 |
| 14.824 | 6.342 | 1.00 | 0.00 | BrD | ATOM | 46 | HA | HIS | 3 | 28.652 |
| 13.972 | 5.775 | 1.00 | 0.00 | BrD | ATOM | 47 | CB | HIS | 3 | 29.356 |
| 15.176 | 7.399 | 1.00 | 0.00 | BrD | ATOM | 48 | HB1 | HIS | 3 | 29.337 |
| 14.428 | 8.178 | 1.00 | 0.00 | BrD | ATOM | 49 | HB2 | HIS | 3 | 30.333 |
| 15.184 | 6.939 | 1.00 | 0.00 | BrD | ATOM | 50 | CG | HIS | 3 | 29.137 |
| 16.512 | 8.039 | 1.00 | 0.00 | BrD | ATOM | 51 | ND1 | HIS | 3 | 28.235 |
| 16.718 | 9.062 | 1.00 | 0.00 | BrD | ATOM | 52 | HD1 | HIS | 3 | 27.659 |
| 16.035 | 9.465 | 1.00 | 0.00 | BrD | ATOM | 53 | CD2 | HIS | 3 | 29.710 |
| 17.715 | 7.796 | 1.00 | 0.00 | BrD | ATOM | 54 | HD2 | HIS | 3 | 30.468 |
| 17.927 | 7.055 | 1.00 | 0.00 | BrD | ATOM | 55 | CE1 | HIS | 3 | 28.262 |
| 17.991 | 9.420 | 1.00 | 0.00 | BrD | ATOM | 56 | HE1 | HIS | 3 | 27.661 |
| 18.442 | 10.196 | 1.00 | 0.00 | BrD | ATOM | 57 | NE2 | HIS | 3 | 29.148 |
| 18.615 | 8.668 | 1.00 | 0.00 | BrD | ATOM | 58 | HE2 | HIS | 3 | 29.368 |
| 19.568 | 8.725 | 1.00 | 0.00 | BrD | ATOM | 59 | C | HIS | 3 | 26.991 |
| 14.463 | 7.020 | 1.00 | 0.00 | BrD | ATOM | 60 | O | HIS | 3 | 26.660 |
| 14.998 | 8.078 | 1.00 | 0.00 | BrD | ATOM | 61 | N | MET | 4 | 26.245 |
| 13.551 | 6.405 | 1.00 | 0.00 | BrD | ATOM | 62 | HN | MET | 4 | 26.563 |
| 13.161 | 5.565 | 1.00 | 0.00 | BrD | ATOM | 63 | CA | MET | 4 | 24.964 |
| 13.119 | 6.951 | 1.00 | 0.00 | BrD | ATOM | 64 | HA | MET | 4 | 25.136 |
| 12.767 | 7.958 | 1.00 | 0.00 | BrD | ATOM | 65 | CE | MET | 4 | 21.985 |
| 14.294 | 6.994 | 1.00 | 0.00 | BrD | ATOM | 66 | HB1 | MET | 4 | 24.445 |
| 15.111 | 7.531 | 1.00 | 0.00 | BrD | ATOM | 67 | HB2 | MET | 4 | 23.776 |
| 14.612 | 5.984 | 1.00 | 0.00 | BrD | ATOM | 68 | CG | MET | 4 | 22.665 |
| 13.962 | 7.672 | 1.00 | 0.00 | BrD | ATOM | 69 | HG1 | MET | 4 | 22.754 |
| 14.176 | 8.727 | 1.00 | 0.00 | BrD | ATOM | 70 | HG2 | MET | 4 | 22.461 |
| 12.911 | 7.535 | 1.00 | 0.00 | BrD | ATOM | 71 | SD | MET | 4 | 21.283 |
| 14.909 | 7.006 | 1.00 | 0.00 | BrD | ATOM | 72 | CE | MET | 4 | 22.027 |
| 16.531 | 6.842 | 1.00 | 0.00 | BrD | ATOM | 73 | HE1 | MET | 4 | 22.811 |
| 16.643 | 7.576 | 1.00 | 0.00 | BrD | ATOM | 74 | HE2 | MET | 4 | 21.274 |
| 17.289 | 7.000 | 1.00 | 0.00 | BrD | ATOM | 75 | HE3 | MET | 4 | 22.443 |
| 16.638 | 5.851 | 1.00 | 0.00 | BrD | ATOM | 76 | C | MET | 4 | 24.376 |
| 11.977 | 6.126 | 1.00 | 0.00 | BrD | ATOM | 77 | O | MET | 4 | 24.500 |
| 11.906 | 4.914 | 1.00 | 0.00 | BrD | ATOM | 78 | N | SER | 5 | 23.650 |
| 11.804 | 6.792 | 1.00 | 0.00 | BrD | ATOM | 79 | HN | SER | 5 | 23.528 |
| 11.194 | 7.758 | 1.00 | 0.00 | BrD | ATOM | 80 | CA | SER | 5 | 23.040 |
| 9.939 | 6.125 | 1.00 | 0.00 | BrD | ATOM | 81 | HA | SER | 5 | 23.836 |

TABLE 6-continued

Atomic Structure Coordinates of the
P/CAF Bromodomain/Acetyl-Histamine Complex

| | | | | | | | | | | |
|---|---|---|---|---|---|---|---|---|---|---|
| 9.303 | 5.767 | 1.00 | 0.00 | BrD | ATOM | 82 | CB | SER | 5 | 22.177 |
| 9.148 | 7.111 | 1.00 | 0.00 | BrD | ATOM | 83 | HB1 | SER | 5 | 21.179 |
| 9.560 | 7.123 | 1.00 | 0.00 | BrD | ATOM | 84 | HB | SER | 5 | 22.136 |
| 8.114 | 6.801 | 1.00 | 0.00 | BrD | ATOM | 85 | OG | SER | 5 | 22.712 |
| 9.210 | 8.421 | 1.00 | 0.00 | BrD | ATOM | 86 | HG | SER | 5 | 23.243 |
| 8.428 | 8.588 | 1.00 | 0.00 | BrD | ATOM | 87 | C | SER | 5 | 22.194 |
| 10.380 | 4.934 | 1.00 | 0.00 | BrD | ATOM | 88 | O | SER | 5 | 21.748 |
| 11.525 | 4.867 | 1.00 | 0.00 | BrD | ATOM | 89 | N | LYS | 6 | 21.973 |
| 9.460 | 3.999 | 1.00 | 0.00 | BrD | ATOM | 90 | HN | LYS | 6 | 22.355 |
| 8.565 | 4.110 | 1.00 | 0.00 | BrD | ATOM | 91 | CA | LYS | 6 | 21.180 |
| 9.753 | 2.811 | 1.00 | 0.00 | BrD | ATOM | 92 | HA | LYS | 6 | 20.720 |
| 10.720 | 2.950 | 1.00 | 0.00 | BrD | ATOM | 93 | CB | LYS | 6 | 22.078 |
| 9.801 | 1.572 | 1.00 | 0.00 | BrD | ATOM | 94 | HB1 | LYS | 6 | 31.474 |
| 10.096 | 0.714 | 1.00 | 0.00 | BrD | ATOM | 95 | HB2 | LYS | 6 | 22.512 |
| 8.824 | 1.418 | 1.00 | 0.00 | BrD | ATOM | 96 | CG | LYS | 6 | 23.208 |
| 10.813 | 1.677 | 1.00 | 0.00 | BrD | ATOM | 97 | HG1 | LYS | 6 | 23.164 |
| 11.290 | 2.645 | 1.00 | 0.00 | BrD | ATOM | 98 | HG2 | LYS | 6 | 24.191 |
| 10.299 | 1.568 | 1.00 | 0.00 | BrD | ATOM | 99 | CD | LYS | 6 | 23.100 |
| 11.879 | 0.598 | 1.00 | 0.00 | BrD | ATOM | 100 | HD1 | LYS | 6 | 22.401 |
| 11.546 | −0.155 | 1.00 | 0.00 | BrD | ATOM | 101 | HD2 | LYS | 6 | 24.072 |
| 12.024 | 0.150 | 1.00 | 0.00 | BrD | ATOM | 102 | CE | LYS | 6 | 22.618 |
| 13.203 | 1.168 | 1.00 | 0.00 | BrD | ATOM | 103 | HE1 | LYS | 6 | 21.595 |
| 13.088 | 1.494 | 1.00 | 0.00 | BrD | ATOM | 104 | HE2 | LYS | 6 | 22.666 |
| 13.953 | 0.393 | 1.00 | 0.00 | BrD | ATOM | 105 | HZ | LYS | 6 | 23.448 |
| 13.645 | 2.322 | 1.00 | 0.00 | BrD | ATOM | 106 | HZ1 | LYS | 6 | 24.293 |
| 13.045 | 2.406 | 1.00 | 0.00 | BrD | ATOM | 107 | HZ2 | LYS | 6 | 22.900 |
| 13.578 | 3.204 | 1.00 | 0.00 | BrD | ATOM | 108 | HZ3 | LYS | 6 | 23.749 |
| 14.632 | 2.189 | 1.00 | 0.00 | BrD | ATOM | 109 | C | LYS | 6 | 20.085 |
| 8.710 | 2.613 | 1.00 | 0.00 | BrD | ATOM | 110 | O | LYS | 6 | 18.897 |
| 9.022 | 2.693 | 1.00 | 0.00 | BrD | ATOM | 111 | N | GLU | 7 | 20.495 |
| 7.474 | 2.334 | 1.00 | 0.00 | BrD | ATOM | 112 | HN | GLU | 7 | 21.457 |
| 7.295 | 2.280 | 1.00 | 0.00 | BrD | ATOM | 113 | CA | GLU | 7 | 19.558 |
| 6.370 | 2.115 | 1.00 | 0.00 | BrD | ATOM | 114 | HA | GLU | 7 | 20.083 |
| 5.603 | 1.565 | 1.00 | 0.00 | BrD | ATOM | 115 | CB | GLU | 7 | 19.091 |
| 5.783 | 3.451 | 1.00 | 0.00 | BrD | ATOM | 116 | HB1 | GLU | 7 | 18.110 |
| 5.354 | 3.317 | 1.00 | 0.00 | BrD | ATOM | 117 | HB2 | GLU | 7 | 19.777 |
| 5.003 | 3.745 | 1.00 | 0.00 | BrD | ATOM | 118 | CG | GLU | 7 | 19.014 |
| 6.799 | 4.579 | 1.00 | 0.00 | BrD | ATOM | 119 | HG1 | GLU | 7 | 18.377 |
| 7.614 | 4.271 | 1.00 | 0.00 | BrD | ATOM | 120 | HG2 | GLU | 7 | 20.007 |
| 7.173 | 4.780 | 1.00 | 0.00 | BrD | ATOM | 121 | CD | GLU | 7 | 18.452 |
| 6.206 | 5.857 | 1.00 | 0.00 | BrD | ATOM | 122 | OE1 | GLU | 7 | 17.289 |
| 6.511 | 6.192 | 1.00 | 0.00 | BrD | ATOM | 123 | OE2 | GLU | 7 | 19.176 |
| 5.434 | 6.521 | 1.00 | 0.00 | BrD | ATOM | 124 | C | GLU | 7 | 18.347 |
| 6.812 | 1.290 | 1.00 | 0.00 | BrD | ATOM | 125 | O | GLU | 7 | 17.342 |
| 7.261 | 1.840 | 1.00 | 0.00 | BrD | ATOM | 126 | N | PRO | 8 | 18.430 |
| 6.681 | −0.045 | 1.00 | 0.00 | BrD | ATOM | 127 | CA | PRO | 8 | 17.346 |
| 7.054 | −0.951 | 1.00 | 0.00 | BrD | ATOM | 128 | HA | PRO | 8 | 16.908 |
| 8.003 | −0.677 | 1.00 | 0.00 | BrD | ATOM | 129 | CB | PRO | 8 | 18.034 |
| 7.176 | −2.321 | 1.00 | 0.00 | BrD | ATOM | 130 | HB1 | PRO | 8 | 17.603 |
| 6.458 | −3.004 | 1.00 | 0.00 | BrD | ATOM | 131 | HB2 | PRO | 8 | 17.887 |
| 8.174 | −2.708 | 1.00 | 0.00 | BrD | ATOM | 132 | CG | PRO | 8 | 19.488 |
| 6.795 | −2.087 | 1.00 | 0.00 | BrD | ATOM | 133 | HG1 | PRO | 8 | 19.876 |
| 6.286 | −2.890 | 1.00 | 0.00 | BrD | ATOM | 134 | HG2 | PRO | 8 | 20.034 |
| 7.825 | −2.026 | 1.00 | 0.00 | BrD | ATOM | 135 | CD | PRO | 8 | 19.578 |
| 6.155 | −0.784 | 1.00 | 0.00 | BrD | ATOM | 136 | HD1 | PRO | 8 | 20.904 |
| 6.384 | −0.278 | 1.00 | 0.00 | BrD | ATOM | 137 | HD2 | PRO | 8 | 19.481 |
| 5.090 | −0.943 | 1.00 | 0.00 | BrD | ATOM | 138 | C | PRO | 8 | 16.259 |
| 5.987 | −1.000 | 1.00 | 0.00 | BrD | ATOM | 139 | O | PRO | 8 | 15.071 |
| 6.286 | −0.874 | 1.00 | 0.00 | BrD | ATOM | 140 | N | ARG | 9 | 16.680 |
| 4.740 | −1.177 | 1.00 | 0.00 | BrD | ATOM | 141 | HN | ARG | 9 | 17.640 |
| 4.570 | −1.269 | 1.00 | 0.00 | BrD | ATOM | 142 | CA | ARG | 9 | 19.754 |
| 3.617 | −1.241 | 1.00 | 0.00 | BrD | ATOM | 143 | HA | ARG | 9 | 18.272 |
| 3.529 | −0.276 | 1.00 | 0.00 | BrD | ATOM | 144 | CE | ARG | 9 | 14.692 |
| 3.864 | −2.314 | 1.00 | 0.00 | BrD | ATOM | 145 | HB1 | ARG | 9 | 14.073 |
| 2.982 | −2.402 | 1.00 | 0.00 | BrD | ATOM | 146 | HB2 | ARG | 9 | 14.076 |
| 4.696 | −2.010 | 1.00 | 0.00 | BrD | ATOM | 147 | CG | ARG | 9 | 15.272 |
| 4.176 | −3.684 | 1.00 | 0.00 | BrD | ATOM | 148 | HG1 | ARG | 9 | 16.153 |
| 3.571 | −3.837 | 1.00 | 0.00 | BrD | ATOM | 149 | HG2 | ARG | 9 | 15.539 |
| 5.221 | −3.721 | 1.00 | 0.00 | BrD | ATOM | 150 | CD | ARG | 9 | 14.274 |
| 3.882 | −4.793 | 1.00 | 0.00 | BrD | ATOM | 151 | HD1 | ARG | 9 | 13.277 |
| 4.055 | −4.417 | 1.00 | 0.00 | BrD | ATOM | 152 | HD2 | ARG | 9 | 14.375 |
| 2.848 | −5.085 | 1.00 | 0.00 | BrD | ATOM | 153 | NE | ARG | 9 | 14.493 |
| 4.728 | −5.963 | 1.00 | 0.00 | BrD | ATOM | 154 | HE | ARG | 9 | 14.761 |
| 4.289 | −6.797 | 1.00 | 0.00 | BrD | ATOM | 155 | CZ | ARG | 9 | 14.350 |
| 6.049 | −5.955 | 1.00 | 0.00 | BrD | ATOM | 156 | NH1 | ARG | 9 | 13.988 |
| 6.672 | −4.842 | 1.00 | 0.00 | BrD | ATOM | 157 | HH11 | ARG | 9 | 13.822 |
| 6.147 | −4.006 | 1.00 | 0.00 | BrD | ATOM | 158 | HH12 | ARG | 9 | 13.880 |

TABLE 6-continued

Atomic Structure Coordinates of the
P/CAF Bromodomain/Acetyl-Histamine Complex

| | | | | | | | | | | |
|---|---|---|---|---|---|---|---|---|---|---|
| 7.666 | −4.837 | 1.00 | 0.00 | BrD | ATOM | 159 | NH2 | ARG | 9 | 14.567 |
| 6.749 | −7.059 | 1.00 | 0.00 | BrD | ATOM | 160 | HH21 | ARG | 9 | 14.458 |
| 7.744 | −7.051 | 1.00 | 0.00 | BrD | ATOM | 161 | HH22 | ARG | 9 | 14.840 |
| 6.284 | −7.901 | 1.00 | 0.00 | BrD | ATOM | 162 | C | ARG | 9 | 16.900 |
| 2.320 | −1.538 | 1.00 | 0.00 | BrD | ATOM | 163 | O | ARG | 9 | 17.367 |
| 2.278 | −2.410 | 1.00 | 0.00 | BrD | ATOM | 164 | N | ASP | 10 | 16.159 |
| 1.267 | −0.803 | 1.00 | 0.00 | BrD | ATOM | 165 | HN | ASP | 10 | 15.462 |
| 1.367 | −0.123 | 1.00 | 0.00 | BrD | ATOM | 166 | CA | ASP | 10 | 16.788 |
| 0.038 | −0.988 | 1.00 | 0.00 | BrD | ATOM | 167 | HA | ASP | 10 | 17.629 |
| 0.088 | −1.658 | 1.00 | 0.00 | BrD | ATOM | 168 | CB | ASP | 10 | 17.296 |
| 0.576 | 0.350 | 1.00 | 0.00 | BrD | ATOM | 168 | HB1 | ASP | 10 | 18.082 |
| 0.067 | 0.715 | 1.00 | 0.00 | BrD | ATOM | 170 | HB2 | ASP | 10 | 17.688 |
| 1.572 | 0.204 | 1.00 | 0.00 | BrD | ATOM | 171 | CG | ASP | 10 | 16.201 |
| 0.641 | 1.399 | 1.00 | 0.00 | BrD | ATOM | 172 | OD1 | ASP | 10 | 16.210 |
| 1.595 | 2.205 | 1.00 | 0.00 | BrD | ATOM | 173 | OD2 | ASP | 10 | 15.340 |
| 0.262 | 1.413 | 1.00 | 0.00 | BrD | ATOM | 174 | C | ASP | 10 | 15.803 |
| 1.028 | −1.606 | 1.00 | 0.00 | BrD | ATOM | 175 | O | ASP | 10 | 14.986 |
| 1.622 | −0.903 | 1.00 | 0.00 | BrD | ATOM | 176 | N | PRO | 11 | 15.866 |
| 1.218 | −2.916 | 1.00 | 0.00 | BrD | ATOM | 177 | CA | PRO | 11 | 14.974 |
| 2.118 | −3.657 | 1.00 | 0.00 | BrD | ATOM | 178 | HA | PRO | 11 | 10.975 |
| 2.098 | −3.247 | 1.00 | 0.00 | BrD | ATOM | 179 | CB | PRO | 11 | 14.958 |
| 1.540 | −5.084 | 1.00 | 0.00 | BrD | ATOM | 180 | HB1 | PRO | 11 | 13.973 |
| 1.156 | −5.002 | 1.00 | 0.00 | BrD | ATOM | 181 | HB2 | PRO | 11 | 19.203 |
| 2.321 | −5.789 | 1.00 | 0.00 | BrD | ATOM | 182 | CG | PRO | 11 | 19.982 |
| 0.443 | −9.113 | 1.00 | 0.00 | BrD | ATOM | 183 | HG1 | PRO | 11 | 19.487 |
| 0.516 | −9.149 | 1.00 | 0.00 | BrD | ATOM | 184 | HG2 | PRO | 11 | 16.620 |
| 0.564 | −5.976 | 1.00 | 0.00 | BrD | ATOM | 185 | CD | PRO | 11 | 16.792 |
| 0.558 | −3.852 | 1.00 | 0.00 | BrD | ATOM | 186 | HD1 | PRO | 11 | 17.066 |
| 0.418 | −3.487 | 1.00 | 0.00 | BrD | ATOM | 187 | HD2 | PRO | 11 | 17.671 |
| 1.163 | −4.018 | 1.00 | 0.00 | BrD | ATOM | 188 | C | PRO | 11 | 19.488 |
| 3.954 | −3.470 | 1.00 | 0.00 | BrD | ATOM | 189 | O | PRO | 11 | 19.981 |
| 4.191 | −4.721 | 1.00 | 0.00 | BrD | ATOM | 190 | N | ASP | 12 | 19.849 |
| 4.061 | −2.496 | 1.00 | 0.00 | BrD | ATOM | 191 | HN | ASP | 12 | 19.780 |
| 3.506 | −1.691 | 1.00 | 0.00 | BrD | ATOM | 192 | CA | ASP | 12 | 16.361 |
| 5.421 | −2.384 | 1.00 | 0.00 | BrD | ATOM | 193 | HA | ASP | 12 | 16.155 |
| 5.927 | −3.315 | 1.00 | 0.00 | BrD | ATOM | 194 | CB | ASP | 12 | 17.873 |
| 5.399 | −2.151 | 1.00 | 0.00 | BrD | ATOM | 195 | HB1 | ASP | 12 | 18.123 |
| 6.112 | −1.340 | 1.00 | 0.00 | BrD | ATOM | 196 | HB2 | ASP | 12 | 18.167 |
| 4.410 | −1.830 | 1.00 | 0.00 | BrD | ATOM | 197 | CG | ASP | 12 | 18.657 |
| 5.749 | −3.400 | 1.00 | 0.00 | BrD | ATOM | 198 | OD1 | ASP | 12 | 18.450 |
| 5.084 | −4.437 | 1.00 | 0.00 | BrD | ATOM | 199 | OD2 | ASP | 12 | 19.478 |
| 6.687 | −3.342 | 1.00 | 0.00 | BrD | ATOM | 200 | C | ASP | 12 | 19.674 |
| 6.179 | −1.253 | 1.00 | 0.00 | BrD | ATOM | 201 | O | ASP | 12 | 15.106 |
| 7.250 | −1.468 | 1.00 | 0.00 | BrD | ATOM | 202 | N | GLN | 13 | 15.740 |
| 5.626 | −0.047 | 1.00 | 0.00 | BrD | ATOM | 203 | HN | GLN | 13 | 16.206 |
| 4.770 | 0.063 | 1.00 | 0.00 | BrD | ATOM | 204 | CA | GLN | 13 | 15.122 |
| 6.258 | 1.113 | 1.00 | 0.00 | BrD | ATOM | 205 | HA | GLN | 13 | 15.336 |
| 7.316 | 1.069 | 1.00 | 0.00 | BrD | ATOM | 206 | CB | GLN | 13 | 15.701 |
| 5.684 | 2.405 | 1.00 | 0.00 | BrD | ATOM | 207 | HB1 | GLN | 13 | 16.666 |
| 9.251 | 2.193 | 1.00 | 0.00 | BrD | ATOM | 208 | HB2 | GLN | 13 | 15.041 |
| 4.910 | 2.768 | 1.00 | 0.00 | BrD | ATOM | 209 | CG | GLN | 13 | 15.870 |
| 6.719 | 3.505 | 1.00 | 0.00 | BrD | ATOM | 210 | HG1 | GLN | 13 | 15.520 |
| 6.297 | 4.416 | 1.00 | 0.00 | BrD | ATOM | 211 | HG2 | GLN | 13 | 15.277 |
| 7.587 | 3.298 | 1.00 | 0.00 | BrD | ATOM | 212 | CD | GLN | 13 | 17.313 |
| 7.150 | 3.683 | 1.00 | 0.00 | BrD | ATOM | 213 | OE1 | GLN | 13 | 18.036 |
| 6.611 | 4.520 | 1.00 | 0.00 | BrD | ATOM | 214 | NE2 | GLN | 13 | 17.739 |
| 8.128 | 2.892 | 1.00 | 0.00 | BrD | ATOM | 215 | HE21 | GLN | 13 | 18.668 |
| 8.427 | 2.985 | 1.00 | 0.00 | BrD | ATOM | 216 | HE22 | GLN | 13 | 17.108 |
| 8.513 | 2.248 | 1.00 | 0.00 | BrD | ATOM | 217 | C | GLN | 13 | 13.615 |
| 6.060 | 1.097 | 1.00 | 0.00 | BrD | ATOM | 218 | O | GLN | 13 | 12.855 |
| 6.950 | 1.478 | 1.00 | 0.00 | BrD | ATOM | 219 | N | LEU | 14 | 13.191 |
| 4.880 | 0.662 | 1.00 | 0.00 | BrD | ATOM | 220 | HN | LEU | 14 | 13.848 |
| 4.214 | 0.371 | 1.00 | 0.00 | BrD | ATOM | 221 | CA | LEU | 14 | 11.774 |
| 4.558 | 0.595 | 1.00 | 0.00 | BrD | ATOM | 222 | HA | LEU | 14 | 11.303 |
| 4.943 | 1.487 | 1.00 | 0.00 | BrD | ATOM | 223 | CB | LEU | 14 | 11.581 |
| 3.042 | 0.541 | 1.00 | 0.00 | BrD | ATOM | 224 | HB1 | LEU | 14 | 12.212 |
| 2.592 | 1.292 | 1.00 | 0.00 | BrD | ATOM | 225 | HB2 | LEU | 14 | 10.592 |
| 2.823 | 0.781 | 1.00 | 0.00 | BrD | ATOM | 226 | CG | LEU | 14 | 11.903 |
| 2.399 | −0.808 | 1.00 | 0.00 | BrD | ATOM | 227 | HG | LEU | 14 | 12.685 |
| 2.967 | −1.292 | 1.00 | 0.00 | BrD | ATOM | 228 | CD1 | LEU | 14 | 12.409 |
| 0.978 | −0.615 | 1.00 | 0.00 | BrD | ATOM | 229 | HD11 | LEU | 14 | 11.569 |
| 0.311 | −0.497 | 1.00 | 0.00 | BrD | ATOM | 230 | HD12 | LEU | 14 | 12.986 |
| 0.482 | −1.479 | 1.00 | 0.00 | BrD | ATOM | 231 | HD13 | LEU | 14 | 13.032 |
| 0.934 | 0.266 | 1.00 | 0.00 | BrD | ATOM | 232 | CD2 | LEU | 14 | 10.682 |
| 2.418 | −1.709 | 1.00 | 0.00 | BrD | ATOM | 233 | HD21 | LEU | 14 | 10.185 |
| 1.461 | −1.660 | 1.00 | 0.00 | BrD | ATOM | 234 | HD22 | LEU | 14 | 10.005 |
| 3.192 | −1.383 | 1.00 | 0.00 | BrD | ATOM | 235 | HD23 | LEU | 14 | 10.989 |

TABLE 6-continued

Atomic Structure Coordinates of the
P/CAF Bromodomain/Acetyl-Histamine Complex

| | | | | | | | | | | |
|---|---|---|---|---|---|---|---|---|---|---|
| 2.612 | −2.727 | 1.00 | 0.00 | BrD | ATOM | 236 | C | LEU | 14 | 11.130 |
| 5.209 | −0.423 | 1.00 | 0.00 | BrD | ATOM | 237 | O | LEU | 14 | 9.989 |
| 5.666 | −0.564 | 1.00 | 0.00 | BrD | ATOM | 238 | N | TYR | 15 | 11.866 |
| 5.241 | −1.729 | 1.00 | 0.00 | BrD | ATOM | 239 | HN | TYR | 15 | 12.772 |
| 4.865 | −1.714 | 1.00 | 0.00 | BrD | ATOM | 240 | CA | TYR | 15 | 11.364 |
| 5.841 | −2.959 | 1.00 | 0.00 | BrD | ATOM | 241 | HA | TYR | 15 | 10.939 |
| 5.237 | −3.312 | 1.00 | 0.00 | BrD | ATOM | 242 | CB | TYR | 15 | 12.460 |
| 5.865 | −4.029 | 1.00 | 0.00 | BrD | ATOM | 243 | HB1 | TYR | 15 | 11.317 |
| 6.097 | −3.642 | 1.00 | 0.00 | BrD | ATOM | 244 | HB2 | TYR | 15 | 12.748 |
| 4.850 | −4.259 | 1.00 | 0.00 | BrD | ATOM | 245 | CG | TYR | 15 | 12.043 |
| 6.533 | −5.323 | 1.00 | 0.00 | BrD | ATOM | 246 | CD1 | TYR | 15 | 12.993 |
| 7.047 | −6.197 | 1.00 | 0.00 | BrD | ATOM | 247 | HD1 | TYR | 15 | 14.040 |
| 6.968 | −5.940 | 1.00 | 0.00 | BrD | ATOM | 248 | CD2 | TYR | 15 | 10.702 |
| 6.642 | −5.675 | 1.00 | 0.00 | BrD | ATOM | 249 | HD2 | TYR | 15 | 9.950 |
| 6.248 | −5.008 | 1.00 | 0.00 | BrD | ATOM | 250 | CE1 | TYR | 15 | 12.620 |
| 7.654 | −7.381 | 1.00 | 0.00 | BrD | ATOM | 251 | HE1 | TYR | 15 | 13.374 |
| 8.049 | −8.046 | 1.00 | 0.00 | BrD | ATOM | 252 | CE2 | TYR | 15 | 10.322 |
| 7.249 | −6.857 | 1.00 | 0.00 | BrD | ATOM | 253 | HE2 | TYR | 15 | 9.275 |
| 7.326 | −7.111 | 1.00 | 0.00 | BrD | ATOM | 254 | CZ | TYR | 15 | 11.284 |
| 7.752 | −7.706 | 1.00 | 0.00 | BrD | ATOM | 255 | OH | TYR | 15 | 10.908 |
| 8.358 | −8.883 | 1.00 | 0.00 | BrD | ATOM | 256 | HH | TYR | 15 | 10.572 |
| 9.238 | −8.697 | 1.00 | 0.00 | BrD | ATOM | 257 | C | TYR | 15 | 10.859 |
| 7.253 | −2.696 | 1.00 | 0.00 | BrD | ATOM | 258 | O | TYR | 15 | 9.778 |
| 7.630 | −3.146 | 1.00 | 0.00 | BrD | ATOM | 259 | N | SER | 16 | 11.641 |
| 8.026 | −1.950 | 1.00 | 0.00 | BrD | ATOM | 260 | HN | SER | 16 | 12.485 |
| 7.666 | −1.605 | 1.00 | 0.00 | BrD | ATOM | 261 | CA | SER | 16 | 11.249 |
| 9.384 | −1.602 | 1.00 | 0.00 | BrD | ATOM | 262 | HA | SER | 16 | 11.148 |
| 9.946 | −2.518 | 1.00 | 0.00 | BrD | ATOM | 263 | CB | SER | 16 | 12.315 |
| 10.040 | −0.722 | 1.00 | 0.00 | BrD | ATOM | 264 | HB1 | SER | 16 | 12.503 |
| 9.416 | 0.139 | 1.00 | 0.00 | BrD | ATOM | 265 | HB2 | SER | 16 | 13.227 |
| 10.155 | −1.289 | 1.00 | 0.00 | BrD | ATOM | 266 | OG | SER | 16 | 11.892 |
| 11.317 | −0.276 | 1.00 | 0.00 | BrD | ATOM | 267 | HG | SER | 16 | 12.601 |
| 11.952 | −0.405 | 1.00 | 0.00 | BrD | ATOM | 268 | C | SER | 16 | 9.909 |
| 9.370 | −0.879 | 1.00 | 0.00 | BrD | ATOM | 269 | O | SER | 16 | 9.028 |
| 10.182 | −1.161 | 1.00 | 0.00 | BrD | ATOM | 270 | N | THR | 17 | 9.756 |
| 8.420 | 0.038 | 1.00 | 0.00 | BrD | ATOM | 271 | HN | THR | 17 | 10.493 |
| 7.796 | 0.207 | 1.00 | 0.00 | BrD | ATOM | 272 | CA | THR | 17 | 8.514 |
| 8.269 | 0.785 | 1.00 | 0.00 | BrD | ATOM | 273 | HA | THR | 17 | 8.318 |
| 9.200 | 1.296 | 1.00 | 0.00 | BrD | ATOM | 274 | CB | THR | 17 | 8.656 |
| 7.144 | 1.820 | 1.00 | 0.00 | BrD | ATOM | 275 | HB | THR | 17 | 9.069 |
| 6.275 | 1.333 | 1.00 | 0.00 | BrD | ATOM | 276 | OG1 | THR | 17 | 9.519 |
| 7.535 | 2.857 | 1.00 | 0.00 | BrD | ATOM | 277 | HG1 | THR | 17 | 10.426 |
| 7.633 | 2.502 | 1.00 | 0.00 | BrD | ATOM | 278 | CG2 | THR | 17 | 7.344 |
| 6.733 | 2.463 | 1.00 | 0.00 | BrD | ATOM | 279 | HG21 | THR | 17 | 6.714 |
| 7.600 | 2.589 | 1.00 | 0.00 | BrD | ATOM | 280 | HG22 | THR | 17 | 6.845 |
| 6.012 | 1.832 | 1.00 | 0.00 | BrD | ATOM | 281 | HG23 | THR | 17 | 7.545 |
| 6.289 | 3.427 | 1.00 | 0.00 | BrD | ATOM | 282 | C | THR | 17 | 7.356 |
| 7.971 | −0.161 | 1.00 | 0.00 | BrD | ATOM | 283 | O | THR | 17 | 6.420 |
| 8.757 | −0.277 | 1.00 | 0.00 | BrD | ATOM | 284 | N | LEU | 18 | 7.438 |
| 6.832 | −0.843 | 1.00 | 0.00 | BrD | ATOM | 285 | HN | LEU | 18 | 8.212 |
| 6.247 | −0.702 | 1.00 | 0.00 | BrD | ATOM | 286 | CA | LEU | 18 | 6.396 |
| 6.414 | −1.776 | 1.00 | 0.00 | BrD | ATOM | 287 | HA | LEU | 18 | 5.534 |
| 6.122 | −1.197 | 1.00 | 0.00 | BrD | ATOM | 288 | CB | LEU | 18 | 6.871 |
| 5.218 | −2.591 | 1.00 | 0.00 | BrD | ATOM | 289 | HB1 | LEU | 18 | 7.669 |
| 5.542 | −3.243 | 1.00 | 0.00 | BrD | ATOM | 290 | HB2 | LEU | 18 | 6.049 |
| 4.869 | −3.198 | 1.00 | 0.00 | BrD | ATOM | 291 | CG | LEU | 18 | 7.377 |
| 4.056 | −1.750 | 1.00 | 0.00 | BrD | ATOM | 292 | HG | LEU | 18 | 8.301 |
| 4.305 | −1.275 | 1.00 | 0.00 | BrD | ATOM | 293 | CD1 | LEU | 18 | 7.653 |
| 2.840 | −2.622 | 1.00 | 0.00 | BrD | ATOM | 294 | HD11 | LEU | 18 | 6.966 |
| 2.832 | −3.455 | 1.00 | 0.00 | BrD | ATOM | 295 | HD12 | LEU | 18 | 8.667 |
| 2.885 | −2.994 | 1.00 | 0.00 | BrD | ATOM | 296 | HD13 | LEU | 18 | 7.523 |
| 1.941 | −2.039 | 1.00 | 0.00 | BrD | ATOM | 297 | CD2 | LEU | 18 | 6.369 |
| 3.727 | −0.658 | 1.00 | 0.00 | BrD | ATOM | 298 | HD21 | LEU | 18 | 5.417 |
| 4.180 | −0.897 | 1.00 | 0.00 | BrD | ATOM | 299 | HD22 | LEU | 18 | 6.252 |
| 2.657 | −0.584 | 1.00 | 0.00 | BrD | ATOM | 300 | HD23 | LEU | 18 | 6.722 |
| 4.117 | 0.284 | 1.00 | 0.00 | BrD | ATOM | 301 | C | LEU | 18 | 5.998 |
| 7.542 | −2.707 | 1.00 | 0.00 | BrD | ATOM | 302 | O | LEU | 18 | 4.869 |
| 8.021 | −2.667 | 1.00 | 0.00 | BrD | ATOM | 303 | N | LYS | 19 | 6.926 |
| 7.967 | −3.552 | 1.00 | 0.00 | BrD | ATOM | 304 | HN | LYS | 19 | 7.813 |
| 7.550 | −3.543 | 1.00 | 0.00 | BrD | ATOM | 305 | CA | LYS | 19 | 6.648 |
| 9.050 | −4.487 | 1.00 | 0.00 | BrD | ATOM | 306 | HA | LYS | 19 | 5.959 |
| 8.673 | −5.228 | 1.00 | 0.00 | BrD | ATOM | 307 | CB | LYS | 19 | 7.935 |
| 9.498 | −5.193 | 1.00 | 0.00 | BrD | ATOM | 308 | HB1 | LYS | 19 | 7.671 |
| 9.974 | −6.126 | 1.00 | 0.00 | BrD | ATOM | 309 | HB2 | LYS | 19 | 8.535 |
| 8.625 | −5.404 | 1.00 | 0.00 | BrD | ATOM | 310 | CG | LYS | 19 | 8.785 |
| 10.472 | −4.390 | 1.00 | 0.00 | BrD | ATOM | 311 | HG1 | LYS | 19 | 8.296 |
| 11.438 | −4.386 | 1.00 | 0.00 | BrD | ATOM | 312 | HG2 | LYS | 19 | 8.878 |

TABLE 6-continued

Atomic Structure Coordinates of the
P/CAF Bromodomain/Acetyl-Histamine Complex

| | | | | | | | | | |
|---|---|---|---|---|---|---|---|---|---|
| 10.106 | −3.378 | 1.00 | 0.00 | BrD | ATOM | 313 | CD | LYS | 19 | 10.172 |
| 10.621 | −4.992 | 1.00 | 0.00 | BrD | ATOM | 314 | HD1 | LYS | 19 | 10.575 |
| 9.638 | −5.190 | 1.00 | 0.00 | BrD | ATOM | 315 | HD2 | LYS | 19 | 10.807 |
| 11.137 | −4.287 | 1.00 | 0.00 | BrD | ATOM | 316 | CE | LYS | 19 | 10.133 |
| 11.409 | −6.290 | 1.00 | 0.00 | BrD | ATOM | 317 | HE1 | LYS | 19 | 9.337 |
| 11.019 | −6.908 | 1.00 | 0.00 | BrD | ATOM | 318 | HE2 | LYS | 19 | 11.077 |
| 11.288 | −6.800 | 1.00 | 0.00 | BrD | ATOM | 319 | HZ | LYS | 19 | 9.893 |
| 12.858 | −6.050 | 1.00 | 0.00 | BrD | ATOM | 320 | HZ1 | LYS | 19 | 9.982 |
| 13.072 | −5.036 | 1.00 | 0.00 | BrD | ATOM | 321 | HZ2 | LYS | 19 | 10.587 |
| 13.427 | −6.576 | 1.00 | 0.00 | BrD | ATOM | 322 | HZ3 | LYS | 19 | 8.937 |
| 13.119 | −6.366 | 1.00 | 0.00 | BrD | ATOM | 323 | C | LYS | 19 | 5.988 |
| 10.223 | −3.761 | 1.00 | 0.00 | BrD | ATOM | 324 | O | LYS | 19 | 5.193 |
| 10.960 | −4.341 | 1.00 | 0.00 | BrD | ATOM | 325 | N | SER | 20 | 6.299 |
| 10.359 | −2.474 | 1.00 | 0.00 | BrD | ATOM | 326 | HN | SER | 20 | 6.925 |
| 9.721 | −2.061 | 1.00 | 0.00 | BrD | ATOM | 327 | CA | SER | 20 | 5.722 |
| 11.425 | −1.661 | 1.00 | 0.00 | BrD | ATOM | 328 | HA | SER | 20 | 5.660 |
| 12.306 | −2.277 | 1.00 | 0.00 | BrD | ATOM | 329 | CB | SER | 20 | 6.608 |
| 11.725 | −0.449 | 1.00 | 0.00 | BrD | ATOM | 330 | HB1 | SER | 20 | 7.086 |
| 10.815 | −0.120 | 1.00 | 0.00 | BrD | ATOM | 331 | HB2 | SER | 20 | 5.999 |
| 12.121 | 0.350 | 1.00 | 0.00 | BrD | ATOM | 332 | OG | SER | 20 | 7.610 |
| 12.674 | −0.772 | 1.00 | 0.00 | BrD | ATOM | 333 | HG | SER | 20 | 7.218 |
| 13.396 | −1.269 | 1.00 | 0.00 | BrD | ATOM | 334 | C | SER | 20 | 4.316 |
| 11.056 | −1.207 | 1.00 | 0.00 | BrD | ATOM | 335 | O | SER | 20 | 3.334 |
| 11.659 | −1.642 | 1.00 | 0.00 | BrD | ATOM | 336 | N | ILE | 21 | 4.218 |
| 10.045 | −0.349 | 1.00 | 0.00 | BrD | ATOM | 337 | HN | ILE | 21 | 5.031 |
| 9.592 | −0.044 | 1.00 | 0.00 | BrD | ATOM | 338 | CA | ILE | 21 | 2.919 |
| 9.583 | 0.129 | 1.00 | 0.00 | BrD | ATOM | 339 | HA | ILE | 21 | 2.508 |
| 10.348 | 0.771 | 1.00 | 0.00 | BrD | ATOM | 340 | CB | ILE | 21 | 3.036 |
| 8.280 | 0.945 | 1.00 | 0.00 | BrD | ATOM | 341 | HB | ILE | 21 | 2.050 |
| 7.850 | 1.036 | 1.00 | 0.00 | BrD | ATOM | 342 | CG1 | ILE | 21 | 3.956 |
| 7.280 | 0.240 | 1.00 | 0.00 | BrD | ATOM | 343 | HG11 | ILE | 21 | 4.639 |
| 6.898 | 0.962 | 1.00 | 0.00 | BrD | ATOM | 344 | HG12 | ILE | 21 | 4.519 |
| 7.792 | −0.921 | 1.00 | 0.00 | BrD | ATOM | 345 | CG2 | ILE | 21 | 3.549 |
| 8.579 | 2.346 | 1.00 | 0.00 | BrD | ATOM | 346 | HG21 | ILE | 21 | 4.618 |
| 8.431 | 2.377 | 1.00 | 0.00 | BrD | ATOM | 347 | HG22 | ILE | 21 | 3.319 |
| 9.603 | 2.603 | 1.00 | 0.00 | BrD | ATOM | 348 | HG23 | ILE | 21 | 3.073 |
| 7.915 | 3.053 | 1.00 | 0.00 | BrD | ATOM | 349 | CD3 | ILE | 21 | 3.222 |
| 6.140 | −0.427 | 1.00 | 0.00 | BrD | ATOM | 350 | HD11 | ILE | 21 | 3.805 |
| 5.235 | −0.338 | 1.00 | 0.00 | BrD | ATOM | 351 | HD12 | ILE | 21 | 2.264 |
| 6.000 | 0.051 | 1.00 | 0.00 | BrD | ATOM | 352 | HD13 | ILE | 21 | 3.075 |
| 6.371 | −1.472 | 1.00 | 0.00 | BrD | ATOM | 353 | C | ILE | 21 | 1.969 |
| 9.361 | −1.044 | 1.00 | 0.00 | BrD | ATOM | 354 | O | ILE | 21 | 0.869 |
| 9.901 | −1.074 | 1.00 | 0.00 | BrD | ATOM | 355 | N | LEU | 22 | 2.433 |
| 8.608 | −2.034 | 1.00 | 0.00 | BrD | ATOM | 356 | HN | LEU | 22 | 3.325 |
| 8.224 | −1.957 | 1.00 | 0.00 | BrD | ATOM | 357 | CA | LEU | 22 | 1.648 |
| 8.337 | −3.229 | 1.00 | 0.00 | BrD | ATOM | 358 | HA | LEU | 22 | 0.757 |
| 7.807 | −2.929 | 1.00 | 0.00 | BrD | ATOM | 359 | CB | LEU | 22 | 2.451 |
| 7.465 | −4.197 | 1.00 | 0.00 | BrD | ATOM | 360 | HB1 | LEU | 22 | 3.352 |
| 7.996 | −4.462 | 1.00 | 0.00 | BrD | ATOM | 361 | HB2 | LEU | 22 | 2.728 |
| 6.556 | −3.683 | 1.00 | 0.00 | BrD | ATOM | 362 | CG | LEU | 22 | 1.722 |
| 7.084 | −5.486 | 1.00 | 0.00 | BrD | ATOM | 363 | HG | LEU | 22 | 1.378 |
| 7.982 | −5.977 | 1.00 | 0.00 | BrD | ATOM | 364 | CD1 | LEU | 22 | 3.665 |
| 6.362 | −6.437 | 1.00 | 0.00 | BrD | ATOM | 365 | HD11 | LEU | 22 | 2.220 |
| 6.314 | −7.419 | 1.00 | 0.00 | BrD | ATOM | 366 | HD12 | LEU | 22 | 3.601 |
| 6.898 | −6.492 | 1.00 | 0.00 | BrD | ATOM | 367 | HD13 | LEU | 22 | 2.845 |
| 5.341 | −6.074 | 1.00 | 0.00 | BrD | ATOM | 368 | CD2 | LEU | 22 | 0.507 |
| 6.222 | −5.178 | 1.00 | 0.00 | BrD | ATOM | 369 | HD21 | LEU | 22 | 0.127 |
| 6.472 | −4.199 | 1.00 | 0.00 | BrD | ATOM | 370 | HD22 | LEU | 22 | −0.259 |
| 6.401 | −5.918 | 1.00 | 0.00 | BrD | ATOM | 371 | HD23 | LEU | 22 | 0.790 |
| 5.180 | −5.199 | 1.00 | 0.00 | BrD | ATOM | 372 | C | LEU | 22 | 1.243 |
| 9.636 | −3.915 | 1.00 | 0.00 | BrD | ATOM | 373 | O | LEU | 22 | 0.086 |
| 9.813 | −4.295 | 1.00 | 0.00 | BrD | ATOM | 374 | N | GLN | 23 | 2.201 |
| 10.552 | −4.058 | 1.00 | 0.00 | BrD | ATOM | 375 | HN | GLN | 23 | 3.107 |
| 10.354 | −3.735 | 1.00 | 0.00 | BrD | ATOM | 376 | CA | GLN | 23 | 1.941 |
| 11.841 | −4.693 | 1.00 | 0.00 | BrD | ATOM | 377 | HA | GLN | 23 | 1.828 |
| 11.670 | −5.754 | 1.00 | 0.00 | BrD | ATOM | 378 | CB | GLN | 23 | 3.118 |
| 12.793 | −4.464 | 1.00 | 0.00 | BrD | ATOM | 379 | HB1 | GLN | 23 | 3.720 |
| 12.412 | −3.653 | 1.00 | 0.00 | BrD | ATOM | 380 | HB2 | GLN | 23 | 2.731 |
| 13.763 | −4.186 | 1.00 | 0.00 | BrD | ATOM | 381 | CG | GLN | 23 | 4.012 |
| 12.969 | −5.682 | 1.00 | 0.00 | BrD | ATOM | 382 | HG1 | GLN | 23 | 4.318 |
| 11.995 | −6.035 | 1.00 | 0.00 | BrD | ATOM | 383 | HG2 | GLN | 23 | 4.886 |
| 13.535 | −5.393 | 1.00 | 0.00 | BrD | ATOM | 384 | CD | GLN | 23 | 3.316 |
| 13.697 | −6.815 | 1.00 | 0.00 | BrD | ATOM | 385 | OE1 | GLN | 23 | 2.624 |
| 14.692 | −6.597 | 1.00 | 0.00 | BrD | ATOM | 386 | NE2 | GLN | 23 | 3.494 |
| 13.203 | −8.034 | 1.00 | 0.00 | BrD | ATOM | 387 | HE21 | GLN | 23 | 4.058 |
| 12.408 | −8.134 | 1.00 | 0.00 | BrD | ATOM | 388 | HE22 | GLN | 24 | 3.055 |
| 13.654 | −8.786 | 1.00 | 0.00 | BrD | ATOM | 389 | C | GLN | 23 | 0.655 |

TABLE 6-continued

Atomic Structure Coordinates of the
P/CAF Bromodomain/Acetyl-Histamine Complex

| | | | | | | | | | | |
|---|---|---|---|---|---|---|---|---|---|---|
| 12.467 | −4.157 | 1.00 | 0.00 | BrD | ATOM | 390 | O | GLN | 23 | −0.207 |
| 12.892 | −4.925 | 1.00 | 0.00 | BrD | ATOM | 391 | N | GLN | 24 | 0.930 |
| 12.519 | −2.833 | 1.00 | 0.00 | BrD | ATOM | 392 | HN | GLN | 24 | 1.252 |
| 12.167 | −2.269 | 1.00 | 0.00 | BrD | ATOM | 393 | CA | GLN | 24 | −0.654 |
| 13.096 | −2.203 | 1.00 | 0.00 | BrD | ATOM | 394 | HA | GLN | 24 | −0.951 |
| 13.947 | −2.797 | 1.00 | 0.00 | BrD | ATOM | 395 | CB | GLN | 24 | −0.325 |
| 13.584 | −0.783 | 1.00 | 0.00 | BrD | ATOM | 396 | HB1 | GLN | 24 | 0.666 |
| 14.012 | −0.785 | 1.00 | 0.00 | BrD | ATOM | 397 | HB2 | GLN | 24 | −1.035 |
| 14.351 | −0.509 | 1.00 | 0.00 | BrD | ATOM | 398 | CG | GLN | 24 | −0.369 |
| 12.498 | 0.284 | 1.00 | 0.00 | BrD | ATOM | 399 | HG1 | GLN | 24 | −1.331 |
| 12.531 | 0.774 | 1.00 | 0.00 | BrD | ATOM | 400 | HG2 | GLN | 24 | −0.243 |
| 11.539 | −0.192 | 1.00 | 0.00 | BrD | ATOM | 401 | CD | GLN | 24 | 0.714 |
| 12.663 | 1.333 | 1.00 | 0.00 | BrD | ATOM | 402 | OE1 | GLN | 24 | 0.426 |
| 12.791 | 2.524 | 1.00 | 0.00 | BrD | ATOM | 403 | NE2 | GLN | 24 | 1.967 |
| 12.659 | 0.897 | 1.00 | 0.00 | BrD | ATOM | 404 | HE21 | GLN | 24 | 2.122 |
| 12.552 | −0.065 | 1.00 | 0.00 | BrD | ATOM | 405 | HE23 | GLN | 24 | 2.687 |
| 12.763 | 1.554 | 1.00 | 0.00 | BrD | ATOM | 406 | C | GLN | 24 | −1.816 |
| 12.099 | −2.179 | 1.00 | 0.00 | BrD | ATOM | 407 | O | GLN | 24 | −2.974 |
| 12.485 | −2.331 | 1.00 | 0.00 | BrD | ATOM | 408 | N | VAL | 25 | −1.501 |
| 10.821 | −1.974 | 1.00 | 0.00 | BrD | ATOM | 409 | HN | VAL | 25 | −0.561 |
| 10.575 | −1.859 | 1.00 | 0.00 | BrD | ATOM | 410 | CA | VAL | 25 | −2.523 |
| 9.776 | −1.922 | 1.00 | 0.00 | BrD | ATOM | 411 | HA | VAL | 25 | −3.121 |
| 9.941 | −1.036 | 1.00 | 0.00 | BrD | ATOM | 412 | CB | VAL | 25 | −1.890 |
| 8.369 | −1.813 | 1.00 | 0.00 | BrD | ATOM | 413 | HB | VAL | 25 | −1.198 |
| 8.243 | −2.632 | 1.00 | 0.00 | BrD | ATOM | 414 | CG1 | VAL | 25 | −1.116 |
| 8.236 | −0.510 | 1.00 | 0.00 | BrD | ATOM | 415 | HG11 | VAL | 25 | −1.590 |
| 7.494 | 0.116 | 1.00 | 0.00 | BrD | ATOM | 416 | HG12 | VAL | 25 | −0.102 |
| 7.932 | −0.722 | 1.00 | 0.00 | BrD | ATOM | 417 | HG13 | VAL | 25 | −1.108 |
| 9.186 | 0.003 | 1.00 | 0.00 | BrD | ATOM | 418 | CG2 | VAL | 25 | −2.945 |
| 7.277 | −1.908 | 1.00 | 0.00 | BrD | ATOM | 419 | HG21 | VAL | 25 | −3.437 |
| 7.331 | −2.868 | 1.00 | 0.00 | BrD | ATOM | 420 | HG22 | VAL | 25 | −2.472 |
| 6.313 | −1.799 | 1.00 | 0.00 | BrD | ATOM | 421 | HG23 | VAL | 25 | −3.672 |
| 7.410 | −1.121 | 1.00 | 0.00 | BrD | ATOM | 422 | C | VAL | 25 | −3.440 |
| 9.846 | −3.141 | 1.00 | 0.00 | BrD | ATOM | 423 | O | VAL | 25 | −4.659 |
| 9.930 | −3.000 | 1.00 | 0.00 | BrD | ATOM | 424 | N | LYS | 26 | −2.898 |
| 9.858 | −4.336 | 1.00 | 0.00 | BrD | ATOM | 425 | HN | LYS | 26 | −1.883 |
| 9.798 | −4.396 | 1.00 | 0.00 | BrD | ATOM | 426 | CA | LYS | 26 | −3.648 |
| 9.943 | −5.562 | 1.00 | 0.00 | BrD | ATOM | 427 | HA | LYS | 26 | −4.174 |
| 9.008 | −5.678 | 1.00 | 0.00 | BrD | ATOM | 428 | CB | LYS | 26 | −2.737 |
| 10.161 | −6.771 | 1.00 | 0.00 | BrD | ATOM | 429 | HB1 | LYS | 26 | −3.314 |
| 10.018 | −7.673 | 1.00 | 0.00 | BrD | ATOM | 430 | HB2 | LYS | 26 | −1.942 |
| 9.430 | −6.744 | 1.00 | 0.00 | BrD | ATOM | 431 | CG | LYS | 26 | −2.111 |
| 11.545 | −6.820 | 1.00 | 0.00 | BrD | ATOM | 432 | HG1 | LYS | 26 | −2.070 |
| 11.947 | −5.818 | 1.00 | 0.00 | BrD | ATOM | 433 | HG2 | LYS | 26 | −2.721 |
| 12.183 | −7.442 | 1.00 | 0.00 | BrD | ATOM | 434 | CD | LYS | 26 | −0.702 |
| 11.500 | −7.391 | 1.00 | 0.00 | BrD | ATOM | 435 | HD1 | LYS | 26 | −0.214 |
| 10.600 | −7.048 | 1.00 | 0.00 | BrD | ATOM | 436 | HD2 | LYS | 26 | −0.156 |
| 12.364 | −7.043 | 1.00 | 0.00 | BrD | ATOM | 437 | CE | LYS | 26 | −0.716 |
| 11.505 | −8.910 | 1.00 | 0.00 | BrD | ATOM | 438 | HE1 | LYS | 26 | 0.003 |
| 10.782 | −9.286 | 1.00 | 0.00 | BrD | ATOM | 439 | HE2 | LYS | 26 | −1.703 |
| 11.228 | −9.249 | 1.00 | 0.00 | BrD | ATOM | 440 | NZ | LYS | 26 | −0.371 |
| 12.844 | −9.465 | 1.00 | 0.00 | BrD | ATOM | 441 | HZ1 | LYS | 26 | −1.215 |
| 13.285 | −9.884 | 1.00 | 0.00 | BrD | ATOM | 442 | HZ2 | LYS | 26 | −0.010 |
| 13.461 | −8.710 | 1.00 | 0.00 | BrD | ATOM | 443 | HZ3 | LYS | 26 | 0.354 |
| 12.749 | −10.199 | 1.00 | 0.00 | BrD | ATOM | 444 | C | LYS | 26 | −4.673 |
| 11.073 | −5.468 | 1.00 | 0.00 | BrD | ATOM | 445 | O | LYS | 26 | −5.762 |
| 10.991 | −6.036 | 1.00 | 0.00 | BrD | ATOM | 446 | N | SER | 27 | −4.315 |
| 12.118 | −4.732 | 1.00 | 0.00 | BrD | ATOM | 447 | HN | SER | 27 | −3.439 |
| 12.109 | −4.293 | 1.00 | 0.00 | BrD | ATOM | 448 | CA | SER | 27 | −9.204 |
| 13.257 | −4.516 | 1.00 | 0.00 | BrD | ATOM | 449 | HA | SER | 27 | −6.104 |
| 13.100 | −5.091 | 1.00 | 0.00 | BrD | ATOM | 450 | CB | SER | 27 | −4.532 |
| 14.593 | −4.976 | 1.00 | 0.00 | BrD | ATOM | 451 | HB1 | SER | 27 | −3.629 |
| 14.710 | −4.404 | 1.00 | 0.00 | BrD | ATOM | 452 | HB2 | SER | 27 | −9.207 |
| 15.381 | −4.818 | 1.00 | 0.00 | BrD | ATOM | 453 | OG | SER | 27 | −4.197 |
| 14.492 | −6.351 | 1.00 | 0.00 | BrD | ATOM | 454 | HG | SER | 27 | −1.746 |
| 19.300 | −4.606 | 1.00 | 0.00 | BrD | ATOM | 455 | C | SER | 27 | −5.591 |
| 13.361 | −3.090 | 1.00 | 0.00 | BrD | ATOM | 456 | O | SER | 27 | −9.962 |
| 14.431 | −2.567 | 1.00 | 0.00 | BrD | ATOM | 457 | N | HIS | 28 | −9.477 |
| 12.246 | −2.339 | 1.00 | 0.00 | BrD | ATOM | 458 | HN | HIS | 28 | −5.215 |
| 11.418 | −2.785 | 1.00 | 0.00 | BrD | ATOM | 459 | CA | HIS | 28 | −5.863 |
| 12.197 | −0.946 | 1.00 | 0.00 | BrD | ATOM | 460 | HA | HIS | 28 | −9.597 |
| 13.142 | −0.497 | 1.00 | 0.00 | BrD | ATOM | 461 | CB | HIS | 28 | −9.125 |
| 11.076 | −0.217 | 1.00 | 0.00 | BrD | ATOM | 462 | HB1 | HIS | 28 | −4.073 |
| 11.308 | −0.210 | 1.00 | 0.00 | BrD | ATOM | 463 | HB2 | HIS | 28 | −9.283 |
| 10.146 | −0.742 | 1.00 | 0.00 | BrD | ATOM | 464 | CG | HIS | 28 | −9.549 |
| 10.884 | 1.205 | 1.00 | 0.00 | BrD | ATOM | 465 | ND1 | HIS | 28 | −5.742 |
| 11.931 | 2.081 | 1.00 | 0.00 | BrD | ATOM | 466 | HD1 | HIS | 28 | −5.645 |

TABLE 6-continued

Atomic Structure Coordinates of the
P/CAF Bromodomain/Acetyl-Histamine Complex

| | | | | | | | | | | |
|---|---|---|---|---|---|---|---|---|---|---|
| 12.883 | 1.866 | 1.00 | 0.00 | BrD | ATOM | 467 | CD2 | HIS | 28 | −5.780 |
| 9.754 | 1.916 | 1.00 | 0.00 | BrD | ATOM | 468 | HD2 | HIS | 28 | −5.717 |
| 8.739 | 1.549 | 1.00 | 0.00 | BrD | ATOM | 469 | CE1 | HIS | 28 | −6.092 |
| 11.496 | 3.262 | 1.00 | 0.00 | BrD | ATOM | 470 | HE1 | HIS | 28 | −6.314 |
| 12.044 | 4.141 | 1.00 | 0.00 | BrD | ATOM | 471 | ME2 | HIS | 28 | −6.119 |
| 10.139 | 3.189 | 1.00 | 0.00 | BrD | ATOM | 472 | HE2 | HIS | 28 | −6.350 |
| 9.536 | 3.925 | 1.00 | 0.00 | BrD | ATOM | 473 | C | HIS | 28 | −7.364 |
| 12.017 | −0.850 | 1.00 | 0.00 | BrD | ATOM | 474 | O | HIS | 28 | −7.979 |
| 11.356 | −1.686 | 1.00 | 0.00 | BrD | ATOM | 475 | N | GLN | 29 | −7.954 |
| 12.666 | 0.128 | 1.00 | 0.00 | BrD | ATOM | 476 | HN | GLN | 29 | −7.404 |
| 13.189 | 0.747 | 1.00 | 0.00 | BrD | ATOM | 477 | CA | GLN | 29 | −9.397 |
| 12.630 | 0.298 | 1.00 | 0.00 | BrD | ATOM | 478 | HA | GLN | 29 | −9.836 |
| 12.688 | −0.687 | 1.00 | 0.00 | BrD | ATOM | 479 | CS | GLN | 29 | −9.840 |
| 13.850 | 1.090 | 1.00 | 0.00 | BrD | ATOM | 480 | HB1 | GLN | 29 | −9.485 |
| 13.761 | 2.106 | 1.00 | 0.00 | BrD | ATOM | 481 | HB2 | GLN | 29 | −10.918 |
| 13.901 | 1.092 | 1.00 | 0.00 | BrD | ATOM | 482 | CG | GLN | 29 | −9.294 |
| 15.138 | 0.496 | 1.00 | 0.00 | BrD | ATOM | 483 | HG1 | GLN | 29 | −8.707 |
| 14.867 | −0.386 | 1.00 | 0.00 | BrD | ATOM | 484 | HG2 | GLN | 29 | −8.660 |
| 15.618 | 1.227 | 1.00 | 0.00 | BrD | ATOM | 485 | CD | GLN | 29 | −10.390 |
| 16.105 | 0.093 | 1.00 | 0.00 | BrD | ATOM | 486 | OE1 | GLN | 29 | −10.358 |
| 16.679 | −0.996 | 1.00 | 0.00 | BrD | ATOM | 487 | NE2 | GLN | 29 | −11.368 |
| 16.290 | 0.971 | 1.00 | 0.00 | BrD | ATOM | 488 | HE21 | GLN | 29 | −12.090 |
| 16.910 | 0.737 | 1.00 | 0.00 | BrD | ATOM | 489 | HE22 | GLN | 29 | −11.329 |
| 15.800 | 1.819 | 1.00 | 0.00 | BrD | ATOM | 490 | C | GLN | 29 | −9.866 |
| 11.332 | 0.951 | 1.00 | 0.00 | BrD | ATOM | 491 | O | GLN | 29 | −11.065 |
| 11.111 | 1.116 | 1.00 | 0.00 | BrD | ATOM | 492 | N | SER | 30 | −8.921 |
| 10.450 | 1.262 | 1.00 | 0.00 | BrD | ATOM | 493 | HN | SER | 30 | −7.985 |
| 10.661 | 1.074 | 1.00 | 0.00 | BrD | ATOM | 494 | CA | SER | 30 | −9.246 |
| 9.143 | 1.805 | 1.00 | 0.00 | BrD | ATOM | 495 | HA | SER | 30 | −10.319 |
| 9.016 | 1.787 | 1.00 | 0.00 | BrD | ATOM | 496 | CB | SER | 30 | −8.759 |
| 9.026 | 3.250 | 1.00 | 0.00 | BrD | ATOM | 497 | HB1 | SER | 30 | −7.829 |
| 8.479 | 3.271 | 1.00 | 0.00 | BrD | ATOM | 498 | HB2 | SER | 30 | −9.499 |
| 8.500 | 3.835 | 1.00 | 0.00 | BrD | ATOM | 499 | OG | SER | 30 | −8.552 |
| 10.307 | 3.823 | 1.00 | 0.00 | BrD | ATOM | 500 | HG | SER | 30 | −9.322 |
| 10.857 | 3.664 | 1.00 | 0.00 | BrD | ATOM | 501 | C | SER | 30 | −8.627 |
| 8.036 | 0.945 | 1.00 | 0.00 | BrD | ATOM | 502 | O | SER | 30 | −8.726 |
| 6.855 | 1.276 | 1.00 | 0.00 | BrD | ATOM | 503 | N | ALA | 31 | −7.977 |
| 8.425 | −0.157 | 1.00 | 0.00 | BrD | ATOM | 504 | HN | ALA | 31 | −7.935 |
| 9.377 | −0.385 | 1.00 | 0.00 | BrD | ATOM | 505 | CA | ALA | 31 | −7.365 |
| 7.462 | −1.066 | 1.00 | 0.00 | BrD | ATOM | 506 | HA | ALA | 31 | −6.927 |
| 6.675 | −0.470 | 1.00 | 0.00 | BrD | ATOM | 507 | CB | ALA | 31 | −6.251 |
| 8.123 | −1.861 | 1.00 | 0.00 | BrD | ATOM | 508 | HB1 | ALA | 31 | −5.395 |
| 8.274 | −1.223 | 1.00 | 0.00 | BrD | ATOM | 509 | HB2 | ALA | 31 | −5.974 |
| 7.489 | −2.691 | 1.00 | 0.00 | BrD | ATOM | 510 | HB3 | ALA | 31 | −6.593 |
| 9.076 | −2.236 | 1.00 | 0.00 | BrD | ATOM | 511 | C | ALA | 31 | −8.397 |
| 6.851 | −2.014 | 1.00 | 0.00 | BrD | ATOM | 512 | O | ALA | 31 | −8.097 |
| 5.900 | −2.736 | 1.00 | 0.00 | BrD | ATOM | 513 | N | TRP | 32 | −9.614 |
| 7.396 | −2.010 | 1.00 | 0.00 | BrD | ATOM | 514 | HW | TRP | 32 | −9.795 |
| 8.160 | −1.427 | 1.00 | 0.00 | BrD | ATOM | 515 | CA | TRP | 32 | −10.669 |
| 6.906 | −2.893 | 1.00 | 0.00 | BrD | ATOM | 516 | HA | TRP | 32 | −10.362 |
| 7.135 | −3.902 | 1.00 | 0.00 | BrD | ATOM | 517 | CB | TRP | 32 | −12.002 |
| 7.630 | −2.628 | 1.00 | 0.00 | BrD | ATOM | 518 | HB1 | TRP | 32 | −12.770 |
| 7.192 | −3.249 | 1.00 | 0.00 | BrD | ATOM | 519 | HB2 | TRP | 32 | −11.894 |
| 8.671 | −2.881 | 1.00 | 0.00 | BrD | ATOM | 520 | CG | TRP | 32 | −12.454 |
| 7.944 | −1.209 | 1.00 | 0.00 | BrD | ATOM | 521 | CD1 | TRP | 32 | −12.415 |
| 8.532 | −0.267 | 1.00 | 0.00 | BrD | ATOM | 522 | HD1 | TRP | 32 | −12.058 |
| 9.535 | −0.450 | 1.00 | 0.00 | BrD | ATOM | 523 | CD2 | TRP | 32 | −12.993 |
| 6.393 | −0.565 | 1.00 | 0.00 | BrD | ATOM | 524 | NE1 | TRP | 32 | −12.895 |
| 8.057 | 0.929 | 1.00 | 0.00 | BrD | ATOM | 525 | HE1 | TRP | 32 | −12.970 |
| 8.974 | 1.758 | 1.00 | 0.00 | BrD | ATOM | 526 | CE2 | TRP | 32 | −10.293 |
| 6.743 | 0.770 | 1.00 | 0.00 | BrD | ATOM | 527 | CE2 | TRP | 32 | −10.270 |
| 5.095 | −0.991 | 1.00 | 0.00 | BrD | ATOM | 528 | HE3 | TRP | 32 | −10.068 |
| 4.788 | −2.006 | 1.00 | 0.00 | BrD | ATOM | 529 | CZ2 | TRP | 32 | −13.784 |
| 5.839 | 1.681 | 1.00 | 0.00 | BrD | ATOM | 530 | HZ2 | TRP | 32 | −10.786 |
| 6.109 | 2.708 | 1.00 | 0.00 | BrD | ATOM | 531 | CZ3 | TRP | 32 | −13.786 |
| 4.196 | −0.084 | 1.00 | 0.00 | BrD | ATOM | 532 | HZ3 | TRP | 32 | −14.003 |
| 3.185 | −0.396 | 1.00 | 0.00 | BrD | ATOM | 533 | CH2 | TRP | 32 | −14.055 |
| 4.577 | 1.230 | 1.00 | 0.00 | BrD | ATOM | 534 | HH2 | TRP | 32 | −14.420 |
| 3.838 | 1.903 | 1.00 | 0.00 | BrD | ATOM | 535 | C | TRP | 32 | −10.855 |
| 5.382 | −2.797 | 1.00 | 0.00 | BrD | ATOM | 536 | O | TRP | 32 | −11.199 |
| 4.752 | −3.797 | 1.00 | 0.00 | BrD | ATOM | 537 | N | PRO | 33 | −10.636 |
| 4.741 | −1.618 | 1.00 | 0.00 | BrD | ATOM | 538 | CA | PRO | 33 | −10.800 |
| 3.297 | −1.491 | 1.00 | 0.00 | BrD | ATOM | 539 | HA | PRO | 33 | −11.693 |
| 2.959 | −1.999 | 1.00 | 0.00 | BrD | ATOM | 540 | CB | PRO | 33 | −10.947 |
| 3.057 | 0.017 | 1.00 | 0.00 | BrD | ATOM | 541 | HB1 | PRO | 33 | −10.191 |
| 2.357 | 0.341 | 1.00 | 0.00 | BrD | ATOM | 542 | HB2 | PRO | 33 | −11.926 |
| 2.646 | 0.219 | 1.00 | 0.00 | BrD | ATOM | 543 | CG | PRO | 33 | −10.771 |

TABLE 6-continued

Atomic Structure Coordinates of the
P/CAF Bromodomain/Acetyl-Histamine Complex

| | | | | | | | | | | |
|---|---|---|---|---|---|---|---|---|---|---|
| 4.386 | 0.685 | 1.00 | 0.00 | BrD | ATOM | 544 | HG1 | PRO | 33 | −11.713 |
| 4.744 | 1.048 | 1.00 | 0.00 | BrD | ATOM | 545 | HG2 | PRO | 33 | −10.075 |
| 4.288 | 1.505 | 1.00 | 0.00 | BrD | ATOM | 546 | CD | PRO | 33 | −10.223 |
| 5.333 | −0.337 | 1.00 | 0.00 | BrD | ATOM | 547 | HD1 | PRO | 33 | −10.632 |
| 6.319 | −0.205 | 1.00 | 0.00 | BrD | ATOM | 548 | HD2 | PRO | 33 | −9.165 |
| 5.358 | −0.254 | 1.00 | 0.00 | BrD | ATOM | 549 | C | PRO | 33 | −9.596 |
| 2.535 | −2.040 | 1.00 | 0.00 | BrD | ATOM | 550 | O | PRO | 33 | −9.687 |
| 1.343 | −2.332 | 1.00 | 0.00 | BrD | ATOM | 551 | N | PHE | 34 | −6.472 |
| 3.233 | −2.187 | 1.00 | 0.00 | BrD | ATOM | 552 | HN | PHE | 34 | −8.458 |
| 4.180 | −1.936 | 1.00 | 0.00 | BrD | ATOM | 553 | CA | PHE | 34 | −7.256 |
| 2.619 | −2.703 | 1.00 | 0.00 | BrD | ATOM | 554 | HA | PHE | 34 | −7.295 |
| 1.564 | −2.475 | 1.00 | 0.00 | BrD | ATOM | 555 | CB | PHE | 34 | −6.026 |
| 3.228 | −2.030 | 1.00 | 0.00 | BrD | ATOM | 556 | HB1 | PHE | 34 | −5.773 |
| 4.150 | −2.531 | 1.00 | 0.00 | BrD | ATOM | 557 | HB2 | PHE | 34 | −5.198 |
| 2.940 | −2.118 | 1.00 | 0.00 | BrD | ATOM | 558 | CG | PHE | 34 | −6.228 |
| 3.531 | −0.973 | 1.00 | 0.00 | BrD | ATOM | 559 | CD1 | PHE | 34 | −6.985 |
| 2.689 | 0.226 | 1.00 | 0.00 | BrD | ATOM | 560 | HD1 | PHE | 34 | −7.430 |
| 1.805 | −0.208 | 1.00 | 0.00 | BrD | ATOM | 561 | CD2 | PHE | 34 | −5.663 |
| 4.659 | −0.003 | 1.00 | 0.00 | BrD | ATOM | 562 | HD2 | PHE | 34 | −5.074 |
| 5.324 | −0.617 | 1.00 | 0.00 | BrD | ATOM | 563 | CE1 | PHE | 34 | −7.175 |
| 2.968 | 1.566 | 1.00 | 0.00 | BrD | ATOM | 564 | HE1 | PHE | 34 | −7.767 |
| 2.303 | 2.179 | 1.00 | 0.00 | BrD | ATOM | 565 | CE2 | PHE | 34 | −5.852 |
| 4.944 | 1.335 | 1.00 | 0.00 | BrD | ATOM | 566 | HE2 | PHE | 34 | −5.409 |
| 5.829 | 1.765 | 1.00 | 0.00 | BrD | ATOM | 567 | CZ | PHE | 34 | −6.607 |
| 4.098 | 2.122 | 1.00 | 0.00 | BrD | ATOM | 568 | HZ | PHE | 34 | −6.753 |
| 4.319 | 3.168 | 1.00 | 0.00 | BrD | ATOM | 569 | C | PHE | 34 | −7.150 |
| 2.790 | −4.213 | 1.00 | 0.00 | BrD | ATOM | 570 | O | PHE | 34 | −6.653 |
| 1.909 | −4.907 | 1.00 | 0.00 | BrD | ATOM | 571 | N | MET | 35 | −7.624 |
| 3.923 | −4.721 | 1.00 | 0.00 | BrD | ATOM | 572 | HN | MET | 35 | −8.000 |
| 4.998 | −4.119 | 1.00 | 0.00 | BrD | ATOM | 573 | CA | MET | 35 | −7.545 |
| 4.205 | −6.151 | 1.00 | 0.00 | BrD | ATOM | 574 | HA | MET | 35 | −6.600 |
| 3.825 | −6.507 | 1.00 | 0.00 | BrD | ATOM | 575 | CB | MET | 35 | −7.593 |
| 5.706 | −6.393 | 1.00 | 0.00 | BrD | ATOM | 576 | HB1 | MET | 35 | −7.670 |
| 5.889 | −7.454 | 1.00 | 0.00 | BrD | ATOM | 577 | HB2 | MET | 35 | −8.463 |
| 6.114 | −5.899 | 1.00 | 0.00 | BrD | ATOM | 578 | CG | MET | 35 | −6.367 |
| 6.423 | −5.871 | 1.00 | 0.00 | BrD | ATOM | 579 | HG1 | MET | 35 | −6.673 |
| 7.114 | −5.107 | 1.00 | 0.00 | BrD | ATOM | 580 | HG2 | MET | 35 | −5.696 |
| 5.692 | −5.444 | 1.00 | 0.00 | BrD | ATOM | 581 | SD | MET | 35 | −5.490 |
| 7.322 | −7.161 | 1.00 | 0.00 | BrD | ATOM | 582 | CE | MET | 35 | −4.012 |
| 6.298 | −7.337 | 1.00 | 0.00 | BrD | ATOM | 583 | HE1 | MET | 35 | −3.284 |
| 6.831 | −7.905 | 1.00 | 0.00 | BrD | ATOM | 584 | HE2 | MET | 35 | −3.639 |
| 6.062 | −6.358 | 1.00 | 0.00 | BrD | ATOM | 585 | HE3 | MET | 35 | −4.294 |
| 5.384 | −7.850 | 1.00 | 0.00 | BrD | ATOM | 586 | C | MET | 35 | −8.661 |
| 3.519 | −6.924 | 1.00 | 0.00 | BrD | ATOM | 587 | O | MET | 35 | −9.396 |
| 4.160 | −7.675 | 1.00 | 0.00 | BrD | ATOM | 588 | N | GLU | 36 | −8.749 |
| 2.208 | −6.762 | 1.00 | 0.00 | BrD | ATOM | 589 | HN | GLU | 36 | −8.116 |
| 1.765 | −6.164 | 1.00 | 0.00 | BrD | ATOM | 590 | CA | GLU | 36 | −9.751 |
| 1.407 | −7.457 | 1.00 | 0.00 | BrD | ATOM | 591 | HA | GLU | 36 | −9.531 |
| 1.453 | −8.515 | 1.00 | 0.00 | BrD | ATOM | 592 | CB | GLU | 36 | −11.156 |
| 1.964 | −7.207 | 1.00 | 0.00 | BrD | ATOM | 593 | HB1 | GLU | 36 | −11.084 |
| 3.018 | −6.987 | 1.00 | 0.00 | BrD | ATOM | 594 | HB2 | GLU | 36 | −11.581 |
| 1.458 | −6.354 | 1.00 | 0.00 | BrD | ATOM | 595 | CG | GLU | 36 | −12.099 |
| 1.787 | −8.365 | 1.00 | 0.00 | BrD | ATOM | 596 | HG1 | GLU | 36 | −11.527 |
| 1.466 | −9.243 | 1.00 | 0.00 | BrD | ATOM | 597 | HG2 | GLU | 36 | −12.569 |
| 2.735 | −8.600 | 1.00 | 0.00 | BrD | ATOM | 598 | CD | GLU | 36 | −13.182 |
| 0.761 | −8.114 | 1.00 | 0.00 | BrD | ATOM | 599 | OE1 | GLU | 36 | −12.865 |
| 0.447 | −8.098 | 1.00 | 0.00 | BrD | ATOM | 600 | OE2 | GLU | 36 | −14.348 |
| 1.165 | −7.919 | 1.00 | 0.00 | BrD | ATOM | 601 | C | GLU | 36 | −9.692 |
| 0.050 | −7.001 | 1.00 | 0.00 | BrD | ATOM | 602 | O | GLU | 36 | −10.470 |
| 0.471 | −6.145 | 1.00 | 0.00 | BrD | ATOM | 603 | N | PRO | 37 | −8.764 |
| 0.842 | −7.565 | 1.00 | 0.00 | BrD | ATOM | 604 | CA | PRO | 37 | −8.604 |
| 2.255 | −7.202 | 1.00 | 0.00 | BrD | ATOM | 605 | HA | PRO | 37 | −8.407 |
| 2.369 | −6.146 | 1.00 | 0.00 | BrD | ATOM | 606 | CB | PRO | 37 | −7.376 |
| 2.709 | −8.004 | 1.00 | 0.00 | BrD | ATOM | 607 | HB1 | PRO | 37 | −7.696 |
| 3.306 | −8.846 | 1.00 | 0.00 | BrD | ATOM | 608 | HB2 | PRO | 37 | −6.728 |
| 3.295 | −7.370 | 1.00 | 0.00 | BrD | ATOM | 609 | CG | PRO | 37 | −6.706 |
| 1.453 | −8.451 | 1.00 | 0.00 | BrD | ATOM | 610 | HG1 | PRO | 37 | −6.222 |
| 1.614 | −9.403 | 1.00 | 0.00 | BrD | ATOM | 611 | HG2 | PRO | 37 | −5.984 |
| 1.139 | −7.711 | 1.00 | 0.00 | BrD | ATOM | 612 | CD | PRO | 37 | −7.793 |
| 0.426 | −8.587 | 1.00 | 0.00 | BrD | ATOM | 613 | HD1 | PRO | 37 | −8.229 |
| 0.465 | −9.574 | 1.00 | 0.00 | BrD | ATOM | 614 | HD2 | PRO | 37 | −7.410 |
| 0.561 | −8.378 | 1.00 | 0.00 | BrD | ATOM | 615 | C | PRO | 37 | −9.822 |
| 3.093 | −7.579 | 1.00 | 0.00 | BrD | ATOM | 616 | O | PRO | 37 | −10.678 |
| 2.655 | −8.344 | 1.00 | 0.00 | BrD | ATOM | 617 | N | VAL | 38 | −9.892 |
| 4.301 | −7.025 | 1.00 | 0.00 | BrD | ATOM | 618 | HN | VAL | 38 | −9.179 |
| 4.594 | −6.422 | 1.00 | 0.00 | BrD | ATOM | 619 | CA | VAL | 38 | −11.006 |
| 5.206 | −7.300 | 1.00 | 0.00 | BrD | ATOM | 620 | HA | VAL | 38 | −11.709 |

TABLE 6-continued

Atomic Structure Coordinates of the
P/CAF Bromodomain/Acetyl-Histamine Complex

| | | | | | | | | | | |
|---|---|---|---|---|---|---|---|---|---|---|
| 4.683 | −7.931 | 1.00 | 0.00 | BrD | ATOM | 621 | CB | VAL | 38 | −11.750 |
| 5.646 | −6.012 | 1.00 | 0.00 | BrD | ATOM | 622 | HB | VAL | 38 | −11.449 |
| 6.657 | −5.781 | 1.00 | 0.00 | BrD | ATOM | 623 | CG1 | VAL | 38 | −11.395 |
| 4.767 | −4.819 | 1.00 | 0.00 | BrD | ATOM | 624 | HG11 | VAL | 38 | −11.868 |
| 5.145 | −3.935 | 1.00 | 0.00 | BrD | ATOM | 625 | HG12 | VAL | 38 | −10.326 |
| 4.779 | −4.667 | 1.00 | 0.00 | BrD | ATOM | 626 | HG13 | VAL | 38 | −11.721 |
| 3.755 | −5.008 | 1.00 | 0.00 | BrD | ATOM | 627 | CG2 | VAL | 38 | −13.253 |
| 5.646 | −6.246 | 1.00 | 0.00 | BrD | ATOM | 628 | HG21 | VAL | 38 | −13.760 |
| 5.374 | −5.333 | 1.00 | 0.00 | BrD | ATOM | 629 | HG22 | VAL | 38 | −13.497 |
| 4.934 | −7.020 | 1.00 | 0.00 | BrD | ATOM | 630 | HG23 | VAL | 38 | −12.570 |
| 6.629 | −6.553 | 1.00 | 0.00 | BrD | ATOM | 631 | C | VAL | 38 | −10.518 |
| 6.451 | −8.035 | 1.00 | 0.00 | BrD | ATOM | 632 | O | VAL | 38 | −9.410 |
| 6.473 | −8.571 | 1.00 | 0.00 | BrD | ATOM | 633 | V | LYS | 39 | −11.349 |
| 7.488 | −8.051 | 1.00 | 0.00 | BrD | ATOM | 634 | HN | LYS | 39 | −12.215 |
| 7.412 | −7.609 | 1.00 | 0.00 | BrD | ATOM | 635 | CA | LYS | 39 | −11.005 |
| 8.737 | −8.715 | 1.00 | 0.00 | BrD | ATOM | 636 | HA | LYS | 39 | −9.947 |
| 8.906 | −8.574 | 1.00 | 0.00 | BrD | ATOM | 637 | CB | LYS | 39 | −11.299 |
| 8.646 | −10.216 | 1.00 | 0.00 | BrD | ATOM | 638 | HB1 | LYS | 39 | −10.419 |
| 8.285 | −10.714 | 1.00 | 0.00 | BrD | ATOM | 639 | HB2 | LYS | 39 | −11.931 |
| 9.633 | −10.587 | 1.00 | 0.00 | BrD | ATOM | 640 | CG | LYS | 39 | −12.452 |
| 7.722 | −10.569 | 1.00 | 0.00 | BrD | ATOM | 641 | HG1 | LYS | 39 | −12.970 |
| 7.450 | −9.664 | 1.00 | 0.00 | BrD | ATOM | 642 | HG2 | LYS | 39 | −13.127 |
| 8.241 | −11.232 | 1.00 | 0.00 | BrD | ATOM | 643 | CD | LYS | 39 | −11.962 |
| 6.458 | −11.256 | 1.00 | 0.00 | BrD | ATOM | 644 | HD1 | LYS | 39 | −12.413 |
| 5.601 | −10.777 | 1.00 | 0.00 | BrD | ATOM | 645 | HD2 | LYS | 39 | −10.888 |
| 6.402 | −11.160 | 1.00 | 0.00 | BrD | ATOM | 646 | CE | LYS | 39 | −12.326 |
| 6.447 | −12.732 | 1.00 | 0.00 | BrD | ATOM | 647 | HE1 | LYS | 39 | −11.779 |
| 5.653 | −13.219 | 1.00 | 0.00 | BrD | ATOM | 648 | HE2 | LYS | 39 | −12.044 |
| 7.395 | −13.166 | 1.00 | 0.00 | BrD | ATOM | 649 | NZ | LYS | 39 | −13.784 |
| 6.232 | −12.945 | 1.00 | 0.00 | BrD | ATOM | 650 | HZ1 | LYS | 39 | −13.963 |
| 5.950 | −13.930 | 1.00 | 0.00 | BrD | ATOM | 651 | HZ2 | LYS | 39 | −14.307 |
| 7.108 | −12.745 | 1.00 | 0.00 | BrD | ATOM | 652 | HZ3 | LYS | 39 | −14.130 |
| 5.482 | −12.313 | 1.00 | 0.00 | BrD | ATOM | 653 | C | LYS | 39 | −11.772 |
| 9.903 | −8.105 | 1.00 | 0.00 | BrD | ATOM | 654 | O | LYS | 39 | −12.487 |
| 9.739 | −7.116 | 1.00 | 0.00 | BrD | ATOM | 655 | B | ARG | 40 | −11.626 |
| 11.078 | −8.706 | 1.00 | 0.00 | BrD | ATOM | 656 | HN | ARG | 40 | −11.040 |
| 11.146 | −9.488 | 1.00 | 0.00 | BrD | ATOM | 657 | CA | ARG | 40 | −12.304 |
| 12.273 | −8.223 | 1.00 | 0.00 | BrD | ATOM | 658 | HA | ARG | 40 | −12.018 |
| 12.419 | −7.191 | 1.00 | 0.00 | BrD | ATOM | 659 | CB | ARG | 40 | −11.866 |
| 13.492 | −9.037 | 1.00 | 0.00 | BrD | ATOM | 660 | HB1 | ARG | 40 | −12.313 |
| 13.435 | −10.019 | 1.00 | 0.00 | BrD | ATOM | 661 | HB2 | ARG | 40 | −10.792 |
| 13.476 | −9.139 | 1.00 | 0.00 | BrD | ATOM | 662 | CG | ARG | 40 | −12.265 |
| 14.819 | −8.410 | 1.00 | 0.00 | BrD | ATOM | 663 | HG1 | ARG | 40 | −12.664 |
| 14.634 | −7.424 | 1.00 | 0.00 | BrD | ATOM | 664 | HG2 | ARG | 40 | −13.020 |
| 15.285 | −9.025 | 1.00 | 0.00 | BrD | ATOM | 665 | CD | ARG | 40 | −11.075 |
| 15.759 | −8.292 | 1.00 | 0.00 | BrD | ATOM | 666 | HD1 | ARG | 40 | −10.715 |
| 15.988 | −9.284 | 1.00 | 0.00 | BrD | ATOM | 667 | HD2 | ARG | 40 | −10.296 |
| 15.263 | −7.732 | 1.00 | 0.00 | BrD | ATOM | 668 | NE | ARG | 40 | −11.426 |
| 17.004 | −7.616 | 1.00 | 0.00 | BrD | ATOM | 669 | HE | ARG | 40 | −11.554 |
| 17.802 | −8.171 | 1.00 | 0.00 | BrD | ATOM | 670 | CZ | ARG | 40 | −11.577 |
| 17.109 | −6.300 | 1.00 | 0.00 | BrD | ATOM | 671 | NH1 | ARG | 40 | −11.409 |
| 16.047 | −5.525 | 1.00 | 0.00 | BrD | ATOM | 672 | HH11 | ARG | 40 | −11.168 |
| 15.165 | −5.930 | 1.00 | 0.00 | BrD | ATOM | 673 | HH12 | ARG | 40 | −11.523 |
| 16.127 | −4.535 | 1.00 | 0.00 | BrD | ATOM | 674 | NH2 | ARG | 40 | −11.897 |
| 18.276 | −5.758 | 1.00 | 0.00 | BrD | ATOM | 675 | HH21 | ARG | 40 | −12.011 |
| 18.353 | −4.767 | 1.00 | 0.00 | BrD | ATOM | 676 | HH22 | ARG | 40 | −12.025 |
| 19.079 | −6.339 | 1.00 | 0.00 | BrD | ATOM | 677 | C | ARG | 40 | −13.824 |
| 12.123 | −8.293 | 1.00 | 0.00 | BrD | ATOM | 678 | O | ARG | 40 | −14.556 |
| 12.915 | −7.700 | 1.00 | 0.00 | BrD | ATOM | 679 | N | THR | 41 | −14.301 |
| 11.109 | −9.017 | 1.00 | 0.00 | BrD | ATOM | 680 | HN | THR | 41 | −13.680 |
| 10.511 | −9.481 | 1.00 | 0.00 | BrD | ATOM | 681 | CA | THR | 41 | −15.727 |
| 10.898 | −9.159 | 1.00 | 0.00 | BrD | ATOM | 682 | HA | THR | 41 | −16.228 |
| 11.725 | −8.681 | 1.00 | 0.00 | BrD | ATOM | 683 | CB | THR | 41 | −16.133 |
| 10.870 | −10.637 | 1.00 | 0.00 | BrD | ATOM | 684 | HB | THR | 41 | −15.862 |
| 11.812 | −11.090 | 1.00 | 0.00 | BrD | ATOM | 685 | OG1 | THR | 41 | −17.533 |
| 10.696 | −10.775 | 1.00 | 0.00 | BrD | ATOM | 686 | HG1 | THR | 41 | −17.988 |
| 11.239 | −10.127 | 1.00 | 0.00 | BrD | ATOM | 687 | CG2 | THR | 41 | −15.453 |
| 9.771 | −11.421 | 1.00 | 0.00 | BrD | ATOM | 688 | HG21 | THR | 41 | −14.433 |
| 9.669 | −11.083 | 1.00 | 0.00 | BrD | ATOM | 689 | HG22 | THR | 41 | −15.462 |
| 10.020 | −12.472 | 1.00 | 0.00 | BrD | ATOM | 690 | HG23 | THR | 41 | −15.979 |
| 8.841 | −11.267 | 1.00 | 0.00 | BrD | ATOM | 691 | C | THR | 41 | −16.197 |
| 9.623 | −8.467 | 1.00 | 0.00 | BrD | ATOM | 692 | O | THR | 41 | −17.123 |
| 9.656 | −7.658 | 1.00 | 0.00 | BrD | ATOM | 693 | N | GLU | 42 | −15.973 |
| 8.498 | −8.792 | 1.00 | 0.00 | BrD | ATOM | 694 | HN | GLU | 42 | −14.835 |
| 8.921 | −9.435 | 1.00 | 0.00 | BrD | ATOM | 695 | CA | GLU | 42 | −19.940 |
| 7.236 | −8.163 | 1.00 | 0.00 | BrD | ATOM | 696 | HA | GLU | 42 | −16.954 |
| 7.002 | −8.454 | 1.00 | 0.00 | BrD | ATOM | 697 | CB | GLU | 42 | −15.013 |

TABLE 6-continued

Atomic Structure Coordinates of the
P/CAF Bromodomain/Acetyl-Histamine Complex

| | | | | | | | | | | |
|---|---|---|---|---|---|---|---|---|---|---|
| 6.109 | −8.623 | 1.00 | 0.00 | BrD | ATOM | 698 | HB1 | GLU | 42 | −15.239 |
| 5.220 | −8.053 | 1.00 | 0.00 | BrD | ATOM | 699 | HB2 | GLU | 42 | −13.993 |
| 6.398 | −8.431 | 1.00 | 0.00 | BrD | ATOM | 700 | CG | GLU | 42 | −15.142 |
| 5.774 | −10.098 | 1.00 | 0.00 | BrD | ATOM | 701 | HG1 | GLU | 42 | −14.284 |
| 5.191 | −10.396 | 1.00 | 0.00 | BrD | ATOM | 702 | HG2 | GLU | 42 | −15.166 |
| 6.694 | −10.663 | 1.00 | 0.00 | BrD | ATOM | 703 | CD | GLU | 42 | −16.397 |
| 4.982 | −10.409 | 1.00 | 0.00 | BrD | ATOM | 704 | OE1 | GLU | 42 | −17.489 |
| 5.589 | −10.443 | 1.00 | 0.00 | BrD | ATOM | 705 | OE2 | GLU | 42 | −16.289 |
| 3.756 | −10.620 | 1.00 | 0.00 | BrD | ATOM | 706 | C | GLU | 42 | −15.881 |
| 7.374 | −6.647 | 1.00 | 0.00 | BrD | ATOM | 707 | O | GLU | 42 | −16.614 |
| 6.703 | −5.920 | 1.00 | 0.00 | BrD | ATOM | 708 | N | ALA | 43 | −15.024 |
| 8.279 | −6.181 | 1.00 | 0.00 | BrD | ATOM | 709 | HN | ALA | 43 | −14.457 |
| 8.774 | −6.817 | 1.00 | 0.00 | BrD | ATOM | 710 | CA | ALA | 43 | −14.861 |
| 8.509 | −4.752 | 1.00 | 0.00 | BrD | ATOM | 711 | HA | ALA | 43 | −15.712 |
| 8.080 | −4.245 | 1.00 | 0.00 | BrD | ATOM | 712 | CB | ALA | 43 | −13.609 |
| 7.810 | −4.245 | 1.00 | 0.00 | BrD | ATOM | 713 | HB1 | ALA | 43 | −12.893 |
| 7.721 | −5.049 | 1.00 | 0.00 | BrD | ATOM | 714 | HB2 | ALA | 43 | −13.866 |
| 6.822 | −3.893 | 1.00 | 0.00 | BrD | ATOM | 715 | HB3 | ALA | 43 | −13.180 |
| 8.381 | −3.435 | 1.00 | 0.00 | BrD | ATOM | 716 | C | ALA | 43 | −14.799 |
| 10.002 | −4.440 | 1.00 | 0.00 | BrD | ATOM | 717 | O | ALA | 47 | −13.721 |
| 10.555 | −4.222 | 1.00 | 0.00 | BrD | ATOM | 718 | N | PRO | 44 | −15.962 |
| 10.676 | −4.414 | 1.00 | 0.00 | BrD | ATOM | 719 | CA | PRO | 44 | −16.038 |
| 12.114 | −4.129 | 1.00 | 0.00 | BrD | ATOM | 720 | HA | PRO | 44 | −15.511 |
| 12.692 | −4.874 | 1.00 | 0.00 | BrD | ATOM | 721 | CB | PRO | 44 | −17.539 |
| 12.422 | −4.207 | 1.00 | 0.00 | BrD | ATOM | 722 | HB1 | PRO | 44 | −17.688 |
| 13.369 | −4.704 | 1.00 | 0.00 | BrD | ATOM | 723 | HB2 | PRO | 44 | −17.991 |
| 12.465 | −3.210 | 1.00 | 0.00 | BrD | ATOM | 724 | CG | PRO | 44 | −18.125 |
| 11.298 | −4.991 | 1.00 | 0.00 | BrD | ATOM | 725 | HG1 | PRO | 44 | −18.071 |
| 11.518 | −6.047 | 1.00 | 0.00 | BrD | ATOM | 726 | HG2 | PRO | 44 | −19.150 |
| 11.137 | −4.692 | 1.00 | 0.00 | BrD | ATOM | 727 | CD | PRO | 44 | −17.291 |
| 10.095 | −4.665 | 1.00 | 0.00 | BrD | ATOM | 728 | HD1 | PRO | 44 | −17.264 |
| 9.413 | −5.500 | 1.00 | 0.00 | BrD | ATOM | 729 | HD2 | PRO | 44 | −17.668 |
| 9.601 | −3.783 | 1.00 | 0.00 | BrD | ATOM | 730 | C | PRO | 44 | −15.498 |
| 12.458 | −2.746 | 1.00 | 0.00 | BrD | ATOM | 731 | O | PRO | 44 | −16.262 |
| 12.635 | −1.797 | 1.00 | 0.00 | BrD | ATOM | 732 | N | GLY | 45 | −14.177 |
| 12.551 | −2.637 | 1.00 | 0.00 | BrD | ATOM | 733 | HN | GLY | 45 | −13.617 |
| 12.400 | −3.427 | 1.00 | 0.00 | BrD | ATOM | 734 | CA | GLY | 45 | −13.560 |
| 12.875 | −1.365 | 1.00 | 0.00 | BrD | ATOM | 735 | HA1 | GLY | 45 | −13.586 |
| 13.946 | −1.228 | 1.00 | 0.00 | BrD | ATOM | 736 | HA2 | GLY | 45 | −14.128 |
| 12.409 | −0.573 | 1.00 | 0.00 | BrD | ATOM | 737 | C | GLY | 45 | −12.121 |
| 12.405 | −1.278 | 1.00 | 0.00 | BrD | ATOM | 738 | O | GLY | 45 | −11.333 |
| 12.942 | −0.499 | 1.00 | 0.00 | BrD | ATOM | 739 | N | TYR | 46 | −11.777 |
| 11.403 | −2.081 | 1.00 | 0.00 | BrD | ATOM | 740 | HN | TYR | 46 | −12.450 |
| 11.015 | −2.678 | 1.00 | 0.00 | BrD | ATOM | 741 | CA | TYR | 46 | −10.423 |
| 10.861 | −2.089 | 1.00 | 0.00 | BrD | ATOM | 742 | HA | TYR | 46 | −10.271 |
| 10.337 | −1.158 | 1.00 | 0.00 | BrD | ATOM | 743 | CB | TYR | 46 | −10.255 |
| 9.878 | −3.249 | 1.00 | 0.00 | BrD | ATOM | 744 | HB1 | TYR | 46 | −11.073 |
| 10.006 | −3.942 | 1.00 | 0.00 | BrD | ATOM | 745 | HB2 | TYR | 46 | −9.324 |
| 10.084 | −3.755 | 1.00 | 0.00 | BrD | ATOM | 746 | CG | TYR | 46 | −10.237 |
| 8.431 | −2.814 | 1.00 | 0.00 | BrD | ATOM | 747 | CD1 | TYR | 46 | −9.262 |
| 7.558 | −3.279 | 1.00 | 0.00 | BrD | ATOM | 748 | HD1 | TYR | 46 | −8.511 |
| 7.926 | −3.962 | 1.00 | 0.00 | BrD | ATOM | 749 | CD1 | TYR | 46 | −11.194 |
| 7.938 | −1.935 | 1.00 | 0.00 | BrD | ATOM | 750 | HD2 | TYR | 46 | −11.958 |
| 8.605 | −1.564 | 1.00 | 0.00 | BrD | ATOM | 751 | CE1 | TYR | 46 | −9.242 |
| 6.235 | −2.884 | 1.00 | 0.00 | BrD | ATOM | 752 | HE1 | TYR | 46 | −8.474 |
| 9.972 | −3.254 | 1.00 | 0.00 | BrD | ATOM | 753 | CE2 | TYR | 46 | −11.180 |
| 6.617 | −1.534 | 1.00 | 0.00 | BrD | ATOM | 754 | HE2 | TYR | 46 | −11.933 |
| 6.253 | −0.850 | 1.00 | 0.00 | BrD | ATOM | 755 | CZ | TYR | 46 | −10.203 |
| 9.769 | −2.010 | 1.00 | 0.00 | BrD | ATOM | 756 | OH | TYR | 46 | −10.186 |
| 4.452 | −1.612 | 1.00 | 0.00 | BrD | ATOM | 757 | HH | TYR | 46 | −9.895 |
| 4.397 | −0.699 | 1.00 | 0.00 | BrD | ATOM | 758 | C | TYR | 46 | −9.386 |
| 11.975 | −2.200 | 1.00 | 0.00 | BrD | ATOM | 759 | O | TYR | 46 | −9.727 |
| 13.132 | −2.446 | 1.00 | 0.00 | BrD | ATOM | 760 | N | TYR | 47 | −8.120 |
| 11.618 | −2.014 | 1.00 | 0.00 | BrD | ATOM | 761 | HN | TYR | 47 | −7.911 |
| 10.680 | −1.823 | 1.00 | 0.00 | BrD | ATOM | 762 | CA | TYR | 47 | −7.033 |
| 12.587 | −2.097 | 1.00 | 0.00 | BrD | ATOM | 763 | HA | TYR | 47 | −6.102 |
| 12.042 | −2.050 | 1.00 | 0.00 | BrD | ATOM | 764 | CB | TYR | 47 | −7.099 |
| 13.345 | −3.424 | 1.00 | 0.00 | BrD | ATOM | 765 | HB1 | TYR | 47 | −7.889 |
| 14.080 | −3.370 | 1.00 | 0.00 | BrD | ATOM | 766 | HB2 | TYR | 47 | −6.158 |
| 13.848 | −3.590 | 1.00 | 0.00 | BrD | ATOM | 767 | CG | TYR | 47 | −7.370 |
| 12.459 | −4.619 | 1.00 | 0.00 | BrD | ATOM | 768 | CD1 | TYR | 47 | −8.056 |
| 12.946 | −5.725 | 1.00 | 0.00 | BrD | ATOM | 769 | HD1 | TYR | 47 | −8.397 |
| 13.971 | −5.722 | 1.00 | 0.00 | BrD | ATOM | 770 | CD2 | TYR | 47 | −6.940 |
| 11.137 | −4.644 | 1.00 | 0.00 | BrD | ATOM | 771 | HD2 | TYR | 47 | −6.405 |
| 10.742 | −3.792 | 1.00 | 0.00 | BrD | ATOM | 772 | CE1 | TYR | 47 | −8.306 |
| 12.143 | −6.821 | 1.00 | 0.00 | BrD | ATOM | 773 | HE1 | TYR | 47 | −8.841 |
| 12.540 | −7.671 | 1.00 | 0.00 | BrD | ATOM | 774 | CE2 | TYR | 47 | −7.186 |

TABLE 6-continued

Atomic Structure Coordinates of the
P/CAF Bromodomain/Acetyl-Histamine Complex

| | | | | | | | | | | |
|---|---|---|---|---|---|---|---|---|---|---|
| 10.328 | −9.738 | 1.00 | 0.00 | BrD | ATOM | 775 | HE2 | TYR | 47 | −6.845 |
| 9.303 | −5.739 | 1.00 | 0.00 | BrD | ATOM | 776 | CZ | TYR | 47 | −7.870 |
| 10.835 | −6.823 | 1.00 | 0.00 | BrD | ATOM | 777 | OH | TYR | 47 | −8.117 |
| 10.032 | −7.912 | 1.00 | 0.00 | BrD | ATOM | 778 | HH | TYR | 47 | −7.972 |
| 10.317 | −8.650 | 1.00 | 0.00 | BrD | ATOM | 778 | C | TYR | 47 | −7.085 |
| 13.572 | −0.933 | 1.00 | 0.00 | BrD | ATOM | 780 | O | TYR | 47 | −6.183 |
| 13.605 | −0.095 | 1.00 | 0.00 | BrD | ATOM | 781 | N | GLU | 48 | −8.144 |
| 14.376 | −0.887 | 1.00 | 0.00 | BrD | ATOM | 782 | HN | GLU | 48 | −8.830 |
| 14.304 | −1.584 | 1.00 | 0.00 | BrD | ATOM | 783 | CA | GLU | 48 | −8.309 |
| 15.365 | 0.174 | 1.00 | 0.00 | BrD | ATOM | 784 | HA | GLU | 48 | −7.569 |
| 16.138 | 0.024 | 1.00 | 0.00 | BrD | ATOM | 785 | CB | GLU | 48 | −9.704 |
| 15.991 | 0.104 | 1.00 | 0.00 | BrD | ATOM | 786 | HB1 | GLU | 48 | −9.746 |
| 16.827 | 0.786 | 1.00 | 0.00 | BrD | ATOM | 787 | HB2 | GLU | 48 | −10.432 |
| 15.254 | 0.408 | 1.00 | 0.00 | BrD | ATOM | 788 | CG | GLU | 48 | −10.079 |
| 16.488 | −1.283 | 1.00 | 0.00 | BrD | ATOM | 789 | HG1 | GLU | 48 | −9.268 |
| 17.086 | −1.669 | 1.00 | 0.00 | BrD | ATOM | 790 | HG2 | GLU | 48 | −10.235 |
| 15.635 | −1.927 | 1.00 | 0.00 | BrD | ATOM | 791 | CD | GLU | 48 | −11.341 |
| 17.328 | −1.282 | 1.00 | 0.00 | BrD | ATOM | 792 | OE1 | GLU | 48 | −12.059 |
| 17.320 | −0.260 | 1.00 | 0.00 | BrD | ATOM | 793 | OE2 | GLU | 48 | −11.612 |
| 17.994 | −2.304 | 1.00 | 0.00 | BrD | ATOM | 794 | C | GLU | 48 | −8.091 |
| 14.736 | 1.547 | 1.00 | 0.00 | BrD | ATOM | 795 | O | GLU | 48 | −7.683 |
| 15.410 | 2.493 | 1.00 | 0.00 | BrD | ATOM | 796 | N | VAL | 49 | −8.360 |
| 13.439 | 1.645 | 1.00 | 0.00 | BrD | ATOM | 797 | HN | VAL | 49 | −8.682 |
| 12.958 | 0.854 | 1.00 | 0.00 | BrD | ATOM | 798 | CA | VAL | 49 | −8.192 |
| 12.712 | 2.899 | 1.00 | 0.00 | BrD | ATOM | 799 | HA | VAL | 49 | −7.919 |
| 13.423 | 3.645 | 1.00 | 0.00 | BrD | ATOM | 800 | CB | VAL | 49 | −9.495 |
| 12.010 | 3.332 | 1.00 | 0.00 | BrD | ATOM | 801 | HB | VAL | 49 | −9.555 |
| 11.064 | 2.815 | 1.00 | 0.00 | BrD | ATOM | 802 | CG1 | VAL | 49 | −10.713 |
| 12.834 | 2.949 | 1.00 | 0.00 | BrD | ATOM | 803 | HG11 | VAL | 49 | −11.006 |
| 12.591 | 1.937 | 1.00 | 0.00 | BrD | ATOM | 804 | HG12 | VAL | 49 | −10.472 |
| 13.884 | 3.011 | 1.00 | 0.00 | BrD | ATOM | 805 | HG13 | VAL | 49 | −11.526 |
| 12.609 | 3.622 | 1.00 | 0.00 | BrD | ATOM | 806 | CG2 | VAL | 49 | −9.475 |
| 11.729 | 4.827 | 1.00 | 0.00 | BrD | ATOM | 807 | HG21 | VAL | 49 | −9.393 |
| 12.661 | 5.367 | 1.00 | 0.00 | BrD | ATOM | 808 | HG22 | VAL | 49 | −8.628 |
| 11.101 | 5.062 | 1.00 | 0.00 | BrD | ATOM | 809 | HG23 | VAL | 49 | −10.387 |
| 11.226 | 5.111 | 1.00 | 0.00 | BrD | ATOM | 810 | C | VAL | 49 | −7.100 |
| 11.656 | 2.787 | 1.00 | 0.00 | BrD | ATOM | 811 | O | VAL | 49 | −6.592 |
| 11.167 | 3.797 | 1.00 | 0.00 | BrD | ATOM | 812 | N | ILE | 50 | −6.763 |
| 11.281 | 1.558 | 1.00 | 0.00 | BrD | ATOM | 813 | HN | ILE | 50 | −7.214 |
| 11.686 | 0.792 | 1.00 | 0.00 | BrD | ATOM | 814 | CA | ILE | 50 | −9.769 |
| 10.245 | 1.324 | 1.00 | 0.00 | BrD | ATOM | 815 | HA | ILE | 50 | −5.942 |
| 9.783 | 2.274 | 1.00 | 0.00 | BrD | ATOM | 816 | CB | ILE | 50 | −6.291 |
| 9.152 | 0.366 | 1.00 | 0.00 | BrD | ATOM | 817 | HB | ILE | 50 | −6.001 |
| 9.428 | −0.635 | 1.00 | 0.00 | BrD | ATOM | 818 | CG1 | ILE | 50 | −7.818 |
| 9.035 | 0.436 | 1.00 | 0.00 | BrD | ATOM | 819 | HG11 | ILE | 50 | −8.256 |
| 10.011 | 0.288 | 1.00 | 0.00 | BrD | ATOM | 820 | HG12 | ILE | 50 | −8.158 |
| 8.371 | −0.344 | 1.00 | 0.00 | BrD | ATOM | 821 | CG2 | ILE | 50 | −5.644 |
| 7.815 | 0.684 | 1.00 | 0.00 | BrD | ATOM | 822 | HG21 | ILE | 50 | −5.490 |
| 7.264 | −0.233 | 1.00 | 0.00 | BrD | ATOM | 823 | HG22 | ILE | 50 | −6.289 |
| 7.250 | 1.339 | 1.00 | 0.00 | BrD | ATOM | 824 | HG23 | ILE | 50 | −4.694 |
| 7.981 | 1.169 | 1.00 | 0.00 | BrD | ATOM | 825 | CD1 | ILE | 50 | −8.324 |
| 8.499 | 1.757 | 1.00 | 0.00 | BrD | ATOM | 826 | HD11 | ILE | 50 | −8.330 |
| 9.293 | 2.489 | 1.00 | 0.00 | BrD | ATOM | 827 | HD12 | ILE | 50 | −7.674 |
| 7.704 | 2.094 | 1.00 | 0.00 | BrD | ATOM | 828 | HD13 | ILE | 50 | −9.326 |
| 8.116 | 1.631 | 1.00 | 0.00 | BrD | ATOM | 829 | C | ILE | 50 | −4.490 |
| 10.827 | 0.738 | 1.00 | 0.00 | BrD | ATOM | 830 | O | ILE | 50 | −4.504 |
| 11.444 | −0.327 | 1.00 | 0.00 | BrD | ATOM | 831 | N | ARG | 51 | −3.384 |
| 10.597 | 1.428 | 1.00 | 0.00 | BrD | ATOM | 832 | HN | ARG | 51 | −3.443 |
| 10.086 | 2.260 | 1.00 | 0.00 | BrD | ATOM | 833 | CA | ARG | 51 | −2.082 |
| 11.061 | 0.969 | 1.00 | 0.00 | BrD | ATOM | 834 | HA | ARG | 51 | −2.068 |
| 12.139 | 1.024 | 1.00 | 0.00 | BrD | ATOM | 835 | CB | ARG | 51 | −0.988 |
| 10.491 | 1.870 | 1.00 | 0.00 | BrD | ATOM | 836 | HB1 | ARG | 51 | −1.452 |
| 10.081 | 2.754 | 1.00 | 0.00 | BrD | ATOM | 837 | HB2 | ARG | 51 | −0.478 |
| 9.698 | 1.341 | 1.00 | 0.00 | BrD | ATOM | 838 | CG | ARG | 51 | 0.048 |
| 11.516 | 2.301 | 1.00 | 0.00 | BrD | ATOM | 839 | HG1 | ARG | 51 | −0.399 |
| 12.185 | 3.022 | 1.00 | 0.00 | BrD | ATOM | 840 | HG2 | ARG | 51 | 0.883 |
| 11.000 | 2.753 | 1.00 | 0.00 | BrD | ATOM | 841 | CD | ARG | 51 | 0.552 |
| 12.329 | 1.120 | 1.00 | 0.00 | BrD | ATOM | 842 | HD1 | ARG | 51 | 0.514 |
| 11.713 | 0.233 | 1.00 | 0.00 | BrD | ATOM | 843 | HD2 | ARG | 51 | −0.090 |
| 13.187 | 0.989 | 1.00 | 0.00 | BrD | ATOM | 844 | NE | ARG | 51 | 1.923 |
| 12.789 | 1.318 | 1.00 | 0.00 | BrD | ATOM | 845 | HE | ARG | 51 | 2.296 |
| 12.730 | 2.222 | 1.00 | 0.00 | BrD | ATOM | 846 | CZ | ARG | 51 | 2.683 |
| 13.279 | 0.344 | 1.00 | 0.00 | BrD | ATOM | 847 | NH1 | ARG | 51 | 3.921 |
| 13.678 | 0.602 | 1.00 | 0.00 | BrD | ATOM | 848 | HH11 | ARG | 51 | 4.491 |
| 14.046 | −0.132 | 1.00 | 0.00 | BrD | ATOM | 849 | HH12 | ARG | 51 | 4.284 |
| 13.610 | 1.532 | 1.00 | 0.00 | BrD | ATOM | 850 | NH2 | ARG | 51 | 2.206 |
| 13.371 | −0.890 | 1.00 | 0.00 | BrD | ATOM | 851 | HH21 | ARG | 51 | 2.779 |

TABLE 6-continued

Atomic Structure Coordinates of the
P/CAF Bromodomain/Acetyl-Histamine Complex

| | | | | | | | | | | |
|---|---|---|---|---|---|---|---|---|---|---|
| 13.739 | −1.622 | 1.00 | 0.00 | BrD | ATOM | 852 | HH22 | ARG | 51 | 1.273 |
| 13.071 | −1.089 | 1.00 | 0.00 | BrD | ATOM | 853 | C | ARG | 51 | −1.836 |
| 10.631 | −0.471 | 1.00 | 0.00 | BrD | ATOM | 854 | O | ARG | 51 | −1.644 |
| 11.461 | −1.360 | 1.00 | 0.00 | BrD | ATOM | 855 | N | SER | 52 | −1.843 |
| 9.322 | −0.687 | 1.00 | 0.00 | BrD | ATOM | 856 | HN | SER | 52 | −2.010 |
| 8.718 | 0.067 | 1.00 | 0.00 | BrD | ATOM | 857 | CA | SER | 52 | −1.634 |
| 8.753 | −2.012 | 1.00 | 0.00 | BrD | ATOM | 858 | HA | SER | 52 | −1.991 |
| 9.462 | −2.740 | 1.00 | 0.00 | BrD | ATOM | 859 | CB | SER | 52 | −0.145 |
| 8.497 | −2.253 | 1.00 | 0.00 | BrD | ATOM | 860 | HB1 | SER | 52 | 0.426 |
| 8.900 | −1.430 | 1.00 | 0.00 | BrD | ATOM | 861 | HB2 | SER | 52 | 0.028 |
| 7.433 | −2.325 | 1.00 | 0.00 | BrD | ATOM | 862 | OG | SER | 52 | 0.290 |
| 9.112 | −3.453 | 1.00 | 0.00 | BrD | ATOM | 863 | HG | SER | 52 | −0.218 |
| 8.768 | −4.192 | 1.00 | 0.00 | BrD | ATOM | 864 | C | SER | 52 | −2.415 |
| 7.450 | −2.148 | 1.00 | 0.00 | BrD | ATOM | 865 | O | SER | 52 | −1.912 |
| 6.382 | −1.801 | 1.00 | 0.00 | BrD | ATOM | 866 | N | PRO | 53 | −3.675 |
| 7.518 | −2.619 | 1.00 | 0.00 | BrD | ATOM | 867 | CA | PRO | 53 | −4.531 |
| 6.344 | −2.745 | 1.00 | 0.00 | BrD | ATOM | 868 | HA | PRO | 53 | −4.993 |
| 6.101 | −1.800 | 1.00 | 0.00 | BrD | ATOM | 869 | CB | PRO | 53 | −5.620 |
| 6.776 | −3.738 | 1.00 | 0.00 | BrD | ATOM | 870 | HB1 | PRO | 53 | −5.555 |
| 6.173 | −4.630 | 1.00 | 0.00 | BrD | ATOM | 871 | HB2 | PRO | 53 | −6.590 |
| 6.638 | −3.284 | 1.00 | 0.00 | BrD | ATOM | 872 | CG | PRO | 53 | −5.371 |
| 8.224 | −4.043 | 1.00 | 0.00 | BrD | ATOM | 873 | HG1 | PRO | 53 | −6.296 |
| 8.775 | −3.959 | 1.00 | 0.00 | BrD | ATOM | 874 | HG2 | PRO | 53 | −4.969 |
| 8.321 | −9.041 | 1.00 | 0.00 | BrD | ATOM | 875 | CO | PRO | 53 | −4.377 |
| 8.735 | −3.034 | 1.00 | 0.00 | BrD | ATOM | 876 | HD1 | PRO | 53 | −4.886 |
| 9.191 | −2.200 | 1.00 | 0.00 | BrD | ATOM | 877 | HD2 | PRO | 53 | −3.704 |
| 9.437 | −3.498 | 1.00 | 0.00 | BrD | ATOM | 878 | C | PRO | 53 | −3.770 |
| 5.120 | −3.252 | 1.00 | 0.00 | BrD | ATOM | 879 | O | PRO | 53 | −3.456 |
| 4.218 | −2.475 | 1.00 | 0.00 | BrD | ATOM | 880 | N | MET | 54 | −3.471 |
| 5.089 | −4.553 | 1.00 | 0.00 | BrD | ATOM | 881 | HN | MET | 54 | −3.738 |
| 5.838 | −5.124 | 1.00 | 0.00 | BrD | ATOM | 882 | CA | MET | 54 | −2.734 |
| 3.970 | −5.149 | 1.00 | 0.00 | BrD | ATOM | 883 | HA | MET | 54 | −2.905 |
| 3.995 | −6.215 | 1.00 | 0.00 | BrD | ATOM | 884 | CB | MET | 54 | −1.236 |
| 4.127 | −4.877 | 1.00 | 0.00 | BrD | ATOM | 885 | HB1 | MET | 54 | −0.936 |
| 5.129 | −5.145 | 1.00 | 0.00 | BrD | ATOM | 886 | HB2 | MET | 54 | −1.057 |
| 3.978 | −3.822 | 1.00 | 0.00 | BrD | ATOM | 887 | CG | MET | 54 | −0.368 |
| 3.147 | −5.649 | 1.00 | 0.00 | BrD | ATOM | 888 | HG1 | MET | 54 | −0.510 |
| 2.160 | −5.235 | 1.00 | 0.00 | BrD | ATOM | 889 | HG2 | MET | 54 | 0.666 |
| 3.438 | −5.537 | 1.00 | 0.00 | BrD | ATOM | 890 | SD | MET | 54 | −0.767 |
| 3.101 | −7.407 | 1.00 | 0.00 | BrD | ATOM | 891 | CE | MET | 54 | −2.176 |
| 1.995 | −7.401 | 1.00 | 0.00 | BrD | ATOM | 892 | HE1 | MET | 54 | −2.086 |
| 1.294 | −8.214 | 1.00 | 0.00 | BrD | ATOM | 893 | HE2 | MET | 54 | −3.085 |
| 2.967 | −7.518 | 1.00 | 0.00 | BrD | ATOM | 894 | HE3 | MET | 54 | −2.208 |
| 1.457 | −6.465 | 1.00 | 0.00 | BrD | ATOM | 895 | C | MET | 54 | −3.229 |
| 2.630 | −4.602 | 1.00 | 0.00 | BrD | ATOM | 896 | O | MET | 54 | −2.556 |
| 1.990 | −3.795 | 1.00 | 0.00 | BrD | ATOM | 897 | N | ASP | 55 | −4.422 |
| 3.232 | −5.029 | 1.00 | 0.00 | BrD | ATOM | 898 | HN | ASP | 55 | −4.919 |
| 2.803 | −5.652 | 1.00 | 0.00 | BrD | ATOM | 899 | CA | ASP | 55 | −5.045 |
| 1.005 | −4.544 | 1.00 | 0.00 | BrD | ATOM | 900 | HA | ASP | 55 | −5.234 |
| 1.142 | −3.490 | 1.00 | 0.00 | BrD | ATOM | 901 | CB | ASP | 55 | −6.391 |
| 0.793 | −5.249 | 1.00 | 0.00 | BrD | ATOM | 902 | HB1 | ASP | 55 | −6.327 |
| 0.045 | −5.917 | 1.00 | 0.00 | BrD | ATOM | 903 | HB2 | ASP | 55 | −6.631 |
| 1.679 | −5.817 | 1.00 | 0.00 | BrD | ATOM | 904 | OG | ASP | 55 | −7.520 |
| 0.536 | −4.269 | 1.00 | 0.00 | BrD | ATOM | 905 | OD1 | ASP | 55 | −8.426 |
| 0.256 | −4.602 | 1.00 | 0.00 | BrD | ATOM | 906 | OD2 | ASP | 55 | −7.496 |
| 1.126 | −3.169 | 1.00 | 0.00 | BrD | ATOM | 907 | C | ASP | 55 | −4.121 |
| 0.212 | −4.704 | 1.00 | 0.00 | BrD | ATOM | 908 | O | ASP | 55 | −3.406 |
| 0.970 | −3.772 | 1.00 | 0.00 | BrD | ATOM | 909 | N | LEU | 56 | −4.142 |
| 0.896 | −9.870 | 1.00 | 0.00 | BrD | ATOM | 910 | HN | LEU | 56 | −4.715 |
| 0.533 | −6.586 | 1.00 | 0.00 | BrD | ATOM | 911 | CA | LEU | 56 | −3.306 |
| 2.030 | −6.111 | 1.00 | 0.00 | BrD | ATOM | 912 | HA | LEU | 56 | −2.301 |
| 1.790 | −5.810 | 1.00 | 0.00 | BrD | ATOM | 913 | CB | LEU | 56 | −3.804 |
| 3.224 | −5.292 | 1.00 | 0.00 | BrD | ATOM | 914 | HB1 | LEU | 56 | −3.692 |
| 4.115 | −5.892 | 1.00 | 0.00 | BrD | ATOM | 915 | HB2 | LEU | 56 | −4.852 |
| 3.082 | −5.089 | 1.00 | 0.00 | BrD | ATOM | 916 | OG | LEU | 56 | −3.088 |
| 3.451 | −3.962 | 1.00 | 0.00 | BrD | ATOM | 917 | HG | LEU | 56 | −3.356 |
| 2.661 | −3.279 | 1.00 | 0.00 | BrD | ATOM | 918 | CD1 | LEU | 56 | −3.521 |
| 4.770 | −3.344 | 1.00 | 0.00 | BrD | ATOM | 919 | HD11 | LEU | 56 | −2.809 |
| 5.539 | −3.606 | 1.00 | 0.00 | BrD | ATOM | 920 | HD12 | LEU | 56 | −4.497 |
| 5.040 | −3.719 | 1.00 | 0.00 | BrD | ATOM | 921 | HD13 | LEU | 56 | −3.562 |
| 4.668 | −2.270 | 1.00 | 0.00 | BrD | ATOM | 922 | CD2 | LEU | 56 | −1.980 |
| 3.419 | −4.153 | 1.00 | 0.00 | BrD | ATOM | 923 | HD21 | LEU | 56 | −1.352 |
| 3.388 | −5.209 | 1.00 | 0.00 | BrD | ATOM | 924 | HD22 | LEU | 56 | −1.144 |
| 4.306 | −3.716 | 1.00 | 0.00 | BrD | ATOM | 925 | HD23 | LEU | 56 | −1.175 |
| 2.542 | −3.671 | 1.00 | 0.00 | BrD | ATOM | 926 | C | LEU | 56 | −3.305 |
| 2.400 | −7.587 | 1.00 | 0.00 | BrD | ATOM | 927 | O | LEU | 56 | −2.271 |
| 2.760 | −8.150 | 1.00 | 0.00 | BrD | ATOM | 928 | N | LYS | 57 | −4.475 |

TABLE 6-continued

Atomic Structure Coordinates of the
P/CAF Bromodomain/Acetyl-Histamine Complex

| | | | | | | | | | | |
|---|---|---|---|---|---|---|---|---|---|---|
| 2.304 | −8.207 | 1.00 | 0.00 | BrD | ATOM | 929 | HN | LYS | 57 | −5.261 |
| 2.020 | −7.696 | 1.00 | 0.00 | BrD | ATOM | 930 | CA | LYS | 57 | −4.634 |
| 2.639 | −9.615 | 1.00 | 0.00 | BrD | ATOM | 931 | HA | LYS | 57 | −4.577 |
| 3.712 | −9.704 | 1.00 | 0.00 | BrD | ATOM | 932 | CB | LYS | 57 | −6.007 |
| 2.179 | −10.108 | 1.00 | 0.00 | BrD | ATOM | 933 | HB1 | LYS | 57 | −6.765 |
| 2.764 | −9.608 | 1.00 | 0.00 | BrD | ATOM | 934 | HB2 | LYS | 57 | −6.139 |
| 1.139 | −9.890 | 1.00 | 0.00 | BrD | ATOM | 935 | CG | LYS | 57 | −6.203 |
| 2.328 | −11.608 | 1.00 | 0.00 | BrD | ATOM | 936 | HG1 | LYS | 57 | −9.383 |
| 1.845 | −12.118 | 1.00 | 0.00 | BrD | ATOM | 937 | HG2 | LYS | 57 | −7.132 |
| 1.856 | −11.889 | 1.00 | 0.00 | BrD | ATOM | 938 | CO | LYS | 57 | −6.248 |
| 3.790 | −12.024 | 1.00 | 0.00 | BrD | ATOM | 939 | HD1 | LYS | 57 | −5.259 |
| 4.098 | −12.327 | 1.00 | 0.00 | BrD | ATOM | 940 | HD2 | LYS | 57 | −6.971 |
| 4.383 | −11.181 | 1.00 | 0.00 | BrD | ATOM | 941 | CE | LYS | 57 | −7.210 |
| 4.011 | −13.180 | 1.00 | 0.00 | BrD | ATOM | 942 | HE1 | LYS | 57 | −7.354 |
| 3.073 | −13.697 | 1.00 | 0.00 | BrD | ATOM | 943 | HE2 | LYS | 57 | −6.778 |
| 4.732 | −13.858 | 1.00 | 0.00 | BrD | ATOM | 944 | NZ | LYS | 57 | −8.532 |
| 4.515 | −12.715 | 1.00 | 0.00 | BrD | ATOM | 945 | HZ1 | LYS | 57 | −8.403 |
| 5.182 | −11.928 | 1.00 | 0.00 | BrD | ATOM | 946 | HZ2 | LYS | 57 | −9.022 |
| 5.003 | −13.492 | 1.00 | 0.00 | BrD | ATOM | 947 | HZ3 | LYS | 57 | −9.122 |
| 3.723 | −12.391 | 1.00 | 0.00 | BrD | ATOM | 948 | C | LYS | 57 | −3.533 |
| 2.015 | −10.473 | 1.00 | 0.00 | BrD | ATOM | 949 | O | LYS | 57 | −3.222 |
| 2.519 | −11.553 | 1.00 | 0.00 | BrD | ATOM | 950 | N | THR | 58 | −2.941 |
| 0.923 | −9.989 | 1.00 | 0.00 | BrD | ATOM | 951 | HN | THR | 58 | −3.240 |
| 0.552 | −9.135 | 1.00 | 0.00 | BrD | ATOM | 952 | CA | THR | 58 | −1.901 |
| 0.230 | −10.742 | 1.00 | 0.00 | BrD | ATOM | 953 | HA | THR | 58 | −1.819 |
| 0.717 | −11.702 | 1.00 | 0.00 | BrD | ATOM | 954 | CB | THR | 58 | −2.307 |
| 1.233 | −10.967 | 1.00 | 0.00 | BrD | ATOM | 955 | HB | THR | 58 | −2.611 |
| 1.660 | −10.024 | 1.00 | 0.00 | BrD | ATOM | 956 | OG1 | THR | 58 | −3.403 |
| 1.313 | −11.862 | 1.00 | 0.00 | BrD | ATOM | 957 | HG1 | THR | 58 | −3.101 |
| 1.133 | −12.755 | 1.00 | 0.00 | BrD | ATOM | 958 | OG2 | THR | 58 | −1.197 |
| 2.099 | −11.525 | 1.00 | 0.00 | BrD | ATOM | 959 | HG21 | THR | 58 | −0.808 |
| 2.734 | −10.743 | 1.00 | 0.00 | BrD | ATOM | 960 | HG22 | THR | 58 | −1.585 |
| 2.710 | −12.326 | 1.00 | 0.00 | BrD | ATOM | 961 | HG23 | THR | 58 | −0.405 |
| 1.469 | −11.904 | 1.00 | 0.00 | BrD | ATOM | 962 | C | THR | 58 | −0.539 |
| 0.305 | −10.045 | 1.00 | 0.00 | BrD | ATOM | 963 | O | THR | 58 | 0.499 |
| 0.220 | −10.701 | 1.00 | 0.00 | BrD | ATOM | 964 | N | MET | 59 | −0.537 |
| 0.445 | −8.721 | 1.00 | 0.00 | BrD | ATOM | 965 | HN | MET | 59 | −1.388 |
| 0.503 | −8.238 | 1.00 | 0.00 | BrD | ATOM | 966 | CA | MET | 59 | 0.718 |
| 0.505 | −7.972 | 1.00 | 0.00 | BrD | ATOM | 967 | HA | MET | 59 | 1.401 |
| 0.191 | −8.436 | 1.00 | 0.00 | BrD | ATOM | 968 | CB | MET | 59 | 0.499 |
| 0.070 | −6.513 | 1.00 | 0.00 | BrD | ATOM | 969 | HB1 | MET | 59 | 1.430 |
| 0.316 | −6.125 | 1.00 | 0.00 | BrD | ATOM | 970 | HB1 | MET | 59 | −0.236 |
| 0.717 | −6.498 | 1.00 | 0.00 | BrD | ATOM | 971 | CG | MET | 59 | 0.022 |
| 1.176 | −5.583 | 1.00 | 0.00 | BrD | ATOM | 972 | HG1 | MET | 59 | −0.422 |
| 0.811 | −5.017 | 1.00 | 0.00 | BrD | ATOM | 973 | HG2 | MET | 59 | −0.286 |
| 2.022 | −6.180 | 1.00 | 0.00 | BrD | ATOM | 974 | SD | MET | 59 | 1.300 |
| 1.715 | −4.431 | 1.00 | 0.00 | BrD | ATOM | 975 | CE | MET | 59 | 1.463 |
| 0.259 | −3.400 | 1.00 | 0.00 | BrD | ATOM | 976 | HE1 | MET | 59 | 0.629 |
| 0.205 | −2.715 | 1.00 | 0.00 | BrD | ATOM | 977 | HE2 | MET | 59 | 1.474 |
| 0.624 | −4.022 | 1.00 | 0.00 | BrD | ATOM | 978 | HE3 | MET | 59 | 2.386 |
| 0.316 | −2.841 | 1.00 | 0.00 | BrD | ATOM | 979 | C | MET | 59 | 1.345 |
| 1.901 | −8.036 | 1.00 | 0.00 | BrD | ATOM | 980 | O | MET | 59 | 2.535 |
| 2.067 | −7.767 | 1.00 | 0.00 | BrD | ATOM | 981 | N | SER | 60 | 0.542 |
| 2.898 | −8.392 | 1.00 | 0.00 | BrD | ATOM | 982 | HN | SER | 60 | −0.399 |
| 2.710 | −8.590 | 1.00 | 0.00 | BrD | ATOM | 983 | CA | SER | 60 | 1.025 |
| 4.271 | −8.478 | 1.00 | 0.00 | BrD | ATOM | 984 | HA | SER | 60 | 1.685 |
| 4.442 | −7.640 | 1.00 | 0.00 | BrD | ATOM | 985 | CB | SER | 60 | −0.147 |
| 5.250 | −8.396 | 1.00 | 0.00 | BrD | ATOM | 986 | HB1 | SER | 60 | −0.610 |
| 5.171 | −7.424 | 1.00 | 0.00 | BrD | ATOM | 987 | HB2 | SER | 60 | −0.871 |
| 5.006 | −9.159 | 1.00 | 0.00 | BrD | ATOM | 988 | OG | SER | 60 | 0.286 |
| 6.585 | −8.588 | 1.00 | 0.00 | BrD | ATOM | 989 | HG | SER | 60 | −0.145 |
| 6.953 | −9.363 | 1.00 | 0.00 | BrD | ATOM | 990 | C | SER | 60 | 1.803 |
| 4.903 | −9.770 | 1.00 | 0.00 | BrD | ATOM | 991 | O | SER | 60 | 2.636 |
| 5.405 | −9.850 | 1.00 | 0.00 | BrD | ATOM | 992 | N | GLU | 61 | 1.519 |
| 3.690 | −10.782 | 1.00 | 0.00 | BrD | ATOM | 993 | HN | GLU | 61 | 0.839 |
| 2.998 | −10.661 | 1.00 | 0.00 | BrD | ATOM | 994 | CA | GLU | 61 | 2.182 |
| 3.820 | −12.075 | 1.00 | 0.00 | BrD | ATOM | 995 | HA | GLU | 61 | 2.295 |
| 4.874 | −12.283 | 1.00 | 0.00 | BrD | ATOM | 996 | CB | GLU | 61 | 1.326 |
| 3.187 | −13.174 | 1.00 | 0.00 | BrD | ATOM | 997 | HB1 | GLU | 61 | 1.820 |
| 3.324 | −14.125 | 1.00 | 0.00 | BrD | ATOM | 998 | HB2 | GLU | 61 | 1.232 |
| 2.129 | −12.977 | 1.00 | 0.00 | BrD | ATOM | 999 | OG | GLU | 61 | −0.071 |
| 3.779 | −13.274 | 1.00 | 0.00 | BrD | ATOM | 1000 | HG1 | GLU | 61 | −0.494 |
| 3.836 | −12.282 | 1.00 | 0.00 | BrD | ATOM | 1001 | HG2 | GLU | 61 | −0.679 |
| 3.132 | −13.889 | 1.00 | 0.00 | BrD | ATOM | 1002 | CD | GLU | 61 | −0.073 |
| 9.167 | −13.883 | 1.00 | 0.00 | BrD | ATOM | 1003 | OE1 | GLU | 61 | −1.024 |
| 9.488 | −14.627 | 1.00 | 0.00 | BrD | ATOM | 1004 | OE2 | GLU | 61 | 0.876 |
| 5.934 | −13.617 | 1.00 | 0.00 | BrD | ATOM | 1005 | C | GLU | 61 | 3.565 |

TABLE 6-continued

Atomic Structure Coordinates of the
P/CAF Bromodomain/Acetyl-Histamine Complex

| | | | | | | | | | | |
|---|---|---|---|---|---|---|---|---|---|---|
| 3.174 | −12.060 | 1.00 | 0.00 | BrD | ATOM | 1006 | O | GLU | 61 | 4.466 |
| 3.601 | −12.782 | 1.00 | 0.00 | BrD | ATOM | 1007 | N | ARG | 62 | 3.726 |
| 2.137 | −11.244 | 1.00 | 0.00 | BrD | ATOM | 1008 | HN | ARG | 62 | 2.971 |
| 1.836 | −10.697 | 1.00 | 0.00 | BrD | ATOM | 1009 | CA | ARG | 62 | 4.999 |
| 1.428 | −11.155 | 1.00 | 0.00 | BrD | ATOM | 1010 | HA | ARG | 62 | 9.352 |
| 1.262 | −12.162 | 1.00 | 0.00 | BrD | ATOM | 1011 | CB | ARG | 62 | 4.807 |
| 0.075 | −10.468 | 1.00 | 0.00 | BrD | ATOM | 1012 | HB1 | ARG | 62 | 5.793 |
| 0.241 | −10.052 | 1.00 | 0.00 | BrD | ATOM | 1013 | HB2 | ARG | 62 | 4.091 |
| 0.187 | −9.668 | 1.00 | 0.00 | BrD | ATOM | 1014 | OG | ARG | 62 | 4.312 |
| 1.018 | −11.404 | 1.00 | 0.00 | BrD | ATOM | 1015 | HG1 | ARG | 62 | 4.852 |
| 1.928 | −11.195 | 1.00 | 0.00 | BrD | ATOM | 1016 | HG2 | ARG | 62 | 4.494 |
| 0.714 | −12.424 | 1.00 | 0.00 | BrD | ATOM | 1017 | CD | ARG | 62 | 2.826 |
| 1.278 | −11.225 | 1.00 | 0.00 | BrD | ATOM | 1018 | HD1 | ARG | 62 | 2.484 |
| 0.738 | −10.356 | 1.00 | 0.00 | BrD | ATOM | 1019 | HD2 | ARG | 62 | 2.675 |
| 2.336 | −11.072 | 1.00 | 0.00 | BrD | ATOM | 1020 | NE | ARG | 62 | 2.052 |
| 0.851 | −12.387 | 1.00 | 0.00 | BrD | ATOM | 1021 | HE | ARG | 62 | 1.621 |
| 0.028 | −12.346 | 1.00 | 0.00 | BrD | ATOM | 1022 | CZ | ARG | 62 | 1.903 |
| 1.585 | −13.485 | 1.00 | 0.00 | BrD | ATOM | 1023 | NH1 | ARG | 62 | 1.183 |
| 1.125 | −14.498 | 1.00 | 0.00 | BrD | ATOM | 1024 | HH11 | ARG | 62 | 1.072 |
| 1.678 | −15.324 | 1.00 | 0.00 | BrD | ATOM | 1025 | HH12 | ARG | 62 | 0.752 |
| 0.224 | −14.437 | 1.00 | 0.00 | BrD | ATOM | 1026 | NH2 | ARG | 62 | 2.473 |
| 2.780 | −13.571 | 1.00 | 0.00 | BrD | ATOM | 1027 | HH21 | ARG | 62 | 2.359 |
| 3.329 | −14.399 | 1.00 | 0.00 | BrD | ATOM | 1028 | HH22 | ARG | 62 | 3.018 |
| 3.130 | −12.809 | 1.00 | 0.00 | BrD | ATOM | 1029 | C | ARG | 62 | 6.040 |
| 2.299 | −10.405 | 1.00 | 0.00 | BrD | ATOM | 1030 | O | ARG | 62 | 7.101 |
| 2.569 | −10.945 | 1.00 | 0.00 | BrD | ATOM | 1031 | N | LEU | 63 | 9.734 |
| 2.606 | −9.158 | 1.00 | 0.00 | BrD | ATOM | 1032 | HN | LEU | 63 | 4.875 |
| 2.326 | −8.780 | 1.00 | 0.00 | BrD | ATOM | 1033 | CA | LEU | 63 | 6.691 |
| 3.396 | −8.339 | 1.00 | 0.00 | BrD | ATOM | 1034 | HA | LEU | 63 | 7.496 |
| 2.771 | −8.093 | 1.00 | 0.00 | BrD | ATOM | 1035 | CB | LEU | 63 | 9.962 |
| 3.840 | −7.043 | 1.00 | 0.00 | BrD | ATOM | 1036 | HB1 | LEU | 63 | 5.009 |
| 4.277 | −7.302 | 1.00 | 0.00 | BrD | ATOM | 1037 | HB2 | LEU | 63 | 5.780 |
| 2.962 | −6.442 | 1.00 | 0.00 | BrD | ATOM | 1038 | CG | LEU | 63 | 6.736 |
| 4.857 | −6.186 | 1.00 | 0.00 | BrD | ATOM | 1039 | HG | LEU | 63 | 6.429 |
| 4.754 | −5.156 | 1.00 | 0.00 | BrD | ATOM | 1040 | CD1 | LEU | 63 | 8.237 |
| 4.605 | −6.247 | 1.00 | 0.00 | BrD | ATOM | 1041 | HD11 | LEU | 63 | 8.420 |
| 3.584 | −6.547 | 1.00 | 0.00 | BrD | ATOM | 1042 | HD12 | LEU | 63 | 8.685 |
| 5.277 | −6.965 | 1.00 | 0.00 | BrD | ATOM | 1043 | HD13 | LEU | 63 | 8.671 |
| 4.779 | −5.273 | 1.00 | 0.00 | BrD | ATOM | 1044 | CD2 | LEU | 63 | 6.414 |
| 6.277 | −6.627 | 1.00 | 0.00 | BrD | ATOM | 1045 | HD21 | LEU | 63 | 7.332 |
| 6.804 | −6.842 | 1.00 | 0.00 | BrD | ATOM | 1046 | HD22 | LEU | 63 | 5.798 |
| 6.248 | −7.514 | 1.00 | 0.00 | BrD | ATOM | 1047 | HD23 | LEU | 63 | 9.883 |
| 6.787 | −5.836 | 1.00 | 0.00 | BrD | ATOM | 1048 | C | LEU | 63 | 7.190 |
| 4.618 | −9.103 | 1.00 | 0.00 | BrD | ATOM | 1049 | O | LEU | 63 | 8.354 |
| 4.853 | −9.203 | 1.00 | 0.00 | BrD | ATOM | 1050 | N | LYS | 64 | 6.214 |
| 9.390 | −9.643 | 1.00 | 0.00 | BrD | ATOM | 1051 | HN | LYS | 64 | 9.271 |
| 9.150 | −9.525 | 1.00 | 0.00 | BrD | ATOM | 1052 | CA | LYS | 64 | 6.551 |
| 6.592 | −10.397 | 1.00 | 0.00 | BrD | ATOM | 1053 | HA | LYS | 64 | 6.929 |
| 7.325 | −9.699 | 1.00 | 0.00 | BrD | ATOM | 1054 | CB | LYS | 64 | 5.303 |
| 7.152 | −11.082 | 1.00 | 0.00 | BrD | ATOM | 1055 | HB1 | LYS | 64 | 4.649 |
| 6.332 | −11.340 | 1.00 | 0.00 | BrD | ATOM | 1056 | HB2 | LYS | 64 | 5.602 |
| 7.661 | −11.987 | 1.00 | 0.00 | BrD | ATOM | 1057 | CG | LYS | 64 | 4.523 |
| 8.131 | −10.221 | 1.00 | 0.00 | BrD | ATOM | 1058 | HG1 | LYS | 64 | 3.533 |
| 7.734 | −10.047 | 1.00 | 0.00 | BrD | ATOM | 1059 | HG2 | LYS | 64 | 5.035 |
| 8.254 | −9.278 | 1.00 | 0.00 | BrD | ATOM | 1060 | CD | LYS | 64 | 4.398 |
| 9.488 | −10.894 | 1.00 | 0.00 | BrD | ATOM | 1061 | HD1 | LYS | 64 | 3.363 |
| 9.798 | −10.870 | 1.00 | 0.00 | BrD | ATOM | 1062 | HD2 | LYS | 64 | 4.726 |
| 9.402 | −11.920 | 1.00 | 0.00 | BrD | ATOM | 1063 | CE | LYS | 64 | 5.243 |
| 10.538 | −10.192 | 1.00 | 0.00 | BrD | ATOM | 1064 | HE1 | LYS | 64 | 9.904 |
| 10.043 | −9.496 | 1.00 | 0.00 | BrD | ATOM | 1065 | HE2 | LYS | 64 | 4.989 |
| 11.207 | −9.653 | 1.00 | 0.00 | BrD | ATOM | 1066 | HZ | LYS | 64 | 4.060 |
| 11.330 | −11.154 | 1.00 | 0.00 | BrD | ATOM | 1067 | HZ1 | LYS | 64 | 6.712 |
| 11.955 | −10.638 | 1.00 | 0.00 | BrD | ATOM | 1068 | HZ2 | LYS | 64 | 6.615 |
| 10.693 | −11.761 | 1.00 | 0.00 | BrD | ATOM | 1069 | HZ3 | LYS | 64 | 5.441 |
| 11.911 | −11.754 | 1.00 | 0.00 | BrD | ATOM | 1070 | C | LYS | 64 | 7.629 |
| 6.305 | −11.439 | 1.00 | 0.00 | BrD | ATOM | 1071 | O | LYS | 64 | 8.376 |
| 7.200 | −11.834 | 1.00 | 0.00 | BrD | ATOM | 1072 | N | ASN | 65 | 7.705 |
| 5.052 | −11.880 | 1.00 | 0.00 | BrD | ATOM | 1073 | HN | ASN | 65 | 7.080 |
| 4.383 | −11.531 | 1.00 | 0.00 | BrD | ATOM | 1074 | CA | ASN | 65 | 8.688 |
| 4.657 | −12.883 | 1.00 | 0.00 | BrD | ATOM | 1075 | HA | ASN | 65 | 9.212 |
| 5.549 | −13.198 | 1.00 | 0.00 | BrD | ATOM | 1076 | CB | ASN | 65 | 7.989 |
| 4.034 | −14.092 | 1.00 | 0.00 | BrD | ATOM | 1077 | HB1 | ASN | 65 | 8.680 |
| 3.376 | −14.600 | 1.00 | 0.00 | BrD | ATOM | 1078 | HB2 | ASN | 65 | 7.137 |
| 3.463 | −13.754 | 1.00 | 0.00 | BrD | ATOM | 1079 | CG | ASN | 65 | 7.506 |
| 5.076 | −19.081 | 1.00 | 0.00 | BrD | ATOM | 1080 | OD1 | ASN | 65 | 8.177 |
| 6.080 | −15.320 | 1.00 | 0.00 | BrD | ATOM | 1081 | ND2 | ASN | 65 | 6.334 |
| 4.844 | −15.660 | 1.00 | 0.00 | BrD | ATOM | 1082 | HD21 | ASN | 65 | 5.854 |

TABLE 6-continued

Atomic Structure Coordinates of the
P/CAF Bromodomain/Acetyl-Histamine Complex

| | | | | | | | | | | |
|---|---|---|---|---|---|---|---|---|---|---|
| 4.024 | −15.421 | 1.00 | 0.00 | BrD | ATOM | 1083 | HD22 | ASN | 65 | 5.997 |
| 5.502 | −16.303 | 1.00 | 0.00 | BrD | ATOM | 1084 | C | ASN | 65 | 9.703 |
| 3.677 | −12.308 | 1.00 | 0.00 | BrD | ATOM | 1085 | O | ASN | 65 | 10.237 |
| 2.829 | −13.023 | 1.00 | 0.00 | BrD | ATOM | 1086 | N | ARG | 66 | 9.973 |
| 3.804 | −11.014 | 1.00 | 0.00 | BrD | ATOM | 1087 | HN | ARG | 66 | 9.523 |
| 4.505 | −10.498 | 1.00 | 0.00 | BrD | ATOM | 1088 | CA | ARG | 66 | 10.942 |
| 2.943 | −10.346 | 1.00 | 0.00 | BrD | ATOM | 1089 | HA | ARG | 66 | 10.826 |
| 3.082 | −9.281 | 1.00 | 0.00 | BrD | ATOM | 1090 | CB | ARG | 66 | 12.357 |
| 3.347 | −10.739 | 1.00 | 0.00 | BrD | ATOM | 1091 | HB1 | ARG | 66 | 12.323 |
| 3.875 | −11.680 | 1.00 | 0.00 | BrD | ATOM | 1092 | HB2 | ARG | 66 | 12.959 |
| 2.458 | −10.854 | 1.00 | 0.00 | BrD | ATOM | 1093 | OG | ARG | 66 | 13.018 |
| 4.243 | −9.713 | 1.00 | 0.00 | BrD | ATOM | 1094 | HG1 | ARG | 66 | 13.744 |
| 3.666 | −9.163 | 1.00 | 0.00 | BrD | ATOM | 1095 | HG2 | ARG | 66 | 12.262 |
| 4.613 | −9.038 | 1.00 | 0.00 | BrD | ATOM | 1096 | CD | ARG | 66 | 13.710 |
| 8.423 | −10.368 | 1.00 | 0.00 | BrD | ATOM | 1097 | HD1 | ARG | 66 | 13.483 |
| 5.439 | −11.416 | 1.00 | 0.00 | BrD | ATOM | 1098 | HD2 | ARG | 66 | 13.398 |
| 6.329 | −9.898 | 1.00 | 0.00 | BrD | ATOM | 1099 | NE | ARG | 66 | 15.162 |
| 5.391 | −10.237 | 1.00 | 0.00 | BrD | ATOM | 1100 | HE | ARG | 66 | 15.688 |
| 9.255 | −11.059 | 1.00 | 0.00 | BrD | ATOM | 1101 | CZ | ARG | 66 | 15.801 |
| 9.407 | −9.074 | 1.00 | 0.00 | BrD | ATOM | 1102 | NH1 | ARG | 66 | 19.117 |
| 9.538 | −7.945 | 1.00 | 0.00 | BrD | ATOM | 1103 | HH11 | ARG | 66 | 15.599 |
| 5.578 | −7.070 | 1.00 | 0.00 | BrD | ATOM | 1104 | HH12 | ARG | 66 | 14.118 |
| 5.591 | −7.969 | 1.00 | 0.00 | BrD | ATOM | 1105 | NH2 | ARG | 66 | 17.125 |
| 5.334 | −9.037 | 1.00 | 0.00 | BrD | ATOM | 1106 | HH21 | ARG | 66 | 17.604 |
| 5.377 | −8.161 | 1.00 | 0.00 | BrD | ATOM | 1107 | HH22 | ARG | 66 | 17.643 |
| 5.237 | −9.887 | 1.00 | 0.00 | BrD | ATOM | 1108 | C | ARG | 66 | 10.708 |
| 1.474 | −10.682 | 1.00 | 0.00 | BrD | ATOM | 1109 | O | ARG | 66 | 11.654 |
| 0.705 | −10.850 | 1.00 | 0.00 | BrD | ATOM | 1110 | N | TYR | 67 | 9.441 |
| 1.097 | −10.781 | 1.00 | 0.00 | BrD | ATOM | 1111 | HN | TYR | 67 | 8.736 |
| 1.759 | −10.633 | 1.00 | 0.00 | BrD | ATOM | 1112 | CA | TYR | 67 | 9.075 |
| 0.280 | −11.094 | 1.00 | 0.00 | BrD | ATOM | 1113 | HA | TYR | 67 | 9.952 |
| 0.780 | −11.472 | 1.00 | 0.00 | BrD | ATOM | 1114 | CB | TYR | 67 | 7.982 |
| 0.309 | −12.164 | 1.00 | 0.00 | BrD | ATOM | 1115 | HB1 | TYR | 67 | 7.062 |
| 0.061 | −11.738 | 1.00 | 0.00 | BrD | ATOM | 1116 | HB2 | TYR | 67 | 8.276 |
| 0.330 | −12.984 | 1.00 | 0.00 | BrD | ATOM | 1117 | OG | TYR | 67 | 7.713 |
| 1.487 | −12.723 | 1.00 | 0.00 | BrD | ATOM | 1118 | CD1 | TYR | 67 | 7.042 |
| 2.639 | −11.970 | 1.00 | 0.00 | BrD | ATOM | 1119 | HD1 | TYR | 67 | 6.718 |
| 2.385 | −10.973 | 1.00 | 0.00 | BrD | ATOM | 1120 | CD2 | TYR | 67 | 8.122 |
| 2.032 | −14.005 | 1.00 | 0.00 | BrD | ATOM | 1121 | HD2 | TYR | 67 | 8.645 |
| 1.301 | −14.604 | 1.00 | 0.00 | BrD | ATOM | 1122 | CE1 | TYR | 67 | 6.787 |
| 3.899 | −12.475 | 1.00 | 0.00 | BrD | ATOM | 1123 | HE1 | TYR | 67 | 6.261 |
| 4.625 | −11.872 | 1.00 | 0.00 | BrD | ATOM | 1124 | CE2 | TYR | 67 | 7.872 |
| 3.291 | −14.518 | 1.00 | 0.00 | BrD | ATOM | 1125 | HE2 | TYR | 67 | 8.198 |
| 3.541 | −15.516 | 1.00 | 0.00 | BrD | ATOM | 1126 | CZ | TYR | 67 | 7.204 |
| 4.220 | −13.749 | 1.00 | 0.00 | BrD | ATOM | 1127 | OH | TYR | 67 | 6.953 |
| 5.475 | −14.256 | 1.00 | 0.00 | BrD | ATOM | 1128 | HH | TYR | 67 | 7.446 |
| 6.127 | −13.753 | 1.00 | 0.00 | BrD | ATOM | 1129 | C | TYR | 67 | 8.606 |
| 1.006 | −9.840 | 1.00 | 0.00 | BrD | ATOM | 1130 | O | TYR | 67 | 8.910 |
| 2.181 | −9.639 | 1.00 | 0.00 | BrD | ATOM | 1131 | N | TYR | 68 | 7.880 |
| 0.291 | −8.990 | 1.00 | 0.00 | BrD | ATOM | 1132 | HN | TYR | 68 | 7.686 |
| 0.647 | −9.197 | 1.00 | 0.00 | BrD | ATOM | 1133 | CA | TYR | 68 | 7.401 |
| 0.855 | −7.736 | 1.00 | 0.00 | BrD | ATOM | 1134 | HA | TYR | 68 | 7.528 |
| 1.924 | −7.788 | 1.00 | 0.00 | BrD | ATOM | 1135 | CB | TYR | 68 | 5.918 |
| 0.531 | −7.538 | 1.00 | 0.00 | BrD | ATOM | 1136 | HB1 | TYR | 68 | 5.646 |
| 0.286 | −8.188 | 1.00 | 0.00 | BrD | ATOM | 1137 | HB2 | TYR | 68 | 5.758 |
| 0.234 | −6.512 | 1.00 | 0.00 | BrD | ATOM | 1138 | CG | TYR | 68 | 4.987 |
| 1.689 | −7.833 | 1.00 | 0.00 | BrD | ATOM | 1139 | CD1 | TYR | 68 | 5.378 |
| 2.734 | −8.664 | 1.00 | 0.00 | BrD | ATOM | 1140 | HD1 | TYR | 68 | 6.364 |
| 2.717 | −9.101 | 1.00 | 0.00 | BrD | ATOM | 1141 | CD2 | TYR | 68 | 3.712 |
| 1.732 | −7.283 | 1.00 | 0.00 | BrD | ATOM | 1142 | HD2 | TYR | 68 | 3.392 |
| 0.927 | −6.638 | 1.00 | 0.00 | BrD | ATOM | 1143 | CE1 | TYR | 68 | 4.926 |
| 3.788 | −8.933 | 1.00 | 0.00 | BrD | ATOM | 1144 | HE1 | TYR | 68 | 4.849 |
| 4.591 | −9.579 | 1.00 | 0.00 | BrD | ATOM | 1145 | CE2 | TYR | 68 | 2.855 |
| 2.782 | −7.549 | 1.00 | 0.00 | BrD | ATOM | 1146 | HE2 | TYR | 68 | 1.868 |
| 2.797 | −7.110 | 1.00 | 0.00 | BrD | ATOM | 1147 | CZ | TYR | 68 | 3.267 |
| 3.807 | −8.374 | 1.00 | 0.00 | BrD | ATOM | 1148 | OH | TYR | 68 | 2.416 |
| 4.855 | −8.639 | 1.00 | 0.00 | BrD | ATOM | 1149 | NH | TYR | 68 | 2.457 |
| 5.490 | −7.920 | 1.00 | 0.00 | BrD | ATOM | 1150 | C | TYR | 68 | 8.206 |
| 0.327 | −6.548 | 1.00 | 0.00 | BrD | ATOM | 1151 | O | TYR | 68 | 8.001 |
| 0.759 | −5.416 | 1.00 | 0.00 | BrD | ATOM | 1152 | B | VAL | 69 | 9.149 |
| 0.579 | −6.816 | 1.00 | 0.00 | BrD | ATOM | 1153 | HN | VAL | 69 | 9.268 |
| 0.888 | −7.735 | 1.00 | 0.00 | BrD | ATOM | 1154 | CA | VAL | 69 | 9.977 |
| 1.170 | −5.769 | 1.00 | 0.00 | BrD | ATOM | 1155 | HA | VAL | 69 | 9.397 |
| 1.941 | −5.285 | 1.00 | 0.00 | BrD | ATOM | 1156 | CB | VAL | 69 | 11.232 |
| 1.825 | −6.366 | 1.00 | 0.00 | BrD | ATOM | 1157 | HB | VAL | 69 | 10.922 |
| 2.537 | −7.117 | 1.00 | 0.00 | BrD | ATOM | 1158 | CG1 | VAL | 69 | 12.107 |
| 0.778 | −7.032 | 1.00 | 0.00 | BrD | ATOM | 1159 | HG11 | VAL | 69 | 11.701 |

TABLE 6-continued

Atomic Structure Coordinates of the
P/CAF Bromodomain/Acetyl-Histamine Complex

| | | | | | | | | | | |
|---|---|---|---|---|---|---|---|---|---|---|
| 0.936 | −8.003 | 1.00 | 0.00 | BrD | ATOM | 1160 | HG12 | VAL | 69 | 13.108 |
| 1.165 | −7.146 | 1.00 | 0.00 | BrD | ATOM | 1161 | HG13 | VAL | 69 | 12.131 |
| 0.111 | −6.420 | 1.00 | 0.00 | BrD | ATOM | 1162 | CG2 | VAL | 69 | 12.001 |
| 2.572 | −5.291 | 1.00 | 0.00 | BrD | ATOM | 1163 | HG21 | VAL | 69 | 11.389 |
| 3.370 | −4.899 | 1.00 | 0.00 | BrD | ATOM | 1164 | HG22 | VAL | 69 | 12.256 |
| 1.889 | −4.494 | 1.00 | 0.00 | BrD | ATOM | 1165 | HG23 | VAL | 69 | 12.904 |
| 2.985 | −5.716 | 1.00 | 0.00 | BrD | ATOM | 1166 | C | VAL | 69 | 10.409 |
| 0.149 | −4.717 | 1.00 | 0.00 | BrD | ATOM | 1167 | O | VAL | 69 | 10.642 |
| 0.506 | −3.565 | 1.00 | 0.00 | BrD | ATOM | 1168 | N | SER | 70 | 10.508 |
| 1.123 | −5.110 | 1.00 | 0.00 | BrD | ATOM | 1169 | HN | SER | 70 | 10.321 |
| 1.350 | −6.044 | 1.00 | 0.00 | BrD | ATOM | 1170 | CA | SER | 70 | 10.909 |
| 2.190 | −4.189 | 1.00 | 0.00 | BrD | ATOM | 1171 | HA | SER | 70 | 11.983 |
| 2.146 | −4.081 | 1.00 | 0.00 | BrD | ATOM | 1172 | CB | SER | 70 | 10.525 |
| 3.552 | −4.767 | 1.00 | 0.00 | BrD | ATOM | 1173 | HB1 | SER | 70 | 11.246 |
| 3.838 | −5.518 | 1.00 | 0.00 | BrD | ATOM | 1174 | HB2 | SER | 70 | 9.546 |
| 3.483 | −5.216 | 1.00 | 0.00 | BrD | ATOM | 1175 | OG | SER | 70 | 10.498 |
| 4.549 | −3.758 | 1.00 | 0.00 | BrD | ATOM | 1176 | HG | SER | 70 | 10.908 |
| 5.349 | −4.088 | 1.00 | 0.00 | BrD | ATOM | 1177 | C | SER | 70 | 10.268 |
| 2.011 | −2.810 | 1.00 | 0.00 | BrD | ATOM | 1178 | O | SER | 70 | 9.252 |
| 1.330 | −2.674 | 1.00 | 0.00 | BrD | ATOM | 1179 | N | LYS | 71 | 10.881 |
| 2.605 | −1.791 | 1.00 | 0.00 | BrD | ATOM | 1180 | HN | LYS | 71 | 11.700 |
| 3.118 | −1.958 | 1.00 | 0.00 | BrD | ATOM | 1181 | CA | LYS | 71 | 10.393 |
| 2.470 | −0.422 | 1.00 | 0.00 | BrD | ATOM | 1182 | HA | LYS | 71 | 10.268 |
| 1.418 | −0.226 | 1.00 | 0.00 | BrD | ATOM | 1183 | CB | LYS | 71 | 11.419 |
| 3.036 | 0.564 | 1.00 | 0.00 | BrD | ATOM | 1184 | HB1 | LYS | 71 | 10.915 |
| 3.287 | 1.485 | 1.00 | 0.00 | BrD | ATOM | 1185 | HB2 | LYS | 71 | 11.848 |
| 3.933 | 0.142 | 1.00 | 0.00 | BrD | ATOM | 1186 | CG | LYS | 71 | 12.550 |
| 2.074 | 0.888 | 1.00 | 0.00 | BrD | ATOM | 1187 | HG1 | LYS | 71 | 13.359 |
| 2.237 | 0.191 | 1.00 | 0.00 | BrD | ATOM | 1188 | HG2 | LYS | 71 | 12.186 |
| 1.061 | 0.791 | 1.00 | 0.00 | BrD | ATOM | 1189 | CD | LYS | 71 | 13.069 |
| 2.279 | 2.102 | 1.00 | 0.00 | BrD | ATOM | 1190 | HD1 | LYS | 71 | 12.295 |
| 2.00 | 3.002 | 1.00 | 0.00 | BrD | ATOM | 1191 | HD2 | LYS | 71 | 13.935 |
| 1.652 | 2.452 | 1.00 | 0.00 | BrD | ATOM | 1192 | CE | LYS | 71 | 13.460 |
| 3.727 | 2.548 | 1.00 | 0.00 | BrD | ATOM | 1193 | HE1 | LYS | 71 | 14.024 |
| 4.084 | 1.699 | 1.00 | 0.00 | BrD | ATOM | 1194 | HE2 | LYS | 71 | 12.561 |
| 4.316 | 2.655 | 1.00 | 0.00 | BrD | ATOM | 1195 | NZ | LYS | 71 | 14.287 |
| 3.879 | 3.777 | 1.00 | 0.00 | BrD | ATOM | 1196 | HZ1 | LYS | 71 | 13.870 |
| 3.334 | 4.558 | 1.00 | 0.00 | BrD | ATOM | 1197 | HZ2 | LYS | 71 | 14.334 |
| 4.880 | 4.055 | 1.00 | 0.00 | BrD | ATOM | 1198 | HZ3 | LYS | 71 | 19.292 |
| 3.933 | 3.604 | 1.00 | 0.00 | BrD | ATOM | 1199 | C | LYS | 71 | 9.041 |
| 3.140 | −0.231 | 1.00 | 0.00 | BrD | ATOM | 1200 | O | LYS | 71 | 7.992 |
| 2.529 | −0.362 | 1.00 | 0.00 | BrD | ATOM | 1201 | N | LYS | 72 | 9.070 |
| 4.447 | 0.109 | 1.00 | 0.00 | BrD | ATOM | 1202 | HN | LYS | 72 | 9.933 |
| 4.898 | 0.211 | 1.00 | 0.00 | BrD | ATOM | 1203 | CA | LYS | 72 | 7.844 |
| 5.201 | 0.351 | 1.00 | 0.00 | BrD | ATOM | 1204 | HA | LYS | 72 | 7.396 |
| 4.818 | 1.255 | 1.00 | 0.00 | BrD | ATOM | 1205 | CB | LYS | 72 | 8.167 |
| 6.684 | 0.947 | 1.00 | 0.00 | BrD | ATOM | 1206 | HB1 | LYS | 72 | 7.249 |
| 7.216 | 0.752 | 1.00 | 0.00 | BrD | ATOM | 1207 | HB2 | LYS | 72 | 8.601 |
| 7.070 | −0.364 | 1.00 | 0.00 | BrD | ATOM | 1208 | CG | LYS | 72 | 9.136 |
| 6.950 | 1.687 | 1.00 | 0.00 | BrD | ATOM | 1209 | HG1 | LYS | 72 | 9.870 |
| 6.158 | 1.715 | 1.00 | 0.00 | BrD | ATOM | 1210 | HG2 | LYS | 72 | 9.629 |
| 7.895 | 1.915 | 1.00 | 0.00 | BrD | ATOM | 1211 | CD | LYS | 72 | 8.419 |
| 7.004 | 3.027 | 1.00 | 0.00 | BrD | ATOM | 1212 | HD1 | LYS | 72 | 7.833 |
| 6.104 | 3.147 | 1.00 | 0.00 | BrD | ATOM | 1213 | HD2 | LYS | 72 | 9.155 |
| 7.065 | 3.816 | 1.00 | 0.00 | BrD | ATOM | 1214 | CE | LYS | 72 | 7.497 |
| 8.208 | 3.117 | 1.00 | 0.00 | BrD | ATOM | 1215 | HE1 | LYS | 72 | 7.708 |
| 8.869 | 2.288 | 1.00 | 0.00 | BrD | ATOM | 1216 | HE2 | LYS | 72 | 6.474 |
| 7.868 | 3.054 | 1.00 | 0.00 | BrD | ATOM | 1217 | NZ | LYS | 72 | 7.681 |
| 8.956 | 4.391 | 1.00 | 0.00 | BrD | ATOM | 1218 | HZ1 | LYS | 72 | 8.150 |
| 8.392 | 5.096 | 1.00 | 0.00 | BrD | ATOM | 1219 | HZ2 | LYS | 72 | 6.798 |
| 9.256 | 4.766 | 1.00 | 0.00 | BrD | ATOM | 1220 | HZ3 | LYS | 72 | 8.267 |
| 9.800 | 4.229 | 1.00 | 0.00 | BrD | ATOM | 1221 | C | LYS | 72 | 6.892 |
| 5.034 | −0.794 | 1.00 | 0.00 | BrD | ATOM | 1222 | O | LYS | 72 | 5.641 |
| 5.001 | −0.578 | 1.00 | 0.00 | BrD | ATOM | 1223 | N | LEU | 73 | 7.370 |
| 4.933 | −2.011 | 1.00 | 0.00 | BrD | ATOM | 1224 | HN | LEU | 73 | 8.343 |
| 4.972 | −2.121 | 1.00 | 0.00 | BrD | ATOM | 1225 | CA | LEU | 73 | 6.528 |
| 4.786 | −3.191 | 1.00 | 0.00 | BrD | ATOM | 1226 | HA | LEU | 73 | 5.982 |
| 5.708 | −3.323 | 1.00 | 0.00 | BrD | ATOM | 1227 | CB | LEU | 73 | 7.394 |
| 4.539 | −4.427 | 1.00 | 0.00 | BrD | ATOM | 1228 | HB1 | LEU | 73 | 7.447 |
| 3.474 | −4.596 | 1.00 | 0.00 | BrD | ATOM | 1229 | HB2 | LEU | 73 | 8.389 |
| 4.903 | −4.219 | 1.00 | 0.00 | BrD | ATOM | 1230 | CG | LEU | 73 | 6.896 |
| 5.206 | −5.711 | 1.00 | 0.00 | BrD | ATOM | 1231 | HG | LEU | 73 | 5.937 |
| 4.747 | −5.978 | 1.00 | 0.00 | BrD | ATOM | 1232 | CD1 | LEU | 73 | 7.860 |
| 4.943 | −6.857 | 1.00 | 0.00 | BrD | ATOM | 1233 | HD11 | LEU | 73 | 8.166 |
| 3.907 | −6.840 | 1.00 | 0.00 | BrD | ATOM | 1234 | HD12 | LEU | 73 | 8.729 |
| 5.576 | −6.750 | 1.00 | 0.00 | BrD | ATOM | 1235 | HD13 | LEU | 73 | 7.372 |
| 5.158 | −7.796 | 1.00 | 0.00 | BrD | ATOM | 1236 | CD2 | LEU | 73 | 6.710 |

TABLE 6-continued

Atomic Structure Coordinates of the
P/CAF Bromodomain/Acetyl-Histamine Complex

| | | | | | | | | | |
|---|---|---|---|---|---|---|---|---|---|
| 6.701 | −5.498 | 1.00 | 0.00 | BrD | ATOM | 1237 | HD21 | LEU | 73 | 7.104 |
| 6.979 | −4.531 | 1.00 | 0.00 | BrD | ATOM | 1238 | HD22 | LEU | 73 | 5.659 |
| 6.943 | −5.541 | 1.00 | 0.00 | BrD | ATOM | 1239 | HD23 | LEU | 73 | 7.237 |
| 7.243 | −6.270 | 1.00 | 0.00 | BrD | ATOM | 1240 | C | LEU | 73 | 5.528 |
| 3.645 | −3.025 | 1.00 | 0.00 | BrD | ATOM | 1241 | O | LEU | 73 | 4.318 |
| 3.860 | −3.061 | 1.00 | 0.00 | BrD | ATOM | 1242 | N | PHE | 74 | 5.041 |
| 2.432 | −2.860 | 1.00 | 0.00 | BrD | ATOM | 1243 | HN | PHE | 74 | 7.014 |
| 2.322 | −2.855 | 1.00 | 0.00 | BrD | ATOM | 1244 | CA | PHE | 74 | 5.192 |
| 1.293 | −2.721 | 1.00 | 0.00 | BrD | ATOM | 1245 | HA | PHE | 74 | 4.364 |
| 1.359 | −3.406 | 1.00 | 0.00 | BrD | ATOM | 1246 | CB | PHE | 74 | 5.984 |
| 0.003 | −3.084 | 1.00 | 0.00 | BrD | ATOM | 1247 | HB1 | PHE | 74 | 6.730 |
| 0.181 | −2.324 | 1.00 | 0.00 | BrD | ATOM | 1248 | HB2 | PHE | 74 | 6.473 |
| 0.154 | −4.030 | 1.00 | 0.00 | BrD | ATOM | 1249 | CG | PHE | 74 | 5.141 |
| 1.240 | −3.202 | 1.00 | 0.00 | BrD | ATOM | 1250 | CD1 | PHE | 74 | 4.992 |
| 1.851 | −4.431 | 1.00 | 0.00 | BrD | ATOM | 1251 | HD1 | PHE | 74 | 5.412 |
| 1.425 | −5.311 | 1.00 | 0.00 | BrD | ATOM | 1252 | CD2 | PHE | 74 | 4.546 |
| 1.797 | −2.082 | 1.00 | 0.00 | BrD | ATOM | 1253 | HD2 | PHE | 74 | 4.691 |
| 1.332 | −1.118 | 1.00 | 0.00 | BrD | ATOM | 1254 | CE1 | PHE | 74 | 4.181 |
| 2.993 | −4.542 | 1.00 | 0.00 | BrD | ATOM | 1255 | HE1 | PHE | 74 | 4.039 |
| 3.458 | −5.506 | 1.00 | 0.00 | BrD | ATOM | 1256 | CE2 | PHE | 74 | 3.780 |
| 2.942 | −2.186 | 1.00 | 0.00 | BrD | ATOM | 1257 | HE2 | PHE | 74 | 3.315 |
| 3.362 | −1.304 | 1.00 | 0.00 | BrD | ATOM | 1258 | CZ | PHE | 74 | 3.593 |
| 3.538 | −3.418 | 1.00 | 0.00 | BrD | ATOM | 1259 | HZ | PHE | 74 | 2.989 |
| 4.430 | −3.502 | 1.00 | 0.00 | BrD | ATOM | 1260 | C | PHE | 74 | 4.643 |
| 1.116 | −1.305 | 1.00 | 0.00 | BrD | ATOM | 1261 | O | PHE | 74 | 3.501 |
| 0.694 | −1.111 | 1.00 | 0.00 | BrD | ATOM | 1262 | N | MET | 75 | 5.466 |
| 1.447 | −0.318 | 1.00 | 0.00 | BrD | ATOM | 1263 | HN | MET | 75 | 6.372 |
| 1.755 | −0.532 | 1.00 | 0.00 | BrD | ATOM | 1264 | CA | MET | 75 | 9.072 |
| 1.308 | 1.078 | 1.00 | 0.00 | BrD | ATOM | 1265 | HA | MET | 75 | 4.403 |
| 0.339 | 1.187 | 1.00 | 0.00 | BrD | ATOM | 1266 | CB | MET | 75 | 6.300 |
| 1.365 | 1.984 | 1.00 | 0.00 | BrD | ATOM | 1267 | HB1 | MET | 75 | 6.001 |
| 1.734 | 2.954 | 1.00 | 0.00 | BrD | ATOM | 1268 | HB2 | MET | 75 | 7.021 |
| 2.043 | 1.554 | 1.00 | 0.00 | BrD | ATOM | 1269 | CG | MET | 75 | 6.966 |
| 0.014 | 2.171 | 1.00 | 0.00 | BrD | ATOM | 1270 | HG1 | MET | 75 | 7.924 |
| 0.029 | 3.092 | 1.00 | 0.00 | BrD | ATOM | 1271 | HG2 | MET | 75 | 6.200 |
| 0.744 | 2.231 | 1.00 | 0.00 | BrD | ATOM | 1272 | SD | MET | 75 | 8.086 |
| 0.403 | 0.822 | 1.00 | 0.00 | BrD | ATOM | 1273 | CE | MET | 75 | 8.173 |
| 2.182 | 1.002 | 1.00 | 0.00 | BrD | ATOM | 1274 | HE1 | MET | 75 | 7.211 |
| 2.557 | 1.319 | 1.00 | 0.00 | BrD | ATOM | 1275 | HE2 | MET | 75 | 8.917 |
| 2.435 | 1.741 | 1.00 | 0.00 | BrD | ATOM | 1276 | HE3 | MET | 75 | 8.438 |
| 2.630 | 0.054 | 1.00 | 0.00 | BrD | ATOM | 1277 | C | MET | 75 | 4.067 |
| 2.374 | 1.496 | 1.00 | 0.00 | BrD | ATOM | 1278 | O | MET | 75 | 2.939 |
| 2.052 | 1.866 | 1.00 | 0.00 | BrD | ATOM | 1279 | N | ALA | 76 | 4.472 |
| 3.642 | 1.462 | 1.00 | 0.00 | BrD | ATOM | 1280 | HN | ALA | 76 | 5.380 |
| 3.854 | 1.163 | 1.00 | 0.00 | BrD | ATOM | 1281 | CA | ALA | 76 | 3.573 |
| 4.722 | 1.861 | 1.00 | 0.00 | BrD | ATOM | 1282 | HA | ALA | 76 | 3.409 |
| 4.638 | 2.922 | 1.00 | 0.00 | BrD | ATOM | 1283 | CE | ALA | 76 | 4.182 |
| 6.083 | 1.595 | 1.00 | 0.00 | BrD | ATOM | 1284 | HB1 | ALA | 76 | 4.234 |
| 6.252 | 0.931 | 1.00 | 0.00 | BrD | ATOM | 1285 | HB2 | ALA | 76 | 5.172 |
| 6.125 | 2.021 | 1.00 | 0.00 | BrD | ATOM | 1286 | HB3 | ALA | 76 | 3.558 |
| 6.842 | 2.049 | 1.00 | 0.00 | BrD | ATOM | 1287 | C | ALA | 76 | 2.240 |
| 4.601 | 1.147 | 1.00 | 0.00 | BrD | ATOM | 1288 | O | ALA | 76 | 1.211 |
| 5.026 | 1.666 | 1.00 | 0.00 | BrD | ATOM | 1289 | N | ASP | 77 | 2.270 |
| 4.014 | −0.044 | 1.00 | 0.00 | BrD | ATOM | 1290 | HN | ASP | 77 | 3.124 |
| 3.685 | −0.394 | 1.00 | 0.00 | BrD | ATOM | 1291 | CA | ASP | 77 | 1.058 |
| 3.804 | −0.818 | 1.00 | 0.00 | BrD | ATOM | 1292 | HA | ASP | 77 | 0.460 |
| 4.701 | −0.750 | 1.00 | 0.00 | BrD | ATOM | 1293 | CB | ASP | 77 | 1.392 |
| 3.934 | −2.283 | 1.00 | 0.00 | BrD | ATOM | 1294 | HB1 | ASP | 77 | 2.196 |
| 2.817 | −2.334 | 1.00 | 0.00 | BrD | ATOM | 1295 | HB2 | ASP | 77 | 0.521 |
| 3.128 | −2.776 | 1.00 | 0.00 | BrD | ATOM | 1296 | CG | ASP | 77 | 1.817 |
| 4.790 | −3.018 | 1.00 | 0.00 | BrD | ATOM | 1297 | OG1 | ASP | 77 | 1.353 |
| 4.995 | −4.159 | 1.00 | 0.00 | BrD | ATOM | 1298 | OD2 | ASP | 77 | 2.613 |
| 5.569 | −2.453 | 1.00 | 0.00 | BrD | ATOM | 1299 | C | ASP | 77 | 0.268 |
| 2.641 | −0.243 | 1.00 | 0.00 | BrD | ATOM | 1300 | O | ASP | 77 | −0.950 |
| 2.717 | −0.113 | 1.00 | 0.00 | BrD | ATOM | 1301 | N | LEU | 78 | 0.970 |
| 1.569 | 0.119 | 1.00 | 0.00 | BrD | ATOM | 1302 | HN | LEU | 78 | 1.944 |
| 1.570 | 0.006 | 1.00 | 0.00 | BrD | ATOM | 1303 | CA | LEU | 78 | 0.319 |
| 0.411 | 0.711 | 1.00 | 0.00 | BrD | ATOM | 1304 | HA | LEU | 78 | −0.493 |
| 0.122 | 0.060 | 1.00 | 0.00 | BrD | ATOM | 1305 | CB | LEU | 78 | 1.280 |
| 0.761 | 0.849 | 1.00 | 0.00 | BrD | ATOM | 1306 | HB1 | LEU | 78 | 2.212 |
| 0.516 | 0.350 | 1.00 | 0.00 | BrD | ATOM | 1307 | HB2 | LEU | 78 | 1.480 |
| 0.922 | 1.900 | 1.00 | 0.00 | BrD | ATOM | 1308 | OG | LEU | 78 | 0.736 |
| 2.092 | 0.259 | 1.00 | 0.00 | BrD | ATOM | 1309 | HG | LEU | 78 | −0.338 |
| 2.023 | 0.293 | 1.00 | 0.00 | BrD | ATOM | 1310 | CD1 | LEU | 78 | 1.143 |
| 2.189 | −1.193 | 1.00 | 0.00 | BrD | ATOM | 1311 | HD11 | LEU | 78 | 1.413 |
| 3.213 | −1.398 | 1.00 | 0.00 | BrD | ATOM | 1312 | HD12 | LEU | 78 | 1.985 |
| 1.543 | −1.388 | 1.00 | 0.00 | BrD | ATOM | 1313 | HD13 | LEU | 78 | 0.317 |

TABLE 6-continued

Atomic Structure Coordinates of the
P/CAF Bromodomain/Acetyl-Histamine Complex

| | | | | | | | | | |
|---|---|---|---|---|---|---|---|---|---|
| 1.901 | −1.625 | 1.00 | 0.00 | BrD | ATOM | 1314 | CD2 | LEU | 78 | 1.189 |
| 3.236 | 1.078 | 1.00 | 0.00 | BrD | ATOM | 1315 | HD12 | LEU | 78 | 2.264 |
| 3.266 | 1.099 | 1.00 | 0.00 | BrD | ATOM | 1316 | HD22 | LEU | 78 | 0.808 |
| 4.145 | 0.640 | 1.00 | 0.00 | BrD | ATOM | 1317 | HD23 | LEU | 78 | 0.809 |
| 3.130 | 2.084 | 1.00 | 0.00 | BrD | ATOM | 1318 | C | LEU | 78 | −0.293 |
| 0.769 | 2.066 | 1.00 | 0.00 | BrD | ATOM | 1319 | O | LEU | 78 | −1.459 |
| 0.663 | 2.292 | 1.00 | 0.00 | BrD | ATOM | 1320 | N | GLN | 79 | 0.611 |
| 1.252 | 2.952 | 1.00 | 0.00 | BrD | ATOM | 1321 | HN | GLN | 79 | 1.551 |
| 1.353 | 2.700 | 1.00 | 0.00 | BrD | ATOM | 1322 | CA | GLN | 79 | 0.171 |
| 1.723 | 4.254 | 1.00 | 0.00 | BrD | ATOM | 1323 | HA | GLN | 79 | −0.198 |
| 0.873 | 4.807 | 1.00 | 0.00 | BrD | ATOM | 1324 | CB | GLN | 79 | 1.338 |
| 2.361 | 5.015 | 1.00 | 0.00 | BrD | ATOM | 1325 | HB1 | GLN | 79 | 1.045 |
| 2.920 | 6.038 | 1.00 | 0.00 | BrD | ATOM | 1326 | HB2 | GLN | 79 | 2.180 |
| 1.686 | 4.991 | 1.00 | 0.00 | BrD | ATOM | 1327 | OG | GLN | 79 | 1.781 |
| 3.694 | 4.448 | 1.00 | 0.00 | BrD | ATOM | 1328 | HG1 | GLN | 79 | 1.501 |
| 3.740 | 3.407 | 1.00 | 0.00 | BrD | ATOM | 1329 | HG2 | GLN | 79 | 2.855 |
| 3.766 | 4.538 | 1.00 | 0.00 | BrD | ATOM | 1330 | CD | GLN | 79 | 1.158 |
| 4.871 | 5.172 | 1.00 | 0.00 | BrD | ATOM | 1331 | OE1 | GLN | 79 | 0.409 |
| 5.651 | 4.585 | 1.00 | 0.00 | BrD | ATOM | 1332 | NE2 | GLN | 79 | 1.467 |
| 5.005 | 6.457 | 1.00 | 0.00 | BrD | ATOM | 1333 | HE21 | GLN | 79 | 1.079 |
| 5.757 | 6.950 | 1.00 | 0.00 | BrD | ATOM | 1334 | HE22 | GLN | 79 | 2.070 |
| 4.346 | 6.859 | 1.00 | 0.00 | BrD | ATOM | 1335 | C | GLN | 79 | −0.960 |
| 2.732 | 4.074 | 1.00 | 0.00 | BrD | ATOM | 1336 | O | GLN | 79 | −1.787 |
| 2.924 | 4.964 | 1.00 | 0.00 | BrD | ATOM | 1337 | N | ARG | 80 | −0.997 |
| 3.356 | 2.895 | 1.00 | 0.00 | BrD | ATOM | 1338 | HN | ARG | 80 | −0.321 |
| 3.140 | 2.216 | 1.00 | 0.00 | BrD | ATOM | 1339 | CA | ARG | 80 | −2.048 |
| 4.306 | 2.560 | 1.00 | 0.00 | BrD | ATOM | 1340 | HA | ARG | 80 | −2.275 |
| 4.880 | 3.447 | 1.00 | 0.00 | BrD | ATOM | 1341 | CB | ARG | 80 | −1.579 |
| 5.253 | 1.451 | 1.00 | 0.00 | BrD | ATOM | 1342 | HB1 | ARG | 80 | −2.401 |
| 5.429 | 0.773 | 1.00 | 0.00 | BrD | ATOM | 1343 | HB2 | ARG | 80 | −0.770 |
| 4.785 | 0.908 | 1.00 | 0.00 | BrD | ATOM | 1344 | CG | ARG | 80 | −1.092 |
| 6.598 | 1.964 | 1.00 | 0.00 | BrD | ATOM | 1345 | HG1 | ARG | 80 | −0.290 |
| 6.434 | 2.669 | 1.00 | 0.00 | BrD | ATOM | 1346 | HG2 | ARG | 80 | −0.728 |
| 7.180 | 1.131 | 1.00 | 0.00 | BrD | ATOM | 1347 | CD | ARG | 80 | −2.206 |
| 7.367 | 2.654 | 1.00 | 0.00 | BrD | ATOM | 1348 | HA1 | ARG | 80 | −3.054 |
| 6.711 | 2.780 | 1.00 | 0.00 | BrD | ATOM | 1349 | HD2 | ARG | 80 | −2.486 |
| 8.203 | 2.031 | 1.00 | 0.00 | BrD | ATOM | 1350 | NE | ARG | 80 | −1.796 |
| 7.867 | 3.962 | 1.00 | 0.00 | BrD | ATOM | 1351 | HE | ARG | 80 | −0.837 |
| 7.874 | 4.166 | 1.00 | 0.00 | BrD | ATOM | 1352 | CZ | ARG | 80 | −2.648 |
| 8.310 | 4.881 | 1.00 | 0.00 | BrD | ATOM | 1353 | HH1 | ARG | 80 | −2.198 |
| 8.750 | 6.047 | 1.00 | 0.00 | BrD | ATOM | 1354 | HH11 | ARG | 80 | −1.216 |
| 8.749 | 6.237 | 1.00 | 0.00 | BrD | ATOM | 1355 | HH12 | ARG | 80 | −2.840 |
| 9.083 | 6.738 | 1.00 | 0.00 | BrD | ATOM | 1356 | HH2 | ARG | 80 | −3.950 |
| 8.314 | 4.633 | 1.00 | 0.00 | BrD | ATOM | 1357 | HH21 | ARG | 80 | −4.590 |
| 8.647 | 5.326 | 1.00 | 0.00 | BrD | ATOM | 1358 | HH22 | ARG | 80 | −4.293 |
| 7.983 | 3.754 | 1.00 | 0.00 | BrD | ATOM | 1359 | C | ARG | 80 | −3.305 |
| 3.568 | 2.114 | 1.00 | 0.00 | BrD | ATOM | 1360 | O | ARG | 80 | −4.417 |
| 3.922 | 2.502 | 1.00 | 0.00 | BrD | ATOM | 1361 | N | VAL | 81 | −3.116 |
| 2.536 | 1.293 | 1.00 | 0.00 | BrD | ATOM | 1362 | HN | VAL | 81 | −2.203 |
| 2.301 | 1.024 | 1.00 | 0.00 | BrD | ATOM | 1363 | CA | VAL | 81 | −4.231 |
| 1.738 | 0.799 | 1.00 | 0.00 | BrD | ATOM | 1364 | HA | VAL | 81 | −4.849 |
| 2.374 | 0.182 | 1.00 | 0.00 | BrD | ATOM | 1364 | CB | VAL | 81 | −3.742 |
| 0.556 | −0.063 | 1.00 | 0.00 | BrD | ATOM | 1366 | HB | VAL | 81 | −3.104 |
| 0.068 | 0.946 | 1.00 | 0.00 | BrD | ATOM | 1367 | CG1 | VAL | 81 | −2.926 |
| 1.057 | −1.244 | 1.00 | 0.00 | BrD | ATOM | 1368 | HG11 | VAL | 81 | −3.462 |
| 0.861 | −2.159 | 1.00 | 0.00 | BrD | ATOM | 1369 | HG12 | VAL | 81 | −1.973 |
| 0.545 | −1.268 | 1.00 | 0.00 | BrD | ATOM | 1370 | HG13 | VAL | 81 | −2.763 |
| 2.119 | −1.146 | 1.00 | 0.00 | BrD | ATOM | 1371 | CG2 | VAL | 81 | −4.916 |
| 0.287 | −0.539 | 1.00 | 0.00 | BrD | ATOM | 1372 | HG21 | VAL | 81 | −4.851 |
| 0.425 | −1.608 | 1.00 | 0.00 | BrD | ATOM | 1373 | HG22 | VAL | 81 | −5.841 |
| 0.215 | −0.297 | 1.00 | 0.00 | BrD | ATOM | 1374 | HG23 | VAL | 81 | −4.890 |
| 1.250 | −0.050 | 1.00 | 0.00 | BrD | ATOM | 1375 | C | VAL | 81 | −5.069 |
| 1.206 | 1.957 | 1.00 | 0.00 | BrD | ATOM | 1376 | O | VAL | 81 | −6.293 |
| 1.339 | 1.964 | 1.00 | 0.00 | BrD | ATOM | 1377 | N | PHE | 82 | −4.400 |
| 0.610 | 2.937 | 1.00 | 0.00 | BrD | ATOM | 1378 | HN | PHE | 82 | −3.424 |
| 0.340 | 2.876 | 1.00 | 0.00 | BrD | ATOM | 1379 | CA | PHE | 82 | −5.079 |
| 0.070 | 4.108 | 1.00 | 0.00 | BrD | ATOM | 1380 | HA | PHE | 82 | −5.919 |
| 0.914 | 3.764 | 1.00 | 0.00 | BrD | ATOM | 1381 | CB | PHE | 82 | −4.131 |
| 0.833 | 4.899 | 1.00 | 0.00 | BrD | ATOM | 1382 | HB1 | PHE | 82 | −3.486 |
| 0.220 | 5.511 | 1.00 | 0.00 | BrD | ATOM | 1383 | HB2 | PHE | 82 | −4.712 |
| 1.484 | 5.536 | 1.00 | 0.00 | BrD | ATOM | 1384 | CG | PHE | 82 | −3.261 |
| 1.695 | 4.028 | 1.00 | 0.00 | BrD | ATOM | 1385 | CD1 | PHE | 82 | −1.979 |
| 2.035 | 4.428 | 1.00 | 0.00 | BrD | ATOM | 1386 | HD1 | PHE | 82 | −1.606 |
| 1.677 | 5.376 | 1.00 | 0.00 | BrD | ATOM | 1387 | CD2 | PHE | 82 | −3.725 |
| 2.162 | 2.809 | 1.00 | 0.00 | BrD | ATOM | 1388 | HD2 | PHE | 82 | −4.723 |
| 1.901 | 2.487 | 1.00 | 0.00 | BrD | ATOM | 1389 | CE1 | PHE | 82 | −1.177 |
| 2.827 | 3.628 | 1.00 | 0.00 | BrD | ATOM | 1390 | HE1 | PHE | 82 | −0.179 |

TABLE 6-continued

Atomic Structure Coordinates of the
P/CAF Bromodomain/Acetyl-Histamine Complex

| | | | | | | | | | |
|---|---|---|---|---|---|---|---|---|---|
| 3.086 | 3.951 | 1.00 | 0.00 | BrD | ATOM | 1391 | CE2 | PHE | 82 | −2.928 |
| 2.952 | 2.004 | 1.00 | 0.00 | BrD | ATOM | 1392 | HE2 | PHE | 82 | −3.302 |
| 3.311 | 1.057 | 1.00 | 0.00 | BrD | ATOM | 1393 | CZ | PHE | 82 | −1.651 |
| 3.284 | 2.413 | 1.00 | 0.00 | BrD | ATOM | 1394 | HZ | PHE | 82 | −1.029 |
| 3.906 | 1.789 | 1.00 | 0.00 | BrD | ATOM | 1395 | C | PHE | 82 | −5.594 |
| 1.197 | 4.994 | 1.00 | 0.00 | BrD | ATOM | 1396 | O | PHE | 82 | −6.745 |
| 1.180 | 5.431 | 1.00 | 0.00 | BrD | ATOM | 1397 | N | THR | 83 | −4.740 |
| 2.185 | 5.241 | 1.00 | 0.00 | BrD | ATOM | 1398 | HN | THR | 83 | −3.841 |
| 2.149 | 4.852 | 1.00 | 0.00 | BrD | ATOM | 1399 | CA | THR | 83 | −5.119 |
| 3.337 | 6.048 | 1.00 | 0.00 | BrD | ATOM | 1400 | HA | THR | 83 | −5.427 |
| 2.977 | 7.019 | 1.00 | 0.00 | BrD | ATOM | 1401 | CB | THR | 83 | −3.927 |
| 4.282 | 6.216 | 1.00 | 0.00 | BrD | ATOM | 1402 | HB | THR | 83 | −3.525 |
| 4.916 | 5.240 | 1.00 | 0.00 | BrD | ATOM | 1403 | OG | THR | 83 | −2.905 |
| 3.666 | 6.982 | 1.00 | 0.00 | BrD | ATOM | 1404 | HG1 | THR | 83 | −3.138 |
| 3.699 | 7.913 | 1.00 | 0.00 | BrD | ATOM | 1405 | CG2 | THR | 83 | −4.263 |
| 9.989 | 6.892 | 1.00 | 0.00 | BrD | ATOM | 1406 | HG21 | THR | 83 | −4.813 |
| 6.222 | 6.196 | 1.00 | 0.00 | BrD | ATOM | 1407 | HG22 | THR | 83 | −3.379 |
| 6.085 | 7.214 | 1.00 | 0.00 | BrD | ATOM | 1408 | HG23 | THR | 83 | −4.910 |
| 9.391 | 7.749 | 1.00 | 0.00 | BrD | ATOM | 1409 | C | THR | 83 | −6.286 |
| 4.077 | 5.402 | 1.00 | 0.00 | BrD | ATOM | 1410 | O | THR | 83 | −7.073 |
| 4.735 | 6.082 | 1.00 | 0.00 | BrD | ATOM | 1411 | N | ASN | 84 | −6.391 |
| 3.996 | 4.082 | 1.00 | 0.00 | BrD | ATOM | 1412 | HN | ASN | 84 | −5.732 |
| 3.418 | 3.597 | 1.00 | 0.00 | BrD | ATOM | 1413 | CA | ASN | 84 | −7.458 |
| 4.609 | 3.334 | 1.00 | 0.00 | BrD | ATOM | 1414 | HA | ASN | 84 | −7.546 |
| 5.622 | 3.698 | 1.00 | 0.00 | BrD | ATOM | 1415 | CB | ASN | 84 | −7.113 |
| 4.640 | 1.844 | 1.00 | 0.00 | BrD | ATOM | 1416 | HB1 | ASN | 84 | −7.095 |
| 3.629 | 1.464 | 1.00 | 0.00 | BrD | ATOM | 1417 | HB2 | ASN | 84 | −6.138 |
| 5.086 | 1.716 | 1.00 | 0.00 | BrD | ATOM | 1418 | CG | ASN | 84 | −8.115 |
| 5.438 | 1.035 | 1.00 | 0.00 | BrD | ATOM | 1419 | OD1 | ASN | 84 | −9.269 |
| 5.596 | 1.433 | 1.00 | 0.00 | BrD | ATOM | 1420 | ND2 | ASN | 84 | −7.677 |
| 5.945 | −0.111 | 1.00 | 0.00 | BrD | ATOM | 1421 | HD21 | ASN | 84 | −6.745 |
| 5.778 | −0.365 | 1.00 | 0.00 | BrD | ATOM | 1422 | HD22 | ASN | 84 | −8.302 |
| 6.465 | −0.655 | 1.00 | 0.00 | BrD | ATOM | 1423 | C | ASN | 84 | −8.788 |
| 3.893 | 3.544 | 1.00 | 0.00 | BrD | ATOM | 1424 | O | ASN | 84 | −9.745 |
| 4.477 | 4.051 | 1.00 | 0.00 | BrD | ATOM | 1425 | N | CYS | 85 | −8.842 |
| 2.623 | 3.150 | 1.00 | 0.00 | BrD | ATOM | 1426 | HN | CYS | 85 | −8.046 |
| 2.213 | 2.791 | 1.00 | 0.00 | BrD | ATOM | 1427 | CA | CYS | 85 | −10.058 |
| 1.827 | 3.291 | 1.00 | 0.00 | BrD | ATOM | 1428 | HA | CYS | 85 | −10.778 |
| 2.193 | 2.575 | 1.00 | 0.00 | BrD | ATOM | 1429 | CB | CYS | 85 | −9.765 |
| 0.394 | 2.995 | 1.00 | 0.00 | BrD | ATOM | 1430 | HB1 | CYS | 85 | −8.806 |
| 0.277 | 2.504 | 1.00 | 0.00 | BrD | ATOM | 1431 | HB2 | CYS | 85 | −9.732 |
| 0.193 | 3.926 | 1.00 | 0.00 | BrD | ATOM | 1432 | SG | CYS | 85 | −10.992 |
| 0.444 | 1.933 | 1.00 | 0.00 | BrD | ATOM | 1433 | HG | CYS | 85 | −10.844 |
| 0.144 | 1.033 | 1.00 | 0.00 | BrD | ATOM | 1434 | C | CYS | 85 | −10.645 |
| 1.965 | 4.692 | 1.00 | 0.00 | BrD | ATOM | 1435 | O | CYS | 85 | −11.842 |
| 2.203 | 4.854 | 1.00 | 0.00 | BrD | ATOM | 1436 | N | LYS | 86 | −9.794 |
| 1.817 | 5.701 | 1.00 | 0.00 | BrD | ATOM | 1437 | HN | LYS | 86 | −8.852 |
| 1.626 | 5.508 | 1.00 | 0.00 | BrD | ATOM | 1438 | CA | LYS | 86 | −10.228 |
| 1.921 | 7.089 | 1.00 | 0.00 | BrD | ATOM | 1439 | HA | LYS | 86 | −11.111 |
| 1.310 | 7.203 | 1.00 | 0.00 | BrD | ATOM | 1440 | CB | LYS | 86 | −9.137 |
| 1.395 | 8.023 | 1.00 | 0.00 | BrD | ATOM | 1441 | HB1 | LYS | 86 | −9.063 |
| 0.325 | 7.903 | 1.00 | 0.00 | BrD | ATOM | 1442 | HB2 | LYS | 86 | −9.416 |
| 1.616 | 9.043 | 1.00 | 0.00 | BrD | ATOM | 1443 | CG | LYS | 86 | −7.768 |
| 1.998 | 7.763 | 1.00 | 0.00 | BrD | ATOM | 1444 | HG1 | LYS | 86 | −7.809 |
| 2.583 | 6.857 | 1.00 | 0.00 | BrD | ATOM | 1445 | HG2 | LYS | 86 | −7.050 |
| 1.199 | 7.645 | 1.00 | 0.00 | BrD | ATOM | 1446 | CD | LYS | 86 | −7.32 |
| 2.892 | 8.910 | 1.00 | 0.00 | BrD | ATOM | 1447 | HD1 | LYS | 86 | −6.477 |
| 3.478 | 8.590 | 1.00 | 0.00 | BrD | ATOM | 1448 | HD2 | LYS | 86 | −8.140 |
| 3.548 | 9.177 | 1.00 | 0.00 | BrD | ATOM | 1449 | CE | LYS | 86 | −6.929 |
| 2.076 | 10.130 | 1.00 | 0.00 | BrD | ATOM | 1450 | HE1 | LYS | 86 | −7.418 |
| 1.114 | 10.078 | 1.00 | 0.00 | BrD | ATOM | 1451 | HE2 | LYS | 86 | −5.858 |
| 1.935 | 10.120 | 1.00 | 0.00 | BrD | ATOM | 1452 | NZ | LYS | 86 | −7.317 |
| 2.749 | 11.400 | 1.00 | 0.00 | BrD | ATOM | 1453 | HZ1 | LYS | 86 | −8.019 |
| 2.174 | 11.909 | 1.00 | 0.00 | BrD | ATOM | 1454 | HZ2 | LYS | 86 | −7.729 |
| 3.682 | 11.199 | 1.00 | 0.00 | BrD | ATOM | 1455 | HZ3 | LYS | 86 | −6.482 |
| 2.874 | 12.008 | 1.00 | 0.00 | BrD | ATOM | 1456 | C | LYS | 86 | −10.579 |
| 3.360 | 7.456 | 1.00 | 0.00 | BrD | ATOM | 1457 | O | LYS | 86 | −11.293 |
| 3.603 | 8.429 | 1.00 | 0.00 | BrD | ATOM | 1458 | N | GLU | 87 | −10.076 |
| 4.314 | 6.676 | 1.00 | 0.00 | BrD | ATOM | 1459 | HN | GLU | 87 | −9.514 |
| 4.064 | 5.914 | 1.00 | 0.00 | BrD | ATOM | 1460 | CA | GLU | 87 | −10.390 |
| 5.724 | 6.926 | 1.00 | 0.00 | BrD | ATOM | 1461 | HA | GLU | 87 | −10.510 |
| 5.848 | 7.986 | 1.00 | 0.00 | BrD | ATOM | 1462 | CB | GLU | 87 | −9.158 |
| 6.583 | 6.498 | 1.00 | 0.00 | BrD | ATOM | 1463 | HB1 | GLU | 87 | −9.513 |
| 7.572 | 6.249 | 1.00 | 0.00 | BrD | ATOM | 1464 | HB2 | GLU | 87 | −8.706 |
| 6.141 | 5.622 | 1.00 | 0.00 | BrD | ATOM | 1465 | CG | GLU | 87 | −8.088 |
| 6.716 | 7.570 | 1.00 | 0.00 | BrD | ATOM | 1466 | HG1 | GLU | 87 | −7.954 |
| 5.757 | 8.048 | 1.00 | 0.00 | BrD | ATOM | 1467 | HG2 | GLU | 87 | −7.163 |

TABLE 6-continued

Atomic Structure Coordinates of the
P/CAF Bromodomain/Acetyl-Histamine Complex

| | | | | | | | | | | |
|---|---|---|---|---|---|---|---|---|---|---|
| 7.016 | 7.101 | 1.00 | 0.00 | BrD | ATOM | 1468 | CD | GLU | 87 | −8.446 |
| 7.740 | 8.629 | 1.00 | 0.00 | BrD | ATOM | 1469 | OE1 | GLU | 87 | −9.092 |
| 8.751 | 8.283 | 1.00 | 0.00 | BrD | ATOM | 1470 | OE2 | GLU | 87 | −8.079 |
| 7.931 | 9.805 | 1.00 | 0.00 | BrD | ATOM | 1471 | C | GLU | 87 | −11.604 |
| 6.172 | 6.183 | 1.00 | 0.00 | BrD | ATOM | 1472 | O | GLU | 87 | −12.942 |
| 6.692 | 6.787 | 1.00 | 0.00 | BrD | ATOM | 1473 | N | TYR | 88 | −11.617 |
| 5.962 | 4.871 | 1.00 | 0.00 | BrD | ATOM | 1474 | HN | TYR | 88 | −10.840 |
| 5.541 | 4.446 | 1.00 | 0.00 | BrD | ATOM | 1475 | CA | TYR | 88 | −12.759 |
| 6.339 | 4.046 | 1.00 | 0.00 | BrD | ATOM | 1476 | HA | TYR | 88 | −13.070 |
| 7.330 | 4.344 | 1.00 | 0.00 | BrD | ATOM | 1477 | CB | TYR | 88 | −12.361 |
| 6.363 | 2.568 | 1.00 | 0.00 | BrD | ATOM | 1478 | HB1 | TYR | 88 | −11.310 |
| 6.602 | 2.489 | 1.00 | 0.00 | BrD | ATOM | 1479 | HB2 | TYR | 88 | −12.537 |
| 5.388 | 2.139 | 1.00 | 0.00 | BrD | ATOM | 1480 | CG | TYR | 88 | −13.128 |
| 7.376 | 1.748 | 1.00 | 0.00 | BrD | ATOM | 1481 | CD1 | TYR | 88 | −12.606 |
| 8.640 | 1.505 | 1.00 | 0.00 | BrD | ATOM | 1482 | HD1 | TYR | 88 | −11.639 |
| 8.896 | 1.914 | 1.00 | 0.00 | BrD | ATOM | 1483 | CD2 | TYR | 88 | −14.372 |
| 7.066 | 1.213 | 1.00 | 0.00 | BrD | ATOM | 1484 | HD2 | TYR | 88 | −14.792 |
| 6.087 | 1.392 | 1.00 | 0.00 | BrD | ATOM | 1485 | CE1 | TYR | 88 | −13.302 |
| 9.568 | 0.795 | 1.00 | 0.00 | BrD | ATOM | 1486 | HE1 | TYR | 88 | −12.880 |
| 10.546 | 0.578 | 1.00 | 0.00 | BrD | ATOM | 1487 | CE2 | TYR | 88 | −15.075 |
| 7.989 | 0.462 | 1.00 | 0.00 | BrD | ATOM | 1488 | HE2 | TYR | 88 | −16.042 |
| 7.730 | 0.055 | 1.00 | 0.00 | BrD | ATOM | 1489 | CZ | TYR | 88 | −14.536 |
| 9.238 | 0.236 | 1.00 | 0.00 | BrD | ATOM | 1490 | OH | TYR | 88 | −15.233 |
| 10.159 | −0.512 | 1.00 | 0.00 | BrD | ATOM | 1491 | HH | TYR | 88 | −15.995 |
| 10.465 | −0.014 | 1.00 | 0.00 | BrD | ATOM | 1492 | C | TYR | 88 | −13.923 |
| 5.374 | 4.256 | 1.00 | 0.00 | BrD | ATOM | 1493 | O | TYR | 88 | −14.369 |
| 4.711 | 3.320 | 1.00 | 0.00 | BrD | ATOM | 1494 | N | ASN | 89 | −14.408 |
| 5.298 | 5.492 | 1.00 | 0.00 | BrD | ATOM | 1495 | HN | ASN | 89 | −14.012 |
| 5.852 | 6.195 | 1.00 | 0.00 | BrD | ATOM | 1496 | CA | ASN | 89 | −15.518 |
| 4.414 | 5.827 | 1.00 | 0.00 | BrD | ATOM | 1497 | HA | ASN | 89 | −16.155 |
| 4.336 | 4.958 | 1.00 | 0.00 | BrD | ATOM | 1498 | CB | ASN | 89 | −14.996 |
| 3.023 | 6.192 | 1.00 | 0.00 | BrD | ATOM | 1499 | HB1 | ASN | 89 | −15.816 |
| 2.421 | 6.557 | 1.00 | 0.00 | BrD | ATOM | 1500 | HB2 | ASN | 89 | −14.578 |
| 2.559 | 5.311 | 1.00 | 0.00 | BrD | ATOM | 1501 | CG | ASN | 89 | −13.925 |
| 3.072 | 7.263 | 1.00 | 0.00 | BrD | ATOM | 1502 | OD1 | ASN | 89 | −13.552 |
| 4.147 | 7.734 | 1.00 | 0.00 | BrD | ATOM | 1503 | ND2 | ASN | 89 | −13.424 |
| 1.904 | 7.655 | 1.00 | 0.00 | BrD | ATOM | 1504 | HD21 | ASN | 89 | −13.770 |
| 1.090 | 7.236 | 1.00 | 0.00 | BrD | ATOM | 1505 | HD22 | ASN | 89 | −12.731 |
| 1.909 | 8.347 | 1.00 | 0.00 | BrD | ATOM | 1506 | C | ASN | 89 | −16.332 |
| 4.982 | 6.985 | 1.00 | 0.00 | BrD | ATOM | 1507 | O | ASN | 89 | −16.088 |
| 4.658 | 8.147 | 1.00 | 0.00 | BrD | ATOM | 1508 | B | ALA | 90 | −17.296 |
| 5.836 | 6.659 | 1.00 | 0.00 | BrD | ATOM | 1509 | HN | ALA | 90 | −17.438 |
| 6.058 | 5.715 | 1.00 | 0.00 | BrD | ATOM | 1510 | CA | ALA | 90 | −18.142 |
| 6.458 | 7.670 | 1.00 | 0.00 | BrD | ATOM | 1511 | HA | ALA | 90 | −17.525 |
| 7.122 | 8.258 | 1.00 | 0.00 | BrD | ATOM | 1512 | CB | ALA | 90 | −19.228 |
| 7.291 | 7.006 | 1.00 | 0.00 | BrD | ATOM | 1513 | HB1 | ALA | 90 | −19.280 |
| 7.045 | 5.956 | 1.00 | 0.00 | BrD | ATOM | 1514 | HB2 | ALA | 90 | −18.997 |
| 8.340 | 7.119 | 1.00 | 0.00 | BrD | ATOM | 1515 | HB3 | ALA | 90 | −20.179 |
| 7.081 | 7.473 | 1.00 | 0.00 | BrD | ATOM | 1516 | C | ALA | 90 | −18.764 |
| 5.414 | 8.594 | 1.00 | 0.00 | BrD | ATOM | 1517 | O | ALA | 90 | −18.728 |
| 5.557 | 9.817 | 1.00 | 0.00 | BrD | ATOM | 1518 | N | PRO | 91 | −19.346 |
| 4.347 | 8.021 | 1.00 | 0.00 | BrD | ATOM | 1519 | CA | PRO | 91 | −20.000 |
| 3.290 | 8.783 | 1.00 | 0.00 | BrD | ATOM | 1520 | HA | PRO | 91 | −20.495 |
| 3.681 | 9.655 | 1.00 | 0.00 | BrD | ATOM | 1521 | CB | PRO | 91 | −21.048 |
| 2.740 | 7.800 | 1.00 | 0.00 | BrD | ATOM | 1522 | HB1 | PRO | 91 | −20.932 |
| 1.670 | 7.715 | 1.00 | 0.00 | BrD | ATOM | 1523 | HB2 | PRO | 91 | −22.038 |
| 2.966 | 8.169 | 1.00 | 0.00 | BrD | ATOM | 1524 | CG | PRO | 91 | −20.794 |
| 3.419 | 6.483 | 1.00 | 0.00 | BrD | ATOM | 1525 | HG1 | PRO | 91 | −20.778 |
| 2.684 | 5.692 | 1.00 | 0.00 | BrD | ATOM | 1526 | HG2 | PRO | 91 | −21.566 |
| 4.151 | 6.296 | 1.00 | 0.00 | BrD | ATOM | 1527 | CD | PRO | 91 | −19.456 |
| 4.095 | 6.587 | 1.00 | 0.00 | BrD | ATOM | 1528 | HD1 | PRO | 91 | −18.670 |
| 3.436 | 6.247 | 1.00 | 0.00 | BrD | ATOM | 1529 | HD2 | PRO | 91 | −19.450 |
| 5.018 | 6.027 | 1.00 | 0.00 | BrD | ATOM | 1530 | C | PRO | 91 | −19.035 |
| 2.183 | 9.196 | 1.00 | 0.00 | BrD | ATOM | 1531 | O | PRO | 91 | −19.458 |
| 1.079 | 9.540 | 1.00 | 0.00 | BrD | ATOM | 1532 | N | GLU | 92 | −17.736 |
| 2.481 | 9.160 | 1.00 | 0.00 | BrD | ATOM | 1533 | HN | GLU | 92 | −17.462 |
| 3.377 | 8.873 | 1.00 | 0.00 | BrD | ATOM | 1534 | CA | GLU | 92 | −16.703 |
| 1.506 | 9.521 | 1.00 | 0.00 | BrD | ATOM | 1535 | HA | GLU | 92 | −15.779 |
| 1.838 | 9.083 | 1.00 | 0.00 | BrD | ATOM | 1536 | CB | GLU | 92 | −16.529 |
| 1.439 | 11.039 | 1.00 | 0.00 | BrD | ATOM | 1537 | HB1 | GLU | 92 | −15.786 |
| 0.690 | 11.272 | 1.00 | 0.00 | BrD | ATOM | 1538 | HB2 | GLU | 92 | −16.182 |
| 2.399 | 11.393 | 1.00 | 0.00 | BrD | ATOM | 1539 | CG | GLU | 92 | −17.809 |
| 1.092 | 11.778 | 1.00 | 0.00 | BrD | ATOM | 1540 | HG1 | GLU | 92 | −18.550 |
| 1.831 | 11.537 | 1.00 | 0.00 | BrD | ATOM | 1541 | HG2 | GLU | 92 | −18.143 |
| 0.119 | 11.452 | 1.00 | 0.00 | BrD | ATOM | 1542 | CD | GLU | 92 | −19.622 |
| 1.062 | 13.283 | 1.00 | 0.00 | BrD | ATOM | 1543 | OE1 | GLU | 92 | −18.536 |
| 1.517 | 14.001 | 1.00 | 0.00 | BrD | ATOM | 1544 | OE2 | GLU | 92 | −16.564 |

TABLE 6-continued

Atomic Structure Coordinates of the
P/CAF Bromodomain/Acetyl-Histamine Complex

| | | | | | | | | | |
|---|---|---|---|---|---|---|---|---|---|
| 0.581 | 13.743 | 1.00 | 0.00 | BrD | ATOM | 1545 | C | GLU | 92 | −17.029 |
| 0.119 | 8.974 | 1.00 | 0.00 | BrD | ATOM | 1546 | O | GLU | 92 | −16.862 |
| 0.887 | 9.663 | 1.00 | 0.00 | BrD | ATOM | 1547 | N | SER | 93 | −17.508 |
| 0.081 | 7.736 | 1.00 | 0.00 | BrD | ATOM | 1548 | HN | SER | 93 | −17.620 |
| 0.919 | 7.240 | 1.00 | 0.00 | BrD | ATOM | 1549 | CA | SER | 93 | −17.863 |
| 1.176 | 7.092 | 1.00 | 0.00 | BrD | ATOM | 1550 | HA | SER | 93 | −18.677 |
| 1.616 | 7.649 | 1.00 | 0.00 | BrD | ATOM | 1551 | CB | SER | 93 | −18.317 |
| 0.925 | 5.653 | 1.00 | 0.00 | BrD | ATOM | 1552 | HB1 | SER | 93 | −17.475 |
| 1.052 | 4.986 | 1.00 | 0.00 | BrD | ATOM | 1553 | HB2 | SER | 93 | −18.695 |
| 0.084 | 5.568 | 1.00 | 0.00 | BrD | ATOM | 1554 | OG | SER | 93 | −19.339 |
| 1.830 | 5.274 | 1.00 | 0.00 | BrD | ATOM | 1555 | HG | SER | 93 | −19.610 |
| 1.648 | 4.371 | 1.00 | 0.00 | BrD | ATOM | 1556 | C | SER | 93 | −16.686 |
| 2.141 | 7.099 | 1.00 | 0.00 | BrD | ATOM | 1557 | O | SER | 93 | −15.700 |
| 1.932 | 7.807 | 1.00 | 0.00 | BrD | ATOM | 1558 | N | GLU | 94 | −16.790 |
| 3.194 | 6.298 | 1.00 | 0.00 | BrD | ATOM | 1559 | HN | GLU | 94 | −17.598 |
| 3.303 | 5.754 | 1.00 | 0.00 | BrD | ATOM | 1560 | CA | GLU | 94 | −15.729 |
| 4.186 | 6.204 | 1.00 | 0.00 | BrD | ATOM | 1561 | HA | GLU | 94 | −15.574 |
| 4.596 | 7.191 | 1.00 | 0.00 | BrD | ATOM | 1562 | CB | GLU | 94 | −16.144 |
| 5.314 | 5.258 | 1.00 | 0.00 | BrD | ATOM | 1563 | HB1 | GLU | 94 | −16.411 |
| 4.887 | 4.302 | 1.00 | 0.00 | BrD | ATOM | 1564 | HB2 | GLU | 94 | −17.006 |
| 5.817 | 5.671 | 1.00 | 0.00 | BrD | ATOM | 1565 | CG | GLU | 94 | −15.054 |
| 6.346 | 5.031 | 1.00 | 0.00 | BrD | ATOM | 1566 | HG1 | GLU | 94 | −14.187 |
| 5.849 | 4.622 | 1.00 | 0.00 | BrD | ATOM | 1567 | HG2 | GLU | 94 | −14.797 |
| 6.793 | 5.981 | 1.00 | 0.00 | BrD | ATOM | 1568 | CD | GLU | 94 | −15.479 |
| 7.446 | 4.078 | 1.00 | 0.00 | BrD | ATOM | 1569 | OE1 | GLU | 94 | −16.617 |
| 7.382 | 3.568 | 1.00 | 0.00 | BrD | ATOM | 1570 | OE2 | GLU | 94 | −14.673 |
| 8.370 | 3.840 | 1.00 | 0.00 | BrD | ATOM | 1571 | C | GLU | 94 | −14.422 |
| 3.556 | 5.725 | 1.00 | 0.00 | BrD | ATOM | 1572 | O | GLU | 94 | −13.351 |
| 4.143 | 5.876 | 1.00 | 0.00 | BrD | ATOM | 1573 | N | TYR | 95 | −14.510 |
| 2.357 | 5.150 | 1.00 | 0.00 | BrD | ATOM | 1574 | HN | TYR | 95 | −15.387 |
| 1.930 | 5.057 | 1.00 | 0.00 | BrD | ATOM | 1575 | CA | TYR | 95 | −13.327 |
| 1.658 | 4.663 | 1.00 | 0.00 | BrD | ATOM | 1576 | HA | TYR | 95 | −12.919 |
| 2.227 | 3.841 | 1.00 | 0.00 | BrD | ATOM | 1577 | CB | TYR | 95 | −13.704 |
| 0.260 | 4.166 | 1.00 | 0.00 | BrD | ATOM | 1578 | HB1 | TYR | 95 | −14.448 |
| 0.160 | 4.827 | 1.00 | 0.00 | BrD | ATOM | 1579 | HB2 | TYR | 95 | −12.825 |
| 0.367 | 4.176 | 1.00 | 0.00 | BrD | ATOM | 1580 | CG | TYR | 95 | −14.270 |
| 0.244 | 2.762 | 1.00 | 0.00 | BrD | ATOM | 1581 | CD1 | TYR | 95 | −14.933 |
| 1.350 | 2.245 | 1.00 | 0.00 | BrD | ATOM | 1582 | HD1 | TYR | 95 | −15.041 |
| 2.232 | 2.859 | 1.00 | 0.00 | BrD | ATOM | 1583 | CD2 | TYR | 95 | −14.141 |
| 0.880 | 1.956 | 1.00 | 0.00 | BrD | ATOM | 1584 | HD2 | TYR | 95 | −13.630 |
| 1.749 | 2.343 | 1.00 | 0.00 | BrD | ATOM | 1585 | CE1 | TYR | 95 | −15.450 |
| 1.337 | 0.963 | 1.00 | 0.00 | BrD | ATOM | 1586 | HE1 | TYR | 95 | −15.961 |
| 2.208 | 0.579 | 1.00 | 0.00 | BrD | ATOM | 1587 | CE2 | TYR | 95 | −14.656 |
| 0.901 | 0.673 | 1.00 | 0.00 | BrD | ATOM | 1588 | HE2 | TYR | 95 | −14.546 |
| 1.785 | 0.062 | 1.00 | 0.00 | BrD | ATOM | 1589 | CZ | TYR | 95 | −15.310 |
| 0.210 | 0.182 | 1.00 | 0.00 | BrD | ATOM | 1590 | OH | TYR | 95 | −19.823 |
| 0.193 | −1.095 | 1.00 | 0.00 | BrD | ATOM | 1591 | HH | TYR | 95 | −16.730 |
| 0.508 | −1.079 | 1.00 | 0.00 | BrD | ATOM | 1592 | C | TYR | 95 | −12.274 |
| 1.552 | 5.761 | 1.00 | 0.00 | BrD | ATOM | 1593 | O | TYR | 95 | −11.076 |
| 1.911 | 5.485 | 1.00 | 0.00 | BrD | ATOM | 1594 | N | TYR | 96 | −12.733 |
| 1.513 | 7.007 | 1.00 | 0.00 | BrD | ATOM | 1595 | HN | TYR | 96 | −13.700 |
| 1.553 | 7.161 | 1.00 | 0.00 | BrD | ATOM | 1596 | CA | TYR | 96 | −11.835 |
| 1.421 | 8.192 | 1.00 | 0.00 | BrD | ATOM | 1597 | HA | TYR | 96 | −11.033 |
| 0.746 | 7.889 | 1.00 | 0.00 | BrD | ATOM | 1598 | CN | TYR | 96 | −12.581 |
| 0.860 | 9.365 | 1.00 | 0.00 | BrD | ATOM | 1599 | HB1 | TYR | 96 | −13.397 |
| 1.522 | 9.615 | 1.00 | 0.00 | BrD | ATOM | 1600 | HB2 | TYR | 96 | −12.977 |
| 0.114 | 9.116 | 1.00 | 0.00 | BrD | ATOM | 1601 | CG | TYR | 96 | −11.712 |
| 0.708 | 10.994 | 1.00 | 0.00 | BrD | ATOM | 1602 | CD1 | TYR | 96 | −10.351 |
| 0.458 | 10.477 | 1.00 | 0.00 | BrD | ATOM | 1603 | HD1 | TYR | 96 | −9.918 |
| 0.375 | 9.493 | 1.00 | 0.00 | BrD | ATOM | 1604 | CD2 | TYR | 96 | −12.252 |
| 0.815 | 11.870 | 1.00 | 0.00 | BrD | ATOM | 1605 | HD2 | TYR | 96 | −13.308 |
| 1.009 | 11.979 | 1.00 | 0.00 | BrD | ATOM | 1606 | CE1 | TYR | 96 | −9.551 |
| 0.319 | 11.594 | 1.00 | 0.00 | BrD | ATOM | 1607 | HE1 | TYR | 96 | −8.495 |
| 0.125 | 11.480 | 1.00 | 0.00 | BrD | ATOM | 1608 | CE2 | TYR | 96 | −11.458 |
| 0.677 | 12.993 | 1.00 | 0.00 | BrD | ATOM | 1609 | HE2 | TYR | 96 | −11.895 |
| 0.763 | 13.977 | 1.00 | 0.00 | BrD | ATOM | 1610 | CZ | TYR | 96 | −10.109 |
| 0.429 | 12.849 | 1.00 | 0.00 | BrD | ATOM | 1611 | OH | TYR | 96 | −9.315 |
| 0.291 | 13.964 | 1.00 | 0.00 | BrD | ATOM | 1612 | HH | TYR | 96 | −8.479 |
| 0.742 | 13.821 | 1.00 | 0.00 | BrD | ATOM | 1613 | C | TYR | 96 | −11.238 |
| 2.783 | 8.497 | 1.00 | 0.00 | BrD | ATOM | 1614 | O | TYR | 96 | −10.238 |
| 2.868 | 9.211 | 1.00 | 0.00 | BrD | ATOM | 1615 | N | LYS | 97 | −11.857 |
| 3.849 | 7.995 | 1.00 | 0.00 | BrD | ATOM | 1616 | HN | LYS | 97 | −12.650 |
| 3.728 | 7.435 | 1.00 | 0.00 | BrD | ATOM | 1617 | CA | LYS | 97 | −11.390 |
| 5.200 | 8.256 | 1.00 | 0.00 | BrD | ATOM | 1618 | HA | LYS | 97 | −11.067 |
| 5.248 | 9.285 | 1.00 | 0.00 | BrD | ATOM | 1619 | CB | LYS | 97 | −12.547 |
| 6.183 | 8.044 | 1.00 | 0.00 | BrD | ATOM | 1620 | HB1 | LYS | 97 | −11.075 |
| 5.901 | 7.145 | 1.00 | 0.00 | BrD | ATOM | 1621 | HB2 | LYS | 97 | −13.223 |

TABLE 6-continued

Atomic Structure Coordinates of the
P/CAF Bromodomain/Acetyl-Histamine Complex

| | | | | | | | | | | |
|---|---|---|---|---|---|---|---|---|---|---|
| 6.110 | 8.884 | 1.00 | 0.00 | BrD | ATOM | 1622 | CG | LYS | 97 | −12.120 |
| 7.632 | 7.902 | 1.00 | 0.00 | BrD | ATOM | 1623 | HG1 | LYS | 97 | −11.914 |
| 7.826 | 6.862 | 1.00 | 0.00 | BrD | ATOM | 1624 | HG2 | LYS | 97 | −11.227 |
| 7.795 | 8.487 | 1.00 | 0.00 | BrD | ATOM | 1625 | CD | LYS | 97 | −13.205 |
| 8.984 | 8.379 | 1.00 | 0.00 | BrD | ATOM | 1626 | HD1 | LYS | 97 | −14.156 |
| 8.255 | 7.989 | 1.00 | 0.00 | BrD | ATOM | 1627 | HD2 | LYS | 97 | −12.986 |
| 9.579 | 8.013 | 1.00 | 0.00 | BrD | ATOM | 1628 | CE | LYS | 97 | −13.282 |
| 8.625 | 9.697 | 1.00 | 0.00 | BrD | ATOM | 1629 | HE1 | LYS | 97 | −13.091 |
| 7.633 | 10.281 | 1.00 | 0.00 | BrD | ATOM | 1630 | HE2 | LYS | 97 | −12.527 |
| 9.304 | 10.265 | 1.00 | 0.00 | BrD | ATOM | 1631 | NZ | LYS | 97 | −14.617 |
| 9.080 | 10.374 | 1.00 | 0.00 | BrD | ATOM | 1632 | HZ1 | LYS | 97 | −14.760 |
| 10.082 | 10.135 | 1.00 | 0.00 | BrD | ATOM | 1633 | HZ2 | LYS | 97 | −15.368 |
| 8.517 | 9.926 | 1.00 | 0.00 | BrD | ATOM | 1634 | HZ3 | LYS | 97 | −14.685 |
| 8.968 | 11.406 | 1.00 | 0.00 | BrD | ATOM | 1635 | C | LYS | 97 | −10.212 |
| 5.550 | 7.349 | 1.00 | 0.00 | BrD | ATOM | 1636 | O | LYS | 97 | −9.123 |
| 5.870 | 7.824 | 1.00 | 0.00 | BrD | ATOM | 1637 | B | CYS | 98 | −10.443 |
| 5.490 | 6.040 | 1.00 | 0.00 | BrD | ATOM | 1638 | HN | CYS | 98 | −11.334 |
| 5.233 | 5.724 | 1.00 | 0.00 | BrD | ATOM | 1639 | CA | CYS | 98 | −9.408 |
| 5.811 | 5.062 | 1.00 | 0.00 | BrD | ATOM | 1640 | HA | CYS | 98 | −9.253 |
| 6.879 | 5.086 | 1.00 | 0.00 | BrD | ATOM | 1641 | CB | CYS | 98 | −9.862 |
| 5.408 | 3.660 | 1.00 | 0.00 | BrD | ATOM | 1642 | HB1 | CYS | 98 | −9.000 |
| 5.351 | 3.012 | 1.00 | 0.00 | BrD | ATOM | 1643 | HB2 | CYS | 98 | −10.337 |
| 4.440 | 3.707 | 1.00 | 0.00 | BrD | ATOM | 1644 | SG | CYS | 98 | −11.036 |
| 6.562 | 2.916 | 1.00 | 0.00 | BrD | ATOM | 1645 | HD | CYS | 98 | −11.755 |
| 6.695 | 3.538 | 1.00 | 0.00 | BrD | ATOM | 1646 | C | CYS | 98 | −8.093 |
| 5.121 | 5.405 | 1.00 | 0.00 | BrD | ATOM | 1647 | O | CYS | 98 | −7.040 |
| 5.757 | 5.442 | 1.00 | 0.00 | BrD | ATOM | 1648 | N | ALA | 99 | −8.159 |
| 3.820 | 5.668 | 1.00 | 0.00 | BrD | ATOM | 1649 | HN | ALA | 99 | −9.028 |
| 3.368 | 5.644 | 1.00 | 0.00 | BrD | ATOM | 1650 | CA | ALA | 99 | −6.975 |
| 3.066 | 6.046 | 1.00 | 0.00 | BrD | ATOM | 1651 | HA | ALA | 99 | −6.290 |
| 3.066 | 5.214 | 1.00 | 0.00 | BrD | ATOM | 1652 | CB | ALA | 99 | −7.339 |
| 1.623 | 6.363 | 1.00 | 0.00 | BrD | ATOM | 1653 | HB1 | ALA | 99 | −8.281 |
| 1.597 | 6.890 | 1.00 | 0.00 | BrD | ATOM | 1654 | HB2 | ALA | 99 | −7.425 |
| 1.063 | 5.443 | 1.00 | 0.00 | BrD | ATOM | 1655 | HB3 | ALA | 99 | −6.568 |
| 1.185 | 6.980 | 1.00 | 0.00 | BrD | ATOM | 1656 | C | ALA | 99 | −6.293 |
| 3.721 | 7.232 | 1.00 | 0.00 | BrD | ATOM | 1657 | O | ALA | 99 | −5.092 |
| 3.963 | 7.207 | 1.00 | 0.00 | BrD | ATOM | 1658 | N | ASN | 100 | −7.080 |
| 4.054 | 8.247 | 1.00 | 0.00 | BrD | ATOM | 1659 | HN | ASN | 100 | −8.019 |
| 3.848 | 8.199 | 1.00 | 0.00 | BrD | ATOM | 1660 | CA | ASN | 100 | −6.550 |
| 4.702 | 9.438 | 1.00 | 0.00 | BrD | ATOM | 1661 | HA | ASN | 100 | −9.922 |
| 3.988 | 9.949 | 1.00 | 0.00 | BrD | ATOM | 1662 | CB | ASN | 100 | −7.697 |
| 5.116 | 10.363 | 1.00 | 0.00 | BrD | ATOM | 1663 | HB1 | ASN | 100 | −8.587 |
| 4.570 | 10.089 | 1.00 | 0.00 | BrD | ATOM | 1664 | HB2 | ASN | 100 | −7.879 |
| 6.174 | 10.247 | 1.00 | 0.00 | BrD | ATOM | 1665 | CG | ASN | 100 | −7.395 |
| 4.838 | 11.822 | 1.00 | 0.00 | BrD | ATOM | 1666 | OD1 | ASN | 100 | −7.283 |
| 3.684 | 12.236 | 1.00 | 0.00 | BrD | ATOM | 1667 | HD2 | ASN | 100 | −7.266 |
| 5.898 | 12.611 | 1.00 | 0.00 | BrD | ATOM | 1668 | HD21 | ASN | 100 | −7.370 |
| 6.787 | 12.212 | 1.00 | 0.00 | BrD | ATOM | 1669 | HD22 | ASN | 100 | −7.072 |
| 5.748 | 13.560 | 1.00 | 0.00 | BrD | ATOM | 1670 | C | ASN | 100 | −5.711 |
| 5.922 | 9.069 | 1.00 | 0.00 | BrD | ATOM | 1671 | O | ASN | 100 | −4.740 |
| 6.251 | 9.753 | 1.00 | 0.00 | BrD | ATOM | 1672 | N | ILE | 101 | −6.088 |
| 6.587 | 7.981 | 1.00 | 0.00 | BrD | ATOM | 1673 | HN | ILE | 101 | −6.870 |
| 6.277 | 7.481 | 1.00 | 0.00 | BrD | ATOM | 1674 | CA | ILE | 101 | −5.377 |
| 7.777 | 7.524 | 1.00 | 0.00 | BrD | ATOM | 1675 | HA | ILE | 101 | −5.132 |
| 8.370 | 8.394 | 1.00 | 0.00 | BrD | ATOM | 1676 | CB | ILE | 101 | −6.254 |
| 8.636 | 6.594 | 1.00 | 0.00 | BrD | ATOM | 1677 | HB | ILE | 101 | −6.469 |
| 8.061 | 5.705 | 1.00 | 0.00 | BrD | ATOM | 1678 | OG1 | ILE | 101 | −7.569 |
| 8.996 | 7.290 | 1.00 | 0.00 | BrD | ATOM | 1679 | HG11 | ILE | 101 | −8.112 |
| 8.090 | 7.513 | 1.00 | 0.00 | BrD | ATOM | 1680 | HG12 | ILE | 101 | −7.350 |
| 9.516 | 8.212 | 1.00 | 0.00 | BrD | ATOM | 1681 | OG2 | ILE | 101 | −9.509 |
| 9.894 | 6.177 | 1.00 | 0.00 | BrD | ATOM | 1682 | HG21 | ILE | 101 | −6.221 |
| 10.659 | 5.902 | 1.00 | 0.00 | BrD | ATOM | 1683 | HG22 | ILE | 101 | −4.905 |
| 10.244 | 7.001 | 1.00 | 0.00 | BrD | ATOM | 1684 | HG23 | ILE | 101 | −4.874 |
| 9.673 | 9.333 | 1.00 | 0.00 | BrD | ATOM | 1685 | CD1 | ILE | 101 | −8.470 |
| 9.885 | 6.461 | 1.00 | 0.00 | BrD | ATOM | 1686 | HD11 | ILE | 101 | −9.158 |
| 10.406 | 7.109 | 1.00 | 0.00 | BrD | ATOM | 1687 | HD12 | ILE | 101 | −7.869 |
| 10.604 | 9.922 | 1.00 | 0.00 | BrD | ATOM | 1688 | HD13 | ILE | 101 | −9.024 |
| 9.281 | 5.758 | 1.00 | 0.00 | BrD | ATOM | 1689 | C | ILE | 101 | −4.084 |
| 7.408 | 6.802 | 1.00 | 0.00 | BrD | ATOM | 1690 | O | ILE | 101 | −2.993 |
| 7.580 | 7.345 | 1.00 | 0.00 | BrD | ATOM | 1691 | N | LEU | 102 | −4.206 |
| 6.890 | 5.579 | 1.00 | 0.00 | BrD | ATOM | 1692 | HN | LEU | 102 | −5.100 |
| 6.770 | 5.196 | 1.00 | 0.00 | BrD | ATOM | 1693 | C | LEU | 102 | −3.033 |
| 6.486 | 4.800 | 1.00 | 0.00 | BrD | ATOM | 1694 | HA | LEU | 102 | −2.519 |
| 7.384 | 4.485 | 1.00 | 0.00 | BrD | ATOM | 1695 | CB | LEU | 102 | −3.454 |
| 5.690 | 3.565 | 1.00 | 0.00 | BrD | ATOM | 1696 | HB1 | LEU | 102 | −4.530 |
| 5.734 | 3.485 | 1.00 | 0.00 | BrD | ATOM | 1697 | HB2 | LEU | 102 | −3.164 |
| 4.661 | 3.717 | 1.00 | 0.00 | BrD | ATOM | 1698 | CG | LEU | 102 | −2.852 |

TABLE 6-continued

Atomic Structure Coordinates of the
P/CAF Bromodomain/Acetyl-Histamine Complex

| | | | | | | | | | | |
|---|---|---|---|---|---|---|---|---|---|---|
| 6.166 | 2.236 | 1.00 | 0.00 | BrD | ATOM | 1699 | HG | LEU | 102 | −2.990 |
| 5.394 | 1.493 | 1.00 | 0.00 | BrD | ATOM | 1700 | CG1 | LEU | 102 | −3.570 |
| 7.417 | 1.745 | 1.00 | 0.00 | BrD | ATOM | 1701 | HD11 | LEU | 102 | −4.201 |
| 7.803 | 2.533 | 1.00 | 0.00 | BrD | ATOM | 1702 | HD12 | LEU | 102 | −2.843 |
| 8.165 | 1.468 | 1.00 | 0.00 | BrD | ATOM | 1703 | HD13 | LEU | 102 | −4.180 |
| 7.170 | 0.887 | 1.00 | 0.00 | BrD | ATOM | 1704 | CD2 | LEU | 102 | −1.353 |
| 6.418 | 2.376 | 1.00 | 0.00 | BrD | ATOM | 1705 | HD21 | LEU | 102 | −1.167 |
| 7.481 | 2.412 | 1.00 | 0.00 | BrD | ATOM | 1706 | HD22 | LEU | 102 | −0.992 |
| 5.959 | 3.285 | 1.00 | 0.00 | BrD | ATOM | 1707 | HD23 | LEU | 102 | −0.833 |
| 5.992 | 1.529 | 1.00 | 0.00 | BrD | ATOM | 1708 | C | LEU | 102 | −2.087 |
| 5.649 | 5.649 | 1.00 | 0.00 | BrD | ATOM | 1709 | O | LEU | 102 | −0.868 |
| 5.770 | 5.546 | 1.00 | 0.00 | BrD | ATOM | 1710 | N | GLU | 103 | −2.661 |
| 4.792 | 6.486 | 1.00 | 0.00 | BrD | ATOM | 1711 | HN | GLU | 103 | −3.639 |
| 4.747 | 6.528 | 1.00 | 0.00 | BrD | ATOM | 1712 | CA | GLU | 103 | −1.872 |
| 3.948 | 7.369 | 1.00 | 0.00 | BrD | ATOM | 1713 | HA | GLU | 103 | −1.199 |
| 3.364 | 6.758 | 1.00 | 0.00 | BrD | ATOM | 1714 | CB | GLU | 103 | −2.781 |
| 3.002 | 8.159 | 1.00 | 0.00 | BrD | ATOM | 1715 | HB1 | GLU | 103 | −3.230 |
| 2.297 | 7.475 | 1.00 | 0.00 | BrD | ATOM | 1716 | HB2 | GLU | 103 | −3.559 |
| 3.579 | 8.627 | 1.00 | 0.00 | BrD | ATOM | 1717 | CG | GLU | 103 | −2.060 |
| 2.222 | 9.242 | 1.00 | 0.00 | BrD | ATOM | 1718 | HG1 | GLU | 103 | −2.356 |
| 2.611 | 10.205 | 1.00 | 0.00 | BrD | ATOM | 1719 | HG2 | GLU | 103 | −0.999 |
| 2.356 | 9.112 | 1.00 | 0.00 | BrD | ATOM | 1720 | CD | GLU | 103 | −2.373 |
| 0.740 | 9.200 | 1.00 | 0.00 | BrD | ATOM | 1721 | OE1 | GLU | 103 | −2.248 |
| 0.077 | 10.251 | 1.00 | 0.00 | BrD | ATOM | 1722 | OE2 | GLU | 103 | −2.745 |
| 0.242 | 8.117 | 1.00 | 0.00 | BrD | ATOM | 1723 | C | GLU | 103 | −1.052 |
| 4.806 | 8.322 | 1.00 | 0.00 | BrD | ATOM | 1724 | O | GLU | 103 | 0.179 |
| 4.759 | 8.317 | 1.00 | 0.00 | BrD | ATOM | 1725 | N | LYS | 104 | −1.740 |
| 5.627 | 9.117 | 1.00 | 0.00 | BrD | ATOM | 1726 | H | LYS | 104 | −2.720 |
| 5.629 | 9.066 | 1.00 | 0.00 | BrD | ATOM | 1727 | CA | LYS | 104 | −1.072 |
| 6.511 | 10.062 | 1.00 | 0.00 | BrD | ATOM | 1728 | HA | LYS | 104 | −0.569 |
| 5.894 | 10.792 | 1.00 | 0.00 | BrD | ATOM | 1729 | CB | LYS | 104 | −2.097 |
| 7.395 | 10.777 | 1.00 | 0.00 | BrD | ATOM | 1730 | HB1 | LYS | 104 | −2.976 |
| 7.479 | 10.157 | 1.00 | 0.00 | BrD | ATOM | 1731 | HB2 | LYS | 104 | −1.670 |
| 8.377 | 10.917 | 1.00 | 0.00 | BrD | ATOM | 1732 | CG | LYS | 104 | −2.520 |
| 6.861 | 12.136 | 1.00 | 0.00 | BrD | ATOM | 1733 | HG1 | LYS | 104 | −3.354 |
| 7.445 | 12.497 | 1.00 | 0.00 | BrD | ATOM | 1734 | HG2 | LYS | 104 | −1.691 |
| 6.951 | 12.822 | 1.00 | 0.00 | BrD | ATOM | 1735 | CD | LYS | 104 | −2.938 |
| 5.401 | 12.056 | 1.00 | 0.00 | BrD | ATOM | 1736 | HD1 | LYS | 104 | −2.817 |
| 5.059 | 11.039 | 1.00 | 0.00 | BrD | ATOM | 1737 | HD2 | LYS | 104 | −2.306 |
| 4.819 | 12.712 | 1.00 | 0.00 | BrD | ATOM | 1738 | CE | LYS | 104 | −4.387 |
| 5.210 | 12.469 | 1.00 | 0.00 | BrD | ATOM | 1739 | HE1 | LYS | 104 | −4.975 |
| 5.002 | 11.567 | 1.00 | 0.00 | BrD | ATOM | 1740 | HE2 | LYS | 104 | −4.741 |
| 6.120 | 12.930 | 1.00 | 0.00 | BrD | ATOM | 1741 | NZ | LYS | 104 | −4.547 |
| 4.085 | 13.432 | 1.00 | 0.00 | BrD | ATOM | 1742 | HZ1 | LYS | 104 | −5.135 |
| 4.384 | 14.236 | 1.00 | 0.00 | BrD | ATOM | 1743 | HZ2 | LYS | 104 | −5.004 |
| 3.277 | 12.964 | 1.00 | 0.00 | BrD | ATOM | 1744 | HZ3 | LYS | 104 | −3.618 |
| 3.785 | 13.788 | 1.00 | 0.00 | BrD | ATOM | 1745 | C | LYS | 104 | −0.039 |
| 7.383 | 9.357 | 1.00 | 0.00 | BrD | ATOM | 1746 | O | LYS | 104 | 1.021 |
| 7.678 | 9.910 | 1.00 | 0.00 | BrD | ATOM | 1747 | N | PHE | 105 | −0.397 |
| 7.796 | 8.139 | 1.00 | 0.00 | BrD | ATOM | 1748 | HN | PHE | 105 | −1.217 |
| 7.526 | 7.749 | 1.00 | 0.00 | BrD | ATOM | 1749 | CA | PHE | 105 | 0.541 |
| 8.636 | 7.352 | 1.00 | 0.00 | BrD | ATOM | 1750 | HA | PHE | 105 | 0.954 |
| 9.385 | 8.011 | 1.00 | 0.00 | BrD | ATOM | 1751 | CB | PHE | 105 | −0.229 |
| 9.331 | 6.228 | 1.00 | 0.00 | BrD | ATOM | 1752 | HB1 | PHE | 105 | 0.455 |
| 9.569 | 5.426 | 1.00 | 0.00 | BrD | ATOM | 1753 | HB2 | PHE | 105 | −0.992 |
| 8.662 | 9.857 | 1.00 | 0.00 | BrD | ATOM | 1754 | CG | PHE | 105 | −0.899 |
| 10.604 | 6.658 | 1.00 | 0.00 | BrD | ATOM | 1755 | CD1 | PHE | 105 | −0.202 |
| 11.559 | 7.301 | 1.00 | 0.00 | BrD | ATOM | 1756 | HD1 | PHE | 105 | 0.833 |
| 11.361 | 7.633 | 1.00 | 0.00 | BrD | ATOM | 1757 | CD2 | PHE | 105 | −2.226 |
| 10.844 | 6.342 | 1.00 | 0.00 | BrD | ATOM | 1758 | HD2 | PHE | 105 | −2.779 |
| 10.106 | 5.780 | 1.00 | 0.00 | BrD | ATOM | 1759 | CE1 | PHE | 105 | −0.816 |
| 12.730 | 7.780 | 1.00 | 0.00 | BrD | ATOM | 1760 | HE1 | PHE | 105 | −0.262 |
| 13.467 | 8.342 | 1.00 | 0.00 | BrD | ATOM | 1761 | CE2 | PHE | 105 | −2.846 |
| 12.013 | 6.738 | 1.00 | 0.00 | BrD | ATOM | 1762 | HE2 | PHE | 105 | −3.861 |
| 12.188 | 6.465 | 1.00 | 0.00 | BrD | ATOM | 1763 | CZ | PHE | 105 | −2.140 |
| 12.958 | 7.458 | 1.00 | 0.00 | BrD | ATOM | 1764 | HZ | PHE | 105 | −2.623 |
| 13.873 | 7.768 | 1.00 | 0.00 | BrD | ATOM | 1765 | C | PHE | 105 | 1.684 |
| 7.817 | 6.766 | 1.00 | 0.00 | BrD | ATOM | 1766 | O | PHE | 105 | 2.845 |
| 7.998 | 7.133 | 1.00 | 0.00 | BrD | ATOM | 1767 | N | PHE | 106 | 1.347 |
| 6.917 | 5.849 | 1.00 | 0.00 | BrD | ATOM | 1768 | HN | PHE | 106 | 0.405 |
| 6.824 | 5.595 | 1.00 | 0.00 | BrD | ATOM | 1769 | CA | PHE | 106 | 2.344 |
| 6.075 | 5.202 | 1.00 | 0.00 | BrD | ATOM | 1770 | HA | PHE | 106 | 2.956 |
| 6.711 | 4.579 | 1.00 | 0.00 | BrD | ATOM | 1770 | CB | PHE | 106 | 1.665 |
| 5.021 | 4.325 | 1.00 | 0.00 | BrD | ATOM | 1772 | HB1 | PHE | 106 | 0.985 |
| 5.512 | 3.644 | 1.00 | 0.00 | BrD | ATOM | 1773 | HB2 | PHE | 106 | 1.110 |
| 4.341 | 4.954 | 1.00 | 0.00 | BrD | ATOM | 1774 | CG | PHE | 106 | 2.633 |
| 4.213 | 3.510 | 1.00 | 0.00 | BrD | ATOM | 1775 | CD1 | PHE | 106 | 3.519 |

TABLE 6-continued

Atomic Structure Coordinates of the
P/CAF Bromodomain/Acetyl-Histamine Complex

| | | | | | | | | | | |
|---|---|---|---|---|---|---|---|---|---|---|
| 4.836 | 2.649 | 1.00 | 0.00 | BrD | ATOM | 1776 | HD1 | PHE | 106 | 3.508 |
| 5.913 | 2.565 | 1.00 | 0.00 | BrD | ATOM | 1777 | CD2 | PHE | 106 | 2.662 |
| 2.831 | 3.612 | 1.00 | 0.00 | BrD | ATOM | 1778 | HD2 | PHE | 106 | 1.974 |
| 2.333 | 4.279 | 1.00 | 0.00 | BrD | ATOM | 1779 | CE1 | PHE | 106 | 4.413 |
| 4.098 | 1.898 | 1.00 | 0.00 | BrD | ATOM | 1780 | HE1 | PHE | 106 | 5.098 |
| 4.598 | 1.229 | 1.00 | 0.00 | BrD | ATOM | 1781 | CE2 | PHE | 106 | 3.548 |
| 2.086 | 2.857 | 1.00 | 0.00 | BrD | ATOM | 1782 | HE2 | PHE | 106 | 3.562 |
| 1.010 | 2.946 | 1.00 | 0.00 | BrD | ATOM | 1783 | CZ | PHE | 106 | 4.432 |
| 2.721 | 2.005 | 1.00 | 0.00 | BrD | ATOM | 1784 | HZ | PHE | 106 | 5.127 |
| 2.142 | 1.417 | 1.00 | 0.00 | BrD | ATOM | 1785 | C | PHE | 106 | 3.236 |
| 5.388 | 6.230 | 1.00 | 0.00 | BrD | ATOM | 1786 | O | PHE | 106 | 4.439 |
| 5.637 | 6.282 | 1.00 | 0.00 | BrD | ATOM | 1787 | N | PHE | 107 | 2.643 |
| 4.516 | 7.043 | 1.00 | 0.00 | BrD | ATOM | 1788 | NH | PHE | 107 | 1.679 |
| 4.349 | 6.948 | 1.00 | 0.00 | BrD | ATOM | 1789 | CA | PHE | 107 | 3.401 |
| 3.784 | 8.098 | 1.00 | 0.00 | BrD | ATOM | 1790 | HA | PHE | 107 | 4.035 |
| 3.076 | 7.543 | 1.00 | 0.00 | BrD | ATOM | 1791 | CB | PHE | 107 | 2.462 |
| 3.014 | 8.995 | 1.00 | 0.00 | BrD | ATOM | 1792 | HB1 | PHE | 107 | 1.719 |
| 3.629 | 9.384 | 1.00 | 0.00 | BrD | ATOM | 1793 | HB2 | PHE | 107 | 3.040 |
| 2.618 | 9.817 | 1.00 | 0.00 | BrD | ATOM | 1794 | CG | PHE | 107 | 1.741 |
| 1.858 | 8.345 | 1.00 | 0.00 | BrD | ATOM | 1795 | CD1 | PHE | 107 | 1.007 |
| 0.971 | 9.117 | 1.00 | 0.00 | BrD | ATOM | 1796 | HD1 | PHE | 107 | 0.954 |
| 1.118 | 10.186 | 1.00 | 0.00 | BrD | ATOM | 1797 | CD2 | PHE | 107 | 1.798 |
| 1.652 | 6.972 | 1.00 | 0.00 | BrD | ATOM | 1798 | HD2 | PHE | 107 | 2.368 |
| 2.334 | 6.357 | 1.00 | 0.00 | BrD | ATOM | 1799 | CE1 | PHE | 107 | 0.345 |
| 0.095 | 8.537 | 1.00 | 0.00 | BrD | ATOM | 1800 | HE1 | PHE | 107 | −0.224 |
| 0.776 | 9.151 | 1.00 | 0.00 | BrD | ATOM | 1801 | CE2 | PHE | 107 | 1.137 |
| 0.588 | 6.387 | 1.00 | 0.00 | BrD | ATOM | 1802 | HE2 | PHE | 107 | 1.192 |
| 0.439 | 5.318 | 1.00 | 0.00 | BrD | ATOM | 1803 | CZ | PHE | 107 | 0.410 |
| 0.286 | 7.171 | 1.00 | 0.00 | BrD | ATOM | 1804 | HZ | PHE | 107 | −0.108 |
| 1.118 | 6.718 | 1.00 | 0.00 | BrD | ATOM | 1805 | C | PHE | 107 | 4.287 |
| 4.727 | 8.867 | 1.00 | 0.00 | BrD | ATOM | 1806 | O | PHE | 107 | 5.369 |
| 4.345 | 9.312 | 1.00 | 0.00 | BrD | ATOM | 1807 | N | SER | 108 | 3.825 |
| 5.960 | 9.054 | 1.00 | 0.00 | BrD | ATOM | 1808 | HN | SER | 108 | 2.968 |
| 6.218 | 8.654 | 1.00 | 0.00 | BrD | ATOM | 1809 | CA | SER | 108 | 4.607 |
| 6.959 | 9.773 | 1.00 | 0.00 | BrD | ATOM | 1810 | HA | SER | 108 | 4.981 |
| 6.503 | 10.678 | 1.00 | 0.00 | BrD | ATOM | 1811 | CB | SER | 108 | 3.740 |
| 8.166 | 10.136 | 1.00 | 0.00 | BrD | ATOM | 1812 | HB1 | SER | 108 | 2.987 |
| 7.864 | 10.848 | 1.00 | 0.00 | BrD | ATOM | 1813 | HB2 | SER | 108 | 3.262 |
| 8.546 | 9.245 | 1.00 | 0.00 | BrD | ATOM | 1814 | OG | SER | 108 | 4.521 |
| 9.200 | 10.711 | 1.00 | 0.00 | BrD | ATOM | 1815 | HG | SER | 108 | 4.902 |
| 9.739 | 10.014 | 1.00 | 0.00 | BrD | ATOM | 1816 | C | SER | 108 | 5.784 |
| 7.395 | 8.915 | 1.00 | 0.00 | BrD | ATOM | 1817 | O | SER | 108 | 6.887 |
| 7.618 | 9.413 | 1.00 | 0.00 | BrD | ATOM | 1818 | N | LYS | 109 | 5.540 |
| 7.475 | 7.613 | 1.00 | 0.00 | BrD | ATOM | 1819 | HN | LYS | 109 | 4.643 |
| 7.256 | 7.283 | 1.00 | 0.00 | BrD | ATOM | 1820 | CA | LYS | 109 | 6.578 |
| 7.819 | 6.656 | 1.00 | 0.00 | BrD | ATOM | 1821 | HA | LYS | 109 | 7.113 |
| 8.679 | 7.032 | 1.00 | 0.00 | BrD | ATOM | 1822 | CB | LYS | 109 | 5.950 |
| 8.163 | 9.306 | 1.00 | 0.00 | BrD | ATOM | 1823 | HB1 | LYS | 109 | 4.898 |
| 7.922 | 5.340 | 1.00 | 0.00 | BrD | ATOM | 1824 | HB2 | LYS | 109 | 6.421 |
| 7.566 | 4.542 | 1.00 | 0.00 | BrD | ATOM | 1825 | CG | LYS | 109 | 6.090 |
| 9.626 | 4.926 | 1.00 | 0.00 | BrD | ATOM | 1826 | HG1 | LYS | 109 | 5.522 |
| 9.811 | 4.026 | 1.00 | 0.00 | BrD | ATOM | 1827 | HG2 | LYS | 109 | 7.133 |
| 9.844 | 4.748 | 1.00 | 0.00 | BrD | ATOM | 1828 | CD | LYS | 109 | 5.577 |
| 10.535 | 6.029 | 1.00 | 0.00 | BrD | ATOM | 1829 | HD1 | LYS | 109 | 6.413 |
| 10.864 | 6.629 | 1.00 | 0.00 | BrD | ATOM | 1830 | HD2 | LYS | 109 | 4.885 |
| 9.981 | 6.646 | 1.00 | 0.00 | BrD | ATOM | 1831 | CE | LYS | 109 | 4.866 |
| 11.751 | 5.462 | 1.00 | 0.00 | BrD | ATOM | 1832 | HE1 | LYS | 109 | 5.179 |
| 11.889 | 4.438 | 1.00 | 0.00 | BrD | ATOM | 1833 | HE2 | LYS | 109 | 3.801 |
| 11.575 | 5.491 | 1.00 | 0.00 | BrD | ATOM | 1834 | NZ | LYS | 109 | 5.175 |
| 12.986 | 6.235 | 1.00 | 0.00 | BrD | ATOM | 1835 | HZ1 | LYS | 109 | 6.202 |
| 13.148 | 6.254 | 1.00 | 0.00 | BrD | ATOM | 1836 | HZ3 | LYS | 109 | 4.715 |
| 13.808 | 5.795 | 1.00 | 0.00 | BrD | ATOM | 1837 | HZ3 | LYS | 109 | 4.831 |
| 12.892 | 7.212 | 1.00 | 0.00 | BrD | ATOM | 1838 | C | LYS | 109 | 7.947 |
| 6.653 | 6.504 | 1.00 | 0.00 | BrD | ATOM | 1839 | O | LYS | 109 | 8.761 |
| 6.842 | 6.428 | 1.00 | 0.00 | BrD | ATOM | 1840 | N | ILE | 110 | 6.994 |
| 5.441 | 6.492 | 1.00 | 0.00 | BrD | ATOM | 1841 | HN | ILE | 110 | 6.022 |
| 5.363 | 6.581 | 1.00 | 0.00 | BrD | ATOM | 1842 | CA | ILE | 110 | 7.796 |
| 4.223 | 6.407 | 1.00 | 0.00 | BrD | ATOM | 1843 | HA | ILE | 110 | 8.198 |
| 4.138 | 5.405 | 1.00 | 0.00 | BrD | ATOM | 1844 | CB | ILE | 110 | 6.935 |
| 2.973 | 6.692 | 1.00 | 0.00 | BrD | ATOM | 1845 | HB | ILE | 110 | 6.496 |
| 3.087 | 7.671 | 1.00 | 0.00 | BrD | ATOM | 1846 | CG1 | ILE | 110 | 5.811 |
| 2.844 | 5.654 | 1.00 | 0.00 | BrD | ATOM | 1847 | HG11 | ILE | 110 | 5.353 |
| 3.811 | 5.511 | 1.00 | 0.00 | BrD | ATOM | 1848 | HG12 | ILE | 110 | 5.068 |
| 2.193 | 6.026 | 1.00 | 0.00 | BrD | ATOM | 1849 | CG2 | ILE | 110 | 7.798 |
| 1.722 | 6.712 | 1.00 | 0.00 | BrD | ATOM | 1850 | HG21 | ILE | 110 | 8.756 |
| 1.945 | 6.264 | 1.00 | 0.00 | BrD | ATOM | 1851 | HG22 | ILE | 110 | 7.944 |
| 1.401 | 7.732 | 1.00 | 0.00 | BrD | ATOM | 1852 | HG23 | ILE | 110 | 7.311 |

TABLE 6-continued

Atomic Structure Coordinates of the
P/CAF Bromodomain/Acetyl-Histamine Complex

| | | | | | | | | | | |
|---|---|---|---|---|---|---|---|---|---|---|
| 0.938 | 6.152 | 1.00 | 0.00 | BrD | ATOM | 1853 | CG1 | ILE | 110 | 6.269 |
| 2.345 | 4.297 | 1.00 | 0.00 | BrD | ATOM | 1854 | HD11 | ILE | 110 | 6.222 |
| 3.153 | 3.583 | 1.00 | 0.00 | BrD | ATOM | 1855 | HD12 | ILE | 110 | 7.283 |
| 1.985 | 4.366 | 1.00 | 0.00 | BrD | ATOM | 1856 | HD13 | ILE | 110 | 5.623 |
| 1.540 | 3.971 | 1.00 | 0.00 | BrD | ATOM | 1857 | C | ILE | 110 | 8.948 |
| 4.274 | 7.411 | 1.00 | 0.00 | BrD | ATOM | 1858 | O | ILE | 110 | 10.104 |
| 4.045 | 7.060 | 1.00 | 0.00 | BrD | ATOM | 1859 | N | LYS | 111 | 8.615 |
| 4.582 | 8.662 | 1.00 | 0.00 | BrD | ATOM | 1860 | HN | LYS | 111 | 7.674 |
| 4.752 | 8.875 | 1.00 | 0.00 | BrD | ATOM | 1861 | CA | LYS | 111 | 9.608 |
| 4.664 | 9.730 | 1.00 | 0.00 | BrD | ATOM | 1862 | HA | LYS | 111 | 9.919 |
| 3.660 | 9.972 | 1.00 | 0.00 | BrD | ATOM | 1863 | CB | LYS | 111 | 8.989 |
| 5.308 | 10.972 | 1.00 | 0.00 | BrD | ATOM | 1864 | HB1 | LYS | 111 | 9.742 |
| 5.373 | 11.743 | 1.00 | 0.00 | BrD | ATOM | 1865 | HB2 | LYS | 111 | 8.661 |
| 6.304 | 10.718 | 1.00 | 0.00 | BrD | ATOM | 1866 | CG | LYS | 111 | 7.801 |
| 4.542 | 11.528 | 1.00 | 0.00 | BrD | ATOM | 1867 | HG1 | LYS | 111 | 7.127 |
| 4.304 | 10.718 | 1.00 | 0.00 | BrD | ATOM | 1868 | HG2 | LYS | 111 | 7.293 |
| 5.162 | 12.292 | 1.00 | 0.00 | BrD | ATOM | 1869 | CD | LYS | 111 | 8.237 |
| 3.252 | 12.203 | 1.00 | 0.00 | BrD | ATOM | 1870 | HD1 | LYS | 111 | 8.872 |
| 2.701 | 11.525 | 1.00 | 0.00 | BrD | ATOM | 1871 | HD2 | LYS | 111 | 7.361 |
| 2.666 | 12.437 | 1.00 | 0.00 | BrD | ATOM | 1872 | CE | LYS | 111 | 9.006 |
| 3.527 | 13.485 | 1.00 | 0.00 | BrD | ATOM | 1873 | HE1 | LYS | 111 | 10.044 |
| 3.698 | 13.239 | 1.00 | 0.00 | BrD | ATOM | 1874 | HE2 | LYS | 111 | 8.597 |
| 4.411 | 13.952 | 1.00 | 0.00 | BrD | ATOM | 1875 | NZ | LYS | 111 | 8.916 |
| 2.389 | 14.442 | 1.00 | 0.00 | BrD | ATOM | 1876 | HZ1 | LYS | 111 | 9.335 |
| 2.656 | 19.356 | 1.00 | 0.00 | BrD | ATOM | 1877 | HZ2 | LYS | 111 | 7.921 |
| 2.127 | 14.593 | 1.00 | 0.00 | BrD | ATOM | 1878 | HZ3 | LYS | 111 | 9.428 |
| 1.565 | 14.066 | 1.00 | 0.00 | BrD | ATOM | 1879 | C | LYS | 111 | 10.828 |
| 5.465 | 9.289 | 1.00 | 0.00 | BrD | ATOM | 1880 | O | LYS | 111 | 11.964 |
| 5.112 | 9.607 | 1.00 | 0.00 | BrD | ATOM | 1881 | N | GLU | 112 | 10.585 |
| 6.549 | 8.961 | 1.00 | 0.00 | BrD | ATOM | 1882 | HN | GLU | 112 | 9.658 |
| 6.780 | 8.344 | 1.00 | 0.00 | BrD | ATOM | 1883 | CA | GLU | 112 | 11.662 |
| 7.407 | 8.085 | 1.00 | 0.00 | BrD | ATOM | 1884 | HA | GLU | 112 | 12.330 |
| 7.588 | 8.914 | 1.00 | 0.00 | BrD | ATOM | 1885 | CB | GLU | 112 | 11.098 |
| 8.745 | 7.600 | 1.00 | 0.00 | BrD | ATOM | 1886 | HB1 | GLU | 112 | 10.589 |
| 8.589 | 6.661 | 1.00 | 0.00 | BrD | ATOM | 1887 | HB2 | GLU | 112 | 11.917 |
| 9.432 | 7.445 | 1.00 | 0.00 | BrD | ATOM | 1888 | CG | GLU | 112 | 10.120 |
| 9.383 | 8.573 | 1.00 | 0.00 | BrD | ATOM | 1889 | HG1 | GLU | 112 | 10.678 |
| 9.856 | 9.367 | 1.00 | 0.00 | BrD | ATOM | 1890 | HG2 | GLU | 112 | 9.489 |
| 8.611 | 6.987 | 1.00 | 0.00 | BrD | ATOM | 1891 | CD | GLU | 112 | 9.240 |
| 10.425 | 7.912 | 1.00 | 0.00 | BrD | ATOM | 1892 | OE1 | GLU | 112 | 9.625 |
| 10.932 | 6.837 | 1.00 | 0.00 | BrD | ATOM | 1893 | OE2 | GLU | 112 | 8.165 |
| 10.734 | 8.468 | 1.00 | 0.00 | BrD | ATOM | 1894 | C | GLU | 112 | 12.467 |
| 6.739 | 6.960 | 1.00 | 0.00 | BrD | ATOM | 1895 | O | GLU | 112 | 13.583 |
| 7.120 | 6.677 | 1.00 | 0.00 | BrD | ATOM | 1896 | N | ALA | 113 | 11.840 |
| 5.744 | 6.318 | 1.00 | 0.00 | BrD | ATOM | 1897 | HN | ALA | 113 | 10.932 |
| 5.486 | 6.579 | 1.00 | 0.00 | BrD | ATOM | 1898 | CA | ALA | 113 | 12.492 |
| 5.046 | 5.216 | 1.00 | 0.00 | BrD | ATOM | 1899 | HA | ALA | 113 | 13.355 |
| 5.620 | 4.936 | 1.00 | 0.00 | BrD | ATOM | 1900 | CB | ALA | 113 | 11.573 |
| 4.989 | 4.008 | 1.00 | 0.00 | BrD | ATOM | 1901 | HB1 | ALA | 113 | 11.649 |
| 5.914 | 3.455 | 1.00 | 0.00 | BrD | ATOM | 1902 | HB2 | ALA | 113 | 11.865 |
| 4.166 | 3.373 | 1.00 | 0.00 | BrD | ATOM | 1903 | HB3 | ALA | 113 | 10.554 |
| 4.848 | 4.336 | 1.00 | 0.00 | BrD | ATOM | 1904 | C | ALA | 113 | 12.953 |
| 3.645 | 5.624 | 1.00 | 0.00 | BrD | ATOM | 1905 | O | ALA | 113 | 13.778 |
| 3.035 | 4.943 | 1.00 | 0.00 | BrD | ATOM | 1906 | N | GLY | 114 | 12.435 |
| 3.146 | 6.743 | 1.00 | 0.00 | BrD | ATOM | 1907 | HN | GLY | 114 | 11.790 |
| 3.678 | 7.255 | 1.00 | 0.00 | BrD | ATOM | 1908 | CA | GLY | 114 | 12.833 |
| 1.836 | 7.229 | 1.00 | 0.00 | BrD | ATOM | 1909 | HA1 | GLY | 114 | 12.506 |
| 1.732 | 8.253 | 1.00 | 0.00 | BrD | ATOM | 1910 | HA2 | GLY | 114 | 13.911 |
| 1.749 | 7.200 | 1.00 | 0.00 | BrD | ATOM | 1911 | C | GLY | 114 | 12.252 |
| 0.695 | 6.414 | 1.00 | 0.00 | BrD | ATOM | 1912 | O | GLY | 114 | 12.991 |
| 0.085 | 5.813 | 1.00 | 0.00 | BrD | ATOM | 1913 | N | LEU | 115 | 10.927 |
| 0.590 | 6.405 | 1.00 | 0.00 | BrD | ATOM | 1914 | HN | LEU | 115 | 10.398 |
| 1.231 | 6.921 | 1.00 | 0.00 | BrD | ATOM | 1915 | CA | LEU | 115 | 10.244 |
| 0.482 | 5.683 | 1.00 | 0.00 | BrD | ATOM | 1916 | HA | LEU | 115 | 10.991 |
| 1.195 | 5.369 | 1.00 | 0.00 | BrD | ATOM | 1917 | CB | LEU | 115 | 9.523 |
| 0.066 | 4.442 | 1.00 | 0.00 | BrD | ATOM | 1918 | HB1 | LEU | 115 | 8.622 |
| 0.563 | 4.768 | 1.00 | 0.00 | BrD | ATOM | 1919 | HB2 | LEU | 115 | 9.240 |
| 0.773 | 3.824 | 1.00 | 0.00 | BrD | ATOM | 1920 | CG | LEU | 115 | 10.312 |
| 1.047 | 3.570 | 1.00 | 0.00 | BrD | ATOM | 1921 | HG | LEU | 115 | 9.929 |
| 1.000 | 2.565 | 1.00 | 0.00 | BrD | ATOM | 1922 | CD1 | LEU | 115 | 10.120 |
| 2.469 | 4.061 | 1.00 | 0.00 | BrD | ATOM | 1923 | HD11 | LEU | 115 | 10.216 |
| 3.149 | 3.228 | 1.00 | 0.00 | BrD | ATOM | 1924 | HD12 | LEU | 115 | 9.137 |
| 3.571 | 4.493 | 1.00 | 0.00 | BrD | ATOM | 1925 | HD13 | LEU | 115 | 10.868 |
| 2.699 | 4.804 | 1.00 | 0.00 | BrD | ATOM | 1926 | CD2 | LEU | 115 | 11.790 |
| 0.683 | 3.517 | 1.00 | 0.00 | BrD | ATOM | 1927 | HD21 | LEU | 115 | 12.358 |
| 1.397 | 4.094 | 1.00 | 0.00 | BrD | ATOM | 1928 | HD22 | LEU | 115 | 11.932 |
| 0.306 | 3.924 | 1.00 | 0.00 | BrD | ATOM | 1929 | HD23 | LEU | 115 | 12.127 |

TABLE 6-continued

Atomic Structure Coordinates of the P/CAF Bromodomain/Acetyl-Histamine Complex

| | | | | | | | | | | |
|---|---|---|---|---|---|---|---|---|---|---|
| 0.701 | 2.491 | 1.00 | 0.00 | BrD | ATOM | 1930 | C | LEU | 115 | 9.246 |
| 1.193 | 6.603 | 1.00 | 0.00 | BrD | ATOM | 1931 | O | LEU | 115 | 9.407 |
| 1.183 | 7.823 | 1.00 | 0.00 | BrD | ATOM | 1932 | N | ILE | 116 | 8.209 |
| 1.801 | 6.018 | 1.00 | 0.00 | BrD | ATOM | 1933 | HN | ILE | 116 | 8.131 |
| 1.787 | 5.043 | 1.00 | 0.00 | BrD | ATOM | 1934 | CA | ILE | 116 | 7.196 |
| 2.518 | 6.794 | 1.00 | 0.00 | BrD | ATOM | 1935 | HA | ILE | 116 | 7.614 |
| 3.470 | 7.083 | 1.00 | 0.00 | BrD | ATOM | 1936 | CE | ILE | 116 | 5.930 |
| 2.786 | 5.936 | 1.00 | 0.00 | BrD | ATOM | 1937 | HB | ILE | 116 | 5.183 |
| 3.218 | 6.605 | 1.00 | 0.00 | BrD | ATOM | 1938 | CG1 | ILE | 116 | 5.388 |
| 1.480 | 5.367 | 1.00 | 0.00 | BrD | ATOM | 1939 | HG11 | ILE | 116 | 4.697 |
| 4.713 | 4.570 | 1.00 | 0.00 | BrD | ATOM | 1940 | HG12 | ILE | 116 | 6.209 |
| 0.904 | 4.968 | 1.00 | 0.00 | BrD | ATOM | 1941 | CG2 | ILE | 116 | 6.228 |
| 3.786 | 4.850 | 1.00 | 0.00 | BrD | ATOM | 1942 | HG21 | ILE | 116 | 5.309 |
| 4.261 | 4.538 | 1.00 | 0.00 | BrD | ATOM | 1943 | HG22 | ILE | 116 | 6.671 |
| 3.271 | 4.010 | 1.00 | 0.00 | BrD | ATOM | 1944 | HG23 | ILE | 116 | 6.914 |
| 4.534 | 5.217 | 1.00 | 0.00 | BrD | ATOM | 1945 | CD1 | ILE | 116 | 4.662 |
| 0.615 | 6.373 | 1.00 | 0.00 | BrD | ATOM | 1946 | HD11 | ILE | 116 | 3.870 |
| 0.073 | 5.875 | 1.00 | 0.00 | BrD | ATOM | 1947 | HD12 | ILE | 116 | 4.240 |
| 1.238 | 7.147 | 1.00 | 0.00 | BrD | ATOM | 1948 | HD13 | ILE | 116 | 5.356 |
| 0.086 | 6.812 | 1.00 | 0.00 | BrD | ATOM | 1949 | C | ILE | 116 | 6.802 |
| 1.751 | 8.053 | 1.00 | 0.00 | BrD | ATOM | 1950 | O | ILE | 116 | 7.024 |
| 0.544 | 8.154 | 1.00 | 0.00 | BrD | ATOM | 1951 | N | ASP | 117 | 6.222 |
| 2.465 | 9.014 | 1.00 | 0.00 | BrD | ATOM | 1952 | HN | ASP | 117 | 6.079 |
| 3.424 | 8.874 | 1.00 | 0.00 | BrD | ATOM | 1953 | CA | ASP | 117 | 5.805 |
| 1.862 | 10.275 | 1.00 | 0.00 | BrD | ATOM | 1954 | HA | ASP | 117 | 5.197 |
| 2.585 | 10.798 | 1.00 | 0.00 | BrD | ATOM | 1955 | CE | ASP | 117 | 4.967 |
| 0.609 | 10.013 | 1.00 | 0.00 | BrD | ATOM | 1956 | HB1 | ASP | 117 | 5.564 |
| 0.267 | 10.220 | 1.00 | 0.00 | BrD | ATOM | 1957 | HB2 | ASP | 117 | 4.664 |
| 0.596 | 8.976 | 1.00 | 0.00 | BrD | ATOM | 1958 | CG | ASP | 117 | 3.722 |
| 0.555 | 10.876 | 1.00 | 0.00 | BrD | ATOM | 1959 | OD1 | ASP | 117 | 2.897 |
| 1.488 | 10.787 | 1.00 | 0.00 | BrD | ATOM | 1960 | OD2 | ASP | 117 | 3.572 |
| 0.421 | 11.641 | 1.00 | 0.00 | BrD | ATOM | 1961 | C | ASP | 117 | 7.006 |
| 1.506 | 11.154 | 1.00 | 0.00 | BrD | ATOM | 1962 | O | ASP | 117 | 6.846 |
| 0.892 | 12.209 | 1.00 | 0.00 | BrD | ATOM | 1963 | N | LYS | 118 | 8.206 |
| 1.897 | 10.725 | 1.00 | 0.00 | BrD | ATOM | 1964 | HN | LYS | 118 | 8.282 |
| 2.384 | 9.879 | 1.00 | 0.00 | BrD | ATOM | 1965 | CA | LYS | 118 | 9.416 |
| 1.613 | 11.488 | 1.00 | 0.00 | BrD | ATOM | 1966 | HA | LYS | 118 | 10.248 |
| 2.063 | 10.968 | 1.00 | 0.00 | BrD | ATOM | 1967 | CB | LYS | 118 | 9.315 |
| 2.220 | 12.889 | 1.00 | 0.00 | BrD | ATOM | 1968 | HB1 | LYS | 118 | 8.636 |
| 1.624 | 13.480 | 1.00 | 0.00 | BrD | ATOM | 1969 | HB2 | LYS | 118 | 10.292 |
| 2.199 | 13.349 | 1.00 | 0.00 | BrD | ATOM | 1970 | CG | LYS | 118 | 5.818 |
| 3.656 | 12.895 | 1.00 | 0.00 | BrD | ATOM | 1971 | HG1 | LYS | 118 | 7.921 |
| 3.719 | 12.296 | 1.00 | 0.00 | BrD | ATOM | 1972 | HG2 | LYS | 118 | 8.595 |
| 3.946 | 13.911 | 1.00 | 0.00 | BrD | ATOM | 1973 | CD | LYS | 118 | 9.857 |
| 4.608 | 12.327 | 1.00 | 0.00 | BrD | ATOM | 1974 | HD1 | LYS | 118 | 10.477 |
| 4.972 | 13.133 | 1.00 | 0.00 | BrD | ATOM | 1975 | HD2 | LYS | 118 | 10.468 |
| 4.075 | 11.613 | 1.00 | 0.00 | BrD | ATOM | 1976 | CE | LYS | 118 | 9.208 |
| 5.794 | 11.631 | 1.00 | 0.00 | BrD | ATOM | 1977 | HE1 | LYS | 118 | 8.502 |
| 5.425 | 10.902 | 1.00 | 0.00 | BrD | ATOM | 1978 | HE2 | LYS | 118 | 8.687 |
| 6.386 | 12.369 | 1.00 | 0.00 | BrD | ATOM | 1979 | NZ | LYS | 118 | 10.212 |
| 6.652 | 10.943 | 1.00 | 0.00 | BrD | ATOM | 1980 | HZ1 | LYS | 118 | 11.163 |
| 6.458 | 11.316 | 1.00 | 0.00 | BrD | ATOM | 1981 | HZ2 | LYS | 118 | 9.989 |
| 7.656 | 11.096 | 1.00 | 0.00 | BrD | ATOM | 1982 | HZ3 | LYS | 118 | 10.206 |
| 6.459 | 9.921 | 1.00 | 0.00 | BrD | ATOM | 1983 | C | LYS | 118 | 9.657 |
| 0.110 | 11.591 | 1.00 | 0.00 | BrD | ATOM | 1984 | OT1 | LYS | 118 | 9.047 |
| 0.641 | 10.802 | 1.00 | 0.00 | BrD | ATOM | 1985 | OT2 | LYS | 118 | 10.454 |
| 0.302 | 12.459 | 1.00 | 0.00 | BrD | END | | | | | |

What is claimed is:

1. An isolated nucleic acid encoding a peptide consisting of about 21 to 40 amino acids consisting essentially of a ZA loop of a bromodomain consisting of the amino acid sequence of SEQ ID NO:3.

2. An isolated nucleic acid encoding a peptide consisting of about 21 to 40 amino acids consisting of a ZA loop of a bromodomain, wherein the bromodomain has an amino acid sequence selected from the group consisting of SEQ ID NO: 7.

* * * * *